United States Patent
Caferro et al.

(10) Patent No.: US 9,688,672 B2
(45) Date of Patent: *Jun. 27, 2017

(54) 3-PYRIMIDIN-4-YL-OXAZOLIDIN-2-ONES AS INHIBITORS OF MUTANT IDH

(71) Applicant: NOVARTIS AG

(72) Inventors: Thomas Raymond Caferro, Abington, MA (US); Zhuoliang Chen, Belmont, MA (US); Young Shin Cho, Cambridge, MA (US); Abran Q. Costales, El Cerrito, CA (US); Julian Roy Levell, Arlington, MA (US); Gang Liu, Waltham, MA (US); James R. Manning, Pleasant Hill, CA (US); Martin Sendzik, Belmont, MA (US); Cynthia Shafer, El Sobrante, CA (US); Michael David Shultz, Lexington, MA (US); James Clifford Sutton, Pleasanton, CA (US); Yaping Wang, Boxborough, MA (US); Qian Zhao, El Cerrito, CA (US)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/209,731

(22) Filed: Jul. 13, 2016

(65) Prior Publication Data
US 2016/0318915 A1    Nov. 3, 2016

Related U.S. Application Data

(63) Continuation of application No. 14/408,418, filed as application No. PCT/IB2014/059695 on Mar. 12, 2014, now Pat. No. 9,434,719.

(60) Provisional application No. 61/783,210, filed on Mar. 14, 2013, provisional application No. 61/892,131, filed on Oct. 17, 2013.

(51) Int. Cl.
C07D 413/14    (2006.01)
A61K 31/506    (2006.01)
C07D 413/04    (2006.01)
C07D 417/14    (2006.01)
A61K 31/5377   (2006.01)

(52) U.S. Cl.
CPC .......... *C07D 413/14* (2013.01); *A61K 31/506* (2013.01); *A61K 31/5377* (2013.01); *C07D 413/04* (2013.01); *C07D 417/14* (2013.01)

(58) Field of Classification Search
CPC .. C07D 413/04; C07D 413/14; C07D 417/14; A61K 31/506
USPC .............. 544/122, 295, 296, 324; 514/235.8, 514/252.19, 275
See application file for complete search history.

(56) References Cited

U.S. PATENT DOCUMENTS

| | | |
|---|---|---|
| 3,975,384 A | 8/1976 | Narr et al. |
| 4,929,726 A | 5/1990 | Strekowski et al. |
| 5,358,945 A | 10/1994 | Mizuchi et al. |
| 5,786,355 A | 7/1998 | Konno et al. |
| 5,976,758 A | 11/1999 | Fukui et al. |
| 5,990,105 A | 11/1999 | Boes et al. |
| 6,251,900 B1 | 6/2001 | Kawashima et al. |
| 6,288,228 B1 | 9/2001 | Henkin et al. |
| 6,495,558 B1 | 12/2002 | Armistead et al. |
| 6,599,926 B2 | 7/2003 | Pinto et al. |
| 6,603,000 B2 | 8/2003 | Yee et al. |
| 6,743,788 B2 | 6/2004 | Cirillo et al. |

(Continued)

FOREIGN PATENT DOCUMENTS

| | | |
|---|---|---|
| AU | 2010291318 | 3/2011 |
| CN | 103483345 A | 1/2014 |
| CN | 103694218 A | 4/2014 |
| DE | 2341925 A1 | 3/1975 |
| EP | 0 330 263 A1 | 8/1989 |

(Continued)

OTHER PUBLICATIONS

Ali et al., Essential role for the p110delta phosphoinositide 3-kinase in the allergic response. Nature. Oct. 21, 2004; 431(7011):1007-11.
Amary et al., Ollier disease and Maffucci syndrome are caused by somatic mosaic mutations of IDH1 and IDH2. Nat Genet. Nov. 6, 2011;43(12):1262-5.

(Continued)

*Primary Examiner* — Deepak Rao
(74) *Attorney, Agent, or Firm* — Laura Madden

(57) ABSTRACT

The invention is directed to a formula (I):

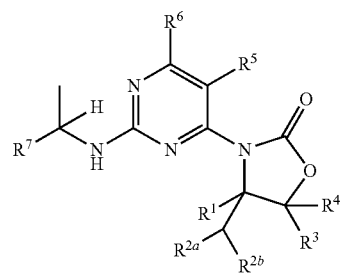

(I)

or a pharmaceutically acceptable salt thereof, wherein $R^1$, $R^{2a}$, $R^{2b}$ and $R^3$-$R^7$ are herein. The invention is also directed to compositions containing a compound of formula (I) and to the use of such compounds in the inhibition of mutant IDH proteins having a neomorphic activity. The invention is further directed to the use of a compound of formula (I) in the treatment of diseases or disorders associated with such mutant IDH proteins including, but not limited to, cell-proliferation disorders, such as cancer.

14 Claims, No Drawings

(56) References Cited

U.S. PATENT DOCUMENTS

| | | | |
|---|---|---|---|
| 6,846,928 | B2 | 1/2005 | Bebbington et al. |
| 7,045,519 | B2 | 5/2006 | Nuss et al. |
| 7,091,343 | B2 | 8/2006 | Bebbington et al. |
| 7,179,826 | B2 | 2/2007 | Bebbington et al. |
| 7,423,148 | B2 | 9/2008 | Nuss et al. |
| 7,566,712 | B2 | 7/2009 | Bakthavatchalam et al. |
| 7,652,009 | B2 | 1/2010 | Kim et al. |
| 7,767,669 | B2 | 8/2010 | Nuss et al. |
| 7,893,063 | B2 | 2/2011 | Pass et al. |
| 7,957,951 | B2 | 6/2011 | Foster et al. |
| 8,173,647 | B2 | 5/2012 | Atallah et al. |
| 8,217,035 | B2 | 7/2012 | Burger et al. |
| 8,563,549 | B2 | 10/2013 | Burger et al. |
| 8,575,338 | B2 | 11/2013 | Tsuzuki et al. |
| 8,865,894 | B2 | 10/2014 | Caravatti et al. |
| 8,957,068 | B2 | 2/2015 | Caferro et al. |
| 9,434,719 | B2 * | 9/2016 | Caferro ............... A61K 31/506 |
| 2004/0002496 | A1 | 1/2004 | Bebbington et al. |
| 2004/0009974 | A1 | 1/2004 | Bebbington et al. |
| 2004/0009981 | A1 | 1/2004 | Bebbington et al. |
| 2005/0014753 | A1 | 1/2005 | Ding et al. |
| 2009/0018134 | A1 | 1/2009 | Pike et al. |
| 2010/0048547 | A1 | 2/2010 | Atallah et al. |
| 2010/0249126 | A1 | 9/2010 | Burger et al. |
| 2011/0195966 | A1 | 8/2011 | Garcia-Echeverria et al. |
| 2011/0288065 | A1 | 11/2011 | Fujihara et al. |
| 2012/0225859 | A1 | 9/2012 | Burger et al. |
| 2013/0123289 | A1 | 5/2013 | Yang et al. |
| 2013/0143862 | A1 | 6/2013 | Ashcraft et al. |
| 2013/0150368 | A1 | 6/2013 | Ashcraft et al. |
| 2013/0225574 | A1 | 8/2013 | Caravatti et al. |
| 2014/0135330 | A1 | 5/2014 | Fairhurst et al. |
| 2015/0152093 | A1 | 6/2015 | Caferro et al. |

FOREIGN PATENT DOCUMENTS

| | | |
|---|---|---|
| EP | 0 459 830 A1 | 12/1991 |
| EP | 0 767 170 B1 | 10/2002 |
| EP | 1 277 738 A1 | 1/2003 |
| EP | 1 277 741 A1 | 1/2003 |
| EP | 2 394 999 A1 | 12/2011 |
| EP | 2 560 488 A1 | 2/2013 |
| EP | 2 563 365 A1 | 3/2013 |
| GB | 0 581 334 A | 10/1946 |
| GB | 2 431 156 A | 4/2007 |
| JP | 49-021148 B | 2/1974 |
| JP | 49-021149 B | 2/1974 |
| JP | 11-158073 A2 | 6/1999 |
| JP | 2001-089452 A | 4/2001 |
| WO | 89/00599 A1 | 1/1989 |
| WO | 99/19305 A2 | 4/1999 |
| WO | 99/65897 A1 | 12/1999 |
| WO | 00/43373 A2 | 7/2000 |
| WO | 01/00207 A1 | 1/2001 |
| WO | 01/00213 A1 | 1/2001 |
| WO | 01/00214 A1 | 1/2001 |
| WO | 01/05783 A1 | 1/2001 |
| WO | 01/60816 A1 | 8/2001 |
| WO | 01/72745 A1 | 10/2001 |
| WO | 01/83456 A1 | 11/2001 |
| WO | 02/20495 A2 | 3/2002 |
| WO | 02/22606 A1 | 3/2002 |
| WO | 02/22608 A1 | 3/2002 |
| WO | 02/36586 A1 | 5/2002 |
| WO | 02/062766 A2 | 8/2002 |
| WO | 02/062789 A1 | 8/2002 |
| WO | 02/064096 A2 | 8/2002 |
| WO | 02/102313 A2 | 12/2002 |
| WO | 03/030909 A1 | 4/2003 |
| WO | 2004/000820 A2 | 12/2003 |
| WO | 2004/029204 A2 | 4/2004 |
| WO | 2004/032716 A2 | 4/2004 |
| WO | 2004/039788 A1 | 5/2004 |
| WO | 2004/048365 A1 | 6/2004 |
| WO | 2004/084824 A2 | 10/2004 |
| WO | 2004/092196 A2 | 10/2004 |
| WO | 2005/007648 A2 | 1/2005 |
| WO | 2005/009977 A1 | 2/2005 |
| WO | 2005/028444 A1 | 3/2005 |
| WO | 2005/099711 A1 | 10/2005 |
| WO | 2006/005914 A1 | 1/2006 |
| WO | 2006/005918 A1 | 1/2006 |
| WO | 2006/021544 A1 | 3/2006 |
| WO | 2006/026135 A2 | 3/2006 |
| WO | 2006/065872 A1 | 6/2006 |
| WO | 2006/071538 A2 | 7/2006 |
| WO | 2006/071960 A2 | 7/2006 |
| WO | 2006/078992 A2 | 7/2006 |
| WO | 2006/090167 A2 | 8/2006 |
| WO | 2006/113704 A2 | 10/2006 |
| WO | 2007/080382 A1 | 7/2007 |
| WO | 2007/084595 A1 | 7/2007 |
| WO | 2007/084786 A1 | 7/2007 |
| WO | 2007/085556 A1 | 8/2007 |
| WO | 2007/087204 A1 | 8/2007 |
| WO | 2008/080937 A1 | 7/2008 |
| WO | 2008/098058 A1 | 8/2008 |
| WO | 2009/007748 A2 | 1/2009 |
| WO | 2009/066084 A1 | 5/2009 |
| WO | 2009/109605 A1 | 9/2009 |
| WO | 2009/118324 A1 | 10/2009 |
| WO | 2009/120094 A2 | 10/2009 |
| WO | 2009/125870 A1 | 10/2009 |
| WO | 2010/020432 A2 | 2/2010 |
| WO | 2010/049481 A1 | 5/2010 |
| WO | 2010/052569 A2 | 5/2010 |
| WO | 2010/068863 A2 | 6/2010 |
| WO | 2010/090290 A1 | 8/2010 |
| WO | 2010/090344 A1 | 8/2010 |
| WO | 2010/105243 A1 | 9/2010 |
| WO | 2010/120994 A2 | 10/2010 |
| WO | 2010/135070 A1 | 11/2010 |
| WO | 2011/005119 A1 | 1/2011 |
| WO | 2011/017296 A1 | 2/2011 |
| WO | 2011/026835 A1 | 3/2011 |
| WO | 2011/031896 A2 | 3/2011 |
| WO | 2011/060816 A1 | 5/2011 |
| WO | 2011/072174 A1 | 6/2011 |
| WO | 2011/114275 A1 | 9/2011 |
| WO | 2011/133888 A1 | 10/2011 |
| WO | 2011/143160 A2 | 11/2011 |
| WO | 2012/009678 A1 | 1/2012 |
| WO | 2012/044727 A2 | 4/2012 |
| WO | 2012/054535 A2 | 4/2012 |
| WO | 2012/055942 A1 | 5/2012 |
| WO | 2012/109423 A1 | 8/2012 |
| WO | 2012/171337 A1 | 12/2012 |
| WO | 2013/030368 A1 | 3/2013 |
| WO | 2013/046136 A1 | 4/2013 |
| WO | 2013/052395 A1 | 4/2013 |
| WO | 2013/124826 A1 | 8/2013 |
| WO | 2013/151938 A1 | 10/2013 |
| WO | 2013/155262 A2 | 10/2013 |
| WO | 2013/173283 A1 | 11/2013 |
| WO | 2013/178569 A1 | 12/2013 |
| WO | 2013/184621 A1 | 12/2013 |
| WO | 2014/028566 A1 | 2/2014 |
| WO | 2014/064058 A1 | 5/2014 |
| WO | 2014/110200 A1 | 7/2014 |
| WO | 2014/141104 A1 | 9/2014 |
| WO | 2014/181287 A1 | 11/2014 |

OTHER PUBLICATIONS

Amine, Utilities of 4-(4'-Benzyl Phenyl) -6-Arylpyrimi-dine-2-Thiones for the synthesis of biologically active condensed and non-condensed hetero-cycles. Egypt J Chem. 1998;41(1-6):267-76.

Andrisano, Pyrimidine. IV. Bollettino Scientifico della Facolta di Chimica Industriale di Bologna. 1947; 5:48-51.

Angelo et al., Synthesis and antifilarial activity of N-[4-[[4-alkoxy-3[(dialkylamino)methyl]phenyl]amino]-2-pyrimidinyl]-N'-phenylguanidines. J Med Chem. Sep. 1983;26(9):1258-67.

(56) References Cited

OTHER PUBLICATIONS

Balant et al., Metabolic Considerations in Prodrug Design. Burger's Medicinal Chemistry and Drug Discovery. 1995; 1:975-7.
Balss et al., Analysis of the IDH1 codon 132 mutation in brain tumors. Acta Neuropathol. Dec. 2008; 116(6):597-602. Epub Nov. 5, 2008.
Banker et al., Modern Pharmaceuticals. 3rd Edition. Marcel Dekker, New York. 1996:451, 596.
Bennet et al., Part XIV, Oncology. Cecil Textbook of Medicine. 20th Edition. W.B. Saunders, Philadelphia. 1996:1004-10.
Brown et al., Some Heterocyclic Analogues of Stilbenes. J Chem Soc. Jan. 1948:2147-53.
Bundy et al., Synthesis of 2,4-diaminopyrrolo[2,3-d]pyrimidines via thermal fisher indolization. Pyrazole formation with ytterbium triflate catalysis. J Heterocyclic Chem. Nov.-Dec. 2000; 37:1471-7.
Bundy et al., Synthesis of novel 2,4-diaminopyrrolo-[2,3-d]pyrimidines with antioxidant, neuroprotective, and antiasthma activity. J. Med. Chem. Oct. 13, 1995; 38(21):4161-3.
Buonamici et al., Interfering with resistance to smoothened antagonists by inhibition of the PI3K pathway in medulloblastoma. Sci. Transl. Med. Sep. 29, 2010; 2(51):1-8.
Burger et al., Identification of NVP-BKM120 as a Potent, Selective, Orally Bioavailable Class I PI3 Kinase Inhibitor for Treating Cancer. ACS Med. Chem. Lett. 2011; 2(10):774-9.
Cabaj et al., Bromine-medicated addition of nucleophiles to the electron-rich pyrimidine subunit of tirilazad. J. Org. Chem. Aug. 1994; 59:5090-2.
Caine et al., Coagulopathic complications in breast cancer. Cancer. Oct. 2003;98(8):1578-86.
Chen et al, Activation of the mammalian target of rapamycin signalling pathway in epidermal tumours and its correlation with cyclin-dependent kinase 2. British Journal of Dermatology Aug. 2009; 160, pp. 442-445.
Clayton et al., A crucial role for the p110delta subunit of phosphatidylinositol 3-kinase in b cell development and activation. J. Exp. Med. Sep. 9, 2002;196(6):753-63.
Crowder et al., Treating breast cancer through novel inhibitors of the phosphatidylinositol 3'-kinase pathway. Breast Cancer Res. 2005; 7(5):212-4.
Dang et al., Cancer-associated IDH1 mutations produce 2-hydroxyglutarate. Nature. Dec. 10, 2009; 462(7274):739-44.
Dang et al., IDH mutations in glioma and acute myeloid leukemia. Trends Mol Med. Sep. 2010;16(9):387-97. Epub Aug. 5, 2010.
Dario et al, Targeting of the Tumor Suppressor GRHL3 by a miR-21-Dependent Proto-Oncogenic Network Results in PTEN Loss and Tumorigenesis. Cancer Cell Nov. 2011; 20(5): 635-648.
Essawy et al., Some reactions of 4-(2-Methoxynaphthyl)-6-(P-Chlorophenyl) Pyrimidin-2 (1H)-One and its corresponding 2-Chloro derivative. Egypt J. Chem. 1994;37(4):413-21.
Falco et al., 2:4-diaminopyrimidines- a new series of antimalarials. Br J Pharmacol Chemother. Jun. 1951;6(2):185-200.
Font et al., Development of an efficient and straightforward methodology toward the synthesis of molecularly diverse 2,6-disubstituted 3,4-dihydropyrimidin-4(3H)-ones. Synthesis. Sep. 2002;13:1833-42.
Gaal et al., Isocitrate dehydrogenase mutations are rare in pheochromocytomas and paragangliomas. J. Clin. Endocrinol Metab. Mar. 2010; 95(3):1274-8. Epub Nov. 13, 2009.
Golub et al., Molecular classification of cancer: class discovery and class prediction by gene expression monitoring. Science. Oct. 15, 1999;286(5439):531-7.
Gross et al., Cancer-associated metabolite 2-hydroxyglutarate accumulates in acute myelogenous leukemia with isocitrate dehydrogenase 1 and 2 mutations. J Exp Med. Feb. 15, 2010;207(2):339-44. Epub Feb. 8, 2010.
Hayden et al., Frequent IDH1 mutations in supratentorial primitive neuroectodermal tumors (sPNET) of adults but not children. Cell Cycle. Jun. 1, 2009; 8(11):1806-7. Epub Jun. 30, 2009.
Jackson et al., PI 3-kinase p110beta: a new target for antithrombotic therapy. Nat. Med. May 2005; 11(5):507-14.

Jaworska et al., SAR applicability domain. Review of Methods for Assessing the Applicabilty Domains of SARS and QSARS. Sep. 27, 2004:1-8.
Jou et al., Essential, nonredundant role for the phosphoinositide 3-kinase p110delta in signaling by the B-cell receptor complex. Mol. Cell. Biol. Dec. 2002;22(24):8580-91.
Katiyar et al., Syntheses of 2,4,6-trisubstituted pyrimidine derivatives as a new class of antifilarial topoisomerase II inhibitors. Bioorg. Med. Chem. Lett. Jan. 3, 2005;15(1):47-50.
Kidwai et al., Base catalysed pyrimidine synthesis using microwave. Bull Korean Chem Society. Nov. 2003;24(11):1575-8.
Kothari et al., A facile one pot conversion of 3',5'-dibromo-4'-hydroxy substituted chalcones to pyrimidine derivatives and their antibacterial and herbicidal activity. Indian Journal of Heterocyclic Chemistry. Apr.-Jun. 1999; 8(4)285-8.
Kowalewski et al., Unfused heterobicycles as amplifiers of phleomycin. IV 4,5'-bipyrimidines with dimethylamino and/or dimethylaminoethylamino substituents. Australian Journal of Chem. 1981; 34(12):2929-33.
Kranendijket et al., IDH2 mutations in patients with D-2-hydroxyglutaric aciduria. Science. Oct. 15, 2010; 330(6002):336. Epub Sep. 16, 2010.
Lala et al., Role of nitric oxide in tumor progression: lessons from experimental tumors. Cancer Metastasis Rev. Mar. 1998; 17(1):91-106.
Li et al., PIK3CA mutations in breast cancer are associated with poor outcome. Breast Cancer Research and Treatment. Mar. 2006; 96(1):91-5.
Mamaev et al., Reaction kinetics of substituted 2-chloropyrimidines with piperdine. Reaktsionnaya Sposobnost Organicheskikh Soedinenii. 1968; 5(3):824-37.
Mikhaleva et al., Pyrimidines. 70. Relative reactivities of the chlorine atoms of 2,2',4-trichloro-4',5-dipyrimidinyl in its reaction with piperidine. Chemistry of Heterocyclic Compounds. Jun. 1979; 15(6):671-6.
Mikhaleva et al., Pyrimidines. 70. Relative reactivity of the chlorine atoms of 2,2',4-trichloro-4',5-bipyrimidine in the reaction with piperidine. Khimiya Geterotsiklicheskikh Soedinenii. 1979;6:821-6.
Ming et al, UVB-induced ERK/AKT-dependent PTEN suppression promotes survival of epidermal keratinocytes. Jan. 2010; 29(4): 492-502.
Mokrosz et al., 4-(3-furyl)-2-(4-methylpiperazino)pyrimidines: Potent 5-HT2A receptor antagonists. Bioorganic & Medicinal Chemistry Letters. Jul. 1997; 7(13):1635-8.
Mokrosz et al., Structure-activity relationship studies of CNS agents. Part 25. 4,6-Di(heteroaryl)-2-(N-methylpiperazino) pyrimidines as new, potent 5-HT2A receptor ligands: a verification of the topographic model. Archiv der Pharmazie. Sep. 1995; 328(9):659-66.
Nahta et al., Signal transduction inhibitors in the treatment of breast cancer. Curr Med Chem Anticancer Agents. May 2003;3(3):201-16.
Ouf et al., Preparation of Some Methyl Pyrimidines Expected to be Antimetabolites. Egyptian Journal of Pharmaceutical Science. 1973; 14(2):180-95.
Pansuriya et al., Somatic mosaic IDH1 and IDH2 mutations are associated with enchondroma and spindle cell hemangioma in Ollier disease and Maffucci syndrome. Nat Genet. Nov. 6, 2011; 43(12):1256-61.
Patani et al., Bioisosterism: A Rational Approach in Drug Design. Chem Rev. Dec. 1996;96(8):3147-76.
Reif et al., Cutting edge: differential roles for phosphoinositide 3-kinases, p110gamma and p110delta, in lymphocyte chemotaxis and homing. J Immunol. Aug. 15, 2004; 173(4):2236-40.
Salasche, Epidemiology of actinic keratoses and squamous cell carcinoma. J Am Acad Dermatol Jan. 2000; 42:S4-7.
Sellner et al., Increased levels of 2-hydroxyglutarate in AML patients with IDH1-R132H and IDH2-R140Q mutations. Eur J Haematol. Nov. 2010;85(5):457-9.
Sharma et al., A convenient one-pot synthesis of 2-substituted-4,6-diaryl pyrimidines. Indian Journal of Chem. 38B. Aug. 1999:966-8.

(56) References Cited

OTHER PUBLICATIONS

Shibata et al., Mutant IDH1 confers an in vivo growth in a melanoma cell line with BRAF mutation. Am. J. Pathol. Mar. 2011;178(3):1395-402.
Silverman, The Organic Chemistry of Drug Design and Drug Action. 2nd Edition. Elsevier Academic Press. Jan. 26, 2004:29-34.
Sukhwal et al., A new route to 2-piperidino-4,6-diarylpyrimidines. Indian Journal of Heterocyclic Chemistry. Jul.-Sep. 1994; 4:67-8.
Tani et al., 2,4,6-Trisubstituted pyrimidines. JP 49021148. May 30, 1974.
U.S. Office Action for U.S. Appl. No. 14/069,400 mailed Feb. 28, 2014.
Voskoglou-Nomikos et al., Clinical predictive value of the in vitro cell line, human xenograft, and mouse allograft preclinical cancer models. Clin. Cancer Res. Sep. 15, 2003;9(11):4227-39.
Wolff, Burger's Medicinal Chemistry and Drug Discovery. 5th Edition. Wiley, New York. 1995; 1:975-7.
U.S. Office Action for U.S. Appl. No. 14/208,015, filed Mar. 13, 2014.
Gura, Systems for identifying New Drugs Are Often Faulty, Cancer Models, Science, vol. 278, No. 5340, pp. 1041-1042, Nov. 1997.
Johnson et al., Relationships between drug activity in NCI preclinical in vitro and in vivo models and early clinical trials, British Journal of Cancer (2001) 64(10): 1424-31.
Pearce et al., Failure modes in anticancer drug discovery and development, Cancer Drug Design and Discovery Edited by Stephen Neidle, Chapter 18, pp. 424-435 (2008).
Simone, Oncology: Introduction, Cecil Textbook of Medicine, 20th Edition, vol. 1, pp. 1004-1010, 1996.
Pickhard A. C. et al., Inhibition of radiation induced migration of human head and neck squamous cell carcinoma cells by blocking of EGF receptor pathways, BMC Cancer, Sep. 6, 2011; 11(388):1-12.

\* cited by examiner

3-PYRIMIDIN-4-YL-OXAZOLIDIN-2-ONES AS INHIBITORS OF MUTANT IDH

This Application is a continuing application of U.S. application Ser. No. 14/408,418, which is a national stage of PCT/IB2014/059695, filed Mar. 12, 2014 and claims priority to both of U.S. Provisional Application No. 61/783,210, filed Mar. 14, 2013 and U.S. Provisional Application No. 61/892,131, filed Oct. 17, 2013. U.S. application Ser. No. 14/408,418 also claims priority to U.S. application Ser. No. 14/208,015, filed Mar. 14, 2014, which claims priority to both U.S. Provisional Application No. 61/783,210, filed Mar. 14, 2013 and U.S. Provisional Application No. 61/892,131, filed Oct. 17, 2013. The contents of all of the foregoing documents are expressly incorporated herein by reference.

FIELD OF THE INVENTION

The present invention is directed to novel 3-pyrimidinyl-4-yl-oxazolidin-2-one compounds, compositions containing these compounds, the use of such compounds in the inhibition of mutant IDH proteins having a neomorphic activity and in the treatment of diseases or disorders associated with such mutant IDH proteins including, but not limited to, cell-proliferation disorders, such as cancer.

BACKGROUND OF THE INVENTION

Isocitrate dehydrogenase (IDH) is a key family of enzymes found in cellular metabolism. They are $NADP^+$/$NAD^+$ and metal dependent oxidoreductases of the enzyme class EC 1.1.1.42. The wild type proteins catalyze the oxidative decarboxylation of isocitrate to alpha-ketoglutarate generating carbon dioxide and NADPH/NADH in the process. They are also known to convert oxalosuccinate into alpha-ketoglutarate. Mutations in IDH1 (cytosolic) and IDH2 (mitochondrial) have been identified in multiple cancer types including, but not limited to, glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, and melanoma. (See L. Dang et al., Trends Mol. Med., 2010, 16, 387; T. Shibata et al., Am. J. Pathol., 2011, 178(3), 1395; Gaal et al., J. Clin. Endocrinol. Metab. 2010; Hayden et al., Cell Cycle, 2009; Balss et al., Acta Neuropathol., 2008). The mutations have been found at or near key residues in the active site: G97D, R100, R132, H133Q, and A134D for IDH1, and R140 and R172 for IDH2. (See L. Dang et al., Nature, 2009, 462, 739; L. Sellner et al., Eur. J. Haematol., 2011, 85, 457).

These mutant forms of IDH are shown to have a neomorphic activity (also known as a gain of function activity), reducing alpha-ketoglutarate to 2-hydroxyglutarate (2-HG). (See P. S. Ward et al., Cancer Cell, 2010, 17, 225) In general, production of 2-HG is enantiospecific, resulting in generation of the D-enantiomer (also known as R enantiomer or R-2-HG). Normal cells have low native levels of 2-HG, whereas cells harboring these mutations in IDH1 or IDH2 show significantly elevated levels of 2-HG. High levels of 2-HG have been detected in tumors harboring the mutations. For example, high levels of 2-HG have been detected in the plasma of patients with mutant IDH containing AML. (See S. Gross et al., J. Exp. Med., 2010, 207(2), 339). High levels of 2-HG are highly associated with tumorigenesis.

Mutant IDH2 is also associated with the rare neurometabolic disorder D-2-hydroxyglutaric aciduria type II (D-2-HGA type II). Germline mutations were found at R140 in IDH2 in 15 pateints having D-2-HGA type II. Patients having this disorder also have consistently increased levels of D-2-HG in their urine, plasma and cerebrospinal fluid. (See Kranendijk, M. et al., Science, 2010, 330, 336). Finally, patients with Ollier Disease and Mafucci Syndrome (two rare disorders that predispose to cartilaginous tumors) have been shown to be somatically mosaic for IDH1 and 2 mutations and exhibit high levels of D-2-HG. (See Amary et al., Nature Genetics, 2011 and Pansuriya et al., Nature Genetics, 2011).

Thus, there is a need for small molecule inhibitors of mutant IDH proteins having a neomorphic activity for the treatment of diseases and disorders associated with these proteins.

SUMMARY OF THE INVENTION

In one aspect, this invention provides for a compound of formula (I)

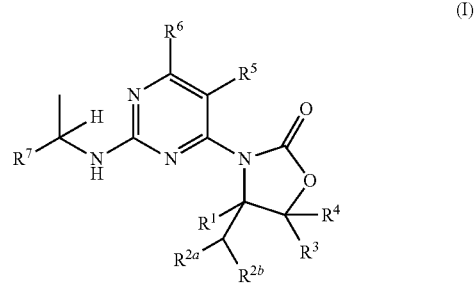

or a pharmaceutically acceptable salt thereof wherein $R^1$, $R^{2a}$, $R^{2b}$ and $R^3$-$R^7$ are defined below.

In a second aspect, this invention provides for a pharmaceutical composition comprising a compound of formula (I), or a pharmaceutically acceptable salt thereof, and a pharmaceutically acceptable carrier or excipient.

In a third aspect, this invention provides for the use of a compound of formula (I), or a pharmaceutically acceptable salt thereof, as an inhibitor of a mutant IDH protein having a neomorphic activity such as reducing alpha-ketoglutarate to 2-hydroxyglutarate (2-HG neomorphic activity). Suitably, this invention provides for the use of a compound of formula (I), or a pharmaceutically acceptable salt thereof, as an inhibitor of mutant IDH1 having a neomorphic activity, such as 2-HG neomorphic activity, and/or mutant IDH2 having a neomorphic activity, such as 2-HG neomorphic activity. This invention further provides for the use of a compound of formula (I), or a pharmaceutically acceptable salt thereof, as an inhibitor of IDH1 having a mutation at residue 97, 100 or 132, for example G97D, R100Q, R132H, R132C, R132S, R132G, R132L, and R132V; and/or an inhibitor of IDH2 having a mutation at residue 140 or 172, for example R172K, R172M, R172S, R172G, and R172W.

In a fourth aspect, this invention provides for a method of treating a disease or disorder associated with a mutant IDH protein having a neomorphic activity comprising administration of an effective amount of a compound according to formula (I), or a pharmaceutically acceptable salt thereof, to a subject in need thereof. In one embodiment, the disease or disorder is a cell proliferation disorder, such as cancer. In another embodiment, the cancer is brain cancer, such as glioma, glioblastoma multiforme, paraganglioma, and supratentorial primordial neuroectodermal tumors (pNET); leukemia, such as acute myeloid leukemia (AML), myelodysplastic syndrome, and chronic myelogenous leukemia (CML); skin cancer, including melanoma; prostate cancer; thyroid cancer; colon cancer; lung cancer; sarcoma, including central chondrosarcoma, central and periosteal chondroma; and fibrosarcoma. In another embodiment the disease or disorder is D-2-hydroxyglutaric aciduria.

In a fifth aspect the invention provides for a compound of formula (I), or a pharmaceutically acceptable salt thereof, in combination with another therapeutic agent.

These and other aspects of the present invention are described further in the following detailed description of the invention.

DETAILED DESCRIPTION OF THE INVENTION

The present invention is directed to a compound of formula (I)

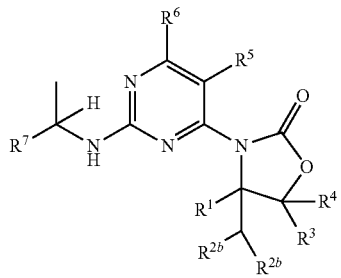

wherein:
$R^1$ is hydrogen, methyl or ethyl;
$R^{2a}$ is hydrogen, methyl or $C_{1-3}$ haloalkyl;
$R^{2b}$ is OH, halo, $C_{1-6}$ alkoxy, $C_{1-3}$ haloalkyl, $NH_2$, $NH(CH_3)$ or $N(CH_3)_2$;
$R^3$ and $R^4$ are each independently hydrogen, methyl or ethyl or $R^3$ and $R^4$ are joined together forming cyclopropyl, cyclobutyl or oxetanyl;
$R^5$ and $R^6$ are each independently hydrogen, deuterium, halo, —C(O)OCH$_3$, $C_{1-3}$ alkyl or $C_{1-3}$ haloalkyl;
$R^7$ is

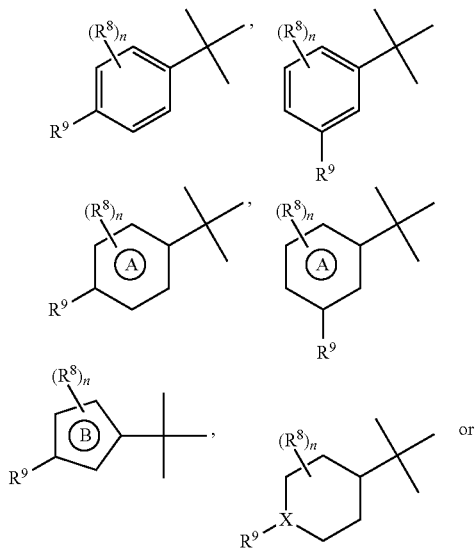

-continued

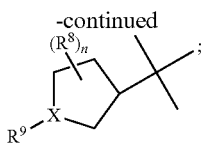

wherein:
ring A is a 6 membered heteroaryl ring having one to three nitrogen atoms;
ring B is a 5 membered heteroaryl ring having one to four heteroatoms each independently selected from the group consisting of N, O and S;
X is N or CH;
each $R^8$ is independently hydrogen, halo, $C_{1-3}$ alkyl, $C_{1-3}$ haloalkyl, $C_{1-3}$ alkoxy or $C_{1-3}$ haloalkoxy;
n is 1 or 2;
$R^9$ is hydrogen, halo, $C_{1-3}$ haloalkyl, optionally substituted $C_{1-6}$ alkyl, optionally substituted $C_{3-6}$ cycloalkyl, optionally substituted aryl, optionally substituted 5 or 6 membered heterocyclic, optionally substituted heteroaryl, —OR$^{9a}$, —SO$_2$R$^{9a}$, —C(O)NHR$^{9a}$, CH$_2$R$^{9b}$ or CHCH$_3$R$^{9b}$, provided that when X is N, $R^9$ is hydrogen, $C_{1-3}$ haloalkyl, optionally substituted $C_{1-6}$ alkyl, optionally substituted $C_{3-6}$ cycloalkyl, optionally substituted aryl, optionally substituted heteroaryl, —SO$_2$R$^{9a}$ or —C(O)NHR$^{9a}$, wherein:
said $C_{1-6}$ alkyl is optionally substituted with one to three substituents each independently selected from the group consisting of: OH, phenyl and phenoxy, and
said $C_{3-6}$ cycloalkyl, 5 or 6 membered heterocyclic, aryl and heteroaryl are each optionally substituted with one to three substituents each independently selected from the group consisting of: halo, hydroxyl, cyano, —NRR, $C_{1-6}$ alkyl, $C_{1-6}$ haloalkyl, $C_{1-3}$ alkoxy, and $C_{1-3}$ haloalkoxy;
$R^{9a}$ is optionally substituted $C_{1-6}$ alkyl, $C_{1-6}$ haloalkyl, optionally substituted $C_{3-6}$ cycloalkyl, optionally substituted phenyl, or optionally substituted heterocyclic, wherein:
said $C_{1-6}$ alkyl is optionally substituted with one $C_{3-6}$ cycloalkyl,
said $C_{3-6}$ cycloalkyl and heterocyclic are each optionally substituted with one to three substituents each independently selected from the group consisting of: hydroxyl, CH$_2$OH, —NRR, cyano, $C_{1-3}$ alkyl, $C_{1-3}$ haloalkyl, and $C_{1-3}$ alkoxy, and
said phenyl is optionally substituted with one to three substituents each independently selected from the group consisting of: halo, hydroxyl, cyano, —NRR, $C_{1-6}$ alkyl, $C_{1-6}$ haloalkyl, $C_{1-3}$ alkoxy, and $C_{1-3}$ haloalkoxy;
$R^{9b}$ is optionally substituted $C_{3-6}$ cycloalkyl, optionally substituted phenyl or optionally substituted heterocyclic,
said $C_{3-6}$ cycloalkyl and heterocyclic are each optionally substituted with one to four substituents each independently selected from the group consisting of: hydroxyl, CH$_2$OH, —NRR, —NRC(O)CH$_3$, 4 to 6 membered heterocyclic, cyano, halo, $C_{1-3}$ alkyl, $C_{1-3}$ haloalkyl, and $C_{1-3}$ alkoxy, and
said phenyl is optionally substituted with one to three substituents each independently selected from the group consisting of: halo, hydroxyl, cyano, $C_{1-6}$ alkyl, $C_{1-6}$ haloalkyl, $C_{1-3}$ alkoxy, and $C_{1-3}$ haloalkoxy; and each R is independently selected from the group consisting of H, $C_{1-3}$ alkyl and $C_{3-6}$ cycloalkyl.

"Alkyl" refers to a monovalent saturated hydrocarbon chain having the specified number of carbon atoms. For example, $C_{1-6}$ alkyl refers to an alkyl group having from 1 to 6 carbon atoms. Alkyl groups may be optionally substituted with one or more substituents as defined in formula (I). Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl.

"Alkoxy" refers to any alkyl moiety attached through an oxygen bridge (i.e. a —O—$C_{1-3}$ alkyl group wherein $C_{1-3}$ alkyl is as defined herein). Examples of such groups include, but are not limited to, methoxy, ethoxy, and propoxy.

"Aryl" refers to a hydrocarbon ring system having an aromatic ring. Aryl groups are monocyclic ring systems or bicyclic ring systems. Monocyclic aryl ring refers to phenyl. Bicyclic aryl rings refer to naphthyl and to rings wherein phenyl is fused to a $C_{5-7}$ cycloalkyl or $C_{5-7}$ cycloalkenyl ring as defined herein. Aryl groups may be optionally substituted with one or more substituents as defined in formula (I).

"Cycloalkyl" refers to a saturated hydrocarbon ring system having the specified number of carbon atoms. Cycloalkyl groups are monocyclic or bicyclic ring systems. For example, $C_{3-6}$ cycloalkyl refers to a cycloalkyl group having from 3 to 6 carbon atoms. Cycloalkyl groups may be optionally substituted with one or more substituents as defined in formula (I). Examples of cycloalkyl groups include, but are not limited to, cyclopropyl, cyclobutyl, cyclopentyl and cyclohexyl.

"Cycloalkenyl" refers to an unsaturated hydrocarbon ring system having the specified number of carbon atoms and having a carbon-carbon double bond within the ring. For example, $C_{5-7}$ cycloalkenyl refers to a cycloalkenyl group having from 5 to 7 carbon atoms. In certain embodiments, cycloalkenyl groups have one carbon-carbon double bond within the ring. In other embodiments, cycloalkeneyl groups have more than one carbon-carbon double bond within the ring. Cycloalkenyl rings are not aromatic. Cycloalkenyl groups may be optionally substituted with one or more substituents as defined in formula (I).

"Halo" refers to the halogen radicals fluoro, chloro, bromo, and iodo.

"Haloalkyl" refers to an alkyl group wherein at least one hydrogen atom attached to a carbon atom within the alkyl group is replaced with halo. The number of halo substituents includes, but is not limited to, 1, 2, 3, 4, 5, or 6 substituents. Haloalkyl includes, but is not limited to, monofluoromethyl, difluoroethyl, and trifluoromethyl.

"Haloalkoxy" refers to a haloalkyl moiety attached through an oxygen bridge (i.e. a —O—$C_{1-3}$ haloalkyl group wherein $C_{1-3}$ haloalkyl is as defined herein). An example of a haloalkoxy group is trifluoromethoxy.

"Heteroaryl" refers to an aromatic ring system containing from 1 to 5 heteroatoms. Heteroaryl groups containing more than one heteroatom may contain different heteroatoms. Heteroaryl groups may be optionally substituted with one or more substituents as defined in formula (I). Heteroaryl groups are monocyclic ring systems or are fused bicyclic ring systems. Monocyclic heteroaryl rings have from 5 to 6 ring atoms. Bicyclic heteroaryl rings have from 8 to 10 member atoms. Bicyclic heteroaryl rings include those ring systems wherein a heteroaryl ring is fused to a phenyl ring. Heteroaryl includes, but is not limited to, pyrrolyl, pyrazolyl, imidazolyl, oxazolyl, isoxazolyl, oxadiazolyl (including 1,3,4-oxadiazolyl and 1,2,4-oxadiazolyl), thiazolyl, isothiazolyl, thiadiazolyl, furanyl, furanzanyl, thienyl, triazolyl, pyridinyl (including 2-, 3-, and 4-pyridinyl), pyrimidinyl, pyridazinyl, pyrazinyl, trazinyl, tetrazinyl, tetrzolyl, indonyl, isoindolyl, indolizinyl, indazolyl, purinyl, quinolinyl, isoquinolinyl, quinoxalinyl, quinazolinyl, benzimidazolyl, benzopyranyl, benzopyranyl, benzoxazolyl, benzoisoxazolyl, benzofuranyl, benzothiazolyl, benzothienyl, naphthyridinyl, 1H-pyrrolo[2,3-b]pyridinyl, tetrazolo[1,5-a]pyridinyl, imidazo[2,1-b][1,3,4]thiadiazolyl and the like.

"Heteroatom" refers to a nitrogen, oxygen, or sulfur atom.

"Heterocyclic" refers to a 3 to 11 membered saturated or unsaturated monocyclic or bicyclic ring containing from 1 to 4 heteroatoms. Heterocyclic ring systems are not aromatic. Heterocyclic groups containing more than one heteroatom may contain different heteroatoms. Heterocyclic includes ring systems wherein a sulfur atom is oxidized to form SO or $SO_2$. Heterocyclic groups may be optionally substituted with one or more substituents as defined in formula (I). Heterocyclic groups are monocyclic, spiro, or fused or bridged bicyclic ring systems. Monocyclic heterocyclic rings have 3 to 7 ring atoms. Examples of monocyclic heterocyclic groups include oxtanyl, tetrahydrofuranyl, dihydrofuranyl, 1,4-dioxanyl, morpholinyl, 1,4-dithianyl, piperazinyl, piperidinyl, 1,3-dioxolanyl, imidazolidinyl, imidazolinyl, pyrrolinyl, pyrrolidinyl, tetrahydropyranyl, dihydropyranyl, oxathiolanyl, dithiolanyl, 1,3-dioxanyl, 1,3-dithianyl, oxathianyl, thiomorpholinyl, tetrahydro-thiopyran1,1-dioxide, 1,4-diazepanyl, and the like. Fused heterocyclic ring systems have from 8 to 11 ring atoms and include groups wherein a heterocyclic ring is fused to a phenyl ring, a heteroaryl ring or another heterocyclic ring. Examples of fused heterocyclic rings include 2,3-dihydrobenzo[b][1,4]dioxinyl, benzo[1,3]dioxyl, octahydro-pyrrolo[1,2-a]pyrazinyl, octahydro-pyrido[1,2-a]pyrazinyl, octahydro-pyrrolo[3,4-c]pyrrolyl, 5,6,7,8-tetrahydro-[1,2,4]triazolo[4,3-a]pyrazinyl, 5,6,7,8-tetrahydro-imidazo[1,2-a]pyrazinyl and the like. Examples of bridged heterocyclic groups include 3,8-diaza-bicyclo[3.2.1]octanyl, 3,8-diaza-bicyclo[4.2.0]octanyl and the like. Examples of spiro heterocyclic groups include 4,7-diaza-spiro[2.5]octanyl and the like.

"5-6 membered heterocylic" refers to a heterocyclic group as defined above, having 5 or 6 ring atoms and containing from 1 to 4 heteroatoms.

"Optionally substituted" indicates that a group, such as an alkyl, cycloalkyl, heteroaryl, heterocyclic, phenyl, and benzyl may be unsubstituted or the group may be substituted with one or more substituents as defined in formula (I).

"Pharmaceutically acceptable" means a compound which is suitable for pharmaceutical use. Salts and solvates (e.g. hydrates and hydrates of salts) of compounds of the invention which are suitable for use in medicine are those where in the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

"Substituted" in reference to a group such as alkyl, phenyl, benzyl, heteroaryl, and heterocyclic, indicates that one or more hydrogen atoms attached to an atom within the group is replaced with a substituent selected from the group of defined substituents. It should be understood that the term "substituted" includes the implicit provision that such substitution be in accordance with permitted valence of the substituted atom and the substituent, and that the substitution results in a stable compound (i.e. one that does not spontaneously undergo transformation, for example, by hydrolysis, rearrangement, cyclization, or elimination and that is sufficiently robust to survive isolation from a reaction mixture). When it is stated that a group may contain one or more substituents, one or more (as appropriate) atoms within the group may be substituted. In addition, a single atom within the group may be substituted with more than one substituent as long as such substitution is accordance with the permitted valence of the atom. Suitable substituents are defined for each substituted or optionally substituted group.

The skilled artisan will appreciate that salts, including pharmaceutically acceptable salts, of the compounds according to formula (I) may be prepared. These salts may be prepared in situ during the final isolation and purification of the compound, or by separately reacting the purified compound in its free acid or free base form with a suitable base or acid, respectively.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Solvates, including pharmaceutically acceptable solvates, of the compounds of formula (I) may also be prepared. "Solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The compounds of formula (I), including salts and solvates thereof, may exist in crystalline forms, non-crystalline forms, or mixtures thereof. The compound or salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of formula (I).

The invention also includes various isomers of the compounds of formula (I). "Isomer" refers to compounds that have the same composition and molecular weight but differ in physical and/or chemical properties. The structural difference may be in constitution (geometric isomers) or in the ability to rotate the plane of polarized light (stereosiomers). With regard to stereoisomers, the compounds of formula (I) may have one or more asymmetric carbon atom and may occur as racemates, racemic mixtures and as individual enantiomers or diastereomers. All such isomeric forms are included within the present invention, including mixtures thereof, unless specifically indicated otherwise. If the compound contains a double bond, the substituent may be in the E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of a compound of formula (I) can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of formula (I) can be in the form of one of the possible isomers, rotamers, atropisomers, tautomers or mixtures thereof, for example, as substantially pure geometric (cis or trans) isomers, diastereomers, optical isomers, racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical isomers by known methods, e.g., by separation of the diastereomeric salts thereof, obtained with an optically active acid or base, and liberating the optically active acidic or basic compound. In particular, a basic moiety may thus be employed to resolve the compounds of the present invention into their optical isomers, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The invention includes unlabeled forms as well as isotopically labeled forms of compounds of formula (I). Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Furthermore, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Representative Embodiments

Various embodiments of the invention are described herein. It will be recognized that features specified in each embodiment may be combined with other specified features to provide for further embodiments.

In one embodiment of the present invention $R^1$ is hydrogen.

In another embodiment of the present invention $R^{2a}$ is hydrogen or methyl. Suitably $R^{2a}$ is methyl.

In another embodiment of the present invention $R^{2b}$ is OH, fluoro, methoxy, t-butoxy, $CHF_2$, $CF_3$, $NH_2$ or $NH(CH_3)$. Suitably $R^{2b}$ is OH, fluoro or $NH_2$.

In another embodiment of the present invention $R^3$ and $R^4$ are each hydrogen.

In another embodiment of the present invention $R^5$ is hydrogen or halo. Suitably $R^5$ is hydrogen, fluoro or chloro. More suitably $R^5$ is hydrogen or fluoro.

In another embodiment of the present invention $R^6$ is hydrogen, halo, methyl, $CH_2F$, $CHF_2$, or $CF_3$. Suitably $R^6$ is hydrogen, fluoro, chloro, methyl, $CH_2F$, $CHF_2$, or $CF_3$. More suitably $R^6$ is hydrogen or methyl.

In another embodiment of the present invention $R^5$ is hydrogen and $R^6$ is hydrogen, halo, methyl, $CH_2F$, $CHF_2$, or $CF_3$. Suitably $R^5$ is hydrogen and $R^6$ is hydrogen, fluoro, chloro, methyl, $CH_2F$, $CHF_2$, or $CF_3$. More suitably $R^5$ is hydrogen and $R^6$ is hydrogen or methyl.

In another embodiment of the present invention $R^6$ is hydrogen and $R^5$ is hydrogen or halo. Suitably $R^6$ is hydrogen and $R^5$ is hydrogen, fluoro or chloro. More suitably $R^6$ is hydrogen and $R^5$ is hydrogen or fluoro.

In another embodiment $R^5$ and $R^6$ are both hydrogen.

In another embodiment $R^7$ is

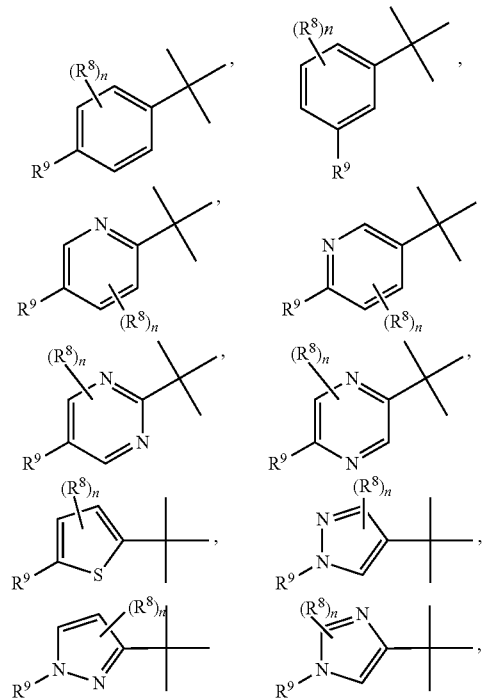

-continued

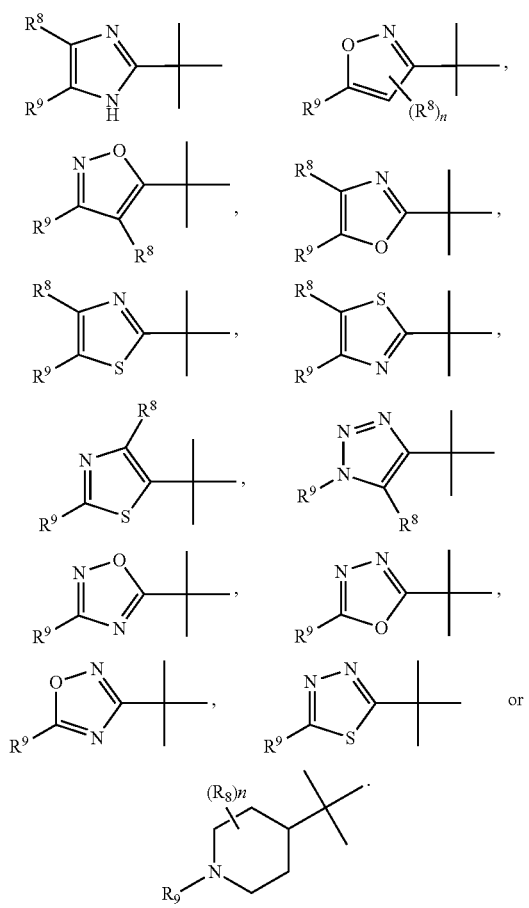

In another embodiment R⁷ is

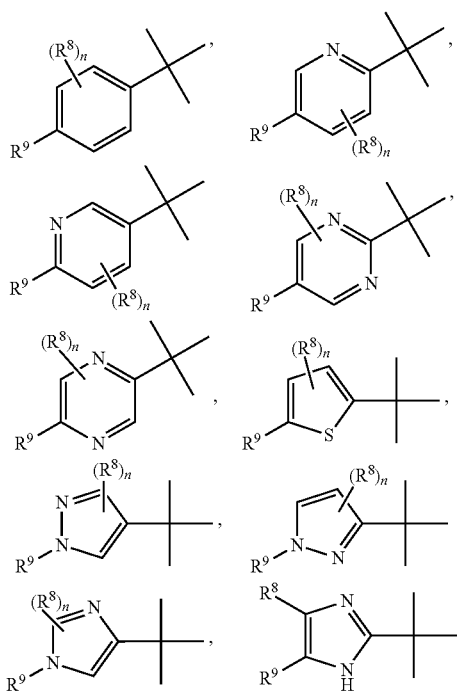

-continued

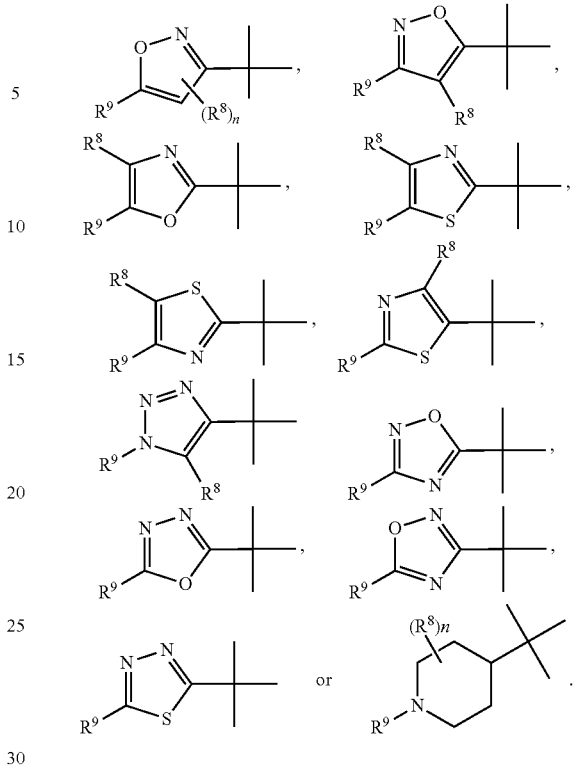

In another embodiment $R^8$ is hydrogen, fluoro, chloro or methyl and n is 1. In another embodiment each $R^8$ is independently fluoro or chloro and n is 2.

In another embodiment $R^9$ is hydrogen, halo, $C_{1-3}$ haloalkyl, optionally substituted $C_{1-6}$ alkyl, optionally substituted $C_{3-6}$ cycloalkyl. Suitably $R^9$ is hydrogen, halo, $CF_2H$, $CF_3$, $CF_2CH_3$, $C(CH_3)_2F$, $C_{1-6}$ alkyl optionally substituted with one substituent selected from the group consisting of: OH, phenyl and phenoxy, or $C_{3-6}$ cycloalkyl optionally substituted with one substituent selected from the group consisting of: cyano, $C_{1-3}$ alkyl, and $C_{1-3}$ alkoxy. Suitably $R^9$ is hydrogen, halo, $CF_2H$, $CF_3$, $CF_2CH_3$, $C(CH_3)_2F$, $C_{1-3}$ alkyl optionally substituted with one substituent selected from the group consisting of: OH, phenyl and phenoxy group, or cyclopropyl optionally substituted with one substituent selected from the group consisting of: cyano, $C_{1-3}$ alkyl, and $C_{1-3}$ alkoxy.

In another embodiment $R^9$ is phenyl or 2,3-dihydro-1H-indenyl optionally substituted with one or two substituents each independently selected from the group consisting of: fluoro, chloro, bromo, cyano, methoxy, $CH_2OH$, $C_{1-4}$ alkyl, $C_{1-4}$ haloalkyl and $C_{1-3}$ haloalkoxy.

In another embodiment $R^9$ is phenyl optionally substituted with one or two substituents each independently selected from the group consisting of: fluoro, chloro, bromo, cyano, methoxy, $CH_2OH$, $C_{1-4}$ alkyl, $C_{1-4}$ haloalkyl and $C_{1-3}$ haloalkoxy. Suitably $R^9$ is phenyl optionally substituted with one or two substituents each independently selected from the group consisting of: fluoro, chloro, bromo, cyano, methoxy, $CH_2OH$, $C_{1-4}$ alkyl, $CF_2H$, $CF_3$, $C(CH_3)_2CF_3$, $OCF_3$, —$OCH_2CF_3$, and —$OCHF_2$. Suitably $R^9$ is phenyl substituted in the para position with chloro, fluoro, methyl, cyano, $CF_3$ or isopropyl. Suitably $R^9$ is phenyl substituted in the para position with chloro, $CF_3$ or isopropyl.

In another embodiment $R^9$ is optionally substituted heteroaryl. Suitably $R^9$ is optionally substituted pyrazolyl, pyridinyl, indolyl or isoquinolinyl. Suitably $R^9$ is pyrazolyl or pyridinyl optionally substituted with one or two substituents each independently selected from the group consisting of halo, $C_{1-6}$ alkyl and $C_{1-6}$ haloalkyl, for example, fluoro, methyl and $CF_3$ or $C(CH_3)_2CF_3$.

In another embodiment $R^9$ is —$OR^{9a}$ wherein $R^{9a}$ is optionally substituted $C_{1-6}$ alkyl, $C_{1-6}$ haloalkyl, optionally substituted phenyl, or optionally substituted 5 or 6 membered heterocyclic. Suitably $R^{9a}$ is tetrahydrofuranyl, $CF_3$, $CHF_2$, $CHCF_3$, $C_{1-6}$ alkyl optionally substituted with one cyclopropyl, or phenyl optionally substituted with one halo.

In another embodiment $R^9$ is —$SO_2R^{9a}$ wherein $R^{9a}$ is $C_{1-6}$ alkyl.

In another embodiment $R^9$ is —$C(O)NHR^{9a}$ wherein $R^{9a}$ is optionally substituted $C_{3-6}$ cycloalkyl. Suitably $R^9$ is —$C(O)NHR^{9a}$ wherein $R^{9a}$ is cyclopentyl.

In another embodiment $R^9$ is $CH_2R^{9b}$ wherein $R^{9b}$ is optionally substituted heterocyclic. Suitably $R^{9b}$ is optionally substituted 5 to 6 membered heterocyclic. Suitably $R^{9b}$ is piperidinyl, piperazinyl or morpholinyl each of which is optionally substituted with one to four substituents each independently selected from the group consisting of: hydroxyl, halo, $CH_2OH$, —NRR, cyano, $C_{1-3}$ alkyl, $C_{1-3}$ haloalkyl, and $C_{1-3}$ alkoxy. Suitably $R^{9b}$ is piperidinyl, piperazinyl or morpholinyl each of which is optionally substituted with one to three substituents each independently selected from the group consisting of: hydroxyl, $CH_2OH$, fluoro, $NH_2$, $N(CH_3)_2$, $NHCH_3$, methyl, and $CF_3$.

In another embodiment of the present invention each R is independently selected from the group consisting of: H, $C_{1-3}$ alkyl.

Another embodiment of the present invention is a compound according to formula (II).

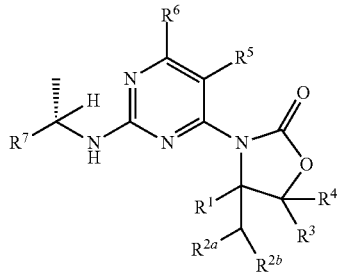

(II)

Another embodiment of the present invention is a compound according to formula (III).

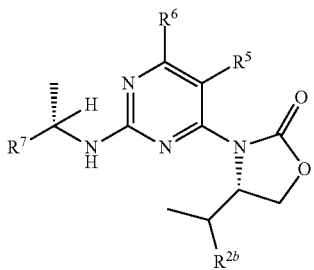

(III)

wherein $R^{2b}$ is OH, $NH_2$ or fluoro.

Another embodiment of the present invention is a compound according to formula (IV).

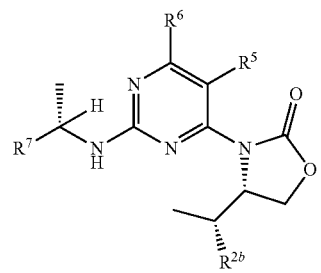

(IV)

wherein $R^{2b}$ is OH or $NH_2$. Suitably $R^{2b}$ is OH. Suitably $R^{2b}$ is $NH_2$.

Another embodiment of the present invention is a compound according to formula (IV), wherein:
$R^{2b}$ is OH;
$R^5$ is hydrogen or fluoro;
$R^6$ is hydrogen, chloro, methyl or $CH_2F$;
$R^7$ is

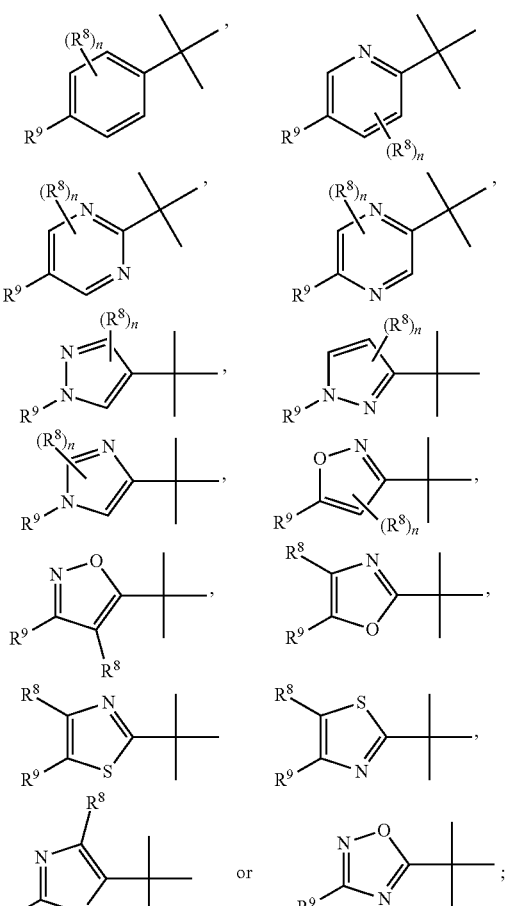

$R^8$ is hydrogen, methyl or fluoro;
n is 1 or 2; and
$R^9$ is methylcyclopropyl, isobutoxy, phenyl optionally substituted with one or two substituents each independently selected from the group consisting of: fluoro, chloro, bromo, $C_{1-4}$ alkyl, $CF_2H$, and $CF_3$, or pyridinyl optionally substituted with one or two substituents each independently selected from the group consisting of: methyl, CF$_3$ and C(CH$_3$)$_2$CF$_3$; Suitably R$^5$ is hydrogen and R$^6$ is chloro, methyl or CH$_2$F or R$^6$ is hydrogen and R$^5$ is fluoro. Suitably R$^5$ is hydrogen and R$^6$ are both hydrogen.

Another embodiment of the present invention is a compound according to formula (V).

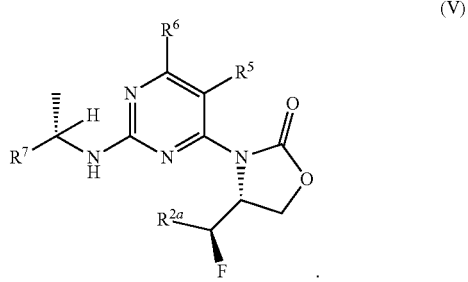

(V)

Another embodiment of the present invention is a compound according to formula (V) wherein:
R$^5$ is hydrogen or fluoro;
R$^6$ is hydrogen;
R$^7$ is

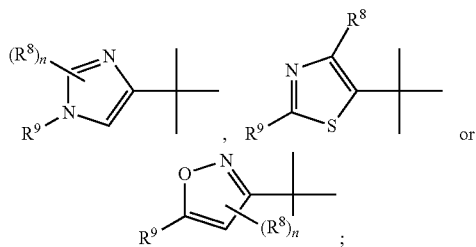

R$^8$ is hydrogen or methyl;
n is 1; and
R$^9$ is phenyl optionally substituted with one chloro.

Another embodiment of the present invention is a compound according to formula (VI)

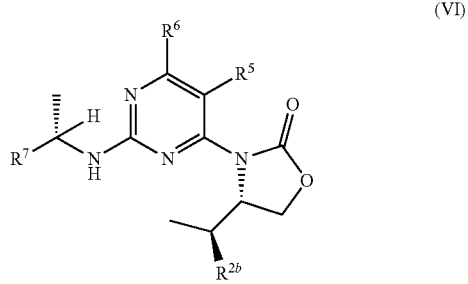

(VI)

wherein:
R$^{2b}$ is fluoro;
R$^5$ is hydrogen or fluoro;
R$^6$ is hydrogen;
R$^7$ is

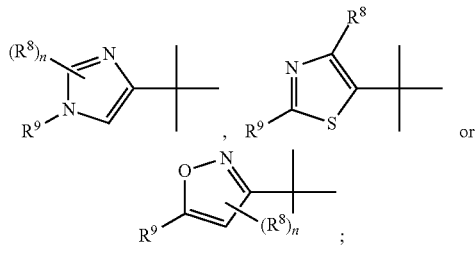

R$^8$ is hydrogen or methyl;
n is 1; and
R$^9$ is phenyl optionally substituted with one chloro; or a pharmaceutically acceptable salt thereof.

Preferred compounds of the invention include:
(R)-4-((R)-1-hydroxy(R)-4-((R)-1-hydroxyethyl)-3-(2-(((S)-1-(5-(3-(trifluoromethyl)phenyl)pyrazin-2-yl)ethyl)amino)pyrimidin-4-yl)oxazolidin-2-onethyl)-3-(2-(((S)-1-(5-(3-(trifluoromethyl)phenyl)pyrazin-2-yl)ethyl)amino)pyrimidin-4-yl)oxazolidin-2-one;
(R)-3-(2-(((S)-1-(5-(4-fluoro-3-methylphenyl)pyridin-2-yl)ethyl)amino)pyrimidin-4-yl)-4-((R)-1-hydroxyethyl)oxazolidin-2-one;
(R)-4-((R)-1-hydroxyethyl)-3-(2-(((S)-1-(5-(3-(trifluoromethyl)phenyl)pyridin-2-yl)ethyl)amino)pyrimidin-4-yl)oxazolidin-2-one;
(R)-4-((R)-1-hydroxyethyl)-3-(2-(((S)-1-(6-(trifluoromethyl)-[2,3'-bipyridin]-6'-yl)ethyl)amino)pyrimidin-4-yl)oxazolidin-2-one;
(R)-4-((R)-1-hydroxyethyl)-3-(2-(((S)-1-(4-methyl-2'-(trifluoromethyl)-[3,4'-bipyridin]-6-yl)ethyl)amino)pyrimidin-4-yl)oxazolidin-2-one;
(R)-3-(2-(((S)-1-(5-(4-chlorophenyl)isoxazol-3-yl)ethyl)amino)pyrimidin-4-yl)-4-((R)-1-hydroxyethyl)oxazolidin-2-one;
(R)-3-(2-(((S)-1-(5-(4-fluoro-3-(trifluoromethyl)phenyl)pyrimidin-2-yl)ethyl)amino)pyrimidin-4-yl)-4-((R)-1-hydroxyethyl)oxazolidin-2-one;
(R)-3-(2-(((S)-1-(5-(4-chloro-3-(trifluoromethyl)phenyl)pyrimidin-2-yl)ethyl)amino)pyrimidin-4-yl)-4-((R)-1-hydroxyethyl)oxazolidin-2-one;
(R)-3-(2-(((S)-1-(5-(3,4-dichlorophenyl)pyrimidin-2-yl)ethyl)amino)pyrimidin-4-yl)-4-((R)-1-hydroxyethyl)oxazolidin-2-one;
(R)-4-((R)-1-hydroxyethyl)-3-(2-(((S)-1-(5-(3-(trifluoromethyl)phenyl)pyrimidin-2-yl)ethyl)amino)pyrimidin-4-yl)oxazolidin-2-one;
(R)-3-(2-(((S)-1-(5-(4-chloro-3-methylphenyl)pyrimidin-2-yl)ethyl)amino)pyrimidin-4-yl)-4-((R)-1-hydroxyethyl)oxazolidin-2-one;
(R)-3-(2-(((S)-1-(5-(3-chloro-5-(trifluoromethyl)phenyl)pyrimidin-2-yl)ethyl)amino)pyrimidin-4-yl)-4-((R)-1-hydroxyethyl)oxazolidin-2-one;
(R)-3-(2-(((S)-1-(3-(4-chlorophenyl)-1,2,4-oxadiazol-5-yl)ethyl)amino)pyrimidin-4-yl)-4-((R)-1-hydroxyethyl)oxazolidin-2-one;
(R)-3-{2-[((R)1-(3-(3-fluoro-4-methylphenyl)-1,2,4-oxadiazol-5-yl)ethyl]amino}pyrimidin-4-yl)-4-((R)-1-hydroxyethyl)oxazolidin-2-one;
(R)-3-(2-{(S)-1-[3-(3,4-Dichloro-phenyl)-isoxazol-5-yl]-ethylamino}-pyrimidin-4-yl)-4-((R)-1-hydroxy-ethyl)-oxazolidin-2-one;
(R)-3-(2-{(S)-1-[3-(3,4-Dichloro-phenyl)-isoxazol-5-yl]-ethylamino}-5-fluoro-pyrimidin-4-yl)-4-((R)-1-hydroxy-ethyl)-oxazolidin-2-one;
(R)-3-(5-fluoro-2-(((S)-1-(3-(4-isopropylphenyl)-1,2,4-oxadiazol-5-yl)ethyl)amino)pyrimidin-4-yl)-4-((R)-1-hydroxyethyl)oxazolidin-2-one;
(R)-4-((R)-1-hydroxyethyl)-3-(2-(((S)-1-(3-(4-(trifluoromethyl)phenyl)-1,2,4-oxadiazol-5-yl)ethyl)amino)pyrimidin-4-yl)oxazolidin-2-one;
(R)-3-(2-(((S)-1-(5-(4-chlorophenyl)-4-methyloxazol-2-yl)ethyl)amino)pyrimidin-4-yl)-4-((R)-1-hydroxyethyl)oxazolidin-2-one;
(R)-3-(2-(((S)-1-(5-(4-chlorophenyl)-4-methyloxazol-2-yl)ethyl)amino)-5-fluoropyrimidin-4-yl)-4-((R)-1-hydroxyethyl)oxazolidin-2-one;

(R)-3-(2-(((S)-1-(4-(4-bromophenyl)thiazol-2-yl)ethyl)amino)-5-fluoropyrimidin-4-yl)-4-((R)-1-hydroxyethyl)oxazolidin-2-one;

(R)-3-(2-(((S)-1-(5-(3,4-dichlorophenyl)pyrimidin-2-yl)ethyl)amino)-5-fluoropyrimidin-4-yl)-4-((R)-1-hydroxyethyl)oxazolidin-2-one;

(R)-4-((R)-1-hydroxyethyl)-3-(2-(((S)-1-(4-methyl-5-(2-(1,1,1-trifluoro-2-methylpropan-2-yl)pyridin-4-yl)thiazol-2-yl)ethyl)amino)pyrimidin-4-yl)oxazolidin-2-one;

(4R)-3-(5-fluoro-2-(((S)-1-(4-methyl-5-(2-(1,1,1-trifluoro-2-methylpropan-2-yl)pyridin-4-yl)thiazol-2-yl)ethyl)amino)pyrimidin-4-yl)-4-((R)-1-hydroxyethyl)oxazolidin-2-one;

(R)-3-(2-(((S)-1-(5-(2-fluoro-3-(trifluoromethyl)phenyl)pyrimidin-2-yl)ethyl)amino)pyrimidin-4-yl)-4-((R)-1-hydroxyethyl)oxazolidin-2-one;

(R)-3-(2-(((S)-1-(5-(4-chlorophenyl)oxazol-2-yl)ethyl)amino)-5-fluoropyrimidin-4-yl)-4-((R)-1-hydroxyethyl)oxazolidin-2-one;

(R)-3-(2-(((S)-1-(5-(4-chlorophenyl)oxazol-2-yl)ethyl)amino)pyrimidin-4-yl)-4-((R)-1-hydroxyethyl)oxazolidin-2-one;

(R)-3-(2-(((S)-1-(2-(4-chlorophenyl)thiazol-5-yl)ethyl)amino)-5-fluoropyrimidin-4-yl)-4-((R)-1-hydroxyethyl)oxazolidin-2-one;

(R)-3-(2-(((S)-1-(2-(4-chlorophenyl)thiazol-5-yl)ethyl)amino)-6-(fluoromethyl)pyrimidin-4-yl)-4-((R)-1-hydroxyethyl)oxazolidin-2-one;

(R)-3-(2-(((S)-1-(2-(4-chlorophenyl)thiazol-5-yl)ethyl)amino)pyrimidin-4-yl)-4-((R)-1-hydroxyethyl)oxazolidin-2-one;

(R)-3-(2-(((S)-1-(1-(4-chlorophenyl)-1H-pyrazol-4-yl)ethyl)amino)pyrimidin-4-yl)-4-((R)-1-hydroxyethyl)oxazolidin-2-one;

(R)-3-(2-(((S)-1-(5-(4-chlorophenyl)isoxazol-3-yl)ethyl)amino)-6-methylpyrimidin-4-yl)-4-((R)-1-hydroxyethyl)oxazolidin-2-one;

(R)-3-(2-(((S)-1-(2-(4-chlorophenyl)thiazol-5-yl)ethyl)amino)-6-methylpyrimidin-4-yl)-4-((R)-1-hydroxyethyl)oxazolidin-2-one;

(R)-3-(2-(((S)-1-(1-(4-chlorophenyl)-1H-imidazol-4-yl)ethyl)amino)-6-methylpyrimidin-4-yl)-4-((R)-1-hydroxyethyl)oxazolidin-2-one;

(R)-3-(2-(((S)-1-(2-(4-(difluoromethyl)phenyl)thiazol-5-yl)ethyl)amino)pyrimidin-4-yl)-4-((R)-1-hydroxyethyl)oxazolidin-2-one;

(R)-3-(2-(((S)-1-(2-fluoro-4-(1-methylcyclopropyl)phenyl)ethylamino)pyrimidin-4-yl)-4-((R)-1-hydroxyethyl)oxazolidin-2-one;

(R)-3-(2-(((S)-1-(1-(4-chlorophenyl)-1H-imidazol-4-yl)ethyl)amino)pyrimidin-4-yl)-4-((R)-1-hydroxyethyl)oxazolidin-2-one;

(R)-3-(6-chloro-2-(((S)-1-(1-(4-chlorophenyl)-1H-imidazol-4-yl)ethyl)amino)pyrimidin-4-yl)-4-((R)-1-hydroxyethyl)oxazolidin-2-one;

(R)-3-(2-(((S)-1-(2,5-difluoro-4-(2-methylpyridin-4-yl)phenyl)ethyl)amino)pyrimidin-4-yl)-4-((R)-1-hydroxyethyl)oxazolidin-2-one;

(R)-3-(5-fluoro-2-(((S)-1-(2-fluoro-4-isobutoxyphenyl)ethyl)amino)pyrimidin-4-yl)-4-((R)-1-hydroxyethyl)oxazolidin-2-one;

(R)-3-(2-(((S)-1-(2-fluoro-4-isobutoxyphenyl)ethyl)amino)pyrimidin-4-yl)-4-((R)-1-hydroxyethyl)oxazolidin-2-one;

(R)-3-(2-(((S)-1-(3-(3-(tert-butyl)phenyl)-1,2,4-oxadiazol-5-yl)ethyl)amino)pyrimidin-4-yl)-4-((R)-1-hydroxyethyl)oxazolidin-2-one;

(R)-3-(6-chloro-2-(((S)-1-(2-(4-chlorophenyl)thiazol-5-yl)ethyl)amino)pyrimidin-4-yl)-4-((R)-1-methoxyethyl)oxazolidin-2-one;

(R)-3-(2-(((S)-1-(1-(4-chlorophenyl)-1H-imidazol-4-yl)ethyl)amino)pyrimidin-4-yl)-4-((R)-1-methoxyethyl)oxazolidin-2-one;

(S)-4-((R)-1-aminoethyl)-3-(2-(((S)-1-(2-(4-chlorophenyl)thiazol-5-yl)ethyl)amino)pyrimidin-4-yl)oxazolidin-2-one;

(R)-3-(2-(((S)-1-(1-(4-chlorophenyl)-1H-imidazol-4-yl)ethyl)amino)pyrimidin-4-yl)-4-((R)-1-fluoroethyl)oxazolidin-2-one;

(R)-3-(2-(((S)-1-(1-(4-chlorophenyl)-1H-imidazol-4-yl)ethyl)amino)pyrimidin-4-yl)-4-((S)-1-fluoroethyl) oxazolidin-2-one;

(R)-3-(2-(((S)-1-(2-(4-chlorophenyl) thiazol-5-yl)ethyl)amino)pyrimidin-4-yl)-4-((S)-1-fluoroethyl)oxazolidin-2-one;

(R)-3-(2-(((S)-1-(5-(4-chlorophenyl) isoxazol-3-yl)ethyl)amino)pyrimidin-4-yl)-4-((S)-1-fluoroethyl)oxazolidin-2-one;

(R)-3-(2-(((S)-1-(1-(4-chlorophenyl)-1H-imidazol-4-yl)ethyl)amino)-5-fluoropyrimidin-4-yl)-4-((R)-1-fluoroethyl) oxazolidin-2-one;

(R)-3-(2-(((S)-1-(1-(4-chlorophenyl)-2-methyl-1H-imidazol-4-yl)ethyl)amino)pyrimidin-4-yl)-4-((S)-1-fluoroethyl) oxazolidin-2-one;

(R)-4-((S)-1-fluoroethyl)-3-(2-(((S)-1-(1-(4-fluorophenyl)-1H-imidazol-4-yl)ethyl)amino)pyrimidin-4-yl)oxazolidin-2-one;

(R)-3-(2-(((S)-1-(1-(4-chlorophenyl)-1H-imidazol-4-yl)ethyl)amino)pyrimidin-4-yl)-4-(fluoromethyl)oxazolidin-2-one;

(S)-3-(2-(((S)-1-(1-(4-chlorophenyl)-1H-imidazol-4-yl)ethyl)amino)pyrimidin-4-yl)-4-((R)-1,1-difluoropropan-2-yl)oxazolidin-2-one;

(R)-4-((S)-1-fluoroethyl)-3-(2-(((S)-1-(4-methyl-2'-(trifluoromethyl)-[3,4'-bipyridin]-6-yl)ethyl)amino)pyrimidin-4-yl)oxazolidin-2-one;

(R)-3-(5-fluoro-2-(((S)-1-(4-methyl-2'-(trifluoromethyl)-[3,4'-bipyridin]-6-yl)ethyl)amino)pyrimidin-4-yl)-4-((S)-1-fluoroethyl)oxazolidin-2-one;

(R)-3-(2-(((S)-1-(1-(3-chloro-4-fluorophenyl)-1H-imidazol-4-yl)ethyl)amino)-5-fluoropyrimidin-4-yl)-4-(fluoromethyl)oxazolidin-2-one; and (R)-3-(2-(((S)-1-(5-(4-chlorophenyl)oxazol-2-yl)ethyl)amino)-5-fluoropyrimidin-4-yl)-4-(fluoromethyl)oxazolidin-2-one.

Certain compounds of the present invention were found to have improved preclinical properties. For example, certain compounds of the present invention were found to have maintained potency against mIDH1 (for example IDH R132H and/or R132C) in biochemical and/or cellular activity assays, while at the same time improving in-vitro absorption, distribution, metabolism and excretion (ADME) properties. For example, certain compounds of the present invention were found to have reduced clearance rates in rat and/or mouse and/or human in vitro liver microsomal stability assays. Stability in the presence of liver microsomes is important because it can be predictive of in-vivo clearance, and therefore also be predictive of whether or not a compound will have an adequate systemic exposure profile in the human body to effect the desired pharmacological response. Lower clearance rates, i.e. the more stable the compound is in the presence of liver microsomes in vitro, suggests the compound is more likely to have adequate systemic exposure in humans.

General Synthetic Procedures

The compounds of the present invention may be made by a variety of methods, including standard chemistry. Suitable synthetic routes are depicted in the Schemes given below.

The compounds of formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of formula (I).

Those skilled in the art will recognize if a stereocenter exists in the compounds of formula (I). Accordingly, the present invention includes both possible stereoisomers and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be effected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Scheme 1.

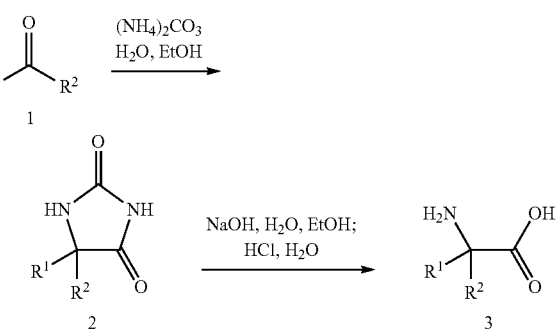

wherein $R^2$ is $CH_2R^{2a}R^{2b}$

Non-commercial aminoacids can be prepared following the procedures of Scheme 1. Conversion of ketone 1 to the corresponding imidazolidine-2,4-dione 2 followed by hydrolysis provides aminoacid 3.

Scheme 2.

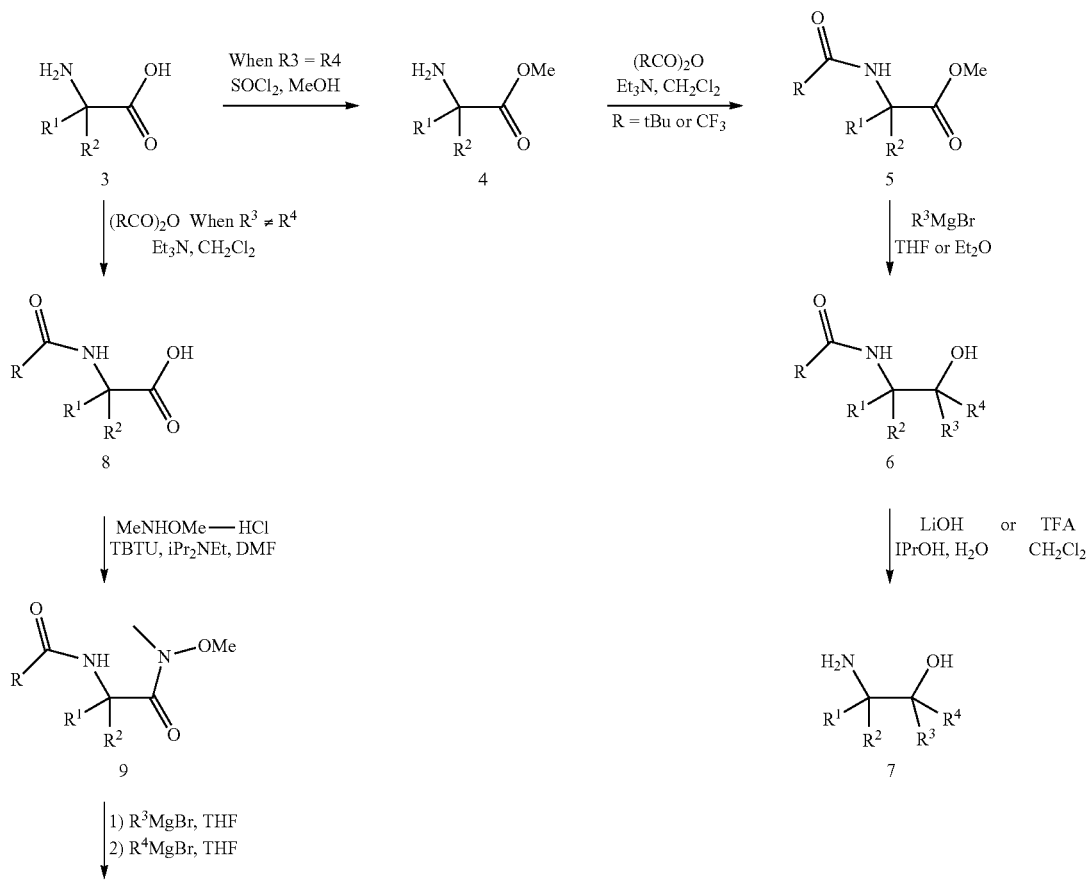

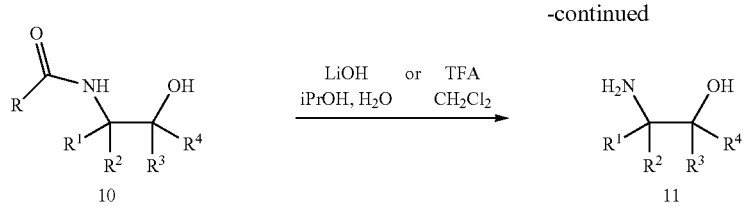
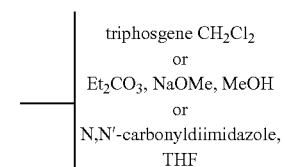
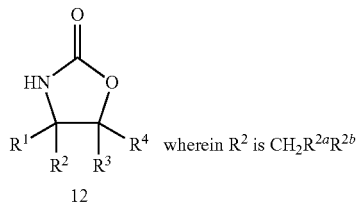

When aminoalcohol, precursor of oxazolidinone, is not commercially available, it can be prepared from aminoacid 3 following the procedures of Scheme 2. When $R^3=R^4$, protected aminoester 5 is treated with an appropriate Grignard reagent to give protected aminoalcohol 6 which goes through basic or acidic deprotection step. When $R^3\ne R^4$, protected aminoacid 8 is converted into Weinreb amide 9 which is treated with different Grignard reagents sequentially to provide protected aminoalcohol 10. Either basic or acidic deprotection of 10 gives 11. Insertion of CO unit into 7 or 11 to provide oxazolidinone 12 is accomplished with several reagents, including (but not limited to) triphosgene, $Et_2CO_3$ or N—N'-darbonyldiimidazole, as shown in Scheme 2.

Oxazolidinone 12 is coupled with dihalogen-pyrimidine 13 in the presence of NaH and the resulting 14 is treated with primary amine 15 under several different reaction conditions as shown in Scheme 3 to provide 16.

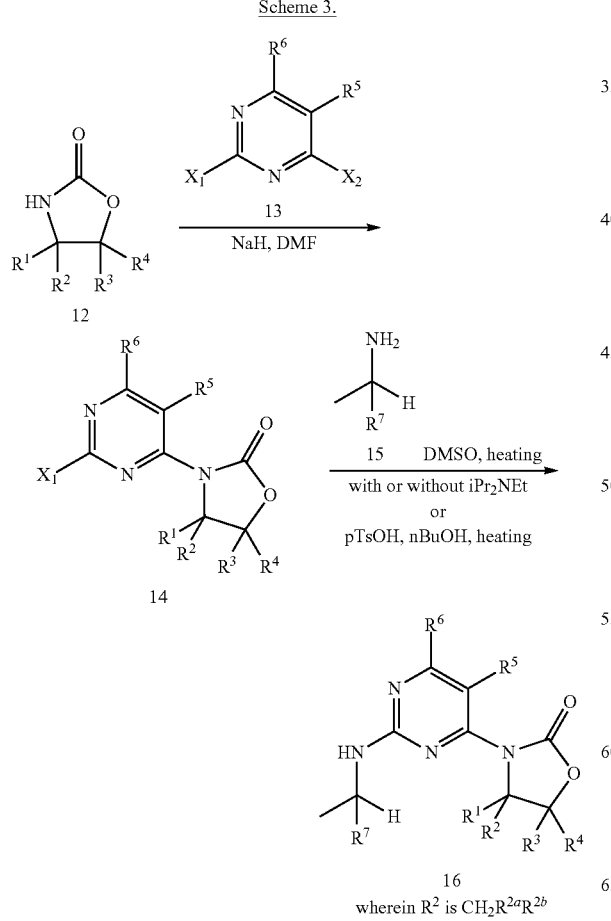

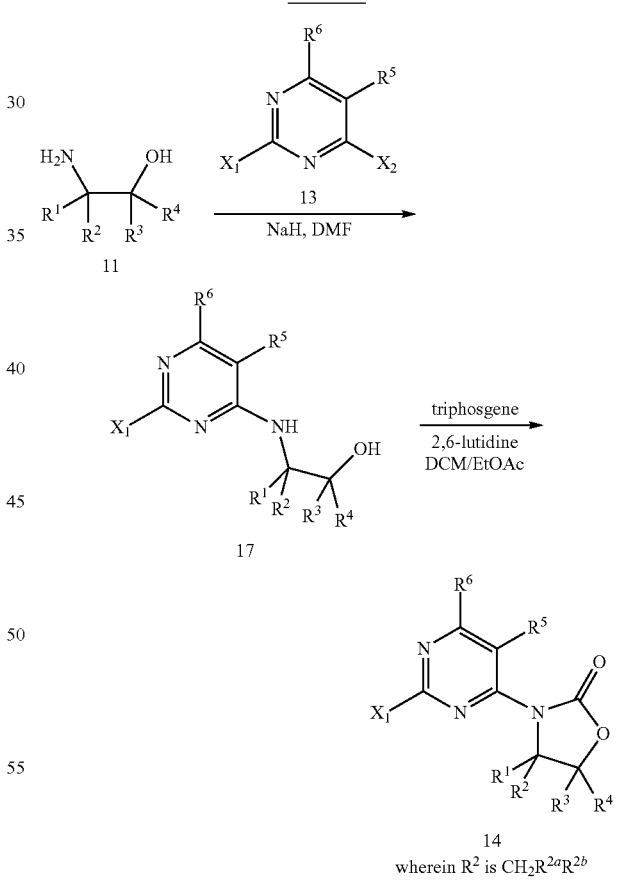

Alternately intermediate 14 can be prepared by coupling the amino alcohol 11 and dihalogen-pyrimidine 13 in the presence of a base such as diisopropylethyl amine resulting in intermediate 17 which can be treated with triphosgene in the presence of a base such as 2,6-lutidine resulting in intermediate 14.

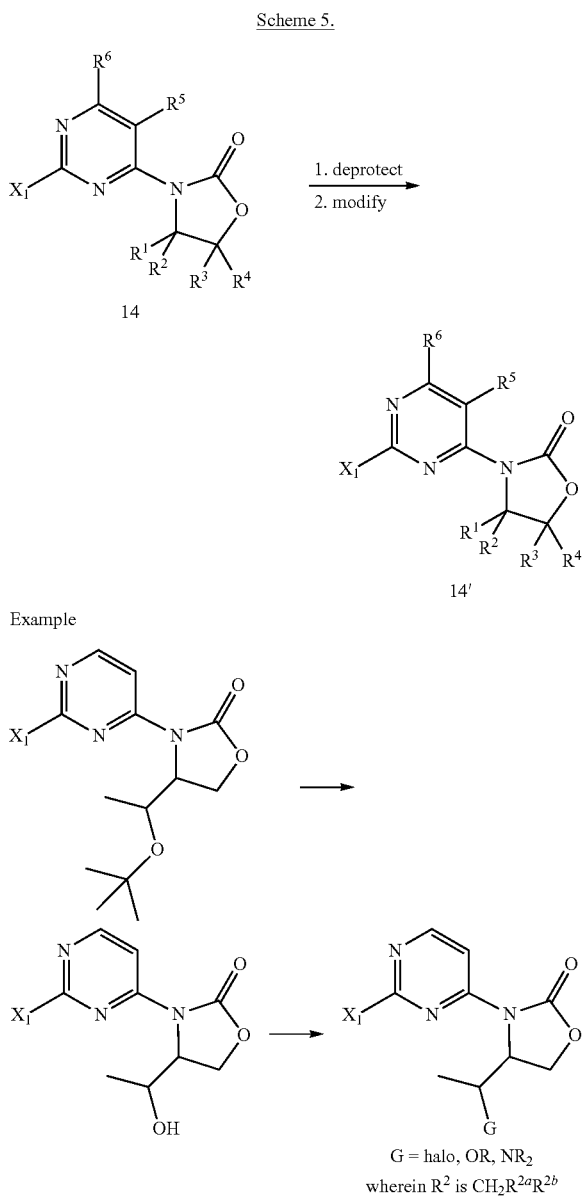

Intermediate 14 can undergo modification of functional groups on $R^1$, $R^2$, $R^3$ or $R^4$ prior to transformation to compound 16 as described in Scheme 3.

Methods of Use

The compounds of the present invention are inhibitors of a mutant IDH protein having a neomorphic activity and are therefore useful in the treatment of diseases or disorders associated with such proteins including, but not limited to, cell proliferation disorders, such as cancer.

Examples of a mutant IDH protein having a neomorphic activity are mutant IDH1 and mutant IDH2. A neomorphic activity associated with mutant IDH1 and mutant IDH2 is the ability to produce 2-hydroxyglutarate (2-HG neomorphic activity), specifically R-2-HG (R-2-HG neomorphic activity). Mutations in IDH1 associated with 2-HG neomorphic activity, specifically R-2-HG neomorphic activity, include mutations at residues 97, 100, and 132, e.g. G97D, R100Q, R132H, R132C, R132S, R132G, R132L, and R132V. Mutations in IDH2 associated with 2-HG neoactivity, specifically R-2-HG neomorphic activity, include mutations at residues 140 and 172, e.g. R140Q, R140G, R172K, R172M, R172S, R172G, and R172W.

Cell-proliferation disorders associated with a mutant IDH protein having a neomorphic activity include, but are not limited to, cancer. Examples of such cancers include Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primaiy; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; steosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

In another embodiment the cancer associated with a mutant IDH protein having a neomorphic activity is brain cancer, such as astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma); oligodendroglial tumor (e.g., oligodendroglioma, and anaplastic oligodendroglioma); oligoastrocytic tumor (e.g., oligoastrocytoma, and anaplastic oligoastrocytoma); ependymoma (e.g., myxopapillary ependymoma, and anaplastic ependymoma); medulloblastoma; primitive neuroectodermal tumor, schwannoma, meningioma, meatypical meningioma, anaplastic meningioma; and pituitary adenoma. In another embodiment, the brain cancer is glioma, glioblastoma multiforme, paraganglioma, or suprantentorial primordial neuroectodermal tumors (sPNET).

In another embodiment the cancer associated with a mutant IDH protein having a neomorphic activity is leukemia, such as acute myeloid leukemia (AML), myelodysplastic syndrome (MDS), chronic myelogenous leukemia (CML), myeloproliferative neoplasm (MPN), MDS.MPN including chronic myelomonocytic leukemia, post MDS AML, post MPN AML, post MDS/MPN AML, del(5q)-associated high risk MDS or AML, blast-phase chronic myelogenous leukemia, angioimmunoblastic lymphoma and acute lymphoblastic leukemia.

In another embodiment the cancer associated with a mutant IDH protein having a neomorphic activity is skin cancer, including melanoma.

In another embodiment the cancer associated with a mutant IDH protein having a neomorphic activity is prostate cancer, thyroid cancer, colon cancer, or lung cancer.

In another embodiment the cancer associated with a mutant IDH protein having a neomorphic activity is sarcoma, including central chondrosarcoma, central and periosteal chondroma, and fibrosarcoma.

In another embodiment the cancer associated with a mutant IDH protein having a neomorphic activity is cholangiocarcinoma.

Another disease or disorder associated with a mutant IDH protein having R-2-HG neomorphic activity is D-2-hydroxyglutaric aciduria.

Another disease or disorder associated with a mutant IDH protein having R-2-HG neomorphic activity is Oilier disease and Mafucci syndrome.

As used herein the term "neomorphic activity" refers to a gain of novel activity of a protein that the wild-type protein does not have or does not exhibit to a significant degree. For example, a neomorphic activity associated with a mutant form of IDH1 and IDH2 is the ability to reduce alpha-ketoglutarate to 2-hydroxyglutarate (i.e. 2-HG, specifically R-2-HG). The wild type form of IDH1 and IDH2 does not have the ability to reduce alpha-ketoglutarate to 2-hydroxyglutarate (i.e. 2-HG, specifically R-2-HG) or if it does have this ability, it does not produce significant (i.e. harmful or disease causing) amounts of 2-HG.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "therapeutically effective amount" in reference to a compound of the invention means an amount of the compound sufficient to treat the subject's disease or condition, but low enough to avoid serious sides effects (at a reasonable benefit/risk ratio) within the scope of sound medical judgment. A therapeutically effective amount of a compound will vary with the particular compound chosen (e.g. consider the potency, efficacy, and half-life of the compound); the route of administration chosen; the condition being treated; the severity of the condition being treated; the age, size, weight, and physical condition of the subject being treated; the medical history of the subject being treated; the duration of the treatment; the nature of the concurrent therapy; the desired therapeutic effect; and like factors and can be routinely determined by the skilled artisan.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

The compounds of the present invention may be administered by any suitable route including oral and parenteral administration. Parenteral administration is typically by injection or infusion and includes intravenous, intramuscular, and subcontaneous injection or infusion.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution and half life which can be determined by the skilled artisan. In addition, suitable dosing regimens, including the duration such regimens are administered, for a compound of the invention depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 5 mg to about 500 mg of a compound of formula (I).

One embodiment of the present invention provides for a method of treating a disease or disorder associated with a mutant form of IDH having a neomorphic activity comprising administration of a therapeutically effective amount of a compound of formula (I) to a subject in need of treatment thereof. In one embodiment, the disease or disorder associated with a mutant form of IDH having a neomorphic activity is a cell proliferation disorder. In another embodiment, the cell proliferation disorder is cancer. In another embodiment, the cancer is a cancer associated with mutant IDH1 having 2-HG neomorphic activity or mutant IDH2 having 2-HG neomorphic activity. In another embodiment the neomorphic activity is R-2-HG neomorphic activity. In another embodiment the cancer is associated with mutant IDH1 having 2-HG or R-2-HG neomorphic activity having a mutation at residues 97, 100, or 132, such as G97D, R100Q, R132H, R132C, R132S, R132G, R132L, and R132V. In another embodiment the cancer is associated with mutant IDH2 having 2-HG or R-2-HG neomorphic activity having a mutation at residues 140 or 172, e.g. R140Q, R140G, R172K, R172M, R172S, R172G, and R172W. In another embodiment the cancer is brain cancer, leukemia, skin cancer, prostate cancer, thyroid cancer, colon cancer, lung cancer or sarcoma. In another embodiment the cancer is glioma, glioblastoma multiforme, paraganglioma, suprantentorial primordial neuroectodermal tumors, acute myeloid leukemia, myelodysplastic syndrome, chronic myelogenous leukemia, melanoma, prostate, thyroid, colon, lung, central chondrosarcoma, central and periosteal chondroma tumors, fibrosarcoma, and cholangiocarcinoma.

Another embodiment of the present invention provides for a method of treating a disease or disorder associated with a mutant form of IDH having R-2-HG neomorphic activity comprising administration of a therapeutically effective amount of a compound according to formula (I) to a subject in need thereof wherein the disease or disorder is D-2-hydroxyglutaric aciduria, Ollier Disease, or Mafucci Syndrome.

Another embodiment of the present invention provides for the use of a compound of formula (I) in therapy. In a further embodiment the therapy is a disease or disorder associated with a mutant form of IDH having a neomorphic activity. In another embodiment the therapy is a cell proliferation disorder associated with a mutant form of IDH having a neomorphic activity. In another embodiment the therapy is cancer. In another embodiment the therapy is a cancer associated with a mutant IDH protein having a neomorphic activity, such as mutant IDH1 having 2-HG neomorphic activity or mutant IDH2 having 2-HG neomorphic activity. In another embodiment the neomorphic activity is R-2-HG neomorphic activity. In another embodiment the cancer is associated with mutant IDH1 having 2-HG or R-2-HG neomorphic activity having a mutation at residues 97, 100, or 132, such as G97D, R100Q, R132H, R132C, R132S, R132G, R132L, and R132V. In another embodiment the cancer is associated with mutant IDH2 having 2-HG or R-2-HG neomorphic activity having a mutation at residue at residues R140 or 172, e.g. R140Q, R140G, R172K, R172M, R172S, R172G, and R172W. In another embodiment the cancer is brain cancer, leukemia, skin cancer, prostate cancer, thyroid cancer, colon cancer, lung cancer or sarcoma. In another embodiment the cancer is glioma, glioblastoma multiforme, paraganglioma, suprantentorial primordial neuroectodermal tumors, acute myeloid leukemia, myelodysplastic syndrome, chronic myelogenous leukemia, melanoma, prostate, thyroid, colon, lung, central chondrosarcoma, central and periosteal chondroma tumors, fibrosarcoma, and cholangiocarcinoma.

Another embodiment of the present invention provides for the use of a compound of formula (I) in therapy wherein the therapy is D-2-hydroxyglutaric aciduria, Ollier Disease, or Mafucci Syndrome.

Another embodiment of the present invention provides for the use of a compound according to formula (I) in the manufacture of a medicament for the treatment of disease or disorder associated with a mutant form of IDH having a neomorphic activity. In one embodiment the disease or disorder associated with a mutant form of IDH having a neomorphic activity is a cell proliferation disorder. In another embodiment, the cell proliferation disorder is cancer. In another embodiment the cancer is a cancer associated with a mutant IDH protein having a neomorphic activity, such as mutant IDH1 having 2-HG neomorphic activity or mutant IDH2 having 2-HG neomorphic activity. In another embodiment the neomorphic activity is R-2-HG neomorphic activity. In another embodiment the cancer is associated with mutant IDH1 having 2-HG or R-2-HG neomorphic activity having a mutation at residues 97, 100, or 132, such as G97D, R100Q, R132H, R132C, R132S, R132G, R132L, and R132V. In another embodiment the cancer is associated with mutant IDH2 having 2-HG or R-2-HG neomorphic activity having a mutation at residue at residues 140 or 172, e.g. R140Q, R140G, R172K, R172M, R172S, R172G, and R172W. In another embodiment the cancer is brain cancer, leukemia, skin cancer, prostate cancer, thyroid cancer, colon cancer, lung cancer or sarcoma. In another embodiment the cancer is glioma, glioblastoma multiforme, paraganglioma, suprantentorial primordial neuroectodermal tumors, acute myeloid leukemia, myelodysplastic syndrome, chronic myelogenous leukemia, melanoma, prostate, thyroid, colon, lung, central chondrosarcoma, central and periosteal chondroma tumors, fibrosarcoma, and cholangiocarcinoma.

Another embodiment of the present invention provides for the use of a compound according to formula (I) in the manufacture of a medicament for the treatment of disease or disorder associated with a mutant form of IDH having R-2-HG neomorphic activity wherein the disease or disorder is D-2-hydroxyglutaric aciduria, Ollier Disease, or Mafucci Syndrome.

Another embodiment of the present invention provides for a compound of formula (I) for use in therapy. In a further embodiment the therapy is a disease or disorder associated with a mutant form of IDH having a neomorphic activity. In another embodiment the therapy is a cell proliferation disorder associated with a mutant form of IDH having a neomorphic activity. In another embodiment the therapy is cancer. In another embodiment the therapy is a cancer associated with a mutant IDH protein having a neomorphic activity, such as mutant IDH1 having 2-HG neomorphic activity or mutant IDH2 having 2-HG neomorphic activity. In another embodiment the neomorphic activity is R-2-HG neomorphic activity. In another embodiment the cancer is associated with mutant IDH1 having 2-HG or R-2-HG neomorphic activity having a mutation at residues 97, 100, or 132, such as G97D, R100Q, R132H, R132C, R132S, R132G, R132L, and R132V. In another embodiment the cancer is associated with mutant IDH2 having 2-HG or R-2-HG neomorphic activity having a mutation at residue at residues R140 or 172, e.g. R140Q, R140G, R172K, R172M, R172S, R172G, and R172W. In another embodiment the cancer is brain cancer, leukemia, skin cancer, prostate cancer, thyroid cancer, colon cancer, lung cancer or sarcoma. In another embodiment the cancer is glioma, glioblastoma multiforme, paraganglioma, suprantentorial primordial neuroectodermal tumors, acute myeloid leukemia, myelodysplastic syndrome, chronic myelogenous leukemia, melanoma, prostate, thyroid, colon, lung, central chondrosarcoma, central and periosteal chondroma tumors, fibrosarcoma, and cholangiocarcinoma.

Another embodiment of the present invention provides for a compound of formula (I) for use in therapy wherein the therapy is D-2-hydroxyglutaric aciduria, Ollier Disease, or Mafucci Syndrome.

Compositions

In another aspect, the present invention provides a pharmaceutical composition comprising a compound of formula (I) and a pharmaceutically acceptable carrier or excipient.

The pharmaceutical compositions of the invention may be prepared and packaged in bulk form wherein a therapeutically effective amount of a compound of the invention can be extracted and then given to a subject, such as with powders or syrups. Alternatively, the pharmaceutical compositions of the invention may be prepared and packaged in unit dosage form wherein each physically discrete unit contains a therapeutically effective amount of a compound of the invention. When prepared in unit dosage form, the pharmaceutical compositions of the invention typically contain from about 5 mg to 500 mg of a compound of formula (I).

As used herein the term "pharmaceutically acceptable carrier or excipient" means a pharmaceutically acceptable material, composition or vehicle that, for example, are involved in giving form or consistency to the pharmaceutical composition. Each excipient must be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided. In addition, each excipient must, of course, be of sufficiently high purity to render it pharmaceutically acceptable.

The compound of the invention and the pharmaceutically acceptable carrier or excipient(s) will typically be formulated into a dosage form adapted for administration to the subject by the desired route of administration. For example, dosage forms include those adapted for (1) oral administration such as tablets, capsules, caplets, pills, troches, powders, syrups, elixirs, suspensions, solutions, emulsions, sachets, and cachets; and (2) parenteral administration such as sterile solutions, suspensions, and powders for reconstitution. Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of the invention, once administered to the subject, from one organ or portion of the body to another organ or another portion of the body. Certain pharmaceutically acceptable excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemecctants, chelating agents, plasticizers, viscosity increasing agents, antioxidants, preservatives, stabilizers, surfactants, and buffering agents.

Skilled artisans possess the knowledge and skill in the art to enable them to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some methods commonly used in the art are described in *Remington's Pharmaceutical Sciences* (Mack Publishing Company).

In one aspect, the invention is directed to a solid oral dosage form such as a tablet or capsule comprising a therapeutically effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds of the invention may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of the invention. Syrups can be prepared by dissolving the compound of the invention in a suitably flavored aqueous solution; while elixirs are prepared through the use of a non-toxic alcoholic vehicle. Suspensions can be formulated by dispersing the compound of the invention in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In another aspect, the invention is directed to parenteral administration. Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

The compound of the present invention may be administered either simultaneously with, or before or after, one or more other therapeutic agent(s). The compound of the present invention may be administered separately, by the same or different route of administration, or together in the same pharmaceutical composition as the other agent(s).

In one embodiment, the invention provides a product comprising a compound of formula (I) and at least one other therapeutic agent as a combined preparation for simultaneous, separate or sequential use in therapy. In one embodiment, the therapy is the treatment of a disease or disorder associated with a mutant form of IDH. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic agent may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or disorder associated with a mutant form of IDH, wherein the medicament is prepared for administration with another therapeutic agent. The invention also provides the use of another therapeutic agent for treating a disease or disorder associated with a mutant form of IDH, wherein the medicament is administered with a compound of formula (I).

The invention also provides a compound of formula (I) for use in a method of treating a disease or disorder associated with a mutant form of IDH, wherein the compound of formula (I) is prepared for administration with another therapeutic agent. The invention also provides another therapeutic agent for use in a method of treating a disease or disorder associated with a mutant form of IDH, wherein the other therapeutic agent is prepared for administration with a compound of formula (I). The invention also provides a compound of formula (I) for use in a method of treating a disease or disorder associated with a mutant form of IDH, wherein the compound of formula (I) is administered with another therapeutic agent. The invention also provides another therapeutic agent for use in a method of treating a disease or disorder associated with a mutant form of IDH, wherein the other therapeutic agent is administered with a compound of formula (I).

The invention also provides the use of a compound of formula (I) for treating a disease or disorder associated with a mutant form of IDH, wherein the patient has previously (e.g. within 24 hours) been treated with another therapeutic agent. The invention also provides the use of another therapeutic agent for treating a disease or disorder associated with a mutant form of IDH, wherein the patient has previously (e.g. within 24 hours) been treated with a compound of formula (I).

In one embodiment, the other therapeutic agent is selected from: vascular endothelial growth factor (VEGF) receptor inhibitors, topoisomerase II inhibitors, smoothened inhibitors, alkylating agents, anti-tumor antibiotics, anti-metabolites, retinoids, and other cytotoxic agents.

Examples of vascular endothelial growth factor (VEGF) receptor inhibitors include, but are not limited to, bevacizumab (sold under the trademark Avastin® by Genentech/Roche), axitinib, (N-methyl-2-[[3-[(E)-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide, and described in PCT Publication No. WO 02/066470), pasireotide (also known as SOM230, and described in PCT Publication No. WO 02/010192), and sorafenib (sold under the tradename Nexavar®).

Examples of topoisomerase II inhibitors, include but are not limited to, etoposide (also known as VP-16 and Etoposide phosphate, sold under the tradenames Toposar®, VePesid® and Etopophos®), and teniposide (also known as VM-26, sold under the tradename Vumon®).

Examples of alkylating agents, include but are not limited to, temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, and sold under the tradename Thioplex®.

Examples of anti-tumor antibiotics include, but are not limited to, doxorubicin (sold under the tradenames Adriamycin® and Rubex®), bleomycin (sold under the tradename Ienoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), and mitomycin C (sold under the tradename Mutamycin®).

Examples of anti-metabolites include, but are not limited to, claribine (2-chlorodeoxyadenosine, sold under the tradename Ieustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™) methotrexate (also known as amethopterin, methotrexate sodium (MTX), sold under the tradenames Rheumatrex® and Trexall™), and pentostatin (sold under the tradename Nipent®).

Examples of retinoids include, but are not limited to, alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Clarus®, Decutan®, Isotane®, Izotech®, Oratane®, Isotret®, and Sotret®), and bexarotene (sold under the tradename Targretin®).

Examples of other cytotoxic agents include, but are not limited to, arsenic trioxide (sold under the tradename Trisenox®), asparaginase (also known as L-asparaginase, and *Erwinia* L-asparaginase, sold under the tradenames Elspar® and Kidrolase®).

Intermediates and Examples

The following examples are intended to be illustrative only and not limiting in any way. Unless otherwise noted, the following Intermediates and Examples were purified vial silica gel column chromatograph using RediSep® Rf columns from Teledyne Isco, Inc. Abbreviations used are those conventional in the art or the following:

ACN acetonitrile
BINAP 2,2'-bis(diphenylphosphino)-1,1'-binaphthyl
BSA bovine serum albumin
C Celsius
d doublet
dd doublet of doublets
DAST diethylaminosulfur trifluoride
DEAD diethyl azodicarboxylate
DIPEA NN-diisopropylethylamine
DMF N,N-dimethylformamide
DMSO dimethylsulfoxide
DTT dithiothreitol
EtOAc ethyl acetate
EtOH ethanol
g gram
h hour(s)
hr hour(s)
HATU 2-(1H-7-azabenzotriazol-1-yl)-1,1,3,3-tetramethyl-uronium hexafluorophosphate
HEPES 4-(2-hydroxyethyl)-1-piperazineethylanesulfonic acid
HPLC high pressure liquid chromatography
IPA isopropyl alcohol
kg kilogram
L liter
LC liquid chromatography LCMS liquid chromatography and mass spectrometry
MeOH methanol
MS mass spectrometry
m multiplet
min minutes
mL milliliter(s)
µM micromolar
m/z mass to charge ratio
nm nanometer
nM nanomolar
N normal
NADPH nicotinamide adenine dinucleotide phosphate
NMP N-methylpyrrolidone
NMR nuclear magnetic resonance
PdCl$_2$(dppf).CH$_2$Cl$_2$ 1,1'-bis(diphenylphosphino)ferrocene-palladium(II)dichloride dichloromethane complex
psi pounds per square inch
rac racemic
Rt retention time
s singlet
sat. saturated
SFC supercritical fluid chromatography
t triplet
tR rentention time
TCEP tris(2-carboxyethyl)phosphine
TEA triethylamine
TFA trifluoroacetic acid
THF tetrahydrofuran
TLC thin layer chromatography
  Instrumentation
  LCMS:
Unless otherwise noted, LCMS data (also reported herein as simply MS) were recorded using a Waters System (Acuity UPLC and a Micromass ZQ mass spectrometer; Column: Acuity HSS C18 1.8-micron, 2.1×50 mm; gradient: 5-95% acetonitrile in water with 0.05% TFA over a 1.8 min period; flow rate 1.2 mL/min; molecular weight range 200-1500; cone Voltage 20 V; column temperature 50° C.). All masses reported are those of the protonated parent ions unless recorded otherwise.

High Resolution Mass Spectrometry (HRMS):
HRMS Method A: ESI-MS data were recorded using a Synapt G2 HDMS (TOF mass spectrometer, Waters) with electrospray ionization source. The resolution of the MS system was approximately 15000. Leucine Enkephalin was used as lock mass (internal standards) infused from lockspary probe. The compound was infused into the mass spectrometer by UPLC (Acquity, Waters) from sample probe. The separation was performed on Acquity UPLC BEH C18 1×50 mm column at 0.2 mL/min flow rate with the gradient from 5% to 95% in 3 min. Solvent A was Water with 0.1% Formic Acid and solvent B was Acetonitrile with 0.1% Formic Acid. The mass accuracy of the system has been found to be <5 ppm with lock mass.

HRMS Method B: LC-MS/ESI-MS data were recorded on an Acquity G2 Xevo QTof-Rs(FWHM)>20000 Accuracy<5 ppm. The separation was performed on Acquity CSH 1.7 µm 2.1×50 mm-50° C. column Eluent A: Water+3.75 mM ammonium acetate. Eluent B: Acetonitrile. Gradient: from 2 to 98% B in 4.4 min—flow 1.0 mL/min.

HRMS Method C: Same as HRMS method B, except Gradient: from 40 to 98% B in 3.4 min-flow 1.0 mL/min.

HRMS Method D: LC-MS/ESI-MS data were recorded on an Acquity LCTp Tof-Rs(FWHM)>12000<5 ppm. The separation was performed on Acquity BEHC18 1.7 µm 2.1×50 mm-50° C. column Eluent A: Water+0.1% Formic Acid+3.75 mM Am acetate. Eluent B: Acetonitrile+0.04% formic+3.75 mM Am Acetate+5% Water. Gradient: from 0.2 to 98% B in 4.4 min-flow 1.0 mL/min.

HRMS methods A, B, C and D are referred to throughout as HRMS(A), HRMS(B), HRMS(C) and HRMS(D) respectively.

Intermediates

Intermediate 1: benzyl ((2R)-(3R)-(tert-butoxy)-1-hydroxybutan-2-yl)carbamate

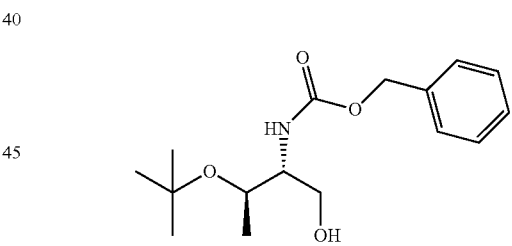

A solution of (S)-2-(((benzyloxy)carbonyl)amino)-(R)-3-(tert-butoxy)butanoic acid dicyclohexylammonium salt (500 mg, 1.0 mmol) in 10 ml of THF and isobutyl chloroformate (167 mg, 1.2 mmol, 1.2 equiv) at −25° C. was added N-methylmorpholine (124 mg, 1.2 mmol, 1.2 equiv), the mixture was stirred at same temperature for 10 min and filtered. The filtrate was cooled to −20° C. and to it was added NaBH$_4$, followed by 2 ml of water immediately afterwards. The reaction mixture was stirred at same temperature for 5 min. then gradually warmed to room temperature for 25 min, poured into water (10 ml) and extracted with EA (2×20 ml). The combined organic phases were washed with water, brine and dried over Na$_2$SO$_4$. The solvent was removed to yield the desired product as the clear oil. No further purification was required for next step. $^1$H NMR (400 MHz, CDCl$_3$) δ 7.37-7.16 (m, 5H), 5.25 (d, J=8.0

Hz, 1H), 5.02 (s, 1H), 4.04 (ddd, J=12.0, 8.9, 2.8 Hz, 1H), 3.92-3.75 (m, 1H), 3.59 (dddd, J=32.3, 14.6, 8.2, 4.3 Hz, 2H), 1.10 (s, 9H), 1.09-1.06 (m, 3H).

Intermediate 2: (R)-4-((R)-1-(tert-butoxy)ethyl)oxazolidin-2-one

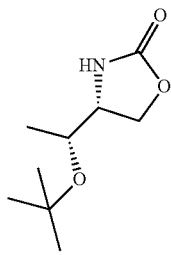

Method A: A solution of benzyl ((2R)-(3R)-(tert-butoxy)-1-hydroxybutan-2-yl)carbamate (134 mg, 0.45 mmol in 5 mL of THF) was pre-cooled to 0° C.) under nitrogen was treated with potassium tert-butoxide (153 mg, 1.4 mmol, 3.0 equiv), it was stirred at same temperature for 2 hours, 5 mL of water was added, it was extracted with EtOAc (2×20 mL), the combined organic layers were washed with water, brine, dried over Na$_2$SO$_4$, the solvent was removed to yield the desired product as a yellow oil, no further purification was required for next step. $^1$H NMR (400 MHz, CDCl$_3$) δ 6.20 (br s, 1H), 4.33 (t, J=8.7 Hz, 1H), 4.07 (dd, J=8.9, 5.5 Hz, 1H), 3.67-3.58 (m, 1H), 3.58-3.49 (m, 1H), 1.13 (s, 9H), 1.02 (d, J=6.0 Hz, 3H).

Method B: (2R,3R)-2-amino-3-(tert-butoxy)butan-1-ol hydrochloride (19.77 g, 100 mmol) was dissolved in DCM (200 mL) at 0° C., and added triethylamine (69.7 ml, 500 mmol). Solution was treated over 90 mins with a solution of triphosgene (12.76 g, 43.0 mmol) in DCM (100 mL) [keep the reaction mixture below 5° C.]. The reaction mixture was stirred at 0° C. for 30 mins before allowing to warm to room temperature and stirring overnight. The reaction mixture was treated with aqueous saturated NH4Cl (200 mL), water (50 mL) and stirred vigorously at room temperature for 1 h. Separated the organics, extracted the aqueous with DCM (500 mL), combined the organics and washed them with 1N HCl (3×150 mL), and aqueous saturated NH4Cl, dried (MgSO4) and concentrated to dryness (careful not to leave under vacuum or heat excessively) to give a pale brown oil. TLC shows mostly product with some small by-product peaks at higher Rf and some baseline materials. Subjected to flash column chromatography on silica with neat heptanes, 20% Et2O/heptanes, 50% Et2O/heptanes, neat Et2O, and 30% EtOAc/Et2O. TLC: neat ether, stain with cupric ammonium sulfate (heat hard for 1 minute to see the blue product stain); product Rf=0.34. Product off mostly with neat Et2O. One of the cleanest single fractions was concentrated to dryness to give 2.02 g of a very pale yellow/brown oil which crystallized upon standing. The remainder of the product fractions were combined and concentrated to dryness to give 15.2 g as a pale brown oil, which was seeded with crystals of the initial batch to give a pale brown crystalline solid. Overall yield ~90%. $^1$H NMR (400 MHz, CDCl$_3$) δ 5.28 (br s, 1H); 4.44 (t, 1H); 4.13-4.09 (m, 1H); 3.7-3.57 (m, 2H); 1.23 (s, 9H); 1.11 (d, 3H).

Intermediate 3: (R)-4-(R)-1-(tert-butoxy)ethyl)-3-(2-fluoropyrimidin-4-yl)oxazolidin-2-one

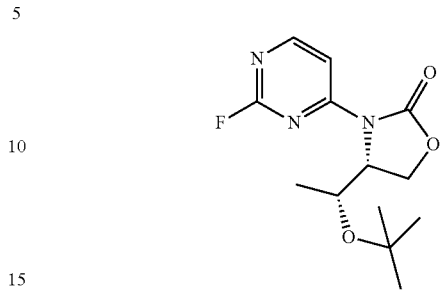

Method A: A solution of (R)-4-((R)-1-(tert-butoxy)ethyl)oxazolidin-2-one (86 mg, 0.46 mmol) and 2,4-difluoropyrimidine (79 mg, 0.55 mmol, 1.2 equiv) in 3 ml of DMF was cooled to 0° C. under N2 before adding NaH (60%, 28 mg, 0.69 mmol, 1.5 equiv) slowly. The reaction mixture was stirred at 0° C. for 45 min., then gradually warmed to room temperature, and stirred at room temperature overnight. The reaction was quenched with 5 ml of water, and extracted with EtOAc (2×10 ml). The solvent was removed to yield the crude product. Silica gel column chromatography (ethyl acetate in heptane 10 to 50%) provided the desired product as a white solid. $^1$H NMR (400 MHz, CDCl$_3$) δ 8.50 (dd, J=5.8, 2.1 Hz, 1H), 8.14 (dd, J=5.8, 3.8 Hz, 1H), 4.85-4.63 (m, 2H), 4.56-4.30 (m, 2H), 1.26 (s, 9H), 1.05 (d, J=6.5 Hz, 3H).

Method B: A solution of (R)-4-((R)-1-(tert-butoxy)ethyl)oxazolidin-2-one (5 g, 26.7 mmol) in DMF (50 mL) was cooled to −5° C. under N2 atmosphere. Internal temperature was monitored and maintained at ca. −5° C. during the portionwise addition of 60% NaH (1.602 g, 40.1 mmol) over 5 mins (no appreciable exotherm seen, but effervescence observed and cloudy suspension resulted). Added 2,4-difluoropyrimidine (2.507 mL, 29.4 mmol) dropwise whilst still maintaining the temperature at ca. −5° C. After complete addition the reaction mixture was stirred at this temperature for 15 mins before removing the cooling bath and allowing the reaction mixture to warm to room temperature (ca. 27° C. internal temp). Left stirring at room temperature for 2 h. Workup: [Safety Note: NaF salt present. Do not acidify workup] Quenched the reaction mixture with water (100 mL) which resulted in considerable effervescence although minimal increase in temperature. Added EtOAc (75 mL) and separated, extracted the aqueous with EtOAc (2×75 mL), combined the organics, washed with water (100 mL), brine (50 mL), dried (MgSO4) and concentrated to dryness to give crude product as a pale yellow oil [8.33 g] which was purified by silica gel chromatography (initial ramp DCM/heptane 5 to 100%, then EtOAc/DCM 0% to 20%, product off with ~5% EtOAc/DCM). Combined and concentrated the pure product fractions to dryness to give a white solid which was placed under high vacuum for 4 h. $^1$H NMR (400 MHz, CDCl$_3$) δ 8.5 (dd, 1H), 8.15 (dd, 1H); 4.77-4.66 (m, 2H); 4.53-4.42 (m, 2H); 1.26 (s, 9H), 1.05 (d, 3H). MS m/z 284.1 (M+H)+.

Intermediate 4: (R)-4-((R)-1-(tert-butoxy)ethyl)-3-(2,5-difluoropyrimidin-4-yl)oxazolidin-2-one

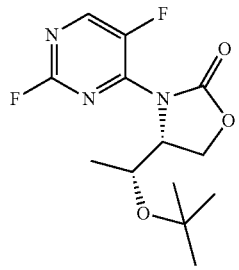 [SMILES: C[C@@H](OC(C)(C)C)[C@H]1COC(=O)N1c1nc(F)ncc1F]

A solution of (R)-4-((R)-1-(tert-butoxy)ethyl)oxazolidin-2-one (5 g, 26.7 mmol) in DMF (50 mL) was cooled to −5° C. under N2 atmosphere. Internal temperature was monitored and maintained at ca. −5° C. during the portionwise addition of 60% NaH (1.28 g, 32 mmol) over 5 mins (no appreciable exotherm seen, but effervescence observed and cloudy suspension resulted). Added 2,4,5-trifluoropyrimidine (3.76 g, 28 mmol) dropwise whilst still maintaining the temperature at ca. −5° C. After complete addition the reaction mixture was stirred at this temperature for 15 mins before removing the cooling bath and allowing the rm to warm to room temperature (ca. 27° C. internal temp). Left stirring at room temperature for 6 h. Sampled reaction mixture and quenched with water, extracted into EtOAc; TLC and LCMS show significant product but remaining oxazolidinone sm. Cooled reaction mixture to 0° C. and added an additional portion of trifluoropyrimidine (1.2 g, 8.95 mmol), warmed to room temperature and left stirring for 3 h at rt. Still faint residual sm seen by TLC of sample, but quenched reaction mixture at this point. Workup: [Safety Note: NaF salt present. Do not acidify workup] Quenched the reaction mixture with water (100 mL) which resulted in considerable effervescence. Added EtOAc (75 mL) and separated, extracted the aqueous with EtOAc (2×75 mL), combined the organics, washed with water (100 mL), brine (50 mL), dried (MgSO4) and concentrated to dryness to give crude product as a pale yellow oil. Crude was purified by silica gel chromatography (initial neat DCM, then ramp to 20% EtOAc/DCM). Pure product fractions were combined and concentrated to dryness to give a colourless oil which was placed under high vacuum. Upon standing the oil converted into a white solid. $^1$H NMR (400 MHz, CDCl$_3$) δ 8.47 (dd, J=3, 1 Hz, 1H); 4.73-4.68 (m, 1H); 4.62-4.52 (m, 2H); 4.34-4.28 (m, 1H); 1.20 (s, 9H); 1.11 (d, 3H). MS m/z 302.1 (M+H)+.

Intermediate 5: (R)-3-(2-fluoropyrimidin-4-yl)-4-((R)-1-hydroxyethyl)oxazolidin-2-one

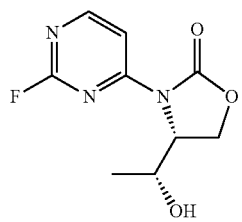

A solution of (R)-4-((R)-1-(tert-butoxy)ethyl)-3-(2-fluoropyrimidin-4-yl)oxazolidin-2-one (1.0 g, 3.35 mmol) in 20 ml of DCM was cooled in an ice bath, and treated with 8.16 mL of TFA. The mixture was stirred at same temperature for 4 hours, and allowed to warm to room temp and stir 16 h. The reaction was poured into 10 mL water. The DCM was removed in vacuo. The aqueous was basified by slow addition of saturated NaHCO3 solution, then extracted with (2×30 mL) EtOAc. The organics were washed with 30 mL brine, and dried over Na2SO4. Filtered and concentrated to give the desired alcohol, (R)-3-(2-fluoropyrimidin-4-yl)-4-((R)-1-hydroxyethyl)oxazolidin-2-one (0.56 g, 70% yield) as a white solid. HRMS(B) tR=0.80 min; MS m/z 228.4 (M+H)+.

Intermediate 6: (R)-methyl 3-(2-fluoropyrimidin-4-yl)-2-oxooxazolidine-4-carboxylate

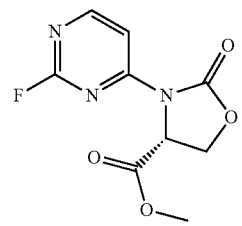 [SMILES: COC(=O)[C@H]1COC(=O)N1c1ccnc(F)n1]

A solution of (R)-methyl 2-oxooxazolidine-4-carboxylate (200 mg, 1.4 mmol) and 2,4-fluoropyrimidine (176 mg, 1.5 mmol, 1.1 equiv) in DMF (3 mL) was treated with NaH (60%, 66.2 mg, 1.2 mmol, 1.2 equiv), then the resulting mixture was stirred at 0° C. for 45 minutes, then room temperature for 12 h. The reaction mixture was diluted with EtOAc (20 mL), washed with sat. NH$_4$Cl (15 mL) and 4% aqueous NaCl (2×100 mL), dried over Na$_2$SO$_4$, filtered and concentrated. Silica gel column chromatography (EtOAc/Heptane 10% to 50%) to provide (R)-methyl 3-(2-fluoropyrimidin-4-yl)-2-oxooxazolidine-4-carboxylate (240 mg, white waxy solid) in 71% yield. $^1$H NMR (400 MHz, CDCl$_3$) δ 8.47 (dd, J=5.8, 2.0 Hz, 1H), 8.07 (dd, J=5.7, 3.7 Hz, 1H), 5.18 (dd, J=9.4, 3.7 Hz, 1H), 4.68 (t, J=9.4 Hz, 1H), 4.45 (dd, J=9.3, 3.7 Hz, 1H), 3.78 (s, 3H).

Intermediate 7: 2-amino-4,4,4-trifluoro-3-methylbutan-1-ol

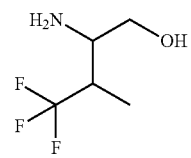

To a chilled (0° C.) solution of 2-amino-4,4,4-trifluoro-3-methylbutanoic acid (736 mg, 4.30 mmol) in THF (9 mL) was added aluminum (III) lithium hydride (2.26 mL, 9.03 mmol, 4M) dropwise. After addition complete, the reaction was allowed to stir at ambient temperature for 1 hour. Cool to 0° C. and quench w/sat. Na$_2$SO$_4$ soln, added EtOAc (50 mL), Na$_2$SO$_4$, filtered, conc. in vacuo afforded material that was a mixture of the title compound and the starting material acid in a 3:2 ratio which was used crude in the next step. $^1$H NMR (400 MHz, CDCl$_3$) δ 3.71 (dd, J=10.7, 3.7 Hz, 1H), 3.57 (dd, J=10.4, 5.2 Hz, 1H), 3.45 (ddd, J=10.7, 8.0, 4.8 Hz, 2H), 3.28 (ddd, J=8.2, 5.3, 2.9 Hz, 1H), 3.06 (td, J=7.3, 3.6 Hz, 1H), 2.44-2.20 (m, 2H), 2.04-1.54 (m, 1H), 1.21-1.08 (m, 7H). $^{19}$F NMR (376 MHz, CDCl$_3$) δ -68.33 (s), -70.12 (s).

Intermediate 8:
4-(1,1,1-trifluoropropan-2-yl)oxazolidin-2-one

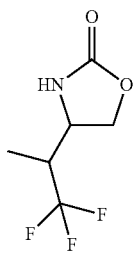

To a solution of 2-amino-4,4,4-trifluoro-3-methylbutan-1-ol (580 mg, 3.69 mmol) in DCM (13 ml) was added triethylamine (1.132 ml, 8.12 mmol) and added dropwise a solution of triphosgene (329 mg, 1.107 mmol) in 1 mL in DCM (3 ml) over 10 min. The reaction mixture was washed with sat. NH$_4$Cl solution (13 ml) dry, and concentrated in vacuo. Afforded 450 mg (lt yellow solid). Used crude in the next step. $^1$H NMR (400 MHz, CDCl$_3$) δ 5.91 (d, J=13.3 Hz, 1H), 4.61-4.34 (m, 1H), 4.22-4.00 (m, 2H), 3.05 (q, J=7.3 Hz, 1H), 2.54-2.14 (m, 1H), 1.34 (t, J=7.3 Hz, 1H), 1.17 (d, J=7.1 Hz, 2H), 1.09 (d, J=7.1 Hz, 1H). MS 183.0507 m/z.

Intermediate 9: 3-(2-fluoropyrimidin-4-yl)-4-(1,1,1-trifluoropropan-2-yl)oxazolidin-2-one

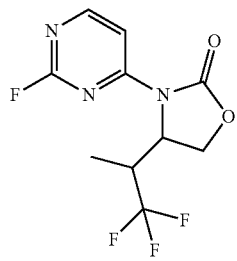

A solution of 4-(1,1,1-trifluoropropan-2-yl)oxazolidin-2-one (270 mg, 1.474 mmol) and 2,4-difluoropyrimidine (171 mg, 1.474 mmol, 1 eq) in DMF (4 mL) was treated with NaH (60%, 88 mg, 2.212 mmol, 1.5 eq), then the resulting mixture was stirred at 0° C. for 10 minutes, then room temperature for 1 h. The reaction mixture was quenched with sat. Na$_2$SO$_4$ (15 mL) diluted with EtOAc (20 mL), washed and 4% aqueous NaCl (3×20 mL), dried over Na$_2$SO$_4$, concentrated in vacuo. Flash column chromatography (silica, 120 g, 15 m) 5% EtOAc/DCM to provide 3-(2-fluoropyrimidin-4-yl)-4-(1,1,1-trifluoropropan-2-yl)oxazolidin-2-one (100 mg, white solid). $^1$H NMR (400 MHz, CDCl$_3$) δ 8.55 (dd, J=5.8, 2.1 Hz, 1H), 8.20 (dd, J=5.8, 3.7 Hz, 1H), 5.04-4.84 (m, 1H), 4.68 (dd, J=9.5, 2.6 Hz, 1H), 4.54 (t, J=9.2 Hz, 1H), 3.34 (ddddd, J=13.3, 9.3, 7.1, 3.9, 1.6 Hz, 1H), 1.29 (d, J=7.3 Hz, 3H). MS 279.0631 m/z.

Intermediate 10: (R)-3-(2,6-dichloropyrimidin-4-yl)-4-((R)-1-methoxyethyl)oxazolidin-2-one

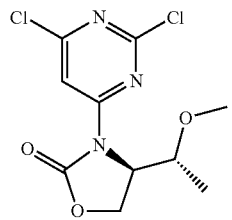 [SMILES: CO[C@H](C)[C@H]1COC(=O)N1c1cc(Cl)nc(Cl)n1]

Step 1

To a round bottom flask was added NaH (0.54 g, 13.5 mmol, 57% dispersion in mineral oil) to a solution of 2,4,6-trichloropyrimidine (1.22 ml, 10.6 mmol) and (R)-4-((R)-1-(tert-butoxy)ethyl)oxazolidin-2-one (1.8 g, 9.61 mmol) in DMF (32 mL) at 0° C. (ice bath) under a bubbler. The yellow suspension was then stirred at 0° C. for 15 min and then the ice bath was removed and reaction mixture allowed to stir 1 hr at room temperature. Reaction mixture was diluted with EtOAc and then carefully quenched with brine. The layers were separated and the aqueous layer was extracted with EtOAc. The combined organic layers were dried (Na$_2$SO$_4$), filtered and concentrated onto silica gel. Silica gel column chromatography (EtOAc/Heptane 0 to 100%) provided (R)-4-((R)-1-(tert-butoxy)ethyl)-3-(2,6-dichloropyrimidin-4-yl)oxazolidin-2-one (2.1 g, 6.28 mmol, 65% yield) as a white solid. $^1$H NMR (400 MHz, CDCl$_3$) δ 1.04 (d, J=6.55 Hz, 3H) 1.26 (s, 9H) 4.38-4.48 (m, 2H) 4.64-4.75 (m, 2H) 8.22 (s, 1H). LCMS m/z 334.1 (M+H)$^+$, Rt 1.10 min.

Step 2

To a round bottom flask containing (R)-4-((R)-1-(tert-butoxy)ethyl)-3-(2,6-dichloropyrimidin-4-yl)oxazolidin-2-one (1 g, 2.99 mmol) was added DCM (7.5 mL) followed by the addition of TFA (7.5 mL). The resulting homogenous reaction mixture allowed to stir 1 hr at room temperature. The volatiles were then removed. Residue dissolved in DCM and neutralized with a saturated solution of NaHCO$_3$. The phases were partioned, the aqueous phase extracted with DCM. Organic phases combined, washed with water, brine, dried (Na$_2$SO$_4$), filtered and concentrated to a white foam of (R)-3-(2,6-dichloropyrimidin-4-yl)-4-((R)-1-hydroxyethyl)oxazolidin-2-one (737 mg, 2.65 mmol, 89% yield). $^1$H NMR (400 MHz, CDCl$_3$) δ 1.19 (d, J=6.46 Hz, 3H) 4.47 (dd, J=9.37, 8.53 Hz, 1H) 4.55 (quin, J=5.69 Hz, 1H) 4.63 (dd, J=9.49, 2.79 Hz, 1H) 4.89 (ddd, J=8.19, 4.96, 2.79 Hz, 1H) 8.24 (s, 1H). LCMS m/z 278.0 (M+H)$^+$, Rt 0.66 min.

Step 3

To a round bottom flask was added (R)-3-(2,6-dichloropyrimidin-4-yl)-4-((R)-1-hydroxyethyl)oxazolidin-2-one (364 mg, 1.31 mmol) followed by the addition of DCM (10.8 mL). The reaction mixture was then cooled to 0° C. in a (ice/water bath) under nitrogen. To this cold solution was added tetrafluoroboric acid (0.20 mL, 1.31 mmol, 50% aqueous solution) followed by the addition of trimethylsilyldiazomethane (1.96 mL, 3.93 mmol, 2 M in hexanes) divided into 3 portions added 20 min apart. A second addition of trimethylsilyldiazomethane in hexanes (1.96 mL, 3.93 mmol, 2 M in hexanes) again divided into 3 portions added 20 min apart was added. Reaction mixture was quenched with water and diluted with DCM. Phases partitioned and the aqueous phase extracted with DCM. Organic phases combined and washed with brine, dried (Na$_2$SO$_4$), filtered and concentrated onto silica gel. Silica gel column chromatography (EtOAc/Heptane 0 to 100%) provided (R)-3-(2,6-dichloropyrimidin-4-yl)-4-((R)-1-methoxyethyl)oxazolidin-2-one (119 mg, 0.41 mmol, 31% yield) as a colorless oil which crystallizes upon standing. $^1$H NMR (400 MHz, CDCl$_3$) δ 1.09 (d, J=6.50 Hz, 3H) 3.44 (s, 3H) 4.09 (qd, J=6.46, 4.16 Hz, 1H) 4.38-4.49 (m, 1H) 4.60 (dd, J=9.49, 2.84 Hz, 1H) 4.99 (ddd, J=8.50, 3.95, 2.96 Hz, 1H) 8.23 (s, 1H). LCMS m/z 292.0 (M+H)$^+$, Rt 0.86 min.

Intermediate 11: (R)-3-(2-fluoropyrimidin-4-yl)-4-((R)-1-methoxyethyl)oxazolidin-2-one

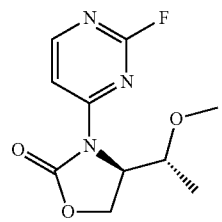 [SMILES: CO[C@H](C)[C@H]1COC(=O)N1c1ccnc(F)n1]

Step 1

To a round bottom flask containing a stir bar and (2S,3R)-2-((tert-butoxycarbonyl)amino)-3-methoxybutanoic acid (2.5 g, 10.7 mmol) in THF (80 mL) under nitrogen was cooled to −30° C. in a dry ice/acetone bath. To this cold solution was added isobutyl chloroformate (1.7 mL, 12.9 mmol) followed by the addition of N-methylmorpholine (1.4 mL, 12.9 mmol). Mixture was stirred for 15 min at −30° C. N-Methylmorpholine salt develops and was filtered from mixture. Mother liquor was cooled to −30° C. where upon sodium borohydride (0.61 g, 16.1 mmol) was added followed by the addition of water (10 mL) immediately afterwards. Reaction mixture allowed to stir for 15 min at −20° C. then gradually allowed to warm to room temperature. Reaction mixture was stirred for 30 min at room temperature. Reaction mixture was then diluted with water and extracted with EtOAc. Organic phases combined, washed with water, brine, dried (Na$_2$SO$_4$), filtered and concentrated to afford tert-butyl ((2R,3R)-1-hydroxy-3-methoxybutan-2-yl)carbamate (2.0 g, 9.1 mmol, 85% yield) as a colorless oil. $^1$H NMR (400 MHz, CDCl$_3$) δ 1.18 (d, J=6.26 Hz, 3H) 1.45 (s, 9H) 3.33 (s, 3H) 3.55-3.84 (m, 4H). LCMS m/z 220.2 (M+H)$^+$, Rt 0.57 min.

Step 2

To a round bottom flask containing tert-butyl ((2R,3R)-1-hydroxy-3-methoxybutan-2-yl) (2 g, 9.1 mmol) and stir bar was added DCM (5.0 mL) followed by the addition of TFA (5.0 mL). Resulting reaction mixture allowed to stir 30 min at room temperature. Volatiles were removed to afford (2R,3R)-2-amino-3-methoxybutan-1-ol (2.1 g, 9.0 mmol, 99% yield) as a TFA salt. Material was used in next step without further purification. LCMS m/z 120.0 (M+H)$^+$, Rt 0.15 min.

Step 3

To a round bottom flask containing (2R,3R)-2-amino-3-methoxybutan-1-ol (2.1 g, 9.0 mmol) and a stir bar was added acetonitrile (100 mL) followed by the addition of 2,4-dichloropyrimidine (1.34 g, 9.0 mmol) and DIEA (4.7 mL, 27.0 mmol). Resulting reaction mixture allowed to stir 18 hr at room temperature. Volatiles were then removed. Residue was partitioned between EtOAc and water. Aqueous layer extracted with EtOAc. Organic phases combined, washed with water, brine, dried (Na$_2$SO$_4$), filtered and concentrated to afford (2R,3R)-2-((2-chloropyrimidin-4-yl)amino)-3-methoxybutan-1-ol (1.68 g, 3.63 mmol, 40% yield) which contains some unreacted 2,4-dichloropyrimidine. LCMS m/z 232.0 (M+H)$^+$, Rt 0.38 min.

Step 4

To a round bottom flask containing (2R,3R)-2-((2-chloropyrimidin-4-yl)amino)-3-methoxybutan-1-ol (1.68 g, 3.63 mmol) and a stir bar under nitrogen was added DCM (18 mL). The resulting reaction mixture cooled to 0° C. in a brine/ice bath. To this cold solution was then added triphosgene (0.59 g, 1.99 mmol) followed by the addition of 2,6-dimethylpyridine (2 mL, 17.0 mmol). Resulting reaction mixture allowed to stir 30 min at 0° C. The reaction mixture was diluted with DCM and water and allowed to stir 1 hr at room temperature. The phases partitioned and the aqueous phase extracted with DCM. Organic phases were combined, washed with water, brine, dried (Na$_2$SO$_4$), filtered and concentrated onto silica gel. Silica gel column chromatography (EtOAc/Heptane 0 to 100%) provided (R)-3-(2-chloropyrimidin-4-yl)-4-((R)-1-methoxyethyl)oxazolidin-2-one (145 mg, 0.56 mmol, 15% yield) as a white crystalline. $^1$H NMR (400 MHz, CDCl$_3$) δ 1.09 (d, J=6.26 Hz, 3H) 3.45 (s, 3H) 4.15 (qd, J=6.39, 4.30 Hz, 1H) 4.39-4.47 (m, 1H) 4.60 (dd, J=9.39, 2.74 Hz, 1H) 5.02 (dt, J=8.61, 3.52 Hz, 1H) 8.17 (d, J=5.87 Hz, 1H) 8.48 (d, J=5.87 Hz, 1H). LCMS m/z 258.1 (M+H)$^+$, Rt 0.69 min.

Step 5

To a microwave vial with stir bar was added (R)-3-(2-chloropyrimidin-4-yl)-4-((R)-1-methoxyethyl)oxazolidin-2-one (145 mg, 0.56 mmol), potassium fluoride (327 mg, 5.63 mmol) and DMSO (4 mL). Vial capped and heated to 120° C. in a sand bath for 3 hr. Reaction mixture was then cooled to room temperature, diluted with water and aqueous mixture extracted with EtOAc. The Organic phases were combined and washed with water, brine, dried (Na$_2$SO$_4$), filtered and concentrated to afford a white crystalline of (R)-3-(2-fluoropyrimidin-4-yl)-4-((R)-1-methoxyethyl)oxazolidin-2-one (117 mg, 0.49 mmol, 86% yield). LCMS m/z 242.1 (M+H)$^+$, Rt 0.63 min.

Intermediate 12: (R)-4-((S)-1-(tert-butoxy)ethyl)-3-(2-chloropyrimidin-4-yl)oxazolidin-2-one

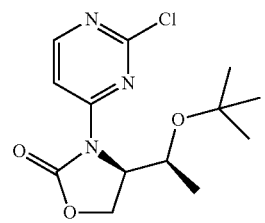 [SMILES: C[C@H](OC(C)(C)C)[C@H]1COC(=O)N1c1ccnc(Cl)n1]

Step 1

To a round bottom flask containing a stir bar and (2S,3S)-2-((((9H-fluoren-9-yl)methoxy)carbonyl)amino)-3-(tert-butoxy)butanoic acid (8.55 g, 21.5 mmol) in THF (72 mL) under nitrogen was cooled to −30° C. in a dry ice/acetonitrile bath. To this cold solution was added isobutyl chloroformate (3.4 mL, 25.8 mmol) followed by the addition of N-methylmorpholine (2.8 mL, 25.8 mmol). Mixture was stirred for 15 min at −30° C. N-Methylmorpholine salt develops and was filtered from mixture. Mother liquor was cooled to −30° C. where upon sodium borohydride (1.22 g, 32.3 mmol) was added followed by the addition of water (25 mL) immediately afterwards. Reaction mixture allowed to stir for 15 min at −20° C. then gradually allowed to warm to room temperature. Reaction mixture was stirred for 30 min at room temperature. Reaction mixture was diluted with water, extracted with EtOAc. Organic phases combined, washed with water, brine, dried (Na$_2$SO$_4$), filtered and concentrated to afford (9H-fluoren-9-yl)methyl ((2R,3S)-3-(tert-butoxy)-1-hydroxybutan-2-yl)carbamate (8.11 g, 21.15 mmol, 98% yield) as a colorless oil. $^1$H NMR (400 MHz, CDCl$_3$) δ 1.18 (s, 9H) 1.24 (d, J=5.87 Hz, 3H) 4.11-4.26 (m, 2H) 4.42 (d, J=7.04 Hz, 2H) 5.73 (d, J=7.43 Hz, 1H) 7.29-7.35 (m, 2H) 7.38-7.45 (m, 2H) 7.61 (t, J=6.06 Hz, 2H) 7.78 (d, J=7.43 Hz, 2H).). LCMS m/z 384.3 (M+H)$^+$, Rt 0.96 min.

Step 2

To a round bottom flask with stir bar was added (9H-fluoren-9-yl)methyl ((2R,3S)-3-(tert-butoxy)-1-hydroxybutan-2-yl)carbamate (4.7 g, 12.3 mmol) and acetonitrile (100 mL) followed by the addition of piperidine (1.8 mL, 18.4 mmol). The flask was capped and stirred for 18 hr at room temperature. The volatiles were then removed. A white solid develops which contains the amino alcohol product and the fmoc deprotection by products. Solids were redissolved in acetonitrile (50 ml) (some of the fmoc polymer is insoluble) and 2,4-dichloropyrimidine (5.48 g, 36.8 mmol) and DIEA (2.141 mL, 12.26 mmol) were added. Resulting reaction mixture allowed to stir 18 hr at room temperature. The volatiles were again removed. Reaction mixture was diluted with water and extracted with EtOAc. Organic phases combined, washed with water, brine, dried (Na$_2$SO$_4$), filtered and concentrated onto silica gel. Silica gel column chromatography (EtOAc/Heptane 0 to 100%) provided (2R,3S)-3-(tert-butoxy)-2-((2-chloropyrimidin-4-yl)amino)butan-1-ol (1.80 g, 6.58 mmol, 54% yield) as a colorless oil which crystallizes upon standing. LCMS m/z 274.1 (M+H)$^+$, Rt 0.56 min.

Step 3

To a round bottom flask containing (2R,3S)-3-(tert-butoxy)-2-((2-chloropyrimidin-4-yl)amino)butan-1-ol (1.8 g, 6.58 mmol) and a stir bar under nitrogen was added DCM (66 ml). The resulting reaction mixture cooled to −70° C. in a dry ice/acetone bath. To this cold solution was added triphosgene (1.07 g, 3.62 mmol) followed by the addition of 2,6-dimethylpyridine (3.6 mL, 30.9 mmol). Resulting reaction mixture allowed to gradually warm to room temperature and stirred for 30 min at room temperature. Reaction mixture diluted with DCM and water and allowed to stir 1 hr at room temperature. The phases were then partioned and aqueous extracted with DCM. Organics phases combined, washed with water, brine, dried (Na$_2$SO$_4$), filtered and concentrated onto silica gel. Silica gel column chromatography (EtOAc/Heptane 0 to 100%) provided (R)-4-((S)-1-(tert-butoxy)ethyl)-3-(2-chloropyrimidin-4-yl)oxazolidin-2-one (1.44 g, 4.80 mmol, 73% yield) as a white crystalline. LCMS m/z 300.1 (M+H)$^+$, Rt 0.91 min.

Intermediate 13: (R)-4-((R)-1-tert-butoxyethyl)-3-(2,6-dichloropyrimidin-4-yl)oxazolidin-2-one

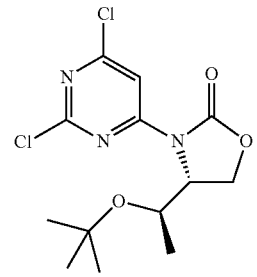 [SMILES: C[C@@H](OC(C)(C)C)[C@H]1COC(=O)N1c1cc(Cl)nc(Cl)n1]

A solution of (R)-4-((R)-1-tert-butoxyethyl)oxazolidin-2-one (0.830 g, 4.43 mmol) and 2,4,6-trichloropyrimidine (0.894 g, 4.88 mmol, 1.10 equiv) in DMF (15 mL) was treated with NaH (60%, 0.248 g, 6.21 mmol, 1.40 equiv), then the resulting mixture (yellow) was stirred at room temperature for 1 h. The reaction mixture was diluted with EtOAc (100 mL) and quenched with saturated aqueous NaCl (100 mL). The layers were separated and the aqueous layer was extracted with ethyl acetate (2×30 mL). The combined organic layers were dried over Na$_2$SO$_4$, filtered and concentrated. Silica gel column chromatography (EtOAc/Heptane 0 to 40%) provided (R)-4-((R)-1-tert-butoxyethyl)-3-(2,6-dichloropyrimidin-4-yl)oxazolidin-2-one (1.0 g, white solid) in 69% yield. $^1$H NMR (400 MHz, CDCl$_3$) δ 8.22 (s, 1H), 4.70-4.66 (m, 2H), 4.45-4.40 (m, 2H), 1.26 (s, 9H), 1.04 (d, J=6.6 Hz, 3H); MS m/z 334.0 (M+H)$^+$; Rt-1.10 min.

Intermediate 14: (R)-4-((R)-1-tert-butoxyethyl)-3-(6-(difluoromethyl)-2-(methylthio)pyrimidin-4-yl)oxazolidin-2-one

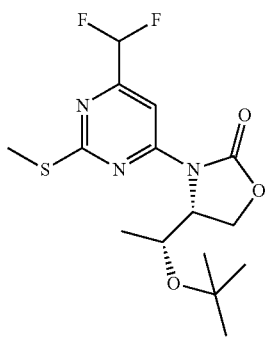 [SMILES: CSc1nc(C(F)F)cc(N2C(=O)OC[C@@H]2[C@@H](C)OC(C)(C)C)n1]

A solution of (R)-4-((R)-1-tert-butoxyethyl)oxazolidin-2-one (0.100 g, 0.534 mmol) and 4-chloro-6-(difluoromethyl)-2-(methylthio)pyrimidine (0.124 g, 0.587 mmol, 1.10 equiv) in DMF (2.7 mL) was treated with NaH (60%, 0.026 g, 0.64 mmol, 1.20 equiv), then the resulting mixture (yellow) was stirred at room temperature for 30 min. The reaction mixture was diluted with EtOAc (20 mL), washed with saturated aqueous NaCl (2×20 mL), dried over Na$_2$SO$_4$, filtered and concentrated. Silica gel column chromatography (EtOAc/Heptane 0 to 40%) provided (R)-4-((R)-1-tert-butoxyethyl)-3-(6-(difluoromethyl)-2-(methylthio)pyrimidin-4-yl)oxazolidin-2-one (0.164 g, white solid) in 85% yield. $^1$H NMR (400 MHz, CDCl$_3$) δ 8.15 (s, 1H), 6.45 (t, J=54 Hz, 1H), 4.80-4.72 (m, 1H), 4.66 (dd, J=9.4, 3.0 Hz, 1H), 4.49-4.34 (m, 2H), 2.58 (s, 3H), 1.25 (s, 9H), 1.02 (d, J=6.5 Hz, 3H); MS m/z 362.3 (M+H)⁺; Rt-1.09 min.

Intermediate 15: (R)-4-((R)-1-tert-butoxyethyl)-3-(6-(difluoromethyl)-2-(methylsulfonyl)pyrimidin-4-yl)oxazolidin-2-one

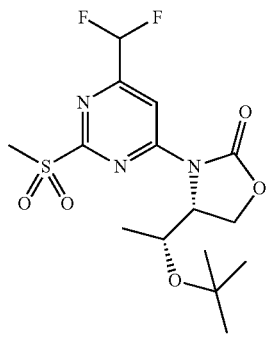 [SMILES: C[C@@H](OC(C)(C)C)[C@H]1COC(=O)N1c1cc(C(F)F)nc(S(C)(=O)=O)n1]

A solution of (R)-4-((R)-1-tert-butoxyethyl)-3-(6-(difluoromethyl)-2-(methylthio)pyrimidin-4-yl)oxazolidin-2-one (0.164 g, 0.454 mmol) in DCM (4.5 mL) was treated with m-CPBA (0.244 g, 1.09 mmol, 2.4 equiv) at 0° C. The mixture was allowed to warm to room temperature and stirred for 4 h. The reaction was carefully quenched with a 1:1 mixture of 1 M aqueous sodium thiosulfate solution and saturated aqueous sodium bicarbonate solution (20 mL). The mixture was extracted with DCM (3×20 mL) and the combined organic extracts were washed with saturated aqueous NaCl (20 mL), dried over Na₂SO₄, filtered and concentrated. Silica gel column chromatography (EtOAc/Heptane 20% to 40%) provided (R)-4-((R)-1-tert-butoxyethyl)-3-(6-(difluoromethyl)-2-(methylsulfonyl)pyrimidin-4-yl)oxazolidin-2-one as a white solid in 82% yield. MS m/z 338.1 (M+H—tert-butyl)⁺; Rt-0.87 min.

Intermediate 16: (R)-4-((R)-1-tert-butoxyethyl)-3-(2-chloro-6-(trifluoromethyl)pyrimidin-4-yl)oxazolidin-2-one

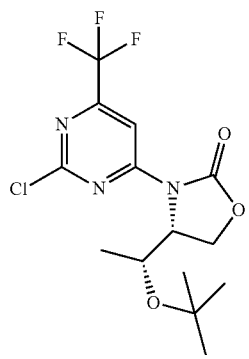 [SMILES: C[C@@H](OC(C)(C)C)[C@H]1COC(=O)N1c1cc(C(F)(F)F)nc(Cl)n1]

A solution of (R)-4-((R)-1-tert-butoxyethyl)oxazolidin-2-one (0.070 g, 0.374 mmol) and 2,4-dichloro-6-(trifluoromethyl)pyrimidine (0.089 g, 0.411 mmol, 1.10 equiv) in DMF (1.3 mL) was treated with NaH (60%, 0.018 g, 0.45 mmol, 1.20 equiv), then the resulting mixture (yellow) was stirred at room temperature for 60 min. The reaction mixture was diluted with EtOAc (20 mL), washed with saturated aqueous NaCl (2×20 mL), dried over Na₂SO₄, filtered and concentrated. Silica gel column chromatography (EtOAc/Heptane 0 to 15%) provided (R)-4-((R)-1-tert-butoxyethyl)-3-(2-chloro-6-(trifluoromethyl)pyrimidin-4-yl)oxazolidin-2-one (0.116 g, white solid) in 84% yield. ¹H NMR (400 MHz, CDCl₃) δ 8.50 (s, 1H), 4.76 (ddd, J=8.5, 4.2, 2.9 Hz, 1H), 4.70 (dd, J=9.5, 2.9 Hz, 1H), 4.50-4.42 (m, 2H), 1.26 (s, 9H), 1.04 (d, J=6.5 Hz, 3H). MS m/z 368.1 (M+H)⁺; Rt-1.10 min.

Intermediate 17: (2R,3R)-3-(tert-butoxy)-2-((2-chloro-6-methylpyrimidin-4-yl)amino)butan-1-ol

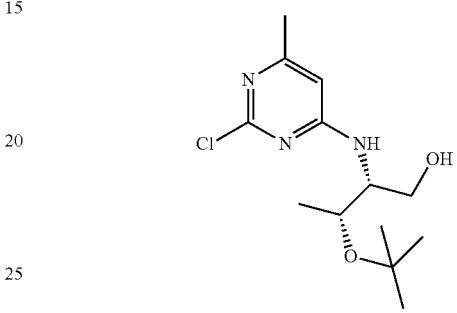

A solution of (2R,3R)-2-amino-3-(tert-butoxy)butan-1-ol (267 mg, 1.35 mmol, 1.1 equiv), 2,4-dichloro-6-methylpyrimidine (200 mg, 1.23 mmol, 1.0 equiv), and N-ethyl-N-isopropylpropan-2-amine (0.54 mL, 3.1 mmol, 2.5 equiv) in 1,4-dioxane (6 mL) was heated at 75° C. for 4 h. The reaction was cooled to room temperature and concentrated in vacuo. Silica gel column chromatography (EtOAc/Heptane) provided (2R,3R)-3-(tert-butoxy)-2-((2-chloro-6-methylpyrimidin-4-yl)amino)butan-1-ol (86 mg, white solid) in 24% yield. ¹H NMR (400 MHz, CDCl₃) δ 6.17 (s, 1H), 4.02 (m, 2H), 3.79-3.64 (m, 2H), 2.30 (s, 3H), 1.22 (s, 9H), 1.18 (d, J=6.2 Hz, 3H); MS m/z 288.1 (M+H)⁺; Rt-0.59 min.

Intermediate 18: (R)-4-((R)-1-(tert-butoxy)ethyl)-3-(2-chloro-6-methylpyrimidin-4-yl)oxazolidin-2-one

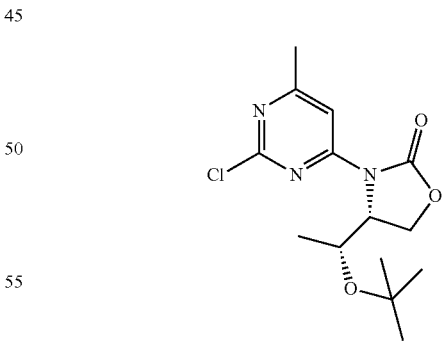

Triphosgene (35 mg, 0.12 mmol, 0.4 equiv) was added to a solution of (2R,3R)-3-(tert-butoxy)-2-((2-chloro-6-methylpyrimidin-4-yl)amino)butan-1-ol (86 mg, 0.30 mmol) in DCM (3 mL) at −78° C., followed by the dropwise addition of 2,6-lutidine (0.14 mL, 1.2 mmol, 4 equiv). The solution was allowed to warm to room temperature and was then heated at 35° C. for 5 hours. The reaction was then cooled to room temperature and diluted with DCM (30 mL) and saturated aqueous sodium chloride (30 mL). The layers were separated and the organic layer was dried over Na₂SO₄, filtered and concentrated. Silica gel column chromatography (EtOAc/Heptane) provided (R)-4-((R)-1-(tert-butoxy)ethyl)-3-(2-chloro-6-methylpyrimidin-4-yl)oxazolidin-2-one (0.057 g, white solid) in 61% yield. ¹H NMR (400 MHz, CDCl₃) δ 8.01 (s, 1H), 4.73 (ddd, J=8.6, 4.1, 3.0 Hz, 1H), 4.65 (dd, J=9.4, 2.9 Hz, 1H), 4.48 (m, 1H), 4.41 (m, 1H), 2.52 (s, 3H), 1.26 (s, 9H), 1.03 (d, J=6.5 Hz, 3H); MS m/z 314.1 (M+H)⁺; Rt-1.02 min.

Intermediate 19: (R)-4-((R)-1-(tert-butoxy)ethyl)-3-(2-fluoro-6-methylpyrimidin-4-yl)oxazolidin-2-one

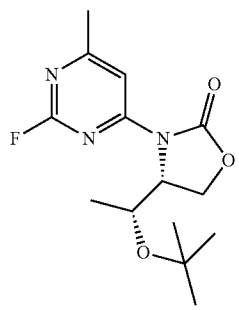

Potassium fluoride (0.063 g, 1.08 mmol, 10 equiv) was added to a solution of (R)-4-((R)-1-(tert-butoxy)ethyl)-3-(2-chloro-6-methylpyrimidin-4-yl)oxazolidin-2-one (34 mg, 0.108 mmol) in DMSO (1.1 mL). The suspension was heated at 120° C. for 3 hours and then cooled to room temperature. The reaction was diluted with ethyl acetate (20 mL) and water (20 mL). The layers were separated and the aqueous layer was extracted with ethyl acetate (20 mL). The combined organic layers were dried over Na₂SO₄, filtered and concentrated to give crude (R)-4-((R)-1-(tert-butoxy)ethyl)-3-(2-fluoro-6-methylpyrimidin-4-yl)oxazolidin-2-one, which was used without further purification. ¹H NMR (400 MHz, CDCl₃) δ 7.99 (d, J=3.8 Hz, 1H), 4.71 (m, 1H), 4.65 (m, 1H), 4.46 (m, 1H), 4.41 (m, 1H), 2.53 (s, 3H), 1.25 (s, 9H), 1.03 (d, J=6.5 Hz, 3H); MS m/z 298.2 (M+H)⁺; Rt-0.96 min.

Intermediate 20: methyl 6-((R)-4-((R)-1-(tert-butoxy)ethyl)-2-oxooxazolidin-3-yl)-2-chloropyrimidine-4-carboxylate

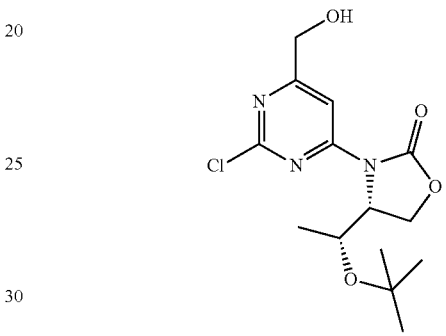

Sodium hydride (60% dispersion in mineral oil, 23 mg, 0.58 mmol, 1.2 equiv) was added to a solution of methyl 2,6-dichloropyrimidine-4-carboxylate (100 mg, 0.483 mmol) and (R)-4-((R)-1-(tert-butoxy)ethyl)oxazolidin-2-one (90 mg, 0.483 mmol, 1 equiv) in DMF (2.4 mL) at 0° C. The suspension was stirred at 0° C. for 1 hour, by which time it turned yellow. The reaction was quenched with dilute aqueous sodium chloride (20 mL) and extracted with ethyl acetate (2×20 mL). The combined extracts were dried over Na₂SO₄, filtered and concentrated. Silica gel column chromatography (EtOAc/Heptane) separated the regioisomers and provided methyl 6-((R)-4-((R)-1-(tert-butoxy)ethyl)-2-oxooxazolidin-3-yl)-2-chloropyrimidine-4-carboxylate (0.111 g, white solid) in 64% yield. ¹H NMR (400 MHz, CDCl₃) δ 8.79 (s, 1H), 4.76 (m, 1H), 4.69 (dd, J=9.4, 2.7 Hz, 1H), 4.52-4.41 (m, 2H), 4.02 (s, 3H), 1.26 (s, 9H), 1.05 (d, J=6.6 Hz, 3H). MS m/z 358.2 (M+H)⁺; Rt-1.00 min.

Intermediate 21: (R)-4-((R)-1-(tert-butoxy)ethyl)-3-(2-chloro-6-(hydroxymethyl)pyrimidin-4-yl)oxazolidin-2-one

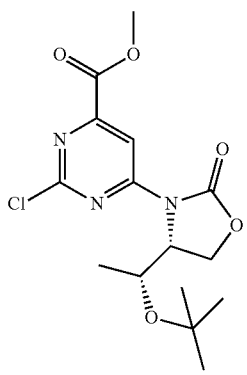 [SMILES: COC(=O)c1cc(N2C(=O)OC[C@@H]2[C@@H](C)OC(C)(C)C)nc(Cl)n1]

Sodium borohydride (60 mg, 1.59 mmol, 1.4 equiv) was added to a suspension of methyl 6-((R)-4-((R)-1-(tert-butoxy)ethyl)-2-oxooxazolidin-3-yl)-2-chloropyrimidine-4-carboxylate (400 mg, 1.12 mmol) in methanol (11.2 mL) at 0° C. The ice bath was removed and the reaction was stirred at room temperature for 1 hour. The reaction was quenched with saturated aqueous ammonium chloride (100 mL) and extracted with ethyl acetate (3×50 mL). The combined extracts were washed with saturated aqueous sodium chloride (30 mL), dried over Na₂SO₄, filtered and concentrated. Silica gel column chromatography (EtOAc/Heptane) provided (R)-4-((R)-1-(tert-butoxy)ethyl)-3-(2-chloro-6-(hydroxymethyl)pyrimidin-4-yl)oxazolidin-2-one (0.220 g, white solid) in 60% yield. ¹H NMR (400 MHz, CDCl₃) δ 8.18 (s, 1H), 4.77-4.72 (m, 3H), 4.66 (dd, J=9.4, 2.9 Hz, 1H), 4.48 (m, 1H), 4.41 (m, 1H), 2.83 (m, 1H), 1.26 (s, 9H), 1.03 (d, J=6.6 Hz, 3H). MS m/z 330.1 (M+H)⁺; Rt-0.86 min.

Intermediate 22: (R)-4-((R)-1-(tert-butoxy)ethyl)-3-(2-chloro-6-(fluoromethyl)pyrimidin-4-yl)oxazolidin-2-one

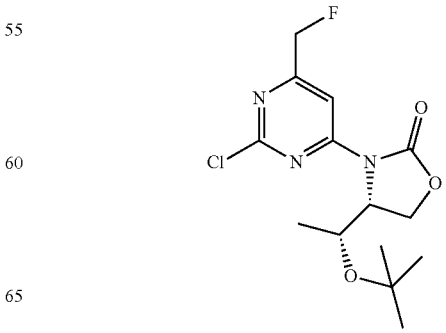

N,N-Diethylaminosulfur trifluoride (0.13 mL, 0.98 mmol, 1.5 equiv) was added to a solution of (R)-4-((R)-1-(tert-butoxy)ethyl)-3-(2-chloro-6-(hydroxymethyl)pyrimidin-4-yl)oxazolidin-2-one (215 mg, 0.652 mmol) in DCM at −78° C. The reaction was stirred at −78° C. for 1 hour, then warmed to room temperature and stirred for another hour. Additional N,N-Diethylaminosulfur trifluoride (0.26 mL, 2.0 mmol, 3 equiv) was added and the reaction stirred for another 1 hour. The reaction was quenched with water (50 mL) and extracted with DCM (3×25 mL). The combined extracts were washed with saturated aqueous sodium chloride (30 mL), dried over Na$_2$SO$_4$, filtered and concentrated. Silica gel column chromatography (EtOAc/Heptane) provided (R)-4-((R)-1-(tert-butoxy)ethyl)-3-(2-chloro-6-(hydroxymethyl)pyrimidin-4-yl)oxazolidin-2-one (0.165 g, white solid) in 76% yield. $^1$H NMR (400 MHz, CDCl$_3$) δ 8.30 (s, 1H), 5.40 (d, J=44 Hz, 1H), 4.75 (ddd, J=8.6, 4.1, 3.0 Hz, 1H), 4.67 (dd, J=9.4, 2.9 Hz, 1H), 4.49 (m, 1H), 4.43 (m, 1H), 1.27 (s, 9H), 1.04 (d, J=6.5 Hz, 3H). MS m/z 332.1 (M+H)$^+$; Rt-1.02 min.

Intermediate 23: (S)-4,6-difluoro-N-(1-(1-(4-fluorophenyl)-1H-pyrazol-4-yl)ethyl)pyrimidin-2-amine

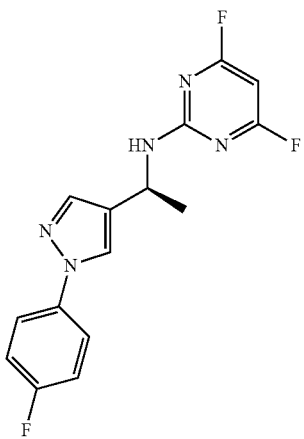 [SMILES: C[C@H](Nc1nc(F)cc(F)n1)c1cnn(-c2ccc(F)cc2)c1]

(S)-1-(1-(4-Fluorophenyl)-1H-pyrazol-4-yl)ethanamine (175 mg, 0.724 mmol) was added to a solution of 2,4,6-trifluoropyrimidine (146 mg, 1.09 mmol, 1.5 equiv) and N-ethyl-N-isopropylpropan-2-amine (0.32 mL, 1.8 mmol, 2.5 equiv) in 1,4-dioxane at room temperature. The mixture was stirred at room temperature for 1 hour and then the reaction was concentrated in vacuo. Silica gel column chromatography (EtOAc/Heptane) provided (R)-4-((R)-1-(tert-butoxy)ethyl)-3-(2-chloro-6-(hydroxymethyl)pyrimidin-4-yl)oxazolidin-2-one (0.085 g) in 37% yield. $^1$H NMR (400 MHz, CDCl$_3$) δ 7.82 (s, 1H), 7.68 (s, 1H), 7.62 (dd, J=8.9, 4.6 Hz, 1H), 7.18-7.11, (m, 2H), 5.80 (t, J=1.2 Hz, 1H), 5.49 (m, 1H), 5.25 (m, 1H), 1.62 (d, J=6.8 Hz, 3H). MS m/z 320.1 (M+H)$^+$; Rt-0.95 min.

The Intermediates in Table 1a were prepared by a method similar to the one described for the preparation of Intermediate 23.

TABLE 1a

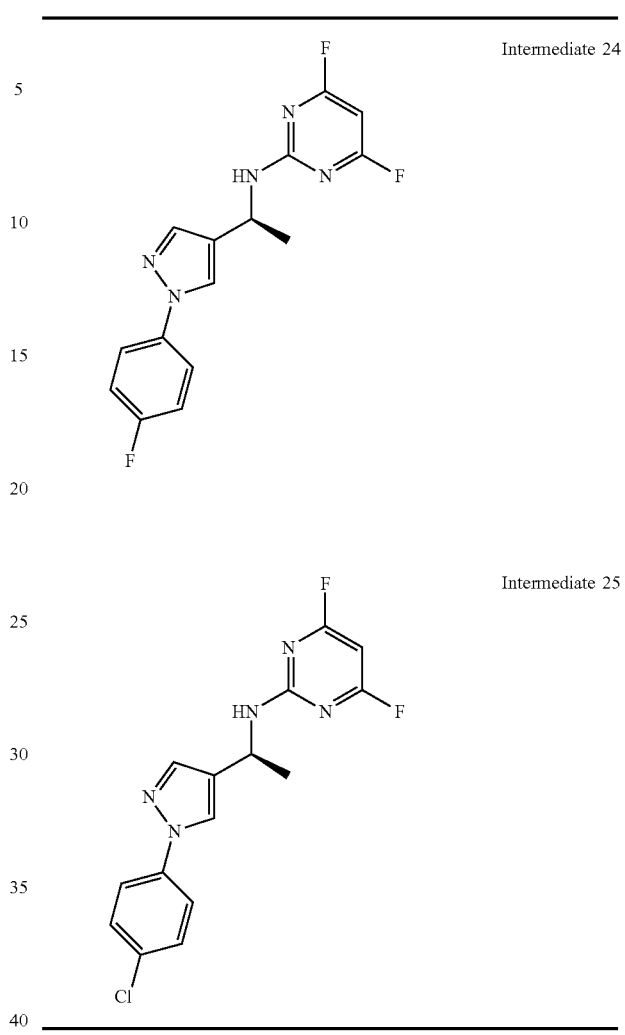

TABLE 1b

Chemical name, NMR chemical shifts and LCMS signal for each intermediate listed in Table 1a.

| Intermediate: Name | $^1$H NMR (400 MHz, CDCl$_3$) δ ppm | LCMS |
|---|---|---|
| 24: (S)-4,6-difluoro-N-(1-(1-(4-fluorophenyl)-1H-pyrazol-4-yl)ethyl)pyrimidin-2-amine | 7.82 (s, 1H), 7.68 (s, 1H), 7.62 (dd, J = 8.9, 4.6 Hz, 1H), 7.18-7.11, (m, 2H), 5.80 (t, J = 1.2 Hz, 1H), 5.49 (m, 1H), 5.25 (m, 1H), 1.62 (d, J = 6.8 Hz, 3H). | MS m/z 320.1 (M + H)$^+$; Rt-0.95 min |
| 25: (S)-N-(1-(1-(4-chlorophenyl)-1H-pyrazol-4-yl)ethyl)-4,6-difluoropyrimidin-2-amine | | MS m/z 336.0 (M + H)$^+$; Rt-1.04 min |

Intermediate 26: (R)-4-(((tert-butyldiphenylsilyl)oxy)methyl)oxazolidin-2-one

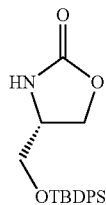

Imidazole (1.74 g, 25.6 mmol, 2.0 equiv) was added to a solution of (S)-4-(hydroxymethyl)oxazolidin-2-one (1.5 g, 12.8 mmol) and tert-butylchlorodiphenylsilane (3.95 mL, 15.4 mmol, 1.2 equiv) in DCM (43 mL) at room temperature. A white precipitate formed. The solution was stirred at room temperature for 16 hours and then diluted with water (50 mL). The layers were separated and the aqueous layer was extracted with DCM (50 mL). The combined organic extracts were washed with saturated aqueous sodium chloride (50 mL), dried over Na$_2$SO$_4$, filtered and concentrated. Silica gel column chromatography (EtOAc/Heptane 20 to 65%) provided (R)-4-(((tert-butyldiphenylsilyl)oxy)methyl)oxazolidin-2-one (3.55 g, sticky colorless oil) in 78% yield. $^1$H NMR (400 MHz, CDCl$_3$) δ 7.64 (m, 4H), 7.50-7.38 (m, 6H), 5.31 (m, 1H), 4.44 (t, J=8.7 Hz, 1H), 4.15 (m, 1H), 4.00 (m, 1H), 3.65 (d, J=5.5 Hz, 2H), 1.07 (s, 9H). MS m/z 356.1 (M+H)$^+$; Rt-1.00 min.

Intermediate 27: (R)-4-(((tert-butyldiphenylsilyl)oxy)methyl)-3-(2-fluoropyrimidin-4-yl)oxazolidin-2-one

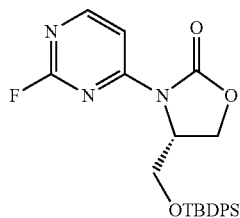

Sodium hydride (34 mg, 0.84 mmol, 1.5 equiv) was carefully added to a solution of (R)-4-(((tert-butyldiphenylsilyl)oxy)methyl)oxazolidin-2-one (200 mg, 0.563 mmol) in DMF (2.8 mL). The mixture was stirred at room temperature for 20 minutes and then 2,4-difluoropyrimidine (0.072 mL, 0.84 mmol, 1.5 equiv) was added (bubbling). The yellow suspension was stirred for 10 minutes and the reaction was then carefully quenched with saturated aqueous ammonium chloride (5 mL). Water (20 mL) was added and the mixture was extracted with ethyl acetate (2×25 mL). The combined organic extracts were washed with saturated aqueous sodium chloride (20 mL), dried over Na$_2$SO$_4$, filtered and concentrated. Silica gel column chromatography (EtOAc/Heptane 30%) provided (R)-4-(((tert-butyldiphenylsilyl)oxy)methyl)-3-(2-fluoropyrimidin-4-yl)oxazolidin-2-one (0.185 g, sticky colorless oil) in 73% yield. $^1$H NMR (400 MHz, CDCl$_3$) δ 8.44 (dd, J=5.8, 2.2 Hz, 1H), 8.12 (dd, J=5.8, 3.4 Hz, 1H), 7.58 (m, 2H), 7.48-7.32 (m, 6H), 7.23 (m, 2H), 4.80 (m, 1H), 4.65 (dd, J=8.6, 3.0 Hz, 1H), 4.55 (m, 1H), 4.18 (dd, J=11.1, 3.5 Hz, 1H), 3.83 (dd, J=11.1, 2.1 Hz, 1H), 1.04 (s, 9H). MS m/z 452.3 (M+H)$^+$; Rt-1.15 min.

Intermediate 28: (S)-3-(2-fluoropyrimidin-4-yl)-4-(hydroxymethyl)oxazolidin-2-one

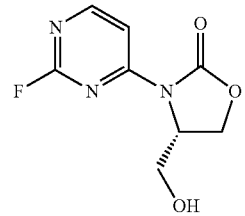

A solution of tetrabutylammonium fluoride (1.0 M in THF, 0.44 mL, 0.44 mmol, 1.1 equiv) was added to a solution of (R)-4-(((tert-butyldiphenylsilyl)oxy)methyl)-3-(2-fluoropyrimidin-4-yl)oxazolidin-2-one (180 mg, 0.40 mmol) in THF (4 mL) at room temperature. The solution was stirred for 1 hour and then diluted with saturated aqueous sodium chloride (30 mL). The mixture was extracted with ethyl acetate (2×30 mL) and the combined extracts were dried over Na$_2$SO$_4$, filtered and concentrated. Silica gel column chromatography (EtOAc/Heptane) provided (S)-3-(2-fluoropyrimidin-4-yl)-4-(hydroxymethyl)oxazolidin-2-one (0.051 g, white solid) in 60% yield. $^1$H NMR (400 MHz, CDCl$_3$) δ 8.51 (dd, J=5.8, 2.1 Hz, 1H), 8.19 (dd, J=5.8, 3.8 Hz, 1H), 4.86 (dq, J=8.1, 4.0 Hz, 1H), 4.55 (m, 2H), 4.09 (m, 1H), 3.96 (m, 1H), 2.18 (t, J=5.4 Hz, 1H). MS m/z 214.0 (M+H)$^+$; Rt-0.37 min.

Intermediate 29: (R)-4-(fluoromethyl)-3-(2-fluoropyrimidin-4-yl)oxazolidin-2-one

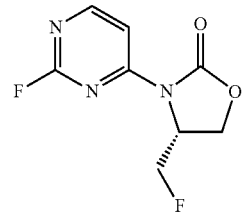 [SMILES: O=C1OC[C@H](CF)N1c1ccnc(F)n1]

Perfluorobutanesulfonyl fluoride (0.18 mL, 0.98 mmol, 4 equiv) was added to a solution of (S)-3-(2-fluoropyrimidin-4-yl)-4-(hydroxymethyl)oxazolidin-2-one (52 mg, 0.24 mmol) in THF (1.2 mL) at room temperature. Triethylamine trihydrofluoride (0.16 mL, 0.98 mmol, 4 equiv) and triethylamine (0.41 mL, 3.0 mmol, 12 equiv) were then added and the solution was stirred at 40° C. for 18 hours. The reaction was then cooled to room temperature and diluted with water (25 mL). The mixture was extracted with ethyl acetate (2×25 mL). The combined organic extracts were washed with saturated aqueous sodium chloride (10 mL), dried over Na$_2$SO$_4$, filtered and concentrated. Silica gel column chromatography (EtOAc/Heptane) provided (R)-4-(fluoromethyl)-3-(2-fluoropyrimidin-4-yl)oxazolidin-2-one (0.021 g, colorless oil) in 40% yield. $^1$H NMR (400 MHz, CDCl$_3$) δ 8.53 (dd, J=5.7, 2.1 Hz, 1H), 8.18 (dd, J=5.7, 3.7 Hz, 1H), 5.08-4.93 (m, 2H), 4.91-4.72 (m, 1H), 4.66-4.55 (m, 2H). MS m/z 215.9 (M+H)$^+$; Rt-0.57 min.

Intermediate 30: (R)-4-((R)-1-fluoroethyl)-3-(2-fluoropyrimidin-4-yl)oxazolidin-2-one

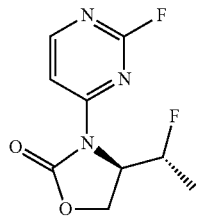 [SMILES: C[C@@H](F)[C@H]1COC(=O)N1c1ccnc(F)n1]

Step 1

To a round bottom flask containing a stir bar and (2S,3S)-2-(((benzyloxy)carbonyl)amino)-3-(tert-butoxy)butanoic acid DCHA (10 g, 20.4 mmol) in THF (160 mL) under nitrogen was cooled to −30° C. in a dry ice/acetone bath. To this cold white suspension was added isobutyl chloroformate (3.2 mL, 24.5 mmol) followed by the addition of N-methylmorpholine (2.7 mL, 24.5 mmol). Mixture was stirred for 20 min at −30° C. A N-Methylmorpholine salt develops and was filtered from mixture. Mother liquor was cooled to −30° C. where upon sodium borohydride (1.16 g, 30.6 mmol) was added followed by the addition of water (20 mL) immediately afterwards. Reaction mixture allowed to stir for 15 min at −20° C. then gradually allowed to warm to room temperature. The reaction mixture was stirred for 30 min at room temperature. The reaction mixture was then diluted with water and extracted with EtOAc. Organic phases combined, washed with water, brine, dried ($Na_2SO_4$), filtered and concentrated to afford benzyl ((2R,3S)-3-(tert-butoxy)-1-hydroxybutan-2-yl)carbamate (5.27 g, 17.8 mmol, 88% yield) as a colorless oil. LCMS m/z 296.1 (M+H)$^+$, Rt 0.84 min.

Step 2

To a round bottom flask containing benzyl ((2R,3S)-3-(tert-butoxy)-1-hydroxybutan-2-yl)carbamate (5.27 g, 17.8 mmol) was added MeOH (100 mL). Solution was degassed with nitrogen for 15 min at which time palladium on carbon (0.95 g, 0.89 mmol) in MeOH (5 mL) was added. A hydrogen atmosphere was then inserted. Resulting reaction mixture allowed to stir 40 min at room temperature at atmospheric pressure when water (2 mL) was added and once again a hydrogen atmosphere was inserted at atmospheric pressure and the subsequent reaction mixture allowed to stir 18 hr at room temperature. The reaction mixture was filtered through a pad of celite and concentrated to a brown oil. Oil redissolved in toluene and concentrated to afford (2R,3S)-2-amino-3-(tert-butoxy)butan-1-ol (2.5 g, 15.5 mmol, 87% yield) as a brown oil. LCMS m/z 162.1 (M+H)$^+$, Rt 0.41 min (Mass ion only, no UV peak).

Step 3

To a round bottom flask containing (2R,3S)-2-amino-3-(tert-butoxy)butan-1-ol (1.25 g, 7.75 mmol) and a stir bar was added acetonitrile (50 mL) followed by the addition of 2,4-difluoropyrimidine (0.99 g, 8.53 mmol) and DIEA (4.1 mL, 23.3 mmol). The resulting reaction mixture allowed to stir 1 hr at room temperature. The volatiles were then removed. Residue was partitioned between EtOAc and water. Aqueous layer extracted with EtOAc. Organic phases combined, washed with water, brine, dried ($Na_2SO_4$), filtered and concentrated to a viscous yellow oil of (2R,3S)-3-(tert-butoxy)-2-((2-fluoropyrimidin-4-yl)amino)butan-1-ol (1.5 g, 5.83 mmol, 75% yield. $^1$H NMR (400 MHz, CDCl$_3$) δ ppm 1.14 (s, 9H) 1.31 (d, J=6.26 Hz, 3H) 3.64 (d, J=12.91 Hz, 2H) 3.86 (br. s., 1H) 4.26 (d, J=10.17 Hz, 1H) 6.09 (br. s., 1H) 6.25 (br. s., 1H) 7.99 (br. s., 1H). LCMS m/z 258.2 (M+H)$^+$, Rt 0.62 min Step 4

To a round bottom flask containing (2R,3S)-3-(tert-butoxy)-2-((2-fluoropyrimidin-4-yl)amino)butan-1-ol (1.5 g, 5.83 mmol) and a stir bar under nitrogen was added DCM (58 mL). The resulting reaction mixture cooled to −70° C. in a dry ice/acetone bath. To this cold solution was added triphosgene (0.95 g, 3.21 mmol) followed by the addition of 2,6-dimethylpyridine (2.7 ml, 23.3 mmol). The resulting reaction mixture allowed to warm to room temperature and stirred for 1 hr.

The reaction mixture was then diluted with DCM and water and allowed to stir 1 hr at room temperature. The phases were then partioned and aqueous phase extracted with DCM. Organic phases combined, washed with water, brine, dried ($Na_2SO_4$), filtered and concentrated onto silica gel. Silica gel column chromatography (EtOAc/Heptane 0 to 100%) provided (R)-4-((S)-1-(tert-butoxy)ethyl)-3-(2-fluoropyrimidin-4-yl)oxazolidin-2-one (502 mg, 1.77 mmol, 30% yield) as a white crystalline. LCMS m/z 284.1 (M+H)$^+$, Rt 0.89 min.

Step 5

To a round bottom flask containing (R)-4-((S)-1-(tert-butoxy)ethyl)-3-(2-fluoropyrimidin-4-yl)oxazolidin-2-one (502 mg, 1.77 mmol) was added DCM (4 mL) and TFA (4 mL). Resulting reaction mixture stirred for 1 hr at room temperature. The volatiles were then removed and the residue neutralized with a saturated solution of NaHCO$_3$. The aqueous mixture was extracted with EtOAc. Organic phases combined, washed with water, brine, dried ($Na_2SO_4$), filtered and concentrated to a colorless residue of (R)-3-(2-fluoropyrimidin-4-yl)-4-((S)-1-hydroxyethyl)oxazolidin-2-one (382 mg, 1.68 mmol, 95% yield). LCMS m/z 228.1 (M+H)$^+$, Rt 0.44 min.

Step 6

To a round bottom flask containing a solution of (R)-3-(2-fluoropyrimidin-4-yl)-4-((S)-1-hydroxyethyl)oxazolidin-2-one (348 mg, 1.53 mmol) in THF (5.1 mL) was added perfluorobutanesulfonyl fluoride (0.83 mL, 4.60 mmol) followed by the addition of triethylamine trihydrofluoride (0.75 mL, 4.60 mmol) and triethylamine (1.9 mL, 13.8 mmol). The resulting reaction mixture allowed to stir at room temperature for 6 hr. The reaction mixture was diluted with water and the aqueous mixture was extracted with EtOAc. Organic phases combined, washed with water, brine, dried ($Na_2SO_4$), filtered and concentrated onto silica gel. Silica gel column chromatography (EtOAc/Heptane 0 to 60%) provided a viscous oil of (R)-4-((R)-1-fluoroethyl)-3-(2-fluoropyrimidin-4-yl)oxazolidin-2-one (125 mg, 0.44 mmol, 28% yield) which crystallizes upon standing. $^1$H NMR (400 MHz, CDCl$_3$) δ 1.34 (dd, J=24.26, 6.65 Hz, 3H) 4.45-4.55 (m, 1H) 4.61-4.68 (m, 1H) 5.11 (dt, J=7.63, 4.01 Hz, 1H)

5.30-5.52 (m, 1H) 8.13-8.17 (m, 1H) 8.52 (d, J=5.87 Hz, 1H). LCMS m/z 230.0 (M+H)⁺, Rt 0.66 min.

Intermediate 31: (R)-3-(2,5-difluoropyrimidin-4-yl)-4-((R)-1-fluoroethyl)oxazolidin-2-one

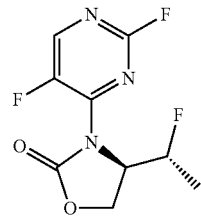 [SMILES: C[C@@H](F)[C@H]1COC(=O)N1c1nc(F)ncc1F]

Step 1

To a round bottom flask containing (2R,3S)-2-amino-3-(tert-butoxy)butan-1-ol (1.25 g, 7.75 mmol) and a stir bar was added acetonitrile (50 mL) followed by the addition of 2,4,5-trifluoropyrimidine (1.04 g, 7.75 mmol) and DIEA (4.1 mL, 23.3 mmol). The resulting reaction mixture allowed to stir 1 hr at room temperature. The volatiles were then removed. Reaction mixture was then partitioned between EtOAc and water. Aqueous layer extracted with EtOAc. Organic phases combined, washed with water, brine, dried (Na₂SO₄), filtered and concentrated to a viscous yellow oil of (2R,3S)-3-(tert-butoxy)-2-((2,5-difluoropyrimidin-4-yl)amino)butan-1-ol (1.56 g, 5.67 mmol, 73% yield). ¹H NMR (400 MHz, CDCl₃) δ 1.15 (s, 9H) 1.32 (d, J=6.26 Hz, 3H) 3.45 (br. s., 1H) 3.67 (d, J=11.35 Hz, 1H) 3.85-3.92 (m, 1H) 4.27 (d, J=11.74 Hz, 1H) 6.29 (d, J=5.48 Hz, 1H) 7.87 (d, J=2.35 Hz, 1H). LCMS m/z 276.4 (M+H)⁺, Rt 0.71 min.

Step 2

To a round bottom flask containing (2R,3S)-3-(tert-butoxy)-2-((2,5-difluoropyrimidin-4-yl)amino)butan-1-ol (1.56 g, 5.67 mmol) and a stir bar under nitrogen was added DCM (57 mL). The resulting reaction mixture cooled to −70° C. in a dry ice/acetone bath. To this cold solution was added triphosgene (0.93 g, 3.12 mmol) followed by the addition of 2,6-dimethylpyridine (2.64 ml, 22.7 mmol). The resulting reaction mixture allowed to warm to room temperature and stirred 90 hr at room temperature. The reaction mixture was then diluted with DCM and water and allowed to stir 1 hr at room temperature. The phases were then partioned and aqueous phase extracted with DCM. Organic phases combined, washed with water, brine, dried (Na₂SO₄), filtered and concentrated onto silica gel. Silica gel column chromatography (EtOAc/Heptane 0 to 100%) provided (R)-4-((S)-1-(tert-butoxy)ethyl)-3-(2,5-difluoropyrimidin-4-yl)oxazolidin-2-one (0.59 g, 1.96 mmol, 35% yield) as a white crystalline. ¹H NMR (400 MHz, CDCl₃) δ 1.03 (s, 9H) 1.16 (d, J=6.65 Hz, 3H) 4.15 (qd, J=6.39, 1.96 Hz, 1H) 4.43-4.52 (m, 1H) 4.59-4.72 (m, 2H) 8.43 (d, J=1.57 Hz, 1H). LCMS m/z 246.0 (−t-butyl fragment) (M+H)⁺, Rt 0.88 min.

Step 3

To a round bottom flask containing (R)-4-((S)-1-(tert-butoxy)ethyl)-3-(2,5-difluoropyrimidin-4-yl)oxazolidin-2-one (590 mg, 1.96 mmol) was added DCM (4 mL) and TFA (4 mL). Resulting reaction mixture stirred for 1 hr at room temperature. The volatiles were then removed. Residue neutralized with a saturated solution of NaHCO₃ and aqueous mixture extracted with EtOAc. Organic phases combined, washed with water, brine, dried (Na₂SO₄), filtered and concentrated to a colorless residue of (R)-3-(2,5-difluoropyrimidin-4-yl)-4-((S)-1-hydroxyethyl)oxazolidin-2-one (470 mg, 1.917 mmol, 98% yield). LCMS m/z 246.0 (M+H)⁺, Rt 0.41 min.

Step 4

To a round bottom flask containing a solution of (R)-3-(2,5-difluoropyrimidin-4-yl)-4-((S)-1-hydroxyethyl)oxazolidin-2-one (0.47 g, 1.917 mmol) in THF (6.4 mL) was added perfluorobutanesulfonyl fluoride (1.03 mL, 5.75 mmol) followed by the addition of triethylamine trihydrofluoride (0.94 mL, 5.75 mmol) and triethylamine (2.40 mL, 17.3 mmol) resulting reaction mixture allowed to stir at room temperature for 6 hr. The reaction mixture was diluted with water and the aqueous mixture was extracted with EtOAc. Organic phases combined, washed with water, brine, dried (Na₂SO₄), filtered and concentrated onto silica gel. Silica gel column chromatography (EtOAc/Heptane 0 to 60%) provided a white crystalline of (R)-3-(2,5-difluoropyrimidin-4-yl)-4-((R)-1-fluoroethyl)oxazolidin-2-one (150 mg, 0.61 mmol, 32% yield). ¹H NMR (400 MHz, CDCl₃) δ 1.37 (dd, J=24.26, 6.26 Hz, 3H) 4.48 (dd, J=9.39, 4.70 Hz, 1H) 4.63 (t, J=8.80 Hz, 1H) 4.90-5.02 (m, 1H) 5.02-5.25 (m, 1H) 8.50 (s, 1H). LCMS m/z 248.0 (M+H)⁺, Rt 0.59 min.

Intermediate 32

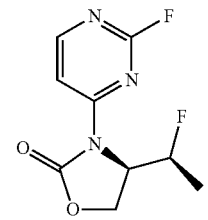 [SMILES: C[C@H](F)[C@H]1COC(=O)N1c1ccnc(F)n1]

Step 1

To a round bottom flask containing (R)-4-((R)-1-(tert-butoxy)ethyl)-3-(2-fluoropyrimidin-4-yl)oxazolidin-2-one (2.1 g, 7.41 mmol) was added DCM (18.5 mL) and TFA (18.5 mL). The resulting reaction mixture stirred for 1 hr at room temperature. The volatiles were then removed and the residue neutralized with a saturated solution of NaHCO₃. The aqueous mixture was then extracted with EtOAc. The organic phases were combined, washed with water, brine, dried (Na₂SO₄), filtered and concentrated to a colorless residue of (R)-3-(2-fluoropyrimidin-4-yl)-4-((R)-1-hydroxyethyl)oxazolidin-2-one (1.52 g, 6.69 mmol, 90% yield) which crystallizes upon standing. LCMS m/z 228.0 (M+H)⁺, Rt 0.44 min.

Step 2

To a round bottom flask containing a solution of (R)-3-(2-fluoropyrimidin-4-yl)-4-((R)-1-hydroxyethyl)oxazolidin-2-one (1.52 g, 6.69 mmol) in THF (22 mL) was added perfluorobutanesulfonyl fluoride (3.6 mL, 20.1 mmol) followed by the addition of triethylamine trihydrofluoride (3.3 mL, 20.1 mmol) and triethylamine (8.4 mL, 60.2 mmol). The resulting reaction mixture allowed to stir at room temperature for 2 hr. The reaction mixture was then diluted with water and the aqueous mixture was extracted with EtOAc. The organic phases combined, washed with water, brine, dried (Na₂SO₄), filtered and concentrated onto silica gel. Silica gel column chromatography (EtOAc/Heptane 0 to 60%) provided a white crystalline of (R)-4-((S)-1-fluoroethyl)-3-(2-fluoropyrimidin-4-yl)oxazolidin-2-one (207 mg, 0.90 mmol, 14% yield). ¹H NMR (400 MHz, CDCl₃) δ 1.44 (dd, J=23.48, 6.26 Hz, 3H) 4.47-4.57 (m, 1H) 4.66 (dd, J=8.80, 3.33 Hz, 1H) 4.71-4.86 (m, 1H) 5.22-5.45 (m, 1H) 8.21 (dd, J=5.48, 3.91 Hz, 1H) 8.52 (dd, J=5.48, 1.96 Hz, 1H). LCMS m/z 230.1 (M+H)⁺, Rt 0.63 min.

Alternative Method for Making Intermediate 32:

To a cooled (0° C.) solution of 2,4-difluoropyrimidine (160 mg, 1.375 mmol) and (R)-4-((S)-1-fluoroethyl)oxazolidin-2-one (183 mg, 1.375 mmol) in DMF (Volume: 4.6 mL) was added NaH (60% in mineral oil, 66.0 mg, 1.650 mmol). The resulting mixture was stirred at 0° C. for 30 min and at room temperature for 2 hr. Desired product was observed from LC-MS. The mixture was quenched with brine (1 ml). Diluted w/ EtOAc (20 ml) and water (10 ml), and separated layers. The organic was extracted with an additional 20 mL EtOAc. The combined organics were washed with brine, dried, and concentrated. Crude was purified through flash column chromatography (10-100% EtOAc/Heptane) to give (R)-4-((S)-1-fluoroethyl)-3-(2-fluoropyrimidin-4-yl)oxazolidin-2-one, 210 mg white solid. 1H NMR (400 MHz, CDCl3) δ 8.51 (dd, J=5.8, 2.1 Hz, 1H), 8.20 (dd, J=5.7, 3.7 Hz, 1H), 5.33 (dqd, J=49.5, 6.6, 1.3 Hz, 1H), 4.77 (dddd, J=26.5, 9.1, 3.4, 1.4 Hz, 1H), 4.65 (dd, J=9.0, 3.4 Hz, 1H), 4.50 (td, J=9.0, 1.3 Hz, 1H), 1.43 (dd, J=23.1, 6.6 Hz, 3H). MS m/z 230.1 (M+H).

Intermediate 33:
4-(2-fluoropropan-2-yl)oxazolidin-2-one

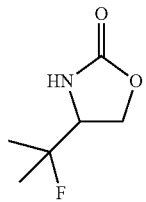

Step 1: Preparation of 2-amino-3-fluoro-3-methylbutan-1-ol

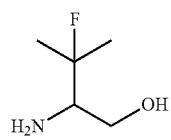

To the solution of LiBH₄ (2M in THF, 7.40 mL, 14.8 mmol) and trimethylchlorosilane (3.78 mL, 29.6 mmol) in THF (7 mL) was added 3-fluoro-D,L-valine (1 g, 7.40 mmol). The resulting mixture was stirred at room temperature for 24 hr. The reaction mixture was quenched with methanol and then concentrated under reduced pressure to give an oily product. The oily product was diluted with DCM and 10% aqueous sodium bicarbonate solution and then stirred at room temperature for ~16 hr. The separated organic layer was washed with saturated aqueous sodium bicarbonate solution and brine, dried over sodium sulfate, filtered off and concentrated under reduced pressure providing 2-amino-3-fluoro-3-methylbutan-1-ol (350 mg) as a solid, which was used without further purification. MS m/z 121.9 (M+H)⁺; Rt-0.16 min.

Step 2: Preparation of 4-(2-fluoropropan-2-yl)oxazolidin-2-one

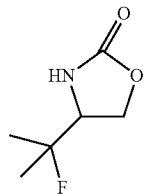

To a solution of N,N'-carbonyldiimidazole (530 mg, 3.27 mmol in THF (5 mL) was added slowly a solution of 2-amino-3-fluoro-3-methylbutan-1-ol (360 mg, 2.97 mmol) in THF (10 mL). The reaction mixture was stirred at room temperature for 18 hr, was diluted with DCM and stirred for additional 30 min. The separated organic layer was washed with water and brine, dried over sodium sulfate, filtered off and concentrated under reduced pressure. The residue was purified by column chromatography [SiO₂, 12 g, EtOAc/heptane=0/100 to 80/20] to provide 4-(2-fluoropropan-2-yl)oxazolidin-2-one (150 mg) as a brown solid. MS m/z 148.0 (M+H)⁺; Rt-0.32 min. ¹H NMR (400 Mhz, CDCl₃) δ ppm 6.30 (br. s., 1H), 4.39-4.54 (m, 1H), 4.26 (dd, J=8.9, 5.1 Hz, 1H), 3.84-3.99 (m, 1H), 1.29-1.45 (m, 6H).

Intermediate 34: 3-(2-chloropyrimidin-4-yl)-4-(2-fluoropropan-2-yl)oxazolidin-2-one

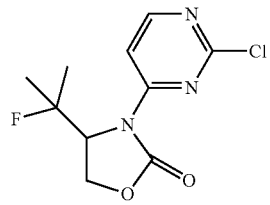 [SMILES: CC(C)(F)C1COC(=O)N1c1ccnc(Cl)n1]

To the solution of 2,4-dichloropyrimidine (150 mg, 1.006 mmol) and 4-(2-fluoropropan-2-yl)oxazolidin-2-one (148 mg, 1.01 mmol) in DMF (4.5 mL), sodium hydride (60% wt. 89 mg, 2.21 mmol) was added to give a pale yellow mixture. The mixture was stirred at room temperature for 2 hr, diluted with EtOAc and stirred for additional 30 min. The separated organic layer was washed with saturated aqueous sodium bicarbonate solution, water and brine. The organic phase was dried over sodium sulfate, filtered off and concentrated under reduced pressure. The residue was purified by column chromatography [SiO₂, 12 g, EtOAc/heptane=0/100 to 80/20] providing 3-(2-chloropyrimidin-4-yl)-4-(2-fluoropropan-2-yl)oxazolidin-2-one (150 mg) as a brown solid. MS m/z 260.1 (M+H)⁺; Rt-0.72 min. ¹H NMR (400 Mhz, CDCl₃) δ ppm 8.51 (d, J=5.9 Hz, 1H), 8.17 (d, J=5.9 Hz, 1H), 5.14 (dd, J=17.4, 8.0 Hz, 1H), 4.66 (d, J=9.4 Hz, 1H), 4.43-4.52 (m, 1H), 1.42-1.52 (m, 3H), 1.30-1.40 (m, 3H).

Intermediate 35: (S)-4-((R)-1,1-difluoropropan-2-yl)oxazolidin-2-one

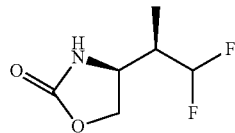

Step 1: Preparation of (S)-benzyl 3-((tert-butoxycarbonyl)amino)-4-hydroxybutanoate

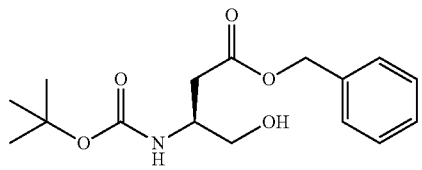 [SMILES: CC(C)(C)OC(=O)N[C@H](CO)CC(=O)OCc1ccccc1]

Reference: V. L. Truong, et al.; *Synlett* 2005, 8, 1279-1280.

To a solution of Boc-Asp(OBnzl)-OH (20 g, 61.9 mmol) in DME (60 mL) at −40° C. (dry ice/acetonitrile bath) was added N-methylmorpholine (7.07 mL, 64.3 mmol) over 5 min followed by isobutyl chloroformate (8.53 ml, 64.9 mmol) dropwise over 15 min, keeping the temperature below −10° C. The mixture was stirred for 30 min (−30° C. to −40° C.). The solids were quickly filtered off and rinsed with DME (60 mL). The clear filtrate was cooled to −35° C. and a solution of NaBH$_4$ (2.93 g, 78 mmol) in 30 mL water was added dropwise maintaining a temperature between −30° C. and −15° C. [Caution: gas development]. Water (332 mL) was added dropwise over 30 min to the white suspension maintaining a temperature below −15° C. The thick white slurry was filtered, rinsed with water (300 mL). The filtered solid was dissolved in DCM (250 mL). The solution was dried over sodium sulfate, filtered off and concentrated under reduced pressure to provide (S)-benzyl 3-((tert-butoxycarbonyl)amino)-4-hydroxybutanoate (16.35 g) as a white solid. MS m/z 254.2 (M-tert-butyl)$^+$; Rt-0.78 min. $^1$H NMR (400 Mhz, D$_3$C(CO)CD$_3$) δ ppm 7.45-7.28 (m, 4H), 5.92-5.80 (m, 1H), 5.11 (s, 2H), 4.07-3.91 (m, 1H), 3.67-3.48 (m, 2H), 2.82-2.77 (m, 1H), 2.74-2.68 (m, 1H), 2.61-2.52 (m, 1H), 1.39 (s, 9H).

Step 2: Preparation of (S)-benzyl 2-(2-oxooxazolidin-4-yl)acetate

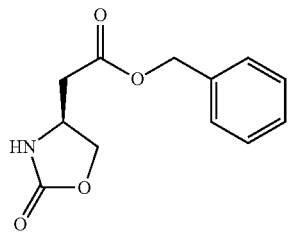 [SMILES: O=C(C[C@H]1COC(=O)N1)OCc1ccccc1]

Reference: V. L. Truong, et al.; *Synlett* 2005, 8, 1279-1280.

To a solution of (S)-benzyl 3-((tert-butoxycarbonyl)amino)-4-hydroxybutanoate (16.3 g, 52.7 mmol) and pyridine (10.65 ml, 132 mmol) in DCE (157 mL) at 0° C. was added p-toluenesulfonic anhydride (17.10 g, 52.4 mmol) in two portions over 5 min. The mixture was stirred for a few minutes, then allowed to warm to room temperature and stirred for 1 hr. The mixture was heated for 6 hr at 92° C. and then allowed to cool to room temperature. The mixture was diluted with DCM (80 mL), washed with 1N aqueous HCl solution (2×200 mL), brine (200 mL), and saturated aqueous sodium bicarbonate solution (100 mL). The organic layer was dried over sodium sulfate, filtered off and concentrated under reduced pressure. The residue was purified by column chromatography [SiO$_2$, 220 g, EtOAc/heptane=5/95 to 75/25] to provide (S)-benzyl 2-(2-oxooxazolidin-4-yl)acetate (10.0 g) as a white solid. MS m/z 236.2 (M+H)$^+$; Rt-0.59 min.

Step 3: Preparation of (R)-benzyl 2-((S)-2-oxooxazolidin-4-yl)propanoate

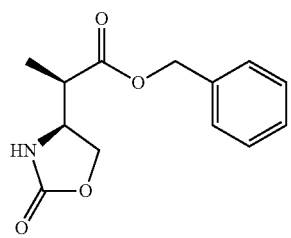 [SMILES: C[C@@H](C(=O)OCc1ccccc1)[C@H]1COC(=O)N1]

To a solution of sodium bis(trimethylsilyl)amide (1M in THF; 68.0 mL) under argon atmosphere was added THF (40.4 mL). The mixture was cooled to −78° C. and a solution of (S)-benzyl 2-(2-oxooxazolidin-4-yl)acetate (7.80 g, 33.2 mmol) in THF (85 mL) was added slowly over −15 min. The mixture was stirred for 1 hr at −78° C. and a solution of iodomethane (4.25 mL, 68.0 mmol) in THF (40.4 mL) was added slowly over −10 min. The reaction mixture was stirred for 1 hr at −78° C. and −1 hr at −40° C. The mixture was quenched with saturated aqueous ammonium chloride solution (~100 mL) and allowed to warm to room temperature. The mixture was extracted with DCM (3×). The combined organic layers were dried over sodium sulfate, filtered off and concentrated under reduced pressure. The residue was purified by column chromatography [SiO$_2$, 220 g, EtOAc/heptane] to provide (R)-benzyl 2-((S)-2-oxooxazolidin-4-yl)propanoate (7.47 g) as a colorless oil. MS m/z 250.1 (M+H)$^+$; Rt-0.65 min. $^1$H NMR (400 Mhz, DMSO-d6) δ ppm 7.85 (s, 1H), 7.44-7.28 (m, 5H), 5.10 (s, 2H), 4.36 (t, J=1.0 Hz, 1H), 4.11 (dd, J=5.4, 8.9 Hz, 1H), 4.06-3.98 (m, 1H), 2.69 (quin, J=6.9 Hz, 1H), 1.08 (d, J=7.1 Hz, 3H).

Step 4: Preparation of (R)-2-((S)-2-oxooxazolidin-4-yl)propanoic acid

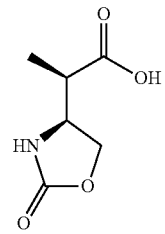

To a solution of (R)-benzyl 2-((S)-2-oxooxazolidin-4-yl)propanoate (1.99 g, 7.98 mmol) in THF (18.7 mL) was added Pd/C (10% wt., Degussa; 0.425 g). The mixture was stirred under hydrogen atmosphere (balloon) at room temperature for 4 hr. The mixture was filtered through a plug of celite and rinsed several times with THF. The filtrate was concentrated under reduced pressure providing (R)-2-((S)-2-oxooxazolidin-4-yl)propanoic acid (1.17 g) as a white solid, which was directly used without further purification. MS m/z 160.0 (M+H)⁺; Rt-0.26 min. ¹H NMR (400 Mhz, CD₃OD) δ ppm 4.53-4.47 (m, 1H), 4.26 (dd, J=5.7, 9.1 Hz, 1H), 4.13 (td, J=6.0, 8.8 Hz, 1H), 2.69-2.61 (m, 1H), 1.18 (d, J=7.2 Hz, 3H).

Step 5: Preparation of (R)—N-methoxy-N-methyl-2-((S)-2-oxooxazolidin-4-yl)propanamide

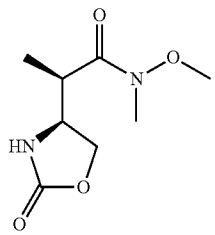

To a mixture of (R)-2-((S)-2-oxooxazolidin-4-yl)propanoic acid (1.1 g, 6.91 mmol) in DCM (20 mL) was added 1-chloro-N,N,2-trimethylprop-1-en-1-amine (1.385 g, 10.37 mmol) at 0° C. The ice bath was removed and the mixture was stirred for 30 min at ambient temperature. A mixture of N,O-dimethylhydroxylamine (1.011 g, 10.37 mmol) and pyridine (1.677 mL, 20.74 mmol) in DCM (20 mL) was added and stirring was continued for ~1 hr. The mixture was diluted with water (~2 mL) and saturated sodium bicarbonate solution (~2 mL) and stirred for ~15 min. The mixture was diluted with dichloromethane (~30 mL). The separated aqueous layer was extracted with DCM (1×), the organic layers were combined, dried over sodium sulfate, filtered and concentrated under reduced pressure providing crude (R)—N-methoxy-N-methyl-2-((S)-2-oxooxazolidin-4-yl)propanamide (2.73 g) as an orange oil which was directly used without further purification. MS m/z 203.1 (M+H)⁺; Rt-0.36 min.

Step 6: Preparation of (R)-2-((S)-3-benzyl-2-oxooxazolidin-4-yl)-N-methoxy-N-methylpropanamide

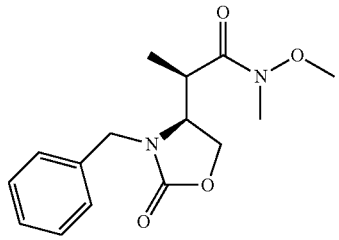 [SMILES: CON(C)C(=O)[C@H](C)[C@H]1COC(=O)N1Cc1ccccc1]

To a mixture of crude (R)—N-methoxy-N-methyl-2-((S)-2-oxooxazolidin-4-yl)propanamide (1.3 g, 6.43 mmol) and (bromomethyl)benzene (1.30 mL, 11.4 mmol) in THF (25 mL) was added slowly sodium hydride (60% wt.; 0.643 g) at 0° C. [Caution: gas development!]. The ice bath was removed and the mixture was stirred for ~2 hr. The mixture were diluted carefully with water and ethyl acetate. The reaction was repeated on the same scale and the mixtures were combined. The aqueous layer was separated and extracted with ethyl acetate (1×). The combined organic layers were dried over sodium sulfate, filtered off and concentrated under reduced pressure. The residue was purified by column chromatography [SiO₂, 80 g, EtOAc/heptane=5/95 to 75/25] to provide (R)-2-((S)-3-benzyl-2-oxooxazolidin-4-yl)-N-methoxy-N-methylpropanamide (1.83 g) as a slightly yellow oil, which contained also N-methoxy-N-methylisobutyramide. MS m/z 293.7 (M+H)⁺; Rt-0.64 min.

Step 7: Preparation of (R)-2-((S)-3-benzyl-2-oxooxazolidin-4-yl)propanal

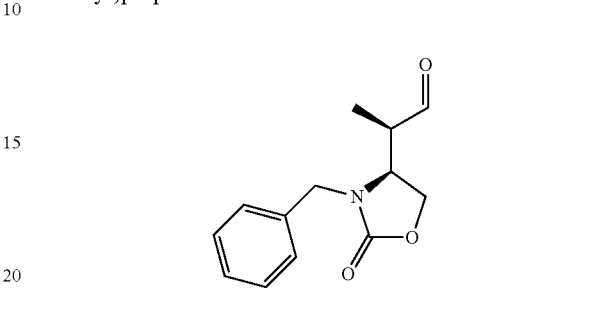

To a solution of (R)-2-((S)-3-benzyl-2-oxooxazolidin-4-yl)-N-methoxy-N-methylpropanamide from Step 6 (1.5 g, 5.13 mmol) in THF (30 mL) was added dropwise DIBAL-H (1M solution in hexane; 11.29 mL) at -78° C. The mixture was stirred for 90 min at -78° C., diluted slowly with Rochelle's salt solution (1M solution in water; ~20 mL) and stirred vigorously for ~15 min. The aqueous layer was separated and extracted with ethyl acetate (3×). The combined organic extracts were washed with saturated sodium bicarbonate solution and brine, filtered through a mixture of celite/silica gel. The filtrate was concentrated under reduced pressure providing crude (R)-2-((S)-3-benzyl-2-oxooxazolidin-4-yl)propanal (1.26 g) as a colorless oil, which was directly used without further purification. MS m/z 234.2 (M+H)⁺; Rt-0.60 min.

Step 8: Preparation of (S)-3-benzyl-4-((R)-1,1-difluoropropan-2-yl)oxazolidin-2-one

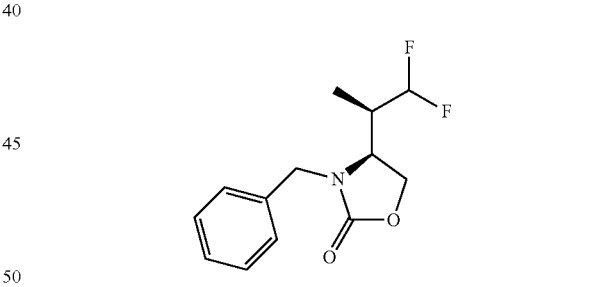

To a solution of (R)-2-((S)-3-benzyl-2-oxooxazolidin-4-yl)propanal (1.26 g, 5.40 mmol) in DCM (13 mL) was added slowly DAST (2.85 mL, 21.6 mmol) at 0° C. The mixture was allowed to warm to room temperature and stirred overnight. The mixture was carefully diluted with ice-water. The separated aqueous layer was extracted with DCM (3×). The combined organic layers were dried over sodium sulfate, filtered off and concentrated under reduced pressure. The residue was purified by column chromatography [SiO₂; 80 g, ethylacetate/heptane] providing (S)-3-benzyl-4-((R)-1,1-difluoropropan-2-yl)oxazolidin-2-one (627 mg) as a slightly yellowish oil. MS m/z 255.7/257.3 (M+H)⁺; Rt-0.80 min. ¹H NMR (400 Mhz, CD₃OD) δ ppm 7.31-7.43 (m, 5H), 5.86 (dt, J=1.0 Hz, 1H), 4.70 (d, J=15.3 Hz, 1H), 4.32 (d, J=7.4 Hz, 2H), 4.23 (d, J=15.7 Hz, 1H), 4.06 (td, J=7.4, 2.7 Hz, 1H), 2.40-2.59 (m, 1H), 0.98 (d, J=7.0 Hz, 3H).

Step 9: Preparation of (S)-4-((R)-1,1-difluoropropan-2-yl)oxazolidin-2-one

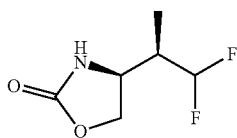

To liquid ammonia at −50° C. under argon was slowly added a solution of (S)-3-benzyl-4-((R)-1,1-difluoropropan-2-yl)oxazolidin-2-one (627 mg) (200 mg, 0.784 mmol) in diethylether (10 mL). Lithium (pellets; 54.4 mg, 7.84 mmol) were added in three portions. The reaction mixture became green then dark greenish blue over ~10 min. The mixture was stirred for additional 15 min and then quenched slowly by the addition of saturated aqueous ammonium chloride solution (3 mL). The mixture was allowed to warm slowly to room temperature. The residue was diluted with diethylether (20 mL) and water (10 mL). The separated aqueous layer was extract with ether (2×25 mL) and DCM (3×20 mL). The DCM and ether layers were separately concentrated under reduced pressure. The residues were dissolved in DCM and combined. The organic layer was dried over magnesium sulfate, filtered off and concentrated under reduced pressure providing crude (S)-4-((R)-1,1-difluoropropan-2-yl)oxazolidin-2-one (114 mg) as a colorless solid, which was directly used without further purification. MS m/z 166.1 (M+H)$^+$; Rt-0.37 min.

Intermediate 36: (S)-4-((R)-1,1-difluoropropan-2-yl)-3-(2-fluoropyrimidin-4-yl)oxazolidin-2-one

To a solution of (S)-4-((R)-1,1-difluoropropan-2-yl)oxazolidin-2-one (223 mg, 1.35 mmol) and 2,4-difluoropyrimidine (157 mg, 1.35 mmol) in DMF (4.09 mL) was added sodium hydride (60% wt.; 70.2 mg) in three portions at <0° C. (sodium chloride/ice). After the first portion of sodium hydride the mixture was stirred for ~5 min. The remaining two portions of sodium hydride were added over ~5 min and stirring was continued for 30 min. The mixture was diluted with ethylacetate (10 mL), stirred for 5 min and further slowly diluted with brine/water (1/1; 10 mL). The mixture was allowed to warm to 5° C. and poured into a mixture of brine/water (1/1; 20 mL) and ethylacetate (20 mL). The aqueous layer was separated and extracted with ethylacetate (25 mL). The combined organic layers were washed with brine (40 mL), dried over sodium sulfate, filtered off and concentrated under reduced pressure. The residue was purified by column chromatography [SiO$_2$, 12 g, EtOAc/heptane] to provide (S)-4-((R)-1,1-difluoropropan-2-yl)-3-(2-fluoropyrimidin-4-yl)oxazolidin-2-one (207 mg) as a white solid.

MS m/z 262.1 (M+H)$^+$; Rt-0.72 min. $^1$H NMR (400 Mhz, CD$_3$OD) δ ppm 8.55 (dd, J=2.3, 5.8 Hz, 1H), 8.17 (dd, J=3.8, 5.8 Hz, 1H), 6.02 (q, J=1.0 Hz, 1H), 5.17 (td, J=3.1, 8.3 Hz, 1H), 4.62-4.52 (m, 2H), 3.11-2.88 (m, 1H), 1.05 (dd, J=0.7, 7.2 Hz, 3H).

Intermediate 37: (S)-3-(2-chloro-5-fluoropyrimidin-4-yl)-4-((R)-1,1-difluoropropan-2-yl)oxazolidin-2-one

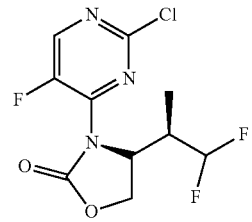

To a solution of (S)-4-((R)-1,1-difluoropropan-2-yl)oxazolidin-2-one (114 mg, 069 mmol) and 2,4-dichloro-5-fluoropyrimidine (115 mg, 0.690 mmol) in DMF (2.26 mL) was added sodium hydride (60% wt.; 35.9 mg) in three portions at <0° C. (sodium chloride/ice). After the first portion of sodium hydride the mixture was stirred for ~5 min. The remaining two portions of sodium hydride were added over ~5 min and stirring was continued for 30 min. The mixture was diluted with ethylacetate (10 mL), stirred for 5 min and further slowly diluted with brine/water (1/1; 10 mL). The mixture was allowed to warm to 5° C. and poured into a mixture of brine/water (1/1; 10 mL) and ethylacetate (10 mL). The aqueous layer was separated and extracted with ethylacetate (25 mL). The combined organic layers were washed with brine (30 mL), dried over sodium sulfate, filtered off and concentrated under reduced pressure. The residue was purified by column chromatography [SiO$_2$, 12 g, EtOAc/heptane] to provide (S)-3-(2-chloro-5-fluoropyrimidin-4-yl)-4-((R)-1,1-difluoropropan-2-yl)oxazolidin-2-one (134 mg) as a white solid. MS m/z 296.1 (M+H)$^+$; Rt-0.75 min. $^1$H NMR (400 Mhz, CD$_3$OD) δ ppm 8.69 (d, J=2.6 Hz, 1H), 5.99 (q, J=1.0 Hz, 1H), 5.17 (ddd, J=3.5, 7.4, 8.6 Hz, 1H), 4.69-4.50 (m, 2H), 2.88-2.70 (m, 1H), 1.04 (d, J=7.1 Hz, 3H).

Intermediate 38: 2-(1-azidoethyl)-5-(4-chlorophenyl)-4-methyloxazole

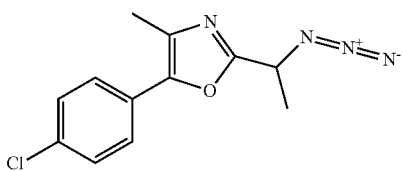 [SMILES: Cc1nc(C(C)N=[N+]=[N-])oc1-c1ccc(Cl)cc1]

Sodium azide (635 mg, 9.760 mmol) and a catalytic amount of 1,4,7,10,13,16-hexaoxacyclooctadecane was added to a solution of 2-(1-chloroethyl)-5-(4-chlorophenyl)-4-methyloxazole (250 mg, 0.976 mmol) in acetonitrile (10 ml) and refluxed at 80° C. for 3 hours. The reaction was concentrated in vacuo. Flash column chromatography (silica, 40 g) eluting with 0-5% EtOAc/DCM provided the title compound (254 mg, clear oil). HRMS(C) tR=1.52 min; MS m/z 262.0621

Intermediate 39: 1-(5-(4-chlorophenyl)-4-methyloxazol-2-yl)ethanamine

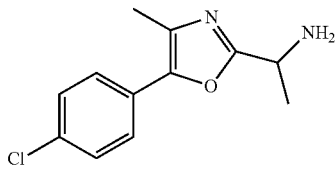 [SMILES: Cc1nc(C(C)N)oc1-c1ccc(Cl)cc1]

SiliaBond® Diphenylphosphine (1500 mg, 1.19 mmol/g) was added to a solution of 2-(1-azidoethyl)-5-(4-chlorophenyl)-4-methyloxazole (366 mg, 1.393 mmol) in anhydrous methanol (15 ml) and shaken for 3 hours. The reaction was filtered and concentrated in vacuo. Flash column chromatography (silica, 40 g) eluting with 2-10% MeOH/DCM afforded 160 mg (white solid). HRMS(B) tR=1.73 min; MS m/z 236.0716

Intermediate 40: (2S)—N-(2-(4-chlorophenyl)-2-hydroxyethyl)-2-(1,3-dioxoisoindolin-2-yl)propanamide

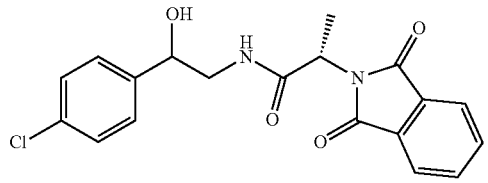 [SMILES: C[C@@H](C(=O)NCC(O)c1ccc(Cl)cc1)N1C(=O)c2ccccc2C1=O]

A solution of 2-amino-1-(4-chlorophenyl)ethanol (1000 mg, 5.83 mmol) and (S)-2-(1,3-dioxoisoindolin-2-yl)propanoic acid (1280 mg, 5.83 mmol) in THF (20 ml) was added N,N'-methanediylidenedicyclohexanamine (1.1 eq, 1322 mg, 6.41 mmol) and allowed to stir at ambient temperature for 12 hours. Concentrate in vacuo, dilute w/ EtOAc, filter washing w/EtOAc, wash w/water, brine, concentrate in vacuo. Used crude directly in the next step. 2 g of white solid. HRMS(B) tR=1.04 min; MS m/z 373.1

Intermediate 41: (S)—N-(2-(4-chlorophenyl)-2-oxoethyl)-2-(1,3-dioxoisoindolin-2-yl)propanamide

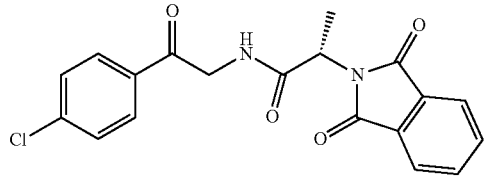 [SMILES: C[C@@H](C(=O)NCC(=O)c1ccc(Cl)cc1)N1C(=O)c2ccccc2C1=O]

1,1,1-Triacetoxy-1,1-dihydro-1,2-benziodoxol-3(1H)-one (3.091 g, 7.29 mmol) was added to a solution of (2S)—N-(2-(4-chlorophenyl)-2-hydroxyethyl)-2-(1,3-dioxoisoindolin-2-yl)propanamide (2.173 g, 5.83 mmol) in dichloromethane (20 ml) and allowed to stir for 2 hours. Dilute w/dichloromethane (50 ml), wash w/a sol'n of sat. sodium bicarbonate and 10% Na₂S₂O₃ solution, dry, concentrate in vacuo. 2.162 g (Used directly in the next step without further purification. HRMS(B) tR=1.24 min; MS m/z 371.2

Intermediate 42: (S)-2-(1-(5-(4-chlorophenyl)oxazol-2-yl)ethyl)isoindoline-1,3-dione

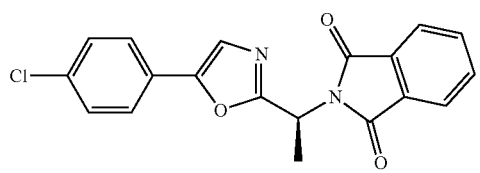 [SMILES: C[C@@H](c1ncc(-c2ccc(Cl)cc2)o1)N1C(=O)c2ccccc2C1=O]

Phosphoryl trichloride (1.m7 ml, 10.8 mmol) was added to a solution of (S)—N-(2-(4-chlorophenyl)-2-oxoethyl)-2-(1,3-dioxoisoindolin-2-yl)propanamide (2.162 g, 5.83 mmol) in toluene and heated at 110° C. for 15 hours. Dilute with dichloromethane (50 ml), wash with saturated sodium bicarbonate solution, water, brine, dried and concentrated in vacuo. Flash column chromatography (silica, 80 g) eluting with 0-50% EtOAc/DCM afforded the pure product 430 mg (yellow foam). HRMS(B) tR=1.42 min; MS m/z 353.1

Intermediate 43: (S)-2-(1-(3-(3-chlorophenyl)-1,2,4-oxadiazol-5-yl)ethyl)isoindoline-1,3-dione

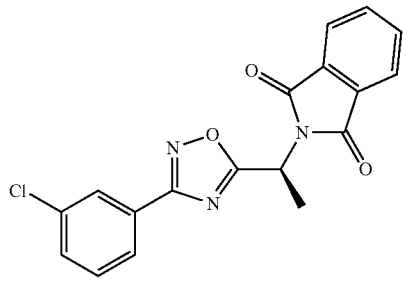 [SMILES: C[C@@H](c1nc(-c2cccc(Cl)c2)no1)N1C(=O)c2ccccc2C1=O]

To a stirred solution of (Z)-3-chloro-N'-hydroxybenzimidamide (500 mg, 2.93 mmol) and (S)-2-(1,3-dioxoisoindolin-2-yl)propanoic acid (642 mg, 2.93 mmol) was added N,N'-methanediylidenedicyclohexanamine (1.1 eq, 665 mg, 3.22 mmol) and allowed to reflux at 100° C. for 12 hours. Concentrate in vacuo, dilute w/ EtOAc, filter washing w/ EtOAc, wash w/water, brine, concentrate in vacuo. Flash column chromatography (silica, 40 g) eluting w/ 0-10% EtOAc/DCM afforded 300 mg. HRMS m/z 353.0567

Intermediate 44: (S)-1-(5-(4-chlorophenyl)oxazol-2-yl)ethanamine

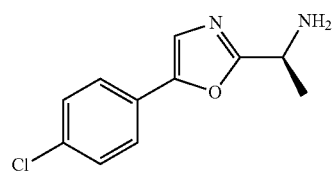

Hydrazine (0.55 ml, 6.09 mmol) was added to a solution of (S)-2-(1-(5-(4-chlorophenyl)oxazol-2-yl)ethyl)isoindoline-1,3-dione (430 mg, 1.219 mmol) in ethanol (15 ml) and heated at 80° C. for 13 hours. The reaction was concentrated in vacuo. Flash column chromatography (silica, 40 g) eluting with 2-10% MeOH/DCM afforded the desired product (200 mg, yellow oil). $^1$H NMR (400 MHz, CDCl$_3$) δ 7.67-7.51 (m, 9H), 7.47-7.35 (m, 8H), 7.31-7.21 (m, 1H), 4.25 (q, J=6.8 Hz, 4H), 1.97-1.66 (m, 15H), 1.63-1.48 (m, 2H). HRMS(B) tR=1.49 min; MS m/z 222.0560

Intermediate 45: (Z)-3-chloro-N'-hydroxy-4-(trifluoromethoxy)benzimidamide

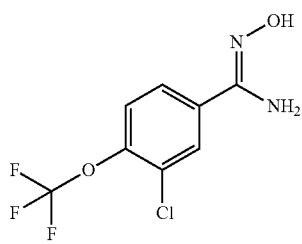 [SMILES: N/C(=N\O)c1ccc(OC(F)(F)F)c(Cl)c1]

To a solution of 3-chloror-4-(trifluoromethoxy)benzonitrile (1.0 g, 4.51 mmol) and hydroxylamine hydrochloride (1.5 eq, 0.47 g, 6.77 mmol) in ethanol (10 ml) was added N-ethyl-N-isopropylpropan-2-amine (1.6 eq, 1.26 ml, 7.22 mmol) and refluxed at 80° C. for 12 hours under N$_2$. Allow to cool to rt. Dilute with EtOAc (25 ml), wash with water (25 ml), brine (25 ml), dry, concentrate in vacuo afforded (Z)-3-chloro-N'-hydroxy-4-(trifluoromethoxy)benzimidamide (0.71 g, 62.1%, white solid). Used crude in the next step. HRMS(B) m/z 254.0070

The intermediates in Table 2a were prepared using a method similar to that described for the preparation of Intermediate 45

TABLE 2a

| | |
|---|---|
| 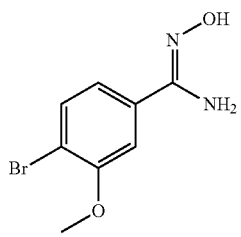 | Intermediate 46 |
| 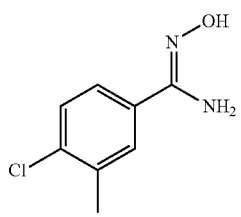 | Intermediate 47 |

TABLE 2a-continued

| | |
|---|---|
| 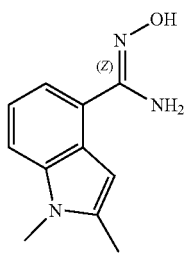 | Intermediate 48 |
| 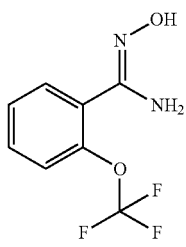 [SMILES: N/C(=N\O)c1ccccc1OC(F)(F)F] | Intermediate 49 |
| 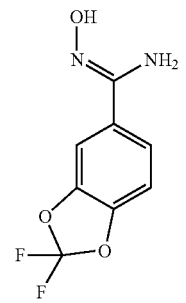 [SMILES: N/C(=N\O)c1ccc2c(c1)OC(F)(F)O2] | Intermediate 50 |
| 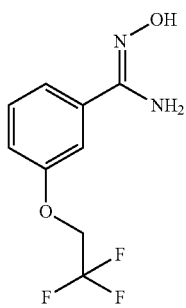 [SMILES: N/C(=N\O)c1cccc(OCC(F)(F)F)c1] | Intermediate 51 |
| 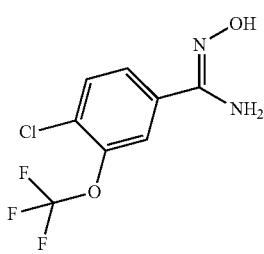 [SMILES: N/C(=N\O)c1ccc(Cl)c(OC(F)(F)F)c1] | Intermediate 52 |
| 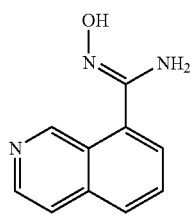 [SMILES: N/C(=N\O)c1cccc2ccncc12] | Intermediate 53 |

TABLE 2a-continued

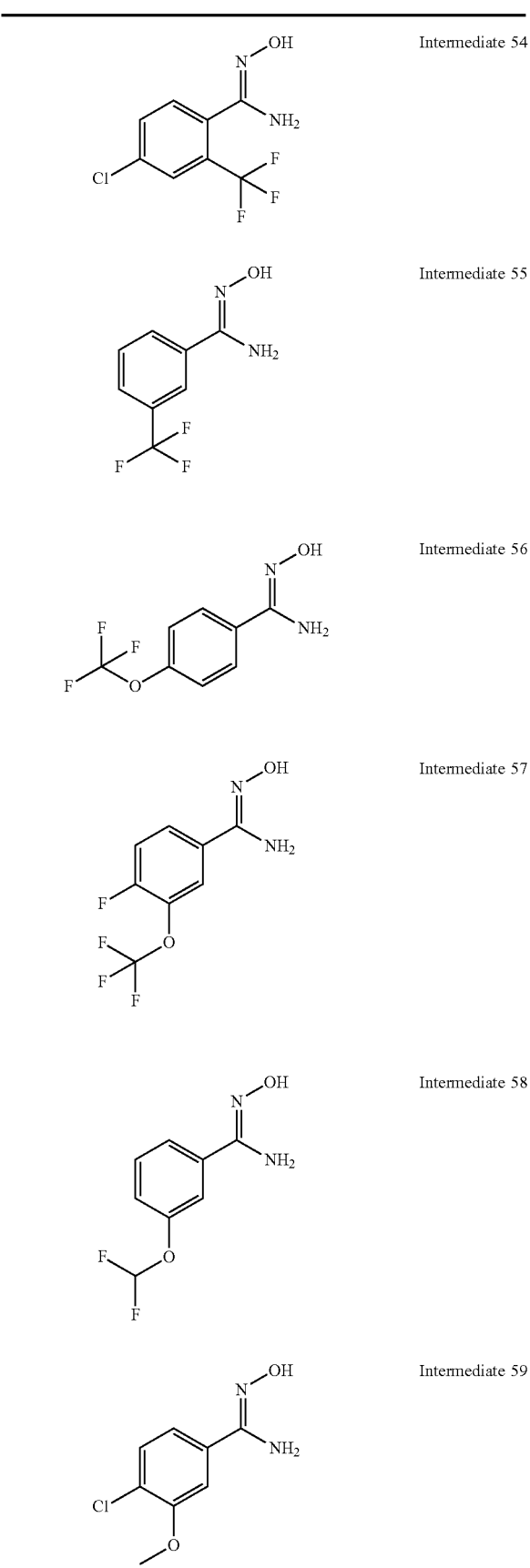

Intermediate 54

Intermediate 55

Intermediate 56

Intermediate 57

Intermediate 58

Intermediate 59

TABLE 2a-continued

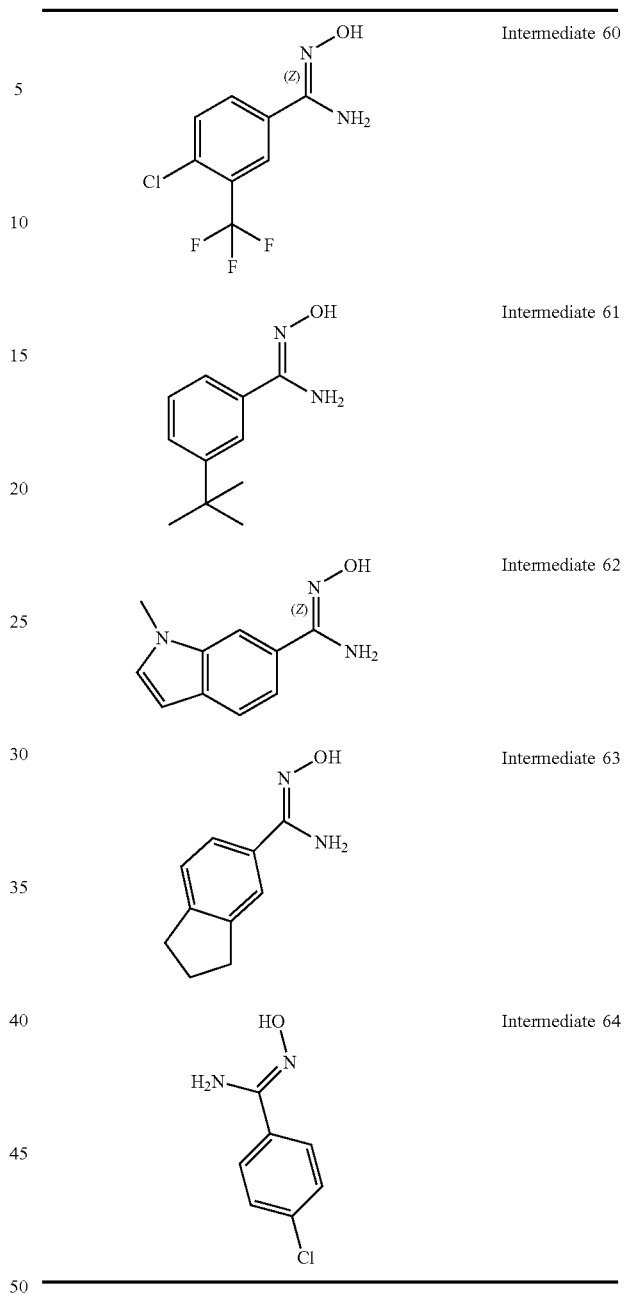

Intermediate 60

Intermediate 61

Intermediate 62

Intermediate 63

Intermediate 64

TABLE 2b

Chemical name and analytical data for each intermediate listed in Table 2a.

| Intermediate: Name | Analytical data |
|---|---|
| 46: (Z)-4-bromo-N'-hydroxy-3-methoxybenzimidamide | HRMS(B) tR = 1.24 min; MS m/z 243.9847. |
| 47: (Z)-4-chloro-N'-hydroxy-3-methylbenzimidamide | HRMS(B) tR = 1.35 min; MS m/z 184.0403 |
| 48: (Z)-N'-hydroxy-1,2-dimethyl-1H-indole-4-carboximidamide | HRMS(B) tR = 1.13 min; MS m/z 203.1059 |
| 49: (Z)-N'-hydroxy-2-(trifluoromethoxy)benzimidamide | HRMS(B) tR = 1.20 min; MS m/z 220.0460 |
| 50: (Z)-2,2-difluoro-N'-hydroxy-benzo[d][1,3]dioxole-5-carboximidamide | HRMS(B) tR = 1.33 min; MS m/z 216.0347 |

TABLE 2b-continued

Chemical name and analytical data for each intermediate listed in Table 2a.

| Intermediate: Name | Analytical data |
|---|---|
| 51: (Z)-N'-hydroxy-3-(2,2,2-trifluoroethoxy)benzimidamide | HRMS(B) tR = 1.46 min; MS m/z 234.061 |
| 52: (Z)-4-chloro-N'-hydroxy-3-(trifluoromethoxy) benzimidamide | HRMS(B) tR = 1.44 min; MS m/z 254.0070 |
| 53: (Z)-N'-hydroxyisoquinoline-8-carboximidamide | Anal. RP-HPLC tR = 0.93 min (Gradient: 1 to 30% B in 3.2 min to 98% in 1.95 min. - flow 1 mL/min. Eluent A: Water + 3.75 mM NH4Ac + 0.001% formic acid. Eluent B: ACN. Column: Acquity CSH 1.7 μm 2.1 × 50 mm - 50° C.) MS m/z 187.0746 |
| 54: (Z)-4-chloro-N'-hydroxy-2-(trifluoromethyl) benzimidamide | HRMS(B) tR = 1.35 min; MS m/z 238.0121 |
| 55: (Z)-N'-hydroxy-3-(trifluoromethyl)benzimidamide | HRMS(B) tR = 1.36 min; MS m/z 204.0510 |
| 56: (Z)-N'-hydroxy-4-(trifluoromethoxy)benzimidamide | HRMS(B) tR = 1.69 min; MS m/z 220.0460 |
| 57: (Z)-4-fluoro-N'-hydroxy-3-(trifluoromethoxy) benzimidamide | HRMS(B) tR = 1.55 min; MS m/z 238.0365 |
| 58: (Z)-3-(difluoromethoxy)-N'-hydroxybenzimidamide | HRMS(B) tR = 1.05 min; MS m/z 202.0554 |
| 59: (Z)-4-chloro-N'-hydroxy-3-methoxybenzimidamide | HRMS(B) tR = 1.14 min; MS m/z 200.0352 |
| 60: (Z)-4-chloro-N'-hydroxy-3-(trifluoromethyl) benzimidamide | HRMS(B) tR = 1.19 min; MS m/z 239.3000 (M + H) |
| 61: (Z)-3-(tert-butyl)-N'-hydroxybenzimidamide | HRMS(B) tR = 1.51 min ; MS m/z 193.1342 (M + H) |
| 62: (Z)-N'-hydroxy-1-methyl-1H-indole-6-carboximidamide | HRMS(B) tR = 1.03 min; MS m/z 190.0883 (M + H) |
| 63: (Z)-N'-hydroxy-2,3-dihydro-1H-indene-5-carboximidamide | HRMS(B) tR = 1.30 min; MS m/z 176.0950 |
| 64: 4-chloro-N'-hydroxybenzimidamide | MS m/z 171.0 (M + H)+; Rt-0.35 min. |

Intermediate 65: (S)-tert-butyl 1-(3-(4-chlorophenyl)-1,2,4-oxadiazol-5-yl)ethylcarbamate

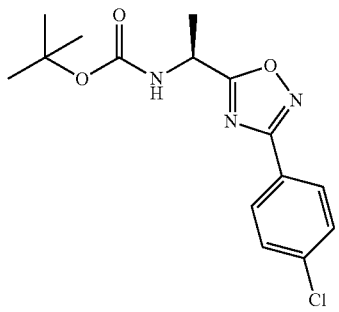

A solution of 4-chloro-N'-hydroxybenzimidamide (1.24 g, 7.27 mmol), (S)-2-(tert-butoxycarbonylamino)propanoic acid (1.38 g, 7.27 mmol, 1.0 equiv), and DCC (1.65 g, 8.00 mmol, 1.1 equiv) in 1,4-dioxane (73 mL) was heated at 100° C. for 18 hours. The reaction was then cooled to room temperature and concentrated in vacuo. Silica gel column chromatography (EtOAc/Heptane, 0 to 35%) provided (S)-tert-butyl 1-(3-(4-chlorophenyl)-1,2,4-oxadiazol-5-yl)ethyl-carbamate (1.13 g, white solid) in 48% yield. $^1$H NMR (400 MHz, CDCl$_3$) δ 8.03 (d, J=8.8 Hz, 2H), 7.47 (d, J=8.8 Hz, 2H), 5.18 (m, 1H), 1.64 (d, J=6.8 Hz, 3H), 1.47 (s, 9H).

Intermediate 66 (S)-tert-butyl (1-(3-(3-chloro-4-(trifluoromethoxy)phenyl)-1,2,4-oxadiazol-5-yl)ethyl)carbamate

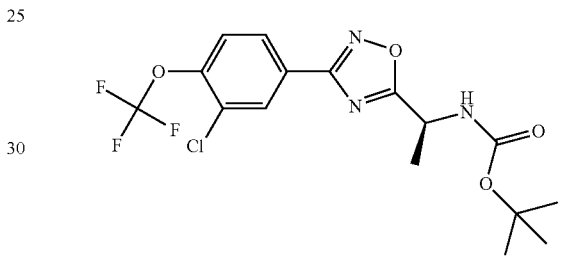

To a stirred solution of (Z)-3-chloro-N'-hydroxy-4-(trifluoromethoxy)benzimidamide (500 mg, 1.964 mmol) and (S)-2-((tert-butoxycarbonyl)amino)propanoic acid (372 mg, 1.964 mmol) was added N,N'-methanediylidenedicyclohexanamine (1.1 eq, 446 mg, 2.160 mmol) and allowed to reflux at 100° C. for 12 hours. Concentrate in vacuo, dilute w/ EtOAc, filter washing w/ EtOAc, wash w/water, brine, concentrate in vacuo. Flash column chromatography (silica, 80 g) eluting w/ 0-5% EtOAc/DCM afforded 230 mg. HRMS m/z 407.0860

The intermediates in Table 3a were prepared using a method similar to that described for the preparation of Intermediate 66

TABLE 3a

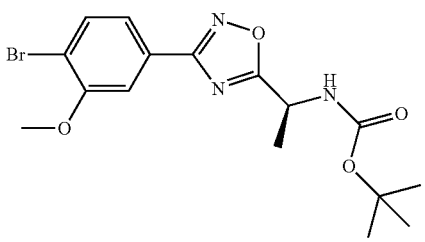 [SMILES: COc1cc(-c2noc([C@H](C)NC(=O)OC(C)(C)C)n2)ccc1Br]

Intermediate 67

TABLE 3a-continued
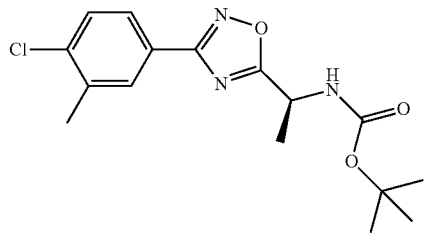 [SMILES: Cc1cc(-c2noc([C@H](C)NC(=O)OC(C)(C)C)n2)ccc1Cl] Intermediate 68
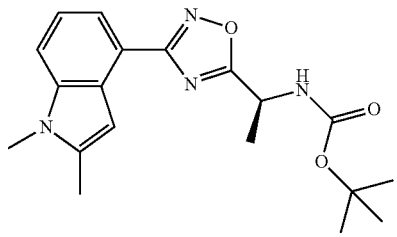 [SMILES: Cc1cc2c(-c3noc([C@H](C)NC(=O)OC(C)(C)C)n3)cccc2n1C] Intermediate 69
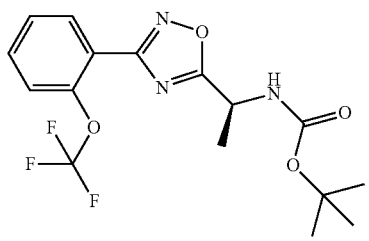 [SMILES: C[C@H](NC(=O)OC(C)(C)C)c1nc(-c2ccccc2OC(F)(F)F)no1] Intermediate 70
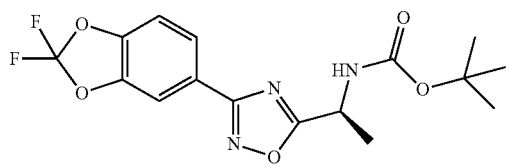 [SMILES: C[C@H](NC(=O)OC(C)(C)C)c1nc(-c2ccc3c(c2)OC(F)(F)O3)no1] Intermediate 71
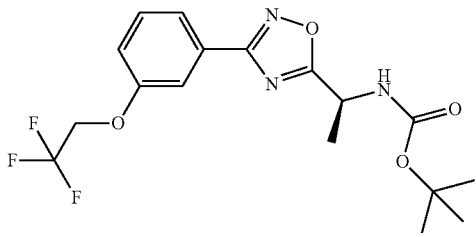 [SMILES: C[C@H](NC(=O)OC(C)(C)C)c1nc(-c2cccc(OCC(F)(F)F)c2)no1] Intermediate 72
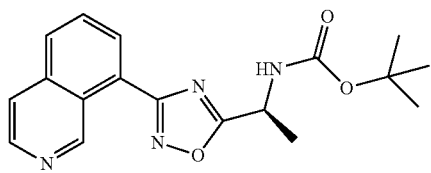 [SMILES: C[C@H](NC(=O)OC(C)(C)C)c1nc(-c2cccc3ccncc23)no1] Intermediate 73
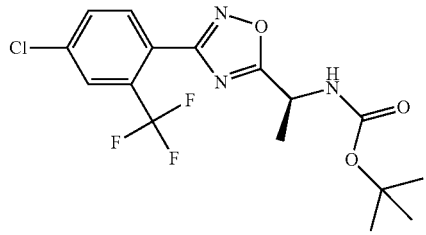 [SMILES: C[C@H](NC(=O)OC(C)(C)C)c1nc(-c2ccc(Cl)cc2C(F)(F)F)no1] Intermediate 74

TABLE 3a-continued
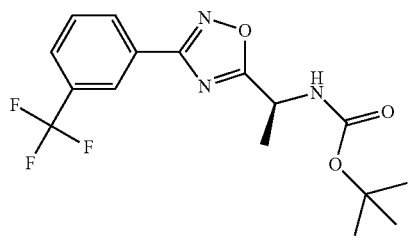 [SMILES: C[C@H](NC(=O)OC(C)(C)C)c1nc(-c2cccc(C(F)(F)F)c2)no1]
Intermediate 75
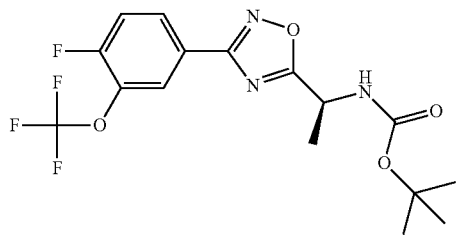 [SMILES: C[C@H](NC(=O)OC(C)(C)C)c1nc(-c2ccc(F)c(OC(F)(F)F)c2)no1]
Intermediate 76
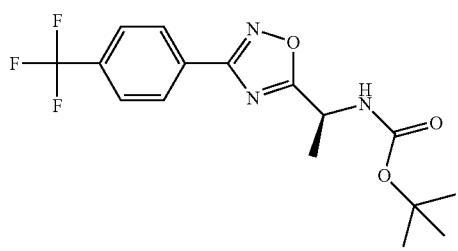 [SMILES: C[C@H](NC(=O)OC(C)(C)C)c1nc(-c2ccc(C(F)(F)F)cc2)no1]
Intermediate 77
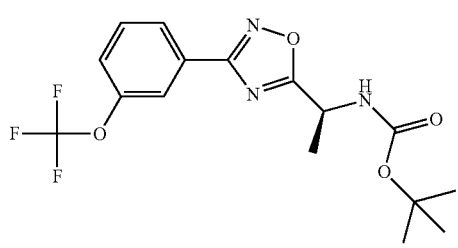 [SMILES: C[C@H](NC(=O)OC(C)(C)C)c1nc(-c2cccc(OC(F)(F)F)c2)no1]
Intermediate 78
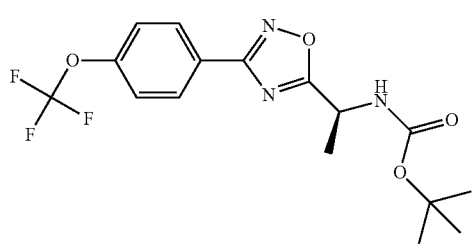
Intermediate 79
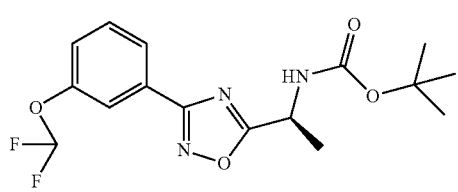 [SMILES: C[C@H](NC(=O)OC(C)(C)C)c1nc(-c2cccc(OC(F)F)c2)no1]
Intermediate 80
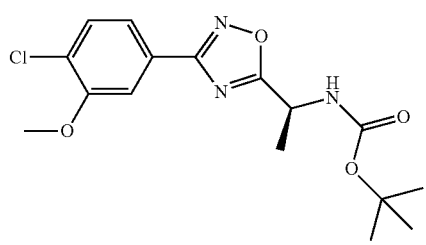 [SMILES: COc1cc(-c2noc([C@H](C)NC(=O)OC(C)(C)C)n2)ccc1Cl]
Intermediate 81

TABLE 3a-continued

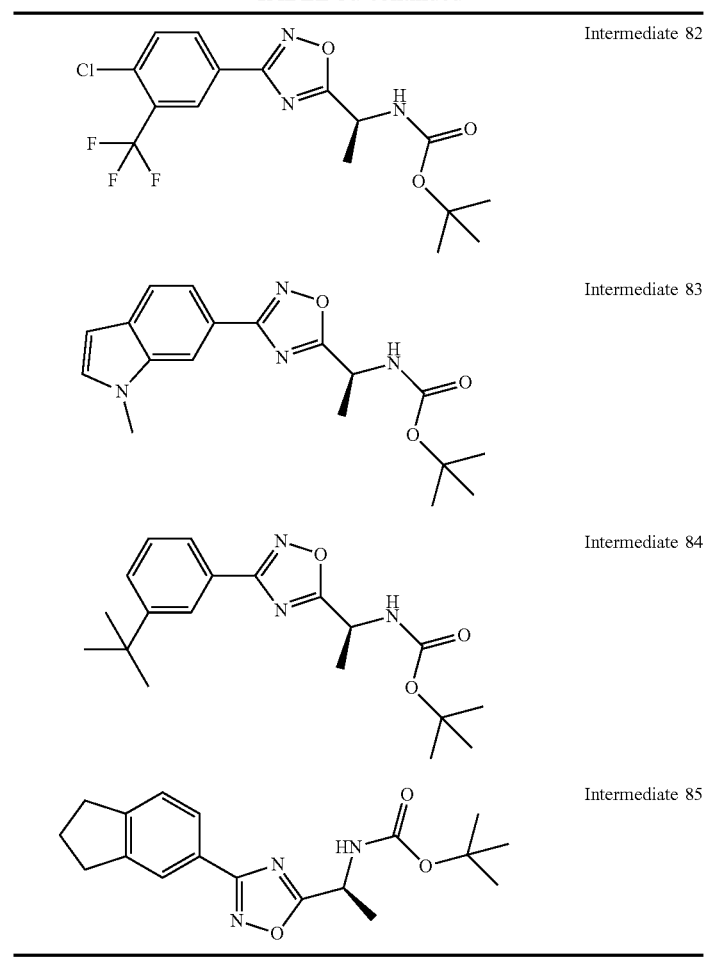

Intermediate 82

Intermediate 83

Intermediate 84

Intermediate 85

TABLE 3b

Chemical name and analytical data for each intermediate listed in Table 3a.

| Intermediate: Name | Analytical data |
| --- | --- |
| 67: (S)-tert-butyl (1-(3-(4-bromo-3-methoxyphenyl)-1,2,4-oxadiazol-5-yl)ethyl)carbamate | HRMS(C) tR = 1.20 min; MS m/z 397.0637 |
| 68: (S)-tert-butyl (1-(3-(4-chloro-3-methylphenyl)-1,2,4-oxadiazol-5-yl)ethyl)carbamate | HRMS(C) tR = 1.42 min; MS m/z 337.1193 |
| 69: (S)-tert-butyl (1-(3-(1,2-dimethyl-1H-indol-4-yl)-1,2,4-oxadiazol-5-yl)ethyl)carbamate | HRMS(C) tR = 1.12 min; MS m/z 356.1848 |
| 70: (S)-tert-butyl (1-(3-(2-(trifluoromethoxy)phenyl)-1,2,4-oxadiazol-5-yl)ethyl)carbamate | HRMS(C) tR = 1.12 min; MS m/z 373.1249 |
| 71: (S)-tert-butyl(1-(3-(2,2-difluorobenzo[d][1,3]dioxol-5-yl)-1,2,4-oxadiazol-5-yl)ethyl)carbamate | HRMS(C) tR = 1.41 min; MS m/z 369.1136 |
| 72: (S)-tert-butyl(1-(3-(3-(2,2,2-trifluoroethoxy)phenyl)-1,2,4-oxadiazol-5-yl)ethyl)carbamate | HRMS(C) tR = 1.33 min; MS m/z 387.1406 |
| 73: (S)-tert-butyl(1-(3-(isoquinolin-8-yl)-1,2,4-oxadiazol-5-yl)ethyl)carbamate | HRMS(C) tR = 0.71 min; MS m/z 340.1535 |
| 74: (S)-tert-butyl(1-(3-(4-chloro-2-(trifluoromethyl)phenyl)-1,2,4-oxadiazol-5-yl)ethyl)carbamate | HRMS(C) tR = 1.35 min; MS m/z 392.1055 |
| 75: (S)-tert-butyl (1-(3-(3-(trifluoromethyl)phenyl)-1,2,4-oxadiazol-5-yl)ethyl)carbamate | HRMS(C) tR = 1.41 min; MS m/z 357.1300 |
| 76: (S)-tert-butyl(1-(3-(4-fluoro-3-(trifluoromethoxy)phenyl)-1,2,4-oxadiazol-5-yl)ethyl)carbamate | HRMS(C) tR = 1.42 min; MS m/z 392.1302 |
| 77: (S)-tert-butyl (1-(3-(4-(trifluoromethyl)phenyl)-1,2,4-oxadiazol-5-yl)ethyl)carbamate | HRMS(C) tR = 1.59 min; MS m/z 357.1300 |
| 78: (S)-tert-butyl (1-(3-(3-(trifluoromethoxy)phenyl)-1,2,4-oxadiazol-5-yl)ethyl)carbamate | HRMS(C) tR = 1.38 min; MS m/z 374.1378 (M + H) |
| 79: (S)-tert-butyl (1-(3-(4-(trifluoromethoxy)phenyl)-1,2,4-oxadiazol-5-yl)ethyl)carbamate | HRMS(C) tR = 1.69 min; MS m/z 373.1249 |
| 80: (S)-tert-butyl (1-(3-(3-(difluoromethoxy)phenyl)-1,2,4-oxadiazol-5-yl)ethyl)carbamate | HRMS(C) tR = 1.12 min; MS m/z 355.1344 |
| 81: (S)-tert-butyl (1-(3-(4-chloro-3-methoxyphenyl)-1,2,4-oxadiazol-5-yl)ethyl)carbamate | HRMS(C) tR = 1.14 min; MS m/z 353.1142 |
| 82: (S)-tert-butyl(1-(3-(4-chloro-3-(trifluoromethyl)phenyl)-1,2,4-oxadiazol-5-yl)ethyl)carbamate | HRMS(C) tR = 1.52 min; MS m/z 391.0911 |
| 83: (S)-tert-butyl (1-(3-(1-methyl-1H-indol-6-yl)-1,2,4-oxadiazol-5-yl)ethyl)carbamate | HRMS(C) tR = 1.03 min; MS m/z 342.1692 |

TABLE 3b-continued

Chemical name and analytical data for each intermediate listed in Table 3a.

| Intermediate: Name | Analytical data |
|---|---|
| 84: (S)-tert-butyl (1-(3-(3-(tert-butyl)phenyl)-1,2,4-oxadiazol-5-yl)ethyl)carbamate | HRMS(C) tR = 1.62 min; MS m/z 345.2052 |
| 85: (S)-tert-butyl (1-(3-(2,3-dihydro-1H-inden-5-yl)-1,2,4-oxadiazol-5-yl)ethyl)carbamate | HRMS(C) tR = 1.50 min; MS m/z 329.1740 |

Intermediate 86: (S)-tert-butyl (1-(5-bromopyridin-2-yl)ethyl)carbamate

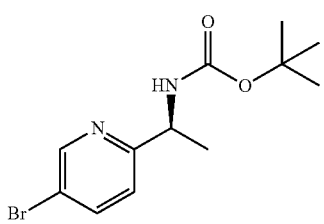 [SMILES: C[C@H](NC(=O)OC(C)(C)C)c1ccc(Br)cn1]

To a solution of (S)-1-(5-bromopyridin-2-yl)ethanamine (300 mg, 1.49 mmol) in DCM (7.5 mL) was added di-tert-butyl dicarbonate (358 mg, 1.64 mmol) and triethylamine (0.31 mL, 2.24 mmol). The solution was stirred for 16 h at room temperature then washed with water and brine. The organic layer was dried over Na2SO4, filtered and concentrated. Silica gel column chromatography (EtOAc/heptane 0 to 80%) provided a white solid (308 mg, 68.5% yield). $^1$H NMR (400 MHz, CDCl3) δ 8.59 (d, J=2.2 Hz, 1H), 7.76 (dd, J=8.3, 2.4 Hz, 1H), 7.16 (d, J=8.3 Hz, 1H), 5.57-5.42 (m, 1H), 4.86-4.73 (m, 1H), 1.43 (t, J=3.4 Hz, 12H); MS m/z 303.4 (M+H).

The intermediates in Table 4a were prepared using a method similar to that described for the preparation of Intermediate 86

TABLE 4a

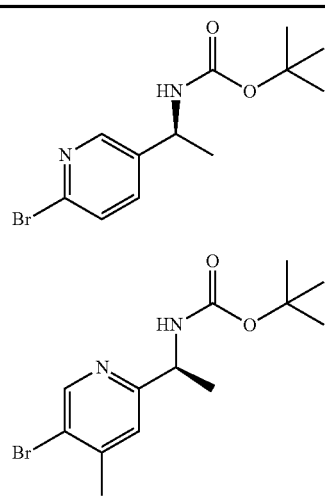

TABLE 4b

Chemical name and analytical data for each intermediate listed in Table 4a.

| Intermediate: Name | Analytical data |
|---|---|
| 87: (S)-tert-butyl (1-(6-bromopyridin-3-yl)ethyl)carbamate | $^1$H NMR (400 MHz, CDCl3) δ 8.33 (d, J = 2.6 Hz, 1H), 7.49 (dd, J = 8.2, 2.5 Hz, 1H), 7.44 (d, J = 8.3 Hz, 1H), 4.88-4.69 (m, 2H), 1.45 (d, J = 7.1 Hz, 3H), 1.41 (s, 9H); MS m/z 303.4 (M + H). |
| 88: (S)-tert-butyl (1-(5-bromo-4-methylpyridin-2-yl)ethyl)carbamate | LCMS tR = 1.31 min; MS m/z 317.0 (M + H) |
| 89: (S)-tert-butyl (1-(5-bromo-6-methylpyridin-2-yl)ethyl)carbamate | LCMS tR = 1.35 min; MS m/z 317.1 (M + H) |
| 90: (S)-tert-butyl (1-(5-bromo-3-fluoropyridin-2-yl)ethyl)carbamate | LCMS tR = 1.31 min; MS m/z 319.0 (M + H) |
| 91: (S)-tert-butyl (1-(5-bromo-3-methylpyridin-2-yl)ethyl)carbamate | LCMS tR = 1.37 min; MS m/z 317.0 (M + H) |

Intermediate 92: (S)-tert-butyl (1-(5-(4-fluoro-3-methylphenyl)pyridin-2-yl)ethyl)carbamate

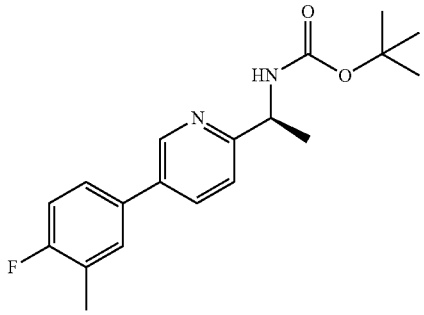 [SMILES: Cc1cc(-c2ccc([C@H](C)NC(=O)OC(C)(C)C)cn2)ccc1F]

In a 5 mL microwave vial a solution of (S)-tert-butyl (1-(5-bromopyridin-2-yl)ethyl)carbamate (60 mg, 0.2 mmol), (4-fluoro-3-methylphenyl)boronic acid (37 mg, 0.24 mmol), Sodium bicarbonate (0.2 mL, 0.4 mmol, 2 M aqueous solution) in Dioxane (2 mL) was bubbled N2 for 3 min then Cl2Pd(dppf)CH2Cl2 (16 mg, 0.02 mmol) was added. The capped tube was heated to 100° C. for 16 h. After cooling the reaction mixture was diluted with EtOAc (10 mL) and washed with water (10 mL). After separation, the aqueous phase was extracted with EtOAc (3×10 mL). Combined organics were dried over Na2SO4, filtered and concentrated. The crude material was purified through silica gel column chromatography (EtOAc in Heptane 12 to 100%) to give a white solid (66 mg, 80% yield). LCMS tR=1.43 min; MS m/z 331.1 (M+H).

The intermediates in Table 5a were prepared using a method similar to that described for the preparation of Intermediate 92

TABLE 5a

Intermediate 93
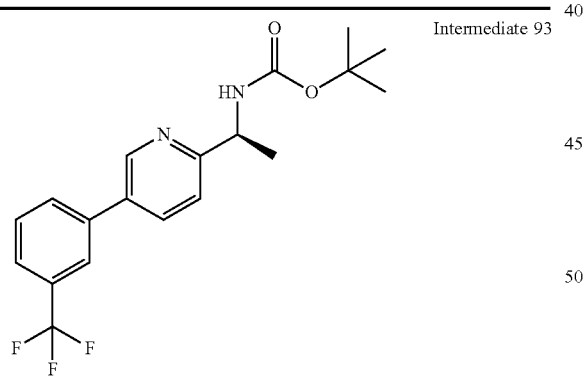

Intermediate 94
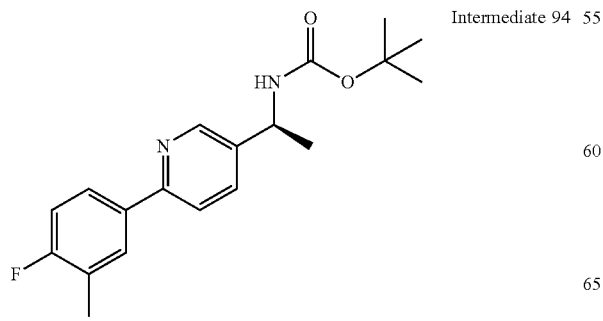

TABLE 5a-continued

Intermediate 95
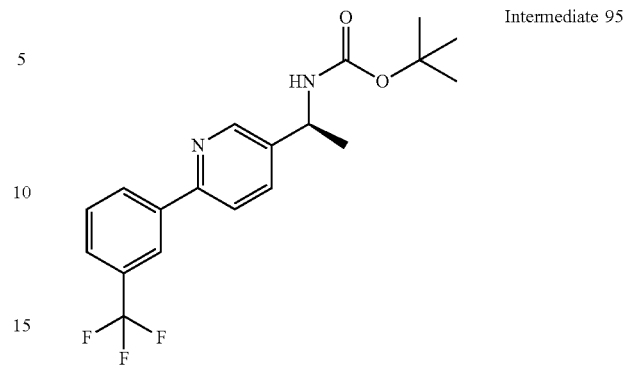

Intermediate 96
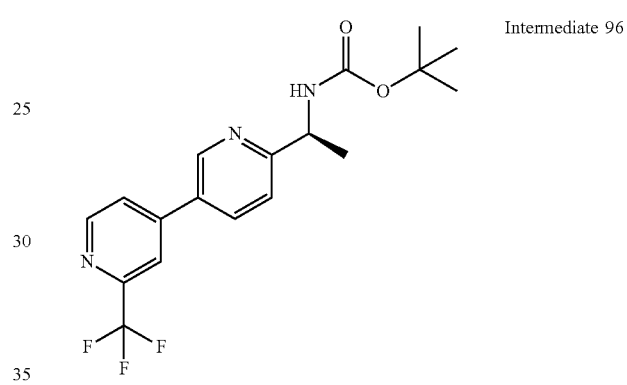

Intermediate 97
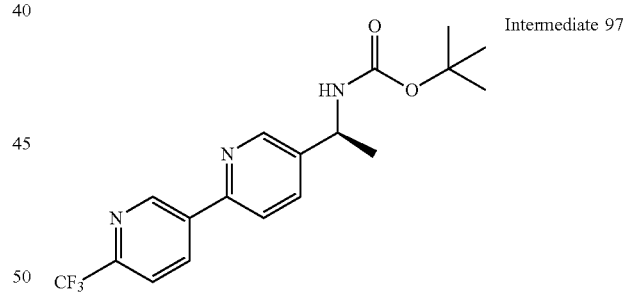

Intermediate 98
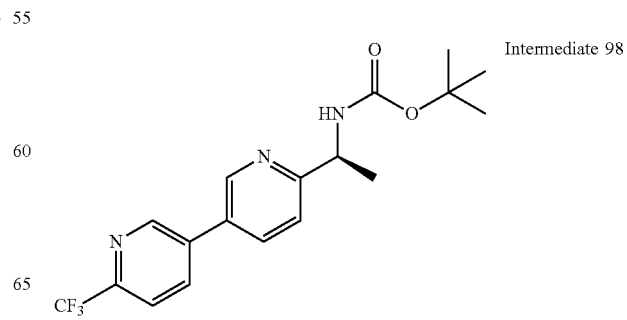

TABLE 5a-continued

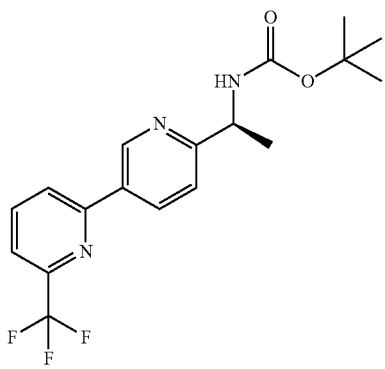 [SMILES: C[C@H](NC(=O)OC(C)(C)C)c1ccc(-c2cccc(C(F)(F)F)n2)cn1]
Intermediate 99

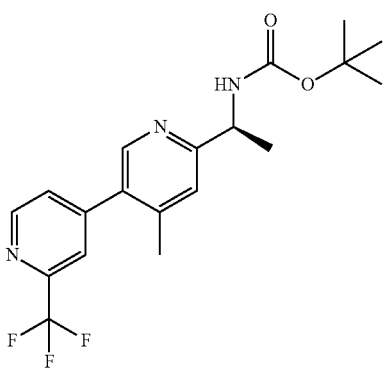 [SMILES: Cc1cc([C@H](C)NC(=O)OC(C)(C)C)ncc1-c1ccnc(C(F)(F)F)c1]
Intermediate 100

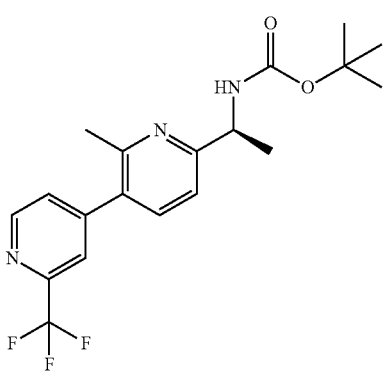 [SMILES: Cc1nc([C@H](C)NC(=O)OC(C)(C)C)ccc1-c1ccnc(C(F)(F)F)c1]
Intermediate 101

TABLE 5a-continued

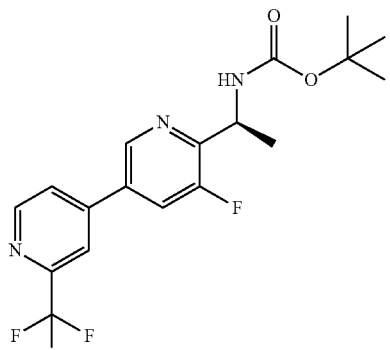
Intermediate 102

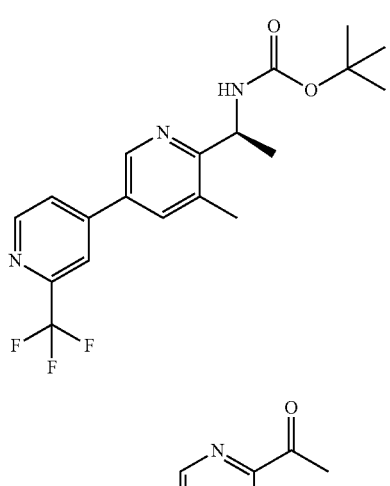
Intermediate 103

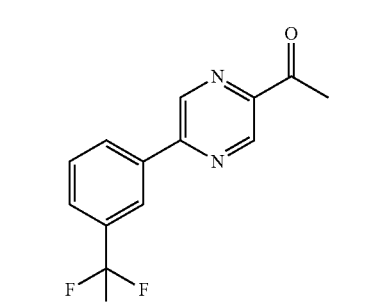
Intermediate 104

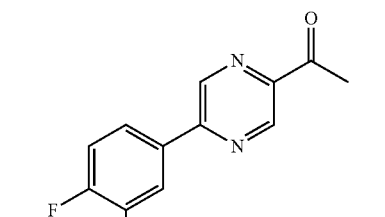
Intermediate 105

TABLE 5b

Chemical name and analytical data for each intermediate listed in Table 5a.

| Intermediate: Name | Analytical data |
| --- | --- |
| 93: (S)-tert-butyl (1-(5-(3-(trifluoromethyl)phenyl)pyridin-2-yl)ethyl)carbamate | LCMS tR = 1.69 min; MS m/z 365.5 (M − H). |
| 94: (S)-tert-butyl (1-(6-(4-fluoro-3-methylphenyl)pyridin-3-yl)ethyl)carbamate | LCMS tR = 1.62 min; MS m/z 329.5 (M − H). |
| 95: (S)-tert-butyl (1-(6-(3-(trifluoromethyl)phenyl)pyridin-3-yl)ethyl)carbamate | LCMS tR = 1.68 min; MS m/z 365.4 (M − H). |

TABLE 5b-continued

Chemical name and analytical data for each intermediate listed in Table 5a.

| Intermediate: Name | Analytical data |
| --- | --- |
| 96: (S)-tert-butyl (1-(2'-(trifluoromethyl)-[3,4'-bipyridin]-6-yl)ethyl)carbamate | $^1$H NMR (400 MHz, CDCl3) δ 8.83 (t, J = 3.9 Hz, 2H), 7.92 (dd, J = 8.3, 2.5 Hz, 1H), 7.87 (d, J = 1.7 Hz, 1H), 7.73-7.66 (m, 1H), 7.42 (d, J = 8.1 Hz, 1H), 5.59 (d, J = 7.6 Hz, 1H), 4.93 (p, J = 6.9 Hz, 1H), 1.50 (d, J = 7.0 Hz, 3H), 1.45 (s, 9H); MS m/z 368.2 (M + H). |
| 97: (S)-tert-butyl (1-(6'-(trifluoromethyl)-[2,3'-bipyridin]-5-yl)ethyl)carbamate | $^1$H NMR (400 MHz, CDCl3) δ 9.27 (d, J = 2.1 Hz, 1H), 8.71 (s, 1H), 8.49 (dd, J = 8.3, 2.1 Hz, 1H), 7.80-7.75 (m, 3H), 4.90 (br s, 1H), 1.52 (d, J = 6.3 Hz, 3H), 1.43 (s, 9H); MS m/z 368.2 (M + H). |
| 98: (S)-tert-butyl (1-(6'-(trifluoromethyl)-[3,3'-bipyridin]-6-yl)ethyl)carbamate | $^1$H NMR (400 MHz, CDCl3) δ 8.93 (d, J = 2.1 Hz, 1H), 8.79 (d, J = 2.3 Hz, 1H), 8.04 (dd, J = 8.2, 2.3 Hz, 1H), 7.88 (dd, J = 8.1, 2.4 Hz, 1H), 7.80 (d, J = 8.2 Hz, 1H), 7.42 (d, J = 8.1 Hz, 1H), 5.60 (d, J = 7.8 Hz, 1H), 4.93 (p, J = 6.9 Hz, 1H), 1.50 (d, J = 6.8 Hz, 3H), 1.44 (s, 9H); MS m/z 368.2 (M + H). |
| 99: (S)-tert-butyl (1-(6-(trifluoromethyl)-[2,3'-bipyridin]-6'-yl)ethyl)carbamate | $^1$H NMR (400 MHz, CDCl3) δ 9.15 (d, J = 2.3 Hz, 1H), 8.36 (dd, J = 7.8, 2.4 Hz, 1H), 8.01-7.89 (m, 2H), 7.66 (dd, J = 7.5, 1.1 Hz, 1H), 7.38 (d, J = 8.0 Hz, 1H), 5.69 (d, J = 7.9 Hz, 1 H), 4.92 (p, J = 6.9 Hz, 1H), 1.49 (d, J = 6.8 Hz, 3H), 1.45 (s, 9H); MS m/z 368.2 (M + H). |
| 100: (S)-tert-butyl (1-(4-methyl-2'-(trifluoromethyl)-[3,4'-bipyridin]-6-yl)ethyl)carbamate | $^1$H NMR (400 MHz, CDCl3) δ 8.83 (d, J = 4.9 Hz, 1H), 8.36 (s, 1H), 7.66 (s, 1H), 7.51-7.42 (m, 1H), 7.21 (s, 1H), 5.60 (d, J = 7.7 Hz, 1H), 4.87 (p, J = 6.9 Hz, 1H), 2.30 (s, 3H), 1.48 (d, J = 6.9 Hz, 3H), 1.45 (s, 9H); MS m/z 326.4 (M + H − 56). |
| 101: (S)-tert-butyl (1-(2-methyl-2'-(trifluoromethyl)-[3,4'-bipyridin]-6-yl)ethyl)carbamate | $^1$H NMR (400 MHz, CDCl3) δ 8.81 (d, J = 5.0 Hz, 1H), 7.66 (s, 1H), 7.50 (d, J = 7.9 Hz, 1H), 7.47 (dd, J = 4.9, 1.6 Hz, 1H), 7.20 (d, J = 7.8 Hz, 1H), 5.75 (d, J = 7.5 Hz, 1H), 4.86 (p, J = 6.9 Hz, 1H), 2.51 (s, 3H), 1.48 (d, J = 6.9 Hz, 3H), 1.46 (s, 9H); MS m/z 326.4 (M + H − 56). |
| 102: (S)-tert-butyl (1-(5-fluoro-2'-(trifluoromethyl)-[3,4'-bipyridin]-6-yl)ethyl)carbamate | $^1$H NMR (400 MHz, CDCl$_3$) δ 8.85 (d, J = 5.1 Hz, 1H), 8.66 (s, 1H), 7.87-7.84 (m, 1H), 7.70-7.67 (m, 1H), 7.65 (dd, J = 9.8, 1.9 Hz, 1H), 5.76 (d, J = 7.7 Hz, 1H), 5.31-5.23 (m, 1 H), 1.47 (d, J = 6.8 Hz, 3H), 1.45 (s, 9H); MS m/z 386.1 (M + H). |
| 103: (S)-tert-butyl (1-(5-methyl-2'-(trifluoromethyl)-[3,4'-bipyridin]-6-yl)ethyl)carbamate | $^1$H NMR (400 MHz, CDCl3) δ 8.81 (d, J = 5.1 Hz, 1H), 8.68 (d, J = 2.2 Hz, 1H), 7.88-7.85 (m, 1H), 7.71 (d, J = 1.7 Hz, 1H), 7.68 (dd, J = 5.0, 1.7 Hz, 1H), 5.99 (d, J = 8.2 Hz, 1H), 5.13 (p, J = 6.7 Hz, 1H), 2.48 (s, 3H), 1.45 (s, 9H), 1.42 (d, J = 6.6 Hz, 3H); MS m/z 382.2 (M + H). |
| 104: 1-(5-(3-(trifluoromethyl)phenyl)pyrazin-2-yl)ethanone | $^1$H NMR (400 MHz, CDCl3) δ 9.30 (d, J = 1.5 Hz, 1H), 9.11 (d, J = 1.5 Hz, 1H), 8.39 (s, 1H), 8.29 (d, J = 8.0 Hz, 1H), 7.78 (s, 1H), 7.69 (t, J = 7.8 Hz, 1H), 2.76 (s, 3H).); MS m/z 266.9 (M + H). |
| 105: 1-(5-(4-fluoro-3-methylphenyl)pyrazin-2-yl)ethanone | $^1$H NMR (400 MHz, CDCl3) δ 9.24 (d, J = 1.5 Hz, 1H), 9.01 (d, J = 1.5 Hz, 1H), 7.97 (dd, J = 7.3, 1.9 Hz, 1H), 7.89 (ddd, J = 7.6, 4.8, 2.3 Hz, 1H), 7.17 (t, J = 8.9 Hz, 1H), 2.74 (s, 3H), 2.39 (d, J = 2.0 Hz, 3H); MS m/z 230.9 (M + H). |

The following intermediates were prepared using a method similar to that described for the preparation of Intermediate 92

Intermediate 106: (R)-4-((R)-1-(tert-butoxy)ethyl)-3-(2-(((S)-1-(2'-(tert-butyl)-[3,4'-bipyridin]-6-yl)ethyl)amino)pyrimidin-4-yl)oxazolidin-2-one

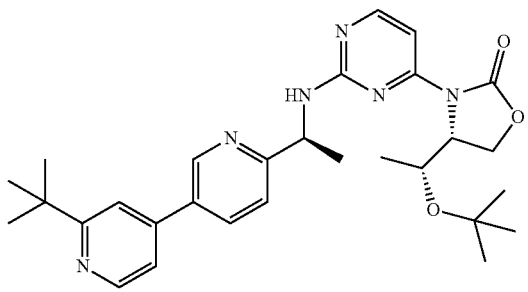 [SMILES: C[C@H](Nc1nccc(N2C(=O)OC[C@@H]2[C@@H](C)OC(C)(C)C)n1)c1ccc(-c2ccnc(C(C)(C)C)c2)cn1]

LCMS tR=1.67 min; MS m/z 519.3 (M+H).

Intermediate 107: (R)-4-((R)-1-(tert-butoxy)ethyl)-3-(2-(((S)-1-(2'-(1,1,1-trifluoro-2-methylpropan-2-yl)-[3,4'-bipyridin]-6-yl)ethyl)amino)pyrimidin-4-yl)oxazolidin-2-one

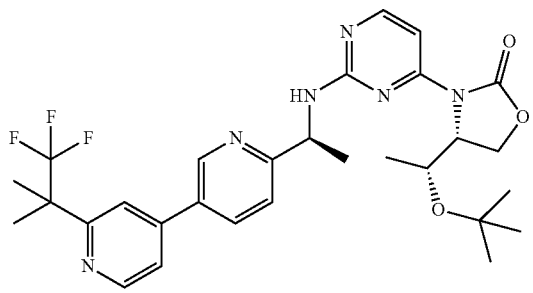 [SMILES: C[C@H](Nc1nccc(N2C(=O)OC[C@@H]2[C@@H](C)OC(C)(C)C)n1)c1ccc(-c2ccnc(C(C)(C)C(F)(F)F)c2)cn1]

¹H NMR (400 MHz, CDCl3) δ 8.83 (d, J=2.2 Hz, 1H), 8.73 (d, J=5.1 Hz, 1H), 8.23 (d, J=5.6 Hz, 1H), 7.90 (dd, J=8.1, 2.3 Hz, 1H), 7.68 (s, 1H), 7.50 (d, J=5.8 Hz, 1H), 7.47-7.41 (m, 2H), 5.34 (p, J=6.9 Hz, 1H), 4.81-4.72 (m, 1H), 4.64 (dd, J=9.3, 2.9 Hz, 1H), 4.45 (p, J=6.3 Hz, 1H), 4.36 (t, J=9.0 Hz, 1H), 1.69 (s, 6H), 1.63 (d, J=6.9 Hz, 3H), 1.26 (s, 9H), 1.04 (d, J=6.4 Hz, 3H); MS m/z 573.3 (M+H).

Intermediate 108: (S)-4-(1-(tert-butoxycarbonylamino)ethyl)-2-fluorobenzoic acid

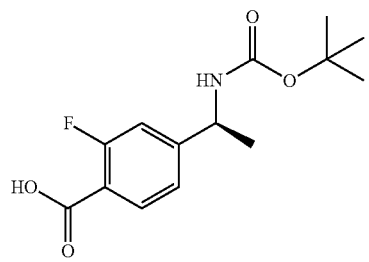 [SMILES: C[C@H](NC(=O)OC(C)(C)C)c1ccc(C(=O)O)c(F)c1]

To a solution of (S)-4-(1-aminoethyl)-2-fluorobenzoic acid (5 g, 22.76 mmol) in water (66 mL) and THF (66 mL) was added di-tert-butyl dicarbonate (6.95 g, 31.9 mmol) and sodium carbonate (5.74 g, 68.3 mmol). The solution was stirred for 16 h at room temperature then THF was removed under reduced pressure. The aqueous solution was acidified with 1N HCl to pH 3-4 and extracted with EtOAc (3×60 mL). Combined organics were dried over Na2SO4, filtered and concentrated to give a white solid (1.94 g, 30.1% yield). The crude product was used to next step without further purification.

¹H NMR (400 MHz, MeOD) δ 7.89 (t, J=7.8 Hz, 1H), 7.20 (dd, J=8.2, 1.7 Hz, 1H), 7.13 (dd, J=12.0, 1.6 Hz, 1H), 4.70 (d, J=7.1 Hz, 1H), 1.47-1.35 (m, 12H); MS m/z 282.0 (M−H).

Intermediate 109: (S)-tert-butyl 1-(3-fluoro-4-(methoxy(methyl)carbamoyl)phenyl)ethylcarbamate

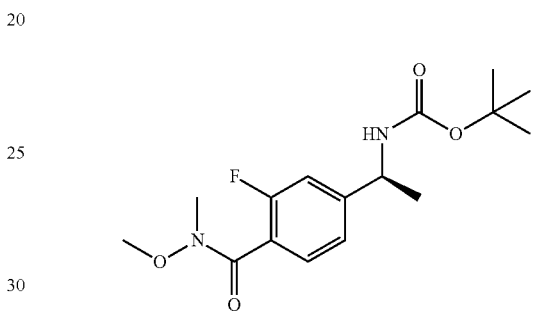

A solution of (S)-4-(1-(tert-butoxycarbonylamino)ethyl)-2-fluorobenzoic acid (1.416 g, 5 mmol), N,O-dimethylhydroxylamine hydrochloride (732 mg, 7.5 mmol), HATU (2.85 g, 7.5 mmol) and DIPEA (3.49 mL, 20 mmol) in DMF (25 mL) was stirred at room temperature for 16 h. The reaction mixture was diluted with EtOAc and washed with water. After separation, the aqueous phase was washed with EtOAc (2×75 mL). Combined organics were dried over Na2SO4, filtered and concentrated. Silica gel column chromatography (EtOAc/heptane 12 to 100%) provided (S)-tert-butyl 1-(3-fluoro-4-(methoxy(methyl)carbamoyl)phenyl)ethylcarbamate as a white solid (1.5 g, 92% yield).

¹H NMR (400 MHz, CDCl3) δ 7.40 (t, J=7.4 Hz, 1H), 7.13 (dd, J=7.8, 1.6 Hz, 1H), 7.04 (dd, J=10.7, 1.6 Hz, 1H), 4.80 (br s, 1H), 3.56 (s, 3H), 3.34 (s, 3H), 1.50-1.29 (m, 12H); MS m/z 327.1 (M+H).

Intermediate 110: (S)-tert-butyl 1-(3-fluoro-4-formylphenyl)ethylcarbamate

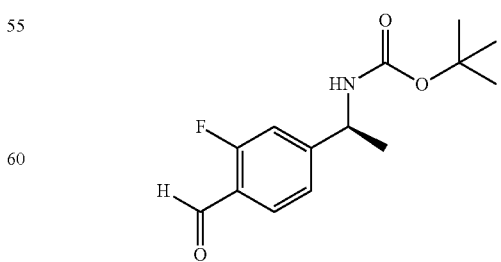

To a cooled (0° C.) solution of (S)-tert-butyl 1-(3-fluoro-4-(methoxy(methyl)carbamoyl)phenyl)ethylcarbamate (1.175 g, 3.6 mmol) in THF (36 mL) was added a solution of LAH in THF (1.0 M, 18 mL, 18 mmol) and the resulting mixture was stirred at 0° C. for 20 min. The reaction mixture was quenched by addition of a saturated Na2SO4 solution until gas evolution ceased. The reaction mixture was extracted with EtOAc (2×100 mL). Combined organics were dried over Na2SO4, filtered and concentrated. Silica gel column chromatography (EtOAc/heptane 12 to 100%) provided (S)-tert-butyl 1-(3-fluoro-4-formylphenyl)ethylcarbamate as a white solid (760 mg, 79% yield).

$^{1}$H NMR (400 MHz, CDCl3) δ 10.31 (s, 1H), 7.87-7.80 (m, 1H), 7.20 (dd, J=8.2, 1.3 Hz, 1H), 7.11 (dd, J=11.5, 1.4 Hz, 1H), 4.80 (br s, 1H), 1.45 (br s, 12H); MS m/z 212.1 (M−56+H).

Intermediate 111: (S)-tert-butyl 1-(3-fluoro-4-((3,3,4-trimethylpiperazin-1-yl)methyl)phenyl)ethylcarbamate

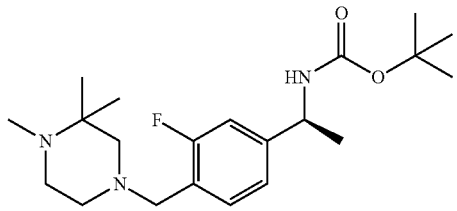 [SMILES: C[C@H](NC(=O)OC(C)(C)C)c1ccc(CN2CCN(C)C(C)(C)C2)c(F)c1]

A solution of (S)-tert-butyl 1-(3-fluoro-4-formylphenyl)ethylcarbamate (267 mg, 1 mmol) and 1,2,2-trimethylpiperazine dihydrochloride (402 mg, 2 mmol) in THF (5 mL) was stirred at room temperature for 1 h and treated with sodium triacetoxyborohydride (848 mg, 4 mmol). The resulting mixture was stirred at room temperature for 16 h. The reaction mixture was quenched with saturated aqueous solution of NaHCO3 (15 mL) and extracted with EtOAc (3×25 mL). Combined organics were dried over Na2SO4, filtered and concentrated. Silica gel column chromatography (MeOH/CH2Cl2 0 to 10%) provided (S)-tert-butyl 1-(3-fluoro-4-((3,3,4-trimethylpiperazin-1-yl)methyl)phenyl)ethylcarbamate as a white solid (186 mg, 49% yield). $^{1}$H NMR (400 MHz, CDCl3) δ 7.35 (t, J=7.7 Hz, 1H), 7.03 (dd, J=7.9, 1.9 Hz, 1H), 6.95 (dd, J=11.1, 1.8 Hz, 1H), 4.77 (s, 1H), 3.49 (s, 2H), 2.56 (br s, 4H), 2.24 (br s, 5H), 1.42 (br s, 12H), 1.04 (s, 6H); MS m/z 380.4 (M+H).

Intermediate 112: (S)-tert-butyl 1-(4-((4,4-difluoropiperidin-1-yl)methyl)-3-fluorophenyl)ethylcarbamate

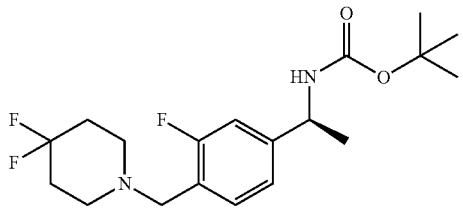 [SMILES: C[C@H](NC(=O)OC(C)(C)C)c1ccc(CN2CCC(F)(F)CC2)c(F)c1]

Following the procedure for intermediate 111: Title compound was prepared from (S)-tert-butyl 1-(3-fluoro-4-form-ylphenyl)ethylcarbamate and 4,4-difluoropiperidine hydrochloride as a white solid. LCMS tR=1.63 min; MS m/z 371.5 (M−H).

Intermediate 113: 1-(5-(3-(trifluoromethyl)phenyl)pyrimidin-2-yl)ethanone

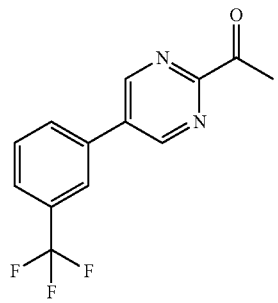 [SMILES: CC(=O)c1ncc(-c2cccc(C(F)(F)F)c2)cn1]

A cloudy solution of 1-(5-bromopyrimidin-2-yl)ethanone (300 mg, 1.49 mmol), 3-(trifluoromethyl)phenylboronic acid (567 mg, 2.98 mmol), K3PO4 (950 mg, 4.48 mmol), DavePhos ligand [2-dicyclohexylphosphino-2'-(N,N-dimethylamino)biphenyl] (59 mg, 0.15 mmol), and Pd(OAc)2 (17 mg, 0.075 mmol) in 6 mL toluene was heated at 100° C. for 1 h. The mixture was cooled to room temperature, and filtered through Celite. Filter cake was rinsed with 30 mL EtOAc. The filtrate was poured into 20 mL water. Layers were separated, and the aqueous was further extracted with EtOAc (20 mL). Combined organics were washed with water (20 mL) and brine (20 mL), dried over Na2SO4, filtered and concentrated directly onto silica gel. Column chromatography (10-100% EtOAc/heptane) gave 0.26 g 1-(5-(3-(trifluoromethyl)phenyl)pyrimidin-2-yl)ethanone as tan solid. MS m/z 267.1 (M+H)+. $^{1}$H NMR (400 MHz, CDCl3) δ 9.16 (s, 2H), 7.93-7.69 (m, 4H), 2.87 (s, 3H).

The intermediates in Table 6a were prepared using a method similar to that described for the preparation of Intermediate 113

TABLE 6a

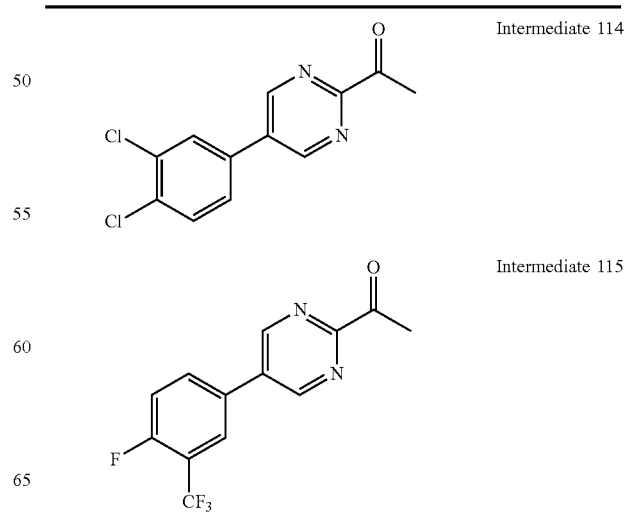

Intermediate 114

Intermediate 115

TABLE 6a-continued

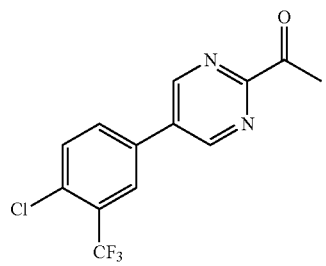 [SMILES: CC(=O)c1ncc(-c2ccc(Cl)c(C(F)(F)F)c2)cn1]

Intermediate 116

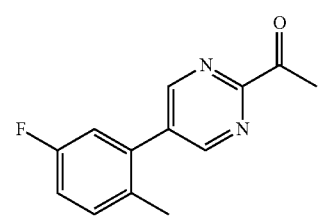 [SMILES: CC(=O)c1ncc(-c2cc(F)ccc2C)cn1]

Intermediate 117

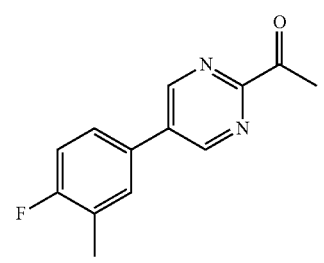 [SMILES: CC(=O)c1ncc(-c2ccc(F)c(C)c2)cn1]

Intermediate 118

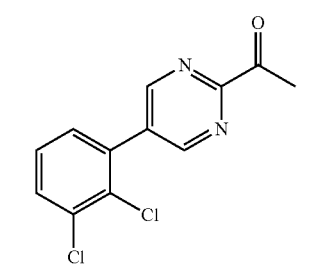 [SMILES: CC(=O)c1ncc(-c2cccc(Cl)c2Cl)cn1]

Intermediate 119

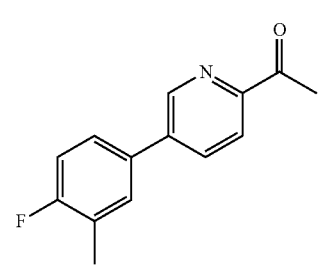 [SMILES: CC(=O)c1ccc(-c2ccc(F)c(C)c2)cn1]

Intermediate 120

TABLE 6a-continued

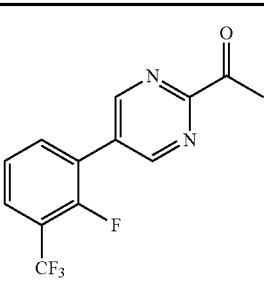

Intermediate 121

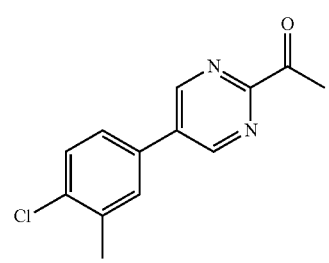 [SMILES: CC(=O)c1ncc(-c2ccc(Cl)c(C)c2)cn1]

Intermediate 122

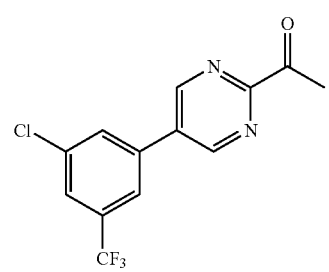 [SMILES: CC(=O)c1ncc(-c2cc(Cl)cc(C(F)(F)F)c2)cn1]

Intermediate 123

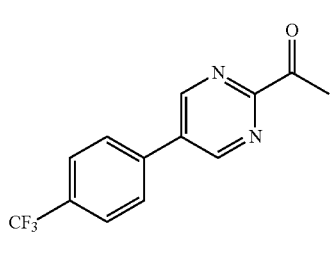 [SMILES: CC(=O)c1ncc(-c2ccc(C(F)(F)F)cc2)cn1]

Intermediate 124

TABLE 6b

Chemical name and analytical data for each intermediate listed in Table 6a, using Anal. RP-HPLC Column = Inertsil C8 Column, 3.0 μm, 3.0 × 30 mm. Column Temperature = 50° C. Eluents = A: Water (5 mM Ammonium formate, 2% ACN); B: ACN. Flow Rate = 2 mL/min. Gradient = 0 min 5% B; 5% to 95% B in 1.70 min; 0.3 min 95% B; 2.1 min 1% B.)

| Intermediate: Name | Analytical data |
| --- | --- |
| 114: 1-(5-(3,4-dichlorophenyl) pyrimidin-2-yl)ethanone. | Anal. RP-HPLC tR = 1.17 min. MS m/z 266.9 (M + H)+. |
| 115: 1-(5-(4-fluoro-3-(trifluoromethyl)phenyl) pyrimidin-2-yl)ethanone. | Anal. RP-HPLC tR = 1.26 min. MS m/z 285.2 (M + H)+. |
| 116: 1-(5-(4-chloro-3-(trifluoromethyl)phenyl) pyrimidin-2-yl)ethanone. | Anal. RP-HPLC tR = 1.33 min. MS m/z 301.3 (M + H)+. |

TABLE 6b-continued

Chemical name and analytical data for each intermediate listed in Table 6a, using Anal. RP-HPLC Column = Inertsil C8 Column, 3.0 µm, 3.0 × 30 mm. Column Temperature = 50° C. Eluents = A: Water (5 mM Ammonium formate, 2% ACN); B: ACN. Flow Rate = 2 mL/min. Gradient = 0 min 5% B; 5% to 95% B in 1.70 min; 0.3 min 95% B; 2.1 min 1% B.)

| Intermediate: Name | Analytical data |
|---|---|
| 117:: 1-(5-(5-fluoro-2-methylphenyl) pyrimidin-2-yl)ethanone | Anal. RP-HPLC tR = 1.16 min. MS m/z 231.2 (M + H)+. |
| 118: 1-(5-(4-fluoro-3-methylphenyl) pyrimidin-2-yl)ethanone. | $^1$H NMR (400 MHz, CDCl$_3$) δ 9.09 (s, 2H), 7.52-7.41 (m, 2H), 7.24-7.16 (m, 1H), 2.85 (s, 3H), 2.41 (d, J = 2.0 Hz, 3H). Anal. RP-HPLC tR = 1.20 min. MS m/z 231.0 (M + H)+. |
| 119: 1-(5-(2,3-dichlorophenyl) pyrimidin-2-yl)ethanone | Anal. RP-HPLC tR = 1.15 min. MS m/z 267.9 (M + H)+. |
| 120: 1-(5-(4-fluoro-3-methylphenyl) pyridin-2-yl)ethanone. | $^1$H NMR (400 MHz, CDCl$^3$) δ 8.88 (dd, J = 2.3, 0.8 Hz, 1H), 8.13 (dd, J = 8.1, 0.8 Hz, 1H), 7.98 (dd, J = 8.1, 2.3 Hz, 1H), 7.50-7.39 (m, 2H), 7.21-7.12 (m, 1H), 2.78 (s, 3H), 2.42-2.36 (m, 3H). Anal. RP-HPLC tR = 1.40 min. MS m/z 230.8 (M + H)+. |
| 121: 1-(5-(2-fluoro-3-(trifluoromethyl)phenyl) pyrimidin-2-yl)ethanone. | Anal. RP-HPLC tR = 1.19 min. MS m/z 285.0 (M + H)+. |
| 122: 1-(5-(4-chloro-3-methylphenyl) pyrimidin-2-yl)ethanone. | Anal. RP-HPLC tR = 1.30 min. MS m/z 247.2 (M + H)+. |
| 123: 1-(5-(3-chloro-5-(trifluoromethyl)phenyl) pyrimidin-2-yl)ethanone. | Anal. RP-HPLC tR = 1.27 min. MS m/z 301.0 (M + H)+. |
| 124: 1-(5-(4-(trifluoromethyl)phenyl) pyrimidin-2-yl)ethanone. | Anal. RP-HPLC tR = 1.22 min. MS m/z 266.8 (M + H)+. |

Intermediate 125: (S)-1-(3-(4-chlorophenyl)-1,2,4-oxadiazol-5-yl)ethanamine

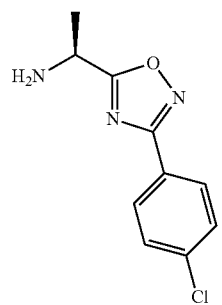

2,2,2-Trifluoroacetic acid (4 mL, 52 mmol) was added to a solution of (S)-tert-butyl 1-(3-(4-chlorophenyl)-1,2,4-oxadiazol-5-yl)ethylcarbamate (0.613 g, 1.89 mmol) in DCM (10 mL) at room temperature. The solution was stirred at room temperature for 1 hour and then concentrated in vacuo. The residue was dissolved in chloroform (100 mL) and washed with saturated aqueous sodium bicarbonate (100 mL). The layers were separated and the aqueous layer was extracted with chloroform (3×30 mL) and the combined organic layers were dried over anhydrous sodium sulfate, filtered and concentrated in vacuo to give (S)-1-(3-(4-chlorophenyl)-1,2,4-oxadiazol-5-yl)ethanamine (500 mg, yellow oil). The material was used without further purification. $^1$H NMR (400 MHz, CDCl$_3$) δ 8.04 (d, J=8.7 Hz, 2H), 7.47 (d, J=8.6 Hz, 2H), 4.37 (q, J=6.9 Hz, 1H), 1.62 (d, J=6.9 Hz, 3H). MS m/z 224.0 (M+H)$^+$; Rt-0.56 min.

Intermediate 126 (S)-1-(3-(3-chloro-4-(trifluoromethoxy)phenyl)-1,2,4-oxadiazol-5-yl)ethanamine

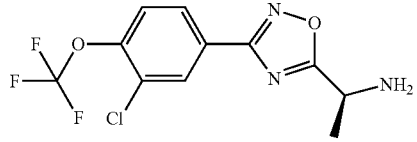 [SMILES: C[C@H](N)c1nc(-c2ccc(OC(F)(F)F)c(Cl)c2)no1]

(S)-tert-butyl (1-(3-(3-chloro-4-(trifluoromethoxy)phenyl)-1,2,4-oxadiazol-5-yl)ethyl)carbamate (2.0 g, 4.90 mmol) was treated with 90% TFA/water for 2 hours. Concentrate in vacuo and neutralized by passing through a column of MP-carbonate resin (6.0 g, 0.55 mmol/g eluting with MeOH/DCM/MeOH afforded 1.4 g waxy off-white solid. HRMS m/z 307.0335

Intermediate 127 (S)-1-(3-(3-chlorophenyl)-1,2,4-oxadiazol-5-yl)ethanamine

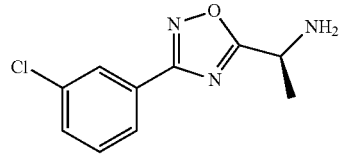

To a stirred solution of (S)-2-(1-(3-(3-chlorophenyl)-1,2,4-oxadiazol-5-yl)ethyl)isoindoline-1,3-dione (100 mg, 0.283 mmol) in ethanol (5 ml) was added methylhydrazine (16 µL, 0.311 mmol). Stir for 13 hours at 80° C. Concentrate in vacuo. Flash column chromatography (silica, 40 g) eluting with dichloromethane afforded 50 mg of desired product. HRMS m/z 224.4 (M+H)

The intermediates in Table 7a were prepared using a method similar to that described for the preparation of Intermediate 126 or Intermediate 127

TABLE 7a

| Structure | Name |
|---|---|
| 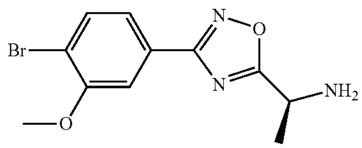 | Intermediate 128 |
| 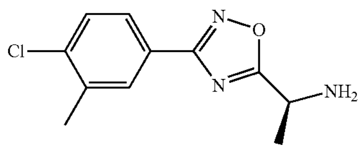 [SMILES: Cc1cc(-c2noc([C@H](C)N)n2)ccc1Cl] | Intermediate 129 |
| 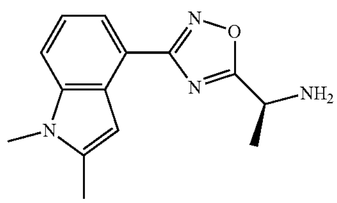 [SMILES: Cc1cc2c(-c3noc([C@H](C)N)n3)cccc2n1C] | Intermediate 130 |
| 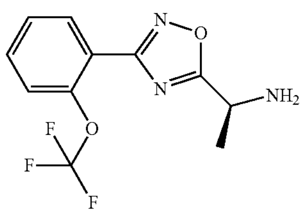 [SMILES: C[C@H](N)c1nc(-c2ccccc2OC(F)(F)F)no1] | Intermediate 131 |
| 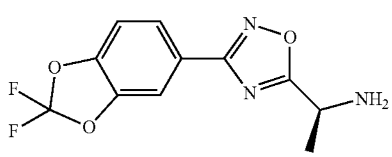 [SMILES: C[C@H](N)c1nc(-c2ccc3c(c2)OC(F)(F)O3)no1] | Intermediate 132 |
| 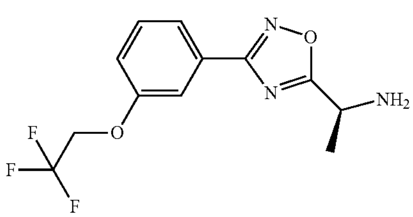 [SMILES: C[C@H](N)c1nc(-c2cccc(OCC(F)(F)F)c2)no1] | Intermediate 133 |
| 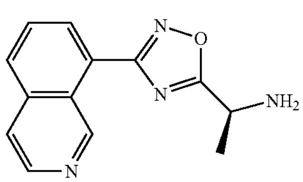 [SMILES: C[C@H](N)c1nc(-c2cccc3ccncc23)no1] | Intermediate 134 |
| 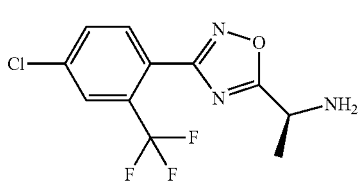 [SMILES: C[C@H](N)c1nc(-c2ccc(Cl)cc2C(F)(F)F)no1] | Intermediate 135 |

TABLE 7a-continued

| Structure | Name |
|---|---|
| 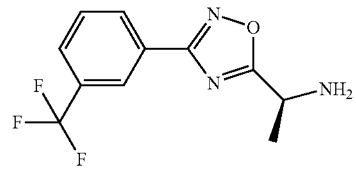 [SMILES: C[C@H](N)c1nc(-c2cccc(C(F)(F)F)c2)no1] | Intermediate 136 |
| 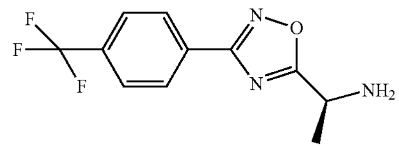 [SMILES: C[C@H](N)c1nc(-c2ccc(C(F)(F)F)cc2)no1] | Intermediate 137 |
| 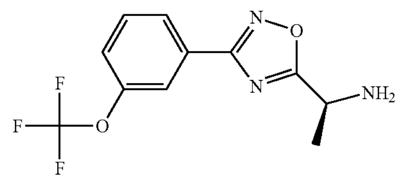 [SMILES: C[C@H](N)c1nc(-c2cccc(OC(F)(F)F)c2)no1] | Intermediate 138 |
| 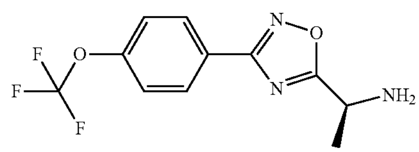 | Intermediate 139 |
| 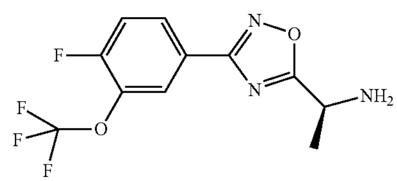 [SMILES: C[C@H](N)c1nc(-c2ccc(F)c(OC(F)(F)F)c2)no1] | Intermediate 140 |
| 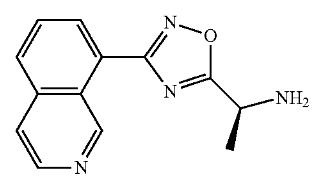 [SMILES: C[C@H](N)c1nc(-c2cccc3ccncc23)no1] | Intermediate 141 |
| 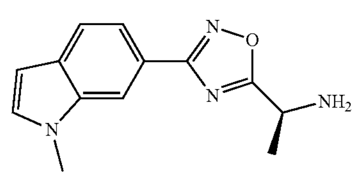 [SMILES: C[C@H](N)c1nc(-c2ccc3ccn(C)c3c2)no1] | Intermediate 142 |
| 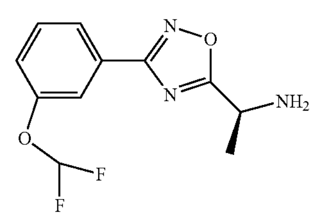 [SMILES: C[C@H](N)c1nc(-c2cccc(OC(F)F)c2)no1] | Intermediate 143 |
| 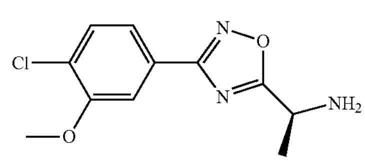 [SMILES: COc1cc(-c2noc([C@H](C)N)n2)ccc1Cl] | Intermediate 144 |

TABLE 7a-continued

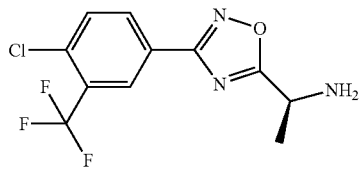
Intermediate 145

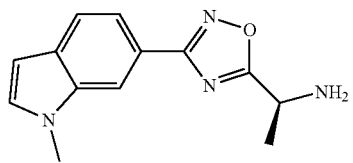 [SMILES: C[C@H](N)c1nc(-c2ccc3ccn(C)c3c2)no1]
Intermediate 146

TABLE 7a-continued

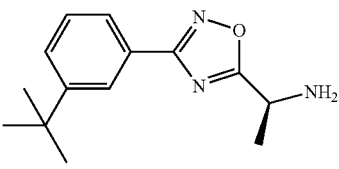 [SMILES: C[C@H](N)c1nc(-c2cccc(C(C)(C)C)c2)no1]
Intermediate 147

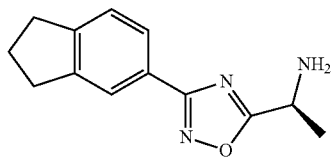 [SMILES: C[C@H](N)c1nc(-c2ccc3c(c2)CCC3)no1]
Intermediate 148

TABLE 7b

Chemical name and analytical data for each intermediate listed in Table 7a.

| Intermediate: Name | Analytical data |
| --- | --- |
| 128: (S)-1-(3-(4-bromo-3-methoxyphenyl)-1,2,4-oxadiazol-5-yl)ethanamine | HRMS(B) tR = 1.88 min; m/z 297.0113 |
| 129: (S)-1-(3-(4-chloro-3-methylphenyl)-1,2,4-oxadiazol-5-yl)ethanamine | HRMS(B) tR = 2.05 min; m/z 237.0669 |
| 130: (S)-1-(3-(1,2-dimethyl-1H-indol-4-yl)-1,2,4-oxadiazol-5-yl)ethanamine | HRMS(B) tR = 1.38 min; m/z 256.1324 |
| 131: (S)-1-(3-(2-(trifluoromethoxy)phenyl)-1,2,4-oxadiazol-5-yl)ethanamine | HRMS(B) tR = 1.92 min; m/z 273.0725 |
| 132: (S)-1-(3-(2,2-difluorobenzo[d][1,3]dioxol-5-yl)-1,2,4-oxadiazol-5-yl)ethanamine | HRMS(B) tR = 2.04 min; m/z 269.0612 |
| 133: (S)-1-(3-(3-(2,2,2-trifluoroethoxy)phenyl)-1,2,4-oxadiazol-5-yl)ethanamine | HRMS(B) tR = 2.02 min; m/z 287.0882 |
| 134: (S)-1-(3-(isoquinolin-8-yl)-1,2,4-oxadiazol-5-yl)ethanamine | HRMS(B) tR = 0.68 min; m/z 240.1011 |
| 135: (S)-1-(3-(4-chloro-2-(trifluoromethyl)phenyl)-1,2,4-oxadiazol-5-yl)ethanamine | HRMS(B) tR = 2.08 min; m/z 291.0386 |
| 136: (S)-1-(3-(3-(trifluoromethyl)phenyl)-1,2,4-oxadiazol-5-yl)ethanamine | HRMS(B) tR = 2.02 min; m/z 257.0776 |
| 137: (S)-1-(3-(4-(trifluoromethyl)phenyl)-1,2,4-oxadiazol-5-yl)ethanamine | HRMS(B) tR = 2.01 min; m/z 257.0776 |
| 138: (S)-1-(3-(3-(trifluoromethoxy)phenyl)-1,2,4-oxadiazol-5-yl)ethanamine | HRMS(B) tR = 1.20 min; m/z 274.0 (M + H) |
| 139: (S)-1-(3-(4-(trifluoromethoxy)phenyl)-1,2,4-oxadiazol-5-yl)ethanamine | HRMS(B) tR = 2.09 min; m/z 273.0725 |
| 140: (S)-1-(3-(4-fluoro-3-(trifluoromethoxy)phenyl)-1,2,4-oxadiazol-5-yl)ethanamine | HRMS(B) tR = 2.16 min; m/z 291.0631 |
| 141: (S)-1-(3-(isoquinolin-8-yl)-1,2,4-oxadiazol-5-yl)ethanamine | HRMS(B) tR = 0.71 min; m/z 240.1011 |
| 142: (S)-1-(3-(1-methyl-1H-indol-6-yl)-1,2,4-oxadiazol-5-yl)ethanamine | HRMS(B) tR = 1.67 min; m/z 242.1168 |
| 143: (S)-1-(3-(3-(difluoromethoxy)phenyl)-1,2,4-oxadiazol-5-yl)ethanamine | HRMS(B) tR = 1.74 min; m/z 255.0819 |
| 144: (S)-1-(3-(4-chloro-3-methoxyphenyl)-1,2,4-oxadiazol-5-yl)ethanamine | HRMS(B) tR = 1.82 min; m/z 253.0618 |
| 145: (S)-1-(3-(4-chloro-3-(trifluoromethyl)phenyl)-1,2,4-oxadiazol-5-yl)ethanamine | HRMS(B) tR = 2.26 min; m/z 291.0386 |
| 146: (S)-1-(3-(1-methyl-1H-indol-6-yl)-1,2,4-oxadiazol-5-yl)ethanamine | HRMS(B) tR = 1.67 min; m/z 242.1168 |
| 147: (S)-1-(3-(3-(tert-butyl)phenyl)-1,2,4-oxadiazol-5-yl)ethanamine | HRMS(B) tR = 2.33 min; m/z 246.1552 |
| 148: (S)-1-(3-(2,3-dihydro-1H-inden-5-yl)-1,2,4-oxadiazol-5-yl)ethanamine | HRMS(B) tR = 2.02 min; m/z 229.1215 |

Intermediate 149: 1-(5-(3-(trifluoromethyl)phenyl)pyrimidin-2-yl)ethanamine

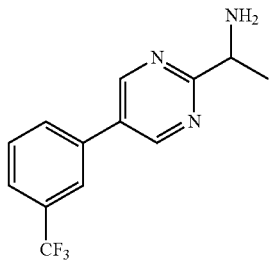 [SMILES: CC(N)c1ncc(-c2cccc(C(F)(F)F)c2)cn1]

1-(5-(3-(Trifluoromethyl)phenyl)pyrimidin-2-yl)ethanone (260 mg, 0.977 mmol), NH4OAc (1.13 g, 14.6 mmol), and NaBH3CN (245 mg, 3.91 mmol) were taken up in 8 mL 200 proof EtOH, and heated at 120° C. for 5 minutes in a microwave apparatus. The mixture was concentrated to remove the EtOH. Crude was taken up in 30 ml water+25 mL EtOAc. 6N NaOH was added until aqueous pH was ~10. Separated layers, and extracted aqueous with EtOAc (25 ml). The combined organic layer was washed with 25 mL brine and dried with Na$_2$SO$_4$. Filtered and concentrated with reduced pressure to give 262 mg crude yellow oil, which was carried forward without further purification. Anal. RP-HPLC tR=0.90 min. (Column=Inertsil C8 Column, 3.0 µm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 268.1 (M+H)+.

The intermediates in Table 8a were prepared using a method similar to that described for the preparation of Intermediate 149

TABLE 8a

| Structure | Intermediate |
|---|---|
| 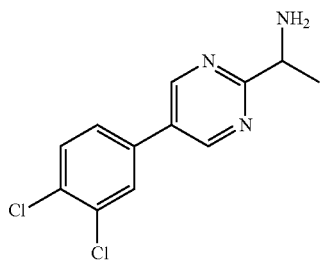 [SMILES: CC(N)c1ncc(-c2ccc(Cl)c(Cl)c2)cn1] | Intermediate 150 |
| 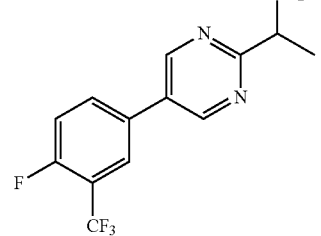 | Intermediate 151 |

TABLE 8a-continued

| Structure | Intermediate |
|---|---|
| 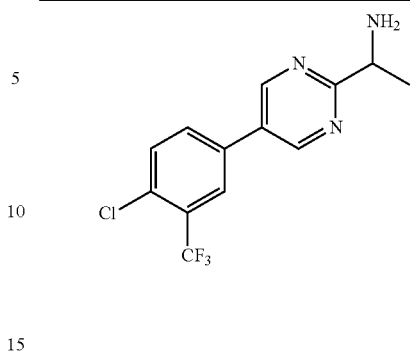 | Intermediate 152 |
| 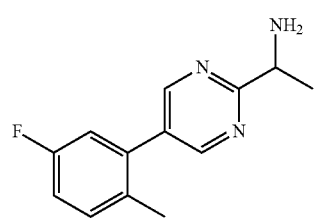 [SMILES: Cc1ccc(F)cc1-c1cnc(C(C)N)nc1] | Intermediate 153 |
| 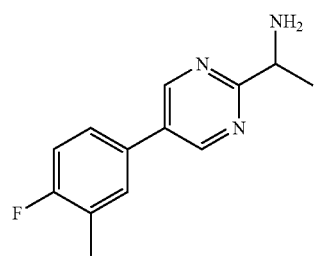 [SMILES: Cc1cc(-c2cnc(C(C)N)nc2)ccc1F] | Intermediate 154 |
| 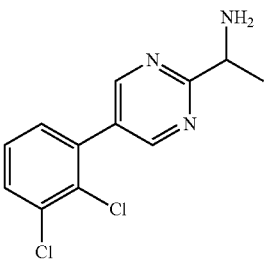 [SMILES: CC(N)c1ncc(-c2cccc(Cl)c2Cl)cn1] | Intermediate 155 |
| 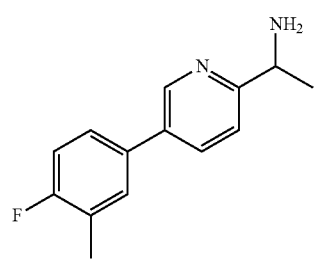 | Intermediate 156 |

TABLE 8a-continued

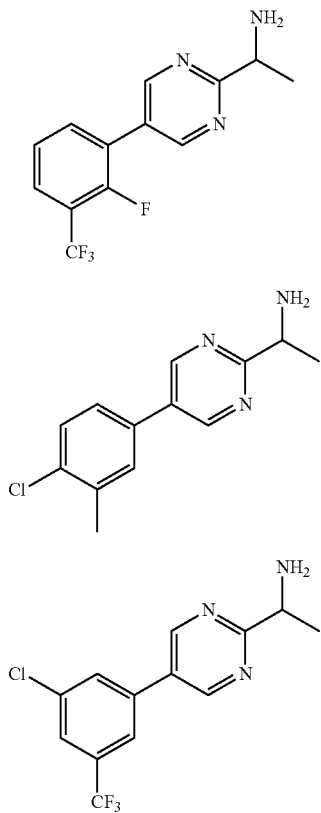
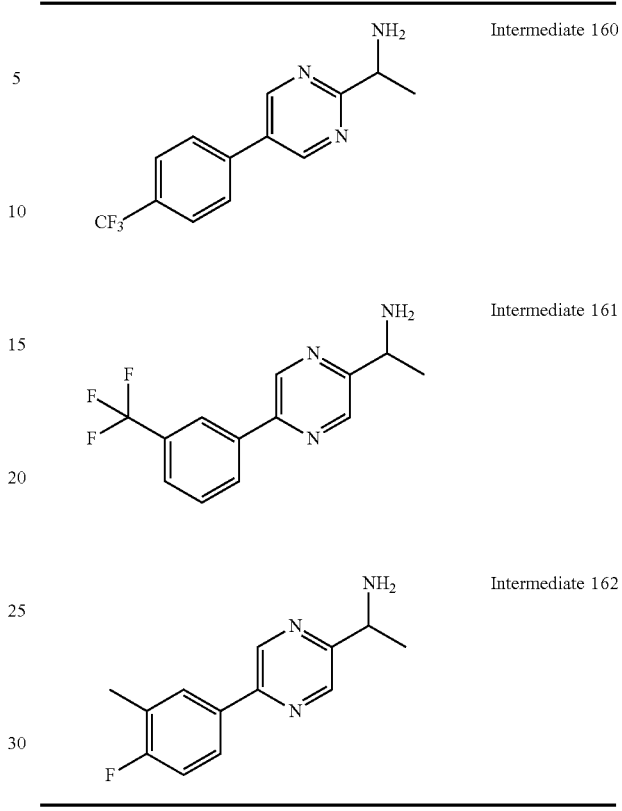

TABLE 8b

Chemical name and analytical data for each intermediate listed in Table 8a.

| Intermediate: Name | Analytical data |
| --- | --- |
| 150: 1-(5-(3,4-dichlorophenyl)pyrimidin-2-yl)ethanamine. | Anal. RP-HPLC tR = 1.09 min; MS m/z 268.4 (M + H)+. |
| 151: 1-(5-(4-fluoro-3-(trifluoromethyl)phenyl)pyrimidin-2-yl)ethanamine. | Anal. RP-HPLC tR = 1.04 min. MS m/z 286.3 (M + H)+. |
| 152: 1-(5-(4-chloro-3-(trifluoromethyl)phenyl)pyrimidin-2-yl)ethanamine. | Anal. RP-HPLC tR = 1.06 min. MS m/z 302.3 (M + H)+. |
| 153: 1-(5-(5-fluoro-2-methylphenyl)pyrimidin-2-yl)ethanamine | Anal. RP-HPLC tR = 0.79 min. MS m/z 232.0 (M + H)+. |
| 154: 1-(5-(4-fluoro-3-methylphenyl)pyrimidin-2-yl)ethanamine | Anal. RP-HPLC tR = 0.81 min. MS m/z 231.9 (M + H)+. |
| 155: 1-(5-(2,3-dichlorophenyl)pyrimidin-2-yl)ethanamine | Anal. RP-HPLC tR = 1.01 min. MS m/z 269.0 (M + H)+. |
| 156: 1-(5-(4-fluoro-3-methylphenyl)pyridin-2-yl)ethanamine | Anal. RP-HPLC tR = 0.92 min. MS m/z 230.9 (M + H)+. |
| 157: 1-(5-(2-fluoro-3-(trifluoromethyl)phenyl)pyrimidin-2-yl)ethanamine. | Anal. RP-HPLC tR = 0.96 min. MS m/z 286.0 (M + H)+. |
| 158: 1-(5-(4-chloro-3-methylphenyl)pyrimidin-2-yl)ethanamine. | Anal. RP-HPLC tR = 0.97 min. MS m/z 247.9 (M + H)+. |
| 159: 1-(5-(3-chloro-5-(trifluoromethyl)phenyl)pyrimidin-2-yl)ethanamine. | Anal. RP-HPLC tR = 1.06 min. MS m/z 301.9 (M + H)+. |
| 160: 1-(5-(4-(trifluoromethyl)phenyl)pyrimidin-2-yl)ethanamine. | Anal. RP-HPLC tR = 1.02 min. MS m/z 268.2 (M + H)+. |
| 161 : 1-(5-(3-(trifluoromethyl)phenyl)pyrazin-2-yl)ethanamine | LCMS tR = 1.04 min; MS m/z 267.9 (M + H)+. |
| 162: 1-(5-(4-fluoro-3-methylphenyl)pyrazin-2-yl)ethanamine | LCMS tR = 0.91 min; MS m/z 231.9 (M + H)+. |

Intermediate 163: 1-(5-(4-fluorophenoxy)pyrimidin-2-yl)ethanamine

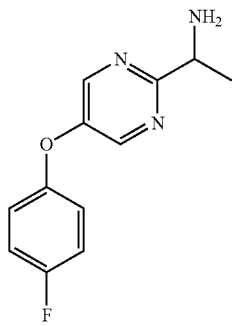 [SMILES: CC(N)c1ncc(Oc2ccc(F)cc2)cn1]

Step 1: A solution of 1-(5-fluoropyrimidin-2-yl)ethanone (700 mg, 5.0 mmol) and 4-fluorophenol (616 mg, 5.50 mmol) in 6 mL DMF was treated with potassium carbonate (829 mg 6.0 mmol) and heated to 50° C. for 3.5 h. The reaction mixture was poured into 20 mL water, and extracted with EtOAc (2×20 mL). Organics were washed with 20 mL each water, brine, and dried over $Na_2SO_4$. Mixture was filtered and concentrated on silica gel. Column chromatography (10-100% EtOAc/hept) gave 295 mg (25%) 1-(5-(4-fluorophenoxy)pyrimidin-2-yl)ethanone as a white solid used directly in the following step. MS m/z 233.2 (M+H)+. $^1$H NMR (400 MHz, $CDCl_3$) δ 8.55 (s, 2H), 7.23-7.07 (m, 4H), 2.78 (s, 3H).

Step 2: 1-(5-(4-fluorophenoxy)pyrimidin-2-yl)ethanone (290 mg, 1.25 mmol), NH4OAc (1.9 g, 24.6 mmol), and $NaBH_3CN$ (314 mg, 5.00 mmol) were taken up in 20 mL 200 proof EtOH, and heated at 130 C for 3 minutes in a microwave apparatus. The mixture was concentrated to remove the EtOH. Crude was taken up in 30 ml water+25 mL EtOAc. 6N NaOH was added until aqueous pH was ~10. Separated layers, and extracted aqueous with EtOAc (25 ml). The combined organic layer was washed with 25 mL brine and dried with $Na_2SO_4$. Filtered and concentrated with reduced pressure to give 275 mg crude tan oil, which was carried forward without further purification. Major product Anal. RP-HPLC tR=1.26 min. (Column=Inertsil C8 Column, 3.0 μm, 3.0×30 mm. Column Temperature=50° C. Eluents=A: Water (5 mM Ammonium formate, 2% ACN); B: ACN. Flow Rate=2 mL/min. Gradient=0 min 5% B; 5% to 95% B in 1.70 min; 0.3 min 95% B; 2.1 min 1% B.) MS m/z 234.1 (M+H)+.

Intermediate 164: 1-(4-methyl-5-(2-(1,1,1-trifluoro-2-methylpropan-2-yl)pyridin-4-yl)thiazol-2-yl)ethanamine

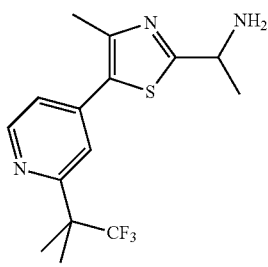 [SMILES: Cc1nc(C(C)N)sc1-c1ccnc(C(C)(C)C(F)(F)F)c1]

Step 1: In a well vented vial, 90% t-butyl nitrite (4.74 mL, 35.8 mmol) and CuCl (2.96 g, 29.9 mmol) were taken up in 30 mL ACN. Over 15 mins, 4-methyl-5-(2-(1,1,1-trifluoro-2-methylpropan-2-yl)pyridin-4-yl)thiazol-2-amine (6.0 g, 19.9 mmol) was added in portions. Gas evolved. The mixture was stirred 30 min at r.t., then warmed to 65 C for another 30 min. The reaction mixture was filtered through Celite. 200 mL Water was added to the filtrate. This was extracted with (2×150 mL) EtOAc. Organics were washed with 200 mL brine, and dried over Na2SO4. Filtered and concentrated on silica gel. Flash column chromatography (10-50% EA/hept) gave 3.35 g (52%) 2-chloro-4-methyl-5-(2-(1,1,1-trifluoro-2-methylpropan-2-yl)pyridin-4-yl)thiazole as a green oil. MS m/z 321.0 (M+H)+. 1H NMR (400 MHz, CDCl3) δ 8.69 (dd, J=5.1, 0.8 Hz, 1H), 7.52 (dq, J=1.7, 0.8 Hz, 1H), 7.31-7.22 (m, 1H), 2.55 (s, 3H), 1.67 (s, 6H).

Step 2: To a solution of 2-chloro-4-methyl-5-(2-(1,1,1-trifluoro-2-methylpropan-2-yl)pyridin-4-yl)thiazole (3.3 g, 10.3 mmol) and Pd(PPh3)2Cl2 (0.72 g, 1.03 mmol) in 50 mL dioxane under nitrogen, tributyl(1-ethoxyvinyl)stannane (3.82 ml, 11.32 mmol) was added. The mixture was heated to 100 C for 16 h. The reaction was cooled to r.t. and diluted with 25 mL EtOAc. 2M KF (15.4 ml) solution was added and stirred for 1 h. Copious precipitate formed. The reaction was filtered through Celite and chased with EtOAc. The organic layer was rinsed with 60 mL water, and concentrated to give grey solid. Crude solid was dissolved in THF (50 mL) and 1N HCl (20.58 mL) was added. The reaction was stirred at r.t. for 2 h. The mixture was neutralized by addition of 1 N NaOH. THF was removed in vacuo. Extracted aqueous with 2×50 mL EtOAc. The organic layers were washed with 50 mL brine, and dried over Na2SO4. Filtered and concentrated on silica gel. Flash chromatography using 10-50% EtOAc in heptane gave 1.65 g (49%) 1-(4-methyl-5-(2-(1,1,1-trifluoro-2-methylpropan-2-yl)pyridin-4-yl)thiazol-2-yl)ethanone as a yellow oil. MS m/z 329.0 (M+H)+. 1H NMR (400 MHz, CDCl3) δ 8.72 (dd, J=5.2, 0.9 Hz, 1H), 7.60 (dq, J=1.8, 0.9 Hz, 1H), 7.34 (dd, J=5.1, 1.6 Hz, 1H), 2.74 (s, 3H), 2.63 (s, 3H), 1.69 (s, 6H).

Step 3: 1-(4-methyl-5-(2-(1,1,1-trifluoro-2-methylpropan-2-yl)pyridin-4-yl)thiazol-2-yl)ethanone ethanone (1.6 g, 4.87 mmol), NH4OAc (5.6 g, 73.1 mmol), and NaBH3CN (1.2 g, 19.5 mmol) were taken up in 40 mL 200 proof EtOH, and heated at 130 C for 10 minutes in a sealed tube. The mixture was concentrated to remove the EtOH. Crude was taken up in 50 ml water+50 mL EtOAc. 6N NaOH was added until aqueous pH was ~9. Separated layers, and extracted aqueous with EtOAc (50 ml). The combined organic layer was washed with 60 mL brine and dried with Na2SO4. Filtered and concentrated with reduced pressure to give 1.58 g crude tan oil. This material was taken up in 20 mL dioxane. 2.2 eq HCl (4N in dioxane) was added, and stirred 1 h. Yellow ppt was formed. The suspension was concentrated in vacuo to give 1.97 g 1-(4-methyl-5-(2-(1,1,1-trifluoro-2-methylpropan-2-yl)pyridin-4-yl)thiazol-2-yl)ethanamine dihydrochloride salt as a yellow-green solid, which was carried forward without further purification. Major product Anal. RP-HPLC tR=1.23 min. MS m/z 330.1 (M+H)+.

Intermediate 165: 4-((S)-1-Amino-ethyl)-piperidine-1-carboxylic acid benzyl ester

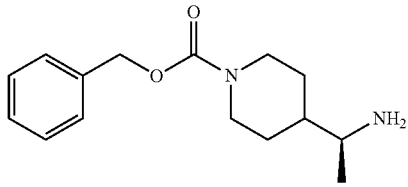 [SMILES: C[C@H](N)C1CCN(C(=O)OCc2ccccc2)CC1]

Benzyl 4-((1S)-1-(1,1-dimethylethylsulfinamido)ethyl)piperidine-1-carboxylate (1.825 g, 4.98 mmole) was dissolved in dioxane (10 mL) and 4N HCl in dioxane (5 mL, 1.3 eq.) was added. The mixture was stirred for 3 hours at room temperature. The solvents were removed by rotary evaporation to give the title compound as a hydrochloride salt (1.3 g). $^1$H NMR (400 MHz, CD2Cl2) δ 8.46 (s, 2H), 7.44-7.27 (m, 5H), 5.11 (s, 2H), 4.26 (d, J=13.57 Hz, 2H), 3.24-3.12 (m, 1H), 2.86-2.61 (m, 2H), 1.99-1.86 (m, 3H), 1.38 (d, J=6.33 Hz, 3H), 1.34-1.23 (m, 2H). HRMS(C) tR=1.87 min; MS m/z 263.1760 (M+H)+

Intermediate 166: (S)-1-(5-(4-fluoro-3-methylphenyl)pyridin-2-yl)ethanamine

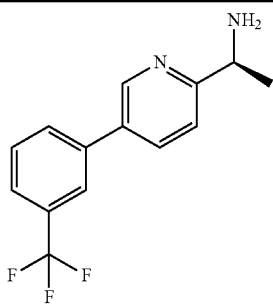

To a solution of (S)-tert-butyl (1-(5-(4-fluoro-3-methylphenyl)pyridin-2-yl)ethyl)carbamate (66 mg, 0.47 mmol) in DCM (2 mL) was added TFA (2 mL, 26 mmol) slowly at −78° C. The reaction was stirred at room temperature for 1 h then concentrated and diluted with DCM (10 mL). The solution was stirred with 3 eq. of MP-carbonate resin (3.28 mmol/g, Biotage) for 1 hr at room temperature. The resin was removed by filtration and washed (2×5 mL) with DCM. The filtrate was concentrated and the crude residue was used to next step without further purification. LCMS tR=0.97 min; MS m/z 231.1 (M+H).

The intermediates in Table 9a were prepared using a method similar to that described for the preparation of Intermediate 166

TABLE 9a

| | |
|---|---|
| 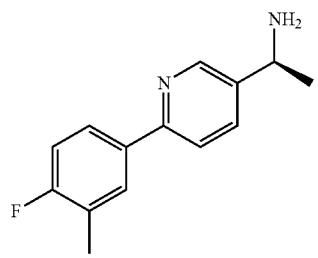 [SMILES: Cc1cc(-c2ccc([C@H](C)N)cn2)ccc1F] | Intermediate 167 |
| 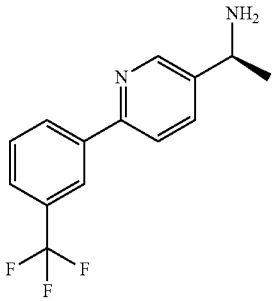 [SMILES: C[C@H](N)c1ccc(-c2cccc(C(F)(F)F)c2)nc1] | Intermediate 168 |
| 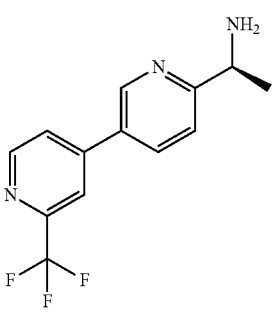 [SMILES: C[C@H](N)c1ccc(-c2ccnc(C(F)(F)F)c2)cn1] | Intermediate 169 |
| 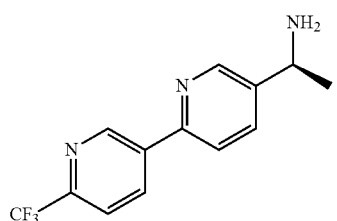 | Intermediate 170 |
| 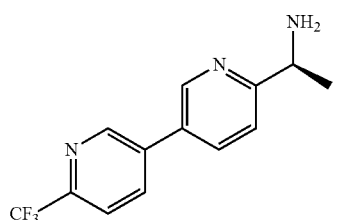 | Intermediate 171 |
| | Intermediate 172 |
| 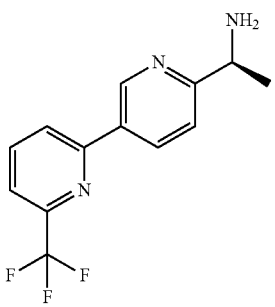 [SMILES: C[C@H](N)c1ccc(-c2cccc(C(F)(F)F)n2)cn1] | Intermediate 173 |

TABLE 9a-continued

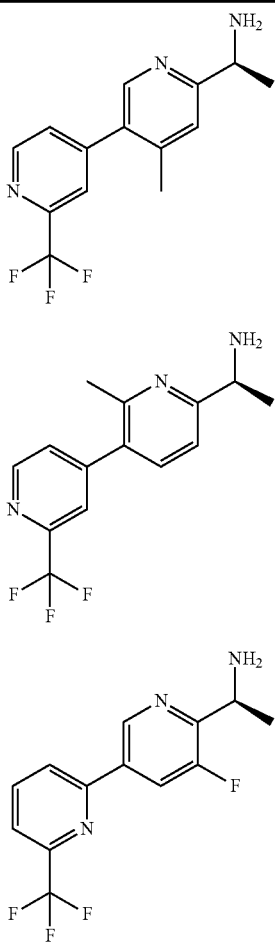

Intermediate 174

Intermediate 175

Intermediate 176

TABLE 9a-continued

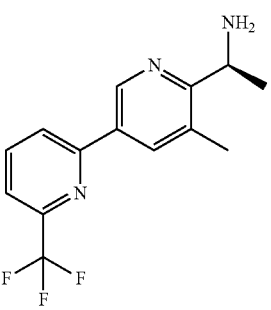 [SMILES: Cc1cc(-c2cccc(C(F)(F)F)n2)cnc1[C@H](C)N]

Intermediate 177

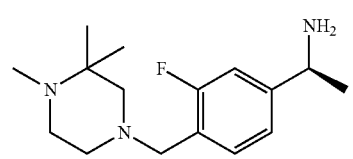 [SMILES: C[C@H](N)c1ccc(CN2CCN(C)C(C)(C)C2)c(F)c1]

Intermediate 178

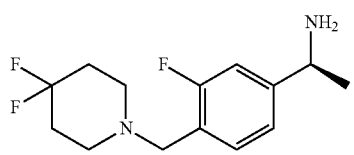 [SMILES: C[C@H](N)c1ccc(CN2CCC(F)(F)CC2)c(F)c1]

Intermediate 179

TABLE 9b

Chemical name and analytical data for each intermediate listed in Table 9a.

| Intermediate: Name | Analytical data |
| --- | --- |
| 167: (S)-1-(5-(3-(trifluoromethyl)phenyl)pyridin-2-yl)ethanamine | LCMS tR = 1.12 min; MS m/z 267.7 (M + H). |
| 168: (S)-1-(6-(4-fluoro-3-methylphenyl)pyridin-3-yl)ethanamine | LCMS tR = 1.05 min; MS m/z 231.4 (M + H). |
| 169: (S)-1-(6-(3-(trifluoromethyl)phenyl)pyridin-3-yl)ethanamine | LCMS tR = 1.14 min; MS m/z 267.4 (M + H). |
| 170: (S)-1-(2'-(trifluoromethyl)-[3,4'-bipyridin]-6-yl)ethanamine | LCMS tR = 0.79 min; MS m/z 268.1 (M + H). |
| 171: (S)-1-(6'-(trifluoromethyl)-[2,3'-bipyridin]-5-yl)ethanamine | LCMS tR = 0.81 min; MS m/z 268.1 (M + H). |
| 172: (S)-1-(6'-(trifluoromethyl)-[3,3'-bipyridin]-6-yl)ethanamine | LCMS tR = 0.81 min; MS m/z 268.1 (M + H). |
| 173: (S)-1-(6-(trifluoromethyl)-[2,3'-bipyridin]-6'-yl)ethanamine | LCMS tR = 0.89 min; MS m/z 268.1 (M + H). |
| 174: (S)-1-(4-methyl-2'-(trifluoromethyl)-[3,4'-bipyridin]-6-yl)ethanamine | LCMS tR = 0.85 min; MS m/z 282.1 (M + H). |
| 175: (S)-1-(2-methyl-2'-(trifluoromethyl)-[3,4'-bipyridin]-6-yl)ethanamine | LCMS tR = 0.86 min; MS m/z 282.1 (M + H). |
| 176: (S)-1-(5-fluoro-2'-(trifluoromethyl)-[3,4'-bipyridin]-6-yl)ethanamine | LCMS tR = 0.88 min; MS m/z 286.1 (M + H). |
| 177: (S)-1-(5-methyl-2'-(trifluoromethyl)-[3,4'-bipyridin]-6-yl)ethanamine | LCMS tR = 0.89 min; MS m/z 282.1 (M + H). |
| 178: (S)-1-(3-fluoro-4-((3,3,4-trimethylpiperazin-1-yl)methyl)phenyl)ethanamine | LCMS tR = 0.29 min; MS m/z 280.2 (M + H). |
| 179: (S)-1-(4-((4,4-difluoropiperidin-1-yl)methyl)-3-fluorophenyl)ethanamine | LCMS tR = 0.29 min; MS m/z 273.2 (M + H). |

Intermediate 180: (S)-tert-butyl (1-hydrazinyl-1-oxopropan-2-yl)carbamate

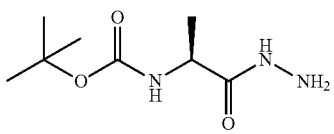

A solution of (S)-methyl 2-((tert-butoxycarbonyl)amino)propanoate (1.00 g, 4.92 mmol) and hydrazine (0.23 mL, 1.5 equiv) in THF (8 mL) was heated in a sealed tube at 72° C. for 15 hours. Additional hydrazine (0.23 mL, 1.5 equiv) was added and heating was continued for another 21 hours. The reaction was then cooled to room temperature and concentrated in vacuo to give crude (S)-tert-butyl (1-hydrazinyl-1-oxopropan-2-yl)carbamate (1 g, white solid), which was used without purification. $^1$H NMR (400 MHz, CDCl$_3$) δ 4.20 (m, 1H), 1.44 (s, 9H), 1.36 (d, J=7.1 Hz, 3H).

Intermediate 181: (S)-tert-butyl (1-(2-(4-chlorobenzoyl)hydrazinyl)-1-oxopropan-2-yl)carbamate

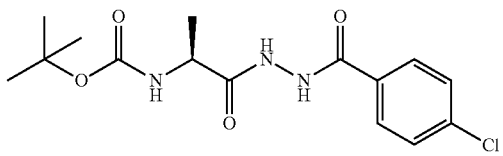 [SMILES: C[C@H](NC(=O)OC(C)(C)C)C(=O)NNC(=O)c1ccc(Cl)cc1]

4-Chlorobenzoyl chloride (0.63 mL, 4.92 mmol, 1.0 equiv) was added to a solution of (S)-tert-butyl (1-hydrazinyl-1-oxopropan-2-yl)carbamate (1.0 g, 4.92 mmol) in DCM (25 mL) at 0° C. A white precipitate formed. The mixture was stirred at 0° C. for 1 hour and the reaction mixture was then concentrated in vacuo to give crude (S)-tert-butyl (1-(2-(4-chlorobenzoyl)hydrazinyl)-1-oxopropan-2-yl)carbamate (1.55 g), which was used without purification. $^1$H NMR (400 MHz, CD$_3$OD) δ 7.85 (d, J=8.7 Hz, 2H), 7.49 (d, J=8.7 Hz, 2H), 4.21 (q, J=7.0 Hz, 1H), 1.45 (s, 9H), 1.41 (d, J=7.2 Hz, 3H). MS m/z 342.1 (M+H)$^+$; Rt-0.69 min.

Intermediate 182: (S)-tert-butyl (1-(5-(4-chlorophenyl)-1,3,4-thiadiazol-2-yl)ethyl)carbamate

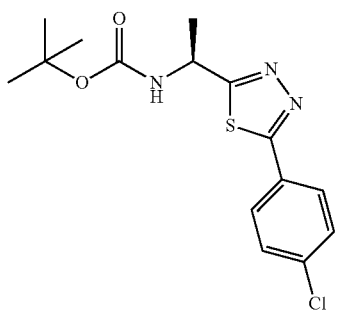 [SMILES: C[C@H](NC(=O)OC(C)(C)C)c1nnc(-c2ccc(Cl)cc2)s1]

A solution of (S)-tert-butyl (1-(2-(4-chlorobenzoyl)hydrazinyl)-1-oxopropan-2-yl)carbamate (1.0 g, 2.93 mmol) and 2,4-bis(4-methoxyphenyl)-1,3,2,4-dithiadiphosphetane 2,4-disulfide (1.18 g, 2.93 mmol, 1.0 equiv) in THF (29 mL) was heated at reflux for 2 hours. The reaction wash then cooled to room temperature and filtered through a pad of celite, using THF to wash through. The filtrate was concentrated in vacuo. Silica gel column chromatography (EtOAc/Heptane, 0 to 30%) provided (S)-tert-butyl (1-(5-(4-chlorophenyl)-1,3,4-thiadiazol-2-yl)ethyl)carbamate (0.600 g, light green solid) in 60% yield. $^1$H NMR (400 MHz, CDCl$_3$) δ 7.89 (d, J=8.5 Hz, 2H), 7.46 (d, J=8.5 Hz, 2H), 5.23 (m, 1H), 1.72 (d, J=6.5 Hz, 3H), 1.48 (s, 9H). MS m/z 340.1 (M+H)$^+$; Rt-0.99 min.

Intermediate 183: (S)-1-(5-(4-chlorophenyl)-1,3,4-thiadiazol-2-yl)ethanamine

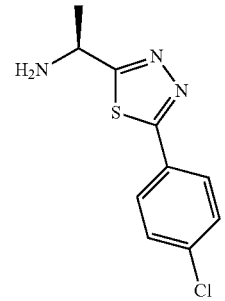

A solution of hydrogen chloride (4.0 M in 1,4-dioxane, 4 mL, 16 mmol, 9 equiv) was added to a solution of (S)-tert-butyl (1-(5-(4-chlorophenyl)-1,3,4-thiadiazol-2-yl)ethyl)carbamate (600 mg, 1.77 mmol) in 1,4-dioxane (5 mL) at room temperature. The solution was stirred for 3 hours, by which time a white precipitate had formed. The reaction was concentrated in vacuo to give the hydrochloride salt of (S)-1-(5-(4-chlorophenyl)-1,3,4-thiadiazol-2-yl)ethanamine (480 mg, white solid) in 97% yield. The material was used without purification. $^1$H NMR (400 MHz, CD$_3$OD) δ 8.00 (d, J=8.7 Hz, 2H), 7.58 (d, J=8.7 Hz, 2H), 5.10 (q, J=6.9 Hz, 1H), 1.82 (d, J=6.9 Hz, 3H). MS m/z 240.0 (M+H)$^+$; Rt-0.54 min.

Intermediate 184: (S)-tert-butyl but-3-yn-2-ylcarbamate

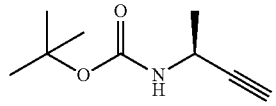

A solution of (S)-tert-butyl (1-oxopropan-2-yl)carbamate (500 mg, 2.89 mmol), dimethyl (1-diazo-2-oxopropyl)phosphonate (610 mg, 3.18 mmol, 1.1 equiv), and potassium carbonate (638 mg, 4.62 mmol, 1.6 equiv) in methanol (14.4 mL) was stirred at room temperature for 18 hours. The reaction was then diluted with ethyl acetate (30 mL) and saturated aqueous sodium chloride (40 mL). The layers were separated and the aqueous layer was extracted with ethyl acetate (30 mL) and the combined organic extracts were dried over Na$_2$SO$_4$, filtered and concentrated. Silica gel column chromatography (20% EtOAc in Heptane) provided (S)-tert-butyl but-3-yn-2-ylcarbamate (0.258 g, white solid) in 53% yield. $^1$H NMR (400 MHz, CDCl$_3$) δ 4.49 (m, 1H), 2.26 (d, J=2.2 Hz, 1H), 1.46 (s, 9H), 1.41 (d, J=6.8 Hz, 3H).

Intermediate 185: (S)-tert-butyl (1-(1-(4-chlorophenyl)-1H-1,2,3-triazol-4-yl)ethyl)carbamate

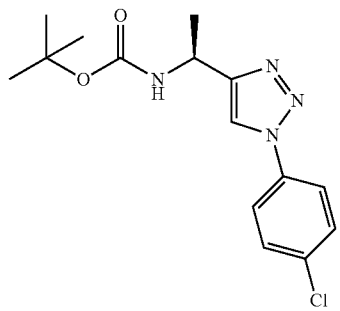 [SMILES: C[C@H](NC(=O)OC(C)(C)C)c1cn(-c2ccc(Cl)cc2)nn1]

A solution of (S)-tert-butyl but-3-yn-2-ylcarbamate (250 mg, 1.48 mmol), 1-azido-4-chlorobenzene (227 mg, 1.48 mmol, 1.0 equiv), and N-ethyl-N-isopropylpropan-2-amine (0.77 mL, 4.43 mmol, 3.0 equiv) in anhydrous acetonitrile (14.8 mL) was stirred at room temperature for 10 min. Copper(I) iodide (563 mg, 2.95 mmol, 2.0 equiv) was then added in portions. The mixture was stirred at room temperature for 30 min. The reaction was quenched with saturated aqueous ammonium chloride (50 mL) and diluted with water (50 mL). The mixture was extracted with ethyl acetate (3×30 mL) and the combined organic extracts were washed with water (30 mL), saturated aqueous sodium chloride (30 mL), dried over $Na_2SO_4$, filtered and concentrated. Silica gel column chromatography (EtOAc/Heptane) provided (S)-tert-butyl (1-(1-(4-chlorophenyl)-1H-1,2,3-triazol-4-yl)ethyl)carbamate (0.428 g, white solid) in 90% yield. $^1$H NMR (400 MHz, CDCl$_3$) δ 7.86 (s, 1H), 7.68 (d, J=8.8 Hz, 2H), 7.50 (d, J=8.8 Hz, 2H), 5.02 (m, 1H), 1.63 (d, J=6.8 Hz, 3H), 1.46 (s, 9H). MS m/z 323.1 (M+H)$^+$; Rt-0.92 min.

Intermediate 186: (S)-1-(1-(4-chlorophenyl)-1H-1,2,3-triazol-4-yl)ethanamine

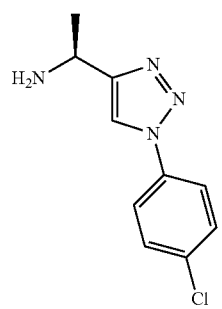

A solution of hydrogen chloride (4.0 M in 1,4-dioxane, 3.3 mL, 13.2 mmol, 10 equiv) was added to a solution of (S)-tert-butyl (1-(1-(4-chlorophenyl)-1H-1,2,3-triazol-4-yl)ethyl)carbamate (425 mg, 1.32 mmol) in 1,4-dioxane (5 mL) at room temperature. The solution was stirred for 1 hour, by which time a white precipitate had formed. The reaction was concentrated in vacuo to give the hydrochloride salt of (S)-1-(1-(4-chlorophenyl)-1H-1,2,3-triazol-4-yl)ethanamine (338 mg, white solid) in 99% yield. The material was used without purification. $^1$H NMR (400 MHz, CD$_3$OD) δ 8.68 (s, 1H), 7.90 (d, J=9.0 Hz, 2H), 7.63 (d, J=9.0 Hz, 2H), 4.77 (q, J=6.9 Hz, 1H), 1.78 (d, J=6.9 Hz, 3H). MS m/z 223.1 (M+H)$^+$; Rt-0.50 min.

Intermediate 187:
2-(6-methylpyridin-3-yl)thiazole-5-carbaldehyde

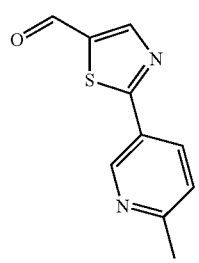

A mixture of 2-bromothiazole-5-carbaldehyde (400 mg, 2.08 mmol), (6-methylpyridin-3-yl)boronic acid (428 mg, 3.12 mmol, 1.5 equiv), [1,1'-bis(diphenylphosphino)ferrocene]dichloropalladium(II), complex with dichloromethane (170 mg, 0.21 mmol, 0.1 equiv) and 2.0 M aqueous sodium carbonate (5.2 mL, 10.4 mmol, 5 equiv) in 1,2-dimethoxyethane (6.9 mL) was heated in a microwave reactor at 110° C. for 20 minutes. The reaction was then diluted with ethyl acetate (50 mL) and water (50 mL). The layers were separated and the aqueous layer was extracted with ethyl acetate (2×25 mL). The combined organic extracts were washed with saturated aqueous sodium chloride (30 mL), dried over $Na_2SO_4$, filtered and concentrated. Silica gel column chromatography (EtOAc) provided 2-(6-methylpyridin-3-yl)thiazole-5-carbaldehyde (0.176 g, brown solid) in 41% yield. $^1$H NMR (400 MHz, CDCl$_3$) δ 10.08 (s, 1H), 9.15 (d, J=2.0 Hz, 1H), 8.47 (s, 1H), 8.19 (dd, J=8.1, 2.4 Hz, 1H), 7.31 (d, J=8.3 Hz, 1H), 2.66 (s, 3H). MS m/z 205.0 (M+H)$^+$; Rt-0.36 min.

The intermediates in Table 10a were prepared using a method similar to that described for the preparation of Intermediate 187

TABLE 10a

| | |
|---|---|
| 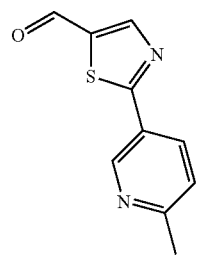 | Intermediate 188 |
| 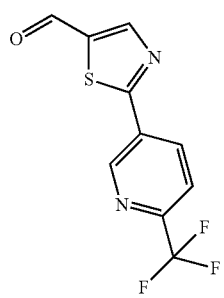 [SMILES: O=Cc1cnc(-c2ccc(C(F)(F)F)nc2)s1] | Intermediate 189 |
| 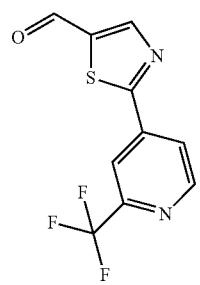 [SMILES: O=Cc1cnc(-c2ccnc(C(F)(F)F)c2)s1] | Intermediate 190 |

TABLE 10b

Chemical name, NMR chemical shifts and LCMS signal for each intermediate listed in Table 10a.

| Intermediate: Name | $^1$H NMR (400 MHz, CDCl$_3$) δ ppm | LCMS |
|---|---|---|
| 188: 2-(6-methylpyridin-3-yl)thiazole-5-carbaldehyde | 10.08 (s, 1H), 9.15 (d, J = 2.0 Hz, 1H), 8.47 (s, 1H), 8.19 (dd, J = 8.1, 2.4 Hz, 1H), 7.31 (d, J = 8.3 Hz, 1H), 2.66 (s, 3H). | MS m/z 205.0 (M + H)$^+$; Rt-0.36 min |
| 189: 2-(6-(trifluoromethyl)pyridin-3-yl)thiazole-5-carbaldehyde | 10.13 (s, 1H), 9.37 (d, J = 1.6 Hz, 1H), 8.55 (s, 1H), 8.50 (dd, J = 8.2, 2.0 Hz, 1H), 7.85 (d, J = 8.2 Hz, 1H) | MS m/z 259.0 (M + H)$^+$; Rt-0.74 min |
| 190: 2-(2-(trifluoromethyl)pyridin-4-yl)thiazole-5-carbaldehyde | 10.14 (s, 1H), 8.91 (d, J = 5.0 Hz, 1H), 8.57 (d, J = 0.6 Hz, 1H), 8.30 (s, 1H), 8.06 (d, J = 5.1 Hz, 1H) | MS m/z 259.0 (M + H)$^+$; Rt-0.76 min |

Intermediate 191: 1-(4-chlorophenyl)-4-(1,3-dioxolan-2-yl)-1H-imidazole

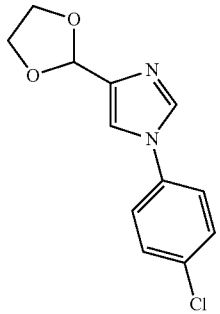 [SMILES: Clc1ccc(-n2cnc(C3OCCO3)c2)cc1]

A solution of ethane-1,2-diol (0.081 mL, 1.45 mmol, 1.5 equiv), 1-(4-chlorophenyl)-1H-imidazole-4-carbaldehyde (200 mg, 0.968 mmol), and camphorsulfonic acid (45 mg, 0.19 mmol, 0.2 equiv) in toluene (10 mL) was heated at reflux with a Dean-Stark apparatus for 1 hour. The reaction was cooled to room temperature and quenched with saturated aqueous sodium bicarbonate (30 mL). The mixture was extracted with ethyl acetate (30 mL) and the organic layer was dried (Na$_2$SO$_4$), filtered, and concentrated in vacuo. Silica gel column chromatography (EtOAc with 7% methanol) provided 1-(4-chlorophenyl)-4-(1,3-dioxolan-2-yl)-1H-imidazole (0.100 g, tan solid) in 41% yield. $^1$H NMR (400 MHz, CDCl$_3$) δ 7.80 (s, 1H), 7.46 (d, J=8.4 Hz, 2H), 7.36 (s, 1H), 7.33 (d, J=8.4 Hz, 2H), 5.96 (s, 1H), 4.20 (m, 2H), 4.05 (m, 2H). MS m/z 251.0 (M+H)$^+$; Rt-0.53 min.

Intermediate 192: 1-(4-chlorophenyl)-4-(1,3-dioxolan-2-yl)-2-methyl-1H-imidazole

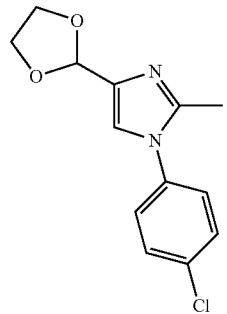 [SMILES: Cc1nc(C2OCCO2)cn1-c1ccc(Cl)cc1]

A solution of n-butyllithium (1.6 M in hexane, 0.37 mL, 0.60 mmol, 1.5 equiv) was added to a solution of N,N-diisopropylamine (0.085 mL, 0.60 mmol, 1.5 equiv) in THF (1.5 mL) at −78° C. The solution was stirred at −78° C. for 10 min and then a solution of 1-(4-chlorophenyl)-4-(1,3-dioxolan-2-yl)-1H-imidazole (100 mg, 0.40 mmol) in THF (1 mL) was added dropwise. The resulting solution was stirred at −78° C. for 30 min, and then iodomethane (0.042 mL, 0.68 mmol, 1.7 equiv) was added. The solution was allowed to warm to room temperature and then quenched with water (20 mL). The mixture was extracted with ethyl acetate (30 mL) and the organic extract was washed with saturated aqueous sodium chloride (15 mL), dried (Na$_2$SO$_4$), filtered, and concentrated in vacuo to give crude 1-(4-chlorophenyl)-4-(1,3-dioxolan-2-yl)-2-methyl-1H-imidazole. The material was used without further purification. $^1$H NMR (400 MHz, CDCl$_3$) δ 7.46 (d, J=8.4 Hz, 2H), 7.23 (d, J=8.4 Hz, 2H), 7.09 (s, 1H), 5.88 (s, 1H), 4.20 (m, 2H), 4.03 (m, 2H), 2.35 (s, 3H). MS m/z 265.0 (M+H)$^+$; Rt-0.57 min.

Intermediate 193: 1-(4-chlorophenyl)-2-methyl-1H-imidazole-4-carbaldehyde

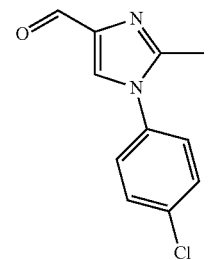

A solution of 1-(4-chlorophenyl)-4-(1,3-dioxolan-2-yl)-2-methyl-1H-imidazole (1.05 g, 3.97 mmol) and camphorsulfonic acid (92 mg, 0.40 mmol, 0.1 equiv) in THF (26.5 mL) and water (13.3 mL) was heated at 60° C. for 1 hour. The reaction was then cooled to room temperature and quenched with saturated aqueous sodium bicarbonate (100 mL). The mixture was extracted with ethyl acetate (100 mL) and the organic layer was washed with saturated aqueous sodium chloride (50 mL), dried (Na$_2$SO$_4$), filtered, and concentrated in vacuo. Silica gel column chromatography (EtOAc with 7% methanol) provided 1-(4-chlorophenyl)-2-methyl-1H-imidazole-4-carbaldehyde (0.600 g, tan solid) in 69% yield. $^1$H NMR (400 MHz, CDCl$_3$) δ 9.89 (s, 1H), 7.67 (s, 1H), 7.53 (d, J=8.7 Hz, 2H), 7.27 (d, J=8.7 Hz, 2H), 2.40 (s, 3H). MS m/z 221.0 (M+H)$^+$; Rt-0.47 min.

Intermediate 194: 1-(6-(trifluoromethyl)pyridin-3-yl)-1H-pyrazole-3-carbaldehyde

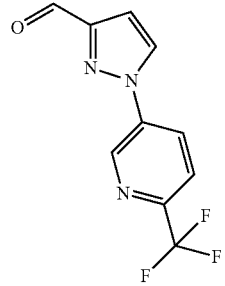 [SMILES: O=Cc1ccn(-c2ccc(C(F)(F)F)nc2)n1]

A mixture of 1H-pyrazole-3-carbaldehyde (0.700 g, 7.29 mmol), 5-bromo-2-(trifluoromethyl)pyridine (2.31 g, 10.2 mmol, 1.4 equiv), cesium carbonate (4.75 g, 14.6 mmol, 2.0 equiv), copper(I) iodide (0.069 g, 0.36 mmol, 0.05 equiv), and (1R,2R)—N1,N2-dimethylcyclohexane-1,2-diamine (0.23 mL, 1.46 mmol, 0.2 equiv) in DMF (9.5 mL) was heated in a sealed reaction vessel at 110° C. for 16 hours. The reaction was then cooled to room temperature and saturated aqueous ammonium chloride (100 mL) was added. The mixture was extracted with ethyl acetate (3×50 mL). The combined organic extracts were washed with saturated aqueous sodium chloride (50 mL), dried (Na$_2$SO$_4$), filtered, and concentrated in vacuo. Silica gel column chromatography (EtOAc/heptane) provided 1-(6-(trifluoromethyl)pyridin-3-yl)-1H-pyrazole-3-carbaldehyde (0.470 g, brown solid) in 27% yield.

$^1$H NMR (400 MHz, CDCl$_3$) δ 10.13 (s, 1H), 9.18 (d, J=2.1 Hz, 1H), 8.34 (dd, J=8.7, 2.0 Hz, 1H), 8.12 (m, 1H), 7.88 (d, J=8.5 Hz, 1H), 7.10 (d, J=1.8 Hz, 1H). MS m/z 241.9 (M+H)$^+$; Rt-0.78 min.

Intermediate 195: (R,E)-N-((5-(4-chlorophenyl)isoxazol-3-yl)methylene)-2-methylpropane-2-sulfinamide

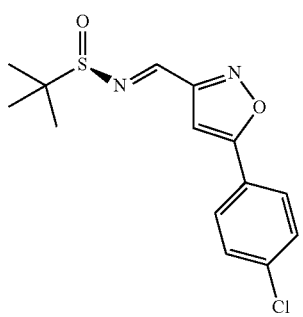 [SMILES: CC(C)(C)[S@@](=O)/N=C/c1cc(-c2ccc(Cl)cc2)on1]

A suspension of 5-(4-chlorophenyl)isoxazole-3-carbaldehyde (2.00 g, 9.63 mmol), (R)-2-methylpropane-2-sulfinamide (1.28 g, 10.6 mmol, 1.1 equiv) and anhydrous copper (II) sulfate (2.31 g, 14.5 mmol, 1.5 equiv) in 1,2-dichloroethane (19 mL) was heated at 55° C. for 2-18 hours. The reaction was then cooled to room temperature and filtered through a pad of celite, using 1,2-dichloroethane to wash through. The filtrate was concentrated in vacuo to give crude (R,E)-N-((5-(4-chlorophenyl)isoxazol-3-yl)methylene)-2-methylpropane-2-sulfinamide as a green solid, which was used without further purification. MS m/z 311.0 (M+H)$^+$; Rt-1.11 min.

The intermediates in Table 11a were prepared using a method similar to that described for the preparation of Intermediate 195

TABLE 11a

| | |
|---|---|
| 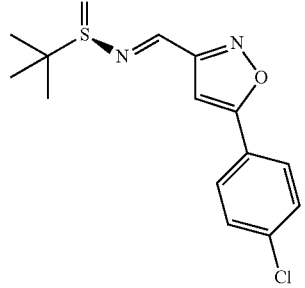 | Intermediate 196 |
| 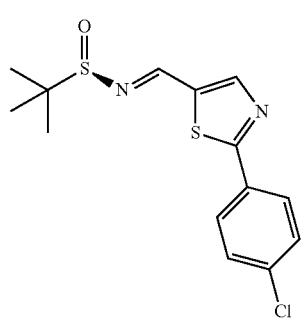 [SMILES: CC(C)(C)[S@@](=O)/N=C/c1cnc(-c2ccc(Cl)cc2)s1] | Intermediate 197 |
| 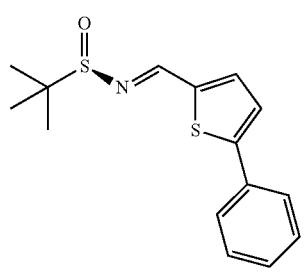 [SMILES: CC(C)(C)[S@@](=O)/N=C/c1ccc(-c2ccccc2)s1] | Intermediate 198 |
| 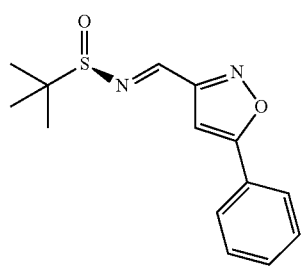 [SMILES: CC(C)(C)[S@@](=O)/N=C/c1cc(-c2ccccc2)on1] | Intermediate 199 |
| 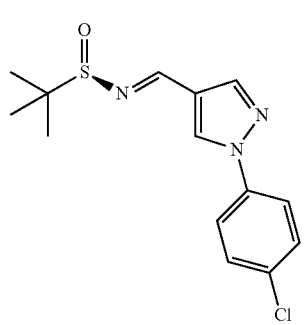 [SMILES: CC(C)(C)[S@@](=O)/N=C/c1cnn(-c2ccc(Cl)cc2)c1] | Intermediate 200 |

TABLE 11a-continued
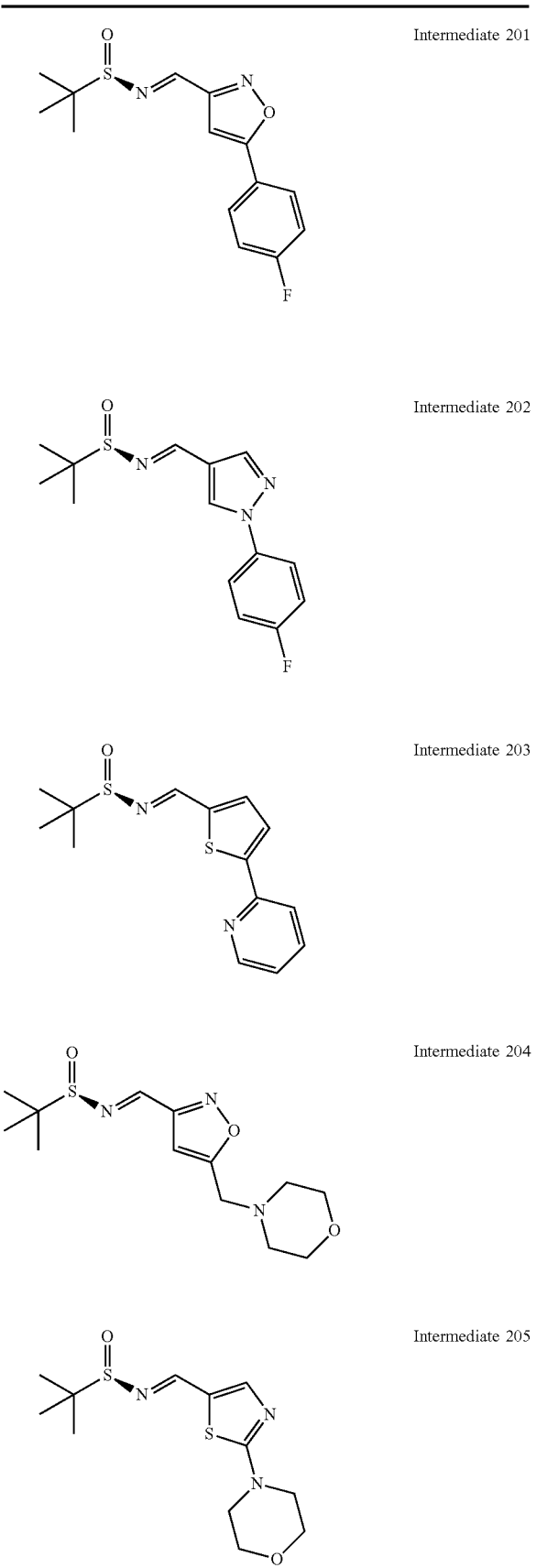
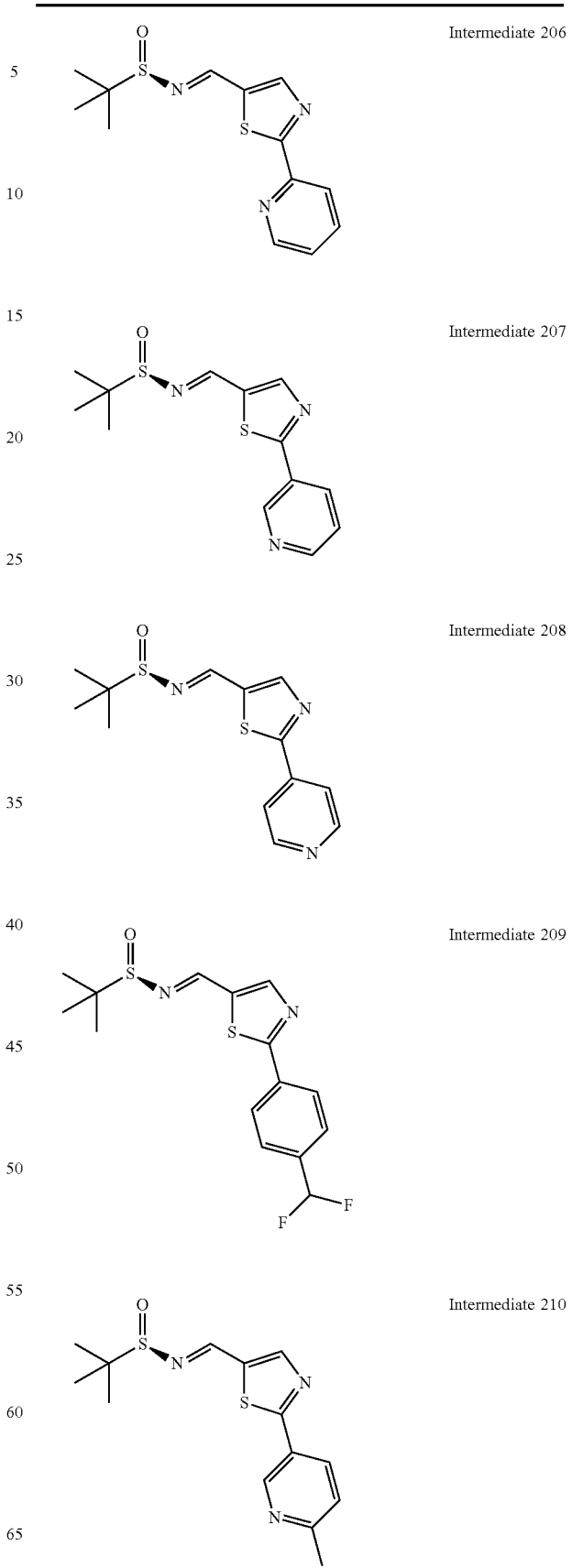

TABLE 11a-continued

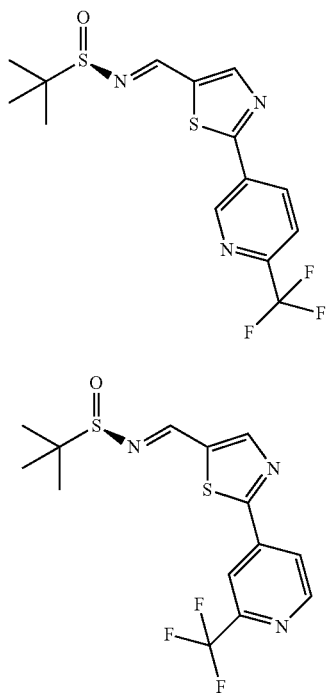

Intermediate 211

Intermediate 212

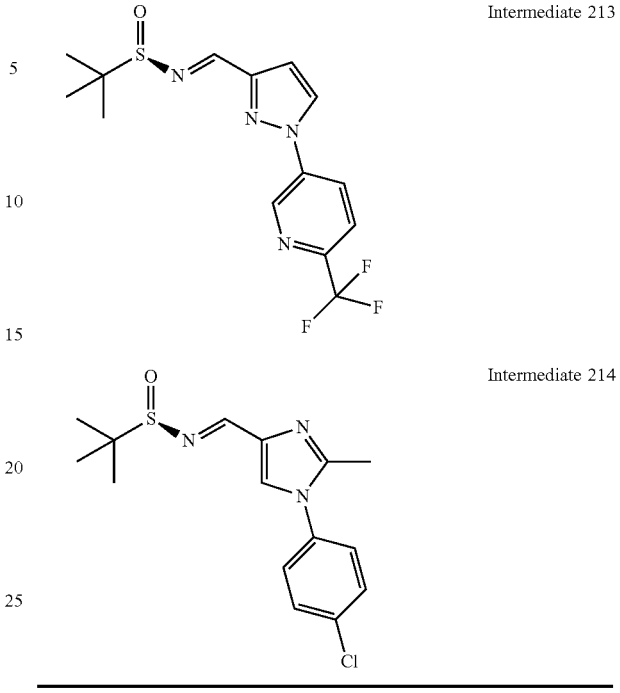

Intermediate 213

Intermediate 214

TABLE 11b

Chemical name and analytical data for each intermediate listed in Table 11a.

| Intermediate: Name | Analytical data |
|---|---|
| 196: (R,E)-N-((5-(4-chlorophenyl)isoxazol-3-yl)methylene)-2-methylpropane-2-sulfinamide | MS m/z 311.0 (M + H)$^+$; Rt-1.11 min |
| 197: (R,E)-N-((2-(4-chlorophenyl)thiazol-5-yl)methylene)-2-methylpropane-2-sulfinamide | MS m/z 327.1 (M + H)$^+$; Rt-1.13 min |
| 198: (R,E)-2-methyl-N-((5-phenylthiophen-2-yl)methylene)propane-2-sulfinamide | MS m/z 292.0 (M + H)$^+$; Rt-1.05 min |
| 199: (R,E)-2-methyl-N-((5-phenylisoxazol-3-yl)methylene)propane-2-sulfinamide | MS m/z 277.1 (M + H)$^+$; Rt-1.02 min |
| 200: (R,E)-N-((1-(4-chlorophenyl)-1H-pyrazol-4-yl)methylene)-2-methylpropane-2-sulfinamide | MS m/z 310.1 (M + H)$^+$; Rt-1.00 min |
| 201: (R,E)-N-((5-(4-fluorophenyl)isoxazol-3-yl)methylene)-2-methylpropane-2-sulfinamide | MS m/z 295.1 (M + H)$^+$; Rt-1.00 min |
| 202: (R,E)-N-((1-(4-fluorophenyl)-1H-pyrazol-4-yl)methylene)-2-methylpropane-2-sulfinamide | MS m/z 294.1 (M + H)$^+$; Rt-0.90 min |
| 203: (R,E)-2-methyl-N-((5-(pyridin-2-yl)thiophen-2-yl)methylene)propane-2-sulfinamide | MS m/z 293.1 (M + H)$^+$; Rt-0.85 min |
| 204: (R,E)-2-methyl-N-((5-(morpholinomethyl)isoxazol-3-yl)methylene)propane-2-sulfinamide | MS m/z 300.1 (M + H)$^+$; Rt-0.43 min |
| 205: (R,E)-2-methyl-N-((2-morpholinothiazol-5-yl)methylene)propane-2-sulfinamide | MS m/z 302.1 (M + H)$^+$; Rt-0.69 min |
| 206: (R,E)-2-methyl-N-((2-(pyridin-2-yl)thiazol-5-yl)methylene)propane-2-sulfinamide | MS m/z 294.2 (M + H)$^+$; Rt-0.92 min |
| 207: (R,E)-2-methyl-N-((2-(pyridin-3-yl)thiazol-5-yl)methylene)propane-2-sulfinamide | MS m/z 294.1 (M + H)$^+$; Rt-0.63 min |
| 208: (R,E)-2-methyl-N-((2-(pyridin-4-yl)thiazol-5-yl)methylene)propane-2-sulfinamide | MS m/z 294.1 (M + H)$^+$; Rt-0.55 min |
| 209: (R,E)-N-((2-(4-(difluoromethyl)phenyl)thiazol-5-yl)methylene)-2-methylpropane-2-sulfinamide | MS m/z 342.9 (M + H)$^+$; Rt-0.86 min |
| 210: (R,E)-2-methyl-N-((2-(6-methylpyridin-3-yl)thiazol-5-yl)methylene)propane-2-sulfinamide | MS m/z 308.1 (M + H)$^+$; Rt-0.58 min |
| 211: (R,E)-2-methyl-N-((2-(6-(trifluoromethyl)pyridin-3-yl)thiazol-5-yl)methylene)propane-2-sulfinamide | MS m/z 362.1 (M + H)$^+$; Rt-0.96 min |
| 212: (R,E)-2-methyl-N-((2-(2-(trifluoromethyl)pyridin-4-yl)thiazol-5-yl)methylene)propane-2-sulfinamide | MS m/z 362.1 (M + H)$^+$; Rt-0.97 min |

TABLE 11b-continued

Chemical name and analytical data for each intermediate listed in Table 11a.

| Intermediate: Name | Analytical data |
|---|---|
| 213: (R,E)-2-methyl-N-((1-(6-(trifluoromethyl)pyridin-3-yl)-1H-pyrazol-3-yl)methylene)propane-2-sulfinamide | MS m/z 345.0 (M + H)+; Rt-0.95 min |
| 214: (R,E)-N-((1-(4-chlorophenyl)-2-methyl-1H-imidazol-4-yl)methylene)-2-methylpropane-2-sulfinamide | MS m/z 324.0 (M + H)+; Rt-0.62 min |

Intermediate 215: (R)—N—((S)-1-(5-(4-chlorophenyl)isoxazol-3-yl)ethyl)-2-methylpropane-2-sulfinamide

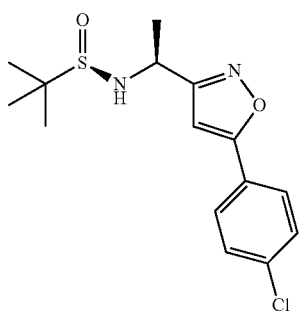

A solution of methylmagnesium bromide (3.0 M in diethyl ether, 12.8 mL, 38.4 mmol, 4 equiv) was added to a solution of (R,E)-N-((5-(4-chlorophenyl)isoxazol-3-yl)methylene)-2-methylpropane-2-sulfinamide (2.98 g, 9.6 mmol) in DCM (96 mL) at 0° C. The solution became orange, then faded to yellow. The reaction was stirred at 0° C. for 30 min and then carefully quenched with saturated aqueous ammonium chloride (100 mL). The layers were separated and the aqueous layer was extracted with DCM (40 mL). The combined organic layers were washed with water (50 mL), saturated aqueous sodium chloride (50 mL), dried over Na$_2$SO$_4$, filtered and concentrated. Silica gel column chromatography (EtOAc/Heptane) provided (R)—N—((S)-1-(5-(4-chlorophenyl)isoxazol-3-yl)ethyl)-2-methylpropane-2-sulfinamide (1.0 g, white solid) in 32% yield. $^1$H NMR (400 MHz, CDCl$_3$) δ 7.71 (d, J=8.6 Hz, 2H), 7.45 (d, J=8.6 Hz, 2H), 6.50 (s, 1H), 4.75 (m, 1H), 3.47 (m, 1H), 1.70 (d, J=6.8 Hz, 3H), 1.25 (s, 9H). MS m/z 327.0 (M+H)+; Rt-0.94 min.

The intermediates in Table 12a were prepared using a method similar to that described for the preparation of Intermediate 215.

TABLE 12a

| Structure | Name |
|---|---|
| | Intermediate 216 |
| | Intermediate 217 |
| | Intermediate 218 |
| | Intermediate 219 |
| | Intermediate 220 |

TABLE 12a-continued
| | |
|---|---|
| 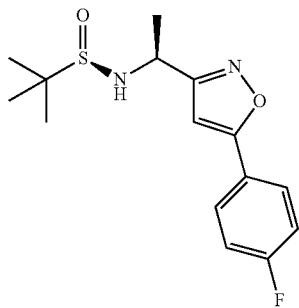 [SMILES: C[C@H](N[S@](=O)C(C)(C)C)c1cc(-c2ccc(F)cc2)on1] | Intermediate 221 |
| 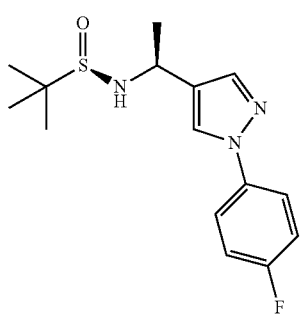 [SMILES: C[C@H](N[S@](=O)C(C)(C)C)c1cnn(-c2ccc(F)cc2)c1] | Intermediate 222 |
| 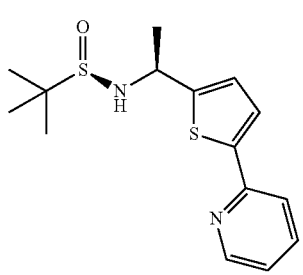 [SMILES: C[C@H](N[S@](=O)C(C)(C)C)c1ccc(-c2ccccn2)s1] | Intermediate 223 |
| 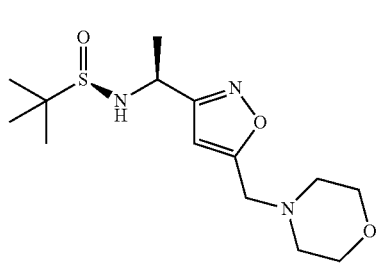 [SMILES: C[C@H](N[S@](=O)C(C)(C)C)c1cc(CN2CCOCC2)on1] | Intermediate 224 |
| 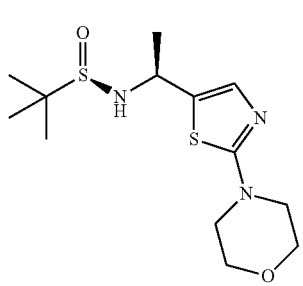 [SMILES: C[C@H](N[S@](=O)C(C)(C)C)c1cnc(N2CCOCC2)s1] | Intermediate 225 |
| 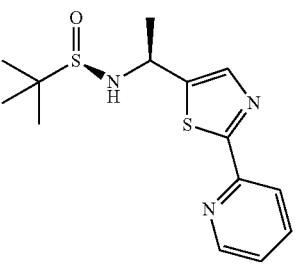 [SMILES: C[C@H](N[S@](=O)C(C)(C)C)c1cnc(-c2ccccn2)s1] | Intermediate 226 |
| 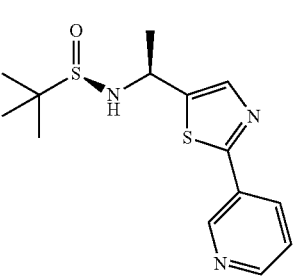 [SMILES: C[C@H](N[S@](=O)C(C)(C)C)c1cnc(-c2cccnc2)s1] | Intermediate 227 |
| 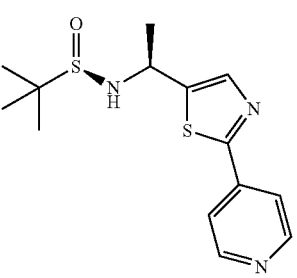 [SMILES: C[C@H](N[S@](=O)C(C)(C)C)c1cnc(-c2ccncc2)s1] | Intermediate 228 |
| 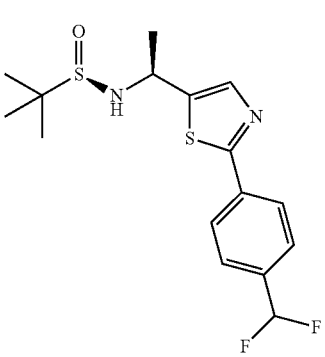 [SMILES: C[C@H](N[S@](=O)C(C)(C)C)c1cnc(-c2ccc(C(F)F)cc2)s1] | Intermediate 229 |
| 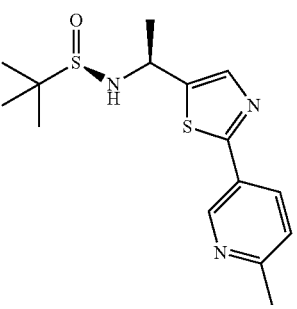 [SMILES: Cc1ccc(-c2ncc([C@H](C)N[S@](=O)C(C)(C)C)s2)cn1] | Intermediate 230 |

TABLE 12a-continued

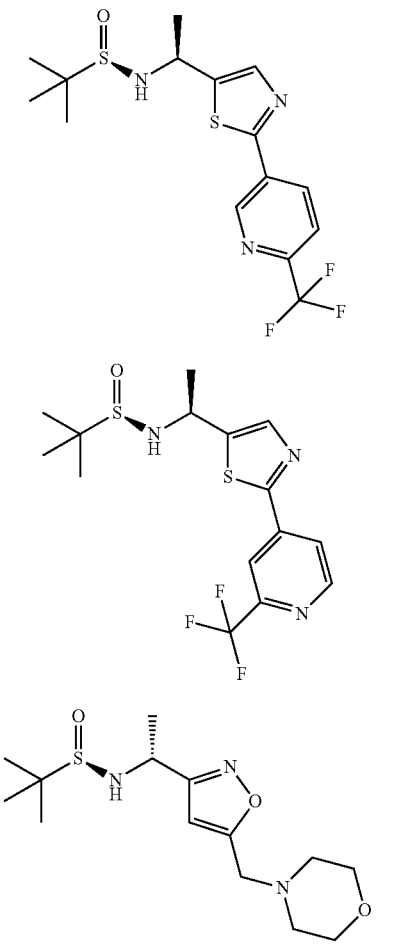

Intermediate 231

Intermediate 232

Intermediate 233

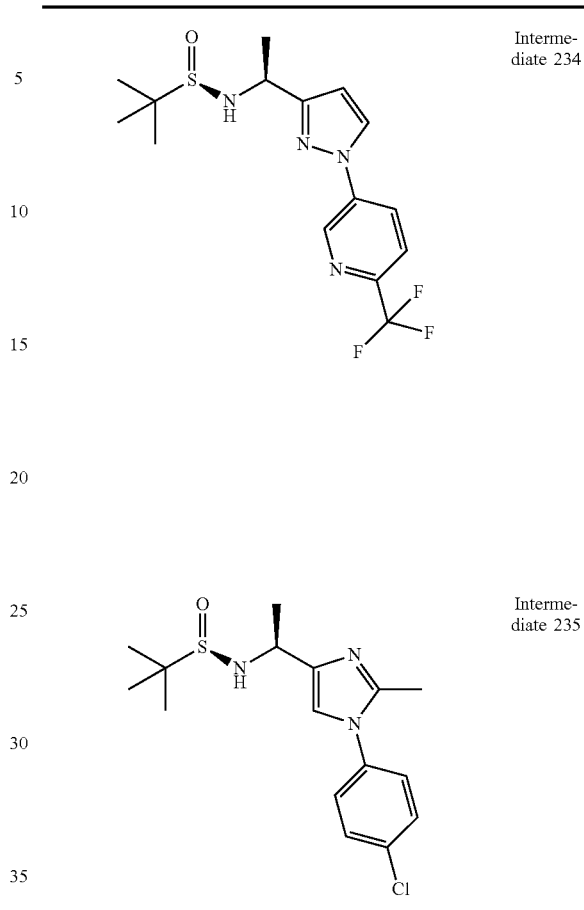

Intermediate 234

Intermediate 235

TABLE 12b

Chemical name, NMR chemical shifts and LCMS signal for each intermediate listed in Table 12a.

| Intermediate: Name | $^1$H NMR (400 MHz, CDCl$_3$) δ ppm | LCMS |
|---|---|---|
| 216: (R)-N-((S)-1-(5-(4-chlorophenyl)isoxazol-3-yl)ethyl)-2-methylpropane-2-sulfinamide | 7.71 (d, J = 8.6 Hz, 2H), 7.45 (d, J = 8.6 Hz, 2H), 6.50 (s, 1H), 4.75 (m, 1H), 3.47 (m, 1H), 1.70 (d, J = 6.8 Hz, 3H), 1.25 (s, 9H). | MS m/z 327.0 (M + H)$^+$; Rt-0.94 min |
| 217: (R)-N-((S)-1-(2-(4-chlorophenyl)thiazol-5-yl)ethyl)-2-methylpropane-2-sulfinamide | CD$_3$OD: 7.88 (d, J = 8.7 Hz, 2H), 7.73 (d, J = 1.0 Hz, 1H), 7.47 (d, J = 8.7 Hz, 2H), 4.83 (m, 1H), 1.71 (d, J = 6.7 Hz, 3H), 1.25 (s, 9H) | MS m/z 343.1 (M + H)$^+$; Rt-0.97 min |
| 218: (R)-2-methyl-N-((S)-1-(5-phenylthiophen-2-yl)ethyl)propane-2-sulfinamide | 7.58 (d, J = 7.4 Hz, 2H), 7.37 (m, 2H), 7.27 (m, 1H), 7.16 (d, J = 3.7 Hz, 1H), 6.95 (d, J = 3.7 Hz, 1H), 4.84 (m, 1H), 3.42 (m, 1H), 1.70 (d, J = 6.6 Hz, 3H), 1.26 (s, 9H) | MS m/z 308.1 (M + H)$^+$; Rt-0.95 min |
| 219: (R)-2-methyl-N-((S)-1-(5-phenylisoxazol-3-yl)ethyl)propane-2-sulfinamide | | MS m/z 293.2 (M + H)$^+$; Rt-0.85 min |
| 220: (R)-N-((S)-1-(1-(4-chlorophenyl)-1H-pyrazol-4-yl)ethyl)-2-methylpropane-2-sulfinamide | 7.84 (s, 1H), 7.63 (s, 1H), 7.61 (d, J = 8.7 Hz, 2H), 7.42 (d, J = 8.7 Hz, 2H), 4.64 (m, 1H), 3.31 (m, 1H), 1.62 (d, J = 6.7 Hz, 3H), 1.24 (s, 9H) | MS m/z 326.1 (M + H)$^+$; Rt-0.89 min |

TABLE 12b-continued

Chemical name, NMR chemical shifts and LCMS signal for each intermediate listed in Table 12a.

| Intermediate: Name | $^1$H NMR (400 MHz, CDCl$_3$) δ ppm | LCMS |
| --- | --- | --- |
| 221: (R)-N-((S)-1-(5-(4-fluorophenyl)isoxazol-3-yl)ethyl)-2-methylpropane-2-sulfinamide | 7.77 (dd, J = 8.9, 5.2 Hz, 2H), 7.16 (t, J = 8.7 Hz, 2H), 6.46 (s, 1H), 4.77 (m, 1H), 3.47 (d, J = 5.7 Hz, 1H), 1.70 (d, J = 6.8 Hz, 3H), 1.25 (s, 9H) | MS m/z 311.1 (M + H)$^+$; Rt-0.85 min |
| 222: (R)-N-((S)-1-(1-(4-fluorophenyl)-1H-pyrazol-4-yl)ethyl)-2-methylpropane-2-sulfinamide | 7.80 (s, 1H), 7.63 (m, 3H), 7.14 (t, J = 8.5 Hz, 2H), 4.63 (m, 1H), 3.31 (d, J = 5.0 Hz, 1H), 1.62 (d, J = 6.7 Hz, 3H), 1.24 (s, 9H) | MS m/z 310.1 (M + H)$^+$; Rt-0.79 min |
| 223: (R)-2-methyl-N-((S)-1-(5-(pyridin-2-yl)thiophen-2-yl)ethyl)propane-2-sulfinamide | 8.53-8.59 (m, 1 H), 7.60-7.73 (m, 2 H), 7.43 (d, J = 3.7 Hz, 1 H), 7.15 (ddd, J = 7.1, 5.0, 1.2 Hz, 1 H), 6.99 (d, J = 3.8 Hz, 1 H), 4.84 (quin, J = 6.3 Hz, 1 H), 3.43 (d, J = 5.5 Hz, 1 H), 1.70 (d, J = 6.6 Hz, 3 H), 1.26 (s, 9 H) | MS m/z 309.1 (M + H)$^+$; Rt-0.58 min |
| 224: (R)-2-methyl-N-((S)-1-(5-(morpholinomethyl)isoxazol-3-yl)ethyl)propane-2-sulfinamide | | MS m/z 316.1 (M + H)$^+$; Rt-0.38 min |
| 225: (R)-2-methyl-N-((S)-1-(2-morpholinothiazol-5-yl)ethyl)propane-2-sulfinamide | 7.06 (s, 1H), 4.69 (quin, J = 6.1 Hz, 1H), 3.81 (m, 4H), 3.44 (m, 4H), 3.32 (d, J = 4.9 Hz, 1H), 1.60 (d, J = 6.6 Hz, 3H), 1.22 (s, 9H) | |
| 226: (R)-2-methyl-N-((S)-1-(2-(pyridin-2-yl)thiazol-5-yl)ethyl)propane-2-sulfinamide | 8.60 (m, 1H), 8.15 (m, 1H), 7.80 (m, 2H), 7.33 (m, 1H), 4.93 (m, 1H), 1.71 (d, J = 6.6 Hz, 3H), 1.25 (s, 9H) | MS m/z 310.0 (M + H)$^+$; Rt-0.69 min |
| 227: (R)-2-methyl-N-((S)-1-(2-(pyridin-3-yl)thiazol-5-yl)ethyl)propane-2-sulfinamide | 9.11 (m, 1H), 8.65 (m, 1H), 8.23 (m, 1H), 7.75 (m, 1H), 7.38 (m, 1H), 4.90 (m, 1H), 3.50 (m, 1H), 1.71 (d, J = 6.6 Hz, 3H), 1.24 (s, 9H) | MS m/z 310.0 (M + H)$^+$; Rt-0.50 min |
| 228: (R)-2-methyl-N-((S)-1-(2-(pyridin-4-yl)thiazol-5-yl)ethyl)propane-2-sulfinamide | 8.70 (m, 2H), 7.79 (m, 3H), 4.94 (m, 1H), 1.72 (d, J = 6.6 Hz, 3H) | MS m/z 310.2 (M + H)$^+$; Rt-0.46 min |
| 229: (R)-N-((S)-1-(2-(4-(difluoromethyl)phenyl)thiazol-5-yl)ethyl)-2-methylpropane-2-sulfinamide | 8.01 (d, J = 8.0 Hz, 2H), 7.74 (s, 1H), 7.59 (d, J = 8.0 Hz, 2H), 6.69 (t, J = 56 Hz, 1H), 4.91 (m, 1H), 3.45 (d, J = 4.7 Hz, 1H), 1.72 (d, J = 6.6 Hz, 3H), 1.25 (s, 9H) | MS m/z 359.1 (M + H)$^+$; Rt-0.89 min |
| 230: (R)-2-methyl-N-((S)-1-(2-(6-methylpyridin-3-yl)thiazol-5-yl)ethyl)propane-2-sulfinamide | 9.01 (d, J = 2.2 Hz, 1H), 8.10 (dd, J = 8.1, 2.3 Hz, 1H), 7.73 (s, 1H), 7.24 (d, J = 8.2 Hz, 1H), 4.91 (m, 1H), 3.46 (d, J = 4.8 Hz, 1H), 2.62 (s, 3H), 1.72 (d, J = 6.6 Hz, 3H), 1.25 (s, 9H) | MS m/z 324.1 (M + H)$^+$; Rt-0.49 min |
| 231: (R)-2-methyl-N-((S)-1-(2-(6-(trifluoromethyl)pyridin-3-yl)thiazol-5-yl)ethyl)propane-2-sulfinamide | 9.23 (s, 1H), 8.40 (d, J = 8.3 Hz, 1H), 7.82 (s, 1H), 7.78 (d, J = 8.3 Hz, 1H), 4.95 (m, 1H), 3.49 (d, J = 4.1 Hz, 1H), 1.74 (d, J = 6.6 Hz, 3H), 1.26 (s, 9H) | MS m/z 378.1 (M + H)$^+$; Rt-0.84 min |
| 232: (R)-2-methyl-N-((S)-1-(2-(2-(trifluoromethyl)pyridin-4-yl)thiazol-5-yl)ethyl)propane-2-sulfinamide | 8.82 (d, J = 5.0 Hz, 1H), 8.19 (s, 1H), 7.97 (dd, J = 5.0, 1.6 Hz, 1H), 7.85 (s, 1H), 4.95 (m, 1H), 3.49 (d, J = 4.5 Hz, 1H), 1.74 (d, J = 6.6 Hz, 3H), 1.26 (s, 9H) | MS m/z 378.1 (M + H)$^+$; Rt-0.85 min |
| 233: (R)-2-methyl-N-((R)-1-(5-(morpholinomethyl)isoxazol-3-yl)ethyl)propane-2-sulfinamide | | MS m/z 316.2 (M + H)$^+$; Rt-0.43 min |
| 234: (R)-2-methyl-N-((S)-1-(1-(6-(trifluoromethyl)pyridin-3-yl)-1H-pyrazol-3-yl)ethyl)propane-2-sulfinamide | 9.06 (d, J = 2.3 Hz, 1H), 8.22 (dd, J = 8.6, 1.9 Hz, 1H), 7.98 (dd, J = 2.6, 0.9 Hz, 1H), 7.78 (d, J = 8.6 Hz, 1H), 6.51 (dd, J = 2.5, 0.9 Hz, 1H), 4.76 (m, 1H), 3.48 (d, J = 4.1 Hz, 1H), 1.68 (d, J = 6.8 Hz, 3H), 1.24 (s, 9H) | MS m/z 361.1 (M + H)$^+$; Rt-0.85 min |

TABLE 12b-continued

Chemical name, NMR chemical shifts and LCMS signal for each intermediate listed in Table 12a.

| Intermediate: Name | $^1$H NMR (400 MHz, CDCl$_3$) δ ppm | LCMS |
|---|---|---|
| 235: (R)-N-((S)-1-(1-(4-chlorophenyl)-2-methyl-1H-imidazol-4-yl)ethyl)-2-methylpropane-2-sulfinamide | 7.45 (d, J = 8.6 Hz, 2H), 7.24 (d, J = 8.6 Hz, 2H), 6.87 (s, 1H), 4.54 (m, 1H), 3.48 (d, J = 5.8 Hz, 1H), 2.33 (s, 3H), 1.65 (d, J = 6.8 Hz, 3H), 1.22 (s, 9H) | MS m/z 340.1 (M + H)$^+$; Rt-0.64 min |

Intermediate 236: (R)—N—((S)-1-(2-fluoro-4-(1-methylcyclopropyl)phenyl)ethyl)-2-methylpropane-2-sulfinamide

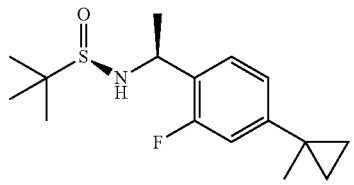 [SMILES: C[C@H](N[S@](=O)C(C)(C)C)c1ccc(C2(C)CC2)cc1F]

Step 1

To an oven dried round bottom flask with stir bar was added 4-bromo-2-fluorobenzaldehyde (5 g, 24.6 mmol), (R)-2-methylpropane-2-sulfinamide (3.28 g, 27.1 mmol) and DCE (49 mL). To this mixture was then added copper (II) sulfate (5.90 g, 36.9 mmol). Reaction mixture was heated in a preheated oil bath to 55° C. for 18 hours. Reaction mixture was filtered through a pad celite, washing the solids with CH$_2$Cl$_2$. The filtrate was concentrated to afford a viscous yellow oil of (R,E)-N-(4-bromo-2-fluorobenzylidene)-2-methylpropane-2-sulfinamide (7.73 g, 25.2 mmol, 103% yield). $^1$H NMR (400 MHz, CDCl$_3$) δ 1.27 (s, 9H) 7.31-7.42 (m, 2H) 7.87 (t, J=7.87 Hz, 1H) 8.83 (s, 1H). LCMS m/z 307.9 (M+H)$^+$, Rt 1.01 min.

Step 2

To a solution of (R,E)-N-(4-bromo-2-fluorobenzylidene)-2-methylpropane-2-sulfinamide (7.73 g, 25.2 mmol) in CH$_2$Cl$_2$ (252 mL), cooled to 0° C. (water/ice bath) under nitrogen, was added 3M methyl magnesium bromide (33.7 mL, 101 mmol) in Et$_2$O. Reaction mixture allowed to stir for 30 min at 0° C., then gradually allowed to warm to room temperature and stirred for 1 hour at room temperature. Reaction mixture was cooled to 0° C. then quenched with the slow addition of a saturated solution of NH$_4$Cl. Aqueous mixture extracted with EtOAc. Organic phases combined, washed with water, brine, dried (Na$_2$SO$_4$), filtered and concentrated onto silica gel. Silica gel column chromatography (EtOAc/Heptane 40 to 100%) provided (R)—N—((S)-1-(4-bromo-2-fluorophenyl)ethyl)-2-methylpropane-2-sulfinamide (4.93 g, 15.3 mmol, 60% yield) as a white crystalline solid. $^1$H NMR (400 MHz, CDCl$_3$) δ 1.20 (s, 9H) 1.56 (d, J=6.70 Hz, 3H) 3.34 (br. s., 1H) 4.77-4.87 (m, 1H) 7.19-7.31 (m, 3H). LCMS m/z 324.0 (M+H)$^+$, Rt 0.90 min.

Step 3

To a microwave vial with stir bar was added (R)—N—((S)-1-(4-bromo-2-fluorophenyl)ethyl)-2-methylpropane-2-sulfinamide (1 g, 3.10 mmol), isopropenyl boronic acid pinacol ester (1.51 ml, 8.07 mmol), DME (8 ml), sodium carbonate (7.76 ml, 15.5 mmol) (2.0 M aq) and PdCl$_2$(dppf).CH$_2$Cl$_2$ adduct (0.127 g, 0.155 mmol). Vessel was capped and heated by microwave irradiation for 20 min at 100° C. Reaction mixture was diluted with a saturated solution of NH$_4$Cl. The aqueous mixture was extracted with EtOAc. Organic phases combined, washed with water, brine, dried (Na$_2$SO$_4$), filtered and concentrated onto silica gel. Silica gel column chromatography (EtOAc/Heptane 50 to 100%) provided (R)—N—((S)-1-(2-fluoro-4-(prop-1-en-2-yl)phenyl)ethyl)-2-methylpropane-2-sulfinamide (830 mg, 2.93 mmol, 94% yield) as a pale brown crystalline. $^1$H NMR (400 MHz, DMSO) δ 1.08-1.11 (m, 9H) 1.47 (d, J=6.80 Hz, 3H) 2.09 (d, J=0.54 Hz, 3H) 4.61-4.71 (m, 1H) 5.14 (t, J=1.32 Hz, 1H) 5.43 (d, J=5.58 Hz, 1H) 5.49 (s, 1H) 7.24-7.30 (m, 1H) 7.31-7.36 (m, 1H) 7.41-7.47 (m, 1H). LCMS m/z 284.0 (M+H)$^+$, Rt 0.93 min.

Step 4

To a round bottom flask containing (R)—N—((S)-1-(2-fluoro-4-(prop-1-en-2-yl)phenyl)ethyl)-2-methylpropane-2-(0.37 g, 1.31 mmol) in DCE (13 mL) at 0° C. was added under argon diethylzinc (1.0M in hexanes) (13.1 mL, 13.1 mmol) followed by the dropwise addition of chloroiodomethane (0.95 mL, 13.1 mmol). Reaction mixture allowed to warm to room temperature and stirred for 1 hour. Reaction mixture was cooled to 0° C. whereupon a second addition of diethylzinc (1.0M in hexanes) (13.1 mL, 13.1 mmol) took place followed by the addition of chloroiodomethane (0.95 mL, 13.1 mmol). Reaction mixture allowed to warm to room temperature and stirred 18 hours under argon. Reaction mixture was cooled to 0° C. in a ice bath and to the cold reaction mixture was slowly added a saturated solution of NH$_4$Cl. The aqueous mixture was extracted with EtOAc. Organic phases combined, washed with water, brine, dried (Na$_2$SO$_4$), filtered and concentrated onto silica gel. Silica gel column chromatography (EtOAc/Heptane 20 to 100%) provided a white crystalline of (R)—N—((S)-1-(2-fluoro-4-(1-methylcyclopropyl)phenyl)ethyl)-2-methylpropane-2-sulfinamide (89 mg, 0.299 mmol, 22.92% yield). $^1$H NMR (400 MHz, CDCl$_3$) δ 0.75-0.79 (m, 2H) 0.85-0.90 (m, 2H) 1.20 (s, 9H) 1.55 (s, 3H) 1.57 (d, J=6.80 Hz, 1H) 3.34 (d, J=5.23 Hz, 1H) 4.75-4.85 (m, 1H) 6.90 (dd, J=12.30, 1.74 Hz, 1H) 6.97 (dd, J=8.05, 1.78 Hz, 1H) 7.22 (t, J=7.97 Hz, 1H). LCMS m/z 298.1 (M+H)$^+$, Rt 1.01 min.

Intermediate 237: (R)—N—((S)-1-(4-(1-ethoxycyclopropyl)-2-fluorophenyl)ethyl)-2-methylpropane-2-sulfinamide

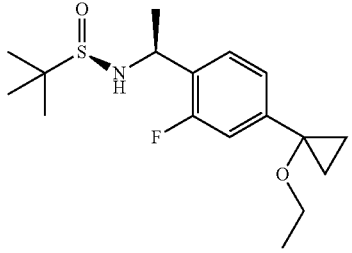 [SMILES: CCOC1(c2ccc([C@H](C)N[S@](=O)C(C)(C)C)c(F)c2)CC1]

Step 1

To a microwave vial with stir bar was added (R)—N—((S)-1-(4-bromo-2-fluorophenyl)ethyl)-2-methylpropane-2-sulfinamide (500 mg, 1.55 mmol) followed by the addition of tributyl(1-ethoxyvinyl)stannane (1.12 g, 3.10 mmol), triethylamine (0.65 ml, 4.65 mmol) and PdCl$_2$(dppf).

CH₂Cl₂ adduct (63 mg, 0.078 mmol). To the solids was added toluene (10 ml). Vial capped and heated in a preheated sand bath at 100° C. for 1 hour. Reaction mixture was loaded onto silica gel column. Silica gel column chromatography (MeOH/CH₂Cl₂ 0 to 10% with 1% NH₄OH buffer) provided (R)—N—((S)-1-(4-(1-ethoxyvinyl)-2-fluorophenyl)ethyl)-2-methylpropane-2-sulfinamide (498 mg, 1.59 mmol, 102% yield) as a brown viscous oil which crystallizes upon standing. ¹H NMR (400 MHz, CDCl₃) δ 1.20 (s, 9H) 1.43 (t, J=6.97 Hz, 3H) 1.58 (d, J=6.75 Hz, 3H) 3.35 (d, J=4.74 Hz, 1H) 3.92 (q, J=6.96 Hz, 2H) 4.23 (d, J=2.79 Hz, 1H) 4.65 (d, J=2.79 Hz, 1H) 4.79-4.89 (m, 1H) 7.16-7.20 (m, 1H) 7.29-7.34 (m, 1H) 7.39 (dd, J=8.07, 1.66 Hz, 1H).

Step 2

To a round bottom flask containing (R)—N—((S)-1-(4-(1-ethoxyvinyl)-2-fluorophenyl)ethyl)-2-methylpropane-2-sulfinamide (0.49 g, 1.56 mmol) and chloroiodomethane (1.14 mL, 15.6 mmol) in toluene (15 mL) at 0° C. under argon was added diethylzinc (1.0M in hexanes) (15.6 mL, 15.6 mmol). Reaction mixture allowed to warm to room temperature and stirred for 1 hour. Reaction mixture was cooled to 0° C. in an ice bath and to the cold reaction mixture was slowly added a saturated solution of NH₄Cl. The aqueous mixture was extracted with EtOAc. Organic phases combined, washed with water, brine, dried (Na₂SO₄), filtered and concentrated onto silica gel. Silica gel column chromatography (MeOH/CH₂Cl₂ 0 to 10%) provided (R)—N—((S)-1-(4-(1-ethoxycyclopropyl)-2-fluorophenyl)ethyl)-2-methylpropane-2-sulfinamide (145 mg, 0.44 mmol, 28% yield) as a viscous brown oil. ¹H NMR (300 MHz, CDCl₃) δ 0.93-0.99 (m, 2H) 1.14-1.20 (m, 3H) 1.21 (s, 9H) 1.22-1.27 (m, 2H) 1.57-1.61 (m, 4H) 3.35 (d, J=4.98 Hz, 1H) 3.45 (q, J=7.07 Hz, 2H) 4.77-4.87 (m, 1H) 6.98 (dd, J=7.58, 1.43 Hz, 3H) 7.00-7.03 (m, 4H) 7.28-7.32 (m, 1H). LCMS m/z 328.1 (M+H)⁺, Rt 0.95 min.

Intermediate 238: (R)—N—((S)-1-(4-(1-cyanocyclopropyl)-2-fluorophenyl)ethyl)-2-methylpropane-2-sulfinamide

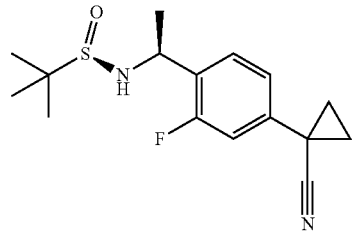 [SMILES: C[C@H](N[S@](=O)C(C)(C)C)c1ccc(C2(C#N)CC2)cc1F]

Step 1

To a microwave vial with a stir bar was added (R)—N—((S)-1-(4-bromo-2-fluorophenyl)ethyl)-2-methylpropane-2-sulfinamide (300 mg, 0.93 mmol), 4-isoxazoleboronic acid pinacol ester (218 mg, 1.12 mmol), PdCl₂(dppf).CH₂Cl₂ adduct (76 mg, 0.09 mmol), potassium fluoride (2.7 mL, 1.0 M in water, 2.79 mmol) and finally DMSO (9 mL). The reaction mixture was degassed with bubbling nitrogen (3 min) and the vial capped and heated in a preheated oil bath at 130° C. for 18 hours. The reaction mixture was diluted with a saturated solution of NH₄Cl and extracted with EtOAc. Organic phases combined, washed with water, brine, dried (Na₂SO₄), filtered and concentrated onto silica gel. Silica gel column chromatography (EtOAc/Heptanes 40 to 100%) provided (R)—N—((S)-1-(4-(cyanomethyl)-2-fluorophenyl)ethyl)-2-methylpropane-2-sulfinamide (136 mg, 0.48 mmol, 52% yield) as a viscous brown oil. ¹H NMR (400 MHz, CDCl₃) δ 1.19 (s, 9H) 1.57 (d, J=6.80 Hz, 3H) 3.39 (d, J=4.35 Hz, 1H) 3.74 (s, 2H) 4.81-4.88 (m, 1H) 7.04 (d, J=10.66 Hz, 1H) 7.11 (d, J=7.97 Hz, 1H) 7.38 (t, J=7.73 Hz, 1H). LCMS m/z 283.0 (M+H)⁺, Rt 0.72 min.

Step 2

To a scintillation vial containing (R)—N—((S)-1-(4-(cyanomethyl)-2-fluorophenyl)ethyl)-2-methylpropane-2- (86 mg, 0.31 mmol) and a stir bar was added toluene (2 mL). To this mixture was then added tetrabutylammonium bromide (19 mg, 0.06 mmol) followed by the addition of NaOH (1.52 ml, 1.0 M (aq), 1.52 mmol) and 1,2-dibromoethane (0.11 ml, 1.22 mmol). Vial capped and reaction mixture was stirred vigorously at room temperature for 18 hours. Whereupon, 1,2-dibromoethane (0.11 ml, 1.22 mmol) and tetrabutylammonium bromide (19 mg, 0.06 mmol) were added and reaction mixture allowed to stir an additional 18 hours. A third addition of 1,2-dibromoethane (0.11 ml, 1.22 mmol) was added and the reaction mixture heated to 50° C. for an additional 18 hours in a preheated aluminum tray. The reaction mixture was quenched with a saturated solution of NH₄Cl and the aqueous mixture extracted with EtOAc. Organics combined and washed twice with water, brine, dried (Na₂SO₄), filtered and concentrated. Crude material was passed through a small plug of silica gel using 10% MeOH:90% DCM to elute product. The solution was concentrated to afford a viscous orange oil of (R)—N—((S)-1-(4-(1-cyanocyclopropyl)-2-fluorophenyl)ethyl)-2-methylpropane-2-sulfinamide (23 mg, 0.08 mmol, 24% yield). ¹H NMR (400 MHz, CDCl₃) δ 1.20 (s, 9H) 1.38-1.44 (m, 2H) 1.56 (d, J=6.75 Hz, 3H) 1.73-1.79 (m, 2H) 3.37 (d, J=4.45 Hz, 1H) 4.78-4.88 (m, 1H) 6.94 (dd, J=11.35, 1.91 Hz, 1H) 7.09 (dd, J=8.07, 1.91 Hz, 1H) 7.34 (t, J=7.90 Hz, 1H). LCMS m/z 309.2 (M+H)⁺, Rt 0.83 min.

Intermediate 239: (R)—N—((S)-1-(2-fluoro-4-isopropylphenyl)ethyl)-2-methylpropane-2-sulfinamide

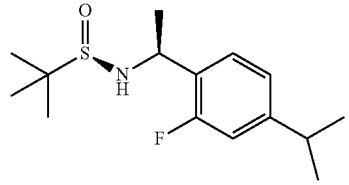 [SMILES: CC(C)c1ccc([C@H](C)N[S@](=O)C(C)(C)C)c(F)c1]

To a round bottom flask containing (R)—N—((S)-1-(2-fluoro-4-(prop-1-en-2-yl)phenyl)ethyl)-2-methylpropane-2-sulfinamide (204 mg, 0.72 mmol) and a stir bar was added MeOH (7.2 mL). To this solution was added palladium on carbon (77 mg, 10%, 0.07 mmol) in MeOH (1 mL). A hydrogen atmosphere was inserted and the resulting reaction mixture stirred at room temperature for 18 hours, at which time more palladium on carbon was added (300 mg) in MeOH (5 mL). A hydrogen atmosphere was inserted again and the reaction mixture allowed to stir an additional 18 hours at room temperature. The reaction mixture was filtered through a syringe filter and concentrated to afford a light brown viscous oil of (R)—N—((S)-1-(2-fluoro-4-isopropylphenyl)ethyl)-2-methylpropane-2-sulfinamide (149 mg, 0.52 mmol, 73% yield) which crystallizes upon standing. ¹H NMR (400 MHz, CDCl₃) δ 1.20 (s, 9H) 1.24 (d, J=5.87 Hz, 6H) 1.58 (d, J=6.70 Hz, 3H) 2.89 (dt, J=13.79, 6.90 Hz, 1H) 3.35 (d, J=5.04 Hz, 1H) 4.76-4.85 (m, 1H) 6.90 (dd, J=12.03, 1.52 Hz, 1H) 6.98 (dd, J=7.90, 1.54 Hz, 1H) 7.24 (t, J=7.97 Hz, 1H). LCMS m/z 286.3 (M+H)⁺, Rt 1.01 min.

Intermediate 240: (R)—N—((S)-1-(2-fluoro-4-(1-methyl-1H-pyrazol-4-yl)phenyl)ethyl)-2-methylpropane-2-sulfinamide

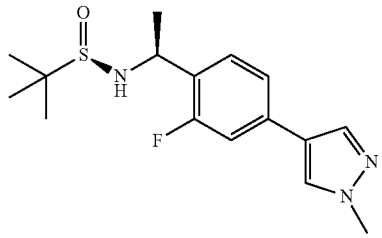 [SMILES: C[C@H](N[S@](=O)C(C)(C)C)c1ccc(-c2cnn(C)c2)cc1F]

To a two microwave vials with stir bars were added (R)—N—((S)-1-(4-bromo-2-fluorophenyl)ethyl)-2-methylpropane-2-sulfinamide (1.5 g, 4.65 mmol), 1-methyl-4-1H-pyrazoleboronic acid pinacol ester (2.91 g, 13.9 mmol), DME (20 mL), sodium carbonate (11.6 mL, 23.3 mmol, 2.0 M aq) and PdCl$_2$(dppf).CH$_2$Cl$_2$ adduct (190 mg, 0.23 mmol) divided between the two vials. The vials were capped and heated by microwave irradiation for 20 min at 100° C. respectively. The reaction mixtures combined, diluted with a saturated solution of NH$_4$Cl and EtOAc. The phases were partitioned and the aqueous phase extracted with EtOAc. Organic phases combined, washed with water, brine, dried (Na$_2$SO$_4$), filtered and concentrated onto silica gel. Silica gel column chromatography (EtOAc/Heptane 40 to 100%) provided a orange crystalline of (R)—N—((S)-1-(2-fluoro-4-(1-methyl-1H-pyrazol-4-yl)phenyl)ethyl)-2-methylpropane-2-sulfinamide (1.07 g, 3.31 mmol, 71% yield. $^1$H NMR (400 MHz, CDCL$_3$) δ ppm 1.21 (s, 9H) 1.60 (d, J=6.80 Hz, 3H) 3.36 (d, J=4.25 Hz, 1H) 3.96 (s, 3H) 4.79-4.91 (m, 1H) 7.13 (dd, J=11.69, 1.61 Hz, 1H) 7.23 (dd, J=8.00, 1.64 Hz, 1H) 7.30-7.37 (m, 1H) 7.60 (s, 1H) 7.74 (s, 1H). LCMS m/z 324.0 (M+H)$^+$, Rt 0.74 min.

The Intermediates in Table 13a were prepared by a method similar to the one described for the preparation of Intermediate 240.

TABLE 13a

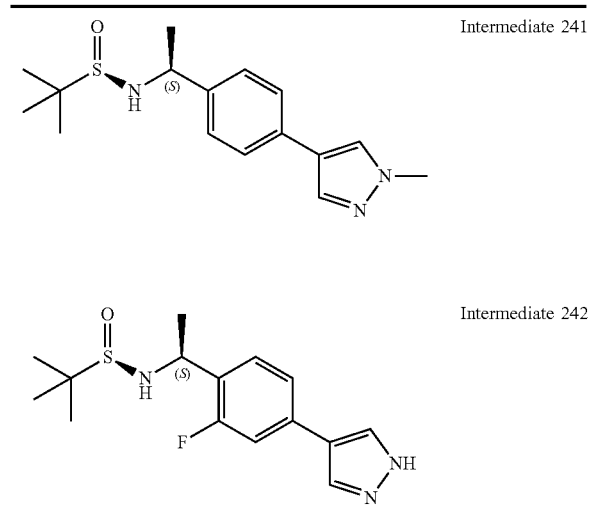

Intermediate 241

Intermediate 242

Intermediate 243: (R)—N—((S)-1-(2-fluoro-4-(trifluoromethyl)phenyl)ethyl)-2-methylpropane-2-sulfinamide

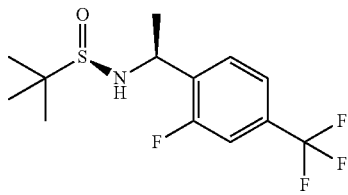 [SMILES: C[C@H](N[S@](=O)C(C)(C)C)c1ccc(C(F)(F)F)cc1F]

Step 1

To a oven dried round bottom flask with stir bar was added 2-fluoro-4-(trifluoromethyl)benzaldehyde (5 g, 26.0 mmol), (R)-2-methylpropane-2-sulfinamide (3.47 g, 28.6 mmol) and DCE (52 mL). To this mixture was then added copper (II) sulfate (6.23 g, 39.0 mmol). The reaction mixture was heated in a preheated oil bath at 55° C. for 18 hours. The reaction mixture was filtered through a pad celite, washing the solids with DCE. The filtrate was concentrated to afford a viscous green oil of (R,E)-N-(2-fluoro-4-(trifluoromethyl)benzylidene)-2-methyl propane-2-sulfinamide (7.3 g, 24.7 mmol, 95% yield). Material was taken onto next step without further purification. $^1$H NMR (400 MHz, CDCl$_3$) δ ppm 1.29 (s, 9H) 7.44 (d, J=10.08 Hz, 1H) 7.51 (d, J=8.27 Hz, 1H) 8.13 (t, J=7.46 Hz, 1H) 8.92 (s, 1H). LCMS m/z 296.0 (M+H)$^+$, Rt 1.02 min.

Step 2

To a solution of (R,E)-N-(2-fluoro-4-(trifluoromethyl)benzylidene)-2-methylpropane-2-sulfinamide (7.3 g, 24.7 mmol) in CH$_2$Cl$_2$ (247 mL) cooled to 0° C. (water/ice bath) under nitrogen, was added 3M methyl magnesium bromide (33 mL, 99 mmol) in Et$_2$O. Reaction mixture allowed to stir for 30 min at 0° C., then gradually allowed to warm to room temperature and stirred for 1 hour at room temperature. Reaction mixture was cooled to 0° C. then quenched with the slow addition of a saturated solution of NH$_4$Cl. Aqueous mixture extracted with EtOAc. Organic phases combined, washed with water, brine, dried (Na$_2$SO$_4$), filtered and concentrated onto silica gel. Silica gel column chromatography (EtOAc/Heptane 40 to 100%) provided (R)—N—

TABLE 13b

Chemical name, NMR chemical shifts and LCMS signal for each intermediate listed in Table 13.

| Intermediate: Name | $^1$H NMR (400 MHz) δ ppm | LCMS |
|---|---|---|
| 241: (R)-2-methyl-N-((S)-1-(4-(1-methyl-1H-pyrazol-4-yl)phenyl)ethyl)propane-2-sulfinamide | | MS m/z 306.0 (M + H)$^+$, Rt 0.71 min. |
| 242: (R)-N-((S)-1-(2-fluoro-4-(1H-pyrazol-4-yl)phenyl)ethyl)-2-methylpropane-2-sulfinamide | (DMSO) 1.10 (s, 9 H) 1.47 (d, J = 6.75 Hz, 3 H) 4.60-4.70 (m, 1 H) 5.41 (d, J = 5.48 Hz, 1 H) 7.38-7.44 (m, 3 H) 7.96 (br. s., 1 H) 8.23 (br. s., 1 H) 12.97 (br. s., 1 H) | MS m/z 310.0 (M + H)$^+$, Rt 0.67 min. |

((S)-1-(2-fluoro-4-(trifluoromethyl)phenyl)ethyl)-2-methyl-propane-2-sulfinamide (4.68 g, 15.0 mmol, 61% yield) as a white crystalline solid. $^1$H NMR (400 MHz, CDCL$_3$) δ 1.22 (s, 9H) 1.60 (d, J=6.80 Hz, 3H) 3.38 (d, J=4.01 Hz, 1H) 4.87-4.97 (m, 1H) 7.33 (d, J=10.32 Hz, 1H) 7.39-7.45 (m, 1H) 7.49-7.55 (m, 1H). LCMS m/z 312.0 (M+H)$^+$, Rt 0.92 min.

Intermediate 244: (S)-tert-butyl 1-(3-chloro-4-(cyclopentylcarbamoyl)phenyl)ethyl carbamate

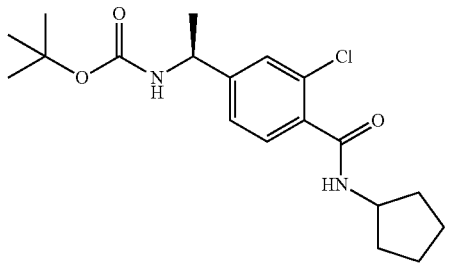 [SMILES: C[C@H](NC(=O)OC(C)(C)C)c1ccc(C(=O)NC2CCCC2)c(Cl)c1]

Step 1

To a round bottom flask with stir bar was added 4-((S)-1aminoethyl-2-chlorobenzoic acid HCl salt (1.05 g, 4.45 mmol) followed by the addition of THF (40 mL). To this solution was added DIEA (1.86 ml, 10.7 mmol). The reaction mixture becomes cloudy white followed by the addition of di-tert-butyl dicarbonate (1.07 g, 4.89 mmol). Resulting reaction mixture allowed to stir for 18 hours at room temperature. At which time the reaction mixture was then heated to 60° C. for 2 hours in a oil bath. Di-tert-butyl dicarbonate (1.07 g, 4.89 mmol) and NMP (20 ml) were then added and the resulting reaction mixture allowed to stir for 2 hours at 60° C. Volatiles were removed. The resulting oil was diluted with a saturated solution of NH$_4$Cl and the aqueous mixture extracted with EtOAc. The organic phases combined, washed twice with water, brine, dried (Na$_2$SO$_4$), filtered and concentrated to a viscous yellow oil of (S)-4-(1-(tert-butoxycarbonylamino)ethyl)-2-chlorobenzoic acid (2.32 g, 6.19 mmol, 139% yield) which contains some excess di-tert-butyl dicarbonate and NMP. LCMS m/z 284.9 (M+H)$^+$ (carboxylic acid fragment+CH$_3$CN adduct), Rt 0.75 min.

Step 2

To a round bottom flask with stir bar was added (S)-4-(1-(tert-butoxycarbonylamino)ethyl)-2-chlorobenzoic acid (450 mg, 1.20 mmol), cyclopentylamine (355 µL, 3.60 mmol), EDC HCl (460 mg, 2.40 mmol), 1-hydroxy-7-azabenzotriazole (229 mg, 1.68 mmol) and DMF (6 mL). To this mixture was then added DIEA (629 µL, 3.60 mmol). Reaction mixture was allowed to stir at room temperature for 18 hours. The reaction mixture was diluted with water and extracted with EtOAc. The organic phases were combined, washed with twice with water, brine, dried (Na$_2$SO$_4$), filtered and concentrated to a brown crystalline of (S)-tert-butyl 1-(3-chloro-4-(cyclopentylcarbamoyl)phenyl)ethyl-carbamate (476 mg, 1.17 mmol, 97% yield). LCMS m/z 367.0 (M+H)$^+$, Rt 0.90 min.

Intermediate 245: (R)—N—((S)-1-(2,5-difluoro-4-(1-methyl-1H-pyrazol-4-yl)phenyl)ethyl)-2-methyl-propane-2-sulfinamide

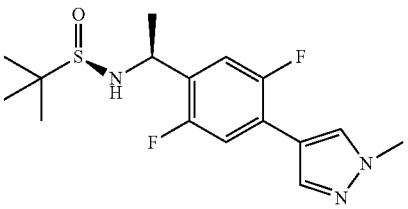 [SMILES: C[C@H](N[S@](=O)C(C)(C)C)c1cc(F)c(-c2cnn(C)c2)cc1F]

Step 1

To a round bottom flask with stir bar was added 4-bromo-2,5-difluorobenzaldehyde (5.3 g, 24.0 mmol), (R)-2-methylpropane-2-sulfinamide (3.2 g, 26.4 mmol) and DCE (80 mL). To this mixture was then added copper (II) sulfate (5.74 g, 36.0 mmol). The reaction mixture was heated in a preheated oil bath at 60° C. for 18 hours. The reaction mixture was filtered through a pad celite, washing the solids with DCE. The filtrate was concentrated to afford a viscous green oil of (R,E)-N-(4-bromo-2,5-difluorobenzylidene)-2-methylpropane-2-sulfinamide (7.2 g, 22.2 mmol, 93% yield). Material was taken onto next step without further purification. LCMS m/z 326.0 (M+H)$^+$, Rt 1.04 min.

Step 2

To a solution of (R,E)-N-(4-bromo-2,5-difluorobenzylidene)-2-methylpropane-2-sulfinamide (7.2 g, 22.2 mmol in CH$_2$Cl$_2$ (200 mL) cooled to 0° C. (water/ice bath) under nitrogen, was added 3M methyl magnesium bromide (29.6 mL, 89 mmol) in Et$_2$O. Reaction mixture allowed to stir for 5 hours at 0° C. then quenched with the slow addition of a saturated solution of NH$_4$Cl. Aqueous mixture adjusted to pH 8 with HCl (1 N) and extracted with DCM. Organic phases combined, washed with water, brine, dried (Na$_2$SO$_4$), filtered and concentrated onto silica gel. Silica gel column chromatography (EtOAc/Heptane 30 to 100%) provided (R)—N—((S)-1-(4-bromo-2,5-difluorophenyl)ethyl)-2-methylpropane-2-sulfinamide (6.86 g, 20.2 mmol, 91% yield) LCMS m/z 342.1 (M+H)$^+$, Rt 0.96 min.

Step 3

To two microwave vials with stir bars were added (R)—N—((S)-1-(4-bromo-2,5-difluorophenyl)ethyl)-2-methyl-propane-2-sulfinamide (500 mg, 1.47 mmol), 1-Methyl-4-1H-pyrazoleboronic acid, pinacol ester (917 mg, 4.41 mmol), DME (6 ml), Na$_2$CO$_3$ (3.67 ml, 7.35 mmol) (2.0 M aq) and PdCl$_2$(dppf).CH$_2$Cl$_2$ adduct (60.0 mg, 0.07 mmol) divided evenly between the two vessels. Vessels were capped and heated by microwave irradiation for 20 min at 100° C. Reaction mixtures were combined, diluted with a saturated solution of NH$_4$Cl and EtOAc. Phases partitioned. Aqueous phase extracted with EtOAc and organic phases combined, washed with water, brine, dried (Na$_2$SO$_4$), filtered and concentrated onto silica gel. Silica gel column chromatography (EtOAc/Heptane 60 to 100%) provided (R)—N—((S)-1-(2,5-difluoro-4-(1-methyl-1H-pyrazol-4-yl)phenyl)ethyl)-2-methylpropane-2-sulfinamide (370 mg, 1.08 mmol, 73.7% yield). $^1$H NMR (400 MHz, CDCL$_3$) δ ppm 1.23 (s, 9H) 1.57-1.60 (m, 3H) 3.33 (d, J=4.06 Hz, 1H) 3.97 (s, 3H) 4.79-4.88 (m, 1H) 7.10 (dd, J=11.20, 6.06 Hz, 1H) 7.20 (dd, J=10.78, 6.19 Hz, 1H) 7.76 (d, J=2.20 Hz, 1H) 7.82 (s, 1H). LCMS m/z 342.1 (M+H)$^+$, Rt 0.77 min.

Intermediate 246: (S)—N—((S)-1-(1-(4-chlorophenyl)-1H-imidazol-4-yl)ethyl)-2-methylpropane-2-sulfinamide

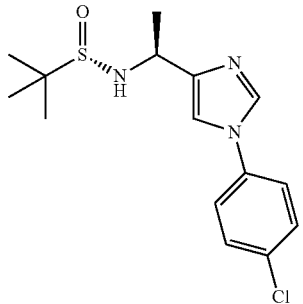 [SMILES: C[C@H](N[S@@](=O)C(C)(C)C)c1cn(-c2ccc(Cl)cc2)cn1]

Step 1

To a mixture of 1H-imidazole-4-carbaldehyde (3.71 g, 38.6 mmol), 1-chloro-4-iodobenzene (13.81 g, 57.9 mmol), (1R,2R)—N1,N2-dimethylcyclohexane-1,2-diamine (1.10 g, 7.72 mmol), copper(I) iodide (0.368 g, 1.93 mmol) and cesium carbonate (25.2 g, 77 mmol) was added DMF (50 mL). The reaction was sealed and heated to 110° C. for 18 hours. The reaction mixture was then cooled to room temperature and diluted with a saturated solution of NH$_4$Cl. A brown solid develops. Solid was collected, washed with water and air dried. Solid material was then dissolved in 10% MeOH:90% DCM solution and dried (Na$_2$SO$_4$), filtered and concentrated to afford a dark brown solid 1-(4-chlorophenyl)-1H-imidazole-4-carbaldehyde (8.55 g, 41.4 mmol, 107% yield). Material as used without further purification. LCMS m/z 207.1 (M+H)$^+$, Rt 0.58 min.

Step 2

To a suspension of (S)-(–)tert-Butanesulfinamide (2.35 g, 19.4 mmol) and 1-(4-chlorophenyl)-1H-imidazole-4-carbaldehyde (4 g, 19.4 mmol) in DCE (39 mL) was added CuSO$_4$ (4.63 g, 29.0 mmol). The reaction mixture was heated at 60° C. for 18 hours in a oil bath. A dark brown suspension resulted. The reaction mixture was then cooled to room temperature, filtered through a pad of celite, rinsed with DCM. The solution was then concentrated onto silica gel. Silica gel column chromatography (EtOAc/Heptane 0 to 100%) provided (S,E)-N-((1-(4-chlorophenyl)-1H-imidazol-4-yl)methylene)-2-methylpropane-2-sulfinamide (1.69 g, 5.45 mmol, 28.2% yield) as a light brown solid. LCMS m/z 310.0 (M+H)$^+$, Rt 0.75 min.

Step 3

To a solution of (S,E)-N-((1-(4-chlorophenyl)-1H-imidazol-4-yl)methylene)-2-methylpropane-2-sulfinamide (1.69 g, 5.45 mmol) in DCM (27 mL), cooled to –40° C. (acetone/dry ice) under N$_2$, was added 3M MeMgBr (7.27 ml, 21.8 mmol) in diethyl ether. Reaction mixture allowed to stir for 1 hr at –40° C. Reaction mixture was quenched with the slow addition of a saturated solution of NH$_4$Cl and diluted with EtOAc. Phases partitioned, aqueous phase extracted with EtOAc and the organic layers combined washed with water, brine, dried (Na$_2$SO$_4$), filtered and concentrated onto silica gel. Silica gel column chromatography (EtOAc/MeOH:EtOAc 0 to 5%) provided (S)—N—((S)-1-(1-(4-chlorophenyl)-1H-imidazol-4-yl)ethyl)-2-methylpropane-2-sulfinamide (1.11 g, 3.41 mmol, 62% yield). $^1$H NMR (400 MHz, CDCL$_3$) δ 1.25 (s, 9H) 1.58 (d, J=6.65 Hz, 3H) 3.80 (d, J=5.48 Hz, 1H) 4.59 (quin, J=6.36 Hz, 1H) 7.26 (s, 1H) 7.33 (d, J=8.61 Hz, 2H) 7.41-7.47 (m, 2H) 7.76 (d, J=1.17 Hz, 1H). LCMS m/z 326.1 (M+H)$^+$, Rt 0.59 min.

Intermediate 247: (S)-1-(5-(4-chlorophenyl)isoxazol-3-yl)ethanamine

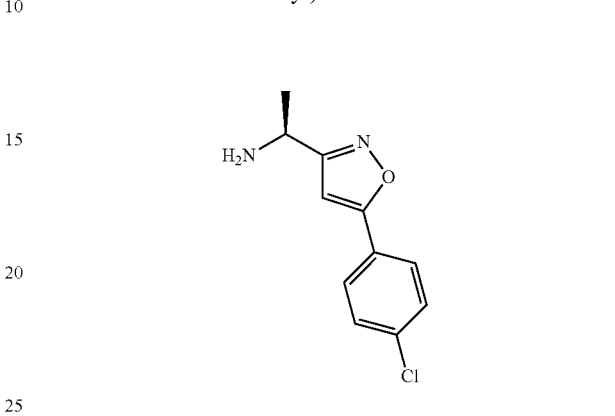

A solution of hydrochloric acid (4.0 M in 1,4-dioxane, 2.1 mL, 8.2 mmol, 2 equiv) was added to a solution of (R)—N—((S)-1-(5-(4-chlorophenyl)isoxazol-3-yl)ethyl)-2-methylpropane-2-sulfinamide (1.34 g, 4.1 mmol) in 1,4-dioxane at room temperature. A precipitate formed. The suspension was stirred for 1 hour and then concentrated in vacuo to give the hydrochloride salt of (S)-1-(5-(4-chlorophenyl)isoxazol-3-yl)ethanamine (1.1 g, light yellow solid), which was used without purification. $^1$H NMR (400 MHz, CD$_3$OD) δ 7.87 (d, J=8.8 Hz, 2H), 7.56 (d, J=8.8 Hz, 2H), 6.98 (s, 1H), 4.72 (q, J=6.9 Hz, 1H), 1.72 (d, J=7.0 Hz, 3H). MS m/z 223.1 (M+H)$^+$; Rt-0.59 min.

The intermediates in Table 14a were prepared using a method similar to that described for the preparation of Intermediate 247.

TABLE 14a

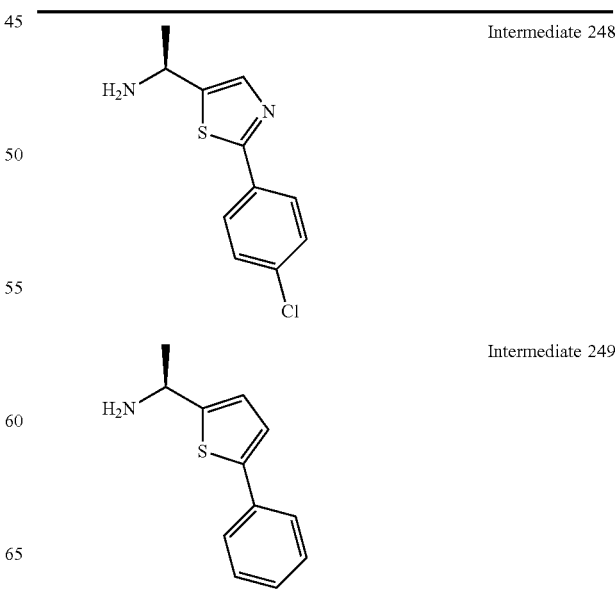

Intermediate 248

Intermediate 249

TABLE 14a-continued
Intermediate 250
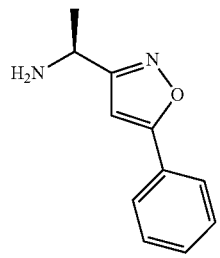
Intermediate 251
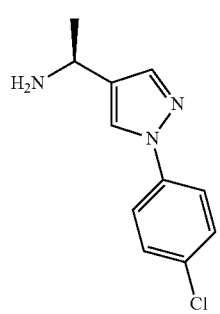
Intermediate 252
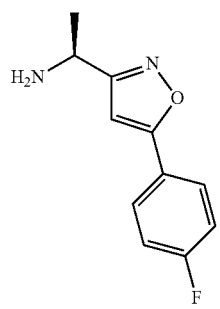
Intermediate 253
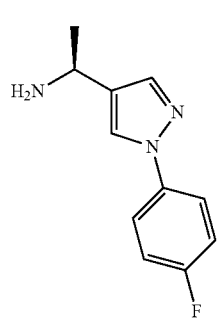
Intermediate 254
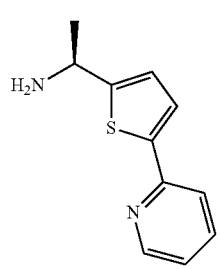
TABLE 14a-continued
Intermediate 255
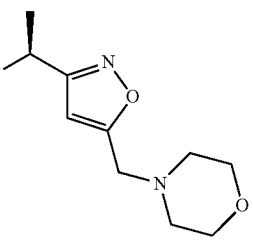
Intermediate 256
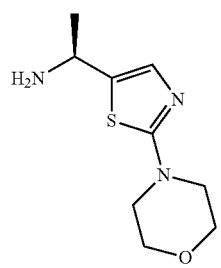
Intermediate 257
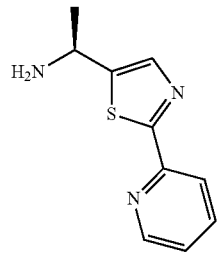
Intermediate 258
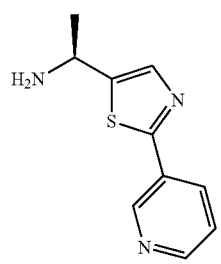
Intermediate 259
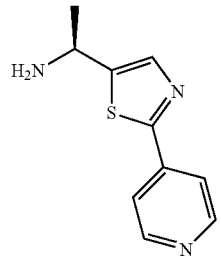
Intermediate 260
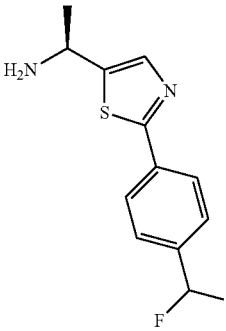

TABLE 14a-continued
| | |
|---|---|
| 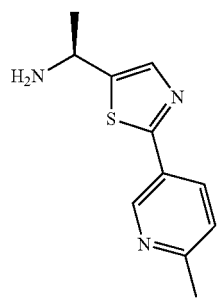 | Intermediate 261 |
| 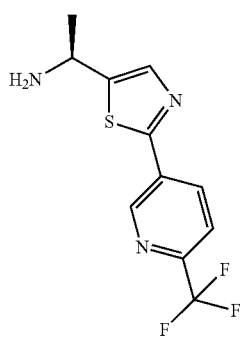 [SMILES: C[C@H](N)c1cnc(-c2ccc(C(F)(F)F)nc2)s1] | Intermediate 262 |
| 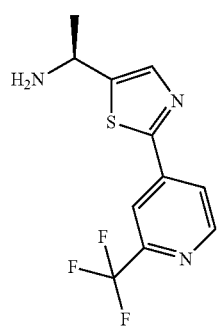 [SMILES: C[C@H](N)c1cnc(-c2ccnc(C(F)(F)F)c2)s1] | Intermediate 263 |
| 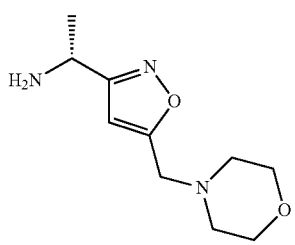 | Intermediate 264 |
| 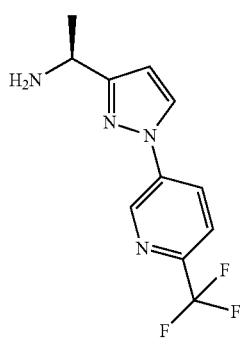 [SMILES: C[C@H](N)c1ccn(-c2ccc(C(F)(F)F)nc2)n1] | Intermediate 265 |
TABLE 14a-continued
| | |
|---|---|
| 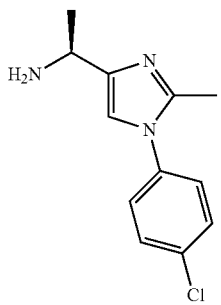 [SMILES: Cc1nc([C@H](C)N)cn1-c1ccc(Cl)cc1] | Intermediate 266 |
| 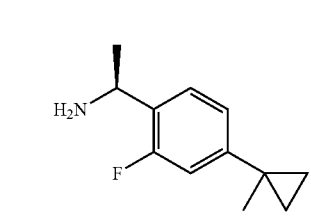 | Intermediate 267 |
| 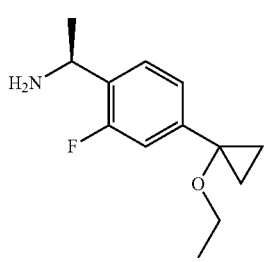 [SMILES: CCOC1(c2ccc([C@H](C)N)c(F)c2)CC1] | Intermediate 268 |
| 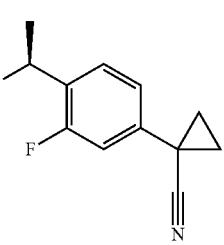 | Intermediate 269 |
| 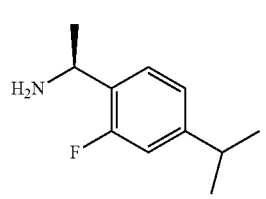 | Intermediate 270 |
| 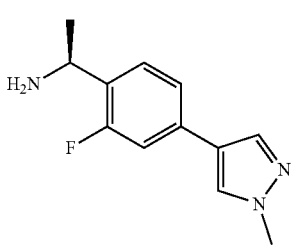 [SMILES: C[C@H](N)c1ccc(-c2cnn(C)c2)cc1F] | Intermediate 271 |

TABLE 14a-continued

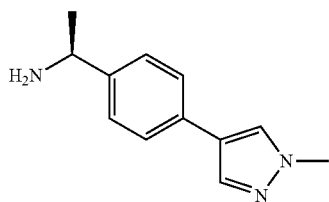
Intermediate 272

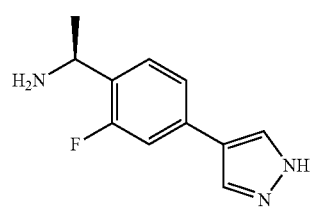
Intermediate 273

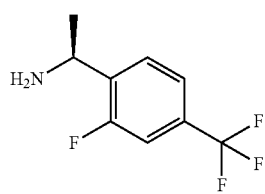
Intermediate 274

TABLE 14a-continued

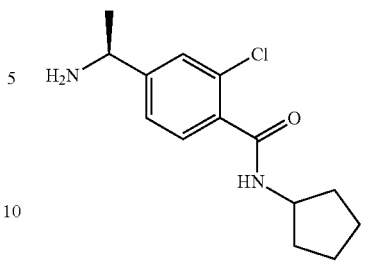
Intermediate 275

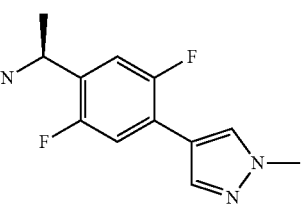
Intermediate 276

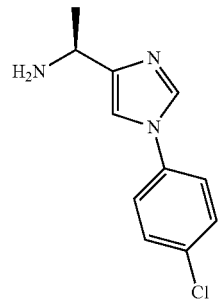
Intermediate 277

TABLE 14b

Chemical name, NMR chemical shifts and LCMS signal for each intermediate listed in Table 14a.

| Intermediate: Name | $^1$H NMR (400 MHz, CD$_3$OD) δ ppm | LCMS |
| --- | --- | --- |
| 248: (S)-1-(2-(4-chlorophenyl)thiazol-5-yl)ethanamine | 7.97 (d, J = 8.7 Hz, 2H), 7.94 (s, 1H), 7.52 (d, J = 8.7 Hz, 2H), 4.95 (m, 1H), 1.78 (d, J = 6.8 Hz, 3H) | MS m/z 239.9 (M + H)$^+$; Rt-0.59 min |
| 249: (S)-1-(5-phenylthiophen-2-yl)ethanamine | 7.29 (dd, J = 8.3, 1.2 Hz, 2H), 7.05 (m, 2H), 6.99 (m, 2H), 6.89 (dd, J = 3.8, 0.6 Hz, 1H), 4.45 (m, 1H), 1.41 (d, J = 6.8 Hz, 3H) | MS m/z 187.1 (M − NH$_2$)$^+$; Rt-0.59 min |
| 250: (S)-1-(5-phenylisoxazol-3-yl)ethanamine | 7.87 (m, 2H), 7.55 (m, 3H), 6.95 (s, 1H), 4.72 (q, J = 6.9 Hz, 1H), 1.73 (d, J = 6.9 Hz, 3H) | MS m/z 189.2 (M + H)$^+$; Rt-0.50 min |
| 251: (S)-1-(1-(4-chlorophenyl)-1H-pyrazol-4-yl)ethanamine | 8.43 (s, 1H), 7.87 (s, 1H), 7.78 (d, J = 9.0 Hz, 2H), 7.51 (d, J = 9.0 Hz, 2H), 4.61 (q, J = 6.9 Hz, 1H), 1.72 (d, J = 6.9 Hz, 3H) | MS m/z 223.1 (M + H)$^+$; Rt-0.54 min |
| 252: (S)-1-(5-(4-fluorophenyl)isoxazol-3-yl)ethanamine | 7.92 (dd, J = 9.0, 5.2 Hz, 2H), 7.30 (t, J = 8.8 Hz, 2H), 6.92 (s, 1H), 4.71 (q, 7.0 Hz, 1H), 1.72 (d, J = 7.0 Hz, 3H) | MS m/z 207.1 (M + H)$^+$; Rt-0.51 min |
| 253: (S)-1-(1-(4-fluorophenyl)-1H-pyrazol-4-yl)ethanamine | 8.39 (s, 1H), 7.86 (s, 1H), 7.78 (dd, J = 9.2, 4.6 Hz, 2H), 7.25 (dd, J = 9.1, 8.4 Hz, 2H), 4.60 (q, J = 6.9 Hz, 1H), 1.71 (d, J = 6.9 Hz, 3H) | MS m/z 207.1 (M + H)$^+$; Rt-0.46 min |

TABLE 14b-continued

Chemical name, NMR chemical shifts and LCMS signal for each intermediate listed in Table 14a.

| Intermediate: Name | $^1$H NMR (400 MHz, CD$_3$OD) δ ppm | LCMS |
|---|---|---|
| 254: (S)-1-(5-(pyridin-2-yl)thiophen-2-yl)ethanamine | 8.73-8.78 (m, 1 H), 8.57 (td, J = 8.0, 1.6 Hz, 1 H), 8.31 (d, J = 8.3 Hz, 1 H), 8.03 (d, J = 4.0 Hz, 1 H), 7.92 (ddd, J = 7.5, 6.0, 1.1 Hz, 1 H), 7.50 (dd, J = 4.0, 0.6 Hz, 1 H), 4.91-4.98 (m, 1 H) 1.80 (d, J = 6.8 Hz, 3 H) | MS m/z 206.0 (M + H)$^+$; Rt-0.35 min |
| 255: (S)-1-(5-(morpholinomethyl)isoxazol-3-yl)ethanamine | 6.97 (s, 1H), 4.72 (m, 3H), 3.96 (m, 4H), 3.38 (m, 4H), 1.70 (d, J = 7.0 Hz, 3H) | MS m/z 212.1 (M + H)$^+$; Rt-0.14 min |
| 256: (S)-1-(2-morpholinothiazol-5-yl)ethanamine | 7.56 (s, 1H), 4.78 (quin, J = 6.8 Hz, 1H), 3.88 (m, 4H), 3.68 (m, 4H), 1.71 (d, J = 6.9 Hz, 3H) | MS m/z 197.0 (M − NH$_2$)$^+$; Rt-0.26 min |
| 257: (S)-1-(2-(pyridin-2-yl)thiazol-5-yl)ethanamine | 8.68 (m, 1H), 8.30 (m, 1H), 8.17 (m, 1H), 8.09 (m, 1H), 7.66 (m, 1H), 4.99 (q, J = 7.1 Hz, 1H), 1.80 (d, J = 6.9 Hz, 3H) | MS m/z 189.0 (M − NH$_2$)$^+$; Rt-0.39 min |
| 258: (S)-1-(2-(pyridin-3-yl)thiazol-5-yl)ethanamine | 9.49 (d, J = 2.0 Hz, 1H), 9.14 (m, 1H), 8.96 (m, 1H), 8.23 (ddd, J = 8.3, 5.8, 0.7 Hz, 1H), 8.17 (d, J = 0.7 Hz, 1H), 5.04 (q, J = 6.9 Hz, 1H), 1.82 (d, J = 6.9 Hz, 3H) | MS m/z 189.0 (M − NH$_2$)$^+$; Rt-0.25 min |
| 259: (S)-1-(2-(pyridin-4-yl)thiazol-5-yl)ethanamine | 8.97 (d, J = 6.9 Hz, 2H), 8.62 (d, J = 6.9 Hz, 2H), 8.29 (d, J = 0.6 Hz, 1H), 5.08 (q, J = 6.8 Hz, 1H), 1.84 (d, J = 6.9 Hz, 3H) | MS m/z 189.0 (M − NH$_2$)$^+$; Rt-0.24 min |
| 260: (S)-1-(2-(4-(difluoromethyl)phenyl)thiazol-5-yl)ethanamine | 8.09 (d, J = 7.7 Hz, 2H), 7.99 (s, 1H), 7.68 (d, J = 7.7 Hz, 2H), 6.84 (t, J = 56 Hz, 1H), 4.96 (m, 1H), 1.78 (d, J = 6.9 Hz, 3H) | MS m/z 256.0 (M + H)$^+$; Rt-0.56 min |
| 261: (S)-1-(2-(6-methylpyridin-3-yl)thiazol-5-yl)ethanamine | 9.30 (d, J = 2.0 Hz, 1H), 8.98 (dd, J = 8.5, 2.0 Hz, 1H), 8.14 (s, 1H), 8.06 (d, J = 8.5 Hz, 1H), 5.03 (q, J = 6.9 Hz, 1H), 2.87 (s, 3H), 1.82 (d, J = 6.9 Hz, 3H) | MS m/z 220.1 (M + H)$^+$; Rt-0.27 min |
| 262: (S)-1-(2-(6-(trifluoromethyl)pyridin-3-yl)thiazol-5-yl)ethanamine | 9.31 (d, J = 2.1 Hz, 1H), 8.59 (dd, J = 8.2, 1.7 Hz, 1H), 8.10 (s, 1H), 7.98 (d, J = 8.3 Hz, 1H), 5.01 (q, J = 6.8 Hz, 1H), 1.81 (d, J = 6.8 Hz, 3H) | MS m/z 274.0 (M + H)$^+$; Rt-0.51 min |
| 263: (S)-1-(2-(2-(trifluoromethyl)pyridin-4-yl)thiazol-5-yl)ethanamine | 8.87 (d, J = 5.1 Hz, 1H), 8.34 (dd, J = 1.5, 0.7 Hz, 1H), 8.17 (m, 1H), 5.02 (q, J = 6.9 Hz, 1H), 1.82 (d, J = 6.9 Hz, 3H) | MS m/z 274.0 (M + H)$^+$; Rt-0.51 min |
| 264: (R)-1-(5-(morpholinomethyl)isoxazol-3-yl)ethanamine | 7.01 (s, 1H), 4.74 (m, 3H), 4.00-3.86 (br m, 4H), 3.45-3.37 (br m, 4H), 1.70 (d, J = 6.9 Hz, 3H) | MS m/z 212.2 (M + H)$^+$; Rt-0.14 min |
| 265: (S)-1-(1-(6-(trifluoromethyl)pyridin-3-yl)-1H-pyrazol-3-yl)ethanamine | 9.29 (d, J = 2.4 Hz, 1H), 8.56 (d, J = 2.6 Hz, 1H), 8.47 (dd, J = 8.6, 2.5 Hz, 1H), 7.98 (d, J = 8.6 Hz, 1H), 6.73 (d, J = 2.6 Hz, 1H), 4.68 (q, J = 7.0 Hz, 1H), 1.72 (d, J = 6.9 Hz, 3H) | MS m/z 257.0 (M + H)$^+$; Rt-0.12 min |
| 266: (S)-1-(1-(4-chlorophenyl)-2-methyl-1H-imidazol-4-yl)ethanamine | 7.83 (d, J = 0.7 Hz, 1H), 7.72 (m, 2H), 7.63 (m, 2H), 4.75 (q, J = 7.0 Hz, 1H), 2.63 (s, 3H), 1.79 (d, J = 7.0 Hz, 3H) | MS m/z 236.1 (M + H)$^+$; Rt-0.45 min |
| 267: (S)-1-(2-fluoro-4-(1-methylcyclopropyl)phenyl)ethanamine | | MS m/z 194.1 (M + H)+, Rt 0.60 min. |
| 268: (S)-1-(4-(1-ethoxycyclopropyl)-2-fluorophenyl)ethanamine | (D2O) 0.98 (s, 1 H) 1.03-1.08 (m, 2 H) 1.14 (t, J = 7.09 Hz, 1 H) 1.25-1.30 (m, 2 H) 1.64 (d, J = 6.99 Hz, 3 H) 3.45-3.59 (m, 2 H) 7.16 (dd, J = 5.58, 1.47 Hz, 1 H) 7.17-7.21 (m, 1 H) 7.40-7.48 (m, 1 H) | MS m/z 224.1 (M + H)+, Rt 0.56 min. |

TABLE 14b-continued

Chemical name, NMR chemical shifts and LCMS signal for each intermediate listed in Table 14a.

| Intermediate: Name | $^1$H NMR (400 MHz, CD$_3$OD) δ ppm | LCMS |
|---|---|---|
| 269: (S)-1-(4-(1-aminoethyl)-3-fluorophenyl)cyclopropanecarbonitrile | | MS m/z 205.1 (M + H)+, Rt 0.44 min. |
| 270: (S)-1-(2-fluoro-4-isopropylphenyl)ethanamine | | MS m/z 182.1 (M + H)+, Rt 0.59 min. |
| 271: (S)-1-(2-fluoro-4-(1-methyl-1H-pyrazol-4-yl)phenyl)ethanamine | | MS m/z 220.1 (M + H)+, Rt 0.43 min. |
| 272: (S)-1-(4-(1-methyl-1H-pyrazol-4-yl)phenyl)ethanamine | | MS m/z 185.1 (M + H)+, Rt 0.41 min. |
| 273: (S)-1-(2-fluoro-4-(1H-pyrazol-4-yl)phenyl)ethanamine | (D2O) 1.66 (d, J = 6.99 Hz, 3 H) 4.76-4.82 (m, 1 H) 7.39-7.52 (m, 3 H) 8.16 (s, 2 H) | MS m/z 206.1 (M + H)+, Rt 0.37 min. |
| 274: (S)-1-(2-fluoro-4-(trifluoromethyl)phenyl)ethanamine | (D2O) 1.67 (d, J = 6.94 Hz, 3 H) 4.84 (q, J = 6.94 Hz, 1 H) 7.54-7.70 (m, 3 H) | MS m/z 208.0 (M + H)+, Rt 0.51 min. |
| 275: (S)-4-(1-aminoethyl)-2-chloro-N-cyclopentylbenzamide | | MS m/z 267.0 (M + H)+, Rt 0.50 min. |
| 276: (S)-1-(2,5-difluoro-4-(1-methyl-1H-pyrazol-4-yl)phenyl)ethanamine | (D2O) 1.65 (d, J = 6.94 Hz, 3 H) 3.53 (q, J = 7.11 Hz, 1 H) 3.91 (s, 3 H) 7.28 (dd, J = 11.10, 6.26 Hz, 1 H) 7.44 (dd, J = 11.18, 6.24 Hz, 1 H) 7.94 (s, 1 H) 8.06 (d, J = 1.86 Hz, 1 H) | MS m/z 239.1 (M + H)+, Rt 0.45 min. |
| 277: (S)-1-(1-(4-chlorophenyl)-1H-imidazol-4-yl)ethanamine | (D2O) 1.74 (d, J = 6.65 Hz, 3 H) 4.76-4.85 (m, 1 H) 7.61 (q, J = 9.00 Hz, 4 H) 8.00 (s, 1 H) 9.04 (s, 1 H) | MS m/z 222.1 (M + H)+, Rt 0.44 min. |

Intermediate 278: (S)-1-(2-fluoro-4-(2-fluoropropan-2-yl)phenyl)ethanamine

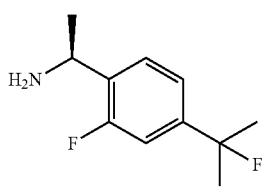

Step 1

To a round bottom flask containing (R)—N—((S)-1-(2-fluoro-4-(prop-1-en-2-yl)phenyl)ethyl)-2-methylpropane-2-sulfinamide (1.02 g, 3.60 mmol) was added dioxane (7 mL). To this homogenous solution was then added HCl in Dioxane (1.80 mL, 7.20 mmol, 4 M). Resulting reaction mixture allowed to stir 10 min at room temperature. Volatiles removed. Et$_2$O was added and mixture sonnicated briefly. Volatiles removed again. Et$_2$O was added and the solid collected and washed with Et$_2$O to afford a white HCl salt of (S)-1-(2-fluoro-4-(prop-1-en-2-yl)phenyl)ethanamine (742 mg, 3.44 mmol, 96% yield). $^1$H NMR (400 MHz, D$_2$O) δ 1.65 (d, J=6.94 Hz, 3H) 2.12 (s, 3H) 5.23 (s, 1H) 5.50 (s, 1H) 7.37 (d, J=13.06 Hz, 1H) 7.43 (m, 2H). LCMS m/z 163.2 (deamino fragment) (M+H)$^+$, Rt 0.56 min.

Step 2

To a RBF containing (S)-1-(2-fluoro-4-(prop-1-en-2-yl)phenyl)ethanamine (742 mg, 3.44 mmol) was added NMP (7 mL). To this solution was then added TEA (959 μl, 6.88 mmol) followed by the addition of Di-tert-butyl dicarbonate (976 mg, 4.47 mmol). Resulting reaction mixture allowed to stir 2 hr at room temperature. Reaction mixture was diluted with water and extracted with EtOAc. Organic phases combined, washed with water, brine, dried (Na$_2$SO$_4$), filtered and concentrated onto silica gel. Silica gel column chromatography (EtOAc/Heptanes 0 to 100%) provided (S)-tert-butyl (1-(2-fluoro-4-(prop-1-en-2-yl)phenyl)ethyl)carbamate (1.28 g, 4.58 mmol, 133% yield) as a white crystalline. $^1$H NMR (400 MHz, CDCl$_3$) δ 1.40-1.48 (m, 12H) 2.12 (d, J=0.44 Hz, 3H) 4.98 (br. s., 2H) 5.10-5.12 (m, 1H) 5.37 (s, 1H) 7.11-7.16 (m, 1H) 7.19-7.24 (m, 2H). LCMS m/z 163.0 (deamino fragment) (M+H)$^+$, Rt 1.13 min.

Step 3

To a round bottom flask containing (S)-tert-butyl (1-(2-fluoro-4-(prop-1-en-2-yl)phenyl)ethyl)carbamate (1.28 g, 4.58 mmol) was added DCM (23 mL). The homogenous solution was cooled to −70° C. in a acetone/dry ice bath. Ozone (g) was then gently bubbled through the solution for 25 min at which time the solution becomes pale blue in color. Dimethyl sulfide (1.02 mL, 13.8 mmol) was then added to the cold solution and mixture gradually allowed to warm to room temperature and stirred for 30 min. Reaction mixture was diluted with a water. Phases partitioned. Aqueous phase extracted with DCM. Organic phases combined, washed with brine, dried (Na₂SO₄), filtered and concentrated onto silica gel. Silica gel column chromatography (EtOAc/Heptane 0 to 60%) provided (S)-tert-butyl (1-(4-acetyl-2-fluorophenyl)ethyl)carbamate (296 mg, 1.05 mmol, 23% yield) as a colorless oil that crystallizes upon standing. ¹H NMR (400 MHz, CDCl₃) δ 1.38-1.49 (m, 12H) 2.59 (s, 3H) 5.01 (br. s., 1H) 7.40 (t, J=7.65 Hz, 1H) 7.62 (dd, J=11.20, 1.57 Hz, 1H) 7.71 (dd, J=7.95, 1.54 Hz, 1H). LCMS m/z 267.1 (carboxylic acid fragment+CH₃CN) (M+H)⁺, Rt 0.89 min.

Step 4

To a solution of (S)-tert-butyl (1-(4-acetyl-2-fluorophenyl)ethyl)carbamate (296 mg, 1.05 mmol) in DCM (5.2 mL), cooled to 0° C. (water/ice bath) under N₂, was added 3M MeMgBr (1.4 mL, 4.21 mmol) in diethyl ether. Reaction mixture allowed to stir for 5 min at 0° C. Then gradually allowed to warm to room temperature and stirred for 30 min at room temperature. Reaction mixture was cooled to 0° C. then quenched with the slow addition of a saturated solution of NH₄Cl and diluted with DCM. Phases partitioned, aqueous phase extracted with DCM and the organic layers combined washed with water, brine, dried (Na₂SO₄), filtered and concentrated to (S)-tert-butyl (1-(2-fluoro-4-(2-hydroxypropan-2-yl)phenyl)ethyl)carbamate (288 mg, 0.97 mmol, 92% yield) afford as a colorless oil which slowly crystallizes upon standing. ¹H NMR (400 MHz, CDCl₃) δ 1.39-1.48 (m, 12H) 1.57 (s, 6H) 7.15-7.25 (m, 2H) 7.31-7.36 (m, 1H).

Step 5

To a RBF containing (S)-tert-butyl (1-(2-fluoro-4-(2-hydroxypropan-2-yl)phenyl)ethyl) carbamate (288 mg, 0.97 mmol) was added DCM (5 mL) the resulting colorless solution was cooled to −70° C. in a dry ice/acetone bath. To this cold solution under N₂ was then added DAST (0.26 mL, 1.94 mmol) resulting reaction mixture allowed to stir 1 hr at −70° C. To the cold solution was added ice and resulting mixture allowed to warm to room temperature. Mixture diluted with DCM, phases partioned and the aqueous phase extracted with DCM. Organic layers combined, washed with brine, dried (Na₂SO₄), filtered and concentrated to onto silica gel. Silica gel column chromatography (EtOAc/Heptane 0 to 50%) provided (S)-tert-butyl (1-(2-fluoro-4-(2-fluoropropan-2-yl)phenyl)ethyl)carbamate (126 mg, 0.42 mmol, 44% yield) as a white solid. ¹H NMR (400 MHz, CDCl₃) δ 1.39-1.49 (m, 12H) 1.66 (d, J=21.52 Hz, 6H) 4.97 (br. s., 1H) 7.04-7.12 (m, 2H) 7.22-7.26 (m, 1H). LCMS m/z 285.1 (carboxylic acid fragment+CH₃CN) (M+H)⁺, Rt 1.06 min.

Step 6

To a round bottom flask containing (S)-tert-butyl (1-(2-fluoro-4-(2-fluoropropan-2-yl)phenyl)ethyl)carbamate (126 mg, 0.42 mmol) was added HCl in dioxane (2.1 mL, 8.42 mmol). Resulting reaction mixture allowed to stir 1 hr at room temperature. Volatiles were removed. Et₂O was then added and the mixture sonnicated briefly. Volatiles were once again removed to a afford an HCl salt of (S)-1-(2-fluoro-4-(2-fluoropropan-2-yl)phenyl)ethanamine (104 mg, 0.44 mmol, 105% yield) as a white solid. ¹H NMR (400 MHz, D₂O) δ 1.59-1.80 (m, 9H) 7.24-7.37 (m, 2H) 7.43-7.56 (m, 1H). LCMS m/z 200.1 (M+H)⁺, Rt 0.54 min.

Intermediate 279: (S)-2-(4-(1-aminoethyl)-3-fluorophenyl)propan-2-ol

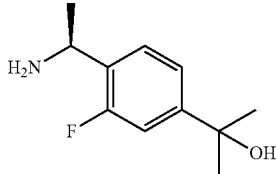

Step 1

To a microwave vial with stir bar was added (R)—N—((S)-1-(4-bromo-2-fluorophenyl)ethyl)-2-methylpropane-2-sulfinamide (1 g, 3.10 mmol) followed by the addition of tributyl(1-ethoxyvinyl)stannane (2.24 g, 6.21 mmol), TEA (1.3 mL, 9.31 mmol) and PdCl₂(dppf).CH₂Cl₂ adduct (0.127 g, 0.155 mmol). To the solids was then added toluene (10 mL). Vial capped and heated by microwave irradiation at 100° C. for 30 min. To this reaction mixture was added 1 ml of TFA to try to convert vinyl ether to the ketone which was unsuccessful. Resulting reaction mixture allowed to stir 5 min at room temperature. Reaction mixture was then quenched with a saturated solution of NaHCO₃ to pH 8. Aqueous mixture extracted with EtOAc. Organic phases combined, washed with water, brine, dried (Na₂SO₄), filtered and concentrated onto silica gel. Silica gel column chromatography (EtOAc/Heptane 40 to 100%) provided (R)—N—((S)-1-(4-(1-ethoxyvinyl)-2-fluorophenyl)ethyl)-2-methylpropane-2-sulfinamide (0.60 g, 1.91 mmol, 62% yield) as a yellow viscous residue. ¹H NMR (400 MHz, CDCl₃) δ 1.20 (s, 9H) 1.43 (t, J=6.94 Hz, 3H) 1.56-1.63 (m, 5H) 3.36 (d, J=3.13 Hz, 1H) 3.92 (q, J=6.96 Hz, 2H) 4.23 (br. s., 1H) 4.65 (s, 1H) 4.79-4.91 (m, 1H) 7.30 (s, 2H) 7.40 (d, J=8.02 Hz, 1H).

Step 2

To a round bottom flask containing (R)—N—((S)-1-(4-(1-ethoxyvinyl)-2-fluorophenyl)ethyl)-2-methylpropane-2-sulfinamide (600 mg, 1.91 mmol) was added MeOH (19 mL). To this homogenous solution was then added HCl (aq) (3.2 mL, 19.1 mmol, 3 M). Resulting reaction mixture stirred at room temperature for 30 min. Volatiles were then removed. Residue triturated with Et₂O to provide (S)-1-(4-(1-aminoethyl)-3-fluorophenyl)ethanone (0.43 g, 1.98 mmol, 103% yield) as a HCl salt. ¹H NMR (400 MHz, D₂O) δ 1.67 (d, J=6.99 Hz, 3H) 2.64 (s, 3H) 4.80-4.87 (m, 1H) 7.61 (t, J=7.73 Hz, 1H) 7.77 (dd, J=11.30, 1.66 Hz, 1H) 7.87 (dd, J=8.09, 1.64 Hz, 1H). LCMS m/z 182.0 (M+H)⁺, Rt 0.36 min.

Step 3

To a round bottom flask with stir bar was added (S)-1-(4-(1-aminoethyl)-3-fluorophenyl) ethanone (0.43 g, 1.98 mmol) followed by the addition of NMP (9.9 mL). To this solution was then added DIEA (0.83 mL, 4.74 mmol) and Di-tert-butyl dicarbonate (0.95 g, 4.35 mmol). The resulting reaction mixture allowed to stir 2 hr at room temperature. Reaction mixture was diluted with water, extracted with EtOAc. Organic phase washed with water, brine, dried (Na₂SO₄), filtered and concentrated onto silica gel. Silica gel column chromatography (EtOAc/Heptane 0 to 100%) provided (S)-tert-butyl 1-(4-acetyl-2-fluorophenyl)ethylcarbamate (369 mg, 1.31 mmol, 66.4% yield) as a colorless oil which crystallizes upon standing. ¹H NMR (400 MHz, CDCl₃) δ 1.38-1.49 (m, 12H) 2.59 (s, 3H) 5.01 (br. s., 1H)

7.40 (t, J=7.65 Hz, 1H) 7.62 (dd, J=11.20, 1.57 Hz, 1H) 7.71 (dd, J=7.95, 1.54 Hz, 1H). LCMS m/z 267.1 (carboxylic acid fragment+CH$_3$CN) (M+H)$^+$, Rt 0.89 min.

Step 4

To a solution of (S)-tert-butyl (1-(4-acetyl-2-fluorophenyl)ethyl)carbamate (200 mg, 0.71 mmol) in DCM (7.1 mL), cooled to 0° C. (water/ice bath) under N$_2$, was added 3M MeMgBr (10.95 mL, 2.84 mmol) in diethyl ether. Reaction mixture allowed to stir for 5 min at 0° C. Then gradually allowed to warm to room temperature and stirred for 30 min at room temperature. Reaction mixture was cooled to 0° C. then quenched with the slow addition of a saturated solution of NH$_4$Cl and diluted with DCM. Phases partitioned, aqueous phase extracted with DCM and the organic layers combined washed with water, brine, dried (Na$_2$SO$_4$), filtered and concentrated to (S)-tert-butyl (1-(2-fluoro-4-(2-hydroxypropan-2-yl)phenyl)ethyl)carbamate (184 mg, 0.62 mmol, 87% yield) afford as a colorless oil which slowly crystallizes upon standing. $^1$H NMR (400 MHz, CDCl$_3$) δ 1.39-1.48 (m, 12H) 1.57 (s, 6H) 7.15-7.25 (m, 2H) 7.31-7.36 (m, 1H).

Step 5

To a round bottom flask containing (S)-tert-butyl (1-(2-fluoro-4-(2-hydroxypropan-2-yl)phenyl)ethyl)carbamate (184 mg, 0.62 mmol) and a stir bar was added dioxane (2 mL). To this reaction mixture was then added HCl in dioxane (0.93 ml, 3.71 mmol, 4.0M). Resulting reaction mixture allowed to stir at room temperature for 18 hr. Volatiles were then removed. Residue triturated with Et$_2$O to afford (S)-2-(4-(1-aminoethyl)-3-fluorophenyl)propan-2-ol (142 mg, 0.61 mmol, 98% yield) as a HCl salt. $^1$H NMR (400 MHz, D$_2$O) δ 1.53 (s, 6H) 1.64 (d, J=7.04 Hz, 3H) 3.73 (s, 1H) 7.28-7.37 (m, 2H) 7.42-7.48 (m, 1H). LCMS m/z 198.1 (M+H)$^+$, Rt 0.37 min.

Intermediate 280: (R)—N—((S)-1-(2,5-difluoro-4-(2,2,2-trifluoroethoxy)phenyl)ethyl)-2-methylpropane-2-sulfinamide

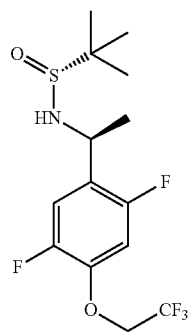 [SMILES: C[C@H](N[S@](=O)C(C)(C)C)c1cc(F)c(OCC(F)(F)F)cc1F]

To a mixture of ethyl 2-oxocyclohexanecarboxylate (58.0 mg, 0.341 mmol), (R)—N—((S)-1-(4-bromo-2,5-difluorophenyl)ethyl)-2-methylpropane-2-sulfinamide (580 mg, 1.705 mmol), Cs$_2$CO$_3$ (1555 mg, 4.77 mmol), copper(I) iodide (32.5 mg, 0.170 mmol) was added 2,2,2-trifluoroethanol (871 µl, 11.93 mmol). The reaction was sealed and heated at 78° C. for 24 hours. LCMS indicated complete conversion to product. The reaction mixture was then cooled to room temperature and diluted with EtOAc (20 mL). The mixture was filtered through a pad of celite and the pad was rinsed with EtOAc (20 mL). The organic was washed with water (2×15 mL), dried (Na$_2$SO$_4$) and concentrated. The residue was then filtered through a pad of silica gel (30 g) with EtOAc/heptane (1:3) to give crude (R)—N—((S)-1-(2,5-difluoro-4-(2,2,2-trifluoroethoxy)phenyl)ethyl)-2-methylpropane-2-sulfinamide (0.601 g). LCMS (B) m/z 360.1 (M+H)$^+$ Intermediate 281: (S)-1-(2,5-difluoro-4-(2,2,2-trifluoroethoxy)phenyl)ethanamine

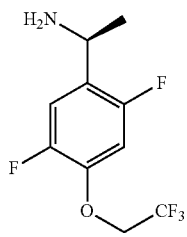 [SMILES: C[C@H](N)c1cc(F)c(OCC(F)(F)F)cc1F]

To a solution of (R)—N—((S)-1-(2,5-difluoro-4-(2,2,2-trifluoroethoxy)phenyl)ethyl)-2-methylpropane-2-sulfinamide (0.601 g, 1.672 mmol) in dioxane (10 ml) was added dropwise HCl (0.836 ml, 3.34 mmol). The reaction was stirred at room temperature for 30 minutes. LCMS indicated complete conversion to product. The reaction mixture was concentrated and DCM (20 mL) and saturated NaHCO$_3$ solution (10 mL) was added to the residue. The mixture was stirred for 10 minutes and phases were separated. Aqueous layer was then extracted with DCM (2×10 mL), and the combined organic was dried (Na$_2$SO$_4$) and concentrated to give crude product. LCMS (B) m/z 256.2 (M+H)$^+$ The intermediates in Table 15a were prepared using a method similar to that described for the preparation of Intermediate 281.

TABLE 15a

| Structure | |
|---|---|
| (structure with H$_2$N, F, pyridine, O-CH$_2$-CF$_3$) | Intermediate 282 |
| (structure with H$_2$N, F, phenyl, O-CH$_2$-CF$_3$) | Intermediate 283 |
| (structure with H$_2$N, F, phenyl, O-CH$_2$-CF$_3$) | Intermediate 284 |

TABLE 15b

Chemical name and analytical data for each intermediate listed in Table 15a.

| Intermediate: Name | Analytical data |
| --- | --- |
| 282: (S)-1-(4-bromo-2,5-difluorophenyl)ethanamine | LCMS m/z (M + H)+ 239.2, RT 0.52 min. |
| 283: (S)-1-(2-fluoro-4-(2,2,2-trifluoroethoxy)phenyl)ethanamine | LCMS m/z (M + H)+ 238.3, RT 0.57 min. |
| 284: (S)-1-(3-fluoro-4-(2,2,2-trifluoroethoxy)phenyl)ethanamine | LCMS m/z (M + H)+ 238.3, RT 0.58 min. |

Intermediate 285: (R,E)-N-((1-(4-chlorophenyl)-1H-pyrazol-3-yl)methylene)-2-methylpropane-2-sulfinamide

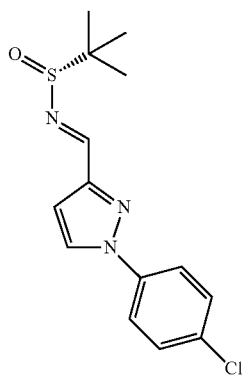 [SMILES: CC(C)(C)[S@@](=O)/N=C/c1ccn(-c2ccc(Cl)cc2)n1]

To a mixture of 1H-pyrazole-3-carbaldehyde (1.52 g, 15.82 mmol), 1-chloro-4-iodobenzene (5.66 g, 23.73 mmol), (1R,2R)—N1,N2-dimethylcyclohexane-1,2-diamine (0.450 g, 3.16 mmol), copper(I) iodide (0.151 g, 0.791 mmol) and K$_2$CO$_3$ (4.37 g, 31.6 mmol) was added toluene (20 mL). The reaction was sealed and heated to 110° C. for 18 hours. The reaction mixture was then cooled to room temperature and diluted with water (50 mL), and extracted with EtOAc (3×30 mL). The combined organic was then dried (Na$_2$SO$_4$) and concentrated to give crude 1-(4-chlorophenyl)-1H-pyrazole-3-carbaldehyde (1.86 g, 9.0 mmol), to which was added (R)-2-methylpropane-2-sulfinamide (1.20 g, 9.90 mmol), CuSO4 (2.155 g, 13.50 mmol) and DCE (30 ml). The reaction was sealed, heated at 60° C. for 18 hours. A dark green suspension resulted. The reaction mixture was then cooled to 20° C., filtered through a pad of celite, rinsed with DCM. The solution was then concentrated to give final crude product as a light green oil. The residue was purified via silica gel chromatography (EtOAc/Heptane). LCMS (B) m/z 310.3 (M+H)+

Intermediate 286: (R)—N—((R)-1-(1-(4-chlorophenyl)-1H-pyrazol-3-yl)ethyl)-2-methylpropane-2-sulfinamide

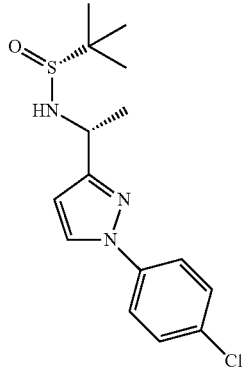 [SMILES: C[C@@H](N[S@](=O)C(C)(C)C)c1ccn(-c2ccc(Cl)cc2)n1]

To a solution of (R,E)-N-((1-(4-chlorophenyl)-1H-pyrazol-3-yl)methylene)-2-methylpropane-2-sulfinamide (2.12 g, 6.84 mmol) in DCM (40 ml) at −40° C. was added methylmagnesium bromide (9.12 ml, 27.4 mmol). The reaction was stirred at −40° C. for 3 hours. The reaction mixture was then quenched with saturated NH$_4$Cl solution (20 mL). The aqueous layer was adjusted to pH=8 with HCl (1M) and extracted with DCM (2×200 mL). The combined organic was dried (Na$_2$SO$_4$) and concentrated. The residue was then purified via silica gel chromatography (EtOAC/heptane) to give (R)—N—((R)-1-(1-(4-chlorophenyl)-1H-pyrazol-3-yl)ethyl)-2-methylpropane-2-sulfinamide (1.11 g). LCMS (B) m/z 326.3 (M+H)+

Intermediate 287: (R)-1-(1-(4-chlorophenyl)-1H-pyrazol-3-yl)ethanamine

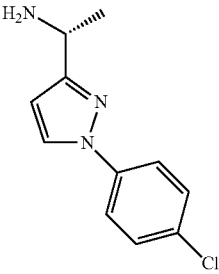

To a solution of (R)—N—((R)-1-(1-(4-chlorophenyl)-1H-pyrazol-3-yl)ethyl)-2-methylpropane-2-sulfinamide (0.98 g, 3.01 mmol) in dioxane (10 ml) was added dropwise HCl (1.504 ml, 6.01 mmol). The reaction was stirred at room temperature for 30 minutes. LCMS indicated complete conversion to product. The reaction mixture was concentrated and DCM (20 mL) and saturated NaHCO$_3$ solution (10 mL) was added to the residue. The mixture was stirred for 10 minutes and phases were separated. Aqueous layer was then extracted with DCM (2×10 mL), and the combined organic was dried (Na$_2$SO$_4$) and concentrated to give product (0.556 g). LCMS (B) m/z 222.2 (M+H)+

Intermediate 288: (R)—N—((S)-1-(1-(4-chlorophenyl)-1H-pyrazol-3-yl)ethyl)-2-methylpropane-2-sulfinamide

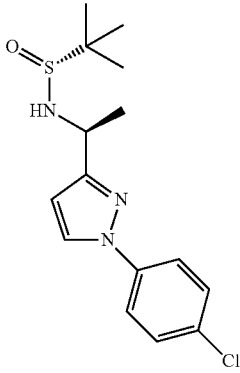 [SMILES: C[C@H](N[S@](=O)C(C)(C)C)c1ccn(-c2ccc(Cl)cc2)n1]

To a solution of (R,E)-N-((1-(4-chlorophenyl)-1H-pyrazol-3-yl)methylene)-2-methylpropane-2-sulfinamide (2.12 g, 6.84 mmol) in DCM (40 ml) at −40° C. was added methylmagnesium bromide (9.12 ml, 27.4 mmol). The reaction was stirred at −40° C. for 3 hours. The reaction mixture was then quenched with saturated NH₄Cl solution (20 mL). The aqueous layer was adjusted to pH=8 with HCl (1M) and extracted with DCM (2×200 mL). The combined organic was dried (Na₂SO₄) and concentrated. The residue was then purified via silica gel chromatography (EtOAC/heptane) to give (R)—N—((R)-1-(1-(4-chlorophenyl)-1H-pyrazol-3-yl)ethyl)-2-methylpropane-2-sulfinamide (1.01 g). LCMS (B) m/z 326.3 (M+H)⁺

Intermediate 289: (S)-1-(1-(4-chlorophenyl)-1H-pyrazol-3-yl)ethanamine

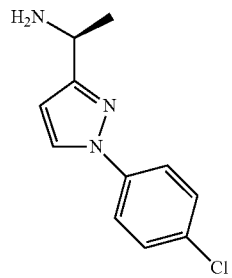

To a solution of (R)—N—((S)-1-(1-(4-chlorophenyl)-1H-pyrazol-3-yl)ethyl)-2-methylpropane-2-sulfinamide (0.98 g, 3.01 mmol) in dioxane (10 ml) was added dropwise HCl (1.504 ml, 6.01 mmol). The reaction was stirred at room temperature for 30 minutes. LCMS indicated complete conversion to product. The reaction mixture was concentrated and DCM (20 mL) and saturated NaHCO₃ solution (10 mL) was added to the residue. The mixture was stirred for 10 minutes and phases were separated. Aqueous layer was then extracted with DCM (2×10 mL), and the combined organic was dried (Na₂SO₄) and concentrated to give crude product (0.501 g). LCMS (B) m/z 222.2 (M+H)⁺

The intermediates in Table 16a were prepared using a method similar to that described for the preparation of Intermediate 289

TABLE 16a

| Structure | Intermediate |
|---|---|
| 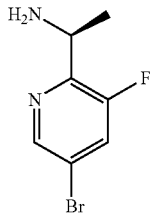 | Intermediate 290 |
| 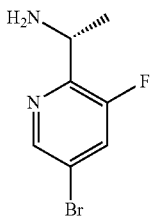 | Intermediate 291 |
| 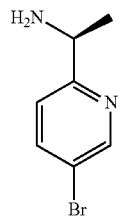 | Intermediate 292 |
| 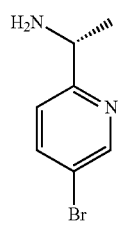 | Intermediate 293 |
| 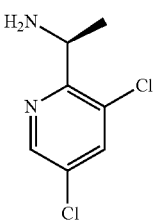 | Intermediate 294 |
| 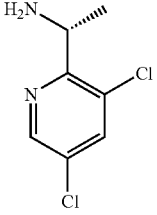 | Intermediate 295 |

TABLE 16b

Chemical name and analytical data for each intermediate listed in Table 16a.

| Intermediate: Name | Analytical data |
|---|---|
| 290: (S)-1-(5-bromo-3-fluoropyridin-2-yl)ethanamine | LCMS(B) m/z (M + H)⁺ 219.0, 221.0, RT 0.37 min. |
| 291: (R)-1-(5-bromo-3-fluoropyridin-2-yl)ethanamine | LCMS(B) m/z (M + H)⁺ 219.0, 221.0, RT 0.38 min. |
| 292: (S)-1-(5-bromopyridin-2-yl)ethanamine | LCMS(B) m/z (M + H)⁺ 201.0, 203.0, RT 0.37 min. |

TABLE 16b-continued

Chemical name and analytical data for each intermediate listed in Table 16a.

| Intermediate: Name | Analytical data |
|---|---|
| 293: (R)-1-(5-bromopyridin-2-yl)ethanamine | LCMS(B) m/z (M + H)+ 201.0, 203.0, RT 0.40 min. |
| 294: (S)-1-(3,5-dichloropyridin-2-yl)ethanamine | LCMS(B) m/z (M + H)+ 191.1, RT 0.45 min. |
| 295: (R)-1-(3,5-dichloropyridin-2-yl)ethanamine | LCMS(B) m/z (M + H)+ 191.1, RT 0.44 min. |

Intermediate 296: (R)—N—((S)-1-(2,5-difluoro-4-(2-(trifluoromethyl)pyridin-4-yl)phenyl)ethyl)-2-methylpropane-2-sulfinamide

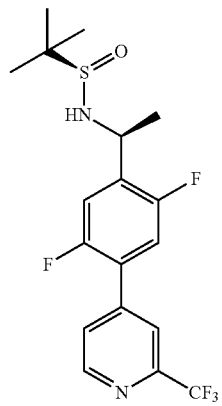 [SMILES: C[C@H](N[S@](=O)C(C)(C)C)c1cc(F)c(-c2ccnc(C(F)(F)F)c2)cc1F]

To a solution of (R)—N—((S)-1-(4-bromo-2,5-difluorophenyl)ethyl)-2-methylpropane-2-sulfinamide (230 mg, 0.676 mmol) in dioxane/H₂O (5 mL/1 mL) was added sodium 2'-(dicyclohexylphosphino)-2,6-dimethoxy-[1,1'-biphenyl]-3-sulfonate (34.7 mg, 0.068 mmol), (2-(trifluoromethyl)pyridin-4-yl)boronic acid (194 mg, 1.014 mmol), K₂CO₃ (234 mg, 1.690 mmol) followed by Pd₂dba₃ (31.0 mg, 0.034 mmol). The reaction mixture was sealed and heated to 110° C. and stirred for 2 hours. LCMS show complete conversion. The reaction mixture was then cooled to room temperature and diluted with EtOAc (20 mL) and water (10 mL). The aqueous layer was then extracted with EtOAc (2×20 mL). The combined organic was then concentrated. The residue was purified by silica gel chromatography (50% heptane in EtOAc to 10% MeOH in EtOAc) to give product. (0.25 g). LCMS (B) m/z 407.6 (M+H)+

Intermediate 297: (S)-1-(2,5-difluoro-4-(2-(trifluoromethyl)pyridin-4-yl)phenyl)ethanamine

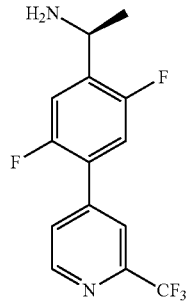

To a solution of (R)—N—((S)-1-(1-(4-chlorophenyl)-1H-pyrazol-3-yl)ethyl)-2-methylpropane-2-sulfinamide (0.98 g, 3.01 mmol) in dioxane (10 ml) was added dropwise HCl (1.504 ml, 6.01 mmol). The reaction was stirred at room temperature for 30 minutes. LCMS indicated complete conversion to product. The reaction mixture was concentrated and DCM (20 mL) and saturated NaHCO₃ solution (10 mL) was added to the residue. The mixture was stirred for 10 minutes and phases were separated. Aqueous layer was then extracted with DCM (2×10 mL), and the combined organic was dried (Na₂SO₄) and concentrated to give crude product (0.501 g). LCMS (B) m/z 303.2 (M+H)+

The intermediates in Table 17a were prepared using a method similar to that described for the preparation of Intermediate 297

TABLE 17a

| | |
|---|---|
| Intermediate 298 | |
| Intermediate 299 | |
| Intermediate 300 | |

TABLE 17b

Chemical name and analytical data for each intermediate listed in Table 17a.

| Intermediate: Name | Analytical data |
|---|---|
| 298: (S)-1-(2,5-difluoro-4-(2-methylpyridin-4-yl)phenyl)ethanamine | LCMS(B) m/z (M + H)+ 249.2, RT 0.34 min. |
| 299: (S)-1-(2,5-difluoro-4-(6-methylpyridin-3-yl)phenyl)ethanamine | LCMS(B) m/z (M + H)+ 249.1, RT 0.32 min. |
| 300: (S)-1-(2,5-difluoro-4-(6-(trifluoromethyl)pyridin-3-yl)phenyl)ethanamine | LCMS(B) m/z (M + H)+ 303.2, RT 0.64 min. |

Intermediate 301: (R)—N—((S)-1-(2,5-difluoro-4-(4-methyl-1H-imidazol-1-yl)phenyl)ethyl)-2-methyl-propane-2-sulfinamide

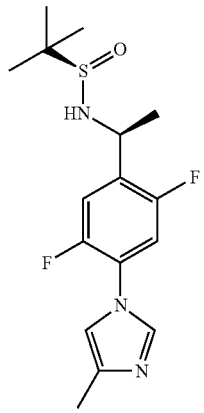 [SMILES: Cc1cn(-c2cc(F)c([C@H](C)N[S@](=O)C(C)(C)C)cc2F)cn1]

To a solution of di-tert-butyl(2',4',6'-triisopropyl-3,4,5,6-tetramethyl-[1,1'-biphenyl]-2-yl)phosphine (80 mg, 0.166 mmol) in toluene/dioxane (8 mL/2 mL) was added Pd$_2$dba$_3$ (60 mg, 0.066 mmol). The reaction mixture was sealed and heated to 120° C. and stirred for 5 minutes. The reaction was cooled to room temperature and 4-methyl-1H-imidazole (157 mg, 1.910 mmol), (R)—N—((S)-1-(4-bromo-2,5-difluorophenyl)ethyl)-2-methylpropane-2-sulfinamide (500 mg, 1.470 mmol) and K$_3$PO$_4$ (624 mg, 2.94 mmol) was added to the reaction mixture. The reaction was sealed and heated to 120° C. for 2 hours. LCMS show complete conversion. The reaction mixture was then cooled to room temperature and diluted with EtOAc (20 mL) and water (10 mL). The aqueous layer was then extracted with EtOAc (2×20 mL). The combined organic was then concentrated. The residue was purified by silica gel chromatography (50% heptane in EtOAc to 10% MeOH in EtOAc) to give (S)-1-(2,5-difluoro-4-(4-methyl-1H-imidazol-1-yl)phenyl)ethanamine (500 mg). LCMS (B) m/z 342.6 (M+H)+

Intermediate 302: (S)-1-(2,5-difluoro-4-(4-methyl-1H-imidazol-1-yl)phenyl)ethanamine

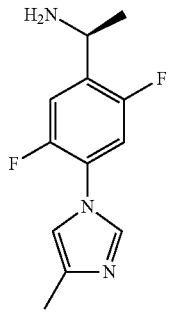 [SMILES: Cc1cn(-c2cc(F)c([C@H](C)N)cc2F)cn1]

To a solution of (R)—N—((S)-1-(2,5-difluoro-4-(4-methyl-1H-imidazol-1-yl)phenyl)ethyl)-2-methylpropane-2-sulfinamide (500 mg) in MeOH (10 mL) was added dropwise HCl (732 µl, 2.93 mmol). The reaction was stirred at room temperature for 30 minutes. LCMS indicated complete conversion to product. The reaction mixture was concentrated and DCM (20 mL) and saturated NaHCO$_3$ solution (10 mL) was added to the residue. The mixture was stirred for 10 minutes and phases were separated. Aqueous layer was then extracted with DCM (2×10 mL), and the combined organic was dried (Na$_2$SO$_4$) and concentrated to give (S)-1-(2,5-difluoro-4-(4-methyl-1H-imidazol-1-yl)phenyl)ethanamine (330 mg). LCMS (B) m/z 238.1 (M+H)+

Intermediate 303: (S)-1-(1-(4-fluorophenyl)-1H-imidazol-4-yl)ethanamine hydrochloride

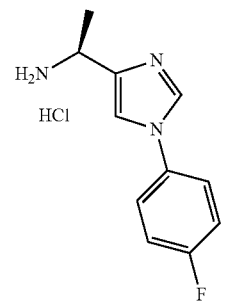

Step 1: preparation of tert-butyl 4-formyl-1H-imidazole-1-carboxylate

To di-tert-butyl dicarbonate (23.25 g, 107 mmol) and 1H-imidazole-4-carbaldehyde (9.75 g, 101 mmol) in THF (200 mL) was added DMAP (100 mg, 0.819 mmol). The reaction was stirred for two hours. The reaction mixture was then diluted with saturated NaHCO$_3$ solution/EtOAc (100 mL/100 mL). The aqueous was then extracted with EtOAc (2×100 mL) and the combined organic was dried (Na$_2$SO$_4$) and concentrated to give crude product (19.9 g). LCMS (B) m/z 197.2 (M+H)+

Step 2: preparation of (S,E)-tert-butyl 4-(((tert-butylsulfinyl)imino)methyl)-1H-imidazole-1-carboxylate To CuSO₄ (24.28 g, 152 mmol) and tert-butyl 4-formyl-1H-imidazole-1-carboxylate (19.9 g, 101 mmol) in DCE (100 mL) was added (S)-2-methylpropane-2-sulfinamide (13.52 g, 112 mmol). The reaction was heated to 65° C. for 18 hours. The reaction mixture was then cooled to room temperature and filtered through a pad of celite. The pad was rinsed with DCM (200 mL) and the filtrated was concentrated. The residue was then run through a pad of silica gel with heptane/EtOAc (3:1) as eluent. The filtrate was concentrated to give crude (S,E)-tert-butyl 4-(((tert-butylsulfinyl)imino)methyl)-1H-imidazole-1-carboxylate (22 g). LCMS (B) m/z 300.2 (M+H)⁺

Step 3: preparation of (S,E)-N-((1H-imidazol-4-yl)methylene)-2-methylpropane-2-sulfinamide To (S,E)-tert-butyl 4-(((tert-butylsulfinyl)imino)methyl)-1H-imidazole-1-carboxylate (18.61 g, 62.2 mmol) in DCM (250 mL) at −70° C. was added dropwise methylmagnesium bromide (83 mL, 249 mmol) in Et₂O. The reaction was stirred at −70° C. for 4 hours. The reaction mixture was then warmed to −40° C. and stirred for one hour. The reaction was then quenched with cautious addition of HCl (1N). Cold bath was removed and while with stirring the aqueous layer was adjusted pH=8. The aqueous layer was separated and extracted with DCM (3×100 mL). The combined organic was dried (Na₂SO₄) and concentrated to give crude product as a mixture of tert-butyl 4-((S)-1-((S)-1,1-dimethylethylsulfinamido)ethyl)-1H-imidazole-1-carboxylate and (S,E)-N-((1H-imidazol-4-yl)methylene)-2-methylpropane-2-sulfinamide, to which was added DCM (300 mL) at 0° C. and formic acid (100 mL, 2651 mmol). The cold bath was then removed and the reaction was stirred for 2 hours. The reaction mixture was then concentrated under reduce pressure to remove DCM and formic acid. The residue was diluted with DCM (400 mL) and washed with saturated Na₂CO₃ aqueous solution (2×200 mL). The combined aqueous was extracted with DCM (2×200 mL). The combined organic was then dried (Na₂SO₄) and concentrated to give (S,E)-N-((1H-imidazol-4-yl)methylene)-2-methylpropane-2-sulfinamide (12.5 g). LCMS (B) m/z 216.1 (M+H)⁺

Step 4: preparation of (S)-1-(1-(4-fluorophenyl)-1H-imidazol-4-yl)ethanamine hydrochloride To a 200 mL RBF was added toluene/dioxane (80 ml/20 mL). The flask was cooled to 0° C. and the mixture of solvents was evacuated under high vacuum for 2 minutes and then recharged with argon. The process was repeated three more times. This solvent was then used for the reaction.

A vial containing di-tert-butyl(2',4',6'-triisopropyl-3,4,5,6-tetramethyl-[1,1'-biphenyl]-2-yl)phosphine (55.8 mg, 0.116 mmol) and Pd₂(dba)₃ (42 mg, 0.046 mmol) was evacuated under high vacuum for 1 minute and then recharged with argon. The process was repeated three more times and the toluene/dioxane solvent (10 mL) prepared as above was added followed by the palladium/ligand complex prepared as above was then added to the reaction vial containing the other starting materials. The reaction mixture was sealed and heated to 120° C. and stirred for 5 minutes. The reaction was cooled to room temperature.

A separate reaction vial was charged with (S,E)-N-((1H-imidazol-4-yl)methylene)-2-methylpropane-2-sulfinamide (500 mg, 2.322 mmol), 1-bromo-4-fluorobenzene (447 mg, 2.55 mmol) and K₃PO₄ (986 mg, 4.64 mmol). The vial was evacuated under high vacuum for 1 minute and then recharged with argon. The process was repeated three more times and the palladium/ligand complex prepared as above was then added to the reaction vial containing the other starting materials. The reaction was sealed and heated to 120° C. for 18 hours. LCMS show complete conversion. The reaction mixture was then cooled to room temperature and filtered through a pad of celite. The solid was rinsed with EtOAc (30 mL). The filtrate was then washed with water (2×20 mL). The aqueous layer was then extracted with EtOAc (20 mL). The combined organic was then concentrated. The residue was purified via silica gel chromatography (EtOAc/Heptane 70%-100% with 5% MeOH) to give (S)—N—((S)-1-(1-(4-fluorophenyl)-1H-imidazol-4-yl)ethyl)-2-methylpropane-2-sulfinamide. LCMS (B) m/z 310.2 (M+H)⁺

To the above intermediate product was added MeOH (5 mL) and HCl (4M in dioxane, 1 mL). The reaction mixture was stirred for one hour and LCMS showed complete conversion, The mixture was then concentrated to give (S)-1-(1-(4-fluorophenyl)-1H-imidazol-4-yl)ethanamine hydrochloride (300 mg). LCMS (B) m/z 206.0 (M+H)⁺

Intermediate 304:
5-chloro-6-(1,1-difluoroethyl)nicotinaldehyde

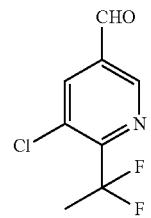

Step 1: Preparation of ethyl 5,6-dichloronicotinate

To a solution of 5,6-dichloronicotinic acid (20.01 g, 104 mmol) in EtOH (500 mL) at 20° C. was added chlorotrimethylsilane (132 mL, 1042 mmol). The reaction was stirred for 72 hours. The reaction mixture was then concentrated and diluted with EtOAc (500 mL), and washed with saturated NaHCO₃ (2×100 mL) and brine (100 mL). The organic was then dried (Na₂SO₄) and concentrated under reduced pressure to give final crude product (21.25 g). LCMS m/z 220.1 (M+H)⁺, Rt 0.94 min.

Step 2: Preparation of ethyl 6-acetyl-5-chloronicotinate

To a suspension of ethyl 5,6-dichloronicotinate (5.26 g, 23.90 mmol) and tetraethylammonium-chloride (11.88 g, 71.7 mmol) in MeCN (50 mL) was added tributyl(1-ethoxyvinyl)stannane (9.50 g, 26.3 mmol) and PdCl₂(PPh₃)₂ (0.671 g, 0.956 mmol). The reaction was sealed, heated at 80° C. for 5 hours. A dark color clear solution resulted. The reaction mixture was then cooled to 20° C., concentrated and diluted with EtOAc (200 mL), and washed with water (50 mL) and brine (50 mL). The organic was then dried (Na₂SO₄) and concentrated to give crude ethyl 5-chloro-6-(1-ethoxyvinyl)nicotinate. The residue was then dissolved in THF (100 mL) and HCl (20 mL, 3M in H₂O) was added. The reaction mixture was stirred at 20° C. for 5 hours, and saturated NaHCO₃ solution was added until pH=8. The mixture was then diluted with EtOAc (200 mL) and water (50 mL). The phases were separated and the aqueous layer was extracted with EtOAc (2×50 mL). The combined organics was washed with brine (20 mL), dried (Na₂SO₄) and concentrated to afford the desired product (3.56 g). LCMS m/z 228.5 (M+H)⁺, Rt 0.83 min.

Step 3: Preparation of ethyl 5-chloro-6-(1,1-difluoroethyl)nicotinate

To a solution of ethyl 6-acetyl-5-chloronicotinate (3.01 g, 13.22 mmol) in CHCl3 (7 mL) was added DAST (5.20 mL, 39.7 mmol) and ethanol (0.061 g, 1.32 mmol). The reaction was sealed, heated at 60° C. for 24 hours. A dark color clear solution resulted. The reaction mixture was then cooled to 20° C., and added cautiously with cold concentrated NaHCO3 aqueous solution (50 mL). The aqueous layer was extracted with DCM (2×100 mL). The combined organic was then dried (Na2SO4) and concentrated. The residue was purified via silica gel flash chromatography (0-20 percent EtOAc-Hexanes) to afford the desired product as yellow oil (2.88 g). LCMS m/z 250.1 (M+H)+, Rt 0.99 min.

Step 4: Preparation of (5-chloro-6-(1,1-difluoroethyl)pyridin-3-yl)methanol

To a solution of ethyl 5-chloro-6-(1,1-difluoroethyl)nicotinate (2.68 g, 10.74 mmol) in Et2O (40 mL) was added LiBH4 (0.351 g, 16.10 mmol), followed by dropwise addition of methanol (0.653 mL, 16.10 mmol). The reaction was refluxed at 40° C. for one hour. The reaction mixture was then cooled to 0° C., and quenched with HCl (1M) until pH=2 for aqueous layer. The phases were separated and the aqueous layer was extracted with DCM (3×50 mL). The organic was then dried (Na2SO4) and concentrated under reduced pressure to give final crude product (2.12 g). LCMS m/z 208.0 (M+H)+, Rt 0.63 min.

Step 5: Preparation of 5-chloro-6-(1,1-difluoroethyl)nicotinaldehyde

To a solution of (5-chloro-6-(1,1-difluoroethyl)pyridin-3-yl)methanol (2.12 g, 10.21 mmol) in DCM (100 ml) was added PCC (3.30 g, 15.32 mmol). The reaction was stirred at 20° C. for 3 hours. A dark color suspension resulted. LCMS showed clean conversion to the product. The reaction mixture was then filtered through a pad of celite, and washed with DCM (200 mL). The filtrate was then concentrated to give crude product (1.78 g). LCMS m/z 224.0 (M+H2O+H)+, Rt 0.72 min.

Intermediate 305:
5-chloro-6-(2,2,2-trifluoroethoxy)nicotinaldehyde

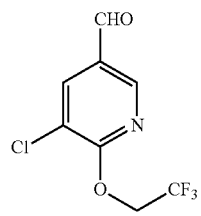

Step 1: Preparation of ethyl 5-chloro-6-(2,2,2-trifluoroethoxy)nicotinate

To a solution of ethyl 5,6-dichloronicotinate (6.28 g, 28.5 mmol) and 2,2,2-trifluoroethanol (2.71 ml, 37.1 mmol) in THF (90 ml) at −73° C. was added NaHMDS (37.1 ml, 37.1 mmol). The reaction was stirred at −73° C. for 30 minutes, then at 0° C. for 5 hours. The reaction was quenched with 30 mL saturated NH4Cl solution. The reaction mixture was then poured into 50 mL brine and phases were separated. The aqueous layer was extracted with DCM (2×100 mL). The combined organics were dried (Na2SO4) and concentrated. Silica gel chromatography with 100% heptane to 30% EtOAc in heptane provided final product (7.51 g). LCMS m/z 284.1 (M+H)+, Rt 1.07 min.

Step 2: Preparation of (5-chloro-6-(2,2,2-trifluoroethoxy)pyridin-3-yl)methanol

To a solution of ethyl 5-chloro-6-(2,2,2-trifluoroethoxy)nicotinate (7.51 g, 26.5 mmol) in Et2O (200 mL) was added LiBH4 (0.865 g, 39.7 mmol), followed by drop wise addition of methanol (1.611 ml, 39.7 mmol). The reaction was refluxed at 40° C. for one hour. The reaction mixture was then cooled to 0° C., and quenched with HCl (1M) until pH=2 for aqueous layer. The phases were separated and the aqueous layer was extracted with DCM (3×200 mL). The organic was then dried (Na2SO4) and concentrated under reduced pressure to give final crude product (6.31 g). LCMS m/z 242.1 (M+H)+, Rt 0.77 min.

Step 3: Preparation of 5-chloro-6-(2,2,2-trifluoroethoxy)nicotinaldehyde

To a solution of (5-chloro-6-(2,2,2-trifluoroethoxy)pyridin-3-yl)methanol (4.00 g, 16.56 mmol) in EtOAc (15 mL) was added manganese(IV) oxide (16.93 g, 166 mmol). The reaction was heated with microwave at 120° C. for 30 minutes. The mixture was then filtered through a pad of celite, and rinsed with EtOAc. The filtrated was concentrated to give crude product (3.38 g).

Intermediate 306:
(S)-1-(2,3-difluorophenyl)ethanamine

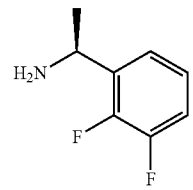

Step 1

To a oven dried round bottom flask with stir bar was added 2,3-difluorobenzaldehyde (0.5 g, 3.52 mmol), (R)-2-methylpropane-2-sulfinamide (0.469 g, 3.87 mmol) and DCE (7.04 mL). To this mixture was then added Copper (II) Sulfate (0.842 g, 5.28 mmol). Reaction mixture heated in a preheated oil bath to 55° C. for 24 hr. The reaction mixture was filtered through a celite pad washing solids with DCE. Combined filtrate was concentrated to afford a viscous yellow oil of (R,E)-N-(2,3-difluorobenzylidene)-2-methylpropane-2-sulfinamide (0.8007 g, 3.26 mmol, 93% yield). MS m/z 246.1 (M+H)+; Rt-0.91 min.

Step 2

To a solution of (R,E)-N-(2,3-difluorobenzylidene)-2-methylpropane-2-sulfinamide (0.800 g, 3.26 mmol) in DCM (32.6 mL), cooled to 0° C. (water/icebath) under N2, was added 3M MeMgBr (4.35 mL, 13.05 mmol) in diethyl ether. Reaction mixture allowed to stir for 30 min at 0° C. Then gradually allowed to warm to room temperature and stirred for 30 min at room temperature. Reaction mixture was cooled to 0° C. then quenched with the slow addition of a saturated solution of NH4Cl and diluted with EtOAc. Phases partitioned aqueous phase extracted with EtOAc and the organic layers combined washed with water, brine, dried with MgSO4, filtered and concentrated to afford (R)—N—((S)-1-(2,3-difluorophenyl)ethyl)-2-methylpropane-2-sulfinamide (0.7868 g, 3.01 mmol, 92% yield) as yellow solid. MS m/z 262.0 (M+H)+; Rt-0.70 min.

Step 3

To a round bottom flask containing (R)—N—((S)-1-(2,3-difluorophenyl)ethyl)-2-methylpropane-2-sulfinamide (786.8 mg, 3.01 mmol) was added Dioxane (10.000 mL). To this solution was added HCl in dioxane 4.0M (1.505 mL, 6.02 mmol) and the solution was allowed to stir 15 min at room temperature. The reaction mixture was concentrated, dissolved in Et2O 10 ml, and concentrated again. Et2O was again added and resulting mixture sonnicated and a solid material was filtered and dried to afford (S)-1-(2,3-difluorophenyl)ethanamine (0.4213 g, 2.176 mmol, 72.3% yield) as a white crystalline HCl salt. 1H NMR (400 MHz, <d2o>) d ppm 1.55 (d, J=6.99 Hz, 3H) 4.71 (q, J=6.96 Hz, 1H) 7.10-7.26 (m, 3H); MS m/z 158.0 (M+H)+; Rt-0.37 min.

The intermediates in Table A were prepared using a method similar to that described for the preparation of Intermediate 306

TABLE 18a

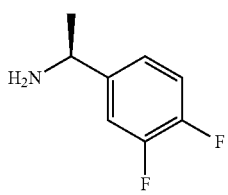

Intermediate 307

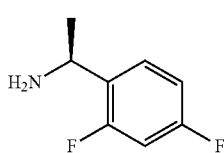

Intermediate 308

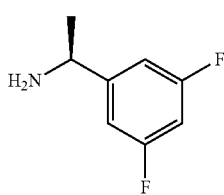

Intermediate 309

TABLE 18b

Chemical name, NMR chemical shifts and LCMS signal for each compound listed in Table 18a.

| Intermediate: Name | Analytical data |
|---|---|
| 307: (S)-1-(3,4-difluorophenyl)ethanamine | ¹H NMR (400 MHz, <cd3od>) δ ppm 1.61 (d, J = 6.90 Hz, 3 H) 4.47 (q, J = 6.90 Hz, 1 H) 7.25-7.30 (m, 1 H) 7.32-7.46 (m, 2 H) LCMS m/z 158.1.1 (M + H)⁺; Rt-0.39 min. |
| 308: (S)-1-(2,4-difluorophenyl)ethanamine | ¹H NMR (400 MHz, <cd3od>) δ ppm 1.65 (d, J = 1.00 Hz, 3 H) 4.71 (q, J = 6.91 Hz, 1 H) 7.05-7.15 (m, 2 H) 7.51-7.61 (m, 1 H) LCMS m/z 158.1.1 (M + H)⁺; Rt-0.37 min. |

Intermediate 310: (S)-1-(4-(1,1-difluoroethyl)-2-fluorophenyl)ethanamine

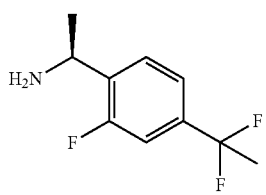

Step 1: Preparation 1-(4-bromo-3-fluorophenyl)ethanol

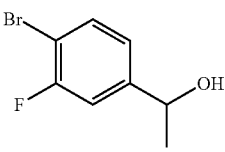

Methylmagnesium bromide (3M in diethylether, 6.77 mL, 20.31 mmol) was added dropwise over ~15 min to a solution of 4-bromo-3-fluorobenzaldehyde (3.1 g, 15.27 mmol) in THF (50 mL) under argon at a temperature of −60° C. to −50° C. The ice bath was removed and the reaction mixture was allowed to warm to room temperature and stirred ~20 hr. The reaction mixture was slowly diluted/quenched with saturated aqueous ammonium chloride solution (20 mL) and further diluted with water (10 mL). The separated aqueous layer was extracted with ethyl acetate (2×40 mL). The combined organic layers were washed with brine (60 mL), dried over sodium sulfate, filtered and concentrated under reduced pressure to provide crude 1-(4-bromo-3-fluorophenyl)ethanol as a pale yellow oil, which was directly used without further purification.

LCMS m/z 201.0 (M−H₂O)⁺, Rt 0.75 min.

Step 2: Preparation 1-(4-bromo-3-fluorophenyl)ethanone

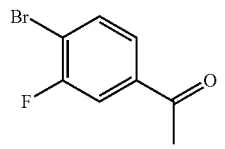

To a solution of crude 1-(4-bromo-3-fluorophenyl)ethanol oil (from Step 1) in DCM (100 mL) was added pyridinium dichromate (8.96 g, 23.82 mmol). The mixture was stirred overnight at room temperature. To the mixture was added celite, the reaction mixture was filtered through a celite pad and rinsed several times with DCM. The filtrate was concentrated under reduced pressure. The crude material was purified by column chromatography [SiO₂, 40 g, heptane/ethyl acetate] providing 1-(4-bromo-3-fluorophenyl)ethanone (3.08 g) as a white solid. ¹H NMR (400 Mhz, CDCl₃) δ ppm 7.72-7.58 (m, 3H), 2.59 (s, 3H).

Step 3: Preparation 1-bromo-4-(1,1-difluoroethyl)-2-fluorobenzene

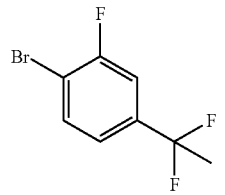

To a solution of 1-(4-bromo-3-fluorophenyl)ethanone (3.08 g, 14.19 mmol) in chloroform (15 mL) was added DAST (5.62 mL, 42.6 mmol) and ethanol (0.083 mL, 1.42 mmol). The orange solution was heated at 60° C. for 24 hr in a sealed container. The reaction mixture was allowed to cool to ~20° C. and to the mixture was added slowly saturated aqueous sodium bicarbonate solution (75 mL). Stirring was continued until off-gased ceased (~15 min). The separated aqueous layer was diluted with additional saturated aqueous sodium bicarbonate solution (25 mL) and carefully mixed. The basic aqueous layer was extracted with DCM (2×100 mL). The combined organic layers were dried over sodium sulfate, filtered and concentrated under reduced pressure. The residue was purified by column chromatography [SiO$_2$, heptane/ethyl acetate] providing 1-bromo-4-(1,1-difluoroethyl)-2-fluorobenzene (2.1 g) as a slightly cloudy colorless oil. $^1$H NMR (400 MHz, CD$_3$OD) δ ppm 7.73 (dd, J=7.2, 8.1 Hz, 1H), 7.40 (dd, J=2.0, 9.4 Hz, 1H), 7.29 (m, J=1.0 Hz, 1H), 1.92 (t, J=18.4 Hz, 3H).

Step 4: Preparation 4-(1,1-difluoroethyl)-2-fluorobenzaldehyde

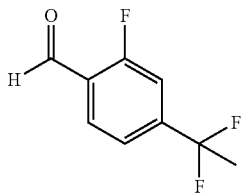

To a solution of 1-bromo-4-(1,1-difluoroethyl)-2-fluorobenzene (2.1 g, 8.79 mmol) in THF (30.3 mL) was added n-butyllithium (1.6M in hexanes, 5.60 mL) over ~20 min at −78° C. The mixture was stirred for 30 min at −78° C. and DMF (1.02 mL, 13.18 mmol) was added dropwise over ~4 min. Stirring was continued for 1 hr, the mixture was diluted/quenched with 1N aqueous HCl/MeOH (2/1, 15 mL) and allowed to warm to room temperature. The reaction mixture was diluted further with water (50 mL) and extracted with diethylether (2×50 mL). The combined organic layers were washed with 1N aqueous sodium hydroxide solution (50 mL) and brine (100 mL), dried over magnesium sulfate, filtered and concentrated under reduced pressure. The crude material was purified by column chromatography [SiO$_2$, 40 g, heptane/ethyl acetate] providing 4-(1,1-difluoroethyl)-2-fluorobenzaldehyde (699 mg) as a dark yellow, volatile oil, which was contaminated with 1-bromo-4-(1,1-difluoroethyl)-2-fluorobenzene. $^1$H NMR (400 Mhz, CDCl$_3$) δ ppm 10.40 (s, 1H), 7.95 (t, J=7.4 Hz, 1H), 7.39-7.47 (m, 2H), 7.35 (d, J=10.6 Hz, 1H), 1.94 (t, J=18.2 Hz, 4H) 7.73 (dd, J=7.2, 8.1 Hz, 1H).

Step 5: Preparation (R,E)-N-(4-(1,1-difluoroethyl)-2-fluorobenzylidene)-2-methylpropane-2-sulfinamide

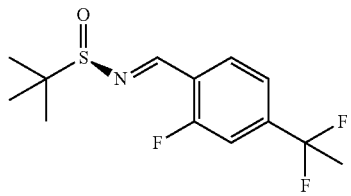 [SMILES: CC(F)(F)c1ccc(/C=N/[S@](=O)C(C)(C)C)c(F)c1]

To a mixture of 4-(1,1-difluoroethyl)-2-fluorobenzaldehyde (693 mg, from Step 4) and (R)-2-methylpropane-2-sulfinamide (513 mg, 4.24 mmol) in DCE (12.9 mL) was added copper(II) sulfate (882 mg, 5.52 mmol). The reaction mixture was placed in a pre-heated oil bath (55° C.) and heated for ~2 d. The mixture was allowed to cool to room temperature, filtered through a pad of celite and rinsed with DCE. The combined filtrates were concentrated under reduced pressure. The residue was purified by column chromatography [SiO$_2$, 24 g, heptane/ethyl acetate] providing (R,E)-N-(4-(1,1-difluoroethyl)-2-fluorobenzylidene)-2-methylpropane-2-sulfinamide (497 mg) as a yellow oil. LCMS m/z 292.1 (M+H)$^+$, Rt 0.97 min.

Step 6: Preparation N—((S)-1-(4-(1,1-difluoroethyl)-2-fluorophenyl)ethyl)-2-methylpropane-2-sulfinamide

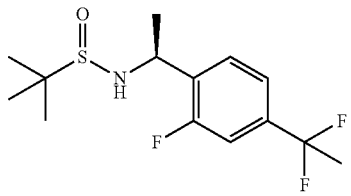 [SMILES: C[C@H](NS(=O)C(C)(C)C)c1ccc(C(C)(F)F)cc1F]

To a solution of (R,E)-N-(4-(1,1-difluoroethyl)-2-fluorobenzylidene)-2-methylpropane-2-sulfinamide (497 mg, 1.706 mmol) in DCM (9.59 mL) was added methylmagnesium bromide (3M in diethylether; 1.20 mL) at 0° C. The reaction mixture was allowed to stir for 1 hr at 0° C., gradually allowed to warm to room temperature and stirred for 1 hr at room temperature. The mixture was cooled to 0° C., additional methylmagnesium bromide (3M in diethylether; 0.5 mL) was added and stirring was continued for 30 min at 0° C. The reaction mixture was carefully quenched with saturated aqueous ammonium chloride solution (6 mL) and diluted with water (20 mL). The separated aqueous phase was extracted with DCM (30 mL). The combined organic layers were washed with brine (50 mL), concentrated under reduced pressure. The residue was purified by column chromatography [SiO$_2$, 24 g, heptane/ethyl acetate] providing N—((S)-1-(4-(1,1-difluoroethyl)-2-fluorophenyl)ethyl)-2-methylpropane-2-sulfinamide (349 mg) as a white solid. LCMS m/z 308.2 (M+H)$^+$, Rt 0.91 min.

Step 7: Preparation (S)-1-(4-(1,1-difluoroethyl)-2-fluorophenyl)ethanamine

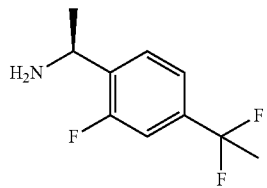

To N—((S)-1-(4-(1,1-difluoroethyl)-2-fluorophenyl)ethyl)-2-methylpropane-2-sulfinamide (349 mg, 1.135 mmol) was added 4M HCl in dioxane (3.01 mL) to give a purple solution. To the mixture was added diethylether (20 mL) and the mixture was stirred for 15 min at −10° C. The mixture was concentrated under reduced pressure to ~2 mL of volume and diethylether (20 mL) was added. The solids were filtered off, rinsed with diethylether (4×10 mL) and dried under reduced pressure providing (S)-1-(4-(1,1-difluoroethyl)-2-fluorophenyl)ethanamine (244 mg) as an off-white solid (HCl salt). LCMS m/z 204.1 (M+H)$^+$, Rt 0.42 min.

Intermediate 311: (S)-tert-butyl 1-(3-hydroxyphenyl)ethylcarbamate

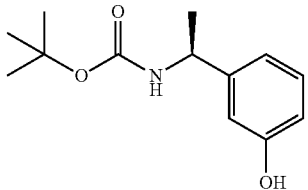 [SMILES: C[C@H](NC(=O)OC(C)(C)C)c1cccc(O)c1]

A slurry of (S)-3-(1-aminoethyl)phenol (1.188 g, 6.84 mmol) and Boc$_2$O (1.747 mL, 7.53 mmol) in DCM (17.10 mL) was stirred at room temperature under N$_2$ while slowly adding DI EA (1.434 mL, 8.21 mmol). The initially insoluble starting materials slowly dissolve. The solution was stirred at room temperature for 16 hours and then concentrated. The oily residue was re-dissolved in EtOAc and washed with Na$_2$CO$_3$ saturated, followed by brine. The original aqueous layer was re-extracted with EtOAc, which was then washed with brine and combined with the previous EtOAc batch. The combined organics were dried over Na$_2$SO$_4$, filtered and concentrated to 2.4 g crude clear yellowish oil which was purified by silica gel column chromatography (EtOAc/Heptane 0 to 30%), yielding (S)-tert-butyl 1-(3-hydroxyphenyl)ethylcarbamate as a clear colourless oil, which solidifies upon sitting (1.79 g, 7.55 mmol, 110% yield). $^1$H NMR (400 MHz, CDCl$_3$) d 1.44 (br. s., 12H) 4.08-4.18 (m, 1H) 4.76 (br. s., 1H) 6.72 (dd, J=7.46, 1.83 Hz, 1H) 6.78 (br. s., 1H) 6.88 (br. s., 1H) 7.16-7.24 (m, 1H). LCMS m/z 223.0/182.0 (the parent not observed, just the Boc fragments) (M+H)$^+$, Rt 0.71 min.

Intermediate 312: (S)-tert-butyl 1-(4-hydroxy-3-methylphenyl)ethylcarbamate

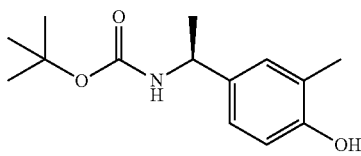 [SMILES: Cc1cc([C@H](C)NC(=O)OC(C)(C)C)ccc1O]

Made as above Intermediate 195: (S)-tert-butyl 1-(4-hydroxy-3-methylphenyl)ethylcarbamate, clear colourless oil. (1.27 g, 5.05 mmol, 103% yield). $^1$H NMR (400 MHz, CDCl$_3$) d 1.42 (s, 9H) 1.54 (s, 3H) 2.24 (s, 3H) 4.70 (br. s., 1H) 6.72 (d, J=8.22 Hz, 1H) 7.01 (d, J=9.00 Hz, 1H) 7.05 (s, 1H). LCMS m/z 252.2 (M+H)$^+$, Rt 0.80 min.

Intermediate 313: (S)-1-(3-(cyclohexyloxy)phenyl)ethanamine hydrochloride

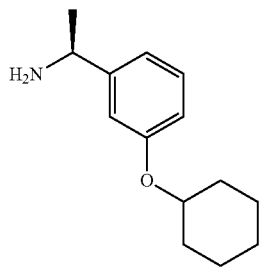

Step 1

To a solution of (S)-tert-butyl 1-(3-hydroxyphenyl)ethylcarbamate (100 mg, 0.421 mmol), cyclohexanol (0.180 ml, 1.686 mmol) and PPh$_3$ (221 mg, 0.843 mmol) in THF (2 ml), was added DEAD (0.133 ml, 0.843 mmol) dropwise, under N$_2$, at room temperature. The resulting yellow solution was stirred for 3 hours, at which point another batch of cyclohexanol (0.180 ml, 1.686 mmol), PPh$_3$ (221 mg, 0.843 mmol), and 10 min later DEAD (0.133 ml, 0.843 mmol), was added at room temperature. The reaction mixture was stirred for 16 hours and then concentrated. The crude clear oil was re-dissolved in DMSO and purified by reverse phase HPLC. The combined product fractions were desalted by addition of equal amount of EtOAc and about 250 mg Na$_2$CO$_3$ in a separatory funnel. The phases were separated and the organic washed with brine, dried over MgSO$_4$, filtered and concentrated in vacuo to yield (S)-tert-butyl 1-(3-(cyclohexyloxy)phenyl)ethylcarbamate (74.1 mg, 0.232 mmol, 55.0% yield) as a clear colourless film. LCMS m/z 305.0/264.0 (the parent not observed, just the Boc fragments) (M+H)$^+$, Rt 1.12 min.

Step 2

(S)-tert-butyl 1-(3-(cyclohexyloxy)phenyl)ethylcarbamate (74.1 mg, 0.232 mmol) was dissolved in 4M HCl in dioxane (1 ml, 4.00 mmol) and the resulting mixture was allowed to sit for 1 hour, then concentrated to yield (S)-1-(3-(cyclohexyloxy)phenyl)ethanamine as an HCl salt (yield assumed quantitative). LCMS m/z 220.1 (M+H)$^+$, Rt 0.66 min.

The Intermediates in Table 19 were prepared using the method described for the preparation of Intermediate 313.

TABLE 19

| Intermediate: Name | Structure | LCMS |
|---|---|---|
| 314: (S)-1-(3-((S)-tetrahydrofuran-3-yloxy)phenyl)ethanamine | 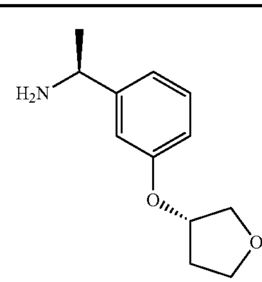 | MS m/z 208.1 (M + H)$^+$, Rt 0.41 min. |

TABLE 19-continued

| Intermediate: Name | Structure | LCMS |
|---|---|---|
| 315: (S)-1-(3-isobutoxyphenyl)ethanamine | 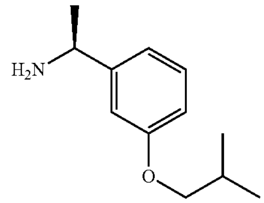 | MS m/z 194.1 (M + H)$^+$, Rt 0.61 min. |
| 316: (S)-1-(4-isobutoxy-3-methylphenyl)ethanamine | 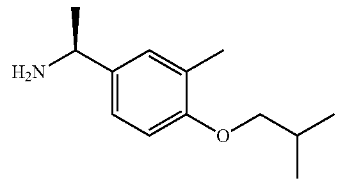 | MS m/z 191.1 (M + H)$^+$, Rt 0.70 min. |
| 317: (S)-1-(2-fluoro-4-isobutoxyphenyl)ethanamine | 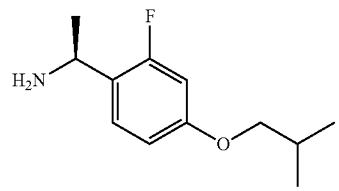 | MS m/z 195.2 (M + H)$^+$, Rt 0.64 min. |
| 318: (S)-1-(4-(cyclopropylmethoxy)phenyl)ethanamine | 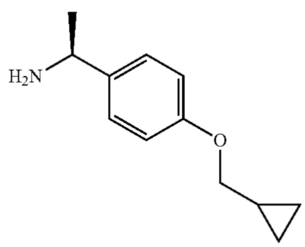 | MS m/z 175.1 (M + H)$^+$, Rt 0.53 min. |

Intermediate 319:
(S)-1-(3-phenoxyphenyl)ethanamine

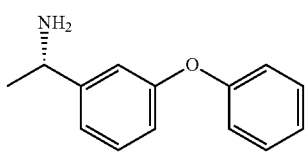 [SMILES: C[C@H](N)c1cccc(Oc2ccccc2)c1]

Into a 20 ml microwave vial was weighted 1-(pyridin-2-yl)propan-2-one ligand (90 mg, 0.665 mmol), phenol (407 mg, 4.32 mmol), CuBr (47.7 mg, 0.332 mmol) and Cs$_2$CO$_3$ (2166 mg, 6.65 mmol). To the mixture was added DMSO (5 ml) and (S)-1-(3-bromophenyl)ethanamine (0.5 ml, 3.32 mmol). The tube was flushed with N$_2$, capped, and the black mixture heated in the oil bath at 90° C. for 18 hours. The heterogenous mixture was diluted with EtOAc and filtered through a glass-fritted funnel, eluting with EtOAc and another 5 mls of DMSO. The volatiles were then removed in vacuo and the crude brown liquid was filtered through 1 um PTFE filter and purified by reverse phase HPLC. The combined product fractions were desalted by addition of equal amount of EtOAc and about 250 mg Na$_2$CO$_3$ in a separatory funnel. The phases were separated and the organic washed with brine, dried over MgSO$_4$, filtered and concentrated in vacuo to yield (S)-1-(3-phenoxyphenyl)ethanamine (361.5 mg, 1.678 mmol, 50.5% yield) as an amber oil. LCMS m/z 214.1 (M+H)$^+$, Rt 0.61 min.

Intermediate 320:
(S)-1-(4-(trifluoromethoxy)phenyl)ethanamine

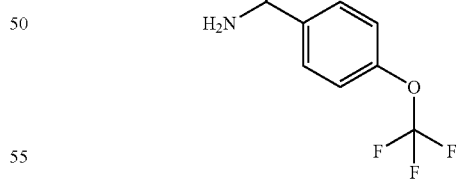

Step 1

To a cloudy solution of 4-(trifluoromethoxy)benzaldehyde (5 g, 26.3 mmol) and (R)-2-methylpropane-2-sulfinamide (3.51 g, 28.9 mmol) in DCE (52 mL), under N$_2$, was added copper (II) sulfate (6.30 g, 39.4 mmol), and the resulting mixture heated in a preheated oil bath at 55° C. for 22 hours. The reaction mixture was filtered through a pad of celite, eluting with DCM. The filtrate was concentrated to afford a viscous yellow oil of (R,E)-2-methyl-N-(4-(trifluoromethoxy)benzylidene)propane-2-sulfinamide (7.9 g, 26.9 mmol, 102% yield). Material was taken onto next step without further purification. ¹H NMR (400 MHz, CDCl₃) δ ppm 1.27 (s, 9H) 7.32 (d, J=8.07 Hz, 2H) 7.91 (d, J=8.75 Hz, 2H) 8.59 (s, 1H). LCMS m/z 294.1 (M+H)⁺, Rt 1.01 min.

Step 2

To a solution of (R,E)-2-methyl-N-(4-(trifluoromethoxy)benzylidene)propane-2-sulfinamide (7.7 g, 26.3 mmol) in CH₂Cl₂ (150 mL), cooled to 0° C. (water/ice bath), under nitrogen, was added 3M methyl magnesium bromide (35 mL, 105 mmol) in Et₂O. The reaction mixture was stirred at 0° C. for 30 min, then allowed to warm up to room temperature and stirred additional 4 hrs. The reaction mixture was cooled again to 0° C. and quenched with the slow addition of a saturated NH₄Cl solution. The by-phasic mixture was diluted with DCM and Water and the aqueous extracted with DCM two times. The organic phases were combined, washed with brine, dried (Na₂SO₄), filtered and concentrated to 11.5 g crude white solid. Silica gel column chromatography (EtOAc/Heptane 0 to 30%) afforded (R)-2-methyl-N—((S)-1-(4-(trifluoromethoxy)phenyl)ethyl)propane-2-sulfinamide (5.08 g, 16.2 mmol, 62% yield) as a white crystalline solid. ¹H NMR (400 MHz, CDCl₃) δ 1.21 (s, 9H) 1.53 (d, J=6.70 Hz, 3H) 3.31 (d, J=2.74 Hz, 1H) 4.59 (qd, J=6.67, 3.37 Hz, 1H) 7.18 (d, J=8.02 Hz, 2H) 7.36 (d, J=8.66 Hz, 2H). LCMS m/z 310.2 (M+H)⁺, Rt 0.90 min.

Step 3

(R)-2-methyl-N—((S)-1-(4-(trifluoromethoxy)phenyl)ethyl)propane-2-sulfinamide (5.08 g, 16.4 mmol) was dissolved by swirling in 4M HCl in dioxane (16.4 ml, 65.6 mmol), at room temperature. The solution was allowed to sit for 1 hr with occasional swirling. To the clear solution was added 45 ml ether and the resulting cloudy solution sonicated for 1 min, upon which time the white solid product precipitates out. The solid was filtered through a Buchner funnel, washed 5 times with ~20 ml ether and allowed to air dry. Obtained (S)-1-(4-(trifluoromethoxy)phenyl)ethanamine (3.2 g, 13.2 mmol, 80% yield), ¹H NMR (400 MHz, CD₃OD) δ 1.64 (d, J=6.90 Hz, 3H) 4.52 (q, J=6.88 Hz, 1H) 7.38 (d, J=8.02 Hz, 2H) 7.57 (d, J=8.71 Hz, 2H). LCMS m/z 206.1 (M+H)⁺, Rt 0.52 min.

The Intermediates in Table 20 were prepared using the method described for the preparation of Intermediate 320.

TABLE 20

| Intermediate: Name | Structure | ¹H NMR (400 MHz, CD₃OD), LCMS |
|---|---|---|
| 321: (S)-1-(2-fluoro-4-(trifluoromethoxy)phenyl)ethanamine | | δ ppm 1.66 (d, J = 6.94 Hz, 3H) 4.75 (q, J = 6.94 Hz, 1H) 7.23-7.31 (m, 2H) 7.60-7.68 (m, 1H). MS m/z 224.1 (M + H)⁺, Rt 0.54 min. |
| 322: (S)-1-(4-(difluoromethoxy)phenyl)ethanamine | | δ ppm 1.63 (d, J = 6.90 Hz, 3H) 4.48 (q, J = 6.88 Hz, 1H) 6.63-7.10 (m, 1H) 7.24 (d, J = 8.71 Hz, 2H) 7.50 (d, J = 8.66 Hz, 2H). MS m/z 171.1 (M + H)⁺ Rt 0.43 min. |
| 323: (S)-1-(3-fluoro-4-(trifluoromethoxy)phenyl)ethanamine | | δ ppm 1.64 (d, J = 6.90 Hz, 3H) 4.54 (q, J = 6.88 Hz, 1H) 7.39 (dt, J = 8.52, 1.56 Hz, 1H) 7.46-7.59 (m, 2H). MS m/z 224.1 (M + H)⁺, Rt 0.55 min. |
| 324: (S)-1-(4-(difluoromethoxy)-3-fluorophenyl)ethanamine | | δ ppm 1.62 (d, J = 6.90 Hz, 3H) 4.49 (q, J = 6.83 Hz, 1H) 6.67-7.10 (m, 1H) 7.27-7.33 (m, 1H) 7.35-7.44 (m, 2H). MS m/z 206.1 (M + H)⁺, Rt 0.46 min. |

TABLE 20-continued

| Intermediate: Name | Structure | $^1$H NMR (400 MHz, CD$_3$OD), LCMS |
|---|---|---|
| 325: (S)-1-(4-(difluoromethoxy)-2-fluorophenyl)ethanamine | 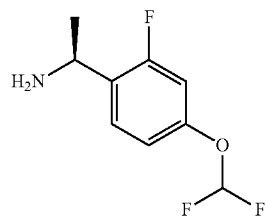 | δ ppm 1.65 (d, J = 6.94 Hz, 3H) 4.71 (q, J = 6.94 Hz, 1H) 6.71-6.97 (m, 1H) 7.05-7.14 (m, 2H) 7.55 (t, J = 8.68 Hz, 1H). MS m/z 206.1 (M + H)$^+$, Rt 0.46 min. |
| 326: (S)-1-(3-(trifluoromethoxy)-phenyl)ethanamine | 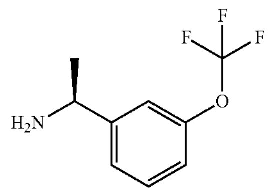 | δ ppm 1.63 (d, J = 6.90 Hz, 3H) 4.53 (q, J = 6.86 Hz, 1H) 7.35 (ddt, J = 8.21, 2.27, 1.09, 1.09 Hz, 1H) 7.41 (s, 1H) 7.47 (d, J = 7.82 Hz, 1H) 7.54-7.61 (m, 1H). MS m/z 206.1 (M + H)$^+$, Rt 0.51 min. |
| 327: (S)-1-(3-(difluoromethoxy)-phenyl)ethanamine | 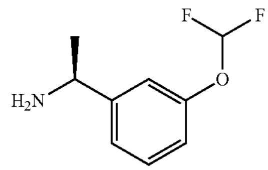 | δ ppm 1.63 (d, J = 6.90 Hz, 3H) 4.49 (q, J = 6.88 Hz, 1H) 6.64-7.08 (m, 1H) 7.21 (dd, J = 8.19, 1.83 Hz, 1H) 7.26 (t, J = 2.03 Hz, 1H) 7.33 (d, J = 7.78 Hz, 1H) 7.45-7.53 (m, 1H). MS m/z 188.1 (M + H)$^+$, Rt 0.43 min. |

Intermediate 328 (R)-4-((S)-1-(tert-butoxy)ethyl)-3-(5-fluoro-2-(((S)-1-(piperidin-4-yl)ethyl)amino)pyrimidin-4-yl)oxazolidin-2-one

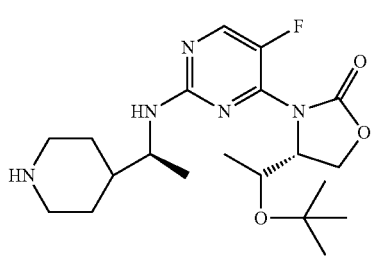 [SMILES: CC(OC(C)(C)C)[C@H]1COC(=O)N1c1nc(N[C@@H](C)C2CCNCC2)ncc1F]

To a Parshaker flask were added benzyl 4-((S)-1-((4-((R)-4-((S)-1-(tert-butoxy)ethyl)-2-oxooxazolidin-3-yl)-5-fluoropyrimidin-2-yl)amino)ethyl)piperidine-1-carboxylate (850 mg, 1.56 mmole) and 20% Pd(OH)$_2$ in Actifed carbon (880 mg, 1.25 mmole), then was added MeOH (100 mL) under nitrogen gas. The reaction mixture was shaked under 50 psi hydrogen overnight. The reaction mixture was filtered through a celite. The celite cake was washed with MeOH and the filtrate was concentrate in vacuo. The resulting crude product was purified by flash column chromatography (basic alumina, 40 g) eluting w/ 0-20% MeOH/DCM to afford the title product as a white solid (230 mg). $^1$H NMR (400 MHz, CD$_2$Cl$_2$) δ 8.18 (d, J=2.87 Hz, 1H), 5.15 (br s, 1H), 4.71-4.63 (m, 1H), 4.56-4.47 (m, 1H), 4.47-4.34 (m, 2H), 4.25-4.14 (m, 1H), 3.96-3.82 (m, 1H), 3.16 (d, J=12.34 Hz, 2H), 2.67-2.54 (m, 2H), 1.85-1.66 (m, 2H), 1.64-1.52 (m, 1H), 1.40-1.26 (m, 2H), 1.20 (d, J=6.60 Hz, 3H), 1.18 (s, 9H), 1.10 (d, J=6.46 Hz, 3H). HRMS(C) tR=2.36 min; MS m/z 410.2571 (M+H)+

Intermediate 329 (R)-4-((S)-1-(tert-butoxy)ethyl)-3-(2-(((S)-1-(1-(4-chloro-3-(trifluoromethoxy)phenyl)piperidin-4-yl)ethyl)amino)-5-fluoropyrimidin-4-yl)oxazolidin-2-one

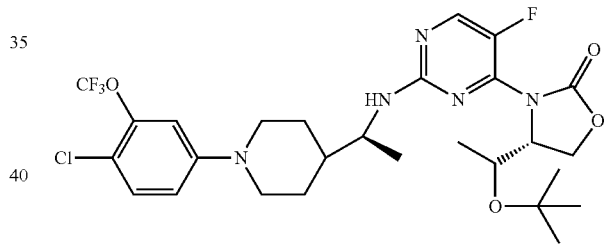

A cloudy solution of (R)-4-((S)-1-(tert-butoxy)ethyl)-3-(5-fluoro-2-(((S)-1-(piperidin-4-yl)ethyl)amino)pyrimidin-4-yl)oxazolidin-2-one (32 mg, 0.078 mmol), 4-bromo-1-chloro-2-(trifluoromethyoxy)benzene (26 mg, 0.094 mmol), Pd(OAc)$_2$ (2 mg, 8 umol), BINAP (5 mg, 8 umol), and Cs$_2$CO$_3$ (51 mg, 0.156 mmol) in 6 mL toluene was heated at 90° C. for 3 days. The mixture was cooled to room temperature, and filtered through Celite. The celite cake was rinsed with 5 mL EtOAc. The filtrate was poured into 5 mL water. Organic layer was separated, and the aqueous was further extracted with EtOAc (5 mL). The organic extracts were combined and concentrated by rotary evaporation. The crude was dissolved in a mixture of MeOH (1 mL) and DMSO (1 mL) and purified by reverse phase HPLC. Selected fractions were collected and concentrated by rotary evaporation to afford the title product as a colorless oil (34 mg). (400 MHz, CD$_2$Cl$_2$) δ 8.19 (d, J=2.95 Hz, 1H), 7.31 (d, J=8.85 Hz, 1H), 6.87-6.80 (m, 2H), 5.05 (br s, 1H), 4.73-4.63 (m, 1H), 4.56-4.44 (m, 2H), 4.25-4.13 (m, 1H), 4.01-3.88 (m, 1H), 3.79-3.69 (m, 2H), 2.82-2.69 (m, 2H), 2.00-1.79 (m, 2H), 1.68-1.56 (m, 1H), 1.54-1.36 (m, 2H), 1.23 (d, J=6.87 Hz, 3H), 1.15 (s, 9H), 1.09 (d, J=6.44 Hz, 3H), HRMS(C) tR=5.61 min; MS m/z 604.2328 (M+H)+

The intermediates in Table 21 were prepared with procedures similar to those used to prepare Intermediate 301

TABLE 21

| Intermediate: Name | Structure | LCMS |
|---|---|---|
| 330: (R)-N-((S)-1-(5-chloro-6-(1,1-difluoroethyl)pyridin-3-yl)ethyl)-2-methylpropane-2-sulfinamide | 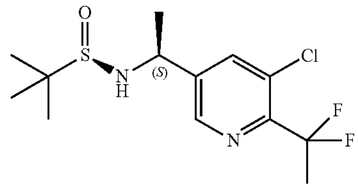 | MS m/z 325.2 (M + H)+, Rt 0.85 min. |
| 331: (R)-N-((S)-1-(5-chloro-6-(2,2,2-trifluoroethoxy)pyridin-3-yl)ethyl)-2-methylpropane-2-sulfinamide | 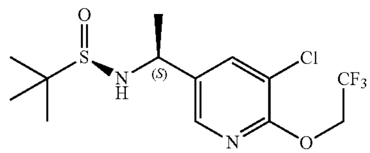 | MS m/z 359.1 (M + H)+, Rt 0.95 min. |

The intermediates in Table 22 were prepared with procedures similar to those used to prepare Intermediate 302

TABLE 22

| Intermediate: Name | Structure | LCMS |
|---|---|---|
| 332: (S)-1-(5-chloro-6-(1,1-difluoroethyl)pyridin-3-yl)ethanamine | 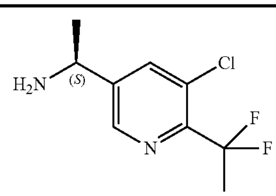 | MS m/z 221.1 (M + H)+, Rt 0.50 min. |
| 333: (S)-1-(5-chloro-6-(2,2,2-trifluoroethoxy)pyridin-3-yl)ethanamine | 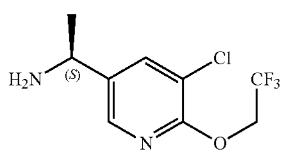 | MS m/z 255.1 (M + H)+, Rt 0.62 min. |

The intermediates in Table 23a were prepared using a method similar to that described for the preparation of Intermediate 306

TABLE 23a

Intermediate 334

Intermediate 335

TABLE 23a-continued

Intermediate 336

Intermediate 337

TABLE 23a-continued

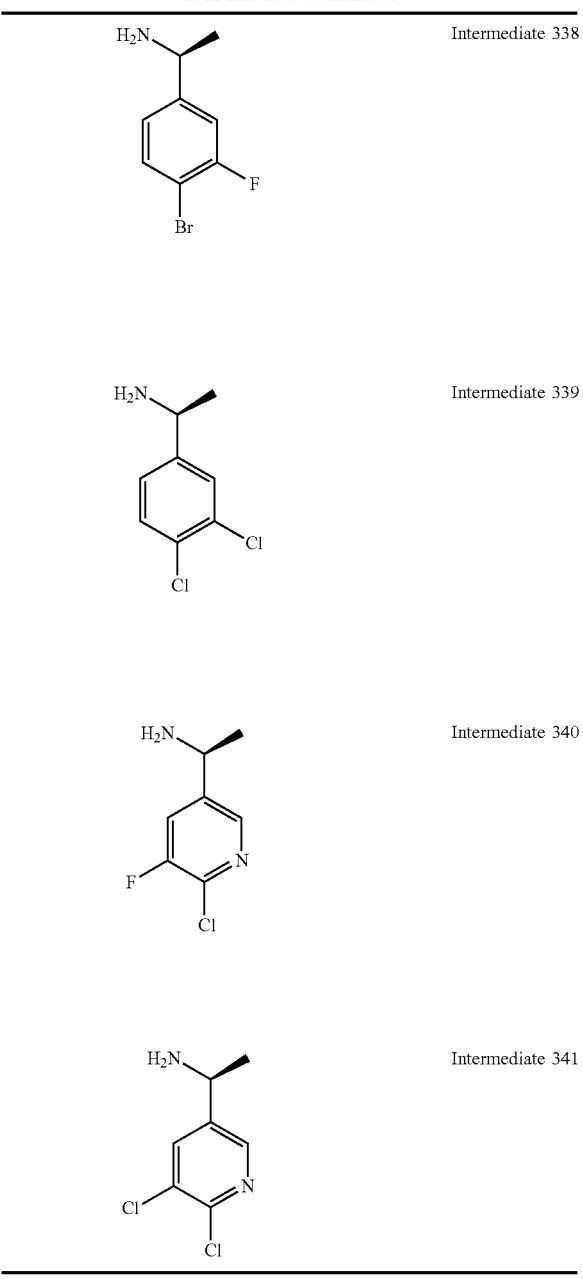

| Intermediate |
|---|
| Intermediate 338 |
| Intermediate 339 |
| Intermediate 340 |
| Intermediate 341 |

Intermediate 342: (R)-4-((R)-1-(tert-butoxy)ethyl)-3-(2-(((S)-1-phenylethyl)amino)pyrimidin-4-yl)oxazolidin-2-one

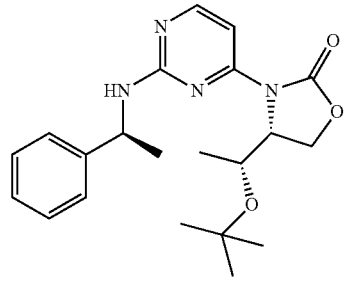 [SMILES: C[C@H](Nc1nccc(N2C(=O)OC[C@@H]2[C@@H](C)OC(C)(C)C)n1)c1ccccc1]

A solution of (R)-4-((R)-1-(tert-butoxy)ethyl)-3-(2-fluoropyrimidin-4-yl)oxazolidin-2-one (112 mg, 0.40 mmol), (S)-1-phenylethanamine (58 mg, 0.48 mmol, 1.2 equiv), and DIPEA (153 mg, 1.2 mmol, 3.0 equiv) in DMSO (4.0 mL) was heated at 100° C. for 90 min. The reaction mixture was poured into 5 ml of water, extracted with EA (2×10 ml), the solvent was removed to yield the crude product. Silica gel column chromatography (ethyl acetate in heptane 10 to 50%) provided the pure product (142 mg, white solid) in a 93% yield. HRMS m/z 385.2231 (M+H)$^+$, RT=3.35 min.

The Following Intermediates were prepared using a method similar to that described for the preparation of Intermediate 342 or Example 3

Intermediate 343: (R)-4-((R)-1-(tert-butoxy)ethyl)-3-(2-(((S)-1-(3-(2,3-dihydro-1H-inden-5-yl)-1,2,4-oxadiazol-5-yl)ethyl)amino)pyrimidin-4-yl)oxazolidin-2-one

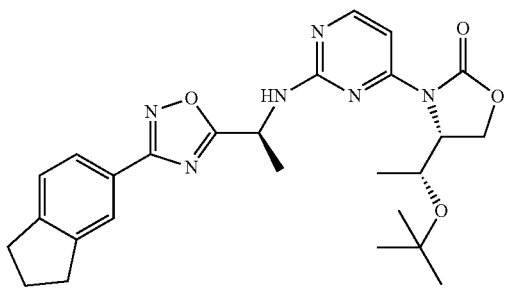 [SMILES: C[C@H](Nc1nccc(N2C(=O)OC[C@@H]2[C@@H](C)OC(C)(C)C)n1)c1nc(-c2ccc3c(c2)CCC3)no1]

HRMS(B) tR=3.54 min; m/z 492.2485

TABLE 23b

Chemical name and analytical data for each intermediate listed in Table 23a.

| Intermediate: Name | Analytical data |
|---|---|
| 334: (S)-1-(4-bromo-2,5-difluorophenyl)ethanamine | LCMS m/z (M + H)$^+$ 236.0, RT 0.5 min. |
| 335: (S)-1-(4-bromo-2,3-difluorophenyl)ethanamine | LCMS m/z (M + H)$^+$ 238.1, RT 0.55 min. |
| 336: (S)-1-(4-bromo-2-fluorophenyl)ethanamine | LCMS m/z (M + H)$^+$ 218.0, 220.1, RT 0.47 min. |
| 337: (S)-1-(4-chloro-2-fluorophenyl)ethanamine | LCMS m/z (M + H)$^+$ 174.2, RT 0.47 min. |
| 338: (S)-1-(4-bromo-3-fluorophenyl)ethanamine | LCMS m/z (M + H)$^+$ 218.1, 220.1, RT 0.52 min. |
| 339: (S)-1-(3,4-dichlorophenyl)ethanamine | LCMS m/z (M + H)$^+$ 190.0, RT 0.57 min. |
| 340: (S)-1-(6-chloro-5-fluoropyridin-3-yl)ethanamine | LCMS m/z (M + H)$^+$ 175.2, RT 0.37 min. |
| 341: (S)-1-(5,6-dichloropyridin-3-yl)ethanamine | LCMS m/z (M + H)$^+$ 191.1, RT 0.42 min. |

Intermediate 344 (4R)-3-(2-((1-(3-(4-bromo-3-methoxyphenyl)-1,2,4-oxadiazol-5-yl)ethyl)amino)pyrimidin-4-yl)-4-((R)-1-(tert-butoxy)ethyl)oxazolidin-2-one

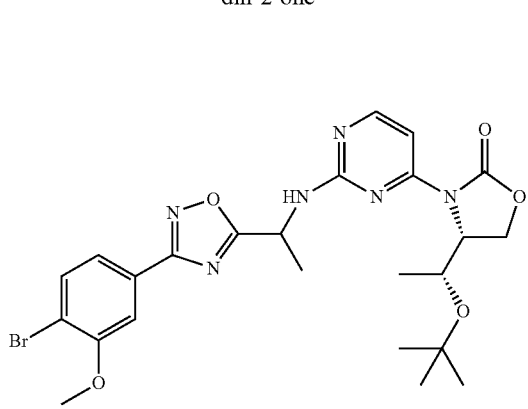

HRMS(C) tR=1.76 min; MS m/z 561.43

Intermediate 345 (4R)-4-((R)-1-(tert-butoxy)ethyl)-3-(2-((1-(3-(4-ethylphenyl)-1,2,4-oxadiazol-5-yl)ethyl)amino)pyrimidin-4-yl)oxazolidin-2-one

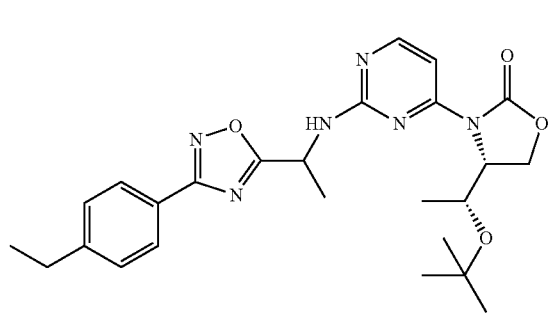 [SMILES: CCc1ccc(-c2noc(C(C)Nc3nccc(N4C(=O)OC[C@@H]4[C@@H](C)OC(C)(C)C)n3)n2)cc1]

HRMS(C) tR=1.94 min; m/z 480.2485

Intermediate 346 (4R)-4-((R)-1-(tert-butoxy)ethyl)-3-(2-((1-(3-(4-ethylphenyl)-1,2,4-oxadiazol-5-yl)ethyl)amino)-5-fluoropyrimidin-4-yl)oxazolidin-2-one

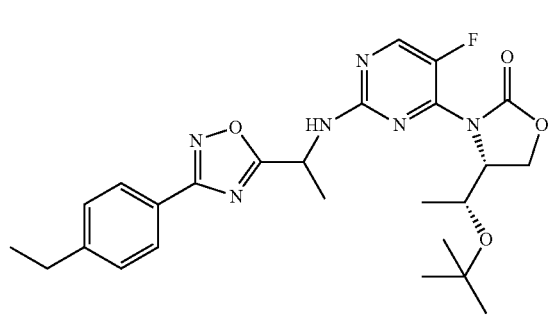 [SMILES: CCc1ccc(-c2noc(C(C)Nc3ncc(F)c(N4C(=O)OC[C@@H]4[C@@H](C)OC(C)(C)C)n3)n2)cc1]

HRMS(C) tR=1.78 min; m/z 498.2391

Intermediate 347 (4R)-4-((R)-1-(tert-butoxy)ethyl)-3-(2-((1-(3-phenethyl-1,2,4-oxadiazol-5-yl)ethyl)amino)pyrimidin-4-yl)oxazolidin-2-one

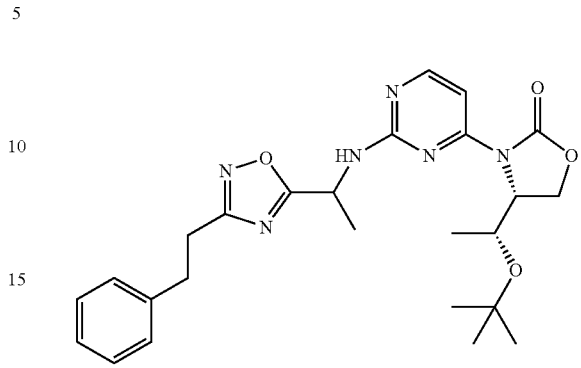

HRMS(C) tR=1.71 min; m/z 480.2485

Intermediate 348 (R)-4-((R)-1-(tert-butoxy)ethyl)-3-(2-(((S)-1-(3-(isoquinolin-8-yl)-1,2,4-oxadiazol-5-yl)ethyl)amino)pyrimidin-4-yl)oxazolidin-2-one

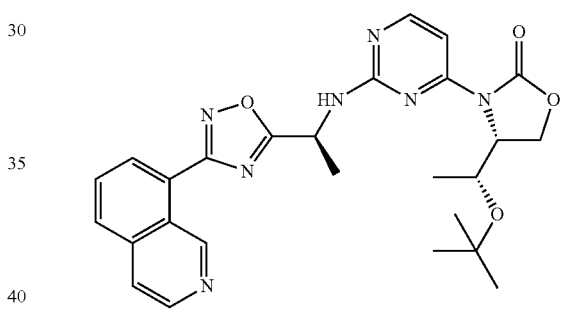

HRMS(B) tR=2.77 min; m/z 504.2337 (M+H)

Intermediate 349 (4R)-4-((R)-1-(tert-butoxy)ethyl)-3-(2-((1-(3-(4-chloro-3-(trifluoromethyl)phenyl)-1,2,4-oxadiazol-5-yl)ethyl)amino)pyrimidin-4-yl)oxazolidin-2-one

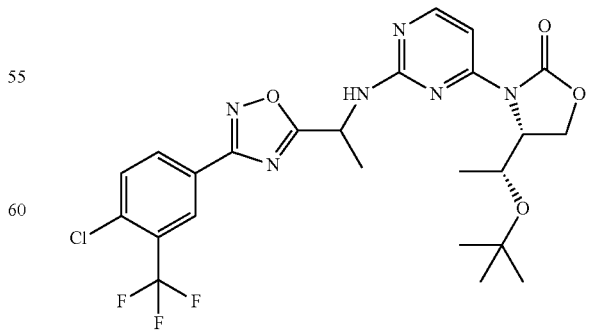

HRMS(C) tR=1.96 min; m/z 554.1656

Intermediate 350 (R)-4-((R)-1-(tert-butoxy)ethyl)-3-(2-(((S)-1-(3-(3-(difluoromethoxy)phenyl)-1,2,4-oxadiazol-5-yl)ethyl)amino)pyrimidin-4-yl)oxazolidin-2-one

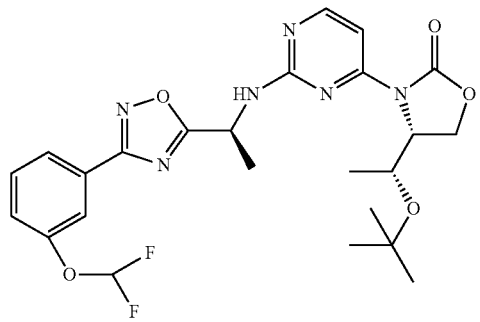 [SMILES: C[C@H](Nc1nccc(N2C(=O)OC[C@@H]2[C@@H](C)OC(C)(C)C)n1)c1nc(-c2cccc(OC(F)F)c2)no1]

HRMS(B) tR=3.13 min; m/z 518.2089

Intermediate 351 (4R)-4-((R)-1-(tert-butoxy)ethyl)-3-(2-((1-(3-(4-(trifluoromethoxy)phenyl)-1,2,4-oxadiazol-5-yl)ethyl)amino)pyrimidin-4-yl)oxazolidin-2-one

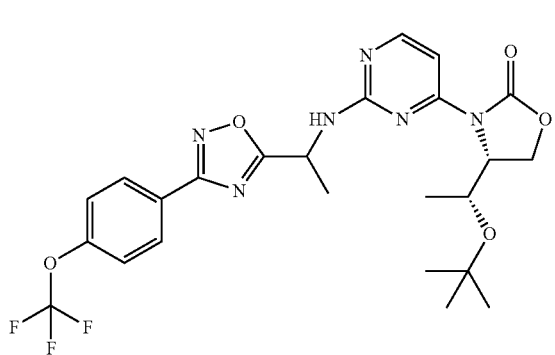 [SMILES: CC(Nc1nccc(N2C(=O)OC[C@@H]2[C@@H](C)OC(C)(C)C)n1)c1nc(-c2ccc(OC(F)(F)F)cc2)no1]

HRMS(C) tR=1.97 min; m/z 536.1995

Intermediate 352 (4R)-4-((R)-1-(tert-butoxy)ethyl)-3-(2-((1-(3-(4-(trifluoromethyl)phenyl)-1,2,4-oxadiazol-5-yl)ethyl)amino)pyrimidin-4-yl)oxazolidin-2-one

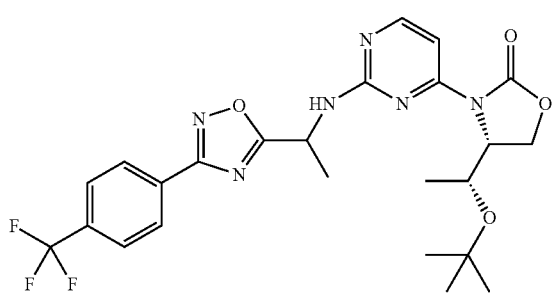 [SMILES: CC(Nc1nccc(N2C(=O)OC[C@@H]2[C@@H](C)OC(C)(C)C)n1)c1nc(-c2ccc(C(F)(F)F)cc2)no1]

HRMS(C) tR=1.91 min; m/z 520.2046

Intermediate 353 (R)-4-((R)-1-(tert-butoxy)ethyl)-3-(2-(((S)-1-(3-(3-(trifluoromethyl)phenyl)-1,2,4-oxadiazol-5-yl)ethyl)amino)pyrimidin-4-yl)oxazolidin-2-one

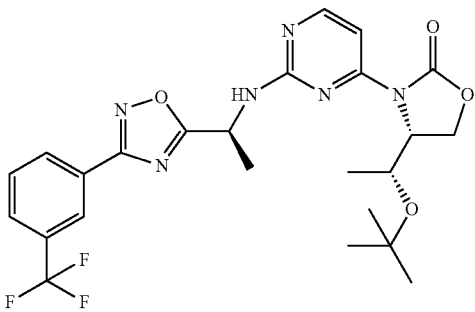 [SMILES: C[C@H](Nc1nccc(N2C(=O)OC[C@@H]2[C@@H](C)OC(C)(C)C)n1)c1nc(-c2cccc(C(F)(F)F)c2)no1]

HRMS(C) tR=1.87 min; m/z 520.2046

Intermediate 354 (R)-4-((R)-1-(tert-butoxy)ethyl)-3-(2-(((S)-1-(3-(2-(trifluoromethoxy)phenyl)-1,2,4-oxadiazol-5-yl)ethyl)amino)pyrimidin-4-yl)oxazolidin-2-one

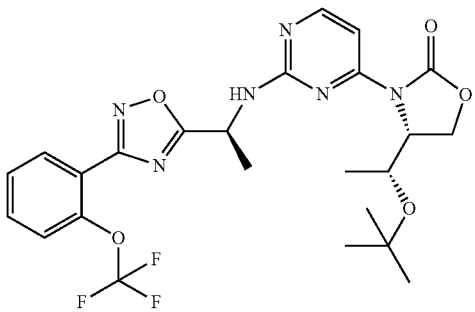 [SMILES: C[C@H](Nc1nccc(N2C(=O)OC[C@@H]2[C@@H](C)OC(C)(C)C)n1)c1nc(-c2ccccc2OC(F)(F)F)no1]

HRMS(C) tR=1.76 min; m/z 536.1995

Intermediate 355 (R)-4-((R)-1-(tert-butoxy)ethyl)-3-(2-(((S)-1-(3-(3-(2,2,2-trifluoroethoxy)phenyl)-1,2,4-oxadiazol-5-yl)ethyl)amino)pyrimidin-4-yl)oxazolidin-2-one

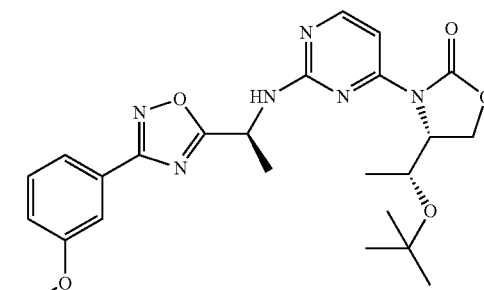

HRMS(C) tR=1.76 min; m/z 550.2151

187

Intermediate 356 (R)-4-((R)-1-(tert-butoxy)ethyl)-3-(2-(((S)-1-(3-(2,2-difluorobenzo[d][1,3]dioxol-5-yl)-1,2,4-oxadiazol-5-yl)ethyl)amino)pyrimidin-4-yl)oxazolidin-2-one

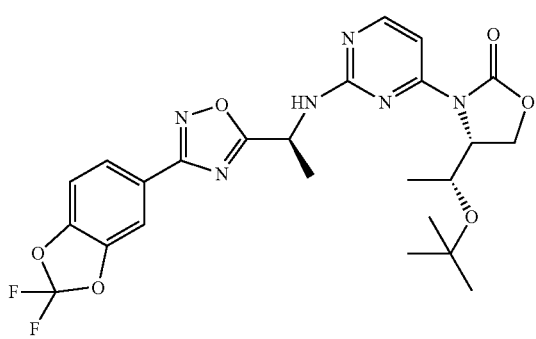 [SMILES: C[C@H](Nc1nccc(N2C(=O)OC[C@@H]2[C@@H](C)OC(C)(C)C)n1)c1nc(-c2ccc3c(c2)OC(F)(F)O3)no1]

HRMS(B) tR=3.38 min; m/z 532.1882

Intermediate 357 (4R)-4-((R)-1-(tert-butoxy)ethyl)-3-(2-((1-(5-(3,4-dimethylphenyl)-1,3,4-oxadiazol-2-yl)ethyl)amino)pyrimidin-4-yl)oxazolidin-2-one

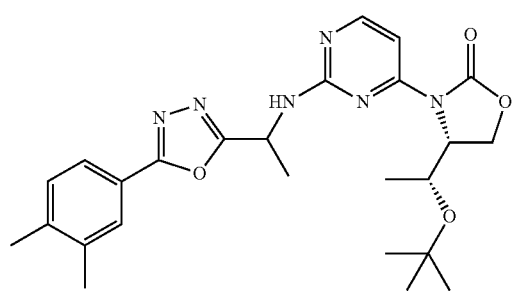 [SMILES: Cc1ccc(-c2nnc(C(C)Nc3nccc(N4C(=O)OC[C@@H]4[C@@H](C)OC(C)(C)C)n3)o2)cc1C]

HRMS(C) tR=1.63 min; m/z 480.2485

Intermediate 358 (4R)-4-((R)-1-(tert-butoxy)ethyl)-3-(2-((1-(5-(4-chlorophenyl)-4-methyloxazol-2-yl)ethyl)amino)-5-fluoropyrimidin-4-yl)oxazolidin-2-one

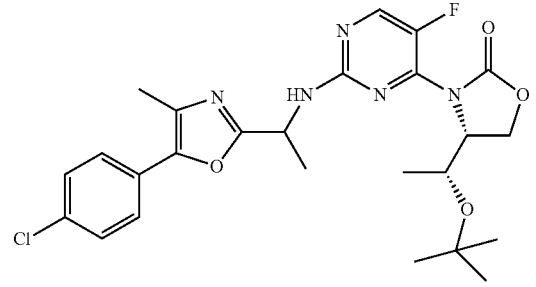 [SMILES: Cc1nc(C(C)Nc2ncc(F)c(N3C(=O)OC[C@@H]3[C@@H](C)OC(C)(C)C)n2)oc1-c1ccc(Cl)cc1]

HRMS(B) tR=1.65 min; MS m/z 518.1 (M+H)

188

Intermediate 359 (R)-4-((R)-1-(tert-butoxy)ethyl)-3-(2-(((S)-1-(5-(4-chlorophenyl)oxazol-2-yl)ethyl)amino)pyrimidin-4-yl)oxazolidin-2-one

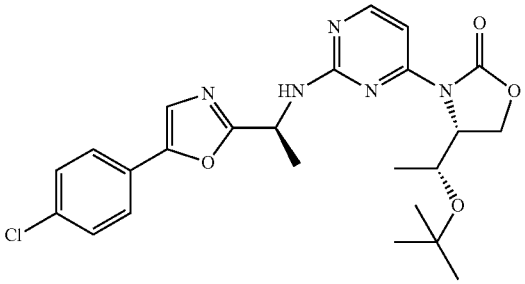 [SMILES: C[C@H](Nc1nccc(N2C(=O)OC[C@@H]2[C@@H](C)OC(C)(C)C)n1)c1ncc(-c2ccc(Cl)cc2)o1]

HRMS(B) tR=1.59 min; MS m/z 486.2

Intermediate 360 (4R)-3-(2-((1-(3-(4-bromo-3-methoxyphenyl)-1,2,4-oxadiazol-5-yl)ethyl)amino)pyrimidin-4-yl)-4-((R)-1-(tert-butoxy)ethyl)oxazolidin-2-one

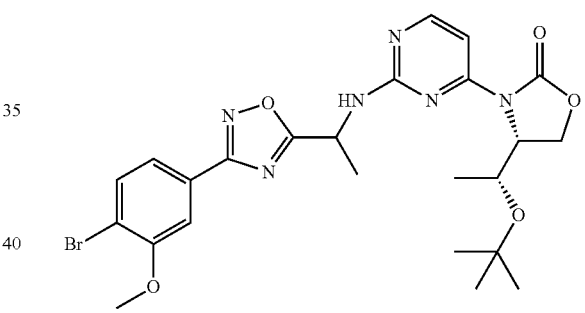

HRMS(C) tR=1.76 min; MS m/z 561.43

Intermediate 361 (4R)-4-((R)-1-(tert-butoxy)ethyl)-3-(2-((1-(3-(4-ethylphenyl)-1,2,4-oxadiazol-5-yl)ethyl)amino)pyrimidin-4-yl)oxazolidin-2-one

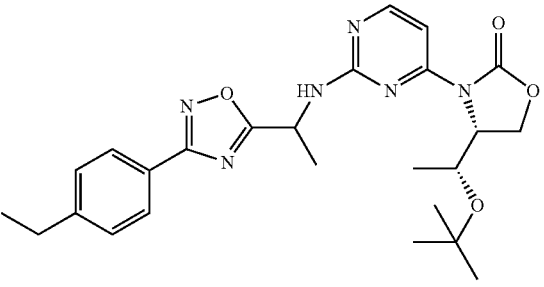 [SMILES: CCc1ccc(-c2noc(C(C)Nc3nccc(N4C(=O)OC[C@@H]4[C@@H](C)OC(C)(C)C)n3)n2)cc1]

HRMS(C) tR=1.94 min; m/z 480.2485

189

Intermediate 362 (4R)-4-((R)-1-(tert-butoxy)ethyl)-3-(5-fluoro-2-((1-(3-(4-isopropylphenyl)-1,2,4-oxadiazol-5-yl)ethyl)amino)pyrimidin-4-yl)oxazolidin-2-one

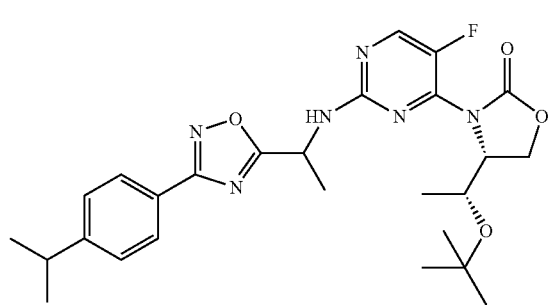 [SMILES: CC(C)c1ccc(-c2noc(C(C)Nc3ncc(F)c(N4C(=O)OC[C@@H]4[C@@H](C)OC(C)(C)C)n3)n2)cc1]

HRMS(C) tR=1.96 min; m/z 512.2548

Intermediate 363 (4R)-4-((R)-1-(tert-butoxy)ethyl)-3-(2-((1-(3-(4-ethylphenyl)-1,2,4-oxadiazol-5-yl)ethyl)amino)-5-fluoropyrimidin-4-yl)oxazolidin-2-one

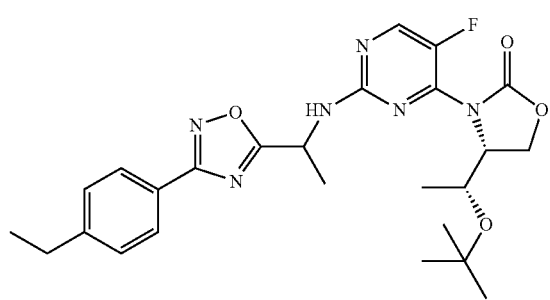 [SMILES: CCc1ccc(-c2noc(C(C)Nc3ncc(F)c(N4C(=O)OC[C@@H]4[C@@H](C)OC(C)(C)C)n3)n2)cc1]

HRMS(C) tR=1.78 min; m/z 498.2391

Intermediate 364 (4R)-4-((R)-1-(tert-butoxy)ethyl)-3-(2-((1-(3-phenethyl-1,2,4-oxadiazol-5-yl)ethyl)amino)pyrimidin-4-yl)oxazolidin-2-one

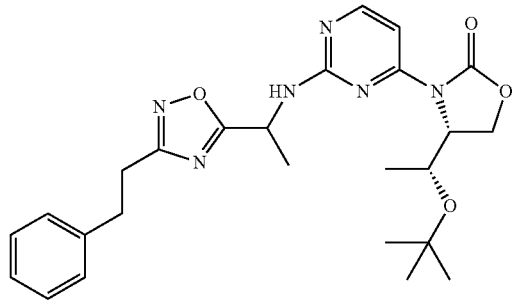 [SMILES: CC(Nc1nccc(N2C(=O)OC[C@@H]2[C@@H](C)OC(C)(C)C)n1)c1nc(CCc2ccccc2)no1]

HRMS(C) tR=1.71 min; m/z 480.2485

190

Intermediate 365 (R)-4-((R)-1-(tert-butoxy)ethyl)-3-(2-(((S)-1-(3-(isoquinolin-8-yl)-1,2,4-oxadiazol-5-yl)ethyl)amino)pyrimidin-4-yl)oxazolidin-2-one

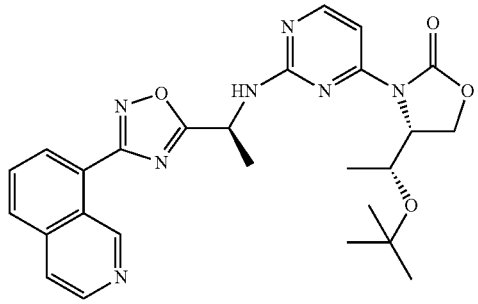 [SMILES: C[C@H](Nc1nccc(N2C(=O)OC[C@@H]2[C@@H](C)OC(C)(C)C)n1)c1nc(-c2cccc3ccncc23)no1]

HRMS(B) tR=2.77 min; m/z 504.2337 (M+H)

Intermediate 366 (4R)-4-((R)-1-(tert-butoxy)ethyl)-3-(2-((1-(3-(4-chloro-3-(trifluoromethyl)phenyl)-1,2,4-oxadiazol-5-yl)ethyl)amino)pyrimidin-4-yl)oxazolidin-2-one

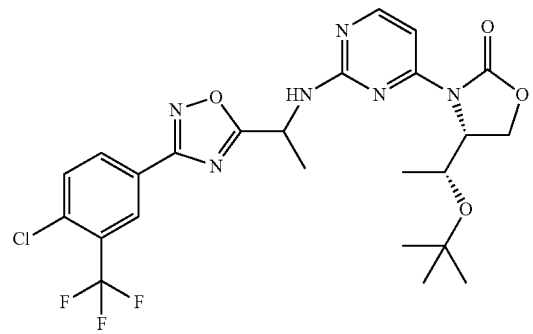 [SMILES: CC(Nc1nccc(N2C(=O)OC[C@@H]2[C@@H](C)OC(C)(C)C)n1)c1nc(-c2ccc(Cl)c(C(F)(F)F)c2)no1]

HRMS(C) tR=1.96 min; m/z 554.1656

Intermediate 367 (R)-4-((R)-1-(tert-butoxy)ethyl)-3-(2-(((S)-1-(3-(3-(difluoromethoxy)phenyl)-1,2,4-oxadiazol-5-yl)ethyl)amino)pyrimidin-4-yl)oxazolidin-2-one

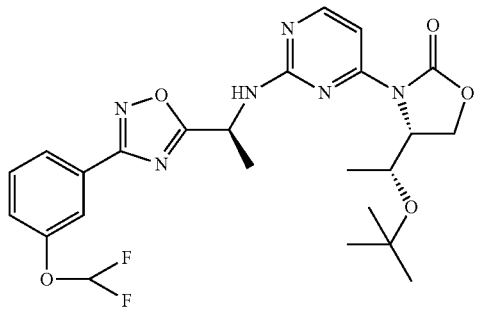 [SMILES: C[C@H](Nc1nccc(N2C(=O)OC[C@@H]2[C@@H](C)OC(C)(C)C)n1)c1nc(-c2cccc(OC(F)F)c2)no1]

HRMS(B) tR=3.13 min; m/z 518.2089

191

Intermediate 368 (4R)-4-((R)-1-(tert-butoxy)ethyl)-3-(2-((1-(3-(4-(trifluoromethoxy)phenyl)-1,2,4-oxadiazol-5-yl)ethyl)amino)pyrimidin-4-yl)oxazolidin-2-one

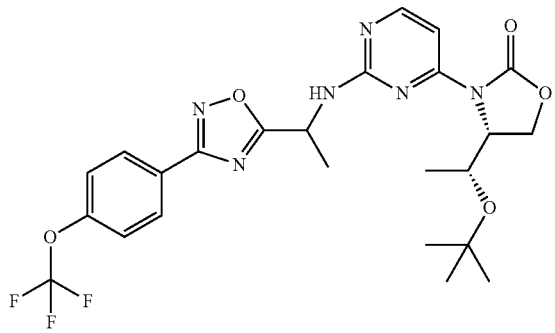 [SMILES: CC(Nc1nccc(N2C(=O)OC[C@@H]2[C@@H](C)OC(C)(C)C)n1)c1nc(-c2ccc(OC(F)(F)F)cc2)no1]

HRMS(C) tR=1.97 min; m/z 536.1995

Intermediate 369 (4R)-4-((R)-1-(tert-butoxy)ethyl)-3-(2-((1-(3-(4-(trifluoromethyl)phenyl)-1,2,4-oxadiazol-5-yl)ethyl)amino)pyrimidin-4-yl)oxazolidin-2-one

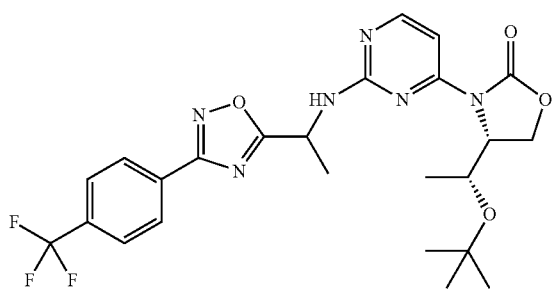 [SMILES: CC(Nc1nccc(N2C(=O)OC[C@@H]2[C@@H](C)OC(C)(C)C)n1)c1nc(-c2ccc(C(F)(F)F)cc2)no1]

HRMS(C) tR=1.91 min; m/z 520.2046

Intermediate 370 (R)-4-((R)-1-(tert-butoxy)ethyl)-3-(2-(((S)-1-(3-(3-(trifluoromethyl)phenyl)-1,2,4-oxadiazol-5-yl)ethyl)amino)pyrimidin-4-yl)oxazolidin-2-one

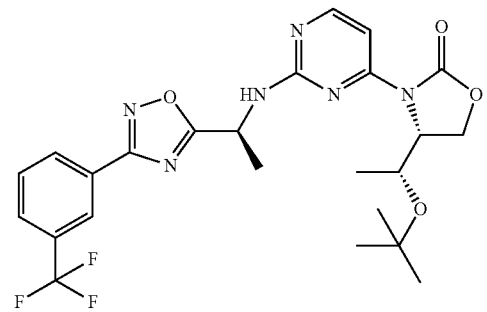 [SMILES: C[C@H](Nc1nccc(N2C(=O)OC[C@@H]2[C@@H](C)OC(C)(C)C)n1)c1nc(-c2cccc(C(F)(F)F)c2)no1]

HRMS(C) tR=1.87 min; m/z 520.2046

192

Intermediate 371 (R)-4-((R)-1-(tert-butoxy)ethyl)-3-(2-(((S)-1-(3-(2-(trifluoromethoxy)phenyl)-1,2,4-oxadiazol-5-yl)ethyl)amino)pyrimidin-4-yl)oxazolidin-2-one

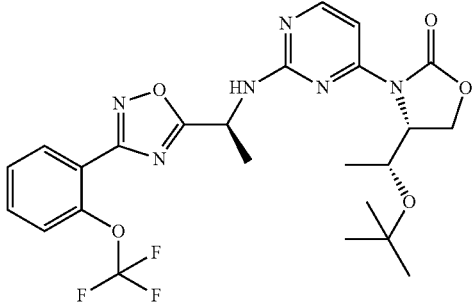 [SMILES: C[C@H](Nc1nccc(N2C(=O)OC[C@@H]2[C@@H](C)OC(C)(C)C)n1)c1nc(-c2ccccc2OC(F)(F)F)no1]

HRMS(C) tR=1.76 min; m/z 536.1995

Intermediate 372 (R)-4-((R)-1-(tert-butoxy)ethyl)-3-(2-(((S)-1-(3-(3-(2,2,2-trifluoroethoxy)phenyl)-1,2,4-oxadiazol-5-yl)ethyl)amino)pyrimidin-4-yl)oxazolidin-2-one

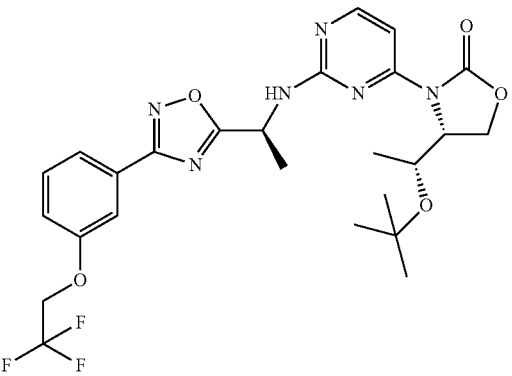 [SMILES: C[C@H](Nc1nccc(N2C(=O)OC[C@@H]2[C@@H](C)OC(C)(C)C)n1)c1nc(-c2cccc(OCC(F)(F)F)c2)no1]

HRMS(C) tR=1.76 min; m/z 550.2151

Intermediate 373 (R)-4-((R)-1-(tert-butoxy)ethyl)-3-(2-(((S)-1-(3-(2,2-difluorobenzo[d][1,3]dioxol-5-yl)-1,2,4-oxadiazol-5-yl)ethyl)amino)pyrimidin-4-yl)oxazolidin-2-one

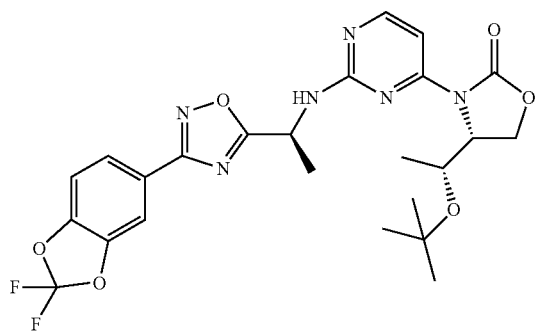 [SMILES: C[C@H](Nc1nccc(N2C(=O)OC[C@@H]2[C@@H](C)OC(C)(C)C)n1)c1nc(-c2ccc3c(c2)OC(F)(F)O3)no1]

HRMS(B) tR=3.38 min; m/z 532.1882

Intermediate 374 (4R)-4-((R)-1-(tert-butoxy)ethyl)-3-(2-((1-(5-(3,4-dimethylphenyl)-1,3,4-oxadiazol-2-yl)ethyl)amino)pyrimidin-4-yl)oxazolidin-2-one

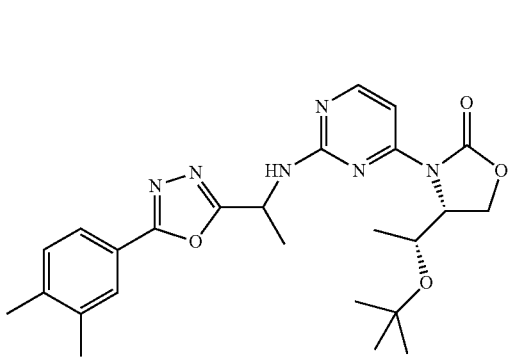 [SMILES: Cc1ccc(-c2nnc(C(C)Nc3nccc(N4C(=O)OC[C@@H]4[C@@H](C)OC(C)(C)C)n3)o2)cc1C]

HRMS(C) tR=1.63 min; m/z 480.2485

Intermediate 375 (4R)-4-((R)-1-(tert-butoxy)ethyl)-3-(2-((1-(5-(4-chlorophenyl)-4-methyloxazol-2-yl)ethyl)amino)-5-fluoropyrimidin-4-yl)oxazolidin-2-one

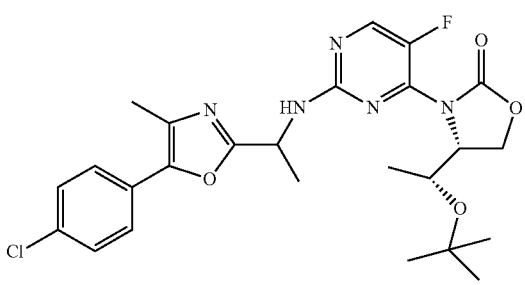 [SMILES: Cc1nc(C(C)Nc2ncc(F)c(N3C(=O)OC[C@@H]3[C@@H](C)OC(C)(C)C)n2)oc1-c1ccc(Cl)cc1]

HRMS(B) tR=1.65 min; MS m/z 518.1 (M+H)

Intermediate 376 (R)-4-((R)-1-(tert-butoxy)ethyl)-3-(2-(((S)-1-(4-(4-chlorophenyl)oxazol-2-yl)ethyl)amino)pyrimidin-4-yl)oxazolidin-2-one

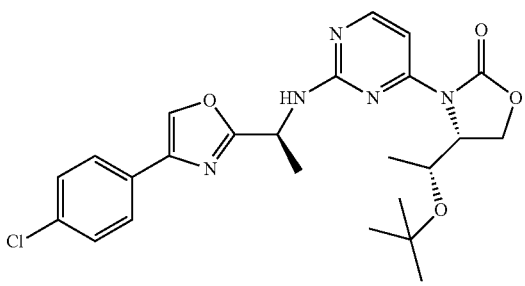 [SMILES: C[C@H](Nc1nccc(N2C(=O)OC[C@@H]2[C@@H](C)OC(C)(C)C)n1)c1nc(-c2ccc(Cl)cc2)co1]

HRMS(B) tR=1.59 min; MS m/z 486.2

Intermediate 377: (4R)-4-((R)-1-(tert-butoxy)ethyl)-3-(5-fluoro-2-((1-(4-methyl-5-(2-(1,1,1-trifluoro-2-methylpropan-2-yl)pyridin-4-yl)thiazol-2-yl)ethyl)amino)pyrimidin-4-yl)oxazolidin-2-one

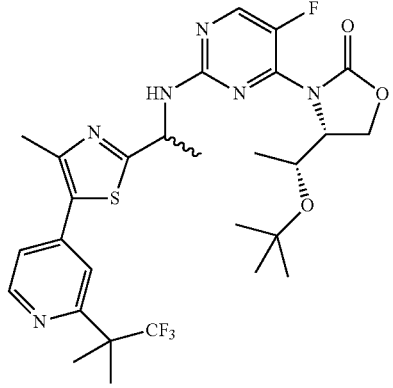 [SMILES: Cc1nc(C(C)Nc2ncc(F)c(N3C(=O)OC[C@@H]3[C@@H](C)OC(C)(C)C)n2)sc1-c1ccnc(C(C)(C)C(F)(F)F)c1]

Anal. RP-HPLC tR=1.69 min; MS m/z 611.1 (M+H)+.

Intermediate 378 benzyl 4-((S)-1-((4-((R)-4-((S)-1-(tert-butoxy)ethyl)-2-oxooxazolidin-3-yl)-5-fluoropyrimidin-2-yl)amino)ethyl)piperidine-1-carboxylate

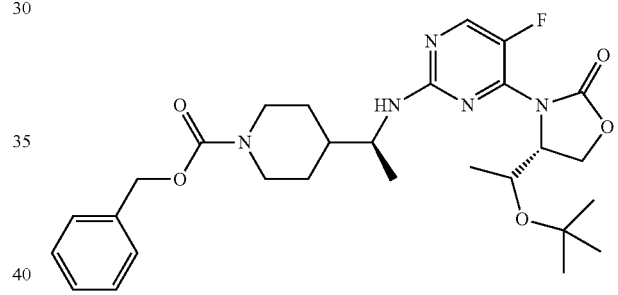

$^1$H NMR (400 MHz, CD$_2$Cl$_2$) δ 8.18 (s, 1H), 7.41-7.30 (m, 5H), 5.15 (s, 2H), 5.03 (br s, 1H), 4.71-4.64 (m, 1H), 4.54-4.45 (m, 2H), 4.30-4.12 (m, 3H), 3.99-3.86 (m, 1H), 2.77 (br s, 2H), 1.87-1.57 (m, 3H), 1.36-1.24 (m, 2H), 1.20 (d, J=6.44 Hz, 3H), 1.16 (s, 9H), 1.09 (d, J=5.91 Hz, 3H). HRMS(C) tR=4.46 min; MS m/z 544.2964 (M+H)+

Intermediate 379: (R)-4-((R)-1-(tert-butoxy)ethyl)-3-(2-(((S)-1-(5-(4-fluoro-3-methylphenyl)pyridin-2-yl)ethyl)amino)pyrimidin-4-yl)oxazolidin-2-one

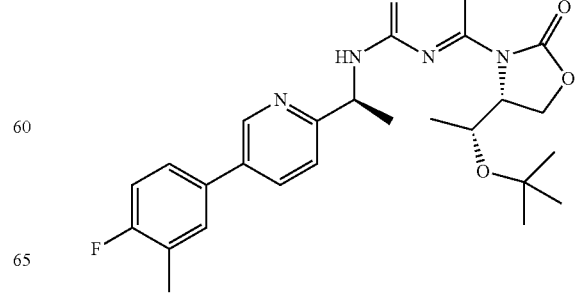

¹H NMR (400 MHz, CDCl3) δ 8.72 (d, J=2.3 Hz, 1H), 8.21 (d, J=5.7 Hz, 1H), 7.79 (dd, J=8.1, 2.4 Hz, 1H), 7.47 (d, J=5.8 Hz, 1H), 7.39-7.28 (m, 3H), 7.13-7.07 (m, 1H), 5.28 (p, J=6.9 Hz, 1H), 4.75 (dt, J=8.1, 3.5 Hz, 1H), 4.62 (dd, J=9.4, 3.1 Hz, 1H), 4.49-4.40 (m, 1H), 4.34 (t, J=9.0 Hz, 1H), 2.35 (d, J=1.9 Hz, 3H), 1.60 (d, J=6.7 Hz, 3H), 1.25 (s, 12H), 1.01 (d, J=6.5 Hz, 3H); MS m/z 492.6 (M−H).

Intermediate 380: (R)-4-((R)-1-(tert-butoxy)ethyl)-3-(2-(((S)-1-(5-(3-(trifluoromethyl)phenyl)pyridin-2-yl)ethyl)amino)pyrimidin-4-yl)oxazolidin-2-one

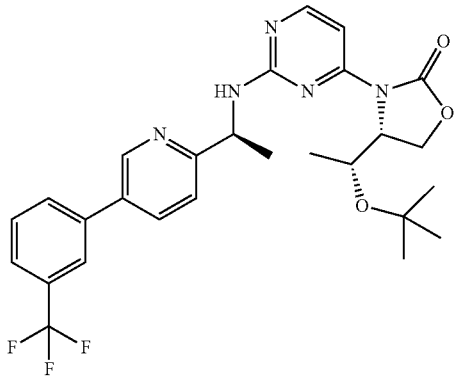

LCMS tR=1.86 min; MS m/z 528.5 (M−H)+.

Intermediate 381: (R)-4-((R)-1-(tert-butoxy)ethyl)-3-(2-(((S)-1-(6-(4-fluoro-3-methylphenyl)pyridin-3-yl)ethyl)amino)pyrimidin-4-yl)oxazolidin-2-one

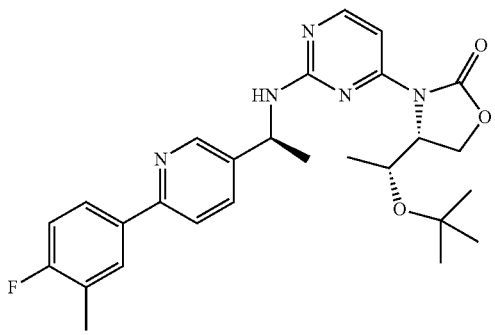

LCMS tR=1.69 min; MS m/z 494.0 (M+H)+.

Intermediate 382: (R)-4-((R)-1-(tert-butoxy)ethyl)-3-(2-(((S)-1-(6-(3-(trifluoromethyl)phenyl)pyridin-3-yl)ethyl)amino)pyrimidin-4-yl)oxazolidin-2-one

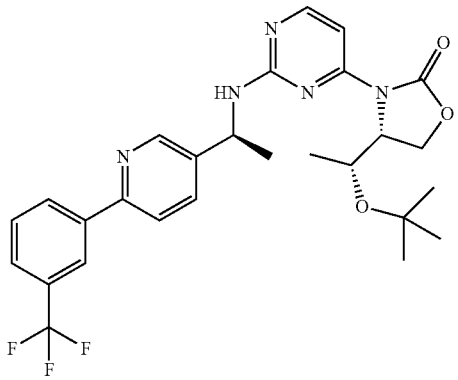

LCMS tR=1.74 min; MS m/z 530.0 (M+H)+.

Intermediate 383: (R)-4-((R)-1-(tert-butoxy)ethyl)-3-(2-(((S)-1-(2'-(trifluoromethyl)-[3,4'-bipyridin]-6-yl)ethyl)amino)pyrimidin-4-yl)oxazolidin-2-one

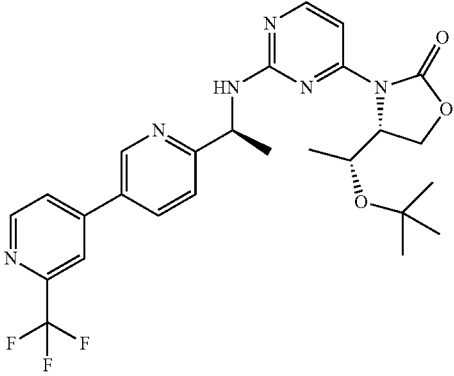 [SMILES: C[C@H](Nc1nccc(N2C(=O)OC[C@@H]2[C@@H](C)OC(C)(C)C)n1)c1ccc(-c2cccc(C(F)(F)F)c2)cn1]

¹H NMR (400 MHz, CDCl3) δ 8.86 (d, J=2.3 Hz, 1H), 8.83 (d, J=5.1 Hz, 1H), 8.20 (d, J=5.7 Hz, 1H), 7.93 (dd, J=8.1, 2.4 Hz, 1H), 7.87 (s, 1H), 7.69 (dd, J=5.2, 1.7 Hz, 1H), 7.48 (d, J=5.8 Hz, 1H), 7.45 (d, J=8.1 Hz, 1H), 6.37-5.79 (m, 1H), 5.33 (p, J=6.9 Hz, 1H), 4.74 (ddd, J=8.2, 4.6, 3.0 Hz, 1H), 4.62 (dd, J=9.3, 3.0 Hz, 1H), 4.43 (qd, J=6.4, 4.2 Hz, 1H), 4.34 (t, J=9.0 Hz, 1H), 1.67 (br s, 1H), 1.62 (d, J=6.8 Hz, 3H), 1.26 (s, 9H), 1.02 (d, J=6.4 Hz, 3H); MS m/z 531.3 (M+H).

Intermediate 384: (R)-4-((R)-1-(tert-butoxy)ethyl)-3-(2-(((S)-1-(6'-(trifluoromethyl)-[2,3'-bipyridin]-5-yl)ethyl)amino)pyrimidin-4-yl)oxazolidin-2-one

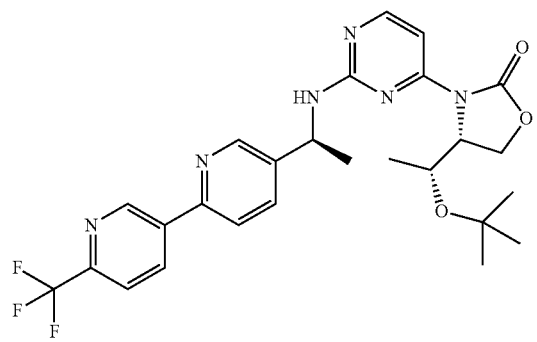 [SMILES: C[C@H](Nc1nccc(N2C(=O)OC[C@@H]2[C@@H](C)OC(C)(C)C)n1)c1ccc(-c2ccc(C(F)(F)F)nc2)nc1]

LCMS tR=1.51 min; MS m/z 531.1 (M+H).

Intermediate 385: (R)-4-((R)-1-(tert-butoxy)ethyl)-3-(2-(((S)-1-(6'-(trifluoromethyl)-[3,3'-bipyridin]-6-yl)ethyl)amino)pyrimidin-4-yl)oxazolidin-2-one

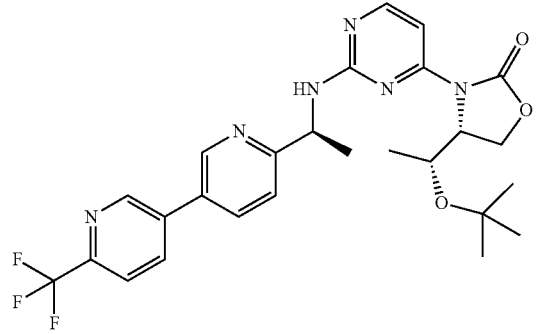 [SMILES: C[C@H](Nc1nccc(N2C(=O)OC[C@@H]2[C@@H](C)OC(C)(C)C)n1)c1ccc(-c2ccc(C(F)(F)F)nc2)cn1]

LCMS tR=1.51 min; MS m/z 531.3 (M+H).

Intermediate 386: (R)-4-((R)-1-(tert-butoxy)ethyl)-3-(2-(((S)-1-(6-(trifluoromethyl)-[2,3'-bipyridin]-6'-yl)ethyl)amino)pyrimidin-4-yl)oxazolidin-2-one

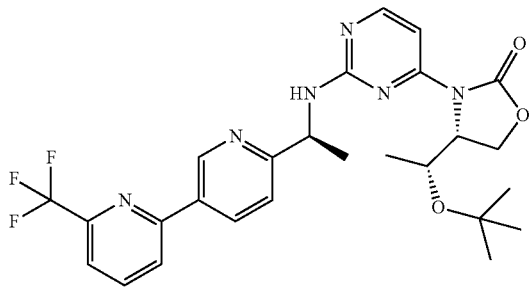 [SMILES: C[C@H](Nc1nccc(N2C(=O)OC[C@@H]2[C@@H](C)OC(C)(C)C)n1)c1ccc(-c2cccc(C(F)(F)F)n2)cn1]

LCMS tR=1.59 min; MS m/z 531.2 (M+H).

Intermediate 387: (R)-4-((R)-1-(tert-butoxy)ethyl)-3-(2-(((S)-1-(4-methyl-2'-(trifluoromethyl)-[3,4'-bipyridin]-6-yl)ethyl)amino)pyrimidin-4-yl)oxazolidin-2-one

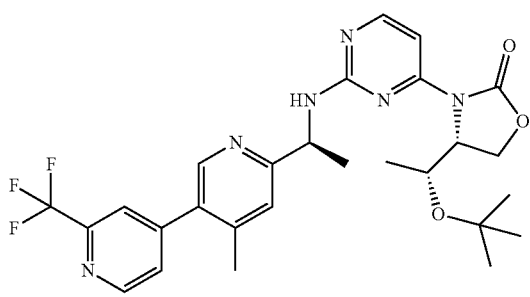 [SMILES: Cc1cc([C@H](C)Nc2nccc(N3C(=O)OC[C@@H]3[C@@H](C)OC(C)(C)C)n2)ncc1-c1ccnc(C(F)(F)F)c1]

LCMS tR=1.60 min; MS m/z 545.2 (M+H).

Intermediate 388: (R)-4-((R)-1-(tert-butoxy)ethyl)-3-(2-(((S)-1-(2-methyl-2'-(trifluoromethyl)-[3,4'-bipyridin]-6-yl)ethyl)amino)pyrimidin-4-yl)oxazolidin-2-one

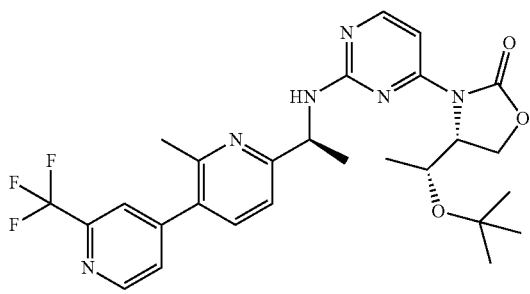 [SMILES: Cc1nc([C@H](C)Nc2nccc(N3C(=O)OC[C@@H]3[C@@H](C)OC(C)(C)C)n2)ccc1-c1ccnc(C(F)(F)F)c1]

LCMS tR=1.65 min; MS m/z 545.2 (M+H).

Intermediate 389: (R)-4-((R)-1-(tert-butoxy)ethyl)-3-(2-(((S)-1-(5-fluoro-2'-(trifluoromethyl)-[3,4'-bipyridin]-6-yl)ethyl)amino)pyrimidin-4-yl)oxazolidin-2-one

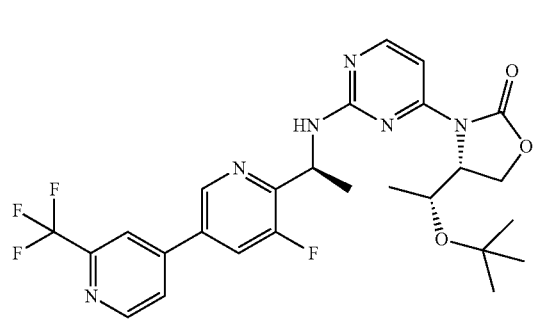 [SMILES: Cc1cc(-c2ccnc(C(F)(F)F)c2)cnc1[C@H](C)Nc1nccc(N2C(=O)OC[C@@H]2[C@@H](C)OC(C)(C)C)n1]

LCMS tR=1.65 min; MS m/z 549.2 (M+H).

Intermediate 390: (R)-4-((R)-1-(tert-butoxy)ethyl)-3-(2-(((S)-1-(5-methyl-2'-(trifluoromethyl)-[3,4'-bipyridin]-6-yl)ethyl)amino)pyrimidin-4-yl)oxazolidin-2-one

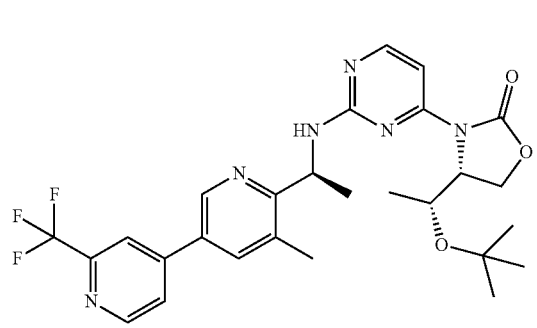

LCMS tR=1.65 min; MS m/z 545.6 (M+H).

Intermediate 391: (R)-4-((S)-1-tert-butoxyethyl)-3-(2-(((S)-1-(3-fluoro-4-((3,3,4-trimethylpiperazin-1-yl)methyl)phenyl)ethylamino)pyrimidin-4-yl)oxazolidin-2-one

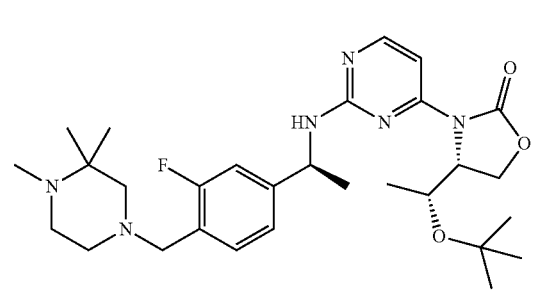 [SMILES: C[C@H](Nc1nccc(N2C(=O)OC[C@@H]2[C@@H](C)OC(C)(C)C)n1)c1ccc(CN2CCN(C)C(C)(C)C2)c(F)c1]

LCMS tR=1.63 min; MS m/z 543.5 (M+H).

Intermediate 392: (R)-4-((R)-1-(tert-butoxy)ethyl)-3-(2-(((S)-1-(5-(4-chlorophenyl)isoxazol-3-yl)ethyl)amino)pyrimidin-4-yl)oxazolidin-2-one

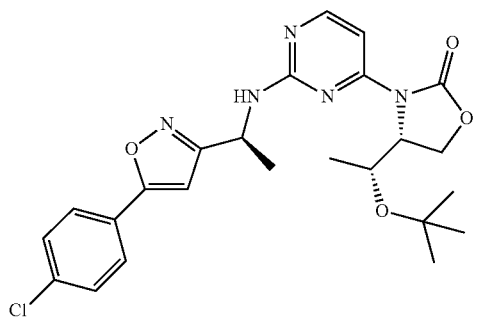 [SMILES: C[C@H](Nc1nccc(N2C(=O)OC[C@@H]2[C@@H](C)OC(C)(C)C)n1)c1cc(-c2ccc(Cl)cc2)on1]

LCMS tR=0.94 min; MS m/z 486.0 (M–H).

Intermediate 393: (R)-4-((R)-1-tert-butoxyethyl)-3-(2-(((S)-1-(4-((4,4-difluoropiperidin-1-yl)methyl)-3-fluorophenyl)ethylamino)pyrimidin-4-yl)oxazolidin-2-one

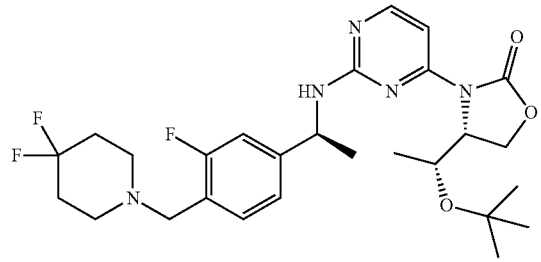 [SMILES: C[C@H](Nc1nccc(N2C(=O)OC[C@@H]2[C@@H](C)OC(C)(C)C)n1)c1ccc(CN2CCC(F)(F)CC2)c(F)c1]

LCMS tR=1.81 min; MS m/z 534.5 (M–H).

Intermediate 394: (R)-4-((R)-1-(tert-butoxy)ethyl)-3-(2-(((S)-1-(5-(3-(trifluoromethyl)phenyl)pyrazin-2-yl)ethyl)amino)pyrimidin-4-yl)oxazolidin-2-one

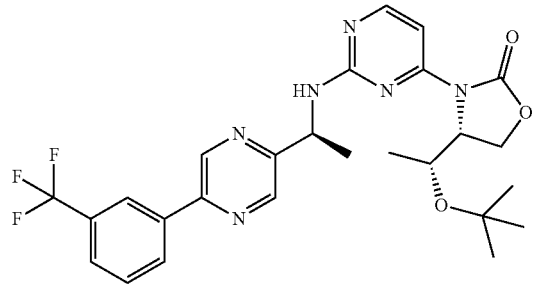 [SMILES: C[C@H](Nc1nccc(N2C(=O)OC[C@@H]2[C@@H](C)OC(C)(C)C)n1)c1cnc(-c2cccc(C(F)(F)F)c2)cn1]

LCMS tR=1.74 min; MS m/z 531.0 (M+H).

Intermediate 395: (R)-4-((R)-1-(tert-butoxy)ethyl)-3-(2-(((S)-1-(5-(4-fluoro-3-methylphenyl)pyrazin-2-yl)ethyl)amino)pyrimidin-4-yl)oxazolidin-2-one

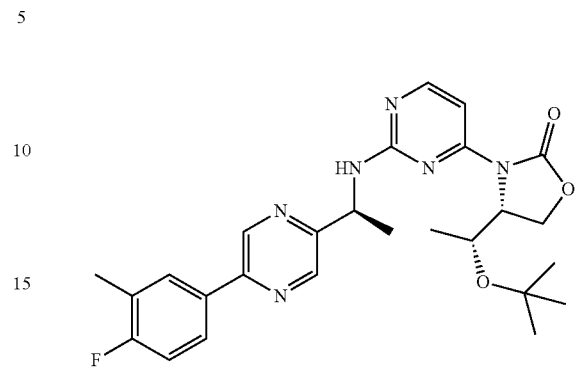

LCMS tR=1.71 min; MS m/z 495.0 (M+H).

Intermediate 396: (R)-4-((R)-1-(tert-butoxy)ethyl)-3-(2-(((S)-1-(4-(2,4-dichlorophenyl)thiazol-2-yl)ethyl)amino)pyrimidin-4-yl)oxazolidin-2-one

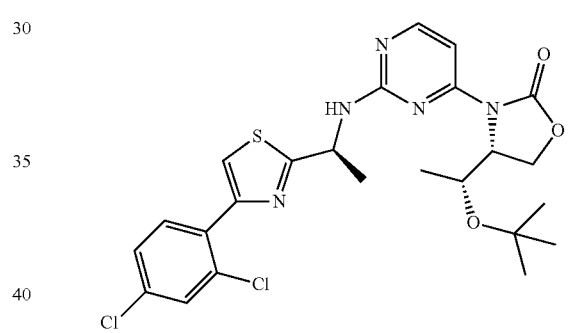

LCMS tR=1.84 min; MS m/z 536.0 (M+H).

Intermediate 397: (R)-3-(2-(((S)-1-(4-(4-bromophenyl)thiazol-2-yl)ethyl)amino)pyrimidin-4-yl)-4-((R)-1-(tert-butoxy)ethyl)oxazolidin-2-one

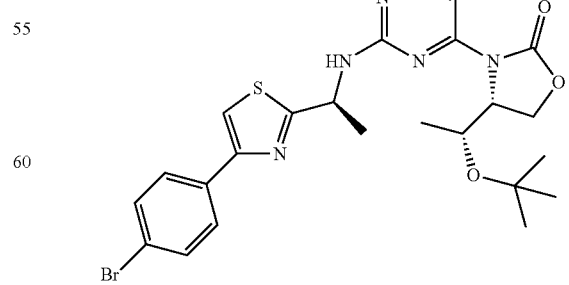

LCMS tR=1.77 min; MS m/z 548.0 (M+H).

Intermediate 398: 4-(2-(((S)-1-((4-((R)-4-((R)-1-(tert-butoxy)ethyl)-2-oxooxazolidin-3-yl)pyrimidin-2-yl)amino)ethyl)thiazol-4-yl)benzonitrile

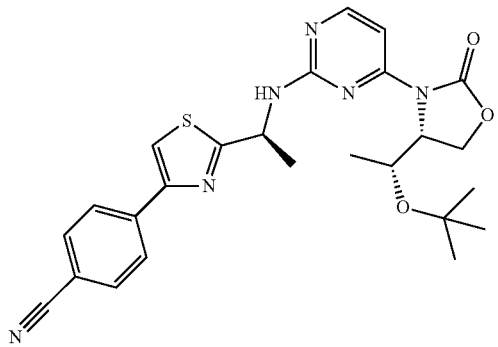 [SMILES: C[C@H](Nc1nccc(N2C(=O)OC[C@@H]2[C@@H](C)OC(C)(C)C)n1)c1nc(-c2ccc(C#N)cc2)cs1]

LCMS tR=1.55 min; MS m/z 493.1 (M+H).

Intermediate 399: (R)-3-(2-(((S)-1-(5-bromopyridin-2-yl)ethyl)amino)pyrimidin-4-yl)-4-((R)-1-(tert-butoxy)ethyl)oxazolidin-2-one

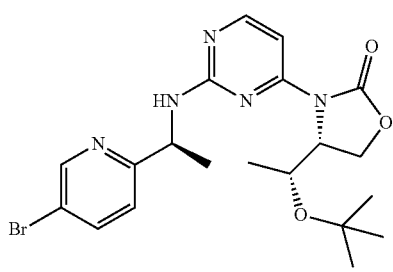 [SMILES: C[C@H](Nc1nccc(N2C(=O)OC[C@@H]2[C@@H](C)OC(C)(C)C)n1)c1ccc(Br)cn1]

$^1$H NMR (400 MHz, CDCl3) δ 8.61 (d, J=2.2 Hz, 1H), 8.15 (d, J=6.0 Hz, 1H), 7.78 (dd, J=8.3, 2.3 Hz, 1H), 7.50 (d, J=5.9 Hz, 1H), 7.21 (d, J=8.3 Hz, 1H), 5.22 (p, J=6.9 Hz, 1H), 4.72 (ddd, J=8.3, 4.7, 3.0 Hz, 1H), 4.62 (dd, J=9.3, 3.0 Hz, 1H), 4.41-4.31 (m, 2H), 1.56 (d, J=6.8 Hz, 3H), 1.21 (s, 9H), 1.00 (d, J=6.4 Hz, 3H). MS m/z 466.2 (M+H).

Intermediate 400: (4R)-4-((R)-1-(tert-butoxy)ethyl)-3-(5-fluoro-2-((1-(5-(3-(trifluoromethyl)phenyl)pyrimidin-2-yl)ethyl)amino)pyrimidin-4-yl)oxazolidin-2-one

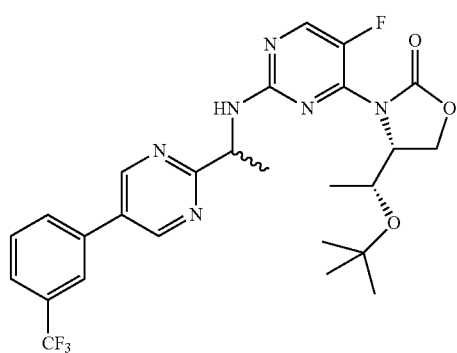 [SMILES: CC(Nc1ncc(F)c(N2C(=O)OC[C@@H]2[C@@H](C)OC(C)(C)C)n1)c1ncc(-c2cccc(C(F)(F)F)c2)cn1]

Anal. RP-HPLC tR=1.54, 1.56 min (Column=Acquity BEH C18 1.7 μm 2.1×50 mm. Column Temperature=50° C.

Eluents=A: Water (3.75 mM Ammonium formate, 2% ACN); B: ACN (3.75 mM Ammonium formate, 5% Water). Flow Rate=1 mL/min. Gradient=2% to 98% B in 1.70 min.; MS m/z 549.3 (M+H)+.

Intermediate 401: (4R)-4-((R)-1-(tert-butoxy)ethyl)-3-(2-((1-(5-(3,4-dichlorophenyl)pyrimidin-2-yl)ethyl)amino)-5-fluoropyrimidin-4-yl)oxazolidin-2-one

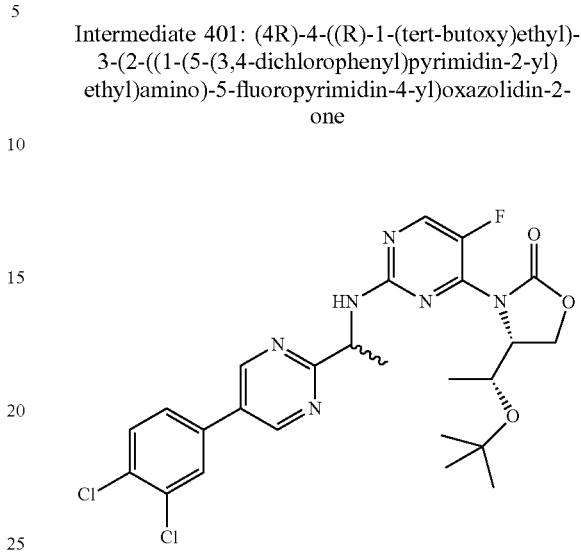

Anal. RP-HPLC tR=1.69 min; MS m/z 549.4 (M+H)+.

Intermediate 402: (R)-4-((R)-1-tert-butoxyethyl)-3-(2-(((S)-1-(3-(4-chlorophenyl)-1,2,4-oxadiazol-5-yl)ethylamino)-6-(difluoromethyl)pyrimidin-4-yl)oxazolidin-2-one

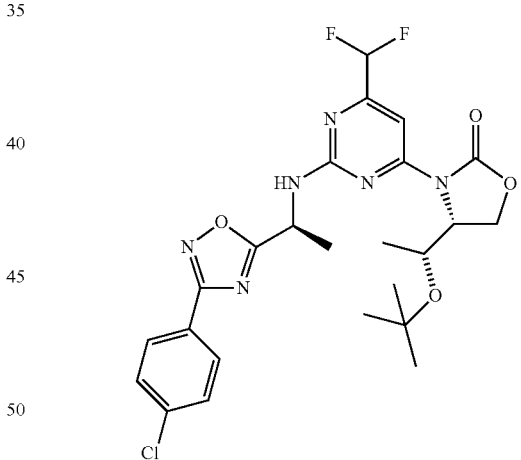

A solution of (R)-4-((R)-1-tert-butoxyethyl)-3-(6-(difluoromethyl)-2-(methylsulfonyl)pyrimidin-4-yl)oxazolidin-2-one (0.146 g, 0.371 mmol), (S)-1-(3-(4-chlorophenyl)-1,2,4-oxadiazol-5-yl)ethanamine (91 mg, 0.41 mmol, 1.1 equiv), and N-ethyl-N-isopropylpropan-2-amine (0.097 mL, 0.56 mmol, 1.5 equiv) in DMSO (2.0 mL) was heated at 85° C. for 18 h. The reaction was cooled to room temperature and diluted with DCM (20 mL) and water (20 mL). The layers were separated and the aqueous layer was extracted with DCM (20 mL). The combined organic layers were washed with saturated aqueous NaCl (10 mL), dried over Na$_2$SO$_4$, filtered and concentrated. Silica gel column chromatography (EtOAc/Heptane 20% to 60%) provided (R)-4-((R)-1-tert-butoxyethyl)-3-(2-(((S)-1-(3-(4-chlorophenyl)-

1,2,4-oxadiazol-5-yl)ethylamino)-6-(difluoromethyl) pyrimidin-4-yl)oxazolidin-2-one as a yellow oily solid in 37% yield. MS m/z 537.2 (M+H)⁺; Rt-1.22 min.

Intermediate 403: (R)-4-((R)-1-(tert-butoxy)ethyl)-3-(6-chloro-2-(((S)-1-(5-(4-chlorophenyl)isoxazol-3-yl)ethyl)amino)pyrimidin-4-yl)oxazolidin-2-one

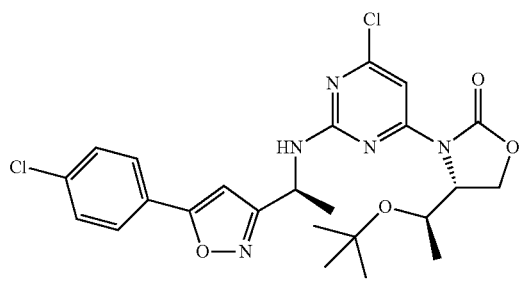 [SMILES: C[C@H](Nc1nc(Cl)cc(N2C(=O)OC[C@@H]2[C@@H](C)OC(C)(C)C)n1)c1cc(-c2ccc(Cl)cc2)on1]

A solution of (R)-4-((R)-1-tert-butoxyethyl)-3-(2,6-dichloropyrimidin-4-yl)oxazolidin-2-one (70 mg, 0.209 mmol), (S)-1-(5-(4-chlorophenyl)isoxazol-3-yl)ethanamine (60 mg, 0.23 mmol, 1.1 equiv), and N-ethyl-N-isopropylpropan-2-amine (0.091 mL, 0.52 mmol, 2.5 equiv) in DMSO (1.0 mL) was heated at 85-110° C. for 3-5 h. The reaction was cooled to room temperature and diluted with ethyl acetate (30 mL) and dilute aqueous sodium chloride (30 mL). The layers were separated and the organic layer was dried over Na₂SO₄, filtered and concentrated to give crude (R)-4-((R)-1-(tert-butoxy)ethyl)-3-(6-chloro-2-(((S)-1-(5-(4-chlorophenyl)isoxazol-3-yl)ethyl)amino)pyrimidin-4-yl)oxazolidin-2-one, which was used without further purification. MS m/z 520.2 (M+H)⁺; Rt-1.31 min.

The intermediates in Table 24a were prepared using a method similar to that described for the preparation of Intermediate 403.

TABLE 24a

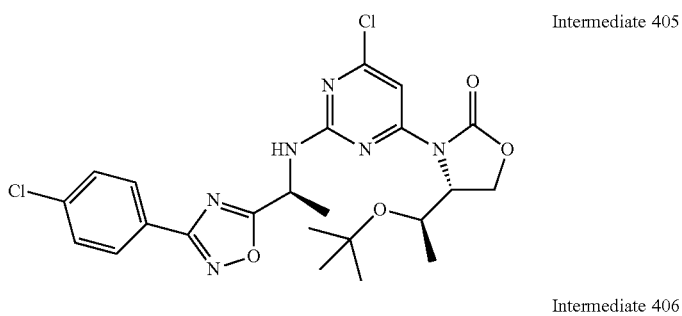

Intermediate 405

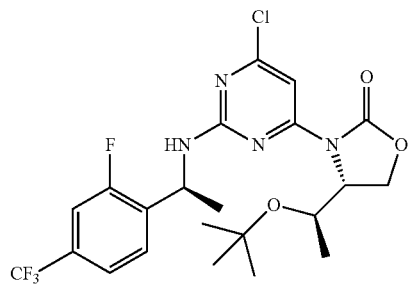 [SMILES: C[C@H](Nc1nc(Cl)cc(N2C(=O)OC[C@@H]2[C@@H](C)OC(C)(C)C)n1)c1ccc(C(F)(F)F)cc1F]

Intermediate 406

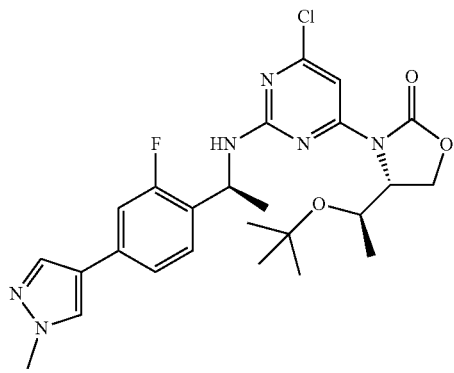 [SMILES: C[C@H](Nc1nc(Cl)cc(N2C(=O)OC[C@@H]2[C@@H](C)OC(C)(C)C)n1)c1ccc(-c2cnn(C)c2)cc1F]

Intermediate 407

TABLE 24a-continued
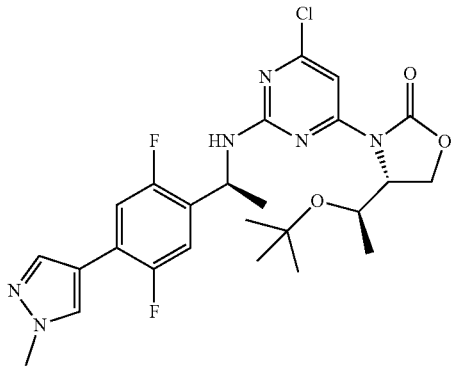 [SMILES: C[C@H](Nc1nc(Cl)cc(N2C(=O)OC[C@@H]2[C@@H](C)OC(C)(C)C)n1)c1cc(F)c(-c2cnn(C)c2)cc1F]
Intermediate 408
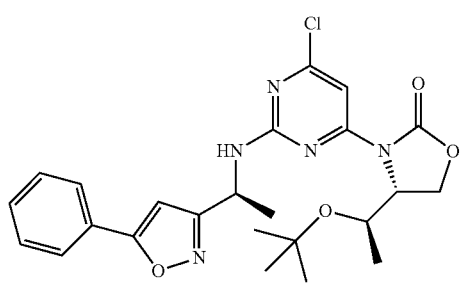 [SMILES: C[C@H](Nc1nc(Cl)cc(N2C(=O)OC[C@@H]2[C@@H](C)OC(C)(C)C)n1)c1cc(-c2ccccc2)on1]
Intermediate 409
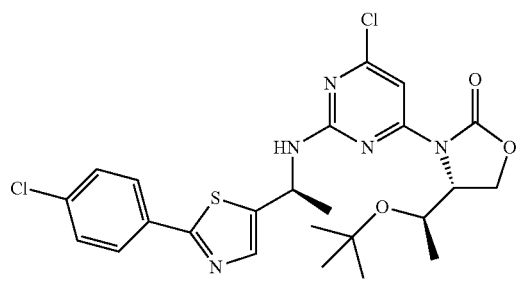 [SMILES: C[C@H](Nc1nc(Cl)cc(N2C(=O)OC[C@@H]2[C@@H](C)OC(C)(C)C)n1)c1cnc(-c2ccc(Cl)cc2)s1]
Intermediate 410
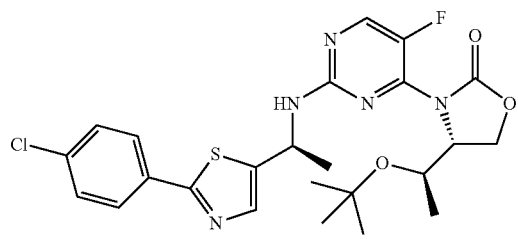 [SMILES: C[C@H](Nc1ncc(F)c(N2C(=O)OC[C@@H]2[C@@H](C)OC(C)(C)C)n1)c1cnc(-c2ccc(Cl)cc2)s1]
Intermediate 411
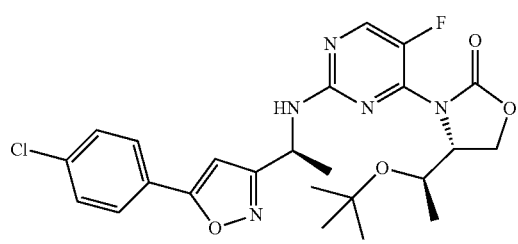 [SMILES: C[C@H](Nc1ncc(F)c(N2C(=O)OC[C@@H]2[C@@H](C)OC(C)(C)C)n1)c1cc(-c2ccc(Cl)cc2)on1]
Intermediate 412

TABLE 24a-continued
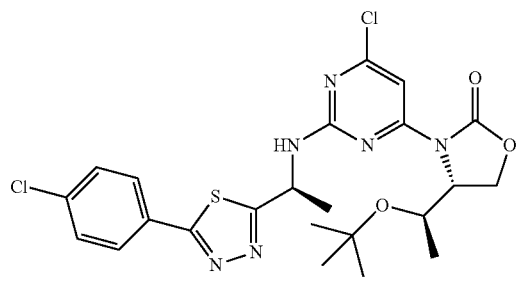 [SMILES: C[C@H](Nc1nc(Cl)cc(N2C(=O)OC[C@@H]2[C@@H](C)OC(C)(C)C)n1)c1nnc(-c2ccc(Cl)cc2)s1]
Intermediate 413
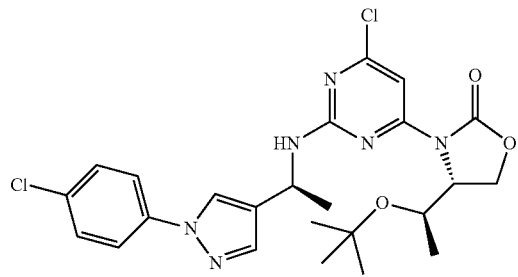 [SMILES: C[C@H](Nc1nc(Cl)cc(N2C(=O)OC[C@@H]2[C@@H](C)OC(C)(C)C)n1)c1cnn(-c2ccc(Cl)cc2)c1]
Intermediate 414
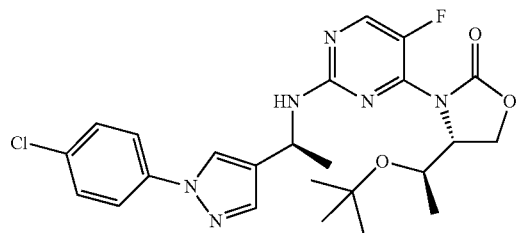 [SMILES: C[C@H](Nc1ncc(F)c(N2C(=O)OC[C@@H]2[C@@H](C)OC(C)(C)C)n1)c1cnn(-c2ccc(Cl)cc2)c1]
Intermediate 415
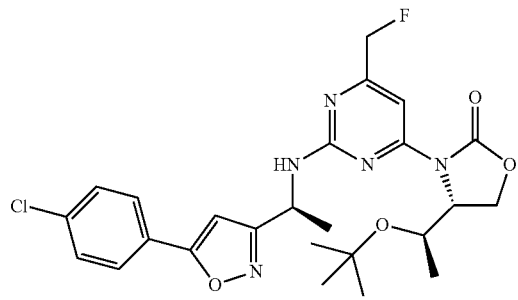 [SMILES: C[C@H](Nc1nc(CF)cc(N2C(=O)OC[C@@H]2[C@@H](C)OC(C)(C)C)n1)c1cc(-c2ccc(Cl)cc2)on1]
Intermediate 416
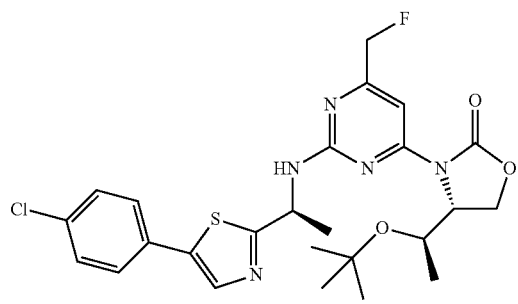 [SMILES: C[C@H](Nc1nc(CF)cc(N2C(=O)OC[C@@H]2[C@@H](C)OC(C)(C)C)n1)c1ncc(-c2ccc(Cl)cc2)s1]
Intermediate 417
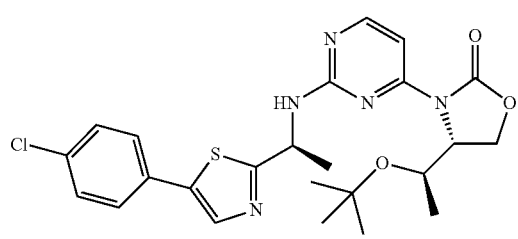 [SMILES: C[C@H](Nc1nccc(N2C(=O)OC[C@@H]2[C@@H](C)OC(C)(C)C)n1)c1ncc(-c2ccc(Cl)cc2)s1]
Intermediate 418

TABLE 24a-continued
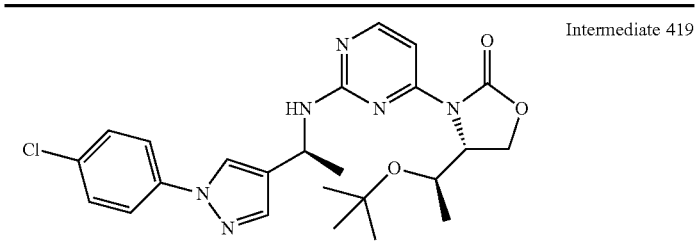
Intermediate 419
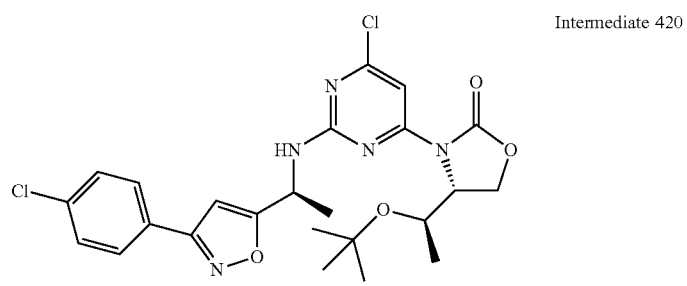
Intermediate 420
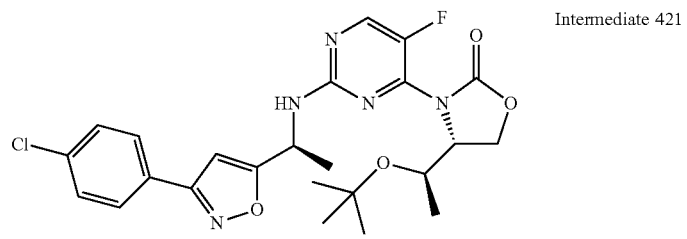
Intermediate 421
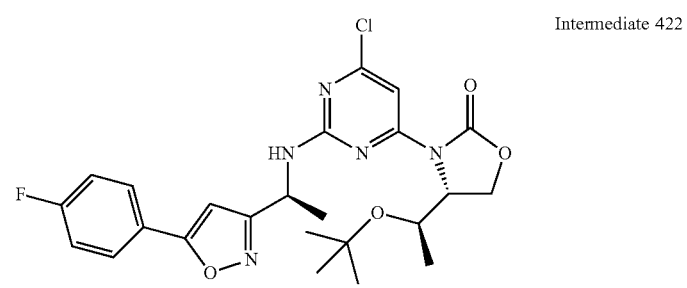
Intermediate 422
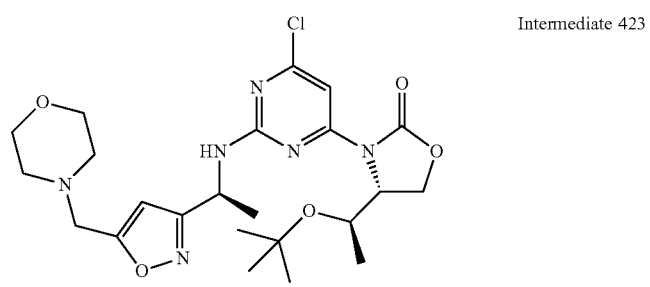
Intermediate 423
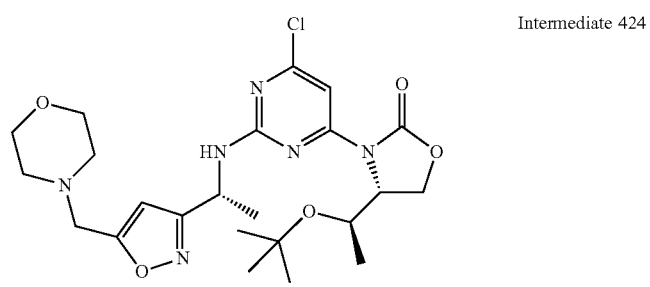
Intermediate 424

TABLE 24a-continued
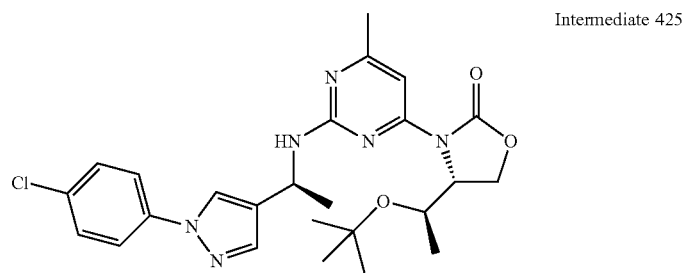
Intermediate 425
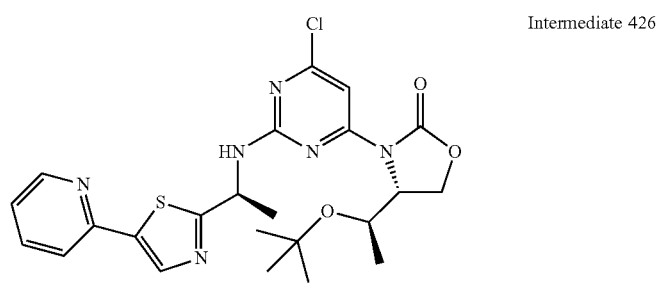
Intermediate 426
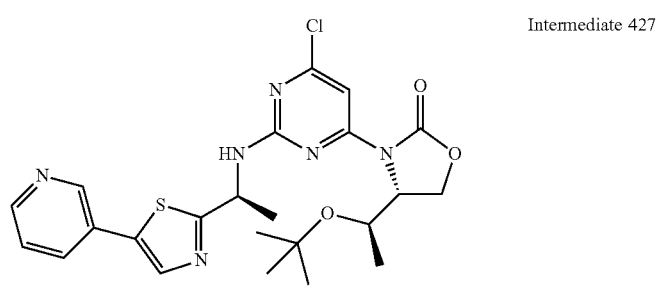
Intermediate 427
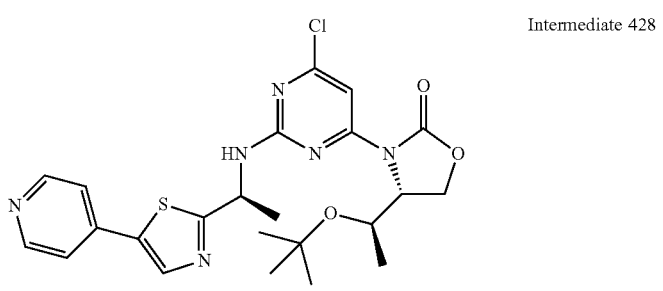
Intermediate 428
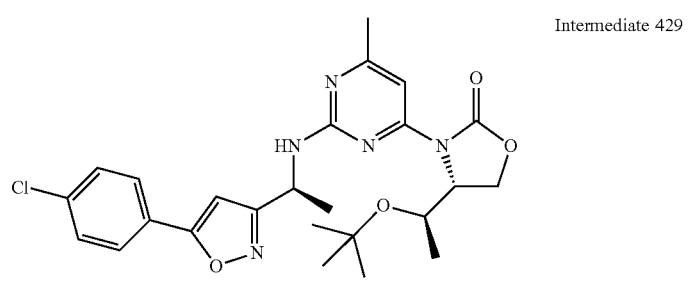
Intermediate 429

TABLE 24a-continued
| | |
|---|---|
| 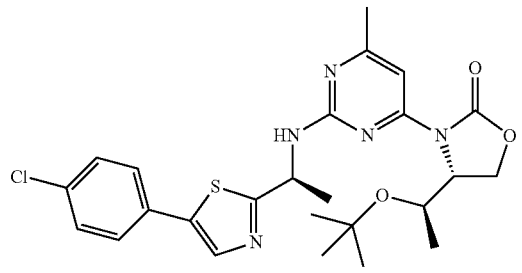 [SMILES: Cc1cc(N2C(=O)OC[C@@H]2[C@@H](C)OC(C)(C)C)nc(N[C@@H](C)c2ncc(-c3ccc(Cl)cc3)s2)n1] | Intermediate 430 |
| 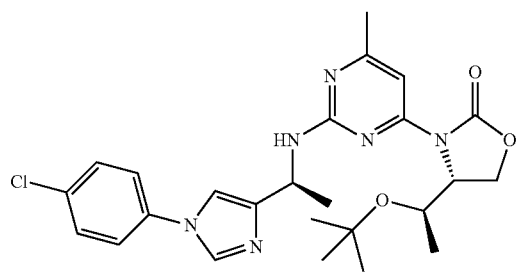 [SMILES: Cc1cc(N2C(=O)OC[C@@H]2[C@@H](C)OC(C)(C)C)nc(N[C@@H](C)c2cn(-c3ccc(Cl)cc3)cn2)n1] | Intermediate 431 |
| 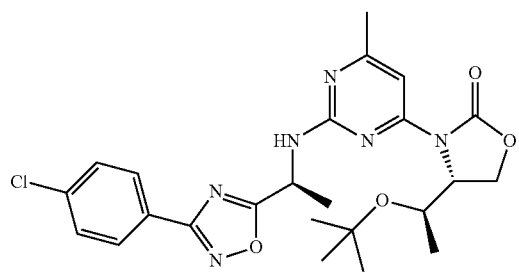 [SMILES: Cc1cc(N2C(=O)OC[C@@H]2[C@@H](C)OC(C)(C)C)nc(N[C@@H](C)c2nc(-c3ccc(Cl)cc3)no2)n1] | Intermediate 432 |
| 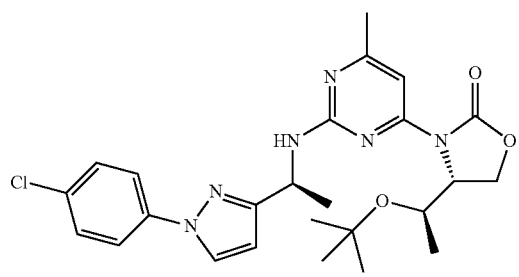 [SMILES: Cc1cc(N2C(=O)OC[C@@H]2[C@@H](C)OC(C)(C)C)nc(N[C@@H](C)c2ccn(-c3ccc(Cl)cc3)n2)n1] | Intermediate 433 |
| 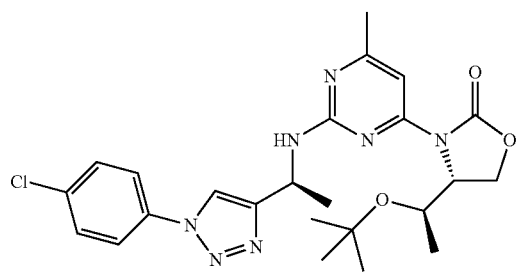 [SMILES: Cc1cc(N2C(=O)OC[C@@H]2[C@@H](C)OC(C)(C)C)nc(N[C@@H](C)c2cn(-c3ccc(Cl)cc3)nn2)n1] | Intermediate 434 |

TABLE 24a-continued
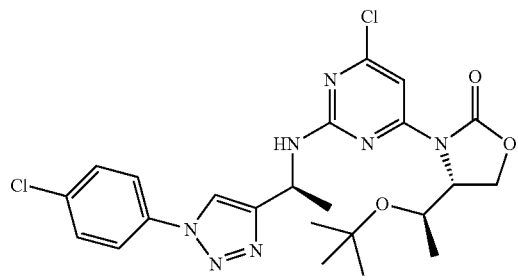 [SMILES: C[C@H](Nc1nc(Cl)cc(N2C(=O)OC[C@@H]2[C@@H](C)OC(C)(C)C)n1)c1cn(-c2ccc(Cl)cc2)nn1]
Intermediate 435
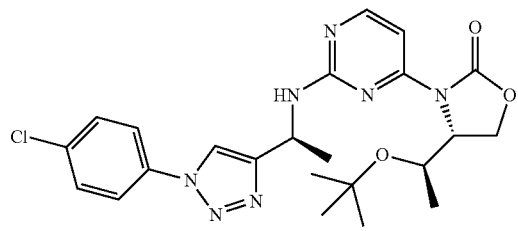 [SMILES: C[C@H](Nc1nccc(N2C(=O)OC[C@@H]2[C@@H](C)OC(C)(C)C)n1)c1cn(-c2ccc(Cl)cc2)nn1]
Intermediate 436
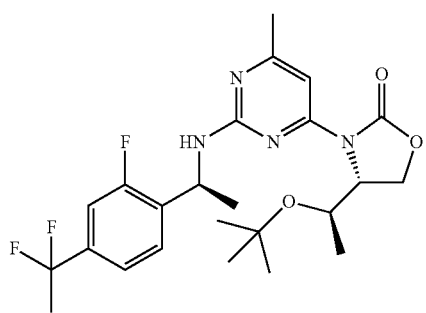 [SMILES: Cc1cc(N2C(=O)OC[C@@H]2[C@@H](C)OC(C)(C)C)nc(N[C@@H](C)c2ccc(C(C)(F)F)cc2F)n1]
Intermediate 437
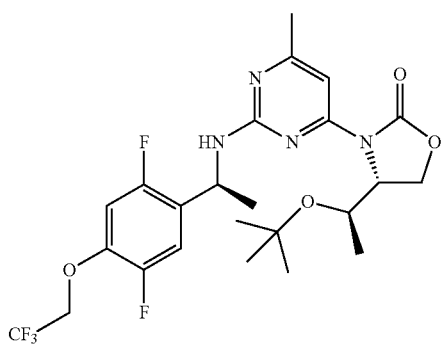 [SMILES: Cc1cc(N2C(=O)OC[C@@H]2[C@@H](C)OC(C)(C)C)nc(N[C@@H](C)c2cc(F)c(OCC(F)(F)F)cc2F)n1]
Intermediate 438
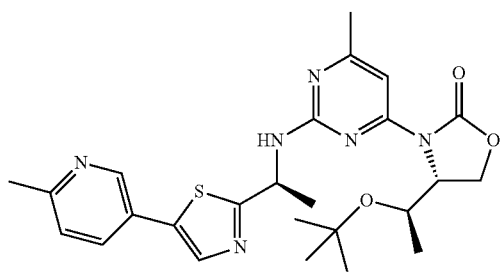 [SMILES: Cc1ccc(-c2cnc([C@H](C)Nc3nc(C)cc(N4C(=O)OC[C@@H]4[C@@H](C)OC(C)(C)C)n3)s2)cn1]
Intermediate 439

TABLE 24a-continued
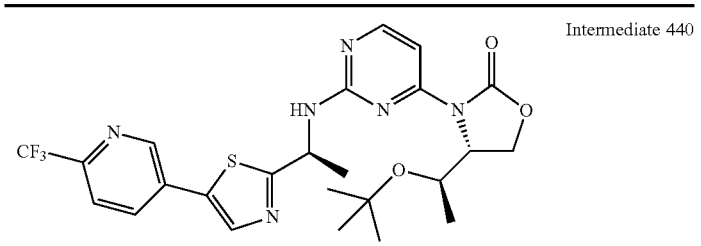
Intermediate 440
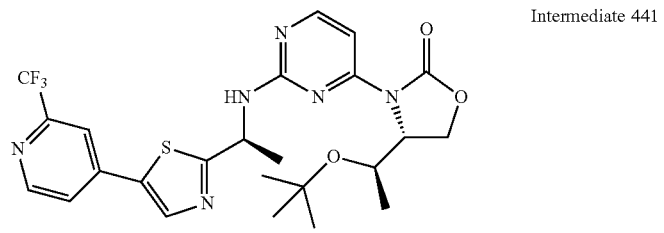
Intermediate 441
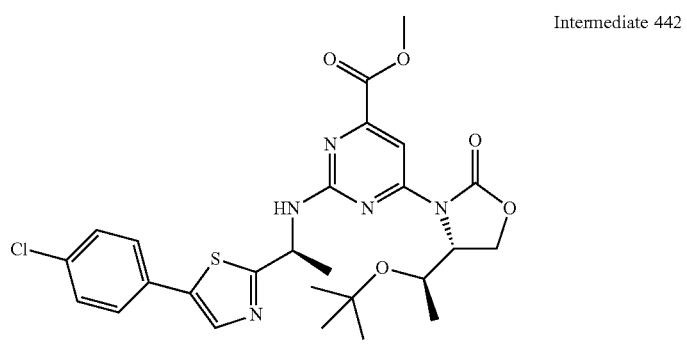
Intermediate 442
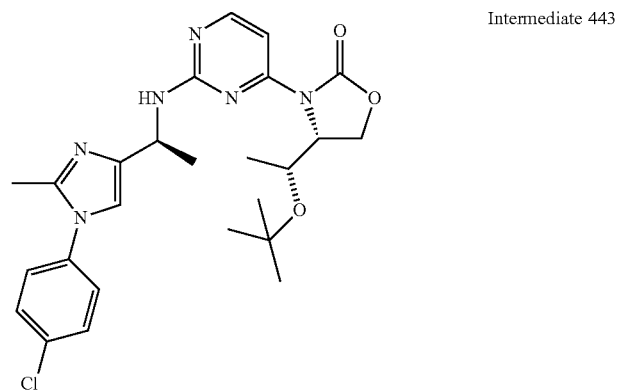
Intermediate 443
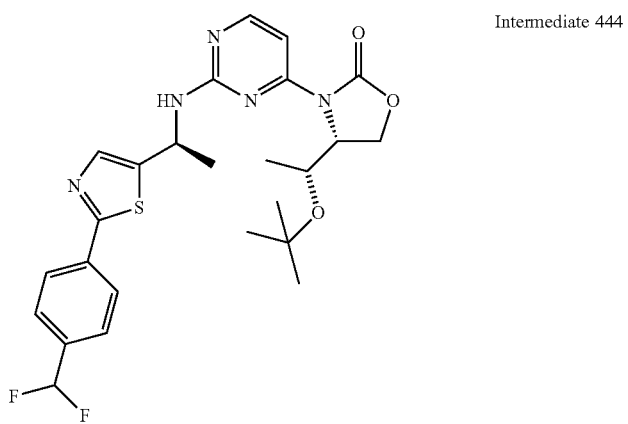
Intermediate 444

TABLE 24a-continued
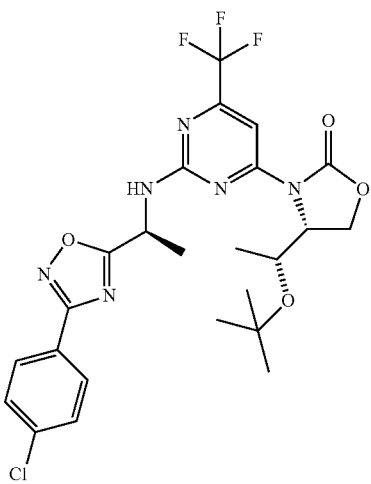 [SMILES: C[C@H](Nc1nc(N2C(=O)OC[C@@H]2[C@@H](C)OC(C)(C)C)cc(C(F)(F)F)n1)c1nc(-c2ccc(Cl)cc2)no1]
Intermediate 445
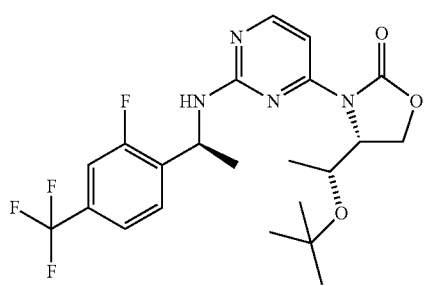 [SMILES: C[C@H](Nc1nccc(N2C(=O)OC[C@@H]2[C@@H](C)OC(C)(C)C)n1)c1ccc(C(F)(F)F)cc1F]
Intermediate 446
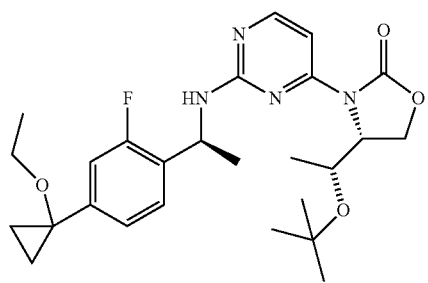 [SMILES: CCOC1(c2ccc([C@H](C)Nc3nccc(N4C(=O)OC[C@@H]4[C@@H](C)OC(C)(C)C)n3)c(F)c2)CC1]
Intermediate 447
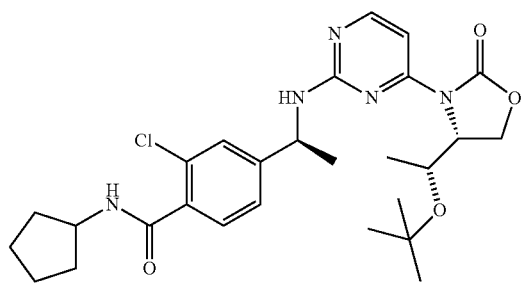 [SMILES: C[C@H](Nc1nccc(N2C(=O)OC[C@@H]2[C@@H](C)OC(C)(C)C)n1)c1ccc(C(=O)NC2CCCC2)c(Cl)c1]
Intermediate 448
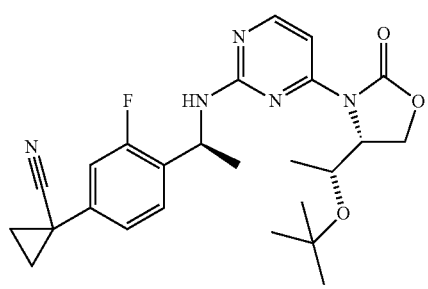 [SMILES: C[C@H](Nc1nccc(N2C(=O)OC[C@@H]2[C@@H](C)OC(C)(C)C)n1)c1ccc(C2(C#N)CC2)cc1F]
Intermediate 449

TABLE 24a-continued
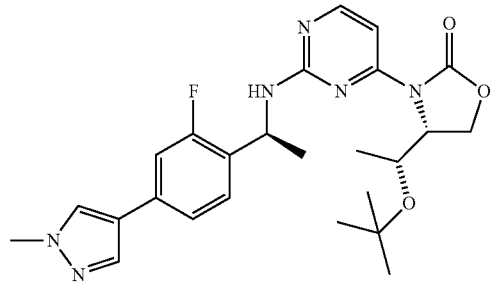 [SMILES: C[C@H](Nc1nccc(N2C(=O)OC[C@@H]2[C@@H](C)OC(C)(C)C)n1)c1ccc(-c2cnn(C)c2)cc1F]
Intermediate 450
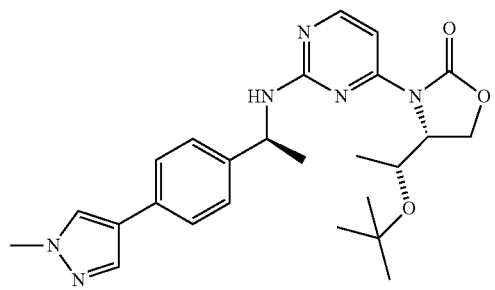 [SMILES: C[C@H](Nc1nccc(N2C(=O)OC[C@@H]2[C@@H](C)OC(C)(C)C)n1)c1ccc(-c2cnn(C)c2)cc1]
Intermediate 451
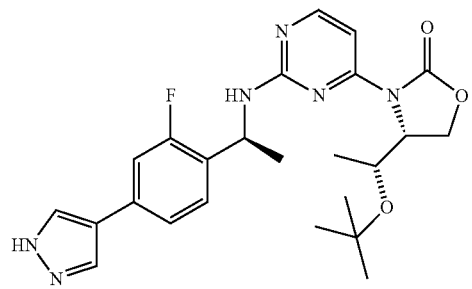 [SMILES: C[C@H](Nc1nccc(N2C(=O)OC[C@@H]2[C@@H](C)OC(C)(C)C)n1)c1ccc(-c2cn[nH]c2)cc1F]
Intermediate 452
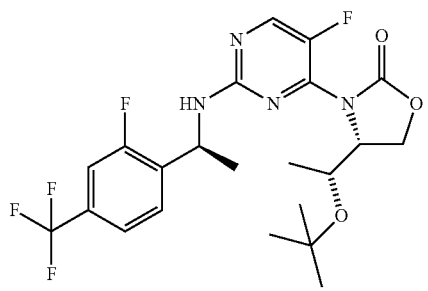 [SMILES: C[C@H](Nc1ncc(F)c(N2C(=O)OC[C@@H]2[C@@H](C)OC(C)(C)C)n1)c1ccc(C(F)(F)F)cc1F]
Intermediate 453
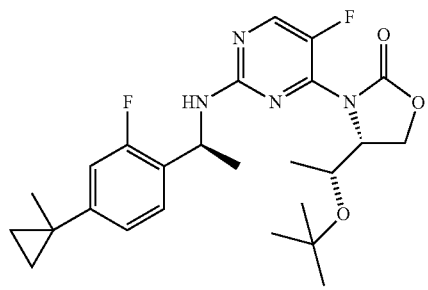 [SMILES: C[C@H](Nc1ncc(F)c(N2C(=O)OC[C@@H]2[C@@H](C)OC(C)(C)C)n1)c1ccc(C2(C)CC2)cc1F]
Intermediate 454

TABLE 24a-continued
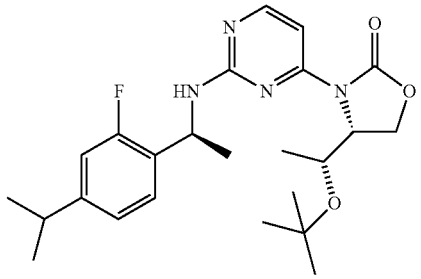 [SMILES: CC(C)c1ccc([C@H](C)Nc2nccc(N3C(=O)OC[C@@H]3[C@@H](C)OC(C)(C)C)n2)c(F)c1]
Intermediate 455
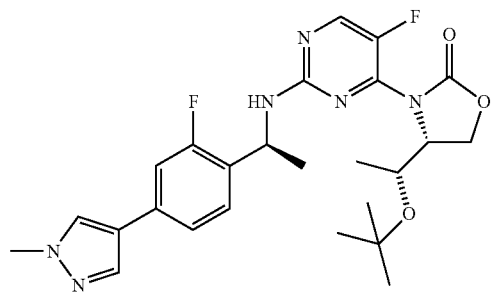 [SMILES: C[C@H](Nc1ncc(F)c(N2C(=O)OC[C@@H]2[C@@H](C)OC(C)(C)C)n1)c1ccc(-c2cnn(C)c2)cc1F]
Intermediate 456
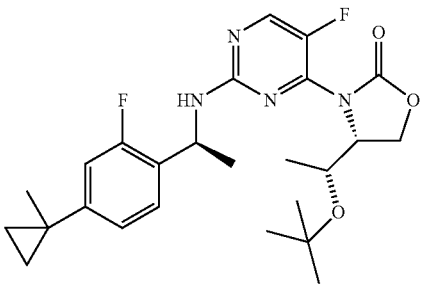 [SMILES: C[C@H](Nc1ncc(F)c(N2C(=O)OC[C@@H]2[C@@H](C)OC(C)(C)C)n1)c1ccc(C2(C)CC2)cc1F]
Intermediate 457
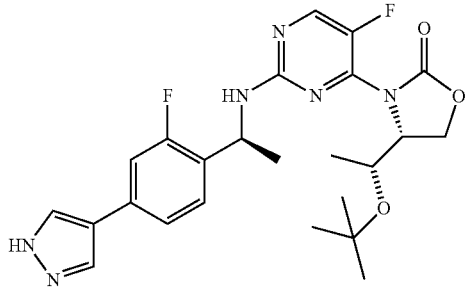 [SMILES: C[C@H](Nc1ncc(F)c(N2C(=O)OC[C@@H]2[C@@H](C)OC(C)(C)C)n1)c1ccc(-c2cn[nH]c2)cc1F]
Intermediate 458
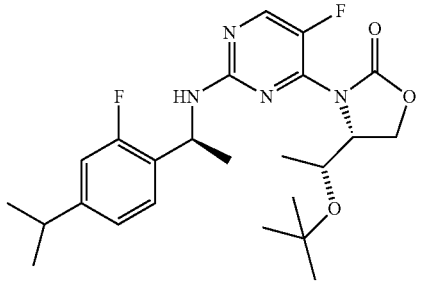 [SMILES: CC(C)c1ccc([C@H](C)Nc2ncc(F)c(N3C(=O)OC[C@@H]3[C@@H](C)OC(C)(C)C)n2)c(F)c1]
Intermediate 459

TABLE 24a-continued
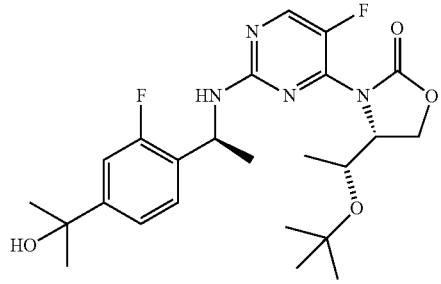 [SMILES: C[C@H](Nc1ncc(F)c(N2C(=O)OC[C@@H]2[C@@H](C)OC(C)(C)C)n1)c1ccc(C(C)(C)O)cc1F]
Intermediate 460
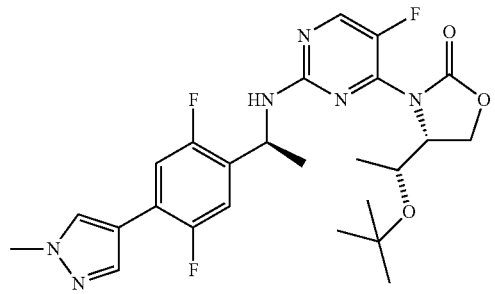 [SMILES: C[C@H](Nc1ncc(F)c(N2C(=O)OC[C@@H]2[C@@H](C)OC(C)(C)C)n1)c1cc(F)c(-c2cnn(C)c2)cc1F]
Intermediate 461
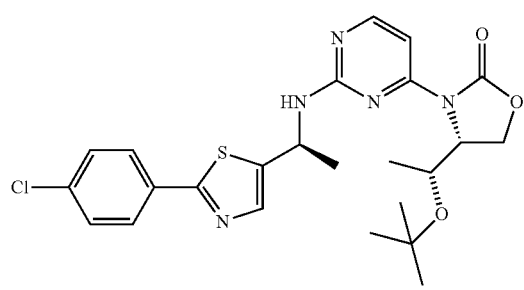 [SMILES: C[C@H](Nc1nccc(N2C(=O)OC[C@@H]2[C@@H](C)OC(C)(C)C)n1)c1cnc(-c2ccc(Cl)cc2)s1]
Intermediate 462
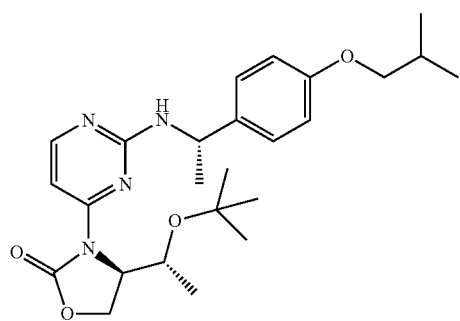 [SMILES: CC(C)COc1ccc([C@H](C)Nc2nccc(N3C(=O)OC[C@@H]3[C@@H](C)OC(C)(C)C)n2)cc1]
Intermediate 463
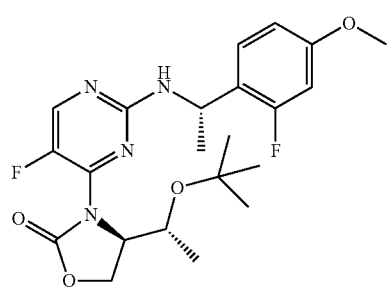 [SMILES: COc1ccc([C@H](C)Nc2ncc(F)c(N3C(=O)OC[C@@H]3[C@@H](C)OC(C)(C)C)n2)c(F)c1]
Intermediate 464

TABLE 24a-continued
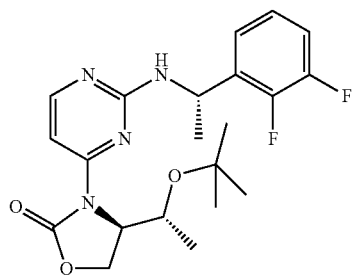 [SMILES: C[C@H](Nc1nccc(N2C(=O)OC[C@@H]2[C@@H](C)OC(C)(C)C)n1)c1cccc(F)c1F]
Intermediate 465
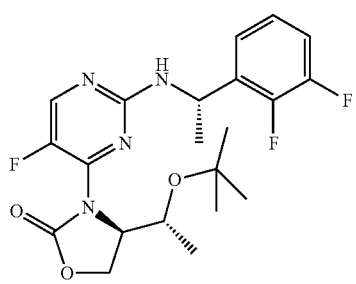 [SMILES: C[C@H](Nc1ncc(F)c(N2C(=O)OC[C@@H]2[C@@H](C)OC(C)(C)C)n1)c1cccc(F)c1F]
Intermediate 466
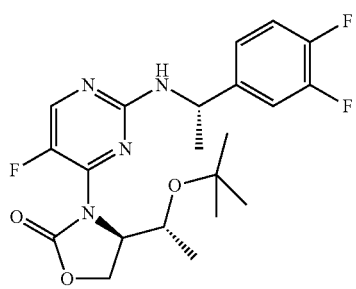 [SMILES: C[C@H](Nc1ncc(F)c(N2C(=O)OC[C@@H]2[C@@H](C)OC(C)(C)C)n1)c1ccc(F)c(F)c1]
Intermediate 467
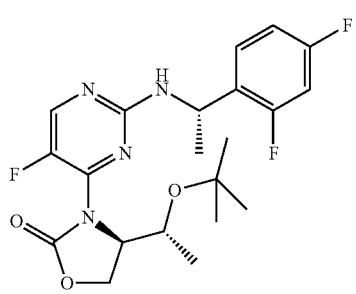 [SMILES: C[C@H](Nc1ncc(F)c(N2C(=O)OC[C@@H]2[C@@H](C)OC(C)(C)C)n1)c1ccc(F)cc1F]
Intermediate 468
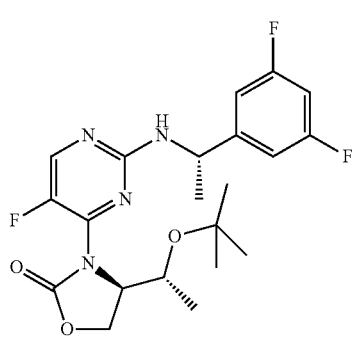 [SMILES: C[C@H](Nc1ncc(F)c(N2C(=O)OC[C@@H]2[C@@H](C)OC(C)(C)C)n1)c1cc(F)cc(F)c1]
Intermediate 469

TABLE 24a-continued

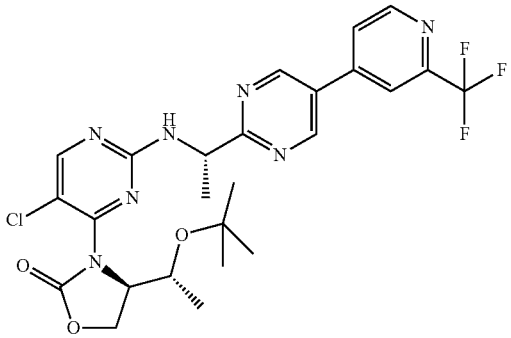 [SMILES: C[C@H](Nc1ncc(Cl)c(N2C(=O)OC[C@@H]2[C@@H](C)OC(C)(C)C)n1)c1ncc(-c2ccnc(C(F)(F)F)c2)cn1]

Intermediate 470

TABLE 24b

Chemical name and analytical data for each intermediate listed in Table 24a.

| Intermediate: Name | Analytical data |
|---|---|
| 405: (R)-4-((R)-1-tert-butoxyethyl)-3-(6-chloro-2-((S)-1-(3-(4-chlorophenyl)-1,2,4-oxadiazol-5-yl)ethylamino)pyrimidin-4-yl)oxazolidin-2-one | MS m/z 521.1 (M + H)+; Rt-1.29 min |
| 406: (R)-4-((R)-1-tert-butoxyethyl)-3-(6-chloro-2-((S)-1-(2-fluoro-4-(trifluoromethyl)phenyl)ethylamino)pyrimidin-4-yl)oxazolidin-2-one | MS m/z 505.3 (M + H)+; Rt-1.29 min |
| 407: (R)-4-((R)-1-tert-butoxyethyl)-3-(6-chloro-2-((S)-1-(2-fluoro-4-(1-methyl-1H-pyrazol-4-yl)phenyl)ethylamino)pyrimidin-4-yl)oxazolidin-2-one | MS m/z 517.2 (M + H)+; Rt-1.13 min |
| 408: (R)-4-((R)-1-(tert-butoxy)ethyl)-3-(6-chloro-2-(((S)-1-(2,5-difluoro-4-(1-methyl-1H-pyrazol-4-yl)phenyl)ethyl)amino)pyrimidin-4-yl)oxazolidin-2-one | MS m/z 535.2 (M + H)+; Rt-1.14 min |
| 409: (R)-4-((R)-1-(tert-butoxy)ethyl)-3-(6-chloro-2-(((S)-1-(5-phenylisoxazol-3-yl)ethyl)amino)pyrimidin-4-yl)oxazolidin-2-one | MS m/z 486.3 (M + H)+; Rt-1.25 min |
| 410: (R)-4-((R)-1-(tert-butoxy)ethyl)-3-(6-chloro-2-(((S)-1-(2-(4-chlorophenyl)thiazol-5-yl)ethyl)amino)pyrimidin-4-yl)oxazolidin-2-one | MS m/z 537.2 (M + H)+; Rt-1.33 min |
| 411: (R)-4-((R)-1-(tert-butoxy)ethyl)-3-(2-(((S)-1-(2-(4-chlorophenyl)thiazol-5-yl)ethyl)amino)-5-fluoropyrimidin-4-yl)oxazolidin-2-one | MS m/z 520.2 (M + H)+; Rt-1.16 min |
| 412: (R)-4-((R)-1-(tert-butoxy)ethyl)-3-(2-(((S)-1-(5-(4-chlorophenyl)isoxazol-3-yl)ethyl)amino)-5-fluoropyrimidin-4-yl)oxazolidin-2-one | MS m/z 504.2 (M + H)+; Rt-1.16 min |
| 413: (R)-4-((R)-1-(tert-butoxy)ethyl)-3-(6-chloro-2-(((S)-1-(5-(4-chlorophenyl)-1,3,4-thiadiazol-2-yl)ethyl)amino)pyrimidin-4-yl)oxazolidin-2-one | MS m/z 537.2 (M + H)+; Rt-1.28 min |
| 414: (R)-4-((R)-1-(tert-butoxy)ethyl)-3-(6-chloro-2-(((S)-1-(1-(4-chlorophenyl)-1H-pyrazol-4-yl)ethyl)amino)pyrimidin-4-yl)oxazolidin-2-one | MS m/z 519.3 (M + H)+; Rt-1.30 min |
| 415: (R)-4-((R)-1-(tert-butoxy)ethyl)-3-(2-(((S)-1-(1-(4-chlorophenyl)-1H-pyrazol-4-yl)ethyl)amino)-5-fluoropyrimidin-4-yl)oxazolidin-2-one | MS m/z 503.4 (M + H)+; Rt-1.11 min |
| 416: (R)-4-((R)-1-(tert-butoxy)ethyl)-3-(2-(((S)-1-(5-(4-chlorophenyl)isoxazol-3-yl)ethyl)amino)-6-(fluoromethyl)pyrimidin-4-yl)oxazolidin-2-one | MS m/z 518.2 (M + H)+; Rt-1.18 min |
| 417: (R)-4-((R)-1-(tert-butoxy)ethyl)-3-(2-(((S)-1-(2-(4-chlorophenyl)thiazol-5-yl)ethyl)amino)-6-(fluoromethyl)pyrimidin-4-yl)oxazolidin-2-one | MS m/z 534.2 (M + H)+; Rt-1.21 min |
| 418: (R)-4-((R)-1-(tert-butoxy)ethyl)-3-(2-(((S)-1-(2-(4-chlorophenyl)thiazol-5-yl)ethyl)amino)pyrimidin-4-yl)oxazolidin-2-one | MS m/z 502.2 (M + H)+; Rt-0.99 min |
| 419: (R)-4-((R)-1-(tert-butoxy)ethyl)-3-(2-(((S)-1-(1-(4-chlorophenyl)-1H-pyrazol-4-yl)ethyl)amino)pyrimidin-4-yl)oxazolidin-2-one | MS m/z 485.4 (M + H)+; Rt-0.93 min |
| 420: (R)-4-((R)-1-(tert-butoxy)ethyl)-3-(6-chloro-2-(((S)-1-(3-(4-chlorophenyl)isoxazol-5-yl)ethyl)amino)pyrimidin-4-yl)oxazolidin-2-one | MS m/z 520.2 (M + H)+; Rt-1.30 min |
| 421: (R)-4-((R)-1-(tert-butoxy)ethyl)-3-(2-(((S)-1-(3-(4-chlorophenyl)isoxazol-5-yl)ethyl)amino)-5-fluoropyrimidin-4-yl)oxazolidin-2-one | MS m/z 504.3 (M + H)+; Rt-1.13 min |

TABLE 24b-continued

Chemical name and analytical data for each intermediate listed in Table 24a.

| Intermediate: Name | Analytical data |
|---|---|
| 422: (R)-4-((R)-1-(tert-butoxy)ethyl)-3-(6-chloro-2-(((S)-1-(5-(4-fluorophenyl)isoxazol-3-yl)ethyl)amino)pyrimidin-4-yl)oxazolidin-2-one | MS m/z 504.3 (M + H)$^+$; Rt-1.22 min |
| 423: (R)-4-((R)-1-(tert-butoxy)ethyl)-3-(6-chloro-2-(((S)-1-(5-(morpholinomethyl)isoxazol-3-yl)ethyl)amino)pyrimidin-4-yl)oxazolidin-2-one | MS m/z 509.4 (M + H)$^+$; Rt-0.80 min |
| 424: (R)-4-((R)-1-(tert-butoxy)ethyl)-3-(6-chloro-2-(((R)-1-(5-(morpholinomethyl)isoxazol-3-yl)ethyl)amino)pyrimidin-4-yl)oxazolidin-2-one | MS m/z 509.4 (M + H)$^+$; Rt-0.83 min |
| 425: (R)-4-((R)-1-(tert-butoxy)ethyl)-3-(2-(((S)-1-(1-(4-chlorophenyl)-1H-pyrazol-4-yl)ethyl)amino)-6-methylpyrimidin-4-yl)oxazolidin-2-one | MS m/z 499.3 (M + H)$^+$; Rt-0.98 min |
| 426: (R)-4-((R)-1-(tert-butoxy)ethyl)-3-(6-chloro-2-(((S)-1-(2-(pyridin-2-yl)thiazol-5-yl)ethyl)amino)pyrimidin-4-yl)oxazolidin-2-one | MS m/z 503.2 (M + H)$^+$; Rt-1.19 min |
| 427: (R)-4-((R)-1-(tert-butoxy)ethyl)-3-(6-chloro-2-(((S)-1-(2-(pyridin-3-yl)thiazol-5-yl)ethyl)amino)pyrimidin-4-yl)oxazolidin-2-one | MS m/z 503.3 (M + H)$^+$; Rt-0.92 min |
| 428: (R)-4-((R)-1-(tert-butoxy)ethyl)-3-(6-chloro-2-(((S)-1-(2-(pyridin-4-yl)thiazol-5-yl)ethyl)amino)pyrimidin-4-yl)oxazolidin-2-one | MS m/z 503.3 (M + H)$^+$; Rt-0.89 min |
| 429: (R)-4-((R)-1-(tert-butoxy)ethyl)-3-(2-(((S)-1-(5-(4-chlorophenyl)isoxazol-3-yl)ethyl)amino)-6-methylpyrimidin-4-yl)oxazolidin-2-one | MS m/z 500.4 (M + H)$^+$; Rt-1.02 min |
| 430: (R)-4-((R)-1-(tert-butoxy)ethyl)-3-(2-(((S)-1-(2-(4-chlorophenyl)thiazol-5-yl)ethyl)amino)-6-methylpyrimidin-4-yl)oxazolidin-2-one | MS m/z 516.3 (M + H)$^+$; Rt-1.04 min |
| 431: (R)-4-((R)-1-(tert-butoxy)ethyl)-3-(2-(((S)-1-(1-(4-chlorophenyl)-1H-imidazol-4-yl)ethyl)amino)-6-methylpyrimidin-4-yl)oxazolidin-2-one | MS m/z 499.3 (M + H)$^+$; Rt-0.76 min |
| 432: (R)-4-((R)-1-(tert-butoxy)ethyl)-3-(2-(((S)-1-(3-(4-chlorophenyl)-1,2,4-oxadiazol-5-yl)ethyl)amino)-6-methylpyrimidin-4-yl)oxazolidin-2-one | MS m/z 501.3 (M + H)$^+$; Rt-1.04 min |
| 433: (R)-4-((R)-1-(tert-butoxy)ethyl)-3-(2-(((S)-1-(1-(4-chlorophenyl)-1H-pyrazol-3-yl)ethyl)amino)-6-methylpyrimidin-4-yl)oxazolidin-2-one | MS m/z 499.3 (M + H)$^+$; Rt-1.02 min |
| 434: (R)-4-((R)-1-(tert-butoxy)ethyl)-3-(2-(((S)-1-(1-(4-chlorophenyl)-1H-1,2,3-triazol-4-yl)ethyl)amino)-6-methylpyrimidin-4-yl)oxazolidin-2-one | MS m/z 500.2 (M + H)$^+$; Rt-0.88 min |
| 435: (R)-4-((R)-1-(tert-butoxy)ethyl)-3-(6-chloro-2-(((S)-1-(1-(4-chlorophenyl)-1H-1,2,3-triazol-4-yl)ethyl)amino)pyrimidin-4-yl)oxazolidin-2-one | MS m/z 520.2 (M + H)$^+$; Rt-1.14 min |
| 436: (R)-4-((R)-1-(tert-butoxy)ethyl)-3-(2-(((S)-1-(1-(4-chlorophenyl)-1H-1,2,3-triazol-4-yl)ethyl)amino)pyrimidin-4-yl)oxazolidin-2-one | MS m/z 486.3 (M + H)$^+$; Rt-0.87 min |
| 437: (R)-4-((R)-1-(tert-butoxy)ethyl)-3-(2-(((S)-1-(4-(1,1-difluoroethyl)-2-fluorophenyl)ethyl)amino)-6-methylpyrimidin-4-yl)oxazolidin-2-one | MS m/z 481.4 (M + H)$^+$; Rt-0.94 min |
| 438: (R)-4-((R)-1-(tert-butoxy)ethyl)-3-(2-(((S)-1-(2,5-difluoro-4-(2,2,2-trifluoroethoxy)phenyl)ethyl)amino)-6-methylpyrimidin-4-yl)oxazolidin-2-one | MS m/z 533.4 (M + H)$^+$; Rt-0.96 min |
| 439: (R)-4-((R)-1-(tert-butoxy)ethyl)-3-(6-methyl-2-(((S)-1-(2-(6-methylpyridin-3-yl)thiazol-5-yl)ethyl)amino)pyrimidin-4-yl)oxazolidin-2-one | MS m/z 497.3 (M + H)$^+$; Rt-0.63 min |
| 440: (R)-4-((R)-1-(tert-butoxy)ethyl)-3-(2-(((S)-1-(2-(6-(trifluoromethyl)pyridin-3-yl)thiazol-5-yl)ethyl)amino)pyrimidin-4-yl)oxazolidin-2-one | MS m/z 537.3 (M + H)$^+$; Rt-0.95 min |
| 441: (R)-4-((R)-1-(tert-butoxy)ethyl)-3-(2-(((S)-1-(2-(2-(trifluoromethyl)pyridin-4-yl)thiazol-5-yl)ethyl)amino)pyrimidin-4-yl)oxazolidin-2-one | MS m/z 537.3 (M + H)$^+$; Rt-0.80 min |
| 442: methyl 6-((R)-4((R)-1-(tert-butoxy)ethyl)-2-oxooxazolidin-3-yl)-2-(((S)-1-(2-(4-chlorophenyl)thiazol-5-yl)ethyl)amino)pyrimidine-4-carboxylate | MS m/z 560.3 (M + H)$^+$; Rt-1.20 min |
| 443: (R)-4-((R)-1-(tert-butoxy)ethyl)-3-(2-(((S)-1-(1-(4-chlorophenyl)-2-methyl-1H-imidazol-4-yl)ethyl)amino)pyrimidin-4-yl)oxazolidin-2-one | MS m/z 499.2 (M + H)$^+$; Rt-0.77 min |
| 444: (R)-4-((R)-1-(tert-butoxy)ethyl)-3-(2-(((S)-1-(2-(4-(difluoromethyl)phenyl)thiazol-5-yl)ethyl)amino)pyrimidin-4-yl)oxazolidin-2-one | MS m/z 518.3 (M + H)$^+$; Rt-0.89 min |
| 445: (R)-4-((R)-1-tert-butoxyethyl)-3-(2-((S)-1-(3-(4-chlorophenyl)-1,2,4-oxadiazol-5-yl)ethylamino)-6-(trifluoromethyl)pyrimidin-4-yl)oxazolidin-2-one | MS m/z 499.2 (M + H)$^+$; Rt-1.27 min. |

TABLE 24b-continued

Chemical name and analytical data for each intermediate listed in Table 24a.

| Intermediate: Name | Analytical data |
|---|---|
| 446: (R)-4-((R)-1-tert-butoxyethyl)-3-(2-((S)-1-(2-fluoro-4-(trifluoromethyl)phenyl)ethylamino)pyrimidin-4-yl)oxazolidin-2-one | MS m/z 471.3 (M + H)+; Rt-1.01 min |
| 447: (R)-4-((R)-1-tert-butoxyethyl)-3-(2-((S)-1-(4-(1-ethoxycyclopropyl)-2-fluorophenyl)ethylamino)pyrimidin-4-yl)oxazolidin-2-one | MS m/z 487.3 (M + H)+; Rt-1.02 min |
| 448: 4-((S)-1-(4-((R)-4-((R)-1-tert-butoxyethyl)-2-oxooxazolidin-3-yl)pyrimidin-2-ylamino)ethyl)-2-chloro-N-cyclopentylbenzamide | MS m/z 530.3 (M + H)+; Rt-0.91 min |
| 449: 1-(4-((S)-1-(4-((R)-4-((R)-1-tert-butoxyethyl)-2-oxooxazolidin-3-yl)pyrimidin-2-ylamino)ethyl)-3-fluorophenyl)cyclopropanecarbonitrile | MS m/z 468.3 (M + H)+; Rt-0.91 min |
| 450: (R)-4-((R)-1-tert-butoxyethyl)-3-(2-((S)-1-(2-fluoro-4-(1-methyl-1H-pyrazol-4-yl)phenyl)ethylamino)pyrimidin-4-yl)oxazolidin-2-one | MS m/z 483.3 (M + H)+; Rt-0.86 min |
| 451: (R)-4-((R)-1-tert-butoxyethyl)-3-(2-((S)-1-(4-(1-methyl-1H-pyrazol-4-yl)phenyl)ethylamino)pyrimidin-4-yl)oxazolidin-2-one | MS m/z 465.3 (M + H)+; Rt-0.83 min |
| 452: (R)-4-((R)-1-tert-butoxyethyl)-3-(2-((S)-1-(2-fluoro-4-(1H-pyrazol-4-yl)phenyl)ethylamino)pyrimidin-4-yl)oxazolidin-2-one | MS m/z 469.3 (M + H)+; Rt-0.80 min |
| 453: (R)-4-((R)-1-tert-butoxyethyl)-3-(5-fluoro-2-((S)-1-(2-fluoro-4-(trifluoromethyl)phenyl)ethylamino)pyrimidin-4-yl)oxazolidin-2-one | MS m/z 489.3 (M + H)+; Rt-1.15 min |
| 454: (R)-4-((R)-1-tert-butoxyethyl)-3-(2-((S)-1-(2-fluoro-4-(1-methylcyclopropyl)phenyl)ethylamino)pyrimidin-4-yl)oxazolidin-2-one | MS m/z 457.4 (M + H)+; Rt-1.06 min |
| 455: (R)-4-((R)-1-tert-butoxyethyl)-3-(2-((S)-1-(2-fluoro-4-isopropylphenyl)ethylamino)pyrimidin-4-yl)oxazolidin-2-one | MS m/z 445.3 (M + H)+; Rt-1.05 min |
| 456: (R)-4-((R)-1-tert-butoxyethyl)-3-(5-fluoro-2-((S)-1-(2-fluoro-4-(1-methyl-1H-pyrazol-4-yl)phenyl)ethylamino)pyrimidin-4-yl)oxazolidin-2-one | MS m/z 501.3 (M + H)+; Rt-0.98 min |
| 457: (R)-4-((R)-1-tert-butoxyethyl)-3-(5-fluoro-2-((S)-1-(2-fluoro-4-(1-methylcyclopropyl)phenyl)ethylamino)pyrimidin-4-yl)oxazolidin-2-one | MS m/z 475.3 (M + H)+; Rt-1.20 min |
| 458: (R)-4-((R)-1-tert-butoxyethyl)-3-(5-fluoro-2-((S)-1-(2-fluoro-4-(1H-pyrazol-4-yl)phenyl)ethylamino)pyrimidin-4-yl)oxazolidin-2-one | MS m/z 487.2 (M + H)+; Rt-0.90 min |
| 459: (R)-4-((R)-1-tert-butoxyethyl)-3-(5-fluoro-2-((S)-1-(2-fluoro-4-isopropylphenyl)ethylamino)pyrimidin-4-yl)oxazolidin-2-one | MS m/z 463.3 (M + H)+; Rt-1.20 min |
| 460: (R)-4-((R)-1-(tert-butoxy)ethyl)-3-(5-fluoro-2-(((S)-1-(2-fluoro-4-(2-hydroxypropan-2-yl)phenyl)ethyl)amino)pyrimidin-4-yl)oxazolidin-2-one | MS m/z 461.3 (M + H)+; Rt-1.14 min |
| 461: (R)-4-((R)-1-(tert-butoxy)ethyl)-3-(2-(((S)-1-(2,5-difluoro-4-(1-methyl-1H-pyrazol-4-yl)phenyl)ethyl)amino)-5-fluoropyrimidin-4-yl)oxazolidin-2-one | MS m/z 519.3 (M + H)+; Rt-0.98 min |
| 462: (R)-4-((S)-1-(tert-butoxy)ethyl)-3-(2-(((S)-1-(2-(4-chlorophenyl)thiazol-5-yl)ethyl)amino)pyrimidin-4-yl)oxazolidin-2-one | MS m/z 502.3 (M + H)+; Rt-0.95 min |
| 463: (R)-4-((R)-1-(tert-butoxy)ethyl)-3-(2-(((S)-1-(4-isobutoxyphenyl)ethyl)amino)pyrimidin-4-yl)oxazolidin-2-one | MS m/z 457.4 (M + H)+; Rt 1.04 min |
| 464: (R)-4-((R)-1-(tert-butoxy)ethyl)-3-(5-fluoro-2-(((S)-1-(2-fluoro-4-methoxyphenyl)ethyl)amino)pyrimidin-4-yl)oxazolidin-2-one | MS m/z 451.3 (M + H)+; Rt 1.03 min |
| 465: (R)-4-((R)-1-(tert-butoxy)ethyl)-3-(2-(((S)-1-(2,3-difluorophenyl)ethyl)amino)pyrimidin-4-yl)oxazolidin-2-one | MS m/z 421.2 (M + H)+; Rt = 0.91 min |
| 466: (R)-4-((R)-1-(tert-butoxy)ethyl)-3-(2-(((S)-1-(2,3-difluorophenyl)ethyl)amino)-5-fluoropyrimidin-4-yl)oxazolidin-2-one | MS m/z 439.2 (M + H)+; Rt = 1.05 min; |
| 467: (R)-4-((R)-1-(tert-butoxy)ethyl)-3-(2-(((S)-1-(3,4-difluorophenyl)ethyl)amino)-5-fluoropyrimidin-4-yl)oxazolidin-2-one | MS m/z 439.2 (M + H)+; Rt = 1.03 min; |
| 468: (R)-4-((R)-1-(tert-butoxy)ethyl)-3-(2-(((S)-1-(2,4-difluorophenyl)ethyl)amino)-5-fluoropyrimidin-4-yl)oxazolidin-2-one | MS m/z 439.3 (M + H)+; Rt = 1.04 min; |
| 469: (R)-4-((R)-1-(tert-butoxy)ethyl)-3-(2-(((S)-1-(3,5-difluorophenyl)ethyl)amino)-5-fluoropyrimidin-4-yl)oxazolidin-2-one | MS m/z 439.2 (M + H)+; Rt = 1.04 min; |

TABLE 24b-continued

Chemical name and analytical data for each intermediate listed in Table 24a.

| Intermediate: Name | Analytical data |
|---|---|
| 470: (R)-4-((R)-1-(tert-butoxy)ethyl)-3-(5-chloro-2-(((S)-1-(5-(2-(trifluoromethyl)pyridin-4-yl)pyrimidin-2-yl)ethyl)amino)pyrimidin-4-yl)oxazolidin-2-one | MS m/z 565.4 (M + H)+; Rt = 0.98 min; |

Intermediate 473: (2R,3R)-3-(tert-butoxy)-2-((6-fluoro-2-(((S)-1-(1-(4-fluorophenyl)-1H-pyrazol-4-yl)ethyl)amino)pyrimidin-4-yl)amino)butan-1-ol

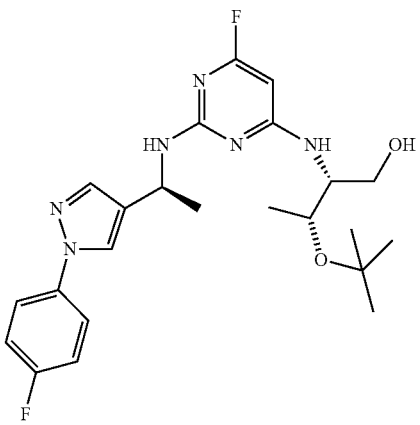 [SMILES: C[C@H](Nc1nc(F)cc(N[C@H](CO)[C@@H](C)OC(C)(C)C)n1)c1cnn(-c2ccc(F)cc2)c1]

A solution of (S)-4,6-difluoro-N-(1-(1-(4-fluorophenyl)-1H-pyrazol-4-yl)ethyl)pyrimidin-2-amine (80 mg, 0.25 mmol), (2R,3R)-2-amino-3-(tert-butoxy)butan-1-ol (55 mg, 0.28 mmol, 1.1 equiv), and N-ethyl-N-isopropylpropan-2-amine (0.11 mL, 0.63 mmol, 2.5 equiv) in DMSO (1.3 mL) was heated at 85° C. for 16 hours. The reaction was cooled to room temperature and diluted with ethyl acetate (30 mL) and dilute aqueous sodium chloride (30 mL). The layers were separated and the aqueous layer was extracted with ethyl acetate (20 mL). The combined organic extracts were dried over $Na_2SO_4$, filtered and concentrated. Silica gel column chromatography (EtOAc/Heptane) provided (2R, 3R)-3-(tert-butoxy)-2-((6-fluoro-2-(((S)-1-(1-(4-fluorophenyl)-1H-pyrazol-4-yl)ethyl)amino)pyrimidin-4-yl)amino)butan-1-ol (0.058 g, white solid) in 50% yield. 1H NMR (400 MHz, CDCl3) δ 7.79 (s, 1H), 7.66 (s, 1H), 7.61 (m, 2H), 7.13 (t, J=8.6 Hz, 2H), 5.35 (s, 1H), 5.30-5.14 (m, 2H), 5.04 (m, 1H), 3.94 (m, 1H), 3.77-3.65 (m, 2H), 1.57 (d, J=6.9 Hz, 3H), 1.21 (s, 9H), 1.15 (d, J=6.0 Hz, 3H). MS m/z 461.3 (M+H)+; Rt-0.88 min.

Intermediate 474 (2R,3R)-3-(tert-butoxy)-2-((2-(((S)-1-(1-(4-chlorophenyl)-1H-pyrazol-4-yl)ethyl)amino)-6-fluoropyrimidin-4-yl)amino)butan-1-ol

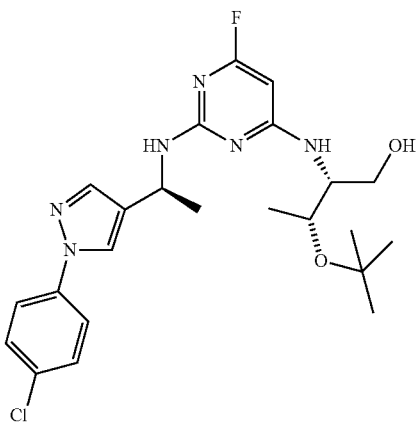 [SMILES: C[C@H](Nc1nc(F)cc(N[C@H](CO)[C@@H](C)OC(C)(C)C)n1)c1cnn(-c2ccc(Cl)cc2)c1]

(2R,3R)-3-(tert-butoxy)-2-((2-(((S)-1-(1-(4-chlorophenyl)-1H-pyrazol-4-yl)ethyl)amino)-6-fluoropyrimidin-4-yl)amino)butan-1-ol was prepared using a method similar to that described for the preparation of Intermediate 473. 1H NMR (400 MHz, CDCl3) δ ppm 7.82 (s, 1H), 7.67 (s, 1H), 7.60 (d, J=8.9 Hz, 2H), 7.41 (d, J=8.8 Hz, 2H), 5.35 (s, 1H), 5.27 (m, 1H), 5.19 (m, 1H), 5.07 (m, 1H), 3.94 (m, 1H), 3.71 (m, 2H), 1.57 (d, J=6.8 Hz, 3H), 1.21 (s, 9H), 1.14 (d, J=5.9 Hz, 3H). MS m/z 477.3 (M+H)+; Rt-0.96 min Intermediate 475: (R)-4-((R)-1-(tert-butoxy)ethyl)-3-(6-fluoro-2-(((S)-1-(1-(4-fluorophenyl)-1H-pyrazol-4-yl)ethyl)amino)pyrimidin-4-yl)oxazolidin-2-one

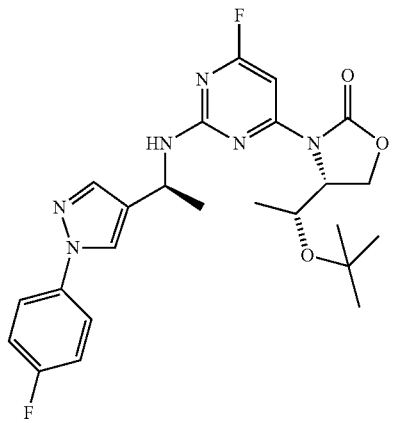

Triphosgene (18 mg, 0.062 mmol, 0.5 equiv) was added to a solution of (2R,3R)-3-(tert-butoxy)-2-((6-fluoro-2-(((S)-1-(1-(4-fluorophenyl)-1H-pyrazol-4-yl)ethyl)amino)pyrimidin-4-yl)amino)butan-1-ol (57 mg, 0.12 mmol) in DCM (1.2 mL) at −78° C., followed by the dropwise addition of 2,6-lutidine (0.058 mL, 0.49 mmol, 4 equiv). The solution was allowed to warm to room temperature and was then heated at 35° C. for 30 min. The reaction was then cooled to room temperature and diluted with DCM (30 mL) and saturated aqueous sodium chloride (30 mL). The layers were separated and the organic layer was dried over $Na_2SO_4$, filtered and concentrated to give crude (R)-4-((R)-1-(tert-butoxy)ethyl)-3-(6-fluoro-2-(((S)-1-(1-(4-fluorophenyl)-1H-pyrazol-4-yl)ethyl)amino)pyrimidin-4-yl)oxazolidin-2-one, which was used without further purification. MS m/z 487.4 (M+H)+; Rt-1.12 min.

Intermediate 476: (R)-4-((R)-1-(tert-butoxy)ethyl)-3-(2-(((S)-1-(1-(4-chlorophenyl)-1H-pyrazol-4-yl)ethyl)amino)-6-fluoropyrimidin-4-yl)oxazolidin-2-one

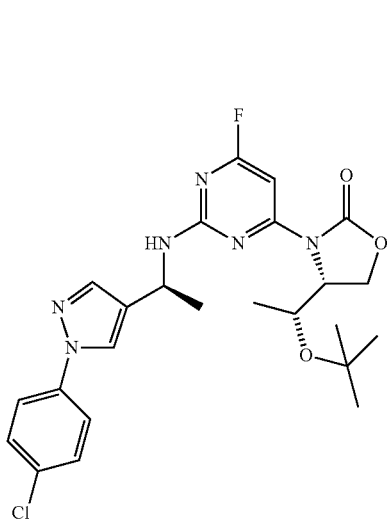 [SMILES: C[C@H](Nc1nc(F)cc(N2C(=O)OC[C@@H]2[C@@H](C)OC(C)(C)C)n1)c1cnn(-c2ccc(F)cc2)c1]

(R)-4-((R)-1-(tert-butoxy)ethyl)-3-(2-(((S)-1-(1-(4-chlorophenyl)-1H-pyrazol-4-yl)ethyl)amino)-6-fluoropyrimidin-4-yl)oxazolidin-2-one was prepared using a method similar to that described for the preparation of Intermediate 475. ¹H NMR (400 MHz, CDCl₃) δ ppm 7.82 (s, 1H), 7.66 (s, 1H), 7.60 (d, J=8.8 Hz, 2H), 7.43 (d, J=8.7 Hz, 2H), 7.17 (s, 1H), 5.31 (m, 1H), 4.70 (m, 1H), 4.62 (dd, J=9.2, 3.0 Hz, 1H), 4.33 (m, 2H), 1.62 (d, J=6.8 Hz, 3H), 1.13 (br s, 9H), 1.02 (d, J=6.5 Hz, 3H). MS m/z 503.3 (M+H)⁺; Rt-1.21 min.

Intermediate 477

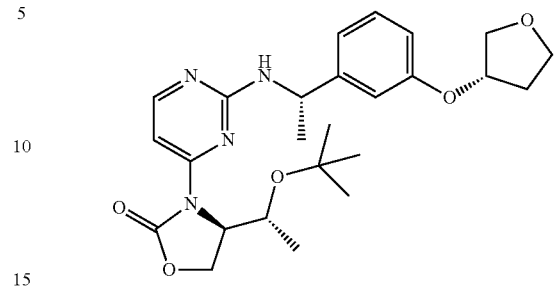

To a microwave vial with a stir bar was added (R)-4-((R)-1-tert-butoxyethyl)-3-(2-chloropyrimidin-4-yl)oxazolidin-2-one (43.6 mg, 0.145 mmol) and (S)-1-(3-((S)-tetrahydrofuran-3-yloxy)phenyl)ethanamine (25.1 mg, 0.121 mmol), followed by DMSO (605 uL) and DIEA (63.5 ul, 0.363 mmol). The vial was capped and the reaction mixture heated in a preheated oil bath at 110° C. for 21 hr. The mixture was diluted with water and extracted with EtOAc two times. The combined organic phases were washed with brine, dried over sodium sulfate, filtered, concentrated and dried on house vacuum to afford crude (R)-4-((R)-1-tert-butoxyethyl)-3-(2-(((S)-1-(3-((S)-tetrahydrofuran-3-yloxy)phenyl)ethylamino)pyrimidin-4-yl)oxazolidin-2-one, as a brown solid film, (yield assumed quantitative). LCMS m/z 471.4 (M+H)⁺, Rt 0.85 min.

The compounds in Table 25 were prepared using methods similar to those described for the preparation of Intermediate 477.

TABLE 25

| Intermediate: Name | Structure | LCMS |
|---|---|---|
| 478: (R)-4-((R)-1-tert-butoxyethyl)-3-(2-((S)-1-(3-isobutoxyphenyl)ethylamino)pyrimidin-4-yl)oxazolidin-2-one | 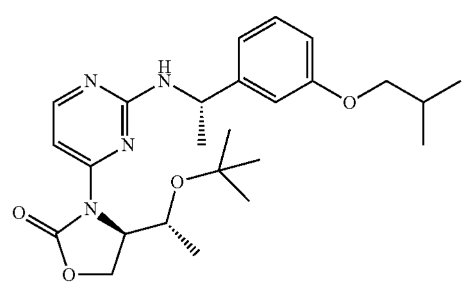 [SMILES: CC(C)COc1cccc([C@H](C)Nc2nccc(N3C(=O)OC[C@@H]3[C@@H](C)OC(C)(C)C)n2)c1] | MS m/z 457.4 (M + H)⁺, Rt 1.04 min. |
| 479: (R)-4-((R)-1-tert-butoxyethyl)-3-(2-((S)-1-(3-phenoxyphenyl)ethylamino)pyrimidin-4-yl)oxazolidin-2-one | 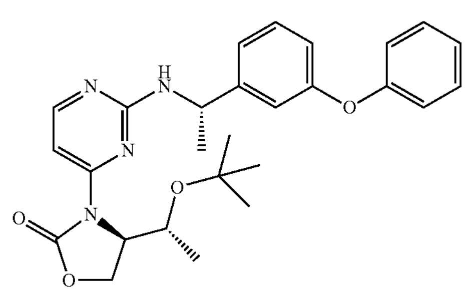 [SMILES: C[C@H](Nc1nccc(N2C(=O)OC[C@@H]2[C@@H](C)OC(C)(C)C)n1)c1cccc(Oc2ccccc2)c1] | MS m/z 477.3 (M + H)⁺, Rt 1.00 min. |

TABLE 25-continued

| Intermediate: Name | Structure | LCMS |
|---|---|---|
| 480: (R)-4-((R)-1-tert-butoxyethyl)-3-(2-((S)-1-(4-isopropoxyphenyl)ethylamino)pyrimidin-4-yl)oxazolidin-2-one | 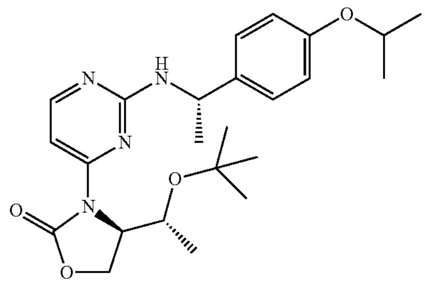 [SMILES: CC(C)Oc1ccc([C@H](C)Nc2nccc(N3C(=O)OC[C@@H]3[C@@H](C)OC(C)(C)C)n2)cc1] | MS m/z 443.4 (M + H)+, Rt 0.94 min. |
| 481: (R)-4-((R)-1-tert-butoxyethyl)-3-(2-((S)-1-(4-isobutoxy-3-methylphenyl)ethylamino)pyrimidin-4-yl)oxazolidin-2-one | 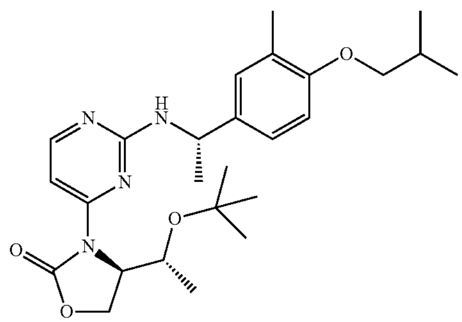 [SMILES: Cc1cc([C@H](C)Nc2nccc(N3C(=O)OC[C@@H]3[C@@H](C)OC(C)(C)C)n2)ccc1OCC(C)C] | MS m/z 471.4 (M + H)+, Rt 1.09 min. |
| 482: (R)-4-((R)-1-(tert-butoxy)ethyl)-3-(5-fluoro-2-(((S)-1-(4-(trifluoromethoxy)phenyl)ethyl)amino)pyrimidin-4-yl)oxazolidin-2-one | 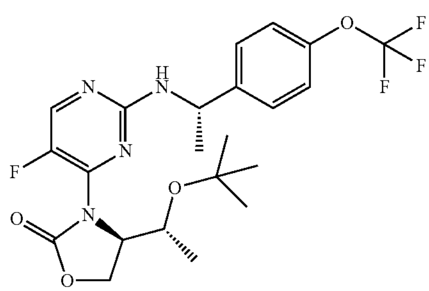 [SMILES: C[C@H](Nc1ncc(F)c(N2C(=O)OC[C@@H]2[C@@H](C)OC(C)(C)C)n1)c1ccc(OC(F)(F)F)cc1] | MS m/z 487.3 (M + H)+, Rt 1.18 min. |
| 483: (R)-4-((R)-1-(tert-butoxy)ethyl)-3-(5-fluoro-2-(((S)-1-(2-fluoro-4-(trifluoromethoxy)phenyl)ethyl)amino)pyrimidin-4-yl)oxazolidin-2-one | 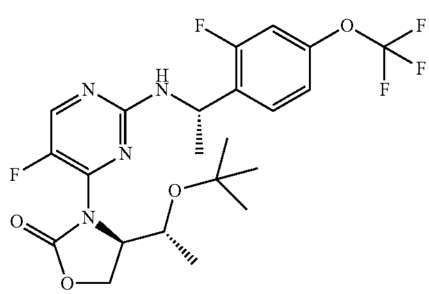 [SMILES: C[C@H](Nc1ncc(F)c(N2C(=O)OC[C@@H]2[C@@H](C)OC(C)(C)C)n1)c1ccc(OC(F)(F)F)cc1F] | MS m/z 505.4 (M + H)+, Rt 1.16 min. |
| 484: (R)-4-((R)-1-(tert-butoxy)ethyl)-3-(2-(((S)-1-(4-(difluoromethoxy)phenyl)ethyl)amino)-5-fluoropyrimidin-4-yl)oxazolidin-2-one | 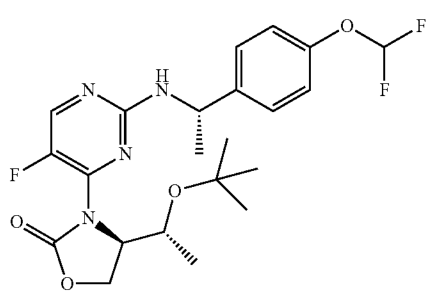 [SMILES: C[C@H](Nc1ncc(F)c(N2C(=O)OC[C@@H]2[C@@H](C)OC(C)(C)C)n1)c1ccc(OC(F)F)cc1] | MS m/z 469.3 (M + H)+, Rt 1.05 min. |

TABLE 25-continued

| Intermediate: Name | Structure | LCMS |
|---|---|---|
| 485: (R)-4-((R)-1-(tert-butoxy)ethyl)-3-(5-fluoro-2-(((S)-1-(3-fluoro-4-(trifluoromethoxy)phenyl)ethyl)amino)pyrimidin-4-yl)oxazolidin-2-one | 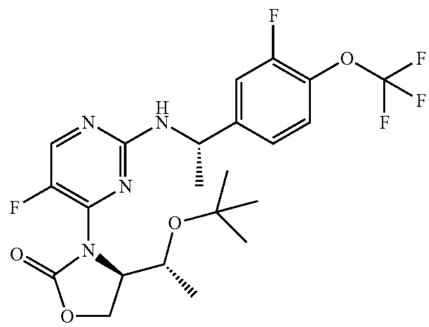 [SMILES: C[C@H](Nc1ncc(F)c(N2C(=O)OC[C@@H]2[C@@H](C)OC(C)(C)C)n1)c1ccc(OC(F)(F)F)c(F)c1] | MS m/z 505.4 (M + H)+, Rt 1.14 min. |
| 486: (R)-4-((R)-1-(tert-butoxy)ethyl)-3-(2-(((S)-1-(4-(difluoromethoxy)-3-fluorophenyl)ethyl)amino)-5-fluoropyrimidin-4-yl)oxazolidin-2-one | 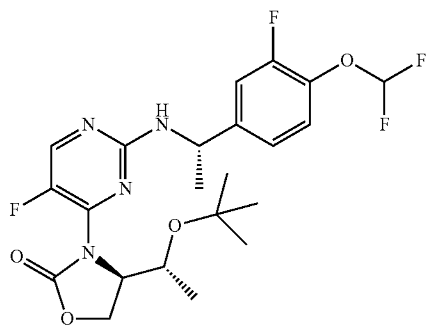 [SMILES: C[C@H](Nc1ncc(F)c(N2C(=O)OC[C@@H]2[C@@H](C)OC(C)(C)C)n1)c1ccc(OC(F)F)c(F)c1] | MS m/z 487.3 (M + H)+, Rt 1.08 min. |
| 487: (R)-4-((R)-1-(tert-butoxy)ethyl)-3-(2-(((S)-1-(4-(difluoromethoxy)-2-fluorophenyl)ethyl)amino)-5-fluoropyrimidin-4-yl)oxazolidin-2-one | 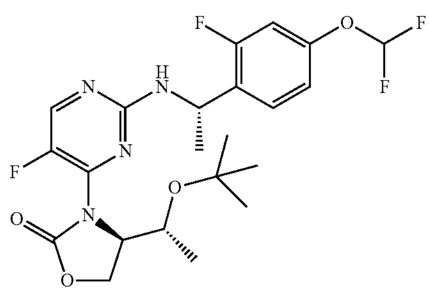 [SMILES: C[C@H](Nc1ncc(F)c(N2C(=O)OC[C@@H]2[C@@H](C)OC(C)(C)C)n1)c1ccc(OC(F)F)cc1F] | MS m/z 487.3 (M + H)+, Rt 1.04 min. |
| 488: (R)-4-((R)-1-(tert-butoxy)ethyl)-3-(5-fluoro-2-(((S)-1-(3-(trifluoromethoxy)phenyl)ethyl)amino)pyrimidin-4-yl)oxazolidin-2-one | 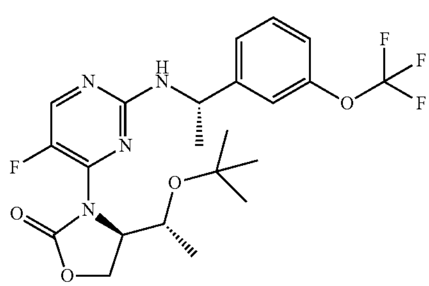 [SMILES: C[C@H](Nc1ncc(F)c(N2C(=O)OC[C@@H]2[C@@H](C)OC(C)(C)C)n1)c1cccc(OC(F)(F)F)c1] | MS m/z 487.3 (M + H)+, Rt 1.10 min. |
| 489: (R)-4-((R)-1-(tert-butoxy)ethyl)-3-(2-(((S)-1-(3-(difluoromethoxy)phenyl)ethyl)amino)-5-fluoropyrimidin-4-yl)oxazolidin-2-one | 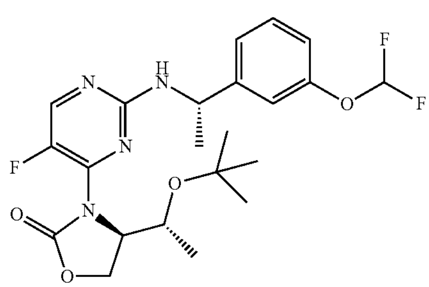 [SMILES: C[C@H](Nc1ncc(F)c(N2C(=O)OC[C@@H]2[C@@H](C)OC(C)(C)C)n1)c1cccc(OC(F)F)c1] | MS m/z 469.3 (M + H)+, Rt 1.03 min. |

Intermediate 490

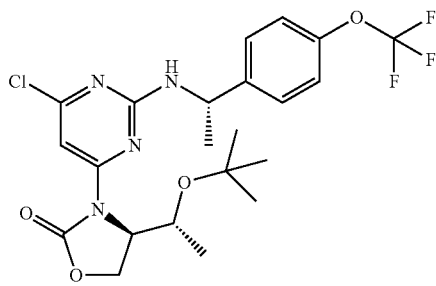 [SMILES: C[C@H](Nc1nc(Cl)cc(N2C(=O)OC[C@@H]2[C@@H](C)OC(C)(C)C)n1)c1ccc(OC(F)(F)F)cc1]

To a microwave vial with a stir bar was added (R)-4-((R)-1-(tert-butoxy)ethyl)-3-(2,6-dichloropyrimidin-4-yl)oxazolidin-2-one (75.0 mg, 0.224 mmol) and (S)-1-(4-(trifluoromethoxy)phenyl)ethanamine (59.7 mg, 0.247 mmol), followed by DMSO (0.9 mL) and DIEA (118 ul, 0.673 mmol). The vial was capped and the reaction mixture heated in a preheated oil bath at 85° C. for 2 hr. The mixture was diluted with brine and extracted with EtOAc two times. The combined organic phases were dried over sodium sulfate, filtered, concentrated and dried on house vacuum to afford crude (R)-4-((R)-1-(tert-butoxy)ethyl)-3-(6-chloro-2-(((S)-1-(4-(trifluoromethoxy)phenyl)ethyl)amino)pyrimidin-4-yl)oxazolidin-2-one as a brown solid film, (yield assumed quantitative). LCMS m/z 503.2 (M+H)$^+$, Rt 1.24 min.

The compounds in Table 26 were prepared using methods similar to those described for the preparation of Intermediate 490

TABLE 26

| Intermediate: Name | Structure | LCMS |
|---|---|---|
| 491: (R)-4-((R)-1-(tert-butoxy)ethyl)-3-(6-chloro-2-(((S)-1-(2-fluoro-4-(trifluoromethoxy)phenyl)ethyl)amino)pyrimidin-4-yl)oxazolidin-2-one | 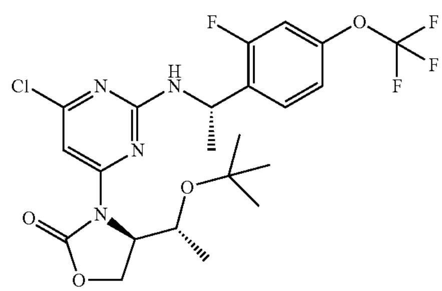 [SMILES: C[C@H](Nc1nc(Cl)cc(N2C(=O)OC[C@@H]2[C@@H](C)OC(C)(C)C)n1)c1ccc(OC(F)(F)F)cc1F] | MS m/z 521.3 (M + H)$^+$, Rt 1.33 min. |
| 492: (R)-4-((R)-1-(tert-butoxy)ethyl)-3-(6-chloro-2-(((S)-1-(4-(difluoromethoxy)phenyl)ethyl)amino)pyrimidin-4-yl)oxazolidin-2-one | 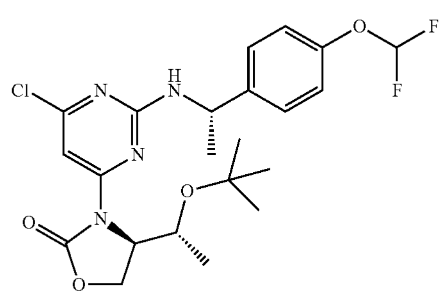 [SMILES: C[C@H](Nc1nc(Cl)cc(N2C(=O)OC[C@@H]2[C@@H](C)OC(C)(C)C)n1)c1ccc(OC(F)F)cc1] | MS m/z 485.2 (M + H)$^+$, Rt 1.20 min. |
| 493: (R)-4-((R)-1-(tert-butoxy)ethyl)-3-(6-chloro-2-(((S)-1-(3-fluoro-4-(trifluoromethoxy)phenyl)ethyl)amino)pyrimidin-4-yl)oxazolidin-2-one | 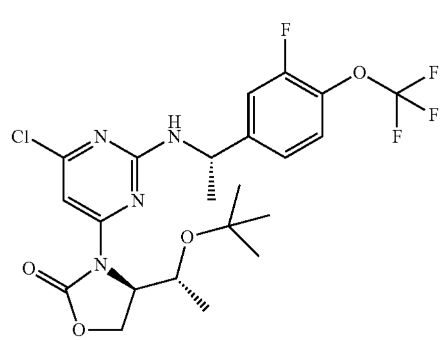 [SMILES: C[C@H](Nc1nc(Cl)cc(N2C(=O)OC[C@@H]2[C@@H](C)OC(C)(C)C)n1)c1ccc(OC(F)(F)F)c(F)c1] | MS m/z 521.3 (M + H)$^+$, Rt 1.31 min. |

Intermediate 494

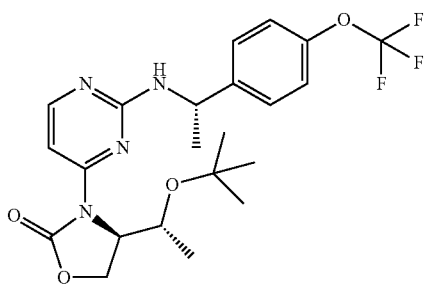 [SMILES: C[C@H](Nc1nccc(N2C(=O)OC[C@@H]2[C@@H](C)OC(C)(C)C)n1)c1ccc(OC(F)(F)F)cc1]

To a suspension of (R)-4-((R)-1-(tert-butoxy)ethyl)-3-(2-fluoropyrimidin-4-yl)oxazolidin-2-one (30.0 mg, 0.106 mmol) and (S)-1-(4-(trifluoromethoxy)phenyl)ethanamine (38.4 mg, 0.159 mmol) in DMSO (0.53 mL), was added DIEA (64.7 ul, 0.371 mmol) in a microwave vial. The vial was capped and the reaction mixture heated in a preheated oil bath at 100° C. for 3 hr. The mixture was diluted with dilute brine and extracted with EtOAc two times. The combined organic phases were washed with brine, dried over magnesium sulfate, filtered, concentrated and dried on house vacuum to afford crude (R)-4-((R)-1-(tert-butoxy)ethyl)-3-(2-(((S)-1-(4-(trifluoromethoxy)phenyl)ethyl)amino)pyrimidin-4-yl)oxazolidin-2-one as a clear colourless oil which was used without further purification (yield assumed quantitative). LCMS m/z 469.3 (M+H)$^+$, Rt 0.98 min.

The compounds in Table 27 were prepared using methods similar to those described for the preparation of Intermediate 494.

TABLE 27

| Intermediate: Name | Structure | LCMS |
| --- | --- | --- |
| 495: (R)-4-((R)-1-(tert-butoxy)ethyl)-3-(2-(((S)-1-(3-fluoro-4-(trifluoromethoxy)phenyl)ethyl)amino)pyrimidin-4-yl)oxazolidin-2-one | 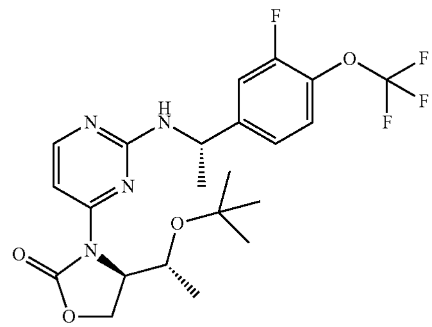 [SMILES: C[C@H](Nc1nccc(N2C(=O)OC[C@@H]2[C@@H](C)OC(C)(C)C)n1)c1ccc(OC(F)(F)F)c(F)c1] | MS m/z 487.3 (M + H)$^+$, Rt 0.99 min. |
| 496: (R)-4-((R)-1-(tert-butoxy)ethyl)-3-(2-(((S)-1-(2-fluoro-4-(trifluoromethoxy)phenyl)ethyl)amino)pyrimidin-4-yl)oxazolidin-2-one | 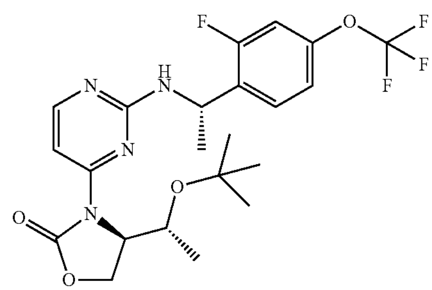 [SMILES: C[C@H](Nc1nccc(N2C(=O)OC[C@@H]2[C@@H](C)OC(C)(C)C)n1)c1ccc(OC(F)(F)F)cc1F] | MS m/z 487.3 (M + H)$^+$, Rt 1.00 min. |
| 497: (R)-4-((R)-1-(tert-butoxy)ethyl)-3-(2-(((S)-1-(4-(difluoromethoxy)-3-fluorophenyl)ethyl)amino)pyrimidin-4-yl)oxazolidin-2-one | 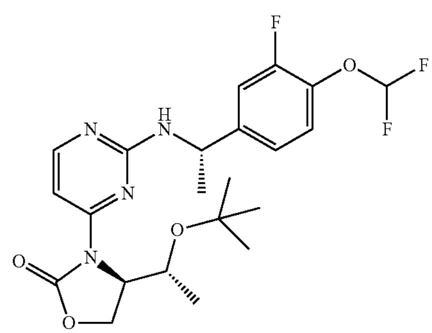 [SMILES: C[C@H](Nc1nccc(N2C(=O)OC[C@@H]2[C@@H](C)OC(C)(C)C)n1)c1ccc(OC(F)F)c(F)c1] | MS m/z 469.4 (M + H)$^+$, Rt 0.91 min. |

TABLE 27-continued

| Intermediate: Name | Structure | LCMS |
|---|---|---|
| 498: (R)-4-((R)-1-(tert-butoxy)ethyl)-3-(2-(((S)-1-(4-(cyclopropylmethoxy)phenyl)ethyl)amino)pyrimidin-4-yl)oxazolidin-2-one | 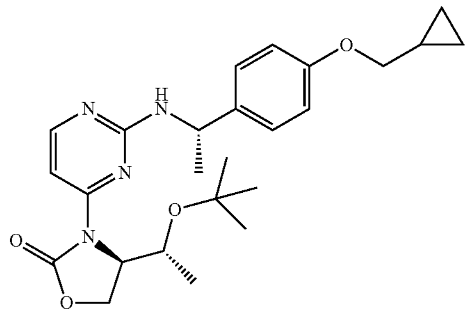 [SMILES: C[C@H](Nc1nccc(N2C(=O)OC[C@@H]2[C@@H](C)OC(C)(C)C)n1)c1ccc(OCC2CC2)cc1] | MS m/z 455.3 (M + H)+, Rt 0.96 min. |
| 499: (R)-4-((R)-1-(tert-butoxy)ethyl)-3-(2-(((S)-1-(2-fluoro-4-isobutoxyphenyl)ethyl)amino)pyrimidin-4-yl)oxazolidin-2-one | 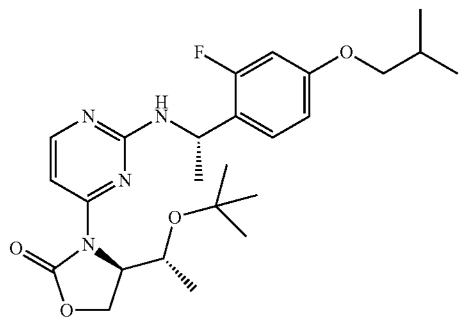 [SMILES: CC(C)COc1ccc([C@H](C)Nc2nccc(N3C(=O)OC[C@@H]3[C@@H](C)OC(C)(C)C)n2)c(F)c1] | MS m/z 475.3 (M + H)+, Rt 1.07 min. |
| 500: (R)-4-((R)-1-(tert-butoxy)ethyl)-3-(2-(((S)-1-(4-(difluoromethoxy)phenyl)ethyl)amino)pyrimidin-4-yl)oxazolidin-2-one | 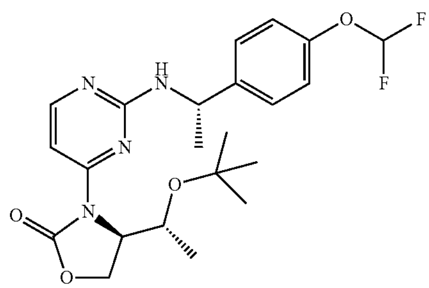 [SMILES: C[C@H](Nc1nccc(N2C(=O)OC[C@@H]2[C@@H](C)OC(C)(C)C)n1)c1ccc(OC(F)F)cc1] | MS m/z 451.3 (M + H)+, Rt 0.90 min. |
| 501: (R)-4-((R)-1-(tert-butoxy)ethyl)-3-(2-(((S)-1-(4-(difluoromethoxy)-2-fluorophenyl)ethyl)amino)pyrimidin-4-yl)oxazolidin-2-one | 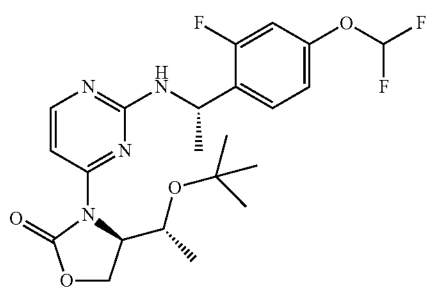 [SMILES: C[C@H](Nc1nccc(N2C(=O)OC[C@@H]2[C@@H](C)OC(C)(C)C)n1)c1ccc(OC(F)F)cc1F] | MS m/z 469.3 (M + H)+, Rt 0.90 min. |
| 502: (R)-4-((R)-1-(tert-butoxy)ethyl)-3-(2-(((S)-1-(3-(trifluoromethoxy)phenyl)ethyl)amino)pyrimidin-4-yl)oxazolidin-2-one | 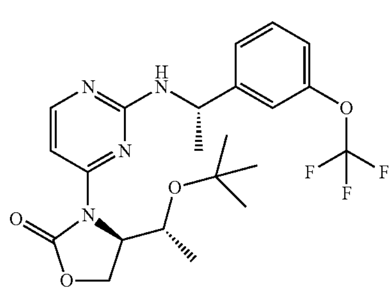 [SMILES: C[C@H](Nc1nccc(N2C(=O)OC[C@@H]2[C@@H](C)OC(C)(C)C)n1)c1cccc(OC(F)(F)F)c1] | MS m/z 469.3 (M + H)+, Rt 0.94 min. |

TABLE 27-continued

| Intermediate: Name | Structure | LCMS |
|---|---|---|
| 503: (R)-4-((R)-1-(tert-butoxy)ethyl)-3-(2-(((S)-1-(3-(difluoromethoxy)phenyl)ethyl)amino)pyrimidin-4-yl)oxazolidin-2-one | 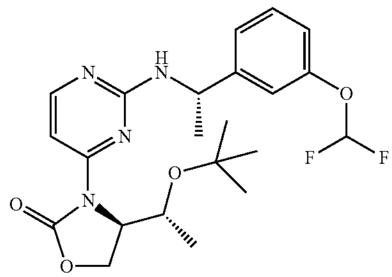 [SMILES: C[C@H](Nc1nccc(N2C(=O)OC[C@@H]2[C@@H](C)OC(C)(C)C)n1)c1cccc(OC(F)F)c1] | MS m/z 451.3 (M + H)+, Rt 0.87 min. |

Intermediate 504 (R)-4-((S)-1-(tert-butoxy)ethyl)-3-(2-(((S)-1-(piperidin-4-yl)ethyl)amino)pyrimidin-4-yl)oxazolidin-2-one

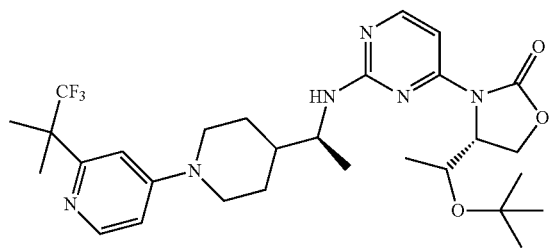 [SMILES: CC(OC(C)(C)C)[C@H]1COC(=O)N1c1ccnc(N[C@@H](C)C2CCN(c3ccnc(C(C)(C)C(F)(F)F)c3)CC2)n1]

To a Parshaker flask were added benzyl 4-((S)-1-((4-((R)-4-((S)-1-(tert-butoxy)ethyl)-2-oxazolidin-3-yl)pyrimidin-2-yl)amino)ethyl)piperidine-1-carboxylate (1 g, 1.90 mmole) and 20% Pd(OH)$_2$ in activated carbon (1 g, 1.42 mmole), then was added MeOH (100 mL) under nitrogen gas. The reaction mixture was shaked under 50 spi hydrogen overnight. The reaction mixture was filtered through a celite. The celite cake was washed with MeOH and the filtrate was concentrate in vacuo to afford the title product as a white solid (630 mg). $^1$H NMR (400 MHz, CD$_2$Cl$_2$) δ 8.18-8.15 (m, 1H), 7.42-7.37 (m, 1H), 4.99 (br, s, 1H), 4.77-4.70 (m, 1H), 4.64-4.57 (m, 1H), 4.52-4.38 (m, 1H), 4.38-4.31 (m, 1H), 4.12-3.93 (m, 2H), 3.40-3.31 (m, 1H), 3.12-3.29 (m, 2H), 2.81-2.70 (m, 1H), 2.02-1.29 (m, 5H), 1.25 (s, 9H), 1.23-1.16 (m, 3H), 1.05-1.00 (m, 3H). HRMS(C) tR=2.65 min; MS m/z 392.2655 (M+H)+

Intermediate 505 (R)-4-((S)-1-(tert-butoxy)ethyl)-3-(2-(((S)-1-(1-(2-(1,1,1-trifluoro-2-methyl propan-2-yl)pyridin-4-yl)piperidin-4-yl)ethyl)amino)pyrimidin-4-yl)oxazolidin-2-one Intermediate 505 was prepared using a method similar to that described for the preparation of Intermediate 329. $^1$H NMR (400 MHz, CD$_2$Cl$_2$) δ 8.23-8.12 (m, 1H), 7.87 (d, J=7.45 Hz, 1H), 7.69 (d, J=6.22 Hz, 1H), 6.81-6.74 (m, 2H), 4.67 (m, 1H), 4.61-4.55 (m, 1H), 4.37-4.29 (m, 1H), 4.25-4.16 (m, 2H), 4.14-4.04 (m, 2H), 3.97-3.85 (m, 1H), 3.21-3.09 (m, 2H), 2.11-1.87 (m, 3H), 1.61 (s, 6H), 1.39-1.23 (m, 1H), 1.21 (d, J=7.45 Hz, 3H), 1.15-1.07 (m, 1H), 1.06 (s, 9H), 0.96 (d, J=6.62 Hz, 3H), HRMS(C) tR=4.80 min; MS m/z 579.3273 (M+H)+

Intermediate 506 (R)-4-((S)-1-(tert-butoxy)ethyl)-3-(2-(((S)-1-(1-(4-chloro-3-(trifluoro methoxy)phenyl)piperidin-4-yl)ethyl)amino)pyrimidin-4-yl)oxazolidin-2-one

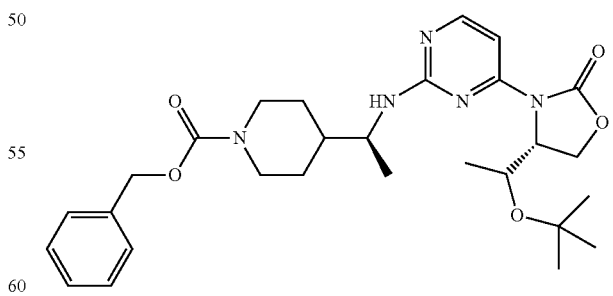

Intermediate 506 was prepared using a method similar to that described for the preparation of Intermediate 329. $^1$H NMR (400 MHz, CD$_2$Cl$_2$) δ 8.17 (br, s, 1H), 7.41 (d, J=6.14 Hz, 1H), 7.31 (d, J=7.98 Hz, 1H), 6.87-6.80 (m, 2H), 4.77-4.71 (m, 1H), 4.64-4.58 (m, 1H), 4.49-4.40 (m, 1H), 4.39-4.32 (m, 1H), 4.11-3.97 (m, 1H), 3.79-3.70 (m, 2H), 2.82-2.71 (m, 2H), 2.04-1.91 (m, 1H), 1.90-1.80 (m, 1H), 1.66-1.35 (m, 3H), 1.34-1.15 (m, 13H), 1.03 (d, J=7.36 Hz, 3H), HRMS(C) tR=5.68 min; MS m/z 586.2419 (M+H)+

Intermediate 507 benzyl 4-((S)-1-((4-((R)-4-((S)-1-(tert-butoxy)ethyl)-2-oxooxazolidin-3-yl)pyrimidin-2-yl)amino)ethyl)piperidine-1-carboxylate Intermediate 507 was prepared using a method similar to that described for the preparation of Intermediate 342. $^1$H NMR (400 MHz, CD$_2$Cl$_2$) δ 8.16 (d, J=5.77 Hz, 1H), 7.41-7.31 (m, 6H), 5.15 (s, 2H), 4.76-4.71 (m, 1H), 4.64-4.58 (m, 1H), 4.48-4.41 (m, 1H), 4.38-4.31 (m, 1H), 4.30-4.18 (m, 2H), 4.09-3.96 (m, 1H), 2.77 (br s, 2H), 1.94-1.54

(m, 3H), 1.37-1.25 (m, 3H), 1.23 (s, 9H), 1.20 (d, J=6.53 Hz, 3H), 1.03 (d, J=5.91 Hz, 3H). HRMS(C) tR=4.64 min; MS m/z 526.3012 (M+H)+

The intermediates in Table 27b were prepared using methods similar to those described for the preparation of Intermediate 303.

TABLE 27b

| Intermediate: Name | Structure | LCMS |
| --- | --- | --- |
| 508: (S)-1-(1-(3,4-difluorophenyl)-1H-imidazol-4-yl)ethanamine | 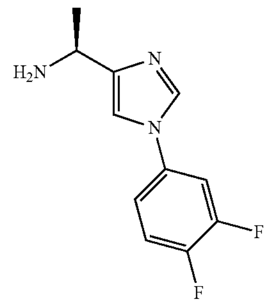 [SMILES: C[C@H](N)c1cn(-c2ccc(F)c(F)c2)cn1] | LCMS(B) m/z (M + H)+ 224.1, RT 0.39 min. |
| 509: (S)-1-(1-(4-chloro-3-fluorophenyl)-1H-imidazol-4-yl)ethanamine | 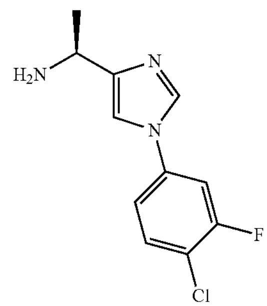 [SMILES: C[C@H](N)c1cn(-c2ccc(Cl)c(F)c2)cn1] | LCMS(B) m/z (M + H)+ 240.0, RT 0.48 min. |
| 510: (S)-1-(1-(3-chloro-4-fluorophenyl)-1H-imidazol-4-yl)ethanamine | 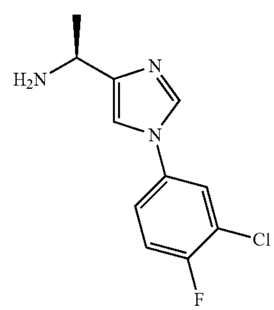 [SMILES: C[C@H](N)c1cn(-c2ccc(F)c(Cl)c2)cn1] | LCMS(B) m/z (M + H)+ 240.1, RT 0.46 min. |
| 511: (S)-1-(1-(4-(difluoromethyl)phenyl)-1H-imidazol-4-yl)ethanamine | 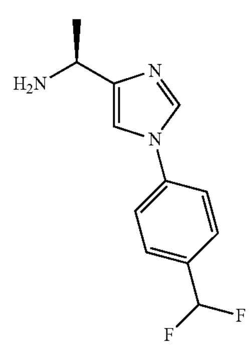 [SMILES: C[C@H](N)c1cn(-c2ccc(C(F)F)cc2)cn1] | LCMS(B) m/z (M + H)+ 238.1, RT 0.41 min. |

TABLE 27b-continued

| Intermediate: Name | Structure | LCMS |
|---|---|---|
| 512: (S)-1-(1-(4-(difluoromethyl)-3-fluorophenyl)-1H-imidazol-4-yl)ethanamine | 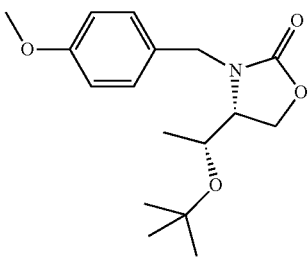 | LCMS(B) m/z (M + H)+ 256.0, RT 0.47 min. |
| 513: (S)-1-(1-(3,5-difluorophenyl)-1H-imidazol-4-yl)ethanamine | 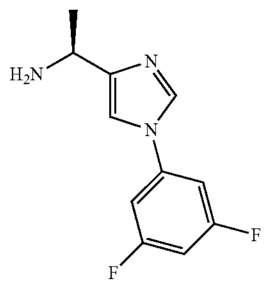 [SMILES: C[C@H](N)c1cn(-c2cc(F)cc(F)c2)cn1] | LCMS(B) m/z (M + H)+ 224.1, RT 0.41 min. |

Intermediate 514: (R)-4-((R)-1-(tert-butoxy)ethyl)-3-(4-methoxybenzyl)oxazolidin-2-one

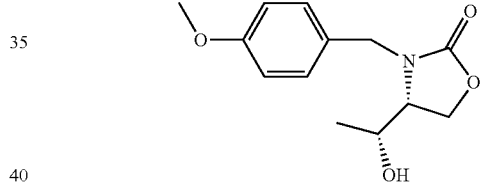

To a solution of benzyl ((2R,3R)-3-(tert-butoxy)-1-hydroxybutan-2-yl)carbamate (5.88 g, 19.9 mmol) in 100 mL DMF was added NaH (60% in mineral oil, 1.62 g, 40.6 mmol) at 0° C. The reaction mixture was stirred for 30 min at 0° C. To the reaction mixture were added 4-methoxybenzyl chloride (4.07 mL, 29.9 mmol) and tetrabutylammonium iodide
(0.74 g, 1.99 mmol) and the resulting mixture was warmed to room temperature and stirred for 15.5 h. The reaction mixture was poured into ice water (200 mL) forming a white suspension. EtOAc (100 mL) was added and the resulting mixture was stirred for 5 min to form a clear two layer solution. After separation, the aqueous phase was extracted with EtOAc (100 mL×3). The combined organic solution was washed with brine (80 mL), dried over Na₂SO₄, filtered and concentrated. Flash column chromatography (EtOAc/Heptane 0 to 70%) gave 5.90 g of the desired product with minor impurities. Major product 1H NMR (400 MHz, MeOD) δ 7.38-7.29 (m, 2H), 6.99-6.93 (m, 2H), 4.68-4.58 (m, 1H), 4.33 (dd, J=9.3, 4.5 Hz, 1H), 4.27-4.17 (m, 2H), 3.89 (dd, J=6.4, 4.8 Hz, 1H), 3.81 (s, 3H), 3.65 (dd, J=9.0, 4.6 Hz, 1H), 1.26 (s, OH), 1.09 (s, 9H), 1.02 (d, J=6.3 Hz, 3H). MS m/z 308.2 (M+H).

Intermediate 515: (R)-4-((R)-1-hydroxyethyl)-3-(4-methoxybenzyl)oxazolidin-2-one A solution of (R)-4-((R)-1-(tert-butoxy)ethyl)-3-(4-methoxybenzyl)oxazolidin-2-one (5.90 g, 19.2 mmol) in CH₂Cl₂ (40 mL) was treated with TFA (40 mL) at room temperature for 20 min. The reaction mixture was concentrated in vacuo, then diluted with CH₂Cl₂ (~50 mL), and again concentrated. This procedure was repeated three times to remove TFA. Flash column chromatography (EtOAc/Heptane 30~100%) gave 3.81 g of the desired product. 1H NMR (400 MHz, MeOD) δ 7.31-7.21 (m, 2H), 7.00-6.87 (m, 2H), 4.67 (d, J=15.0 Hz, 1H), 4.34-4.18 (m, 3H), 3.95 (q, J=6.2 Hz, 1H), 3.80 (s, 3H), 3.68 (dt, J=8.7, 5.5 Hz, 1H), 1.09 (d, J=6.4 Hz, 3H). MS m/z 252.2 (M+H).

Intermediate 516: (R)-4-((S)-1-fluoroethyl)-3-(4-methoxybenzyl)oxazolidin-2-one

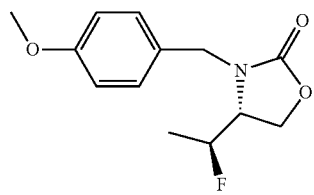 [SMILES: COc1ccc(CN2C(=O)OC[C@@H]2[C@H](C)F)cc1]

To a cooled (0° C.) solution of (R)-4-((R)-1-hydroxyethyl)-3-(4-methoxybenzyl)oxazolidin-2-one (2.27 g, 9.04 mmol) in 30 mL MeCN were added triethylamine (11.4 mL, 82 mmol) followed by perfluoro-1-butanesulfonyl fluoride (4.9 mL, 27.3 mmol) and NEt$_3$(HF)$_3$ (4.5 mL, 27.6 mmol) and the resulting mixture was stirred at 0° C. for 70 min. The reaction mixture was diluted with water (60 mL) and extracted with EtOAc (3×60 mL). Combined organics were washed with water (70 mL), brine (70 mL), dried over Na$_2$SO$_4$, filtered and concentrated. Flash column chromatography (EtOAc/heptane 5 to 70%) gave 2.19 g of the desired product. 1H NMR (400 MHz, CDCl3) δ 7.25-7.20 (m, 2H), 6.92-6.83 (m, 2H), 4.87 (d, J=15.1 Hz, 1H), 4.75 (dqd, J=47.6, 6.6, 2.1 Hz, 1H), 4.26 (td, J=9.2, 1.4 Hz, 1H), 4.17-4.05 (m, 2H), 3.81 (s, 3H), 3.71 (dddd, J=19.8, 9.5, 5.8, 2.1 Hz, 1H), 1.29 (dd, J=23.1, 6.2 Hz, 3H). MS m/z 254.5 (M+H).

Intermediate 517: (R)-4-((S)-1-fluoroethyl)-3-(4-methoxybenzyl)oxazolidin-2-one

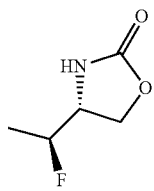

A solution of (R)-4-((S)-1-fluoroethyl)-3-(4-methoxybenzyl)oxazolidin-2-one (1.98 g 7.8 mmol) in 40 mL TFA was heated at 65° C. for 16 h. The reaction mixture was concentrated to remove TFA. Flash column chromatography (EtOAc/CH$_2$Cl$_2$, 0 to 100%) gave 0.91 g pale brown solid. TLC (1:2 heptane:EtOAc) Rf=0.25. 1H NMR (400 MHz, CDCl3) δ 5.60 (br s, 1H), 4.72-4.54 (m, 1H), 4.51 (td, J=8.9, 0.9 Hz, 1H), 4.32 (dd, J=9.2, 4.8 Hz, 1H), 4.02-3.88 (m, 1H), 1.38 (dd, J=24.0, 6.3 Hz, 3H).

Intermediate 518: (R)-3-(2,5-difluoropyrimidin-4-yl)-4-((S)-1-fluoroethyl)oxazolidin-2-one

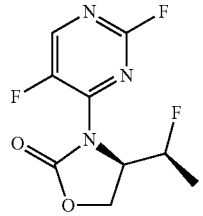 [SMILES: C[C@H](F)[C@H]1COC(=O)N1c1nc(F)ncc1F]

Step 1: To a solution of (R)-4-((R)-1-(tert-butoxy)ethyl)oxazolidin-2-one (6.35 g, 33.9 mmol) in DMF (170 mL) under a nitrogen atmosphere at 0° C. was added sodium hydride (2.14 g, 50.9 mmol, 60%) portion wise over 3 minutes. The reaction mixture was then stirred for 2 hr at 0° C. whereupon 2,4,5-Trifluoropyrimidine (5 g, 37.3 mmol) was added and the reaction mixture allowed to stir 75 minutes at 0° C. then the mixture was allowed to warm to RT and stirred for 1 hr at RT. The reaction mixture was quenched with the slow addition of saturated solution of NH$_4$Cl and the aqueous mixture extracted with EtOAc. Organic phases combined, washed with water, brine, dried (Na$_2$SO$_4$), filtered and concentrated onto silica gel. Silica gel column chromatography (EtOAc/Heptane 0 to 50%) provided a colorless oil of (R)-4-((R)-1-(tert-butoxy)ethyl)-3-(2,5-difluoropyrimidin-4-yl)oxazolidin-2-one (6.97 g, 23.1 mmol, 68% yield) which crystallizes upon standing. $^1$H NMR (400 MHz, CDCl$_3$) n 1.10 (d, J=6.26 Hz, 3H) 1.18 (s, 9H) 4.25-4.35 (m, 1H) 4.49-4.62 (m, 2H) 4.65-4.73 (m, 1H) 8.45 (d, J=1.57 Hz, 1H). LCMS m/z 246.1 (–t-butyl fragment) (M+H)$^+$, Rt 0.91 min.

Step 2: To a round bottom flask containing (R)-4-((R)-1-(tert-butoxy)ethyl)-3-(2,5-difluoropyrimidin-4-yl)oxazolidin-2-one (6.97 g, 23.1 mmol) was added DCM (23 mL) and TFA (23 mL). The resulting reaction mixture stirred for 1 hr at room temperature. The volatiles were then removed and the residue neutralized with a saturated solution of NaHCO$_3$. The aqueous mixture was then extracted with EtOAc. The organic phases were combined, washed with water, brine, dried (Na$_2$SO$_4$), filtered and concentrated to a colorless residue of (R)-4-((R)-1-(tert-butoxy)ethyl)-3-(2,5-difluoropyrimidin-4-yl)oxazolidin-2-one (5.08 g, 20.7 mmol, 90% yield) which crystallizes upon standing. LCMS m/z 246.1 (M+H)$^+$, Rt 0.34 min.

Step 3: To a round bottom flask containing a solution of (R)-3-(2,5-difluoropyrimidin-4-yl)-4-((R)-1-hydroxyethyl) oxazolidin-2-one (4.64 g, 18.9 mmol) in Acetonitrile (63 mL) cooled to 0° C. was added perfluorobutanesulfonyl fluoride (10.2 mL, 56.8 mmol) followed by the addition of triethylamine trihydrofluoride (9.2 mL, 56.8 mmol) and triethylamine (23.7 mL, 170 mmol). The resulting reaction mixture allowed to stir at 0° C. for 4 hr. The reaction mixture was then diluted with water and the aqueous mixture was extracted with EtOAc. The organic phases combined, washed with water, brine, dried (Na$_2$SO$_4$), filtered and concentrated onto silica gel. Silica gel column chromatography (EtOAc/Heptane 0 to 100%) provided a white crystalline of (R)-3-(2,5-difluoropyrimidin-4-yl)-4-((S)-1-fluoroethyl)oxazolidin-2-one (2.24 g, 8.97 mmol, 47% yield). $^1$H NMR (400 MHz, CDCl$_3$) n 8.50 (s, 1H), 5.00-5.25 (m, 1H), 4.75-4.92 (m, 1H), 4.54-4.68 (m, 2H), 1.39 (dd, J=23.1, 7.0 Hz, 3H). LCMS m/z 248.0 (M+H)$^+$, Rt 0.52 min.

The intermediates in Table 27c were prepared using a method similar to that described for the preparation of Intermediate 247.

TABLE 27c

| | |
|---|---|
| 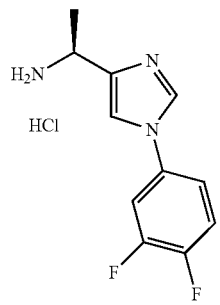 | Intermediate 519 |
| 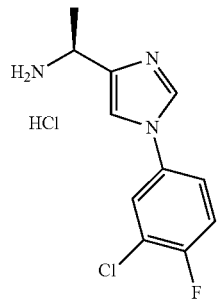 [SMILES: Cl ; C[C@H](N)c1cn(-c2ccc(F)c(Cl)c2)cn1] | Intermediate 520 |
| 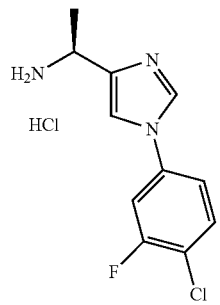 [SMILES: Cl ; C[C@H](N)c1cn(-c2ccc(Cl)c(F)c2)cn1] | Intermediate 521 |

TABLE 27c-continued

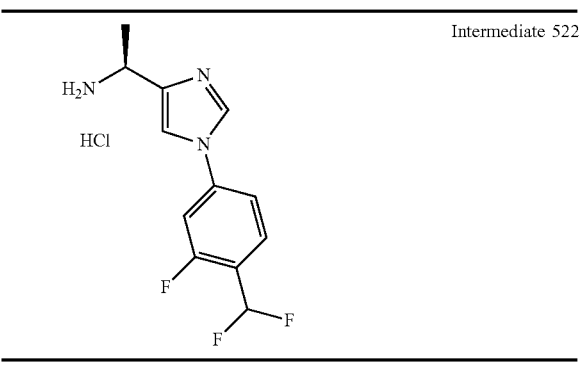

Intermediate 522

TABLE 27d

Chemical name, NMR chemical shifts and LCMS signal for each intermediate listed in Table 27c.

| Intermediate: Name | ¹H NMR (400 MHz, CD₃OD) δ ppm | LCMS |
|---|---|---|
| 519: (S)-1-(1-(3,4-difluorophenyl)-1H-imidazol-4-yl)ethanamine hydrochloride | | MS m/z 224.1 (M + H)⁺; Rt-0.40 min |
| 520: (S)-1-(1-(3-chloro-4-fluorophenyl)-1H-imidazol-4-yl)ethanamine hydrochloride | | MS m/z 240.1 (M + H)⁺; Rt-0.46 min |
| 521: (S)-1-(1-(4-chloro-3-fluorophenyl)-1H-imidazol-4-yl)ethanamine hydrochloride | | MS m/z 240.0 (M + H)⁺; Rt-0.48 min |
| 522: (S)-1-(1-(4-(difluoromethyl)-3-fluorophenyl)-1H-imidazol-4-yl)ethanamine hydrochloride | | MS m/z 256.0 (M – NH₂)⁺; Rt-0.47 min |

EXAMPLES

Example 1

(4R)-4-((R)-1-(tert-butoxy)ethyl)-3-(2-((1-(3-(4-chlorophenyl)isoxazol-5-yl)ethyl)amino)pyrimidin-4-yl)oxazolidin-2-one

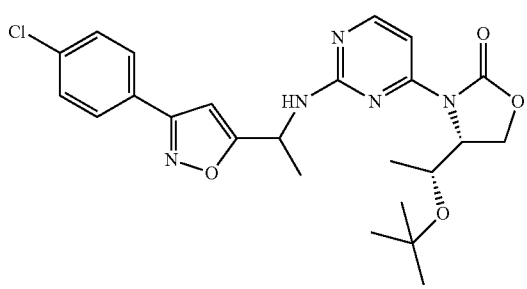 [SMILES: CC(Nc1nccc(N2C(=O)OC[C@@H]2[C@@H](C)OC(C)(C)C)n1)c1cc(-c2ccc(Cl)cc2)no1]

To a solution of 1-(3-(4-chlorophenyl)isoxazol-5-yl)ethanamine (610 mg, 2.74 mmol) and (R)-4-((R)-1-(tert-butoxy)ethyl)-3-(2-fluoropyrimidin-4-yl)oxazolidin-2-one (774 mg, 2.74 mmol) in DMSO (5 ml) was added N-ethyl-N-isopropylpropan-2-amine (2 eq, 0.96 mL, 5.48 mmol) and heated in a microwave at 120° C. for 2 hours. Dilute with EtOAc (50 ml), wash with water (50 ml), brine (50 ml), concentrate in vacuo. Flash column chromatography (silica, 40 g) eluting w/0-25% EtOAc/DCM afforded 500 mg of white solid: ¹H NMR (400 MHz, CDCl₃) δ 8.24 (dd, J=5.8, 1.6 Hz, 1H), 7.80-7.65 (m, 2H), 7.58 (dd, J=5.8, 1.6 Hz, 1H), 7.49-7.37 (m, 2H), 6.48-6.35 (m, 1H), 5.66-5.44 (m, 1H), 4.71 (dddd, J=9.8, 8.5, 4.6, 3.0 Hz, 1H), 4.63 (ddd, J=9.4, 3.1, 2.1 Hz, 1H), 4.50-4.26 (m, 2H), 1.71 (s, 1H), 1.25 (s, 5H), 1.15 (s, 5H), 1.03 (dd, J=22.4, 6.4 Hz, 3H), 5.44-5.13 (m, 1H). HRMS(B) tR=3.36 min; m/z 485.1830

Example 2

(4R)-4-((R)-1-(tert-butoxy)ethyl)-3-(2-((1-(5-(4-chlorophenyl)oxazol-2-yl)ethyl)amino)-5-fluoropyrimidin-4-yl)oxazolidin-2-one

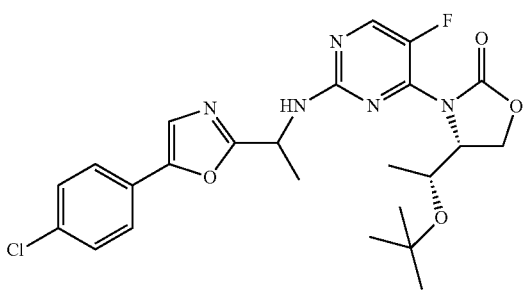 [SMILES: CC(Nc1ncc(F)c(N2C(=O)OC[C@@H]2[C@@H](C)OC(C)(C)C)n1)c1ncc(-c2ccc(Cl)cc2)o1]

To a solution of (S)-1-(5-(4-chlorophenyl)oxazol-2-yl)ethanamine 75 mg, 0.337 mmol) and (R)-4-((R)-1-(tert-butoxy)ethyl)-3-(2,5-difluoropyrimidin-4-yl)oxazolidin-2-one (101 mg, 0.337 mmol) in DMSO (1 ml) was added N-ethyl-N-isopropylpropan-2-amine (2 eq, 0.118 mL, 0.674 mmol) and heated in a microwave at 120° C. for 2 hours. Dilute with EtOAc (25 ml), wash with water (25 ml), brine (25 ml), concentrate in vacuo. Flash column chromatography (silica, 40 g) eluting w/ 0-10% EtOAc/DCM afforded 124 mg yellow foam: ¹H NMR (400 MHz, CDCl₃) δ 8.25 (d, J=2.8 Hz, 1H), 7.61-7.49 (m, 2H), 7.45-7.36 (m, 2H), 7.28 (d, J=6.2 Hz, 1H), 5.65 (d, J=8.9 Hz, 1H), 5.43-5.27 (m, 1H), 4.69 (qd, J=5.6, 2.9 Hz, 1H), 4.62-4.35 (m, 2H), 4.23-4.01 (m, 1H), 1.68 (d, J=12.8 Hz, 2H), 1.26-1.16 (m, 2H), 1.12 (s, 8H), 1.05 (d, J=6.4 Hz, 3H). HRMS(C) tR=1.55 min; m/z 503.1736

Example 3

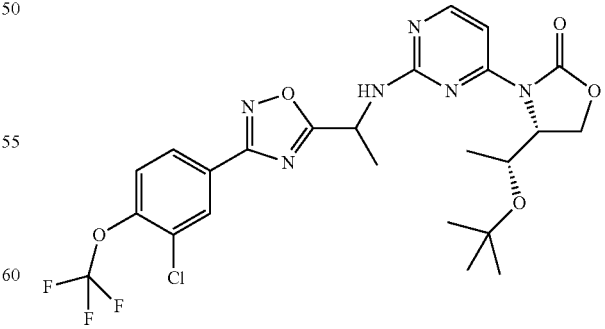

To a solution of (S)-1-(3-(3-chloro-4-(trifluoromethoxy)phenyl)-1,2,4-oxadiazol-5-yl)ethanamine (150 mg, 0.488 mmol) and (R)-4-((R)-1-(tert-butoxy)ethyl)-3-(2-fluoropyrimidin-4-yl)oxazolidin-2-one (138 mg, 0.488 mmol) in DMSO (1 ml) was added N-ethyl-N-isopropylpropan-2-amine (2 eq, 170 uL, 0.975 mmol) and heated in a microwave at 115° C. for 2 hours. Dilute with EtOAc (25 ml), wash with water (25 ml), brine (25 ml), concentrate in vacuo. Flash column chromatography (silica, 40 g) eluting w/ 0-5% EtOAc/DCM afforded 140 mg. ¹H NMR (400 MHz, CDCl₃) δ 8.30-8.19 (m, 4H), 8.01 (dd, J=8.6, 2.1 Hz, 2H), 7.54 (d, J=5.7 Hz, 2H), 7.45 (dq, J=8.4, 1.5 Hz, 2H), 4.53 (dd, J=9.3, 2.4 Hz, 2H), 4.05 (p, J=6.1 Hz, 1H), 3.51 (s, 5H), 1.80 (s, 1H), 1.22 (t, J=6.5 Hz, 12H). Anal. RP-HPLC tR=2.73 min (Gradient: 2 to 98% B in 4.4 min—flow 1 mL/min. Eluent A: Water+3.75 mM NH4Ac+0.001% formic acid. Eluent B: ACN. Column: Acquity CSH 1.7 μm 2.1×50 mm—50° C.) HRMS m/z 514.1039

The Following Examples were prepared using a method similar to that described for the preparation of Intermediate 342 or Example 3

Example 4

(4R)-4-((R)-1-(tert-butoxy)ethyl)-3-(2-((1-(3-(4-chloro-3-methylphenyl)-1,2,4-oxadiazol-5-yl)ethyl)amino)pyrimidin-4-yl)oxazolidin-2-one

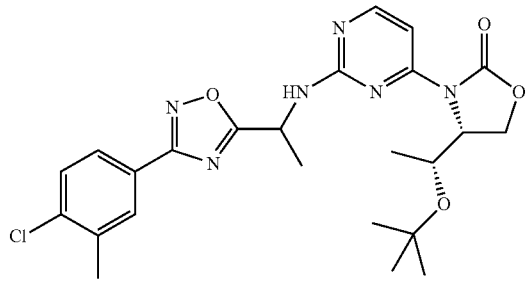 [SMILES: Cc1cc(-c2noc(C(C)Nc3nccc(N4C(=O)OC[C@@H]4[C@@H](C)OC(C)(C)C)n3)n2)ccc1Cl]

¹H NMR (400 MHz, CDCl₃) δ 8.24 (dd, J=5.6, 2.2 Hz, 3H), 7.96 (d, J=2.0 Hz, 3H), 7.84 (dd, J=8.3, 2.1 Hz, 3H), 7.59 (dd, J=5.8, 3.0 Hz, 3H), 7.46 (d, J=8.3 Hz, 3H), 5.71-5.42 (m, 3H), 5.32 (s, 1H), 4.75 (dtd, J=10.3, 5.2, 2.9 Hz, 3H), 1.67-1.60 (m, 3H), 4.64 (ddd, J=9.2, 6.2, 2.9 Hz, 3H), 4.49-4.31 (m, 6H), 4.14 (q, J=7.1 Hz, 1H), 2.46 (s, 9H), 2.07 (s, 1H), 1.77 (dd, J=6.8, 3.2 Hz, 9H), 1.27 (d, J=23.6 Hz, 29H), 1.05 (dd, J=11.3, 6.5 Hz, 9H). HRMS(C) tR=2.00 min; MS m/z 500.98

Example 5

(4R)-4-((R)-1-(tert-butoxy)ethyl)-3-(2-((1-(3-(4-fluoro-3-methylphenyl)-1,2,4-oxadiazol-5-yl)ethyl)amino)pyrimidin-4-yl)oxazolidin-2-one

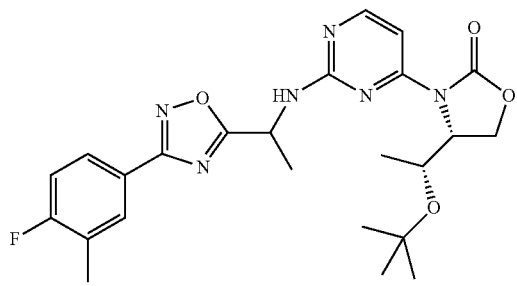 [SMILES: Cc1cc(-c2noc(C(C)Nc3nccc(N4C(=O)OC[C@@H]4[C@@H](C)OC(C)(C)C)n3)n2)ccc1F]

¹H NMR (400 MHz, CDCl₃) δ 8.25 (dd, J=5.8, 2.4 Hz, 3H), 8.02-7.83 (m, 6H), 7.59 (dd, J=5.8, 2.9 Hz, 3H), 7.12 (t, J=8.9 Hz, 3H), 5.72-5.47 (m, 5H), 5.32 (s, 1H), 4.75 (dtd, J=8.7, 4.8, 2.9 Hz, 3H), 4.64 (ddd, J=9.3, 6.2, 2.9 Hz, 3H), 4.49-4.28 (m, 6H), 3.52 (s, 2H), 2.36 (d, J=2.0 Hz, 9H), 1.78 (s, 2H), 1.65 (s, 3H), 1.30 (s, 22H), 1.24 (d, J=2.4 Hz, 6H), 1.05 (dd, J=11.3, 6.4 Hz, 10H). HRMS(C) tR=1.95 min; m/z 484.2234

Example 6

(4R)-4-((R)-1-(tert-butoxy)ethyl)-3-(2-((1-(3-(4-chloro-3-methoxyphenyl)-1,2,4-oxadiazol-5-yl)ethyl)amino)pyrimidin-4-yl)oxazolidin-2-one


¹H NMR (400 MHz, CDCl₃) δ 8.25 (dd, J=5.8, 1.7 Hz, 3H), 7.74-7.57 (m, 9H), 7.53-7.44 (m, 3H), 5.61 (qt, J=16.2, 9.7, 8.6 Hz, 7H), 5.32 (s, 1H), 4.75 (ddd, J=8.6, 4.6, 2.9 Hz, 3H), 4.64 (ddd, J=8.8, 5.8, 2.9 Hz, 3H), 4.50-4.30 (m, 6H), 4.14 (q, J=7.2 Hz, 2H), 4.01 (s, 9H), 2.07 (s, 2H), 1.85-1.73 (m, 9H), 1.62 (s, 2H), 1.36-1.18 (m, 30H), 1.05 (dd, J=10.8, 6.5 Hz, 9H). HRMS(C) tR=1.61 min; m/z 516.1888

Example 7

(4R)-4-((R)-1-(tert-butoxy)ethyl)-3-(2-((1-(3-(4-chloro-3-(trifluoromethoxy)phenyl)-1,2,4-oxadiazol-5-yl)ethyl)amino)pyrimidin-4-yl)oxazolidin-2-one

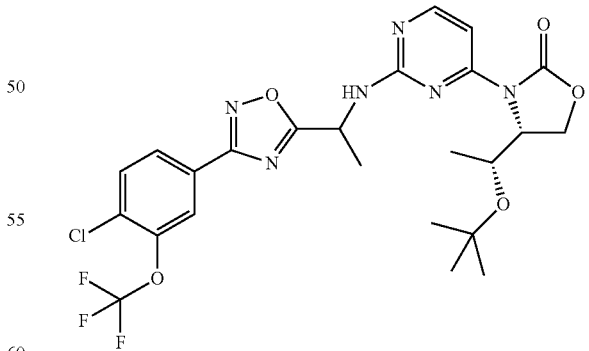

¹H NMR (400 MHz, CDCl₃) δ 8.24 (dd, J=5.8, 3.2 Hz, 1H), 8.11-7.93 (m, 2H), 7.70-7.54 (m, 2H), 5.80-5.40 (m, 2H), 4.75 (dtd, J=8.6, 4.3, 2.2 Hz, 1H), 1.67-1.60 (m, 1H), 4.64 (ddd, J=9.4, 4.2, 2.9 Hz, 1H), 4.50-4.30 (m, 2H), 1.77 (dd, J=6.9, 3.4 Hz, 3H), 1.27 (d, J=21.9 Hz, 9H), 1.06 (dd, J=9.8, 6.5 Hz, 3H). HRMS(C) tR=2.05 min; m/z 570.1605

Example 8

(4R)-4-((R)-1-(tert-butoxy)ethyl)-3-(2-((1-(3-(1-methyl-1H-indol-6-yl)-1,2,4-oxadiazol-5-yl)ethyl)amino)pyrimidin-4-yl)oxazolidin-2-one

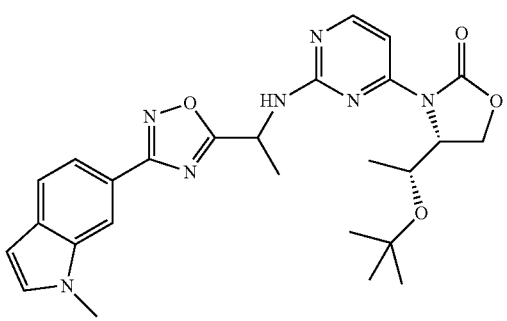 [SMILES: CC(Nc1nccc(N2C(=O)OC[C@@H]2[C@@H](C)OC(C)(C)C)n1)c1nc(-c2ccc3ccn(C)c3c2)no1]

¹H NMR (400 MHz, CDCl₃) δ 8.26 (d, J=5.7 Hz, 3H), 8.10 (d, J=1.3 Hz, 3H), 7.84 (dd, J=8.3, 1.4 Hz, 3H), 7.71 (d, J=8.3 Hz, 3H), 7.64-7.55 (m, 3H), 7.20 (d, J=3.1 Hz, 3H), 6.55 (dd, J=3.1, 0.8 Hz, 3H), 5.64 (p, J=7.2 Hz, 5H), 5.32 (s, 1H), 1.69-1.61 (m, 4H), 4.77 (ddd, J=8.7, 4.7, 2.9 Hz, 3H), 4.65 (td, J=8.8, 8.4, 2.9 Hz, 3H), 4.52-4.27 (m, 6H), 3.90 (s, 9H), 3.51 (s, 2H), 1.89-1.75 (m, 9H), 1.28 (d, J=23.5 Hz, 27H), 1.06 (dd, J=10.9, 6.4 Hz, 10H). HRMS(C) tR=1.77 min; m/z 505.2437

Example 9

(4R)-4-((R)-1-(tert-butoxy)ethyl)-3-(2-((1-(3-(3-(tert-butyl)phenyl)-1,2,4-oxadiazol-5-yl)ethyl)amino)pyrimidin-4-yl)oxazolidin-2-one

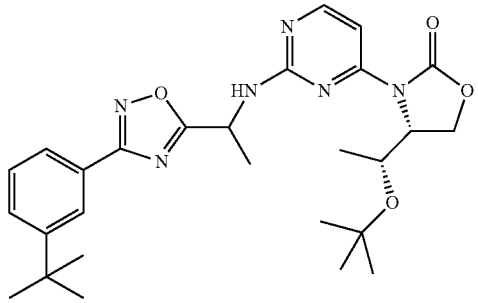 [SMILES: CC(Nc1nccc(N2C(=O)OC[C@@H]2[C@@H](C)OC(C)(C)C)n1)c1nc(-c2cccc(C(C)(C)C)c2)no1]

¹H NMR (400 MHz, CDCl₃) δ 4.64 (ddd, J=9.9, 7.1, 2.9 Hz, 1H), 4.47-4.30 (m, 2H), 1.06 (dd, J=9.3, 6.4 Hz, 3H), 1.85-1.72 (m, 3H), 1.63 (s, 1H), 1.39 (s, 9H), 1.28 (d, J=21.1 Hz, 9H), 4.84-4.71 (m, 1H), 8.25 (d, J=5.7 Hz, 1H), 8.11 (q, J=2.0 Hz, 1H), 7.89 (dt, J=7.7, 1.4 Hz, 1H), 7.66-7.52 (m, 2H), 7.43 (t, J=7.8 Hz, 1H), 5.63 (p, J=7.3 Hz, 2H), 5.39-5.29 (m, OH). HRMS(C) tR=2.02 min; m/z 508.2798

Example 10

(4R)-4-((R)-1-(tert-butoxy)ethyl)-3-(2-((1-(3-(3-(trifluoromethoxy)phenyl)-1,2,4-oxadiazol-5-yl)ethyl)amino)pyrimidin-4-yl)oxazolidin-2-one

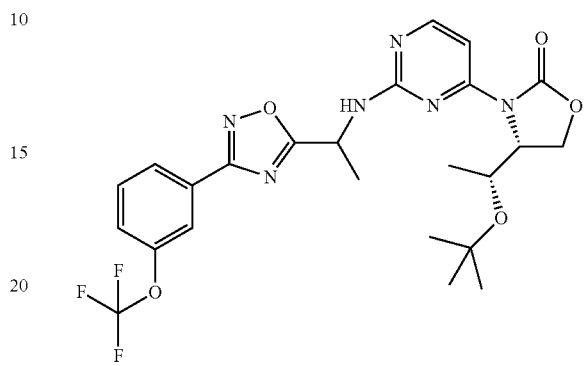

¹H NMR (400 MHz, CDCl₃) δ 8.25 (dd, J=5.7, 2.9 Hz, 1H), 8.04 (dq, J=7.8, 1.3 Hz, 1H), 7.95 (dt, J=2.5, 1.2 Hz, 1H), 7.67-7.49 (m, 2H), 7.39 (ddt, J=8.2, 2.5, 1.2 Hz, 1H), 5.62 (h, J=6.7, 6.1 Hz, 2H), 4.75 (dtd, J=9.1, 4.7, 2.9 Hz, 1H), 4.64 (ddd, J=9.3, 4.9, 2.9 Hz, 1H), 4.49-4.26 (m, 2H), 1.78 (dd, J=6.8, 3.6 Hz, 3H), 1.61 (s, 1H), 1.27 (d, J=23.8 Hz, 9H), 1.06 (dd, J=10.0, 6.5 Hz, 3H). HRMS(C) tR=1.82 min; m/z 536.1995

Example 11

(4R)-4-((R)-1-(tert-butoxy)ethyl)-3-(2-((1-(3-(4-fluoro-3-(trifluoromethoxy)phenyl)-1,2,4-oxadiazol-5-yl)ethyl)amino)pyrimidin-4-yl)oxazolidin-2-one

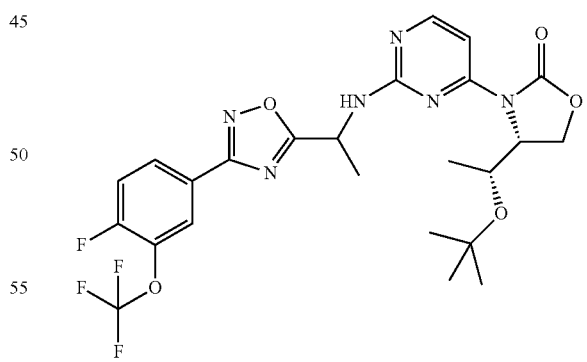

¹H NMR (400 MHz, CDCl₃) δ 8.24 (dd, J=5.8, 3.3 Hz, 1H), 8.13-7.99 (m, 2H), 7.60 (dd, J=5.8, 2.0 Hz, 1H), 5.72-5.56 (m, 1H), 5.48 (s, 1H), 4.85-4.69 (m, 1H), 1.67-1.56 (m, 1H), 4.64 (ddd, J=9.5, 4.5, 2.9 Hz, 1H), 4.53-4.28 (m, 2H), 1.77 (dd, J=7.0, 3.4 Hz, 3H), 1.27 (d, J=22.0 Hz, 9H), 1.06 (dd, J=9.8, 6.4 Hz, 3H). HRMS(C) tR=1.87 min; m/z 554.1901

Example 12

(4R)-4-((R)-1-(tert-butoxy)ethyl)-3-(2-((1-(3-(4-isopropylphenyl)-1,2,4-oxadiazol-5-yl)ethyl)amino)pyrimidin-4-yl)oxazolidin-2-one

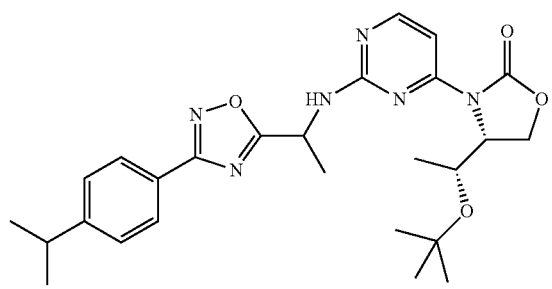 [SMILES: CC(C)c1ccc(-c2noc(C(C)Nc3nccc(N4C(=O)OC[C@@H]4[C@@H](C)OC(C)(C)C)n3)n2)cc1]

$^1$H NMR (400 MHz, CDCl$_3$) δ 8.25 (dd, J=5.9, 1.9 Hz, 1H), 8.09-7.92 (m, 2H), 7.59 (dd, J=5.7, 3.1 Hz, 1H), 7.43-7.32 (m, 2H), 5.60 (dt, J=15.5, 7.8 Hz, 2H), 4.75 (dtd, J=8.4, 5.0, 2.9 Hz, 1H), 4.64 (ddd, J=9.5, 7.1, 2.9 Hz, 1H), 4.49-4.27 (m, 2H), 2.99 (hept, J=6.9 Hz, 1H), 1.76 (dd, J=7.0, 2.8 Hz, 3H), 1.60 (dd, J=6.9, 2.8 Hz, 1H), 1.40-1.19 (m, 15H), 1.05 (dd, J=11.0, 6.5 Hz, 3H). HRMS(C) tR=2.23 min; m/z 494.2642

Example 13

(4R)-4-((R)-1-(tert-butoxy)ethyl)-3-(2-((1-(3-(1,2-dimethyl-1H-indol-4-yl)-1,2,4-oxadiazol-5-yl)ethyl)amino)pyrimidin-4-yl)oxazolidin-2-one

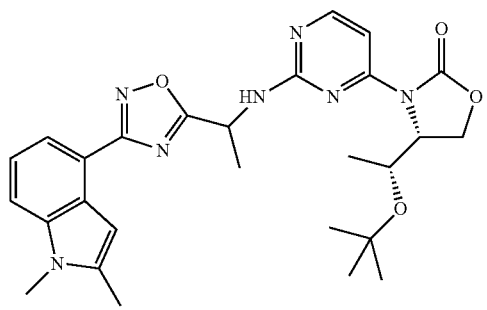 [SMILES: Cc1cc2c(-c3noc(C(C)Nc4nccc(N5C(=O)OC[C@@H]5[C@@H](C)OC(C)(C)C)n4)n3)cccc2n1C]

$^1$H NMR (400 MHz, CDCl$_3$) δ 8.26 (d, J=5.8 Hz, 1H), 7.91 (dd, J=7.5, 0.9 Hz, 1H), 7.60 (d, J=5.8 Hz, 1H), 7.44 (dt, J=8.2, 1.1 Hz, 1H), 7.33-7.20 (m, 1H), 6.99-6.89 (m, 1H), 5.66 (p, J=7.3 Hz, 1H), 4.77 (ddd, J=8.7, 4.7, 3.0 Hz, 1H), 1.66-1.60 (m, 1H), 4.66 (dd, J=9.5, 3.0 Hz, 1H), 4.53-4.44 (m, 1H), 4.38 (q, J=9.0, 8.3 Hz, 1H), 3.75 (s, 3H), 2.51 (d, J=0.9 Hz, 3H), 1.84-1.76 (m, 3H), 1.28 (d, J=26.5 Hz, 9H), 1.04 (d, J=6.5 Hz, 3H). HRMS(C) tR=1.65 min; MS m/z 519.60

Example 14

(4R)-4-((R)-1-(tert-butoxy)ethyl)-3-(2-((1-(5-(4-chlorophenyl)-4-methyloxazol-2-yl)ethyl)amino)pyrimidin-4-yl)oxazolidin-2-one

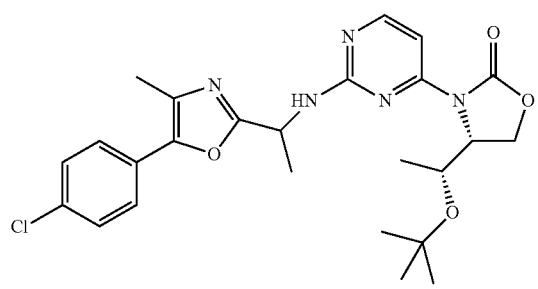 [SMILES: Cc1nc(C(C)Nc2nccc(N3C(=O)OC[C@@H]3[C@@H](C)OC(C)(C)C)n2)oc1-c1ccc(Cl)cc1]

135 mg orangish-red resin (solidified upon standing). $^1$H NMR (400 MHz, CDCl$_3$) δ 8.25 (d, J=5.7 Hz, 1H), 7.62-7.46 (m, 3H), 7.45-7.36 (m, 2H), 4.85-4.69 (m, 1H), 4.64 (ddd, J=9.1, 5.6, 3.0 Hz, 1H), 4.44 (qd, J=6.4, 4.6 Hz, 1H), 4.34 (dt, J=15.4, 9.0 Hz, 1H), 2.40 (d, J=1.3 Hz, 3H), 1.79-1.60 (m, 3H), 1.34-1.18 (m, 11H), 1.04 (dd, J=14.8, 6.5 Hz, 3H). HRMS(C) tR=2.00 min; m/z 499.1986

Example 15

(4R)-4-((R)-1-(tert-butoxy)ethyl)-3-(2-((1-(3-(4-chloro-3-methylphenyl)-1,2,4-oxadiazol-5-yl)ethyl)amino)pyrimidin-4-yl)oxazolidin-2-one $^1$H NMR (400 MHz, CDCl$_3$) δ 8.24 (dd, J=5.6, 2.2 Hz, 3H), 7.96 (d, J=2.0 Hz, 3H), 7.84 (dd, J=8.3, 2.1 Hz, 3H), 7.59 (dd, J=5.8, 3.0 Hz, 3H), 7.46 (d, J=8.3 Hz, 3H), 5.71-5.42 (m, 3H), 5.32 (s, 1H), 4.75 (dtd, J=10.3, 5.2, 2.9 Hz, 3H), 1.67-1.60 (m, 3H), 4.64 (ddd, J=9.2, 6.2, 2.9 Hz, 3H), 4.49-4.31 (m, 6H), 4.14 (q, J=7.1 Hz, 1H), 2.46 (s, 9H), 2.07 (s, 1H), 1.77 (dd, J=6.8, 3.2 Hz, 9H), 1.27 (d, J=23.6 Hz, 29H), 1.05 (dd, J=11.3, 6.5 Hz, 9H). HRMS(C) tR=2.00 min; m/z 500.98

Example 16

(4R)-4-((R)-1-(tert-butoxy)ethyl)-3-(2-((1-(3-(4-fluoro-3-methylphenyl)-1,2,4-oxadiazol-5-yl)ethyl)amino)pyrimidin-4-yl)oxazolidin-2-one

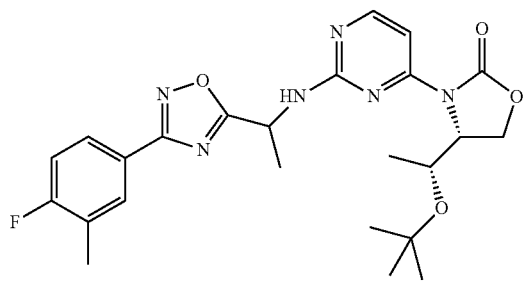 [SMILES: Cc1cc(-c2noc(C(C)Nc3nccc(N4C(=O)OC[C@@H]4[C@@H](C)OC(C)(C)C)n3)n2)ccc1F]

$^1$H NMR (400 MHz, CDCl$_3$) δ 8.25 (dd, J=5.8, 2.4 Hz, 3H), 8.02-7.83 (m, 6H), 7.59 (dd, J=5.8, 2.9 Hz, 3H), 7.12 (t, J=8.9 Hz, 3H), 5.72-5.47 (m, 5H), 5.32 (s, 1H), 4.75 (dtd, J=8.7, 4.8, 2.9 Hz, 3H), 4.64 (ddd, J=9.3, 6.2, 2.9 Hz, 3H), 4.49-4.28 (m, 6H), 3.52 (s, 2H), 2.36 (d, J=2.0 Hz, 9H), 1.78 (s, 2H), 1.65 (s, 3H), 1.30 (s, 22H), 1.24 (d, J=2.4 Hz, 6H), 1.05 (dd, J=11.3, 6.4 Hz, 10H). HRMS(C) tR=1.95 min; m/z 484.2234

Example 17

(4R)-4-((R)-1-(tert-butoxy)ethyl)-3-(2-((1-(3-(4-chloro-3-methoxyphenyl)-1,2,4-oxadiazol-5-yl)ethyl)amino)pyrimidin-4-yl)oxazolidin-2-one

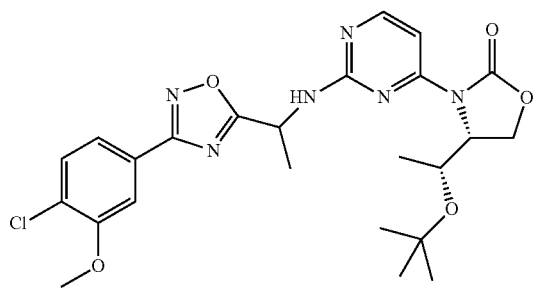 [SMILES: COc1cc(-c2noc(C(C)Nc3nccc(N4C(=O)OC[C@@H]4[C@@H](C)OC(C)(C)C)n3)n2)ccc1Cl]

$^1$H NMR (400 MHz, CDCl$_3$) δ 8.25 (dd, J=5.8, 1.7 Hz, 3H), 7.74-7.57 (m, 9H), 7.53-7.44 (m, 3H), 5.61 (qt, J=16.2, 9.7, 8.6 Hz, 7H), 5.32 (s, 1H), 4.75 (ddd, J=8.6, 4.6, 2.9 Hz, 3H), 4.64 (ddd, J=8.8, 5.8, 2.9 Hz, 3H), 4.50-4.30 (m, 6H), 4.14 (q, J=7.2 Hz, 2H), 4.01 (s, 9H), 2.07 (s, 2H), 1.85-1.73 (m, 9H), 1.62 (s, 2H), 1.36-1.18 (m, 30H), 1.05 (dd, J=10.8, 6.5 Hz, 9H). HRMS(C) tR=1.61 min; m/z 516.1888

Example 18

(4R)-4-((R)-1-(tert-butoxy)ethyl)-3-(2-((1-(3-(4-chloro-3-(trifluoromethoxy)phenyl)-1,2,4-oxadiazol-5-yl)ethyl)amino)pyrimidin-4-yl)oxazolidin-2-one

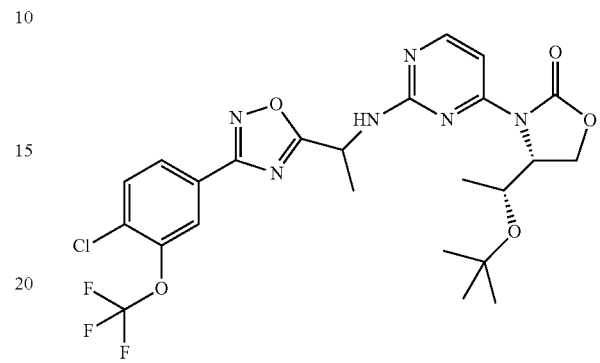

$^1$H NMR (400 MHz, CDCl$_3$) δ 8.24 (dd, J=5.8, 3.2 Hz, 1H), 8.11-7.93 (m, 2H), 7.70-7.54 (m, 2H), 5.80-5.40 (m, 2H), 4.75 (dtd, J=8.6, 4.3, 2.2 Hz, 1H), 1.67-1.60 (m, 1H), 4.64 (ddd, J=9.4, 4.2, 2.9 Hz, 1H), 4.50-4.30 (m, 2H), 1.77 (dd, J=6.9, 3.4 Hz, 3H), 1.27 (d, J=21.9 Hz, 9H), 1.06 (dd, J=9.8, 6.5 Hz, 3H). HRMS(C) tR=2.05 min; m/z 570.1605

Example 19

(4R)-4-((R)-1-(tert-butoxy)ethyl)-3-(2-((1-(3-(1-methyl-1H-indol-6-yl)-1,2,4-oxadiazol-5-yl)ethyl)amino)pyrimidin-4-yl)oxazolidin-2-one

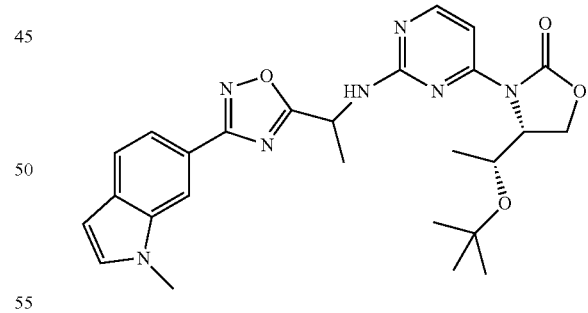

$^1$H NMR (400 MHz, CDCl$_3$) δ 8.26 (d, J=5.7 Hz, 3H), 8.10 (d, J=1.3 Hz, 3H), 7.84 (dd, J=8.3, 1.4 Hz, 3H), 7.71 (d, J=8.3 Hz, 3H), 7.64-7.55 (m, 3H), 7.20 (d, J=3.1 Hz, 3H), 6.55 (dd, J=3.1, 0.8 Hz, 3H), 5.64 (p, J=7.2 Hz, 5H), 5.32 (s, 1H), 1.69-1.61 (m, 4H), 4.77 (ddd, J=8.7, 4.7, 2.9 Hz, 3H), 4.65 (td, J=8.8, 8.4, 2.9 Hz, 3H), 4.52-4.27 (m, 6H), 3.90 (s, 9H), 3.51 (s, 2H), 1.89-1.75 (m, 9H), 1.28 (d, J=23.5 Hz, 27H), 1.06 (dd, J=10.9, 6.4 Hz, 10H). HRMS(C) tR=1.77 min; m/z 505.2437

Example 20

(4R)-4-((R)-1-(tert-butoxy)ethyl)-3-(2-((1-(3-(3-(tert-butyl)phenyl)-1,2,4-oxadiazol-5-yl)ethyl)amino)pyrimidin-4-yl)oxazolidin-2-one

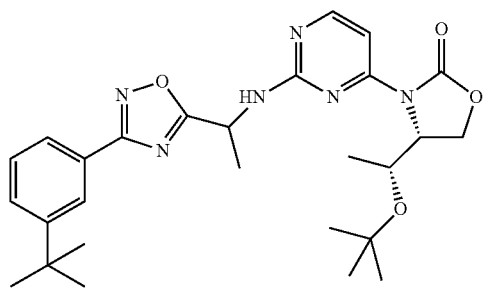 [SMILES: CC(Nc1nccc(N2C(=O)OC[C@@H]2[C@@H](C)OC(C)(C)C)n1)c1nc(-c2cccc(C(C)(C)C)c2)no1]

$^1$H NMR (400 MHz, CDCl$_3$) δ 4.64 (ddd, J=9.9, 7.1, 2.9 Hz, 1H), 4.47-4.30 (m, 2H), 1.06 (dd, J=9.3, 6.4 Hz, 3H), 1.85-1.72 (m, 3H), 1.63 (s, 1H), 1.39 (s, 9H), 1.28 (d, J=21.1 Hz, 9H), 4.84-4.71 (m, 1H), 8.25 (d, J=5.7 Hz, 1H), 8.11 (q, J=2.0 Hz, 1H), 7.89 (dt, J=7.7, 1.4 Hz, 1H), 7.66-7.52 (m, 2H), 7.43 (t, J=7.8 Hz, 1H), 5.63 (p, J=7.3 Hz, 2H), 5.39-5.29 (m, OH). HRMS(C) tR=2.02 min; m/z 508.2798

Example 21

(4R)-4-((R)-1-(tert-butoxy)ethyl)-3-(2-((1-(3-(3-(trifluoromethoxy)phenyl)-1,2,4-oxadiazol-5-yl)ethyl)amino)pyrimidin-4-yl)oxazolidin-2-one

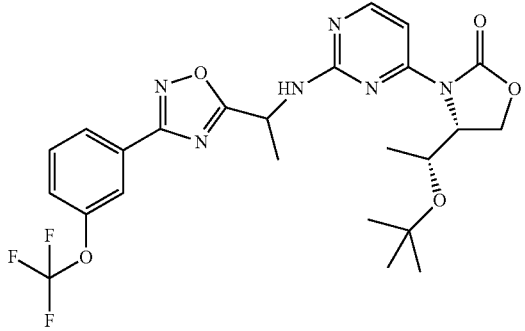 [SMILES: CC(Nc1nccc(N2C(=O)OC[C@@H]2[C@@H](C)OC(C)(C)C)n1)c1nc(-c2cccc(OC(F)(F)F)c2)no1]

$^1$H NMR (400 MHz, CDCl$_3$) δ 8.25 (dd, J=5.7, 2.9 Hz, 1H), 8.04 (dq, J=7.8, 1.3 Hz, 1H), 7.95 (dt, J=2.5, 1.2 Hz, 1H), 7.67-7.49 (m, 2H), 7.39 (ddt, J=8.2, 2.5, 1.2 Hz, 1H), 5.62 (h, J=6.7, 6.1 Hz, 2H), 4.75 (dtd, J=9.1, 4.7, 2.9 Hz, 1H), 4.64 (ddd, J=9.3, 4.9, 2.9 Hz, 1H), 4.49-4.26 (m, 2H), 1.78 (dd, J=6.8, 3.6 Hz, 3H), 1.61 (s, 1H), 1.27 (d, J=23.8 Hz, 9H), 1.06 (dd, J=10.0, 6.5 Hz, 3H). HRMS(C) tR=1.82 min; m/z 536.1995

Example 22

(4R)-4-((R)-1-(tert-butoxy)ethyl)-3-(2-((1-(3-(4-fluoro-3-(trifluoromethoxy)phenyl)-1,2,4-oxadiazol-5-yl)ethyl)amino)pyrimidin-4-yl)oxazolidin-2-one

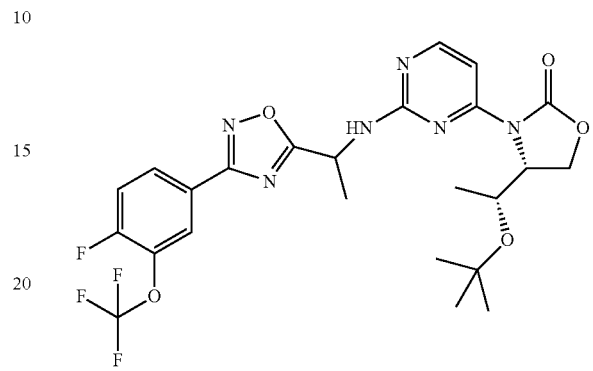

$^1$H NMR (400 MHz, CDCl$_3$) δ 8.24 (dd, J=5.8, 3.3 Hz, 1H), 8.13-7.99 (m, 2H), 7.60 (dd, J=5.8, 2.0 Hz, 1H), 5.72-5.56 (m, 1H), 5.48 (s, 1H), 4.85-4.69 (m, 1H), 1.67-1.56 (m, 1H), 4.64 (ddd, J=9.5, 4.5, 2.9 Hz, 1H), 4.53-4.28 (m, 2H), 1.77 (dd, J=7.0, 3.4 Hz, 3H), 1.27 (d, J=22.0 Hz, 9H), 1.06 (dd, J=9.8, 6.4 Hz, 3H). HRMS(C) tR=1.87 min; m/z 554.1901

Example 23

(4R)-4-((R)-1-(tert-butoxy)ethyl)-3-(2-((1-(3-(4-isopropylphenyl)-1,2,4-oxadiazol-5-yl)ethyl)amino)pyrimidin-4-yl)oxazolidin-2-one

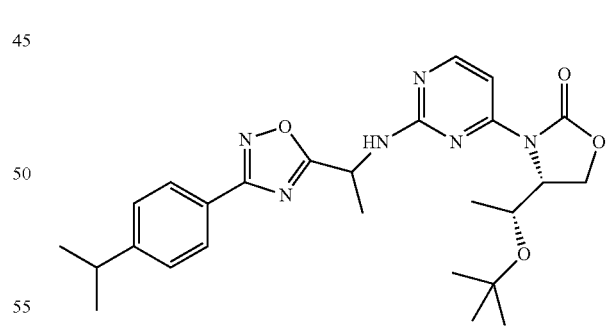

$^1$H NMR (400 MHz, CDCl$_3$) δ 8.25 (dd, J=5.9, 1.9 Hz, 1H), 8.09-7.92 (m, 2H), 7.59 (dd, J=5.7, 3.1 Hz, 1H), 7.43-7.32 (m, 2H), 5.60 (dt, J=15.5, 7.8 Hz, 2H), 4.75 (dtd, J=8.4, 5.0, 2.9 Hz, 1H), 4.64 (ddd, J=9.5, 7.1, 2.9 Hz, 1H), 4.49-4.27 (m, 2H), 2.99 (hept, J=6.9, 1H), 1.76 (dd, J=7.0, 2.8 Hz, 3H), 1.60 (dd, J=6.9, 2.8 Hz, 1H), 1.40-1.19 (m, 15H), 1.05 (dd, J=11.0, 6.5 Hz, 3H). HRMS(C) tR=2.23 min; m/z 494.2642

Example 24

(4R)-4-((R)-1-(tert-butoxy)ethyl)-3-(2-((1-(3-(1,2-dimethyl-1H-indol-4-yl)-1,2,4-oxadiazol-5-yl)ethyl)amino)pyrimidin-4-yl)oxazolidin-2-one

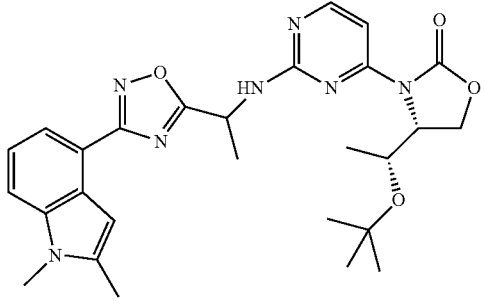 [SMILES: Cc1cc2c(-c3noc(C(C)Nc4nccc(N5C(=O)OC[C@@H]5[C@@H](C)OC(C)(C)C)n4)n3)cccc2n1C]

¹H NMR (400 MHz, CDCl₃) δ 8.26 (d, J=5.8 Hz, 1H), 7.91 (dd, J=7.5, 0.9 Hz, 1H), 7.60 (d, J=5.8 Hz, 1H), 7.44 (dt, J=8.2, 1.1 Hz, 1H), 7.33-7.20 (m, 1H), 6.99-6.89 (m, 1H), 5.66 (p, J=7.3 Hz, 1H), 4.77 (ddd, J=8.7, 4.7, 3.0 Hz, 1H), 1.66-1.60 (m, 1H), 4.66 (dd, J=9.5, 3.0 Hz, 1H), 4.53-4.44 (m, 1H), 4.38 (q, J=9.0, 8.3 Hz, 1H), 3.75 (s, 3H), 2.51 (d, J=0.9 Hz, 3H), 1.84-1.76 (m, 3H), 1.28 (d, J=26.5 Hz, 9H), 1.04 (d, J=6.5 Hz, 3H). HRMS(C) tR=1.65 min; MS m/z 519.60

Example 25

(4R)-4-((R)-1-(tert-butoxy)ethyl)-3-(2-((1-(5-(4-chlorophenyl)-4-methyloxazol-2-yl)ethyl)amino)pyrimidin-4-yl)oxazolidin-2-one

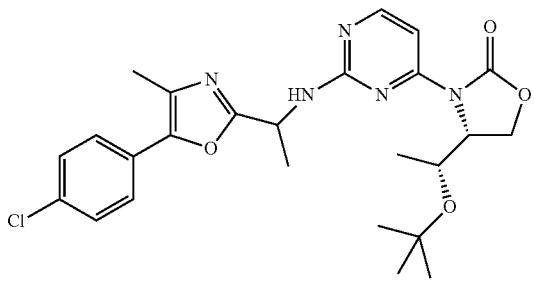 [SMILES: Cc1nc(C(C)Nc2nccc(N3C(=O)OC[C@@H]3[C@@H](C)OC(C)(C)C)n2)oc1-c1ccc(Cl)cc1]

135 mg orange-red resin (solidified upon standing). ¹H NMR (400 MHz, CDCl₃) δ 8.25 (d, J=5.7 Hz, 1H), 7.62-7.46 (m, 3H), 7.45-7.36 (m, 2H), 4.85-4.69 (m, 1H), 4.64 (ddd, J=9.1, 5.6, 3.0 Hz, 1H), 4.44 (qd, J=6.4, 4.6 Hz, 1H), 4.34 (dt, J=15.4, 9.0 Hz, 1H), 2.40 (d, J=1.3 Hz, 3H), 1.79-1.60 (m, 3H), 1.34-1.18 (m, 11H), 1.04 (dd, J=14.8, 6.5 Hz, 3H). HRMS(C) tR=2.00 min; m/z 499.1986

Example 26

(4R)-4-((R)-1-(tert-butoxy)ethyl)-3-(2-((1-(4-(4-chlorophenyl)-5-methylthiazol-2-yl)ethyl)amino)-5-fluoropyrimidin-4-yl)oxazolidin-2-one

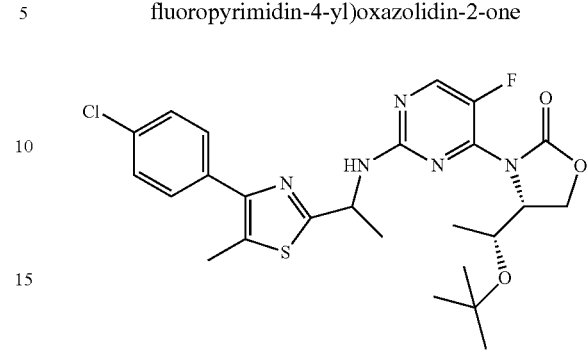

200 mg (white solid). ¹H NMR (400 MHz, CDCl₃) δ 8.25 (dd, J=2.9, 1.0 Hz, 1H), 7.68-7.52 (m, 2H), 7.47-7.35 (m, 2H), 5.99-5.65 (m, 1H), 5.49-5.20 (m, 1H), 4.67 (ddt, J=21.5, 8.9, 5.4 Hz, 1H), 4.58-4.40 (m, 2H), 4.22-4.05 (m, 1H), 2.53 (d, J=6.0 Hz, 3H), 1.74 (s, 1H), 1.16 (s, 5H), 1.13-1.05 (m, 6H), 1.01 (d, J=6.4 Hz, 3H). HRMS(B) tR=5.16 min; m/z 534.1744

Example 27

(4R)-3-(2-((1-(4-(4-bromophenyl)thiazol-2-yl)ethyl)amino)-5-fluoropyrimidin-4-yl)-4-((R)-1-(tert-butoxy)ethyl)oxazolidin-2-one

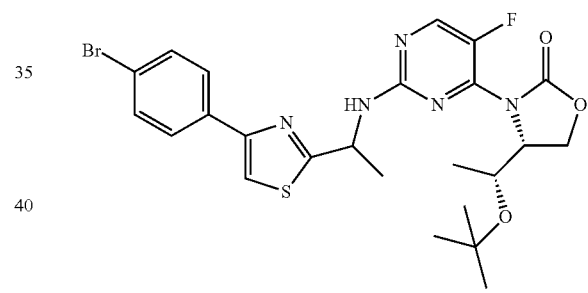

210 mg (white solid). ¹H NMR (400 MHz, CDCl₃) δ 8.25 (dd, J=2.9, 1.9 Hz, 1H), 7.87-7.71 (m, 2H), 7.62-7.50 (m, 2H), 7.40 (d, J=8.7 Hz, 1H), 5.85 (d, J=15.8 Hz, 1H), 5.58-5.36 (m, 1H), 4.81-4.57 (m, 1H), 4.57-4.39 (m, 2H), 4.23-4.00 (m, 1H), 2.07 (s, 2H), 1.77 (s, 1H), 1.16 (s, 5H), 1.11 (d, J=6.4 Hz, 2H), 1.06 (s, 5H), 0.98 (d, J=6.4 Hz, 2H). HRMS(B) tR=5.15 min; m/z 566.1079 (M+H).

Example 28

(R)-3-(2-(((S)-1-(1-(4-chloro-3-(trifluoromethoxy)phenyl)piperidin-4-yl)ethyl)amino)-5-fluoropyrimidin-4-yl)-4-((S)-1-hydroxyethyl)oxazolidin-2-one

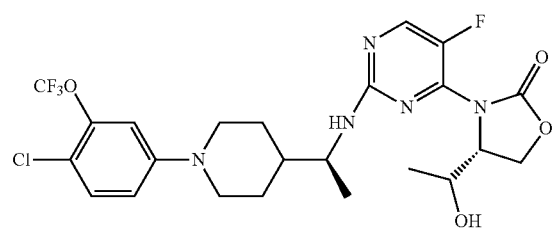

(R)-4-((S)-1-(tert-butoxy)ethyl)-3-(2-(((S)-1-(1-(4-chloro-3-(trifluoromethoxy)phenyl)piperidin-4-yl)ethyl)amino)-5-fluoropyrimidin-4-yl)oxazolidin-2-one (34 mg, 0.058 mmole) was dissolved in DCM (1 mL), TFA (1 mL) was added. The reaction solution was stirred for 2 hour at room temperature and was concentrated by rotary evaporation. The resulting residue was dissolved in DCM (2 mL) and water 2 mL) and the pH was adjusted to ~9 with NH4OH. The DCM layer was separated and concentrated by rotary evaporation to afford 28 mg of the title product as a yellow oil (ratio of two peaks with same MS: 96/4% by LC-MS). (400 MHz, CD$_2$Cl$_2$) δ 8.22 (d, J=2.27 Hz, 1H), 7.31 (d, J=8.85 Hz, 1H), 6.88-6.79 (m, 2H), 5.12 (br s, 1H), 4.61-4.50 (m, 2H), 4.46-4.37 (m, 1H), 4.26-4.15 (m, 1H), 3.93 (br s, 1H), 3.77-3.68 (m, 2H), 3.20 (br s, 1H), 2.79-2.67 (m, 2H), 1.96-1.78 (m, 2H), 1.70-1.58 (m, 1H), 1.55-1.28 (m, 2H), 1.23 (d, J=6.63 Hz, 3H), 1.19 (d, J=7.19 Hz, 3H), HRMS(C) tR=4.47 min; MS m/z 548.1689 (M+H)+

Example 29

(R)-3-(5-fluoro-2-(((S)-1-(1-(2-(1,1,1-trifluoro-2-methylpropan-2-yl)pyridin-4-yl)piperidin-4-yl)ethyl)amino)pyrimidin-4-yl)-4-((S)-1-hydroxyethyl)oxazolidin-2-one

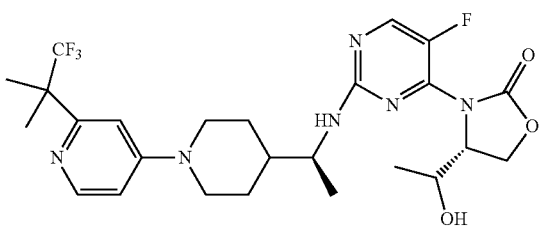 [SMILES: CC(O)[C@H]1COC(=O)N1c1nc(N[C@@H](C)C2CCN(c3ccnc(C(C)(C)C(F)(F)F)c3)CC2)ncc1F]

A cloudy solution of (R)-4-((S)-1-(tert-butoxy)ethyl)-3-(5-fluoro-2-(((S)-1-(piperidin-4-yl)ethyl)amino)pyrimidin-4-yl)oxazolidin-2-one (21 mg, 0.051 mmol), 4-bromo-2-(1,1,1-trifluoro-2-methylpropan-2-yl)pyridine (14 mg, 0.051 mmol), Pd(OAc)$_2$ (1 mg, 5 umol), BINAP (3 mg, 5 umol), and Cs$_2$CO$_3$ (25 mg, 0.077 mmol) in 6 mL toluene was heated at 90° C. overnight. The mixture was cooled to room temperature, and filtered through Celite. The celite cake was rinsed with 5 mL EtOAc. The filtrate was poured into 5 mL water. Organic layer was separated, and the aqueous was further extracted with EtOAc (5 mL). The organic extracts were combined and concentrated by rotary evaporation. The resulting crude was dissolved in DCM (1 mL), TFA (1 mL) was added. The reaction solution was stirred for 2 hour at room temperature and was concentrated by rotary evaporation. The resulting residue was dissolved in DCM (2 mL) and water (2 mL) and the pH was adjusted to ~9 with NH4OH. The DCM layer was separated and concentrated by rotary evaporation. The crude was dissolved in a mixture of MeOH (1 mL) and DMSO (1 mL) and purified by reverse phase HPLC. Selected fractions were collected and concentrated by rotary evaporation to afford the title product as a colorless oil (5 mg) (ratio of two peaks with same MS: 93/7% by LC-MS). (400 MHz, CD$_2$Cl$_2$) δ 8.16-8.08 (m, 2H), 6.79-6.75 (m, 1H), 6.57-6.52 (m, 1H), 4.97-4.86 (m, 1H), 4.47-4.39 (m, 2H), 4.33-4.25 (m, 1H), 4.11-4.02 (m, 1H), 3.89-3.75 (m, 3H), 2.97 (br s, 1H), 2.80-2.67 (m, 2H), 1.84-1.67 (m, 2H), 1.67-1.55 (m, 1H), 1.48 (s, 6H), 1.38- 1.15 (m, 2H), 1.11 (d, J=5.91 Hz, 3H), 1.07 (d, J=5.91 Hz, 3H), HRMS(C) tR=3.59 min; MS m/z 541.2557 (M+H)+

Examples 30, 31, 32, and 33

3-(2-(((S)-1-(3-(4-chlorophenyl)-1,2,4-oxadiazol-5-yl)ethyl)amino)pyrimidin-4-yl)-4-(1,1,1-trifluoropropan-2-yl)oxazolidin-2-one

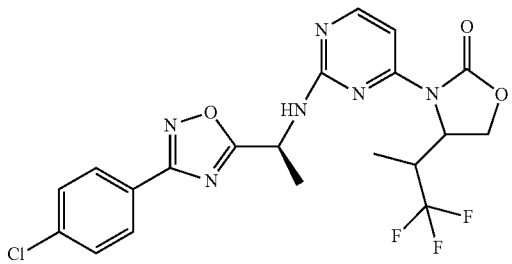 [SMILES: CC(C1COC(=O)N1c1ccnc(N[C@@H](C)c2nc(-c3ccc(Cl)cc3)no2)n1)C(F)(F)F]

To a solution of (S)-1-(5-(4-chlorophenyl)oxazol-2-yl)ethanamine 72 mg, 0.322 mmol) and 3-(2-fluoropyrimidin-4-yl)-4-(1,1,1-trifluoropropan-2-yl)oxazolidin-2-one (90 mg, 0.322 mmol) in DMSO (1 ml) was added N-ethyl-N-isopropylpropan-2-amine (2 eq, 0.113 mL, 0.645 mmol) and heated in a microwave at 120° C. for 2 hours. Dilute with EtOAc (25 ml), wash with water (25 ml), brine (25 ml), concentrate in vacuo. Flash column (silica, 40 g, 50μ) eluting w/ 0-5% EtOAc/DCM followed by Flash column (silica, 80 g, 15μ) eluting w/ 0-5% EtOAc/heptane separated 2 major peaks which were further separated via chiral SFC chromatography on an ID column (75 g/min, 120 bar, 21×250 mm) eluting 35% IPA/CO$_2$ (v/v) to give:

Example 30, Peak 1: 10 mg (white foam): $^1$H NMR (400 MHz, CDCl$_3$) δ 8.27 (d, J=5.8 Hz, 1H), 8.09-7.95 (m, 2H), 7.58 (d, J=5.7 Hz, 1H), 7.54-7.41 (m, 2H), 5.83 (s, 1H), 5.28 (s, 1H), 4.72 (s, 1H), 4.54 (dd, J=9.6, 2.5 Hz, 1H), 4.37 (d, J=9.5 Hz, 1H), 3.44-3.15 (m, 1H), 1.78 (d, J=7.0 Hz, 3H), 1.63 (s, 1H), 1.32 (d, J=7.3 Hz, 3H), 1.23 (d, J=6.1 Hz, 3H). HRMS m/z 482.1081, RT=2.90 min. Chiral RT=2.15 min Example 31, Peak 2: 38 mg (white foam): $^1$H NMR (400 MHz, CDCl$_3$) δ 8.27 (d, J=5.7 Hz, 1H), 8.09-7.93 (m, 2H), 7.58 (d, J=5.7 Hz, 1H), 7.53-7.41 (m, 2H), 5.84 (s, 1H), 5.33 (s, 1H), 4.72 (s, 1H), 4.55 (dd, J=9.6, 2.4 Hz, 1H), 4.35 (t, J=8.8 Hz, 1H), 3.39-3.17 (m, 1H), 1.78 (d, J=7.0 Hz, 3H), 1.62 (d, J=6.9 Hz, 1H), 1.32 (d, J=7.3 Hz, 3H), 1.23 (d, J=6.2 Hz, 1H). HRMS m/z 482.1081, RT=2.89 min. Chiral RT=2.43 min Example 32, Peak 3: 45 mg (white foam)$^1$H NMR (400 MHz, CDCl$_3$) δ 8.27 (d, J=5.8 Hz, 1H), 8.09-7.91 (m, 2H), 7.59 (d, J=5.7 Hz, 1H), 7.52-7.38 (m, 2H), 6.22 (s, 1H), 5.38 (d, J=48.6 Hz, 1H), 4.86 (dd, J=8.2, 4.2 Hz, 1H), 1.83-1.75 (m, 3H), 4.56 (dd, J=9.3, 2.5 Hz, 1H), 4.43 (t, J=9.2 Hz, 1H), 3.50 (s, 1H), 2.97 (d, J=46.0 Hz, 1H), 1.23 (d, J=6.2 Hz, 1H), 1.12 (d, J=7.6 Hz, 3H). HRMS m/z 482.1081, RT=2.86 min. Chiral RT=2.55 min Example 33, Peak 4: 12 mg (white foam)$^1$H NMR (400 MHz, CDCl$_3$) δ 8.28 (d, J=5.8 Hz, 1H), 8.11-7.92 (m, 2H), 7.60 (d, J=5.6 Hz, 1H), 7.53-7.40 (m, 2H), 5.77 (s, 1H), 5.45 (s, 1H), 4.96-4.77 (m, 1H), 4.57 (dd, J=9.5, 2.4 Hz, 1H), 4.44 (t, J=9.1 Hz, 1H), 2.94 (s, 1H), 1.79 (d, J=7.1 Hz, 3H), 1.63 (d, J=7.1 Hz, 1H), 1.23 (d, J=6.1 Hz, 2H), 1.20-1.08 (m, 3H). HRMS m/z 482.1081, RT=2.86 min. Chiral RT=2.66 min

Example 34

3-(5-fluoro-2-(((S)-1-(3-fluoro-4-(hydroxymethyl)phenyl)ethyl)amino)pyrimidin-4-yl)-4-(1,1,1-trifluoropropan-2-yl)oxazolidin-2-one

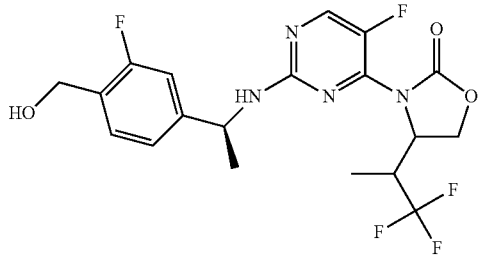 [SMILES: CC(C1COC(=O)N1c1nc(N[C@@H](C)c2ccc(CO)c(F)c2)ncc1F)C(F)(F)F]

To a solution of (S)-(4-(1-aminoethyl)-2-fluorophenyl)methanol (62.6 mg, 0.37 mmol) and 3-(2-fluoropyrimidin-4-yl)-4-(1,1,1-trifluoropropan-2-yl)oxazolidin-2-one (110 mg, 0.37 mmol) in DMSO (1 ml) was added N-ethyl-N-isopropylpropan-2-amine (2 eq, 0.129 mL, 0.74 mmol) and heated in a microwave at 120° C. for 2 hours. Dilute with EtOAc (25 ml), wash with water (25 ml), brine (25 ml), concentrate in vacuo. Flash column (silica, 40 g, 50μ) eluting w/ 5-50% EtOAc/DCM afforded 155 mg (white foam): $^1$H NMR (400 MHz, CDCl$_3$) δ 8.22 (dd, J=6.6, 2.6 Hz, 1H), 7.40 (td, J=7.8, 5.2 Hz, 1H), 7.12 (ddd, J=7.8, 4.6, 1.6 Hz, 1H), 7.03 (ddd, J=10.9, 6.3, 1.7 Hz, 1H), 5.52 (d, J=22.7 Hz, 1H), 4.90 (p, J=7.0 Hz, 1H), 4.75 (d, J=9.6 Hz, 3H), 4.59 (dt, J=15.7, 9.1 Hz, 1H), 4.41 (ddd, J=12.4, 9.1, 6.2 Hz, 1H), 1.89 (d, J=18.6 Hz, 1H), 1.16 (d, J=7.2 Hz, 1H), 1.04-0.74 (m, 2H). HRMS m/z 446.1377, RT=2.03 min.

Example 35

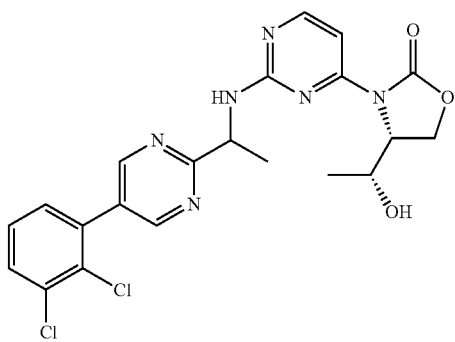 [SMILES: CC(Nc1nccc(N2C(=O)OC[C@@H]2[C@@H](C)O)n1)c1ncc(-c2cccc(Cl)c2Cl)cn1]

A solution of (R)-3-(2-fluoropyrimidin-4-yl)-4-((R)-1-hydroxyethyl)oxazolidin-2-one (18.6 mg, 0.082 mmol) and 1-(5-(2,3-dichlorophenyl)pyrimidin-2-yl)ethanamine (22 mg, 0.082 mmol) in DMSO (2 mL) was heated at 100° C. for 2 h. The reaction mixture was poured into water (20 mL), and extracted with EtOAc (2×20 mL). Combined organics were dried over Na$_2$SO$_4$, filtered and concentrated. Silica gel column chromatography ((25% MeOH in EtOAc)/Heptane 10 to 100%) provided (4R)-3-(2-(1-(5-(2,3-dichlorophenyl)pyrimidin-2-yl)ethylamino)pyrimidin-4-yl)-4-((R)-1-hydroxyethyl)oxazolidin-2-one (12 mg, approx 1:1 mixture of diastereomers) as a white solid. $^1$H NMR (400 MHz, CDCl$_3$) δ 8.72 (s, 4H), 8.15 (d, J=5.7 Hz, 2H), 7.51 (ddd, J=8.1, 2.8, 1.6 Hz, 2H), 7.40-7.11 (m, 6H), 6.07-5.96 (m, 2H), 5.32 (t, J=7.4 Hz, 1H), 5.09 (s, 1H), 4.81 (s, 1H), 4.68 (s, 1H), 4.43 (dd, J=7.3, 4.8 Hz, 2H), 4.33 (dd, J=9.4, 8.3 Hz, 1H), 4.18 (d, J=9.0 Hz, 2H), 3.62 (s, 1H), 3.23 (s, 1H), 1.62-1.58 (m, 6H), 1.07-0.97 (m, 3H), 0.87-0.77 (m, 3H). HRMS m/z 475.1039 and 475.1042 (M+H)$^+$.

Example 36

(R)-4-((R)-1-hydroxyethyl)-3-(2-(((S)-1-phenylethyl)amino)pyrimidin-4-yl)oxazolidin-2-one

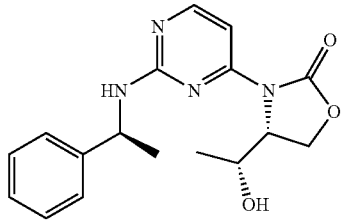 [SMILES: C[C@H](Nc1nccc(N2C(=O)OC[C@@H]2[C@@H](C)O)n1)c1ccccc1]

A solution of (R)-4-((R)-1-(tert-butoxy)ethyl)-3-(2-(((S)-1-phenylethyl)amino)pyrimidin-4-yl)oxazolidin-2-one (68 mg, 0.18 mmol) in 3 ml of DCM was cooled to 0° C., treated with 1 ml of TFA, it was stirred at same temperature for 4 hours, the solvent was removed to yield the product as a TFA salt form, it was dissolved in 2 ml of MeOH, the TFA was removed by using a PL-HCO3 MP SPE (0.9 mmol) cartridge, the solvent was removed to yield the pure product (R)-4-((R)-1-hydroxyethyl)-3-(2-(((S)-1-phenylethyl)amino)pyrimidin-4-yl)oxazolidin-2-one as a white solid (52 mg). $^1$H NMR (400 MHz, CDCl$_3$) δ 8.19 (d, J=5.8 Hz, 1H), 7.43 (d, J=5.8 Hz, 1H), 7.40-7.31 (m, 4H), 7.31-7.24 (m, 1H), 5.84 (s, 1H), 4.94 (s, 1H), 4.58 (q, J=4.9, 3.2 Hz, 1H), 4.40 (dd, J=9.3, 2.8 Hz, 1H), 4.31 (t, J=8.9 Hz, 1H), 1.56 (d, J=7.0 Hz, 3H), 0.98-0.74 (m, 3H). HRMS m/z 329.1619 (M+H)$^+$, RT=2.23 min.

Example 37 and 38

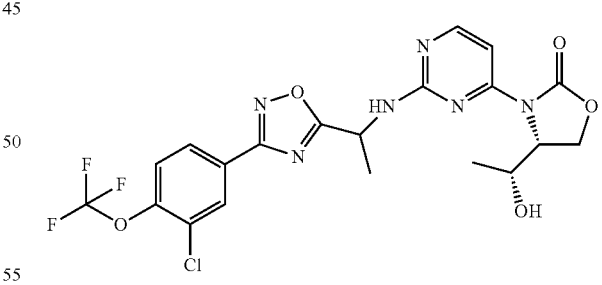

(4R)-4-((R)-1-(tert-butoxy)ethyl)-3-(2-((1-(3-(3-chloro-4-(trifluoromethoxy)phenyl)-1,2,4-oxadiazol-5-yl)ethyl)amino)pyrimidin-4-yl)oxazolidin-2-one (97 mg, 0.17 mmol) was treated with 90% TFA/water for 2 hours. Concentrate in vacuo and neutralized by passing through a column of MP-carbonate resin (2.0 g, 0.55 mmol/g eluting with MeOH/DCM/MeOH afforded 58 mg of (R)-3-(2-(((R)-1-(3-(3-chloro-4-(trifluoromethoxy)phenyl)-1,2,4-oxadiazol-5-yl)ethyl)amino)pyrimidin-4-yl)-4-(1-hydroxyethyl)oxazolidin-2-one as a waxy off-white foam. Separated the diastereomers via chiral SFC chromatography on an AD-H column (75 g/min, 120 bar, 21×250 mm) eluting 25% IPA/CO$_2$ (v/v) to give (R)-3-(2-(((R)-1-(3-(3-chloro-4-(trifluoromethoxy)phenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(3-chloro-4-(trifluoromethoxy)phenyl)-1,2,4-oxadiazol-5-yl)ethyl)amino)pyrimidin-4-yl)-4-((R)-1-hydroxyethyl)oxazolidin-2-one Example 37 Peak 1: 23 mg (off-white foam). $^1$H NMR (400 MHz, CDCl$_3$) δ 8.32-8.17 (m, 4H), 8.01 (dd, J=8.6, 2.1 Hz, 2H), 7.54 (d, J=5.7 Hz, 2H), 7.45 (dq, J=8.4, 1.5 Hz, 2H), 6.16 (s, 2H), 5.32 (s, 3H), 4.82-4.60 (m, 2H), 4.53 (dd, J=9.3, 2.4 Hz, 2H), 4.43 (s, 2H), 4.29 (q, J=8.9 Hz, 2H), 4.05 (p, J=6.1 Hz, 1H), 3.51 (s, 5H), 1.80 (s, 1H), 1.22 (t, J=6.5 Hz, 12H). HRMS(B) tR=2.75 min. MS m/z 514.0979 Chiral RT=2.10 min Example 38 Peak 2: 58 mg (off-white foam). $^1$H NMR (400 MHz, CDCl$_3$) δ 8.23 (dd, J=12.4, 3.9 Hz, 8H), 8.01 (dd, J=8.5, 2.1 Hz, 4H), 7.71-7.36 (m, 8H), 6.29 (s, 4H), 5.37 (d, J=37.2 Hz, 5H), 4.86 (ddd, J=7.7, 4.9, 2.4 Hz, 4H), 4.55 (dd, J=9.5, 2.6 Hz, 4H), 4.41 (t, J=8.9 Hz, 4H), 4.19-3.77 (m, 5H), 3.51 (s, 3H), 1.83 (s, 1H), 1.23 (d, J=6.1 Hz, 4H), 1.12-0.95 (m, 12H). HRMS(B) tR=2.73 min. MS m/z 514.0979 Chiral RT=3.70 min The compounds in Table 28a were prepared using methods similar to those described for the preparation of Examples 35, 36, or 37/38.

TABLE 28a

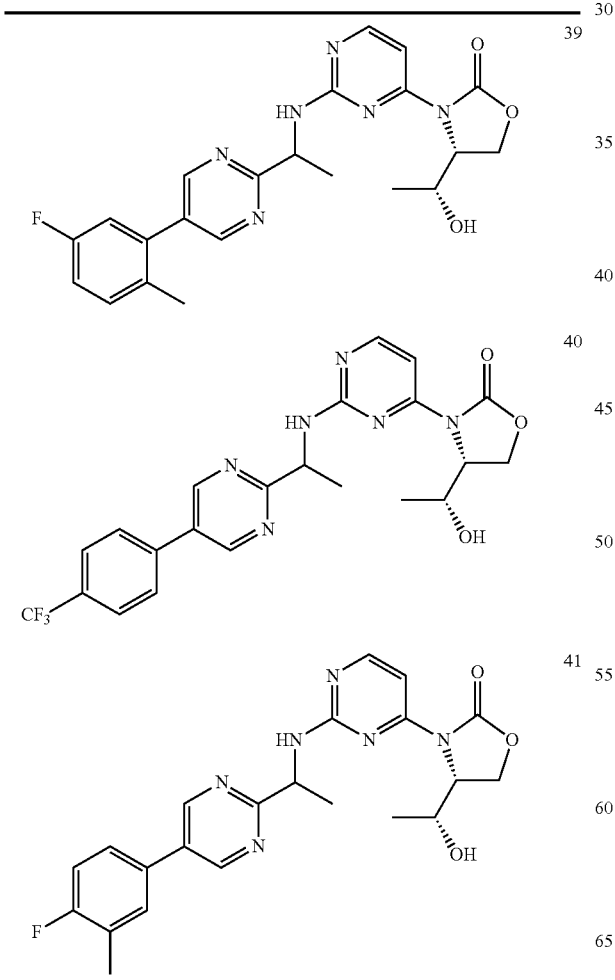

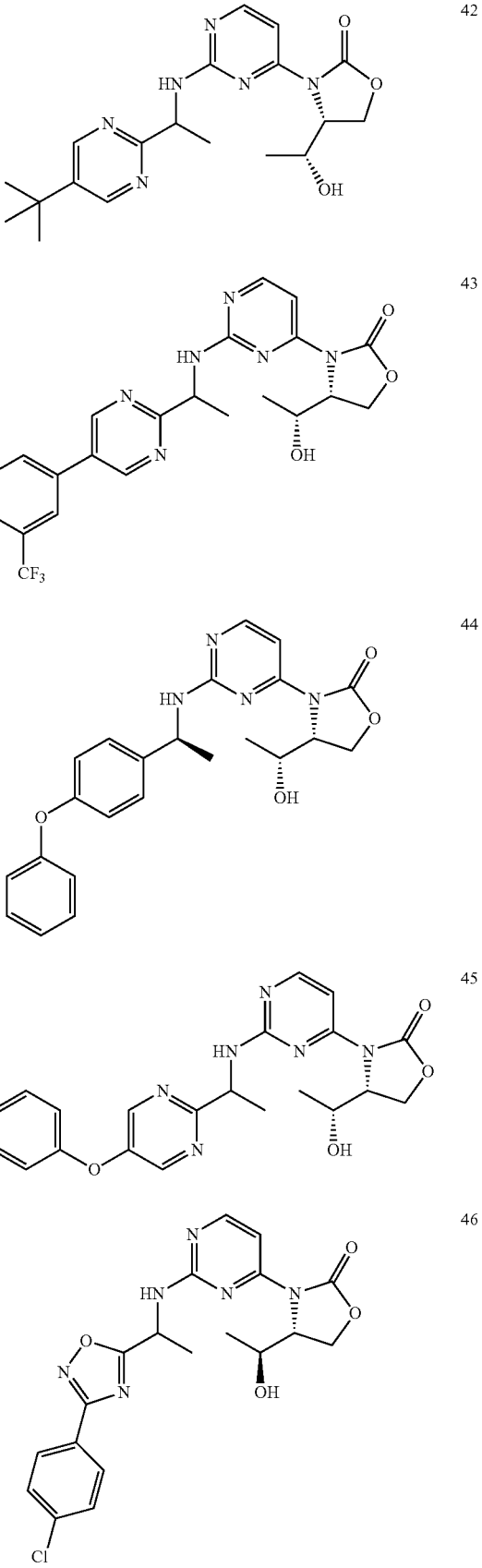

TABLE 28a-continued
| | |
|---|---|
| 47 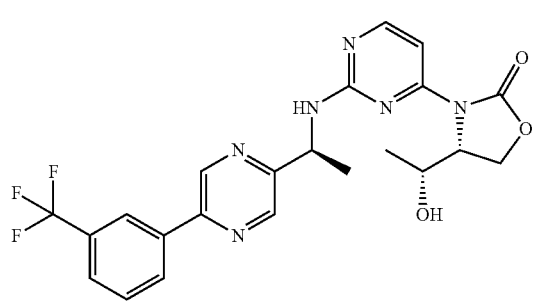 [SMILES: C[C@H](Nc1nccc(N2C(=O)OC[C@@H]2[C@@H](C)O)n1)c1cnc(-c2cccc(C(F)(F)F)c2)cn1] | 52 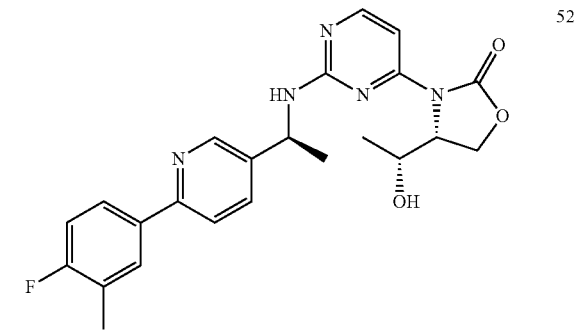 |
| 48 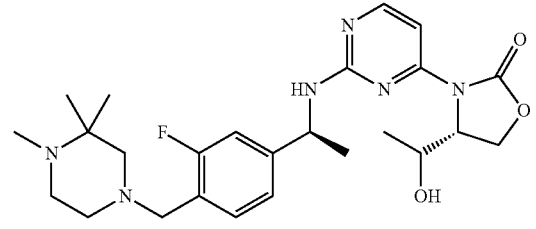 [SMILES: CC(O)[C@H]1COC(=O)N1c1ccnc(N[C@@H](C)c2ccc(CN3CCN(C)C(C)(C)C3)c(F)c2)n1] | 53 |
| 49 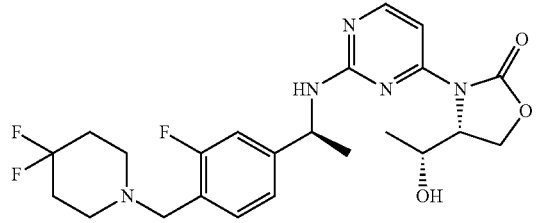 [SMILES: C[C@H](Nc1nccc(N2C(=O)OC[C@@H]2[C@@H](C)O)n1)c1ccc(CN2CCC(F)(F)CC2)c(F)c1] | 54 |
| 50 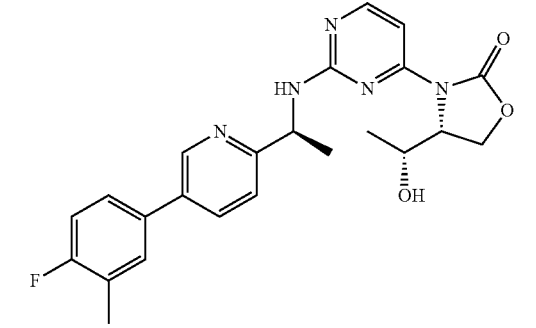 [SMILES: Cc1cc(-c2ccc([C@H](C)Nc3nccc(N4C(=O)OC[C@@H]4[C@@H](C)O)n3)nc2)ccc1F] | 55 |
| 51 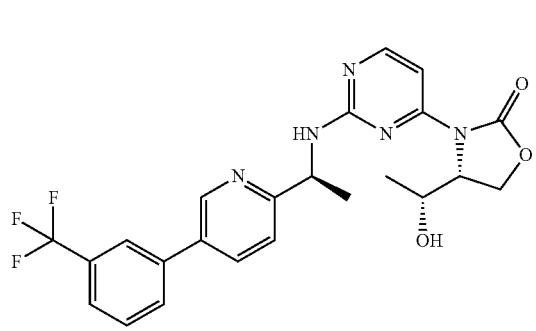 [SMILES: C[C@H](Nc1nccc(N2C(=O)OC[C@@H]2[C@@H](C)O)n1)c1ccc(-c2ccnc(C(F)(F)F)c2)cn1] | 56 |

TABLE 28a-continued
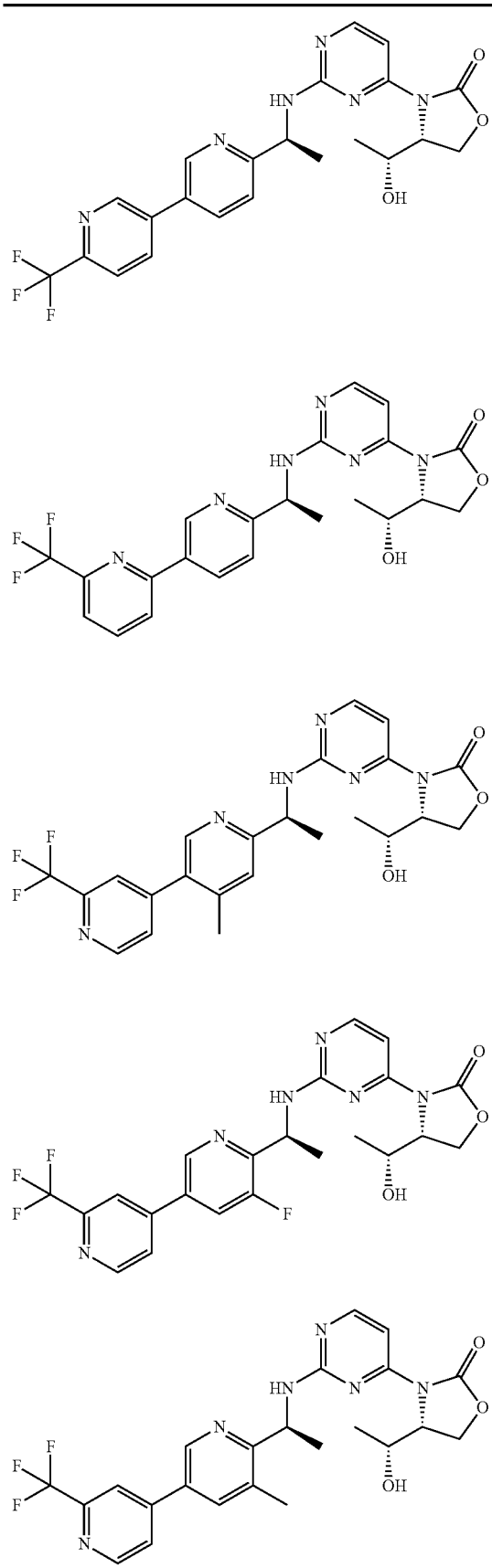
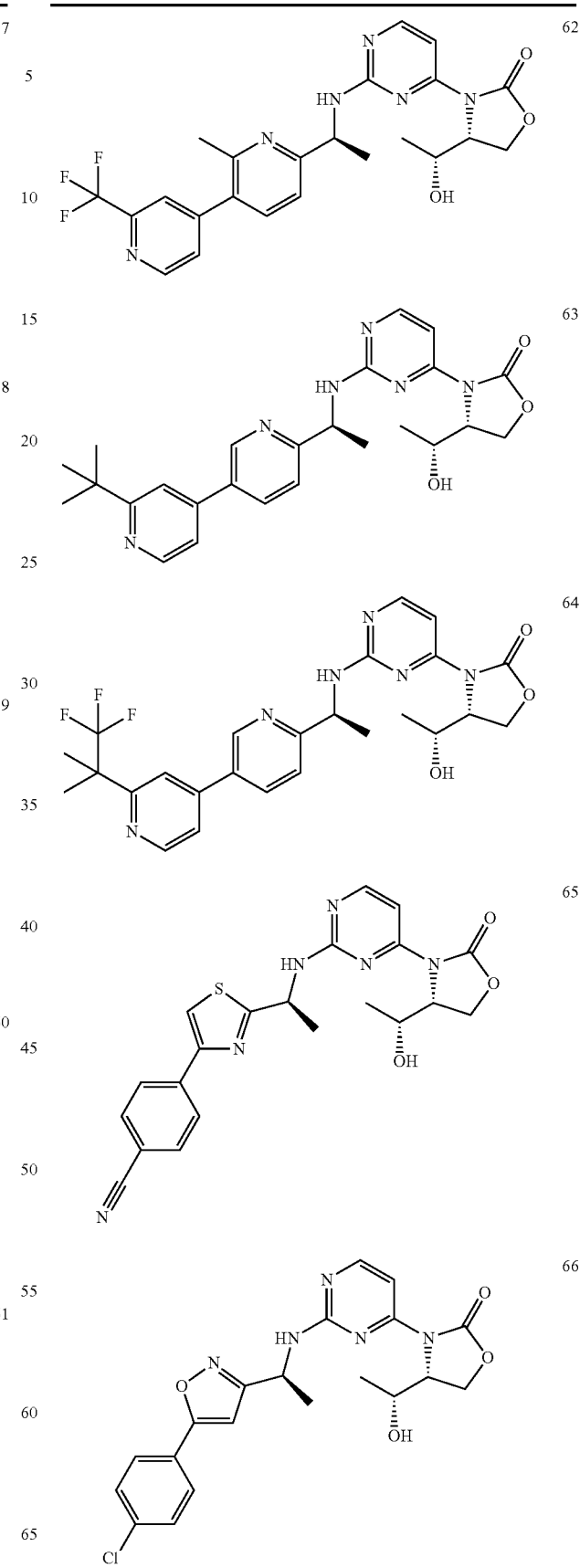

TABLE 28a-continued
| | |
|---|---|
| 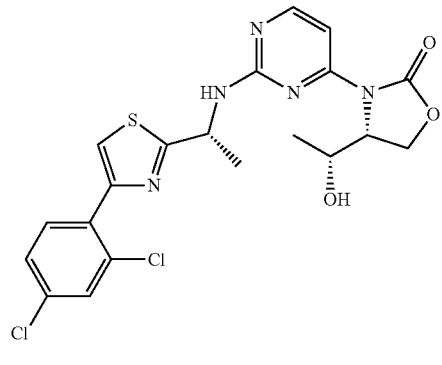 [SMILES: C[C@@H](Nc1nccc(N2C(=O)OC[C@@H]2[C@@H](C)O)n1)c1nc(-c2ccc(Cl)cc2Cl)cs1] | 67 |
| 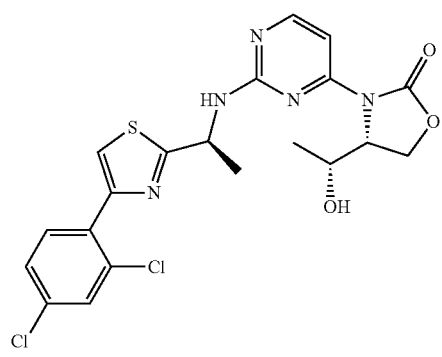 [SMILES: C[C@H](Nc1nccc(N2C(=O)OC[C@@H]2[C@@H](C)O)n1)c1nc(-c2ccc(Cl)cc2Cl)cs1] | 68 |
| 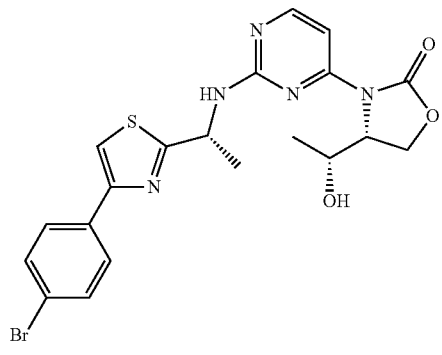 [SMILES: C[C@@H](Nc1nccc(N2C(=O)OC[C@@H]2[C@@H](C)O)n1)c1nc(-c2ccc(Br)cc2)cs1] | 69 |
| 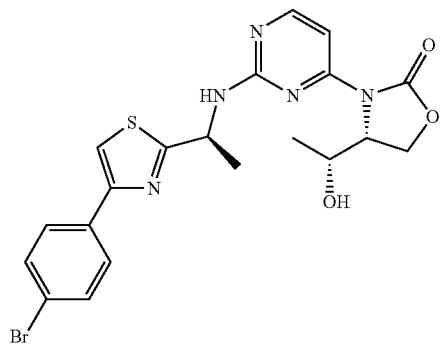 | 70 |
TABLE 28a-continued
| | |
|---|---|
| 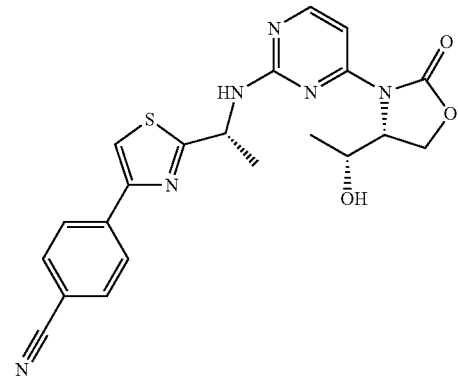 [SMILES: C[C@@H](Nc1nccc(N2C(=O)OC[C@@H]2[C@@H](C)O)n1)c1nc(-c2ccc(C#N)cc2)cs1] | 71 |
| 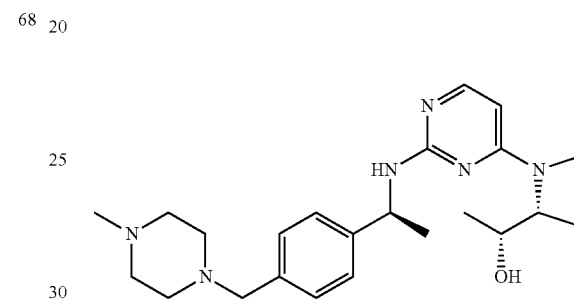 | 72 |
| 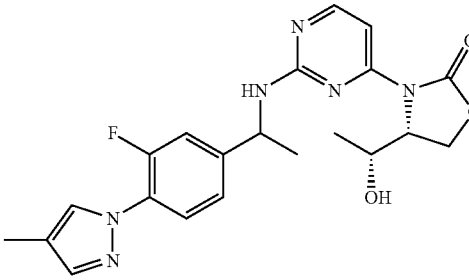 | 73 |
| 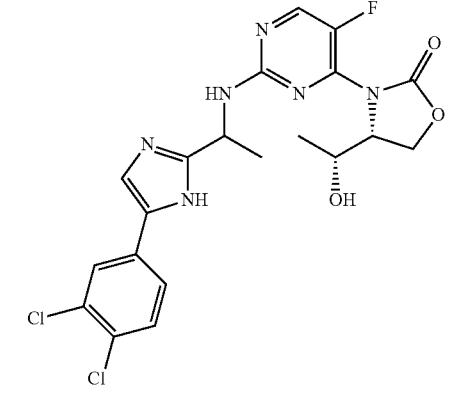 [SMILES: CC(Nc1ncc(F)c(N2C(=O)OC[C@@H]2[C@@H](C)O)n1)c1ncc(-c2ccc(Cl)c(Cl)c2)[nH]1] | 74 |

TABLE 28a-continued

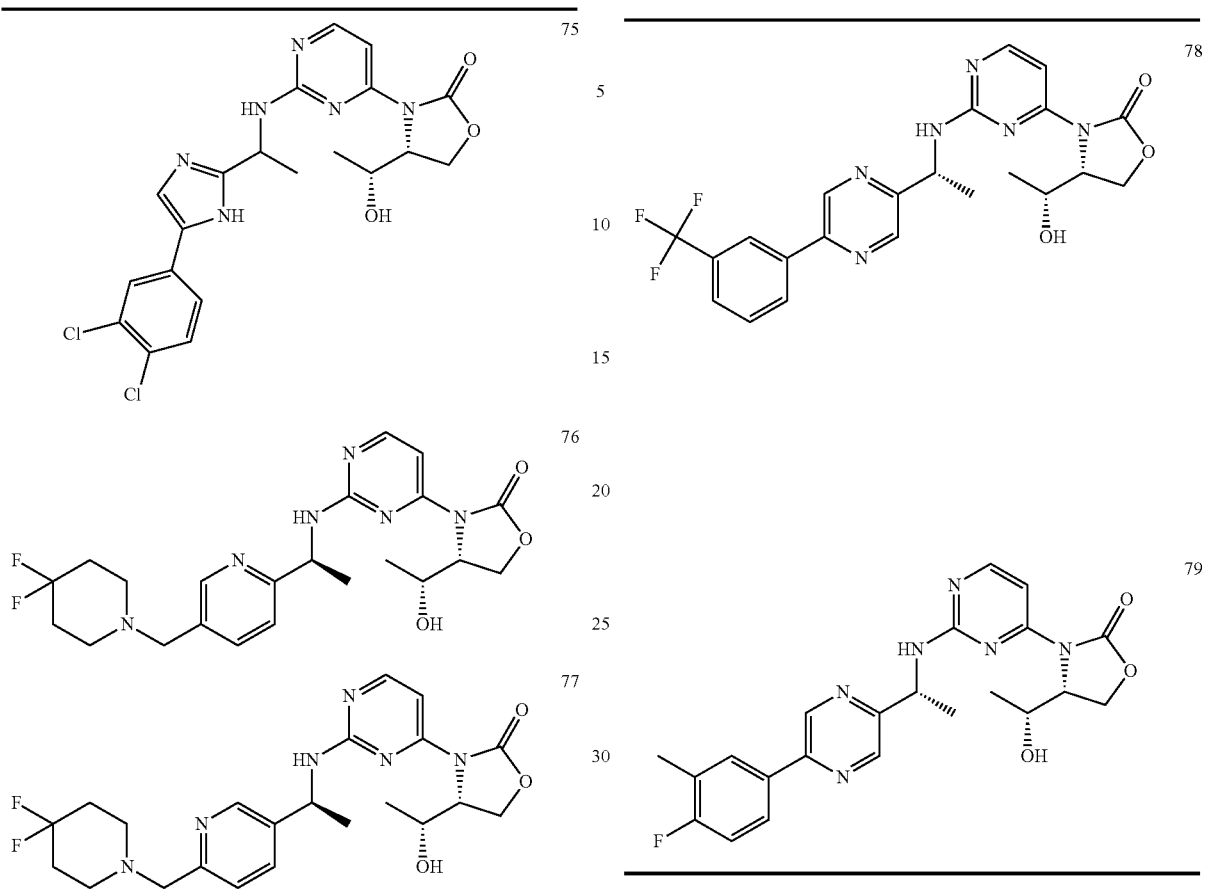

TABLE 28b

Chemical name, NMR chemical shifts and LCMS signal for each compound listed in Table 28a.

| Example: Name | $^1$H NMR (400 MHz) δ ppm | LCMS |
| --- | --- | --- |
| 39: (4R)-3-(2-(1-(5-(5-fluoro-2-methylphenyl)pyrimidin-2-yl)ethylamino)pyrimidin-4-yl)-4-((R)-1-hydroxyethyl)oxazolidin-2-one | (CDCl$_3$) δ 8.71 (d, J = 1.8 Hz, 4H), 8.23 (dd, J = 5.8, 1.0 Hz, 2H), 7.44 (dd, J = 12.1, 5.7 Hz, 2H), 7.35-7.26 (m, 3H), 7.08 (tt, J = 8.4, 2.8 Hz, 2H), 6.95 (dt, J = 9.0, 2.7 Hz, 2H), 6.16 (t, J = 8.5 Hz, 2H), 5.41 (p, J = 7.0 Hz, 1H), 5.20 (s, 1H), 4.91 (s, 1H), 4.78 (s, 1H), 4.58-4.49 (m, 2H), 4.42 (dd, J = 9.4, 8.3 Hz, 2H), 4.29 (s, 2H), 3.84 (s, 1H), 3.48 (br s, 1H), 2.27 (s, 6H), 1.95 (br s, 2H), 1.71-1.67 (m, 3H), 1.38-1.18 (m, 6H), 1.12 (br s, 3H) (approx 1:1 mixture of diastereomers) | HRMS (B) m/z 439.1865 and 439.1865 (M + H)$^+$ |
| 40: (4R)-4-((R)-1-hydroxyethyl)-3-(2-((1-(5-(4-(trifluoromethyl)phenyl)pyrimidin-2-yl)ethyl)amino)pyrimidin-4-yl)oxazolidin-2-one | (CDCl$_3$) δ 8.95 (s, 4H), 8.41 (d, J = 5.8, 1H), 8.21 (d, J = 5.8 Hz, 1H), 7.92-7.66 (m, 7H), 7.48-7.44 (m, 3H), 6.45-6.35 (m, 2H), 5.41 (p, J = 6.9 Hz, 1H), 5.22 (br s, 1H), 4.94-4.90 (m, 2H), 4.78 (br s, 1H), 4.65-4.35 (m, 4H), 4.30 (br s, 1H), 3.49 (br s, 1H), 2.77 (br s, 1H), 1.70-1.66 (m, 6H), 1.25-1.21 (m, 3H), 1.09 (br s, 3H) (approx 1:1 mixture of diastereomers) | HRMS (B) m/z 475.1684 (M + H)$^+$ |

TABLE 28b-continued

Chemical name, NMR chemical shifts and LCMS signal for each compound listed in Table 28a.

| Example: Name | ¹H NMR (400 MHz) δ ppm | LCMS |
|---|---|---|
| 41: (4R)-3-(2-(1-(5-(4-fluoro-3-methylphenyl)pyrimidin-2-yl)ethylamino)pyrimidin-4-yl)-4-((R)-1-hydroxyethyl)oxazolidin-2-one | (CDCl$_3$) δ 8.85-8.75 (m, 4H), 8.16-8.08 (m, 2H), 7.38-7.20 (m, 6H), 7.09-7.05 (m, 2H), 6.08-6.04 (m, 2H), 5.34-5.25 (m, 1H), 5.14-5.10 (m, 1H), 4.86-4.78 (m, 1H), 4.57 (dd, J = 9.5, 2.8 Hz, 1H), 4.49-4.28 (m, 3H), 3.54 (br s, 1H), 2.29 (br s, 6H), 1.58-1.53 (m, 6H), 1.19-1.12 (m, 3H), 1.00 (br s, 3H) (approx 1:1 mixture of diastereomers) | HRMS (B) m/z 439.1875 (M + H)⁺. |
| 42: (4R)-3-(2-((1-(5-(tert-butyl)pyrimidin-2-yl)ethyl)amino)pyrimidin-4-yl)-4-((R)-1-hydroxyethyl)oxazolidin-2-one | (CDCl$_3$) δ 8.74-8.72 (m, 4H), 8.20 (d, J = 5.8 Hz, 2H), 7.46-7.40 (m, 2H), 6.19-6.15 (m, 2H), 5.37-5.29 (m, 1H), 5.30 (s, 1H), 4.98-4.86 (m, 1H), 4.82 (s, 1H), 4.61-4.50 (m, 3H), 4.47-4.37 (m, 2H), 4.32-4.21 (m, 2H), 3.84 (s, 1H), 1.63-1.58 (m, 6H), 1.39-1.37 (m, 18H), 1.24-1.20 (m, 3H), 1.14-1.00 (m, 3H) (approx 1:1 mixture of diastereomers) | HRMS (B) m/z 387.2135 (M + H)⁺ |
| 43: (4R)-4-((R)-1-hydroxyethyl)-3-(2-(1-(5-(3-(trifluoromethyl)phenyl)pyrimidin-2-yl)ethylamino)pyrimidin-4-yl)oxazolidin-2-one | (CDCl$_3$) δ 8.94 (d, J = 4.4 Hz, 4H), 8.23 (dd, J = 5.8, 2.2 Hz, 2H), 7.86-7.63 (m, 8H), 7.44 (dd, J = 13.5, 5.7 Hz, 2H), 6.12 (dd, J = 15.1, 7.4 Hz, 2H), 5.41 (t, J = 7.4 Hz, 1H), 5.20 (br s, 1H), 4.89 (d, J = 6.7 Hz, 1H), 4.80 (s, 1H), 4.58-4.48 (m, 2H), 4.43 (dd, J = 9.3, 8.2 Hz, 2H), 4.30 (br s, 1H), 3.77 (br s, 1H), 3.36 (br s, 1H), 1.90 (br s, 3H), 1.69 (d, J = 2.2 Hz, 3H), 1.37-1.17 (m, 3H), 1.12 (br s, 3H) (approx 1:1 mixture of diastereomers) | HRMS (B) m/z 475.1682 and 475.1689 (M + H)⁺. |
| 44: (R)-4-((R)-1-hydroxyethyl)-3-(2-(((S)-1-(4-phenoxyphenyl)ethyl)amino)pyrimidin-4-yl)oxazolidin-2-one | (CDCl$_3$) δ 8.21 (d, J = 5.9 Hz, 1H), 7.45 (d, J = 5.7 Hz, 1H), 7.42-7.26 (m, 4H), 7.13 (dd, J = 8.1, 6.7 Hz, 1H), 7.07-6.88 (m, 4H), 5.66 (b, 1H), 4.97 (s, 1H), 4.67 (ddd, J = 8.2, 5.1, 2.5 Hz, 1H), 4.51-4.25 (m, 2H), 3.61 (b, 1H), 1.56 (d, J = 6.9 Hz, 3H), 0.95 (d, J = 22.9 Hz, 3H). | HRMS (B) m/z 421.1875, (M + H)⁺, RT = 2.56 min. |
| 45: (4R)-3-(2-((1-(5-(4-fluorophenoxy)pyrimidin-2-yl)ethyl)amino)pyrimidin-4-yl)-4-((R)-1-hydroxyethyl)oxazolidin-2-one | | HRMS (B) m/z 441.1676, (M + H)⁺, RT = 2.13 min. |
| 46: (4R)-3-(2-((1-(3-(4-chlorophenyl)-1,2,4-oxadiazol-5-yl)ethyl)amino)pyrimidin-4-yl)-4-((S)-1-hydroxyethyl)oxazolidin-2-one. | | HRMS (B) m/z 431.1219, (M + H)⁺, RT = 2.16 min. |
| 47: (R)-4-((R)-1-hydroxyethyl)-3-(2-(((S)-1-(5-(3-(trifluoromethyl)phenyl)pyrazin-2-yl)ethyl)amino)pyrimidin-4-yl)oxazolidin-2-one | ¹H NMR (400 MHz, MeOD) δ 9.13 (d, J = 1.5 Hz, 1H), 8.73 (d, J = 1.4 Hz, 1H), 8.39 (s, 1H), 8.32 (d, J = 7.9 Hz, 1H), 8.16 (d, J = 5.9 Hz, 1H), 7.78 (d, J = 7.8 Hz, 1H), 7.72 (t, J = 7.8 Hz, 1H), 7.39 (d, J = 5.8 Hz, 1H), 5.28 (q, J = 7.0 Hz, 1H), 4.51 (dd, J = 9.2, 2.8 Hz, 1H), 4.39 (t, J = 8.9 Hz, 1H), 3.81 (br s, 0H), 1.65 (d, J = 7.1 Hz, 3H), 0.80 (br s, 3H); | HRMS m/z 475.1686 (M + H)⁺. |
| 48: (R)-3-(2-((S)-1-(3-fluoro-4-((3,3,4-trimethylpiperazin-1-yl)methyl)phenyl)ethylamino)pyrimidin-4-yl)-4-((S)-1-hydroxyethyl)oxazolidin-2-one | ¹H NMR (400 MHz, MeOD) δ 8.11 (d, J = 5.8 Hz, 1H), 7.40-7.30 (m, 2H), 7.16 (dd, J = 8.0, 1.7 Hz, 1H), 7.07 (dd, J = 11.2, 1.7 Hz, 1H), 5.08 (q, J = 7.0 Hz, 1H), 4.80 (br s, 1H), 4.52 (dd, J = 9.2, 2.8 Hz, 1H), 4.38 (t, J = 8.9 Hz, 1H), 3.99 (br s, 1H), 3.48 (s, 2H), 2.55 (t, J = 4.9 Hz, 2H), 2.48 (br s, 2H), 2.20-2.18 (m, 5H), 1.50 (d, J = 7.0 Hz, 3H), 1.04 (s, 6H), 0.78 (br s, 3H); | HRMS m/z 487.2808 (M + H)⁺. |

TABLE 28b-continued

Chemical name, NMR chemical shifts and LCMS signal for each compound listed in Table 28a.

| Example: Name | $^1$H NMR (400 MHz) δ ppm | LCMS |
|---|---|---|
| 49: (R)-3-(2-((S)-1-(4-((4,4-difluoropiperidin-1-yl)methyl)-3-fluorophenyl)ethylamino)pyrimidin-4-yl)-4-((R)-1-hydroxyethyl)oxazolidin-2-one | $^1$H NMR (400 MHz, MeOD) δ 8.11 (d, J = 5.8 Hz, 1H), 7.38-7.30 (m, 2H), 7.18 (dd, J = 7.9, 1.7 Hz, 1H), 7.10 (d, J = 11.3 Hz, 1H), 5.08 (q, J = 6.9 Hz, 1H), 4.80 (br s, 1H), 4.52 (dd, J = 9.1, 2.8 Hz, 1H), 4.38 (t, J = 8.9 Hz, 1H), 4.01 (br s, 1H), 3.60 (s, 2H), 2.60-2.58 (m, 4H), 2.05-1.89 (m, 4H), 1.50 (d, J = 7.0 Hz, 3H), 0.77 (br s, 3H) | HRMS m/z 480.2204 (M + H)$^+$. |
| 50: (R)-3-(2-(((S)-1-(5-(4-fluoro-3-methylphenyl)pyridin-2-yl)ethyl)amino)pyrimidin-4-yl)-4-((R)-1-hydroxyethyl)oxazolidin-2-one | $^1$H NMR (400 MHz, MeOD) δ 8.70 (d, J = 2.5 Hz, 1H), 8.14 (s, 1H), 7.97 (dd, J = 8.2, 2.3 Hz, 1H), 7.55-7.43 (m, 3H), 7.36 (d, J = 5.8 Hz, 1H), 7.13 (dd, J = 9.5, 8.5 Hz, 1H), 5.16 (q, J = 7.0 Hz, 1H), 4.78 (br s, 1H), 4.51 (dd, J = 9.3, 2.7 Hz, 1H), 4.37 (t, J = 8.9 Hz, 1H), 3.67 (br s, 1H), 2.33 (d, J = 1.9 Hz, 3H), 1.59 (d, J = 7.1 Hz, 3H), 0.68 (br s, 3H); | HRMS m/z 438.1927 (M + H)$^+$. |
| 51: (R)-4-((R)-1-hydroxyethyl)-3-(2-(((S)-1-(5-(3-(trifluoromethyl)phenyl)pyridin-2-yl)amino)pyrimidin-4-yl)oxazolidin-2-one | $^1$H NMR (400 MHz, MeOD) δ 8.79 (d, J = 2.5 Hz, 1H), 8.14 (s, 1H), 8.06 (dd, J = 8.3, 2.4 Hz, 1H), 7.95-7.89 (m, 2H), 7.74-7.64 (m, 2H), 7.55 (d, J = 8.2 Hz, 1H), 7.36 (d, J = 5.7 Hz, 1H), 5.18 (q, J = 7.0 Hz, 1H), 4.79 (s, 1H), 4.51 (dd, J = 9.1, 2.7 Hz, 1H), 4.37 (t, J = 8.9 Hz, 1H), 3.63 (br s, 1H), 1.60 (d, J = 7.0 Hz, 3H), 0.68 (br s, 3H); | HRMS m/z 474.1739 (M + H)$^+$. |
| 52: (R)-3-(2-(((S)-1-(6-(4-fluoro-3-methylphenyl)pyridin-3-yl)ethyl)amino)pyrimidin-4-yl)-4-((R)-1-hydroxyethyl)oxazolidin-2-one | $^1$H NMR (400 MHz, MeOD) δ 8.60 (d, J = 2.2 Hz, 1H), 8.13 (d, J = 6.0 Hz, 1H), 7.88 (dd, J = 8.3, 2.3 Hz, 1H), 7.84-7.69 (m, 3H), 7.35 (d, J = 5.8 Hz, 1H), 7.12 (t, J = 9.0 Hz, 1H), 5.17 (q, J = 7.0 Hz, 1H), 4.83 (br s, 1H), 4.52 (dd, J = 9.3, 2.7 Hz, 1H), 4.39 (t, J = 8.9 Hz, 1H), 3.87 (br s, 1H), 2.33 (d, J = 1.9 Hz, 3H), 1.59 (d, J = 7.0 Hz, 3H), 0.76 (br s, 3H); | HRMS m/z 438.1985 (M + H)$^+$. |
| 53: (R)-4-((R)-1-hydroxyethyl)-3-(2-(((S)-1-(6-(3-(trifluoromethyl)phenyl)pyridin-3-yl)ethyl)amino)pyrimidin-4-yl)oxazolidin-2-one | $^1$H NMR (400 MHz, MeOD) δ 8.68 (d, J = 2.1 Hz, 1H), 8.27 (s, 1H), 8.19 (d, J = 7.7 Hz, 1H), 8.14 (d, J = 5.8 Hz, 1H), 7.98-7.85 (m, 2H), 7.76-7.62 (m, 2H), 7.35 (d, J = 5.8 Hz, 1H), 5.19 (q, J = 7.0 Hz, 1H), 4.83 (s, 1H), 4.52 (dd, J = 9.1, 2.7 Hz, 1H), 4.39 (t, J = 8.9 Hz, 1H), 3.84 (br s, 1H), 1.60 (d, J = 7.1 Hz, 3H), 0.75 (br s, 3H); | HRMS m/z 474.1816 (M + H)$^+$. |
| 54: (R)-3-(2-(((S)-1-(5-(4-fluoro-3-methylphenyl)pyrazin-2-yl)ethyl)amino)pyrimidin-4-yl)-4-((R)-1-hydroxyethyl)oxazolidin-2-one | $^1$H NMR (400 MHz, MeOD) δ 9.00 (d, J = 1.5 Hz, 1H), 8.65 (d, J = 1.5 Hz, 1H), 8.15 (d, J = 5.9 Hz, 1H), 7.94 (ddd, J = 7.3, 2.3, 0.9 Hz, 1H), 7.87 (ddd, J = 7.7, 4.9, 2.4 Hz, 1H), 7.38 (d, J = 5.8 Hz, 1H), 7.16 (dd, J = 9.5, 8.6 Hz, 1H), 5.25 (q, J = 7.0 Hz, 1H), 4.82 (br s, 1H), 4.51 (dd, J = 9.3, 2.8 Hz, 1H), 4.38 (t, J = 8.9 Hz, 1H), 3.84 (br s, 1H), 2.35 (d, J = 1.8 Hz, 3H), 1.63 (d, J = 7.1 Hz, 3H), 0.80 (br s, 3H); | HRMS m/z 439.1872 (M + H)$^+$. |
| 55: (R)-4-((R)-1-hydroxyethyl)-3-(2-(((S)-1-(2'-(trifluoromethyl)-[3,4'-bipyridin]-6-yl)ethyl)amino)pyrimidin-4-yl)oxazolidin-2-one | 1H NMR (400 MHz, MeOD) δ 8.95 (d, J = 2.3 Hz, 1H), 8.79 (d, J = 5.1 Hz, 1H), 8.22 (dd, J = 8.3, 2.4 Hz, 1H), 8.19-8.11 (m, 2H), 7.99 (dd, J = 5.1, 1.7 Hz, 1H), 7.61 (d, J = 8.3 Hz, 1H), 7.37 (d, J = 5.8 Hz, 1H), 5.19 (q, J = 7.0 Hz, 1H), 4.78 (s, 1H), 4.55-4.45 (m, 1H), 4.37 (t, J = 8.9 Hz, 1H), 3.73-3.44 (m, 1H), 1.60 (d, J = 7.0 Hz, 3H), 0.69 (br s, 3H); | HRMS m/z 475.1685 (M + H)$^+$. |

TABLE 28b-continued

Chemical name, NMR chemical shifts and LCMS signal for each compound listed in Table 28a.

| Example: Name | $^1$H NMR (400 MHz) δ ppm | LCMS |
|---|---|---|
| 56: (R)-4-((R)-1-hydroxyethyl)-3-(2-(((S)-1-(6'-(trifluoromethyl)-[2,3'-bipyridin]-5-yl)ethyl)amino)pyrimidin-4-yl)oxazolidin-2-one | $^1$H NMR (400 MHz, MeOD) δ 9.30 (d, J = 2.0 Hz, 1H), 8.75 (s, 1H), 8.60 (dd, J = 8.2, 2.1 Hz, 1H), 8.14 (d, J = 5.8 Hz, 5H), 7.98 (t, J = 1.4 Hz, 2H), 7.93 (d, J = 8.4 Hz, 1H), 7.36 (d, J = 5.8 Hz, 1H), 5.20 (q, J = 7.0 Hz, 1H), 4.83 (br s, 1H), 4.52 (dd, J = 9.2, 2.7 Hz, 1H), 4.39 (t, J = 8.9 Hz, 1H), 3.80 (br s, 1H), 1.61 (d, J = 7.0 Hz, 3H), 0.75 (br s, 3H); | HRMS m/z 475.1689 (M + H)$^+$. |
| 57: (R)-4-((R)-1-hydroxyethyl)-3-(2-(((S)-1-(6'-(trifluoromethyl)-[3,3'-bipyridin]-6-yl)ethyl)amino)pyrimidin-4-yl)oxazolidin-2-one | $^1$H NMR (400 MHz, MeOD) δ 9.03 (d, J = 2.2 Hz, 1H), 8.88 (d, J = 1.8 Hz, 1H), 8.34 (dd, J = 8.3, 2.2 Hz, 1H), 8.15 (dd, J = 8.1, 2.5 Hz, 2H), 7.93 (d, J = 8.4 Hz, 1H), 7.63-7.58 (m, 1H), 7.37 (d, J = 5.8 Hz, 1H), 5.19 (q, J = 7.1 Hz, 1H), 4.79 (br s, 1H), 4.51 (dd, J = 9.1, 2.7 Hz, 1H), 4.38 (t, J = 8.9 Hz, 1H), 3.71-3.47 (m, 1H), 1.61 (d, J = 7.1 Hz, 3H), 0.70 (br s, 3H); | HRMS m/z 475.1689 (M + H)$^+$. |
| 58: (R)-4-((R)-1-hydroxyethyl)-3-(2-(((S)-1-(6-(trifluoromethyl)-[2,3'-bipyridin]-6'-yl)ethyl)amino)pyrimidin-4-yl)oxazolidin-2-one | $^1$H NMR (400 MHz, MeOD) δ 9.24-9.19 (m, 1H), 8.47 (dd, J = 8.3, 2.3 Hz, 1H), 8.24-8.07 (m, 3H), 7.79 (dd, J = 7.7, 0.9 Hz, 1H), 7.60 (d, J = 8.2 Hz, 2H), 7.39 (d, J = 5.9 Hz, 1H), 5.21 (q, J = 7.0 Hz, 1H), 4.80 (br s, 1H), 4.58-4.44 (m, 1H), 4.38 (t, J = 8.8 Hz, 1H), 3.69 (br s, 1H), 1.61 (d, J = 7.1 Hz, 3H), 0.69 (br s, 3H); | HRMS m/z 475.1721 (M + H)$^+$. |
| 59: (R)-4-((R)-1-hydroxyethyl)-3-(2-(((S)-1-(4-methyl-2'-(trifluoromethyl)-[3,4'-bipyridin]-6-yl)ethyl)amino)pyrimidin-4-yl)oxazolidin-2-one | $^1$H NMR (400 MHz, MeOD) δ 8.81 (d, J = 5.0 Hz, 1H), 8.38 (s, 1H), 8.15 (d, J = 5.1 Hz, 1H), 7.90 (s, 1H), 7.72 (dd, J = 5.0, 1.6 Hz, 1H), 7.45 (s, 1H), 7.37 (d, J = 5.8 Hz, 1H), 5.14 (q, J = 7.0 Hz, 1H), 4.79 (br s, 1H), 4.52 (dd, J = 9.3, 2.7 Hz, 1H), 4.38 (t, J = 8.9 Hz, 1H), 3.65 (br s, 1H), 2.32 (s, 3H), 1.58 (d, J = 7.1 Hz, 3H), 0.77 (br s, 3H); | HRMS m/z 489.1881 (M + H)$^+$. |
| 60: (R)-3-(2-(((S)-1-(5-fluoro-2'-(trifluoromethyl)-[3,4'-bipyridin]-6-yl)ethyl)amino)pyrimidin-4-yl)-4-((R)-1-hydroxyethyl)oxazolidin-2-one | $^1$H NMR (400 MHz, MeOD) δ 8.82-8.80 (m, 2H), 8.19 (d, J = 1.5 Hz, 1H), 8.14 (d, J = 5.8 Hz, 1H), 8.10 (dd, J = 10.8, 1.9 Hz, 1H), 8.00 (dd, J = 5.2, 1.7 Hz, 1H), 7.38 (d, J = 5.8 Hz, 1H), 5.54 (q, J = 6.9 Hz, 1H), 4.64 (s, 1H), 4.55 (dd, J = 9.3, 2.7 Hz, 1H), 4.41 (t, J = 8.8 Hz, 1H), 3.93 (br s, 1H), 1.60 (d, J = 6.9 Hz, 3H) 0.87 (br s, 3H); | HRMS m/z 493.1575 (M + H)$^+$. |
| 61: (R)-4-((R)-1-hydroxyethyl)-3-(2-(((S)-1-(5-methyl-2'-(trifluoromethyl)-[3,4'-bipyridin]-6-yl)ethyl)amino)pyrimidin-4-yl)oxazolidin-2-one | $^1$H NMR (400 MHz, MeOD) δ 8.79 (s, 1H), 8.78 (d, J = 4.6 Hz, 1H), 8.15 (d, J = 6.3 Hz, 1H), 8.05 (s, 1H), 7.98 (d, J = 5.0 Hz, 1H), 7.37 (d, J = 5.8 Hz, 0H), 5.49-5.38 (m, 1H), 4.90-4.84 (m, 1H), 4.55 (dd, J = 9.2, 2.6 Hz, 1H), 4.41 (t, J = 8.8 Hz, 1H), 3.96 (br s, 1H), 2.57 (s, 3H), 1.53 (d, J = 6.7 Hz, 3H), 0.87 (br s, 3H); | HRMS m/z 489.1829 (M + H)$^+$. |
| 62: (R)-4-((R)-1-hydroxyethyl)-3-(2-(((S)-1-(2-methyl-2'-(trifluoromethyl)-[3,4'-bipyridin]-6-yl)ethyl)amino)pyrimidin-4-yl)oxazolidin-2-one | $^1$H NMR (400 MHz, MeOD) δ 8.79 (d, J = 5.0 Hz, 1H), 8.15 (d, J = 5.9 Hz, 1H), 7.88 (s, 1H), 7.74-7.65 (m, 2H), 7.39 (d, J = 8.0 Hz, 1H), 7.37 (d, J = 5.8 Hz, 1H), 5.14 (t, J = 7.1 Hz, 1H), 4.79 (br s, 1H), 4.52 (dd, J = 9.3, 2.7 Hz, 1H), 4.38 (t, J = 8.9 Hz, 1H), 3.61 (br s, 1H), 2.53 (s, 3H), 1.59 (d, J = 7.0 Hz, 3H), 0.76 (br s, 3H); | HRMS m/z 489.1840 (M + H)$^+$. |
| 63: (R)-3-(2-(((S)-1-(2'-(tert-butyl)-[3,4'-bipyridin]-6-yl)ethyl)amino)pyrimidin-4-yl)-4-((R)-1-hydroxyethyl)oxazolidin-2-one | 1H NMR (400 MHz, MeOD) δ 8.85 (d, J = 1.8 Hz, 1H), 8.56 (dd, J = 5.3, 0.8 Hz, 1H), 8.16-8.08 (m, 1H), 7.73 (d, J = 0.7 Hz, 1H), 7.58 (d, J = 8.2 Hz, 1H), 7.54 (dd, J = 5.2, 1.7 Hz, 1H), 7.36 (d, J = 5.8 Hz, 1H), 5.18 (q, J = 7.0 Hz, 1H), 4.78 (br s, 1H), 4.56-4.46 (m, 1H), 4.37 (t, J = 8.8 Hz, 1H), 3.59 (br s, 1H), 1.60 (d, J = 7.1 Hz, 3H), 1.42 (s, 9H), 0.67 (br s, 3H); | HRMS m/z 463.2439 (M + H)+. |

TABLE 28b-continued

Chemical name, NMR chemical shifts and LCMS signal for each compound listed in Table 28a.

| Example: Name | $^1$H NMR (400 MHz) δ ppm | LCMS |
|---|---|---|
| 64: (R)-4-((R)-1-hydroxyethyl)-3-(2-(((S)-1-(2'-(1,1,1-trifluoro-2-methylpropan-2-yl)-[3,4'-bipyridin]-6-yl)ethyl)amino)pyrimidin-4-yl)oxazolidin-2-one | $^1$H NMR (400 MHz, MeOD) δ 8.84 (d, J = 2.2 Hz, 1H), 8.64 (d, J = 5.1 Hz, 1H), 8.16-8.03 (m, 2H), 7.86 (s, 1H), 7.64 (dd, J = 5.1, 1.6 Hz, 1H), 7.58 (d, J = 8.2 Hz, 1H), 7.35 (d, J = 5.8 Hz, 1H), 5.18 (q, J = 7.0 Hz, 1H), 4.78 (br s, 1H), 4.50 (dd, J = 9.3, 2.7 Hz, 1H), 4.37 (t, J = 8.8 Hz, 1H), 3.57 (br s, 1H), 1.68 (s, 6H), 1.60 (d, J = 7.1 Hz, 3H), 0.67 (br s, 3H); | HRMS m/z 517.2167 (M + H)$^+$. |
| 65: 4-(2-((S)-1-((4-((R)-4-((R)-1-hydroxyethyl)-2-oxooxazolidin-3-yl)pyrimidin-2-yl)amino)ethyl)thiazol-4-yl)benzonitrile | $^1$H NMR (400 MHz, MeOD) δ 8.19 (d, J = 5.8 Hz, 1H), 8.15-8.09 (m, 2H), 7.90 (s, 1H), 7.80-7.74 (m, 2H), 7.43 (d, J = 5.8 Hz, 1H), 5.51 (q, J = 7.5 Hz, 1H), 4.82 (br s, 1H), 4.49 (dd, J = 9.0, 3.1 Hz, 1H), 4.38 (t, J = 8.9 Hz, 1H), 4.10 (br s, 1H), 1.73 (d, J = 7.1 Hz, 3H), 0.78 (br s, 3H); | HRMS m/z 437.1375 (M + H)$^+$. |
| 66: (R)-3-(2-(((S)-1-(5-(4-chlorophenyl)isoxazol-3-yl)ethyl)amino)pyrimidin-4-yl)-4-((R)-1-hydroxyethyl)oxazolidin-2-one | $^1$H NMR (400 MHz, MeOD) δ 8.16 (d, J = 5.8 Hz, 1H), 7.82-7.76 (m, 2H), 7.53-7.47 (m, 2H), 7.40 (d, J = 5.8 Hz, 1H), 6.78 (s, 1H), 5.34 (q, J = 7.1 Hz, 1H), 4.87 (ddd, J = 8.4, 4.2, 2.7 Hz, 1H), 4.54 (dd, J = 9.2, 2.7 Hz, 1H), 4.41 (t, J = 8.9 Hz, 1H), 4.31 (br s, 1H), 1.63 (d, J = 7.0 Hz, 3H), 0.93 (br s, 3H); | HRMS m/z 430.1260 (M + H)$^+$. |
| 67: (R)-3-(2-(((R)-1-(4-(2,4-dichlorophenyl)thiazol-2-yl)ethyl)amino)pyrimidin-4-yl)-4-((R)-1-hydroxyethyl)oxazolidin-2-one | $^1$H NMR (400 MHz, MeOD) δ 8.18 (d, J = 5.8 Hz, 1H), 7.86 (d, J = 8.4 Hz, 1H), 7.78 (s, 1H), 7.58 (d, J = 2.2 Hz, 1H), 7.44-7.39 (m, 2H), 5.43 (q, J = 7.0 Hz, 1H), 4.64 (br s, 1H), 4.56-4.49 (m, 2H), 4.30 (br s, 1H), 1.71 (d, J = 7.0 Hz, 3H), 1.06 (d, J = 6.5 Hz, 3H); | HRMS m/z 480.0639 (M + H)$^+$. |
| 68: (R)-3-(2-(((S)-1-(4-(2,4-dichlorophenyl)thiazol-2-yl)ethyl)amino)pyrimidin-4-yl)-4-((R)-1-hydroxyethyl)oxazolidin-2-one | $^1$H NMR (400 MHz, MeOD) δ 8.19 (d, J = 5.8 Hz, 1H), 7.91 (d, J = 8.5 Hz, 1H), 7.81 (s, 1H), 7.58 (d, J = 2.1 Hz, 1H), 7.46-7.39 (m, 2H), 5.50 (q, J = 7.0 Hz, 1H), 4.82 (br s, 1H), 4.51 (dd, J = 9.0, 2.7 Hz, 1H), 4.38 (t, J = 8.9 Hz, 1H), 4.04 (br s, 1H), 1.72 (d, J = 7.0 Hz, 3H), 0.82 (br s, 3H); | HRMS m/z 480.0637 (M + H)$^+$. |
| 69: (R)-3-(2-(((R)-1-(4-(4-bromophenyl)thiazol-2-yl)ethyl)amino)pyrimidin-4-yl)-4-((R)-1-hydroxyethyl)oxazolidin-2-one | $^1$H NMR (400 MHz, MeOD) δ 8.17 (d, J = 5.8 Hz, 1H), 7.86-7.81 (m, 2H), 7.69 (s, 1H), 7.59-7.54 (m, 2H), 7.42 (d, J = 5.8 Hz, 1H), 5.44 (q, J = 7.0 Hz, 1H), 4.69 (br s, 1H), 4.52 (ddt, J = 19.3, 9.1, 4.6 Hz, 2H), 4.26 (br s, 1H), 1.71 (d, J = 7.0 Hz, 3H), 1.08 (d, J = 6.5 Hz, 3H); | HRMS m/z 490.0533 (M + H)$^+$. |
| 70: (R)-3-(2-(((S)-1-(4-(4-bromophenyl)thiazol-2-yl)ethyl)amino)pyrimidin-4-yl)-4-((R)-1-hydroxyethyl)oxazolidin-2-one | $^1$H NMR (400 MHz, MeOD) δ 8.21 (d, J = 5.8 Hz, 1H), 7.89-7.84 (m, 2H), 7.71 (s, 1H), 7.61-7.56 (m, 2H), 7.44 (d, J = 5.8 Hz, 1H), 5.52 (t, J = 3.5 Hz, 1H), 4.84 (br s, 1H), 4.52 (dd, J = 9.4, 2.8 Hz, 1H), 4.40 (t, J = 8.9 Hz, 1H), 4.13 (br s, 1H), 1.74 (d, J = 7.0 Hz, 3H), 0.81 (br s, 3H); | HRMS m/z 490.0533 (M + H)$^+$. |
| 71: 4-(2-((R)-1-((4-((R)-4-((R)-1-hydroxyethyl)-2-oxooxazolidin-3-yl)pyrimidin-2-yl)amino)ethyl)thiazol-4-yl)benzonitrile | $^1$H NMR (400 MHz, MeOD) δ 8.17 (d, J = 5.8 Hz, 1H), 8.14-8.09 (m, 2H), 7.91 (s, 1H), 7.80-7.74 (m, 2H), 7.42 (d, J = 5.8 Hz, 1H), 5.46 (q, J = 7.0 Hz, 1H), 4.70 (br s, 1H), 4.59-4.45 (m, 2H), 4.27 (br s, 1H), 1.73 (d, J = 7.0 Hz, 3H), 1.08 (d, J = 6.5 Hz, 3H); | HRMS m/z 437.1382 (M + H)$^+$. |
| 72: (R)-4-((R)-1-hydroxyethyl)-3-(2-((S)-1-(4-((4-methylpiperazin-1-yl)methyl)phenyl)ethylamino)pyrimidin-4-yl)oxazolidin-2-one | $^1$H NMR (400 MHz, MeOD) δ 8.12 (d, J = 5.8 Hz, 1H), 7.41-7.22 (m, 5H), 5.09 (q, J = 7.0 Hz, 1H), 4.53 (dd, J = 9.3, 2.8 Hz, 1H), 4.39 (t, J = 8.9 Hz, 1H), 3.99 (s, 1H), 3.52 (d, J = 1.5 Hz, 2H), 2.56 (bs, 8H), 2.28 (s, 3H), 1.52 (d, J = 7.0 Hz, 3H), 0.78 (s, 3H). | HRMS m/z 441.2593 (M + H)$^+$. |

TABLE 28b-continued

Chemical name, NMR chemical shifts and LCMS signal for each compound listed in Table 28a.

| Example: Name | $^1$H NMR (400 MHz) δ ppm | LCMS |
|---|---|---|
| 73: (4R)-3-(2-((1-(3-fluoro-4-(4-methyl-1H-pyrazol-1-yl)phenyl)ethyl)amino)pyrimidin-4-yl)-4-((R)-1-hydroxyethyl)oxazolidin-2-one | $^1$H NMR (400 MHz, MeOD) δ 8.14 (t, J = 5.7 Hz, 1H), 7.86-7.77 (m, 1H), 7.64 (td, J = 8.3, 2.2 Hz, 1H), 7.56 (d, J = 3.0 Hz, 1H), 7.42-7.28 (m, 3H), 5.20-4.99 (m, 1H), 4.75-4.47 (m, 2H), 4.37 (dt, J = 17.1, 8.9 Hz, 1H), 2.17 (s, 3H), 1.56 (d, J = 7.1 Hz, 3H), 1.10 (d, J = 6.5 Hz, 1.5H), 0.82 (br s, 1.5H). | HRMS m/z 427.1870 (M + H)$^+$. |
| 74: (4R)-3-(2-((1-(5-(3,4-dichlorophenyl)-1H-imidazol-2-yl)ethyl)amino)-5-fluoropyrimidin-4-yl)-4-((R)-1-hydroxyethyl)oxazolidin-2-one | $^1$H NMR (400 MHz, MeOD) δ 8.27 (d, J = 3.1 Hz, 1H), 7.63 (d, J = 5.0 Hz, 1H), 7.50 (dd, J = 8.4, 1.6 Hz, 1H), 7.41 (s, 1H), 5.14 (q, J = 7.0 Hz, 1H), 4.72 (td, J = 7.1, 5.1 Hz, 1H), 4.56-4.42 (m, 2H), 4.16 (qd, J = 6.4, 5.1 Hz, 1H), 1.63 (dd, J = 10.1, 7.1 Hz, 3H), 1.11 (d, J = 6.5 Hz, 3H). | HRMS m/z 481.0930 (M + H)$^+$. |
| 75: (4R)-3-(2-((1-(5-(3,4-dichlorophenyl)-1H-imidazol-2-yl)ethyl)amino)pyrimidin-4-yl)-4-((R)-1-hydroxyethyl)oxazolidin-2-one | $^1$H NMR (400 MHz, MeOD) δ 8.19 (d, J = 5.8 Hz, 1H), 7.91 (s, 1H), 7.63 (s, 1H), 7.50 (d, J = 8.4 Hz, 1H), 7.41 (d, J = 5.8 Hz, 1H), 5.27-5.12 (m, 1H), 4.67 (s, 1H), 4.62-4.47 (m, 2H), 4.26 (s, 1H), 1.65 (d, J = 7.1 Hz, 3H), 1.08 (d, J = 6.5 Hz, 3H). | HRMS m/z 463.1018 (M + H)$^+$. |
| 76: (R)-3-(2-(((S)-1-(5-((4,4-difluoropiperidin-1-yl)methyl)pyridin-2-yl)ethyl)amino)pyrimidin-4-yl)-4-((R)-1-hydroxyethyl)oxazolidin-2-one | $^1$H NMR (400 MHz, MeOD) δ 8.47 (d, J = 2.0 Hz, 1H), 8.15 (d, J = 5.9 Hz, 1H), 7.78 (dd, J = 8.0, 2.2 Hz, 1H), 7.45 (d, J = 8.1 Hz, 1H), 7.37 (d, J = 5.7 Hz, 1H), 5.26-5.08 (m, 1H), 4.81 (d, J = 6.4 Hz, 1H), 4.53 (dd, J = 9.1, 2.7 Hz, 1H), 4.39 (t, J = 8.9 Hz, 1H), 3.95-3.64 (m, 1H), 3.61 (s, 2H), 2.59 (t, J = 5.6 Hz, 4H), 1.99 (tt, J = 13.7, 5.6 Hz, 4H), 1.56 (d, J = 7.0 Hz, 3H), 0.77 (s, 3H). | HRMS m/z 463.2250 (M + H)$^+$. |
| 77: (R)-3-(2-(((S)-1-(6-((4,4-difluoropiperidin-1-yl)methyl)pyridin-3-yl)ethyl)amino)pyrimidin-4-yl)-4-((R)-1-hydroxyethyl)oxazolidin-2-one | $^1$H NMR (400 MHz, MeOD) δ 8.52 (d, J = 2.3 Hz, 1H), 8.14 (d, J = 5.9 Hz, 1H), 7.85 (dd, J = 8.1, 2.3 Hz, 1H), 7.51 (d, J = 8.0 Hz, 1H), 7.36 (d, J = 5.8 Hz, 1H), 5.16 (q, J = 7.1 Hz, 1H), 4.83 (d, J = 4.5 Hz, 1H), 4.54 (dd, J = 9.3, 2.7 Hz, 1H), 4.40 (t, J = 8.9 Hz, 1H), 4.16-3.76 (br s, 1H), 3.69 (s, 2H), 2.61 (t, J = 5.7 Hz, 4H), 1.99 (tt, J = 13.5, 5.6 Hz, 4H), 1.57 (d, J = 7.0 Hz, 3H), 0.83 (s, 3H). | HRMS m/z 463.2267 (M + H)$^+$. |
| 78: (R)-4-((R)-1-hydroxyethyl)-3-(2-(((R)-1-(5-(3-(trifluoromethyl)phenyl)pyrazin-2-yl)ethyl)amino)pyrimidin-4-yl)oxazolidin-2-one | $^1$H NMR (400 MHz, MeOD) δ 9.13 (d, J = 1.5 Hz, 1H), 8.79 (d, J = 1.5 Hz, 1H), 8.40 (s, 1H), 8.33 (d, J = 7.8 Hz, 1H), 8.15 (d, J = 5.8 Hz, 1H), 7.78 (d, J = 7.9 Hz, 1H), 7.72 (t, J = 7.8 Hz, 1H), 7.38 (d, J = 5.8 Hz, 1H), 5.25 (q, J = 7.0 Hz, 1H), 4.59-4.51 (m, 2H), 4.33 (br s, 1H), 1.64 (d, J = 7.0 Hz, 3H), 1.09 (d, J = 6.5 Hz, 3H); | HRMS m/z 475.1685 (M + H)$^+$. |
| 79: (R)-3-(2-(((R)-1-(5-(4-fluoro-3-methylphenyl)pyrazin-2-yl)ethyl)amino)pyrimidin-4-yl)-4-((R)-1-hydroxyethyl)oxazolidin-2-one | $^1$H NMR (400 MHz, MeOD) δ 8.99 (d, J = 1.5 Hz, 1H), 8.70 (d, J = 1.6 Hz, 1H), 8.14 (d, J = 5.8 Hz, 1H), 7.99-7.92 (m, 1H), 7.88 (ddd, J = 8.4, 4.9, 2.4 Hz, 1H), 7.37 (d, J = 5.8 Hz, 1H), 7.16 (dd, J = 9.5, 8.6 Hz, 1H), 5.22 (q, J = 7.0 Hz, 1H), 4.64 (br s, 1H), 4.60-4.51 (m, 2H), 4.32 (t, J = 8.7 Hz, 1H), 2.35 (d, J = 2.0 Hz, 3H), 1.62 (d, J = 7.0 Hz, 3H), 1.08 (d, J = 6.5 Hz, 3H); | HRMS m/z 439.1869 (M + H)$^+$. |

The compounds in Table 29a were prepared using methods similar to those described for the preparation of Examples 35, 36, or 37/38.
TABLE 29a
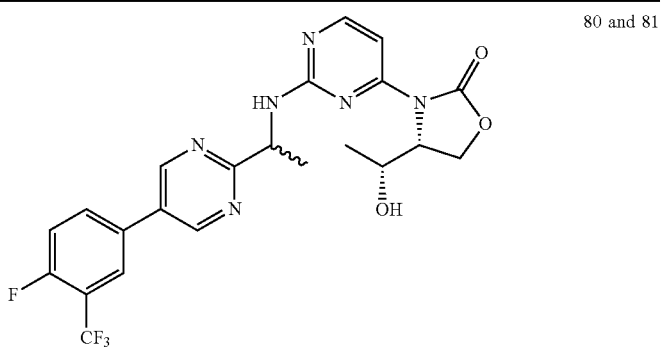
80 and 81
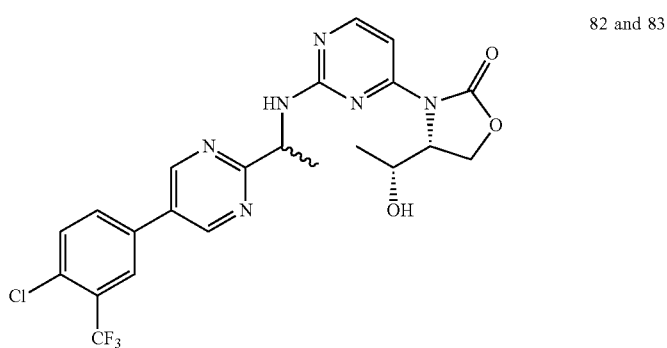
82 and 83
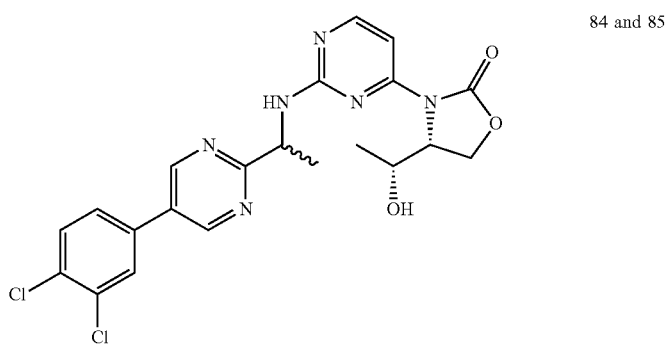
84 and 85
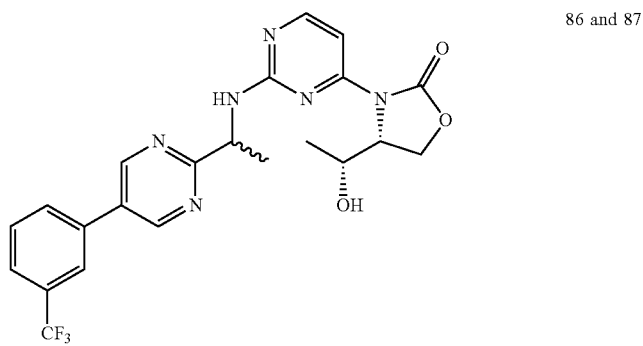
86 and 87

TABLE 29a-continued
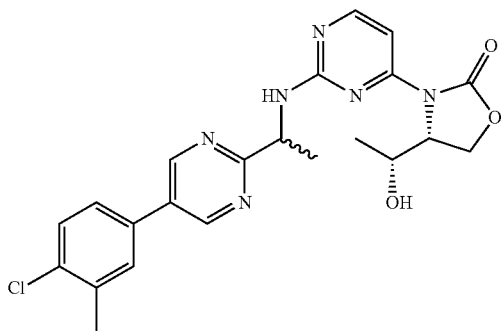 [SMILES: Cc1cc(-c2cnc(C(C)Nc3nccc(N4C(=O)OC[C@@H]4[C@@H](C)O)n3)nc2)ccc1Cl]
88 and 89
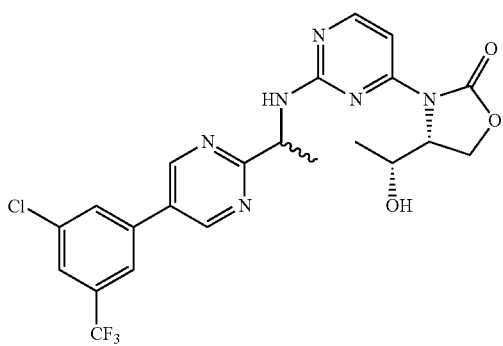 [SMILES: CC(Nc1nccc(N2C(=O)OC[C@@H]2[C@@H](C)O)n1)c1ncc(-c2cc(Cl)cc(C(F)(F)F)c2)cn1]
90 and 91
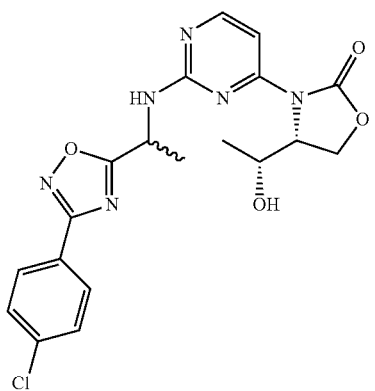 [SMILES: CC(Nc1nccc(N2C(=O)OC[C@@H]2[C@@H](C)O)n1)c1nc(-c2ccc(Cl)cc2)no1]
92 and 93
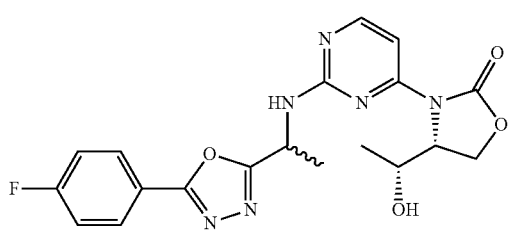 [SMILES: CC(Nc1nccc(N2C(=O)OC[C@@H]2[C@@H](C)O)n1)c1nnc(-c2ccc(F)cc2)o1]
94 and 95

TABLE 29a-continued
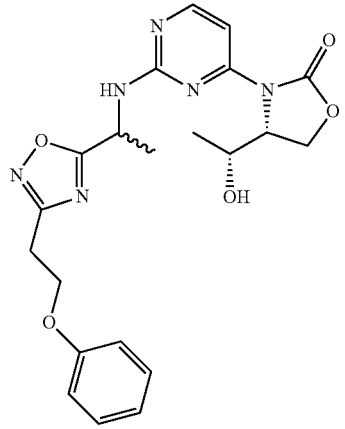 [SMILES: CC(Nc1nccc(N2C(=O)OC[C@@H]2[C@@H](C)O)n1)c1nc(CCOc2ccccc2)no1]
96 and 97
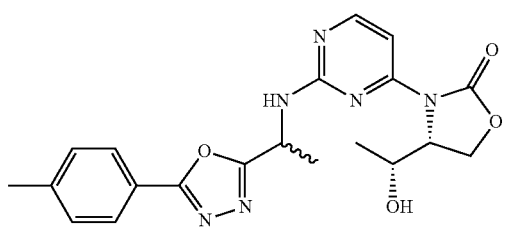 [SMILES: Cc1ccc(-c2nnc(C(C)Nc3nccc(N4C(=O)OC[C@@H]4[C@@H](C)O)n3)o2)cc1]
98 and 99
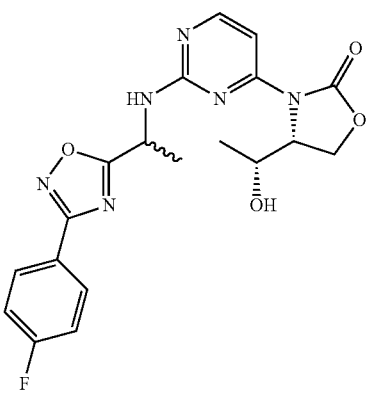 [SMILES: CC(Nc1nccc(N2C(=O)OC[C@@H]2[C@@H](C)O)n1)c1nc(-c2ccc(F)cc2)no1]
100 and 101
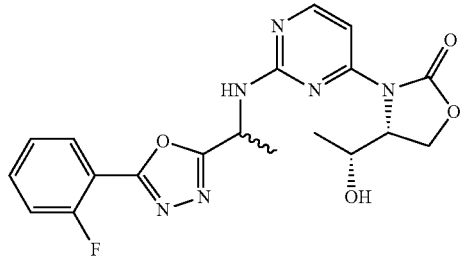 [SMILES: CC(Nc1nccc(N2C(=O)OC[C@@H]2[C@@H](C)O)n1)c1nnc(-c2ccccc2F)o1]
102 and 103
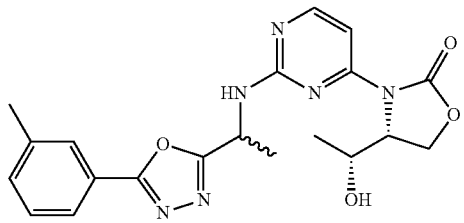 [SMILES: Cc1cccc(-c2nnc(C(C)Nc3nccc(N4C(=O)OC[C@@H]4[C@@H](C)O)n3)o2)c1]
104 and 105

TABLE 29a-continued
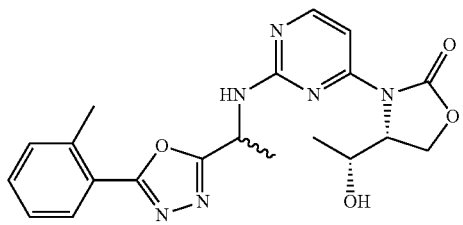 [SMILES: Cc1ccccc1-c1nnc(C(C)Nc2nccc(N3C(=O)OC[C@@H]3[C@@H](C)O)n2)o1]
106 and 107
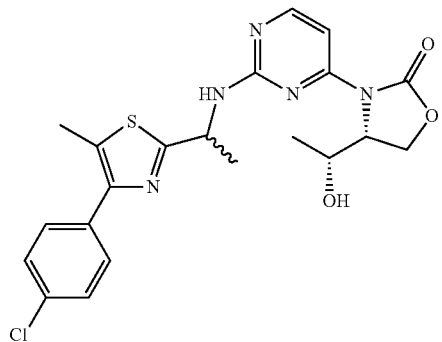 [SMILES: Cc1sc(C(C)Nc2nccc(N3C(=O)OC[C@@H]3[C@@H](C)O)n2)nc1-c1ccc(Cl)cc1]
108 and 109
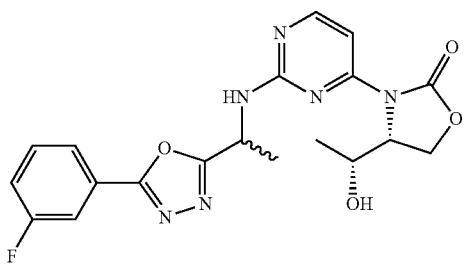 [SMILES: CC(Nc1nccc(N2C(=O)OC[C@@H]2[C@@H](C)O)n1)c1nnc(-c2cccc(F)c2)o1]
110 and 111
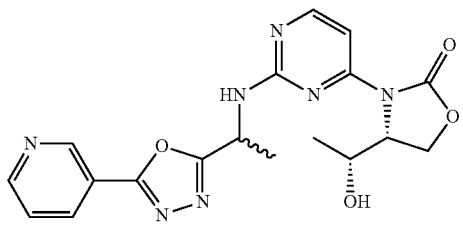 [SMILES: CC(Nc1nccc(N2C(=O)OC[C@@H]2[C@@H](C)O)n1)c1nnc(-c2cccnc2)o1]
112 and 113
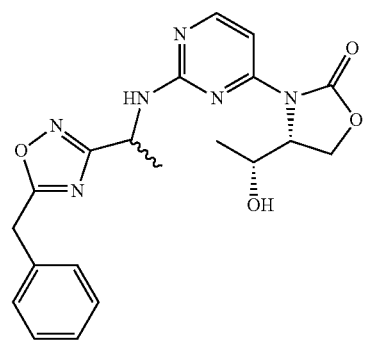 [SMILES: CC(Nc1nccc(N2C(=O)OC[C@@H]2[C@@H](C)O)n1)c1noc(Cc2ccccc2)n1]
114 and 115

TABLE 29a-continued
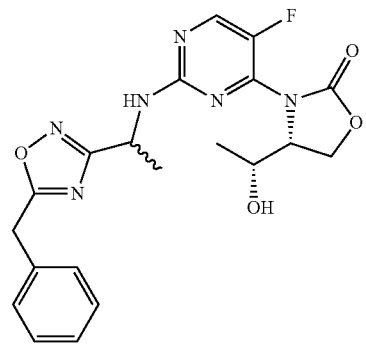 [SMILES: CC(Nc1ncc(F)c(N2C(=O)OC[C@@H]2[C@@H](C)O)n1)c1noc(Cc2ccccc2)n1]
116 and 117
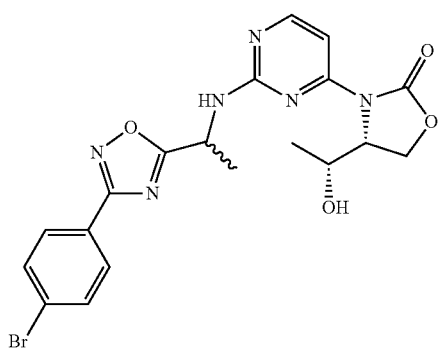
118 and 119
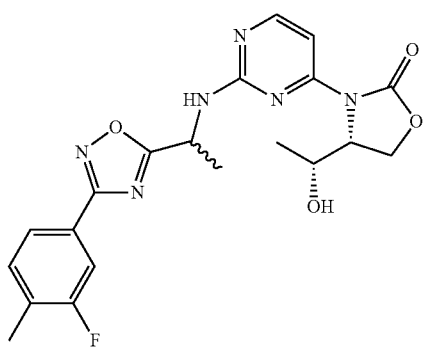 [SMILES: Cc1ccc(-c2noc(C(C)Nc3nccc(N4C(=O)OC[C@@H]4[C@@H](C)O)n3)n2)cc1F]
120 and 121
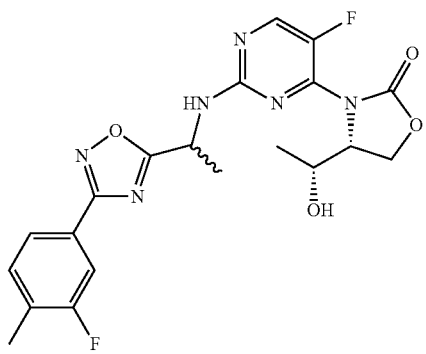 [SMILES: Cc1ccc(-c2noc(C(C)Nc3ncc(F)c(N4C(=O)OC[C@@H]4[C@@H](C)O)n3)n2)cc1F]
122 and 123
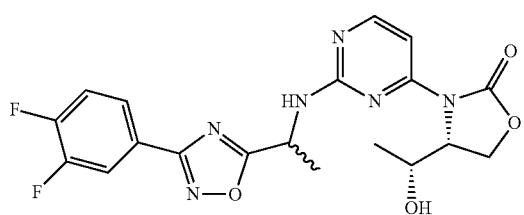 [SMILES: CC(Nc1nccc(N2C(=O)OC[C@@H]2[C@@H](C)O)n1)c1nc(-c2ccc(F)c(F)c2)no1]
124 and 125

TABLE 29a-continued
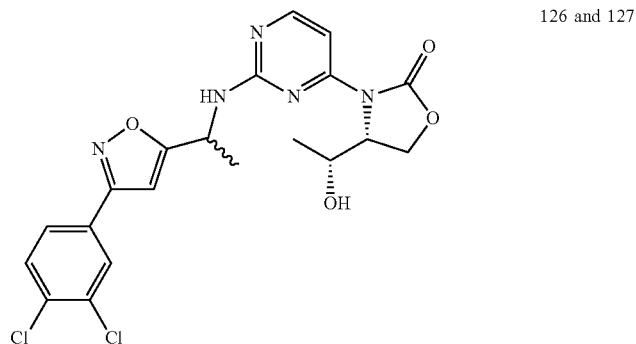
126 and 127
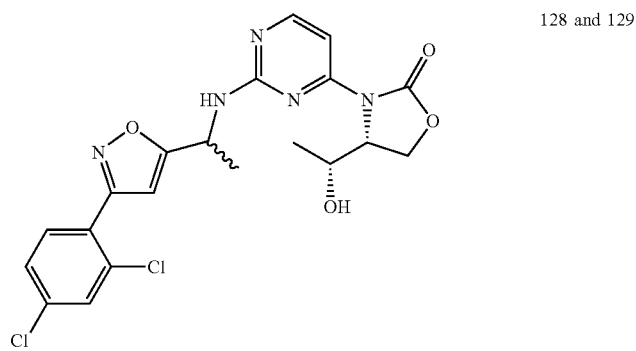
128 and 129
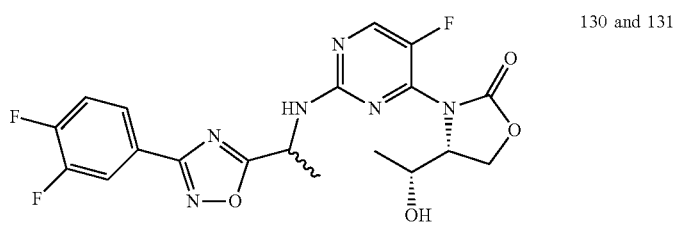
130 and 131
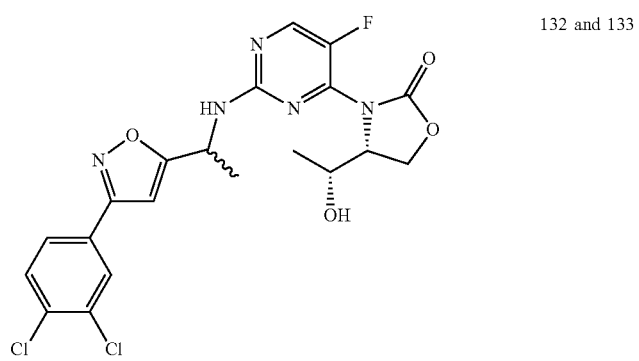
132 and 133
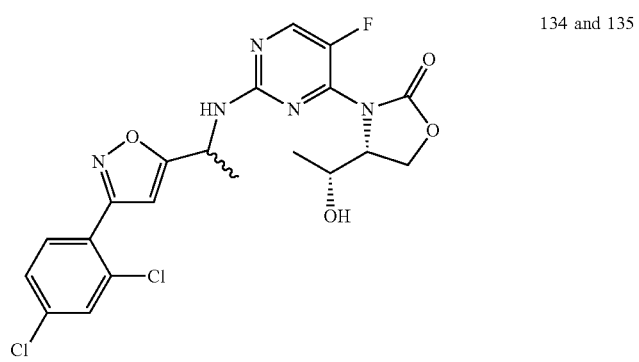
134 and 135

TABLE 29a-continued
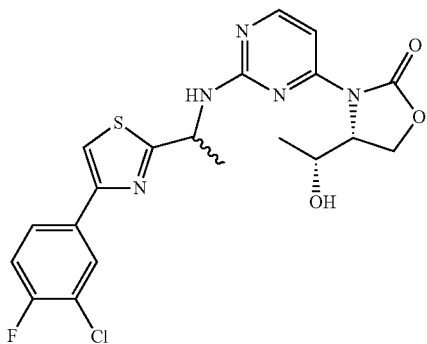
136 and 137
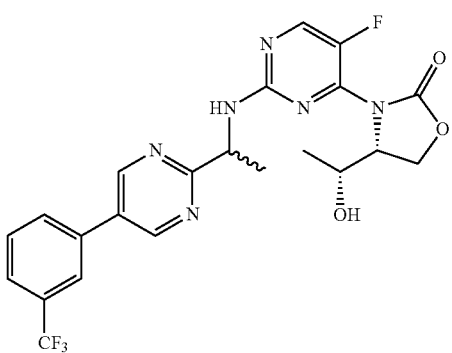 [SMILES: CC(Nc1ncc(F)c(N2C(=O)OC[C@@H]2[C@@H](C)O)n1)c1ncc(-c2cccc(C(F)(F)F)c2)cn1]
138 and 139
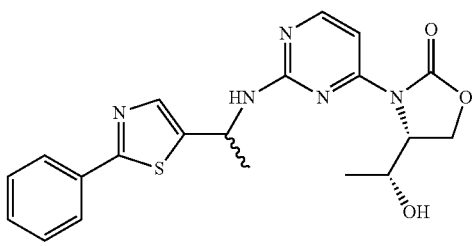 [SMILES: CC(Nc1nccc(N2C(=O)OC[C@@H]2[C@@H](C)O)n1)c1cnc(-c2ccccc2)s1]
140 and 141
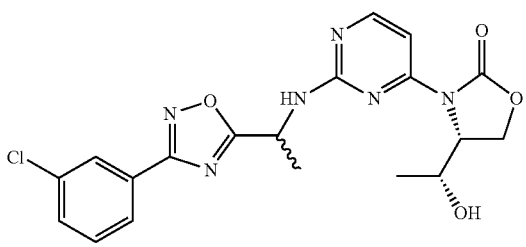 [SMILES: CC(Nc1nccc(N2C(=O)OC[C@@H]2[C@@H](C)O)n1)c1nc(-c2cccc(Cl)c2)no1]
142 and 143
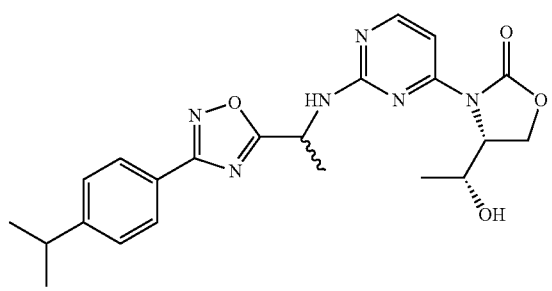 [SMILES: CC(C)c1ccc(-c2noc(C(C)Nc3nccc(N4C(=O)OC[C@@H]4[C@@H](C)O)n3)n2)cc1]
144 and 145

TABLE 29a-continued
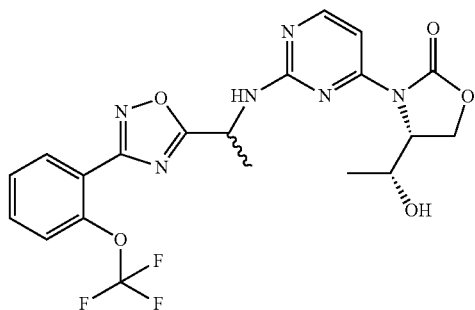 [SMILES: CC(Nc1nccc(N2C(=O)OC[C@@H]2[C@@H](C)O)n1)c1nc(-c2ccccc2OC(F)(F)F)no1]
146 and 147
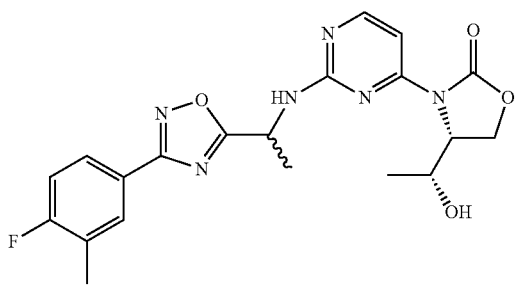 [SMILES: Cc1cc(-c2noc(C(C)Nc3nccc(N4C(=O)OC[C@@H]4[C@@H](C)O)n3)n2)ccc1F]
148 and 149
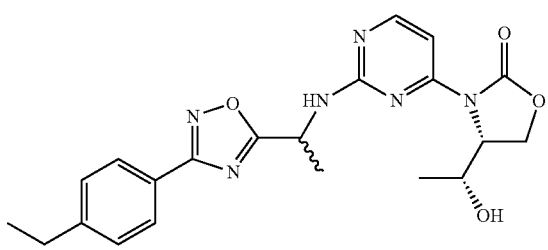 [SMILES: CCc1ccc(-c2noc(C(C)Nc3nccc(N4C(=O)OC[C@@H]4[C@@H](C)O)n3)n2)cc1]
150 and 151
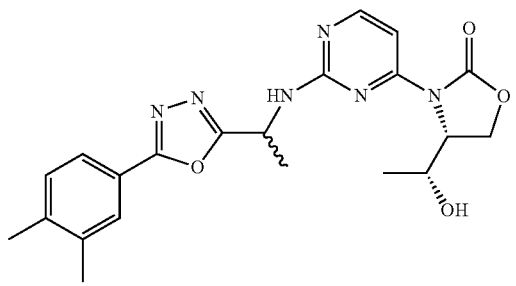 [SMILES: Cc1ccc(-c2nnc(C(C)Nc3nccc(N4C(=O)OC[C@@H]4[C@@H](C)O)n3)o2)cc1C]
152 and 153
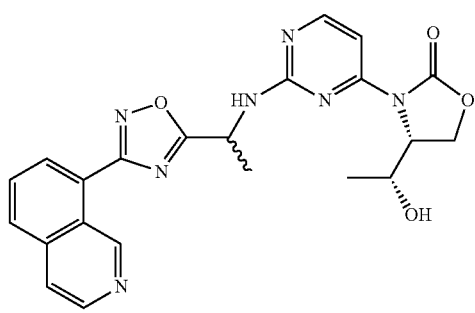 [SMILES: CC(Nc1nccc(N2C(=O)OC[C@@H]2[C@@H](C)O)n1)c1nc(-c2cccc3ccncc23)no1]
154 and 155

TABLE 29a-continued
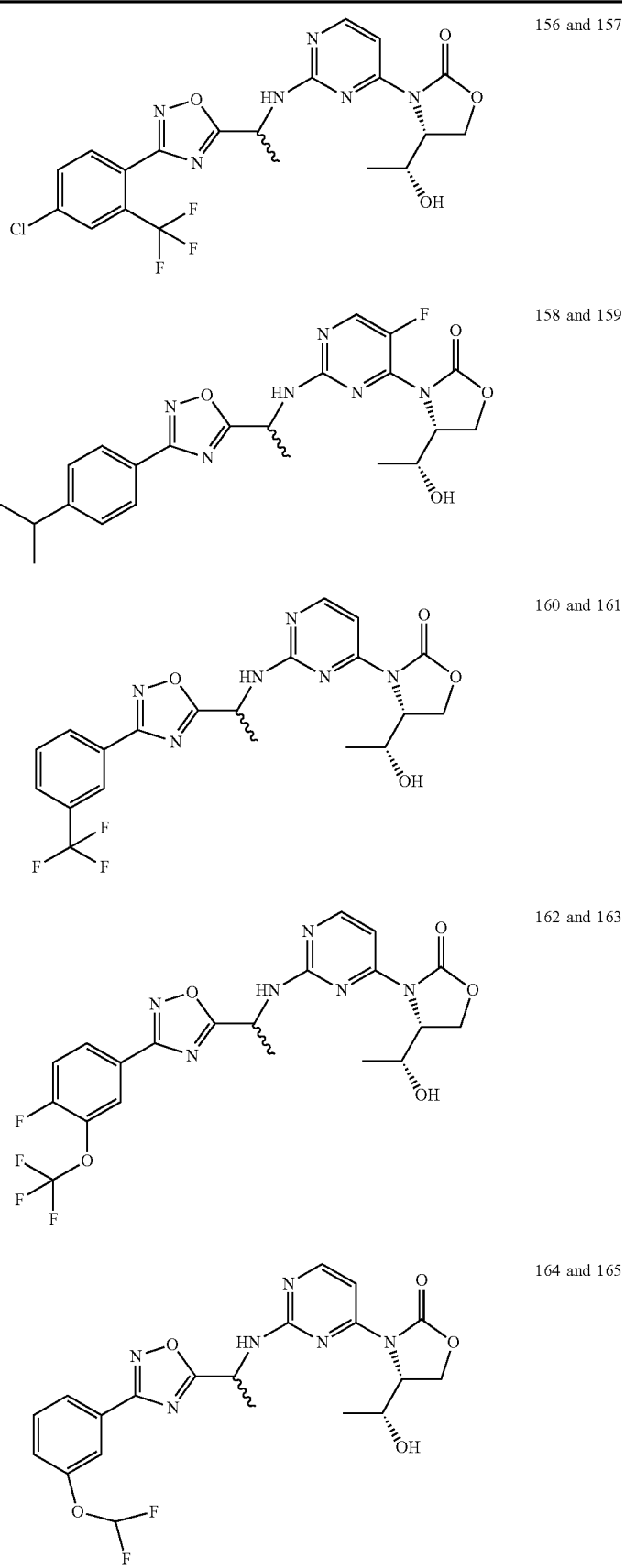
156 and 157
158 and 159
160 and 161
162 and 163
164 and 165

TABLE 29a-continued
| | |
|---|---|
| 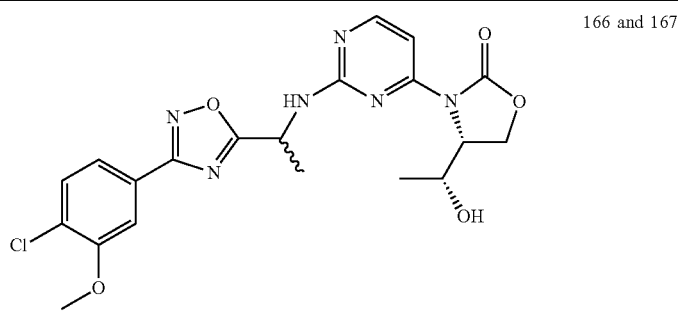 | 166 and 167 |
| 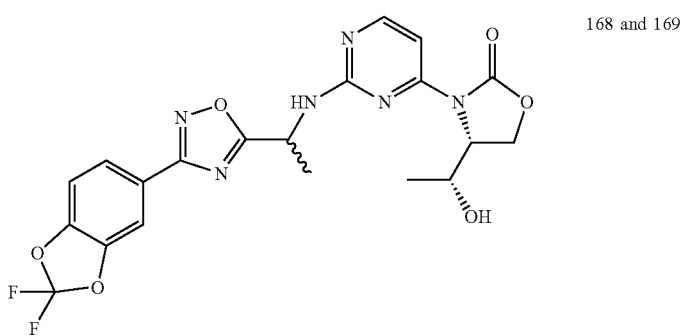 | 168 and 169 |
| 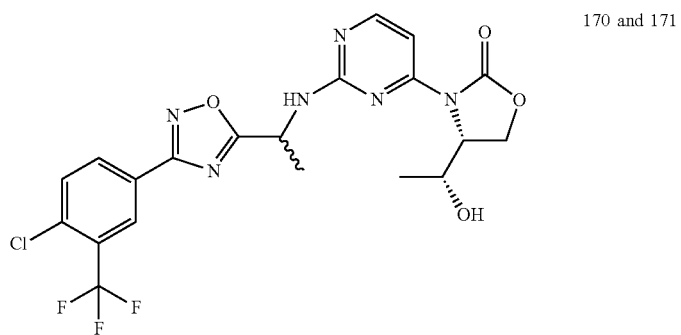 | 170 and 171 |
| 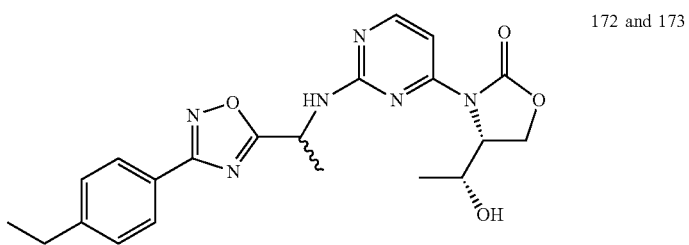 | 172 and 173 |
| 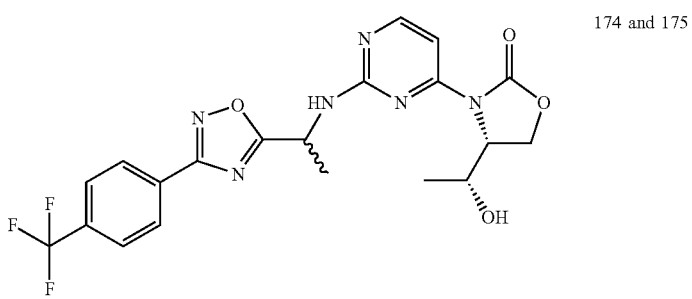 | 174 and 175 |

TABLE 29a-continued
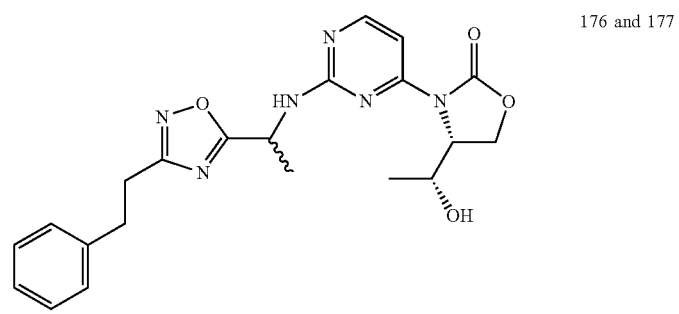
176 and 177
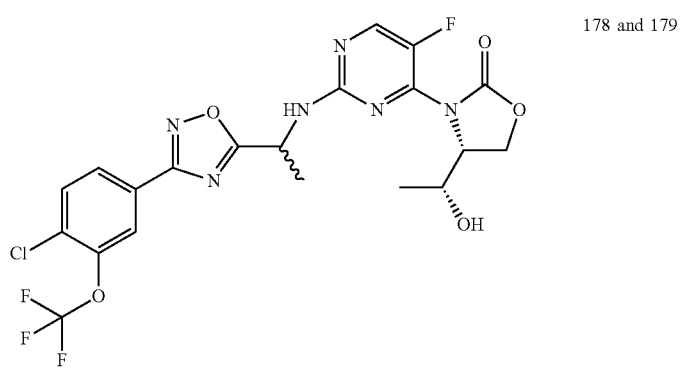
178 and 179
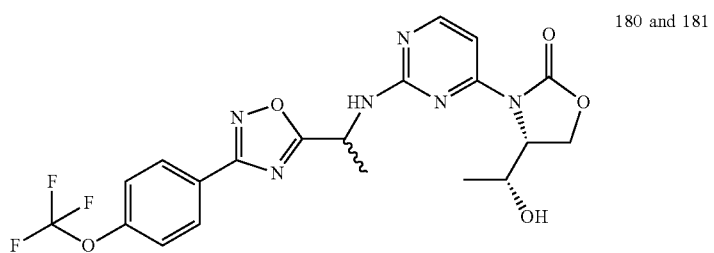
180 and 181
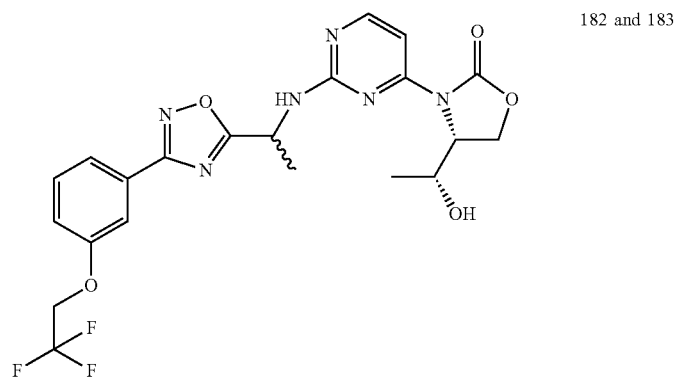
182 and 183
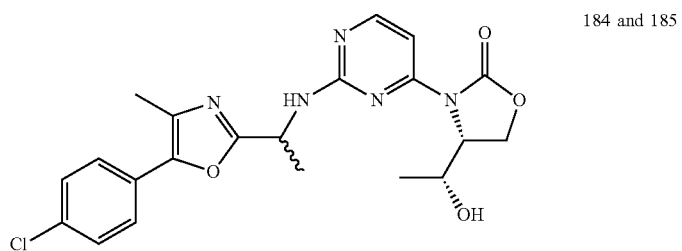
184 and 185

TABLE 29a-continued
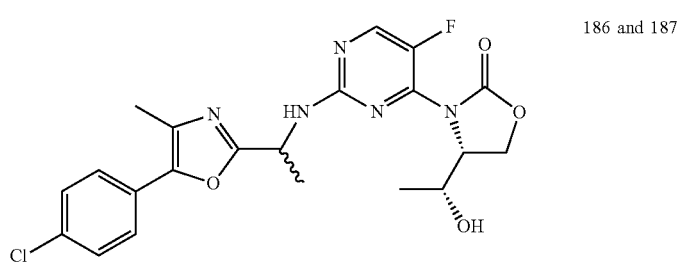
186 and 187
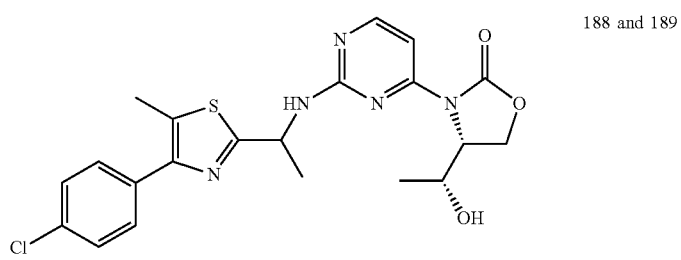
188 and 189
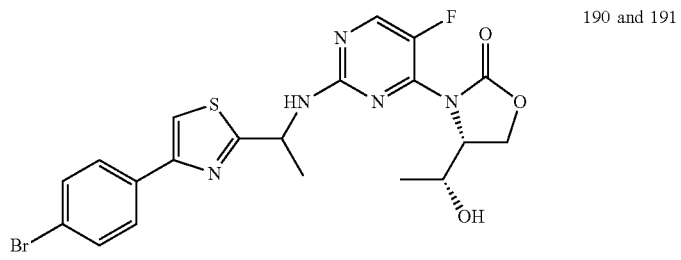
190 and 191
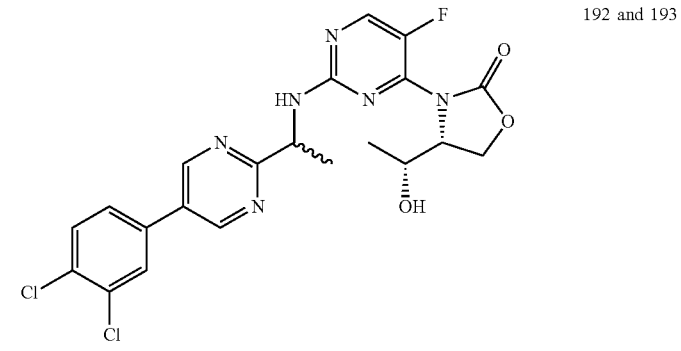
192 and 193
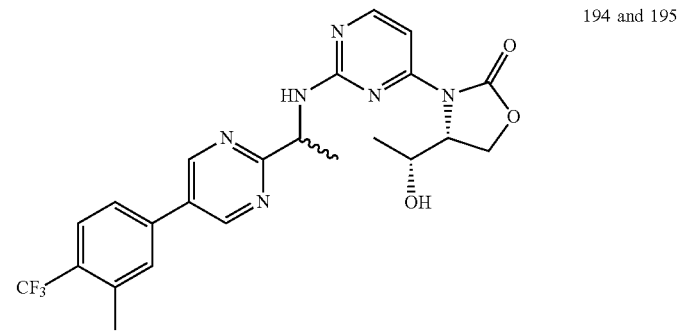
194 and 195

TABLE 29a-continued

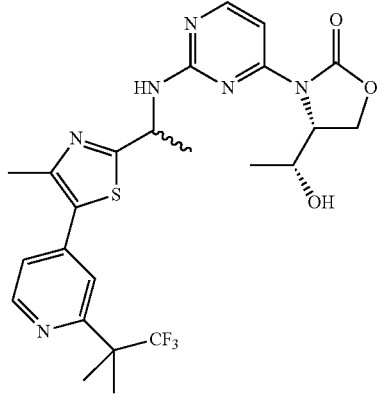 [SMILES: Cc1nc(C(C)Nc2nccc(N3C(=O)OC[C@@H]3[C@@H](C)O)n2)sc1-c1ccnc(C(C)(C)C(F)(F)F)c1]

196 and 197

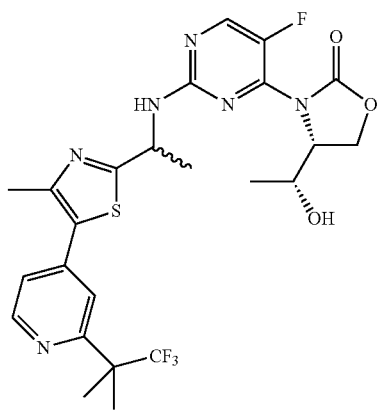 [SMILES: Cc1nc(C(C)Nc2ncc(F)c(N3C(=O)OC[C@@H]3[C@@H](C)O)n2)sc1-c1ccnc(C(C)(C)C(F)(F)F)c1]

198 and 199

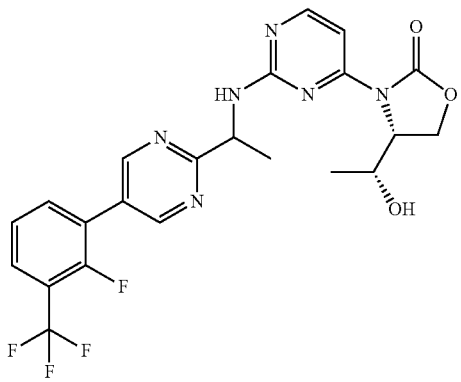 [SMILES: CC(Nc1nccc(N2C(=O)OC[C@@H]2[C@@H](C)O)n1)c1ncc(-c2cccc(C(F)(F)F)c2F)cn1]

200 and 201

TABLE 29b

Chemical name, NMR chemical shifts, chiral separation conditions and LCMS signal for compounds listed in Table 29a.

| Example: Name | Chiral separation conditions, peak identification and analytical data |
|---|---|
| 80 and 81: (R)-3-(2-((1-(5-(4-fluoro-3-(trifluoromethyl)phenyl)pyrimidin-2-yl)ethyl)amino)pyrimidin-4-yl)-4-((R)-1-hydroxyethyl)oxazolidin-2-one | Chiral separation was achieved by chiral SFC column chromatography (Column AD-H 20 × 250 mm 35% IPA 10 mM NH4OH in CO$_2$, flow 75 g/min, 232 nm UV collection) to give (R)-3-(2-(((S)-1-(5-(4-fluoro-3-(trifluoromethyl)phenyl)pyrimidin-2-yl)ethyl)amino)pyrimidin-4-yl)-4-((R)-1-hydroxyethyl)oxazolidin-2-one and (R)-3-(2-(((R)-1-(5-(4-fluoro-3-(trifluoromethyl)phenyl)pyrimidin-2-yl)ethyl)amino)pyrimidin-4-yl)-4-((R)-1-hydroxyethyl)oxazolidin-2-one. |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
| | 80: First eluted product (40 mg) $^1$H NMR (400 MHz, CDCl$_3$) δ 8.90 (s, 2H), 8.22 (d, J = 5.76 Hz, 1H), 7.83-7.70 (m, 2H), 7.49-7.35 (m, 2H), 6.12 (d, J = 8.09 Hz, 1H), 5.40 (p, J = 7.25 Hz, 1H), 4.89 (s, 1H), 4.51 (dd, J = 2.70, 9.45 Hz, 1H), 4.42 (dd, J = 8.23, 9.37 Hz, 1H), 3.30 (s, 1H), 1.68 (d, J = 7.25 Hz, 3H), 1.12 (br s, 3H). HRMS(B) m/z 493.1599 (M + H)$^+$.<br>81: Second eluted product (45 mg) $^1$H NMR (400 MHz, CDCl$_3$) δ 8.91 (s, 2H), 8.22 (d, J = 5.7 Hz, 1H), 7.84-7.71 (m, 2H), 7.40 (dd, J = 11.6, 7.2 Hz, 2H), 6.14 (d, J = 6.8 Hz, 1H), 5.21 (s, 1H), 4.79 (s, 1H), 4.58-4.48 (m, 1H), 4.30 (s, 1H), 3.81 (s, 1H), 1.66 (m, 3H), 1.24 (m, 3H). HRMS(B) m/z 493.1600 (M + H)$^+$. |
| 82 and 83:<br>(R)-3-(2-((1-(5-(4-chloro-3-(trifluoromethyl)phenyl)pyrimidin-2-yl)ethyl)amino)pyrimidin-4-yl)-4-((R)-1-hydroxyethyl)oxazolidin-2-one | Chiral separation was achieved by chiral SFC column chromatography (Column AD-H 20 × 250 mm 30% IPA 10 mM NH4OH in CO$_2$, flow 75 g/min, 232 nm UV collection) to give (R)-3-(2-(((S)-1-(5-(4-chloro-3-(trifluoromethyl)phenyl)pyrimidin-2-yl)ethyl)amino)pyrimidin-4-yl)-4-((R)-1-hydroxyethyl)oxazolidin-2-one and (R)-3-(2-(((R)-1-(5-(4-chloro-3-(trifluoromethyl)phenyl)pyrimidin-2-yl)ethyl)amino)pyrimidin-4-yl)-4-((R)-1-hydroxyethyl)oxazolidin-2-one.<br>82: First eluted product (13 mg) $^1$H NMR (400 MHz, CDCl$_3$) δ 8.91 (s, 2H), 8.22 (d, J = 5.8 Hz, 1H), 7.90-7.85 (m, 1H), 7.68 (d, J = 1.8 Hz, 2H), 7.45 (d, J = 5.7 Hz, 1H), 6.08 (d, J = 8.2 Hz, 1H), 5.40 (q, J = 7.5 Hz, 1H), 4.89 (s, 1H), 4.51 (dd, J = 9.4, 2.7 Hz, 1H), 4.42 (dd, J = 9.4, 8.3 Hz, 1H), 4.09 (s, 1H), 3.29 (s, 1H), 1.68 (d, J = 7.5 Hz, 3H), 1.12 (br s, 3H). HRMS(B) m/z 509.1306 (M + H)$^+$.<br>83: Second eluted product (12 mg) $^1$H NMR (400 MHz, CDCl$_3$) δ 8.93 (s, 2H), 8.23 (d, J = 5.7 Hz, 1H), 7.88 (d, J = 1.7 Hz, 1H), 7.69 (d, J = 1.4 Hz, 2H), 7.42 (d, J = 5.7 Hz, 1H), 6.09 (d, J = 6.8 Hz, 1H), 5.21 (s, 1H), 4.78 (s, 1H), 4.53 (d, J = 8.9 Hz, 1H), 4.31 (s, 1H), 3.70 (s, 1H), 1.66 (m, 3H), 1.24 (m, 3H). HRMS(B) m/z 509.1312 (M + H)$^+$. |
| 84 and 85:<br>(R)-3-(2-((1-(5-(3,4-dichlorophenyl)pyrimidin-2-yl)ethyl)amino)pyrimidin-4-yl)-4-((R)-1-hydroxyethyl)oxazolidin-2-one | Chiral separation was achieved by chiral SFC column chromatography (Column C6 AD-H 20 × 250 mm 35% IPA 5 mM NH$_4$OH in CO$_2$, flow 80 mL/min, 232 nm UV collection) to give (R)-3-(2-(((S)-1-(5-(3,4-dichlorophenyl)pyrimidin-2-yl)ethyl)amino)pyrimidin-4-yl)-4-((R)-1-hydroxyethyl)oxazolidin-2-one and (R)-3-(2-(((R)-1-(5-(3,4-dichlorophenyl)pyrimidin-2-yl)ethyl)amino)pyrimidin-4-yl)-4-((R)-1-hydroxyethyl)oxazolidin-2-one.<br>84: First eluted product (28 mg) $^1$H NMR (400 MHz, CDCl$_3$) δ 8.89 (s, 2H), 8.22 (d, J = 5.7 Hz, 1H), 7.70-7.58 (m, 2H), 7.49-7.37 (m, 2H), 6.03 (d, J = 7.5 Hz, 1H), 5.39 (t, J = 7.4 Hz, 1H), 4.89 (s, 1H), 4.55-4.47 (m, 1H), 4.42 (dd, J = 9.4, 8.3 Hz, 1H), 3.25 (s, 1H), 1.67 (dd, J = 7.0, 4.3 Hz, 3H), 1.12 (br s, 3H). HRMS(B) m/z 475.1026 (M + H)$^+$.<br>85: Second eluted product (22 mg) $^1$H NMR (400 MHz, CDCl$_3$) δ 8.90 (s, 2H), 8.23 (d, J = 5.7 Hz, 1H), 7.71-7.57 (m, 2H), 7.46-7.38 (m, 2H), 6.01 (s, 1H), 5.18 (s, 1H), 4.78 (s, 1H), 4.53 (d, J = 9.0 Hz, 1H), 4.31 (s, 2H), 3.64 (s, 1H), 1.66 (d, J = 6.9 Hz, 3H), 1.26-1.21 (m, 3H). HRMS(B) m/z 475.1032 (M + H)$^+$. |
| 86 and 87: (R)-4-((R)-1-hydroxyethyl)-3-(2-((1-(5-(3-(trifluoromethyl)phenyl)pyrimidin-2-yl)ethyl)amino)pyrimidin-4-yl)oxazolidin-2-one | Chiral separation was achieved by chiral SFC column chromatography (Column AD-H 20 × 250 mm 35% IPA 10 mM NH4OH in CO$_2$, flow 75 g/min, 232 nm UV collection) to give (R)-4-((R)-1-hydroxyethyl)-3-(2-(((S)-1-(5-(3-(trifluoromethyl)phenyl)pyrimidin-2-yl)ethyl)amino)pyrimidin-4-yl)oxazolidin-2-one and (R)-4-((R)-1-hydroxyethyl)-3-(2-(((R)-1-(5-(3-(trifluoromethyl)phenyl)pyrimidin-2-yl)ethyl)amino)pyrimidin-4-yl)oxazolidin-2-one.<br>86:: First eluted product (80 mg) $^1$H NMR (400 MHz, CDCl$_3$) δ 8.94 (s, 2H), 8.23 (d, J = 5.7 Hz, 1H), 7.85-7.63 (m, 4H), 7.46 (d, J = 5.7 Hz, 1H), 6.11 (d, J = 8.2 Hz, 1H), 5.41 (p, J = 7.2 Hz, 1H), 4.90 (s, 1H), 4.52 (dd, J = 9.5, 2.6 Hz, 1H), 4.43 (dd, J = 9.4, 8.3 Hz, 1H), 3.34 (s, 1H), 1.67 (d, J = 7.2 Hz, 3H), 1.12 br (s, 3H). HRMS(B) m/z 475.1681 (M + H)$^+$. |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
|  | 87: Second eluted product (67 mg) $^1$H NMR (400 MHz, CDCl$_3$) δ 8.95 (s, 2H), 8.20 (d, J = 5.9 Hz, 1H), 7.86-7.64 (m, 4H), 7.46 (d, J = 5.9 Hz, 1H), 6.48 (br s, 1H), 5.20 (br s, 1H), 4.79 (br s, 1H), 4.55 (d, J = 8.6 Hz, 1H), 4.34-4.30 (m, 2H), 3.65 (br s, 1H), 1.67 (d, J = 7.2 Hz, 3H), 1.25 (d, J = 6.5 Hz, 3H). HRMS(B) m/z 475.1677 (M + H)$^+$. |
| 88 and 89: (R)-3-(2-((1-(5-(4-chloro-3-methylphenyl)pyrimidin-2-yl)ethyl)amino)pyrimidin-4-yl)-4-((R)-1-hydroxyethyl)oxazolidin-2-one | Chiral separation was achieved by chiral SFC column chromatography (Column C6 AD-H 20 × 250 mm 35% IPA 5 mM NH4OH in CO$_2$, flow 80 mL/min, 232 nm UV collection) to give (R)-3-(2-(((S)-1-(5-(4-chloro-3-methylphenyl)pyrimidin-2-yl)ethyl)amino)pyrimidin-4-yl)-4-((R)-1-hydroxyethyl)oxazolidin-2-one and (R)-3-(2-(((R)-1-(5-(4-chloro-3-methylphenyl)pyrimidin-2-yl)ethyl)amino)pyrimidin-4-yl)-4-((R)-1-hydroxyethyl)oxazolidin-2-one. 88: First eluted product (16 mg) $^1$H NMR (400 MHz, CDCl$_3$) δ 8.79 (s, 2H), 8.13 (d, J = 5.7, 1H), 7.44-7.17 (m, 4H), 6.07-5.96 (m, 1H), 5.29 (t, J = 7.7 Hz, 1H), 5.12 (s, 1H), 4.81 (d, J = 7.3 Hz, 1H), 4.55 (s, 1H), 4.43 (dd, J = 9.4, 2.6 Hz, 1H), 3.38 (s, 1H), 2.39 (s, 3H), 1.57 (d, J = 7.7 Hz, 3H), 1.02 (br s, 3H). HRMS(B) m/z 455.1575 (M + H)$^+$. 89: Second eluted product (9 mg) $^1$H NMR (400 MHz, CDCl$_3$) δ 8.80 (s, 2H), 8.13 (d, J = 5.7 Hz, 1H), 7.41 (d, J = 8.3 Hz, 1H), 7.37-7.23 (m, 3H), 5.97 (br s, 1H), 5.08 (br s, 1H), 4.71 (br s, 1H), 4.45 (d, J = 9.0 Hz, 1H), 4.40-4.18 (m, 2H), 3.86 (br s, 1H), 2.39 (s, 3H), 1.57 (d, J = 7.7 Hz, 3H), 1.16-1.13 (m, 3H). HRMS(B) m/z 455.1578 (M + H)$^+$. |
| 90 and 91: (R)-3-(2-((1-(5-(3-chloro-5-(trifluoromethyl)phenyl)pyrimidin-2-yl)ethyl)amino)pyrimidin-4-yl)-4-((R)-1-hydroxyethyl)oxazolidin-2-one | Chiral separation was achieved by chiral SFC column chromatography (Column Coated 1 P9: AD-H 4.6 × 100 mm 5-55% IPA 5 mM NH$_3$ in CO$_2$, flow 5 mL/min, 177 nm UV collection) to give (R)-3-(2-(((S)-1-(5-(3-chloro-5-(trifluoromethyl)phenyl)pyrimidin-2-yl)ethyl)amino)pyrimidin-4-yl)-4-((R)-1-hydroxyethyl)oxazolidin-2-one and (R)-3-(2-(((R)-1-(5-(3-chloro-5-(trifluoromethyl)phenyl)pyrimidin-2-yl)ethyl)amino)pyrimidin-4-yl)-4-((R)-1-hydroxyethyl)oxazolidin-2-one. 90: First eluted product (4 mg) $^1$H NMR (400 MHz, CDCl$_3$) δ 8.83 (s, 2H), 8.14 (d, J = 5.8 Hz, 1H), 7.69-7.57 (m, 3H), 7.37 (d, J = 5.8 Hz, 1H), 5.99 (d, J = 7.7 Hz, 1H), 5.32 (p, J = 7.1 Hz, 1H), 4.81 (d, J = 7.5 Hz, 1H), 4.42 (dd, J = 9.4, 2.4 Hz, 1H), 4.33 (dd, J = 9.4, 8.3 Hz, 1H), 3.18 (br s, 1H), 1.57 (d, J = 9.5 Hz, 3H), 1.03 (br s, 3H). HRMS(B) m/z 509.1299 (M + H)$^+$. 91: Second eluted product (4 mg) $^1$H NMR (400 MHz, CDCl$_3$) δ 8.83 (s, 2H), 8.13 (d, J = 5.7 Hz, 1H), 7.69-7.58 (m, 3H), 7.34 (d, J = 5.7 Hz, 1H), 5.97 (d, J = 7.5 Hz, 1H), 5.35-5.31 (m, 1H), 5.13 (br s, 1H), 4.45 (d, J = 9.0 Hz, 1H), 4.35-4.24 (m, 1H), 4.22 (s, 1H), 3.62 (br s, 1H), 1.57 (d, J = 7.0 Hz, 3H), 1.19-1.16 (m, 3H). HRMS(B) m/z 509.1298 (M + H)$^+$. |
| 92 and 93: (R)-3-(2-((1-(3-(4-chlorophenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography IA, 5UM, 20 × 250 MM column, 74 ml/min, 60 bar, eluting 25% IPA with 5 mM NH4OH/CO2 (v/v) to give (R)-3-(2-(((R)-1-(3-(4-chlorophenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(4-chlorophenyl)-1,2,4-oxadiazol-5-yl)ethyl)amino)pyrimidin-4-yl)-4-((R)-1-hydroxyethyl)oxazolidin-2-one. 92: First eluted product (12.4 mg). HRMS(B) m/z 431.1225 (M + H)$^+$. RT = 2.39 min. 93: Second eluted product (14.3 mg). $^1$H NMR (400 MHz, CDCl$_3$) δ 8.25 (d, J = 6.0 Hz, 1H), 8.10-7.94 (m, 2H), 7.57 (d, J = 5.7 Hz, 1H), 7.53-7.43 (m, 2H), 5.96 (b, 1H), 5.38 (s, 1H), 4.84 (ddd, J = 8.3, 4.5, 2.5 Hz, 1H), 4.54 (dd, J = 9.4, 2.5 Hz, 1H), 4.40 (dd, J = 9.4, 8.3 Hz, 1H), 4.18-3.59 (b, 1H), 1.79 (d, J = 7.1 Hz, 3H), 1.01 (b, 3H). HRMS(B) m/z 431.1219 (M + H)$^+$, RT = 2.40 min. |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
| 94 and 95:<br>(R)-3-(2-((1-(5-(4-fluorophenyl)-1,3,4-oxadiazol-2-yl)ethyl)amino)pyrimidin-4-yl)-4-((R)-1-hydroxyethyl)oxazolidin-2-one | Chiral separation was achieved by chiral SFC column chromatography ID-H, 5UM, 20 × 250 MM column, 80 ml/min, 99 bar, eluting 30% IPA with 5 mM NH4OH/CO2 (v/v) to give (R)-3-(2-(((R)-1-(5-(4-fluorophenyl)-1,3,4-oxadiazol-2-yl)ethyl)amino)pyrimidin-4-yl)-4-((R)-1-hydroxyethyl)oxazolidin-2-one and (R)-3-(2-(((S)-1-(5-(4-fluorophenyl)-1,3,4-oxadiazol-2-yl)ethyl)amino)pyrimidin-4-yl)-4-((R)-1-hydroxyethyl)oxazolidin-2-one.<br>94: First eluted product (30.1 mg). HRMS (B) m/z 415.1519 (M + H)$^+$. RT = 1.80 min.<br>95: Second eluted product (32.3 mg). HRMS(B) m/z 415.1521 (M + H)$^+$, RT = 1.79 min. |
| 96 and 97:<br>(R)-4-((R)-1-hydroxyethyl)-3-(2-((1-(3-(2-phenoxyethyl)-1,2,4-oxadiazol-5-yl)ethyl)amino)pyrimidin-4-yl)oxazolidin-2-one | Chiral separation was achieved by chiral SFC column chromatography IA, 5UM, 20 × 250 MM column, 80 ml/min, 99 bar, eluting 20% IPA with 5 mM NH4OH/CO2 (v/v) to give(R)-4-((R)-1-hydroxyethyl)-3-(2-(((R)-1-(3-(2-phenoxyethyl)-1,2,4-oxadiazol-5-yl)ethyl)amino)pyrimidin-4-yl)oxazolidin-2-one and (R)-4-((R)-1-hydroxyethyl)-3-(2-(((S)-1-(3-(2-phenoxyethyl)-1,2,4-oxadiazol-5-yl)ethyl)amino)pyrimidin-4-yl)oxazolidin-2-one.<br>96: First eluted product (19.2 mg). HRMS(B) m/z 441.1867 (M + H)$^+$. RT = 1.90 min.<br>97: Second eluted product (31.2 mg). HRMS(B) m/z 441.1864 (M + H)$^+$, RT = 1.94 min. |
| 98 and 99:<br>(R)-4-((R)-1-hydroxyethyl)-3-(2-((1-(5-(p-tolyl)-1,3,4-oxadiazol-2-yl)ethyl)amino)pyrimidin-4-yl)oxazolidin-2-one. | Chiral separation was achieved by chiral SFC column chromatography IA, 5UM, 20 × 250 MM column, 80 ml/min, 100 bar, eluting 15% IPA with 0.5% NH4OH/CO2 (v/v) to give (R)-4-((R)-1-hydroxyethyl)-3-(2-(((R)-1-(5-(p-tolyl)-1,3,4-oxadiazol-2-yl)ethyl)amino)pyrimidin-4-yl)oxazolidin-2-one and (R)-4-((R)-1-hydroxyethyl)-3-(2-(((S)-1-(5-(p-tolyl)-1,3,4-oxadiazol-2-yl)ethyl)amino)pyrimidin-4-yl)oxazolidin-2-one.<br>98: First eluted product (48 mg). HRMS(B) m/z 411.1768 (M + H)$^+$. RT = 1.82 min.<br>99: Second eluted product (50 mg). HRMS(B) m/z 411.1768 (M + H)$^+$, RT = 1.82 min. |
| 100 and 101:<br>(R)-3-(2-((1-(3-(4-fluorophenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography IA, 5UM, 20 × 250 MM column, 80 ml/min, 100 bar, eluting 15% IPA with 0.5% NH4OH/CO2 (v/v) to give (R)-3-(2-(((R)-1-(3-(4-fluorophenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(4-fluorophenyl)-1,2,4-oxadiazol-5-yl)ethyl)amino)pyrimidin-4-yl)-4-((R)-1-hydroxyethyl)oxazolidin-2-one.<br>100: First eluted product (40 mg). HRMS(B) m/z 415.1516 (M + H)$^+$. RT = 1.96 min.<br>101: Second eluted product (13 mg). HRMS(B) m/z 415.1518 (M + H)$^+$. RT = 1.97 min. |
| 102 and 103:<br>(R)-3-(2-((1-(5-(2-fluorophenyl)-1,3,4-oxadiazol-2-yl)ethyl)amino)pyrimidin-4-yl)-4-((R)-1-hydroxyethyl)oxazolidin-2-one. | Chiral separation was achieved by chiral SFC column chromatography IA, 5UM, 20 × 250 MM column, 74 ml/min, 99 bar, eluting 35% IPA with 5 mM NH4OH/CO2 (v/v) to give (R)-3-(2-(((R)-1-(5-(2-fluorophenyl)-1,3,4-oxadiazol-2-yl)ethyl)amino)pyrimidin-4-yl)-4-((R)-1-hydroxyethyl)oxazolidin-2-one and (R)-3-(2-(((S)-1-(5-(2-fluorophenyl)-1,3,4-oxadiazol-2-yl)ethyl)amino)pyrimidin-4-yl)-4-((R)-1-hydroxyethyl)oxazolidin-2-one.<br>102: First eluted product (44 mg). HRMS(B) m/z 415.1514 (M + H)$^+$. RT = 1.58 min.<br>103: Second eluted product (51 mg). HRMS(B) m/z 415.1510 (M + H)$^+$. RT = 1.58 min. |
| 104 and 105:<br>(R)-4-((R)-1-hydroxyethyl)-3-(2-((1-(5-(m-tolyl)-1,3,4-oxadiazol-2-yl)ethyl)amino)pyrimidin-4-yl)oxazolidin-2-one | Chiral separation was achieved by chiral SFC column chromatography IA, 5UM, 20 × 250 MM column, 74 ml/min, 99 bar, eluting 35% IPA with 5 mM NH4OH/CO2 (v/v) to give (R)-4-((R)-1-hydroxyethyl)-3-(2-(((R)-1-(5-(m-tolyl)-1,3,4-oxadiazol-2-yl)ethyl)amino)pyrimidin-4-yl)oxazolidin-2-one and (R)-4-((R)-1-hydroxyethyl)-3-(2-(((S)-1-(5-(m-tolyl)-1,3,4-oxadiazol-2-yl)ethyl)amino)pyrimidin-4-yl)oxazolidin-2-one.<br>104: First eluted product (42 mg). HRMS(B) m/z 411.1762 (M + H)$^+$. RT = 1.78 min.<br>105: Second eluted product (51 mg). HRMS(B) m/z 411.1762 (M + H)$^+$. RT = 1.82 min. |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
| 106 and 107:<br>(R)-4-((R)-1-hydroxyethyl)-3-(2-((1-(5-(o-tolyl)-1,3,4-oxadiazol-2-yl)ethyl)amino)pyrimidin-4-yl)oxazolidin-2-one | Chiral separation was achieved by chiral SFC column chromatography IA, 5UM, 20 × 250 MM column, 74 ml/min, 99 bar, eluting 35% IPA with 5 mM NH4OH/CO2 (v/v) to give (R)-4-((R)-1-hydroxyethyl)-3-(2-(((R)-1-(5-(o-tolyl)-1,3,4-oxadiazol-2-yl)ethyl)amino)pyrimidin-4-yl)oxazolidin-2-one and (R)-4-((R)-1-hydroxyethyl)-3-(2-(((S)-1-(5-(o-tolyl)-1,3,4-oxadiazol-2-yl)ethyl)amino)pyrimidin-4-yl)oxazolidin-2-one.<br>106: First eluted product (44 mg). HRMS(B) m/z 411.1766 (M + H)$^+$. RT = 1.80 min.<br>107: Second eluted product (42 mg). HRMS(B) m/z 411.1764 (M + H)$^+$. RT = 1.80 min. |
| 108 and 109:<br>(R)-3-(2-((1-(4-(4-chlorophenyl)-5-methylthiazol-2-yl)ethyl)amino)pyrimidin-4-yl)-4-((R)-1-hydroxyethyl)oxazolidin-2-one | Chiral separation was achieved by chiral SFC column chromatography ID, 5UM, 20 × 250 MM column, 89 ml/min, 99 bar, eluting 22% MeOH/CO2 (v/v) to give (R)-3-(2-(((R)-1-(4-(4-chlorophenyl)-5-methylthiazol-2-yl)ethyl)amino)pyrimidin-4-yl)-4-((R)-1-hydroxyethyl)oxazolidin-2-one and (R)-3-(2-(((S)-1-(4-(4-chlorophenyl)-5-methylthiazol-2-yl)ethyl)amino)pyrimidin-4-yl)-4-((R)-1-hydroxyethyl)oxazolidin-2-one.<br>108: First eluted product (44 mg). HRMS(B) m/z 411.1766 (M + H)$^+$. RT = 1.80 min.<br>109: Second eluted product (34 mg). HRMS(B) m/z 460.1198 (M + H)$^+$. RT = 2.41 min. |
| 110 and 111:<br>(R)-3-(2-{1-[5-(3-fluoro-phenyl)-[1,3,4]oxadiazol-2-yl]-ethylamino}-pyrimidin-4-yl)-4-((R)-1-hydroxy-ethyl)-oxazolidin-2-one. | Chiral separation was achieved by chiral SFC column chromatography IA, 5UM, 20 × 250 MM column, 80 ml/min, eluting 20% IPA with 5 mM NH4OH/CO2 (v/v) to give (R)-3-(2-{(R)-1-[5-(3-fluoro-phenyl)-[1,3,4]oxadiazol-2-yl]-ethylamino}-pyrimidin-4-yl)-4-((R)-1-hydroxy-ethyl)-oxazolidin-2-one and (R)-3-(2-{(S)-1-[5-(3-fluoro-phenyl)-[1,3,4]oxadiazol-2-yl]-ethylamino}-pyrimidin-4-yl)-4-((R)-1-hydroxy-ethyl)-oxazolidin-2-one.<br>110: First eluted product (34.1 mg). HRMS(B) m/z 415.1510 (M + H)$^+$. RT = 1.70 min.<br>111: Second eluted product (41.9 mg). $^1$H NMR (400 MHz, CDCl$_3$) δ 8.23 (s, 1H), 7.82 (dt, J = 7.7, 1.2 Hz, 1H), 7.72 (ddd, J = 9.1, 2.6, 1.6 Hz, 1H), 7.64-7.42 (m, 2H), 7.35-7.17 (m, 1H), 6.21 (s, 1H), 5.57-5.35 (m, 1H), 4.93 (dt, J = 6.7, 2.9 Hz, 1H), 4.61 (dd, J = 9.5, 2.4 Hz, 2H), 4.42 (dd, J = 9.3, 8.3 Hz, 2H), 3.98 (s, 1H), 1.08 (d, J = 6.4 Hz, 3H), 0.92-0.77 (m, 3H). HRMS(B) m/z 415.1515 (M + H)$^+$, RT = 1.70 min. |
| 112 and 113:<br>(R)-4-((R)-1-Hydroxy-ethyl)-3-{2-[1-(5-pyridin-3-yl-[1,3,4]oxadiazol-2-yl)-ethylamino]-pyrimidin-4-yl}-oxazolidin-2-one | Chiral separation was achieved by chiral SFC column chromatography AD-H 20 × 250 mm, 20% MeOH in CO$_2$, 80 g/min, UV220 nm to give (R)-4-((R)-1-Hydroxy-ethyl)-3-{2-[(R)-1-(5-pyridin-3-yl-[1,3,4]oxadiazol-2-yl)-ethylamino]-pyrimidin-4-yl}-oxazolidin-2-one and (R)-4-((R)-1-Hydroxy-ethyl)-3-{2-[(S)-1-(5-pyridin-3-yl-[1,3,4]oxadiazol-2-yl)-ethylamino]-pyrimidin-4-yl}-oxazolidin-2-one.<br>112: First eluted product (39.9 mg). HRMS(B) m/z 398.1566 (M + H)$^+$. RT = 1.18 min.<br>113: Second eluted product (40.2 mg). $^1$H NMR (400 MHz, CDCl$_3$) δ 9.26 (s, 1H), 8.80 (s, 1H), 8.33 (d, J = 7.9 Hz, 1H), 8.23 (s, 1H), 7.54 (d, J = 5.3 Hz, 1H), 7.48 (dd, J = 8.2, 4.6 Hz, 1H), 6.17 (s, 1H), 5.46 (s, 1H), 4.99-4.84 (m, 1H), 4.60 (dd, J = 9.3, 2.3 Hz, 2H), 4.42 (dd, J = 9.3, 8.3 Hz, 2H), 4.01 (s, 1H), 1.09 (d, J = 6.5 Hz, 3H), 0.91-0.81 (m, 3H). HRMS(B) m/z 398.1660, (M + H)$^+$. RT = 1.17 min. |
| 114 and 115:<br>(R)-3-{2-[1-(5-Benzyl-[1,2,4]oxadiazol-3-yl)-ethylamino]-pyrimidin-4-yl}-4-((R)-1-hydroxy-ethyl)-oxazolidin-2-one | Chiral separation was achieved by chiral SFC column chromatography AD-H 21 × 250 mm, 25% MeOH in CO$_2$, 75 g/min, UV224 nm to give (R)-3-{2-[(R)-1-(5-Benzyl-[1,2,4]oxadiazol-3-yl)-ethylamino]-pyrimidin-4-yl}-4-((R)-1-hydroxy-ethyl)-oxazolidin-2-one and (R)-3-{2-[(S)-1-(5-Benzyl-[1,2,4]oxadiazol-3-yl)-ethylamino]-pyrimidin-4-yl}-4-((R)-1-hydroxy-ethyl)-oxazolidin-2-one.<br>114: First eluted product (48.9 mg). HRMS(B) m/z 411.1855 (M + H)$^+$. RT = 1.85 min.<br>115: Second eluted product (52.2 mg). $^1$H NMR (400 MHz, CDCl$_3$) δ 8.13 (d, J = 5.7 Hz, 1H), 7.38 (d, J = 5.8 Hz, 1H), 7.31-7.13 (m, 5H), 6.09 (s, 1H), 5.21 (dq, J = 14.4, 7.1 Hz, 1H), 4.90-4.69 (m, 1H), 4.42 (dd, J = 9.4, 2.5 Hz, 1H), 4.33-4.20 (m, 1H), 4.12 (s, 2H), 3.99 (d, J = 24.4 Hz, 1H), 1.54 (d, J = 7.1 Hz, 3H), 0.96 (d, J = 6.6 Hz, 3H). HRMS(B) m/z 411.1864, (M + H)$^+$. RT = 1.86 min. |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
| 116 and 117:<br>(R)-3-{2-[1-(5-Benzyl-[1,2,4]oxadiazol-3-yl)-ethylamino]-5-fluoro-pyrimidin-4-yl}-4-((R)-1-hydroxy-ethyl)-oxazolidin-2-one | Chiral separation was achieved by chiral SFC column chromatography AD-H 21 × 250 mm, 25% MeOH in $CO_2$, 75 g/min, UV231 nm to give (R)-3-{2-[(R)-1-(5-Benzyl-[1,2,4]oxadiazol-3-yl)-ethylamino]-5-fluoro-pyrimidin-4-yl}-4-((R)-1-hydroxy-ethyl)-oxazolidin-2-one and (R)-3-{2-[(S)-1-(5-Benzyl-[1,2,4]oxadiazol-3-yl)-ethylamino]-5-fluoro-pyrimidin-4-yl}-4-((R)-1-hydroxy-ethyl)-oxazolidin-2-one.<br>116: First eluted product (29.4 mg). HRMS(B) m/z 429.1667 (M + H)$^+$. RT = 1.84 min.<br>117: Second eluted product (52.2 mg). $^1$H NMR (400 MHz, CDCl$_3$) δ 8.14 (d, J = 2.8 Hz, 1H), 7.38-7.13 (m, 5H), 5.64 (d, J = 8.3 Hz, 1H), 5.25-5.08 (m, 1H), 4.66 (s, 1H), 4.44 (t, J = 9.0 Hz, 1H), 4.28 (dd, J = 9.1, 5.8 Hz, 1H), 4.12 (s, 2H), 3.84 (s, 1H), 1.58-1.50 (m, 3H), 0.99 (d, J = 6.4 Hz, 3H). HRMS(B) m/z 429.1671, (M + H)$^+$. RT = 1.84 min. |
| 118 and 119:<br>(4R)-3-{2-[1-(3-(4-bromophenyl)-1,2,4-oxadiazol-5-yl)ethyl]amino}-pyrimidin-4-yl}-4-((R)-1-hydroxyethyl)-oxazolidin-2-one | Chiral separation was achieved by chiral SFC column chromatography AD-H 21 × 250 mm, 25% IPA in $CO_2$, 75 g/min, UV240 nm to give (R)-3-{2-[(R)1-(3-(4-bromophenyl)-1,2,4-oxadiazol-5-yl)ethyl]amino}-pyrimidin-4-yl}-4-((S)-1-hydroxyethyl)-oxazolidin-2-one and (R)-3-{2-[1-(3-(4-bromophenyl)-1,2,4-oxadiazol-5-yl)ethyl]amino}-pyrimidin-4-yl}-4-((R)-1-hydroxyethyl)-oxazolidin-2-one<br>118: First eluted product (34.3 mg). HRMS(B) m/z 477.0856 (M + H)$^+$. RT = 2.31 min.<br>119: Second eluted product (33.5 mg). $^1$H NMR (400 MHz, CDCl$_3$) δ 8.25 (d, J = 5.8 Hz, 1H), 8.04-7.81 (m, 2H), 7.76-7.58 (m, 2H), 7.55 (d, J = 5.8 Hz, 1H), 5.38 (s, 1H), 4.84 (ddd, J = 8.3, 4.5, 2.5 Hz, 1H), 4.54 (dd, J = 9.4, 2.5 Hz, 1H), 4.39 (dd, J = 9.4, 8.3 Hz, 1H), 3.92 (s, 1H), 1.78 (d, J = 7.1 Hz, 3H), 1.01 (d, J = 7.2 Hz, 3H). HRMS(B) m/z 477.0856 (M + H)$^+$. RT = 2.32 min. |
| 120 and 121:<br>(4R)-3-{2-[(1-(3-(3-fluoro-4-methylphenyl)-1,2,4-oxadiazol-5-yl)-ethyl]amino}pyrimidin-4-yl}-4-((R)-1-hydroxyethyl)oxazolidin-2-one | Chiral separation was achieved by chiral SFC column chromatography OJ-H 21 × 250 mm, 15% MeOH in $CO_2$, 80 g/min, UV233 nm to give (R)-3-{2-[((R)1-(3-(3-fluoro-4-methylphenyl)-1,2,4-oxadiazol-5-yl)ethyl]amino}pyrimidin-4-yl}-4-((R)-1-hydroxyethyl)oxazolidin-2-one and (R)-3-{2-[(1(S)-(3-(3-fluoro-4-methylphenyl)-1,2,4-oxadiazol-5-yl)ethyl]amino}pyrimidin-4-yl}-4-((R)-1-hydroxyethyl)oxazolidin-2-one<br>120: First eluted product (40.1 mg). HRMS(B) m/z 429.1785 (M + H)$^+$. RT = 2.23 min.<br>121: Second eluted product (42.9 mg). $^1$H NMR (400 MHz, CDCl$_3$) δ 8.25 (d, J = 5.8 Hz, 1H), 7.87-7.63 (m, 2H), 7.55 (d, J = 5.8 Hz, 1H), 7.39-7.13 (m, 1H), 6.13 (s, 1H), 5.34 (d, J = 20.8 Hz, 1H), 4.84 (ddd, J = 8.3, 4.5, 2.5 Hz, 1H), 4.54 (dd, J = 9.4, 2.5 Hz, 1H), 4.39 (t, J = 8.9 Hz, 1H), 3.86 (d, J = 36.7 Hz, 1H), 2.34 (d, J = 1.9 Hz, 3H), 1.77 (d, J = 7.1 Hz, 3H), 1.01 (d, J = 6.8 Hz, 4H). HRMS(B) m/z 429.1783 (M + H)$^+$. RT = 2.24 min. |
| 122 and 123:<br>(R)-3-(5-Fluoro-2-{1-[3-(3-fluoro-4-methyl-phenyl)-[1,2,4]oxadiazol-5-yl]-ethylamino}-pyrimidin-4-yl)-4-((R)-1-hydroxy-ethyl)-oxazolidin-2-one | Chiral separation was achieved by chiral SFC column chromatography OJ-H 21 × 250 mm, 15% MeOH in $CO_2$, 80 g/min, UV233 nm to give (R)-3-(5-Fluoro-2-{(R)-1-[3-(3-fluoro-4-methyl-phenyl)-[1,2,4]oxadiazol-5-yl]-ethylamino}-pyrimidin-4-yl)-4-((R)-1-hydroxy-ethyl)-oxazolidin-2-one and (R)-3-{2-[(S)-1-(5-Benzyl-[1,2,4]oxadiazol-3-yl)-ethylamino]-5-fluoro-pyrimidin-4-yl}-4-((R)-1-hydroxy-ethyl)-oxazolidin-2-one.<br>122: First eluted product (58.7 mg). HRMS(B) m/z 447.1573 (M + H)$^+$. RT = 2.22 min.<br>123: Second eluted product (36.4 mg). $^1$H NMR (400 MHz, CDCl$_3$) δ 8.17 (d, J = 2.7 Hz, 1H), 7.63 (dddd, J = 17.6, 9.8, 8.0, 1.7 Hz, 2H), 7.32-7.14 (m, 1H), 5.96-5.72 (m, 1H), 5.22 (q, J = 6.9, 5.9 Hz, 1H), 4.69-4.57 (m, 1H), 4.45 (t, J = 9.0 Hz, 1H), 4.35 (dd, J = 9.2, 5.6 Hz, 1H), 4.14-3.96 (m, 1H), 2.25 (d, J = 1.9 Hz, 3H), 1.67 (dd, J = 11.7, 7.0 Hz, 3H), 0.95 (t, J = 7.8 Hz, 3H). HRMS(B) m/z 447.1573 (M + H)$^+$. RT = 2.22 min. |
| 124 and 125:<br>(R)-3-(2-{1-[3-(3,4-Difluoro-phenyl)-[1,2,4]oxadiazol-5-yl]-ethylamino}-pyrimidin-4-yl)-4-((R)-1-hydroxy-ethyl)-oxazolidin-2-one | Chiral separation was achieved by chiral SFC column chromatography AD-H 21 × 250 mm, 25% IPA in $CO_2$, 75 g/min, UV226 nm to give (R)-3-(2-{(R)-1-[3-(3,4-Difluoro-phenyl)-[1,2,4]oxadiazol-5-yl]-ethylamino}-pyrimidin-4-yl)-4-((R)-1-hydroxy-ethyl)-oxazolidin-2-one and (R)-3-(2-{(S)-1-[3-(3,4-Difluoro-phenyl)-[1,2,4]oxadiazol-5-yl]-ethylamino}-pyrimidin-4-yl)-4-((R)-1-hydroxy-ethyl)-oxazolidin-2-one. |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
|  | 124: First eluted product (43.2 mg). HRMS(B) m/z 443.1112 (M + H)$^+$. RT = 2.09 min.<br>125: Second eluted product (40.7 mg). $^1$H NMR (400 MHz, CDCl$_3$) δ 8.16 (d, J = 5.8 Hz, 1H), 7.93-7.67 (m, 2H), 7.47 (d, J = 5.7 Hz, 1H), 7.30-7.10 (m, 1H), 6.07 (s, 1H), 5.30 (s, 1H), 4.76 (ddd, J = 8.3, 4.6, 2.5 Hz, 1H), 4.45 (dd, J = 9.4, 2.5 Hz, 1H), 4.31 (dd, J = 9.4, 8.4 Hz, 1H), 4.02-3.52 (m, 1H), 1.69 (d, J = 7.1 Hz, 3H), 1.07-0.88 (m, 3H). HRMS(B) m/z 433.1109, (M + H)$^+$. RT = 2.18 min. |
| 126 and 127:<br>(R)-3-(2-{1-[3-(3,4-Dichloro-phenyl)-isoxazol-5-yl]-ethylamino}-pyrimidin-4-yl)-4-((R)-1-hydroxy-ethyl)-oxazolidin-2-one | Chiral separation was achieved by chiral SFC column chromatography IA. 21 × 250 mm, 30% (70% MeOH:30% DCM) in CO$_2$, 70 g/min, UV239 nm to give (R)-3-(2-{(R)-1-[3-(3,4-Dichloro-phenyl)-isoxazol-5-yl]-ethylamino}-pyrimidin-4-yl)-4-((R)-1-hydroxy-ethyl)-oxazolidin-2-one and (R)-3-(2-{(S)-1-[3-(3,4-Dichloro-phenyl)-isoxazol-5-yl]-ethylamino}-pyrimidin-4-yl)-4-((R)-1-hydroxy-ethyl)-oxazolidin-2-one.<br>126: First eluted product (37.4 mg). HRMS(B) m/z 464.0869 (M + H)$^+$. RT = 2.63 min.<br>127: Second eluted product (27.3 mg). $^1$H NMR (400 MHz, CDCl$_3$) δ 8.15 (s, 1H), 7.76 (d, J = 2.0 Hz, 1H), 7.53 (dd, J = 8.3, 2.0 Hz, 1H), 7.45 (d, J = 8.3 Hz, 2H), 6.37 (s, 1H), 5.70 (s, 1H), 5.11 (s, 1H), 4.77 (ddd, J = 7.4, 4.6, 2.6 Hz, 1H), 4.46 (dd, J = 9.4, 2.5 Hz, 1H), 4.31 (dd, J = 9.4, 8.4 Hz, 1H), 1.61 (d, J = 7.0 Hz, 3H), 0.86 (d, J = 7.5 Hz, 3H). HRMS(B) m/z 464.0855, (M + H)$^+$. RT = 2.56 min. |
| 128 and 129:<br>(R)-3-(2-{1-[3-(2,4-Dichloro-phenyl)-isoxazol-5-yl]-ethylamino}-pyrimidin-4-yl)-4-((R)-1-hydroxy-ethyl)-oxazolidin-2-one | Chiral separation was achieved by chiral SFC column chromatography OJ-H. 21 × 250 mm, 15% MeOH in CO$_2$, 75 g/min, UV231 nm to give (R)-3-(2-{(R)-1-[3-(2,4-Dichloro-phenyl)-isoxazol-5-yl]-ethylamino}-pyrimidin-4-yl)-4-((R)-1-hydroxy-ethyl)-oxazolidin-2-one and (R)-3-(2-{(S)-1-[3-(2,4-Dichloro-phenyl)-isoxazol-5-yl]-ethylamino}-pyrimidin-4-yl)-4-((R)-1-hydroxy-ethyl)-oxazolidin-2-one.<br>128: First eluted product (72.9 mg). HRMS(B) m/z 464.0869 (M + H)$^+$. RT = 2.54 min.<br>129: Second eluted product (36.5 mg). $^1$H NMR (400 MHz, CDCl$_3$) δ 8.39-8.11 (m, 1H), 7.65 (d, J = 8.4 Hz, 1H), 7.56-7.47 (m, 2H), 7.42-7.28 (m, 1H), 6.60 (s, 1H), 5.80 (s, 1H), 5.27 (d, J = 37.0 Hz, 1H), 4.72-4.45 (m, 3H), 4.31 (t, J = 8.7 Hz, 1H), 1.71 (d, J = 6.9 Hz, 3H), 1.19 (d, J = 6.4 Hz, 3H). HRMS(B) m/z 464.0876, (M + H)$^+$. RT = 2.55 min. |
| 130 and 131:<br>(R)-3-(2-{1-[3-(3,4-Difluoro-phenyl)-[1,2,4]oxadiazol-5-yl]-ethylamino}-5-fluoro-pyrimidin-4-yl)-4-((R)-1-hydroxy-ethyl)-oxazolidin-2-one | Chiral separation was achieved by chiral SFC column chromatography ID 21 × 250 mm, 30% iIPA in CO$_2$, 75 g/min, UV233 nm to give and (R)-3-(2-{(S)-1-[3-(3,4-Difluorophenyl)-[1,2,4]oxadiazol-5-yl]-ethylamino}-5-fluoro-pyrimidin-4-yl)-4-((R)-1-hydroxy-ethyl)-oxazolidin-2-one.<br>130: First eluted product (63.9 mg). HRMS(B) m/z 451.1324 (M + H)$^+$. RT = 2.20 min.<br>131: Second eluted product (58.1 mg). $^1$H NMR (400 MHz, CDCl$_3$) δ 8.25 (d, J = 2.8 Hz, 1H), 7.97-7.72 (m, 2H), 7.27 (dt, J = 9.9, 8.4 Hz, 1H), 6.09 (s, 1H), 5.47-5.16 (m, 1H), 4.84-4.64 (m, 1H), 4.54 (t, J = 9.0 Hz, 1H), 4.43 (dd, J = 9.1, 5.4 Hz, 1H), 3.87 (s, 1H), 1.76 (d, J = 7.1 Hz, 3H), 1.04 (d, J = 6.5 Hz, 3H). HRMS(B) m/z 451.1324 (M + H)$^+$. RT = 2.20 min. |
| 132 and 133:<br>(R)-3-(2-{1-[3-(3,4-Dichloro-phenyl)-isoxazol-5-yl]-ethylamino}-5-fluoro-pyrimidin-4-yl)-4-((R)-1-hydroxy-ethyl)-oxazolidin-2-one | Chiral separation was achieved by chiral SFC column chromatography IC. 21 × 250 mm, 40% MeOH in CO$_2$, 80 g/min, UV239 nm to give (R)-3-(2-{(R)-1-[3-(3,4-Dichloro-phenyl)-isoxazol-5-yl]-ethylamino}-5-fluoro-pyrimidin-4-yl)-4-((R)-1-hydroxy-ethyl)-oxazolidin-2-one and (R)-3-(2-{(S)-1-[3-(3,4-Dichloro-phenyl)-isoxazol-5-yl]-ethylamino}-5-fluoro-pyrimidin-4-yl)-4-((R)-1-hydroxy-ethyl)-oxazolidin-2-one.<br>132: First eluted product (107 mg). HRMS(B) m/z 482.0781 (M + H)$^+$. RT = 2.63 min.<br>133: Second eluted product (61.1 mg). $^1$H NMR (400 MHz, CDCl$_3$) δ 8.22 (d, J = 2.8 Hz, 1H), 7.86 (d, J = 1.9 Hz, 1H), 7.61 (dd, J = 8.3, 2.0 Hz, 1H), 7.52 (d, J = 8.3 Hz, 1H), 6.45 (s, 1H), 5.72 (d, J = 7.6 Hz, 1H), 5.25 (t, J = 7.1 Hz, 1H), 4.66-4.42 (m, 2H), 4.26 (t, J = 6.2 Hz, 1H), 1.68 (d, J = 6.9 Hz, 3H), 1.19 (d, J = 6.4 Hz, 3H). HRMS(B) m/z 482.0777 (M + H)$^+$. RT = 2.63 min. |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
| 134 and 135:<br>(R)-3-(2-{1-[3-(2,4-Dichloro-phenyl)-isoxazol-5-yl]-ethylamino}-5-fluoro-pyrimidin-4-yl)-4-((R)-1-hydroxy-ethyl)-oxazolidin-2-one | Chiral separation was achieved by chiral SFC column chromatography AD-H, 21 × 250 mm, 35% IPA in $CO_2$, 75 g/min, UV237 nm to give (R)-3-(2-{(R)-1-[3-(2,4-Dichloro-phenyl)-isoxazol-5-yl]-ethylamino}-5-fluoro-pyrimidin-4-yl)-4-((R)-1-hydroxy-ethyl)-oxazolidin-2-one and (R)-3-(2-{(S)-1-[3-(2,4-Dichloro-phenyl)-isoxazol-5-yl]-ethylamino}-5-fluoro-pyrimidin-4-yl)-4-((R)-1-hydroxy-ethyl)-oxazolidin-2-one.<br>134: First eluted product (53.4 mg). HRMS(B) m/z 482.0778 (M + H)$^+$. RT = 2.54 min.<br>135: Second eluted product (107 mg) $^1$H NMR (400 MHz, $CDCl_3$) δ 8.21 (d, J = 2.8 Hz, 1H), 7.63 (d, J = 8.5 Hz, 1H), 7.50 (d, J = 2.0 Hz, 1H), 7.42-7.22 (m, 1H), 6.60 (s, 1H), 5.88 (s, 1H), 5.24 (t, J = 6.7 Hz, 1H), 4.98-4.71 (m, 1H), 4.63-4.40 (m, 2H), 3.83 (s, 1H), 1.70 (d, J = 7.1 Hz, 3H), 1.05 (d, J = 6.4 Hz, 3H) . HRMS(B) m/z 482.0774 (M + H)$^+$. RT = 2.53 min. |
| 136 and 137:<br>(R)-3-(2-{1-[4-(3-Chloro-4-fluoro-phenyl)-thiazol-2-yl]-ethylamino}-pyrimidin-4-yl)-4-((R)-1-hydroxy-ethyl)-oxazolidin-2-one | Chiral separation was achieved by chiral SFC column chromatography OD-H, 21 × 250 mm, 30% IPA in $CO_2$, 75 g/min, UV220 nm to give (R)-3-(2-{(R)-1-[4-(3-Chloro-4-fluoro-phenyl)-thiazol-2-yl]-ethylamino}-pyrimidin-4-yl)-4-((R)-1-hydroxy-ethyl)-oxazolidin-2-one and (R)-3-(2-{(S)-1-[4-(3-Chloro-4-fluoro-phenyl)-thiazol-2-yl]-ethylamino}-pyrimidin-4-yl)-4-((R)-1-hydroxy-ethyl)-oxazolidin-2-one.<br>136: First eluted product (76.9 mg). HRMS(B) m/z 464.0930 (M + H)$^+$. RT = 2.50 min.<br>137: Second eluted product (88.6 mg). $^1$H NMR (400 MHz, $CDCl_3$) δ 8.22 (d, J = 6.0 Hz, 1H), 7.95 (dd, J = 7.0, 2.2 Hz, 1H), 7.72 (ddd, J = 8.6, 4.5, 2.2 Hz, 1H), 7.50 (d, J = 5.7 Hz, 1H), 7.34 (s, 1H), 7.18 (t, J = 8.6 Hz, 1H), 5.61-5.35 (m, 1H), 4.75 (ddd, J = 8.1, 4.4, 2.4 Hz, 1H), 4.45 (dd, J = 9.3, 2.7 Hz, 1H), 4.34 (t, J = 8.9 Hz, 1H), 3.87 (s, 1H), 1.73 (d, J = 6.9 Hz, 3H), 0.90 (q, J = 6.9, 6.3 Hz, 3H). HRMS(B) m/z 464.0940 (M + H)$^+$. RT = 2.49 min. |
| 138 and 139:<br>(R)-3-(5-fluoro-2-((1-(5-(3-(trifluoromethyl)phenyl)pyrimidin-2-yl)ethyl)amino)pyrimidin-4-yl)-4-((R)-1-hydroxyethyl)oxazolidin-2-one | Chiral separation was achieved by chiral SFC column chromatography (Column AD-H 20 × 250 mm 45% IPA 10 mM $NH_4OH$ in $CO_2$, flow 75 g/min, 238 nm UV collection) to give (R)-3-(5-fluoro-2-(((S)-1-(5-(3-(trifluoromethyl)phenyl)pyrimidin-2-yl)ethyl)amino)pyrimidin-4-yl)-4-((R)-1-hydroxyethyl)oxazolidin-2-one and (R)-3-(5-fluoro-2-(((R)-1-(5-(3-(trifluoromethyl)phenyl)pyrimidin-2-yl)ethyl)amino)pyrimidin-4-yl)-4-((R)-1-hydroxyethyl)oxazolidin-2-one.<br>138: First eluted product (6 mg) $^1$H NMR (400 MHz, $CDCl_3$) δ 8.84 (s, 2H), 8.15 (d, J = 2.8 Hz, 1H), 7.76-7.55 (m, 3H), 6.17 (br s, 1H), 5.24 (t, J = 7.1 Hz, 1H), 4.56 (d, J = 7.4 Hz, 1H), 4.47 (t, J = 8.8 Hz, 1H), 4.33 (dd, J = 9.0, 5.1 Hz, 1H), 4.00 (br s, 1H), 1.59 (d, J = 6.9 Hz, 3H), 1.06 (br d, J = 5.7 Hz, 3H). HRMS(B) m/z 493.1587 (M + H)$^+$.<br>139: Second eluted product (10 mg) $^1$H NMR (400 MHz, $CDCl_3$) δ 8.86 (s, 2H), 8.14 (d, J = 2.9 Hz, 1H), 7.77-7.55 (m, 4H), 6.32 (br s, 1H), 5.18 (br s, 1H), 4.49-4.29 (m, 3H), 3.96 (p, J = 6.1 Hz, 1H), 2.69 (br s, 1H), 1.58 (d, J = 7.0 Hz, 3H), 1.15 (d, J = 5.9 Hz, 3H). HRMS(B) m/z 493.1591 (M + H)$^+$. |
| 140 and 141:<br>(4R)-4-((R)-1-hydroxyethyl)-3-(2-((1-(2-phenylthiazol-5-yl)ethyl)amino)pyrimidin-4-yl)oxazolidin-2-one | Chiral separation was achieved by chiral SFC column chromatography (Column OD 20 × 250 mm 25% MeOH in $CO_2$, flow 75 g/min, 238 nm UV collection) to give(R)-4-((R)-1-hydroxyethyl)-3-(2-(((R)-1-(2-phenylthiazol-5-yl)ethyl)amino)pyrimidin-4-yl)oxazolidin-2-one and (R)-4-((R)-1-hydroxyethyl)-3-(2-(((S)-1-(2-phenylthiazol-5-yl)ethyl)amino)pyrimidin-4-yl)oxazolidin-2-one<br>140: First eluted product (48 mg) $^1$H NMR (400 MHz, $CDCl_3$) δ 10.83 (s, 1H), 8.13-7.69 (m, 5H), 7.47 (d, J = 4.6 Hz, 4H), 5.31-5.14 (m, 1H), 4.82 (d, J = 7.7 Hz, 1H), 4.66 (dd, J = 9.6, 2.2 Hz, 1H), 4.46 (dd, J = 9.6, 8.0 Hz, 1H), 3.38 (d, J = 9.6 Hz, 1H), 1.84 (d, J = 6.8 Hz, 3H), 1.55-1.09 (m, 1H), 1.03-0.71 (m, 4H). HRMS(B) m/z 411.1365. Chiral RT = 2.90 min |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
| | 141: Second eluted product (46 mg) $^1$H NMR (400 MHz, CDCl$_3$) δ 11.03 (s, 1H), 8.11-7.64 (m, 5H), 7.49 (d, J = 4.9 Hz, 3H), 5.52-5.10 (m, 1H), 4.70 (dd, J = 23.0, 8.0 Hz, 2H), 4.42 (t, J = 8.6 Hz, 2H), 1.86 (d, J = 6.8 Hz, 3H), 1.53-1.08 (m, 4H), 0.99-0.61 (m, 1H). HRMS(B) m/z 411.1365. Chiral RT = 4.00 min |
| 142 and 143:<br>(4R)-3-(2-((1-(3-(3-chlorophenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column AD 20 × 250 mm 20% MeOH in CO$_2$, flow 90 g/min, 238 nm UV collection) to give (R)-3-(2-(((R)-1-(3-(3-chlorophenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(3-chlorophenyl)-1,2,4-oxadiazol-5-yl)ethyl)amino)pyrimidin-4-yl)-4-((R)-1-hydroxyethyl)oxazolidin-2-one<br>142: First eluted product (15.5 mg): $^1$H NMR (400 MHz, CDCl$_3$) δ 8.16 (d, J = 5.8 Hz, 4H), 7.79 (dd, J = 7.6, 1.8 Hz, 4H), 7.56-7.26 (m, 15H), 5.83 (s, 4H), 5.17 (s, 4H), 4.57 (q, J = 6.1 Hz, 4H), 4.39 (dd, J = 9.3, 2.5 Hz, 4H), 4.29-4.04 (m, 9H), 3.96 (p, J = 6.2 Hz, 1H), 2.96 (s, 4H), 1.88-1.56 (m, 5H), 1.49-1.01 (m, 28H), 0.93-0.59 (m, 4H). HRMS(B) m/z 430.1156. Chiral RT = 3.40 min<br>143: Second eluted product (10 mg) $^1$H NMR (400 MHz, CDCl$_3$) δ 8.25 (d, J = 5.8 Hz, 3H), 7.91 (dd, J = 7.7, 1.8 Hz, 3H), 7.62-7.52 (m, 6H), 7.43 (dtd, J = 25.2, 7.5, 1.6 Hz, 6H), 6.30 (s, 3H), 5.40 (s, 3H), 4.87 (ddd, J = 8.3, 4.3, 2.3 Hz, 3H), 4.55 (dd, J = 9.5, 2.5 Hz, 3H), 4.39 (t, J = 8.9 Hz, 3H), 4.10-3.75 (m, 4H), 3.50 (s, 3H), 3.18-2.93 (m, 3H), 1.72 (d, J = 6.8 Hz, 0H), 1.39-1.16 (m, 5H), 1.10-0.93 (m, 9H), 0.93-0.76 (m, 2H). HRMS(B) m/z 430.1156. Chiral RT = 4.80 min |
| 144 and 145:<br>(4R)-4-((R)-1-hydroxyethyl)-3-(2-((1-(3-(4-isopropylphenyl)-1,2,4-oxadiazol-5-yl)ethyl)amino)pyrimidin-4-yl)oxazolidin-2-one | Chiral separation was achieved by chiral SFC column chromatography (Column ID 21 × 250 mm 25% MeOH in CO$_2$, flow 75 g/min, 238 nm UV collection) to give (R)-4-((R)-1-hydroxyethyl)-3-(2-(((R)-1-(3-(4-isopropylphenyl)-1,2,4-oxadiazol-5-yl)ethyl)amino)pyrimidin-4-yl)oxazolidin-2-one and (R)-4-((R)-1-hydroxyethyl)-3-(2-(((S)-1-(3-(4-isopropylphenyl)-1,2,4-oxadiazol-5-yl)ethyl)amino)pyrimidin-4-yl)oxazolidin-2-one<br>144: First eluted product (36 mg): (CDCl$_3$) δ 8.24 (d, J = 5.7 Hz, 1H), 8.06-7.88 (m, 2H), 7.50 (d, J = 5.8 Hz, 1H), 7.41-7.32 (m, 2H), 6.05 (s, 1H), 5.22 (s, 1H), 4.71 (s, 1H), 4.49 (dd, J = 9.3, 2.5 Hz, 1H), 4.43-4.14 (m, 2H), 4.12-3.99 (m, 0H), 3.51 (s, 1H), 3.37 (s, 1H), 2.98 (hept, J = 6.9 Hz, 1H), 2.04-1.73 (m, 1H), 1.44-1.17 (m, 11H). HRMS(B) m/z 438.2016. Chiral RT = 3.20 min<br>145: Second eluted product (36 mg): CDCl$_3$) δ 8.25 (d, J = 5.7 Hz, 1H), 8.05-7.91 (m, 2H), 7.54 (d, J = 5.7 Hz, 1H), 7.42-7.31 (m, 2H), 6.23 (s, 1H), 5.33 (d, J = 10.8 Hz, 1H), 4.85 (ddd, J = 8.5, 4.5, 2.3 Hz, 1H), 4.56 (dd, J = 9.4, 2.5 Hz, 1H), 1.84-1.73 (m, 3H), 4.39 (t, J = 8.9 Hz, 1H), 3.86 (s, 1H), 3.51 (s, 1H), 3.15 (s, 1H), 2.97 (hept, J = 7.0 Hz, 1H), 1.94 (d, J = 7.1 Hz, 1H), 1.28 (d, J = 6.9 Hz, 6H), 0.99 (d, J = 6.9 Hz, 3H). HRMS(B) m/z 438.2016. Chiral RT = 4.60 min |
| 146 and 147:<br>(4R)-4-((R)-1-hydroxyethyl)-3-(2-((1-(3-(2-(trifluoromethoxy)phenyl)-1,2,4-oxadiazol-5-yl)ethyl)amino)pyrimidin-4-yl)oxazolidin-2-one | Chiral separation was achieved by chiral SFC column chromatography (Column AD-H 21 × 250 mm 25% MeOH in CO$_2$, flow 75 g/min, 238 nm UV collection) to give (R)-4-((R)-1-hydroxyethyl)-3-(2-(((R)-1-(3-(2-(trifluoromethoxy)phenyl)-1,2,4-oxadiazol-5-yl)ethyl)amino)pyrimidin-4-yl)oxazolidin-2-one and (R)-4-((R)-1-hydroxyethyl)-3-(2-(((S)-1-(3-(2-(trifluoromethoxy)phenyl)-1,2,4-oxadiazol-5-yl)ethyl)amino)pyrimidin-4-yl)oxazolidin-2-one<br>146: First eluted product (8.3 mg): (CDCl$_3$) δ 8.25 (d, J = 5.9 Hz, 1H), 8.07 (dd, J = 7.8, 1.8 Hz, 1H), 7.69-7.39 (m, 4H), 5.73 (s, 1H), 5.26 (s, 1H), 4.78-4.57 (m, 1H), 4.48 (dd, J = 9.3, 2.3 Hz, 1H), 4.39-4.00 (m, 2H), 3.52 (s, 1H), 2.93 (s, 1H), 1.80 (d, J = 7.1 Hz, 3H), 1.62 (s, 3H), 1.21 (dd, J = 18.6, 6.3 Hz, 5H). HRMS(B) m/z 480.1369. Chiral RT = 2.10 min<br>147: Second eluted product (38.5 mg): (CDCl$_3$) δ 8.25 (d, J = 5.8 Hz, 1H), 8.10 (dd, J = 8.0, 1.7 Hz, 1H), 7.67-7.52 (m, 2H), 7.51-7.40 (m, 2H), 5.88 (s, 1H), 5.39 (s, 1H), |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
| | 4.86 (ddd, J = 8.5, 4.6, 2.5 Hz, 1H), 1.75-1.64 (m, 1H), 4.55 (dd, J = 9.4, 2.5 Hz, 1H), 4.39 (t, J = 8.9 Hz, 1H), 4.14-3.58 (m, 1H), 2.86 (s, 1H), 1.80 (d, J = 7.1 Hz, 3H), 1.23 (d, J = 6.1 Hz, 1H), 1.00 (s, 3H). HRMS(B) m/z 480.1369. Chiral RT = 2.55 min |
| 148 and 149: (4R)-3-(2-((1-(3-(4-fluoro-3-methylphenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column AD-H 21 × 250 mm 15% MeOH in $CO_2$, flow 80 g/min, 238 nm UV collection) to give(R)-3-(2-(((R)-1-(3-(4-fluoro-3-methylphenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(4-fluoro-3-methylphenyl)-1,2,4-oxadiazol-5-yl)ethyl)amino)pyrimidin-4-yl)-4-((R)-1-hydroxyethyl)oxazolidin-2-one 148: First eluted product (13 mg): ($CDCl_3$) δ 8.25 (d, J = 5.8 Hz, 1H), 8.03-7.80 (m, 2H), 7.52 (d, J = 5.7 Hz, 1H), 7.13 (t, J = 8.9 Hz, 1H), 5.85 (s, 1H), 5.23 (s, 1H), 4.69 (d, J = 8.4 Hz, 1H), 4.50 (dd, J = 9.5, 2.5 Hz, 1H), 4.41-4.04 (m, 2H), 3.51 (s, 2H), 3.11 (s, 1H), 2.36 (d, J = 2.0 Hz, 3H), 1.78 (d, J = 7.1 Hz, 3H), 1.21 (d, J = 6.4 Hz, 4H). HRMS(B) m/z 428.1608 Chiral RT = 4.25 min 149: Second eluted product (49 mg): ($CDCl_3$) δ 8.25 (d, J = 5.7 Hz, 1H), 8.01-7.80 (m, 2H), 7.56 (d, J = 5.7 Hz, 1H), 7.12 (t, J = 8.9 Hz, 1H), 5.76 (s, 1H), 5.46-5.12 (m, 1H), 4.85 (ddd, J = 8.4, 4.6, 2.4 Hz, 1H), 4.55 (dd, J = 9.5, 2.5 Hz, 1H), 4.40 (t, J = 8.9 Hz, 1H), 2.89 (s, 1H), 2.35 (d, J = 2.0 Hz, 3H), 1.79 (d, J = 7.1 Hz, 3H), 1.43-1.13 (m, 2H), 1.16-0.74 (m, 3H). HRMS(B) m/z 428.1608 Chiral RT = 6.15 min |
| 150 and 151: (4R)-3-(2-((1-(3-(4-ethylphenyl)-1,2,4-oxadiazol-5-yl)ethyl)amino)-5-fluoropyrimidin-4-yl)-4-((R)-1-hydroxyethyl)oxazolidin-2-one | Chiral separation was achieved by chiral SFC column chromatography (Column ID 21 × 250 mm 40% MeOH + 10 mM NH4OH in $CO_2$, flow 75 g/min, 238 nm UV collection) to give (R)-3-(2-(((R)-1-(3-(4-ethylphenyl)-1,2,4-oxadiazol-5-yl)ethyl)amino)-5-fluoropyrimidin-4-yl)-4-((R)-1-hydroxyethyl)oxazolidin-2-one and (R)-3-(2-(((S)-1-(3-(4-ethylphenyl)-1,2,4-oxadiazol-5-yl)ethyl)amino)-5-fluoropyrimidin-4-yl)-4-((R)-1-hydroxyethyl)oxazolidin-2-one 150: First eluted product (106 mg): ($CDCl_3$) δ 8.24 (d, J = 2.9 Hz, 1H), 7.99-7.87 (m, 2H), 7.38-7.22 (m, 2H), 5.96 (d, J = 7.1 Hz, 1H), 5.31 (d, J = 9.1 Hz, 1H), 4.56-4.25 (m, 4H), 3.49 (s, 4H), 3.30 (d, J = 13.4 Hz, 1H), 2.72 (q, J = 7.6 Hz, 2H), 1.68 (s, 0H), 1.66-1.38 (m, 2H), 1.35-1.08 (m, 7H). HRMS(B) m/z 442.1765 Chiral RT = 2.80 min 151: Second eluted product (10.6 mg): ($CDCl_3$) δ 8.27 (d, J = 2.7 Hz, 2H), 8.05-7.87 (m, 4H), 7.39-7.23 (m, 4H), 5.77 (d, J = 6.7 Hz, 2H), 5.30-5.17 (m, 2H), 4.73 (dt, J = 10.7, 5.1 Hz, 2H), 4.54 (t, J = 9.1 Hz, 2H), 1.85-1.73 (m, 6H), 4.44 (dd, J = 9.2, 5.6 Hz, 2H), 3.86-3.59 (m, 2H), 3.51 (s, 2H), 2.72 (q, J = 7.6 Hz, 6H), 1.37-1.19 (m, 8H), 1.01 (d, J = 6.9 Hz, 8H), 0.92-0.69 (m, 1H). HRMS(B) m/z 442.1765 Chiral RT = 4.05 min |
| 152 and 153: (4R)-3-(2-((1-(5-(3,4-dimethylphenyl)-1,3,4-oxadiazol-2-yl)ethyl)amino)pyrimidin-4-yl)-4-((R)-1-hydroxyethyl)oxazolidin-2-one | Chiral separation was achieved by chiral SFC column chromatography (Column IC 4.6 × 100 mm 5-55% IPA + 20 mM NH4OH/in $CO_2$, flow 75 g/min, 238 nm UV collection) to give(R)-3-(2-(((S)-1-(5-(3,4-dimethylphenyl)-1,3,4-oxadiazol-2-yl)ethyl)amino)pyrimidin-4-yl)-4-((R)-1-hydroxyethyl)oxazolidin-2-one and (R)-3-(2-(((R)-1-(5-(3,4-dimethylphenyl)-1,3,4-oxadiazol-2-yl)ethyl)amino)pyrimidin-4-yl)-4-((R)-1-hydroxyethyl)oxazolidin-2-one 152: First eluted product (25 mg): ($CDCl_3$) δ 8.22 (d, J = 5.8 Hz, 1H), 7.84-7.79 (m, 1H), 7.75 (dd, J = 8.0, 1.8 Hz, 1H), 7.48 (d, J = 5.7 Hz, 1H), 7.34-7.20 (m, 1H), 5.90 (d, J = 4.6 Hz, 1H), 5.18 (s, 1H), 4.93-4.74 (m, 1H), 1.85-1.71 (m, 3H), 4.61 (dd, J = 9.3, 2.2 Hz, 1H), 4.50-4.38 (m, 1H), 4.33 (t, J = 8.8 Hz, 1H), 4.21 (s, 1H), 4.11-4.00 (m, 0H), 2.34 (s, 6H), 1.22 (dd, J = 10.3, 6.3 Hz, 5H). HRMS(B) m/z 425.1982. Chiral RT = 1.75 min 153: Second eluted product (25 mg): ($CDCl_3$) δ 8.23 (d, J = 5.7 Hz, 1H), 7.81 (d, J = 1.9 Hz, 1H), 7.75 (dd, J = 7.8, 1.9 Hz, 1H), 7.53 (d, J = 5.7 Hz, 1H), 7.28 (d, J = 3.6 Hz, 1H), 5.67 (d, J = 6.0 Hz, 1H), 5.48-5.30 (m, 1H), 5.02-4.91 (m, 1H), 4.62 (dd, J = 9.5, 2.3 Hz, 1H), 4.42 (dd, J = 9.4, 8.3 Hz, 1H), 3.88 (s, 2H), 2.34 (s, 6H), 1.79 (d, J = 7.2 Hz, 3H), 1.63 (s, 1H), 1.33-1.16 (m, 1H), 1.06 (d, J = 6.4 Hz, 3H). HRMS(B) m/z 425.1981. Chiral RT = 2.15 min |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
| 154 and 155:<br>(4R)-4-((R)-1-hydroxyethyl)-3-(2-((1-(3-(isoquinolin-8-yl)-1,2,4-oxadiazol-5-yl)ethyl)amino)pyrimidin-4-yl)oxazolidin-2-one | Chiral separation was achieved by chiral SFC column chromatography (Column OJ-H 21 × 250 mm 20% MeOH + 5 mM NH4OH/CO$_2$/in CO$_2$, flow 75 g/min, 238 nm UV collection) to give (R)-4-((R)-1-hydroxyethyl)-3-(2-(((R)-1-(3-(isoquinolin-8-yl)-1,2,4-oxadiazol-5-yl)ethyl)amino)pyrimidin-4-yl)oxazolidin-2-one and (R)-4-((R)-1-hydroxyethyl)-3-(2-(((S)-1-(3-(isoquinolin-8-yl)-1,2,4-oxadiazol-5-yl)ethyl)amino)pyrimidin-4-yl)oxazolidin-2-one<br>154: First eluted product (10 mg): (CDCl$_3$) δ 8.47-8.11 (m, 4H), 7.99 (d, J = 8.1 Hz, 2H), 7.83 (t, J = 7.9 Hz, 3H), 7.57 (s, 4H), 5.94 (s, 2H), 5.47 (s, 2H), 4.95-4.65 (m, 2H), 4.42 (d, J = 88.6 Hz, 6H), 3.52 (s, 5H), 2.09-1.51 (m, 1H), 1.47-0.99 (m, 7H), 0.96-0.68 (m, 1H). HRMS(B) m/z 447.1655. Chiral RT = 2.55 min<br>155: Second eluted product (28.7 mg): (CDCl$_3$) δ 10.26 (s, 2H), 8.63 (s, 2H), 8.28 (d, J = 7.3 Hz, 4H), 7.97 (d, J = 8.2 Hz, 2H), 7.77 (t, J = 7.8 Hz, 3H), 7.58 (d, J = 5.3 Hz, 2H), 6.08 (s, 2H), 5.62 (p, J = 7.1 Hz, 2H), 5.11-4.84 (m, 2H), 4.61 (dd, J = 8.8, 2.7 Hz, 2H), 4.41 (t, J = 8.9 Hz, 2H), 4.30 (s, 2H), 3.89 (s, 2H), 3.63-3.43 (m, 8H), 1.73 (d, J = 33.4 Hz, 0H), 1.32 (q, J = 5.2 Hz, 3H), 1.04 (d, J = 7.1 Hz, 6H). HRMS(B) m/z 447.1655. Chiral RT = 2.90 min |
| 156 and 157:<br>(4R)-3-(2-((1-(3-(4-chloro-2-(trifluoromethyl)phenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column IC 4.6 × 100 mm 5-55% IPA + 20 mM NH4OH in CO$_2$, flow 75 g/min, 238 nm UV collection) to give (R)-3-(2-(((R)-1-(3-(4-chloro-2-(trifluoromethyl)phenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(4-chloro-2-(trifluoromethyl)phenyl)-1,2,4-oxadiazol-5-yl)ethyl)amino)pyrimidin-4-yl)-4-((R)-1-hydroxyethyl)oxazolidin-2-one<br>156: First eluted product (50 mg): (CDCl$_3$) δ 8.16 (d, J = 5.9 Hz, 1H), 7.81-7.64 (m, 1H), 7.57 (dd, J = 8.3, 2.1 Hz, 1H), 7.48 (d, J = 5.8 Hz, 1H), 6.50 (s, 1H), 5.35 (s, 1H), 4.78 (ddd, J = 7.4, 4.6, 2.4 Hz, 1H), 4.45 (dd, J = 9.3, 2.5 Hz, 1H), 4.31 (dd, J = 9.4, 8.3 Hz, 1H), 3.92 (d, J = 48.4 Hz, 1H), 3.41 (s, 1H), 3.18-2.11 (m, 1H), 1.70 (d, J = 7.1 Hz, 3H), 1.30-1.08 (m, 1H), 0.93 (d, J = 7.6 Hz, 3H). HRMS(B) m/z 498.1030. Chiral RT = 2.03 min<br>157: Second eluted product (15 mg): (CDCl$_3$) δ 8.15 (d, J = 6.2 Hz, 1H), 7.76 (d, J = 2.0 Hz, 1H), 7.68 (d, J = 8.3 Hz, 1H), 7.59 (dd, J = 8.4, 2.1 Hz, 1H), 7.47 (d, J = 5.6 Hz, 1H), 5.96 (s, 1H), 5.17 (s, 1H), 4.73-4.47 (m, 1H), 4.40 (dd, J = 9.2, 2.4 Hz, 1H), 4.21 (d, J = 37.9 Hz, 1H), 3.42 (s, 3H), 1.60 (s, 3H), 1.33-0.99 (m, 1H), 0.92-0.64 (m, 1H). HRMS(B) m/z 498.1030. Chiral RT = 2.18 min |
| 158 and 159:<br>(4R)-3-(5-fluoro-2-((1-(3-(4-isopropylphenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column ID 21 × 250 mm 40% MeOH + 10 mM NH4OH in CO$_2$, flow 75 g/min, 238 nm UV collection) to give (R)-3-(5-fluoro-2-(((R)-1-(3-(4-isopropylphenyl)-1,2,4-oxadiazol-5-yl)ethyl)amino)pyrimidin-4-yl)-4-((R)-1-hydroxyethyl)oxazolidin-2-one and (R)-3-(5-fluoro-2-(((S)-1-(3-(4-isopropylphenyl)-1,2,4-oxadiazol-5-yl)ethyl)amino)pyrimidin-4-yl)-4-((R)-1-hydroxyethyl)oxazolidin-2-one<br>158: First eluted product (51 mg): (CDCl$_3$) δ 8.17 (d, J = 2.7 Hz, 1H), 7.92-7.83 (m, 2H), 7.30-7.21 (m, 2H), 5.83 (d, J = 6.5 Hz, 1H), 5.21 (dd, J = 13.8, 6.9 Hz, 1H), 4.77-4.57 (m, 1H), 4.46 (t, J = 9.1 Hz, 1H), 4.36 (dd, J = 9.2, 5.6 Hz, 1H), 3.96 (p, J = 6.1 Hz, 1H), 3.63 (s, 1H), 2.88 (hept, J = 7.0 Hz, 1H), 1.76-1.60 (m, 3H), 1.19 (d, J = 7.0 Hz, 7H), 1.14 (d, J = 6.1 Hz, 4H), 0.93 (d, J = 7.0 Hz, 3H). HRMS(B) m/z 456.1921 Chiral RT = 2.60 min<br>159: Second eluted product (54 mg): (CDCl$_3$) δ 8.24 (d, J = 3.0 Hz, 1H), 8.02-7.89 (m, 2H), 7.39-7.30 (m, 2H), 5.98 (d, J = 7.2 Hz, 1H), 5.31 (d, J = 8.6 Hz, 1H), 4.52-4.27 (m, 4H), 1.83-1.67 (m, 3H), 3.49 (s, 1H), 2.97 (hept, J = 6.9 Hz, 1H), 1.28 (d, J = 6.9 Hz, 6H), 1.21 (dd, J = 11.1, 6.2 Hz, 5H). HRMS(B) m/z 456.1921. Chiral RT = 3.70 min |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
| 160 and 161:<br>(4R)-4-((R)-1-hydroxyethyl)-3-(2-((1-(3-(3-(trifluoromethyl)phenyl)-1,2,4-oxadiazol-5-yl)ethyl)amino)pyrimidin-4-yl)oxazolidin-2-one | Chiral separation was achieved by chiral SFC column chromatography (Column AD-H 21 × 250 mm 25% IPA in $CO_2$, flow 75 g/min, 238 nm UV collection) to give(R)-4-((R)-1-hydroxyethyl)-3-(2-(((R)-1-(3-(3-(trifluoromethyl)phenyl)-1,2,4-oxadiazol-5-yl)ethyl)amino)pyrimidin-4-yl)oxazolidin-2-one and (R)-4-((R)-1-hydroxyethyl)-3-(2-(((S)-1-(3-(3-(trifluoromethyl)phenyl)-1,2,4-oxadiazol-5-yl)ethyl)amino)pyrimidin-4-yl)oxazolidin-2-one<br>160: First eluted product (15 mg): ($CDCl_3$) δ 8.27 (d, J = 2.0 Hz, 1H), 8.16 (t, J = 7.3 Hz, 2H), 7.71 (d, J = 7.9 Hz, 1H), 7.56 (t, J = 7.8 Hz, 1H), 1.74-1.56 (m, 3H), 7.50-7.37 (m, 1H), 6.06 (s, 1H), 5.26 (d, J = 47.9 Hz, 1H), 4.59 (d, J = 9.5 Hz, 1H), 4.52-4.23 (m, 2H), 1.14 (dd, J = 6.3, 4.8 Hz, 5H), 1.03-0.88 (m, 2H), 0.88-0.71 (m, 0H), 4.85-4.72 (m, 0H), 4.16 (s, 1H), 3.97 (p, J = 6.1 Hz, 0H), 2.88 (s, 1H), 2.34-1.77 (m, 1H). HRMS(B) m/z 464.1420. Chiral RT = 2.10 min<br>161: Second eluted product (38.5 mg): ($CDCl_3$) δ 8.36 (d, J = 1.8 Hz, 1H), 8.31-8.19 (m, 2H), 7.87-7.76 (m, 1H), 7.64 (t, J = 7.8 Hz, 1H), 7.57 (d, J = 5.7 Hz, 1H), 6.04 (s, 1H), 5.42 (s, 1H), 4.87 (ddd, J = 8.4, 4.7, 2.5 Hz, 1H), 4.55 (dd, J = 9.5, 2.5 Hz, 1H), 4.41 (dd, J = 9.5, 8.3 Hz, 1H), 4.11-3.72 (m, 1H), 2.83 (s, 1H), 2.13-1.57 (m, 1H), 1.23 (d, J = 6.1 Hz, 2H), 1.05 (d, J = 9.5 Hz, 3H). HRMS(B) m/z 464.1420 Chiral RT = 2.55 min |
| 162 and 163:<br>(4R)-3-(2-((1-(3-(4-fluoro-3-(trifluoromethoxy)phenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column AD-H 21 × 250 mm 10% MeOH in $CO_2$, flow 80 g/min, 238 nm UV collection) to give (R)-3-(2-(((R)-1-(3-(4-fluoro-3-(trifluoromethoxy)phenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(4-fluoro-3-(trifluoromethoxy)phenyl)-1,2,4-oxadiazol-5-yl)ethyl)amino)pyrimidin-4-yl)-4-((R)-1-hydroxyethyl)oxazolidin-2-one<br>162: First eluted product (13 mg): ($CDCl_3$) δ 8.24 (d, J = 5.9 Hz, 1H), 8.04 (ddt, J = 13.4, 6.5, 1.9 Hz, 2H), 7.55 (d, J = 5.7 Hz, 1H), 7.35 (t, J = 9.0 Hz, 1H), 6.08 (s, 1H), 5.27 (s, 1H), 4.78-4.58 (m, 1H), 4.52 (dd, J = 9.3, 2.5 Hz, 1H), 4.44 (d, J = 15.7 Hz, 1H), 4.25 (d, J = 11.2 Hz, 1H), 3.51 (s, 2H), 2.97 (s, 1H), 1.98-1.67 (m, 0H), 1.22 (d, J = 6.5 Hz, 4H). HRMS(B) m/z 498.1275 Chiral RT = 3.60 min<br>163: Second eluted product (40 mg): ($CDCl_3$) δ 8.25 (d, J = 6.2 Hz, 1H), 8.13-7.98 (m, 2H), 7.57 (d, J = 5.6 Hz, 1H), 7.35 (dd, J = 9.4, 8.6 Hz, 1H), 5.77 (s, 1H), 5.40 (s, 1H), 4.85 (ddd, J = 8.2, 4.7, 2.5 Hz, 1H), 4.54 (dd, J = 9.4, 2.5 Hz, 1H), 4.41 (dd, J = 9.4, 8.3 Hz, 1H), 3.87 (t, J = 65.5 Hz, 1H), 3.52 (s, 1H), 2.76 (s, 1H), 1.79 (d, J = 7.1 Hz, 3H), 1.34-1.25 (m, 1H), 1.05 (s, 3H).). HRMS(B) m/z 498.1275 Chiral RT = 4.80 min |
| 164 and 165:<br>(4R)-3-(2-((1-(3-(3-(difluoromethoxy)phenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column AD-H 21 × 250 mm 35% IPA in $CO_2$, flow 75 g/min, 238 nm UV collection) to give (R)-3-(2-(((R)-1-(3-(3-(difluoromethoxy)phenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(3-(difluoromethoxy)phenyl)-1,2,4-oxadiazol-5-yl)ethyl)amino)pyrimidin-4-yl)-4-((R)-1-hydroxyethyl)oxazolidin-2-one<br>164: First eluted product (18 mg): ($CDCl_3$) δ 8.25 (d, J = 5.8 Hz, 1H), 7.92 (dt, J = 7.7, 1.4 Hz, 1H), 7.83 (t, J = 2.0 Hz, 1H), 7.62-7.43 (m, 2H), 7.36-7.24 (m, 1H), 6.61 (t, J = 73.3 Hz, 1H), 6.25 (d, J = 59.0 Hz, 1H), 5.36 (d, J = 30.2 Hz, 1H), 4.86 (ddd, J = 8.5, 4.8, 2.5 Hz, 1H), 4.55 (dd, J = 9.3, 2.5 Hz, 1H), 4.40 (t, J = 8.9 Hz, 1H), 3.51 (s, 2H), 1.83 (s, 1H), 1.34-1.16 (m, 1H), 1.02 (s, 3H). HRMS(B) m/z 462.1463 Chiral RT = 1.65 min<br>165: Second eluted product (63 mg): ($CDCl_3$) δ 8.25 (d, J = 5.8 Hz, 1H), 7.92 (dt, J = 7.7, 1.4 Hz, 1H), 7.83 (t, J = 2.0 Hz, 1H), 7.62-7.43 (m, 2H), 7.36-7.24 (m, 1H), 6.61 (t, J = 73.3 Hz, 1H), 6.25 (d, J = 59.0 Hz, 1H), 5.36 (d, J = 30.2 Hz, |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
| | 1H), 4.86 (ddd, J = 8.5, 4.8, 2.5 Hz, 1H), 4.55 (dd, J = 9.3, 2.5 Hz, 1H), 4.40 (t, J = 8.9 Hz, 1H), 3.51 (s, 2H), 1.83 (s, 1H), 1.34-1.16 (m, 1H), 1.02 (s, 3H). HRMS(B) m/z 462.1463 Chiral RT = 2.10 min |
| 166 and 167: (4R)-3-(2-((1-(3-(4-chloro-3-methoxyphenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column AD-H 21 × 250 mm 30% MeOH in $CO_2$, flow 80 g/min, 238 nm UV collection) to give (R)-3-(2-(((R)-1-(3-(4-chloro-3-methoxyphenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(4-chloro-3-methoxyphenyl)-1,2,4-oxadiazol-5-yl)ethyl)amino)pyrimidin-4-yl)-4-((R)-1-hydroxyethyl)oxazolidin-2-one 166: First eluted product (10 mg): $CDCl_3$ δ 8.38-8.18 (m, 1H), 7.61 (hept, J = 2.3, 1.9 Hz, 2H), 7.57-7.45 (m, 2H), 5.89 (s, 1H), 5.33 (s, 2H), 4.70 (s, 1H), 4.50 (dd, J = 9.4, 2.4 Hz, 1H), 4.00 (s, 2H), 3.07 (s, 1H), 1.75 (s, 2H), 1.34-1.11 (m, 6H). HRMS(B) m/z 461.1464. RT = 2.24 min. Chiral RT = 2.85 min 167: Second eluted product (120 mg): ($CDCl_3$) δ 8.25 (d, J = 5.8 Hz, 1H), 7.63 (d, J = 7.5 Hz, 2H), 7.57 (d, J = 5.7 Hz, 1H), 7.52-7.46 (m, 1H), 5.74 (s, 1H), 5.35 (d, J = 20.7 Hz, 1H), 4.85 (ddd, J = 8.3, 4.7, 2.4 Hz, 1H), 4.54 (dd, J = 9.5, 2.5 Hz, 1H), 4.40 (dd, J = 9.4, 8.3 Hz, 1H), 4.01 (s, 3H), 3.52 (s, 3H), 2.85 (s, 1H), 1.88-1.76 (m, 2H), 1.67 (s, 1H), 1.23 (d, J = 6.1 Hz, 1H), 1.03 (s, 3H). HRMS(B) m/z 461.1464. RT = 2.23 min. Chiral RT = 3.55 min |
| 168 and 169: (4R)-3-(2-((1-(3-(2,2-difluorobenzo[d][1,3]dioxol-5-yl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column AD-H 21 × 250 mm 35% IPA in $CO_2$, flow 75 g/min, 238 nm UV collection) to give (R)-3-(2-(((R)-1-(3-(2,2-difluorobenzo[d][1,3]dioxol-5-yl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(2,2-difluorobenzo[d][1,3]dioxol-5-yl)-1,2,4-oxadiazol-5-yl)ethyl)amino)pyrimidin-4-yl)-4-((R)-1-hydroxyethyl)oxazolidin-2-one 168: First eluted product (14 mg): ($CDCl_3$) δ 8.23 (d, J = 6.2 Hz, 1H), 7.86 (dd, J = 8.2, 1.8 Hz, 1H), 7.78 (d, J = 1.7 Hz, 1H), 7.55 (d, J = 5.7 Hz, 1H), 7.19 (d, J = 8.3 Hz, 1H), 6.46 (s, 1H), 5.29 (d, J = 27.6 Hz, 1H), 4.90-4.58 (m, 1H), 4.52 (dd, J = 9.4, 2.5 Hz, 1H), 4.46-4.17 (m, 2H), 3.51 (s, 1H), 2.93 (s, 2H), 1.22 (dd, J = 8.8, 6.2 Hz, 4H). HRMS(B) m/z 476.1256. RT = 2.42 min. Chiral RT = 1.65 min 169: Second eluted product (62 mg): ($CDCl_3$) δ 8.15 (d, J = 5.8 Hz, 1H), 7.79 (dd, J = 8.3, 1.7 Hz, 1H), 7.69 (d, J = 1.7 Hz, 1H), 7.47 (d, J = 5.8 Hz, 1H), 7.09 (d, J = 8.4 Hz, 1H), 6.38 (s, 1H), 5.26 (d, J = 24.5 Hz, 1H), 4.76 (ddd, J = 8.5, 4.6, 2.4 Hz, 1H), 4.46 (dd, J = 9.3, 2.5 Hz, 1H), 4.32 (t, J = 8.9 Hz, 1H), 4.06-3.60 (m, 1H), 3.42 (s, 2H), 1.86 (d, J = 7.1 Hz, 3H), 1.14 (d, J = 6.1 Hz, 1H), 1.04-0.72 (m, 3H). HRMS(B) m/z 476.1256. RT = 2.43 min. Chiral RT = 1.95 min |
| 170 and 171: (4R)-3-(2-((1-(3-(4-chloro-3-(trifluoromethyl)phenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column AD-H 21 × 250 mm 20% MeOH in $CO_2$, flow 80 g/min, 238 nm UV collection) to give (R)-3-(2-(((R)-1-(3-(4-chloro-3-(trifluoromethyl)phenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(4-chloro-3-(trifluoromethyl)phenyl)-1,2,4-oxadiazol-5-yl)ethyl)amino)pyrimidin-4-yl)-4-((R)-1-hydroxyethyl)oxazolidin-2-one 170: First eluted product (23 mg): ($CDCl_3$) δ 8.42 (d, J = 2.0 Hz, 1H), 8.25 (d, J = 5.9 Hz, 1H), 8.18 (dd, J = 8.4, 2.1 Hz, 1H), 7.66 (d, J = 8.4 Hz, 1H), 7.55 (d, J = 5.7 Hz, 1H), 5.81 (s, 1H), 5.33 (s, 2H), 4.66 (s, 1H), 4.52 (dd, J = 9.3, 2.5 Hz, 1H), 4.46-4.14 (m, 2H), 2.84 (s, 1H), 1.79 (d, J = 7.0 Hz, 3H), 1.23 (d, J = 6.5 Hz, 4H). HRMS(B) m/z 498.1030. RT = 2.57 min. Chiral RT = 2.70 min 171: Second eluted product (83 mg): ($CDCl_3$) δ 8.42 (d, J = 2.0 Hz, 1H), 8.31-8.12 (m, 2H), 7.62 (dd, J = 26.0, 7.1 Hz, 2H), 1.92-1.70 (m, 3H), 6.31 (s, 1H), 5.32 (s, 2H), 4.86 (ddd, J = 8.3, 4.8, 2.4 Hz, 1H), 4.54 (dd, J = 9.3, 2.5 Hz, 1H), 4.42 (dd, J = 9.4, 8.3 Hz, 1H), 4.13-3.77 (m, 1H), 2.71 (s, 2H), 1.44-0.84 (m, 4H). HRMS(B) m/z 498.1030. RT = 2.57 min. Chiral RT = 3.60 min |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
| 172 and 173: (4R)-3-(2-((1-(3-(4-ethylphenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column IA 21 × 250 mm 40% IPA + 10 mM NH4OH in $CO_2$, flow 75 g/min, 238 nm UV collection) to give (R)-3-(2-(((R)-1-(3-(4-ethylphenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(4-ethylphenyl)-1,2,4-oxadiazol-5-yl)ethyl)amino)pyrimidin-4-yl)-4-((R)-1-hydroxyethyl)oxazolidin-2-one<br>172: First eluted product (73 mg): ($CDCl_3$) δ 8.24 (d, J = 5.8 Hz, 1H), 8.05-7.87 (m, 2H), 7.50 (d, J = 5.8 Hz, 1H), 7.41-7.30 (m, 2H), 5.98 (s, 1H), 1.57-1.47 (m, 0H), 5.22 (s, 1H), 4.71 (s, 1H), 4.13-4.00 (m, 0H), 4.48 (dd, J = 9.5, 2.4 Hz, 1H), 4.33 (s, 1H), 4.18 (s, 1H), 3.51 (d, J = 5.3 Hz, 0H), 3.30 (s, 1H), 2.73 (q, J = 7.6 Hz, 2H), 1.78 (d, J = 7.1 Hz, 3H), 1.39-1.08 (m, 7H). HRMS(B) m/z 424.1859. RT = 2.39 min. Chiral RT = 2.15 min<br>173: Second eluted product (17 mg): ($CDCl_3$) δ 8.25 (d, J = 5.8 Hz, 2H), 8.04-7.89 (m, 4H), 7.54 (d, J = 5.8 Hz, 2H), 7.39-7.29 (m, 4H), 5.97 (s, 2H), 5.53-5.22 (m, 2H), 4.85 (ddd, J = 8.2, 4.4, 2.4 Hz, 2H), 4.55 (dd, J = 9.3, 2.5 Hz, 2H), 4.39 (dd, J = 9.4, 8.3 Hz, 2H), 4.12-3.97 (m, 0H), 3.76 (d, J = 62.5 Hz, 2H), 3.51 (s, 2H), 3.03 (s, 2H), 2.72 (q, J = 7.6 Hz, 4H), 1.98-1.71 (m, 1H), 1.45-1.13 (m, 10H), 1.12-0.80 (m, 7H). HRMS(B) m/z 424.1859. RT = 2.40 min. Chiral RT = 3.25 min |
| 174 and 175: (4R)-4-((R)-1-hydroxyethyl)-3-(2-((1-(3-(4-(trifluoromethyl)phenyl)-1,2,4-oxadiazol-5-yl)ethyl)amino)pyrimidin-4-yl)oxazolidin-2-one | Chiral separation was achieved by chiral SFC column chromatography (Column AD-H 21 × 250 mm 25% IPA in $CO_2$, flow 75 g/min, 238 nm UV collection) to give (R)-4-((R)-1-hydroxyethyl)-3-(2-(((R)-1-(3-(4-(trifluoromethyl)phenyl)-1,2,4-oxadiazol-5-yl)ethyl)amino)pyrimidin-4-yl)oxazolidin-2-one and (R)-4-((R)-1-hydroxyethyl)-3-(2-(((S)-1-(3-(4-(trifluoromethyl)phenyl)-1,2,4-oxadiazol-5-yl)ethyl)amino)pyrimidin-4-yl)oxazolidin-2-one<br>174: First eluted product (55 mg): ($CDCl_3$) δ 8.30-8.14 (m, 3H), 7.76 (dd, J = 8.7, 2.5 Hz, 2H), 7.55 (dd, J = 12.4, 5.8 Hz, 1H), 6.61 (s, 1H), 5.32 (s, 1H), 4.77-4.62 (m, 1H), 4.62-4.46 (m, 1H), 4.40 (t, J = 8.8 Hz, 1H), 4.24 (t, J = 9.0 Hz, 1H), 3.51 (s, 1H), 1.81 (s, 2H), 1.22 (dd, J = 9.6, 6.3 Hz, 4H). HRMS(B) m/z 464.1420. RT = 2.43 min. Chiral RT = 2.55 min<br>175: Second eluted product (51 mg): ($CDCl_3$) δ 8.22 (dd, J = 21.0, 7.0 Hz, 3H), 7.75 (d, J = 8.1 Hz, 2H), 7.56 (d, J = 5.8 Hz, 1H), 6.47 (s, 1H), 5.37 (d, J = 39.2 Hz, 1H), 4.86 (ddd, J = 8.7, 4.7, 2.5 Hz, 1H), 4.55 (dd, J = 9.3, 2.5 Hz, 1H), 4.40 (t, J = 8.9 Hz, 1H), 4.19-3.70 (m, 1H), 3.50 (s, 1H), 2.01-1.70 (m, 0H), 1.23 (d, J = 6.1 Hz, 1H), 1.01 (s, 3H). HRMS(B) m/z 464.1420. RT = 2.44 min. Chiral RT = 3.25 min |
| 176 and 177: (4R)-4-((R)-1-hydroxyethyl)-3-(2-((1-(3-phenethyl-1,2,4-oxadiazol-5-yl)ethyl)amino)pyrimidin-4-yl)oxazolidin-2-one | Chiral separation was achieved by chiral SFC column chromatography (Column AD-H 21 × 250 mm 15% IPA in $CO_2$, flow 80 g/min, 238 nm UV collection) to give (R)-4-((R)-1-hydroxyethyl)-3-(2-(((R)-1-(3-phenethyl-1,2,4-oxadiazol-5-yl)ethyl)amino)pyrimidin-4-yl)oxazolidin-2-one and (R)-4-((R)-1-hydroxyethyl)-3-(2-(((S)-1-(3-phenethyl-1,2,4-oxadiazol-5-yl)ethyl)amino)pyrimidin-4-yl)oxazolidin-2-one<br>176: First eluted product (17 mg): ($CDCl_3$) δ 8.25 (d, J = 6.2 Hz, 1H), 7.54 (d, J = 5.5 Hz, 1H), 7.36-7.07 (m, 5H), 5.83 (s, 1H), 5.10 (s, 1H), 4.67 (d, J = 7.6 Hz, 1H), 4.57-4.41 (m, 1H), 4.10 (d, J = 38.8 Hz, 2H), 3.36-3.14 (m, 1H), 3.07 (d, J = 2.1 Hz, 4H), 1.94-1.67 (m, 1H), 1.28 (d, J = 3.8 Hz, 1H), 1.18 (d, J = 6.5 Hz, 3H). HRMS(B) m/z 424.1859. RT = 2.24 min. Chiral RT = 4.50 min<br>177: Second eluted product (19 mg): ($CDCl_3$) δ 8.25 (d, J = 5.9 Hz, 1H), 7.56 (d, J = 5.7 Hz, 1H), 7.38-7.08 (m, 5H), 6.03 (s, 1H), 5.31 (d, J = 11.3 Hz, 1H), 4.84 (ddd, J = 8.3, 4.5, 2.3 Hz, 1H), 4.56 (dd, J = 9.3, 2.5 Hz, 1H), 4.40 (dd, J = 9.3, 8.3 Hz, 1H), 3.91-3.62 (m, 1H), 3.51 (s, 2H), 3.36-3.10 (m, 1H), 3.06 (s, 4H), 1.72 (d, J = 7.0 Hz, 3H), 1.59-1.35 (m, 1H), 1.06 (d, J = 6.8 Hz, 3H).). HRMS(B) m/z 424.1859. RT = 2.30 min. Chiral RT = 5.90 min |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
| 178 and 179: (4R)-3-(2-((1-(3-(4-chloro-3-(trifluoromethoxy)phenyl)-1,2,4-oxadiazol-5-yl)ethyl)amino)-5-fluoropyrimidin-4-yl)-4-((R)-1-hydroxyethyl)oxazolidin-2-one | Chiral separation was achieved by chiral SFC column chromatography (Column AD-H 21 × 250 mm 20% IPA in $CO_2$, flow 75 g/min, 238 nm UV collection) to give (R)-3-(2-(((R)-1-(3-(4-chloro-3-(trifluoromethoxy)phenyl)-1,2,4-oxadiazol-5-yl)ethyl)amino)-5-fluoropyrimidin-4-yl)-4-((R)-1-hydroxyethyl)oxazolidin-2-one and (R)-3-(2-(((S)-1-(3-(4-chloro-3-(trifluoromethoxy)phenyl)-1,2,4-oxadiazol-5-yl)ethyl)amino)-5-fluoropyrimidin-4-yl)-4-((R)-1-hydroxyethyl)oxazolidin-2-one<br>178: First eluted product (49 mg): ($CDCl_3$) δ 8.26 (d, J = 2.8 Hz, 1H), 8.05 (p, J = 1.4 Hz, 1H), 8.03-7.92 (m, 1H), 7.62 (d, J = 8.4 Hz, 1H), 5.73 (d, J = 7.6 Hz, 1H), 5.44-5.25 (m, 1H), 4.60-4.40 (m, 3H), 4.32 (p, J = 5.7, 5.3 Hz, 1H), 2.81-1.89 (m, 2H), 1.80 (s, 3H), 1.22 (d, J = 6.3 Hz, 3H).). HRMS(B) m/z 533.1171. RT = 2.64 min. Chiral RT = 3.05 min<br>179: Second eluted product (81 mg): ($CDCl_3$) δ 8.27 (d, J = 2.7 Hz, 1H), 8.04 (p, J = 1.4 Hz, 1H), 7.97 (dd, J = 8.4, 1.9 Hz, 1H), 7.62 (d, J = 8.4 Hz, 1H), 5.68 (t, J = 4.0 Hz, 1H), 5.33 (s, 1H), 4.68 (dt, J = 10.9, 4.6 Hz, 1H), 4.56 (t, J = 9.0 Hz, 1H), 4.44 (dd, J = 9.2, 5.3 Hz, 1H), 3.85 (s, 1H), 1.95 (d, J = 7.0 Hz, 2H), 1.84-1.73 (m, 3H), 1.36-1.19 (m, 1H), 1.08 (s, 3H). HRMS(B) m/z 533.1173. RT = 2.64 min. Chiral RT = 3.75 min |
| 180 and 181: (4R)-4-((R)-1-hydroxyethyl)-3-(2-((1-(3-(4-(trifluoromethoxy)phenyl)-1,2,4-oxadiazol-5-yl)ethyl)amino)pyrimidin-4-yl)oxazolidin-2-one | Chiral separation was achieved by chiral SFC column chromatography (Column AD-H 21 × 250 mm 25% IPA in $CO_2$, flow 80 g/min, 238 nm UV collection) to (R)-4-((R)-1-hydroxyethyl)-3-(2-(((R)-1-(3-(4-(trifluoromethoxy)phenyl)-1,2,4-oxadiazol-5-yl)ethyl)amino)pyrimidin-4-yl)oxazolidin-2-one and (R)-4-((R)-1-hydroxyethyl)-3-(2-(((S)-1-(3-(4-(trifluoromethoxy)phenyl)-1,2,4-oxadiazol-5-yl)ethyl)amino)pyrimidin-4-yl)oxazolidin-2-one<br>180: First eluted product (19 mg): ($CDCl_3$) δ 8.24 (d, J = 5.8 Hz, 1H), 8.16-8.06 (m, 2H), 7.53 (d, J = 5.8 Hz, 1H), 7.34 (d, J = 8.3 Hz, 2H), 6.24 (s, 1H), 5.29 (d, J = 24.7 Hz, 1H), 4.81-4.61 (m, 1H), 1.85-1.74 (m, 3H), 4.51 (dd, J = 9.4, 2.4 Hz, 1H), 4.46-4.32 (m, 1H), 4.31-4.13 (m, 1H), 3.51 (s, 1H), 3.25 (d, J = 66.2 Hz, 1H), 1.22 (dd, J = 8.9, 6.3 Hz, 4H). HRMS(B) m/z 480.1369. RT = 2.50 min. Chiral RT = 2.20 min<br>181: Second eluted product (44 mg): ($CDCl_3$) δ 8.25 (d, J = 5.8 Hz, 1H), 8.17-8.05 (m, 2H), 7.55 (d, J = 5.7 Hz, 1H), 7.33 (d, J = 8.3 Hz, 2H), 6.41 (s, 1H), 5.35 (d, J = 27.1 Hz, 1H), 4.96-4.77 (m, 1H), 4.55 (dd, J = 9.3, 2.5 Hz, 1H), 4.40 (t, J = 8.9 Hz, 1H), 4.16-3.55 (m, 1H), 3.03 (s, 1H), 1.78 (d, J = 7.1 Hz, 3H), 1.23 (d, J = 6.1 Hz, 1H), 1.01 (s, 3H). HRMS(B) m/z 480.1369. RT = 2.51 min. Chiral RT = 2.45 min |
| 182 and 183: (4R)-4-((R)-1-hydroxyethyl)-3-(2-((1-(3-(3-(2,2,2-trifluoroethoxy)phenyl)-1,2,4-oxadiazol-5-yl)ethyl)amino)pyrimidin-4-yl)oxazolidin-2-one | Chiral separation was achieved by chiral SFC column chromatography (Column AD-H 21 × 250 mm 30% IPA in $CO_2$, flow 75 g/min, 238 nm UV collection) to give (R)-4-((R)-1-hydroxyethyl)-3-(2-(((R)-1-(3-(3-(2,2,2-trifluoroethoxy)phenyl)-1,2,4-oxadiazol-5-yl)ethyl)amino)pyrimidin-4-yl)oxazolidin-2-one and (R)-4-((R)-1-hydroxyethyl)-3-(2-(((S)-1-(3-(3-(2,2,2-trifluoroethoxy)phenyl)-1,2,4-oxadiazol-5-yl)ethyl)amino)pyrimidin-4-yl)oxazolidin-2-one<br>182: First eluted product (13.8 mg): ($CDCl_3$) δ 8.14 (d, J = 5.9 Hz, 1H), 7.67 (t, J = 6.8 Hz, 1H), 7.60-7.52 (m, 1H), 7.46 (dd, J = 14.2, 5.8 Hz, 1H), 7.37 (td, J = 8.0, 2.8 Hz, 1H), 7.05 (dd, J = 8.2, 2.7 Hz, 1H), 4.71-4.51 (m, 1H), 4.51-4.23 (m, 4H), 4.23-4.04 (m, 1H), 3.97 (hept, J = 6.1 Hz, 1H), 1.64 (d, J = 1.5 Hz, 3H), 1.13 (dd, J = 10.4, 6.3 Hz, 6H). HRMS(B) m/z 494.1526. RT = 2.38 min. Chiral RT = 1.95 min<br>183: Second eluted product (65 mg): ($CDCl_3$) δ 8.25 (d, J = 5.8 Hz, 1H), 7.77 (dt, J = 7.7, 1.2 Hz, 1H), 7.63 (dd, J = 2.7, 1.4 Hz, 1H), 7.56 (d, J = 5.7 Hz, 1H), 7.45 (t, J = 8.0 Hz, 1H), 7.14 (ddd, J = 8.3, 2.7, 1.0 Hz, 1H), 6.06 (s, 1H), 5.35 (d, J = 24.3 Hz, 1H), 4.85 (ddd, J = 8.3, 4.5, 2.5 Hz, 1H), 4.55 (dd, J = 9.3, 2.5 Hz, 1H), 4.51-4.34 (m, 4H), 4.05 (hept, J = 6.1 Hz, 1H), 3.89 (s, 1H), 2.96 (s, 1H), 1.84-1.75 (m, 3H), 1.23 (d, J = 6.2 Hz, 6H), 1.02 (s, 3H). HRMS(B) m/z 494.1526. RT = 2.39 min. Chiral RT = 2.45 min |

TABLE 29b-continued

Chemical name, NMR chemical shifts, chiral separation conditions and LCMS
signal for compounds listed in Table 29a.

| Example: Name | Chiral separation conditions, peak identification and analytical data |
| --- | --- |
| 184 and 185:<br>(4R)-3-(2-((1-(5-(4-chlorophenyl)-4-methyloxazol-2-yl)ethyl)amino)pyrimidin-4-yl)-4-((R)-1-hydroxyethyl)oxazolidin-2-one | Chiral separation was achieved by chiral SFC column chromatography (Column AD-H 21 × 250 mm 20% MeOH in $CO_2$, flow 80 g/min, 238 nm UV collection) to give (R)-3-(2-(((R)-1-(5-(4-chlorophenyl)-4-methyloxazol-2-yl)ethyl)amino)pyrimidin-4-yl)-4-((R)-1-hydroxyethyl)oxazolidin-2-one and (R)-3-(2-(((S)-1-(5-(4-chlorophenyl)-4-methyloxazol-2-yl)ethyl)amino)pyrimidin-4-yl)-4-((R)-1-hydroxyethyl)oxazolidin-2-one<br>184: First eluted product (48 mg): ($CDCl_3$) δ 8.21 (d, J = 5.7 Hz, 1H), 7.58-7.35 (m, 5H), 5.94 (s, 1H), 4.62 (dd, J = 9.2, 2.5 Hz, 1H), 4.55-4.42 (m, 1H), 1.74-1.65 (m, 3H), 4.32 (t, J = 8.9 Hz, 1H), 3.51 (s, 2H), 2.38 (s, 3H), 2.27-1.93 (m, 1H), 1.22 (d, J = 6.6 Hz, 3H). HRMS(B) m/z 443.1360. RT = 2.51 min. Chiral RT = 2.90 min<br>185: Second eluted product (31 mg): ($CDCl_3$) δ 7.61-7.47 (m, 3H), 7.45-7.35 (m, 2H), 5.84 (s, 1H), 5.31 (d, J = 10.0 Hz, 1H), 4.94 (s, 1H), 4.58 (d, J = 9.8 Hz, 2H), 1.78-1.66 (m, 3H), 4.44 (t, J = 8.8 Hz, 1H), 4.22 (s, 1H), 3.52 (s, 2H), 2.38 (s, 3H), 1.16 (d, J = 6.4 Hz, 3H). HRMS(B) m/z 443.1360. RT = 2.52 min. Chiral RT = 4.00 min |
| 186 and 187:<br>(4R)-3-(2-((1-(5-(4-chlorophenyl)-4-methyloxazol-2-yl)ethyl)amino)-5-fluoropyrimidin-4-yl)-4-((R)-1-hydroxyethyl)oxazolidin-2-one | Chiral separation was achieved by chiral SFC column chromatography (Column AD-H 21 × 250 mm 30% IPA in $CO_2$, flow 75 g/min, 238 nm UV collection) to give (R)-3-(2-(((R)-1-(5-(4-chlorophenyl)-4-methyloxazol-2-yl)ethyl)amino)-5-fluoropyrimidin-4-yl)-4-((R)-1-hydroxyethyl)oxazolidin-2-one and (R)-3-(2-(((S)-1-(5-(4-chlorophenyl)-4-methyloxazol-2-yl)ethyl)amino)-5-fluoropyrimidin-4-yl)-4-((R)-1-hydroxyethyl)oxazolidin-2-one<br>186: First eluted product (114 mg): (MeOD) δ 8.14 (dd, J = 111.8, 3.1 Hz, 1H), 7.64-7.53 (m, 2H), 7.53-7.42 (m, 2H), 5.35-5.18 (m, 1H), 5.18-5.05 (m, 1H), 4.80-4.70 (m, 1H), 4.55-4.45 (m, 2H), 4.17 (td, J = 6.7, 3.9 Hz, 1H), 4.07 (dt, J = 8.9, 5.4 Hz, 1H), 2.38 (d, J = 1.9 Hz, 3H), 1.67 (dd, J = 7.1, 5.4 Hz, 3H), 1.14 (dd, J = 27.1, 6.3 Hz, 3H). HRMS(B) m/z 461.1266. RT = 2.29 min. Chiral RT = 3.60 min<br>187: Second eluted product (14 mg): (MeOD) δ 8.14 (dd, J = 115.3, 3.2 Hz, 1H), 7.59 (ddt, J = 6.7, 4.3, 2.1 Hz, 2H), 7.53-7.42 (m, 2H), 5.14 (dq, J = 30.9, 6.9 Hz, 1H), 4.71 (dt, J = 9.6, 4.6 Hz, 1H), 4.39 (q, J = 7.4, 5.0 Hz, 1H), 3.98 (ddt, J = 28.7, 12.3, 5.6 Hz, 2H), 2.37 (d, J = 2.3 Hz, 3H), 1.67 (dd, J = 7.1, 4.0 Hz, 3H), 1.32 (d, J = 6.5 Hz, 2H), 1.17 (d, J = 6.1 Hz, 2H), 1.08-0.76 (m, 2H). HRMS(B) m/z 461.1266. RT = 2.37 min. Chiral RT = 6.05 min |
| 188 and 189:<br>(4R)-3-(2-((1-(4-(4-chlorophenyl)-5-methylthiazol-2-yl)ethyl)amino)-5-fluoropyrimidin-4-yl)-4-((R)-1-hydroxyethyl)oxazolidin-2-one | Chiral separation was achieved by chiral SFC column chromatography (Column ID 21 × 250 mm 25% MeOH 10 mM $NH_4OH$ in $CO_2$, flow 75 g/min, 230 nm UV collection) to give (R)-3-(2-(((R)-1-(4-(4-chlorophenyl)-5-methylthiazol-2-yl)ethyl)amino)-5-fluoropyrimidin-4-yl)-4-((R)-1-hydroxyethyl)oxazolidin-2-one and (R)-3-(2-(((S)-1-(4-(4-chlorophenyl)-5-methylthiazol-2-yl)ethyl)amino)-5-fluoropyrimidin-4-yl)-4-((R)-1-hydroxyethyl)oxazolidin-2-one<br>188: First eluted product (61.8 mg): $^1$H NMR (400 MHz, $CDCl_3$) δ 8.24 (d, J = 3.2 Hz, 1H), 7.64-7.53 (m, 2H), 7.49-7.38 (m, 2H), 5.75 (d, J = 6.1 Hz, 1H), 5.22 (s, 1H), 4.54-4.24 (m, 4H), 3.49 (s, 2H), 2.52 (s, 3H), 1.17 (d, J = 6.4 Hz, 3H). HRMS(E) m/z 478.1114 (M + H). RT = 5.98 min. Chiral RT = 3.90 min.<br>189: Second eluted product (82 mg): $^1$H NMR (400 MHz, $CDCl_3$) δ 8.32-7.93 (m, 1H), 7.68-7.52 (m, 2H), 7.43 (dd, J = 8.6, 2.5 Hz, 2H), 5.75 (d, J = 6.8 Hz, 1H), 5.35-5.21 (m, 1H), 4.58 (dt, J = 8.6, 5.3 Hz, 1H), 1.77-1.64 (m, 3H), 4.53-4.43 (m, 1H), 4.38 (dd, J = 9.0, 5.0 Hz, 1H), 3.96 (d, J = 11.1 Hz, 1H), 3.50 (s, 2H), 2.52 (d, J = 6.1 Hz, 3H), 1.04 (d, J = 49.6 Hz, 3H). HRMS(B) m/z 477.1038. RT = 2.48 min. Chiral RT = 5.80 min. |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
| 190 and 191:<br>(4R)-3-(2-((1-(4-(4-bromophenyl)thiazol-2-yl)ethyl)amino)-5-fluoropyrimidin-4-yl)-4-((R)-1-hydroxyethyl)oxazolidin-2-one | Chiral separation was achieved by chiral SFC column chromatography (Column ID 21 × 250 mm 30% MeOH 10 mM NH4OH in $CO_2$, flow 75 g/min, 230 nm UV collection) to give (R)-3-(2-(((S)-1-(4-(4-bromophenyl)thiazol-2-yl)ethyl)amino)-5-fluoropyrimidin-4-yl)-4-((R)-1-hydroxyethyl)oxazolidin-2-one and (R)-3-(2-(((R)-1-(4-(4-bromophenyl)thiazol-2-yl)ethyl)amino)-5-fluoropyrimidin-4-yl)-4-((R)-1-hydroxyethyl)oxazolidin-2-one<br>190: First eluted product (63.7 mg): $^1$H NMR (400 MHz, CDCl$_3$) δ 8.26 (d, J = 3.0 Hz, 1H), 7.86-7.71 (m, 2H), 7.62-7.50 (m, 2H), 7.41 (s, 1H), 5.80 (d, J = 6.7 Hz, 1H), 1.83-1.68 (m, 3H), 5.33 (t, J = 5.2 Hz, 1H), 4.38 (t, J = 13.2 Hz, 4H), 3.51 (s, 1H), 1.20 (d, J = 6.2 Hz, 3H). HRMS(E) m/z 510.0447 (M + H). RT = 5.95 min. Chiral RT = 3.30 min.<br>191: Second eluted product (77.1): $^1$H NMR (400 MHz, CDCl$_3$) δ 8.13 (dd, J = 109.6, 2.8 Hz, 1H), 7.78 (dd, J = 8.6, 2.1 Hz, 2H), 7.57 (dd, J = 8.8, 2.3 Hz, 2H), 7.40 (s, 1H), 5.78 (d, J = 6.5 Hz, 1H), 1.82-1.67 (m, 3H), 5.46-5.24 (m, 1H), 4.64-4.26 (m, 2H), 4.05-3.74 (m, 1H), 3.51 (s, 1H), 0.96 (s, 3H). HRMS(E) m/z 510.0445 (M + H). RT = 5.91 min. Chiral RT = 5.40 min. |
| 192 and 193:<br>(R)-3-(2-((1-(5-(3,4-dichlorophenyl)pyrimidin-2-yl)ethyl)amino)-5-fluoropyrimidin-4-yl)-4-((R)-1-hydroxyethyl)oxazolidin-2-one | Chiral separation was achieved by chiral SFC column chromatography (Column IC 21 × 250 mm, 45% MeOH in CO2, flow 75 g/min, 220 nm UV collection) to give (R)-3-(2-(((S)-1-(5-(3,4-dichlorophenyl)pyrimidin-2-yl)ethyl)amino)-5-fluoropyrimidin-4-yl)-4-((R)-1-hydroxyethyl)oxazolidin-2-one and (R)-3-(2-(((R)-1-(5-(3,4-dichlorophenyl)pyrimidin-2-yl)ethyl)amino)-5-fluoropyrimidin-4-yl)-4-((R)-1-hydroxyethyl)oxazolidin-2-one.<br>192: First eluted product (49 mg $^1$H NMR (400 MHz, CDCl$_3$) δ 8.88 (s, 2H), 8.24 (d, J = 2.8 Hz, 1H), 7.76-7.51 (m, 2H), 7.48-7.35 (m, 1H), 6.17 (d, J = 7.9 Hz, 1H), 5.30 (tt, J = 12.5, 5.8 Hz, 1H), 4.69-4.47 (m, 2H), 4.41 (dd, J = 8.9, 5.1 Hz, 1H), 4.09 (br s, 1H), 1.69-1.65 (m, 3H), 1.15 (d, J = 6.2 Hz, 3H). HRMS(B) m/z 493.0948 (M + H)$^+$.<br>193: Second eluted product (40 mg) $^1$H NMR (400 MHz, CDCl$_3$) δ 8.89 (d, J = 1.6 Hz, 2H), 8.25 (d, J = 2.9 Hz, 1H), 7.76-7.53 (m, 2H), 7.43 (ddd, J = 8.3, 3.9, 2.2 Hz, 1H), 6.24 (d, J = 7.5 Hz, 1H), 5.26 (br s, 1H), 4.60-4.36 (m, 4H), 1.64 (d, J = 4.8 Hz, 2H), 1.29-1.25 (m, 3H). HRMS(B) m/z 493.0949 (M + H)$^+$. |
| 194 and 195:<br>(R)-4-((R)-1-hydroxyethyl)-3-(2-((1-(5-(3-methyl-4-(trifluoromethyl)phenyl)pyrimidin-2-yl)ethyl)amino)pyrimidin-4-yl)oxazolidin-2-one | Chiral separation was achieved by chiral SFC column chromatography (Column IA 21 × 250 mm, 35% IPA 10 mM NH4OH in CO2, flow 75 g/min, 235 nm UV collection) to give (R)-4-((R)-1-hydroxyethyl)-3-(2-(((S)-1-(5-(3-methyl-4-(trifluoromethyl)phenyl)pyrimidin-2-yl)ethyl)amino)pyrimidin-4-yl)oxazolidin-2-one and (R)-4-((R)-1-hydroxyethyl)-3-(2-(((R)-1-(5-(3-methyl-4-(trifluoromethyl)phenyl)pyrimidin-2-yl)ethyl)amino)pyrimidin-4-yl)oxazolidin-2-one.<br>194: First eluted product (15 mg) $^1$H NMR (400 MHz, CDCl$_3$) δ 8.95 (s, 2H), 8.23 (d, J = 5.7 Hz, 1H), 7.77 (d, J = 8.5 Hz, 1H), 7.54-7.42 (m, 4H), 6.07 (d, J = 8.2 Hz, 1H), 5.45-5.36 (m, 1H), 4.89 (s, 1H), 4.52 (dd, J = 9.5, 2.6 Hz, 1H), 4.42 (dd, J = 9.4, 8.3 Hz, 1H), 3.36 (br s, 1H), 2.60 (dq, J = 3.7, 1.7 Hz, 3H), 1.71-1.60 (m, 3H), 1.11 (br s, 3H). HRMS(D) m/z 489.1850 (M + H)$^+$.<br>195: Second eluted product (11 mg) $^1$H NMR (400 MHz, CDCl$_3$) δ 8.94 (s, 2H), 8.23 (d, J = 5.7 Hz, 1H), 7.81-7.74 (m, 1H), 7.49 (d, J = 6.9 Hz, 1H), 7.42 (d, J = 5.7 Hz, 1H), 6.02 (br s, 1H), 5.18 (br s, 1H), 4.80 (br s, 1H), 4.53 (d, J = 8.8 Hz, 1H), 4.30 (br s, 2H), 3.71 (br s, 1H), 2.60 (q, J = 1.8 Hz, 3H), 1.69-1.65 (m, 3H), 1.25-1.19 (m, 3H). HRMS(D) m/z 489.1862 (M + H)$^+$. |

TABLE 29b-continued

Chemical name, NMR chemical shifts, chiral separation conditions and LCMS signal for compounds listed in Table 29a.

| Example: Name | Chiral separation conditions, peak identification and analytical data |
|---|---|
| 196 and 197: (R)-4-((R)-1-hydroxyethyl)-3-(2-((1-(4-methyl-5-(2-(1,1,1-trifluoro-2-methylpropan-2-yl)pyridin-4-yl)thiazol-2-yl)ethyl)amino)pyrimidin-4-yl)oxazolidin-2-one | Chiral separation was achieved by chiral SFC column chromatography (Column IC 21 × 250 mm, 30% IPA 10 mM NH4OH in CO2, flow 75 g/min, 227 nm UV collection) to give (R)-4-((R)-1-hydroxyethyl)-3-(2-(((S)-1-(4-methyl-5-(2-(1,1,1-trifluoro-2-methylpropan-2-yl)pyridin-4-yl)thiazol-2-yl)ethyl)amino)pyrimidin-4-yl)oxazolidin-2-one and (R)-4-((R)-1-hydroxyethyl)-3-(2-(((R)-1-(4-methyl-5-(2-(1,1,1-trifluoro-2-methylpropan-2-yl)pyridin-4-yl)thiazol-2-yl)ethyl)amino)pyrimidin-4-yl)oxazolidin-2-one. 198: First eluted product (50 mg) $^1$H NMR (400 MHz, CDCl$_3$) δ 8.65 (dd, J = 5.1, 0.8 Hz, 1H), 8.26 (d, J = 5.8 Hz, 1H), 7.59-7.49 (m, 2H), 7.24 (dd, J = 5.2, 1.6 Hz, 1H), 5.63 (d, J = 6.4 Hz, 1H), 5.38 (s, 1H), 4.80 (ddd, J = 8.3, 4.5, 2.5 Hz, 1H), 4.51 (dd, J = 9.4, 2.5 Hz, 1H), 4.40 (dd, J = 9.4, 8.3 Hz, 1H), 3.93 (br s, 1H), 2.79 (br s, 1H), 2.54 (s, 3H), 1.73 (d, J = 7.0 Hz, 3H), 1.67 (s, 6H), 1.05 (d, J = 6.9 Hz, 3H). HRMS(D) m/z 537.1898 (M + H)$^+$. 199: Second eluted product (50 mg) $^1$H NMR (400 MHz, CDCl$_3$) δ 8.65 (dd, J = 5.2, 0.8 Hz, 1H), 8.25 (d, J = 5.8 Hz, 1H), 7.59-7.46 (m, 2H), 7.26 (dd, J = 5.1, 1.6 Hz, 1H), 5.69 (s, 1H), 5.13 (br s, 1H), 4.82 (br s, 1H), 4.58 (d, J = 6.7 Hz, 1H), 4.31 (t, J = 8.4 Hz, 2H), 4.15 (br s, 1H), 2.53 (s, 3H), 1.76-1.65 (m, 9H), 1.25-1.18 (m, 3H). HRMS(D) m/z 537.1900 (M + H)$^+$. |
| 198 and 199: (4R)-3-(5-fluoro-2-((1-(4-methyl-5-(2-(1,1,1-trifluoro-2-methylpropan-2-yl)pyridin-4-yl)thiazol-2-yl)ethyl)amino)pyrimidin-4-yl)-4-((R)-1-hydroxyethyl)oxazolidin-2-one | Chiral separation was achieved by chiral SFC column chromatography (Column ID 21 × 250 mm, 25% IPA 10 mM NH4OH in CO2, flow 75 g/min, 230 nm UV collection) to give (4R)-3-(5-fluoro-2-(((S)-1-(4-methyl-5-(2-(1,1,1-trifluoro-2-methylpropan-2-yl)pyridin-4-yl)thiazol-2-yl)ethyl)amino)pyrimidin-4-yl)-4-((R)-1-hydroxyethyl)oxazolidin-2-one and (4R)-3-(5-fluoro-2-(((R)-1-(4-methyl-5-(2-(1,1,1-trifluoro-2-methylpropan-2-yl)pyridin-4-yl)thiazol-2-yl)ethyl)amino)pyrimidin-4-yl)-4-((R)-1-hydroxyethyl)oxazolidin-2-one. 200: First eluted product (7 mg) $^1$H NMR (400 MHz, CDCl$_3$) δ 8.55 (td, J = 5.4, 0.8 Hz, 1H), 8.17 (dd, J = 4.5, 2.8 Hz, 1H), 7.46-7.40 (m, 1H), 7.16 (ddd, J = 8.1, 5.1, 1.6 Hz, 1H), 5.56 (dd, J = 14.8, 6.8 Hz, 1H), 5.20-5.13 (m, 1H), 4.49-4.37 (m, 2H), 4.30 (d, J = 6.8 Hz, 1H), 3.32 (d, J = 3.7 Hz, 1H), 2.46 (s, 3H), 1.67-1.50 (m, 9H), 1.18-1.12 (m, 3H). HRMS(D) m/z 555.1821 (M + H)$^+$. 201: Second eluted product (33 mg) $^1$H NMR (400 MHz, CDCl$_3$) δ 8.60-8.52 (m, 1H), 8.17 (d, J = 2.8 Hz, 1H), 7.42 (dt, J = 1.7, 0.8 Hz, 1H), 7.21-7.12 (m, 1H), 5.56 (d, J = 6.9 Hz, 1H), 5.24 (p, J = 7.0 Hz, 1H), 4.55 (dt, J = 8.6, 5.5 Hz, 1H), 4.45 (t, J = 8.8 Hz, 1H), 4.31 (dd, J = 9.0, 5.2 Hz, 1H), 3.95 (td, J = 13.7, 13.0, 6.9 Hz, 1H), 2.45 (s, 3H), 1.64 (d, J = 6.9 Hz, 3H), 1.57 (s, 6H), 1.00 (d, J = 6.0 Hz, 3H). HRMS(D) m/z 555.1839 (M + H)$^+$. |
| 200 and 201: (R)-3-(2-((1-(5-(2-fluoro-3-(trifluoromethyl)phenyl)pyrimidin-2-yl)ethyl)amino)pyrimidin-4-yl)-4-((R)-1-hydroxyethyl)oxazolidin-2-one | Chiral separation was achieved by chiral SFC column chromatography (Column IA 21 × 250 mm, 25% MeOH 10 mM NH4OH in CO2, flow 75 g/min, 232 nm UV collection) to give (R)-3-(2-(((S)-1-(5-(2-fluoro-3-(trifluoromethyl)phenyl)pyrimidin-2-yl)ethyl)amino)pyrimidin-4-yl)-4-((R)-1-hydroxyethyl)oxazolidin-2-one and (R)-3-(2-(((R)-1-(5-(2-fluoro-3-(trifluoromethyl)phenyl)pyrimidin-2-yl)ethyl)amino)pyrimidin-4-yl)-4-((R)-1-hydroxyethyl)oxazolidin-2-one. 192: First eluted product (35 mg) $^1$H NMR (400 MHz, CDCl$_3$) δ 8.85-8.79 (m, 2H), 8.12 (dd, J = 6.1, 4.0 Hz, 1H), 7.70-7.52 (m, 2H), 7.41-7.30 (m, 2H), 6.14 (s, 1H), 5.36-5.27 (m, 1H), 4.85-4.76 (m, 1H), 4.43 (dd, J = 9.4, 2.6 Hz, 1H), 4.38-4.24 (m, 1H), 4.13-3.93 (m, 1H), 3.15 (br s, 1H), 1.60 (d, J = 7.0 Hz, 3H), 1.02 (br s, 3H). HRMS(D) m/z 493.1605 (M + H)$^+$. 193: Second eluted product (36 mg) $^1$H NMR (400 MHz, CDCl$_3$) δ 8.83 (d, J = 1.4 Hz, 2H), 8.12 (d, J = 5.8 Hz, 1H), 7.71-7.53 (m, 2H), 7.42-7.31 (m, 2H), 6.19 (br s, 1H), 5.08 (br s, 1H), 4.68 (br s, 1H), 4.46 (d, J = 8.3 Hz, 1H), 4.21 (br s, 2H), 3.50 (br s, 1H), 1.60 (d, J = 7.0 Hz, 3H), 1.19-1.12 (m, 3H). HRMS(D) m/z 493.1630 (M + H)$^+$. |

Examples 202 and 203

(4R)-3-(2-((1-(5-(4-chlorophenyl)oxazol-2-yl)ethyl)amino)-5-fluoropyrimidin-4-yl)-4-((R)-1-hydroxyethyl)oxazolidin-2-one

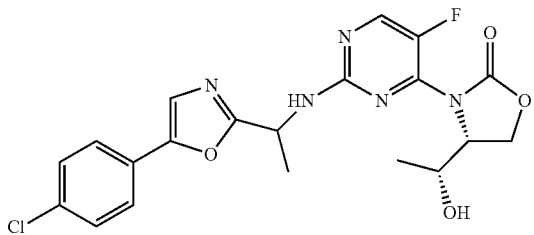 [SMILES: CC(Nc1ncc(F)c(N2C(=O)OC[C@@H]2[C@@H](C)O)n1)c1ncc(-c2ccc(Cl)cc2)o1]

(4R)-4-((R)-1-(tert-butoxy)ethyl)-3-(2-((1-(5-(4-chlorophenyl)oxazol-2-yl)ethyl)amino)-5-fluoropyrimidin-4-yl)oxazolidin-2-one (124 mg, 0.246 mmol) was treated with 90% TFA/water for 2 hours. Concentrated in vacuo and neutralized by passing through a column of MP-carbonate resin (2.0 g, 0.55 mmol/g eluting with MeOH/DCM/MeOH afforded the diastereomeric mixture. Chiral SFC chromatography on an ID column (75 g/min, 120 bar, 21×250 mm) eluting 45% IPA/CO₂ (v/v) to give (R)-3-(2-(((R)-1-(5-(4-chlorophenyl)oxazol-2-yl)ethyl)amino)-5-fluoropyrimidin-4-yl)-4-((R)-1-hydroxyethyl)oxazolidin-2-one and (R)-3-(2-(((S)-1-(5-(4-chlorophenyl)oxazol-2-yl)ethyl)amino)-5-fluoropyrimidin-4-yl)-4-((R)-1-hydroxyethyl)oxazolidin-2-one.

202: Peak 1: 15 mg (pale orange foam): (CDCl₃) δ 8.22 (d, J=3.2 Hz, 1H), 7.63-7.50 (m, 2H), 7.45-7.38 (m, 2H), 7.28 (s, 1H), 5.65 (d, J=7.0 Hz, 1H), 5.16 (s, 1H), 4.80-4.25 (m, 3H), 3.51 (s, 1H), 1.71 (d, J=7.0 Hz, 3H), 1.38-1.15 (m, 4H). HRMS(B) m/z 447.1110. RT=2.20 min.

203: Peak 2: 87 mg (pale orange foam): (CDCl₃) δ 8.24 (d, J=2.9 Hz, 1H), 7.59-7.49 (m, 2H), 7.46-7.37 (m, 2H), 7.24-7.18 (m, 1H), 5.66 (d, J=8.1 Hz, 1H), 5.32 (dd, J=8.3, 6.6 Hz, 1H), 4.79 (s, 1H), 4.56 (t, J=8.9 Hz, 1H), 4.39 (dd, J=9.1, 5.7 Hz, 1H), 4.04 (td, J=11.0, 9.7, 4.8 Hz, 1H), 3.51 (s, 1H), 1.70 (s, 1H), 1.23 (d, J=6.2 Hz, 2H), 1.16 (d, J=6.4 Hz, 3H). HRMS(B) m/z 447.1110. RT=2.20 min.

Examples 204 and 205

(4R)-3-(2-((1-(3-(4-chlorophenyl)isoxazol-5-yl)ethyl)amino)pyrimidin-4-yl)-4-((R)-1-hydroxyethyl)oxazolidin-2-one

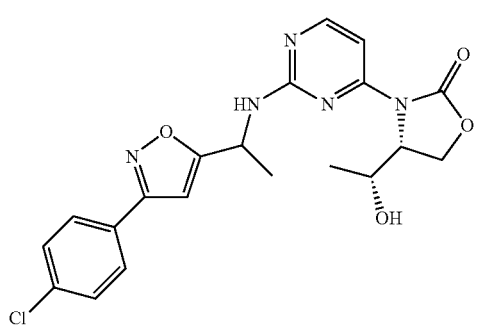 [SMILES: CC(Nc1nccc(N2C(=O)OC[C@@H]2[C@@H](C)O)n1)c1cc(-c2ccc(Cl)cc2)no1]

(4R)-4-((R)-1-(tert-butoxy)ethyl)-3-(2-((1-(3-(4-chlorophenyl)isoxazol-5-yl)ethyl)amino)pyrimidin-4-yl)oxazolidin-2-one (3.50 g, 2.88 mmol) was treated with 90% TFA/water for 2 hours. Concentrated in vacuo and neutralized by passing through a column of MP-carbonate resin (6.0 g, 0.55 mmol/g eluting with MeOH/DCM/MeOH afforded the diastereomeric mixture. Chiral SFC chromatography on an OJ-H column (75 g/min, 120 bar, 21×250 mm) eluting 30% IPA+10 mM NH4OH/CO₂ (v/v) to give (R)-3-(2-(((S)-1-(3-(4-chlorophenyl)isoxazol-5-yl)ethyl)amino)pyrimidin-4-yl)-4-((R)-1-hydroxyethyl)oxazolidin-2-one and (R)-3-(2-(((R)-1-(3-(4-chlorophenyl)isoxazol-5-yl)ethyl)amino)pyrimidin-4-yl)-4-((R)-1-hydroxyethyl)oxazolidin-2-one.

204: Peak 1: 1.40 g (white powder crystals): ¹H NMR (400 MHz, CDCl₃) δ 8.22 (d, J=5.8 Hz, 1H), 7.76-7.63 (m, 2H), 7.54 (d, J=5.7 Hz, 1H), 7.50-7.37 (m, 2H), 6.46 (s, 1H), 5.90-5.55 (m, 1H), 5.27-5.04 (m, 1H), 4.93-4.79 (m, 1H), 4.56 (dd, J=9.3, 2.5 Hz, 1H), 4.40 (dd, J=9.4, 8.4 Hz, 1H), 3.51 (s, 2H), 3.25 (d, J=68.4 Hz, 1H), 1.98-1.55 (m, 2H), 0.91 (s, 3H). HRMS(B) m/z 429.1204. RT=2.45 min.

205: Peak 2: 1.35 g (off-white foam): ¹H NMR (400 MHz, CDCl₃) δ 8.22 (d, J=6.0 Hz, 1H), 7.79-7.64 (m, 2H), 7.54 (d, J=5.8 Hz, 1H), 7.49-7.37 (m, 2H), 6.47 (s, 1H), 5.77 (s, 1H), 1.80-1.61 (m, 4H), 5.16 (s, 1H), 4.71-4.45 (m, 2H), 4.46-4.22 (m, 2H), 3.51 (s, 2H), 2.87 (s, 1H), 1.20 (d, J=6.5 Hz, 4H). HRMS(B) m/z 429.1204. RT=2.45 min.

Example 206

(R)-3-(2-(((S)-1-(5-(4-chlorophenyl)oxazol-2-yl)ethyl)amino)pyrimidin-4-yl)-4-((R)-1-hydroxyethyl)oxazolidin-2-one

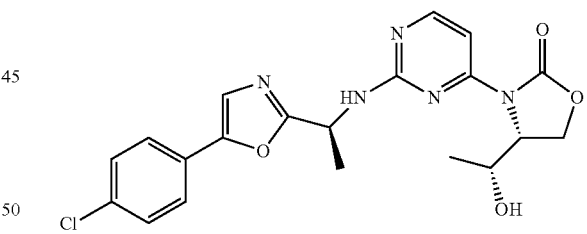

(R)-4-((R)-1-(tert-butoxy)ethyl)-3-(2-(((S)-1-(5-(4-chlorophenyl)oxazol-2-yl)ethyl)amino)pyrimidin-4-yl)oxazolidin-2-one (360 mg, 0.741 mg) was treated with 90% TFA/water for 2 hours. Concentrated in vacuo and neutralized by passing through a column of MP-carbonate resin (2.0 g, 0.55 mmol/g eluting with MeOH/DCM/MeOH afforded the desired product (120 mg, pale yellow foam). ¹H NMR (400 MHz, CDCl₃) δ 8.15 (d, J=6.0 Hz, 1H), 7.64-7.49 (m, 3H), 7.49-7.35 (m, 2H), 7.29 (s, 1H), 5.33 (dd, J=9.4, 5.1 Hz, 1H), 5.04-4.81 (m, 1H), 1.80-1.69 (m, 3H), 4.71-4.53 (m, 1H), 4.45 (dd, J=9.4, 8.1 Hz, 1H), 4.28-3.97 (m, 1H), 3.51 (s, 3H), 1.14 (d, J=6.4 Hz, 3H). HRMS(B) m/z 429.1204. RT=2.22 min.

Example 207

(R)-3-(6-chloro-2-((S)-1-(3-(4-chlorophenyl)-1,2,4-oxadiazol-5-yl)ethylamino)pyrimidin-4-yl)-4-((R)-1-hydroxyethyl)oxazolidin-2-one

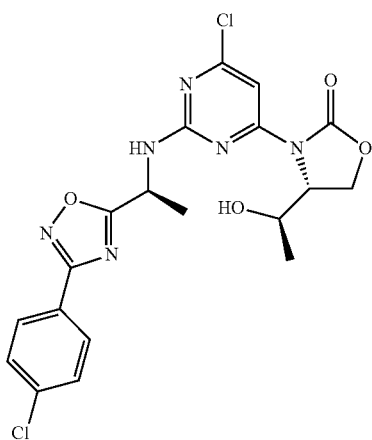 [SMILES: C[C@H](Nc1nc(Cl)cc(N2C(=O)OC[C@@H]2[C@@H](C)O)n1)c1nc(-c2ccc(Cl)cc2)no1]

Trifluoroacetic acid (2 mL) was added to a solution of (R)-4-((R)-1-tert-butoxyethyl)-3-(6-chloro-2-((S)-1-(3-(4-chlorophenyl)-1,2,4-oxadiazol-5-yl)ethylamino)pyrimidin-4-yl)oxazolidin-2-one (25.0 mg, 0.039 mmol), in DCM (2 mL) and the solution was stirred at room temperature for 1 h. The reaction mixture was then concentrated and purification by reverse phase HPLC provided the trifluoroacetate salt of (R)-3-(6-chloro-2-((S)-1-(3-(4-chlorophenyl)-1,2,4-oxadiazol-5-yl)ethylamino)pyrimidin-4-yl)-4-((R)-1-hydroxyethyl)oxazolidin-2-one (10.0 mg, white solid) in 44% yield. $^1$H NMR (400 MHz, CDCl$_3$) δ 8.00 (d, J=8.4 Hz, 2H), 7.63 (s, 1H), 7.48 (d, J=8.4 Hz, 2H), 5.30 (br m, 1H), 4.80-4.77 (m, 1H), 4.55-4.52 (m, 1H), 4.41-4.36 (m, 1H), 3.77-3.62 (br m, 1H), 1.78 (d, J=7.1 Hz, 3H), 0.95 (br m, 3H); HRMS m/z 465.0847 (M+H)$^+$; Rt-2.25 min.

The compounds in Table 30a were prepared using methods similar to those described for the preparation of Examples 35, 36, 37/38, or 207.

TABLE 30a

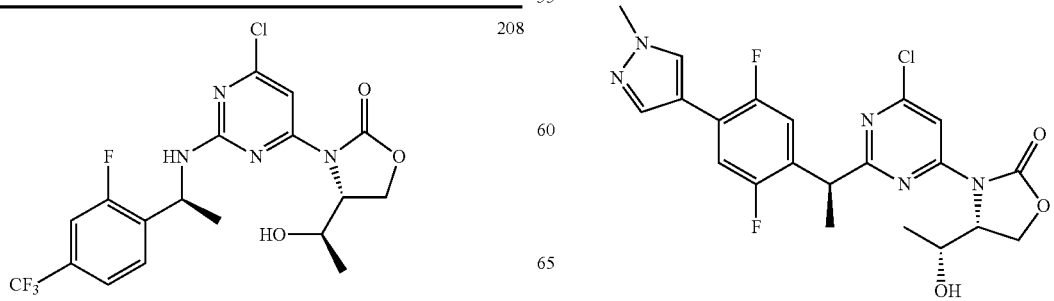

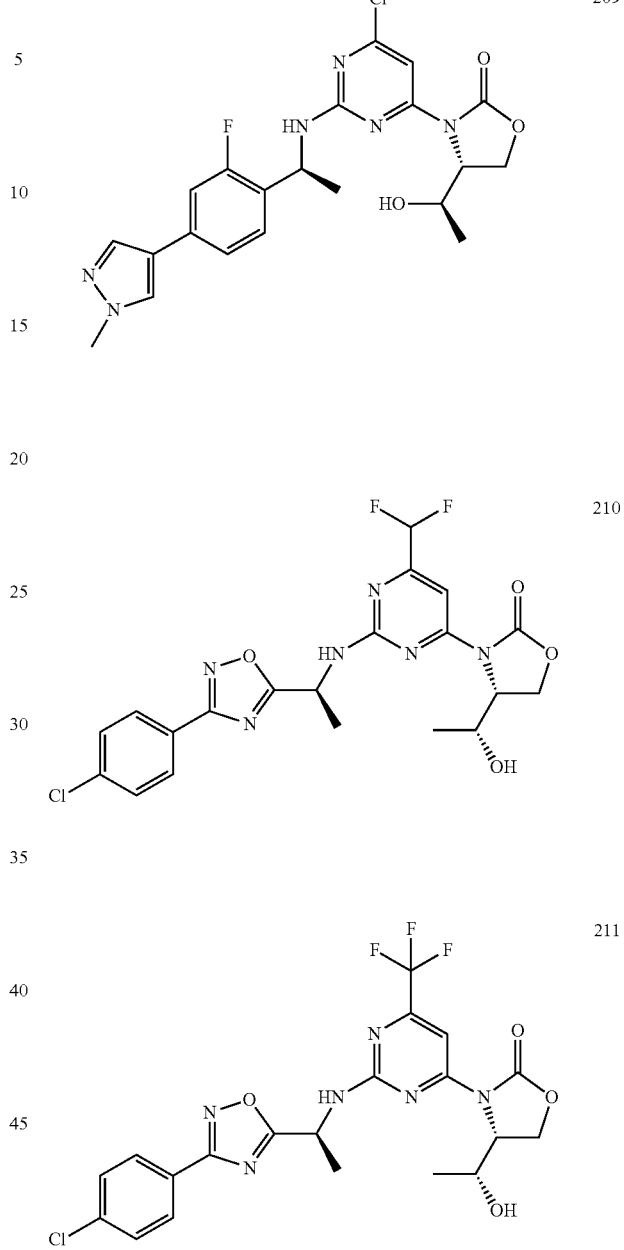

TABLE 30a-continued
| 213 | 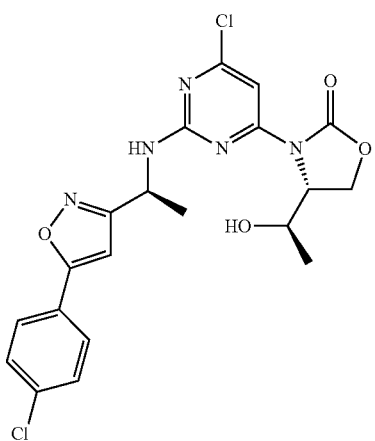 [SMILES: C[C@H](Nc1nc(Cl)cc(N2C(=O)OC[C@@H]2[C@@H](C)O)n1)c1cc(-c2ccc(Cl)cc2)on1] |
| 214 | 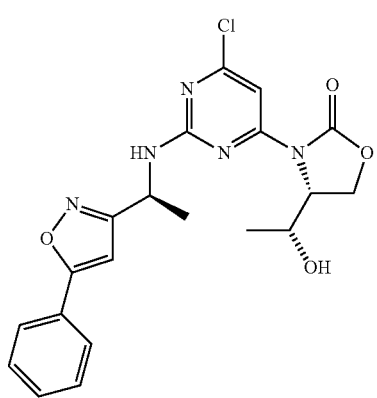 [SMILES: C[C@H](Nc1nc(Cl)cc(N2C(=O)OC[C@@H]2[C@@H](C)O)n1)c1cc(-c2ccccc2)on1] |
| 215 | 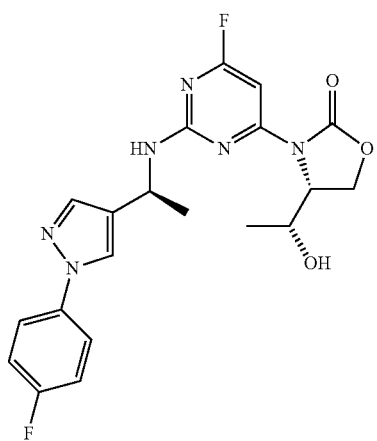 |
| 216 | 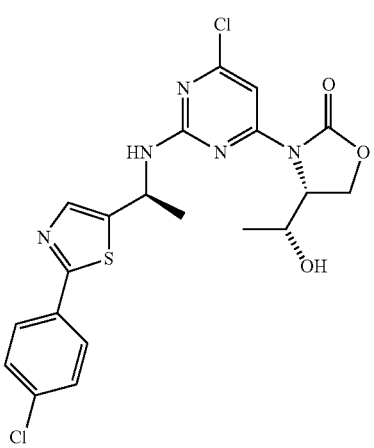 [SMILES: C[C@H](Nc1nc(Cl)cc(N2C(=O)OC[C@@H]2[C@@H](C)O)n1)c1cnc(-c2ccc(Cl)cc2)s1] |
| 217 | 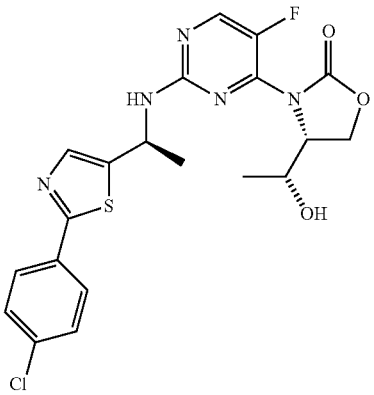 [SMILES: C[C@H](Nc1ncc(F)c(N2C(=O)OC[C@@H]2[C@@H](C)O)n1)c1cnc(-c2ccc(Cl)cc2)s1] |
| 218 | 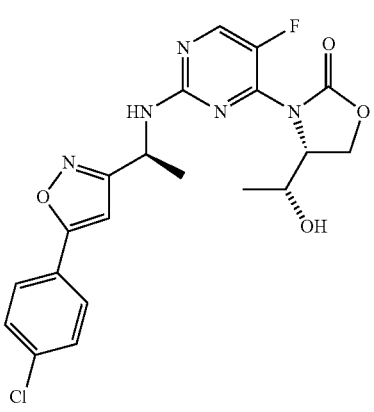 [SMILES: C[C@H](Nc1ncc(F)c(N2C(=O)OC[C@@H]2[C@@H](C)O)n1)c1cc(-c2ccc(Cl)cc2)on1] |

TABLE 30a-continued
| | |
|---|---|
| 219 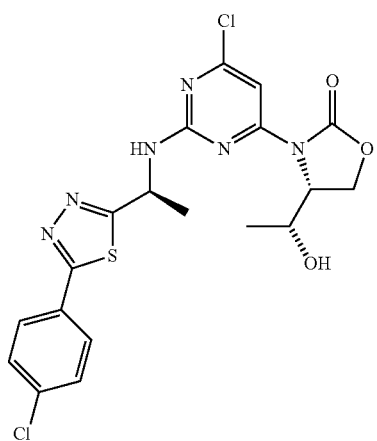 | 222 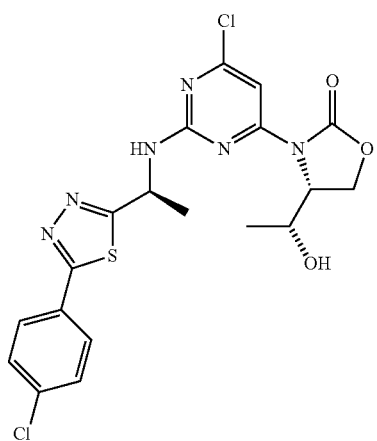 |
| 220 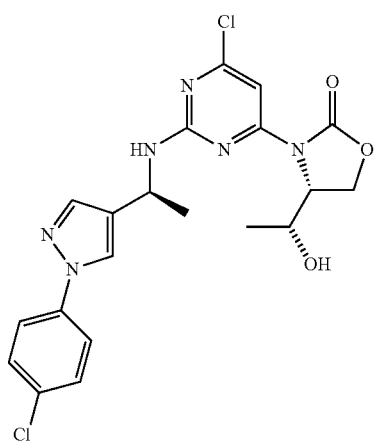 | 223 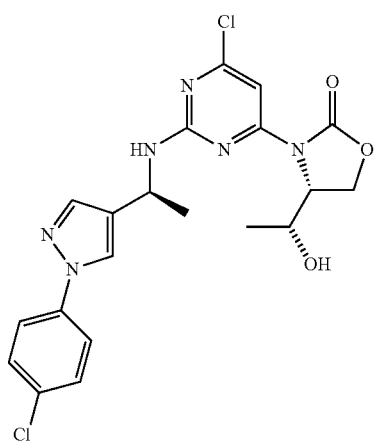 |
| 221 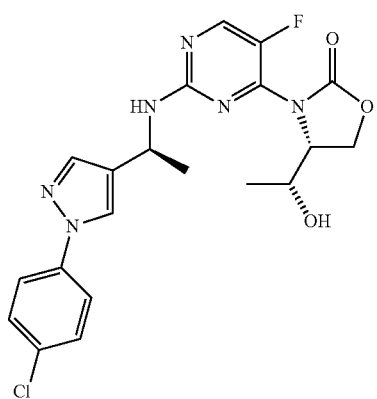 [SMILES: C[C@H](Nc1ncc(F)c(N2C(=O)OC[C@@H]2[C@@H](C)O)n1)c1cnn(-c2ccc(Cl)cc2)c1] | 224 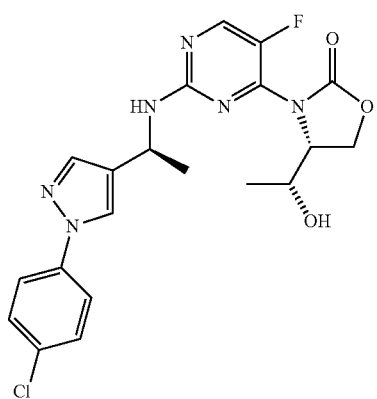 [SMILES: C[C@H](Nc1ncc(F)c(N2C(=O)OC[C@@H]2[C@@H](C)O)n1)c1cnn(-c2ccc(Cl)cc2)c1] |

| | |
|---|---|
| 225 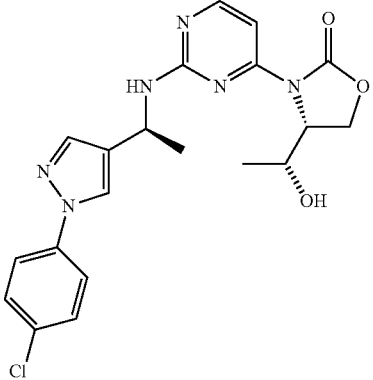 [SMILES: C[C@H](Nc1nccc(N2C(=O)OC[C@@H]2[C@@H](C)O)n1)c1cnn(-c2ccc(Cl)cc2)c1] | 228 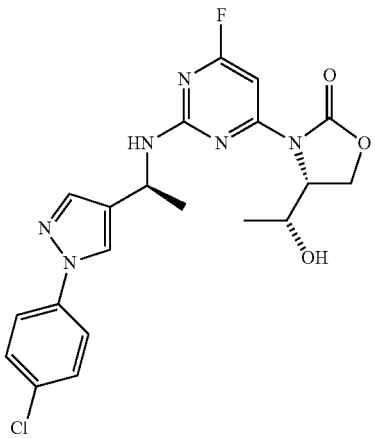 |
| 226 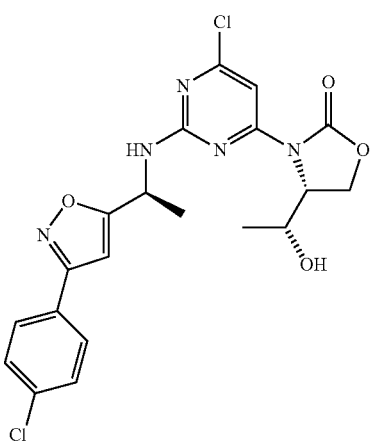 [SMILES: C[C@H](Nc1nc(Cl)cc(N2C(=O)OC[C@@H]2[C@@H](C)O)n1)c1cc(-c2ccc(Cl)cc2)no1] | 229 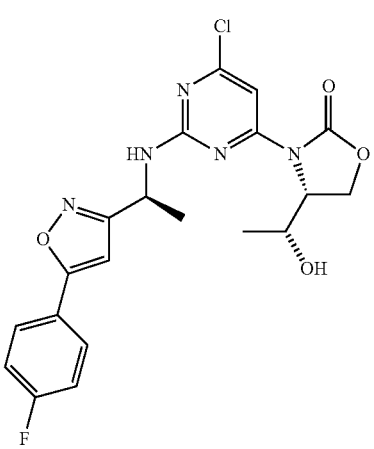 |
| 227 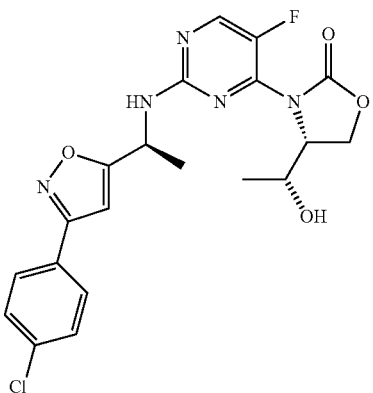 [SMILES: C[C@H](Nc1ncc(F)c(N2C(=O)OC[C@@H]2[C@@H](C)O)n1)c1cc(-c2ccc(Cl)cc2)no1] | 230 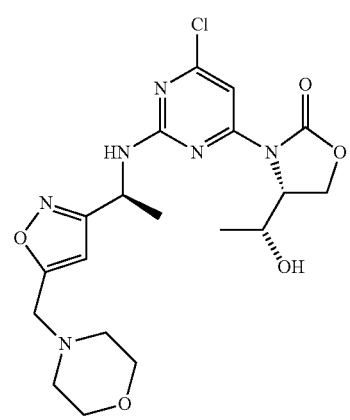 [SMILES: C[C@H](Nc1nc(Cl)cc(N2C(=O)OC[C@@H]2[C@@H](C)O)n1)c1cc(CN2CCOCC2)on1] |

TABLE 30a-continued
231 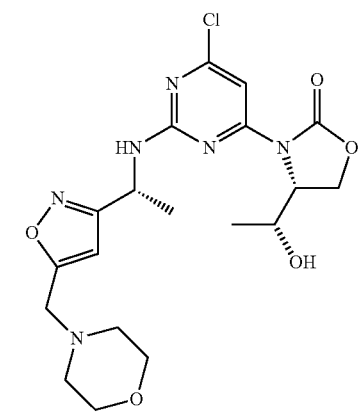 [SMILES: C[C@@H](Nc1nc(Cl)cc(N2C(=O)OC[C@@H]2[C@@H](C)O)n1)c1cc(CN2CCOCC2)on1]
232 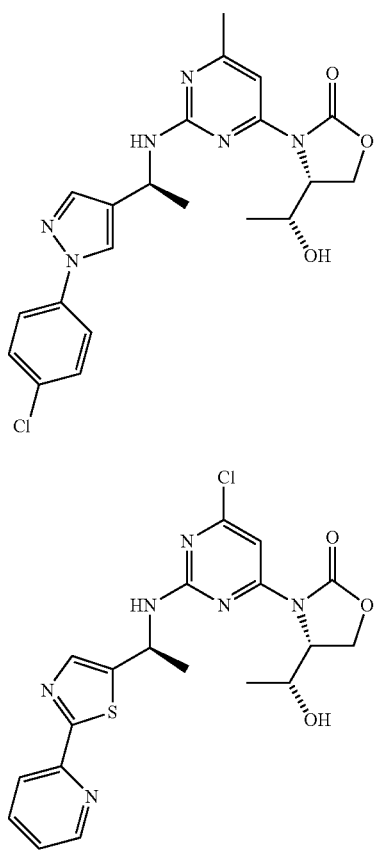
233 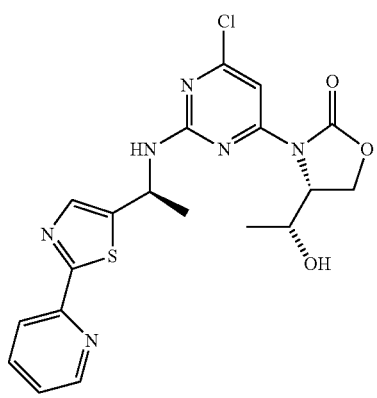 [SMILES: C[C@H](Nc1nc(Cl)cc(N2C(=O)OC[C@@H]2[C@@H](C)O)n1)c1cnc(-c2ccccn2)s1]
234 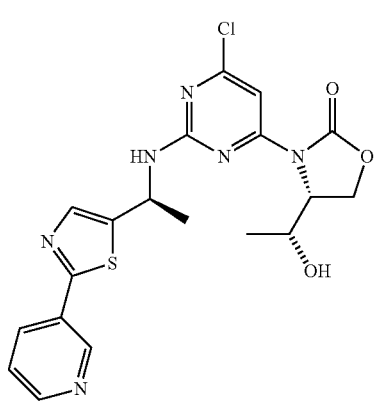 [SMILES: C[C@H](Nc1nc(Cl)cc(N2C(=O)OC[C@@H]2[C@@H](C)O)n1)c1cnc(-c2cccnc2)s1]
TABLE 30a-continued
235 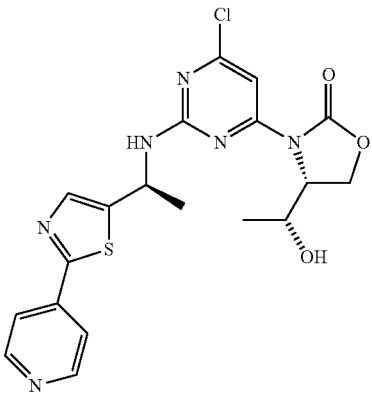 [SMILES: C[C@H](Nc1nc(Cl)cc(N2C(=O)OC[C@@H]2[C@@H](C)O)n1)c1cnc(-c2ccncc2)s1]
236 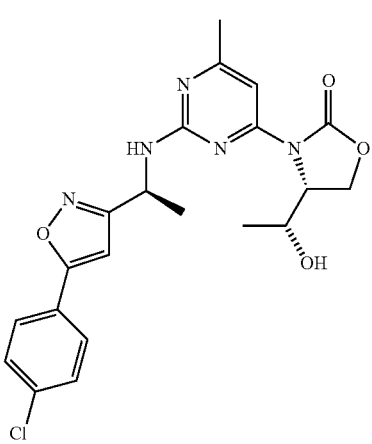 [SMILES: Cc1cc(N2C(=O)OC[C@@H]2[C@@H](C)O)nc(N[C@@H](C)c2cc(-c3ccc(Cl)cc3)on2)n1]
237 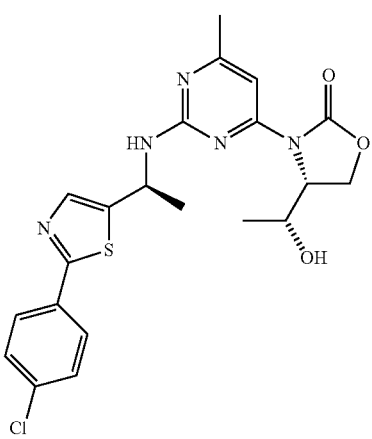 [SMILES: Cc1cc(N2C(=O)OC[C@@H]2[C@@H](C)O)nc(N[C@@H](C)c2cnc(-c3ccc(Cl)cc3)s2)n1]

TABLE 30a-continued
238 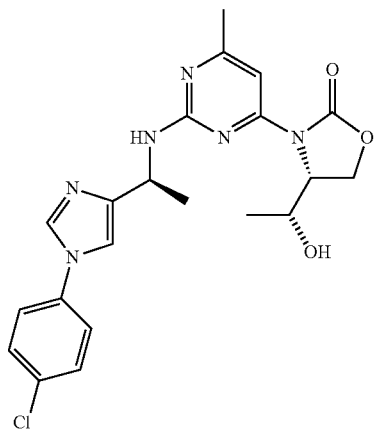
239 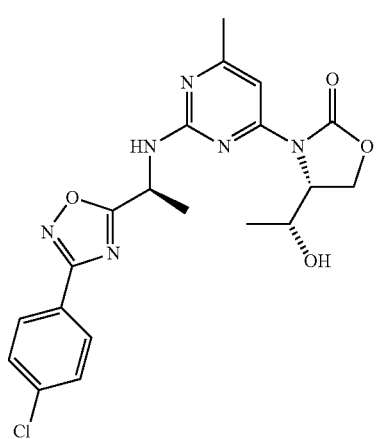 [SMILES: Cc1cc(N2C(=O)OC[C@@H]2[C@@H](C)O)nc(N[C@@H](C)c2nc(-c3ccc(Cl)cc3)no2)n1]
240 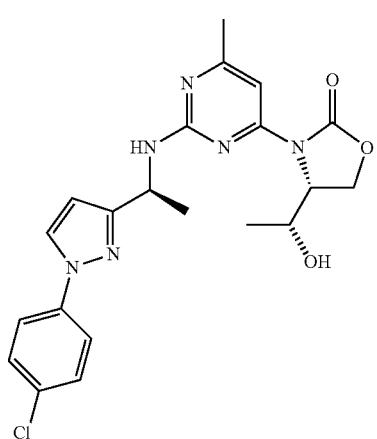 [SMILES: Cc1cc(N2C(=O)OC[C@@H]2[C@@H](C)O)nc(N[C@@H](C)c2ccn(-c3ccc(Cl)cc3)n2)n1]
TABLE 30a-continued
241 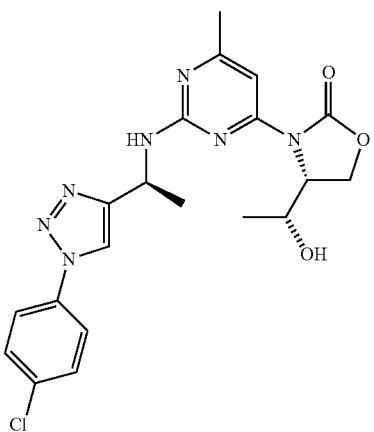 [SMILES: Cc1cc(N2C(=O)OC[C@@H]2[C@@H](C)O)nc(N[C@@H](C)c2cn(-c3ccc(Cl)cc3)nn2)n1]
242 
243 
244 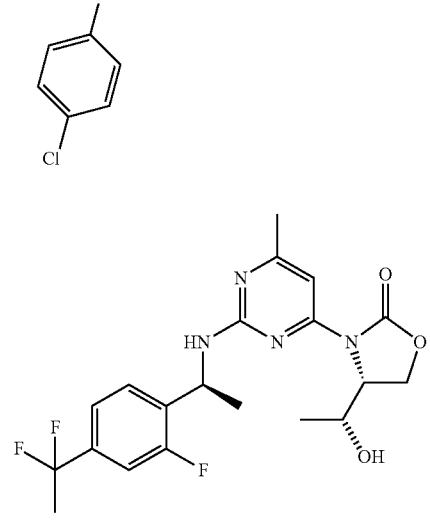

TABLE 30a-continued
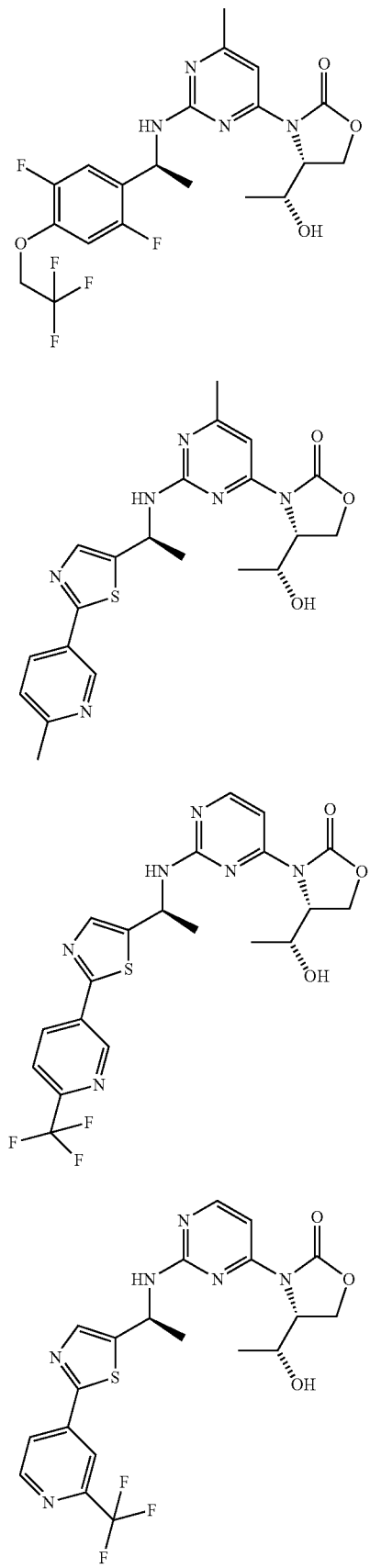
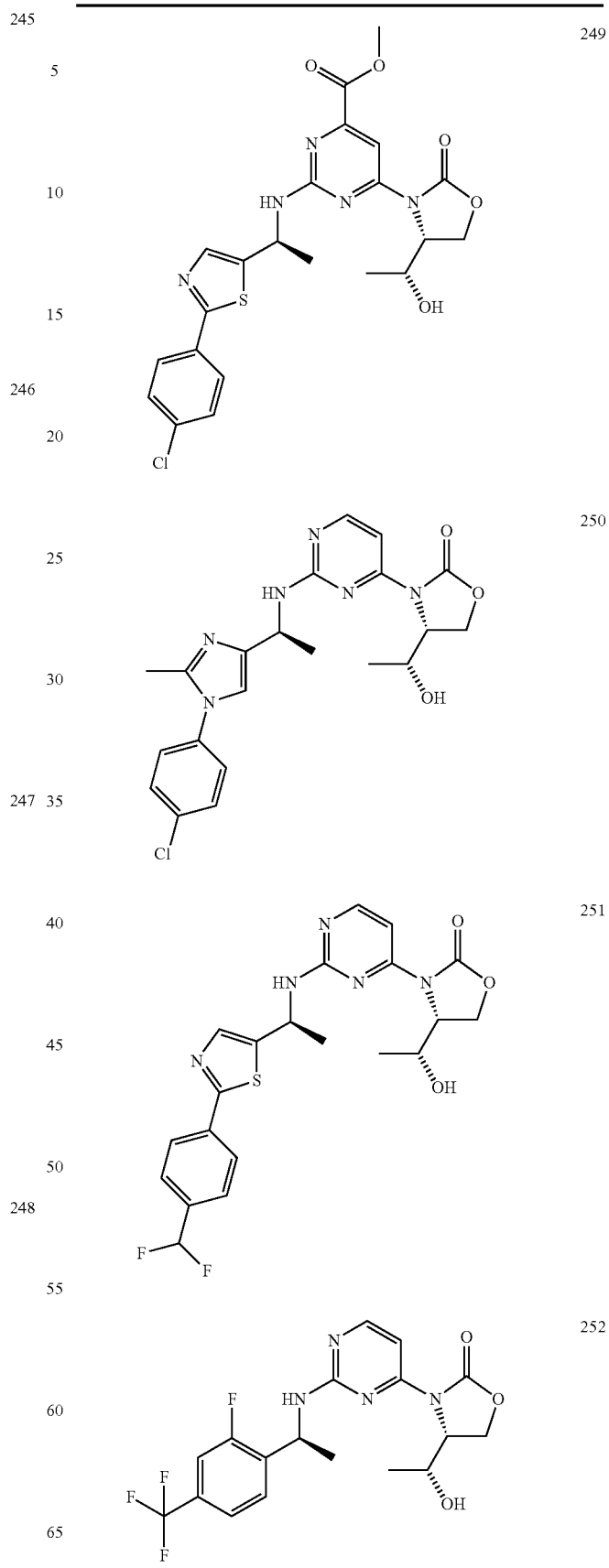

TABLE 30a-continued
| | |
|---|---|
| 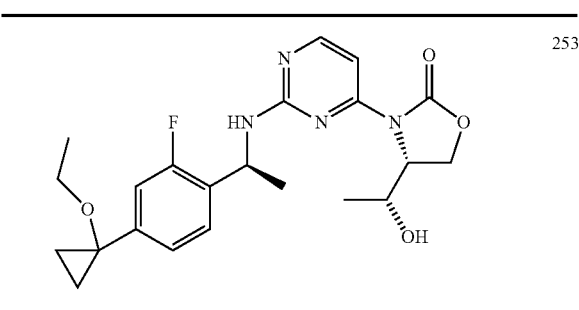 | 253 |
| 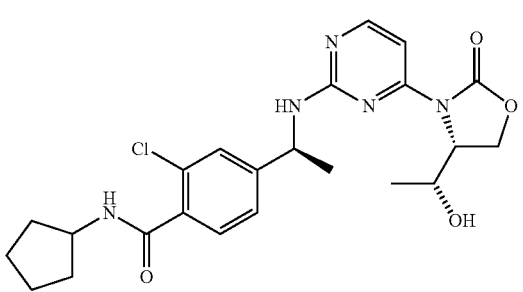 [SMILES: C[C@H](Nc1nccc(N2C(=O)OC[C@@H]2[C@@H](C)O)n1)c1ccc(C(=O)NC2CCCC2)c(Cl)c1] | 254 |
| 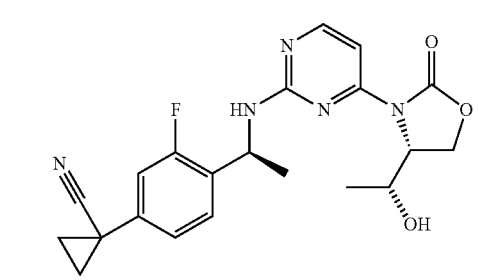 [SMILES: C[C@H](Nc1nccc(N2C(=O)OC[C@@H]2[C@@H](C)O)n1)c1ccc(C2(C#N)CC2)cc1F] | 255 |
| 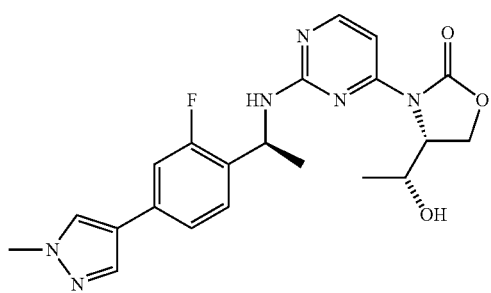 [SMILES: C[C@H](Nc1nccc(N2C(=O)OC[C@@H]2[C@@H](C)O)n1)c1ccc(-c2cnn(C)c2)cc1F] | 256 |
| 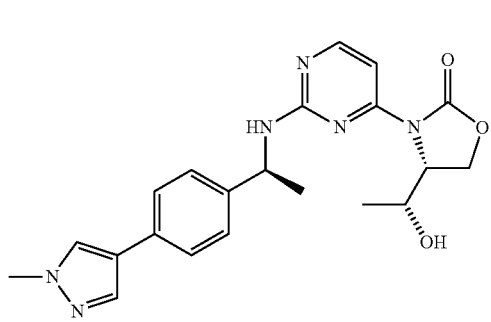 [SMILES: C[C@H](Nc1nccc(N2C(=O)OC[C@@H]2[C@@H](C)O)n1)c1ccc(-c2cnn(C)c2)cc1] | 257 |
| 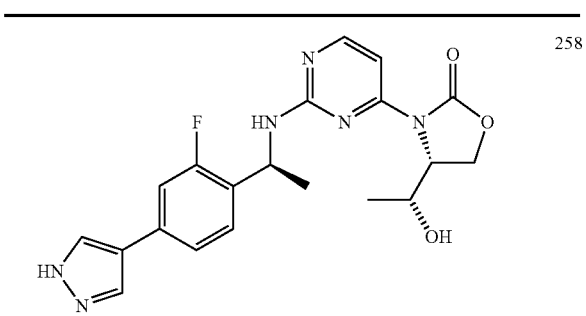 | 258 |
| 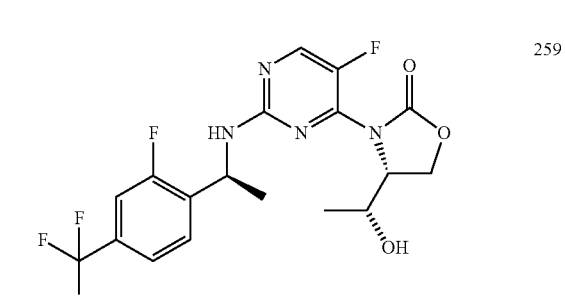 | 259 |
| 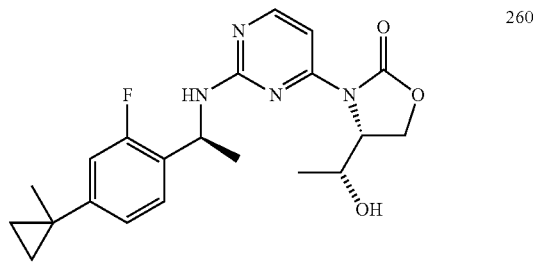 | 260 |
| 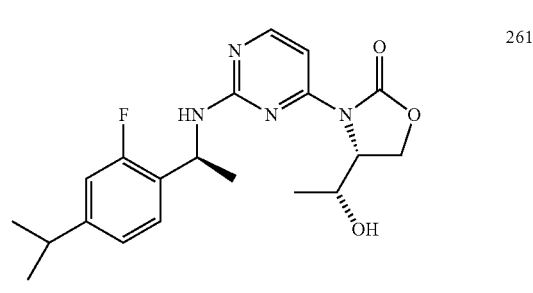 | 261 |
| 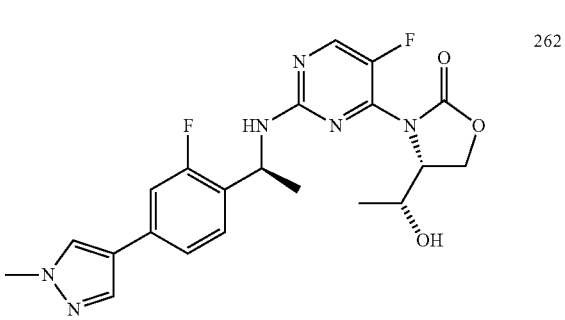 | 262 |

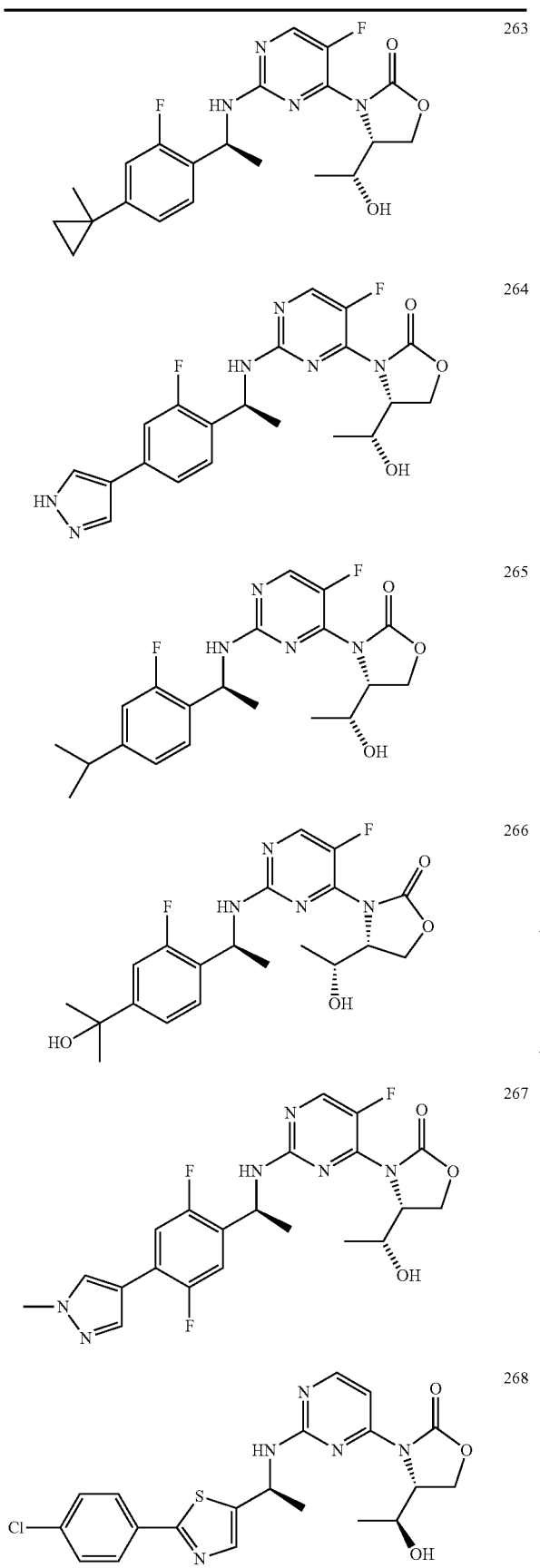

TABLE 30a-continued
| | |
|---|---|
| 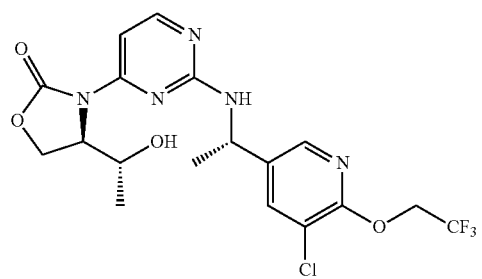 [SMILES: C[C@H](Nc1nccc(N2C(=O)OC[C@@H]2[C@@H](C)O)n1)c1cnc(OCC(F)(F)F)c(Cl)c1] | 274 |
| 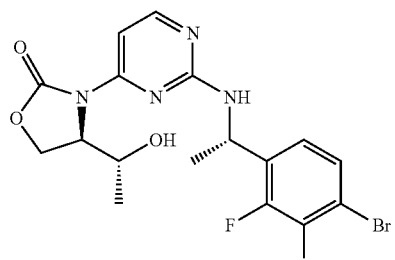 | 275 |
| 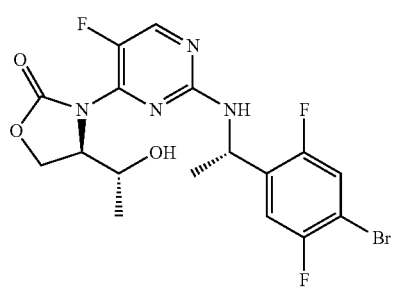 [SMILES: C[C@H](Nc1ncc(F)c(N2C(=O)OC[C@@H]2[C@@H](C)O)n1)c1cc(F)c(Br)cc1F] | 276 |
| 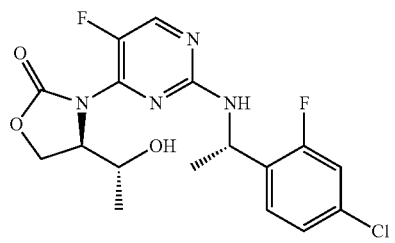 | 277 |
| 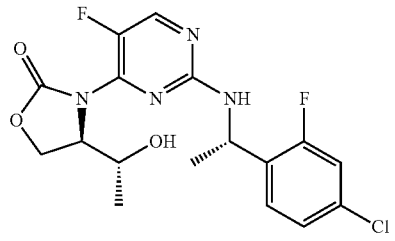 [SMILES: C[C@H](Nc1ncc(F)c(N2C(=O)OC[C@@H]2[C@@H](C)O)n1)c1ncc(Br)cc1F] | 278 |
| 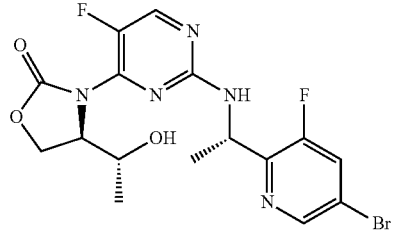 | 279 |
TABLE 30a-continued
| | |
|---|---|
| 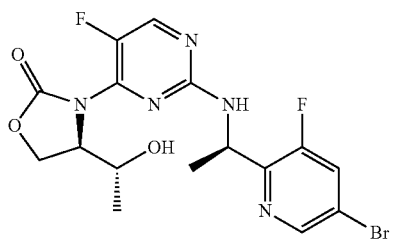 [SMILES: C[C@@H](Nc1ncc(F)c(N2C(=O)OC[C@@H]2[C@@H](C)O)n1)c1ncc(Br)cc1F] | 280 |
| 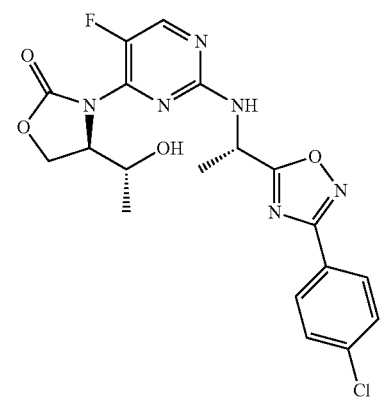 [SMILES: C[C@H](Nc1ncc(F)c(N2C(=O)OC[C@@H]2[C@@H](C)O)n1)c1nc(-c2ccc(Cl)cc2)no1] | 281 |
| 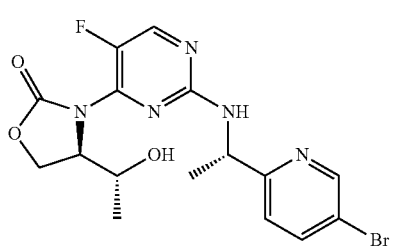 [SMILES: C[C@H](Nc1ncc(F)c(N2C(=O)OC[C@@H]2[C@@H](C)O)n1)c1ccc(Br)cn1] | 282 |
| 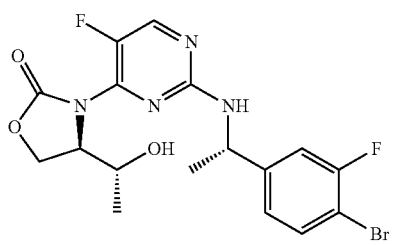 [SMILES: C[C@H](Nc1ncc(F)c(N2C(=O)OC[C@@H]2[C@@H](C)O)n1)c1ccc(Br)c(F)c1] | 283 |
| 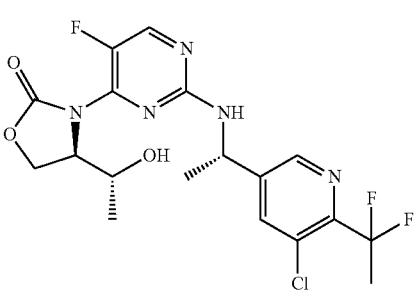 [SMILES: C[C@H](Nc1ncc(F)c(N2C(=O)OC[C@@H]2[C@@H](C)O)n1)c1cnc(C(C)(F)F)c(Cl)c1] | 284 |

TABLE 30a-continued
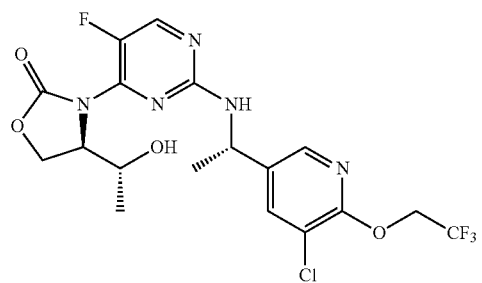 [SMILES: C[C@H](Nc1ncc(F)c(N2C(=O)OC[C@@H]2[C@@H](C)O)n1)c1cnc(OCC(F)(F)F)c(Cl)c1]
285
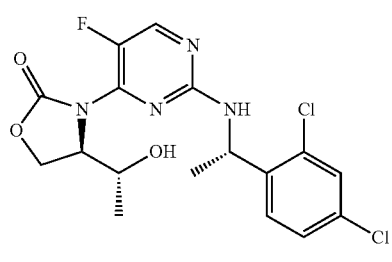
286
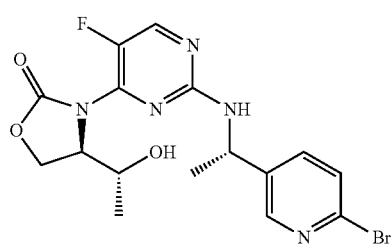 [SMILES: C[C@H](Nc1ncc(F)c(N2C(=O)OC[C@@H]2[C@@H](C)O)n1)c1ccc(Br)nc1]
287
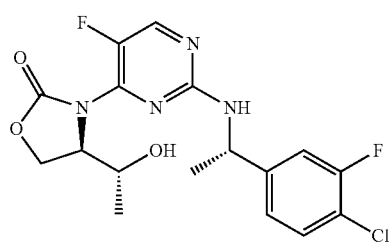
288
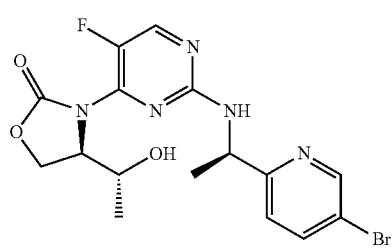 [SMILES: C[C@@H](Nc1ncc(F)c(N2C(=O)OC[C@@H]2[C@@H](C)O)n1)c1ccc(Br)cn1]
289
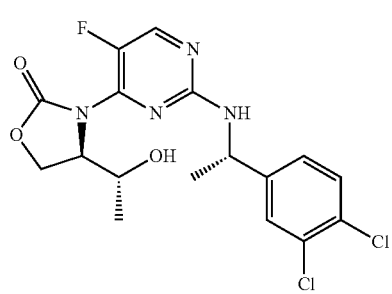
290
TABLE 30a-continued
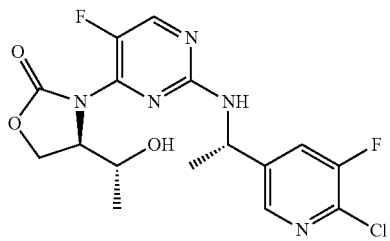 [SMILES: C[C@H](Nc1ncc(F)c(N2C(=O)OC[C@@H]2[C@@H](C)O)n1)c1cnc(Cl)c(F)c1]
291
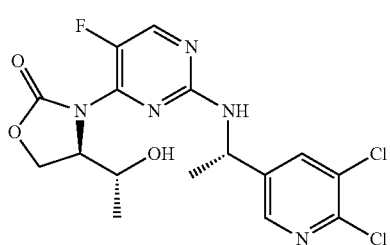 [SMILES: C[C@H](Nc1ncc(F)c(N2C(=O)OC[C@@H]2[C@@H](C)O)n1)c1cnc(Cl)c(Cl)c1]
292
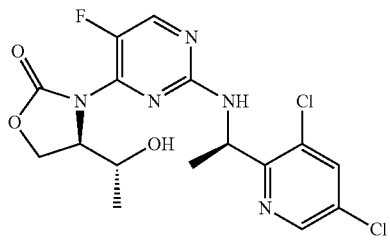 [SMILES: C[C@@H](Nc1ncc(F)c(N2C(=O)OC[C@@H]2[C@@H](C)O)n1)c1ncc(Cl)cc1Cl]
293
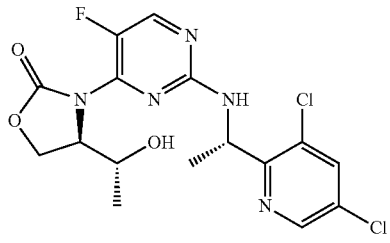 [SMILES: C[C@H](Nc1ncc(F)c(N2C(=O)OC[C@@H]2[C@@H](C)O)n1)c1ncc(Cl)cc1Cl]
294
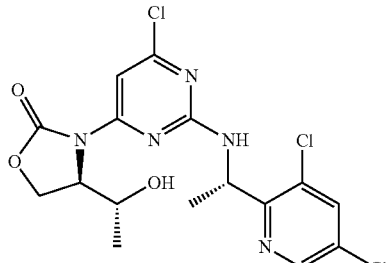
295
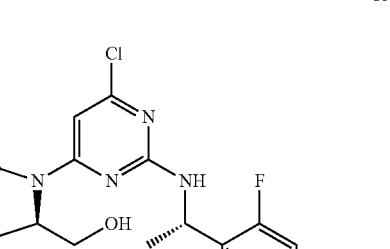
296

TABLE 30a-continued
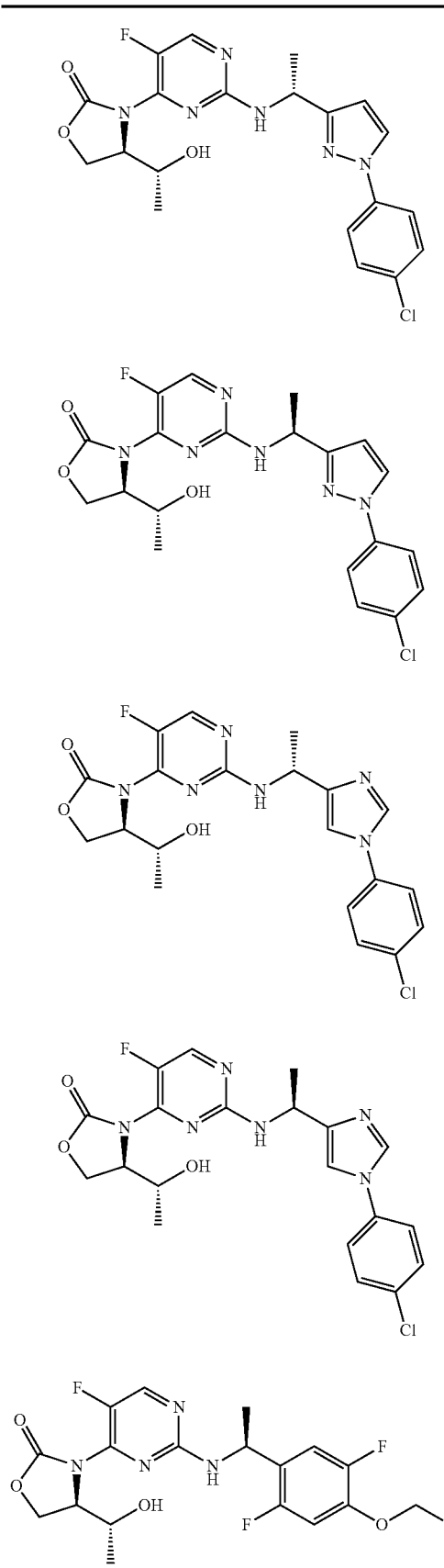
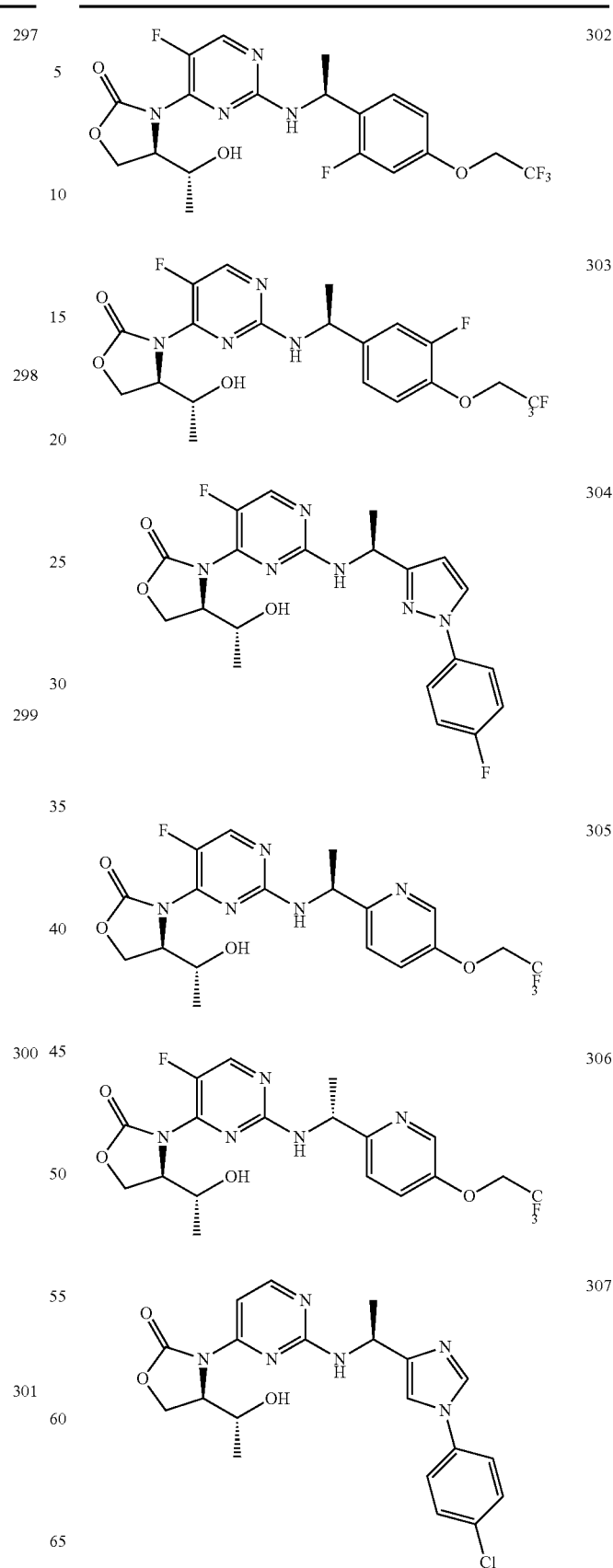

TABLE 30a-continued
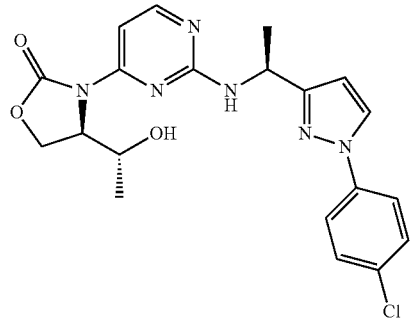 [SMILES: C[C@H](Nc1nccc(N2C(=O)OC[C@@H]2[C@@H](C)O)n1)c1ccn(-c2ccc(Cl)cc2)n1] 308
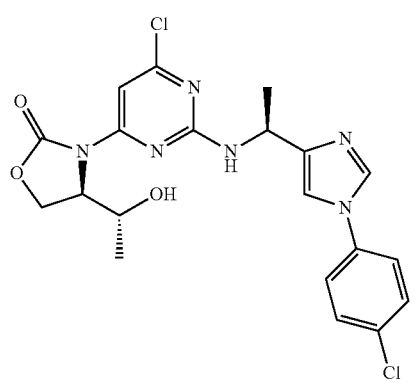 [SMILES: C[C@H](Nc1nc(Cl)cc(N2C(=O)OC[C@@H]2[C@@H](C)O)n1)c1cn(-c2ccc(Cl)cc2)cn1] 309
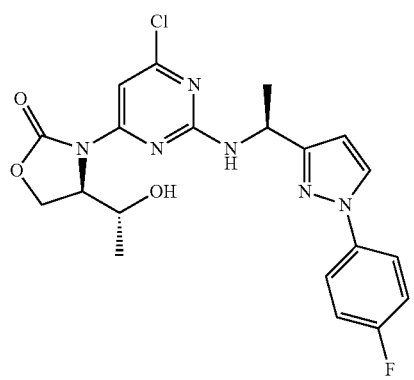 310
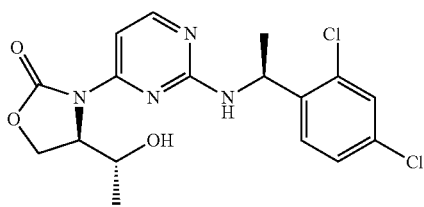 [SMILES: C[C@H](Nc1nccc(N2C(=O)OC[C@@H]2[C@@H](C)O)n1)c1ccc(Cl)cc1Cl] 311
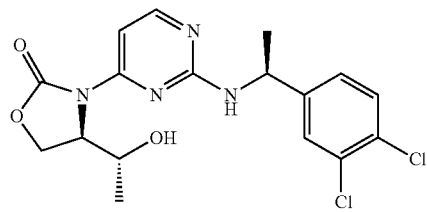 [SMILES: C[C@H](Nc1nccc(N2C(=O)OC[C@@H]2[C@@H](C)O)n1)c1ccc(Cl)c(Cl)c1] 312
TABLE 30a-continued
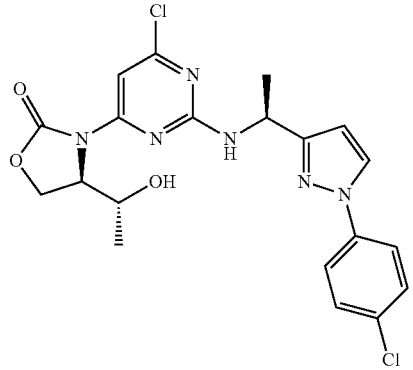 [SMILES: C[C@H](Nc1nc(Cl)cc(N2C(=O)OC[C@@H]2[C@@H](C)O)n1)c1ccn(-c2ccc(Cl)cc2)n1] 313
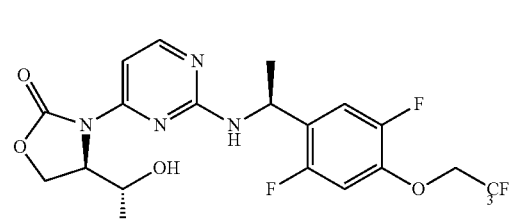 314
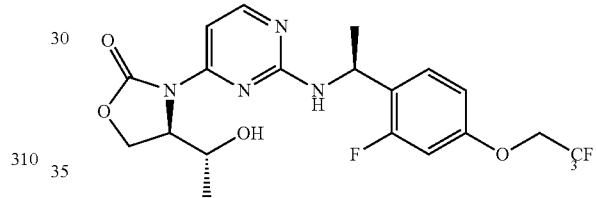 315
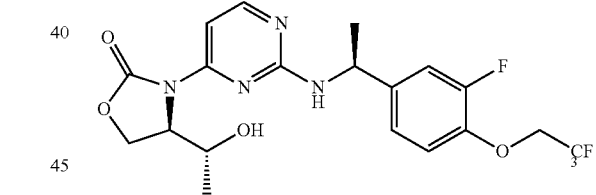 316
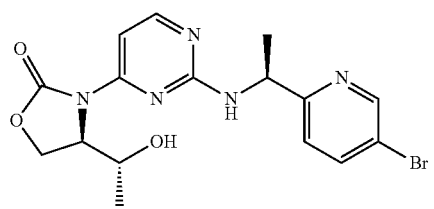 [SMILES: C[C@H](Nc1nccc(N2C(=O)OC[C@@H]2[C@@H](C)O)n1)c1ccc(Br)cn1] 317
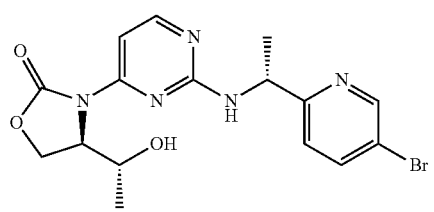 [SMILES: C[C@@H](Nc1nccc(N2C(=O)OC[C@@H]2[C@@H](C)O)n1)c1ccc(Br)cn1] 318

TABLE 30a-continued
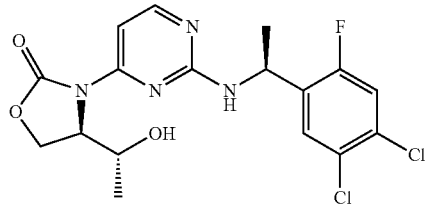 [SMILES: C[C@H](Nc1nccc(N2C(=O)OC[C@@H]2[C@@H](C)O)n1)c1cc(Cl)c(Cl)cc1F] 319
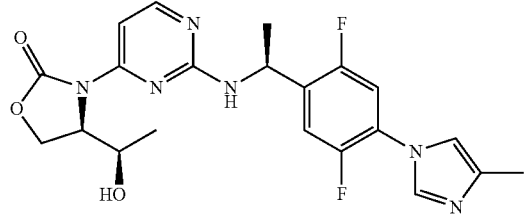 [SMILES: Cc1cn(-c2cc(F)c([C@H](C)Nc3nccc(N4C(=O)OC[C@@H]4[C@@H](C)O)n3)cc2F)cn1] 320
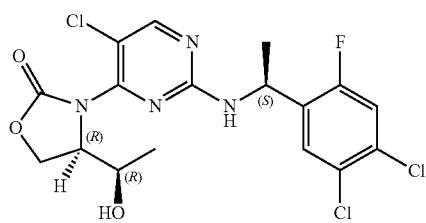 321
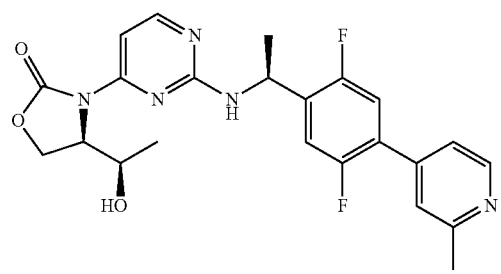 [SMILES: Cc1cc(-c2cc(F)c([C@H](C)Nc3nccc(N4C(=O)OC[C@@H]4[C@@H](C)O)n3)cc2F)ccn1] 322
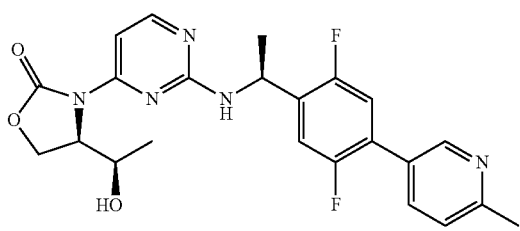 [SMILES: Cc1ccc(-c2cc(F)c([C@H](C)Nc3nccc(N4C(=O)OC[C@@H]4[C@@H](C)O)n3)cc2F)cn1] 323
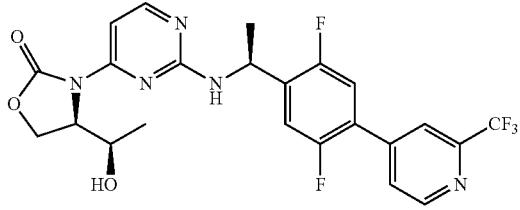 [SMILES: C[C@H](Nc1nccc(N2C(=O)OC[C@@H]2[C@@H](C)O)n1)c1cc(F)c(-c2ccnc(C(F)(F)F)c2)cc1F] 324
TABLE 30a-continued
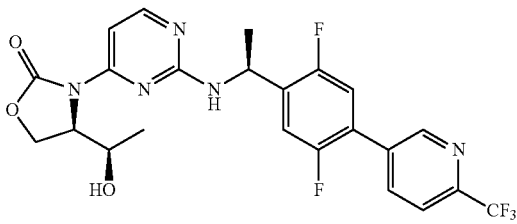 [SMILES: C[C@H](Nc1nccc(N2C(=O)OC[C@@H]2[C@@H](C)O)n1)c1cc(F)c(-c2ccc(C(F)(F)F)nc2)cc1F] 325
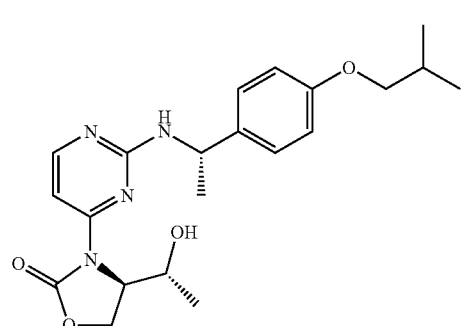 326
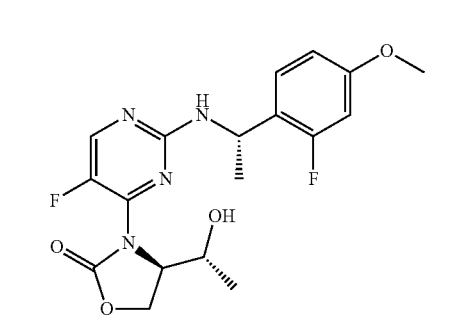 [SMILES: COc1ccc([C@H](C)Nc2ncc(F)c(N3C(=O)OC[C@@H]3[C@@H](C)O)n2)c(F)c1] 327
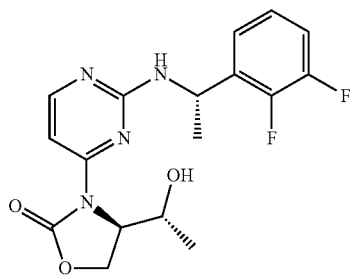 [SMILES: C[C@H](Nc1nccc(N2C(=O)OC[C@@H]2[C@@H](C)O)n1)c1cccc(F)c1F] 328
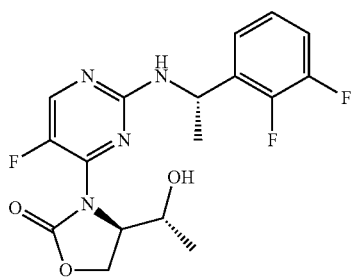 329

TABLE 30a-continued

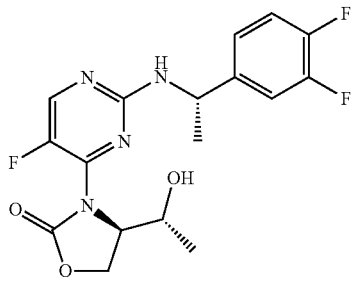 [SMILES: C[C@H](Nc1ncc(F)c(N2C(=O)OC[C@@H]2[C@@H](C)O)n1)c1ccc(F)c(F)c1]

330

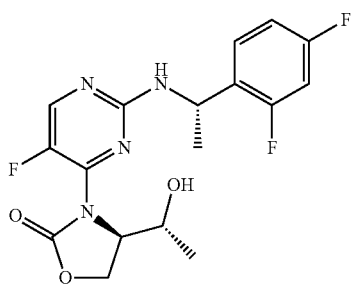 [SMILES: C[C@H](Nc1ncc(F)c(N2C(=O)OC[C@@H]2[C@@H](C)O)n1)c1ccc(F)cc1F]

331

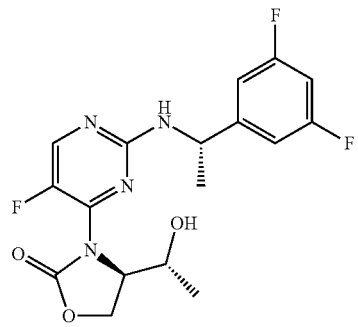 [SMILES: C[C@H](Nc1ncc(F)c(N2C(=O)OC[C@@H]2[C@@H](C)O)n1)c1cc(F)cc(F)c1]

332

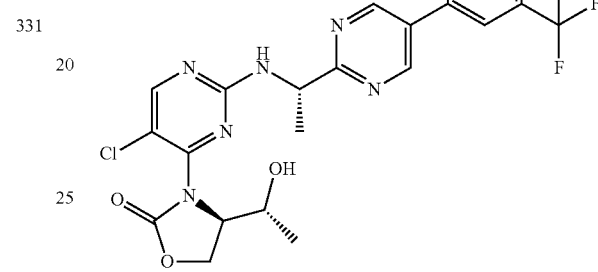

333

TABLE 30b

Chemical name, NMR chemical shifts and LCMS signal for each compound listed in Table 30a.

| Example: Name | $^1$H NMR (400 MHz, CDCl$_3$) δ ppm | LCMS |
|---|---|---|
| 208: (R)-3-(6-chloro-2-((S)-1-(2-fluoro-4-(trifluoromethyl)phenyl)ethyl-amino)pyrimidin-4-yl)-4-((R)-1-hydroxyethyl)oxazolidin-2-one | 7.59 (s, 1H), 7.52-7.48 (m, 1H), 7.44-7.42 (m, 1H), 7.37 (d, J = 9.7 Hz, 1H), 5.31 (br m, 1H), 4.68-4.66 (m, 1H), 4.49-4.46 (m, 1H), 4.38-4.34 (m, 1H), 3.43 (br m, 1H), 1.59 (d, J = 7.0 Hz, 3H), 0.83 (br m, 3H) | HRMS m/z 449.1009 (M + H)$^+$; Rt-2.39 min |
| 209: (R)-3-(6-chloro-2-((S)-1-(2-fluoro-4-(1-methyl-1H-pyrazol-4-yl)phenyl)ethylamino)pyrimidin-4-yl)-4-((R)-1-hydroxyethyl)oxazolidin-2-one | 7.77 (s, 1H), 7.61 (s, 1H), 7.55 (s, 1H), 7.36-7.30 (m, 1H), 7.25-7.21 (m, 1H), 7.17 (dd, J = 11.4, 1.5 Hz, 1H), 5.26 (br m, 1H), 4.70 (ddd, J = 8.1, 5.2, 2.5 Hz, 1H), 4.45 (dd, J = 9.4, 2.5 Hz, 1H), 4.39-4.31 (m, 1H), 3.98 (s, 3H), 3.67-3.55 (m, 1H), 1.57 (d, J = 6.9 Hz, 3H), 0.82 (br m, 3H) | HRMS m/z 461.1505 (M + H)$^+$; Rt-2.00 |
| 210: (R)-3-(2-((S)-1-(3-(4-chlorophenyl)-1,2,4-oxadiazol-5-yl)ethylamino)-6-(difluoromethyl)pyrimidin-4-yl)-4-((R)-1-hydroxyethyl)oxazolidin-2-one | 8.00 (d, J = 8.6 Hz, 2H), 7.91 (s, 1H), 7.48 (d, J = 8.6 Hz, 2H), 6.45 (t, J = 56 Hz, 1H), 4.84 (m, 1H), 4.83 (dt, J = 5.3, 2.5 Hz, 1H), 4.57 (d, J = 9.0 Hz, 1H), 4.46-4.37 (m, 1H), 3.69 (m, 1H), 1.83 (d, J = 7.0 Hz, 3H), 0.96 (br m, 3H) | HRMS m/z 481.1206 (M + H)$^+$; Rt-2.32 |
| 211: (R)-3-(2-((S)-1-(3-(4-chlorophenyl)-1,2,4-oxadiazol-5-yl)ethylamino)-6-(trifluoromethyl)pyrimidin-4-yl)-4-((R)-1-hydroxyethyl)oxazolidin-2-one | 8.00 (d, J = 8.6 Hz, 2H), 7.93 (s, 1H), 7.48 (d, J = 8.6 Hz, 2H), 5.31 (br. s., 1 H), 4.90-4.80 (m, 1H), 4.57 (dd, J = 9.6, 1.8 Hz, 1H), 4.48-4.35 (m, 1H), 3.74 (br m, 1H), 1.81 (d, J = 7.1 Hz, 3H), 1.25-0.84 (br m, 3H) | HRMS m/z 499.1106 (M + H)$^+$; Rt-2.50 |
| 212: (R)-3-(6-chloro-2-(((S)-1-(2,5-difluoro-4-(1-methyl-1H-pyrazol-4-yl)phenyl)ethyl)amino)pyrimidin-4-yl)-4-((R)-1-hydroxyethyl)oxazolidin-2-one | 7.90 (s, 1H), 7.80 (s, 1H), 7.59 (br s, 1H), 7.25-7.21 (m, 1H), 7.12 (dd, J = 11.0, 6.3 Hz, 1H), 5.25 (br m, 1H), 4.72 (m, 1H), 4.49 (d, J = 9.4 Hz, 1H), 4.43-4.33 (m, 1H), 4.02 (s, 3H), 3.72 (br m, 1H), 1.58 (d, J = 7.0 Hz, 3H), 0.88 (br s, 3H) | HRMS m/z 479.1415 (M + H)$^+$; Rt-2.04 |

TABLE 30b-continued

Chemical name, NMR chemical shifts and LCMS
signal for each compound listed in Table 30a.

| Example: Name | $^1$H NMR (400 MHz, CDCl$_3$) δ ppm | LCMS |
|---|---|---|
| 213: (R)-3-(6-chloro-2-(((S)-1-(5-(4-chlorophenyl)isoxazol-3-yl)ethyl)amino)pyrimidin-4-yl)-4-((R)-1-hydroxyethyl)oxazolidin-2-one | 7.70 (d, J = 8.6 Hz, 2H), 7.60 (s, 1H), 7.46 (d, J = 8.6 Hz, 2H), 6.54 (s, 1H), 5.23 (m, 1H), 4.87 (m, 1H), 4.58 (d, J = 9.5 Hz, 1H), 4.47-4.39 (m, 1H), 3.89 (m, 1H), 1.67 (d, J = 7.1 Hz, 3H), 1.05 (d, J = 5.7 Hz, 3H) | HRMS m/z 464.0894 (M + H)$^+$; Rt-2.38 |
| 214: (R)-3-(6-chloro-2-(((S)-1-(5-phenylisoxazol-3-yl)ethyl)amino)pyrimidin-4-yl)-4-((R)-1-hydroxyethyl)oxazolidin-2-one | 7.78-7.73 (m, 2H), 7.59 (s, 1H), 7.50-7.44 (m, 3H), 6.54 (s, 1H), 5.23 (m, 1H), 4.87 (m, 1H), 4.58 (d, J = 9.5 Hz, 1H), 4.42 (d, J = 9.3, 8.4 Hz, 1H), 3.89 (m, 1H), 1.67 (d, J = 7.1 Hz, 3H), 1.05 (d, J = 5.7 Hz, 3H) | HRMS m/z 430.1278 (M + H)$^+$; Rt-2.19 |
| 215: (R)-3-(6-fluoro-2-(((S)-1-(1-(4-fluorophenyl)-1H-pyrazol-4-yl)ethyl)amino)pyrimidin-4-yl)-4-((R)-1-hydroxyethyl)oxazolidin-2-one | 7.80 (s, 1H), 7.73 (s, 1H), 7.63-7.55 (m, 2H), 7.19-7.10 (m, 3H), 5.04 (m, 1H), 4.72 (m, 1H), 4.47 (m, 1H), 4.43-4.34 (m, 1H), 3.73 (m, 1H), 1.62 (d, J = 6.9 Hz, 3H), 0.97 (br m, 3H) | HRMS m/z 431.1644 (M + H)$^+$; Rt-2.06 |
| 216: (R)-3-(6-chloro-2-(((S)-1-(2-(4-chlorophenyl)thiazol-5-yl)ethyl)amino)pyrimidin-4-yl)-4-((R)-1-hydroxyethyl)oxazolidin-2-one | 7.95 (s, 1H), 7.80 (d, J = 8.7 Hz, 2H), 7.65 (s, 1H), 7.48 (d, J = 8.7 Hz, 2H), 5.35 (m, 1H), 4.80 (m, 1H), 4.59 (d, J = 8.5 Hz, 1H), 4.40 (m, 1H), 3.72 (m, 1H), 1.74 (d, J = 6.9 Hz, 3H), 0.97 (br s, 3H) | HRMS m/z 480.0666 (M + H)$^+$; Rt-2.46 |
| 217: (R)-3-(2-(((S)-1-(2-(4-chlorophenyl)thiazol-5-yl)ethyl)amino)-5-fluoropyrimidin-4-yl)-4-((R)-1-hydroxyethyl)oxazolidin-2-one | 8.14 (d, J = 3.4 Hz, 1H), 7.93 (s, 1H), 7.79 (d, J = 8.8 Hz, 2H), 7.46 (d, J = 8.8 Hz, 2H), 5.33 (m, 1H), 4.71 (m, 1H), 4.58 (t, J = 9.0 Hz, 1H), 4.48 (dd, J = 9.3, 5.3 Hz, 1H), 3.72 (m, 1H), 1.79 (d, J = 7.0 Hz, 3H), 1.02 (d, J = 6.2 Hz, 3H) | HRMS m/z 464.0964 (M + H)$^+$; Rt-2.08 |
| 218: (R)-3-(2-(((S)-1-(5-(4-chlorophenyl)isoxazol-3-yl)ethyl)amino)-5-fluoropyrimidin-4-yl)-4-((R)-1-hydroxyethyl)oxazolidin-2-one | 8.07 (d, J = 3.8 Hz, 1H), 7.69 (d, J = 8.8 Hz, 2H), 7.46 (d, J = 8.8 Hz, 2H), 6.62 (s, 1H), 5.31 (m, 1H), 4.95 (m, 1H), 4.62 (t, J = 9.0 Hz, 1H), 4.43 (dd, J = 9.3, 5.4 Hz, 1H), 3.98-3.88 (m, 1H), 1.73 (d, J = 7.1 Hz, 3H), 1.18 (d, J = 6.5 Hz, 3H) | HRMS m/z 448.1186 (M + H)$^+$; Rt-2.03 |
| 219: (R)-3-(6-chloro-2-(((S)-1-(5-(4-chlorophenyl)-1,3,4-thiadiazol-2-yl)ethyl)amino)pyrimidin-4-yl)-4-((R)-1-hydroxyethyl)oxazolidin-2-one | 7.85 (d, J = 8.4 Hz, 2H), 7.65 (s, 1H), 7.48 (d, J = 8.4 Hz, 2H), 5.44 (m, 1H), 4.86 (m, 1H), 4.59 (d, J = 9.5 Hz, 1H), 4.40 (t, J = 8.9 Hz, 1H), 3.33 (m, 1H), 1.80 (d, J = 7.0 Hz, 3H), 0.91 (br s, 3H) | HRMS m/z 481.0618 (M + H)$^+$; Rt-2.25 |
| 220: (R)-3-(6-chloro-2-(((S)-1-(1-(4-chlorophenyl)-1H-pyrazol-4-yl)ethyl)amino)pyrimidin-4-yl)-4-((R)-1-hydroxyethyl)oxazolidin-2-one | 7.86 (s, 1H), 7.79 (s, 1H), 7.60 (s, 1H), 7.56 (d, J = 9.0 Hz, 2H), 7.44 (d, J = 9.0 Hz, 2H), 5.03 (m, 1H), 4.76 (m, 1H), 4.51 (m, 1H), 4.45-4.33 (m, 1H), 3.75 (m, 1H), 1.63 (d, J = 6.9 Hz, 3H), 0.96 (br m, 3H) | HRMS m/z 463.1055 (M + H)$^+$; Rt-2.31 |
| 221: (R)-3-(2-(((S)-1-(1-(4-chlorophenyl)-1H-pyrazol-4-yl)ethyl)amino)-5-fluoropyrimidin-4-yl)-4-((R)-1-hydroxyethyl)oxazolidin-2-one | 8.24 (d, J = 2.7 Hz, 1H), 7.85 (s, 1H), 7.70 (s, 1H), 7.59 (d, J = 8.9 Hz, 2H), 7.41 (d, J = 8.9 Hz, 2H), 5.34 (m, 1H), 5.04 (m, 1H), 4.57-4.48 (m, 2H), 4.43-4.34 (m, 1H), 3.84 (m, 1H), 1.61 (d, J = 6.9 Hz, 3H), 1.08 (d, J = 6.2 Hz, 3H) | HRMS m/z 447.1350 (M + H)$^+$; Rt-1.98 |
| 222: (R)-3-(2-(((S)-1-(5-(4-chlorophenyl)isoxazol-3-yl)ethyl)amino)-6-(fluoromethyl)pyrimidin-4-yl)-4-((R)-1-hydroxyethyl)oxazolidin-2-one | 7.82 (s, 1H), 7.71 (d, J = 8.5 Hz, 2H), 7.46 (d, J = 8.5 Hz, 2H), 6.65 (s, 1H), 5.46 (s, 1H), 5.36-5.29 (m, 2H), 4.96 (m, 1H), 4.62 (d, J = 9.0 Hz, 1H), 4.53-4.45 (m, 1H), 3.99 (m, 1H), 1.73 (d, J = 7.2 Hz, 3H), 1.13 (d, J = 6.6 Hz, 3H) | HRMS m/z 462.1347 (M + H)$^+$; Rt-2.22 |

TABLE 30b-continued

Chemical name, NMR chemical shifts and LCMS signal for each compound listed in Table 30a.

| Example: Name | $^1$H NMR (400 MHz, CDCl$_3$) δ ppm | LCMS |
|---|---|---|
| 223: (R)-3-(2-(((S)-1-(2-(4-chlorophenyl)thiazol-5-yl)ethyl)amino)-6-(fluoromethyl)pyrimidin-4-yl)-4-((R)-1-hydroxyethyl)oxazolidin-2-one | 7.88 (s, 1H), 7.87 (s, 1H), 7.80 (d, J = 8.6 Hz, 2H), 7.46 (d, J = 8.6 Hz, 2H), 5.47 (s, 1H), 5.38-5.30 (m, 2H), 4.86 (ddd, J = 8.1, 4.3, 2.2 Hz, 1H), 4.69-4.62 (m, 1H), 4.45 (dd, J = 9.5, 8.2 Hz, 1H), 3.61 (m, 1H), 1.80 (d, J = 7.0 Hz, 3H), 0.95 (d, J = 6.4 Hz, 3H) | HRMS m/z 478.1116 (M + H)$^+$; Rt-2.28 |
| 224: (R)-3-(2-(((S)-1-(2-(4-chlorophenyl)thiazol-5-yl)ethyl)amino)pyrimidin-4-yl)-4-((R)-1-hydroxyethyl)oxazolidin-2-one | 7.99 (d, J = 7.1 Hz, 1H), 7.93 (s, 1H), 7.85-7.78 (m, 3H), 7.47 (d, J = 8.7 Hz, 2H), 5.43-5.34 (m, 1H), 4.89 (ddd, J = 8.1, 4.1, 2.2 Hz, 1H), 4.69 (dd, J = 9.4, 8.2 Hz, 1H), 3.69 (dd, J = 6.3, 4.4 Hz, 1H), 1.83 (d, J = 7.0 Hz, 3H), 0.97 (d, J = 6.5 Hz, 3H) | HRMS m/z 446.1065 (M + H)$^+$; Rt-1.90 |
| 225: (R)-3-(2-(((S)-1-(1-(4-chlorophenyl)-1H-pyrazol-4-yl)ethyl)amino)pyrimidin-4-yl)-4-((R)-1-hydroxyethyl)oxazolidin-2-one | 10.64 (d, J = 5.9 Hz, 1H), 7.98 (s, 1H), 7.95 (d, J = 7.1 Hz, 1H), 7.78-7.74 (m, 2H), 7.59 (d, J = 9.0 Hz, 2H), 7.43 (d, J = 9.0 Hz, 2H), 5.06 (quin, J = 6.7 Hz, 1H), 4.84 (ddd, J = 8.2, 4.4, 2.3 Hz, 1H), 4.62 (dd, J = 9.6 2.3 Hz, 1H), 4.45 (dd, J = 9.5, 8.2 Hz, 1H), 3.80-3.69 (m, 1H), 1.70 (d, J = 7.0 Hz, 3H), 0.96 (d, J = 6.5 Hz, 3H) | HRMS m/z 429.1441 (M + H)$^+$; Rt-1.62 |
| 226: (R)-3-(6-chloro-2-(((S)-1-(3-(4-chlorophenyl)isoxazol-5-yl)ethyl)amino)pyrimidin-4-yl)-4-((R)-1-hydroxyethyl)oxazolidin-2-one | 7.70 (d, J = 8.6 Hz, 2H), 7.65 (s, 1H), 7.45 (d, J = 8.6 Hz, 2H), 6.50 (s, 1H), 5.09 (m, 1H), 4.87 (m, 1H), 4.59 (d, J = 9.1 Hz, 1H), 4.46-4.37 (m, 1H), 3.49 (m, 1H), 1.72 (d, J = 7.1 Hz, 3H), 0.89 (br s, 3H) | HRMS m/z 464.0898 (M + H)$^+$; Rt-2.37 |
| 227: (R)-3-(2-(((S)-1-(3-(4-chlorophenyl)isoxazol-5-yl)ethyl)amino)-5-fluoropyrimidin-4-yl)-4-((R)-1-hydroxyethyl)oxazolidin-2-one | 8.13 (d, J = 3.5 Hz, 1H), 7.69 (d, J = 8.5 Hz, 2H), 7.44 (d, J = 8.5 Hz, 2H), 6.52 (s, 1H), 5.17 (m, 1H), 4.94 (m, 1H), 4.64-4.57 (m, 1H), 4.52 (dd, J = 9.4, 5.4 Hz, 1H), 3.66 (m, 1H), 1.76 (d, J = 7.1 Hz, 3H), 1.04 (d, J = 6.4 Hz, 3H) | HRMS m/z 448.1190 (M + H)$^+$; Rt-2.07 |
| 228: (R)-3-(2-(((S)-1-(1-(4-chlorophenyl)-1H-pyrazol-4-yl)ethyl)amino)-6-fluoropyrimidin-4-yl)-4-((R)-1-hydroxyethyl)oxazolidin-2-one | 7.84 (br s, 1H), 7.76 (s, 1H), 7.57 (d, J = 8.9 Hz, 2H), 7.44 (d, J = 9.0 Hz, 2H), 7.13 (s, 1H), 5.05 (m, 1H), 4.72 (m, 1H), 4.47 (m, 1H), 4.43-4.35 (m, 1H), 1.62 (d, J = 6.9 Hz, 3H), 0.96 (br m, 3H) | HRMS m/z 447.1347 (M + H)$^+$; Rt-2.23 |
| 229: (R)-3-(6-chloro-2-(((S)-1-(5-(4-fluorophenyl)isoxazol-3-yl)ethyl)amino)pyrimidin-4-yl)-4-((R)-1-hydroxyethyl)oxazolidin-2-one | 7.82-7.69 (m, 2H), 7.62 (s, 1H), 7.17 (t, J = 8.6 Hz, 2H), 6.51 (s, 1H), 5.23 (d, J = 5.8 Hz, 1H), 4.89 (m, 1H), 4.59 (m, 1H), 4.47-4.40 (m, 1H), 3.91 (m, 1H), 1.68 (d, J = 7.1 Hz, 3H), 1.07 (d, J = 6.3 Hz, 3H) | HRMS m/z 448.1192 (M + H)$^+$; Rt-2.23 |
| 230: (R)-3-(6-chloro-2-(((S)-1-(5-(morpholinomethyl)isoxazol-3-yl)ethyl)amino)pyrimidin-4-yl)-4-((R)-1-hydroxyethyl)oxazolidin-2-one | 7.59 (s, 1H), 6.57 (s, 1H), 5.23 (m, 1H), 4.82 (m, 1H), 4.56 (m, 1H), 4.43-4.34 (m, 2H), 4.20 (m, 1H), 3.97 (m, 4H), 3.24 (m, 4H), 1.61 (d, J = 7.2 Hz, 3H), 1.04 (br s, 3H) | HRMS m/z 453.1662 (M + H)$^+$; Rt-1.26 |
| 231: (R)-3-(6-chloro-2-(((R)-1-(5-(morpholinomethyl)isoxazol-3-yl)ethyl)amino)pyrimidin-4-yl)-4-((R)-1-hydroxyethyl)oxazolidin-2-one | 7.55 (s, 1H), 6.55 (s, 1H), 5.87 (m, 1H), 5.05 (m, 1H), 4.65 (m, 1H), 4.56 (m, 1H), 4.34-4.31 (m, 2H), 4.20 (m, 1H), 3.97-3.95 (m, 4H), 3.18 (m, 4H), 1.62 (d, J = 7.0 Hz, 3H), 1.18 (d, J = 6.5 Hz, 3H) | HRMS m/z 453.1651 (M + H)$^+$; Rt-1.27 |
| 232: (R)-3-(2-(((S)-1-(1-(4-chlorophenyl)-1H-pyrazol-4-yl)ethyl)amino)-6-methylpyrimidin-4-yl)-4-((R)-1-hydroxyethyl)oxazolidin-2-one | 10.78 (d, J = 5.8 Hz, 1H), 7.98 (s, 1H), 7.73 (s, 1H), 7.59 (d, J = 8.7 Hz, 2H), 7.56 (s, 1H), 7.43 (d, J = 8.7 Hz, 2H), 5.00 (m, 1H), 4.89-4.74 (m, 1H), 4.60 (dd, J = 9.6, 2.2 Hz, 1H), 4.52-4.35 (m, 1H), 3.69 (dd, J = 6.5, 4.6 Hz, 1H), 2.52 (s, 3H), 1.69 (d, J = 7.0 Hz, 3H), 0.94 (d, J = 6.5 Hz, 3H) | HRMS m/z 443.1596 (M + H)$^+$; Rt-1.62 |

TABLE 30b-continued

Chemical name, NMR chemical shifts and LCMS signal for each compound listed in Table 30a.

| Example: Name | ¹H NMR (400 MHz, CDCl₃) δ ppm | LCMS |
|---|---|---|
| 233: (R)-3-(6-chloro-2-(((S)-1-(2-(pyridin-2-yl)thiazol-5-yl)ethyl)amino)pyrimidin-4-yl)-4-((R)-1-hydroxyethyl)oxazolidin-2-one | 8.63 (m, 1H), 8.14 (s, 1H), 7.95-7.89 (m, 2H), 7.61 (s, 1H), 7.42 (m, 1H), 5.28 (m, 1H), 4.52 (m, 1H), 4.47-4.35 (m, 3H), 1.77 (m, 3H), 0.96 (br s, 3H) | HRMS m/z 447.1011 (M + H)⁺; Rt-1.99 |
| 234: (R)-3-(6-chloro-2-(((S)-1-(2-(pyridin-3-yl)thiazol-5-yl)ethyl)amino)pyrimidin-4-yl)-4-((R)-1-hydroxyethyl)oxazolidin-2-one | 9.30 (m, 1H), 8.70 (m, 1H), 8.54 (m, 1H), 7.88 (s, 1H), 7.69 (m, 1H), 7.61 (s, 1H), 5.30 (m, 1H), 4.52 (m, 1H), 4.42-4.36 (m, 3H), 1.76 (d, J = 6.9 Hz, 3H), 1.03 (br s, 3H) | HRMS m/z 447.1011 (M + H)⁺; Rt-1.72 |
| 235: (R)-3-(6-chloro-2-(((S)-1-(2-(pyridin-4-yl)thiazol-5-yl)ethyl)amino)pyrimidin-4-yl)-4-((R)-1-hydroxyethyl)oxazolidin-2-one | 8.83 (m, 2H), 8.12 (m, 2H), 7.98 (s, 1H), 7.63 (s, 1H), 5.40 (m, 1H), 4.73 (m, 1H), 4.52 (m, 1H), 4.39 (m, 1H), 1.77 (m, 3H), 1.00 (br s, 3H) | HRMS m/z 447.1006 (M + H)⁺; Rt-1.52 |
| 236: (R)-3-(2-(((S)-1-(5-(4-chlorophenyl)isoxazol-3-yl)ethyl)amino)-6-methylpyrimidin-4-yl)-4-((R)-1-hydroxyethyl)oxazolidin-2-one | 11.03 (d, J = 6.8 Hz, 1H), 7.71 (d, J = 8.7 Hz, 2H), 7.56 (s, 1H), 7.46 (d, J = 8.7 Hz, 2H), 6.70 (s, 1H), 5.32 (quin, J = 7.1 Hz, 1H), 4.95 (ddd, J = 7.9, 4.4, 1.9 Hz, 1H), 4.62 (dd, J = 9.5, 1.9 Hz, 1H), 4.53-4.43 (m, 1H), 4.06-3.94 (m, 1H), 2.51 (s, 3H), 1.74 (d, J = 7.2 Hz, 3H), 1.13 (d, J = 6.6 Hz, 3H) | HRMS m/z 444.1443 (M + H)⁺; Rt-1.81 |
| 237: (R)-3-(2-(((S)-1-(2-(4-chlorophenyl)thiazol-5-yl)ethyl)amino)-6-methylpyrimidin-4-yl)-4-((R)-1-hydroxyethyl)oxazolidin-2-one | 11.12 (d, J = 5.4 Hz, 1H), 7.88 (s, 1H), 7.81 (d, J = 8.7 Hz, 2H), 7.62 (s, 1H), 7.45 (d, J = 8.7 Hz, 2H), 5.37-5.27 (m, 1H), 4.84 (ddd, J = 8.2, 4.2, 2.2 Hz, 1H), 4.65 (dd, J = 9.6, 2.2 Hz, 1H), 4.44 (dd, J = 9.4, 8.3 Hz, 1H), 3.61-3.52 (m, 1H), 2.52 (s, 3H), 1.81 (d, J = 7.0 Hz, 3H), 0.93 (d, J = 6.5 Hz, 3H) | HRMS m/z 460.1213 (M + H)⁺; Rt-1.88 |
| 238: (R)-3-(2-(((S)-1-(1-(4-chlorophenyl)-1H-imidazol-4-yl)ethyl)amino)-6-methylpyrimidin-4-yl)-4-((R)-1-hydroxyethyl)oxazolidin-2-one | 11.13 (d, J = 8.3 Hz, 1H), 8.43 (s, 1H), 7.91 (s, 1H), 7.67 (s, 1H), 7.60 (d, J = 8.8 Hz, 2H), 7.46 (d, J = 8.8 Hz, 2H), 5.97 (quin, J = 7.0 Hz, 1H), 4.98 (ddd, J = 8.1, 4.4, 2.4 Hz, 1H), 4.77 (dd, J = 9.6, 2.3 Hz, 1H), 4.53-4.46 (m, 1H), 4.44-4.36 (m, 1H), 2.55 (s, 3H), 1.70 (d, J = 6.8 Hz, 3H), 1.06 (d, J = 6.6 Hz, 3H) | HRMS m/z 443.1599 (M + H)⁺; Rt-1.35 |
| 239: (R)-3-(2-(((S)-1-(3-(4-chlorophenyl)-1,2,4-oxadiazol-5-yl)ethyl)amino)-6-methylpyrimidin-4-yl)-4-((R)-1-hydroxyethyl)oxazolidin-2-one | 11.42 (d, J = 5.0 Hz, 1H), 8.00 (d, J = 8.6 Hz, 2H), 7.64 (s, 1H), 7.48 (d, J = 8.6 Hz, 2H), 5.30-5.20 (m, 1H), 4.77 (ddd, J = 7.9, 4.5, 2.0 Hz, 1H), 4.57 (dd, J = 9.5, 1.9 Hz, 1H), 4.40 (dd, J = 9.4, 8.2 Hz, 1H), 3.65-3.55 (m, 1H), 2.56 (s, 3H), 1.90 (d, J = 7.2 Hz, 3H), 0.92 (d, J = 6.5 Hz, 3H) | HRMS m/z 445.1393 (M + H)⁺; Rt-1.96 |
| 240: (R)-3-(2-(((S)-1-(1-(4-chlorophenyl)-1H-pyrazol-3-yl)ethyl)amino)-6-methylpyrimidin-4-yl)-4-((R)-1-hydroxyethyl)oxazolidin-2-one | 10.80 (d, J = 7.3 Hz, 1H), 7.79 (d, J = 2.5 Hz, 1H), 7.54-7.48 (m, 3H), 7.46-7.41 (m, 2H), 6.58 (d, J = 2.5 Hz, 1H), 5.40-5.30 (m, 1H), 4.85 (ddd, J = 7.7, 5.1, 2.3 Hz, 1H), 4.50-4.38 (m, 2H), 4.02-3.93 (m, 1H), 2.50 (s, 3H), 1.71 (d, J = 7.1 Hz, 3H), 0.94 (d, J = 6.5 Hz, 3H) | HRMS m/z 443.1601 (M + H)⁺; Rt-1.66 |
| 241: (R)-3-(2-(((S)-1-(1-(4-chlorophenyl)-1H-1,2,3-triazol-4-yl)ethyl)amino)-6-methylpyrimidin-4-yl)-4-((R)-1-hydroxyethyl)oxazolidin-2-one | 11.00 (m, 1H), 8.15 (s, 1H), 7.69 (d, J = 8.5 Hz, 2H), 7.53 (s, 1H), 7.51 (d, J = 8.5 Hz, 2H), 5.51 (m, 1H), 4.70 (m, 1H), 4.58 (m, 1H), 4.51 (m, 1H), 3.96 (m, 1H), 2.50 (s, 3H), 1.78 (d, J = 6.5 Hz, 3H), 1.17 (d, J = 6.5 Hz, 3H) | HRMS m/z 444.1548 (M + H)⁺; Rt-1.54 |
| 242: (R)-3-(6-chloro-2-(((S)-1-(1-(4-chlorophenyl)-1H-1,2,3-triazol-4-yl)ethyl)amino)pyrimidin-4-yl)-4-((R)-1-hydroxyethyl)oxazolidin-2-one | 7.97 (s, 1H), 7.69 (m, 2H), 7.60 (s, 1H), 7.52 (d, J = 8.9 Hz, 2H), 5.41 (m, 1H), 4.97 (m, 1H), 4.54 (m, 1H), 4.43 (m, 1H), 3.77 (m, 1H), 1.71 (d, J = 7.0 Hz, 3H), 1.05 (br s, 3H) | HRMS m/z 464.1003 (M + H)⁺; Rt-2.15 |

TABLE 30b-continued

Chemical name, NMR chemical shifts and LCMS signal for each compound listed in Table 30a.

| Example: Name | $^1$H NMR (400 MHz, CDCl$_3$) δ ppm | LCMS |
|---|---|---|
| 243: (R)-3-(2-(((S)-1-(1-(4-chlorophenyl)-1H-1,2,3-triazol-4-yl)ethyl)amino)pyrimidin-4-yl)-4-((R)-1-hydroxyethyl)oxazolidin-2-one | 10.91 (d, J = 7.3 Hz, 1H), 8.15 (s, 1H), 7.89 (d, J = 7.0 Hz, 1H), 7.75 (d, J = 7.0 Hz, 1H), 7.70 (d, J = 8.5 Hz, 2H), 7.52 (d, J = 8.5 Hz, 2H), 5.53 (quin, J = 6.9 Hz, 1H), 5.04 (m, 1H), 4.60-4.50 (m, 2H), 3.99 (m, 1H), 1.79 (d, J = 7.2 Hz, 3H), 1.19 (d, J = 6.5 Hz, 3H) | HRMS m/z 430.1398 (M + H)$^+$; Rt-1.56 |
| 244: (R)-3-(2-(((S)-1-(4-(1,1-difluoroethyl)-2-fluorophenyl)ethyl)amino)-6-methylpyrimidin-4-yl)-4-((R)-1-hydroxyethyl)oxazolidin-2-one | 11.05 (d, J = 5.9 Hz, 1H), 7.56 (s, 1H), 7.52 (t, J = 7.8 Hz, 1H), 7.31 (d, J = 8.7 Hz, 1H), 7.24 (s, 1H), 5.37 (quin, J = 6.7 Hz, 1H), 4.75 (m, 1H), 4.56 (dd, J = 9.6, 2.3 Hz, 1H), 4.40 (m, 1H), 3.47 (m, 1H), 2.53 (s, 3H), 1.92 (t, J = 18.2, Hz, 3H), 1.66 (d, J = 7.0 Hz, 3H), 0.84 (d, J = 6.5 Hz, 3H) | HRMS m/z 425.1803 (M + H)$^+$; Rt-1.68 |
| 245: (R)-3-(2-(((S)-1-(2,5-difluoro-4-(2,2,2-trifluoroethoxy)phenyl)ethyl)amino)-6-methylpyrimidin-4-yl)-4-((R)-1-hydroxyethyl)oxazolidin-2-one | 11.1 (d, J = 6.6 Hz, 1H), 7.58 (s, 1H), 7.25 (m, 1H), 6.83 (dd, J = 10.5, 6.6 Hz, 1H), 5.33 (quin, J = 6.9 Hz, 1H), 4.83 (ddd, J = 8.1, 4.7, 2.3 Hz, 1H), 4.59 (dd, J = 9.6, 2.3 Hz, 1H), 4.48-4.37 (m, 3H), 3.83 (m, 1H), 2.53 (s, 3H), 1.61 (d, J = 7.0 Hz, 3H), 0.96 (d, J = 6.5 Hz, 3H) | HRMS m/z 477.1574 (M + H)$^+$; Rt-1.78 |
| 246: (R)-4-((R)-1-hydroxyethyl)-3-(6-methyl-2-(((S)-1-(2-(6-methylpyridin-3-yl)thiazol-5-yl)ethyl)amino)pyrimidin-4-yl)oxazolidin-2-one | 11.16 (d, J = 6.9 Hz, 1H), 9.54 (d, J = 1.9 Hz, 1H), 8.76 (dd, J = 8.3, 2.1 Hz, 1H), 8.00 (s, 1H), 7.67 (d, J = 8.4 Hz, 1H), 7.63 (s, 1H), 5.43 (quin, J = 6.9 Hz, 1H), 5.06 (ddd, J = 7.9, 4.2, 1.8 Hz, 1H), 4.74 (dd, J = 9.6, 1.9 Hz, 1H), 4.14 (m, 1H), 2.86 (s, 3H), 2.52 (s, 3H), 1.87 (d, J = 7.1 Hz, 3H), 1.13 (d, J = 6.4 Hz, 3H) | HRMS m/z 441.1710 (M + H)$^+$; Rt-1.16 |
| 247: (R)-4-((R)-1-hydroxyethyl)-3-(2-(((S)-1-(2-(6-(trifluoromethyl)pyridin-3-yl)thiazol-5-yl)ethyl)amino)pyrimidin-4-yl)oxazolidin-2-one | 11.05 (br s, 1H), 9.21 (s, 1H), 8.34 (d, J = 8.8 Hz, 1H), 7.97 (d, J = 7.0 Hz, 1H), 7.92 (s, 1H), 7.82 (d, J = 7.0 Hz, 1H), 7.79 (d, J = 8.3 Hz, 1H), 5.35 (m, 1H), 4.85 (m, 1H), 4.64 (m, 1H), 4.46 (m, 1H), 3.58 (m, 1H), 1.85 (d, J = 6.9 Hz, 3H), 0.96 (d, J = 6.4 Hz, 3H) | HRMS m/z 481.1272 (M + H)$^+$; Rt-1.77 |
| 248: (R)-4-((R)-1-hydroxyethyl)-3-(2-(((S)-1-(2-(2-(trifluoromethyl)pyridin-4-yl)thiazol-5-yl)ethyl)amino)pyrimidin-4-yl)oxazolidin-2-one | 11.05 (br s, 1H), 8.84 (d, J = 5.1 Hz, 1H), 8.15 (s, 1H), 7.99 (d, J = 7.1 Hz, 1H), 7.95 (s, 1H), 7.92 (dd, J = 5.1, 1.3 Hz, 1H), 7.83 (d, J = 7.0 Hz, 1H), 5.36 (m, 1H), 4.85 (m, 1H), 4.65 (dd, J = 9.7, 2.0 Hz, 1H), 4.46 (m, 1H), 3.62 (m, 1H), 1.85 (d, J = 6.9 Hz, 3H), 0.97 (d, J = 6.5 Hz, 3H) | HRMS m/z 481.1268 (M + H)$^+$; Rt-1.72 |
| 249: methyl 2-(((S)-1-(2-(4-chlorophenyl)thiazol-5-yl)ethyl)amino)-6-((R)-4-((R)-1-hydroxyethyl)-2-oxooxazolidin-3-yl)pyrimidine-4-carboxylate | 8.27 (s, 1H), 7.96 (s, 1H), 7.80 (d, J = 8.6 Hz, 2H), 7.47 (d, J = 8.6 Hz, 2H), 5.41 (m, 1H), 4.66 (m, 1H), 4.45 (m, 1H), 4.01 (s, 3H), 3.75 (m, 1H), 1.78 (d, J = 6.9 Hz, 3H), 0.98 (d, J = 6.1 Hz, 3H) | HRMS m/z 504.1111 (M + H)$^+$; Rt-2.17 |
| 250: (R)-3-(2-(((S)-1-(1-(4-chlorophenyl)-2-methyl-1H-imidazol-4-yl)ethyl)amino)pyrimidin-4-yl)-4-((R)-1-hydroxyethyl)oxazolidin-2-one | 11.00 (d, J = 8.5 Hz, 1H), 7.95 (m, 1H), 7.87 (m, 1H), 7.61 (m, 2H), 7.43 (d, J = 1.8 Hz, 1H), 7.35 (m, 2H), 5.95 (m, 1H), 5.02 (m, 1H), 4.80 (dd, J = 9.6, 2.4 Hz, 1H), 4.50 (m, 1H), 4.40 (m, 1H), 2.60 (m, 3H), 1.70 (m, 3H), 1.07 (m, 3H) | LCMS m/z 443.2 (M + H)$^+$; Rt-0.60 |
| 251: (R)-3-(2-(((S)-1-(2-(4-(difluoromethyl)phenyl)thiazol-5-yl)ethyl)amino)pyrimidin-4-yl)-4-((R)-1-hydroxyethyl)oxazolidin-2-one | 10.92 (br s, 1H), 7.95 (m, 3H), 7.84 (s, 1H), 7.80 (d, J = 7.0 Hz, 1H), 7.60 (d, J = 8.2 Hz, 2H), 6.69 (t, J = 56 Hz, 1H), 5.27 (m, 1H), 4.81 (ddd, J = 8.2, 4.3, 2.1 Hz, 1H), 4.64 (dd, J = 9.6, 2.1 Hz, 1H), 4.45 (m, 1H), 3.39 (br m, 1H), 1.84 (d, J = 7.0 Hz, 3H), 0.89 (d, J = 6.5 Hz, 3H) | LCMS m/z 462.2 (M + H)$^+$; Rt-0.70 |
| 252: (R)-3-(2-((S)-1-(2-fluoro-4-(trifluoromethyl)phenyl)ethylamino)pyrimidin-4-yl)-4-((R)-1-hydroxyethyl)oxazolidin-2-one | (CD$_3$OD) 0.77 (br. s., 3 H) 1.64 (d, J = 6.99 Hz, 3 H) 4.40-4.47 (m, 1 H) 4.57 (dd, J = 9.22, 2.52 Hz, 1 H) 5.43-5.51 (m, 1 H) 7.50 (d, J = 9.15 Hz, 2 H) 7.62 (t, J = 7.73 Hz, 1 H) 7.67 (d, J = 6.85 Hz, 1 H) 8.15 (d, J = 6.80 Hz, 1 H) | HRMS (B) m/z 415.1402 (M + H)$^+$; Rt-2.18 min |

TABLE 30b-continued

Chemical name, NMR chemical shifts and LCMS
signal for each compound listed in Table 30a.

| Example: Name | $^1$H NMR (400 MHz, CDCl$_3$) δ ppm | LCMS |
|---|---|---|
| 253: (R)-3-(2-((S)-1-(4-(1-ethoxycyclopropyl)-2-fluorophenyl)ethylamino)pyrimidin-4-yl)-4-((R)-1-hydroxyethyl)oxazolidin-2-one | (CD$_3$OD) 0.80 (br. s., 3 H) 0.95-1.00 (m, 2 H) 1.15 (t, J = 7.07 Hz, 3 H) 1.19-1.23 (m, 2 H) 1.61 (d, J = 6.99 Hz, 3 H) 3.44 (qd, J = 7.05, 1.34 Hz, 2 H) 4.41-4.49 (m, 1 H) 4.59 (dd, J = 9.19, 2.49 Hz, 1 H) 5.40 (br. s., 1 H) 7.06 (d, J = 2.15 Hz, 1 H) 7.09 (s, 1 H) 7.36 (t, J = 7.92 Hz, 1 H) 7.66 (d, J = 6.85 Hz, 1 H) 8.12 (d, J = 7.14 Hz, 1 H) | HRMS (B) m/z 431.2090 (M + H)$^+$; Rt-1.72 min |
| 254: 2-chloro-N-cyclopentyl-4-((S)-1-(4-((R)-4-((R)-1-hydroxyethyl)-2-oxooxazolidin-3-yl)pyrimidin-2-ylamino)ethyl)benzamide | (CD$_3$OD) 0.86 (br. s., 3 H) 1.57 (d, J = 6.99 Hz, 3 H) 1.59-1.69 (m, 3 H) 1.74 (d, J = 4.99 Hz, 2 H) 1.95-2.06 (m, 2 H) 2.66 (s, 1 H) 4.29 (d, J = 6.46 Hz, 1 H) 4.38-4.46 (m, 1 H) 4.57 (dd, J = 9.24, 2.54 Hz, 1 H) 5.13 (br. s., 1 H) 7.39 (s, 2 H) 7.47 (s, 1 H) 7.61 (d, J = 6.21 Hz, 1 H) 8.13 (br. s., 1 H) 8.40 (br. s., 1 H) | HRMS (B) m/z 474.1908 (M + H)$^+$; Rt-1.58 min |
| 255: 1-(3-fluoro-4-((S)-1-(4-((R)-4-((R)-1-hydroxyethyl)-2-oxooxazolidin-3-yl)pyrimidin-2-ylamino)ethyl)phenyl)cyclopropanecarbonitrile | (CD$_3$OD) 0.80 (br. s., 3 H) 1.47-1.51 (m, 2 H) 1.60 (d, J = 6.94 Hz, 3 H) 1.72-1.76 (m, 2 H) 4.41-4.47 (m, 1 H) 4.58 (dd, J = 9.22, 2.57 Hz, 1 H) 5.39 (br. s., 1 H) 7.12 (dd, J = 11.64, 1.91 Hz, 1 H) 7.18 (dd, J = 8.09, 1.79 Hz, 1 H) 7.41 (t, J = 8.05 Hz, 1 H) 7.64 (d, J = 6.65 Hz, 1 H) 8.13 (d, J = 6.80 Hz, 1 H) | HRMS (B) m/z 412.1785 (M + H)$^+$; Rt-1.51 min |
| 256: (R)-3-(2-((S)-1-(2-fluoro-4-(1-methyl-1H-pyrazol-4-yl)phenyl)ethylamino)pyrimidin-4-yl)-4-((R)-1-hydroxyethyl)oxazolidin-2-one | (CD$_3$OD) 0.82 (br. s., 3 H) 1.64 (d, J = 6.94 Hz, 3 H) 3.92 (s, 3 H) 4.07 (d, J = 16.09 Hz, 1 H) 4.43-4.50 (m, 1 H) 4.60 (dd, J = 9.22, 2.47 Hz, 1 H) 4.91 (ddd, J = 8.20, 3.97, 2.45 Hz, 2 H) 5.45 (br. s., 1 H) 7.31-7.44 (m, 3 H) 7.73 (d, J = 7.09 Hz, 1 H) 7.82 (d, J = 0.68 Hz, 1 H) 7.98 (s, 1 H) 8.13 (d, J = 7.04 Hz, 1 H) | HRMS (B) m/z 427.1890 (M + H)$^+$; Rt-1.37 min |
| 257: (R)-4-((R)-1-hydroxyethyl)-3-(2-((S)-1-(4-(1-methyl-1H-pyrazol-4-yl)phenyl)ethylamino)pyrimidin-4-yl)oxazolidin-2-one | (CD$_3$OD) 0.80 (br. s., 3 H) 1.62 (d, J = 6.94 Hz, 3 H) 3.92 (s, 3 H) 3.99 (br. s., 1 H) 4.42-4.50 (m, 1 H) 4.60 (dd, J = 9.24, 2.45 Hz, 1 H) 5.21 (br. s., 1 H) 7.38 (d, J = 8.17 Hz, 2 H) 7.53-7.59 (m, 2 H) 7.73 (d, J = 7.14 Hz, 1 H) 7.79 (d, J = 0.68 Hz, 1 H) 7.93 (s, 1 H) 8.12 (d, J = 6.11 Hz, 1 H) | HRMS (B) m/z 409.1982 (M + H)$^+$; Rt-1.27 min |
| 258: (R)-3-(2-((S)-1-(2-fluoro-4-(1H-pyrazol-4-yl)phenyl)ethylamino)pyrimidin-4-yl)-4-((R)-1-hydroxyethyl)oxazolidin-2-one | (CD$_3$OD) 0.83 (br. s., 3 H) 1.65 (d, J = 6.99 Hz, 3 H) 4.07 (br. s., 1 H) 4.43-4.52 (m, 1 H) 4.61 (dd, J = 9.24, 2.45 Hz, 1 H) 4.90-4.94 (m, 2 H) 5.45 (br. s., 1 H) 7.36-7.42 (m, 3 H) 7.73 (d, J = 7.04 Hz, 1 H) 7.98 (s, 2 H) 8.13 (d, J = 6.90 Hz, 1 H) | HRMS (B) m/z 413.1732 (M + H)$^+$; Rt-1.26 min |
| 259: (R)-3-(5-fluoro-2-((S)-1-(2-fluoro-4-(trifluoromethyl)phenyl)ethylamino)pyrimidin-4-yl)-4-((R)-1-hydroxyethyl)oxazolidin-2-one | (CD$_3$OD) 0.75 (br. s., 3 H) 1.54 (d, J = 7.04 Hz, 3 H) 3.85 (br. s., 1 H) 4.42-4.55 (m, 2 H) 5.27 (q, J = 6.99 Hz, 1 H) 7.42 (d, J = 8.90 Hz, 2 H) 7.58 (t, J = 7.92 Hz, 1 H) 8.21 (d, J = 2.74 Hz, 1 H) | HRMS (B) m/z 433.1299 (M + H)$^+$; Rt-2.03 min |
| 260: (R)-3-(2-((S)-1-(2-fluoro-4-(1-methylcyclopropyl)phenyl)ethylamino)pyrimidin-4-yl)-4-((R)-1-hydroxyethyl)oxazolidin-2-one | (CD$_3$OD) 0.73-0.87 (m, 7 H) 1.39 (s, 3 H) 1.60 (d, J = 6.94 Hz, 3 H) 3.99 (br. s., 1 H) 4.40-4.49 (m, 1 H) 4.59 (dd, J = 9.19, 2.54 Hz, 1 H) 5.39 (br. s., 1 H) 7.01 (dd, J = 12.40, 1.74 Hz, 1 H) 7.05 (dd, J = 8.00, 1.79 Hz, 1 H) 7.29 (t, J = 8.09 Hz, 1 H) 7.69 (d, J = 6.99 Hz, 1 H) 8.12 (d, J = 6.94 Hz, 1 H) | HRMS (B) m/z 401.1992 (M + H)$^+$; Rt-1.87 min |
| 261: (R)-3-(2-((S)-1-(2-fluoro-4-isopropylphenyl)ethylamino)pyrimidin-4-yl)-4-((R)-1-hydroxyethyloxazolidin-2-one | (CD$_3$OD) 8.12 (d, J = 6.7 Hz, 1 H), 7.69 (d, J = 7.0 Hz, 1 H), 7.31 (t, J = 8.0 Hz, 1 H), 6.98-7.09 (m, 2 H), 5.42 (d, J = 12.9 Hz, 1 H), 4.59 (dd, J = 9.2, 2.5 Hz, 1 H), 4.40-4.49 (m, 1 H), 2.91 (spt, J = 6.8 Hz, 1 H), 1.61 (d, J = 6.7 Hz, 3 H), 1.23 (d, J = 7.0 Hz, 6 H), 0.80 (br. s., 3 H) | HRMS (B) m/z 389.1987 (M + H)$^+$; Rt-1.83 min |
| 262: (R)-3-(5-fluoro-2-((S)-1-(2-fluoro-4-(1-methyl-1H-pyrazol-4-yl)phenyl)ethylamino)pyrimidin-4-yl)-4-((R)-1-hydroxyethyl)oxazolidin-2-one | (CD$_3$OD) 0.75 (br. s., 3 H) 1.53 (d, J = 6.94 Hz, 3 H) 3.91 (s, 3 H) 4.42-4.56 (m, 2 H) 4.65 (br. s., 1 H) 5.22 (m, J = 7.04 Hz, 1 H) 7.22-7.31 (m, 2 H) 7.31-7.40 (m, 1 H) 7.79 (s, 1 H) 7.94 (s, 1 H) 8.21 (br. s., 1 H) | HRMS (B) m/z 445.1800 (M + H)$^+$; Rt-1.64 min |

TABLE 30b-continued

Chemical name, NMR chemical shifts and LCMS signal for each compound listed in Table 30a.

| Example: Name | $^1$H NMR (400 MHz, CDCl$_3$) δ ppm | LCMS |
|---|---|---|
| 263: (R)-3-(5-fluoro-2-((S)-1-(2-fluoro-4-(1-methylcyclopropyl)phenyl)ethylamino)pyrimidin-4-yl)-4-((R)-1-hydroxyethyl)oxazolidin-2-one | (CD$_3$OD) 0.52-0.78 (m, 5 H) 0.82 (br. s., 2 H) 1.36 (s, 3 H) 1.49 (d, J = 6.99 Hz, 3 H) 3.86 (br. s., 1 H) 4.42-4.56 (m, 2 H) 4.62 (br. s., 1 H) 5.18 (m, J = 6.31 Hz, 1 H) 6.90-7.00 (m, 2 H) 7.24 (t, J = 8.17 Hz, 1 H) 8.20 (d, J = 2.93 Hz, 1 H) | HRMS (B) m/z 419.1895 (M + H)$^+$; Rt-2.21 min |
| 264: (R)-3-(5-fluoro-2-((S)-1-(2-fluoro-4-(1H-pyrazol-4-yl)phenyl)ethylamino)pyrimidin-4-yl)-4-((R)-1-hydroxyethyl)oxazolidin-2-one | (CD$_3$OD) 0.76 (br. s., 3 H) 1.53 (d, J = 6.90 Hz, 3 H) 3.91 (br. s., 1 H) 4.42-4.57 (m, 2 H) 4.66 (br. s., 1 H) 5.23 (d, J = 6.41 Hz, 1 H) 7.28-7.40 (m, 3 H) 7.97 (s, 2 H) 8.21 (br. s., 1 H) | HRMS (B) m/z 431.1640 (M + H)$^+$; Rt-1.55 min |
| 265: (R)-3-(5-fluoro-2-((S)-1-(2-fluoro-4-isopropylphenyl)ethylamino)pyrimidin-4-yl)-4-((R)-1-hydroxyethyl)oxazolidin-2-one | (CD$_3$OD) 0.71 (br. s., 3 H) 1.21 (d, J = 6.94 Hz, 6 H) 1.50 (d, J = 6.99 Hz, 3 H) 2.87 (dt, J = 13.72, 6.83 Hz, 1 H) 3.89 (br. s., 1 H) 4.43-4.56 (m, 2 H) 4.63 (br. s., 1 H) 5.20 (q, J = 6.52 Hz, 1 H) 6.90-7.00 (m, 2 H) 7.26 (t, J = 7.90 Hz, 1 H) 8.21 (d, J = 2.84 Hz, 1 H) | HRMS (B) m/z 407.1890 (M + H)$^+$; Rt-2.18 min |
| 266: (R)-3-(5-fluoro-2-((S)-1-(2-fluoro-4-(2-hydroxypropan-2-yl)phenyl)ethylamino)pyrimidin-4-yl)-4-((R)-1-hydroxyethyl)oxazolidin-2-one | (CD$_3$OD) 0.73 (br. s., 3 H) 1.47-1.52 (m, 9 H) 4.43-4.55 (m, 3 H) 4.59-4.67 (m, 1 H) 5.15-5.27 (m, 1 H) 7.15-7.23 (m, 2 H) 7.30 (t, J = 8.09 Hz, 1 H) 8.20 (d, J = 3.08 Hz, 1 H) | HRMS (B) m/z 423.1838 (M + H)$^+$; Rt-1.59 min |
| 267: (R)-3-(2-(((S)-1-(2,5-difluoro-4-(1-methyl-1H-pyrazol-4-yl)phenyl)ethyl)amino)-5-fluoropyrimidin-4-yl)-4-((R)-1-hydroxyethyl)oxazolidin-2-one | (CD$_3$OD) 0.79 (br. s., 3 H) 1.52 (d, J = 6.99 Hz, 3 H) 3.92 (s, 3 H) 4.43-4.56 (m, 2 H) 4.64 (d, J = 3.42 Hz, 1 H) 5.21 (q, J = 6.83 Hz, 1 H) 7.14 (dd, J = 11.40, 6.31 Hz, 1 H) 7.39 (dd, J = 10.93, 6.14 Hz, 1 H) 7.86 (d, J = 0.59 Hz, 1 H) 8.00 (d, J = 1.86 Hz, 1 H) 8.23 (d, J = 3.03 Hz, 1 H) | HRMS (B) m/z 463.1708 (M + H)$^+$; Rt-1.72 min |
| 268: (R)-3-(2-(((S)-1-(2-(4-chlorophenyl)thiazol-5-yl)ethyl)amino)pyrimidin-4-yl)-4-((S)-1-hydroxyethyl)oxazolidin-2-one | (CD$_3$CN) 0.98 (d, J = 6.65 Hz, 3 H) 1.72 (d, J = 7.04 Hz, 3 H) 4.00 (br. s., 1 H) 4.26-4.42 (m, 1 H) 4.51 (dd, J = 8.80, 2.93 Hz, 1 H) 4.62 (dd, J = 7.24, 1.37 Hz, 1 H) 5.49 (quin, J = 6.85 Hz, 1 H) 7.49 (d, J = 8.61 Hz, 2 H) 7.66-7.78 (m, 2 H) 7.91 (d, J = 8.61 Hz, 2 H) 8.05 (d, J = 7.04 Hz, 1 H) 10.52 (br. s., 1 H) | HRMS (B) m/z 446.1060 (M + H)$^+$; Rt-1.81 min |
| 269: (R)-3-(6-chloro-2-(((S)-1-(2-fluoro-4-(2-fluoropropan-2-yl)phenyl)ethyl)amino)pyrimidin-4-yl)-4-((R)-1-hydroxyethyl)oxazolidin-2-one | (CDCl$_3$) 0.80 (br. s., 3 H) 1.26 (s, 3 H) 1.63-1.73 (m, 9 H) 4.28-4.36 (m, 1 H) 4.44 (dd, J = 9.39, 2.54 Hz, 1 H) 4.64 (br. s., 1 H) 5.21 (br. s., 1 H) 7.07-7.18 (m, 2 H) 7.28-7.33 (m, 1 H) 7.51 (s, 1 H) | HRMS (B) m/z 441.1501 (M + H)$^+$; Rt-2.35 min |
| 270: (R)-3-(5-chloro-2-(((S)-1-(1-(4-chlorophenyl)-1H-imidazol-4-yl)ethyl)amino)pyrimidin-4-yl)-4-((R)-1-hydroxyethyl)oxazolidin-2-one | (CD$_3$OD) δ 8.20 (s, 1 H), 8.03 (d, J = 1.2 Hz, 1 H), 7.30-7.52 (m, 6 H), 5.06 (d, J = 6.7 Hz, 1 H), 4.67 (dt, J = 8.6, 6.1 Hz, 1 H), 4.45 (t, J = 8.8 Hz, 1 H), 4.31 (dd, J = 9.0, 6.3 Hz, 1 H), 3.81 (br. s., 1 H), 1.49 (d, J = 6.7 Hz, 3 H), 0.91 (br. s., 3 H) | HRMS (B) m/z 399.1029 (M + H)$^+$ RT = 1.95 min. |
| 271: (R)-3-(2-((S)-1-(2,5-difluoro-4-isopropylphenyl)ethylamino)pyrimidin-4-yl)-4-((R)-1-hydroxyethyl)oxazolidin-2-one | (CD$_3$OD) 8.14 (br. s., 1 H), 7.64 (d, J = 6.7 Hz, 1 H), 7.07 (dd, J = 10.2, 6.3 Hz, 2 H), 5.37 (d, J = 5.1 Hz, 1 H), 4.85 (s, 1H), 4.57 (dd, J = 9.4, 2.3 Hz, 1 H), 4.38-4.49 (m, 1 H), 3.96 (br. s., 1 H), 3.11-3.25 (m, 1 H), 1.57 (d, J = 7.0 Hz, 3 H), 1.23 (dd, J = 7.0, 2.0 Hz, 6 H), 0.80 (br. s., 3 H) | HRMS (B) m/z 407.1895, (M + H)$^+$, RT = 1.95 min. |
| 272: (R)-3-(2-(((S)-1-(4-bromo-2,5-difluorophenyl)ethyl)amino)pyrimidin-4-yl)-4-((R)-1-hydroxyethyl)oxazolidin-2-one | (CD$_3$OD) 8.14 (d, J = 5.9 Hz, 1 H), 7.51 (d, J = 6.3 Hz, 1 H), 7.44 (dd, J = 9.4, 5.5 Hz, 1 H), 7.24 (dd, J = 9.0, 6.3 Hz, 1 H), 5.33 (q, J = 6.7 Hz, 1 H), 4.85 (s, 8 H), 4.54 (dd, J = 9.2, 2.5 Hz, 2 H), 4.34-4.47 (m, 1 H), 1.54 (d, J = 6.7 Hz, 3 H), 0.83 (br. s., 3 H) | HRMS (B) m/z 443.0527, (M + H)$^+$, RT = 1.74 min. |

TABLE 30b-continued

Chemical name, NMR chemical shifts and LCMS signal for each compound listed in Table 30a.

| Example: Name | $^1$H NMR (400 MHz, CDCl$_3$) δ ppm | LCMS |
|---|---|---|
| 273: (R)-3-(2-((S)-1-(5-chloro-6-(1,1-difluoroethyl)pyridin-3-yl)ethylamino)pyrimidin-4-yl)-4-((R)-1-hydroxyethyl)oxazolidin-2-one | (CD$_3$OD) 8.55 (d, J = 1.2 Hz, 1 H), 8.16 (d, J = 5.9 Hz, 1 H), 7.99 (s, 1 H), 7.64 (d, J = 5.9 Hz, 1 H), 5.27 (br. s., 1 H), 4.85 (s, 2 H), 4.56 (dd, J = 9.0, 2.3 Hz, 1 H), 4.39-4.47 (m, 1 H), 2.04 (t, J = 19.0 Hz, 3 H), 1.63 (d, J = 7.0 Hz, 3 H), 0.82 (br. s., 3 H) | HRMS (B) m/z 428.1299, (M + H)$^+$, RT = 1.65 min. |
| 274: (R)-3-(2-((S)-1-(5-chloro-6-(2,2,2-trifluoroethoxy)pyridin-3-yl)ethylamino)pyrimidin-4-yl)-4-((R)-1-hydroxyethyl)oxazolidin-2-one | (CD$_3$OD) 8.15 (d, J = 2.0 Hz, 2 H), 7.92 (d, J = 2.3 Hz, 1 H), 7.71 (d, J = 7.0 Hz, 1 H), 5.25 (br. s., 1 H), 4.89-4.99 (m, 3H), 4.59 (dd, J = 9.4, 2.3 Hz, 1 H), 4.41-4.50 (m, 1 H), 4.00 (br. s., 1 H), 1.62 (d, J = 7.0 Hz, 6 H) | HRMS (B) m/z 462.1149, (M + H)$^+$, RT = 1.87 min. |
| 275: (R)-3-(2-((S)-1-(4-bromo-2,3-difluorophenyl)ethylamino)pyrimidin-4-yl)-4-((R)-1-hydroxyethyl)oxazolidin-2-one | (CD$_3$OD) 8.16 (br. s., 1 H), 7.71 (d, J = 6.7 Hz, 1 H), 7.36-7.48 (m, 1 H), 7.09-7.22 (m, 1 H), 5.42 (br. s., 1 H), 4.87 (s, 1 H), 4.57 (dd, J = 9.0, 2.3 Hz, 1 H), 4.39-4.50 (m, 1 H), 3.82 (br. s., 1 H), 1.62 (d, J = 7.0 Hz, 6 H) | HRMS (B) m/z 443.0532, (M + H)$^+$, RT = 1.81 min. |
| 276: (R)-3-(2-(((S)-1-(4-bromo-2,5-difluorophenyl)ethyl)amino)-5-fluoropyrimidin-4-yl)-4-((R)-1-hydroxyethyl)oxazolidin-2-one | (CD$_3$OD) 8.22 (d, J = 2.3 Hz, 1 H), 7.41 (dd, J = 9.0, 5.5 Hz, 1 H), 7.21 (dd, J = 9.2, 6.5 Hz, 1 H), 5.13-5.23 (m, 1 H), 4.86 (s, 1 H), 4.38-4.55 (m, 2 H), 3.99-4.16 (m, 1 H), 1.49 (d, J = 7.0 Hz, 6 H) | HRMS (B) m/z 461.0432, (M + H)$^+$, RT = 2.01 min. |
| 277: (R)-3-(2-(((S)-1-(4-bromo-2-fluorophenyl)ethyl)amino)-5-fluoropyrimidin-4-yl)-4-((R)-1-hydroxyethyl)oxazolidin-2-one | (CD$_3$OD) 8.20 (d, J = 2.3 Hz, 1 H), 7.18-7.38 (m, 3 H), 5.18 (q, J = 7.0 Hz, 1 H), 4.61 (t, J = 9.0 Hz, 1 H), 4.42-4.55 (m, 2 H), 3.89 (br. s., 1 H), 1.49 (d, J = 7.0 Hz, 6 H) | HRMS (B) m/z 443.0534, (M + H)$^+$, RT = 1.99 min. |
| 278: (R)-3-(2-(((S)-1-(4-chloro-2-fluorophenyl)ethyl)amino)-5-fluoropyrimidin-4-yl)-4-((R)-1-hydroxyethyl)oxazolidin-2-one | (CD$_3$OD) 8.21 (d, J = 2.7 Hz, 1 H), 7.36 (t, J = 8.4 Hz, 1 H), 7.05-7.21 (m, 2 H), 5.20 (q, J = 7.0 Hz, 1 H), 4.62 (d, J = 8.6 Hz, 1 H), 4.42-4.56 (m, 2 H), 3.90 (br. s., 1 H), 1.50 (d, J = 7.0 Hz, 6 H) | HRMS (B) m/z 399.1029, (M + H)$^+$, RT = 1.95 min. |
| 279: (R)-3-(2-((S)-1-(5-bromo-3-fluoropyridin-2-yl)ethylamino)-5-fluoropyrimidin-4-yl)-4-((R)-1-hydroxyethyl)oxazolidin-2-one | (CD$_3$OD) 8.45 (s, 1 H), 8.21 (d, J = 2.7 Hz, 1 H), 7.86 (dd, J = 9.4, 2.0 Hz, 1 H), 5.35 (q, J = 6.7 Hz, 1 H), 4.67-4.77 (m, 1H), 4.43-4.58 (m, 2 H), 4.08-4.20 (m, 1 H), 1.51 (d, J = 6.7 Hz, 3 H), 1.09 (d, J = 6.7 Hz, 3 H) | HRMS (B) m/z 444.0483, (M + H)$^+$, RT = 1.75 min. |
| 280: (R)-3-(2-((R)-1-(5-bromo-3-fluoropyridin-2-yl)ethylamino)-5-fluoropyrimidin-4-yl)-4-((R)-1-hydroxyethyl)oxazolidin-2-one | (CD$_3$OD) 8.44 (s, 1 H), 8.22 (d, J = 2.7 Hz, 1 H), 7.86 (dd, J = 9.4, 1.6 Hz, 1 H), 5.30-5.38 (m, 1 H), 4.61-4.71 (m, 1H), 4.50-4.58 (m, 1 H), 4.43-4.49 (m, 1 H), 3.92 (br. s., 1 H), 1.52 (d, J = 7.0 Hz, 6 H) | HRMS (B) m/z 444.0478, (M + H)$^+$, RT = 1.75 min. |
| 281: (R)-3-(2-((S)-1-(3-(4-chlorophenyl)-1,2,4-oxadiazol-5-yl)ethylamino)-5-fluoropyrimidin-4-yl)-4-((R)-1-hydroxyethyl)oxazolidin-2-one | (CD$_3$OD) 8.27 (br. s., 1 H), 8.01 (dd, J = 8.6, 2.3 Hz, 2 H), 7.47-7.56 (m, 2 H), 5.30-5.43 (m, 1 H), 4.68 (d, J = 13.7 Hz, 1 H), 4.40-4.57 (m, 2 H), 4.00 (br. s., 1 H), 1.72 (d, J = 7.0 Hz, 6 H) | HRMS (B) m/z 449.1140, (M + H)$^+$, RT = 2.04 min. |
| 282: (R)-3-(2-((S)-1-(5-bromopyridin-2-yl)ethylamino)-5-fluoropyrimidin-4-yl)-4-((R)-1-hydroxyethyl)oxazolidin-2-one | (CD$_3$OD) 8.65 (d, J = 2.0 Hz, 1 H), 8.22 (d, J = 2.3 Hz, 1 H), 8.07 (dd, J = 8.6, 2.3 Hz, 1 H), 7.51 (d, J = 8.2 Hz, 1 H), 5.00-5.08 (m, 1 H), 4.61 (br. s., 1 H), 4.42-4.55 (m, 2 H), 4.06-4.17 (m, 1 H), 1.55 (d, J = 7.0 Hz, 3H), 1.08 (d, J = 6.7 Hz, 3 H) | HRMS (B) m/z 426.0574, (M + H)$^+$, RT = 1.61 min. |

TABLE 30b-continued

Chemical name, NMR chemical shifts and LCMS
signal for each compound listed in Table 30a.

| Example: Name | $^1$H NMR (400 MHz, CDCl$_3$) δ ppm | LCMS |
|---|---|---|
| 283: (R)-3-(2-(((S)-1-(4-bromo-3-fluorophenyl)ethyl)amino)-5-fluoropyrimidin-4-yl)-4-((R)-1-hydroxyethyl)oxazolidin-2-one | (CD$_3$OD) 8.21 (d, J = 2.7 Hz, 1 H), 7.52 (t, J = 7.6 Hz, 1 H), 7.21 (dd, J = 9.8, 2.0 Hz, 1 H), 7.12 (dd, J = 8.2, 2.0 Hz, 1 H), 4.88-4.97 (m, 1 H), 4.59 (d, J = 8.2 Hz, 1 H), 4.42-4.55 (m, 2 H), 3.88 (br. s., 1 H), 1.49 (d, J = 7.0 Hz, 3 H), 0.80 (br. s., 3 H) | HRMS (B) m/z 443.0526, (M + H)$^+$, RT = 1.96 min. |
| 284: (R)-3-(2-(((S)-1-(5-chloro-6-(1,1-difluoroethyl)pyridin-3-yl)ethyl)amino)-5-fluoropyrimidin-4-yl)-4-((R)-1-hydroxyethyl)oxazolidin-2-one | (CD$_3$OD) 8.51 (s, 1H), 8.24 (s, 1H), 7.76 (s, 1H), 5.13 (m, 1 H), 4.91 (m, 1H), 4.42-4.55 (m, 2H), 4.41 (br. s., 1 H), 2.12 (t, J = 7.0 Hz, 3H), 1.22 (m, 6H) | HRMS (B) m/z 446.1208, (M + H)$^+$, RT = 1.85 min. |
| 285: (R)-3-(2-(((S)-1-(5-chloro-6-(2,2,2-trifluoroethoxy)pyridin-3-yl)ethyl)amino)-5-fluoropyrimidin-4-yl)-4-((R)-1-hydroxyethyl)oxazolidin-2-one | (CD$_3$OD) 8.22 (d, J = 2.7 Hz, 1 H), 8.11 (d, J = 2.0 Hz, 1 H), 7.84 (d, J = 2.0 Hz, 1 H), 4.89-5.02 (m, 3 H), 4.62 (d, J = 3.5 Hz, 1 H), 4.42-4.57 (m, 2 H), 3.90 (br. s., 1 H), 1.52 (d, J = 7.0 Hz, 3 H), 0.85 (br. s., 3 H) | HRMS (B) m/z 480.1065, (M + H)$^+$, RT = 2.10 min. |
| 286: (R)-3-(2-(((S)-1-(2,4-dichlorophenyl)ethyl)amino)-5-fluoropyrimidin-4-yl)-4-((R)-1-hydroxyethyl)oxazolidin-2-one | (CD$_3$OD) 8.21 (d, J = 2.3 Hz, 1 H), 7.36-7.46 (m, 2 H), 7.24 (dd, J = 8.2, 2.0 Hz, 1 H), 5.25 (q, J = 6.7 Hz, 1 H), 4.59 (br. s., 1 H), 4.40-4.54 (m, 2 H), 3.81 (br. s., 1 H), 1.47 (d, J = 7.0 Hz, 6 H) | HRMS (B) m/z 415.0741, (M + H)$^+$, RT = 2.07 min. |
| 287: (R)-3-(2-(((S)-1-(6-bromopyridin-3-yl)ethyl)amino)-5-fluoropyrimidin-4-yl)-4-((R)-1-hydroxyethyl)oxazolidin-2-one | (CD$_3$OD) 8.40 (d, J = 2.3 Hz, 1 H), 8.12 (br. s., 1 H), 7.75 (dd, J = 8.4, 2.5 Hz, 1 H), 7.59 (d, J = 8.2 Hz, 1 H), 5.17 (br. s., 1 H), 5.05 (q, J = 7.0 Hz, 1 H), 4.43 (t, J = 8.6 Hz, 1 H), 4.00-4.14 (m, 2 H), 1.59 (d, J = 7.0 Hz, 3 H), 1.40 (d, J = 6.7 Hz, 3 H) | HRMS (B) m/z 426.0570, (M + H)$^+$, RT = 1.51 min. |
| 288: (R)-3-(2-(((S)-1-(4-chloro-3-fluorophenyl)ethyl)amino)-5-fluoropyrimidin-4-yl)-4-((R)-1-hydroxyethyl)oxazolidin-2-one | (CD$_3$OD) 8.21 (d, J = 3.1 Hz, 1 H), 7.38 (t, J = 8.0 Hz, 1 H), 7.12-7.28 (m, 2 H), 4.88-5.00 (m, 1 H), 4.59 (br. s., 1 H), 4.42-4.55 (m, 2 H), 3.89 (br. s., 1 H), 1.49 (d, J = 7.0 Hz, 3 H), 0.81 (br. s., 3 H) | HRMS (B) m/z 399.1031, (M + H)$^+$, RT = 1.91 min. |
| 289: (R)-3-(2-(((R)-1-(5-bromopyridin-2-yl)ethyl)amino)-5-fluoropyrimidin-4-yl)-4-((R)-1-hydroxyethyl)oxazolidin-2-one | (CD$_3$OD) 8.57 (d, J = 2.3 Hz, 1 H), 7.88-7.97 (m, 2 H), 7.37 (d, J = 8.6 Hz, 1 H), 5.09 (br. s., 1 H), 4.94 (d, J = 7.0 Hz, 1H), 4.38 (t, J = 8.8 Hz, 1 H), 3.93-4.12 (m, 2 H), 1.51 (d, J = 7.0 Hz, 3 H), 1.31 (d, J = 6.3 Hz, 3 H) | HRMS (B) m/z 426.0574, (M + H)$^+$, RT = 1.55 min. |
| 290: (R)-3-(2-(((S)-1-(3,4-dichlorophenyl)ethyl)amino)-5-fluoropyrimidin-4-yl)-4-((R)-1-hydroxyethyl)oxazolidin-2-one | (CD$_3$OD) 8.20 (d, J = 2.7 Hz, 1 H), 7.51 (d, J = 2.0 Hz, 1 H), 7.43 (d, J = 8.2 Hz, 1 H), 7.29 (dd, J = 8.4, 1.8 Hz, 1 H), 4.87-4.97 (m, 1 H), 4.59 (br. s., 1 H), 4.40-4.55 (m, 2 H), 3.89 (br. s., 1 H), 1.49 (d, J = 7.0 Hz, 6 H) | HRMS (B) m/z 415.0738, (M + H)$^+$, RT = 2.02 min. |
| 291: (R)-3-(2-(((S)-1-(6-chloro-5-fluoropyridin-3-yl)ethyl)amino)-5-fluoropyrimidin-4-yl)-4-((R)-1-hydroxyethyl)oxazolidin-2-one | (CDCl$_3$) 8.25 (s, 1H), 8.22 (m, 1H), 7.51 (m, 1H), 5.51 (s, 1H), 4.91 (m, 1 H), 4.51 (m, 2H), 4.41 (m, 1 H), 3.62 (m, 1H), 1.45 (d, J = 7.0 Hz, 3 H), 1.01 (br. s., 3H) | HRMS (B) m/z 400.0981, (M + H)$^+$, RT = 1.61 min. |
| 292: (R)-3-(2-(((S)-1-(5,6-dichloropyridin-3-yl)ethyl)amino)-5-fluoropyrimidin-4-yl)-4-((R)-1-hydroxyethyl)oxazolidin-2-one | (CDCl$_3$) 8.37 (s, 1H), 8.15 (m, 1H), 7.76 (m, 1H), 5.68 (s, 1H), 4.94 (m, 1 H), 4.51 (m, 2H), 4.45 (m, 1 H), 3.68 (m, 1H), 1.58 (d, J = 7.0 Hz, 3 H), 1.01 (br. s., 3H) | HRMS (B) m/z 416.0690, (M + H)$^+$, RT = 1.73 min. |

TABLE 30b-continued

Chemical name, NMR chemical shifts and LCMS
signal for each compound listed in Table 30a.

| Example: Name | ¹H NMR (400 MHz, CDCl₃) δ ppm | LCMS |
|---|---|---|
| 293: (R)-3-(2-(((R)-1-(3,5-dichloropyridin-2-yl)ethyl)amino)-5-fluoropyrimidin-4-yl)-4-((R)-1-hydroxyethyl)oxazolidin-2-one | (cdcl3) 8.43 (d, J = 2.0 Hz, 1 H), 8.23 (d, J = 2.3 Hz, 1 H), 7.72 (d, J = 2.0 Hz, 1 H), 6.29 (d, J = 7.8 Hz, 1 H), 5.50 (br. s., 1 H), 4.48-4.59 (m, 2 H), 4.37-4.47 (m, 1 H), 4.24 (br. s., 1 H), 1.48 (d, J = 6.7 Hz, 3 H), 1.22 (d, J = 6.7 Hz, 3 H) | HRMS (B) m/z 416.0685, (M + H)⁺, RT = 1.83 min. |
| 294: (R)-3-(2-(((S)-1-(3,5-dichloropyridin-2-yl)ethyl)amino)-5-fluoropyrimidin-4-yl)-4-((R)-1-hydroxyethyl)oxazolidin-2-one | (CDCl₃) 8.42 (d, J = 2.0 Hz, 1 H), 8.22 (d, J = 2.7 Hz, 1 H), 7.72 (d, J = 2.0 Hz, 1 H), 6.22 (d, J = 8.2 Hz, 1 H), 5.51 (br. s., 1 H), 4.47-4.67 (m, 2 H), 4.34-4.45 (m, 1 H), 1.49 (d, J = 7.0 Hz, 3 H), 1.14 (br. s., 3 H) | HRMS (B) m/z 416.0687, (M + H)⁺, RT = 1.82 min. |
| 295: (R)-3-(6-chloro-2-(((S)-1-(3,5-dichloropyridin-2-yl)ethyl)amino)pyrimidin-4-yl)-4-((R)-1-hydroxyethyl)oxazolidin-2-one | (CDCl₃) 8.43 (d, J = 2.0 Hz, 1 H), 7.73 (d, J = 2.0 Hz, 1 H), 7.50 (s, 1 H), 6.39 (d, J = 7.4 Hz, 1 H), 5.52 (br. s., 1 H), 4.72-4.93 (m, 1 H), 4.32-4.62 (m, 2 H), 4.13 (br. s., 1 H), 1.50 (d, J = 6.7 Hz, 3 H), 1.07 (br. s., 3 H) | HRMS (B) m/z 432.0391, (M + H)⁺, RT = 2.27 min. |
| 296: (R)-3-(6-chloro-2-(((S)-1-(3-fluoro-5-(2,2,2-trifluoroethoxy)pyridin-2-yl)ethyl)amino)pyrimidin-4-yl)-4-((R)-1-hydroxyethyl)oxazolidin-2-one | (CDCl₃) 8.13 (br. s., 1 H), 7.49 (s, 1 H), 7.07 (dd, J = 10.8, 2.2 Hz, 1 H), 6.17 (br. s., 1 H), 5.40 (br. s., 1 H), 4.70-5.04(m, 1 H), 4.52 (br. s., 1 H), 4.41 (q, J = 7.8 Hz, 3 H), 4.18 (br. s., 1 H), 1.53 (br. s., 3 H), 1.01-1.18 (m, 3 H) | HRMS (B) m/z 480.1066, (M + H)⁺, RT = 2.21 min. |
| 297: (R)-3-(2-(((R)-1-(1-(4-chlorophenyl)-1H-pyrazol-3-yl)ethyl)amino)-5-fluoropyrimidin-4-yl)-4-((R)-1-hydroxyethyl)oxazolidin-2-one | (CDCl₃) 8.19 (d, J = 2.7 Hz, 1 H), 7.81 (d, J = 2.3 Hz, 1 H), 7.59 (d, J = 9.0 Hz, 2 H), 7.41 (d, J = 9.0 Hz, 2 H), 6.39 (d, J = 2.3 Hz, 1 H), 5.12 (br. s., 1 H), 4.25-4.58 (m, 4 H), 3.03 (br. s., 1 H), 1.61 (d, J = 7.0 Hz, 3 H), 1.20 (d, J = 6.3 Hz, 3 H) | HRMS (B) m/z 447.1348, (M + H)⁺, RT = 2.00 min. |
| 298: (R)-3-(2-(((S)-1-(1-(4-chlorophenyl)-1H-pyrazol-3-yl)ethyl)amino)-5-fluoropyrimidin-4-yl)-4-((R)-1-hydroxyethyl)oxazolidin-2-one | (CDCl₃) 8.19 (d, J = 2.0 Hz, 1 H), 7.80 (d, J = 2.0 Hz, 1 H), 7.58 (d, J = 9.0 Hz, 2 H), 7.41 (d, J = 9.0 Hz, 2 H), 6.39 (d, J = 2.3 Hz, 1 H), 5.18 (br. s., 1 H), 4.60 (t, J = 5.5 Hz, 1 H), 4.51 (t, J = 8.6 Hz, 1 H), 4.34 (dd, J = 8.8, 5.3 Hz, 1 H), 4.00 (br. s., 1 H), 1.62 (d, J = 7.0 Hz, 3 H), 1.03 (br. s., 3 H) | HRMS (B) m/z 447.1345, (M + H)⁺, RT = 1.98 min. |
| 299: (R)-3-(2-(((R)-1-(1-(4-chlorophenyl)-1H-imidazol-4-yl)ethyl)amino)-5-fluoropyrimidin-4-yl)-4-((R)-1-hydroxyethyl)oxazolidin-2-one | (CDCl₃) 8.20 (d, J = 2.7 Hz, 1 H), 7.76 (s, 1 H), 7.45 (d, J = 8.6 Hz, 2 H), 7.31 (d, J = 8.6 Hz, 2 H), 7.14 (s, 1 H), 5.61 (d, J = 7.4 Hz, 1 H), 5.07 (d, J = 5.9 Hz, 1 H), 4.32-4.57 (m, 4 H), 1.59 (d, J = 6.7 Hz, 3 H), 1.21 (d, J = 6.3 Hz, 3 H) | HRMS (B) m/z 447.1346, (M + H)⁺, RT = 1.32 min. |
| 300: (R)-3-(2-(((S)-1-(1-(4-chlorophenyl)-1H-imidazol-4-yl)ethyl)amino)-5-fluoropyrimidin-4-yl)-4-((R)-1-hydroxyethyl)oxazolidin-2-one | (CDCl₃) 8.19 (d, J = 2.7 Hz, 1 H), 7.71 (s, 1 H), 7.45 (d, J = 8.6 Hz, 2 H), 7.30 (d, J = 8.6 Hz, 2 H), 7.12 (s, 1 H), 5.42 (d, J = 7.8 Hz, 1 H), 5.20 (quin, J = 7.1 Hz, 1 H), 4.74 (br. s., 1 H), 4.54 (t, J = 8.8 Hz, 1 H), 4.29 (dd, J = 8.6, 5.9 Hz, 1 H), 3.99 (br. s., 1 H), 1.62 (d, J = 7.0 Hz, 3 H), 1.15 (d, J = 6.3 Hz, 3 H) | HRMS (B) m/z 447.1350, (M + H)⁺, RT = 1.34 min. |
| 301: (R)-3-(2-(((S)-1-(2,5-difluoro-4-(2,2,2-trifluoroethoxy)phenyl)ethyl)amino)-5-fluoropyrimidin-4-yl)-4-((R)-1-hydroxyethyl)oxazolidin-2-one | (CDCl₃) 8.20 (d, J = 2.7 Hz, 1 H), 7.09 (dd, J = 11.3, 7.0 Hz, 1 H), 6.79 (dd, J = 10.4, 6.8 Hz, 1 H), 5.52 (br. s., 1 H), 5.11(quin, J = 6.7 Hz, 1 H), 4.45-4.59 (m, 2 H), 4.31-4.44 (m, 3 H), 3.87 (br. s., 1 H), 1.53 (d, J = 7.0 Hz, 3 H), 1.03 (d, J = 4.3 Hz, 3 H) | HRMS (B) m/z 481.1315, (M + H)⁺, RT = 2.04 min. |
| 302: (R)-3-(5-fluoro-2-(((S)-1-(2-fluoro-4-(2,2,2-trifluoroethoxy)phenyl)ethyl)amino)pyrimidin-4-yl)-4-((R)-1-hydroxyethyl)oxazolidin-2-one | (CDCl₃) 8.19 (d, J = 2.3 Hz, 1 H), 6.62-6.75 (m, 3 H), 5.48 (br. s., 1 H), 5.14 (t, J = 6.8 Hz, 1 H), 4.43-4.54 (m, 2 H), 4.24-4.40 (m, 3 H), 3.82 (br. s., 1 H), 1.53 (d, J = 6.7 Hz, 3 H), 0.99 (br. s., 3 H) | HRMS (B) m/z 463.1403, (M + H)⁺, RT = 2.03 min. |

TABLE 30b-continued

Chemical name, NMR chemical shifts and LCMS signal for each compound listed in Table 30a.

| Example: Name | ¹H NMR (400 MHz, CDCl₃) δ ppm | LCMS |
|---|---|---|
| 303: (R)-3-(5-fluoro-2-(((S)-1-(3-fluoro-4-(2,2,2-trifluoroethoxy)phenyl)ethyl)amino)pyrimidin-4-yl)-4-((R)-1-hydroxyethyl)oxazolidin-2-one | (CDCl₃) 8.20 (d, J = 2.3 Hz, 1 H), 7.12 (dd, J = 11.7, 2.0 Hz, 1 H), 7.04-7.09 (m, 1 H), 6.93-7.03 (m, 1 H), 5.44 (br. s., 1 H), 4.86 (d, J = 6.3 Hz, 1 H), 4.45-4.55 (m, 1 H), 4.27-4.45 (m, 3 H), 3.76 (br. s., 1 H), 1.51 (d, J = 7.0 Hz, 3 H), 1.01 (br. s., 3H) | HRMS (B) m/z 463.1403, (M + H)⁺, RT = 1.99 min. |
| 304: (R)-3-(5-fluoro-2-(((S)-1-(1-(4-fluorophenyl)-1H-pyrazol-3-yl)ethyl)amino)pyrimidin-4-yl)-4-((R)-1-hydroxyethyl)oxazolidin-2-one | (CDCl₃) 8.22 (d, J = 2.7 Hz, 1 H), 7.77 (d, J = 2.3 Hz, 1 H), 7.54-7.67 (m, 2 H), 7.14 (t, J = 8.4 Hz, 2 H), 6.36 (d, J = 2.3 Hz, 1 H), 5.66 (d, J = 7.8 Hz, 1 H), 5.10-5.25 (m, 1 H), 4.55-4.64 (m, 1 H), 4.47-4.54 (m, 1 H), 4.34 (dd, J = 8.6, 5.1 Hz, 1 H), 4.02 (br. s., 1 H), 1.61 (d, J = 7.0 Hz, 6 H) | HRMS (B) m/z 431.1643, (M + H)⁺, RT = 1.80 min. |
| 305: (R)-3-(5-fluoro-2-(((S)-1-(5-(2,2,2-trifluoroethoxy)pyridin-2-yl)ethyl)amino)pyrimidin-4-yl)-4-((R)-1-hydroxyethyl)oxazolidin-2-one | (CDCl₃) 8.30 (d, J = 2.7 Hz, 1 H), 8.20 (d, J = 2.7 Hz, 1 H), 7.23-7.37 (m, 2 H), 5.96-6.10 (m, 1 H), 4.97-5.14 (m, 1H), 4.44-4.57 (m, 2 H), 4.28-4.44 (m, 3 H), 3.96 (br. s., 1 H), 1.54 (d, J = 6.7 Hz, 6 H) | HRMS (B) m/z 446.1449, (M + H)⁺, RT = 1.58 min. |
| 306: (R)-3-(5-fluoro-2-(((R)-1-(5-(2,2,2-trifluoroethoxy)pyridin-2-yl)ethyl)amino)pyrimidin-4-yl)-4-((R)-1-hydroxyethyl)oxazolidin-2-one | (CDCl₃) 8.28 (d, J = 2.3 Hz, 1 H), 8.20 (d, J = 3.1 Hz, 1 H), 7.21-7.36 (m, 2 H), 6.02 (d, J = 6.7 Hz, 1 H), 5.00 (br. s., 1H), 4.25-4.57 (m, 5 H), 1.52 (d, J = 6.7 Hz, 3 H), 1.20 (d, J = 6.3 Hz, 3 H) | HRMS (B) m/z 446.1447, (M + H)⁺, RT = 1.59 min. |
| 307: (R)-3-(2-(((S)-1-(1-(4-chlorophenyl)-1H-imidazol-4-yl)ethyl)amino)pyrimidin-4-yl)-4-((R)-1-hydroxyethyl)oxazolidin-2-one | (CD₃OD) 9.02 (br. s., 1 H), 8.20 (d, J = 6.7 Hz, 1 H), 7.89 (s, 1 H), 7.64-7.72 (m, 3 H), 7.56-7.64 (m, 2 H), 5.37 (d, J = 6.3 Hz, 1 H), 4.75-5.01 (m, 2 H), 4.56 (dd, J = 9.4, 2.3 Hz, 1 H), 4.40-4.50 (m, 1 H), 1.72 (d, J = 7.0 Hz, 3 H), 1.02 (d, J = 6.3 Hz, 3 H) | HRMS (B) m/z 429.1438, (M + H)⁺, RT = 1.30 min. |
| 308: (R)-3-(2-(((S)-1-(1-(4-chlorophenyl)-1H-pyrazol-3-yl)ethyl)amino)pyrimidin-4-yl)-4-((R)-1-hydroxyethyl)oxazolidin-2-one | (CD₃OD) 8.19 (d, J = 2.3 Hz, 1 H), 8.15 (d, J = 7.0 Hz, 1 H), 7.74 (dd, J = 7.8, 6.7 Hz, 3 H), 7.45 (d, J = 9.0 Hz, 2 H), 6.53(d, J = 2.3 Hz, 1 H), 5.46 (br. s., 1 H), 4.81-4.97 (m, 2 H), 4.60 (dd, J = 9.4, 2.3 Hz, 1 H), 4.42-4.53 (m, 1 H), 4.32 (br. s., 1 H), 1.69 (d, J = 7.0 Hz, 3H), 0.91 (br. s., 3 H) | HRMS (B) m/z 429.1441, (M + H)⁺, RT = 1.65 min. |
| 309: (R)-3-(6-chloro-2-(((S)-1-(1-(4-chlorophenyl)-1H-imidazol-4-yl)ethyl)amino)pyrimidin-4-yl)-4-((R)-1-hydroxyethyl)oxazolidin-2-one | (CD₃OD) 9.34 (s, 1 H), 7.95 (s, 1 H), 7.67-7.75 (m, 2 H), 7.60-7.67 (m, 2 H), 7.44 (s, 1 H), 5.34 (br. s., 1 H), 4.75-4.88 (m, 2 H), 4.52 (d, J = 9.8 Hz, 1 H), 4.36-4.45 (m, 1 H), 1.68 (d, J = 7.0 Hz, 3 H), 0.99 (br. s., 3 H) | HRMS (B) m/z 463.1056, (M + H)⁺, RT = 1.68 min. |
| 310: (R)-3-(6-chloro-2-(((S)-1-(1-(4-fluorophenyl)-1H-pyrazol-3-yl)ethyl)amino)pyrimidin-4-yl)-4-((R)-1-hydroxyethyl)oxazolidin-2-one | (cd3od) 8.04 (d, J = 2.3 Hz, 1 H), 7.71 (dd, J = 9.0, 4.7 Hz, 2 H), 7.35 (s, 1 H), 7.19 (t, J = 8.8 Hz, 2 H), 6.43 (d, J = 2.7 Hz, 1 H), 5.29 (q, J = 7.0 Hz, 1 H), 4.79-4.87 (m, 2 H), 4.52 (dd, J = 9.2, 2.5 Hz, 1 H), 4.35-4.44 (m, 1 H), 1.59 (d, J = 7.0 Hz, 3 H), 0.85 (br. s., 3 H) | HRMS (B) m/z 447.1346, (M + H)⁺, RT = 2.18 min. |
| 311: (R)-3-(2-(((S)-1-(2,4-dichlorophenyl)ethyl)amino)pyrimidin-4-yl)-4-((R)-1-hydroxyethyl)oxazolidin-2-one | (CD₃OD) 8.15 (d, J = 6.7 Hz, 1 H), 7.70 (d, J = 7.0 Hz, 1 H), 7.51 (d, J = 2.0 Hz, 1 H), 7.46 (d, J = 8.6 Hz, 1 H), 7.34 (dd, J = 8.6, 2.0 Hz, 1 H), 5.47 (d, J = 5.1 Hz, 1 H), 4.57 (dd, J = 9.0, 2.3 Hz, 2 H), 4.33-4.50 (m, 2 H), 3.80 (br. s., 2 H), 1.58 (d, J = 7.0 Hz, 6 H) | HRMS (B) m/z 397.0834, (M + H)⁺, RT = 1.77 min. |
| 312: (R)-3-(2-(((S)-1-(3,4-dichlorophenyl)ethyl)amino)pyrimidin-4-yl)-4-((R)-1-hydroxyethyl)oxazolidin-2-one | (CD₃OD) 8.13 (d, J = 6.7 Hz, 1 H), 7.70 (d, J = 7.0 Hz, 1 H), 7.57 (d, J = 2.0 Hz, 1 H), 7.51 (d, J = 8.2 Hz, 1 H), 7.33 (dd, J = 8.4, 2.2 Hz, 1 H), 5.19 (br. s., 1 H), 4.75-5.00 (m, 2 H), 4.58 (dd, J = 9.4, 2.3 Hz, 1 H), 4.34-4.51 (m, 1 H), 3.92 (br. s., 1 H), 1.59 (d, J = 6.7 Hz, 6 H) | HRMS (B) m/z 397.0831, (M + H)⁺, RT = 1.72 min. |

TABLE 30b-continued

Chemical name, NMR chemical shifts and LCMS
signal for each compound listed in Table 30a.

| Example: Name | $^1$H NMR (400 MHz, CDCl$_3$) δ ppm | LCMS |
|---|---|---|
| 313: (R)-3-(6-chloro-2-(((S)-1-(1-(4-chlorophenyl)-1H-pyrazol-3-yl)ethyl)amino)pyrimidin-4-yl)-4-((R)-1-hydroxyethyl)oxazolidin-2-one | (CDCl$_3$) 7.80 (d, J = 2.3 Hz, 1 H), 7.56 (d, J = 8.6 Hz, 2 H), 7.51 (s, 1 H), 7.42 (d, J = 8.6 Hz, 3 H), 6.39 (d, J = 2.3 Hz, 1H), 6.08 (br. s., 1 H), 5.22 (br. s., 1 H), 4.76 (ddd, J = 7.9, 5.0, 2.3 Hz, 1 H), 4.40-4.49 (m, 1 H), 4.31-4.39 (m, 1 H), 3.99 (br. s., 1 H), 1.61 (d, J = 7.0 Hz, 6 H) | HRMS (B) m/z 463.1056, (M + H)$^+$, RT = 2.34 min. |
| 314: (R)-3-(2-(((S)-1-(2,5-difluoro-4-(2,2,2-trifluoroethoxy)phenyl)ethyl)amino)pyrimidin-4-yl)-4-((R)-1-hydroxyethyl)oxazolidin-2-one | (CDCl$_3$) 10.88 (br. s., 1 H), 7.93 (d, J = 7.0 Hz, 1 H), 7.75 (d, J = 7.0 Hz, 1 H), 7.20-7.30 (m, 1 H), 6.83 (dd, J = 10.6, 6.7 Hz, 1 H), 5.34 (t, J = 6.8 Hz, 1 H), 4.85 (ddd, J = 7.4, 4.7, 2.0 Hz, 1 H), 4.61 (dd, J = 9.4, 2.0 Hz, 1 H), 4.34-4.52 (m, 3 H), 3.78-3.96 (m, 1 H), 1.61(d, J = 7.0 Hz, 3 H), 0.96 (d, J = 6.3 Hz, 3 H) | HRMS (B) m/z 463.1410, (M + H)$^+$, RT = 1.79 min. |
| 315: (R)-3-(2-(((S)-1-(2-fluoro-4-(2,2,2-trifluoroethoxy)phenyl)ethyl)amino)pyrimidin-4-yl)-4-((R)-1-hydroxyethyl)oxazolidin-2-one | (CDCl$_3$) 10.61 (d, J = 4.7 Hz, 1 H), 7.98 (d, J = 5.5 Hz, 1 H), 7.75 (d, J = 5.9 Hz, 1 H), 7.41 (t, J = 8.8 Hz, 1 H), 6.64-6.85(m, 2 H), 5.39 (t, J = 6.5 Hz, 1 H), 4.85 (ddd, J = 7.6, 4.9, 2.0 Hz, 1 H), 4.60 (dd, J = 9.8, 2.0 Hz, 1 H), 4.40-4.50 (m, 1 H), 4.35 (q, J = 8.2 Hz, 2 H), 3.79-3.96 (m, 1 H), 1.61 (d, J = 7.0 Hz, 3 H), 0.94 (d, J = 6.3 Hz, 3 H) | HRMS (B) m/z 445.1492, (M + H)$^+$, RT = 1.74 min. |
| 316: (R)-3-(2-(((S)-1-(3-fluoro-4-(2,2,2-trifluoroethoxy)phenyl)ethyl)amino)pyrimidin-4-yl)-4-((R)-1-hydroxyethyl)oxazolidin-2-one | (cdcl3) 10.84 (d, J = 3.9 Hz, 1 H), 7.92 (d, J = 7.0 Hz, 1 H), 7.73 (d, J = 7.0 Hz, 1 H), 7.09-7.20 (m, 2 H), 6.97-7.10 (m, 1 H), 4.93 (t, J = 6.7 Hz, 1 H), 4.78 (td, J = 5.1, 2.3 Hz, 1 H), 4.56 (dd, J = 9.4, 2.0 Hz, 1 H), 4.35-4.47 (m, 3 H), 3.64-3.75 (m, 1 H), 1.62 (d, J = 7.0 Hz, 3 H), 0.94 (d, J = 6.3 Hz, 3 H) | HRMS (B) m/z 445.1491, (M + H)$^+$, RT = 1.69 min. |
| 317: (R)-3-(2-(((S)-1-(5-bromopyridin-2-yl)ethyl)amino)pyrimidin-4-yl)-4-((R)-1-hydroxyethyl)oxazolidin-2-one | (CDCl$_3$) 11.02 (d, J = 6.7 Hz, 1 H), 8.59 (d, J = 1.6 Hz, 1 H), 8.03 (dd, J = 8.4, 1.8 Hz, 1 H), 7.94 (d, J = 6.7 Hz, 1 H), 7.76(d, J = 6.7 Hz, 1 H), 7.58 (d, J = 8.6 Hz, 1 H), 5.40 (t, J = 7.0 Hz, 1 H), 4.83-4.95 (m, 1 H), 4.62 (dd, J = 9.4, 1.6 Hz, 1 H), 4.40-4.51 (m, 1 H), 3.70-3.84 (m, 1 H), 1.70 (d, J = 7.0 Hz, 3H), 1.02 (d, J = 6.3 Hz, 3 H) | HRMS (B) m/z 408.0668, (M + H)$^+$, RT = 1.29 min. |
| 318: (R)-3-(2-(((R)-1-(5-bromopyridin-2-yl)ethyl)amino)pyrimidin-4-yl)-4-((R)-1-hydroxyethyl)oxazolidin-2-one | (CDCl$_3$) 10.97 (d, J = 4.3 Hz, 1 H), 8.62 (d, J = 1.6 Hz, 1 H), 8.09 (dd, J = 8.2, 1.6 Hz, 1 H), 7.99 (d, J = 6.7 Hz, 1 H), 7.77(d, J = 6.7 Hz, 1 H), 7.63 (d, J = 8.2 Hz, 1 H), 5.37 (t, J = 6.5 Hz, 1 H), 4.59-4.74 (m, 2 H), 4.29-4.46 (m, 2 H), 1.70 (d, J = 6.7 Hz, 3 H), 1.17 (d, J = 6.3 Hz, 3 H) | HRMS (B) m/z 408.0670, (M + H)$^+$, RT = 1.33 min. |
| 319: (R)-3-(2-(((S)-1-(4,5-dichloro-2-fluorophenyl)ethyl)amino)pyrimidin-4-yl)-4-((R)-1-hydroxyethyl)oxazolidin-2-one | (CD$_3$OD) 8.15 (d, J = 7.0 Hz, 1 H), 7.70 (d, J = 6.3 Hz, 1 H), 7.58 (d, J = 7.0 Hz, 1 H), 7.41 (d, J = 9.8 Hz, 1 H), 5.42 (d, J = 3.5 Hz, 1 H), 4.87 (d, J = 5.5 Hz, 2 H), 4.58 (dd, J = 9.0, 2.3 Hz, 1 H), 4.38-4.50 (m, 1 H), 3.91 (br. s., 1 H), 1.60 (d, J = 7.0 Hz, 3 H), 0.84 (br. s., 3H) | HRMS (B) m/z 415.0733, (M + H)$^+$, RT = 1.84 min. |
| 320: (R)-3-(2-(((S)-1-(2,5-difluoro-4-(4-methyl-1H-imidazol-1-yl)phenyl)ethyl)amino)pyrimidin-4-yl)-4-((R)-1-hydroxyethyl)oxazolidin-2-one | (CD$_3$OD) 9.26 (s, 1 H), 8.19 (d, J = 7.0 Hz, 1 H), 7.77 (d, J = 6.7 Hz, 1 H), 7.54-7.71 (m, 3 H), 5.51 (d, J = 5.9 Hz, 1 H), 4.81-4.90 (m, 1 H), 4.58 (dd, J = 9.2, 2.2 Hz, 1 H), 4.41-4.51 (m, 1 H), 3.75 (br. s., 1 H), 2.44 (s, 3 H), 1.66 (d, J = 6.7 Hz, 3 H), 0.87 (br. s., 3 H) | HRMS (B) m/z 445.1794, (M + H)$^+$, RT = 1.02 min. |
| 321: (R)-3-(5-chloro-2-(((S)-1-(4,5-dichloro-2-fluorophenyl)ethyl)amino)pyrimidin-4-yl)-4-((R)-1-hydroxyethyl)oxazolidin-2-one | (CD$_3$OD) 8.20 (s, 1 H), 7.43 (d, J = 7.0 Hz, 1 H), 7.26 (d, J = 9.4 Hz, 1 H), 5.11 (br. s., 1 H), 4.68-4.90 (m, 1 H), 4.43 (t, J = 8.2 Hz, 1 H), 4.25-4.37 (m, 1 H), 3.44-3.86 (m, 1 H), 1.42 (d, J = 7.0 Hz, 3 H), 0.73 (br. s., 3 H) | HRMS (B) m/z 449.0347, (M + H)$^+$, RT = 2.14 min. |
| 322: (R)-3-(2-(((S)-1-(2,5-difluoro-4-(2-methylpyridin-4-yl)phenyl)ethyl)amino)pyrimidin-4-yl)-4-((R)-1-hydroxyethyl)oxazolidin-2-one | (CD$_3$OD) 8.74 (d, J = 6.3 Hz, 1 H), 8.11-8.22 (m, 2 H), 8.07 (d, J = 6.3 Hz, 1 H), 7.59-7.77 (m, 2 H), 7.40-7.53 (m, 1H), 5.48 (d, J = 5.5 Hz, 1 H), 4.77-5.01 (m, 2 H), 4.57 (dd, J = 9.0, 2.3 Hz, 1 H), 4.38-4.51 (m, 1 H), 2.83 (s, 3 H), 1.66 (d, J = 7.0 Hz, 2 H), 0.82 (br. s., 3 H) | HRMS (B) m/z 456.1840, (M + H)$^+$, RT = 1.10 min. |

TABLE 30b-continued

Chemical name, NMR chemical shifts and LCMS signal for each compound listed in Table 30a.

| Example: Name | ¹H NMR (400 MHz, CDCl₃) δ ppm | LCMS |
|---|---|---|
| 323: (R)-3-(2-(((S)-1-(2,5-difluoro-4-(6-methylpyridin-3-yl)phenyl)ethyl)amino)pyrimidin-4-yl)-4-((R)-1-hydroxyethyl)oxazolidin-2-one | (CD₃OD) 8.91 (s, 1 H), 8.60 (d, J = 8.2 Hz, 1 H), 8.18 (d, J = 6.3 Hz, 1 H), 7.95 (d, J = 8.2 Hz, 1 H), 7.73 (d, J = 6.3 Hz, 1H), 7.54 (dd, J = 10.2, 6.7 Hz, 1 H), 7.42 (dd, J = 10.8, 6.1 Hz, 1 H), 5.49 (d, J = 4.7 Hz, 1 H), 4.88 (s, 1 H), 4.58 (dd, J = 9.2, 2.2 Hz, 1 H), 4.39-4.51(m, 1 H), 3.83 (br. s., 1 H), 2.82 (s, 3 H), 1.66 (d, J = 7.0 Hz, 3 H), 0.83 (br. s., 3 H) | HRMS (B) m/z 456.1847, (M + H)⁺, RT = 1.18 min. |
| 324: (R)-3-(2-(((S)-1-(2,5-difluoro-4-(2-(trifluoromethyl)pyridin-4-yl)phenyl)ethyl)amino)pyrimidin-4-yl)-4-((R)-1-hydroxyethyl)oxazolidin-2-one | (CD₃OD) 8.80 (d, J = 5.1 Hz, 1 H), 8.18 (d, J = 6.7 Hz, 1 H), 7.97-8.07 (m, 1 H), 7.77-7.90 (m, 2 H), 7.54 (dd, J = 10.6,6.3 Hz, 1 H), 7.40 (dd, J = 11.0, 6.3 Hz, 1 H), 5.49 (br. s., 1 H), 4.79-5.02 (m, 1 H), 4.53-4.68 (m, 1 H), 4.39-4.52 (m, 1 H), 3.80 (br. s., 1 H), 1.61-1.73 (m, 6 H) | HRMS (B) m/z 510.1560, (M + H)⁺, RT = 1.94 min. |
| 325: (R)-3-(2-(((S)-1-(2,5-difluoro-4-(6-(trifluoromethyl)pyridin-3-yl)phenyl)ethyl)amino)pyrimidin-4-yl)-4-((R)-1-hydroxyethyl)oxazolidin-2-one | (CD₃OD) 8.90 (s, 1 H), 8.12-8.29 (m, 2 H), 7.92 (d, J = 8.2 Hz, 1 H), 7.75 (d, J = 6.7 Hz, 1 H), 7.43-7.55 (m, 1 H), 7.37(dd, J = 10.8, 6.1 Hz, 1 H), 5.47 (br. s., 1 H), 4.81-4.97 (m, 1 H), 4.58 (dd, J = 9.0, 2.3 Hz, 1 H), 4.39-4.51 (m, 1 H), 3.82 (br. s., 1 H), 1.66 (d, J = 7.0 Hz, 3 H), 0.82 (br. s., 3 H) | HRMS (B) m/z 510.1565, (M + H)⁺, RT = 1.98 min. |
| 326: (R)-4-((R)-1-hydroxyethyl)-3-(2-(((S)-1-(4-isobutoxyphenyl)ethyl)amino)pyrimidin-4-yl)oxazolidin-2-one | | HRMS (B) m/z 401.2188 (M + H)⁺; Rt 1.80 min |
| 327: (R)-3-(5-fluoro-2-(((S)-1-(2-fluoro-4-methoxyphenyl)-ethyl)amino)pyrimidin-4-yl)-4-((R)-1-hydroxy-ethyl)oxazolidin-2-one | (CD₃OD) 8.22 (d, J = 3.13 Hz, 1H), 7.14-7.41 (m, 1H), 6.55-6.79 (m, 2H), 5.19 (q, J = 7.04 Hz, 1H), 4.68 (d, J = 3.91 Hz, 1H), 4.43-4.60 (m, 2H), 3.92 (d, J = 17.22 Hz, 1H), 3.78 (s, 3H), 1.50 (d, J = 6.65 Hz, 3H) | HRMS (B) m/z 395.1525 (M + H)⁺; Rt 1.78 min |
| 328: (R)-3-(2-(((S)-1-(2,3-difluorophenyl)ethyl)amino)pyrimidin-4-yl)-4-((R)-1-hydroxyethyl)oxazolidin-2-one | 1H NMR (400 MHz, <cd3od>) 0.83 (br. s., 3 H) 1.60 (d, J = 6.65 Hz, 3 H) 4.40-4.45 (m, 1 H) 4.56 (d, J = 7.43 Hz, 1 H) 4.85 (m, 2H) 5.39-5.47 (m, 1 H) 7.11-7.21 (m, 3 H) 7.61-7.68 (m, 1 H) 8.12 (d, J = 6.65 Hz, 1 H) | HRMS (B) m/z 365.1414, (M + H)⁺, RT = 1.49 min. |
| 329: (R)-3-(2-(((S)-1-(2,3-difluorophenyl)ethyl)amino)-5-fluoropyrimidin-4-yl)-4-((R)-1-hydroxyethyl)oxazolidin-2-one | 1H NMR (400 MHz, <cd3od>) 0.81 (br. s., 3 H) 1.52 (d, J = 7.04 Hz, 3 H) 3.81-3.96 (m, 1 H) 4.44-4.56 (m, 2 H) 4.57-4.68 (m, 1 H) 5.21-5.32 (m, 1 H) 7.01-7.22 (m, 3H) 8.21 (d, J = 3.08 Hz, 1 H) | HRMS (B) m/z 383.1327, (M + H)⁺, RT = 1.81 min. |
| 330: (R)-3-(2-(((S)-1-(3,4-difluorophenyl)ethyl)amino)-5-fluoropyrimidin-4-yl)-4-((R)-1-hydroxyethyl)oxazolidin-2-one | 1H NMR (400 MHz, <cd3od>) 0.83 (br. s., 3 H) 1.48 (d, J = 7.04 Hz, 3 H) 3.81-3.97 (m, 1 H) 4.39-4.57 (m, 2 H) 4.59-4.68 (m, 1 H) 4.89-5.01 (m, 2 H) 7.11-7.32 (m, 3 H) 8.21 (d, J = 3.13 Hz, 1 H) | HRMS (B) m/z 383.1328, (M + H)⁺, RT = 1.81 min. |
| 331: (R)-3-(2-(((S)-1-(2,4-difluorophenyl)ethyl)amino)-5-fluoropyrimidin-4-yl)-4-((R)-1-hydroxyethyl)oxazolidin-2-one | 1H NMR (400 MHz, <cd3od>) 0.73 (br. s., 3 H) 1.41 (d, J = 6.99 Hz, 3 H) 3.81 (br. s., 1 H) 4.32-4.47 (m, 2 H) 4.54 (d, J = 3.03 Hz, 1 H) 5.11 (d, J = 6.94 Hz, 1 H) 6.73-6.89 (m, 2 H) 7.29 (td, J = 8.57, 6.53 Hz, 1 H) 8.11 (d, J = 2.98 Hz, 1 H) | HRMS (B) m/z 383.1323, (M + H)⁺, RT = 1.80 min. |
| 332: (R)-3-(2-(((S)-1-(3,5-difluorophenyl)ethyl)amino)-5-fluoropyrimidin-4-yl)-4-((R)-1-hydroxyethyl)oxazolidin-2-one | | HRMS (B) m/z 383.1328, (M + H)⁺, RT = 1.81 min. |

TABLE 30b-continued

Chemical name, NMR chemical shifts and LCMS signal for each compound listed in Table 30a.

| Example: Name | ¹H NMR (400 MHz, CDCl₃) δ ppm | LCMS |
|---|---|---|
| 333: (R)-3-(5-chloro-2-(((S)-1-(5-(2-(trifluoromethyl)pyridin-4-yl)pyrimidin-2-yl)ethyl)amino)pyrimidin-4-yl)-4-((R)-1-hydroxyethyl)oxazolidin-2-one | 1H NMR (400 MHz, <cd3od>) 1.26-1.39 (m, 3 H) 1.61 (d, J = 7.04 Hz, 3 H) 4.74-4.79 (m, 3 H) 4.96 (br. s., 1 H) 5.13 (d, J = 7.04 Hz, 1 H) 7.69 (d, J = 7.83 Hz, 1 H) 7.99 (d, J = 4.30 Hz, 1 H) 8.17 (s, 1 H) 8.29 (d, J = 8.22 Hz, 1 H) 8.80 (d, J = 5.09 Hz, 1 H) 8.96 (s, 1 H) | LCMS m/z 509.2, (M + H)⁺, RT = 0.69 min. |

Example 334

(R)-3-(5-fluoro-2-(((S)-1-(6-(2,2,2-trifluoroehoxy)pyridin-3-yl)ethyl)amino)pyrimidin-4-yl)-4-((R)-1-hydroxyethyl)oxazolidin-2-one

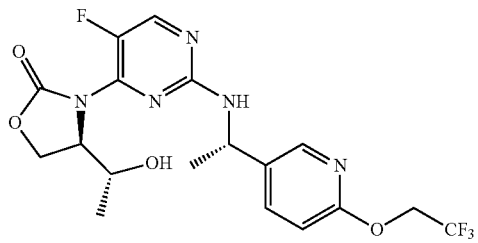 [SMILES: C[C@H](Nc1ncc(F)c(N2C(=O)OC[C@@H]2[C@@H](C)O)n1)c1ccc(OCC(F)(F)F)nc1]

To (R)-3-(2-(((S)-1-(5-chloro-6-(2,2,2-trifluoroethoxy)pyridin-3-yl)ethyl)amino)-5-fluoropyrimidin-4-yl)-4-((R)-1-hydroxyethyl)oxazolidin-2-one (20 mg, 0.042 mmol) in MeOH (10 mL) was added Pd(OH)₂ (10 mg, 0.014 mmol). The reaction was purged with N₂ and H₂ three times each. A hydrogen balloon was applied to the reaction. The reaction mixture was stirred for one hour and concentrated. The residue was applied directly to HPLC separation to give product (15 mg) as a trifluoroacetic acid salt. 1HNMR (CD3OD) δ ppm 8.21 (d, J=3.1 Hz, 1H), 7.38 (t, J=8.0 Hz, 1H), 7.12-7.28 (m, 2H), 4.88-5.00 (m, 1H), 4.59 (br. s., 1H), 4.42-4.55 (m, 2H), 3.89 (br. s., 1H), 1.49 (d, J=7.0 Hz, 3H), 0.81 (br. s., 3H). HRMS (B) m/z 446.1448 (M+H)+, RT=1.90 min.

Example 335

(R)-3-(2-(((S)-1-(4-(difluoromethyl)-2-fluorophenyl)ethylamino)-5-fluoropyrimidin-4-yl)-4-((R)-1-hydroxyethyl)oxazolidin-2-one

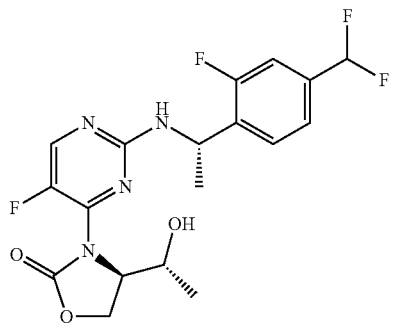 [SMILES: C[C@H](Nc1ncc(F)c(N2C(=O)OC[C@@H]2[C@@H](C)O)n1)c1ccc(C(F)F)cc1F]

A mixture of (R)-4-((R)-1-tert-butoxyethyl)-3-(2-chloro-5-fluoropyrimidin-4-yl)oxazolidin-2-one (40 mg, 0.126 mmol), (S)-1-(4-(difluoromethyl)-2-fluorophenyl)ethanamine (36.9 mg, 0.164 mmol) and Huenig's base (0.11 mL, 0.629 mmol) in DMSO (0.25 mL) under argon atmosphere was heated at ~120° C. for ~16 hr in a sealed vial. The mixture was allowed to cool to room temperature and diluted with ethyl acetate and water. The aqueous layer was extracted with ethyl acetate (2×), the combined organic layers were washed with brine and dried over sodium sulfate, filtered off and concentrated under reduced pressure. The residue was dissolved in DCM (0.8 mL) and cooled to 0° C. To the mixture was added trifluoroacetic acid (0.3 mL), the ice-bath was removed and the mixture was stirred for ~1 hr at room temperature. The mixture was diluted with methanol (2 mL) and concentrated under reduced pressure. The residue was dissolved in DMSO/water (~9/1), filtered through a syringe filter, and purified by reverse phase HPLC. Selected fractions were collected and lyophilized providing (R)-3-(2-(((S)-1-(4-(difluoromethyl)-2-fluorophenyl)ethylamino)-5-fluoropyrimidin-4-yl)-4-((R)-1-hydroxyethyl)oxazolidin-2-one as its trifluoroacetic acid salt (19 mg) as a white solid. ¹H NMR (400 Mhz, CD₃OD) δ ppm 9.77 (d, J=2.7 Hz, 1H), 9.06 (t, J=7.8 Hz, 1H), 8.80-8.87 (m, 2H), 8.12-8.44 (m, 1H), 6.82 (q, J=6.7 Hz, 1H), 6.12-6.21 (m, 1H), 5.99-6.11 (m, 2H), 5.30-5.52 (m, 1H), 3.09 (d, J=7.0 Hz, 3H), 2.14-2.51 (m, 3H). HRMS m/z 415.1390 (M+H)+; Rt-1.84 min.

The following Example was prepared using a method similar to that described for the preparation of Example 335

Example 336

(R)-3-(2-(((S)-1-(4-(1,1-difluoroethyl)-2-fluorophenyl)ethyl)amino)-5-fluoropyrimidin-4-yl)-4-((R)-1-hydroxyethyl)oxazolidin-2-one

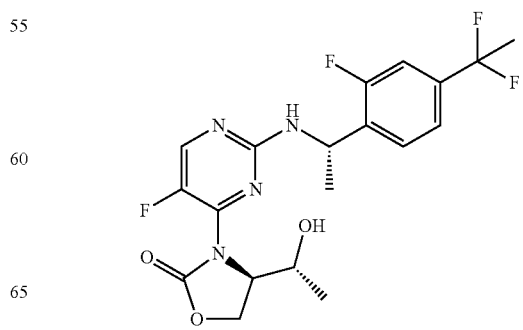

¹H NMR (400 Mhz, CCl₃D) δ ppm 8.19 (d, J=2.7 Hz, 1H), 7.33-7.44 (m, 1H), 7.18-7.30 (m, 2H), 5.49 (m, J=5.9 Hz, 1H), 5.19 (m, J=6.7, 6.7 Hz, 1H), 4.41-4.52 (m, 2H), 4.34 (m, J=7.2, 3.7 Hz, 1H), 1.90 (t, J=18.2 Hz, 3H), 1.51-1.60 (m, 3H), 0.80-1.00 (m, 3H). HRMS m/z 429.1553 (M+H)+; Rt-1.98 min.

Example 337

(R)-3-(6-chloro-2-(((S)-1-(4-(difluoromethyl)-2-fluorophenyl)ethyl)amino)pyrimidin-4-yl)-4-((R)-1-hydroxyethyl)oxazolidin-2-one

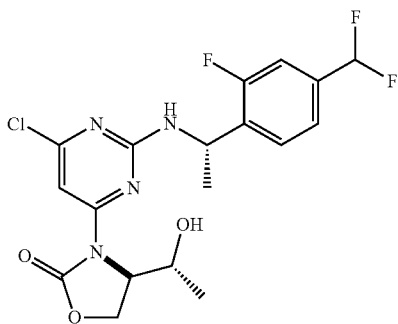 [SMILES: C[C@H](Nc1nc(Cl)cc(N2C(=O)OC[C@@H]2[C@@H](C)O)n1)c1ccc(C(F)F)cc1F]

A mixture of (R)-4-((R)-1-(tert-butoxy)ethyl)-3-(2,6-dichloropyrimidin-4-yl)oxazolidin-2-one (55 mg, 0.165 mmol), (S)-1-(4-(difluoromethyl)-2-fluorophenyl)ethanamine hydrochloride (35 mg, 0.155 mmol) and Huenig's base (0.072 mL, 0.411 mmol) in DMSO (0.6 mL) under argon atmosphere was heated at ~85° C. for ~3 hr in a sealed vial. The mixture was allowed to cool to room temperature and diluted with ethyl acetate and water. The aqueous layer was extracted with ethyl acetate (2×), the combined organic layers were washed with brine and dried over sodium sulfate, filtered off and concentrated under reduced pressure. The residue was dissolved in DCM (0.8 mL) and cooled to 0° C. To the mixture was added trifluoroacetic acid (0.4 mL), the ice-bath was removed and the mixture was stirred for ~1 hr at room temperature. The mixture was diluted with methanol (2 mL) and concentrated under reduced pressure. The residue was dissolved in DMSO/water (~9/1), filtered through a syringe filter, and purified by reverse phase HPLC. Selected fractions were collected and lyophilized providing (R)-3-(6-chloro-2-(((S)-1-(4-(difluoromethyl)-2-fluorophenyl)ethyl)amino)pyrimidin-4-yl)-4-((R)-1-hydroxyethyl)oxazolidin-2-one as its trifluoroacetic acid salt (8.2 mg) as a white solid.

¹H NMR (400 Mhz, CD₃OD) δ ppm 7.50 (m, J=7.60, 7.6 Hz, 1H), 7.25-7.38 (m, 3H), 6.76 (t, J=1.0 Hz, 1H), 5.31-5.43 (m, 1H), 4.72-4.81 (m, 1H), 4.52 (m, J=7.0 Hz, 1H), 4.34-4.44 (m, 1H), 1.55 (d, J=7.0 Hz, 3H), 0.54-0.75 (m, CH₃). HRMS m/z 431.1097 (M+H)+; Rt-2.21 min.

The following Example was prepared using a method similar to that described for the preparation of Example 337

Example 338

(R)-3-(6-chloro-2-(((S)-1-(4-(1,1-difluoroethyl)-2-fluorophenyl)ethyl)amino)pyrimidin-4-yl)-4-((R)-1-hydroxyethyl)oxazolidin-2-one

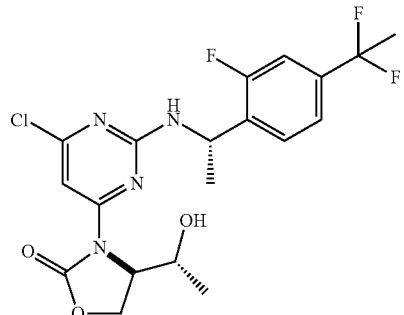

¹H NMR (400 Mhz, CD₃OD) δ ppm 7.45 (m, J=7.6, 7.6 Hz, 1H), 7.21-7.36 (m, 3H), 5.34 (m, J=7.0 Hz, 1H), 4.71-4.79 (m, 1H), 4.45-4.55 (m, 1H), 4.32-4.41 (m, 1H), 1.89 (t, J=18.2 Hz, 3H), 1.52 (d, J=7.0 Hz, 3H), 0.55-0.71 (m, CH₃). HRMS m/z 445.1257 (M+H)+; Rt-2.32 min.

Example 339

(R)-3-(6-chloro-2-(((S)-1-(5-phenylthiophen-2-yl)ethyl)amino)pyrimidin-4-yl)-4-((R)-1-hydroxyethyl)oxazolidin-2-one

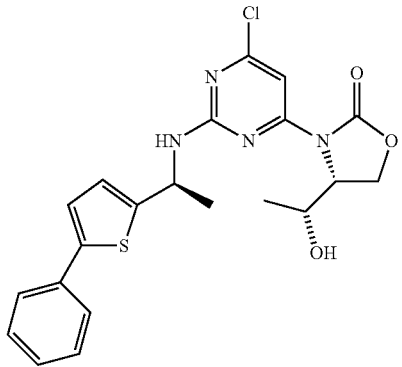 [SMILES: C[C@H](Nc1nc(Cl)cc(N2C(=O)OC[C@@H]2[C@@H](C)O)n1)c1ccc(-c2ccccc2)s1]

A solution of (R)-3-(2,6-dichloropyrimidin-4-yl)-4-((R)-1-hydroxyethyl)oxazolidin-2-one (0.040 g, 0.144 mmol), (S)-1-(5-(pyridin-2-yl)thiophen-2-yl)ethanamine hydrochloride (0.083 g, 0.346 mmol, 2.4 equiv) and N-ethyl-N-isopropylpropan-2-amine (0.075 mL, 0.432 mmol, 3.0 equiv) in DMSO (0.72 mL) was heated at 100° C. for 1 h. Purification by reverse phase HPLC separated the regioisomeric products and provided the trifluoroacetate salt of (R)-3-(6-chloro-2-(((S)-1-(5-phenylthiophen-2-yl)ethyl)amino)pyrimidin-4-yl)-4-((R)-1-hydroxyethyl)oxazolidin-2-one (7.0 mg, white solid) in 8% yield. ¹H NMR (400 MHz, CDCl₃) δ 7.59 (s, 1H), 7.56-7.52 (m, 2H), 7.40-7.34 (m, 2H), 7.29 (d, J=7.4 Hz, 1H), 7.15 (d, J=3.6 hz, 1H), 6.93 (br s, 1H), 5.21 (m, 1H), 4.78-4.68 (m, 1H), 4.50-4.31 (m, 2H), 3.85 (m, 1H), 1.69 (d, J=6.9 Hz, 3H), 0.93 (br s, 3H); HRMS m/z 445.1109 (M+H)⁺; Rt-2.49 min.

The following Example was prepared using a method similar to that described for the preparation of Example 339

Example 340

(R)-3-(6-chloro-2-(((S)-1-(5-(pyridin-2-yl)thiophen-2-yl)ethyl)amino)pyrimidin-4-yl)-4-((R)-1-hydroxyethyl)oxazolidin-2-one

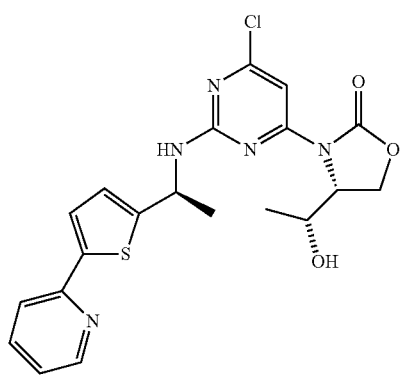 [SMILES: C[C@H](Nc1nc(Cl)cc(N2C(=O)OC[C@@H]2[C@@H](C)O)n1)c1ccc(-c2ccccn2)s1]

$^1$H NMR (400 MHz, CDCl$_3$) δ ppm 8.84 (d, J=5.0 Hz, 1H), 8.05 (t, J=7.8 Hz, 1H), 7.77-7.70 (m, 2H), 7.60 (s, 1H), 7.47 (t, J=6.5 Hz, 1H), 7.13 (d, J=3.9 Hz, 1H), 5.19 (m, 1H), 4.87 (m, 1H), 4.62 (m, 1H), 4.37 (t, J=9.0 Hz, 1H), 3.61 (m, 1H), 1.70 (d, J=7.0 Hz, 3H), 0.89 (br s, 3H). HRMS m/z 446.1054 (M+H)$^+$; Rt-2.04

Example 341

1:1 TFA:DCM

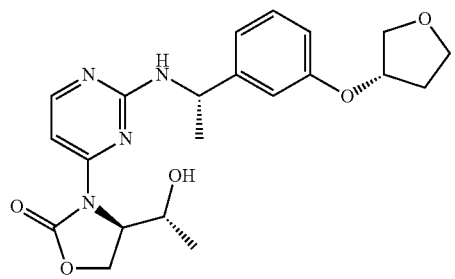 [SMILES: C[C@H](Nc1nccc(N2C(=O)OC[C@@H]2[C@@H](C)O)n1)c1cccc(O[C@H]2CCOC2)c1]

A solution of (R)-4-((R)-1-hydroxyethyl)-3-(2-(((S)-1-(3-((S)-tetrahydrofuran-3-yloxy)phenyl)ethylamino)pyrimidin-4-yl)oxazolidin-2-one (56.5 mg, 0.12 mmol) in DCM (0.6 ml) was treated with TFA (0.6 ml) at room temperature. The resulting solution was let sit for 2 hours, then concentrated. The crude material was purified by reverse phase HPLC. Product fractions were combined and lyophilized to afford (R)-4-((R)-1-hydroxyethyl)-3-(2-(((S)-1-(3-((S)-tetrahydrofuran-3-yloxy)phenyl)ethylamino)pyrimidin-4-yl)oxazolidin-2-one (15.2 mg, 0.036 mmol, 30% yield) as a TFA salt. $^1$H NMR (400 MHz, DMSO-d6) δ 0.65 (br. s., 3H) 1.41 (d, J=6.99 Hz, 3H) 1.84-1.94 (m, 1H) 2.10-2.22 (m, 1H) 3.67-3.89 (m, 4H) 4.33-4.47 (m, 2H) 4.70-4.77 (m, 1H) 4.96 (dd, J=6.06, 4.60 Hz, 1H) 5.01-5.11 (m, 1H) 6.73 (dd, J=8.07, 2.05 Hz, 1H) 6.89-6.97 (m, 2H) 7.19 (t, J=7.85 Hz, 1H) 7.24 (d, J=6.06 Hz, 1H) 8.14 (br. s., 1H). LCMS m/z 415.3 (M+H)$^+$, Rt 0.55 min. HRMS(A) m/z 415.1981 (M+H)$^+$, Rt 1.33 min.

The compounds in Table 31a were prepared using methods similar to those described for the preparation of Example 341.

TABLE 31a

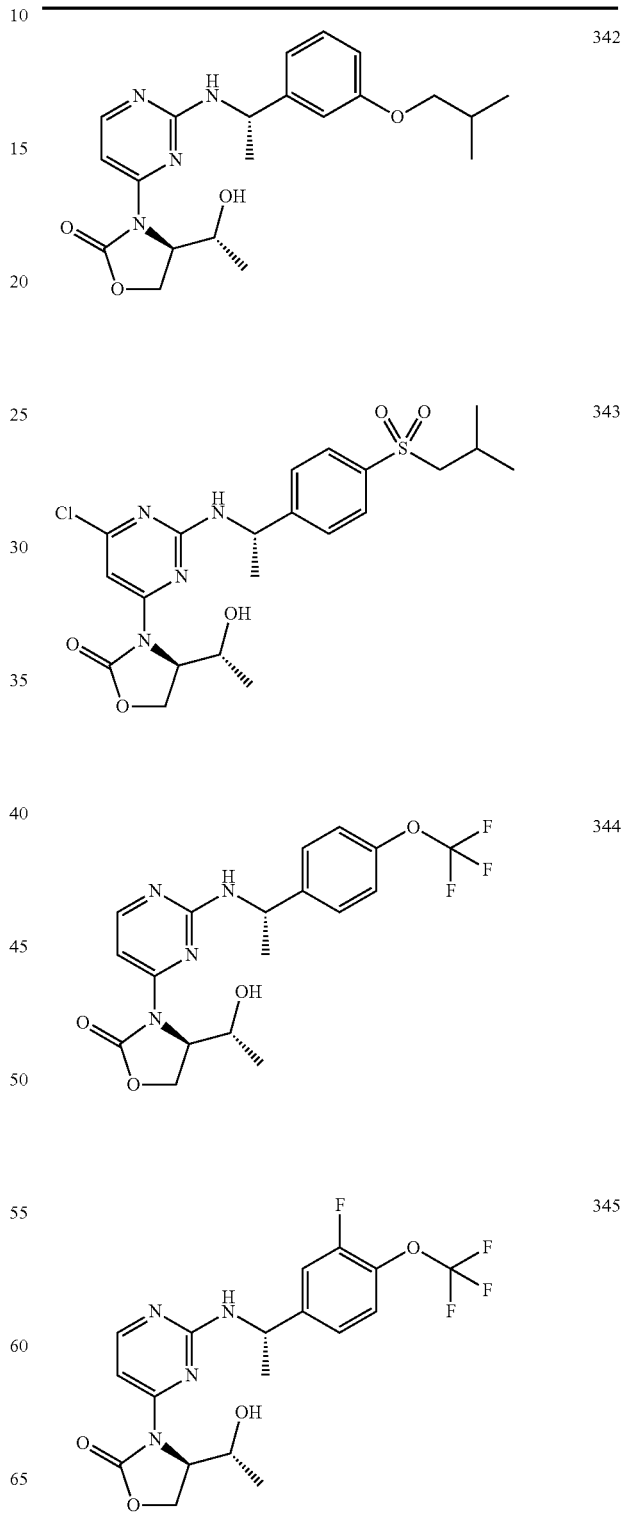

TABLE 31a-continued
| | |
|---|---|
| 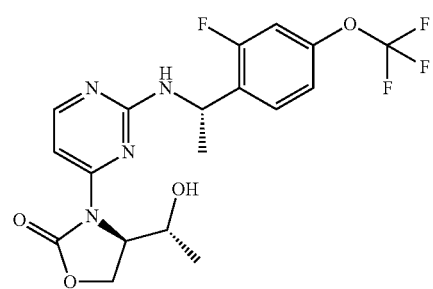 [SMILES: C[C@H](Nc1nccc(N2C(=O)OC[C@@H]2[C@@H](C)O)n1)c1ccc(OC(F)(F)F)cc1F] | 346 |
| 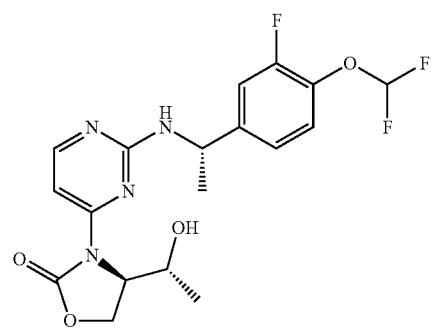 [SMILES: C[C@H](Nc1nccc(N2C(=O)OC[C@@H]2[C@@H](C)O)n1)c1ccc(OC(F)F)c(F)c1] | 347 |
| 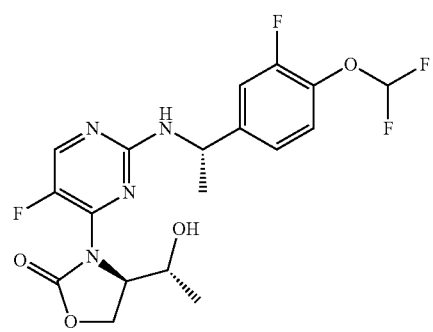 [SMILES: C[C@H](Nc1ncc(F)c(N2C(=O)OC[C@@H]2[C@@H](C)O)n1)c1ccc(OC(F)F)c(F)c1] | 348 |
| 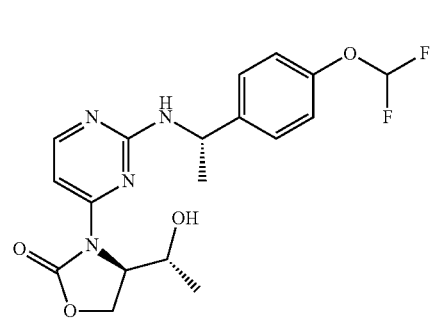 [SMILES: C[C@H](Nc1nccc(N2C(=O)OC[C@@H]2[C@@H](C)O)n1)c1ccc(OC(F)F)cc1] | 349 |
| 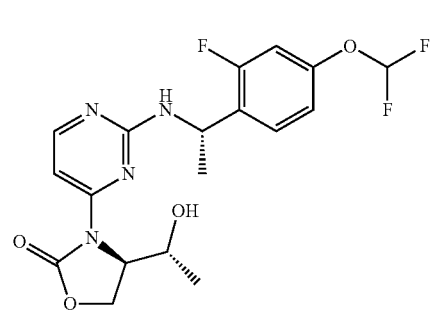 [SMILES: C[C@H](Nc1nccc(N2C(=O)OC[C@@H]2[C@@H](C)O)n1)c1ccc(OC(F)F)cc1F] | 350 |
TABLE 31a-continued
| | |
|---|---|
| 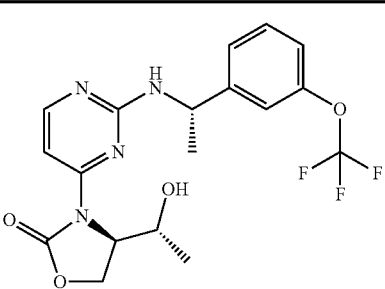 | 351 |
| 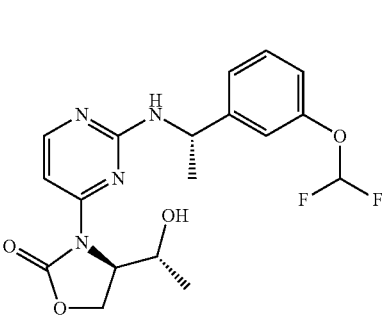 [SMILES: C[C@H](Nc1nccc(N2C(=O)OC[C@@H]2[C@@H](C)O)n1)c1cccc(OC(F)(F)F)c1] | 352 |
| 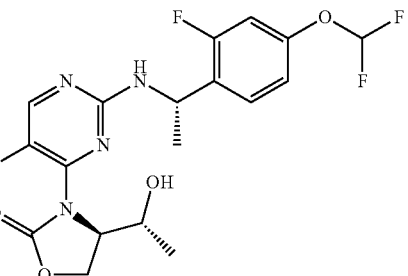 | 353 |
| 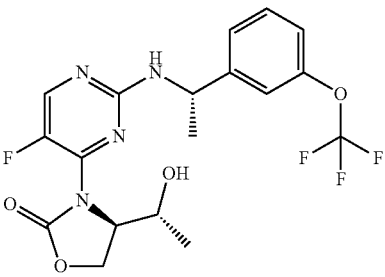 [SMILES: C[C@H](Nc1ncc(F)c(N2C(=O)OC[C@@H]2[C@@H](C)O)n1)c1cccc(OC(F)(F)F)c1] | 354 |
| 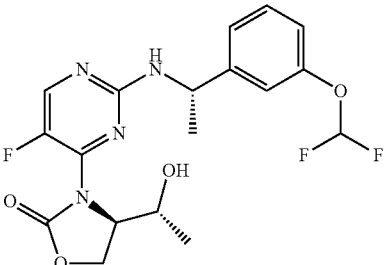 | 355 |

TABLE 31b

Chemical name, NMR chemical shifts and LCMS
signal for each compound listed in Table 31a.

| Example: Name | ¹H NMR (400 MHz) d ppm | LCMS |
|---|---|---|
| 342: (R)-4-((R)-1-hydroxyethyl)-3-(2-((S)-1-(3-isobutoxyphenyl)ethylamino)pyrimidin-4-yl)oxazolidin-2-one | (DMSO-d6) δ 0.93 (s, 3 H) 0.95 (s, 3 H) 1.41 (d, J = 6.99 Hz, 3 H) 1.96 (dquin, J = 13.30, 6.64, 6.64, 6.64, 6.64 Hz, 1 H) 3.55-3.89 (m, 4 H) 4.34-4.41 (m, 1 H) 4.42-4.48 (m, 1 H) 4.71-4.78 (m, 1 H) 5.06 (br. s., 1 H) 6.73 (dd, J = 8.14, 1.93 Hz, 1 H) 6.87-6.99 (m, 2 H) 7.17 (t, J = 7.87 Hz, 1 H) 7.23 (d, J = 6.02 Hz, 1 H) 8.13 (br. s., 1 H) | HRMS m/z 401.2189 (M + H)⁺; Rt-1.86 min |
| 343: (R)-3-(6-chloro-2-(((S)-1-(4-(isobutylsulfonyl)phenyl)ethyl)amino)pyrimidin-4-yl)-4-((R)-1-hydroxyethyl)oxazolidin-2-one | (DMSO-d6) δ 0.55 (d, J = 6.31 Hz, 3 H) 0.94 (dd, J = 6.70, 1.91 Hz, 6 H) 1.43 (d, J = 6.85 Hz, 3 H) 1.97 (dt, J = 13.11, 6.70 Hz, 1 H) 3.14 (d, J = 6.36 Hz, 2 H) 4.31-4.49 (m, 3 H) 4.71 (br. s., 1 H) 5.09 (t, J = 7.19 Hz, 1 H) 7.17 (s, 1 H) 7.61 (d, J = 8.22 Hz, 2 H) 7.83 (d, J = 8.31 Hz, 2 H) 8.49 (d, J = 7.78 Hz, 1 H) | HRMS m/z 483.1472 (M + H)⁺; Rt-2.10 min |
| 344: (R)-4-((R)-1-hydroxyethyl)-3-(2-(((S)-1-(4-(trifluoromethoxy)phenyl)ethyl)amino)pyrimidin-4-yl)oxazolidin-2-one | (DMSO-d6) δ 0.59 (br. s., 3 H) 1.44 (d, J = 6.99 Hz, 3 H) 3.83 (br. s., 1 H) 4.34-4.41 (m, 1 H) 4.41-4.47 (m, 1 H) 4.70-4.76 (m, 2 H) 5.09 (quin, J = 7.24 Hz, 1 H) 7.24 (d, J = 6.02 Hz, 1 H) 7.28 (d, J = 7.97 Hz, 2 H) 7.49 (d, J = 8.61 Hz, 2 H) 8.16 (br. s., 1 H) 8.24 (br. s., 1 H) | HRMS m/z 413.1435 (M + H)⁺; Rt-1.72 min |
| 345: (R)-3-(2-(((S)-1-(3-fluoro-4-(trifluoromethoxy)phenyl)ethyl)amino)pyrimidin-4-yl)-4-((R)-1-hydroxyethyl)oxazolidin-2-one | (DMSO-d6) δ 0.57 (br. s., 3 H) 1.43 (d, J = 7.04 Hz, 3 H) 4.31-4.47 (m, 3 H) 4.71 (br. s., 1 H) 5.08 (t, J = 7.16 Hz, 1 H) 7.23 (d, J = 5.87 Hz, 1 H) 7.29 (d, J = 8.66 Hz, 1 H) 7.42-7.52 (m, 2 H) 8.09 (br. s., 1 H) 8.16 (br. s., 1 H) | HRMS m/z 431.1345 (M + H)⁺; Rt-1.83 min |
| 346: (R)-3-(2-(((S)-1-(2-fluoro-4-(trifluoromethoxy)phenyl)ethyl)amino)pyrimidin-4-yl)-4-((R)-1-hydroxyethyl)oxazolidin-2-one | (DMSO-d6) δ 0.37-0.66 (m, 3 H) 1.43 (d, J = 7.04 Hz, 3 H) 4.32-4.46 (m, 2 H) 4.71 (br. s., 1 H) 5.26 (br. s., 1 H) 7.18 (d, J = 8.51 Hz, 1 H) 7.22 (d, J = 5.82 Hz, 1 H) 7.29 (d, J = 10.86 Hz, 1 H) 7.49 (t, J = 8.49 Hz, 1 H) 8.03 (br. s., 1 H) 8.16 (br. s., 1 H) | HRMS m/z 431.1341 (M + H)⁺; Rt-1.85 min |
| 347: (R)-3-(2-(((S)-1-(4-(difluoromethoxy)-3-fluorophenyl)ethyl)amino)pyrimidin-4-yl)-4-((R)-1-hydroxyethyl)oxazolidin-2-one | (DMSO-d6) δ 0.64 (br. s., 3 H) 1.42 (d, J = 6.99 Hz, 3 H) 4.34-4.47 (m, 3 H) 4.67-4.78 (m, 1 H) 5.06 (quin, J = 7.27 Hz, 1 H) 6.93-7.18 (m, 1 H) 7.19-7.32 (m, 3 H) 7.38 (d, J = 11.84 Hz, 1 H) 8.03-8.11 (m, 1 H) 8.15 (br. s., 1 H) | HRMS m/z 413.1436 (M + H)⁺; Rt-1.60 min |
| 348: (R)-3-(2-(((S)-1-(4-(difluoromethoxy)-3-fluorophenyl)ethyl)amino)-5-fluoropyrimidin-4-yl)-4-((R)-1-hydroxyethyl)oxazolidin-2-one | (DMSO-d6) δ 0.60 (br. s., 3 H) 1.41 (d, J = 7.04 Hz, 3 H) 4.35-4.43 (m, 1 H) 4.45-4.57 (m, 2 H) 4.89 (br. s., 1 H) 6.91-7.17 (m, 1 H) 7.17-7.31 (m, 2 H) 7.31-7.41 (m, 1 H) 7.82-8.03 (m, 1 H) 8.34 (br. s., 1 H) | HRMS m/z 431.1333 (M + H)⁺; Rt-1.89 min |
| 349: (R)-3-(2-(((S)-1-(4-(difluoromethoxy)phenyl)ethyl)amino)pyrimidin-4-yl)-4-((R)-1-hydroxyethyl)oxazolidin-2-one | (DMSO-d6) δ 0.61 (br. s., 3 H) 1.37 (d, J = 7.04 Hz, 3 H) 4.29-4.42 (m, 3 H) 4.65-4.73 (m, 1 H) 5.01 (quin, J = 7.20 Hz, 1 H) 7.04 (d, J = 8.51 Hz, 2 H) 7.09 (s, 1 H) 7.17 (d, J = 5.92 Hz, 1 H) 7.37 (d, J = 8.51 Hz, 2 H) 8.08 (br. s., 1 H) | HRMS m/z 395.1523 (M + H)⁺; Rt-1.49 min |

TABLE 31b-continued

Chemical name, NMR chemical shifts and LCMS
signal for each compound listed in Table 31a.

| Example: Name | $^1$H NMR (400 MHz) d ppm | LCMS |
|---|---|---|
| 350: (R)-3-(2-(((S)-1-(4-(difluoromethoxy)-2-fluorophenyl)ethyl)amino)pyrimidin-4-yl)-4-((R)-1-hydroxyethyl)oxazolidin-2-one | (DMSO-d6) δ 0.61 (br. s., 3 H) 0.93 (br. s., 1 H) 1.44 (d, J = 6.94 Hz, 3 H) 3.76 (br. s., 1 H) 4.34-4.47 (m, 2 H) 4.73 (d, J = 3.57 Hz, 1 H) 5.26 (quin, J = 6.90 Hz, 1 H) 6.98 (dd, J = 8.46, 2.20 Hz, 1 H) 7.06 (dd, J = 11.20, 2.30 Hz, 1 H) 7.26 (d, J = 5.77 Hz, 1 H) 7.43 (t, J = 8.66 Hz, 1 H) 8.17 (br. s., 1 H) | HRMS m/z 413.1431 (M + H)$^+$; Rt-1.60 min |
| 351: (R)-4-((R)-1-hydroxyethyl)-3-(2-(((S)-1-(3-(trifluoromethoxy)phenyl)ethyl)amino)pyrimidin-4-yl)oxazolidin-2-one | (DMSO-d6) δ 0.60 (br. s., 3 H) 1.44 (d, J = 7.04 Hz, 3 H) 3.87 (br. s., 1 H) 4.34-4.47 (m, 2 H) 4.71-4.76 (m, 2 H) 5.14 (quin, J = 7.23 Hz, 1 H) 7.13-7.21 (m, 1 H) 7.25 (d, J = 5.97 Hz, 1 H) 7.34 (s, 1 H) 7.38-7.46 (m, 2 H) 8.16 (br. s., 1 H) | HRMS m/z 413.1432 (M + H)$^+$; Rt-1.73 min |
| 352: (R)-3-(2-(((S)-1-(3-(difluoromethoxy)phenyl)ethyl)amino)pyrimidin-4-yl)-4-((R)-1-hydroxyethyl)oxazolidin-2-one | (DMSO-d6) δ 0.63 (br. s., 3 H) 1.43 (d, J = 7.04 Hz, 3 H) 3.85 (br. s., 4 H) 4.35-4.47 (m, 2 H) 4.71-4.76 (m, 1 H) 5.09 (quin, J = 7.30 Hz, 1 H) 6.96-7.02 (m, 1 H) 7.17 (d, J = 7.48 Hz, 1 H) 7.21-7.27 (m, 2 H) 7.31-7.37(m, 1 H) 8.15 (br. s., 1 H) | HRMS m/z 395.1534 (M + H)$^+$; Rt-1.52 min |
| 353: (R)-3-(2-(((S)-1-(4-(difluoromethoxy)-2-fluorophenyl)ethyl)amino)-5-fluoropyrimidin-4-yl)-4-((R)-1-hydroxyethyl)oxazolidin-2-one | (DMSO-d6) δ 0.33-1.02 (m, 3 H) 1.40 (d, J = 6.99 Hz, 3 H) 4.32-4.55 (m, 3 H) 5.13 (br. s., 1 H) 6.96 (dd, J = 8.53, 2.37 Hz, 1 H) 7.04 (dd, J = 11.10, 2.40 Hz, 1 H) 7.17-7.38 (m, 1 H) 7.41 (t, J = 8.58 Hz, 1 H) 7.97 (br. s., 1 H) 8.34 (br. s., 1 H) | HRMS m/z 431.1334 (M + H)$^+$; Rt-1.92 min |
| 354: (R)-3-(5-fluoro-2-(((S)-1-(3-(trifluoromethoxy)phenyl)ethyl)amino)pyrimidin-4-yl)-4-((R)-1-hydroxyethyl)oxazolidin-2-one | (DMSO-d6) δ 0.15-0.91 (m, 3 H) 1.41 (d, J = 7.04 Hz, 3 H) 4.27-4.56 (m, 3 H) 4.94 (br. s., 2 H) 7.15 (d, J = 7.34 Hz, 1 H) 7.30 (s, 1 H) 7.34-7.45 (m, 2 H) 7.97 (br. s., 1 H) 8.33 (br. s., 1 H) | HRMS m/z 431.1337 (M + H)$^+$; Rt-2.04 min |
| 355: (R)-3-(2-(((S)-1-(3-(difluoromethoxy)phenyl)ethyl)amino)-5-fluoropyrimidin-4-yl)-4-((R)-1-hydroxyethyl)oxazolidin-2-one | (DMSO-d6) δ 0.58 (br. s., 3 H) 1.41 (d, J = 7.04 Hz, 3 H) 3.89 (br. s., 2 H) 4.33-4.57 (m, 3 H) 4.90 (br. s., 1 H) 6.93-7.00 (m, 1 H) 7.11-7.18 (m, 1 H) 7.21 (d, J = 7.78 Hz, 1 H) 7.32 (t, J = 8.00 Hz, 1 H) 7.93 (br. s., 1 H) 8.32 (br. s., 1 H) | HRMS m/z 413.1435 (M + H)$^+$; Rt-1.83 min |

Example 356

1:3 TFA:DCM

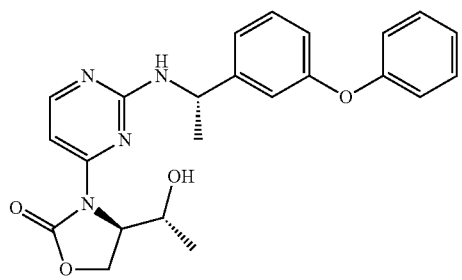 [SMILES: C[C@H](Nc1nccc(N2C(=O)OC[C@@H]2[C@@H](C)O)n1)c1cccc(Oc2ccccc2)c1]

A solution of (R)-4-((R)-1-tert-butoxyethyl)-3-(2-(((S)-1-(3-phenoxyphenyl)ethylamino)pyrimidin-4-yl)oxazolidin-2-one (70.1 mg, 0.147 mmol) in DCM (1.1 ml) was treated with TFA (368 ul) at room temperature. The resulting solution was let sit for 30 min, then concentrated. The crude material was purified by reverse phase HPLC. Product fractions were combined and lyophilized to afford (R)-4-((R)-1-hydroxyethyl)-3-(2-(((S)-1-(3-phenoxyphenyl)ethylamino)pyrimidin-4-yl)oxazolidin-2-one (41.3 mg, 0.097 mmol, 66% yield) as a TFA salt. $^1$H NMR (400 MHz, DMSO-d6) δ 0.64 (br. s., 3H) 1.42 (d, J=6.90 Hz, 3H) 3.70 (br. s., 1H) 4.32-4.48 (m, 3H) 4.67-4.75 (m, 1H) 5.08 (br. s., 1H) 6.78 (d, J=7.87 Hz, 1H) 6.91 (d, J=7.87 Hz, 2H) 7.00-7.18 (m, 3H) 7.22-7.37 (m, 4H) 8.14 (br. s., 1H). LCMS m/z 421.3 (M+H)$^+$, Rt 0.72 min. HRMS(A) m/z 421.1873 (M+H)$^+$, Rt 1.84 min.

The compounds in Table 32a were prepared using methods similar to those described for the preparation of Example 356

TABLE 32a
| | |
|---|---|
| 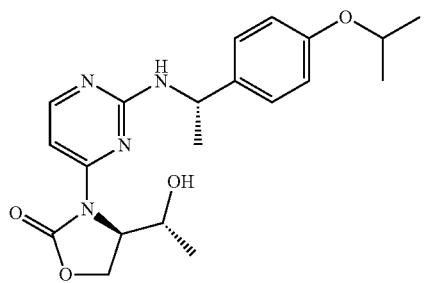 [SMILES: CC(C)Oc1ccc([C@H](C)Nc2nccc(N3C(=O)OC[C@@H]3[C@@H](C)O)n2)cc1] | 357 |
| 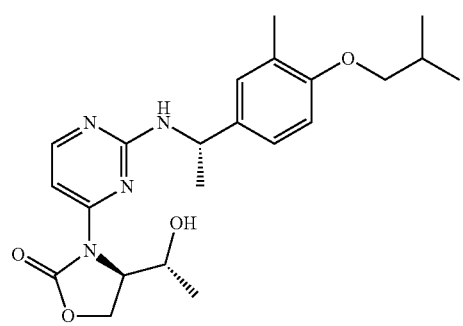 [SMILES: Cc1cc([C@H](C)Nc2nccc(N3C(=O)OC[C@@H]3[C@@H](C)O)n2)ccc1OCC(C)C] | 358 |
| 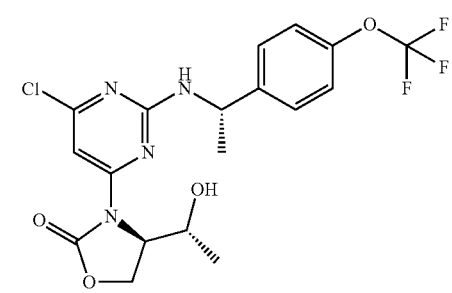 [SMILES: C[C@H](Nc1nc(Cl)cc(N2C(=O)OC[C@@H]2[C@@H](C)O)n1)c1ccc(OC(F)(F)F)cc1] | 359 |
| 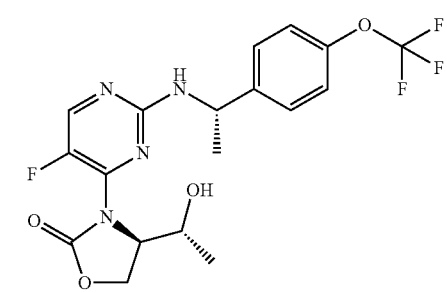 [SMILES: C[C@H](Nc1ncc(F)c(N2C(=O)OC[C@@H]2[C@@H](C)O)n1)c1ccc(OC(F)(F)F)cc1] | 360 |
| 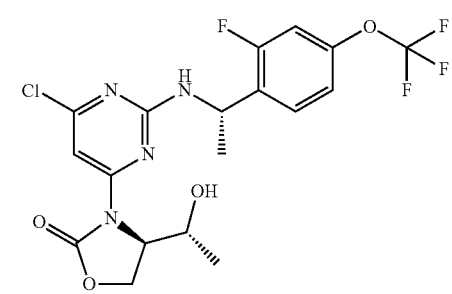 [SMILES: C[C@H](Nc1nc(Cl)cc(N2C(=O)OC[C@@H]2[C@@H](C)O)n1)c1ccc(OC(F)(F)F)cc1F] | 361 |
TABLE 32a-continued
| | |
|---|---|
| 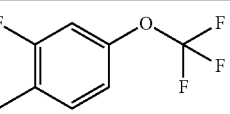 | 362 |
| 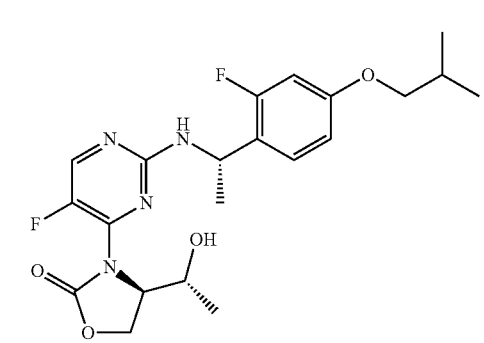 [SMILES: CC(C)COc1ccc([C@H](C)Nc2ncc(F)c(N3C(=O)OC[C@@H]3[C@@H](C)O)n2)c(F)c1] | 363 |
| 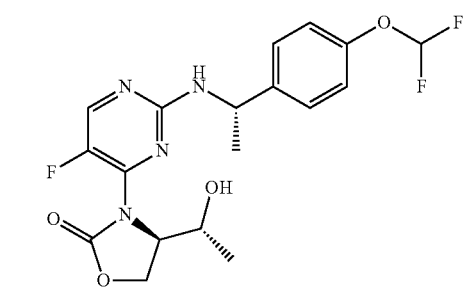 [SMILES: C[C@H](Nc1ncc(F)c(N2C(=O)OC[C@@H]2[C@@H](C)O)n1)c1ccc(OC(F)F)cc1] | 364 |
| 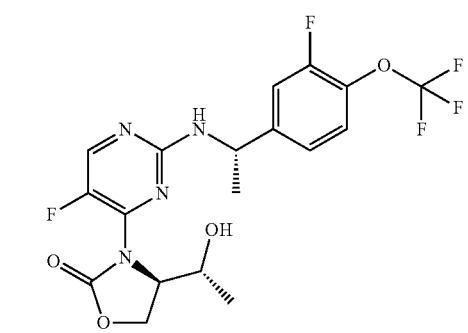 [SMILES: C[C@H](Nc1ncc(F)c(N2C(=O)OC[C@@H]2[C@@H](C)O)n1)c1ccc(OC(F)(F)F)c(F)c1] | 365 |
| 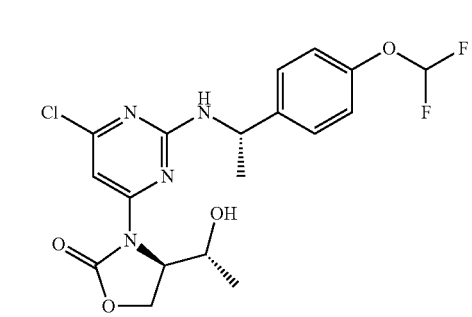 [SMILES: C[C@H](Nc1nc(Cl)cc(N2C(=O)OC[C@@H]2[C@@H](C)O)n1)c1ccc(OC(F)F)cc1] | 366 |

TABLE 32a-continued

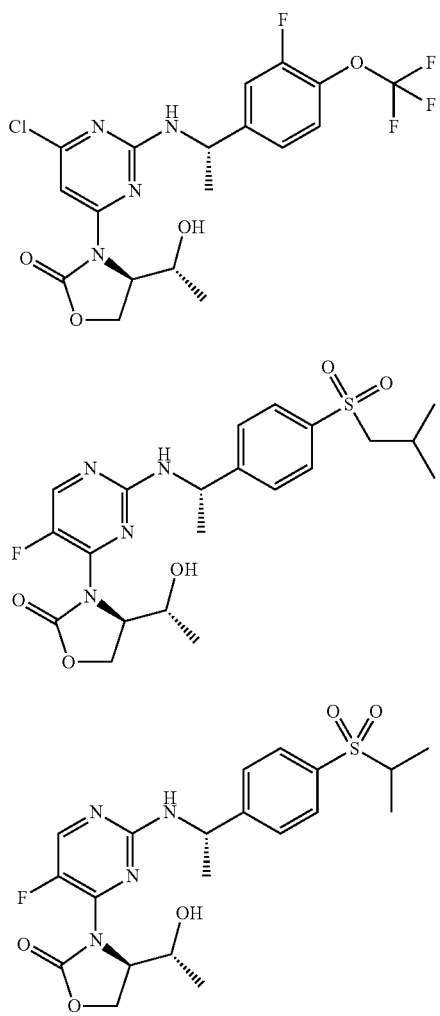

367

368

369

TABLE 32a-continued

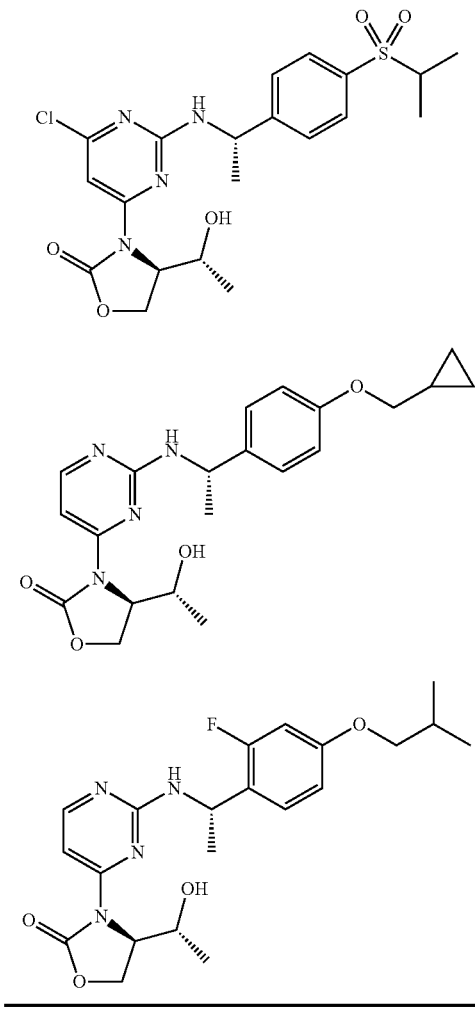

370

371

372

TABLE 32b

Chemical name, NMR chemical shifts and LCMS signal for each compound listed in Table 32a.

| Example: Name | $^1$H NMR (400 MHz) δ ppm | LCMS |
| --- | --- | --- |
| 357: (R)-4-((R)-1-hydroxyethyl)-3-(2-((S)-1-(4-isopropoxyphenyl)ethylamino)pyrimidin-4-yl)oxazolidin-2-one | (DMSO-d6) δ 0.69 (br. s., 3 H) 1.20 (d, J = 6.02 Hz, 6 H) 1.39 (d, J = 6.90 Hz, 3 H) 4.33-4.46 (m, 2 H) 4.51 (dt, J = 11.93, 5.87 Hz, 1 H) 4.74 (br. s., 1 H) 4.94-5.05 (m, 1 H) 6.80 (d, J = 8.41 Hz, 2 H) 7.17-7.29 (m, 3 H) 8.12 (d, J = 5.67 Hz, 1 H) | HRMS m/z 387.2032 (M + H)$^+$; Rt-1.54 min |
| 358: (R)-4-((R)-1-hydroxyethyl)-3-(2-((S)-1-(4-isobutoxy-3-methylphenyl)ethylamino)pyrimidin-4-yl)oxazolidin-2-one | The NMR not taken (not enough material made). | HRMS m/z 415.2340 (M + H)$^+$; Rt-1.98 min |
| 359: (R)-3-(6-chloro-2-(((S)-1-(4-(trifluoromethoxy)phenyl)ethyl)amino)pyrimidin-4-yl)-4-((R)-1-hydroxyethyl)oxazolidin-2-one | (DMSO-d6) δ 0.56 (d, J = 6.11 Hz, 3 H) 0.78-1.00 (m, 1 H) 1.41 (d, J = 6.85 Hz, 3 H) 3.78 (br. s., 1 H) 4.66-4.74 (m, 1 H) 4.97-5.10 (m, 1 H) 7.16 (s, 1 H) 7.28 (d, J = 8.22 Hz, 2 H) 7.47 (d, J = 8.66 Hz, 2 H) 8.40 (d, J = 7.63 Hz, 1 H) | HRMS m/z 477.1054 (M + H)$^+$; Rt-2.39 min |

TABLE 32b-continued

Chemical name, NMR chemical shifts and LCMS
signal for each compound listed in Table 32a.

| Example: Name | $^1$H NMR (400 MHz) δ ppm | LCMS |
| --- | --- | --- |
| 360: (R)-3-(5-fluoro-2-(((S)-1-(4-(trifluoromethoxy)phenyl)ethyl)amino)pyrimidin-4-yl)-4-((R)-1-hydroxyethyl)oxazolidin-2-one | (DMSO-d6) δ 0.49 (br. s., 3 H) 1.43 (d, J = 7.04 Hz, 3 H) 4.39 (dd, J = 8.31, 4.30 Hz, 1 H) 4.46-4.60 (m, 2 H) 4.92 (br. s., 2 H) 7.23-7.31 (m, 2 H) 7.47 (d, J = 8.61 Hz, 2 H) 7.98 (br. s., 1 H) 8.34 (d, J = 2.20 Hz, 1 H) | HRMS m/z 431.1345 (M + H)$^+$; Rt-2.05 min |
| 361: (R)-3-(6-chloro-2-(((S)-1-(2-fluoro-4-(trifluoromethoxy)phenyl)ethyl)amino)pyrimidin-4-yl)-4-((R)-1-hydroxyethyl)oxazolidin-2-one | (DMSO-d6) δ 0.50 (d, J = 6.02 Hz, 3 H) 0.93 (dd, J = 12.30, 6.33 Hz, 1 H) 1.42 (d, J = 6.99 Hz, 3 H) 4.25-4.57 (m, 3 H) 4.66 (br. s., 1 H) 5.14-5.27 (m, 1 H) 7.13-7.25 (m, 2 H) 7.29 (d, J = 10.07 Hz, 1 H) 7.40-7.59 (m, 1 H) 8.36-8.49 (m, 1 H) | HRMS m/z 465.0958 (M + H)$^+$; Rt-2.45 min |
| 362: (R)-3-(5-fluoro-2-(((S)-1-(2-fluoro-4-(trifluoromethoxy)phenyl)ethyl)amino)pyrimidin-4-yl)-4-((R)-1-hydroxyethyl)oxazolidin-2-one | (DMSO-d6) δ 0.48 (br. s., 3 H) 0.91-1.34 (m, 1 H) 1.45 (d, J = 7.04 Hz, 3 H) 4.34-4.59 (m, 3 H) 5.16 (br. s., 1 H) 7.20 (d, J = 8.51 Hz, 1 H) 7.32 (d, J = 10.51 Hz, 1 H) 7.52 (t, J = 8.56 Hz, 1 H) 8.06 (br. s., 1 H) 8.37 (br. s., 1 H) | HRMS m/z 449.1243 (M + H)$^+$; Rt-2.09 min |
| 363: (R)-3-(5-fluoro-2-(((S)-1-(2-fluoro-4-isobutoxyphenyl)ethyl)amino)pyrimidin-4-yl)-4-((R)-1-hydroxyethyl)oxazolidin-2-one | (DMSO-d6) δ 0.40-0.82 (m, 3 H) 0.95 (d, J = 6.65 Hz, 6 H) 1.40 (d, J = 6.99 Hz, 3 H) 1.98 (dquin, J = 13.29, 6.64, 6.64, 6.64, 6.64 Hz, 1 H) 3.71 (d, J = 6.50 Hz, 2 H) 4.38-4.70 (m, 4 H) 5.12 (br. s., 1 H) 6.65-6.78 (m, 2 H) 7.29 (t, J = 9.00 Hz, 1 H) 7.89 (br. s., 1 H) 8.35 (br. s., 1 H) | HRMS m/z 437.2005 (M + H)$^+$; Rt-2.28 min |
| 364: (R)-3-(2-(((S)-1-(4-(difluoromethoxy)phenyl)ethyl)amino)-5-fluoropyrimidin-4-yl)-4-((R)-1-hydroxyethyl)oxazolidin-2-one | (DMSO-d6) δ 0.62 (br. s., 3 H) 1.42 (d, J = 6.99 Hz, 3 H) 4.35-4.44 (m, 1 H) 4.47-4.54 (m, 1 H) 4.56 (br. s., 1 H) 4.91 (br. s., 1 H) 7.10 (d, J = 8.51 Hz, 2 H) 6.95-7.35 (m, 1 H) 7.41 (d, J = 8.61 Hz, 2 H) 7.94 (br. s., 1 H) 8.34 (d, J = 2.64 Hz, 1 H) | HRMS m/z 413.1433 (M + H)$^+$; Rt-1.83 min |
| 365: (R)-3-(5-fluoro-2-(((S)-1-(3-fluoro-4-(trifluoromethoxy)phenyl)ethyl)amino)pyrimidin-4-yl)-4-((R)-1-hydroxyethyl)oxazolidin-2-one | (DMSO-d6) δ 0.26-1.06 (m, 3 H) 1.44 (d, J = 6.99 Hz, 3 H) 4.35-4.61 (m, 2 H) 5.21 (br. s., 3 H) 7.25-7.38 (m, 1 H) 7.42-7.55 (m, 2 H) 8.00 (br. s., 1 H) 8.37 (br. s., 1 H) | HRMS m/z 449.1244 (M + H)$^+$; Rt-2.09 min |
| 366: (R)-3-(6-chloro-2-(((S)-1-(4-(difluoromethoxy)phenyl)ethyl)amino)pyrimidin-4-yl)-4-((R)-1-hydroxyethyl)oxazolidin-2-one | (DMSO-d6) δ 0.65 (d, J = 6.06 Hz, 3 H) 0.87-1.02 (m, 1 H) 1.42 (d, J = 6.70 Hz, 3 H) 4.36-4.54 (m, 2 H) 4.69-4.79 (m, 1 H) 4.99-5.11 (m, 1 H) 6.96-7.39 (m, 1 H) 7.12 (d, J = 8.51 Hz, 2 H) 7.17 (d, J = 7.24 Hz, 1 H) 7.43 (d, J = 8.51 Hz, 2 H) 8.39 (d, J = 8.02 Hz, 1 H) | HRMS m/z 429.1139 (M + H)$^+$; Rt-2.20 min |
| 367: (R)-3-(6-chloro-2-(((S)-1-(3-fluoro-4-(trifluoromethoxy)phenyl)ethyl)amino)pyrimidin-4-yl)-4-((R)-1-hydroxyethyl)oxazolidin-2-one | (DMSO-d6) δ 0.57 (d, J = 6.21 Hz, 3 H) 1.43 (d, J = 6.75 Hz, 3 H) 4.31-4.55 (m, 3 H) 4.71 (br. s., 1 H) 4.99-5.13 (m, 1 H) 7.20 (s, 1 H) 7.30 (d, J = 8.56 Hz, 1 H) 7.40-7.58 (m, 2 H) 8.41 (d, J = 7.19 Hz, 1 H) | HRMS m/z 465.0959 (M + H)$^+$; Rt-2.43 min |

TABLE 32b-continued

Chemical name, NMR chemical shifts and LCMS
signal for each compound listed in Table 32a.

| Example: Name | ¹H NMR (400 MHz) δ ppm | LCMS |
| --- | --- | --- |
| 368: (R)-3-(5-fluoro-2-(((S)-1-(4-(isobutylsulfonyl)phenyl)ethyl)amino)pyrimidin-4-yl)-4-((R)-1-hydroxyethyl)oxazolidin-2-one | (DMSO-d6) δ 0.48 (br. s., 3 H) 0.96 (dd, J = 6.70, 1.12 Hz, 6 H) 1.46 (d, J = 7.04 Hz, 3 H) 2.00 (dquin, J = 13.27, 6.60, 6.60, 6.60, 6.60 Hz, 1 H) 3.15 (d, J = 6.46 Hz, 2 H) 4.34-4.61 (m, 4 H) 4.98 (br. s., 1 H) 7.62 (d, J = 8.31 Hz, 2 H) 7.83 (d, J = 8.31 Hz, 2 H) 8.07 (br. s., 1 H) 8.35 (br. s., 1 H) | HRMS m/z 467.1758 (M + H)⁺; Rt-1.78 min |
| 369: (R)-3-(5-fluoro-2-(((S)-1-(4-(isopropylsulfonyl)phenyl)ethyl)amino)pyrimidin-4-yl)-4-((R)-1-hydroxyethyl)oxazolidin-2-one | (DMSO-d6) δ 0.45 (br. s., 3 H) 1.11 (d, J = 6.80 Hz, 6 H) 1.43 (d, J = 7.04 Hz, 3 H) 3.33 (dt, J = 13.58, 6.78 Hz, 1 H) 4.37 (dd, J = 8.05, 4.13 Hz, 1 H) 4.43-4.58 (m, 2 H) 4.97 (br. s., 1 H) 7.61 (d, J = 8.36 Hz, 2 H) 7.76 (d, J = 8.36 Hz, 2 H) 8.06 (br. s., 1 H) 8.33 (br. s., 1 H) | HRMS m/z 453.1604 (M + H)⁺; Rt-1.57 min |
| 370: (R)-3-(6-chloro-2-(((S)-1-(4-(isopropylsulfonyl)phenyl)ethyl)amino)pyrimidin-4-yl)-4-((R)-1-hydroxyethyl)oxazolidin-2-one | (DMSO-d6) δ 0.53 (d, J = 6.21 Hz, 3 H) 1.11 (dd, J = 6.77, 3.74 Hz, 6 H) 1.43 (d, J = 6.75 Hz, 3 H) 3.34 (dt, J = 13.17, 6.50 Hz, 1 H) 3.68 (br. s., 1 H) 4.38 (dd, J = 16.43, 7.97 Hz, 2 H) 4.64-4.76 (m, 1 H) 4.98-5.17 (m, 1 H) 7.18 (s, 1 H) 7.62 (d, J = 8.31 Hz, 2 H) 7.78 (d, J = 8.27 Hz, 2 H) 8.50 (d, J = 7.34 Hz, 1 H) | HRMS m/z 469.1314 (M + H)⁺; Rt-1.92 min |
| 371: (R)-3-(2-(((S)-1-(4-(cyclopropylmethoxy)phenyl)ethyl)amino)pyrimidin-4-yl)-4-((R)-1-hydroxyethyl)oxazolidin-2-one | (DMSO-d6) δ 0.24-0.35 (m, 2 H) 0.54 (dd, J = 8.09, 1.74 Hz, 2 H) 0.74 (br. s., 3 H) 1.12-1.24 (m, 1 H) 1.42 (d, J = 6.99 Hz, 3 H) 3.76 (d, J = 6.99 Hz, 2 H) 4.36-4.50 (m, 3 H) 4.78 (d, J = 2.89 Hz, 1 H) 4.98-5.10 (m, 1 H) 6.84 (d, J = 8.61 Hz, 2 H) 7.18-7.36 (m, 3 H) 8.15 (d, J = 5.62 Hz, 1 H) | HRMS m/z 399.2034 (M + H)⁺; Rt-1.59 min |
| 372: (R)-3-(2-(((S)-1-(2-fluoro-4-isobutoxyphenyl)ethyl)amino)pyrimidin-4-yl)-4-((R)-1-hydroxyethyl)oxazolidin-2-one | (DMSO-d6) δ 0.51-0.82 (m, 3 H) 0.94 (d, J = 6.70 Hz, 6 H) 1.42 (d, J = 6.85 Hz, 3 H) 1.97 (dquin, J = 13.32, 6.70, 6.70, 6.70, 6.70 Hz, 1 H) 3.70 (d, J = 6.55 Hz, 2 H) 4.35-4.48 (m, 2 H) 4.71-4.79 (m, 1 H) 5.24 (quin, J = 7.10 Hz, 1 H) 6.65-6.79 (m, 2 H) 7.19-7.34 (m, 2 H) 8.15 (br. s., 1 H) | HRMS m/z 419.2102 (M + H)⁺; Rt-1.95 min |

Example 373

(R)-3-(2-(((S)-1-(2-(4-chlorophenyl)thiazol-5-yl)ethyl)amino)pyrimidin-4-yl)-4-((R)-1-methoxyethyl)oxazolidin-2-one

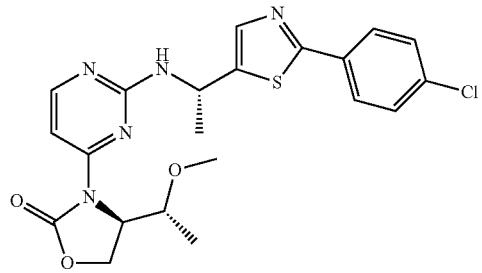 [SMILES: CO[C@H](C)[C@H]1COC(=O)N1c1ccnc(N[C@@H](C)c2cnc(-c3ccc(Cl)cc3)s2)n1]

To a microwave vial with stir bar was added (R)-3-(2-fluoropyrimidin-4-yl)-4-((R)-1-methoxyethyl)oxazolidin-2-one (28 mg, 0.12 mmol) and DMSO (1 mL). To this reaction mixture was added (S)-1-(2-(4-chlorophenyl)thiazol-5-yl)ethanamine (48 mg, 0.17 mmol) and DIEA (61 ul, 0.35 mmol). Vial was capped and the reaction mixture was heated in a preheated sand bath at 80° C. for 18 hr. Reaction mixture was purified by reverse phase HPLC. Product fractions combined, frozen and lyopholyzed to afford a TFA salt of (R)-3-(2-(((S)-1-(2-(4-chlorophenyl)thiazol-5-yl)ethyl)amino)pyrimidin-4-yl)-4-((R)-1-methoxyethyl)oxazolidin-2-one (28 mg, 0.04 mmol, 38% yield). $^1$H NMR (400 MHz, CDCl$_3$) δ 1.01 (d, J=6.65 Hz, 3H) 1.82 (d, J=7.04 Hz, 3H) 3.24 (s, 3H) 3.72-3.86 (m, 1H) 4.36-4.47 (m, 1H) 4.60 (dd, J=9.39, 2.35 Hz, 1H) 4.92-5.01 (m, 1H) 5.48 (t, J=7.04 Hz, 1H) 7.43 (d, J=8.61 Hz, 2H) 7.72 (s, 1H) 7.77-7.85 (m, 4H) 8.02 (d, J=7.04 Hz, 1H) 10.95 (d, J=6.65 Hz, 1H).). LCMS m/z 460.2 (M+H)$^+$, Rt 0.82 min. HRMS (B) m/z 460.1213 (M+H)$^+$, Rt 2.28 min.

The compounds in Table 33a were prepared using methods similar to those described for the preparation of Example 373.

TABLE 33a

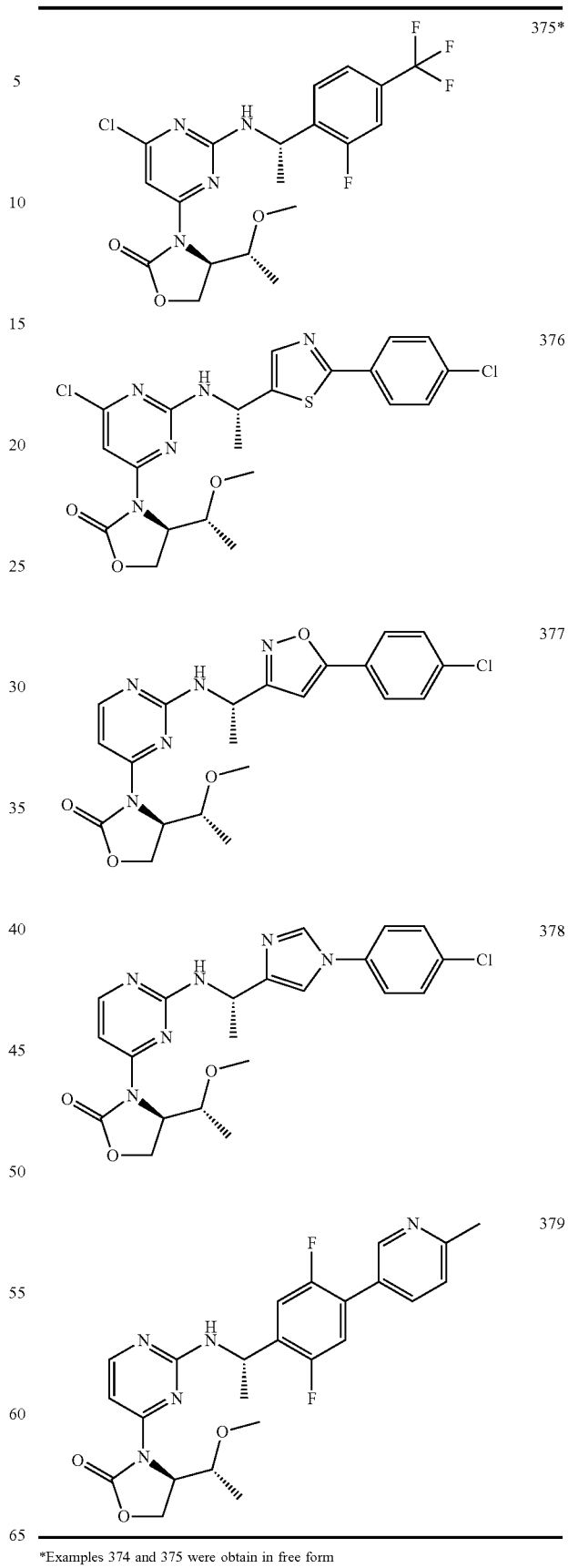

*Examples 374 and 375 were obtain in free form

TABLE 33b

Chemical name, NMR chemical shifts and LCMS signal for each compound listed in Table33a.

| Example: Name | 1H NMR (400 MHz, CDCl$_3$) δ ppm | HRMS |
|---|---|---|
| 374: (R)-3-(6-chloro-2-(((S)-1-(2,5-difluoro-4-(1-methyl-1H-pyrazol-4-yl)phenyl)ethyl)amino)pyrimidin-4-yl)-4-((R)-1-methoxyethyl)oxazolidin-2-one | 0.89 (br. s., 3 H) 1.56 (br. s., 3 H) 3.20 (br. s., 3 H) 3.96 (s, 3 H) 4.28-4.37 (m, 1 H) 4.50 (dd, J = 9.39, 2.89 Hz, 1 H) 4.88 (ddd, J = 8.50, 4.32, 2.98 Hz, 1 H) 5.30 (quin, J = 6.97 Hz, 1 H) 5.50 (br. s., 1 H) 7.07 (dd, J = 10.91, 6.36 Hz, 1 H) 7.21 (dd, J = 10.88, 6.04 Hz, 1 H) 7.55 (s, 1 H) 7.76 (d, J = 2.45 Hz, 1 H) 7.79 (s, 1 H) | HRMS (B) m/z 493.1567 (M + H)$^+$; Rt-2.35 min |
| 375: (R)-3-(6-chloro-2-(((S)-1-(2-fluoro-4-(trifluoromethyl)phenyl)ethyl)amino)pyrimidin-4-yl)-4-((R)-1-methoxyethyl)oxazolidin-2-one | 0.69-0.95 (m, 3 H) 1.57-1.61 (m, 3 H) 3.16 (br. s., 3 H) 4.26-4.37 (m, 1 H) 4.49 (dd, J = 9.39, 2.74 Hz, 1 H) 4.78-4.90 (m, 1 H) 5.37 (quin, J = 6.93 Hz, 1 H) 5.51 (br. s., 1 H) 7.33 (d, J = 9.44 Hz, 1 H) 7.38-7.43 (m, 1 H) 7.44-7.51 (m, 1 H) 7.56 (s, 1 H) | HRMS (B) m/z 463.1170 (M + H)$^+$; Rt-2.74 min |
| 376: (R)-3-(6-chloro-2-(((S)-1-(2-(4-chlorophenyl)thiazol-5-yl)ethyl)amino)pyrimidin-4-yl)-4-((R)-1-methoxyethyl)oxazolidin-2-one | 1.01 (d, J = 4.21 Hz, 3 H) 1.72-1.77 (m, 3 H) 3.21 (br. s., 3 H) 4.31-4.42 (m, 1 H) 4.53 (dd, J = 9.46, 2.76 Hz, 1 H) 4.89 (ddd, J = 8.36, 4.21, 2.79 Hz, 1 H) 5.46 (br. s., 1 H) 7.42-7.48 (m, 2 H) 7.65 (s, 1 H) 7.80 (d, J = 8.56 Hz, 3 H) | HRMS (B) m/z 494.0823 (M + H)$^+$; Rt-2.80 min |
| 377: (R)-3-(2-(((S)-1-(5-(4-chlorophenyl)isoxazol-3-yl)ethyl)amino)pyrimidin-4-yl)-4-((R)-1-methoxyethyl)oxazolidin-2-one | 1.00 (d, J = 6.26 Hz, 3 H) 1.74 (d, J = 7.04 Hz, 3 H) 3.46 (s, 3 H) 4.03-4.19 (m, 1 H) 4.43 (t, J = 8.80 Hz, 1 H) 4.65 (dd, J = 9.59, 2.54 Hz, 1 H) 5.03 (ddd, J = 7.92, 4.60, 2.74 Hz, 1 H) 5.44 (quin, J = 7.14 Hz, 1 H) 6.69 (s, 1 H) 7.45 (d, J = 8.61 Hz, 2 H) 7.71 (d, J = 8.61 Hz, 2 H) 7.80 (d, J = 7.04 Hz, 1 H) 7.94 (d, J = 7.04 Hz, 1 H) 10.98 (d, J = 7.43 Hz, 1 H) | HRMS (B) m/z 444.1433 (M + H)$^+$; Rt-2.21 min |
| 378: (R)-3-(2-(((S)-1-(1-(4-chlorophenyl)-1H-imidazol-4-yl)ethyl)amino)pyrimidin-4-yl)-4-((R)-1-methoxyethyl)oxazolidin-2-one | 1.04 (d, J = 5.87 Hz, 3 H) 1.75 (d, J = 6.26 Hz, 3 H) 3.31 (s, 3 H) 3.95 (br. s., 1 H) 4.46 (t, J = 8.61 Hz, 1 H) 4.60 (dd, J = 9.39, 2.35 Hz, 1 H) 5.07 (m, 3.13 Hz, 1 H) 5.57 (br. s., 1 H) 7.44 (d, J = 8.61 Hz, 2 H) 7.57 (d, J = 8.22 Hz, 2 H) 7.61 (br. s., 1 H) 7.85 (d, J = 7.04 Hz, 1 H) 7.96 (d, J = 6.65 Hz, 1 H) 8.53 (br. s., 1 H) 10.90 (d, J = 6.65 Hz, 1 H) | HRMS (B) m/z 443.1598 (M + H)$^+$; Rt-1.57 min |
| 379: (R)-3-(2-(((S)-1-(2,5-difluoro-4-(6-methylpyridin-3-yl)phenyl)ethyl)amino)pyrimidin-4-yl)-4-((R)-1-methoxyethyl)oxazolidin-2-one | 0.97 (d, J = 6.65 Hz, 3 H) 1.67 (d, J = 7.04 Hz, 3 H) 2.88 (s, 3 H) 3.30 (s, 3 H) 3.67-3.89 (m, 1 H) 4.37-4.49 (m, 1 H) 4.61 (dd, J = 9.39, 2.35 Hz, 1 H) 4.94-5.07 (m, 1 H) 5.62 (quin, J = 6.95 Hz, 1 H) 7.22-7.26 (m, 1 H) 7.48 (dd, J = 10.37, 6.06 Hz, 1 H) 7.66 (d, J = 8.22 Hz, 1 H) 7.82 (d, J = 7.04 Hz, 1 H) 7.97 (d, J = 7.04 Hz, 1 H) 8.34 (d, J = 8.22 Hz, 1 H) 9.00 (s, 1 H) 11.04 (d, J = 7.83 Hz, 1 H) | HRMS (B) m/z 470.2007 (M + H)$^+$; Rt-1.53 min |

Example 380

(S)-4-((R)-1-aminoethyl)-3-(2-(((S)-1-(2-(4-chlorophenyl)thiazol-5-yl)ethyl)amino)pyrimidin-4-yl)oxazolidin-2-one

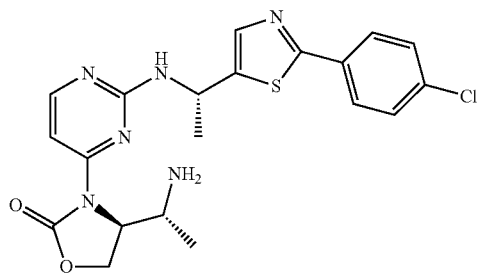 [SMILES: C[C@H](Nc1nccc(N2C(=O)OC[C@@H]2[C@@H](C)N)n1)c1cnc(-c2ccc(Cl)cc2)s1]

Step 1

To a microwave vial with stir bar was added (R)-4-((S)-1-(tert-butoxy)ethyl)-3-(2-chloropyrimidin-4-yl)oxazolidin-2-one (147 mg, 0.49 mmol) and DMSO (4 mL). To this reaction mixture was added (S)-1-(2-(4-chlorophenyl)thiazol-5-yl)ethanamine HCl (148 mg, 0.54 mmol) and DIEA (0.26 mL, 1.47 mmol). Vial capped and the reaction mixture was heated in a preheated sand bath at 110° C. for 42 hr. The reaction mixture was diluted with water and extracted with EtOAc. Organic phases combined, washed with water, brine, dried (Na$_2$SO$_4$), filtered and concentrated onto silica gel. Silica gel column chromatography (EtOAc/Heptane 0 to 100%) provided (R)-4-((S)-1-(tert-butoxy)ethyl)-3-(2-(((S)-1-(2-(4-chlorophenyl)thiazol-5-yl)ethyl)amino)pyrimidin-4-yl)oxazolidin-2-one (82 mg, 0.16 mmol, 33% yield). $^1$H NMR (400 MHz, CDCl$_3$) δ 0.82 (br. s., 9H) 0.90-0.98 (m, 3H) 1.71 (d, J=6.90 Hz, 3H) 4.13 (q, J=7.16 Hz, 1H) 4.21-4.32 (m, 1H) 4.42-4.51 (m, 1H) 4.56 (dd, J=8.31, 2.79 Hz, 1H) 5.39 (br. s., 1H) 7.34-7.45 (m, 2H) 7.57 (d, J=5.77 Hz, 1H) 7.64 (s, 1H) 7.76-7.86 (m, 2H) 8.22 (d, J=5.82 Hz, 1H). LCMS m/z 502.3 (M+H)$^+$, Rt 0.92 min.

Step 2

To a round bottom flask containing a stir bar and (R)-4-((S)-1-(tert-butoxy)ethyl)-3-(2-(((S)-1-(2-(4-chlorophenyl)

thiazol-5-yl)ethyl)amino)pyrimidin-4-yl)oxazolidin-2-one (82 mg, 0.16 mmol) was added DCM (1 mL) followed by the addition of TFA (1 mL). Resulting reaction mixture allowed to stir 30 min at RT. The volatiles were then removed and the residue neutralized by the addition of a saturated solution of NaHCO$_3$. The aqueous mixture was then extracted with DCM. Organic phases combined, washed with water, brine, dried (Na$_2$SO$_4$), filtered and concentrated to a brown foam of (R)-3-(2-(((S)-1-(2-(4-chlorophenyl)thiazol-5-yl)ethyl)amino)pyrimidin-4-yl)-4-((S)-1-hydroxyethyl)oxazolidin-2-one (61 mg, 0.14 mmol, 84% yield) which was used without further purification. LCMS m/z 446.2 (M+H)$^+$, Rt 0.71 min.

Step 3

To a round bottom flask with stir bar was added (R)-3-(2-(((S)-1-(2-(4-chlorophenyl)thiazol-5-yl)ethyl)amino)pyrimidin-4-yl)-4-((S)-1-hydroxyethyl)oxazolidin-2-one (19 mg, 0.04 mmol) followed by the addition of DCM (1 mL) under nitrogen. Mixture was cooled to 0° C. in a ice/water bath. To this cold solution was added DIEA (0.03 mL, 0.17 mmol) followed by the addition of methanesulfonyl chloride (10 µL, 0.13 mmol). Reaction mixture stirred for 1 hr at 0° C. The reaction mixture was then quenched with water and diluted with DCM. Phases partitioned and the aqueous phase extracted with DCM. Organic layers combined and washed with brine, dried (Na$_2$SO$_4$), filtered and concentrated to afford a orange residue of (S)-1-((R)-3-(2-(((S)-1-(2-(4-chlorophenyl)thiazol-5-yl)ethyl)amino)pyrimidin-4-yl)-2-oxooxazolidin-4-yl)ethyl methanesulfonate (21 mg, 0.04 mmol, 94% yield). LCMS m/z 524.2 (M+H)$^+$, Rt 0.75 min.

Step 4

To a microwave vial containing (S)-1-((R)-3-(2-(((S)-1-(2-(4-chlorophenyl)thiazol-5-yl)ethyl)amino)pyrimidin-4-yl)-2-oxooxazolidin-4-yl)ethyl methanesulfonate (21 mg, 0.04 mmol) in DMF (1 mL) was added sodium azide (13 mg, 0.20 mmol). Resulting reaction mixture heated to 50° C. for 1 hr in a sand bath then to 80° C. for 42 hr. Reaction mixture was diluted with water and extracted with EtOAc. Organic phases combined, washed with brine, dried (Na$_2$SO$_4$), filtered and concentrated to a yellow residue of (S)-4-((R)-1-azidoethyl)-3-(2-(((S)-1-(2-(4-chlorophenyl)thiazol-5-yl)ethyl)amino)pyrimidin-4-yl)oxazolidin-2-one (14 mg, 0.030 mmol, 74.2% yield). LCMS m/z 471.2 (M+H)$^+$, Rt 0.92 min.

Step 5

To a round bottom flask containing (S)-4-((R)-1-azidoethyl)-3-(2-(((S)-1-(2-(4-chlorophenyl)thiazol-5-yl)ethyl)amino)pyrimidin-4-yl)oxazolidin-2-one (14 mg, 0.03 mmol) and stir bar was added THF (1 mL) and trimethylphosphine (0.06 mL, 0.06 mmol, 1.0 M in THF). The resulting reaction mixture allowed to stir 2 hr at RT. A second addition of trimethylphosphine (0.06 mL, 0.06 mmol) occurred and the mixture allowed to stir 1.5 hr at RT. Reaction was quenched by the addition of a saturated solution of NH$_4$Cl and EtOAc. The phases were partitioned and aqueous phase extracted with EtOAc. Organic phases combined and washed with brine, dried (Na$_2$SO$_4$), filtered and concentrated to a yellow residue. Residue dissolved in DMSO and purified by reverse phase HPLC. Product fractions combined, frozen and lyopholyzed to afford (S)-4-((R)-1-aminoethyl)-3-(2-(((S)-1-(2-(4-chlorophenyl)thiazol-5-yl)ethyl)amino)pyrimidin-4-yl)oxazolidin-2-one (2.6 mg, 4.60 µmol, 15% yield) as a TFA salt. $^1$H NMR (400 MHz, CD$_3$CN) δ 1.26-1.44 (m, 3H) 1.68 (d, J=6.65 Hz, 3H) 3.83 (quin, J=6.26 Hz, 1H) 4.43-4.53 (m, 1H) 7.46 (d, J=8.61 Hz, 2H) 7.76 (s, 1H) 7.89 (d, J=8.61 Hz, 2H) 8.20 (br. s., 1H). LCMS m/z 445.2 (M+H)$^+$, Rt 0.65 min. HRMS (B) m/z 445.1211 (M+H)$^+$, Rt 1.58 min.

The compounds in Table 34a were prepared using methods similar to those described for the preparation of Example 380

TABLE 34a

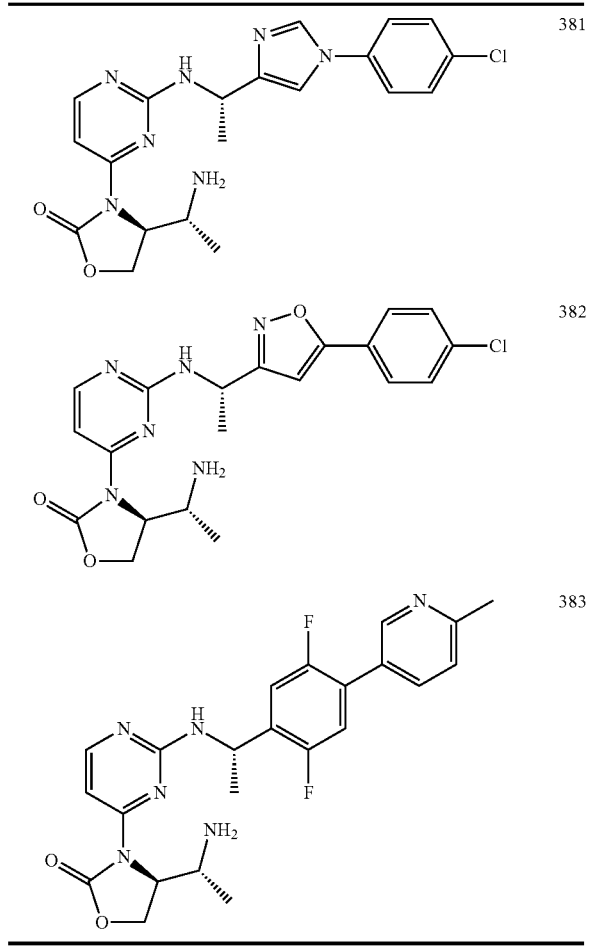

TABLE 34b

| Chemical name, NMR chemical shifts and LCMS signal for each compound listed in Table 34a. | | |
|---|---|---|
| Example: Name | 1H NMR (400 MHz) δ ppm | HRMS |
| 381: (S)-4-((R)-1-aminoethyl)-3-(2-(((S)-1-(1-(4-chlorophenyl)-1H-imidazol-4-yl)ethyl)amino)pyrimidin-4-yl)oxazolidin-2-one | (DMSO) 1.03-1.32 (m, 3 H) 1.55 (d, J = 6.65 Hz, 3 H) 3.86 (br. s., 1 H) 4.51 (d, J = 7.04 Hz, 1 H) 5.23 (br. s., 1 H) 7.28 (d, J = 5.87 Hz, 1 H) 7.60-7.68 (m, 2 H) 7.73 (d, J = 8.61 Hz, 2 H) 7.83 (br. s., 1 H) 8.25 (d, J = 5.87 Hz, 1 H) | HRMS (B) m/z 428.1598 (M + H)$^+$; Rt-1.12 min |

TABLE 34b-continued

Chemical name, NMR chemical shifts and LCMS signal for each compound listed in Table 34a.

| Example: Name | 1H NMR (400 MHz) δ ppm | HRMS |
|---|---|---|
| 382: (S)-4-((R)-1-aminoethyl)-3-(2-(((S)-1-(5-(4-chlorophenyl)isoxazol-3-yl)ethyl)amino)pyrimidin-4-yl)oxazolidin-2-one | (DMSO) 1.09 (br. s., 3 H) 1.56 (d, J = 7.04 Hz, 3 H) 4.45-4.54 (m, 1 H) 5.37 (br. s., 1 H) 7.00 (s, 1 H) 7.26 (d, J = 5.87 Hz, 1 H) 7.60 (d, J = 8.61 Hz, 2 H) 7.87 (d, J = 8.61 Hz, 2 H) 8.07 (br. s., 1 H) 8.24 (d, J = 5.87 Hz, 1 H) | HRMS (B) m/z 429.1438 (M + H)+; Rt-1.49 min |
| 383: (S)-4-((R)-1-aminoethyl)-3-(2-(((S)-1-(2,5-difluoro-4-(6-methylpyridin-3-yl)phenyl)ethyl)amino)pyrimidin-4-yl)oxazolidin-2-one | (CDCl3) 1.24 (br. s., 1 H) 1.53 (d, J = 5.87 Hz, 3 H) 2.64 (br. s., 3 H) 3.31 (br. s., 3 H) 4.42 (br. s., 1 H) 7.23-7.26 (m, 3 H) 7.40 (br. s., 1 H) 7.95-8.12 (m, 2 H) 8.67 (br. s., 1 H) | HRMS (B) m/z 455.2005 (M + H)+; Rt-1.06 min |

Example 384

(S)-3-(2-(((S)-1-(2-(4-chlorophenyl)thiazol-5-yl)ethyl)amino)pyrimidin-4-yl)-4-((R)-1-(methylamino)ethyl)oxazolidin-2-one

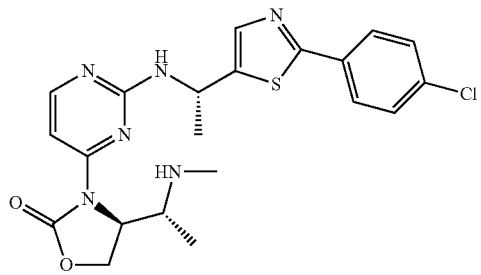 [SMILES: CN[C@H](C)[C@H]1COC(=O)N1c1ccnc(N[C@@H](C)c2cnc(-c3ccc(Cl)cc3)s2)n1]

To a microwave vial containing (S)-1-((R)-3-(2-(((S)-1-(2-(4-chlorophenyl)thiazol-5-yl)ethyl)amino)pyrimidin-4-yl)-2-oxooxazolidin-4-yl)ethyl methanesulfonate (20 mg, 0.04 mmol) in DMF (1 mL) was added methyl amine (30 mg, 0.38 mmol, 40% wt in H2O). Resulting reaction mixture allowed to stir at 80° C. for 18 hr whereupon a second addition of methylamine (0.1 mL, 40% wt in H2O) occurred. The reaction mixture was stirred at 80° C. for 18 hr. The reaction mixture was then diluted with water and extracted with EtOAc. Organic phases combined and washed with brine, dried (Na2SO4), filtered and concentrated. Residue dissolved in DMSO and purified by reverse phase HPLC. Product fractions combined, frozen and lyopholyzed to afford a TFA salt of (S)-3-(2-(((S)-1-(2-(4-chlorophenyl)thiazol-5-yl)ethyl)amino)pyrimidin-4-yl)-4-((R)-1-(methylamino)ethyl)oxazolidin-2-one (3.4 mg, 5.87 μmol, 15% yield). $^1$H NMR (400 MHz, CDCl3) δ 1.47 (d, J=5.87 Hz, 3H) 1.78 (d, J=7.04 Hz, 3H) 2.70 (s, 3H) 4.02 (br. s., 1H) 4.14 (br. s., 2H) 5.33 (br. s., 1H) 5.73 (d, J=6.26 Hz, 1H) 6.23 (d, J=5.48 Hz, 1H) 7.41 (d, J=8.61 Hz, 2H) 7.78 (s, 1H) 7.83 (d, J=8.22 Hz, 2H) 8.05 (d, J=5.48 Hz, 1H). LCMS m/z 459.2 (M+H)+, Rt 0.73 min. HRMS (B) m/z 459.1373 (M+H)+, Rt 1.68 min.

Example 385

(R)-3-(2-(((S)-1-(1-(4-chlorophenyl)-1H-imidazol-4-yl)ethyl)amino)pyrimidin-4-yl)-4-((R)-1-fluoroethyl)oxazolidin-2-one

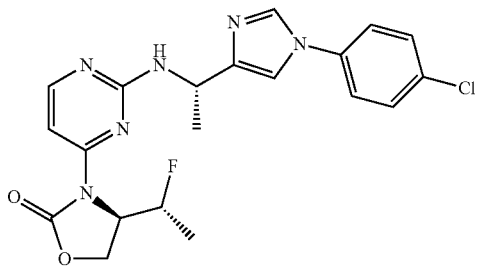 [SMILES: C[C@H](Nc1nccc(N2C(=O)OC[C@@H]2[C@@H](C)F)n1)c1cn(-c2ccc(Cl)cc2)cn1]

To a microwave vial with stir bar was added (R)-4-((R)-1-fluoroethyl)-3-(2-fluoropyrimidin-4-yl)oxazolidin-2-one (20 mg, 0.09 mmol) and DMSO (1 mL). To this reaction mixture was added (S)-1-(1-(4-chlorophenyl)-1H-imidazol-4-yl)ethanamine (34 mg, 0.13 mmol) and DIEA (46 uL, 0.26 mmol). Vial was then capped and heated in a preheated sand bath at 80° C. for 2 hr. Reaction mixture was then purified by reverse phase HPLC. Product fractions combined, frozen and lyopholyzed to afford a TFA salt of (R)-3-(2-(((S)-1-(1-(4-chlorophenyl)-1H-imidazol-4-yl)ethyl)amino)pyrimidin-4-yl)-4-((R)-1-fluoroethyl)oxazolidin-2-one (4.2 mg, 7.63 μmol, 8.74% yield). $^1$H NMR (400 MHz, CDCl3) δ 1.21 (dd, J=24.26, 6.26 Hz, 3H) 1.74 (d, J=6.65 Hz, 3H) 4.52-4.58 (m, 2H) 4.79-5.06 (m, 1H) 5.29 (br. s., 1H) 5.65 (t, J=6.85 Hz, 1H) 7.41 (d, J=8.61 Hz, 2H) 7.52 (s, 1H) 7.57 (d, J=9.00 Hz, 2H) 7.82 (d, J=6.65 Hz, 1H) 7.98 (d, J=7.04 Hz, 1H) 8.48 (s, 1H) 10.97 (d, J=6.65 Hz, 1H).). LCMS m/z 431.1 (M+H)+, Rt 0.61 min. HRMS (B) m/z 431.1392 (M+H)+, Rt 1.54 min.

The compounds in Table 35a were prepared using methods similar to those described for the preparation of Example 385.

TABLE 35a
| | |
|---|---|
| 386 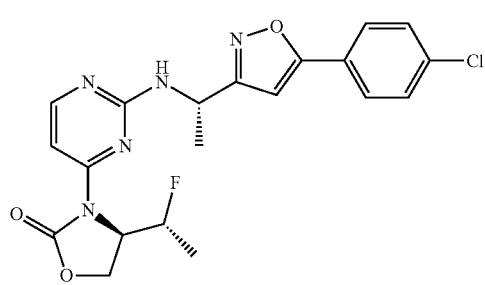 [SMILES: C[C@H](Nc1nccc(N2C(=O)OC[C@@H]2[C@@H](C)F)n1)c1cc(-c2ccc(Cl)cc2)on1] | 391 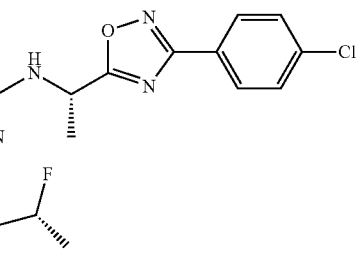 |
| 387 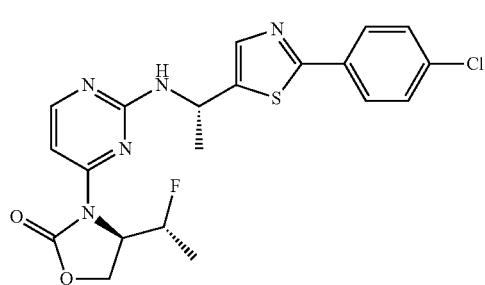 [SMILES: C[C@H](Nc1nccc(N2C(=O)OC[C@@H]2[C@@H](C)F)n1)c1cnc(-c2ccc(Cl)cc2)s1] | 392 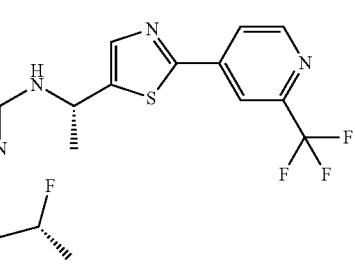 |
| 388 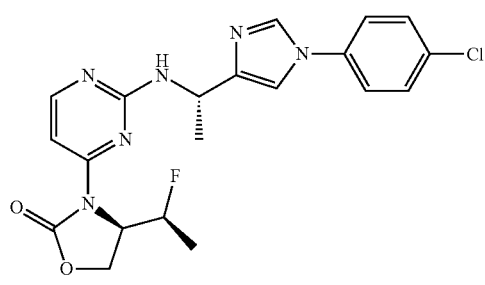 [SMILES: C[C@H](Nc1nccc(N2C(=O)OC[C@@H]2[C@H](C)F)n1)c1cn(-c2ccc(Cl)cc2)cn1] | 393 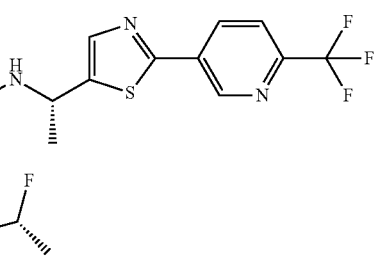 |
| 389 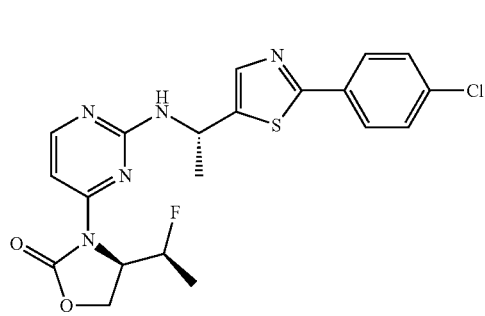 [SMILES: C[C@H](Nc1nccc(N2C(=O)OC[C@@H]2[C@H](C)F)n1)c1cnc(-c2ccc(Cl)cc2)s1] | 394 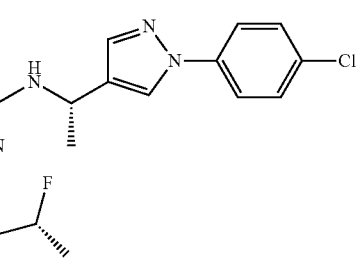 |
| 390 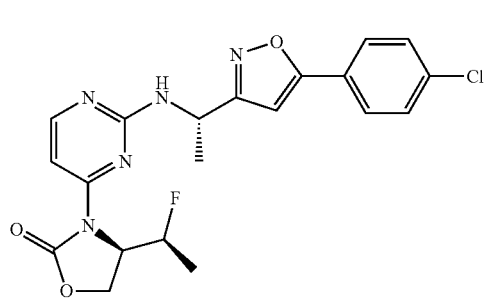 [SMILES: C[C@H](Nc1nccc(N2C(=O)OC[C@@H]2[C@H](C)F)n1)c1cc(-c2ccc(Cl)cc2)on1] | 395 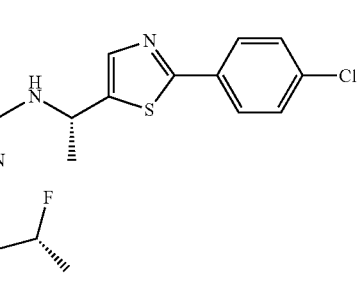 |

TABLE 35a-continued

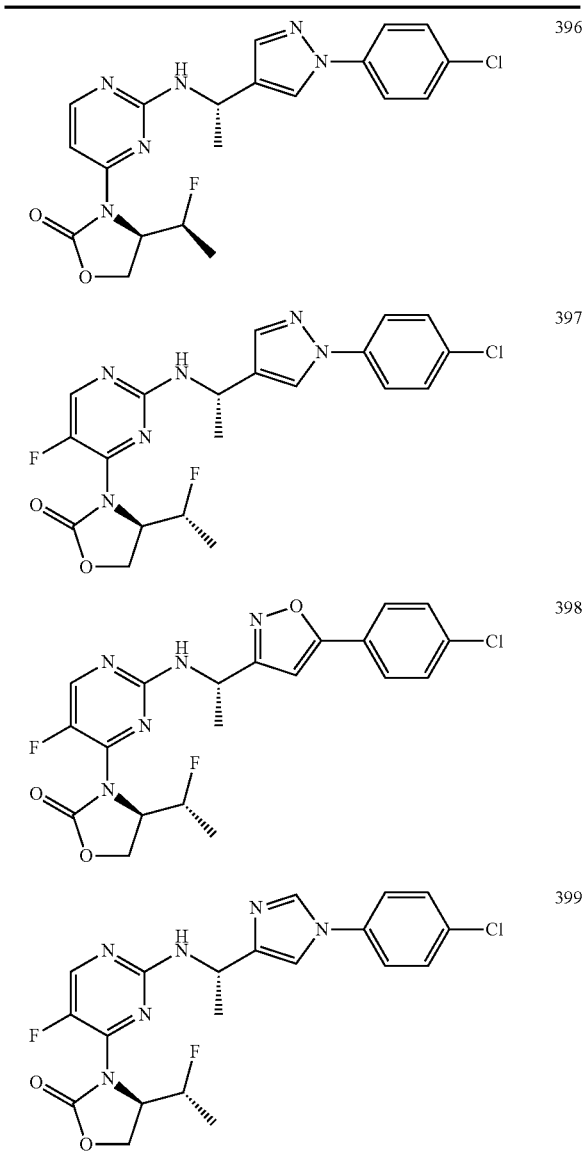

396
397
398
399

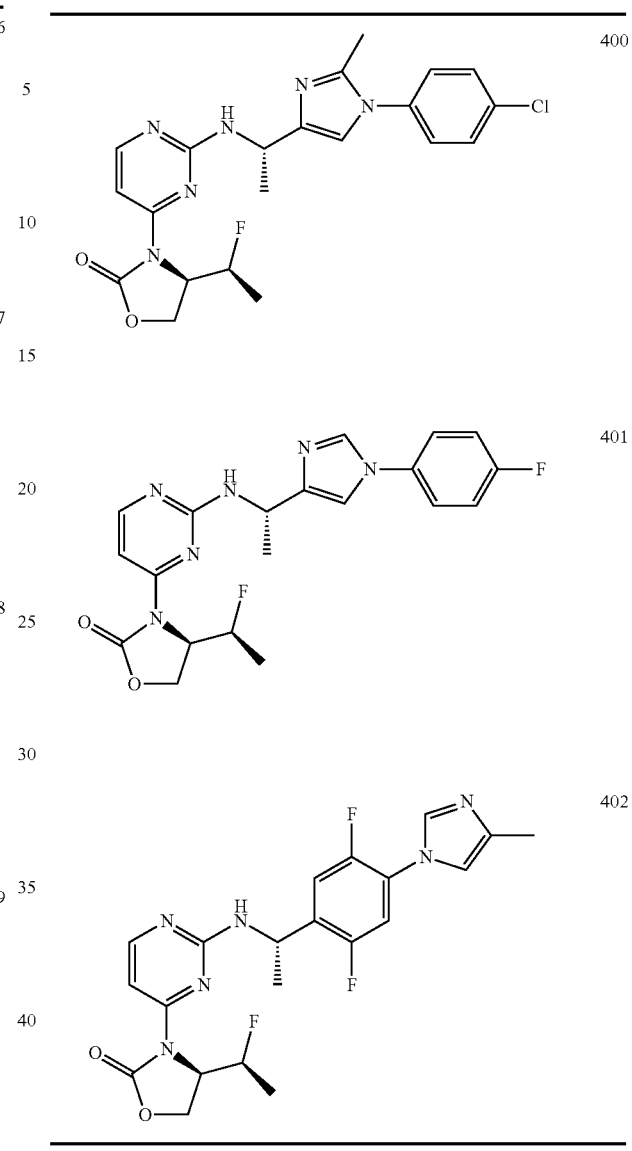

400
401
402

TABLE 35b

Chemical name, NMR chemical shifts and LCMS signal for each compound listed in Table 35a.

| Example: Name | 1H NMR (400 MHz, CDCl$_3$) δ ppm | HRMS |
| --- | --- | --- |
| 386: (R)-3-(2-(((S)-1-(5-(4-chlorophenyl)isoxazol-3-yl)ethyl)amino)pyrimidin-4-yl)-4-((R)-1-fluoroethyl)oxazolidin-2-one | 10.84 (d, J = 6.7 Hz, 1 H), 8.02 (d, J = 7.0 Hz, 1 H), 7.79 (d, J = 7.0 Hz, 1 H), 7.71 (d, J = 8.6 Hz, 2 H), 7.46 (d, J = 8.2 Hz, 2 H), 6.63 (s, 1 H), 5.33 (quin, J = 6.9 Hz, 1 H), 4.95-5.21 (m, 2 H), 4.58-4.71 (m, 1 H), 4.43-4.56 (m, 1 H), 1.75 (d, J = 7.0 Hz, 3 H), 1.17 (dd, J = 23.9, 5.9 Hz, 3 H) | HRMS (B) m/z 432.1242 (M + H)$^+$; Rt-2.18 min |
| 387: (R)-3-(2-(((S)-1-(2-(4-chlorophenyl)thiazol-5-yl)ethyl)amino)pyrimidin-4-yl)-4-((R)-1-fluoroethyl)oxazolidin-2-one | 1.18 (dd, J = 24.26, 6.65 Hz, 3 H) 1.82 (d, J = 7.04 Hz, 3 H) 4.44-4.55 (m, 1 H) 4.57-4.66 (m, 1 H) 4.69-4.94 (m, 1 H) 5.00-5.13 (m, 1 H) 5.40 (quin, J = 6.65 Hz, 1 H) 7.43 (d, J = 8.22 Hz, 2 H) 7.75 (s, 1 H) 7.77-7.88 (m, 3 H) 8.04 (d, J = 6.65 Hz, 1 H) 11.00 (d, J = 5.48 Hz, 1 H) | HRMS (B) m/z 448.1014 (M + H)$^+$; Rt-2.27 min |

TABLE 35b-continued

Chemical name, NMR chemical shifts and LCMS
signal for each compound listed in Table 35a.

| Example: Name | 1H NMR (400 MHz, CDCl$_3$) δ ppm | HRMS |
| --- | --- | --- |
| 388: (R)-3-(2-(((S)-1-(1-(4-chlorophenyl)-1H-imidazol-4-yl)ethyl)amino)pyrimidin-4-yl)-4-((S)-1-fluoroethyl)oxazolidin-2-one | 1.36 (dd, J = 23.87, 6.26 Hz, 3 H) 1.71 (d, J = 6.26 Hz, 3 H) 4.46-4.58 (m, 1 H) 4.59-4.69 (m, 1 H) 4.86-5.12 (m, 2 H) 5.59 (br. s., 1 H) 7.42 (d, J = 8.61 Hz, 2 H) 7.57 (d, J = 9.00 Hz, 3 H) 7.90 (d, J = 6.65 Hz, 1 H) 7.99 (d, J = 7.04 Hz, 1 H) 8.41 (br. s., 1 H) 11.02 (d, J = 7.04 Hz, 1 H) | HRMS (B) m/z 431.1400 (M + H)$^+$; Rt-1.55 min |
| 389: (R)-3-(2-(((S)-1-(2-(4-chlorophenyl)thiazol-5-yl)ethyl)amino)pyrimidin-4-yl)-4-((S)-1-fluoroethyl)oxazolidin-2-one | 1.26 (dd, J = 21.91, 6.65 Hz, 3 H) 1.81 (d, J = 7.04 Hz, 3 H) 4.43-4.55 (m, 1 H) 4.57-4.65 (m, 1 H) 4.65-4.93 (m, 2 H) 5.33 (quin, J = 6.65 Hz, 1 H) 7.45 (d, J = 8.22 Hz, 2 H) 7.71 (s, 1 H) 7.81 (d, J = 8.61 Hz, 2 H) 7.91 (d, J = 7.04 Hz, 1 H) 8.08 (d, J = 7.04 Hz, 1 H) 10.94 (d, J = 5.87 Hz, 1 H) | HRMS (B) m/z 448.1007 (M + H)$^+$; Rt-2.22 min |
| 390: (R)-3-(2-(((S)-1-(5-(4-chlorophenyl)isoxazol-3-yl)ethyl)amino)pyrimidin-4-yl)-4-((S)-1-fluoroethyl)oxazolidin-2-one | 1.48 (dd, J = 23.48, 6.26 Hz, 3 H) 1.73 (d, J = 7.04 Hz, 3 H) 4.41-4.56 (m, 1 H) 4.67 (dd, J = 9.20, 2.54 Hz, 1 H) 4.74-5.05 (m, 2 H) 5.22 (t, J = 6.65 Hz, 1 H) 6.62 (s, 1 H) 7.46 (d, J = 8.22 Hz, 2 H) 7.70 (d, J = 8.22 Hz, 2 H) 7.86 (d, J = 7.04 Hz, 1 H) 7.99 (d, J = 7.04 Hz, 1 H) 10.88 (d, J = 6.26 Hz, 1 H) | HRMS (B) m/z 432.1233 (M + H)$^+$; Rt-2.16 min |
| 391: (R)-3-(2-(((S)-1-(3-(4-chlorophenyl)-1,2,4-oxadiazol-5-yl)ethyl)amino)pyrimidin-4-yl)-4-((R)-1-fluoroethyl)oxazolidin-2-one | 1.11 (dd, J = 24.26, 7.04 Hz, 3 H) 1.90 (d, J = 7.04 Hz, 3 H) 4.40-4.48 (m, 1 H) 4.50-4.57 (m, 1 H) 4.66-4.89 (m, 1 H) 4.93-5.02 (m, 1 H) 5.30-5.41 (m, 1 H) 7.47 (d, J = 8.61 Hz, 2 H) 7.84 (d, J = 7.04 Hz, 1 H) 8.00 (d, J = 8.61 Hz, 2 H) 8.10 (d, J = 6.65 Hz, 1 H) 11.06 (d, J = 4.30 Hz, 1 H) | HRMS (B) m/z 433.1190 (M + H)$^+$; Rt-2.30 min |
| 392: (R)-4-((R)-1-fluoroethyl)-3-(2-(((S)-1-(2-(2-(trifluoromethyl)pyridin-4-yl)thiazol-5-yl)ethyl)amino)pyrimidin-4-yl)oxazolidin-2-one | 1.20 (dd, J = 23.87, 6.26 Hz, 3 H) 1.84 (d, J = 7.04 Hz, 3 H) 4.46-4.55 (m, 1 H) 4.57-4.65 (m, 1 H) 4.68-4.93 (m, 1 H) 5.07 (d, J = 5.87 Hz, 1 H) 5.46 (t, J = 6.85 Hz, 1 H) 7.80 (d, J = 7.04 Hz, 1 H) 7.86 (s, 1 H) 7.94 (d, J = 5.09 Hz, 1 H) 8.04 (d, J = 7.04 Hz, 1 H) 8.17 (s, 1 H) 8.83 (d, J = 5.09 Hz, 1 H) 11.14 (br. s., 1 H) | HRMS (B) m/z 483.1232 (M + H)$^+$; Rt-2.06 min |
| 393: (R)-4-((R)-1-fluoroethyl)-3-(2-(((S)-1-(2-(6-(trifluoromethyl)pyridin-3-yl)thiazol-5-yl)ethyl)amino)pyrimidin-4-yl)oxazolidin-2-one | 1.20 (dd, J = 23.87, 6.26 Hz, 3 H) 1.84 (d, J = 7.04 Hz, 3 H) 4.44-4.56 (m, 1 H) 4.57-4.65 (m, 1 H) 4.68-4.94 (m, 1 H) 5.07 (d, J = 5.48 Hz, 1 H) 5.45 (t, J = 6.65 Hz, 1 H) 7.72-7.88 (m, 3 H) 8.03 (d, J = 7.04 Hz, 1 H) 8.36 (d, J = 7.83 Hz, 1 H) 9.21 (s, 1 H) 11.12 (br. s., 1 H) | HRMS (B) m/z 483.1233 (M + H)$^+$; Rt-2.07 min |
| 394: (R)-3-(2-(((S)-1-(1-(4-chlorophenyl)-1H-pyrazol-4-yl)ethyl)amino)pyrimidin-4-yl)-4-((R)-1-fluoroethyl)oxazolidin-2-one | 1.21 (dd, J = 23.48, 6.65 Hz, 3 H) 1.69 (d, J = 6.65 Hz, 3 H) 4.48-4.56 (m, 1 H) 4.59-4.64 (m, 1 H) 4.87-5.25 (m, 3 H) 7.43 (d, J = 8.61 Hz, 2 H) 7.62 (d, J = 8.61 Hz, 2 H) 7.67 (s, 1 H) 7.74 (d, J = 6.65 Hz, 1 H) 7.95-8.02 (m, 2 H) 10.74 (d, J = 5.48 Hz, 1 H) | HRMS (B) m/z 431.1407 (M + H)$^+$; Rt-1.95 min |
| 395: (R)-3-(2-(((S)-1-(2-(4-chlorophenyl)thiazol-5-yl)ethyl)amino)-5-fluoropyrimidin-4-yl)-4-((R)-1-fluoroethyl)oxazolidin-2-one | 1.17 (dd, J = 23.48, 4.70 Hz, 3 H) 1.76 (d, J = 6.65 Hz, 3 H) 4.39 (dd, J = 9.39, 4.30 Hz, 1 H) 4.60 (t, J = 9.00 Hz, 1 H) 4.68-4.90 (m, 2 H) 5.32 (d, J = 5.09 Hz, 1 H) 7.44 (d, J = 8.61 Hz, 2 H) 7.79 (d, J = 8.61 Hz, 2 H) 7.85 (s, 1 H) 8.19 (d, J = 3.13 Hz, 1 H) | HRMS (B) m/z 466.0916 (M + H)$^+$; Rt-2.32 min |
| 396: (R)-3-(2-(((S)-1-(1-(4-chlorophenyl)-1H-pyrazol-4-yl)ethyl)amino)pyrimidin-4-yl)-4-((S)-1-fluoroethyl)oxazolidin-2-one | 1.28 (dd, J = 23.09, 6.65 Hz, 3 H) 1.68 (d, J = 6.65 Hz, 3 H) 4.44-4.55 (m, 1 H) 4.57-4.65 (m, 1 H) 4.67-4.78 (m, 1 H) 4.81-5.04 (m, 1 H) 5.09 (t, J = 6.65 Hz, 1 H) 7.43 (d, J = 8.61 Hz, 2 H) 7.56-7.67 (m, 3 H) 7.84 (d, J = 6.65 Hz, 1 H) 7.93 (s, 1 H) 8.00 (d, J = 7.04 Hz, 1 H) 10.73 (d, J = 5.87 Hz, 1 H) | HRMS (B) m/z 431.1407 (M + H)$^+$; Rt-1.88 min |
| 397: (R)-3-(2-(((S)-1-(1-(4-chlorophenyl)-1H-pyrazol-4-yl)ethyl)amino)-5-fluoropyrimidin-4-yl)-4-((R)-1-fluoroethyl)oxazolidin-2-one | 1.24 (dd, J = 23.87, 5.87 Hz, 3 H) 1.68 (d, J = 6.65 Hz, 3 H) 4.39 (dd, J = 9.39, 3.91 Hz, 1 H) 4.62 (t, J = 9.00 Hz, 1 H) 4.76-4.99 (m, 2 H) 5.14 (q, J = 7.04 Hz, 1 H) 7.43 (d, J = 8.61 Hz, 2 H) 7.57 (d, J = 8.61 Hz, 2 H) 7.76 (s, 1 H) 7.96 (s, 1 H) 8.15 (d, J = 3.91 Hz, 1H) | HRMS (B) m/z 449.1303 (M + H)$^+$; Rt-2.20 min |
| 398: (R)-3-(2-(((S)-1-(5-(4-chlorophenyl)isoxazol-3-yl)ethyl)amino)-5-fluoropyrimidin-4-yl)-4-((R)-1-fluoroethyl)oxazolidin-2-one | 1.15 (dd, J = 24.26, 6.26 Hz, 3 H) 1.72 (d, J = 7.04 Hz, 3 H) 4.42 (dd, J = 9.39, 4.30 Hz, 1 H) 4.62 (t, J = 9.00 Hz, 1 H) 4.73-5.07 (m, 2 H) 5.17-5.23 (m, 1 H) 6.54 (s, 1 H) 7.45 (d, J = 8.61 Hz, 2 H) 7.68 (d, J = 8.22 Hz, 2 H) 8.15 (d, J = 3.52 Hz, 1 H) | HRMS (B) m/z 450.1145 (M + H)$^+$; Rt-2.26 min |

TABLE 35b-continued

Chemical name, NMR chemical shifts and LCMS signal for each compound listed in Table 35a.

| Example: Name | 1H NMR (400 MHz, CDCl₃) δ ppm | HRMS |
|---|---|---|
| 399: (R)-3-(2-(((S)-1-(1-(4-chlorophenyl)-1H-imidazol-4-yl)ethyl)amino)-5-fluoropyrimidin-4-yl)-4-((R)-1-fluoroethyl)oxazolidin-2-one | 1.29 (dd, J = 23.87, 5.09 Hz, 3 H) 1.75 (d, J = 6.65 Hz, 3 H) 4.38 (d, J = 6.26 Hz, 1 H) 4.58 (t, J = 8.80 Hz, 1 H) 4.93 (br. s., 1 H) 5.32 (br. s., 1 H) 7.42 (d, J = 7.83 Hz, 3 H) 7.56 (d, J = 7.83 Hz, 2 H) 8.19 (br. s., 1 H) 8.62 (br. s., 1 H) | HRMS (B) m/z 449.1313 (M + H)⁺; Rt-1.52 min |
| 400: (R)-3-(2-(((S)-1-(1-(4-chlorophenyl)-2-methyl-1H-imidazol-4-yl)ethyl)amino)pyrimidin-4-yl)-4-((S)-1-fluoroethyl)oxazolidin-2-one | 1.33-1.53 (m, 3 H) 1.71 (br. s., 3 H) 2.60 (s, 3 H) 4.54 (br. s., 1 H) 4.62 (d, J = 7.04 Hz, 1 H) 4.94-5.20 (m, 1 H) 5.69 (br. s., 1 H) 7.30 (d, J = 8.22 Hz, 2 H) 7.59 (d, J = 8.61 Hz, 2 H) 7.82-8.02 (m, 1 H) | HRMS (B) m/z 445.1556 (M + H)⁺; Rt-1.42 min |
| 401: (R)-4-((S)-1-fluoroethyl)-3-(2-(((S)-1-(1-(4-fluorophenyl)-1H-imidazol-4-yl)ethyl)amino)pyrimidin-4-yl)oxazolidin-2-one | 1.36 (dd, J = 24.26, 5.87 Hz, 3 H) 1.72 (d, J = 5.87 Hz, 3 H) 4.44-4.58 (m, 1 H) 4.63 (dd, J = 9.19, 2.93 Hz, 1 H) 4.87-5.18 (m, 2 H) 5.54 (br. s., 1 H) 7.39-7.58 (m, 3 H) 7.87 (d, J = 6.65 Hz, 1 H) 7.97 (d, J = 5.87 Hz, 1 H) 8.26 (br. s., 1 H) 10.95 (br. s., 1 H) | HRMS (B) m/z 415.1695 (M + H)⁺; Rt-1.34 min |
| 402: (R)-3-(2-(((S)-1-(2,5-difluoro-4-(4-methyl-1H-imidazol-1-yl)phenyl)ethyl)amino)pyrimidin-4-yl)-4-((S)-1-fluoroethyl)oxazolidin-2-one | 1.32 (dd, J = 23.09, 6.26 Hz, 3 H) 1.66 (d, J = 7.04 Hz, 3 H) 2.45 (s, 3 H) 4.45-4.56 (m, 1 H) 4.63 (dd, J = 9.00, 2.74 Hz, 1 H) 4.70-4.97 (m, 2 H) 5.48 (quin, J = 6.95 Hz, 1 H) 7.11 (s, 1 H) 7.56 (dd, J = 10.17, 6.65 Hz, 1 H) 7.86 (d, J = 7.04 Hz, 1 H) 8.00 (d, J = 7.04 Hz, 1 H) 8.59 (s, 1 H) 11.07 (br. s., 1 H) | HRMS (B) m/z 447.1761 (M + H)⁺; Rt-1.20 min |

Example 403

(R)-4-((S)-1-fluoroethyl)-3-(2-(((S)-1-(1-(6-(trifluoromethyl)pyridin-3-yl)-1H-pyrazol-3-yl)ethyl)amino)pyrimidin-4-yl)oxazolidin-2-one

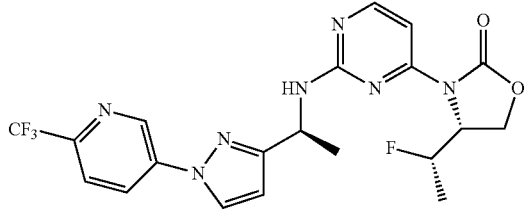 [SMILES: C[C@H](Nc1nccc(N2C(=O)OC[C@@H]2[C@H](C)F)n1)c1ccn(-c2ccc(C(F)(F)F)nc2)n1]

A solution of (R)-4-((S)-1-fluoroethyl)-3-(2-fluoropyrimidin-4-yl)oxazolidin-2-one (10 mg, 0.044 mmol), (S)-1-(1-(6-(trifluoromethyl)pyridin-3-yl)-1H-pyrazol-3-yl)ethanamine (19 mg, 0.065 mmol, 1.5 equiv), and N-ethyl-N-isopropylpropan-2-amine (0.031 mL, 0.175 mmol, 4 equiv) in DMSO (0.5 mL) was heated at 90° C. for 3 hours. The reaction was then cooled to room temperature. Purification by reverse phase HPLC provided the trifluoroacetate salt of (R)-4-((S)-1-fluoroethyl)-3-(2-(((S)-1-(1-(6-(trifluoromethyl)pyridin-3-yl)-1H-pyrazol-3-yl)ethyl)amino)pyrimidin-4-yl)oxazolidin-2-one (14 mg, white solid) in 55% yield. ¹H NMR (400 MHz, CDCl₃) δ 10.83 (d, J=7.1 Hz, 1H), 9.06 (d, J=2.3 Hz, 1H), 8.15 (dd, J=8.5, 2.4 Hz, 1H), 7.93-8.04 (m, 2H), 7.81 (dd, J=7.7, 6.3 Hz, 2H), 6.61 (d, J=2.6 Hz, 1H), 5.28 (quin, J=7.1 Hz, 1H), 4.96-5.17 (m, 1H), 4.68-4.81 (m, 1H), 4.62 (dd, J=9.1, 3.2 Hz, 1H), 4.45-4.54 (m, 1H), 1.72 (d, J=7.1 Hz, 3H), 1.14-1.29 (m, 3H); HRMS m/z 466.1625 (M+H)⁺; Rt-1.83 min.

The compounds in Table 36a were prepared using methods similar to those described for the preparation of Example 403.

TABLE 36a

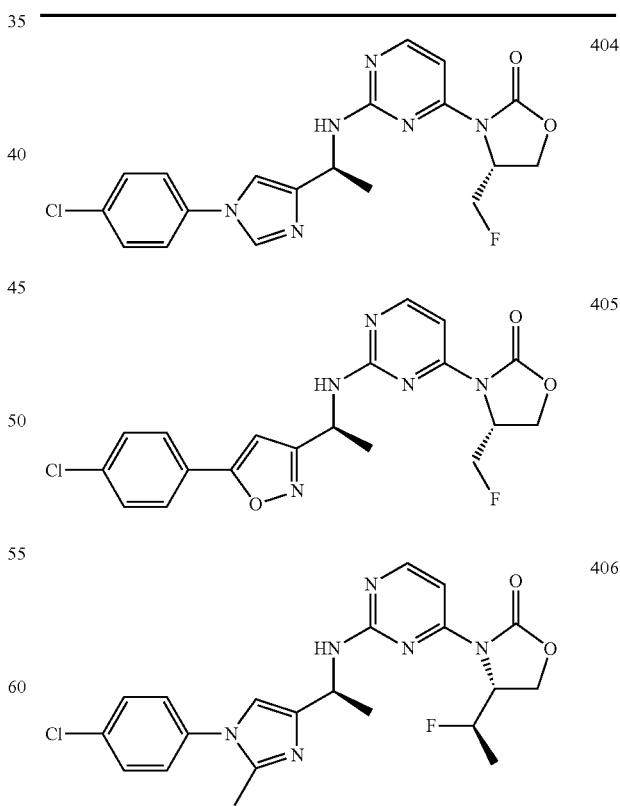

TABLE 36b

Chemical name, NMR chemical shifts and LCMS
signal for each compound listed in Table 36a.

| Example: Name | $^1$H NMR (400 MHz, CDCl$_3$) δ ppm | LCMS |
|---|---|---|
| 404: (R)-3-(2-(((S)-1-(1-(4-chlorophenyl)-1H-imidazol-4-yl)ethyl)amino)pyrimidin-4-yl)-4-(fluoromethyl)oxazolidin-2-one | 8.22 (d, J = 5.5 Hz, 1H), 7.77 (s, 1H), 7.45 (m, 3H), 7.30 (d, J = 8.7 Hz, 2H), 7.11 (s, 1H), 5.14 (m, 1H), 4.93 (m, 1H), 4.48 (m, 4H), 1.63 (d, J = 6.8 Hz, 3H) | LCMS m/z 417.1 (M + H)$^+$; Rt-0.59 min. |
| 405: (R)-3-(2-(((S)-1-(5-(4-chlorophenyl)isoxazol-3-yl)ethyl)amino)pyrimidin-4-yl)-4-(fluoromethyl)oxazolidin-2-one | 8.25 (m, 1H), 7.68 (m, 2H), 7.53 (m, 1H), 7.44 (m, 2H), 6.48 (s, 1H), 5.47 (m, 1H), 4.95 (m, 1H), 4.50 (m, 4H), 1.66 (d, J = 6.8 Hz, 3H) | LCMS m/z 418.2 (M + H)$^+$; Rt-0.82 min. |
| 406: (R)-3-(2-(((S)-1-(1-(4-chlorophenyl)-2-methyl-1H-imidazol-4-yl)ethyl)amino)pyrimidin-4-yl)-4-((R)-1-fluoroethyl)oxazolidin-2-one | 7.96 (m, 1H), 7.82 (m, 1H), 7.60 (d, J = 8.4 Hz, 2H), 7.30 (d, J = 8.4 Hz, 2H), 7.22 (s, 1H), 5.73 (m, 1H), 5.42 (m, 1H), 5.05-4.90 (m, 1H), 4.54 (m, 2H), 2.60 (s, 3H), 1.72 (d, J = 6.7 Hz, 3H), 1.34-1.20 (m, 3H) | LCMS m/z 445.2 (M + H)$^+$; Rt-0.67 min. |

Example 407

(R)-4-((S)-1-hydroxyethyl)-3-(2-(((S)-1-(1-(2-(1,1,1-trifluoro-2-methylpropan-2-yl)pyridin-4-yl)piperidin-4-yl)ethyl)amino)pyrimidin-4-yl)oxazolidin-2-one

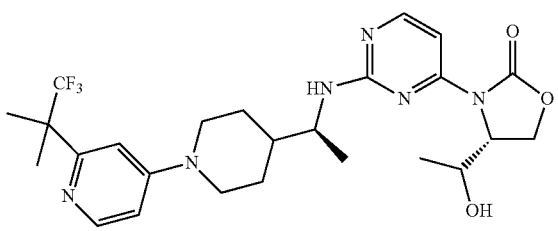 [SMILES: CC(O)[C@H]1COC(=O)N1c1ccnc(N[C@@H](C)C2CCN(c3ccnc(C(C)(C)C(F)(F)F)c3)CC2)n1]

Example 407 was prepared using a method similar to that described for the preparation of Example 28. Product was purified by reverse phase HPLC. $^1$H NMR (400 MHz, CD$_2$Cl$_2$) δ 8.23 (d, J=4.18 Hz, 1H), 8.19 (d, J=4.88 Hz, 1H), 7.37 (d, J=4.88 Hz, 1H), 6.68 (br, s, 1H), 6.68-6.63 (m, 1H), 5.03 (br, s, 1H), 4.80 (br, s, 1H), 4.50-4.36 (m, 3H), 4.09-3.91 (m, 3H), 2.90-2.79 (m, 2H), 1.99-1.79 (m, 2H), 1.78-1.65 (m, 2H), 1.59 (s, 6H), 1.52-1.32 (m, 2H), 1.23 (d, J=6.97 Hz, 3H), 1.18 (d, J=6.27 Hz, 3H), HRMS(C) tR=3.62 min; MS m/z 523.2649 (M+H)+

Example 408

(R)-3-(2-(((S)-1-(1-(4-chloro-3-(trifluoromethoxy)phenyl)piperidin-4-yl)ethyl)amino)pyrimidin-4-yl)-4-((S)-1-hydroxyethyl)oxazolidin-2-one

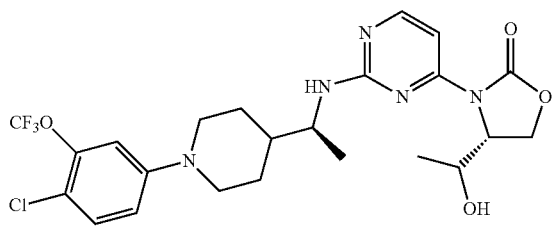

Example 408 was prepared using a method similar to that described for the preparation of Example 28. TFA salt form of product was converted to free base form by using a PL-HCO3 MP SPE cartrage, eluting with MeOH. $^1$H NMR (400 MHz, CD$_2$Cl$_2$) δ 8.07 (d, J=5.33 Hz, 1H), 7.25 (d, J=4.33 Hz, 1H), 7.19 (d, J=9.48 Hz, 1H), 6.76-6.68 (m, 2H), 4.98 (br, s, 1H), 4.69 (br, s, 1H), 4.39-4.25 (m, 3H), 3.90 (br, s, 1H), 3.65-3.56 (m, 2H), 2.68-2.56 (m, 2H), 1.86-1.15 (m, 6H), 1.12 (d, J=6.52 Hz, 3H), 1.07 (d, J=4.74 Hz, 3H), HRMS(C) tR=4.44 min; MS m/z 530.1782 (M+H)+

Example 409

(S)-3-(2-(((S)-1-(4-(difluoromethyl)-2-fluorophenyl)ethyl)amino)-5-fluoropyrimidin-4-yl)-4-((R)-1,1-difluoropropan-2-yl)oxazolidin-2-one

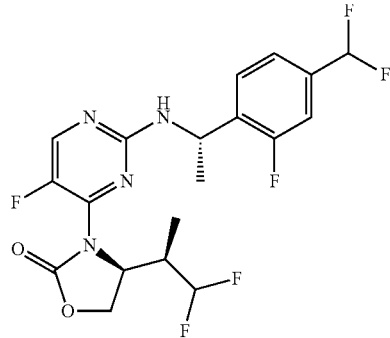

A mixture of (S)-3-(2-chloro-5-fluoropyrimidin-4-yl)-4-((R)-1,1-difluoropropan-2-yl)oxazolidin-2-one (40 mg, 0.135 mmol), (S)-1-(4-(difluoromethyl)-2-fluorophenyl)ethanamine hydrochloride (61.1 mg, 0.271 mmol), Huenig's base (0.095 mL, 0.541 mmol) in DMSO (0.7 mL) under argon atmosphere was heated at 107° C. for ~16 hr. The mixture was diluted with DMSO and water, filtered through a syringe filter and purified by reverse phase HPLC. Selected fractions were collected and lyophilized providing (S)-3-(2-(((S)-1-(4-(difluoromethyl)-2-fluorophenyl)ethyl)amino)-5-fluoropyrimidin-4-yl)-4-((R)-1,1-difluoropropan-2-yl)oxazolidin-2-one as its trifluoroacetic acid salt (35.4 mg).

$^1$H NMR (400 Mhz, CD$_3$OD) δ ppm 8.26 (br. s., 1H), 7.42-7.54 (m, 1H), 7.23-7.33 (m, 2H), 6.55-6.91 (m, 1H), 5.26 (q, J=6.9 Hz, 1H), 4.52 (t, J=9.0 Hz, 1H), 4.36-4.45 (m, 1H), 1.53 (d, J=7.0 Hz, 4H), 0.78 (br. s., 3H). HRMS m/z 449.1412 (M+H)+; Rt-2.27 min.

Examples 410 and 411

(S)-3-(2-(((S)-1-(3-(4-chlorophenyl)-1,2,4-oxadiazol-5-yl)ethyl)amino)pyrimidin-4-yl)-4-((R)-1,1-difluoropropan-2-yl)oxazolidin-2-one/(S)-3-(2-(((R)-1-(3-(4-chlorophenyl)-1,2,4-oxadiazol-5-yl)ethyl)amino)pyrimidin-4-yl)-4-((R)-1,1-difluoropropan-2-yl)oxazolidin-2-one

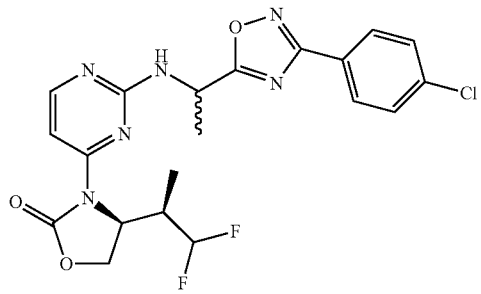 [SMILES: CC(Nc1nccc(N2C(=O)OC[C@@H]2[C@@H](C)C(F)F)n1)c1nc(-c2ccc(Cl)cc2)no1]

A mixture of (S)-4-((R)-1,1-difluoropropan-2-yl)-3-(2-fluoropyrimidin-4-yl)oxazolidin-2-one (40 mg, 0.153 mmol), (S)-1-(3-(4-chlorophenyl)-1,2,4-oxadiazol-5-yl)ethanamine/(R)-1-(3-(4-chlorophenyl)-1,2,4-oxadiazol-5-yl)ethanamine (mixture of diastereomers ~3/1, 37.7 mg, 0.168 mmol) and Huenig's base (0.059 mL, 0.337 mmol) in DMSO (0.7 mmol) under argon atmosphere was heated/radiated in the microwave at 140° C. for 15 min. The mixture was diluted with DMSO and water, filtered through a syringe filter and purified by reverse phase HPLC. Selected fractions were collected and lyophilized providing (S)-3-(2-(((S)-1-(3-(4-chlorophenyl)-1,2,4-oxadiazol-5-yl)ethyl)amino)pyrimidin-4-yl)-4-((R)-1,1-difluoropropan-2-yl)oxazolidin-2-one (31.8 mg; first eluted product) and (S)-3-(2-(((R)-1-(3-(4-chlorophenyl)-1,2,4-oxadiazol-5-yl)ethyl)amino)pyrimidin-4-yl)-4-((R)-1,1-difluoropropan-2-yl)oxazolidin-2-one (11.5 mg; second eluted product) as their trifluoroacetic acid salts.

410: First eluted product: ¹H NMR (500 Mhz, CD₃OD) δ ppm 8.22 (s, 1H), 8.03-7.93 (m, 2H), 7.54-7.46 (m, 3H), 5.84 (m, 1H), 5.49 (q, J=7.2 Hz, 1H), 5.13 (dt, J=8.4, 3.1 Hz, 1H), 4.60-4.21 (m, 2H), 2.74 (m, 1H), 1.75 (d, J=7.2 Hz, 3H), 0.90 (br. s, 3H). HRMS m/z 465.1260 (M+H)+; Rt-2.41 min.

411: Second eluted product: ¹H NMR (500 Mhz, CD₃OD) δ ppm 8.19 (dd, J=7.5, 6.0 Hz, 1H), 8.10-7.91 (m, 2H), 7.55-7.50 (m, 2H), 7.47 (d, J=5.8 Hz, 1H), 6.08 (td, J=55.6, 3.5 Hz, 1H), 5.40 (t, J=7.1 Hz, 1H), 4.59-4.42 (m, 1H), 4.39 (s, 1H), 3.03 (s, 1H), 1.72 (d, J=7.2 Hz, 3H), 1.03 (d, J=7.2 Hz, 3H). HRMS m/z 465.1250 (M+H)+; Rt-2.42 min.

The following Examples were prepared using a method similar to that described for the preparation of Examples 410/411

Example 412

(S)-3-(2-(((S)-1-(4-(difluoromethyl)-2-fluorophenyl)ethyl)amino)pyrimidin-4-yl)-4-((R)-1,1-difluoropropan-2-yl)oxazolidin-2-one

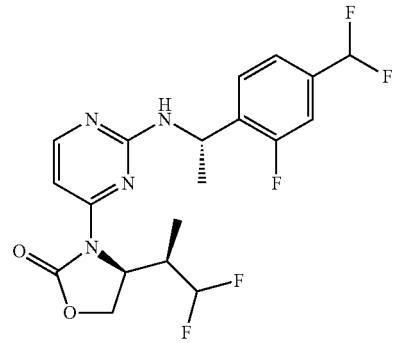 [SMILES: C[C@H](Nc1nccc(N2C(=O)OC[C@@H]2[C@@H](C)C(F)F)n1)c1ccc(C(F)F)cc1F]

¹H NMR (400 Mhz, CD₃OD) δ ppm 8.19 (d, J=6.7 Hz, 1H), 7.70 (d, J=6.7 Hz, 1H), 7.47-7.56 (m, 1H), 7.28-7.40 (m, 2H), 6.60-6.95 (m, 1H), 5.57-5.95 (m, 1H), 5.47 (m, J=5.1 Hz, 1H), 5.12 (dt, J=7.8, 3.13 Hz, 1H), 4.46-4.60 (m, 2H), 1.63 (d, J=7.0 Hz, 3H), 0.77-0.95 (m, 3H). HRMS m/z 431.1506 (M+H)+; Rt-2.09 min.

Example 413 and 414

(S)-4-((R)-1,1-difluoropropan-2-yl)-3-(2-(((S)-1-(5-(4-fluoro-3-methylphenyl)pyrimidin-2-yl)ethyl)amino)pyrimidin-4-yl)oxazolidin-2-one/(S)-4-((R)-1,1-difluoropropan-2-yl)-3-(2-(((R)-1-(5-(4-fluoro-3-methylphenyl)pyrimidin-2-yl)ethyl)amino)pyrimidin-4-yl)oxazolidin-2-one

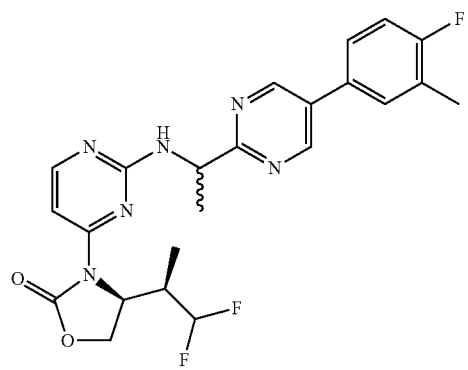 [SMILES: Cc1cc(-c2cnc(C(C)Nc3nccc(N4C(=O)OC[C@@H]4[C@@H](C)C(F)F)n3)nc2)ccc1F]

A mixture of (S)-4-((R)-1,1-difluoropropan-2-yl)-3-(2-fluoropyrimidin-4-yl)oxazolidin-2-one 30 mg, 0.115 mmol), 1-(5-(4-fluoro-3-methylphenyl)pyrimidin-2-yl)ethanamine (53.1 mg, 0.230 mmol), Huenig's Base 0.05 mL, 0.287 mmol) in DMSO (0.7 mL) under argon atmosphere was heated at 120° C. for ~16 hr. Additional amine (2 eq) was added and heating was continued for 3 hrs. More amine (2 eq) was added and heating was continued for 3 hr. The mixture was diluted with DMSO and water, filtered through a syringe filter and purified by reverse phase HPLC. Selected fractions were collected and lyophilized providing (S)-4-

((R)-1,1-difluoropropan-2-yl)-3-(2-(((S)-1-(5-(4-fluoro-3-methylphenyl)pyrimidin-2-yl)ethyl)amino)pyrimidin-4-yl)oxazolidin-2-one/(S)-4-((R)-1,1-difluoropropan-2-yl)-3-(2-(((R)-1-(5-(4-fluoro-3-methylphenyl)pyrimidin-2-yl)ethyl)amino)pyrimidin-4-yl)oxazolidin-2-one as their trifluoroacetic acid salts as off-white solids.

413: First eluted product (2.8 mg): $^1$H NMR (500 Mhz, CD$_3$OD) δ ppm 8.98 (s, 2H), 8.16 (s, 1H), 7.59 (dd, J=7.3, 2.3 Hz, 1H), 7.56-7.45 (m, 2H), 7.18 (t, J=9.0 Hz, 1H), 6.40-5.96 (m, 1H), 5.25 (q, J=6.9 Hz, 1H), 4.52 (dd, J=9.4, 2.8 Hz, 1H), 4.42 (t, J=8.4 Hz, 1H), 3.08 (s, 1H), 2.34 (d, J=2.0 Hz, 3H), 1.62 (d, J=7.0 Hz, 3H), 1.05 (d, J=7.2 Hz, 3H). HRMS m/z 473.1916 (M+H)+; Rt-2.12 min.

414: Second eluted product (2.9 mg): $^1$H NMR (500 Mhz, CD$_3$OD) δ ppm 8.96 (s, 2H), 8.16 (s, 1H), 7.57 (dd, J=7.5, 2.4 Hz, 1H), 7.53-7.43 (m, 2H), 7.17 (t, J=9.0 Hz, 1H), 5.92 (t, J=56.9 Hz, 1H), 5.30 (q, J=7.0 Hz, 1H), 5.13 (dt, J=6.9, 3.3 Hz, 1H), 4.57-4.40 (m, 2H), 2.53 (s, 1H), 2.34 (d, J=2.0 Hz, 3H), 1.64 (d, J=7.0 Hz, 3H), 0.87 (s, 3H). HRMS m/z 473.1919 (M+H)+; Rt-2.17 min.

The compounds in Table 37a were prepared using methods similar to those described for the preparation of Examples 35, 36, or 37/38.

TABLE 37a

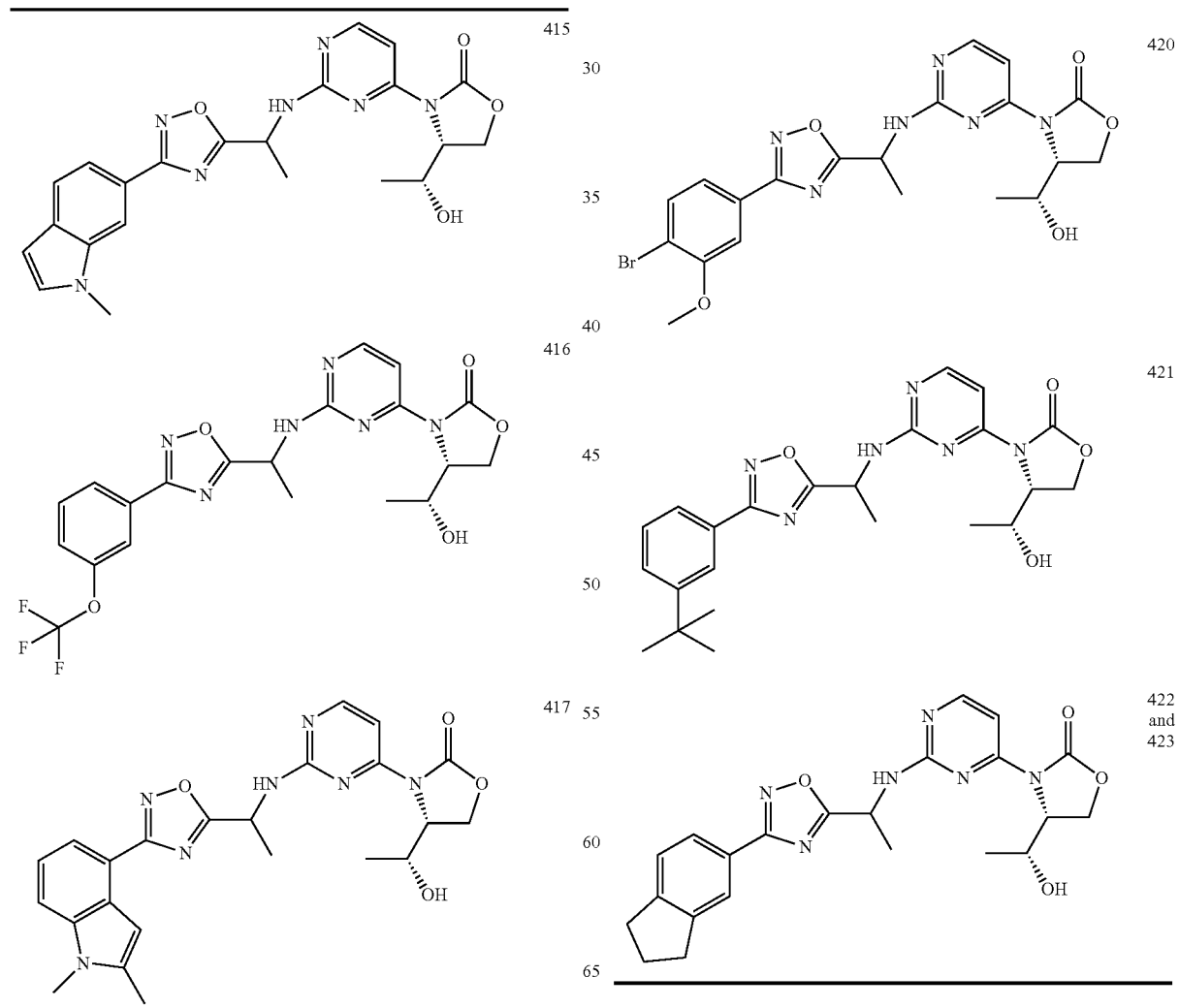

TABLE 37b

Chemical name, NMR chemical shifts, chiral separation conditions
and LCMS signal for compounds listed in Table 37a.

| Example: Name | Chiral separation conditions, peak identification and analytical data |
|---|---|
| 415: (R)-4-((R)-1-hydroxyethyl)-3-(2-(((S)-1-(3-(1-methyl-1H-indol-6-yl)-1,2,4-oxadiazol-5-yl)ethyl)amino)pyrimidin-4-yl)oxazolidin-2-one | Chiral separation was achieved by chiral SFC column chromatography (Column OD-H 21 × 250 mm 30% MeOH + 20 mM NH4OH in $CO_2$, flow 80 g/min, 238 nm UV collection) to give (R)-4-((R)-1-hydroxyethyl)-3-(2-(((R)-1-(3-(1-methyl-1H-indol-6-yl)-1,2,4-oxadiazol-5-yl)ethyl)amino)pyrimidin-4-yl)oxazolidin-2-one and (R)-4-((R)-1-hydroxyethyl)-3-(2-(((S)-1-(3-(1-methyl-1H-indol-6-yl)-1,2,4-oxadiazol-5-yl)ethyl)amino)pyrimidin-4-yl)oxazolidin-2-one<br>415: Peak 2: (11 mg): ($CDCl_3$) δ 8.25 (d, J = 5.7 Hz, 1H), 8.08 (d, J = 1.1 Hz, 1H), 7.80 (dd, J = 8.3, 1.4 Hz, 1H), 7.70 (d, J = 8.3 Hz, 1H), 7.54 (d, J = 5.7 Hz, 1H), 7.19 (d, J = 3.1 Hz, 1H), 6.54 (dd, J = 3.0, 0.9 Hz, 1H), 5.96 (s, 1H), 5.35 (s, 1H), 4.96-4.81 (m, 1H), 4.55 (dd, J = 9.5, 2.5 Hz, 1H), 4.38 (dd, J = 9.3, 8.4 Hz, 1H), 3.88 (s, 4H), 3.19 (s, 1H), 2.63 (s, 8H), 1.80 (d, J = 6.7 Hz, 1H), 0.96 (d, J = 6.4 Hz, 3H). HRMS(B) m/z 449.1812RT = 2.18 min. |
| 416: (R)-4-((R)-1-hydroxyethyl)-3-(2-(((S)-1-(3-(3-(trifluoromethoxy)phenyl)-1,2,4-oxadiazol-5-yl)ethyl)amino)pyrimidin-4-yl)oxazolidin-2-one | Chiral separation was achieved by chiral SFC column chromatography (Column IA-H 21 × 250 mm 15% MeOH in $CO_2$, flow 80 g/min, 238 nm UV collection) to give (R)-4-((R)-1-hydroxyethyl)-3-(2-(((R)-1-(3-(3-(trifluoromethoxy)phenyl)-1,2,4-oxadiazol-5-yl)ethyl)amino)pyrimidin-4-yl)oxazolidin-2-one and (R)-4-((R)-1-hydroxyethyl)-3-(2-(((S)-1-(3-(3-(trifluoromethoxy)phenyl)-1,2,4-oxadiazol-5-yl)ethyl)amino)pyrimidin-4-yl)oxazolidin-2-one<br>416: Peak 2 (62 mg): ($CDCl_3$) δ 8.25 (d, J = 5.8 Hz, 1H), 8.02 (dt, J = 7.7, 1.3 Hz, 1H), 7.95 (dt, J = 2.3, 1.3 Hz, 1H), 7.67-7.46 (m, 2H), 7.40 (ddt, J = 8.3, 2.5, 1.1 Hz, 1H), 5.90 (s, 1H), 5.40 (s, 1H), 4.86 (ddd, J = 8.4, 4.7, 2.5 Hz, 1H), 4.55 (dd, J = 9.5, 2.5 Hz, 1H), 4.41 (t, J = 8.9 Hz, 1H), 3.90 (s, 1H), 3.52 (s, 1H), 2.77 (s, 1H), 1.86-1.77 (m, 3H), 1.34-1.19 (m, 1H), 1.03 (s, 3H). HRMS(B) m/z 480.1369. RT = 2.67 min. Chiral RT = 4.80 min |
| 417: (R)-3-(2-(((S)-1-(3-(1,2-dimethyl-1H-indol-4-yl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column IA 21 × 250 mm 40% MeOH in $CO_2$, flow 75 g/min, 238 nm UV collection) to give (R)-3-(2-(((R)-1-(3-(1,2-dimethyl-1H-indol-4-yl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(1,2-dimethyl-1H-indol-4-yl)-1,2,4-oxadiazol-5-yl)ethyl)amino)pyrimidin-4-yl)-4-((R)-1-hydroxyethyl)oxazolidin-2-one.<br>417: Peak 2 (120 mg): ($CDCl_3$) δ 8.16 (d, J = 6.2 Hz, 1H), 7.89 (dd, J = 7.5, 0.9 Hz, 1H), 7.63 (d, J = 6.2 Hz, 1H), 7.45 (dt, J = 8.1, 1.0 Hz, 1H), 7.34-7.21 (m, 1H), 6.95-6.85 (m, 1H), 5.47-5.19 (m, 1H), 1.91-1.79 (m, 3H), 4.81 (ddd, J = 8.3, 4.3, 2.4 Hz, 1H), 4.52 (dd, J = 9.5, 2.4 Hz, 1H), 4.35 (dd, J = 9.5, 8.3 Hz, 1H), 3.75 (s, 4H), 3.52 (s, 2H), 2.51 (d, J = 1.0 Hz, 3H), 0.86 (d, J = 5.5 Hz, 3H). HRMS(B) m/z 463.1968. RT = 2.23 min. Chiral RT = 3.35 min |
| 418: (R)-3-(2-(((S)-1-(3-(4-chloro-3-(trifluoromethoxy)phenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column AD-H 21 × 250 mm 15% MeOH + 10 mM NH4OH in $CO_2$, flow 75 g/min, 238 nm UV collection) to give (R)-3-(2-(((R)-1-(3-(4-chloro-3-(trifluoromethoxy)phenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(4-chloro-3-(trifluoromethoxy)phenyl)-1,2,4-oxadiazol-5-yl)ethyl)amino)pyrimidin-4-yl)-4-((R)-1-hydroxyethyl)oxazolidin-2-one<br>418: Peak 2 (120 mg): $CDCl_3$) δ 8.25 (d, J = 5.8 Hz, 1H), 8.05 (p, J = 1.4 Hz, 1H), 7.98 (dd, J = 8.4, 1.9 Hz, 1H), 7.70-7.49 (m, 2H), 5.74 (s, 1H), 5.51-5.35 (m, 1H), 4.85 (ddd, J = 8.3, 4.8, 2.5 Hz, 1H), 4.54 (dd, J = 9.3, 2.5 Hz, 1H), 4.41 (dd, J = 9.4, 8.3 Hz, 1H), 2.72 (s, 1H), 1.79 (d, J = 7.1 Hz, 3H), 1.63 (d, J = 7.1 Hz, 2H), 1.05 (s, 3H). HRMS(B) m/z 515.1243. Chiral RT = 4.20 min |

TABLE 37b-continued

Chemical name, NMR chemical shifts, chiral separation conditions and LCMS signal for compounds listed in Table 37a.

| Example: Name | Chiral separation conditions, peak identification and analytical data |
|---|---|
| 419: (R)-3-(2-(((S)-1-(3-(4-chloro-3-methylphenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column IA 21 × 250 mm 30% MeOH in $CO_2$, flow 75 g/min, 238 nm UV collection) to give (R)-3-(2-(((R)-1-(3-(4-chloro-3-methylphenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(4-chloro-3-methylphenyl)-1,2,4-oxadiazol-5-yl)ethyl)amino)pyrimidin-4-yl)-4-((R)-1-hydroxyethyl)oxazolidin-2-one<br>419: Peak 2 (92 mg) (CDCl$_3$) δ 8.20 (d, J = 6.0 Hz, 1H), 7.95 (d, J = 2.1 Hz, 1H), 7.83 (dd, J = 8.3, 2.2 Hz, 1H), 7.61 (d, J = 6.0 Hz, 1H), 7.47 (d, J = 8.3 Hz, 1H), 5.33 (d, J = 7.1 Hz, 1H), 4.84 (ddd, J = 8.4, 4.7, 2.4 Hz, 1H), 1.89-1.74 (m, 3H), 4.56 (dd, J = 9.4, 2.5 Hz, 1H), 4.41 (dd, J = 9.4, 8.3 Hz, 1H), 3.74 (d, J = 41.0 Hz, 1H), 3.52 (s, 1H), 2.46 (s, 3H), 1.12-0.85 (m, 3H). HRMS(B) m/z 411.1365. Chiral RT = 2.85 min |
| 420: (R)-3-(2-(((S)-1-(3-(4-bromo-3-methoxyphenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column IA 21 × 250 mm 30% MeOH in $CO_2$, flow 90 g/min, 238 nm UV collection) to give (R)-3-(2-(((R)-1-(3-(4-bromo-3-methoxyphenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(4-bromo-3-methoxyphenyl)-1,2,4-oxadiazol-5-yl)ethyl)amino)pyrimidin-4-yl)-4-((R)-1-hydroxyethyl)oxazolidin-2-one<br>420: Peak 2 (96 mg) (CDCl$_3$) δ 8.22 (d, J = 6.0 Hz, 1H), 7.67 (d, J = 8.1 Hz, 1H), 7.63-7.52 (m, 3H), 5.37 (s, 1H), 4.84 (ddd, J = 8.3, 4.7, 2.4 Hz, 1H), 1.91-1.72 (m, 3H), 4.55 (dd, J = 9.5, 2.5 Hz, 1H), 4.41 (t, J = 8.9 Hz, 1H), 4.00 (s, 3H), 3.52 (s, 1H), 1.02 (s, 3H). HRMS(B) m/z 504.0757. Chiral RT = 3.50 min |
| 421: (R)-3-(2-(((S)-1-(3-(3-(tert-butyl)phenyl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column IA-H 21 × 250 mm 15% MeOH in $CO_2$, flow 80 g/min, 238 nm UV collection) to give (R)-3-(2-(((R)-1-(3-(3-(tert-butyl)phenyl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(3-(tert-butyl)phenyl)-1,2,4-oxadiazol-5-yl)ethyl)amino)pyrimidin-4-yl)-4-((R)-1-hydroxyethyl)oxazolidin-2-one<br>421: Peak 2 (62 mg): (CDCl$_3$) δ 8.25 (d, J = 5.7 Hz, 1H), 8.08 (t, J = 1.8 Hz, 1H), 7.87 (dt, J = 7.6, 1.4 Hz, 1H), 7.66-7.51 (m, 1H), 7.43 (t, J = 7.8 Hz, 1H), 5.92-5.68 (m, 1H), 5.35 (d, J = 9.3 Hz, 1H), 4.86 (ddd, J = 8.4, 4.4, 2.4 Hz, 1H), 1.74-1.64 (m, 1H), 4.55 (dd, J = 9.5, 2.5 Hz, 1H), 4.39 (dd, J = 9.4, 8.3 Hz, 1H), 3.51 (d, J = 5.3 Hz, 3H), 3.00 (d, J = 4.9 Hz, 1H), 1.79 (d, J = 7.2 Hz, 3H), 1.38 (s, 9H), 1.08 (q, J = 5.5 Hz, 1H), 1.00 (s, 3H). HRMS(B) m/z 452.2172. RT = 2.88 min. Chiral RT = 5.20 min |
| 422 and 423: (R)-3-(2-(((R)-1-(3-(2,3-dihydro-1H-inden-5-yl)-1,2,4-oxadiazol-5-yl)ethyl)amino)pyrimidin-4-yl)-4-((R)-1-hydroxyethyl)oxazolidin-2-one | Chiral separation was achieved by chiral SFC column chromatography (Column ID 21 × 250 mm 40% IPA + 10 mM NH4OH in $CO_2$, flow 75 g/min, 222 nm UV collection) to give (R)-3-(2-(((R)-1-(3-(2,3-dihydro-1H-inden-5-yl)-1,2,4-oxadiazol-5-yl)ethyl)amino)pyrimidin-4-yl)-4-((R)-1-hydroxyethyl)oxazolidin-2-one and (R)-3-(2-(((S)-1-(3-(2,3-dihydro-1H-inden-5-yl)-1,2,4-oxadiazol-5-yl)ethyl)amino)pyrimidin-4-yl)-4-((R)-1-hydroxyethyl)oxazolidin-2-one<br>422: First eluted product (15 mg): $^1$H NMR (400 MHz, CDCl$_3$) δ 8.24 (d, J = 5.8 Hz, 1H), 7.89 (d, J = 1.7 Hz, 1H), 7.81 (dd, J = 7.8, 1.7 Hz, 1H), 7.50 (d, J = 5.7 Hz, 1H), 7.34 (d, J = 7.8 Hz, 1H), 5.81 (s, 1H), 5.27 (d, J = 43.6 Hz, 1H), 4.70 (d, J = 7.9 Hz, 1H), 4.49 (dd, J = 9.3, 2.4 Hz, 1H), 4.42-4.09 (m, 2H), 3.51 (d, J = 3.1 Hz, 3H), 3.23 (s, 1H), 2.98 (t, J = 7.4 Hz, 4H), 2.14 (p, J = 7.5 Hz, 2H), 1.78 (d, J = 7.0 Hz, 3H), 1.75-1.62 (m, 0H), 1.21 (dd, J = 14.9, 6.3 Hz, 4H), 1.14 (d, J = 5.5 Hz, 1H). HRMS(D) m/z 437.1944 (M + H). RT = 3.57 min. Chiral RT = 2.35 min. |

TABLE 37b-continued

Chemical name, NMR chemical shifts, chiral separation conditions and LCMS signal for compounds listed in Table 37a.

| Example: Name | Chiral separation conditions, peak identification and analytical data |
|---|---|
| | 423: Second eluted product (63 mg): $^1$H NMR (400 MHz, CDCl$_3$) δ 8.25 (d, J = 5.7 Hz, 1H), 7.91 (d, J = 1.6 Hz, 1H), 7.83 (dd, J = 7.8, 1.6 Hz, 1H), 7.54 (d, J = 5.7 Hz, 1H), 7.33 (d, J = 7.8 Hz, 1H), 5.79 (s, 1H), 5.32 (s, 1H), 4.85 (ddd, J = 8.4, 4.5, 2.5 Hz, 1H), 4.55 (dd, J = 9.5, 2.5 Hz, 1H), 4.39 (t, J = 8.9 Hz, 1H), 3.75 (d, J = 49.5 Hz, 1H), 3.51 (s, 1H), 2.97 (t, J = 7.4 Hz, 5H), 2.13 (p, J = 7.5 Hz, 2H), 1.78 (d, J = 7.2 Hz, 3H), 1.63 (s, 1H), 1.23 (d, J = 6.1 Hz, 1H), 0.98 (d, J = 7.1 Hz, 4H). HRMS(D) m/z 437.1942 (M + H). RT = 3.58 min. Chiral RT = 3.50 min. |

Example 424 and 425

(4R)-3-(2-((1-(5-(4-chlorophenyl)-1,2,4-oxadiazol-3-yl)ethyl)amino)pyrimidin-4-yl)-4-((R)-1-hydroxy-ethyl)oxazolidin-2-one

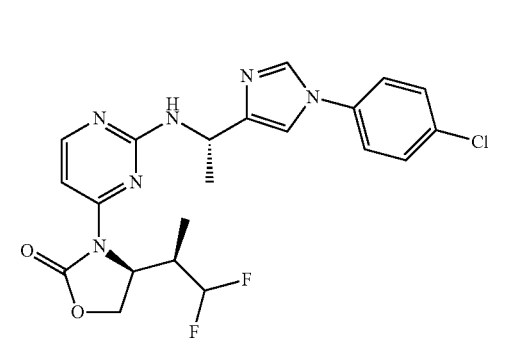 [SMILES: C[C@H](Nc1nccc(N2C(=O)OC[C@@H]2[C@@H](C)C(F)F)n1)c1cn(-c2ccc(Cl)cc2)cn1]

A solution of (R)-4-((R)-1-(tert-butoxy)ethyl)-3-(2-fluoropyrimidin-4-yl)oxazolidin-2-one (150 mg, 0.529 mmol), 1-[3-(4-chloro-phenyl)-[1,2,4]oxadiazol-5-yl]-ethylamine (118 mg, 0.529 mmol, 1.0 equiv), and DIEA (0.185 mL, 1.059 mmol, 2.0 equiv) in DMSO (2 mL) was heated at 110° C. for 120 min. The reaction mixture was diluted with EtOAc (20 mL) and washed with water (10 mL), 4% brine (10 mL), concentrated in vacuo. The crude material, (R)-5-((R)-1-tert-Butoxy-ethyl)-1-(2-{1-[3-(4-chloro-phenyl)-[1,2,4]oxadiazol-5-yl]-ethylamino}-pyrimidin-4-yl)-imidazolidin-2-one, was carried to the next step without further purification.

(R)-5-((R)-1-tert-Butoxy-ethyl)-1-(2-{1-[3-(4-chloro-phenyl)-[1,2,4]oxadiazol-5-yl]-ethylamino}-pyrimidin-4-yl)-imidazolidin-2-one (200 mg, 0.411 mmol) was treated with 10:1 TFA/water (10 ml) for 2 hours. The reaction was conc. in vacuo and neutralized by passing through a column of MP-carbonate eluting with MeOH/DCM/MeOH and Flash column (silica, 15µ, 40 g) eluting w/ 5-60% EtOAc/heptane over 2.5 hours to give (R)-3-(((R)-1-(5-(4-chlorophenyl)-1,2,4-oxadiazol-3-yl)ethyl)amino)pyrimidin-4-yl)-4-((R)-1-hydroxyethyl)oxazolidin-2-one and (R)-3-(2-(((S)-1-(5-(4-chlorophenyl)-1,2,4-oxadiazol-3-yl)ethyl)amino)pyrimidin-4-yl)-4-((R)-1-hydroxyethyl)oxazolidin-2-one 424: first eluted product (45 mg, 50.8%). HRMS m/z 430.1156.

425: Second eluted product (46 mg, 52.0%). $^1$H NMR (400 MHz, CDCl$_3$) δ 8.67 (s, 1H), 8.09 (dq, J=8.4, 2.0, 1.6 Hz, 3H), 7.64 (d, J=6.4 Hz, 1H), 7.58-7.48 (m, 2H), 5.48-5.27 (m, 1H), 4.94 (t, J=6.6 Hz, 1H), 4.63-4.40 (m, 2H), 1.13 (d, J=6.5 Hz, 3H), 0.89 (d, J=7.1 Hz, 0H), 1.83-1.72 (m, 3H). HRMS m/z 430.1156.

Example 426

(S)-3-(2-(((S)-1-(1-(4-chlorophenyl)-1H-imidazol-4-yl)ethyl)amino)pyrimidin-4-yl)-4-((R)-1,1-difluoro-propan-2-yl)oxazolidin-2-one A mixture of (S)-4-((R)-1,1-difluoropropan-2-yl)-3-(2-fluoropyrimidin-4-yl)oxazolidin-2-one (23.35 mg, 0.089 mmol), (S)-1-(1-(4-chlorophenyl)-1H-imidazol-4-yl)ethanamine hydrochloride (30 mg, 0.116 mmol) and Huenig's base (0.047 mL, 0.268 mmol) in DMSO (0.6 mL) under argon atmosphere was heated at 80° C. for ~16 hr. The mixture was diluted with DMSO and water, filtered through a syringe filter and purified by reverse phase HPLC. Selected fractions were collected and lyophilized providing (S)-3-(2-(((S)-1-(1-(4-chlorophenyl)-1H-imidazol-4-yl)ethyl)amino)pyrimidin-4-yl)-4-((R)-1,1-difluoropropan-2-yl)oxazolidin-2-one as its trifluoroacetic acid salt (30.2 mg) as a white solid.

$^1$H NMR (400 Mhz, CD$_3$OD) δ ppm 9.07 (br. s., 1H), 8.24 (d, J=6.3 Hz, 1H), 7.85 (s, 1H), 7.53-7.72 (m, 5H), 5.64-6.06 (m, 1H), 5.36 (q, J=6.9 Hz, 1H), 5.07-5.23 (m, 1H), 4.41-4.62 (m, 2H), 2.62-2.90 (m, 1H), 1.71 (d, J=6.7 Hz, 3H), 0.97 (d, J=7.0 Hz, 3H); LCMS m/z 463.2 (M+H)$^+$, Rt 0.64 min.

The following Example was prepared using a method similar to that described for the preparation of Example 426.

Example 427
(S)-4-((R)-1,1-difluoropropan-2-yl)-3-(2-(((S)-1-(1-(4-fluorophenyl)-1H-imidazol-4-yl)ethyl)amino)pyrimidin-4-yl)oxazolidin-2-one
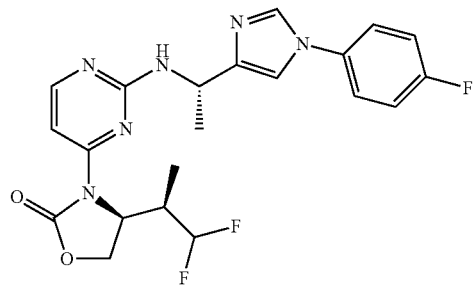 [SMILES: C[C@H](Nc1nccc(N2C(=O)OC[C@@H]2[C@@H](C)C(F)F)n1)c1cn(-c2ccc(F)cc2)cn1]
$^1$H NMR (400 Mhz, CD$_3$OD) δ ppm 9.13 (s, 1H), 8.25 (d, J=6.7 Hz, 1H), 7.86 (s, 1H), 7.61-7.73 (m, 3H), 7.36 (m, J=8.6, 8.6 Hz, 2H), 5.69-6.06 (m, 1H), 5.37 (q, J=6.7 Hz, 1H), 5.10-5.18 (m, 1H), 4.46-4.59 (m, 2H), 2.67-2.82 (m, 1H), 1.72 (d, J=7.0 Hz, 3H), 0.98 (d, J=7.4 Hz, 3H)
LCMS m/z 447.2 (M+H)$^+$, Rt 0.57 min.
The Examples in Table 38a were prepared using methods similar to those described for the preparation of Examples 385 and 403.
TABLE 38a
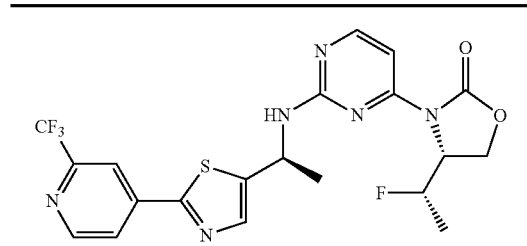
428
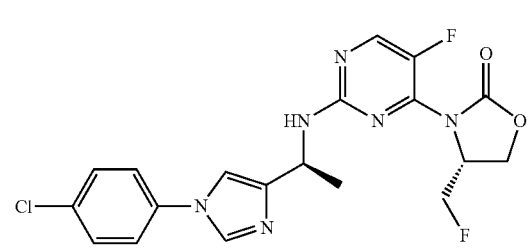 [SMILES: C[C@H](Nc1ncc(F)c(N2C(=O)OC[C@@H]2CF)n1)c1cn(-c2ccc(Cl)cc2)cn1]
429
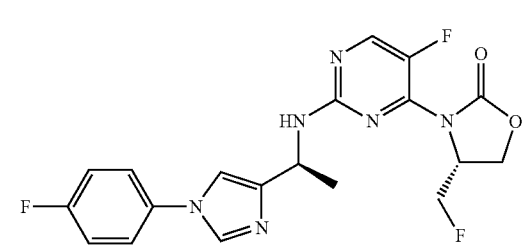 [SMILES: C[C@H](Nc1ncc(F)c(N2C(=O)OC[C@@H]2CF)n1)c1cn(-c2ccc(F)cc2)cn1]
430
TABLE 38a-continued
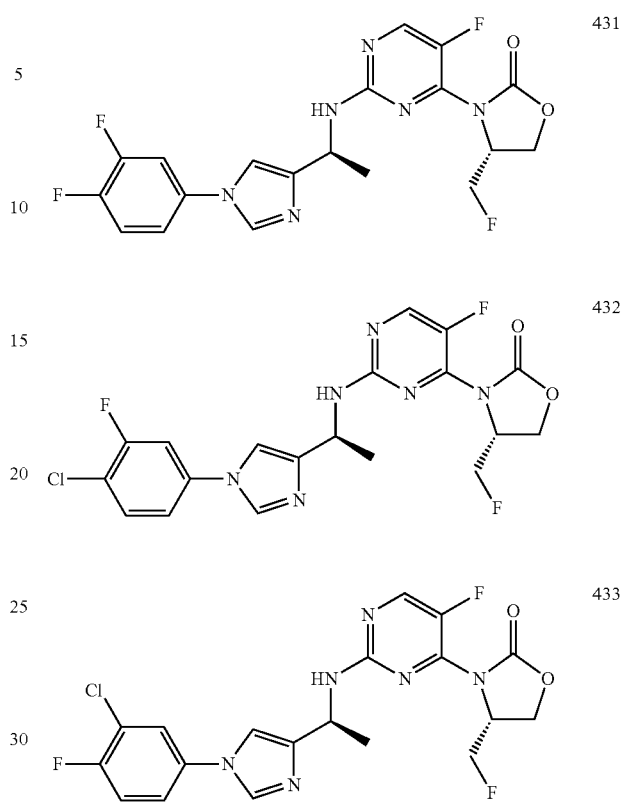
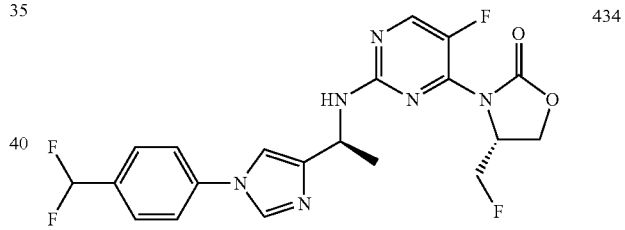
434
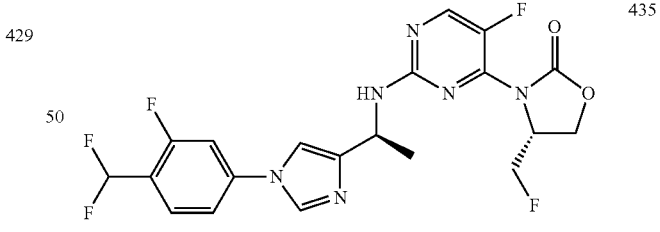
435
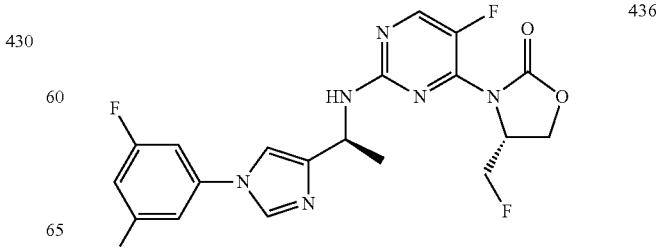
436

TABLE 38a-continued
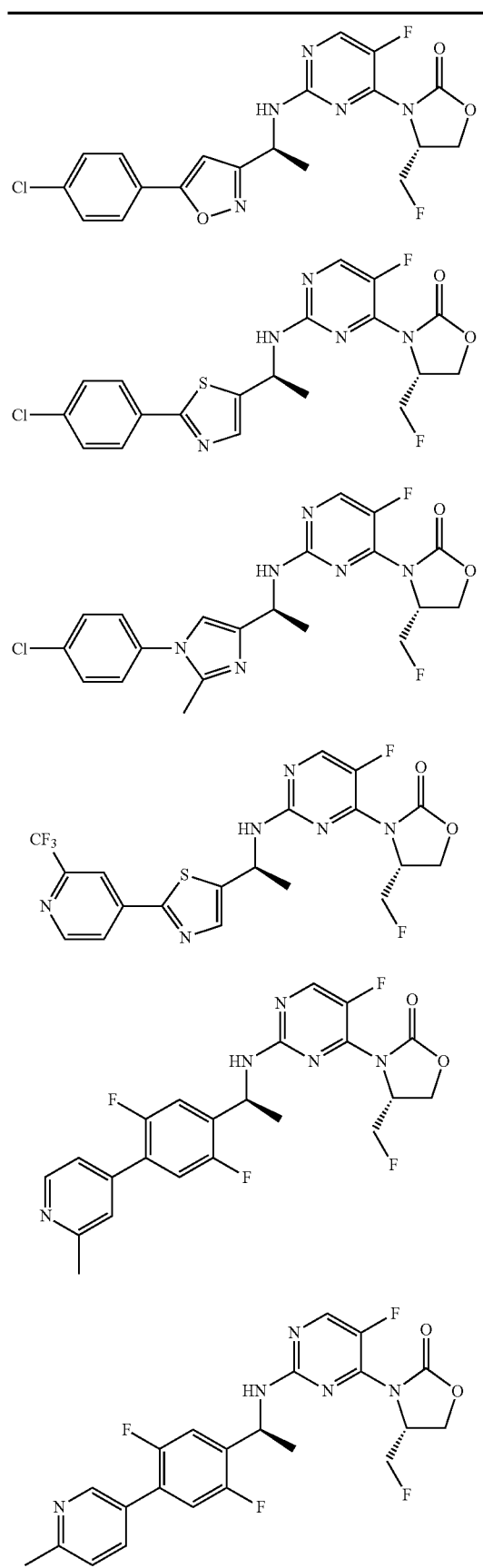
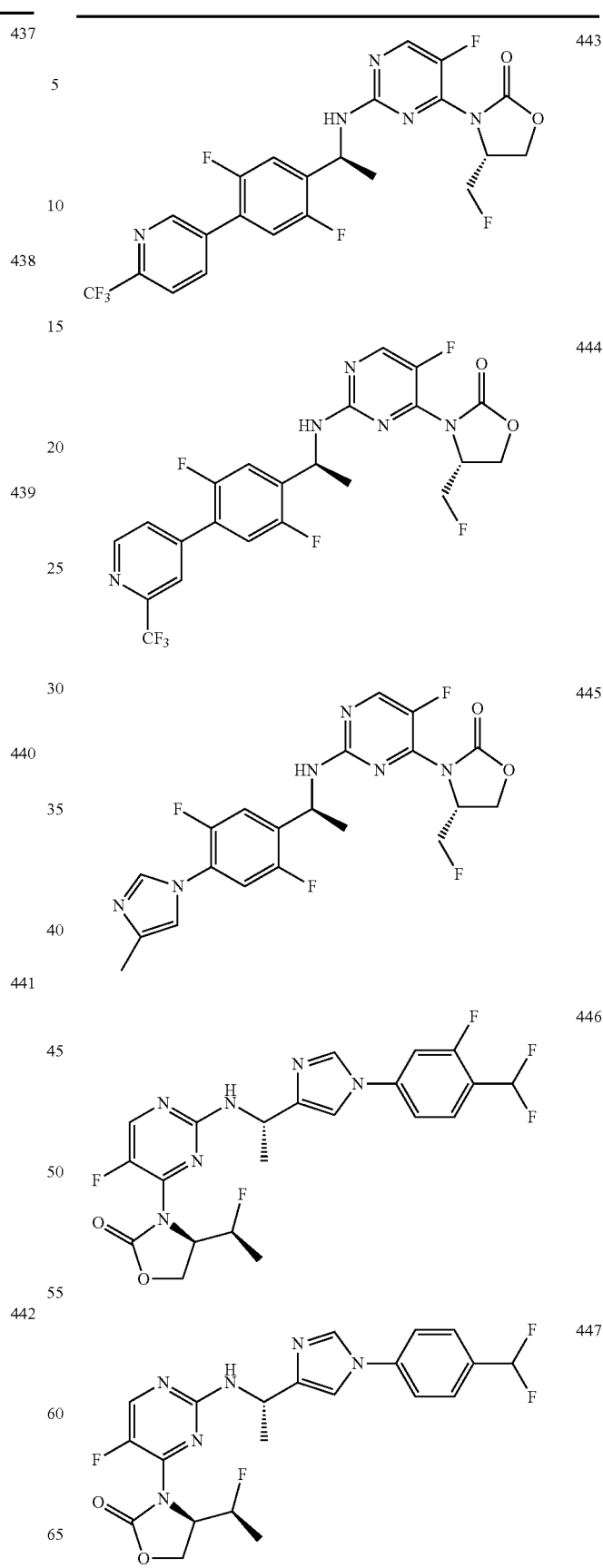

TABLE 38a-continued
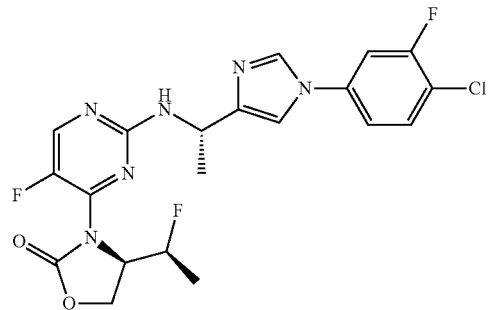 [SMILES: C[C@H](Nc1ncc(F)c(N2C(=O)OC[C@@H]2[C@H](C)F)n1)c1cn(-c2ccc(Cl)c(F)c2)cn1] 448
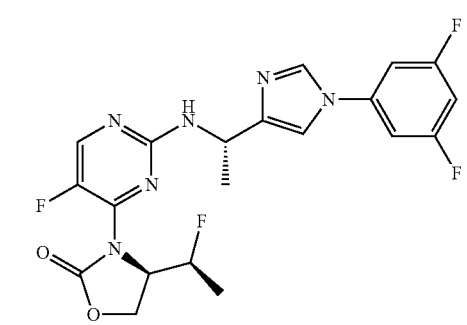 [SMILES: C[C@H](Nc1ncc(F)c(N2C(=O)OC[C@@H]2[C@H](C)F)n1)c1cn(-c2cc(F)cc(F)c2)cn1] 449
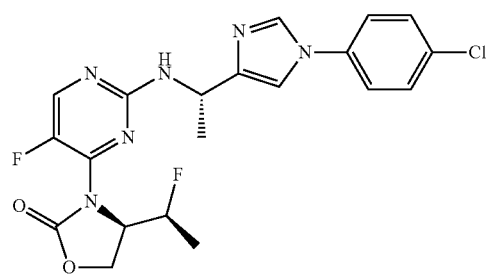 450
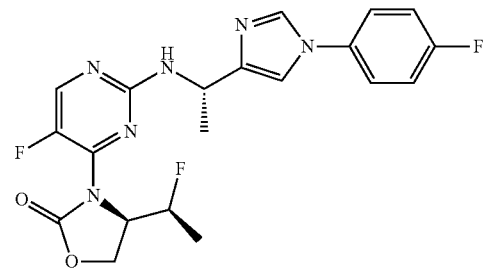 [SMILES: C[C@H](Nc1ncc(F)c(N2C(=O)OC[C@@H]2[C@H](C)F)n1)c1cn(-c2ccc(F)cc2)cn1] 451
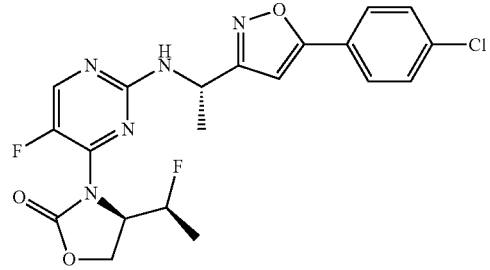 [SMILES: C[C@H](Nc1ncc(F)c(N2C(=O)OC[C@@H]2[C@H](C)F)n1)c1cc(-c2ccc(Cl)cc2)on1] 452
TABLE 38a-continued
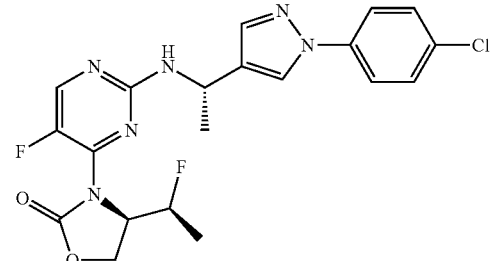 453
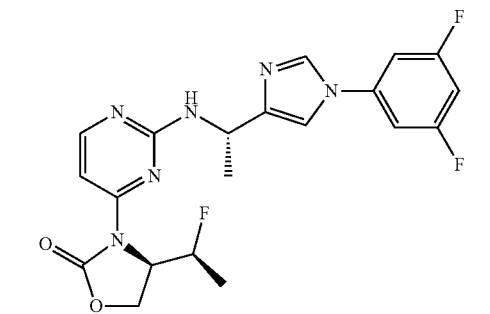 [SMILES: C[C@H](Nc1nccc(N2C(=O)OC[C@@H]2[C@H](C)F)n1)c1cn(-c2cc(F)cc(F)c2)cn1] 454
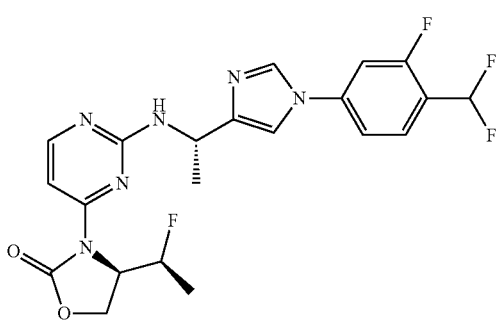 [SMILES: C[C@H](Nc1nccc(N2C(=O)OC[C@@H]2[C@H](C)F)n1)c1cn(-c2ccc(C(F)F)c(F)c2)cn1] 455
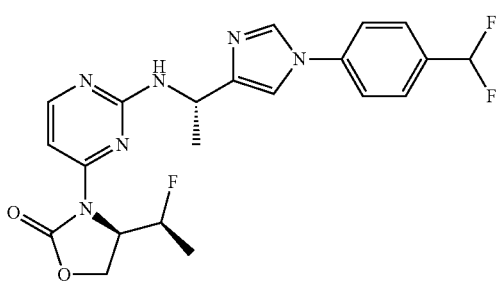 [SMILES: C[C@H](Nc1nccc(N2C(=O)OC[C@@H]2[C@H](C)F)n1)c1cn(-c2ccc(C(F)F)cc2)cn1] 456
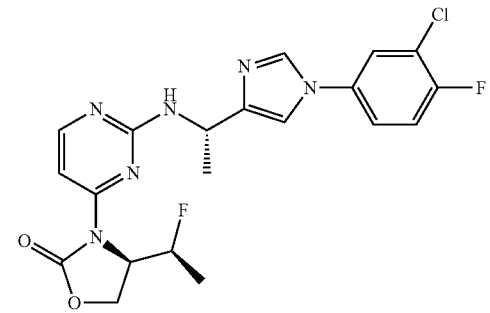 [SMILES: C[C@H](Nc1nccc(N2C(=O)OC[C@@H]2[C@H](C)F)n1)c1cn(-c2ccc(F)c(F)c2)cn1] 457

TABLE 38a-continued
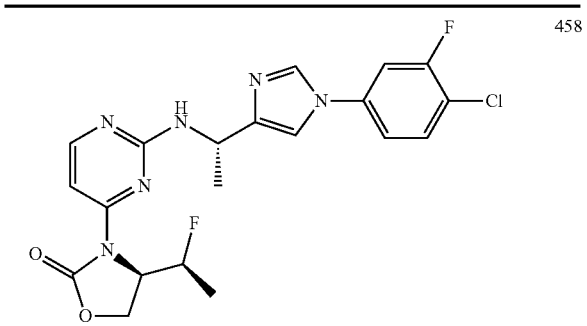
458
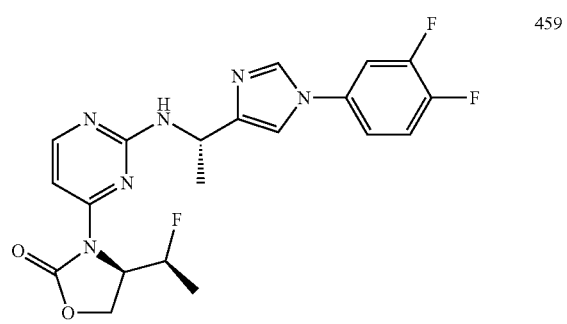
459
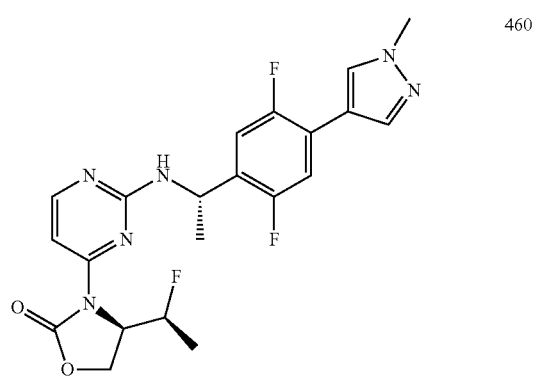
460
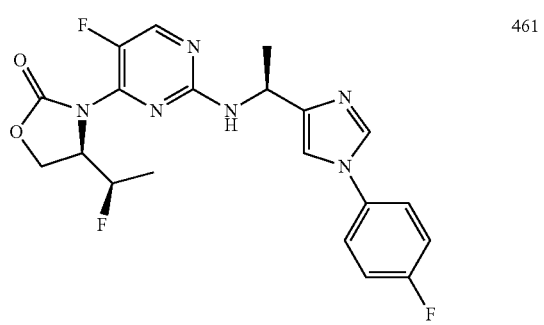
461
TABLE 38a-continued
462
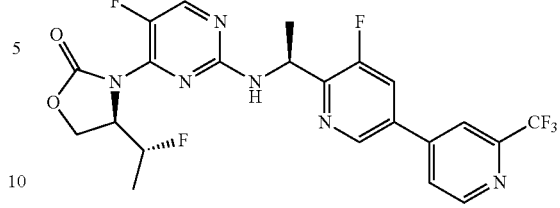
463
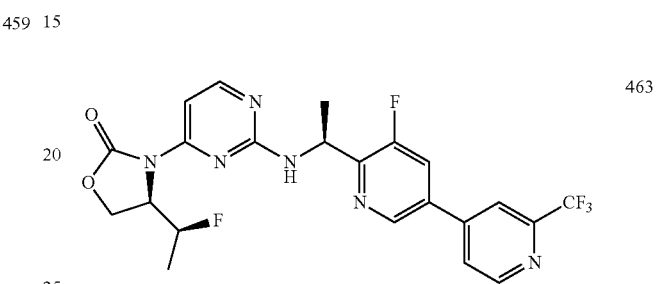
464
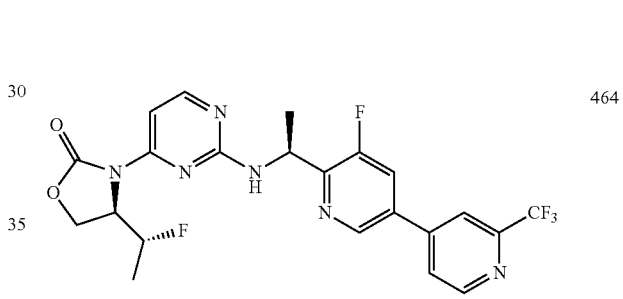
465
TABLE 38b
Chemical name, NMR chemical shifts, chiral separation conditions and LCMS signal for compounds listed in Table 38a.
| Example: Name | $^1$H NMR (400 MHz) δ ppm | LCMS |
|---|---|---|
| 428: (R)-4-((S)-1-fluoroethyl)-3-(2-(((S)-1-(2-(2-(trifluoromethyl)pyridin-4-yl)thiazol-5-yl)ethyl)amino)pyrimidin-4-yl)oxazolidin-2-one | (CDCl$_3$) 11.13 (d, J = 5.9 Hz, 1 H), 8.84 (d, J = 5.0 Hz, 1 H), 8.17 (s, 1 H), 8.06 (d, J = 7.0 Hz, 1 H), 7.89-7.96 (m, 2 H), 7.80 (s, 1 H), 5.34-5.44 (m, 1 H), 4.81-4.90 (m, 1 H), | LCMS (B) m/z 483.1; Rt = 0.79 min. |

TABLE 38b-continued

Chemical name, NMR chemical shifts, chiral separation conditions and LCMS signal for compounds listed in Table 38a.

| Example: Name | $^1$H NMR (400 MHz) δ ppm | LCMS |
|---|---|---|
| | 4.66-4.78 (m, 2 H), 4.59-4.65 (m, 1 H), 4.47-4.55 (m, 1 H), 1.83 (d, J = 7.0 Hz, 3 H), 1.21-1.32 (m, 3 H) | |
| 429: (R)-3-(2-(((S)-1-(1-(4-chlorophenyl)-1H-imidazol-4-yl)ethyl)amino)-5-fluoropyrimidin-4-yl)-4-(fluoromethyl)oxazolidin-2-one | (CDCl$_3$) 8.22 (d, J = 2.9 Hz, 1 H), 7.75 (d, J = 1.2 Hz, 1 H), 7.44 (d, J = 8.9 Hz, 2 H), 7.30 (d, J = 8.9 Hz, 2 H), 7.11 (s, 1H), 5.57 (d, J = 7.7 Hz, 1 H), 5.02-5.14 (m, 1 H), 4.75-4.89 (m, 1 H), 4.56-4.64 (m, 2 H), 4.43-4.53 (m, 2 H), 1.61 (d, J = 6.8 Hz, 3 H) | LCMS (B) m/z 435.1; Rt = 0.62 min. |
| 430: (R)-3-(5-fluoro-2-(((S)-1-(1-(4-fluorophenyl)-1H-imidazol-4-yl)ethyl)amino)pyrimidin-4-yl)-4-(fluoromethyl)oxazolidin-2-one | (CDCl$_3$) 8.62 (d, J = 3.9 Hz, 1 H), 8.14-8.21 (m, 1 H), 7.48 (dd, J = 8.9, 4.4 Hz, 3 H), 7.24-7.34 (m, 2 H), 5.38 (br. s., 1 H), 4.88-5.03 (m, 1 H), 4.42-4.73 (m, 4 H), 1.75 (t, J = 6.3 Hz, 3 H) | LCMS (B) m/z 419.2; Rt = 0.57 min. |
| 431: (R)-3-(2-(((S)-1-(1-(3,4-difluorophenyl)-1H-imidazol-4-yl)ethyl)amino)-5-fluoropyrimidin-4-yl)-4-(fluoromethyl)oxazolidin-2-one | (CDCl$_3$) 8.63 (br. s., 1 H), 8.17 (d, J = 3.3 Hz, 1 H), 7.36-7.52 (m, 4 H), 5.36 (br. s., 1 H), 4.94 (d, J = 18.7 Hz, 1 H), 4.43-4.74 (m, 4 H), 1.74 (d, J = 7.1 Hz, 3 H) | LCMS (B) m/z 437.2; Rt = 0.59 min. |
| 432: (R)-3-(2-(((S)-1-(1-(4-chloro-3-fluorophenyl)-1H-imidazol-4-yl)ethyl)amino)-5-fluoropyrimidin-4-yl)-4-(fluoromethyl)oxazolidin-2-one | (CDCl$_3$) 8.57 (s, 1 H), 8.18 (d, J = 1.9 Hz, 1 H), 7.63 (t, J = 7.6 Hz, 1 H), 7.48 (br. s., 1 H), 7.35 (d, J = 8.5 Hz, 1 H), 7.24-7.29 (m, 1 H), 5.33 (d, J = 5.3 Hz, 1 H), 4.84-4.98 (m, 1 H), 4.54-4.74 (m, 3 H), 4.48 (t, J = 7.5 Hz, 1 H), 1.73 (d, J = 6.5 Hz, 3 H) | LCMS (B) m/z 453.1; Rt = 0.64 min. |
| 433: (R)-3-(2-(((S)-1-(1-(3-chloro-4-fluorophenyl)-1H-imidazol-4-yl)ethyl)amino)-5-fluoropyrimidin-4-yl)-4-(fluoromethyl)oxazolidin-2-one | (CDCl$_3$) 8.56 (s, 1 H), 8.18 (d, J = 1.9 Hz, 1H), 7.57-7.63 (m, 1 H), 7.33-7.48 (m, 3 H), 5.34 (br. s., 1 H), 4.85-5.00 (m, 1 H), 4.41-4.75 (m, 4 H), 1.73 (d, J = 7.0 Hz, 3 H) | LCMS (B) m/z 453.1; Rt = 0.64 min. |
| 434: (R)-3-(2-(((S)-1-(1-(4-(difluoromethyl)phenyl)-1H-imidazol-4-yl)ethyl)amino)-5-fluoropyrimidin-4-yl)-4-(fluoromethyl)oxazolidin-2-one | (CDCl$_3$) 8.67 (s, 1 H), 8.17 (d, J = 3.3 Hz, 1 H), 7.76 (d, J = 8.3 Hz, 2 H), 7.60 (d, J = 8.4 Hz, 2 H), 7.51-7.57 (m, 1H), 6.58-6.90 (m, 1 H), 5.38 (d, J = 6.5 Hz, 1 H), 4.86-5.01 (m, 1 H), 4.41-4.75 (m, 4 H), 1.75 (d, J = 7.1 Hz, 3 H) | LCMS (B) m/z 451.2; Rt = 0.61 min. |
| 435: (R)-3-(2-(((S)-1-(1-(4-(difluoromethyl)-3-fluorophenyl)-1H-imidazol-4-yl)ethyl)amino)-5-fluoropyrimidin-4-yl)-4-(fluoromethyl)oxazolidin-2-one | (CDCl$_3$) 8.60 (d, J = 1.1 Hz, 1 H), 8.17 (d, J = 3.3 Hz, 1 H), 7.84 (t, J = 7.8 Hz, 1 H), 7.53 (d, J = 4.0 Hz, 1 H), 7.41 (d, J = 8.3 Hz, 1 H), 7.35 (d, J = 9.7 Hz, 1 H), 6.78-7.10 (m, 1 H), 5.33 (d, J = 6.4 Hz, 1 H), 4.85-4.99 (m, 1 H), 4.42-4.73 (m, 4 H), 1.73 (d, J = 7.1 Hz, 3 H) | LCMS (B) m/z 469.2; Rt = 0.63 min. |
| 436: (R)-3-(2-(((S)-1-(1-(3,5-difluorophenyl)-1H-imidazol-4-yl)ethyl)amino)-5-fluoropyrimidin-4-yl)-4-(fluoromethyl)oxazolidin-2-one | (CDCl$_3$) 8.63 (s, 1 H), 8.16 (dd, J = 3.3, 2.0 Hz, 1 H), 7.51 (br. s., 1 H), 7.09 (d, J = 6.6 Hz, 2 H), 6.97-7.05 (m, 1 H), 5.35 (d, J = 6.4 Hz, 1 H), 4.40-4.93 (m, 5 H), 1.73 (d, J = 7.0 Hz, 3 H) | LCMS (B) m/z 437.1; Rt = 0.59 min. |
| 437: (R)-3-(2-(((S)-1-(5-(4-chlorophenyl)isoxazol-3-yl)ethyl)amino)-5-fluoropyrimidin-4-yl)-4-(fluoromethyl)oxazolidin-2-one | (CDCl$_3$) 8.13 (d, J = 3.9 Hz, 1 H), 7.69 (d, J = 8.4 Hz, 2 H), 7.46 (d, J = 8.4 Hz, 2 H), 6.57 (s, 1 H), 5.18 (d, J = 7.1 Hz, 1 H), 4.93-5.08 (m, 1 H), 4.64-4.72 (m, 1 H), 4.55 (dd, J = 8.7, 7.2 Hz, 1 H), 4.27-4.52 (m, 2 H), 1.71 (d, J = 7.1 Hz, 3 H) | LCMS (B) m/z 436.1; Rt = 0.91 min. |

TABLE 38b-continued

Chemical name, NMR chemical shifts, chiral separation conditions
and LCMS signal for compounds listed in Table 38a.

| Example: Name | $^1$H NMR (400 MHz) δ ppm | LCMS |
|---|---|---|
| 438: (R)-3-(2-(((S)-1-(2-(4-chlorophenyl)thiazol-5-yl)ethyl)amino)-5-fluoropyrimidin-4-yl)-4-(fluoromethyl)oxazolidin-2-one | (CDCl$_3$) 8.18 (d, J = 3.5 Hz, 1 H), 7.89 (s, 1 H), 7.75-7.80 (m, 2 H), 7.44-7.50 (m, 2 H), 5.28 (d, J = 6.6 Hz, 1 H), 4.80-4.93 (m, 1 H), 4.68 (t, J = 8.9 Hz, 1 H), 4.42-4.49 (m, 1 H), 4.16-4.41 (m, 2 H), 1.77 (d, J = 7.0 Hz, 3 H) | LCMS (B) m/z 452.1; Rt = 0.93 min. |
| 439: (R)-3-(2-(((S)-1-(1-(4-chlorophenyl)-2-methyl-1H-imidazol-4-yl)ethyl)amino)-5-fluoropyrimidin-4-yl)-4-(fluoromethyl)oxazolidin-2-one | (CDCl$_3$) 8.13 (d, J = 3.1 Hz, 1 H), 7.58-7.63 (m, 2 H), 7.31-7.37 (m, 2 H), 7.14-7.18 (m, 1 H), 5.41 (br. s., 1 H), 4.77-4.96 (m, 1 H), 4.46-4.72 (m, 4 H), 2.60 (s, 3 H), 1.70 (d, J = 6.9 Hz, 3 H) | LCMS (B) m/z 449.2; Rt = 0.65 min. |
| 440: (R)-3-(5-fluoro-2-(((S)-1-(2-(2-(trifluoromethyl)pyridin-4-yl)thiazol-5-yl)ethyl)amino)pyrimidin-4-yl)-4-(fluoromethyl)oxazolidin-2-one | (CDCl$_3$) 8.85 (d, J = 5.1 Hz, 1 H), 8.20 (d, J = 3.5 Hz, 1 H), 8.16 (s, 1 H), 7.92-7.96 (m, 1 H), 7.90 (s, 1 H), 5.36 (d, J = 7.0 Hz, 1 H), 4.78-4.91 (m, 1 H), 4.24-4.72 (m, 4 H), 1.79 (d, J = 6.9 Hz, 3 H) | LCMS (B) m/z 487.1; Rt = 0.86 min. |
| 441: (R)-3-(2-(((S)-1-(2,5-difluoro-4-(2-methylpyridin-4-yl)phenyl)ethyl)amino)-5-fluoropyrimidin-4-yl)-4-(fluoromethyl)oxazolidin-2-one | (CDCl$_3$) 8.88 (d, J = 6.0 Hz, 1 H), 8.19 (d, J = 3.0 Hz, 1 H), 7.76 (d, J = 6.2 Hz, 1 H), 7.72 (s, 1 H), 7.21-7.33 (m, 2 H), 5.19-5.30 (m, 1 H), 4.78 (br. s., 1 H), 4.64 (t, J = 8.8 Hz, 1 H), 4.41-4.49 (m, 1 H), 4.09-4.37 (m, 2 H), 2.90 (s, 3 H), 1.63 (d, J = 6.9 Hz, 3 H) | LCMS (B) m/z 462.2; Rt = 0.60 min. |
| 442: (R)-3-(2-(((S)-1-(2,5-difluoro-4-(6-methylpyridin-3-yl)phenyl)ethyl)amino)-5-fluoropyrimidin-4-yl)-4-(fluoromethyl)oxazolidin-2-one | (CDCl$_3$) 9.01 (s, 1 H), 8.33 (d, J = 8.2 Hz, 1 H), 8.17 (d, J = 3.2 Hz, 1 H), 7.67 (d, J = 8.3 Hz, 1 H), 7.21-7.29 (m, 2 H), 5.18-5.29 (m, 1 H), 4.06-4.83 (m, 5 H), 2.89 (s, 3 H), 1.62 (d, J = 7.0 Hz, 3 H) | LCMS (B) m/z 462.1; Rt = 0.61 min. |
| 443: (R)-3-(2-(((S)-1-(2,5-difluoro-4-(6-(trifluoromethyl)pyridin-3-yl)phenyl)ethyl)amino)-5-fluoropyrimidin-4-yl)-4-(fluoromethyl)oxazolidin-2-one | (CDCl$_3$) 8.89 (s, 1 H), 8.15 (dd, J = 3.7, 1.2 Hz, 1 H), 8.06 (d, J = 8.2 Hz, 1 H), 7.82 (d, J = 8.2 Hz, 1 H), 7.17-7.30 (m, 2 H), 5.28 (d, J = 5.7 Hz, 1 H), 4.77-4.90 (m, 1 H), 4.67 (t, J = 8.8 Hz, 1 H), 4.49 (t, J = 7.8 Hz, 1 H), 4.07-4.29 (m, 2 H), 1.66 (d, J = 6.7 Hz, 3 H) | LCMS (B) m/z 516.1; Rt = 0.97 min. |
| 444: (R)-3-(2-(((S)-1-(2,5-difluoro-4-(2-(trifluoromethyl)pyridin-4-yl)phenyl)ethyl)amino)-5-fluoropyrimidin-4-yl)-4-(fluoromethyl)oxazolidin-2-one | (CDCl$_3$) 8.85 (d, J = 5.0 Hz, 1 H), 8.15 (dd, J = 3.4, 2.4 Hz, 1 H), 7.84 (s, 1 H), 7.67 (d, J = 4.9 Hz, 1 H), 7.21-7.33 (m, 2 H), 5.28 (br. s., 1 H), 4.81 (d, J = 14.6 Hz, 1 H), 4.67 (t, J = 8.8 Hz, 1 H), 4.45-4.53 (m, 1 H), 4.07-4.33 (m, 2 H), 1.63-1.68 (m, 3 H) | LCMS (B) m/z 516.0; Rt = 0.96 min. |
| 445: (R)-3-(2-(((S)-1-(2,5-difluoro-4-(4-methyl-1H-imidazol-1-yl)phenyl)ethyl)amino)-5-fluoropyrimidin-4-yl)-4-(fluoromethyl)oxazolidin-2-one | (CDCl$_3$) 8.82 (s, 1 H), 8.18 (d, J = 3.1 Hz, 1 H), 7.39 (dd, J = 10.3, 6.0 Hz, 1 H), 7.27-7.30 (m, 1 H), 7.11 (s, 1 H), 5.19-5.28 (m, 1 H), 4.74 (br. s., 1 H), 4.64 (t, J = 8.6 Hz, 1 H), 4.39-4.47 (m, 1 H), 4.13-4.32 (m, 2 H), 2.49 (s, 3 H), 1.63 (d, J = 7.0 Hz, 3 H) | LCMS (B) m/z 451.1; Rt = 0.58 min. |
| 446: (R)-3-(2-(((S)-1-(1-(4-(difluoromethyl)-3-fluorophenyl)-1H-imidazol-4-yl)ethyl)amino)-5-fluoropyrimidin-4-yl)-4-((S)-1-fluoroethyl)oxazolidin-2-one | (CDCl$_3$) 8.72 (s, 1 H), 8.18 (d, J = 3.1 Hz, 1 H), 7.79-7.91 (m, 1 H), 7.61 (br. s., 1 H), 7.33-7.48 (m, 2 H), 6.94 (t, J = 54.0 Hz, 1 H), 5.34 (d, J = 6.7 Hz, 1 H), 4.71-5.05 (m, 2 H), 4.55-4.65 (m, 1 H), 4.50 (dd, J = 8.4, 6.5 Hz, 1 H), 1.74 (d, J = 7.0 Hz, 3 H), 1.33 (dd, J = 23.5, 6.7 Hz, 3 H) | LCMS m/z 483.0 (M + H)$^+$, Rt 0.68 min; HPLC 2.801 min. |
| 447: (R)-3-(2-(((S)-1-(1-(4-(difluoromethyl)phenyl)-1H-imidazol-4-yl)ethyl)amino)-5-fluoropyrimidin-4-yl)-4-((S)-1-fluoroethyl)oxazolidin-2-one | (CDCl$_3$) 8.81 (s, 1 H), 8.18 (d, J = 3.1 Hz, 1 H), 7.76 (d, J = 8.2 Hz, 2 H), 7.62 (d, J = 8.2 Hz, 2 H), 6.74 (t, J = 56.0 Hz, 1 H), 5.38 (q, J = 6.7 Hz, 1 H), 4.73-5.06 (m, 2 H), 4.59 (t, J = 8.8 Hz, 1 H), 4.45-4.53 (m, 1 H), 1.76 (d, J = 7.0 Hz, 3 H), 1.34 (dd, J = 23.5, 6.3 Hz, 3 H). | LCMS m/z 465.0 (M + H)$^+$, Rt 0.65 min; HPLC 2.624 min. |

TABLE 38b-continued

Chemical name, NMR chemical shifts, chiral separation conditions
and LCMS signal for compounds listed in Table 38a.

| Example: Name | $^1$H NMR (400 MHz) δ ppm | LCMS |
|---|---|---|
| 448: (R)-3-(2-(((S)-1-(1-(4-chloro-3-fluorophenyl)-1H-imidazol-4-yl)ethyl)amino)-5-fluoropyrimidin-4-yl)-4-((S)-1-fluoroethyl)oxazolidin-2-one | (CDCl$_3$) 8.73 (s, 1 H), 8.18 (d, J = 3.1 Hz, 1 H), 7.64 (t, J = 8.0 Hz, 1 H), 7.57 (br. s., 1 H), 7.29-7.44 (m, 2 H), 5.34 (d, J = 6.7 Hz, 1 H), 4.73-4.87 (m, 1 H), 4.59 (t, J = 8.8 Hz, 1 H), 4.45-4.53 (m, 1 H), 1.74 (d, J = 7.0 Hz, 3 H), 1.33 (dd, J = 23.1, 6.3 Hz, 3 H) | LCMS m/z 467.0 (M + H)$^+$, Rt 0.69 min; HPLC 2.847 min. |
| 449: (R)-3-(2-(((S)-1-(1-(3,5-difluorophenyl)-1H-imidazol-4-yl)ethyl)amino)-5-fluoropyrimidin-4-yl)-4-((S)-1-fluoroethyl)oxazolidin-2-one | (CDCl$_3$) 8.58 (s, 1 H), 8.18 (d, J = 2.7 Hz, 1 H), 7.53 (br. s., 1 H), 7.09 (d, J = 5.1 Hz, 2 H), 7.00 (t, J = 8.4 Hz, 1 H), 5.29-5.36 (m, 1 H), 5.00 (br. s., 1 H), 4.87 (br. s., 1 H), 4.70-4.83 (m, 1 H), 4.54-4.64 (m, 1 H), 4.46-4.53 (m, 1 H), 1.73 (d, J = 7.0 Hz, 3 H), 1.33 (dd, J = 23.1, 6.3 Hz, 3 H). | LCMS m/z 451.1 (M + H)$^+$, Rt 0.64 min; HPLC 2.132 min. |
| 450: (R)-3-(2-(((S)-1-(1-(4-chlorophenyl)-1H-imidazol-4-yl)ethyl)amino)-5-fluoropyrimidin-4-yl)-4-((S)-1-fluoroethyl)oxazolidin-2-one | (CDCl$_3$) 8.64 (s, 1 H), 8.18 (d, J = 3.1 Hz, 1 H), 7.57 (d, J = 8.6 Hz, 2 H), 7.51 (br. s., 1 H), 7.44 (d, J = 8.6 Hz, 2 H), 5.35 (d, J = 6.7 Hz, 1 H), 5.01 (br. s., 1 H), 4.89 (br. s., 1 H), 4.71-4.86 (m, 1 H), 4.54-4.64 (m, 1 H), 4.44-4.53 (m, 1 H), 1.74 (d, J = 7.0 Hz, 3 H), 1.33 (dd, J = 23.5, 6.7 Hz, 3 H). | LCMS m/z 449.0 (M + H)$^+$, Rt 0.67 min; HPLC 2.354 min. |
| 451: (R)-3-(5-fluoro-2-(((S)-1-(1-(4-fluorophenyl)-1H-imidazol-4-yl)ethyl)amino)pyrimidin-4-yl)-4-((S)-1-fluoroethyl)oxazolidin-2-one | (CDCl$_3$) 8.61 (s, 1 H), 8.18 (d, J = 2.7 Hz, 1 H), 7.48 (dd, J = 8.4, 4.1 Hz, 3 H), 7.28-7.34 (m, 2 H), 5.35 (d, J = 6.7 Hz, 1 H), 4.70-4.85 (m, 1 H), 4.54-4.62 (m, 1 H), 4.45-4.53 (m, 1 H), 1.75 (d, J = 7.0 Hz, 3 H), 1.33 (dd, J = 23.1, 6.3 Hz, 3 H). | LCMS m/z 433.1 (M + H)$^+$, Rt 0.61 min; HPLC 1.997 min. |
| 452: (R)-3-(2-(((S)-1-(5-(4-chlorophenyl)isoxazol-3-yl)ethyl)amino)-5-fluoropyrimidin-4-yl)-4-((S)-1-fluoroethyl)oxazolidin-2-one | (CDCl$_3$) 8.11 (d, J = 3.5 Hz, 1 H), 7.69 (d, J = 8.6 Hz, 2 H), 7.46 (d, J = 8.6 Hz, 2 H), 6.54 (s, 1 H), 5.17 (d, J = 5.1 Hz, 1 H), 4.69-4.92 (m, 2 H), 4.51-4.65 (m, 2 H), 1.70 (d, J = 7.0 Hz, 3 H), 1.30 (dd, J = 23.1, 6.3 Hz, 3 H). | LCMS m/z 450.0 (M + H)$^+$, Rt 0.96 min; HPLC 4.131 min. |
| 453: (R)-3-(2-(((S)-1-(1-(4-chlorophenyl)-1H-pyrazol-4-yl)ethyl)amino)-5-fluoropyrimidin-4-yl)-4-((S)-1-fluoroethyl)oxazolidin-2-one | (CDCl$_3$) 8.14 (d, J = 3.5 Hz, 1 H), 7.94 (s, 1 H), 7.68 (s, 1 H), 7.59 (d, J = 8.6 Hz, 2 H), 7.43 (d, J = 8.6 Hz, 2 H), 5.08 (q, J = 6.7 Hz, 1 H), 4.65-4.87 (m, 2 H), 4.59 (t, J = 8.8 Hz, 1 H), 4.47-4.55 (m, 1 H), 1.66 (d, J = 7.0 Hz, 3 H), 1.22 (dd, J = 23.5, 6.7 Hz, 3 H). | LCMS m/z 449.0 (M + H)$^+$, Rt 0.92 min; HPLC 3.864 min. |
| 454: (R)-3-(2-(((S)-1-(1-(3,5-difluorophenyl)-1H-imidazol-4-yl)ethyl)amino)pyrimidin-4-yl)-4-((S)-1-fluoroethyl)oxazolidin-2-one | (CDCl$_3$) 10.92 (d, J = 6.7 Hz, 1 H), 8.30 (br. s., 1 H), 7.99 (d, J = 6.7 Hz, 1 H), 7.88 (d, J = 7.0 Hz, 1 H), 7.57 (br. s., 1 H), 6.92-7.11 (m, 3 H), 5.48 (d, J = 6.3 Hz, 1 H), 4.84-5.14 (m, 2 H), 4.59-4.70 (m, 1 H), 4.48-4.57 (m, 1 H), 1.69 (d, J = 6.7 Hz, 3 H), 1.34 (dd, J = 23.5, 5.9 Hz, 3 H). | LCMS m/z 433.2 (M + H)$^+$, Rt 0.59 min; HPLC 1.946 min. |
| 455: (R)-3-(2-(((S)-1-(1-(4-(difluoromethyl)-3-fluorophenyl)-1H-imidazol-4-yl)ethyl)amino)pyrimidin-4-yl)-4-((S)-1-fluoroethyl)oxazolidin-2-one | (CDCl$_3$) 10.91 (d, J = 7.0 Hz, 1 H), 8.24 (br. s., 1 H), 7.98 (d, J = 6.7 Hz, 1 H), 7.88 (d, J = 7.0 Hz, 1 H), 7.82 (t, J = 7.4 Hz, 1 H), 7.58 (br. s., 1 H), 7.30-7.43 (m, 2 H), 6.94 (dt, J = 55.6, 1.0 Hz, 1 H), 5.44 (br. s., 1 H), 4.80-5.22 (m, 2 H), 4.64 (d, J = 9.0 Hz, 1 H), 4.54 (t, J = 8.8 Hz, 1 H), 1.71 (d, J = 6.3 Hz, 3 H), 1.36 (dd, J = 23.5, 6.3 Hz, 3 H). | LCMS m/z 465.2 (M + H)$^+$, Rt 0.63 min; HPLC 2.191 min. |

TABLE 38b-continued

Chemical name, NMR chemical shifts, chiral separation conditions and LCMS signal for compounds listed in Table 38a.

| Example: Name | $^1$H NMR (400 MHz) δ ppm | LCMS |
|---|---|---|
| 456: (R)-3-(2-(((S)-1-(1-(4-(difluoromethyl)phenyl)-1H-imidazol-4-yl)ethyl)amino)pyrimidin-4-yl)-4-((S)-1-fluoroethyl)oxazolidin-2-one | (CDCl$_3$) 11.00 (d, J = 7.0 Hz, 1 H), 8.46 (s, 1 H), 7.99 (d, J = 7.0 Hz, 1 H), 7.90 (d, J = 7.0 Hz, 1 H), 7.75 (d, J = 8.2 Hz, 2 H), 7.66 (s, 1 H), 7.59 (d, J = 8.2 Hz, 2 H), 6.74 (t, J = 55.6 Hz, 1 H), 5.58 (t, J = 6.8 Hz, 1 H), 4.91-5.14 (m, 2 H), 4.60-4.68 (m, 1 H), 4.49-4.59 (m, 1 H), 1.72 (d, J = 6.7 Hz, 3 H), 1.36 (dd, J = 23.5, 6.3 Hz, 3 H). | LCMS m/z 447.3 (M + H)$^+$, Rt 0.58 min; HPLC 1.898 min. |
| 457: (R)-3-(2-(((S)-1-(1-(3-chloro-4-fluorophenyl)-1H-imidazol-4-yl)ethyl)amino)pyrimidin-4-yl)-4-((S)-1-fluoroethyl)oxazolidin-2-one | (CDCl$_3$) 10.97 (d, J = 7.4 Hz, 1 H), 8.33 (s, 1 H), 7.99 (d, J = 6.7 Hz, 1 H), 7.90 (d, J = 7.0 Hz, 1 H), 7.50-7.65 (m, 2 H), 7.37 (d, J = 5.9 Hz, 2 H), 5.53 (t, J = 6.7 Hz, 1 H), 4.87-5.19 (m, 2 H), 4.60-4.70 (m, 1 H), 4.44-4.59 (m, 1 H), 1.71 (d, J = 6.7 Hz, 3 H), 1.36 (dd, J = 23.5, 5.9 Hz, 3 H). | LCMS m/z 449.1 (M + H)$^+$, Rt 0.63 min; HPLC 2.193 min. |
| 458: (R)-3-(2-(((S)-1-(1-(4-chloro-3-fluorophenyl)-1H-imidazol-4-yl)ethyl)amino)pyrimidin-4-yl)-4-((S)-1-fluoroethyl)oxazolidin-2-one | (CDCl$_3$) 10.94 (d, J = 7.0 Hz, 1 H), 8.27 (s, 1 H), 7.98 (d, J = 7.0 Hz, 1 H), 7.88 (d, J = 6.7 Hz, 1 H), 7.62 (t, J = 8.0 Hz, 1 H), 7.55 (s, 1 H), 7.31 (dd, J = 9.0, 2.3 Hz, 1 H), 7.23 (br. s., 1 H), 5.48 (t, J = 6.8 Hz, 1 H), 4.83-5.19 (m, 2 H), 4.60-4.69 (m, 1 H), 4.46-4.58 (m, 1 H), 1.70 (d, J = 6.7 Hz, 3 H), 1.35 (dd, J = 23.5, 6.3 Hz, 3 H). | LCMS m/z 449.2 (M + H)$^+$, Rt 0.64 min; HPLC 2.279 min. |
| 459: (R)-3-(2-(((S)-1-(1-(3,4-difluorophenyl)-1H-imidazol-4-yl)ethyl)amino)pyrimidin-4-yl)-4-((S)-1-fluoroethyl)oxazolidin-2-one | (CDCl$_3$) 10.96 (d, J = 7.0 Hz, 1 H), 8.27 (s, 1 H), 7.98 (d, J = 7.0 Hz, 1 H), 7.89 (d, J = 7.0 Hz, 1 H), 7.53 (s, 1 H), 7.31-7.45 (m, 2 H), 5.51 (t, J = 6.7 Hz, 1 H), 4.84-5.19 (m, 2 H), 4.60-4.72 (m, 1 H), 4.43-4.58 (m, 1 H), 1.70 (d, J = 6.7 Hz, 3 H), 1.36 (dd, J = 23.5, 6.3 Hz, 3 H). | LCMS m/z 433.2 (M + H)$^+$, Rt 0.59 min; HPLC 1.870 min. |
| 460: (R)-3-(2-(((S)-1-(2,5-difluoro-4-(1-methyl-1H-pyrazol-4-yl)phenyl)ethyl)amino)pyrimidin-4-yl)-4-((S)-1-fluoroethyl)oxazolidin-2-one | (CDCl$_3$) 10.96 (d, J = 6.7 Hz, 1 H), 7.99 (d, J = 7.0 Hz, 1 H), 7.71-7.89 (m, 3 H), 7.20 (ddd, J = 14.6, 10.7, 6.1 Hz, 2 H), 5.33 (quin, J = 6.7 Hz, 1 H), 4.64-4.77 (m, 2 H), 4.52-4.64 (m, 2 H), 4.45-4.51 (m, 1 H), 3.99 (s, 3 H), 1.64 (d, J = 7.0 Hz, 3 H), 1.23 (dd, J = 23.5, 6.7 Hz, 3 H). | LCMS m/z 447.3 (M + H)$^+$, Rt 0.68 min; HPLC 2.612 min. |
| 461: (R)-3-(5-fluoro-2-(((S)-1-(1-(4-fluorophenyl)-1H-imidazol-4-yl)ethyl)amino)pyrimidin-4-yl)-4-((R)-1-fluoroethyl)oxazolidin-2-one | (CD3OD) 9.32 (s, 1 H), 8.33 (d, J = 2.7 Hz, 1 H), 7.94 (s, 1 H), 7.72 (dd, J = 9.0, 4.3 Hz, 2 H), 7.37 (t, J = 8.4 Hz, 2 H), 5.21 (q, J = 6.4 Hz, 1 H), 4.78-4.95 (m, 2 H), 4.63 (t, J = 9.2 Hz, 1 H), 4.41 (dd, J = 9.2, 4.5 Hz, 1 H), 1.70 (d, J = 7.0 Hz, 3 H), 1.12-1.29 (m, 3 H) | LCMS (B) m/z 433.1; Rt = 0.60 min. |
| 462: (R)-3-(5-fluoro-2-(((S)-1-(5-fluoro-2'-(trifluoromethyl)-[3,4'-bipyridin]-6-yl)ethyl)amino)pyrimidin-4-yl)-4-((R)-1-fluoroethyl)oxazolidin-2-one | (CD3OD) 8.74-8.84 (m, 2 H), 8.24 (br.s., 1 H), 8.14 (s, 1 H), 8.09 (dd, J = 10.8, 1.4 Hz, 1 H), 7.97 (d, J = 4.7 Hz, 1 H), 5.41 (d, J = 6.3 Hz, 1 H), 4.75-4.94 (m, 2 H), 4.60 (t, J = 9.2 Hz, 1 H), 4.41 (dd, J = 9.2, 4.9 Hz, 1 H), 1.59 (d, J = 7.0 Hz, 3 H), 1.04 (br. s., 3 H) | LCMS (B) m/z 513.2; Rt = 0.87 min |
| 463: (R)-3-(2-(((S)-1-(5-fluoro-2'-(trifluoromethyl)-[3,4'-bipyridin]-6-yl)ethyl)amino)pyrimidin-4-yl)-4-((S)-1-fluoroethyl)oxazolidin-2-one | (CD3OD) 8.87 (s, 1 H), 8.82 (d, J = 5.1 Hz, 1 H), 8.15-8.27 (m, 3 H), 8.00 (d, J = 4.7 Hz, 1 H), 7.81 (d, J = 6.7 Hz, 1 H), 5.63 (d, J = 5.5 Hz, 1 H), 4.75-5.02 (m, 2 H), 4.64 (dd, J = 9.0, 2.7 Hz, 1 H), 4.48-4.58 (m, 1 H), 1.68 (d, J = 7.0 Hz, 3 H), 1.21-1.46 (m, 3 H) | LCMS (B) m/z 495.2; Rt = 0.75 min |

TABLE 38b-continued

Chemical name, NMR chemical shifts, chiral separation conditions and LCMS signal for compounds listed in Table 38a.

| Example: Name | ¹H NMR (400 MHz) δ ppm | LCMS |
|---|---|---|
| 464: (R)-3-(2-(((S)-1-(5-fluoro-2'-(trifluoromethyl)-[3,4'-bipyridin]-6-yl)ethyl)amino)pyrimidin-4-yl)-4-((R)-1-fluoroethyl)oxazolidin-2-one | (CD3OD) 8.76-8.88 (m, 2 H), 8.11-8.25 (m, 3 H), 7.99 (d, J = 5.1 Hz, 1 H), 7.67 (d, J = 4.7 Hz, 1 H), 5.57 (d, J = 6.7 Hz, 1 H), 5.10 (br. s., 1 H), 4.76-4.96 (m, 2 H), 4.47-4.62 (m, 2 H), 1.67 (d, J = 6.7 Hz, 3 H), 0.92-1.21 (m, 3 H) | LCMS (B) m/z 495.2; Rt = 0.75 min |
| 465: (R)-3-(5-fluoro-2-(((S)-1-(5-fluoro-2'-(trifluoromethyl)-[3,4'-bipyridin]-6-yl)ethyl)amino)pyrimidin-4-yl)-4-((S)-1-fluoroethyl)oxazolidin-2-one | (CD3OD) 8.73-8.86 (m, 2 H), 8.24 (br. s., 1 H), 8.16 (s, 1 H), 8.11 (d, J = 11.0 Hz, 1 H), 7.98 (d, J = 5.1 Hz, 1 H), 5.43 (d, J = 6.7 Hz, 1 H), 4.85 (s, 2 H), 4.61 (t, J = 9.0 Hz, 1 H), 4.42-4.52 (m, 1 H), 1.58 (d, J = 7.0 Hz, 3 H), 1.17 (d, J = 19.2 Hz, 3 H) | LCMS (B) m/z 513.2; Rt = 0.95 min |

Example 466

(R)-4-((S)-1-fluoroethyl)-3-(2-(((S)-1-(4-methyl-2'-(trifluoromethyl)-[3,4'-bipyridin]-6-yl)ethyl)amino)pyrimidin-4-yl)oxazolidin-2-one

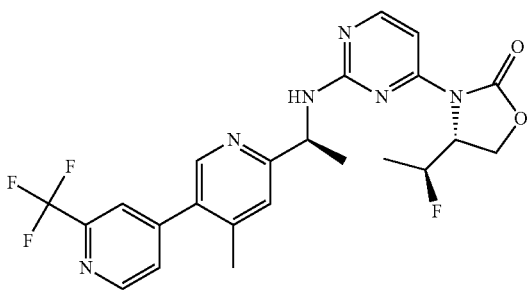 [SMILES: Cc1cc([C@H](C)Nc2nccc(N3C(=O)OC[C@@H]3[C@H](C)F)n2)ncc1-c1ccnc(C(F)(F)F)c1]

Example 466 was prepared by a convergent route. Steps 1a-1c give (S)-1-(4-methyl-2'-(trifluoromethyl)-[3,4'-bipyridin]-6-yl)ethanamine. Steps 2a-2f give (R)-4-((S)-1-fluoroethyl)-3-(2-fluoropyrimidin-4-yl)oxazolidin-2-one. These intermediates were combined in Step 3 to give (R)-4-((S)-1-fluoroethyl)-3-(2-(((S)-1-(4-methyl-2'-(trifluoromethyl)-[3,4'-bipyridin]-6-yl)ethyl)amino)pyrimidin-4-yl)oxazolidin-2-one.

Step 1a: To a solution of (S)-1-(5-bromo-4-methylpyridin-2-yl)ethanamine hydrochloride (750 mg, 2.98 mmol) in DCM (30 mL) was added di-tert-butyl dicarbonate (0.761 mL, 3.28 mmol) and triethylamine (1.25 mL, 8.94 mmol). The resulting solution was stirred at r.t. overnight. Mixture was concentrated under reduced pressure and diluted with 40 mL EtOAc, washed with water, brine, dried over Na₂SO₄ and concentrated to give 940 mg of (S)-tert-butyl (1-(5-bromo-4-methylpyridin-2-yl)ethyl)carbamate as a light brown oil. MS m/z 317.2 (M+H). ¹H NMR (400 MHz, CDCl₃) δ 8.57 (s, 1H), 7.14 (s, 1H), 5.57-5.50 (m, 1H), 4.79 (p, J=7.0 Hz, 1H), 2.40 (s, 3H), 1.47-1.43 (m, 12H).

Step 1b: N₂ was bubbled through a solution of (S)-tert-butyl (1-(5-bromo-4-methylpyridin-2-yl)ethyl)carbamate (200 mg, 0.635 mmol), (2-(trifluoromethyl)pyridin-4-yl)boronic acid (145 mg, 0.761 mmol) and Na₂CO₃ (2.0 M, 635 μl, 1.269 mmol) in dioxane for 5 min. Cl₂Pd(dppf) (CH₂Cl₂ adduct) (51.8 mg, 0.063 mmol) was added. The reaction mixture was stirred at 90° C. for 16 hr. The mixture was diluted with EtOAc, washed with water, brine, dried over Na₂SO₄, filtered, concentrated and purified through flash column chromatography (0-100% EtOAc/Heptane) to give 200 mg (S)-tert-butyl (1-(4-methyl-2'-(trifluoromethyl)-[3,4'-bipyridin]-6-yl)ethyl)carbamate as a white solid. 1H NMR (400 MHz, CDCl3) δ 8.83 (d, J=4.9 Hz, 1H), 8.36 (s, 1H), 7.66 (s, 1H), 7.51-7.42 (m, 1H), 7.21 (s, 1H), 5.60 (d, J=7.7 Hz, 1H), 4.87 (p, J=6.9 Hz, 1H), 2.30 (s, 3H), 1.48 (d, J=6.9 Hz, 3H), 1.45 (s, 9H). MS m/z 382.3 (M+H).

Step 1c: To a solution of (S)-tert-butyl (1-(4-methyl-2'-(trifluoromethyl)-[3,4'-bipyridin]-6-yl)ethyl)carbamate (200 mg, 0.524 mmol) in DCM (2 ml) at −78° C. was added trifluoroacetic acid (2 mL, 12.98 mmol). The solution was stirred at r.t. for 1 hr. The mixture was concentrated, diluted with 10 mL DCM and stirred with solid MP-carbonate to remove TFA. Filtered and concentrated to give 147 mg (S)-1-(4-methyl-2'-(trifluoromethyl)-[3,4'-bipyridin]-6-yl)ethanamine as a light brown sticky oil. MS m/z 282.1 (M+H). Rt=0.85 min. (Column: XBridge C18 3.5 um 2.1× 50 mm. Solvent A: 2% Acetonitrile, 3.75 mM Ammonium Acetate, Water. Solvent B: Acetonitrile. Gradient: 5-95% B over 1.70 min. Flow rate: 2 mL/min.) The crude product was used to next step without further purification.

Step 2a: A solution of (2S,3R)-2-(((benzyloxy)carbonyl)amino)-3-(tert-butoxy)butanoic acid dicyclohexylammonium salt (500 mg, 1.0 mmol) in 10 ml of THF and isobutyl chloroformate (167 mg, 1.2 mmol, 1.2 equiv) at −25° C. was added N-methylmorpholine (124 mg, 1.2 mmol, 1.2 equiv), the mixture was stirred at same temperature for 10 min and filtered. The filtrate was cooled to −20° C. and to it was added NaBH₄, followed by 2 ml of water immediately afterwards. The reaction mixture was stirred at same temperature for 5 min. then gradually warmed to room temperature for 25 min, poured into water (10 ml) and extracted with ethyl acetate (2×20 ml). The combined organic phases were washed with water, brine and dried over Na₂SO₄. The solvent was removed to yield benzyl ((2R)-(3R)-3-(tert-butoxy)-1-hydroxybutan-2-yl)carbamate as a clear oil. No further purification was required for next step. ¹H NMR (400 MHz, CDCl₃) δ 7.37-7.16 (m, 5H), 5.25 (d, J=8.0 Hz, 1H), 5.02 (s, 1H), 4.04 (ddd, J=12.0, 8.9, 2.8 Hz, 1H), 3.92-3.75 (m, 1H), 3.59 (dddd, J=32.3, 14.6, 8.2, 4.3 Hz, 2H), 1.10 (s, 9H), 1.09-1.06 (m, 3H).

Step 2b: To a solution of benzyl ((2R,3R)-3-(tert-butoxy)-1-hydroxybutan-2-yl)carbamate (5.88 g, 19.9 mmol) in 100 mL DMF was added NaH (60% in mineral oil, 1.62 g, 40.6 mmol) at 0° C. The reaction mixture was stirred for 30 min at 0° C. To the reaction mixture were added 4-methoxybenzyl chloride (4.07 mL, 29.9 mmol) and tetrabutylammonium iodide (0.74 g, 1.99 mmol) and the resulting mixture was warmed to room temperature and stirred for 15.5 h. The reaction mixture was poured into ice water (200 mL) forming a white suspension. EtOAc (100 mL) was added and the resulting mixture was stirred for 5 min to form a clear two layer solution. After separation, the aqueous phase was extracted with EtOAc (100 mL×3). The combined organic solution was washed with brine (80 mL), dried over $Na_2SO_4$, filtered and concentrated. Flash column chromatography (EtOAc/Heptane 0 to 70%) gave 5.90 g of (R)-4-((R)-1-(tert-butoxy)ethyl)-3-(4-methoxybenzyl)oxazolidin-2-one with minor impurities. Major product 1H NMR (400 MHz, MeOD) δ 7.38-7.29 (m, 2H), 6.99-6.93 (m, 2H), 4.68-4.58 (m, 1H), 4.33 (dd, J=9.3, 4.5 Hz, 1H), 4.27-4.17 (m, 2H), 3.89 (dd, J=6.4, 4.8 Hz, 1H), 3.81 (s, 3H), 3.65 (dd, J=9.0, 4.6 Hz, 1H), 1.09 (s, 9H), 1.02 (d, J=6.3 Hz, 3H). MS m/z 308.2 (M+H).

Step 2c: A solution of (R)-4-((R)-1-(tert-butoxy)ethyl)-3-(4-methoxybenzyl)oxazolidin-2-one (5.90 g, 19.2 mmol) in $CH_2Cl_2$ (40 mL) was treated with TFA (40 mL) at room temperature for 20 min. The reaction mixture was concentrated in vacuo, then diluted with $CH_2Cl_2$ (~50 mL), and again concentrated. This procedure was repeated three times to remove TFA. Flash column chromatography (EtOAc/Heptane 30-100%) gave 3.81 g (R)-4-((R)-1-hydroxyethyl)-3-(4-methoxybenzyl)oxazolidin-2-one. 1H NMR (400 MHz, MeOD) δ 7.31-7.21 (m, 2H), 7.00-6.87 (m, 2H), 4.67 (d, J=15.0 Hz, 1H), 4.34-4.18 (m, 3H), 3.95 (q, J=6.2 Hz, 1H), 3.80 (s, 3H), 3.68 (dt, J=8.7, 5.5 Hz, 1H), 1.09 (d, J=6.4 Hz, 3H). MS m/z 252.2 (M+H).

Step 2d: To a cooled (0° C.) solution of (R)-4-((R)-1-hydroxyethyl)-3-(4-methoxybenzyl)oxazolidin-2-one (2.27 g, 9.04 mmol) in 30 mL MeCN were added triethylamine (11.4 mL, 82 mmol) followed by perfluoro-1-butanesulfonyl fluoride (4.9 mL, 27.3 mmol) and $NEt_3(HF)_3$ (4.5 mL, 27.6 mmol) and the resulting mixture was stirred at 0° C. for 70 min. The reaction mixture was diluted with water (60 mL) and extracted with EtOAc (3×60 mL). Combined organics were washed with water (70 mL), brine (70 mL), dried over $Na_2SO_4$, filtered and concentrated. Flash column chromatography (EtOAc/heptane 5 to 70%) gave 2.19 g (R)-4-((S)-1-fluoroethyl)-3-(4-methoxybenzyl)oxazolidin-2-one. 1H NMR (400 MHz, CDCl3) δ 7.25-7.20 (m, 2H), 6.92-6.83 (m, 2H), 4.87 (d, J=15.1 Hz, 1H), 4.75 (dqd, J=47.6, 6.6, 2.1 Hz, 1H), 4.26 (td, J=9.2, 1.4 Hz, 1H), 4.17-4.05 (m, 2H), 3.81 (s, 3H), 3.71 (dddd, J=19.8, 9.5, 5.8, 2.1 Hz, 1H), 1.29 (dd, J=23.1, 6.2 Hz, 3H). MS m/z 254.5 (M+H).

Step 2e: A solution of (R)-4-((S)-1-fluoroethyl)-3-(4-methoxybenzyl)oxazolidin-2-one (1.98 g 7.8 mmol) in 40 mL TFA was heated at 65° C. for 16 h. The reaction mixture was concentrated to remove TFA. Flash column chromatography (EtOAc/$CH_2Cl_2$, 0 to 100%) gave 0.91 g (R)-4-((S)-1-fluoroethyl)-oxazolidin-2-one as a pale brown solid. TLC (1:2 heptane:EtOAc) Rf=0.25. 1H NMR (400 MHz, CDCl3) δ 5.60 (br s, 1H), 4.72-4.54 (m, 1H), 4.51 (td, J=8.9, 0.9 Hz, 1H), 4.32 (dd, J=9.2, 4.8 Hz, 1H), 4.02-3.88 (m, 1H), 1.38 (dd, J=24.0, 6.3 Hz, 3H).

Step 2f: To a cooled (0° C.) solution of 2,4-difluoropyrimidine (160 mg, 1.375 mmol) and (R)-4-((S)-1-fluoroethyl)oxazolidin-2-one (183 mg, 1.375 mmol) in DMF (Volume: 4.6 mL) was added NaH (60% in mineral oil, 66.0 mg, 1.650 mmol). The resulting mixture was stirred at 0° C. for 30 min and at room temperature for 2 hr. Desired product was observed from LC-MS. The mixture was quenched with brine (1 ml). Diluted w/ EtOAc (20 ml) and water (10 ml), and separated layers. The organic was extracted with an additional 20 mL EtOAc. The combined organics were washed with brine, dried, and concentrated. Crude was purified through flash column chromatography (10-100% EtOAc/Heptane) to give 210 mg (R)-4-((S)-1-fluoroethyl)-3-(2-fluoropyrimidin-4-yl)oxazolidin-2-one as a white solid. 1H NMR (400 MHz, CDCl3) δ 8.51 (dd, J=5.8, 2.1 Hz, 1H), 8.20 (dd, J=5.7, 3.7 Hz, 1H), 5.33 (dqd, J=49.5, 6.6, 1.3 Hz, 1H), 4.77 (dddd, J=26.5, 9.1, 3.4, 1.4 Hz, 1H), 4.65 (dd, J=9.0, 3.4 Hz, 1H), 4.50 (td, J=9.0, 1.3 Hz, 1H), 1.43 (dd, J=23.1, 6.6 Hz, 3H). MS m/z 230.1 (M+H).

Step 3: A solution of (S)-1-(4-methyl-2'-(trifluoromethyl)-[3,4'-bipyridin]-6-yl)ethanamine (28.1 mg, 0.1 mmol), (R)-4-((S)-1-fluoroethyl)-3-(2-fluoropyrimidin-4-yl)oxazolidin-2-one (22.9 mg, 0.100 mmol) and DIPEA (52.4 μl, 0.300 mmol) in DMSO (Volume: 500 μl) was heated at 110° C. for 1 hr. The solution was then cooled to rt, and RP-HPLC (acetonitrile:water) purification provided a white solid. This material was purified again with flash column chromatography (0-10% MeOH/EtOAc) to give 14 mg (R)-4-((S)-1-fluoroethyl)-3-(2-(((S)-1-(4-methyl-2'-(trifluoromethyl)-[3,4'-bipyridin]-6-yl)ethyl)amino)pyrimidin-4-yl)oxazolidin-2-one as a white solid. 1H NMR (400 MHz, MeOD) δ 8.81 (d, J=5.0 Hz, 1H), 8.41 (s, 1H), 8.18 (s, 1H), 7.86 (s, 1H), 7.69 (dd, J=5.0, 1.6 Hz, 1H), 7.44 (s, 1H), 7.41 (d, J=5.8 Hz, 1H), 5.08 (br s, 1H), 4.73 (br d, J=26.0 Hz, 1H), 4.56-4.27 (m, 3H), 2.32 (s, 3H), 1.58 (d, J=7.1 Hz, 3H), 1.12 (br s, 3H); HRMS (B) m/z 491.1782 (M+H)⁺. Anal. RP-HPLC $t_R$=3.42 min. Purity 100%/100%.

Example 467

(R)-3-(2-(((S)-1-(5-(2-fluoro-3-(trifluoromethyl)phenyl)pyrimidin-2-yl)ethyl)amino)pyrimidin-4-yl)-4-((S)-1-fluoroethyl)oxazolidin-2-one

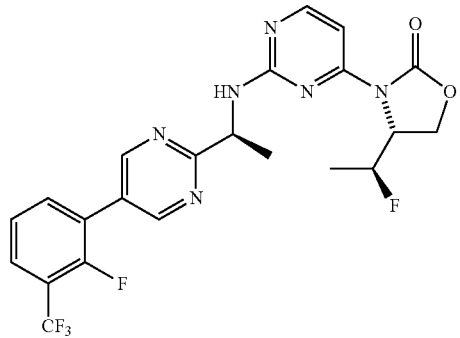

(R)-4-((S)-1-fluoroethyl)-3-(2-fluoropyrimidin-4-yl)oxazolidin-2-one (50 mg, 0.218 mmol) and (S)-1-(5-(2-fluoro-3-(trifluoromethyl)phenyl)pyrimidin-2-yl)ethanamine (75 mg, 0.262 mmol) were taken up in 3 mL DMSO. Hunig's base (57 uL, 0.327 mmol) was added. The mixture was heated to 110 C for 1.5 h. The reaction mixture was poured into 30 mL water, and extracted with EtOAc (2×30 mL). Organics were washed with 20 mL each water, and brine. Combined organics were dried over $Na_2SO_4$, filtered and concentrated on silica gel. Column chromatography (25-100% EtOAc/heptane) gave 82 mg white solid. ¹H NMR (400 MHz, CDCl₃) δ 8.91 (d, J=1.4 Hz, 2H), 8.25 (d, J=5.7

Hz, 1H), 7.79-7.61 (m, 2H), 7.52 (d, J=5.7 Hz, 1H), 7.44 (tt, J=7.7, 0.8 Hz, 1H), 6.12 (s, 1H), 5.32 (s, 1H), 5.08 (br s, 1H), 4.80 (dddd, J=26.5, 9.1, 3.4, 1.5 Hz, 1H), 4.58 (dd, J=8.8, 3.4 Hz, 1H), 4.44 (td, J=9.0, 1.3 Hz, 1H), 1.68 (d, J=8.8 Hz, 3H), 1.43-1.24 (m, 3H). HRMS (A) m/z 495.1611 (M+H)+. Anal. RP-HPLC $t_R$=3.68 min. Purity 96%/100%.

Example 468

(R)-4-((S)-1-fluoroethyl)-3-(2-(((S)-1-(2'-(trifluoromethyl)-[3,4'-bipyridin]-6-yl)ethyl)amino)pyrimidin-4-yl)oxazolidin-2-one

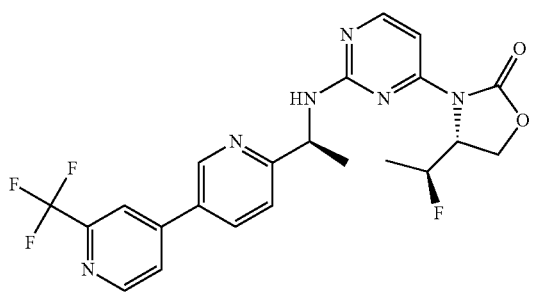 [SMILES: C[C@H](Nc1nccc(N2C(=O)OC[C@@H]2[C@H](C)F)n1)c1ccc(-c2ccnc(C(F)(F)F)c2)cn1]

A solution of (S)-1-(2'-(trifluoromethyl)-[3,4'-bipyridin]-6-yl)ethanamine (27 mg, 0.10 mmol), (R)-4-((S)-1-fluoroethyl)-3-(2-fluoropyrimidin-4-yl)oxazolidin-2-one (23 mg, 0.10 mmol) and DIPEA (52.4 μl, 0.30 mmol) in DMSO (500 μl) was heated at 110° C. for 1 hr. The solution was then cooled to rt and RP-HPLC purification (acetonitrile:water) provided the 32 mg of the major product as a white solid. 1H NMR (400 MHz, MeOD) δ 8.98 (s, 1H), 8.79 (d, J=5.1 Hz, 1H), 8.23 (dd, J=8.2, 2.4 Hz, 1H), 8.17 (br s, 1H), 8.17-8.12 (m, 1H), 7.98 (dd, J=5.1, 1.7 Hz, 1H), 7.59 (d, J=8.3 Hz, 1H), 7.40 (d, J=5.8 Hz, 1H), 5.11 (br s, 1H), 4.69 (br d, J=27.2 Hz, 1H), 4.55-4.12 (m, 3H), 1.60 (d, J=7.1 Hz, 3H), 1.03 (br s, 3H); HRMS (B) m/z 477.1699 (M+H)+.

Example 469

(R)-3-(2-(((S)-1-(5-(4-fluoro-3-methylphenyl)pyrimidin-2-yl)ethyl)amino)pyrimidin-4-yl)-4-((S)-1-fluoroethyl)oxazolidin-2-one

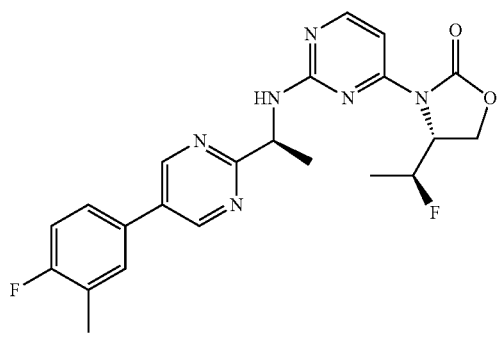 [SMILES: Cc1cc(-c2cnc([C@H](C)Nc3nccc(N4C(=O)OC[C@@H]4[C@H](C)F)n3)nc2)ccc1F]

(R)-4-((S)-1-fluoroethyl)-3-(2-fluoropyrimidin-4-yl)oxazolidin-2-one (50 mg, 0.218 mmol), (S)-1-(5-(4-fluoro-3-methylphenyl)pyrimidin-2-yl)ethanamine (60.5 mg, 0.262 mmol), and DIPEA (57 ul, 0.327 mmol) were taken up in 3 mL DMSO. Heated to 110 C for 1 h. The reaction mixture was poured into 30 mL water and extracted with EtOAc (2×30 mL). Organics were washed with 20 mL each water, brine, and dried over $Na_2SO_4$, and filtered and concentrated on silica gel. Column chromatography (25-100% EtOAc/hept) gave the desired product (92 mg) as a white solid. 1H NMR (400 MHz, CDCl3) δ 8.87 (s, 2H), 8.25 (d, J=5.7 Hz, 1H), 7.51 (d, J=5.7 Hz, 1H), 7.42-7.31 (m, 2H), 7.21-7.12 (m, 1H), 6.15 (s, 1H), 5.28 (s, 2H), 4.80 (dddd, J=26.6, 9.0, 3.5, 1.6 Hz, 1H), 4.57 (dd, J=8.8, 3.4 Hz, 1H), 4.44 (td, J=9.0, 1.3 Hz, 1H), 2.39 (d, J=1.9 Hz, 3H), 1.66 (d, J=6.9 Hz, 3H), 1.35-1.24 (m, 3H). HRMS (A) m/z 441.1849 (M+H)+. Anal. RP-HPLC $t_R$=3.10 min. Purity 100%/100%.

Example 470

(R)-3-(5-fluoro-2-(((S)-1-(4-methyl-2'-(trifluoromethyl)-[3,4'-bipyridin]-6-yl)ethyl)amino)pyrimidin-4-yl)-4-((S)-1-fluoroethyl)oxazolidin-2-one

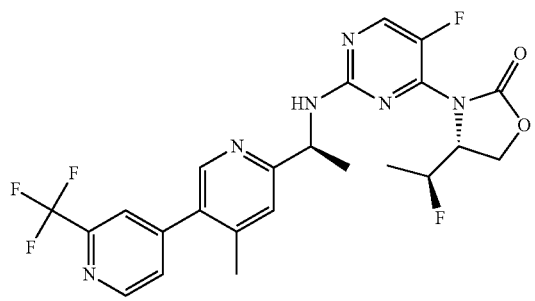 [SMILES: Cc1cc([C@H](C)Nc2ncc(F)c(N3C(=O)OC[C@@H]3[C@H](C)F)n2)ncc1-c1ccnc(C(F)(F)F)c1]

A solution of (S)-1-(4-methyl-2'-(trifluoromethyl)-[3,4'-bipyridin]-6-yl)ethanamine (50 mg, 0.178 mmol), (R)-3-(2,5-difluoropyrimidin-4-yl)-4-((S)-1-fluoroethyl)oxazolidin-2-one, (46.1 mg, 0.187 mmol) and DIPEA (93 μl, 0.533 mmol) in DMSO (889 μl) was heated at 110° C. for 1 hr. The the solution was then cooled to rt diluted with 10 mL EtOAc, washed with water, brine, dried over $Na_2SO_4$, concentrated and purified through RP-HPLC (acetonitrile:water) to provide 37 mg white solid. 1H NMR (400 MHz, MeOD) δ 8.81 (d, J=5.0 Hz, 1H), 8.39 (s, 1H), 8.26 (s, 1H), 7.85 (s, 1H), 7.69 (dd, J=5.1, 1.6 Hz, 1H), 7.46 (s, 1H), 5.00 br (s, 1H), 4.66-4.37 (m, 4H), 2.32 (s, 3H), 1.57 (d, J=7.1 Hz, 3H), 1.04 (br s, 3H); HRMS (B) m/z 509.1701 (M+H)+.

Example 471

(R)-4-(fluoromethyl)-3-(2-(((S)-1-(1-(4-fluorophenyl)-1H-imidazol-4-yl)ethyl)amino)pyrimidin-4-yl)oxazolidin-2-one

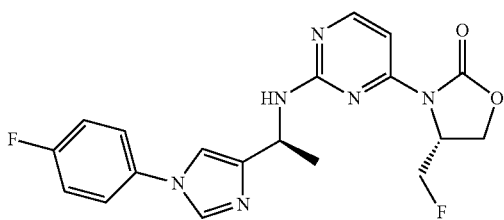 [SMILES: C[C@H](Nc1nccc(N2C(=O)OC[C@@H]2CF)n1)c1cn(-c2ccc(F)cc2)cn1]

A solution of (R)-4-(fluoromethyl)-3-(2-fluoropyrimidin-4-yl)oxazolidin-2-one (15 mg, 0.070 mmol), (S)-1-(1-(4- fluorophenyl)-1H-imidazol-4-yl)ethanamine hydrochloride (20 mg, 0.084 mmol, 1.2 equiv), and N-ethyl-N-isopropylpropan-2-amine (0.043 mL, 0.24 mmol, 3.5 equiv) in DMSO (1.0 mL) was heated at 85° C. for 14 hours. The reaction was then cooled to room temperature. Purification by reverse phase HPLC provided the trifluoroacetate salt of (R)-4-(fluoromethyl)-3-(2-(((S)-1-(1-(4-fluorophenyl)-1H-imidazol-4-yl)ethyl)amino)pyrimidin-4-yl)oxazolidin-2-one (6 mg, white solid) in 17% yield. $^1$H NMR (400 MHz, CDCl$_3$) δ 11.11 (d, J=6.9 Hz, 1H), 8.40 (s, 1H), 7.97 (d, J=7.0 Hz, 1H), 7.88 (d, J=6.9 Hz, 1H), 7.62 (s, 1H), 7.47 (dd, J=8.7, 4.3 Hz, 2H), 7.28-7.34 (m, 2H), 5.75 (t, J=7.1 Hz, 1H), 5.20-5.33 (m, 1H), 4.45-4.75 (m, 4H), 1.71 (d, J=6.8 Hz, 3H); HRMS (A) m/z 401.1537 (M+H)$^+$; Rt-1.22 min.

Example 472

(R)-3-(2-(((S)-1-(1-(3-chloro-4-fluorophenyl)-1H-imidazol-4-yl)ethyl)amino)-5-fluoropyrimidin-4-yl)-4-(fluoromethyl)oxazolidin-2-one

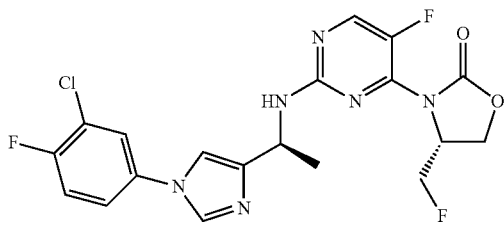 [SMILES: C[C@H](Nc1ncc(F)c(N2C(=O)OC[C@@H]2CF)n1)c1cn(-c2ccc(F)c(Cl)c2)cn1]

A solution of (R)-3-(2,5-difluoropyrimidin-4-yl)-4-(fluoromethyl)oxazolidin-2-one (15 mg, 0.064 mmol), (S)-1-(1-(3-chloro-4-fluorophenyl)-1H-imidazol-4-yl)ethanamine hydrochloride (21 mg, 0.077 mmol, 1.2 equiv), and N-ethyl-N-isopropylpropan-2-amine (0.039 mL, 0.23 mmol, 3.5 equiv) in DMSO (1.0 mL) was heated at 85° C. for 14 hours. The reaction was then cooled to room temperature. Purification by reverse phase HPLC provided the trifluoroacetate salt of (R)-3-(2-(((S)-1-(1-(3-chloro-4-fluorophenyl)-1H-imidazol-4-yl)ethyl)amino)-5-fluoropyrimidin-4-yl)-4-(fluoromethyl)oxazolidin-2-one (11 mg, white solid) in 30% yield. $^1$H NMR (400 MHz, CDCl$_3$) δ 8.56 (s, 1H), 8.18 (d, J=1.9 Hz, 1H), 7.57-7.63 (m, 1H), 7.33-7.48 (m, 3H), 5.34 (br. s., 1H), 4.85-5.00 (m, 1H), 4.41-4.75 (m, 4H), 1.73 (d, J=7.0 Hz, 3H); HRMS(A) m/z 453.1058 (M+H)$^+$; Rt-1.51 min.

Example 473

(R)-3-(2-(((S)-1-(1-(4-chloro-3-fluorophenyl)-1H-imidazol-4-yl)ethyl)amino)pyrimidin-4-yl)-4-(fluoromethyl)oxazolidin-2-one

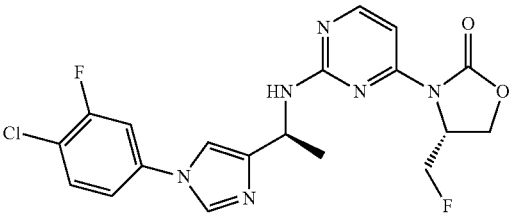 [SMILES: C[C@H](Nc1nccc(N2C(=O)OC[C@@H]2CF)n1)c1cn(-c2ccc(Cl)c(F)c2)cn1]

A solution of (R)-4-(fluoromethyl)-3-(2-fluoropyrimidin-4-yl)oxazolidin-2-one (15 mg, 0.070 mmol), (S)-1-(1-(4-chloro-3-fluorophenyl)-1H-imidazol-4-yl)ethanamine hydrochloride (22 mg, 0.084 mmol, 1.2 equiv), and N-ethyl-N-isopropylpropan-2-amine (0.043 mL, 0.24 mmol, 3.5 equiv) in DMSO (1.0 mL) was heated at 85° C. for 14 hours. The reaction was then cooled to room temperature. Purification by reverse phase HPLC provided the trifluoroacetate salt of (R)-3-(2-(((S)-1-(1-(4-chloro-3-fluorophenyl)-1H-imidazol-4-yl)ethyl)amino)pyrimidin-4-yl)-4-(fluoromethyl)oxazolidin-2-one (14 mg, white solid) in 35% yield. $^1$H NMR (400 MHz, CDCl$_3$) δ 11.04 (d, J=7.0 Hz, 1H), 8.29 (s, 1H), 7.97 (d, J=7.1 Hz, 1H), 7.86 (d, J=6.9 Hz, 1H), 7.57-7.67 (m, 2H), 7.32 (dd, J=8.7, 2.5 Hz, 1H), 7.24 (d, J=1.0 Hz, 1H), 5.64 (t, J=7.1 Hz, 1H), 5.12-5.27 (m, 1H), 4.43-4.75 (m, 4H), 1.70 (d, J=6.8 Hz, 3H); HRMS(A) m/z 435.1151 (M+H)$^+$; Rt-1.51 min.

Example 474

(R)-3-(2-(((S)-1-(1-(3,4-difluorophenyl)-1H-imidazol-4-yl)ethyl)amino)pyrimidin-4-yl)-4-(fluoromethyl)oxazolidin-2-one

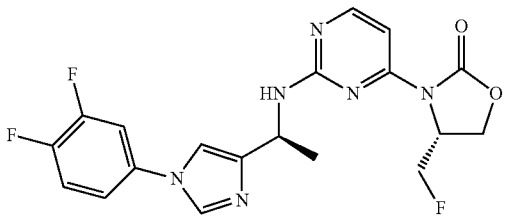 [SMILES: C[C@H](Nc1nccc(N2C(=O)OC[C@@H]2CF)n1)c1cn(-c2ccc(F)c(F)c2)cn1]

A solution of (R)-4-(fluoromethyl)-3-(2-fluoropyrimidin-4-yl)oxazolidin-2-one (15 mg, 0.070 mmol), (S)-1-(1-(3,4-difluorophenyl)-1H-imidazol-4-yl)ethanamine hydrochloride (22 mg, 0.084 mmol, 1.2 equiv), and N-ethyl-N-isopropylpropan-2-amine (0.043 mL, 0.24 mmol, 3.5 equiv) in DMSO (1.0 mL) was heated at 85° C. for 14 hours. The reaction was then cooled to room temperature. Purification by reverse phase HPLC provided the trifluoroacetate salt of (R)-3-(2-(((S)-1-(1-(3,4-difluorophenyl)-1H-imidazol-4-yl)ethyl)amino)pyrimidin-4-yl)-4-(fluoromethyl)oxazolidin-2-one (10 mg, white solid) in 26% yield. $^1$H NMR (400 MHz, CDCl$_3$) δ 11.05 (d, J=8.2 Hz, 1H), 8.30 (s, 1H), 7.98 (d, J=7.2 Hz, 1H), 7.87 (d, J=7.0 Hz, 1H), 7.59 (s, 1H), 7.31-7.46 (m, 2H), 7.24 (br. s., 1H), 5.61-5.71 (m, 1H), 5.14-5.28 (m, 1H), 4.44-4.76 (m, 4H), 1.70 (d, J=6.8 Hz, 3H); HRMS(A) m/z 419.1444 (M+H)$^+$; Rt-1.35 min.

Example 475

(R)-3-(2-(((S)-1-(1-(4-(difluoromethyl)-3-fluorophenyl)-1H-imidazol-4-yl)ethyl)amino)pyrimidin-4-yl)-4-(fluoromethyl)oxazolidin-2-one

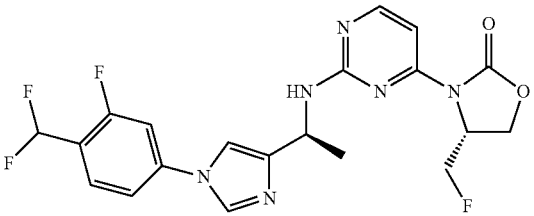 [SMILES: C[C@H](Nc1nccc(N2C(=O)OC[C@@H]2CF)n1)c1cn(-c2ccc(C(F)F)c(F)c2)cn1]

A solution of (R)-4-(fluoromethyl)-3-(2-fluoropyrimidin-4-yl)oxazolidin-2-one (15 mg, 0.070 mmol), (S)-1-(1-(4-(difluoromethyl)-3-fluorophenyl)-1H-imidazol-4-yl)ethanamine hydrochloride (24 mg, 0.084 mmol, 1.2 equiv), and N-ethyl-N-isopropylpropan-2-amine (0.043 mL, 0.24 mmol, 3.5 equiv) in DMSO (1.0 mL) was heated at 85° C. for 14 hours. The reaction was then cooled to room temperature. Purification by reverse phase HPLC provided the trifluoroacetate salt of (R)-3-(2-(((S)-1-(1-(4-(difluoromethyl)-3-fluorophenyl)-1H-imidazol-4-yl)ethyl)amino)pyrimidin-4-yl)-4-(fluoromethyl)oxazolidin-2-one (15 mg, white solid) in 37% yield. $^1$H NMR (400 MHz, CDCl$_3$) δ 10.99 (d, J=7.2 Hz, 1H), 8.24 (s, 1H), 7.97 (d, J=6.8 Hz, 1H), 7.78-7.87 (m, 2H), 7.61 (s, 1H), 7.38 (d, J=8.8 Hz, 1H), 7.31 (d, J=1.0 Hz, 1H), 6.79-7.09 (m, 1H), 5.57 (t, J=7.0 Hz, 1H), 5.09-5.23 (m, 1H), 4.44-4.77 (m, 4H), 1.70 (d, J=6.9 Hz, 3H); HRMS (A) m/z 451.1512 (M+H)$^+$; Rt-1.48 min.

Example 476

(R)-3-(2-(((S)-1-(1-(4-chloro-2-fluorophenyl)-1H-imidazol-4-yl)ethyl)amino)pyrimidin-4-yl)-4-((S)-1-fluoroethyl)oxazolidin-2-one

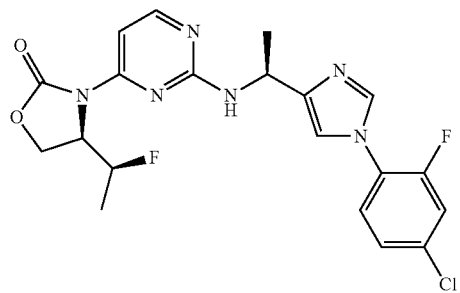 [SMILES: C[C@H](Nc1nccc(N2C(=O)OC[C@@H]2[C@H](C)F)n1)c1cn(-c2ccc(Cl)cc2F)cn1]

Step 1: Preparation of (S)-1-(1-(4-chloro-2-fluorophenyl)-1H-imidazol-4-yl)ethanamine hydrochloride To 1H-imidazole-4-carbaldehyde (2.56 g, 26.6 mmol), 4-chloro-2-fluoro-1-iodobenzene (0.739 g, 2.88 mmol) and Cs$_2$CO$_3$ (1.564 g, 4.80 mmol) in DMF (50 mL) was added copper(I) iodide (0.023 g, 0.120 mmol) and (1R,2R)—N1,N2-dimethylcyclohexane-1,2-diamine (0.068 g, 0.480 mmol). The reaction was heated to 110° C. for 18 hours. The reaction mixture was then cooled to room temperature and filtered, and washed with EtOAc (100 mL). The organic was washed with water (2×30 mL) and brine (30 mL), dried (Na$_2$SO$_4$) and concentrated. The residue was purified by silica gel chromotography to give 1-(4-chloro-2-fluorophenyl)-1H-imidazole-4-carbaldehyde (451 mg), to which was added (S)-2-methylpropane-2-sulfinamide (0.29 g, 2.4 mmol), CuSO$_4$ (0.638 g, 4 mmol) and DCE (10 mL). The reaction was heated at 65° C. for 18 hours. The reaction was cooled to rt, filtered and concentrated to give (S,E)-N-((1-(4-chloro-2-fluorophenyl)-1H-imidazol-4-yl)methylene)-2-methylpropane-2-sulfinamide, to which was added DCM (20 mL). The reaction mixture was cooled to −70° C. and methylmagnesium bromide (1.33 ml, 4 mmol) was added dropwise to the solution. The reaction was stirred for two hours and the cold bath was then removed, and the reaction was allowed to warm to rt and stir for 30 minutes. The reaction was cooled to 0° C. and HCl (1M) was added cautiously to quench until aqueous pH=8. The phases were separated and the aqueous layer was extracted with DCM (2×30 mL). Combined organic was dried (Na2SO4) and concentrated to give (S)—N—((S)-1-(1-(4-chloro-2-fluorophenyl)-1H-imidazol-4-yl)ethyl)-2-methylpropane-2-sulfinamide (130 mg), which was then dissolved in MeOH (5 mL) and HCl (0.5 mL, 4M) was added. The reaction was stirred for one hour and concentrated to give product (100 mg). LCMS m/z 240.1 (M+H)$^+$; Rt-0.50 min.

Step 2: Preparation of (R)-3-(2-(((S)-1-(1-(4-chloro-2-fluorophenyl)-1H-imidazol-4-yl)ethyl)amino)pyrimidin-4-yl)-4-((S)-1-fluoroethyl)oxazolidin-2-one A solution of (S)-1-(1-(4-chloro-2-fluorophenyl)-1H-imidazol-4-yl)ethanamine hydrochloride (20 mg, 0.072 mmol), (S)-4-((S)-1-fluoroethyl)-3-(2-fluoropyrimidin-4-yl)oxazolidin-2-one (15 mg, 0.065 mmol), and N-ethyl-N-isopropylpropan-2-amine (0.040 mL, 0.23 mmol) in DMSO (0.5 mL) was heated at 90° C. for 8 hours. The reaction was then cooled to room temperature. Purification by reverse phase HPLC provided the trifluoroacetate salt of (R)-3-(2-(((S)-1-(1-(4-chloro-2-fluorophenyl)-1H-imidazol-4-yl)ethyl)amino)pyrimidin-4-yl)-4-((S)-1-fluoroethyl)oxazolidin-2-one (12 mg). $^1$H NMR (400 MHz, CD$_3$OD) δ 8.68 (br. s., 1H), 8.22 (d, J=6.7 Hz, 1H), 7.76 (d, J=4.7 Hz, 1H), 7.70-7.55 (m, 3H), 7.45 (d, J=8.6 Hz, 1H), 5.36-5.24 (m, 1H), 4.9-4.75 (m, 2H), 4.62 (dd, J=2.7, 9.4 Hz, 1H), 4.56-4.47 (m, 1H), 1.71 (d, J=6.7 Hz, 3H), 1.35-1.17 (m, 3H); HRMS(A) m/z 449.1306 (M+H)$^+$; Rt-1.57 min.

Example 477

(R)-3-(2-(((S)-1-(1-(4-chloro-2-fluorophenyl)-1H-imidazol-4-yl)ethyl)amino)-5-fluoropyrimidin-4-yl)-4-((S)-1-fluoroethyl)oxazolidin-2-one

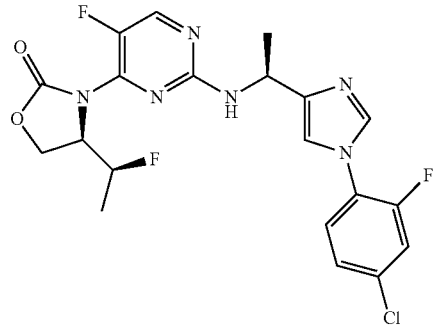

A solution of (S)-1-(1-(4-chloro-2-fluorophenyl)-1H-imidazol-4-yl)ethanamine hydrochloride (20 mg, 0.072 mmol), (R)-3-(2,5-difluoropyrimidin-4-yl)-4-((S)-1-fluoroethyl)oxazolidin-2-one (15 mg, 0.061 mmol), and N-ethyl-N-isopropylpropan-2-amine (0.040 mL, 0.23 mmol) in DMSO (0.5 mL) was heated at 90° C. for 8 hours. The reaction was then cooled to room temperature. Purification by reverse phase HPLC provided the trifluoroacetate salt of (R)-3-(2-(((S)-1-(1-(4-chloro-2-fluorophenyl)-1H-imidazol-4-yl)ethyl)amino)-5-fluoropyrimidin-4-yl)-4-((S)-1-fluoroethyl)oxazolidin-2-one (10 mg). $^1$H NMR (400 MHz, CD$_3$OD) δ 8.25 (d, J=3.1 Hz, 1H), 7.96 (s, 1H), 7.58-7.45 (m, 2H), 7.36 (d, J=8.6 Hz, 1H), 7.26 (s, 1H), 5.06 (d, J=6.7 Hz, 1H), 4.9-4.75 (m, 2H), 4.67-4.55 (m, 2H), 4.53-4.43 (m, 1H), 1.57 (d, J=7.0 Hz, 3H), 1.26-1.06 (m, 3H); HRMS(A) m/z 467.1217 (M+H)$^+$; Rt-1.66 min.

Example 478

(R)-3-(2-(((S)-1-(1-(2,4-difluorophenyl)-1H-imidazol-4-yl)ethyl)amino)pyrimidin-4-yl)-4-((S)-1-fluoroethyl)oxazolidin-2-one

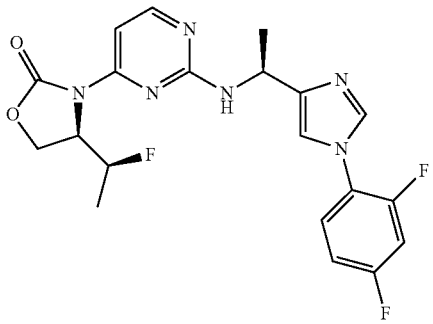 [SMILES: C[C@H](Nc1nccc(N2C(=O)OC[C@@H]2[C@H](C)F)n1)c1cn(-c2ccc(F)cc2F)cn1]

Step 1: Preparation of (S)-1-(1-(2,4-difluorophenyl)-1H-imidazol-4-yl)ethanamine hydrochloride To 1H-imidazole-4-carbaldehyde (3.01 g, 31.3 mmol), 2,4-difluoro-1-iodobenzene (1.008 g, 4.20 mmol), $Cs_2CO_3$ (2.281 g, 7.00 mmol) in DMF (50 mL) was added copper(I) iodide (0.033 g, 0.175 mmol) and (1R,2R)—N1,N2-dimethylcyclohexane-1,2-diamine (0.100 g, 0.700 mmol). The reaction was heated to 110° C. for 18 hours. The reaction mixture was then cooled to room temperature and filtered, and washed with EtOAc (100 mL). The organic was washed with water (2×30 mL) and brine (30 mL), dried ($Na_2SO_4$) and concentrated. The residue was purified by silica gel chromotography to give 1-(2,4-difluorophenyl)-1H-imidazole-4-carbaldehyde (651 mg), to which was added (S)-2-methylpropane-2-sulfinamide (0.424 g, 3.5 mmol), $CuSO_4$ (0.798 g, 5 mmol) and DCE (10 mL). The reaction was heated to 65° C. for 18 hours. The reaction was cooled to rt, filtered and concentrated to give (S,E)-N-((1-(2,4-difluorophenyl)-1H-imidazol-4-yl)methylene)-2-methylpropane-2-sulfinamide, to which was added DCM (20 mL). The reaction mixture was cooled to −70° C. and methylmagnesium bromide (1.667 ml, 5 mmol) was added dropwise to the solution. The reaction was stirred for two hours and the cold bath was then removed, and the reaction was allowed to warm to rt and stir for 30 minutes. The reaction was cooled to 0° C. and HCl (1M) was added cautiously to quench until aqueous pH=8. The phases were separated and the aqueous layer was extracted with DCM (2×30 mL). Combined organic was dried ($Na_2SO_4$) and concentrated to give (S)—N—((S)-1-(1-(2,4-difluorophenyl)-1H-imidazol-4-yl)ethyl)-2-methylpropane-2-sulfinamide (230 mg), which was then dissolved in MeOH (5 mL) and HCl (0.5 mL, 4M) was added. The reaction was stirred for one hour and concentrated to give product (212 mg). LCMS m/z 224.1 $(M+H)^+$; Rt-0.39 min.

Step 2: Preparation of (R)-3-(2-(((S)-1-(1-(2,4-difluorophenyl)-1H-imidazol-4-yl)ethyl)amino)pyrimidin-4-yl)-4-((S)-1-fluoroethyl)oxazolidin-2-one A solution of (S)-1-(1-(2,4-difluorophenyl)-1H-imidazol-4-yl)ethanamine hydrochloride (18 mg, 0.069 mmol), (S)-4-((S)-1-fluoroethyl)-3-(2-fluoropyrimidin-4-yl)oxazolidin-2-one (13 mg, 0.057 mmol), and N-ethyl-N-isopropylpropan-2-amine (0.040 mL, 0.23 mmol) in DMSO (0.5 mL) was heated at 90° C. for 8 hours. The reaction was then cooled to room temperature. Purification by reverse phase HPLC provided the trifluoroacetate salt of (R)-3-(2-(((S)-1-(1-(2,4-difluorophenyl)-1H-imidazol-4-yl)ethyl)amino)pyrimidin-4-yl)-4-((S)-1-fluoroethyl)oxazolidin-2-one (10 mg). $^1$H NMR (400 MHz, $CD_3OD$) δ 8.22 (d, J=6.7 Hz, 1H), 7.88 (q, J=8.7 Hz, 6H), 7.71 (d, J=5.5 Hz, 1H), 5.27 (d, J=7.0 Hz, 1H), 4.86 (s, 2H), 4.68-4.44 (m, 2H), 1.71 (d, J=7.0 Hz, 3H), 1.34-1.15 (m, 3H); HRMS(A) m/z 433.1603 $(M+H)^+$; Rt-1.40 min.

Example 479

(R)-3-(2-(((S)-1-(1-(2,4-difluorophenyl)-1H-imidazol-4-yl)ethyl)amino)-5-fluoropyrimidin-4-yl)-4-((S)-1-fluoroethyl)oxazolidin-2-one

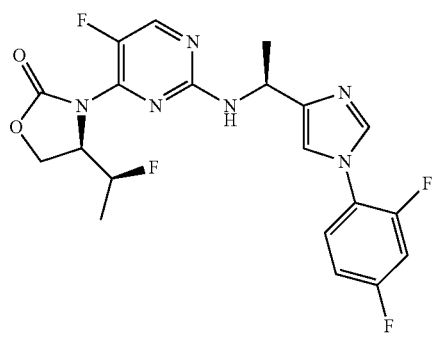 [SMILES: C[C@H](Nc1ncc(F)c(N2C(=O)OC[C@@H]2[C@H](C)F)n1)c1cn(-c2ccc(F)cc2F)cn1]

A solution of (S)-1-(1-(2,4-difluorophenyl)-1H-imidazol-4-yl)ethanamine hydrochloride (18 mg, 0.069 mmol), (R)-3-(2,5-difluoropyrimidin-4-yl)-4-((S)-1-fluoroethyl)oxazolidin-2-one (15 mg, 0.061 mmol), and N-ethyl-N-isopropylpropan-2-amine (0.040 mL, 0.23 mmol) in DMSO (0.5 mL) was heated at 90° C. for 8 hours. The reaction was then cooled to room temperature. Purification by reverse phase HPLC provided the trifluoroacetate salt of (R)-3-(2-(((S)-1-(1-(2,4-difluorophenyl)-1H-imidazol-4-yl)ethyl)amino)-5-fluoropyrimidin-4-yl)-4-((S)-1-fluoroethyl)oxazolidin-2-one (18 mg). $^1$H NMR (400 MHz, $CD_3OD$) δ 9.18 (s, 1H), 8.33 (d, J=3.1 Hz, 1H), 7.82 (s, 1H), 7.74 (dt, J=5.7, 8.7 Hz, 1H), 7.39 (ddd, J=2.5, 8.5, 10.9 Hz, 1H), 7.24 (t, J=8.4 Hz, 1H), 5.21 (d, J=6.7 Hz, 1H), 5.06-4.77 (m, 2H), 4.63 (t, J=9.0 Hz, 1H), 4.50 (dd, J=5.9, 8.6 Hz, 1H), 1.69 (d, J=6.7 Hz, 3H), 1.35-1.22 (m, 3H); HRMS(A) m/z 451.1514 $(M+H)^+$; Rt-1.47 min.

Example 480

(R)-3-(2-(((S)-1-(5-(4-chlorophenyl)oxazol-2-yl)ethyl)amino)-5-fluoropyrimidin-4-yl)-4-(fluoromethyl)oxazolidin-2-one

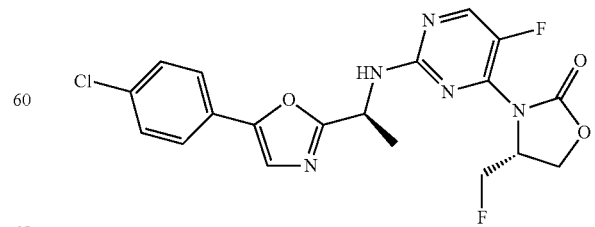

(R)-3-(2,5-difluoropyrimidin-4-yl)-4-(fluoromethyl)oxazolidin-2-one (105 mg, 0.449 mmol), (S)-1-(5-(4-chlorophenyl)oxazol-2-yl)ethanamine (100 mg, 0.449 mmol), and DIPEA (157 ul, 0.898 mmol) were dissolved in DMSO (1 mL) and the reaction mixture was heated at 120° C. for 2 h. The reaction mixture was cooled, diluted with EtOAc, washed with water and brine, and concentrated in vacuo. Column chromatography (5-50% EtOAc/DCM) gave the desired product (169 mg) as a white foam. $^1$H NMR (400 MHz, CDCl$_3$) δ 8.26 (d, J=2.8 Hz, 1H), 7.59-7.50 (m, 2H), 7.45-7.36 (m, 2H), 7.25 (s, 1H), 5.66 (d, J=7.6 Hz, 1H), 5.21 (br s, 1H), 4.86 (ddddd, J=20.0, 8.6, 7.0, 4.3, 2.8 Hz, 1H), 4.66-4.44 (m, 3H), 4.41 (br s, 1H), 1.71 (d, J=7.0 Hz, 3H).

HRMS-Acidic. LC-UV/ESI-MS data was recorded on an Acquity LCTp Tof-Rs(FWHM)>12000 Accuracy<5 ppm. Column: Acquity BEHC18 1.7 μm 2.1×50 mm—50° C. Eluent A: Water+0.1% formic acid. Eluent B: Acetonitrile+ 0.1% formic acid. Gradient: from 0.2 to 98% B in 8.05 min—flow 0.9 mL/min. m/z 436.0996 (M+H)$^+$. Anal. RP-HPLC t$_R$=3.46 min. Purity 100%/100%.

The compounds listed in Table 39 are made using methods similar to those described for Examples 1-465 and as outlined in the general synthetic procedures.

TABLE 39

The compounds in Table 39 are prepared following chemistry similar to that described for Examples 1-465 or as outlined in the Schemes given above.

| Example | Name |
|---|---|
| [structure] | (R)-4-(fluoromethyl)-3-(2-(((S)-1-(1-(4-fluorophenyl)-1H-imidazol-4-yl)ethyl)amino)pyrimidin-4-yl)oxazolidin-2-one |
| [structure] | (R)-3-(2-(((S)-1-(1-(3-chloro-4-fluorophenyl)-1H-imidazol-4-yl)ethyl)amino)-5-fluoropyrimidin-4-yl)-4-(fluoromethyl)oxazolidin-2-one |
| [structure] | (R)-3-(2-(((S)-1-(1-(4-chloro-3-fluorophenyl)-1H-imidazol-4-yl)ethyl)amino)pyrimidin-4-yl)-4-(fluoromethyl)oxazolidin-2-one |
| [structure] | (R)-3-(2-(((S)-1-(1-(3,4-difluorophenyl)-1H-imidazol-4-yl)ethyl)amino)pyrimidin-4-yl)-4-(fluoromethyl)oxazolidin-2-one |

TABLE 39-continued

The compounds in Table 39 are prepared following chemistry similar to that described for Examples 1-465 or as outlined in the Schemes given above.

| Example | | Name |
|---|---|---|
| | 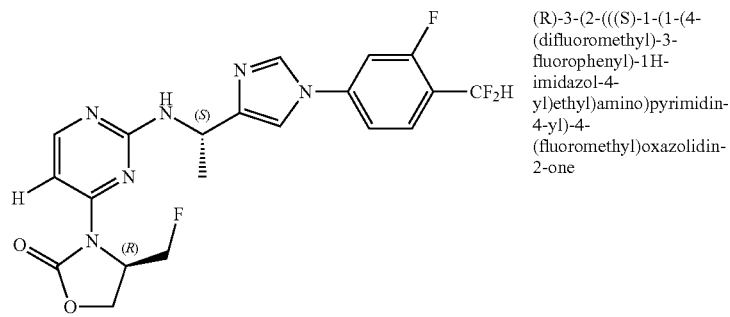 | (R)-3-(2-(((S)-1-(1-(4-(difluoromethyl)-3-fluorophenyl)-1H-imidazol-4-yl)ethyl)amino)pyrimidin-4-yl)-4-(fluoromethyl)oxazolidin-2-one |
| | 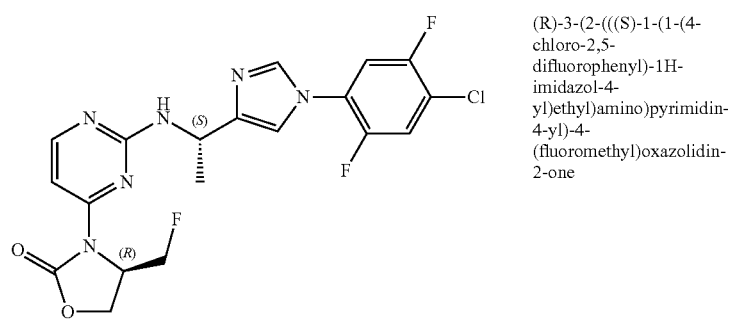 | (R)-3-(2-(((S)-1-(1-(4-chloro-2,5-difluorophenyl)-1H-imidazol-4-yl)ethyl)amino)pyrimidin-4-yl)-4-(fluoromethyl)oxazolidin-2-one |
| | 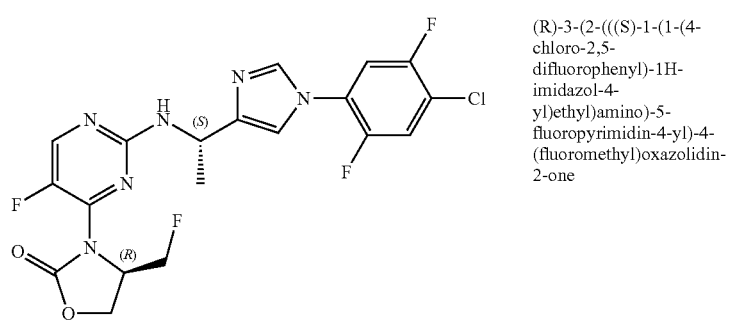 | (R)-3-(2-(((S)-1-(1-(4-chloro-2,5-difluorophenyl)-1H-imidazol-4-yl)ethyl)amino)-5-fluoropyrimidin-4-yl)-4-(fluoromethyl)oxazolidin-2-one |
| | 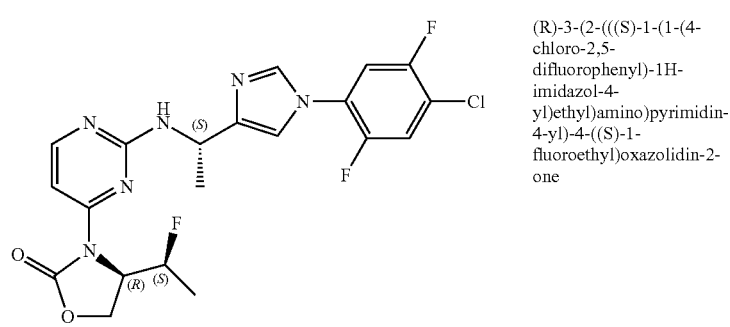 | (R)-3-(2-(((S)-1-(1-(4-chloro-2,5-difluorophenyl)-1H-imidazol-4-yl)ethyl)amino)pyrimidin-4-yl)-4-((S)-1-fluoroethyl)oxazolidin-2-one |

TABLE 39-continued

The compounds in Table 39 are prepared following chemistry similar to that described for Examples 1-465 or as outlined in the Schemes given above.

| Example | Name |
|---|---|
| 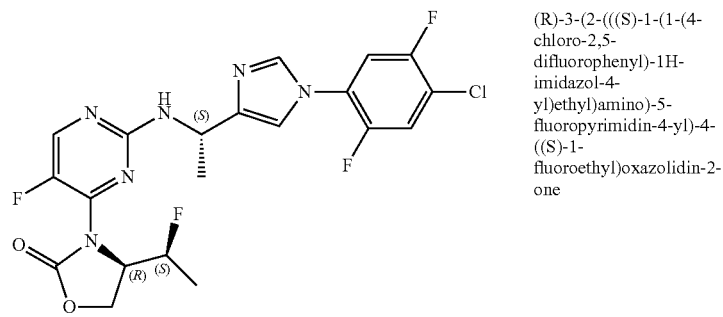 | (R)-3-(2-(((S)-1-(1-(4-chloro-2,5-difluorophenyl)-1H-imidazol-4-yl)ethyl)amino)-5-fluoropyrimidin-4-yl)-4-((S)-1-fluoroethyl)oxazolidin-2-one |
| 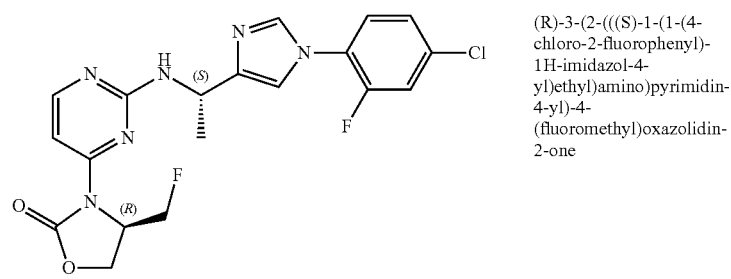 | (R)-3-(2-(((S)-1-(1-(4-chloro-2-fluorophenyl)-1H-imidazol-4-yl)ethyl)amino)pyrimidin-4-yl)-4-(fluoromethyl)oxazolidin-2-one |
| 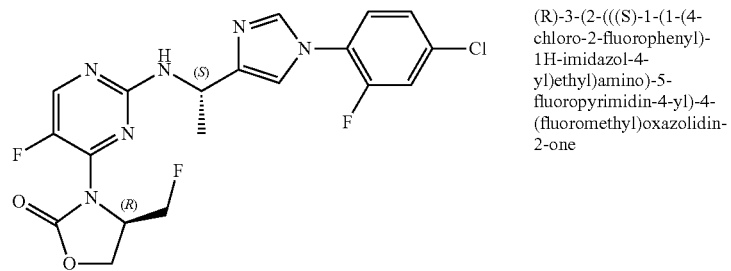 | (R)-3-(2-(((S)-1-(1-(4-chloro-2-fluorophenyl)-1H-imidazol-4-yl)ethyl)amino)-5-fluoropyrimidin-4-yl)-4-(fluoromethyl)oxazolidin-2-one |
| 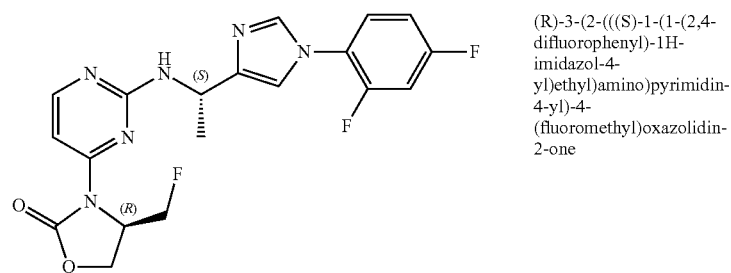 | (R)-3-(2-(((S)-1-(1-(2,4-difluorophenyl)-1H-imidazol-4-yl)ethyl)amino)pyrimidin-4-yl)-4-(fluoromethyl)oxazolidin-2-one |
| 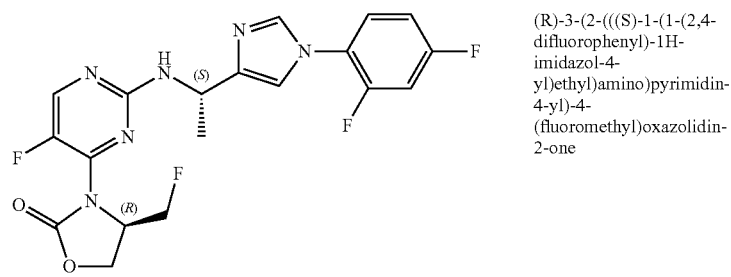 | (R)-3-(2-(((S)-1-(1-(2,4-difluorophenyl)-1H-imidazol-4-yl)ethyl)amino)pyrimidin-4-yl)-4-(fluoromethyl)oxazolidin-2-one |

TABLE 39-continued

The compounds in Table 39 are prepared following chemistry similar to that described for Examples 1-465 or as outlined in the Schemes given above.

| Example | Name |
|---|---|
| 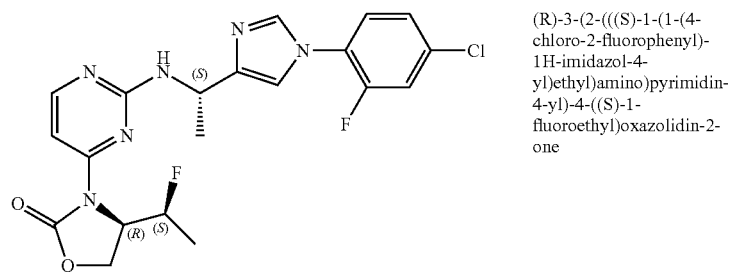 | (R)-3-(2-(((S)-1-(1-(4-chloro-2-fluorophenyl)-1H-imidazol-4-yl)ethyl)amino)pyrimidin-4-yl)-4-((S)-1-fluoroethyl)oxazolidin-2-one |
| 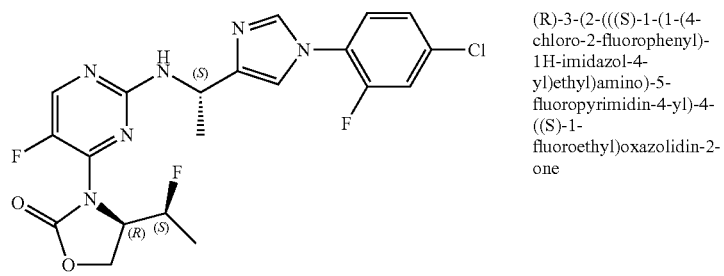 | (R)-3-(2-(((S)-1-(1-(4-chloro-2-fluorophenyl)-1H-imidazol-4-yl)ethyl)amino)-5-fluoropyrimidin-4-yl)-4-((S)-1-fluoroethyl)oxazolidin-2-one |
| 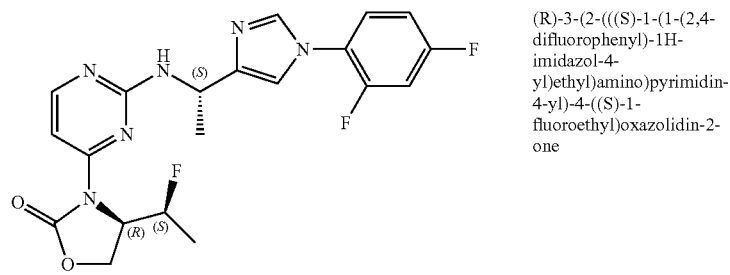 | (R)-3-(2-(((S)-1-(1-(2,4-difluorophenyl)-1H-imidazol-4-yl)ethyl)amino)pyrimidin-4-yl)-4-((S)-1-fluoroethyl)oxazolidin-2-one |
| 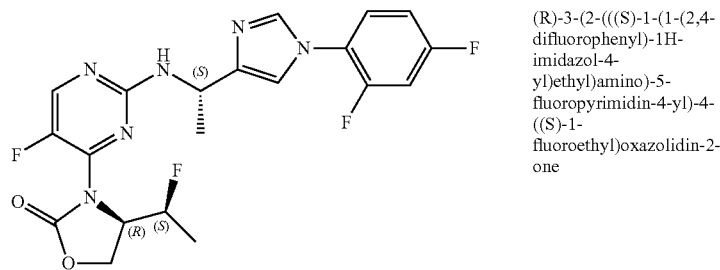 | (R)-3-(2-(((S)-1-(1-(2,4-difluorophenyl)-1H-imidazol-4-yl)ethyl)amino)-5-fluoropyrimidin-4-yl)-4-((S)-1-fluoroethyl)oxazolidin-2-one |
| 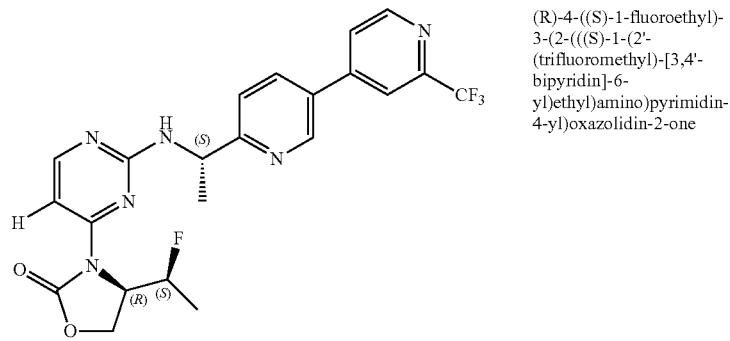 | (R)-4-((S)-1-fluoroethyl)-3-(2-(((S)-1-(2'-(trifluoromethyl)-[3,4'-bipyridin]-6-yl)ethyl)amino)pyrimidin-4-yl)oxazolidin-2-one |

TABLE 39-continued

The compounds in Table 39 are prepared following chemistry similar to that described for Examples 1-465 or as outlined in the Schemes given above.

| Example | | Name |
|---|---|---|
| | 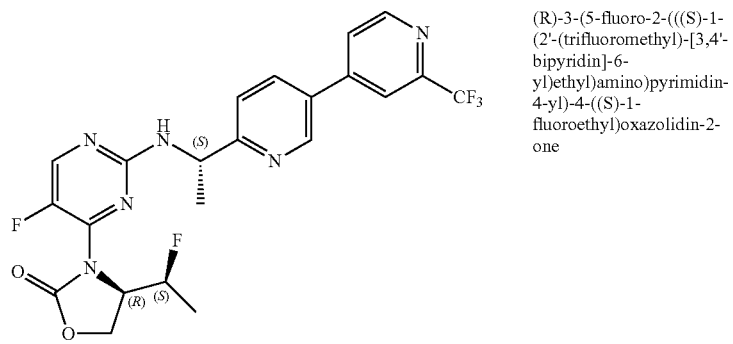 | (R)-3-(5-fluoro-2-(((S)-1-(2'-(trifluoromethyl)-[3,4'-bipyridin]-6-yl)ethyl)amino)pyrimidin-4-yl)-4-((S)-1-fluoroethyl)oxazolidin-2-one |
| | 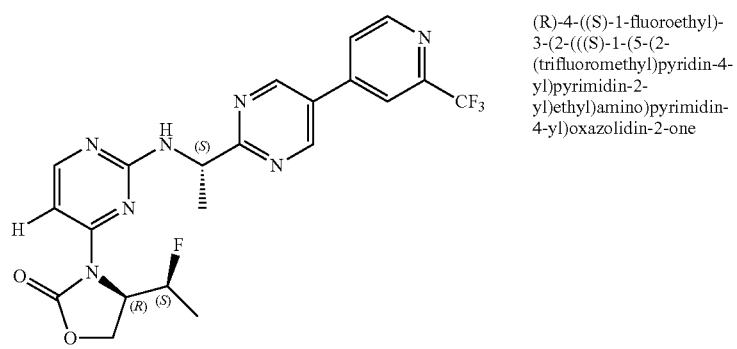 | (R)-4-((S)-1-fluoroethyl)-3-(2-(((S)-1-(5-(2-(trifluoromethyl)pyridin-4-yl)pyrimidin-2-yl)ethyl)amino)pyrimidin-4-yl)oxazolidin-2-one |
| | 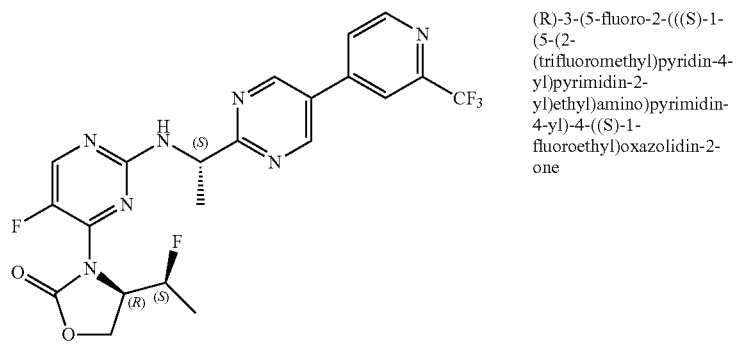 | (R)-3-(5-fluoro-2-(((S)-1-(5-(2-(trifluoromethyl)pyridin-4-yl)pyrimidin-2-yl)ethyl)amino)pyrimidin-4-yl)-4-((S)-1-fluoroethyl)oxazolidin-2-one |
| | 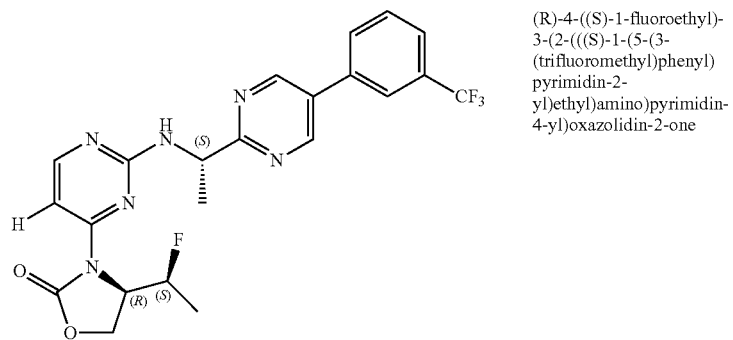 | (R)-4-((S)-1-fluoroethyl)-3-(2-(((S)-1-(5-(3-(trifluoromethyl)phenyl)pyrimidin-2-yl)ethyl)amino)pyrimidin-4-yl)oxazolidin-2-one |

TABLE 39-continued

The compounds in Table 39 are prepared following chemistry similar to that described for Examples 1-465 or as outlined in the Schemes given above.

| Example | | Name |
|---|---|---|
| | 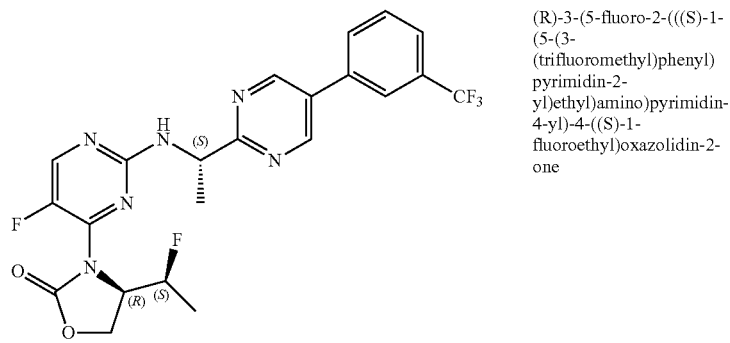 | (R)-3-(5-fluoro-2-(((S)-1-(5-(3-(trifluoromethyl)phenyl)pyrimidin-2-yl)ethyl)amino)pyrimidin-4-yl)-4-((S)-1-fluoroethyl)oxazolidin-2-one |
| | 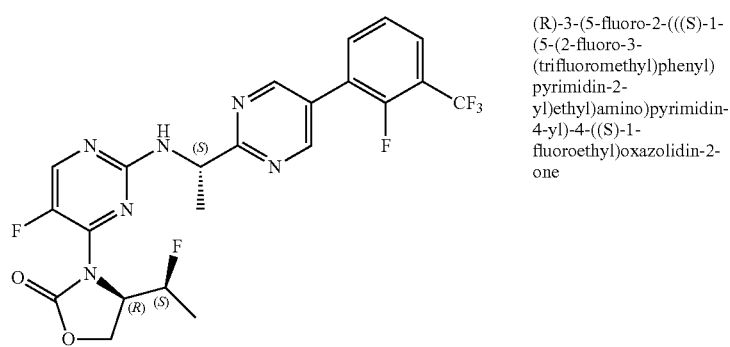 | (R)-3-(5-fluoro-2-(((S)-1-(5-(2-fluoro-3-(trifluoromethyl)phenyl)pyrimidin-2-yl)ethyl)amino)pyrimidin-4-yl)-4-((S)-1-fluoroethyl)oxazolidin-2-one |
| | 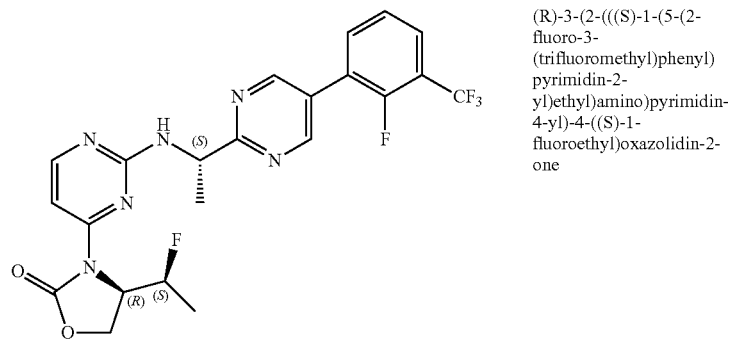 | (R)-3-(2-(((S)-1-(5-(2-fluoro-3-(trifluoromethyl)phenyl)pyrimidin-2-yl)ethyl)amino)pyrimidin-4-yl)-4-((S)-1-fluoroethyl)oxazolidin-2-one |
| | 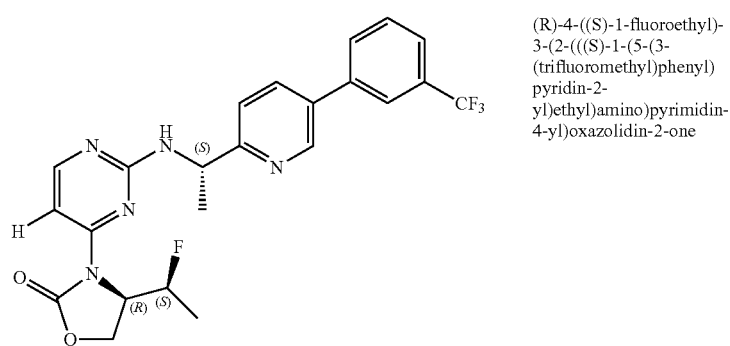 | (R)-4-((S)-1-fluoroethyl)-3-(2-(((S)-1-(5-(3-(trifluoromethyl)phenyl)pyridin-2-yl)ethyl)amino)pyrimidin-4-yl)oxazolidin-2-one |

TABLE 39-continued

The compounds in Table 39 are prepared following chemistry similar to that described for Examples 1-465 or as outlined in the Schemes given above.

| Example | | Name |
|---|---|---|
| | (structure) | (R)-3-(5-fluoro-2-(((S)-1-(5-(3-(trifluoromethyl)phenyl)pyridin-2-yl)ethyl)amino)pyrimidin-4-yl)-4-((S)-1-fluoroethyl)oxazolidin-2-one |
| | (structure) | (R)-4-((S)-1-fluoroethyl)-3-(2-(((S)-1-(5-(4-(trifluoromethyl)phenyl)pyrimidin-2-yl)ethyl)amino)pyrimidin-4-yl)oxazolidin-2-one |
| | (structure) | (R)-3-(5-fluoro-2-(((S)-1-(5-(4-(trifluoromethyl)phenyl)pyrimidin-2-yl)ethyl)amino)pyrimidin-4-yl)-4-((S)-1-fluoroethyl)oxazolidin-2-one |
| | (structure) | (R)-3-(2-(((S)-1-(5-(4-chloro-3-(trifluoromethyl)phenyl)pyrimidin-2-yl)ethyl)amino)pyrimidin-4-yl)-4-((S)-1-fluoroethyl)oxazolidin-2-one |

TABLE 39-continued

The compounds in Table 39 are prepared following chemistry similar to that described for Examples 1-465 or as outlined in the Schemes given above.

| Example | | Name |
|---|---|---|
| | 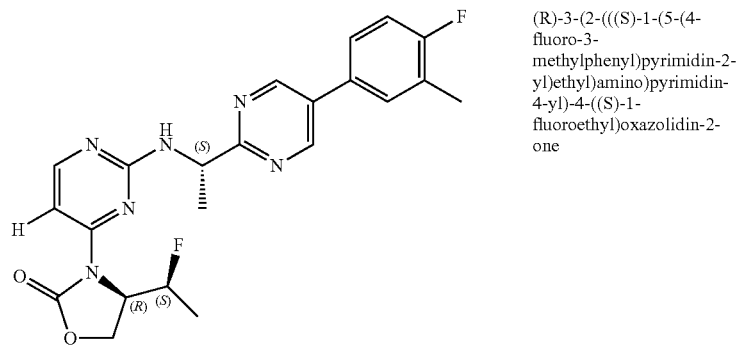 | (R)-3-(2-(((S)-1-(5-(4-fluoro-3-methylphenyl)pyrimidin-2-yl)ethyl)amino)pyrimidin-4-yl)-4-((S)-1-fluoroethyl)oxazolidin-2-one |
| | 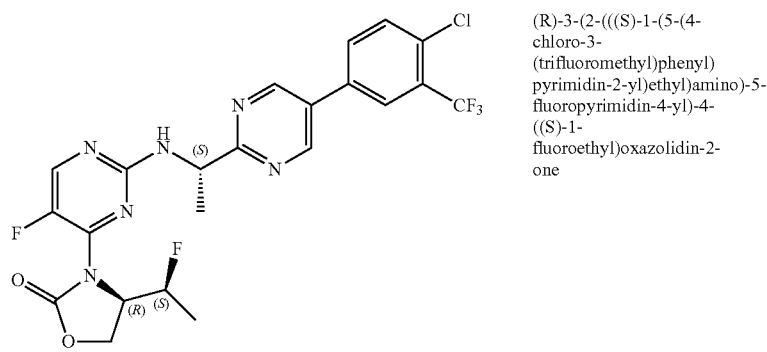 | (R)-3-(2-(((S)-1-(5-(4-chloro-3-(trifluoromethyl)phenyl)pyrimidin-2-yl)ethyl)amino)-5-fluoropyrimidin-4-yl)-4-((S)-1-fluoroethyl)oxazolidin-2-one |
| | 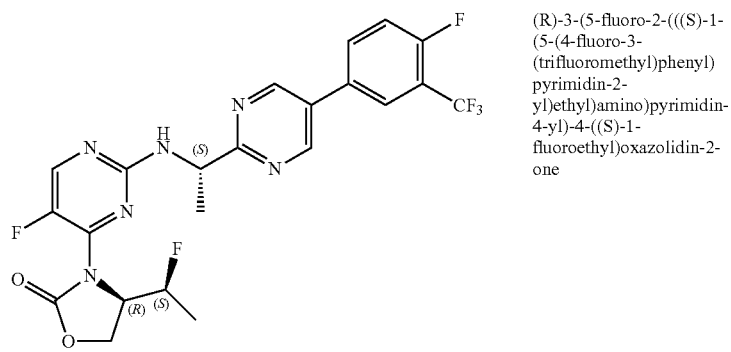 | (R)-3-(5-fluoro-2-(((S)-1-(5-(4-fluoro-3-(trifluoromethyl)phenyl)pyrimidin-2-yl)ethyl)amino)pyrimidin-4-yl)-4-((S)-1-fluoroethyl)oxazolidin-2-one |
| | 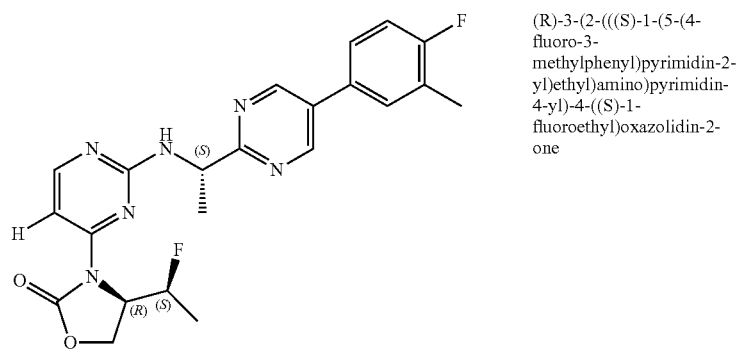 | (R)-3-(2-(((S)-1-(5-(4-fluoro-3-methylphenyl)pyrimidin-2-yl)ethyl)amino)pyrimidin-4-yl)-4-((S)-1-fluoroethyl)oxazolidin-2-one |

TABLE 39-continued

The compounds in Table 39 are prepared following chemistry similar to that described for Examples 1-465 or as outlined in the Schemes given above.

| Example | Name |
|---|---|
|  | (R)-3-(5-fluoro-2-(((S)-1-(5-(4-fluoro-3-methylphenyl)pyrimidin-2-yl)ethyl)amino)pyrimidin-4-yl)-4-((S)-1-fluoroethyl)oxazolidin-2-one |
|  | (R)-3-(2-(((S)-1-(5-(4-chloro-3-fluorophenyl)-4-methylpyrimidin-2-yl)ethyl)amino)pyrimidin-4-yl)-4-((S)-1-fluoroethyl)oxazolidin-2-one |
|  | (R)-3-(2-(((S)-1-(5-(4-chloro-3-fluorophenyl)-4-methylpyrimidin-2-yl)ethyl)amino)-5-fluoropyrimidin-4-yl)-4-((S)-1-fluoroethyl)oxazolidin-2-one |
|  | (R)-3-(2-(((S)-1-(5-(3-chlorophenyl)-4-methylpyrimidin-2-yl)ethyl)amino)pyrimidin-4-yl)-4-((S)-1-fluoroethyl)oxazolidin-2-one |

TABLE 39-continued

The compounds in Table 39 are prepared following chemistry similar to that described for Examples 1-465 or as outlined in the Schemes given above.

| Example | | Name |
|---|---|---|
| | 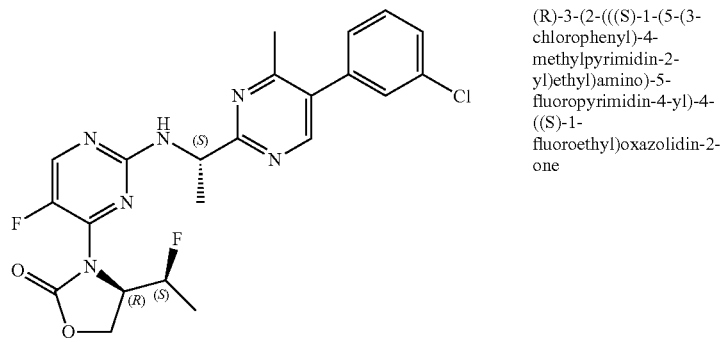 | (R)-3-(2-(((S)-1-(5-(3-chlorophenyl)-4-methylpyrimidin-2-yl)ethyl)amino)-5-fluoropyrimidin-4-yl)-4-((S)-1-fluoroethyl)oxazolidin-2-one |
| | 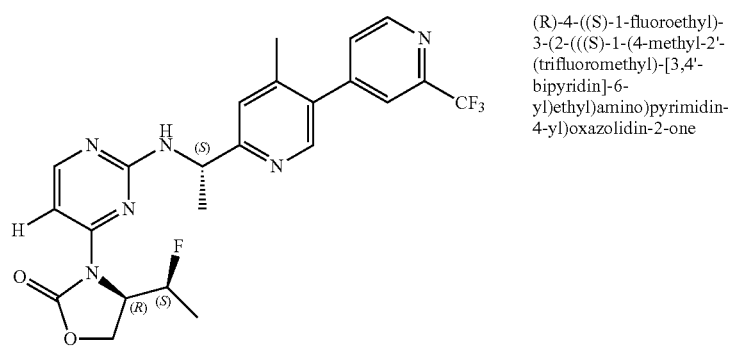 | (R)-4-((S)-1-fluoroethyl)-3-(2-(((S)-1-(4-methyl-2'-(trifluoromethyl)-[3,4'-bipyridin]-6-yl)ethyl)amino)pyrimidin-4-yl)oxazolidin-2-one |
| | 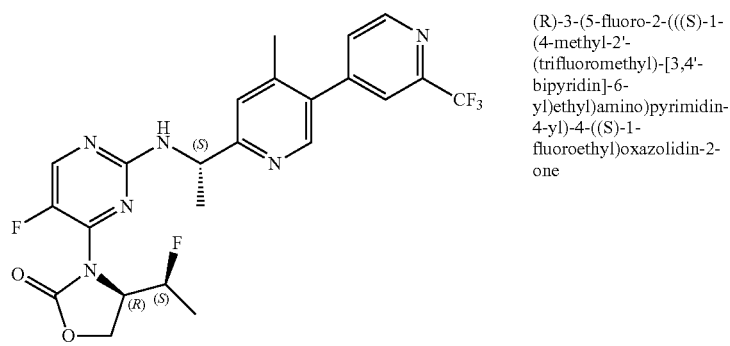 | (R)-3-(5-fluoro-2-(((S)-1-(4-methyl-2'-(trifluoromethyl)-[3,4'-bipyridin]-6-yl)ethyl)amino)pyrimidin-4-yl)-4-((S)-1-fluoroethyl)oxazolidin-2-one |
| | 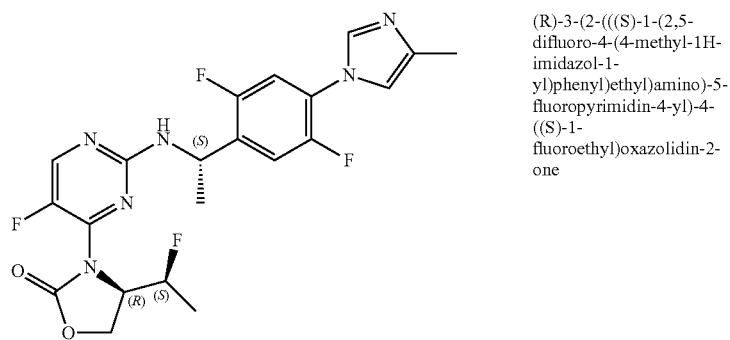 | (R)-3-(2-(((S)-1-(2,5-difluoro-4-(4-methyl-1H-imidazol-1-yl)phenyl)ethyl)amino)-5-fluoropyrimidin-4-yl)-4-((S)-1-fluoroethyl)oxazolidin-2-one |

TABLE 39-continued

The compounds in Table 39 are prepared following chemistry similar to that described for Examples 1-465 or as outlined in the Schemes given above.

| Example | Name |
|---|---|
| 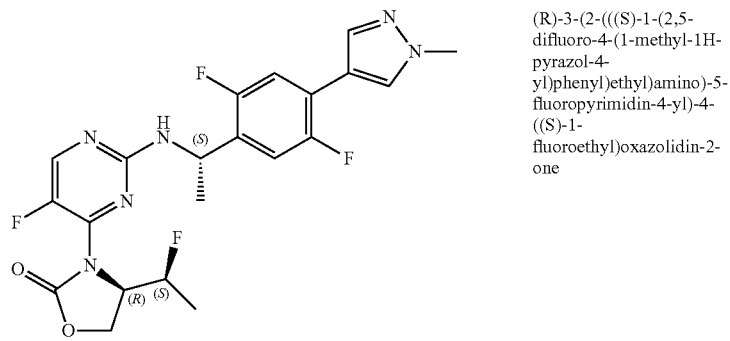 | (R)-3-(2-(((S)-1-(2,5-difluoro-4-(1-methyl-1H-pyrazol-4-yl)phenyl)ethyl)amino)-5-fluoropyrimidin-4-yl)-4-((S)-1-fluoroethyl)oxazolidin-2-one |
| 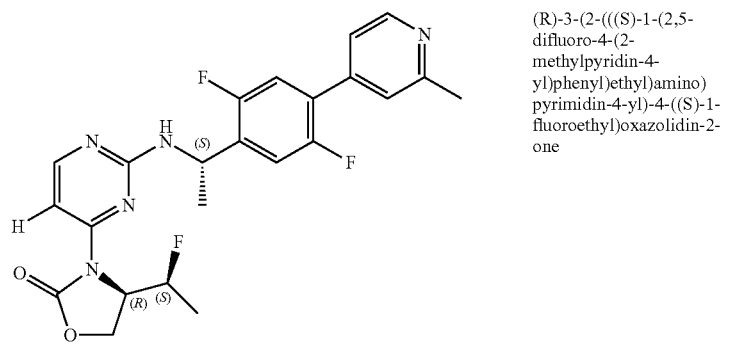 | (R)-3-(2-(((S)-1-(2,5-difluoro-4-(2-methylpyridin-4-yl)phenyl)ethyl)amino)pyrimidin-4-yl)-4-((S)-1-fluoroethyl)oxazolidin-2-one |
| 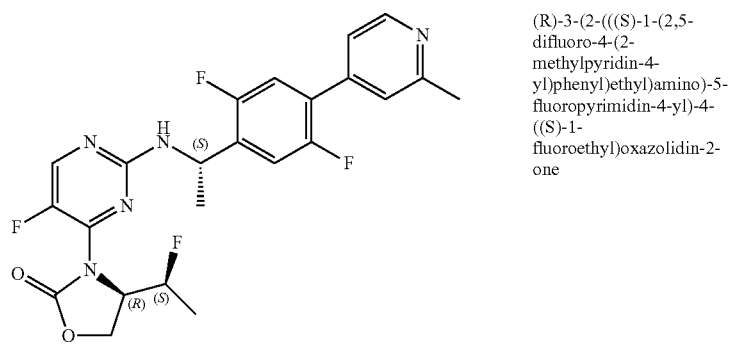 | (R)-3-(2-(((S)-1-(2,5-difluoro-4-(2-methylpyridin-4-yl)phenyl)ethyl)amino)-5-fluoropyrimidin-4-yl)-4-((S)-1-fluoroethyl)oxazolidin-2-one |
| 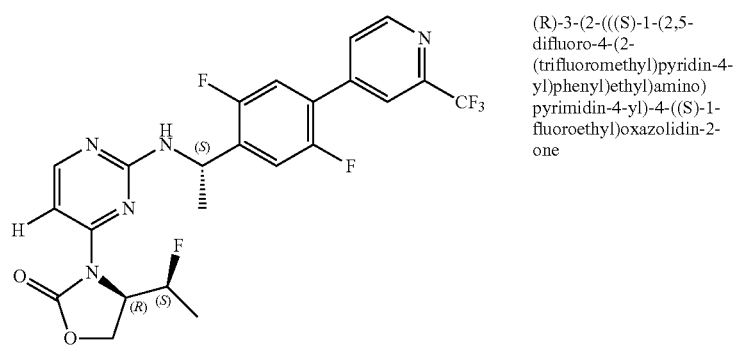 | (R)-3-(2-(((S)-1-(2,5-difluoro-4-(2-(trifluoromethyl)pyridin-4-yl)phenyl)ethyl)amino)pyrimidin-4-yl)-4-((S)-1-fluoroethyl)oxazolidin-2-one |

TABLE 39-continued

The compounds in Table 39 are prepared following chemistry similar to that described for Examples 1-465 or as outlined in the Schemes given above.

| Example | Name |
|---|---|
| 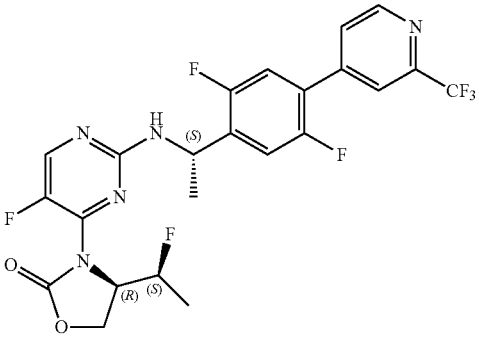 | (R)-3-(2-(((S)-1-(2,5-difluoro-4-(2-(trifluoromethyl)pyridin-4-yl)phenyl)ethyl)amino)-5-fluoropyrimidin-4-yl)-4-((S)-1-fluoroethyl)oxazolidin-2-one |

Biological Assays and Data

Mutant IDH1 Biochemical Assay: LC-MS Detection of 2-HG.

Mutant IDH1 R132H catalytic activity was monitored using the quantitative liquid chromatography/mass spectrometry (LC-MS) detection of 2-HG, a product of the NADPH-dependent alpha-KG reduction reaction.

More specifically, the biochemical reactions were performed at room temperature in 384-well Greiner flat-bottom plates (Costar, Cat. No. 781201) using a final reaction volume of 30 µL and the following assay buffer conditions: 50 mM HEPES pH 7.4, 10 mM $MgCl_2$, 50 mM KCl, 1 mM DTT, 0.02% BSA, 5 uM NADPH and 100 uM alpha-KG.

The final reaction mixture contained 3.3% DMSO and inhibitors with concentrations ranging 0.02-50 µM. The IDH1 enzyme was used at a final concentration of 0.25 nM. Following 45 minutes incubation, the reaction mixtures were quenched by the addition of 10 µL of 16% formic acid containing 800 nM of 5-carbon labeled $^{13}C$-2-HG). The protein was then precipitated by the addition of 2.5 volumes of acetonitrile followed by centrifugation (3000×g, 20 minutes). The concentration of 2-HG in the resulting supernatants was measured by LC-MS (see below).

LC-MS method. Reaction mixture supernatants were submitted to chromatographic separation on a BiobasicAX column (2.1 mm×20 mm, 5 µm particle, Thermo Scientific Inc.). The chromatographic mobile phases were A) 25 mM ammonium biocarbonate and B) acetonitrile (0.1% ammonium hydroxide). Nicotinamide was eluted at 1 ml/min using a 85-5% B gradient over 0.9 minutes (Agilent 1200SL LC system, Thermofisher LX-4 autosampler) and analyzed by multiple reaction monitoring (MRM) on a API4000 QTrap mass spectrometer (ABSciex, Framingham, Mass.) in the positive electrospray ionization (ESI+) mode. The mass transition for 2-HG and $^{13}C$-2-HG were 147→129 and 152→134, respectively. The relative responses (2-HG/$^{13}C$-2-HG) were measured at varied inhibitor concentrations and used to calculate inhibitory IC50 values (normalized IC50 regression curves).

R132 Protein Expression and Purification.

IDH1 R132H was cloned into the pET47b vector using the restriction sites XmaI/XhoI which yields an in frame, N-terminal $His_6$ site cleavable with Prescission protease. This plasmid was transformed into Rosetta™ 2 (DE3) (Novagen) cells. In shake flasks, 8 L of cells were grown in Terrific Broth (Teknova) (plus kanamycin 50 µg/mL and chloramphenicol 34 µg/mL) at 37° C. to an $OD_{600}$ of 0.8 and protein expression was induced by addition of IPTG to a concentration of 0.20 mM. The cells were subsequently grown for 18 hours at 18° C.

$His_6$-IDH1 (R132H) Uncut protein
(SEQ ID NO: 1)
MAHHHHHHSAALEVLFQGPGMSKKISGGSVVEMQGDEMTRIIWELIKEKL

IFPYVELDLHSYDLGIENRDATNDQVTKDAAEAIKKHNVGVKCATITPDE

KRVEEFKLKQMWKSPNGTIRNILGGTVFREAIICKNIPRLVSGVVVKPII

IGHHAYGDQYRATDFVVPGPGKVEITYTPSDGTQKVTYLVHNFEEGGGVA

MGMYNQDKSIEDFAHSSFQMALSKGWPLYLSTKNTILKKYDGRFKDIFQE

IYDKQYKSQFEAQKIVVYEHRLIDDMVAQAMKSEGGFIWACKNYDGDVQS

DSVAQGYGSLGMMTSVLVCPDGKTVEAEAAHGTVTRHYRMYQKGQETSTN

PIASIFAVVTRGLAHRAKLDNNKELAFFANALEEVSIETIEAGFMTKDLA

ACIKGLPNVQRSDYLNTFEFMDKLGENLKIKLAQAKL(stop)

IDH1 (R132H) Prescission Cut Protein (N-term gpg is cloning artifact)
(SEQ ID NO: 2)
GPGMSKKISGGSVVEMQGDEMTRIIWELIKEKLIFPYVELDLHSYDLGIE

NRDATNDQVTKDAAEAIKKHNVGVKCATITPDEKRVEEFKLKQMWKSPNG

TIRNILGGTVFREAIICKNIPRLVSGVVVKPIIIGHHAYGDQYRATDFVV

PGPGKVEITYTPSDGTQKVTYLVHNFEEGGGVAMGMYNQDKSIEDFAHSS

FQMALSKGWPLYLSTKNTILKKYDGRFKDIFQEIYDKQYKSQFEAQKIVV

YEHRLIDDMVAQAMKSEGGFIWACKNYDGDVQSDSVAQGYGSLGMMTSVL

VCPDGKTVEAEAAHGTVTRHYRMYQKGQETSTNPIASIFAVVTRGLAHRA

KLDNNKELAFFANALEEVSIETIEAGFMTKDLAACIKGLPNVQRSDYLNT

FEFMDKLGENLKIKLAQAKL (stop)

Purification

The cells were homogenized in Lysis Buffer with protease inhibitors (cOmplete EDTA-free protease inhibitor tablets (Roche), 1 tablet per 50 mL of buffer), DNAse, and to 200 µM PMSF and lysed in a Microfluidizer. After lysis, Triton X-100 was added to 0.1% and stirred at 4° C. for 30 minutes.

The cleared lysate was loaded onto 2×5 mL HisTrap FF crude columns (GE), washed extensively with Lysis Buffer until the $A_{280}$ stabilized and eluted with Ni Elution Buffer. Peak eluted fractions were concentrated to 30 mL, EDTA was added to 1 mM and GST-Prescission protease was added to 3 U/100 μg of protein. The sample was dialyzed against 2 L Dialysis Buffer I (MWCO 50 kDa) for 6 hours at 4° C. then dialyzed against 2 L of Dialysis Buffer II for at least 6 more hours. GST-Prescission cleaved sample was rocked with Glutathione Agarose Beads, spun down and then the supernatant was loaded through a 5 mL HisTrap HP column and the flow through was collected.

Flow through was then diluted with ice cold 20 mM Tris pH 7.4 and 1 mM TCEP until the conductivity dropped to less than 5 mS/cm (a roughly three fold dilution). This sample was then flowed through a HiTrap Q column and the flow through was concentrated to 10 mL and loaded onto an equilibrated 26/60 Superdex 200 column using SEC Buffer as the mobile phase. Peak fractions were collected, concentrated and aliquoted.

Lysis Buffer:

50 mM Tris pH=7.4, 500 mM NaCl, 20 mM Imidazole, and 1 mM TCEP

Ni Elution Buffer:

50 mM Tris pH=7.4, 150 mM NaCl, 200 mM Imidazole, and 1 mM TCEP

Dialysis Buffer I:

20 mM Tris pH=7.4, 150 mM NaCl, 1 mM TCEP, and 50 mM Imidazole Dialysis Buffer II: 20 mM Tris pH=7.4, 150 mM NaCl, and 1 mM TCEP SEC Buffer:

20 mM Tris pH=7.4, 150 mM NaCl, and 1 mM TCEP

The results of the mutant IDH1 biochemical assay (mIDH R132H) are given in Table 40. Some of the examples were run in the assay multiple times and therefore the $IC_{50}$ values are expressed as a range of activity.

Fluorescence Biochemical Assay

The IDH1 (R132H) mutant catalyzes the reduced form of NADP+(NADPH) and α-ketoglutarate (α-KG) to form nicotinamide adenine dinucleotide phosphate (NADP+) and R (−)-2-hydroxyglutarate (2HG). The reaction can be monitored kinetically by following the oxidation of NADPH to NADP+ which is measured using fluorescence, excitation at 355 nm and emission at 530 nm. Reactions were monitored using the Perkin-Elmer Envision, Model 2101. More specifically, the biochemical reactions were performed at room temperature in 384-well Greiner flat-bottom plates (Cat. No. 781076) using a final reaction volume of 20 μL and the following assay buffer conditions: 50 mM HEPES pH 7.5, 10 mM $MgCl_2$, 1 mM DTT, 0.02% BSA, 0.02% Tween-20, 10 μM NADPH and 100 μM α-KG. The final reaction mixture contained 2.5% DMSO and test compounds with concentrations ranging 0.0000008-25 μM. The IDH1 (R132H) enzyme was used at a final concentration of 10 nM. Curve fitting for dose response IC50 determinations was done using a 4-parameter logistic model: $y=min+((max-min)/1+(x/IC_{50})^{slope})$ The results of the fluorescence biochemical assay (mIDH R132H) are given in Table 40. Some of the examples were run in the assay multiple times and therefore the $IC_{50}$ values are expressed as a range of activity.

TABLE 40

Results of the LC-MS and fluorescence biochemical assays.

| Example Number | Fluorescence biochemical assay IC50 (μM) | LC-MS biochemical assay $IC_{50}$ (μM) |
|---|---|---|
| 1 | 1.410 | Not determined |
| 2 | 0.406 to 0.412 | Not determined |
| 3 | Not determined | Not determined |
| 4 | 1.420 | 2.010 |
| 5 | 17.800 | 3.684 |
| 6 | 1.270 | 1.185 |
| 7 | 2.950 | 1.609 to 4.527 |
| 8 | 2.040 | 0.314 to 2.79 |
| 9 | 2.200 | 3.019 |
| 10 | 11.700 | 1.710 |
| 11 | 3.050 | 2.453 |
| 12 | 3.270 | 0.892 |
| 13 | 2.190 | >5 |
| 14 | 0.405 | 0.813 |
| 15 | Not determined | Not determined |
| 16 | Not determined | Not determined |
| 17 | Not determined | Not determined |
| 18 | Not determined | Not determined |
| 19 | Not determined | Not determined |
| 20 | Not determined | Not determined |
| 21 | Not determined | Not determined |
| 22 | Not determined | Not determined |
| 23 | Not determined | Not determined |
| 24 | Not determined | Not determined |
| 25 | Not determined | Not determined |
| 26 | 3.350 | Not determined |
| 27 | 2.800 | Not determined |
| 28 | Not determined | 0.005 |
| 29 | Not determined | 0.027 |
| 30 | 1.090 | 0.472 |
| 31 | 0.627 | 0.757 |
| 32 | 0.016 | 0.010 |
| 33 | 3.660 | 2.085 |
| 34 | 0.889 to 0.893 | 0.590 |
| 35 | 0.033 | 0.055 |
| 36 | 1.410 | 3.497 |
| 37 | 2.690 | 3.745 |
| 38 | 0.055 | 0.056 |
| 39 | 0.202 | 0.211 |
| 40 | 0.175 | 0.370 |
| 41 | 0.253 | 0.179 |
| 42 | >25 | 1.557 |
| 43 | Not determined | 0.045 |
| 44 | 0.029 | 0.033 to 0.034 |
| 45 | 1.000 | 1.237 |
| 46 | 2.530 | 1.930 |
| 47 | 0.033 | 0.036 |
| 48 | 0.463 | 0.775 |
| 49 | Not determined | 0.094 |
| 50 | 0.037 | 0.043 |
| 51 | 0.013 | 0.016 |
| 52 | 0.131 to 0.289 | 0.194 |
| 53 | 0.042 to 0.051 | 0.059 |
| 54 | 0.116 | 0.119 |
| 55 | 0.267 to 0.291 | 0.323 |
| 56 | 2.920 | 1.549 |
| 57 | 1.270 | 1.131 |
| 58 | 0.027 | 0.029 |
| 59 | 0.079 to 0.085 | 0.033 |
| 60 | 1.100 | 0.201 |
| 61 | 0.313 | 0.156 |
| 62 | 0.53 to 0.599 | 0.087 |
| 63 | <0.0159 | 0.005 |
| 64 | <0.0159 | 0.008 |
| 65 | 0.797 | 0.582 |
| 66 | 0.061 to 0.082 | 0.066 |
| 67 | 1.010 | 1.437 |
| 68 | 0.050 | 0.112 |
| 69 | 0.639 | >5 |
| 70 | 0.073 | 0.080 |
| 71 | >25 | >5 |
| 72 | Not determined | 12.152 |
| 73 | 0.181 | 0.571 |

TABLE 40-continued

Results of the LC-MS and fluorescence biochemical assays.

| Example Number | Fluorescence biochemical assay IC50 (μM) | LC-MS biochemical assay $IC_{50}$ (μM) |
|---|---|---|
| 74 | Not determined | >5 |
| 75 | Not determined | Not determined |
| 76 | Not determined | 0.546 to 0.568 |
| 77 | Not determined | 0.911 |
| 78 | 1.630 | 2.560 |
| 79 | 5.310 | >5 |
| 80 | 0.037 | 0.031 |
| 81 | Not determined | 1.089 |
| 82 | 0.019 | 0.022 |
| 83 | 0.662 to 0.683 | 0.489 |
| 84 | 0.012 to 0.083 | 0.013 |
| 85 | 1.930 | 0.524 |
| 86 | 0.032 to 0.049 | 0.019 |
| 87 | 6.690 | >5 |
| 88 | 0.048 to 0.058 | 0.034 |
| 89 | 1.360 | 1.776 |
| 90 | 0.034 | 0.013 |
| 91 | 0.274 | Not determined |
| 92 | 2.74 to 8.91 | 2.301 to 3.074 |
| 93 | 0.043 to 0.383 | 0.029 to 0.134 |
| 94 | 14.900 | 25.642 |
| 95 | 1.530 | 1.113 |
| 96 | Not determined | >50 |
| 97 | 0.972 | 0.984 |
| 98 | 0.351 | 0.487 |
| 99 | 9.790 | 3.057 |
| 100 | Not determined | 18.066 |
| 101 | Not determined | 0.572 |
| 102 | Not determined | >50 |
| 103 | Not determined | 6.354 |
| 104 | >25 | >50 |
| 105 | 2.430 | 1.720 |
| 106 | >25 | 32.926 |
| 107 | 1.220 | 1.416 |
| 108 | 11.700 | 5.902 |
| 109 | 0.0486 to 0.193 | 0.136 to 0.167 |
| 110 | >25 | 23.402 |
| 111 | 2.780 | 3.511 |
| 112 | >25 | >50 |
| 113 | >25 | 42.325 |
| 114 | >25 | >50 |
| 115 | 7.890 | 3.760 |
| 116 | >25 | >50 |
| 117 | 1.410 | 2.010 |
| 118 | 3.560 | 1.539 |
| 119 | 0.045 | 0.029 to 0.042 |
| 120 | Not determined | 2.668 |
| 121 | 0.182 | 0.045 to 0.081 |
| 122 | 0.370 | 0.268 |
| 123 | 0.017 to 0.044 | 0.024 to 0.029 |
| 124 | 18.8 | >25 |
| 125 | 0.158 | 0.206 |
| 126 | 0.274 | 0.216 |
| 127 | 0.032 | 0.025 to 0.033 |
| 128 | 0.050 | 0.071 |
| 129 | 1.800 | 2.814 |
| 130 | 1.510 | 2.999 |
| 131 | 0.056 | 0.153 to 0.171 |
| 132 | 0.956 | 1.421 |
| 133 | 0.007 | 0.004 to 0.008 |
| 134 | 1.460 | 2.360 |
| 135 | 0.011 | 0.016 |
| 136 | 11.300 | >5 |
| 137 | 1.190 | 0.294 |
| 138 | 0.012 | 0.024 |
| 139 | 0.260 | 0.146 |
| 140 | 10.600 | 4.032 |
| 141 | 0.660 | 0.116 |
| 142 | >25 | 3.977 |
| 143 | 0.756 | 0.572 |
| 144 | 1.670 | 1.685 |
| 145 | 0.020 | 0.036 |
| 146 | Not determined | >5 |
| 147 | Not determined | 0.368 |
| 148 | 9.590 | >5 |
| 149 | 0.194 | 0.168 to 0.216 |
| 150 | Not determined | >5 |
| 151 | 0.043 to 0.044 | 0.012 |
| 152 | 5.990 | >5 |
| 153 | 0.329 | 0.288 |
| 154 | 1.790 | 3.839 |
| 155 | 0.756 | 0.857 |
| 156 | 2.700 | 1.145 |
| 157 | 0.033 | 0.032 |
| 158 | Not determined | 4.374 |
| 159 | <0.0159 | 0.006 |
| 160 | 1.230 | 1.115 |
| 161 | 0.158 | 0.305 |
| 162 | 3.620 | >5 |
| 163 | 0.079 | 0.152 |
| 164 | 4.680 | >5 |
| 165 | 0.152 | 0.304 |
| 166 | 0.871 | 0.243 |
| 167 | 0.131 | 0.067 to 0.076 |
| 168 | 3.200 | >5 |
| 169 | 0.038 | 0.044 to 0.086 |
| 170 | 3.690 | 1.884 |
| 171 | 0.056 | 0.031 to 0.052 |
| 172 | Not determined | 3.407 |
| 173 | 0.051 to 0.078 | 0.040 |
| 174 | 0.230 | 0.238 |
| 175 | 0.298 to 0.538 | 0.049 |
| 176 | 12.400 | 4.591 |
| 177 | 1.230 | 1.587 |
| 178 | 0.364 | 0.077 |
| 179 | 0.007 | 0.005 to 0.006 |
| 180 | >25 | 2.728 |
| 181 | 0.138 | 0.122 |
| 182 | 1.920 | 1.378 |
| 183 | 0.128 | 0.243 |
| 184 | 0.502 | 0.757 |
| 185 | 0.023 | 0.021 |
| 186 | 2.32 to 2.58 | 2.583 |
| 187 | 0.022 | 0.010 |
| 188 | 8.380 | |
| 189 | 0.064 | 0.156 |
| 190 | 0.037 | 0.014 |
| 191 | >50 | |
| 192 | Not determined | 0.010 |
| 193 | Not determined | 0.358 |
| 194 | 0.051 | Not determined |
| 195 | 2.930 | Not determined |
| 196 | <0.0159 | 0.005 |
| 197 | 2.010 | Not determined |
| 198 | 0.020 | Not determined |
| 199 | 1.200 | Not determined |
| 200 | 0.043 | 0.005 |
| 201 | 0.344 | Not determined |
| 202 | 1.680 | 1.093 |
| 203 | 0.016 | 0.008 |
| 204 | 0.026 to 0.059 | 0.02 to 0.05 |
| 205 | 2.700 | 2.052 |
| 206 | 0.03 to 0.051 | 0.022 |
| 207 as TFA salt | 0.011 | <0.0228624 |
| 208 as TFA salt | 0.101 | Not determined |
| 209 as TFA salt | 0.087 | 0.164 |
| 210 as TFA salt | 0.153 | 0.374 |
| 211 as TFA salt | 0.496 | 2.628 |
| 212 as TFA salt | 0.035 | 0.057 |
| 213 as TFA salt | 0.011 | <0.0228624 |
| 213 | 0.019 | 0.018 |
| 214 as TFA salt | 0.046 | 0.107 |
| 215 as TFA salt | 0.055 | 0.106 to 0.138 |
| 216 as TFA salt | 0.004 | 0.011 |
| 217 as TFA salt | 0.012 to 0.033 | 0.019 to 0.025 |
| 218 as TFA salt | 0.019 | 0.018 to 0.044 |

TABLE 40-continued

Results of the LC-MS and fluorescence biochemical assays.

| Example Number | Fluorescence biochemical assay IC50 (μM) | LC-MS biochemical assay IC$_{50}$ (μM) |
|---|---|---|
| 219 as TFA salt | 0.014 | 0.015 |
| 220 as TFA salt | 0.014 | 0.017 |
| 221 | 0.061 | 0.046 |
| 222 as TFA salt | 0.047 | 0.053 |
| 223 as TFA salt | 0.023 to 0.046 | 0.014 |
| 224 as TFA salt | 0.029 | 0.027 |
| 224 | <0.016 | <0.022 |
| 225 as TFA salt | 0.037 | 0.063 |
| 225 | 0.028 to 0.042 | 0.038 to 0.043 |
| 226 as TFA salt | 0.009 | Not determined |
| 227 as TFA salt | 0.015 | 0.22 to 0.023 |
| 228 as TFA salt | 0.019 | 0.045 |
| 228 | 0.018 | 0.014 to 0.035 |
| 229 as TFA salt | 0.054 | 0.081 |
| 230 as TFA salt | >25 | Not determined |
| 231 as TFA salt | >25 | Not determined |
| 232 as TFA salt | 0.024 | 0.026 |
| 233 as TFA salt | 0.377 | Not determined |
| 234 as TFA salt | 0.213 | Not determined |
| 235 as TFA salt | 0.964 | Not determined |
| 236 as TFA salt | 0.024 to 0.042 | 0.023 |
| 237 as TFA salt | 0.02 to 0.025 | 0.013 |
| 238 as TFA salt | 0.017 to 0.024 | 0.012 |
| 239 as TFA salt | 0.049 to 0.058 | 0.020 |
| 240 as TFA salt | 0.142 | 0.067 |
| 241 as TFA salt | 0.114 | 0.157 |
| 242 as TFA salt | 0.042 | 0.053 |
| 243 as TFA salt | 0.141 | 0.172 |
| 244 as TFA salt | 0.300 | Not determined |
| 245 as TFA salt | 0.115 | Not determined |
| 246 as TFA salt | 0.273 | Not determined |
| 247 as TFA salt | 0.079 | Not determined |
| 248 as TFA salt | 0.172 | Not determined |
| 249 as TFA salt | 0.635 | Not determined |
| 250 as TFA salt | 0.025 to 0.047 | Not determined |
| 251 as TFA salt | 0.020 | Not determined |
| 252 as TFA salt | 0.309 | 0.353 to 0.482 |
| 253 as TFA salt | 0.109 | 0.121 |
| 254 as TFA salt | 0.234 | Not determined |
| 255 as TFA salt | 0.450 | Not determined |
| 256 as TFA salt | 0.570 | 0.489 |
| 257 as TFA salt | 1.200 | Not determined |
| 258 as TFA salt | 0.737 | 0.435 |
| 259 as TFA salt | 0.105 | 0.103 |
| 259 | 0.049 | Not determined |
| 260 as TFA salt | 0.040 | 0.039 |
| 261 as TFA salt | 0.064 | 0.089 |
| 262 as TFA salt | 0.088 | 0.167 |
| 263 as TFA salt | 0.014 | Not determined |
| 264 as TFA salt | 0.152 | 0.249 |
| 265 as TFA salt | Not determined | 0.036 |
| 266 as TFA salt | 0.453 | Not determined |
| 267 as TFA salt | 0.048 | 0.095 |
| 268 as TFA salt | 0.338 | Not determined |
| 269 | 0.251 | Not determined |
| 270 as TFA salt | 0.174 | 0.163 |
| 271 as TFA salt | 0.339 | Not determined |
| 272 as TFA salt | 0.117 | Not determined |
| 273 as TFA salt | Not determined | 0.585 |
| 274 as TFA salt | Not determined | 0.265 |
| 275 as TFA salt | Not determined | 0.311 |
| 276 as TFA salt | Not determined | 0.051 |
| 277 as TFA salt | Not determined | 0.086 |
| 278 as TFA salt | 0.174 | 0.163 |
| 279 as TFA salt | 12.700 | Not determined |
| 280 as TFA salt | 3.640 | Not determined |
| 281 as TFA salt | 0.026 | 0.064 |
| 282 as TFA salt | 4.270 | Not determined |
| 283 as TFA salt | 0.068 | 0.248 |
| 284 as TFA salt | 0.266 | Not determined |
| 285 as TFA salt | 0.053 | 0.146 |
| 286 as TFA salt | 0.036 | 0.145 |
| 287 as TFA salt | 2.250 | 46.301 |
| 288 as TFA salt | 0.055 | 0.178 |
| 289 as TFA salt | 2.110 | Not determined |
| 290 as TFA salt | 0.034 | 0.053 |
| 291 | >25 | Not determined |
| 292 | 1.850 | Not determined |
| 293 | >7.91 | Not determined |
| 294 | 0.466 | 0.563 |
| 295 | >25 | Not determined |
| 296 | 0.251 | 0.277 |
| 297 | 2.960 | Not determined |
| 298 | 0.020 | 0.038 |
| 299 | 0.457 | Not determined |
| 300 | 0.010 | 0.017 |
| 301 | 0.021 | 0.033 |
| 302 | 0.045 | Not determined |
| 303 | 0.009 | 0.097 |
| 304 | 0.304 | Not determined |
| 305 | 0.968 | 0.772 to 1.781 |
| 306 | 2.570 | Not determined |
| 307 as TFA salt | 0.029 to 0.049 | 0.038 |
| 308 as TFA salt | 0.049 to 0.097 | 0.073 |
| 309 as TFA salt | 0.003 | 0.004 |
| 309 | 0.003 | 0.004 to 0.005 |
| 310 as TFA salt | 0.072 | 0.128 |
| 311 as TFA salt | 0.518 | 0.445 |
| 312 as TFA salt | 0.066 | 0.144 |
| 313 as TFA salt | 0.020 | 0.019 |
| 314 as TFA salt | 0.106 to 0.121 | 0.157 to 0.182 |
| 315 as TFA salt | 0.161 to 0.514 | 0.35 to 0.463 |
| 316 as TFA salt | 0.123 to 0.29 | 0.261 |
| 317 as TFA salt | 3.7 to 5.63 | Not determined |
| 318 as TFA salt | >25 | Not determined |
| 319 as TFA salt | 0.035 | 0.086 |
| 320 as TFA salt | 0.426 | 0.381 |
| 321 as TFA salt | 0.013 | 0.087 |
| 322 as TFA salt | 0.055 to 0.088 | 0.042 |
| 323 as TFA salt | 0.071 to 0.122 | 0.072 |
| 324 as TFA salt | 0.030 | Not determined |
| 325 as TFA salt | 0.041 | 0.181 |
| 326 as TFA salt | 0.063 | Not determined |
| 327 as TFA salt | 0.236 | 0.562 |
| 328 as TFA salt | 1.800 | Not determined |
| 329 as TFA salt | 0.863 | 0.435 |
| 330 as TFA salt | 0.268 | 0.850 |
| 331 as TFA salt | 0.190 | 0.780 |
| 332 as TFA salt | 1.020 | 0.704 |
| 333 as TFA salt | 0.944 | 0.640 |
| 334 as TFA salt | 0.341 | 0.943 |
| 335 as TFA salt | 0.257 | 0.166 to 0.167 |
| 336 as TFA salt | 0.035 | 0.049 |
| 336 | 0.027 | 0.048 |
| 337 as TFA salt | 0.313 | 0.119 |
| 338 as TFA salt | 0.091 | 0.093 |
| 339 as TFA salt | 0.017 | 0.024 to 0.027 |
| 340 as TFA salt | 0.061 | 0.120 |
| 341 as TFA salt | 7.050 | Not determined |
| 342 as TFA salt | 0.465 | 4.001 |
| 343 as TFA salt | 0.073 | 0.225 |
| 344 as TFA salt | 0.190 | 0.300 |
| 345 as TFA salt | 0.201 | 0.378 |
| 346 as TFA salt | 0.189 | 0.290 |
| 347 as TFA salt | 0.395 | 0.564 |
| 348 as TFA salt | 0.177 | 0.128 |
| 349 as TFA salt | 0.681 | Not determined |
| 350 as TFA salt | 0.413 | Not determined |
| 351 as TFA salt | 0.168 | Not determined |
| 352 as TFA salt | 0.770 | Not determined |
| 353 as TFA salt | 0.103 | 0.117 |
| 354 as TFA salt | 0.051 | 0.286 |
| 355 as TFA salt | 0.152 | 0.381 |
| 356 as TFA salt | 0.120 | 0.132 |
| 357 as TFA salt | 0.358 | 0.439 |
| 358 as TFA salt | 0.123 | Not determined |

TABLE 40-continued

Results of the LC-MS and fluorescence biochemical assays.

| Example Number | Fluorescence biochemical assay IC50 (µM) | LC-MS biochemical assay $IC_{50}$ (µM) |
|---|---|---|
| 359 as TFA salt | 0.171 | 0.193 |
| 360 as TFA salt | 0.056 | 0.119 |
| 361 as TFA salt | 0.107 | 0.170 |
| 362 as TFA salt | 0.072 | 0.142 |
| 363 as TFA salt | 0.007 | 0.009 |
| 364 as TFA salt | 0.124 | 0.286 to 0.472 |
| 365 as TFA salt | 0.033 | 0.137 |
| 366 as TFA salt | 0.151 | 0.345 |
| 367 as TFA salt | 0.127 | 0.209 |
| 368 as TFA salt | 0.091 | 0.127 |
| 369 as TFA salt | 0.397 | 1.277 |
| 370 as TFA salt | 0.441 | 1.303 |
| 371 as TFA salt | 0.125 | 0.110 |
| 372 as TFA salt | 0.014 to 0.044 | 0.029 |
| 373 as TFA salt | 0.051 | Not determined |
| 374 | 0.032 | 0.021 |
| 375 | 0.093 | 0.241 |
| 376 as TFA salt | 0.023 | 0.027 |
| 377 as TFA salt | 0.052 | Not determined |
| 378 as TFA salt | 0.025 to 0.028 | Not determined |
| 379 as TFA salt | 0.053 | Not determined |
| 380 as TFA salt | 0.036 to 0.037 | 0.050 |
| 380 | 0.036 to 0.055 | Not determined |
| 381 as TFA salt | 0.139 | 0.059 |
| 382 as TFA salt | 0.219 | 0.098 |
| 383 as TFA salt | 0.164 | Not determined |
| 384 as TFA salt | 10.5 to >25 | Not determined |
| 385 as TFA salt | 0.017 | <0.023 |
| 385 | <0.016 to 0.027 | 0.007 |
| 386 as TFA salt | 0.059 | Not determined |
| 387 as TFA salt | 0.032 to 0.036 | Not determined |
| 388 as TFA salt | <0.0159 | 0.006 |
| 389 as TFA salt | 0.020 | Not determined |
| 390 as TFA salt | 0.022 to 0.037 | 0.022 |
| 391 as TFA salt | 0.038 to 0.067 | Not determined |
| 392 as TFA salt | 0.101 to 0.142 | Not determined |
| 393 as TFA salt | 0.057 to 0.081 | Not determined |
| 394 as TFA salt | 0.037 to 0.046 | Not determined |
| 395 as TFA salt | 0.034 to 0.045 | Not determined |
| 396 as TFA salt | 0.024 to 0.041 | Not determined |
| 397 as TFA salt | 0.064 to 0.067 | Not determined |
| 398 as TFA salt | 0.038 to 0.04 | Not determined |
| 399 as TFA salt | 0.018 | Not determined |
| 400 as TFA salt | 0.018 to 0.033 | Not determined |
| 401 as TFA salt | 0.023 to 0.03 | Not determined |
| 401 | 0.018 | Not determined |
| 402 as TFA salt | 0.044 to 0.05 | Not determined |
| 403 as TFA salt | 0.137 | Not determined |
| 404 | 0.021 to 0.025 | Not determined |
| 405 | 0.027 to 0.037 | Not determined |
| 406 as TFA salt | 0.028 to 0.03 | Not determined |
| 407 | 0.071 | Not determined |
| 408 | 0.043 | Not determined |
| 409 as TFA salt | 0.209 | 0.501 to 0.515 |
| 410 as TFA salt | 0.020 | 0.034 |
| 411 as TFA salt | 0.756 | 1.601 |
| 412 as TFA salt | 0.108 | 0.223 to 0.347 |
| 413 as TFA salt | 0.023 | Not determined |
| 414 as TFA salt | 2.210 | Not determined |
| 415 | 0.483 to 0.859 | 0.204 |
| 416 | 0.097 | 0.110 |
| 417 | 0.207 | 0.078 to 0.147 |
| 418 | 0.015 to 0.044 | 0.016 to 0.075 |
| 419 | 0.096 | 0.039 to 0.06 |
| 420 | 0.089 | 0.047 to 0.078 |
| 421 | 0.023 | 0.021 |
| 422 | 1.76 to 2.03 | Not determined |
| 423 | 0.036 to 0.042 | Not determined |
| 424 | 7.710 | 6.429 |
| 425 | 0.303 | 0.202 to 0.214 |
| 426 as TFA salt | <0.0159 | Not determined |
| 427 as TFA salt | 0.039 to 0.55 | Not determined |
| 428 as TFA salt | 0.0678 | Not determined |
| 429 | <0.016 | Not determined |
| 430 as TFA salt | 0.050 | Not determined |
| 431 as TFA salt | 0.047 | Not determined |
| 432 as TFA salt | 0.016 | Not determined |
| 433 as TFA salt | 0.032 | Not determined |
| 434 as TFA salt | 0.017 | Not determined |
| 435 as TFA salt | 0.017 | Not determined |
| 436 as TFA salt | 0.06 | Not determined |
| 437 as TFA salt | 0.036 | Not determined |
| 438 as TFA salt | 0.045 | Not determined |
| 439 as TFA salt | 0.392 | Not determined |
| 440 as TFA salt | 0.172 | Not determined |
| 441 as TFA salt | <0.016 | Not determined |
| 442 as TFA salt | 0.038 | Not determined |
| 443 as TFA salt | 0.029 | Not determined |
| 444 as TFA salt | <0.016 | Not determined |
| 445 as TFA salt | 0.112 | Not determined |
| 446 as TFA salt | 0.0268 | Not determined |
| 447 as TFA salt | 0.028 | Not determined |
| 448 as TFA salt | <0.016 | Not determined |
| 449 as TFA salt | 0.0297 | Not determined |
| 450 as TFA salt | <0.016 | Not determined |
| 451 as TFA salt | 0.0435 | Not determined |
| 452 as TFA salt | 0.0293 | Not determined |
| 453 as TFA salt | 0.0357 | Not determined |
| 454 as TFA salt | 0.0234 | Not determined |
| 455 as TFA salt | <0.016 | Not determined |
| 456 as TFA salt | <0.016 | Not determined |
| 456 | 0.0010 | Not determined |
| 457 as TFA salt | 0.017 | Not determined |
| 458 as TFA salt | <0.016 | Not determined |
| 459 as TFA salt | 0.0246 | Not determined |
| 460 as TFA salt | 0.024 to 0.043 | Not determined |
| 461 as TFA salt | 0.045 to 0.064 | Not determined |
| 462 as TFA salt | 0.0738 | Not determined |
| 463 as TFA salt | 0.038 | 0.010 |
| 463 | 0.035 to 0.040 | 0.039 |
| 464 as TFA salt | 0.0937 | Not determined |
| 465 as TFA salt | 0.0681 | Not determined |
| 466 | 0.024 to 0.027 | 0.011 |
| 467 | 0.008 to 0.010 | <0.00229 |
| 468 | 0.128 | 0.023 |
| 469 | 0.020 | Not determined |
| 470 | Not determined | 0.0128 |
| 471 as TFA salt | 0.049 | Not determined |
| 472 as TFA salt | 0.032 | Not determined |
| 473 as TFA salt | 0.019 | Not determined |
| 474 as TFA salt | 0.077 | Not determined |
| 475 as TFA salt | 0.022 | Not determined |
| 476 as TFA salt | 0.012 | Not determined |
| 477 | 0.017 | Not determined |
| 478 as TFA salt | 0.051 | Not determined |
| 479 as TFA salt. | 0.087 | Not determined |
| 480 | 0.014-0.020 | 0.005 |

IDH Cellular Assay

The IDH cellular assay consisted of two side-by-side comparator assays: 1) 2HG oncometabolite detection assay using LC-MS (See Mutant IDH1 biochemical assay for LC-MS detection details) and 2) Cell proliferation assay to monitor off-target killing of cells and to normalize 2HG level change.

IDH1 cellular screens were run with the HCT-116 cell line (express endogenous level of IDH1mut R132H, available from Horizon Discoveries X-Man isogenic human cell lines, catalog #HD104-013). The cells were grown in DMEM (LONZA Cat#12-540F) with 10% Fetal bovine serum (Gibco cat #10099) and 1× non-essential amino acids (NEAA LONZA cat #13-114E). Panel assays were run periodically to test compound activity in cell lines with different endogenous mutations—HT1080 (IDH1mut R132C, EMEM+10% FBS), SNU-1079 (IDH1mut R132C, RPMI+10% FBS+1% sodium pyruvate), and SW1353 (IDH2mut R172S, RPMI+10% FBS+1% sodium pyruvate).

The assay process was as follows:

Day 1: cells were seeded in 384-well plates (Corning Cat#3707) in triplicates for both the cell proliferation and 2HG assay, and incubated at 37 C, 95% Rh, 5% CO2 overnight.

Day 2: compounds were serially diluted 1:3 (10 point dilution from 10 mM solutions in DMSO) and delivered to the cell assay plates via acoustic dispenser, with final concentration ranging from 30 uM to 1.5 nM. The plates were returned to the incubator after treatment and incubated for 48 hours.

Day 4 Proliferation assay: CTG (cell titer-glo, Promega part #G755B) was added to the assay plates and luminescence signal was read on the plate reader.

Day 4 2HG assay: Extraction sample preparation consisted of aspirating all media from the assay plates, adding 70 ul of 90% methanol in water, dry ice incubation for 15 minutes, centrifuging at 2000 rpm for 30 min to ensure all particulates have settled, and transferring 30 ul of the supernatant into LC-MS ready plates. LC-MS analysis followed.

Certain compounds of the invention were tested in the IDH Cellular Assay.

Determination of Metabolic Stability in Liver Microsomes—Method I

The in vitro metabolic stability assay was performed in a 96-well glass plate with shaking incubation at 37° C. A 10 mM DMSO stock solution of the test compound was sequentially diluted 1:1000 to yield a final reaction concentration of 1 μM in 50 mM KPi. Immediately prior to the start of the experiment, respective animal or human liver microsomes (male Sprague-dawley rat, male CD-1 mouse, or pooled human liver microsomes) were diluted in 50 mM KPi to 1.25 mg/mL liver microsomal protein. 30 μL of the 10 μM solution containing the test compound was added to 120 μL of microsomal protein for 150 μL enzyme-compound mixture. The reaction was initiated by adding 150 μL of cofactor solution (2 mM NADPH, 4 mM MgCl in 50 mM KPi) to the enzyme-compound mixture, and the final reaction concentrations are listed in the table below.

| Final Reaction Concentrations | |
| --- | --- |
| Reaction component | Final reaction concentration |
| Potassium phosphate (KPi) buffer, pH 7.4 | 50 mM |
| MgCl₂ | 2.0 mM |
| NADPH | 1.0 mM |
| Liver microsomes | 0.5 mg/mL |
| Test compound | 1.0 μM |
| DMSO (test compound solvent) | 0.01% (v/v) |

At 0, 5, 10 and 30 minute time points in the reaction, reaction aliquots (50 μL) were removed and the reactions were terminated by the addition of acetonitrile (150 μL) containing a mass spectrometry internal standard (1 μM glyburide). The samples were centrifuged and the supernatants analyzed by LC-MS/MS for quantization of remaining compound. The percentage of compound remaining, relative to 0 minutes, was used to estimate in vitro elimination-rate constant ($k_{mic}$) which was used to calculate in vitro metabolic clearance rates.

Analysis of the samples was performed on a high performance liquid chromatography-tandem mass spectrometry (LC/MS) system consisting of a Thermo TSQ Quantum Ultra mass spectrometer, an H-ESI ion source, a CTC-HTS Pal autosampler, and an Agilent LC Pump. Samples were separated on an XTerra C18 column, 2.1×20 mm, 3.5 μm using the fast mobile phase gradient outlined below.

| Time (min) | % B |
| --- | --- |
| 0.0 | 5 |
| 0.2 | 5 |
| 0.85 | 95 |
| 1.02 | 95 |
| 1.05 | 5 |

Mobile phase A consisted of purified water containing 0.01% formic acid. Mobile phase B consisted of acetonitrile containing 0.01% formic acid. The flow rate was 1 mL/min. The injection volume was 10 μL. Compounds were detected using the Thermo QuikQuan software which collects intensity data for all fragments related to the molecular weight of the test compound. After collection of the raw data, the software identifies and integrates the peak of the strongest intensity.

Each microsomal elimination rate, $k_{mic}$, was based on a 4-point elimination curve tested in singlet. LC-MS/MS raw data for a reaction plate was returned as integrated analyte peak areas for the test compound and internal standard used in the quench solution for the reaction to enable use of analyte:internal standard peak area ratios (PARs) for all data comparisons. The reaction time point (e.g. 0, 5, 20 or 30 minutes) was plotted versus the natural logarithm of percent test compound remaining relative to 0 minutes (based on relative PAR). The slope of this clearance plot, $k_{mic}$, was used to calculate the in vitro half-life, $t_{1/2}$. In order to focus on linear reaction kinetics, whenever possible, data points representing <10% test compound remaining were generally omitted from the definition of the clearance plot slope.

Determination of Metabolic Stability in Liver Microsomes—Method II

The in vitro metabolic stability assay was performed in a 96-deep-well plate with incubation at 37° C. 10 mM DMSO stock solution of the test compound was diluted 1:20 in acetonitrile, followed by an additional 1:10 dilution in 100 mM potassium phosphate buffer (KPi) to yield a final reaction concentration of 1 μM. Immediately prior to the start of the experiment, respective animal or human liver microsomes (male Sprague-dawley rat, male CD-1 mouse, or pooled human liver microsomes) were diluted in 100 mM KPi to 1.25 mg/mL liver microsomal protein. 290 μL of cofactor solution (1.7 mM NADPH, 1.7 mM UDPGA, 3.4 mM MgCl in 100 mM KPi) was added to 200 μL of microsomal protein for a final volume of 490 μL. The reaction was initiated by adding 10 μL of the 50 μM test solution to 490 μL of microsomal protein for a final volume 500 μL enzyme-compound mixture.

The final reaction concentrations are listed in the table below:

| Final Reaction Concentrations | |
| --- | --- |
| Reaction component | Final reaction concentration |
| Potassium phosphate (KPi) buffer, pH 7.4 | 50 mM |
| MgCl₂ | 2.0 mM |

-continued

| Final Reaction Concentrations | |
| --- | --- |
| Reaction component | Final reaction concentration |
| NADPH | 1.0 mM |
| UDPGA | 1.0 mM |
| Liver microsomes | 0.5 mg/mL |
| Test compound | 1.0 μM |
| DMSO (test compound solvent) | 0.01% (v/v) |

At 0, 5, 15 and 30 minute time points in the reaction, reaction aliquots (75 μL) were removed and the reactions were terminated by the addition of 50:50 acetonitrile/methanol solution (75 μL) containing a mass spectrometry internal standard (0.5 μM glyburide). The samples were centrifuged at 4000 RPM for 10 minutes. Supernatants (15 μL aliquots) were transferred to a new plate where each well contains 90 μL of deionized water. The supernatants solution were analyzed by UPLC/MS/MS for quantitation of parent remaining compound under multiple reactions monitoring mode (MRM) in positive mode. The percentage of compound remaining, relative to 0 minutes, was used to estimate in vitro elimination-rate constant (k) which was used to calculate in vitro metabolic clearance rates.

Analysis of the samples was performed on an ultra-performance liquid chromatography-tandem mass spectrometry (UPLC/MS/MS) system consisting of an AB Sciex Qtrap 5500 mass spectrometer, AB Sciex Turbo V ion source, Waters Acquity Sample Organizer, Waters Acquity Column manager, Waters Acquity Sample manager, and a Waters Acquity Binary Solvent Manager. Chromatographic separation of analyte and internal standard was achieved using a reverse phase C-18 column (50×2.1 mm, 1.7 μm, Acquity UPLC BEH C-18) with the following UPLC mobile phases and elution gradient:

UPLC mobile phase A: 0.25% formic acid in 5% methanol; mobile phase B: 0.25% formic acid in 95% water.

LC gradient and flow rate are listed below:

| | | |
| --- | --- | --- |
| 0-.01 min | 10% B | 700 μL/min |
| 0.01-1.0 min | 10-95% B | 700 μL/min |
| 1.0-1.1 min | 95% B | 700 μL/min |
| 1.1-1.2 min | 95-10% B | 700 μL/min |
| 1.2-1.5 min | 10% B | 700 μL/min |

The injection volume was 5 μL. Compounds were detected using Analyst 1.5.1 software which collects intensity data for all fragments related to the molecular weight of the test compound. After collection of the raw data, the software identifies and integrates the peak of the strongest intensity.

Each microsomal elimination rate, k, was based on a 4-point elimination curve tested in duplicates. LC-MS/MS raw data for a reaction plate was returned as integrated analyte peak areas for the test compound and internal standard used in the quench solution for the reaction to enable use of analyte:internal standard peak area ratios (PARs) for all data comparisons. The reaction time point (e.g. 0, 5, 15 and 30 minutes) was plotted versus the natural logarithm of percent test compound remaining relative to 0 minutes (based on relative PAR). The slope of this clearance plot, k, was used to calculate the in vitro half-life.

$$\text{Half life } (t_{1/2})(\text{min}) = \frac{-0.693}{k}$$

The intrinsic clearance value, $CL_{int}$ (expressed as μL/min/mg microsomal protein) calculation is shown below:

$$CL_{int} = \frac{0.693}{t_{1/2}} \cdot \frac{V}{M}$$

Where V=the incubation volume (mL) and M=the microsomal protein content in the incubation (mg)

TABLE 41

Results of the metabolic stability assays

| Example Number | Rat microsomal stability $CL_{int}$ [μl min−1 mg−1] | Mouse microsomal stability $CL_{int}$ [μl min−1 mg−1] | Human microsomal stability $CL_{int}$ [μl min−1 mg−1] | Method |
| --- | --- | --- | --- | --- |
| 48 | 49.09 | 173.08 | 120.53 | I |
| 55 | 58.41 | 63.12 | Not determined | I |
| 61 | 34.65 | 67.65 | 66.43 | I |
| 122 | 69.39 | Not determined | Not determined | I |
| 169 | 68.78 | Not determined | Not determined | I |
| | 60.93 | | | |
| 174 | 48.53 | Not determined | Not determined | I |
| 175 | 50.51 | 56.29 | 39.77 | I |
| 181 | 56.58 | Not determined | Not determined | I |
| 380 | 42.93 | | | I |
| | 30.16 | 51.00 | 31.15 | II |
| 401 | 30.38 | | | I |
| | 92.37 | 33.13 | <7.70 | II |
| 404 | 44.6 | | | I |
| | 75.44 | 18.72 | <7.70 | II |
| 434 as TFA salt | 40.97 | | | I |
| | 10.81 | 10.68 | <7.70 | II |
| 456 as TFA salt | 44.66 | | | I |
| | 72.50 | 63.03 | 16.79 | II |
| 463 | 50.8 | | | I |
| | 49.78 | 35.45 | 28.27 | II |
| 466 | 44.90 | 57.89 | 55.93 | I |
| 467 | 75.56 | | | I |
| | 85.38 | 274.97 | 53.27 | II |
| 468 | 30.46 | 28.95 | 70.11 | I |
| 469 | 131.74 | Not determined | Not determined | I |
| 470 | 52.76 | 47.31 | 83.59 | I |
| 471 as TFA salt | <7.70 | 14.75 | <7.70 | II |
| 472 as TFA salt | 12.03 | 45.59 | <7.70 | II |
| 473 as TFA salt | 72.47 | | | I |
| | 33.29 | 17.66 | <7.70 | II |
| 474 as TFA salt | 24.78 | <7.70 | <7.70 | II |
| 475 as TFA salt | 53.95 | | | I |
| | 16.24 | 15.72 | <7.70 | II |
| 476 as TFA salt | 344.08 | 110.74 | 41.35 | II |
| 477 | 437.89 | 167.04 | 30.44 | II |
| 478 as TFA salt | 219.31 | 55.30 | 10.94 | II |
| 479 as TFA salt | 172.65 | 116.32 | 11.86 | II |
| 480 | 65.24 | 51.46 | 35.57 | I |

Enumerated Embodiments

Embodiment 1

A Compound According to Formula (I)

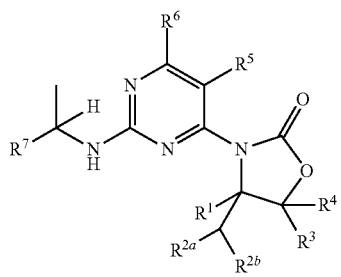

(I)

wherein:
R$^1$ is hydrogen, methyl or ethyl;
R$^{2a}$ is hydrogen, methyl or C$_{1-3}$ haloalkyl;
R$^{2b}$ is OH, halo, C$_{1-6}$ alkoxy, C$_{1-3}$ haloalkyl, NH$_2$, NH(CH$_3$) or N(CH$_3$)$_2$;
R$^3$ and R$^4$ are each independently hydrogen, methyl or ethyl or R$^3$ and R$^4$ are joined together forming cyclopropyl, cyclobutyl or oxetanyl;
R$^5$ and R$^6$ are each independently hydrogen, deuterium, halo, —C(O)OCH$_3$, C$_{1-3}$ alkyl or C$_{1-3}$ haloalkyl;
R$^7$ is

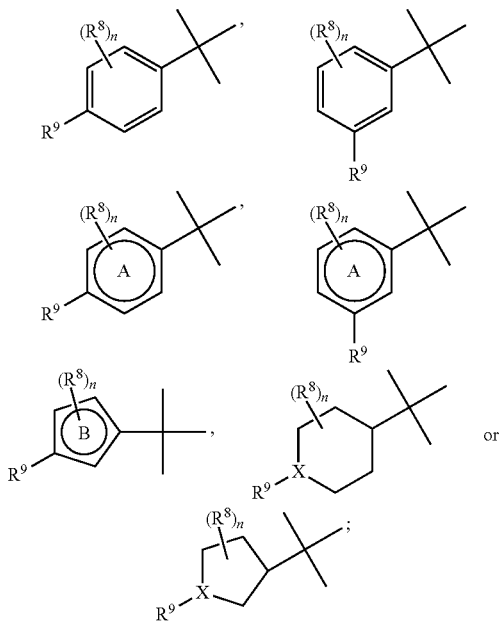

wherein:
ring A is a 6 membered heteroaryl ring having one to three nitrogen atoms;
ring B is a 5 membered heteroaryl ring having one to four heteroatoms each independently selected from the group consisting of N, O and S;
X is N or CH;
each R$^8$ is independently hydrogen, halo, C$_{1-3}$ alkyl, C$_{1-3}$ haloalkyl, C$_{1-3}$ alkoxy or C$_{1-3}$ haloalkoxy;
n is 1 or 2;

R$^9$ is hydrogen, halo, C$_{1-3}$ haloalkyl, optionally substituted C$_{1-6}$ alkyl, optionally substituted C$_{3-6}$ cycloalkyl, optionally substituted aryl, optionally substituted 5 or 6 membered heterocyclic, optionally substituted heteroaryl, —OR$^{9a}$, —SO$_2$R$^{9a}$, —C(O)NHR$^{9a}$, CH$_2$R$^{9b}$ or CHCH$_3$R$^{9b}$, provided that when X is N, R$^9$ is hydrogen, C$_{1-3}$ haloalkyl, optionally substituted C$_{1-6}$ alkyl, optionally substituted C$_{3-6}$ cycloalkyl, optionally substituted aryl, optionally substituted heteroaryl, —SO$_2$R$^{9a}$ or —C(O)NHR$^{9a}$, wherein:
said C$_{1-6}$ alkyl is optionally substituted with one to three substituents each independently selected from the group consisting of: OH, phenyl and phenoxy, and
said C$_{3-6}$ cycloalkyl, 5 or 6 membered heterocyclic, aryl and heteroaryl are each optionally substituted with one to three substituents each independently selected from the group consisting of: halo, hydroxyl, cyano, —NRR, C$_{1-6}$ alkyl, C$_{1-6}$ haloalkyl, C$_{1-3}$ alkoxy, and C$_{1-3}$ haloalkoxy;
R$^{9a}$ is optionally substituted C$_{1-6}$ alkyl, C$_{1-6}$ haloalkyl, optionally substituted C$_{3-6}$ cycloalkyl, optionally substituted phenyl, or optionally substituted heterocyclic, wherein:
said C$_{1-6}$ alkyl is optionally substituted with one C$_{3-6}$ cycloalkyl,
said C$_{3-6}$ cycloalkyl and heterocyclic are each optionally substituted with one to three substituents each independently selected from the group consisting of: hydroxyl, CH$_2$OH, —NRR, cyano, C$_{1-3}$ alkyl, C$_{1-3}$ haloalkyl, and C$_{1-3}$ alkoxy, and
said phenyl is optionally substituted with one to three substituents each independently selected from the group consisting of: halo, hydroxyl, cyano, —NRR, C$_{1-6}$ alkyl, C$_{1-6}$ haloalkyl, C$_{1-3}$ alkoxy, and C$_{1-3}$ haloalkoxy;
R$^{9b}$ is optionally substituted C$_{3-6}$ cycloalkyl, optionally substituted phenyl or optionally substituted heterocyclic,
said C$_{3-6}$ cycloalkyl and heterocyclic are each optionally substituted with one to four substituents each independently selected from the group consisting of: hydroxyl, CH$_2$OH, —NRR, —NRC(O)CH$_3$ 4 to 6 membered heterocyclic, cyano, halo, C$_{1-3}$ alkyl, C$_{1-3}$ haloalkyl, and C$_{1-3}$ alkoxy, and
said phenyl is optionally substituted with one to three substituents each independently selected from the group consisting of: halo, hydroxyl, cyano, C$_{1-6}$ alkyl, C$_{1-6}$ haloalkyl, C$_{1-3}$ alkoxy, and C$_{1-3}$ haloalkoxy; and each R is independently selected from the group consisting of H, C$_{1-3}$ alkyl and C$_{3-6}$ cycloalkyl; or a pharmaceutically acceptable salt thereof.

Embodiment 2

The compound according to embodiment 1 wherein R$^3$ and R$^4$ are both hydrogen; or a pharmaceutically acceptable salt thereof.

Embodiment 3

The compound according to embodiment 1 or 2 wherein R$^1$ is hydrogen; or a pharmaceutically acceptable salt thereof.

Embodiment 4

The compound according to any one of embodiments 1-3 according to formula (II):

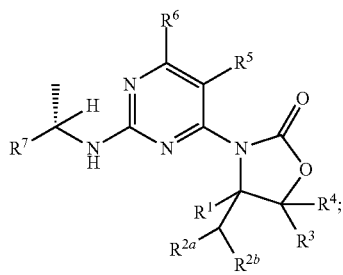

(II)

or a pharmaceutically acceptable salt thereof.

Embodiment 5

The compound according to any one of embodiments 1-4 wherein:
$R^5$ is hydrogen or halo; and
$R^6$ is hydrogen, halo, methyl, $CH_2F$, $CHF_2$, or $CF_3$; or a pharmaceutically acceptable salt thereof.

Embodiment 6

The compound according to embodiment 5 wherein $R^5$ is hydrogen; or a pharmaceutically acceptable salt thereof.

Embodiment 7

The compound according embodiment 5 wherein $R^6$ is hydrogen; or a pharmaceutically acceptable salt thereof.

Embodiment 8

The compound according to embodiment 5 wherein $R^5$ and $R^6$ are both hydrogen; or a pharmaceutically acceptable salt thereof.

Embodiment 9

The compound according to any one of embodiments 1-8 wherein $R^{2a}$ is methyl; or a pharmaceutically acceptable salt thereof.

Embodiment 10

The compound according to any one of embodiments 1-9 wherein $R^{2b}$ is OH, fluoro, methoxy, t-butoxy, $CHF_2$, $CF_3$, $NH_2$ or $NH(CH_3)$; or a pharmaceutically acceptable salt thereof.

Embodiment 11

The compound according to any one of embodiments 1-10 having the following formula:

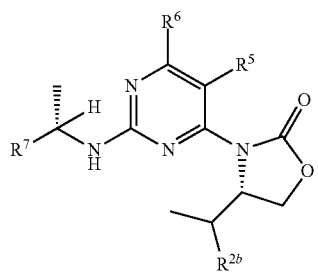

(III)

wherein $R^{2b}$ is OH, $NH_2$ or fluoro; or a pharmaceutically acceptable salt thereof.

Embodiment 12

The compound according to any one of embodiments 1-11 according to formula (IV):

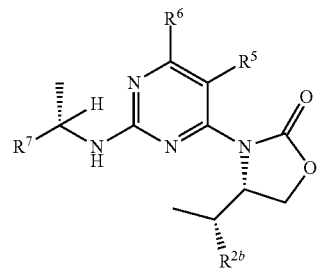

(IV)

wherein $R^{2b}$ is OH or $NH_2$; or a pharmaceutically acceptable salt thereof.

Embodiment 13

The compound according to embodiment 12 wherein $R^{2b}$ is OH; or a pharmaceutically acceptable salt thereof.

Embodiment 14

The compound according to embodiment 12 wherein $R^{2b}$ is $NH_2$; or a pharmaceutically acceptable salt thereof.

Embodiment 15

The compound according to any one of embodiments 1-11 according to formula (V):

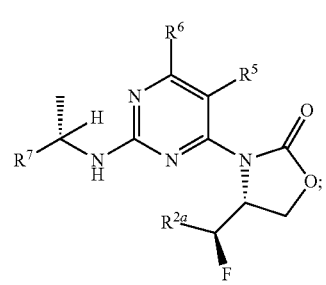

(V)

or a pharmaceutically acceptable salt thereof.

Embodiment 16

The compound according to embodiment 15 wherein $R^{2a}$ is methyl; or a pharmaceutically acceptable salt thereof.

Embodiment 17

The compound according to any one of embodiments 1-16 wherein $R^7$ is:

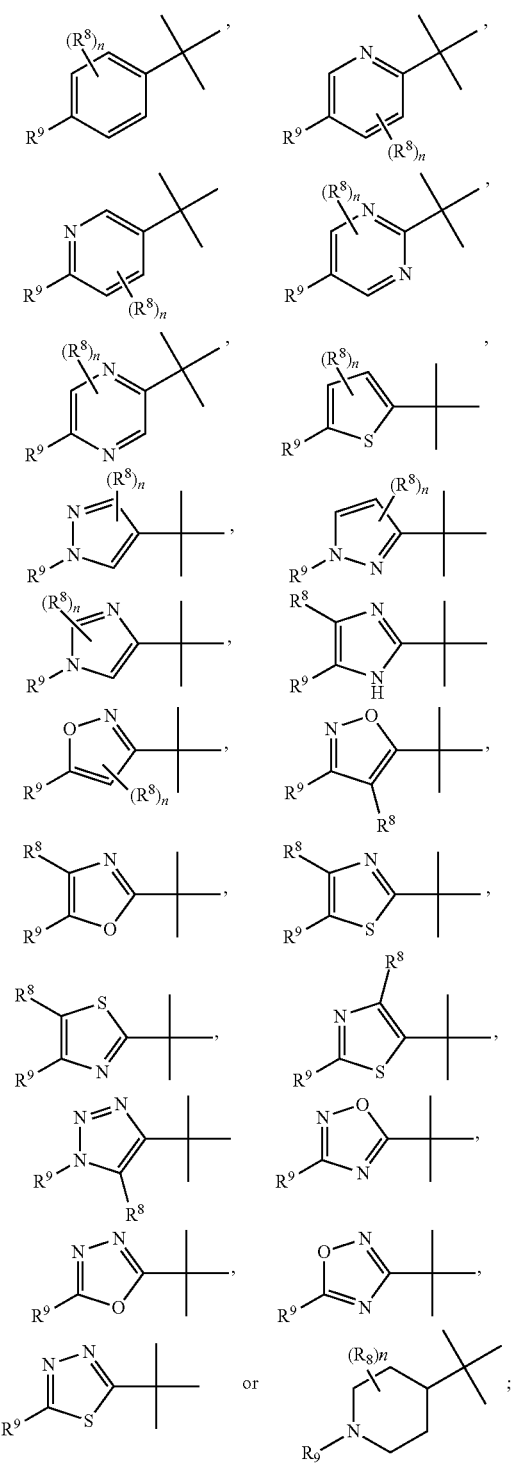

or a pharmaceutically acceptable salt thereof.

Embodiment 18

The compound according to any one of embodiments 1-17 wherein $R^9$ is hydrogen, halo, $C_{1-3}$ haloalkyl, optionally substituted $C_{1-6}$ alkyl or optionally substituted $C_{3-6}$ cycloalkyl; or a pharmaceutically acceptable salt thereof.

Embodiment 19

The compound according to any one of embodiments 1-17 wherein $R^9$ is phenyl optionally substituted with one or two substituents each independently selected from the group consisting of: fluoro, chloro, bromo, cyano, methoxy, $CH_2OH$, $C_{1-4}$ alkyl, $C_{1-4}$ haloalkyl and $C_{1-3}$ haloalkoxy; or a pharmaceutically acceptable salt thereof.

Embodiment 20

The compound according to any one of embodiments 1-17 wherein $R^9$ is pyrazolyl, pyridinyl, indolyl or isoquinolinyl each of which is optionally substituted; or a pharmaceutically acceptable salt thereof.

Embodiment 21

The compound according to any one of embodiments 1-17 wherein $R^9$ is $CH_2R^{9b}$ wherein $R^{9b}$ is piperidinyl, piperazinyl or morpholinyl each of which is optionally substituted with one to three substituents each independently selected from the group consisting of: hydroxyl, halo, $CH_2OH$, —NRR, cyano, $C_{1-3}$ alkyl, $C_{1-3}$ haloalkyl, and $C_{1-3}$ alkoxy.

Embodiment 22

The compound according to embodiment 1 according to formula (IV)

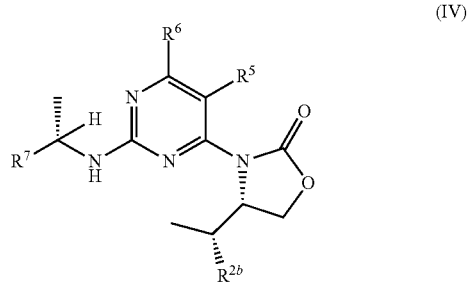

(IV)

wherein:
$R^{2b}$ is OH;
$R^5$ is hydrogen or fluoro;
$R^6$ is hydrogen, chloro, methyl or $CH_2F$;
$R^7$ is

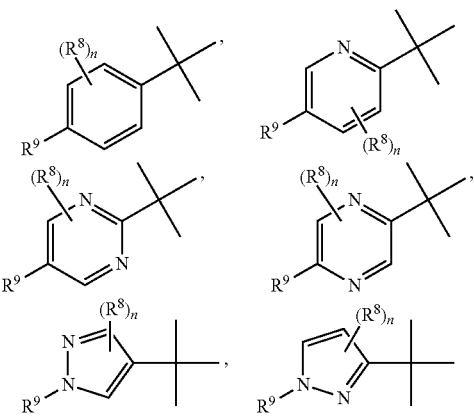

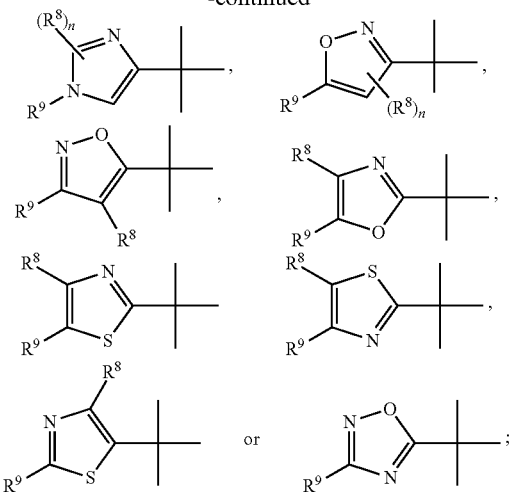

$R^8$ is hydrogen, methyl or fluoro;
n is 1 or 2; and
$R^9$ is methylcyclopropyl, isobutoxy, phenyl optionally substituted with one or two substituents each independently selected from the group consisting of: fluoro, chloro, bromo, $C_{1-4}$ alkyl, $CF_2H$ and $CF_3$ or pyridinyl optionally substituted with one or two substituents each independently selected from the group consisting of: methyl, $CF_3$ and $C(CH_3)_2CF_3$; or a pharmaceutically acceptable salt thereof.

Embodiment 23

The compound according to embodiment 22 wherein:
$R^5$ is hydrogen and $R^6$ is chloro, methyl or $CH_2F$
or
$R^6$ is hydrogen and $R^5$ is fluoro; or a pharmaceutically acceptable salt thereof.

Embodiment 24

The compound according to embodiment 22 wherein $R^5$ and $R^6$ are both hydrogen; or a pharmaceutically acceptable salt thereof.

Embodiment 25

The compound according to embodiment 1 according to formula (VI)

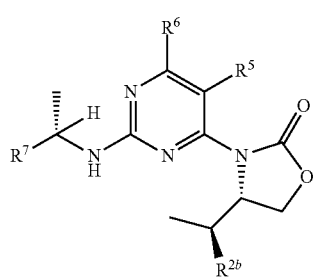

wherein:
$R^{2b}$ is fluoro;
$R^5$ is hydrogen or fluoro;
$R^6$ is hydrogen;

$R^7$ is

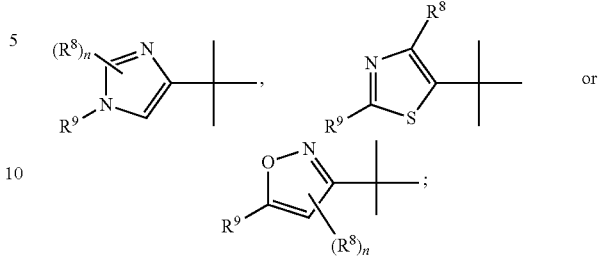

$R^8$ is hydrogen or methyl;
n is 1; and
$R^9$ is phenyl optionally substituted with one chloro; or a pharmaceutically acceptable salt thereof.

Embodiment 26

The compound according to embodiment 1 selected from the group consisting of:
(R)-4-((R)-1-hydroxy(R)-4-((R)-1-hydroxyethyl)-3-(2-(((S)-1-(5-(3-(trifluoromethyl)phenyl)pyrazin-2-yl)ethyl)amino)pyrimidin-4-yl)oxazolidin-2-onethyl)-3-(2-(((S)-1-(5-(3-(trifluoromethyl)phenyl)pyrazin-2-yl)ethyl)amino)pyrimidin-4-yl)oxazolidin-2-one;
(R)-3-(2-(((S)-1-(5-(4-fluoro-3-methylphenyl)pyridin-2-yl)ethyl)amino)pyrimidin-4-yl)-4-((R)-1-hydroxyethyl)oxazolidin-2-one;
(R)-4-((R)-1-hydroxyethyl)-3-(2-(((S)-1-(5-(3-(trifluoromethyl)phenyl)pyridin-2-yl)ethyl)amino)pyrimidin-4-yl)oxazolidin-2-one;
(R)-4-((R)-1-hydroxyethyl)-3-(2-(((S)-1-(6-(trifluoromethyl)-[2,3'-bipyridin]-6'-yl)ethyl)amino)pyrimidin-4-yl)oxazolidin-2-one;
(R)-4-((R)-1-hydroxyethyl)-3-(2-(((S)-1-(4-methyl-2'-(trifluoromethyl)-[3,4'-bipyridin]-6-yl)ethyl)amino)pyrimidin-4-yl)oxazolidin-2-one;
(R)-3-(2-(((S)-1-(5-(4-fluoro-3-(trifluoromethyl)phenyl)pyrimidin-2-yl)ethyl)amino)pyrimidin-4-yl)-4-((R)-1-hydroxyethyl)oxazolidin-2-one;
(R)-3-(2-(((S)-1-(5-(4-chloro-3-(trifluoromethyl)phenyl)pyrimidin-2-yl)ethyl)amino)pyrimidin-4-yl)-4-((R)-1-hydroxyethyl)oxazolidin-2-one;
(R)-3-(2-(((S)-1-(5-(3,4-dichlorophenyl)pyrimidin-2-yl)ethyl)amino)pyrimidin-4-yl)-4-((R)-1-hydroxyethyl)oxazolidin-2-one;
(R)-4-((R)-1-hydroxyethyl)-3-(2-(((S)-1-(5-(3-(trifluoromethyl)phenyl)pyrimidin-2-yl)ethyl)amino)pyrimidin-4-yl)oxazolidin-2-one;
(R)-3-(2-(((S)-1-(5-(4-chloro-3-methylphenyl)pyrimidin-2-yl)ethyl)amino)pyrimidin-4-yl)-4-((R)-1-hydroxyethyl)oxazolidin-2-one;
(R)-3-(2-(((S)-1-(5-(3-chloro-5-(trifluoromethyl)phenyl)pyrimidin-2-yl)ethyl)amino)pyrimidin-4-yl)-4-((R)-1-hydroxyethyl)oxazolidin-2-one;
(R)-3-(2-(((S)-1-(5-(3,4-dichlorophenyl)pyrimidin-2-yl)ethyl)amino)-5-fluoropyrimidin-4-yl)-4-((R)-1-hydroxyethyl)oxazolidin-2-one;
(R)-4-((R)-1-hydroxyethyl)-3-(2-(((S)-1-(4-methyl-5-(2-(1,1,1-trifluoro-2-methylpropan-2-yl)pyridin-4-yl)thiazol-2-yl)ethyl)amino)pyrimidin-4-yl)oxazolidin-2-one;
(4R)-3-(5-fluoro-2-(((S)-1-(4-methyl-5-(2-(1,1,1-trifluoro-2-methylpropan-2-yl)pyridin-4-yl)thiazol-2-yl)ethyl)amino)pyrimidin-4-yl)-4-((R)-1-hydroxyethyl)oxazolidin-2-one;

(R)-3-(2-(((S)-1-(5-(2-fluoro-3-(trifluoromethyl)phenyl)py-rimidin-2-yl)ethyl)amino)pyrimidin-4-yl)-4-((R)-1-hy-droxyethyl)oxazolidin-2-one; and (R)-3-(2-(((S)-1-(2,5-difluoro-4-(2-methylpyridin-4-yl)phe-nyl)ethyl)amino)pyrimidin-4-yl)-4-((R)-1-hydroxyethyl) oxazolidin-2-one; or a pharmaceutically acceptable salt thereof.

Embodiment 27

The compound according to embodiment 1 selected from the group consisting of:
(R)-3-(2-(((S)-1-(5-(4-chlorophenyl)isoxazol-3-yl)ethyl) amino)pyrimidin-4-yl)-4-((R)-1-hydroxyethyl)oxazoli-din-2-one;
(R)-3-(2-(((S)-1-(3-(4-chlorophenyl)-1,2,4-oxadiazol-5-yl) ethyl)amino)pyrimidin-4-yl)-4-((R)-1-hydroxyethyl)ox-azolidin-2-one;
(R)-3-{2-[((R)1-(3-(3-fluoro-4-methylphenyl)-1,2,4-oxadi-azol-5-yl)ethyl]amino}pyrimidin-4-yl}-4-((R)-1-hy-droxyethyl)oxazolidin-2-one;
(R)-3-(2-{(S)-1-[3-(3,4-Dichloro-phenyl)-isoxazol-5-yl]-ethylamino}-pyrimidin-4-yl)-4-((R)-1-hydroxy-ethyl)-oxazolidin-2-one;
(R)-3-(2-{(S)-1-[3-(3,4-Dichloro-phenyl)-isoxazol-5-yl]-ethylamino}-5-fluoro-pyrimidin-4-yl)-4-((R)-1-hydroxy-ethyl)-oxazolidin-2-one;
(R)-3-(5-fluoro-2-(((S)-1-(3-(4-isopropylphenyl)-1,2,4-ox-adiazol-5-yl)ethyl)amino)pyrimidin-4-yl)-4-((R)-1-hy-droxyethyl)oxazolidin-2-one;
(R)-4-((R)-1-hydroxyethyl)-3-(2-(((S)-1-(3-(4-(trifluorom-ethyl)phenyl)-1,2,4-oxadiazol-5-yl)ethyl)amino)pyrimi-din-4-yl)oxazolidin-2-one;
(R)-3-(2-(((S)-1-(5-(4-chlorophenyl)-4-methyloxazol-2-yl) ethyl)amino)pyrimidin-4-yl)-4-((R)-1-hydroxyethyl)ox-azolidin-2-one;
(R)-3-(2-(((S)-1-(5-(4-chlorophenyl)-4-methyloxazol-2-yl) ethyl)amino)-5-fluoropyrimidin-4-yl)-4-((R)-1-hydroxy-ethyl)oxazolidin-2-one;
(R)-3-(2-(((S)-1-(4-(4-bromophenyl)thiazol-2-yl)ethyl) amino)-5-fluoropyrimidin-4-yl)-4-((R)-1-hydroxyethyl) oxazolidin-2-one;
(R)-3-(2-(((S)-1-(5-(4-chlorophenyl)oxazol-2-yl)ethyl) amino)-5-fluoropyrimidin-4-yl)-4-((R)-1-hydroxyethyl) oxazolidin-2-one;
(R)-3-(2-(((S)-1-(5-(4-chlorophenyl)oxazol-2-yl)ethyl) amino)pyrimidin-4-yl)-4-((R)-1-hydroxyethyl)oxazoli-din-2-one;
(R)-3-(2-(((S)-1-(2-(4-chlorophenyl)thiazol-5-yl)ethyl) amino)-5-fluoropyrimidin-4-yl)-4-((R)-1-hydroxyethyl) oxazolidin-2-one;
(R)-3-(2-(((S)-1-(2-(4-chlorophenyl)thiazol-5-yl)ethyl) amino)-6-(fluoromethyl)pyrimidin-4-yl)-4-((R)-1-hy-droxyethyl)oxazolidin-2-one;
(R)-3-(2-(((S)-1-(2-(4-chlorophenyl)thiazol-5-yl)ethyl) amino)pyrimidin-4-yl)-4-((R)-1-hydroxyethyl)oxazoli-din-2-one;
(R)-3-(2-(((S)-1-(1-(4-chlorophenyl)-1H-pyrazol-4-yl) ethyl)amino)pyrimidin-4-yl)-4-((R)-1-hydroxyethyl)ox-azolidin-2-one;
(R)-3-(2-(((S)-1-(5-(4-chlorophenyl)isoxazol-3-yl)ethyl) amino)-6-methylpyrimidin-4-yl)-4-((R)-1-hydroxyethyl) oxazolidin-2-one;
(R)-3-(2-(((S)-1-(2-(4-chlorophenyl)thiazol-5-yl)ethyl) amino)-6-methylpyrimidin-4-yl)-4-((R)-1-hydroxyethyl) oxazolidin-2-one;

(R)-3-(2-(((S)-1-(1-(4-chlorophenyl)-1H-imidazol-4-yl) ethyl)amino)-6-methylpyrimidin-4-yl)-4-((R)-1-hydroxy-ethyl)oxazolidin-2-one;
(R)-3-(2-(((S)-1-(2-(4-(difluoromethyl)phenyl)thiazol-5-yl) ethyl)amino)pyrimidin-4-yl)-4-((R)-1-hydroxyethyl)ox-azolidin-2-one;
(R)-3-(2-(((S)-1-(1-(4-chlorophenyl)-1H-imidazol-4-yl) ethyl)amino)pyrimidin-4-yl)-4-((R)-1-hydroxyethyl)ox-azolidin-2-one;
(R)-3-(6-chloro-2-(((S)-1-(1-(4-chlorophenyl)-1H-imida-zol-4-yl)ethyl)amino)pyrimidin-4-yl)-4-((R)-1-hydroxy-ethyl)oxazolidin-2-one; and
(R)-3-(2-(((S)-1-(3-(3-(tert-butyl)phenyl)-1,2,4-oxadiazol-5-yl)ethyl)amino)pyrimidin-4-yl)-4-((R)-1-hydroxyethyl) oxazolidin-2-one; or a pharmaceutically acceptable salt thereof.

Embodiment 28

The compound according to embodiment 1 selected from the group consisting of:
(R)-3-(2-((S)-1-(2-fluoro-4-(1-methylcyclopropyl)phenyl) ethylamino)pyrimidin-4-yl)-4-((R)-1-hydroxyethyl) oxazolidin-2-one;
(R)-3-(5-fluoro-2-(((S)-1-(2-fluoro-4-isobutoxyphenyl) ethyl)amino)pyrimidin-4-yl)-4-((R)-1-hydroxyethyl)ox-azolidin-2-one; and
(R)-3-(2-(((S)-1-(2-fluoro-4-isobutoxyphenyl)ethyl)amino) pyrimidin-4-yl)-4-((R)-1-hydroxyethyl)oxazolidin-2-one; or a pharmaceutically acceptable salt thereof.

Embodiment 29

The compound according to embodiment 1 selected from the group consisting of:
(R)-3-(6-chloro-2-(((S)-1-(2-(4-chlorophenyl)thiazol-5-yl) ethyl)amino)pyrimidin-4-yl)-4-((R)-1-methoxyethyl)ox-azolidin-2-one;
(R)-3-(2-(((S)-1-(1-(4-chlorophenyl)-1H-imidazol-4-yl) ethyl)amino)pyrimidin-4-yl)-4-((R)-1-methoxyethyl) oxazolidin-2-one; and
(S)-4-((R)-1-aminoethyl)-3-(2-(((S)-1-(2-(4-chlorophenyl) thiazol-5-yl)ethyl)amino)pyrimidin-4-yl)oxazolidin-2-one; or a pharmaceutically acceptable salt thereof.

Embodiment 30

The compound according to embodiment 1 selected from the group consisting of:
(R)-3-(2-(((S)-1-(1-(4-chlorophenyl)-1H-imidazol-4-yl) ethyl)amino)pyrimidin-4-yl)-4-((R)-1-fluoroethyl)oxazo-lidin-2-one;
(R)-3-(2-(((S)-1-(1-(4-chlorophenyl)-1H-imidazol-4-yl) ethyl)amino)pyrimidin-4-yl)-4-((S)-1-fluoroethyl) oxazo-lidin-2-one;
(R)-3-(2-(((S)-1-(2-(4-chlorophenyl) thiazol-5-yl)ethyl) amino)pyrimidin-4-yl)-4-((S)-1-fluoroethyl)oxazolidin-2-one;
(R)-3-(2-(((S)-1-(5-(4-chlorophenyl) isoxazol-3-yl)ethyl) amino)pyrimidin-4-yl)-4-((S)-1-fluoroethyl)oxazolidin-2-one;
(R)-3-(2-(((S)-1-(1-(4-chlorophenyl)-1H-imidazol-4-yl) ethyl)amino)-5-fluoropyrimidin-4-yl)-4-((R)-1-fluoro-ethyl) oxazolidin-2-one;
(R)-3-(2-(((S)-1-(1-(4-chlorophenyl)-2-methyl-1H-imida-zol-4-yl)ethyl)amino)pyrimidin-4-yl)-4-((S)-1-fluoro-ethyl) oxazolidin-2-one;

(R)-4-((S)-1-fluoroethyl)-3-(2-(((S)-1-(1-(4-fluorophenyl)-1H-imidazol-4-yl)ethyl)amino)pyrimidin-4-yl)oxazolidin-2-one;

(R)-3-(2-(((S)-1-(1-(4-chlorophenyl)-1H-imidazol-4-yl)ethyl)amino)pyrimidin-4-yl)-4-(fluoromethyl)oxazolidin-2-one; and (S)-3-(2-(((S)-1-(1-(4-chlorophenyl)-1H-imidazol-4-yl)ethyl)amino)pyrimidin-4-yl)-4-((R)-1,1-difluoropropan-2-yl)oxazolidin-2-one; or a pharmaceutically acceptable salt thereof.

Embodiment 31

The compound according to embodiment 1 which is (R)-4-((R)-1-hydroxyethyl)-3-(2-(((S)-1-(3-(4-(trifluoromethyl)phenyl)-1,2,4-oxadiazol-5-yl)ethyl)amino)pyrimidin-4-yl)oxazolidin-2-one or a pharmaceutically acceptable salt thereof.

Embodiment 32

The compound according to embodiment 1 which is (S)-4-((R)-1-aminoethyl)-3-(2-(((S)-1-(2-(4-chlorophenyl)thiazol-5-yl)ethyl)amino)pyrimidin-4-yl)oxazolidin-2-one or a pharmaceutically acceptable salt thereof.

Embodiment 33

The compound according to embodiment 1 which is (R)-4-((S)-1-fluoroethyl)-3-(2-(((S)-1-(1-(4-fluorophenyl)-1H-imidazol-4-yl)ethyl)amino)pyrimidin-4-yl)oxazolidin-2-one or a pharmaceutically acceptable salt.

Embodiment 34

The compound according to embodiment 1 which is (R)-3-(2-(((S)-1-(1-(4-chlorophenyl)-1H-imidazol-4-yl)ethyl)amino)pyrimidin-4-yl)-4-(fluoromethyl)oxazolidin-2-one or a pharmaceutically acceptable salt thereof.

Embodiment 35

The compound according to embodiment 1 which is (R)-4-((S)-1-fluoroethyl)-3-(2-(((S)-1-(4-methyl-2'-(trifluoromethyl)-[3,4'-bipyridin]-6-yl)ethyl)amino)pyrimidin-4-yl)oxazolidin-2-one or a pharmaceutically acceptable salt thereof.

Embodiment 36

The compound according to embodiment 1 which is (R)-3-(5-fluoro-2-(((S)-1-(4-methyl-2'-(trifluoromethyl)-[3,4'-bipyridin]-6-yl)ethyl)amino)pyrimidin-4-yl)-4-((S)-1-fluoroethyl)oxazolidin-2-one or a pharmaceutically acceptable salt thereof.

Embodiment 37

The compound according to embodiment 1 which is (R)-3-(2-(((S)-1-(1-(3-chloro-4-fluorophenyl)-1H-imidazol-4-yl)ethyl)amino)-5-fluoropyrimidin-4-yl)-4-(fluoromethyl)oxazolidin-2-one or a pharmaceutically acceptable salt thereof.

Embodiment 38

A pharmaceutical composition comprising a compound according to any one of embodiments 1-37, or a pharmaceutically acceptable salt thereof, and a pharmaceutically acceptable carrier or excipient.

Embodiment 39

A method for the treatment of a disease or disorder associated with a mutant IDH protein having a neomorphic activity comprising administration of a therapeutically effective amount of a compound according to any one of embodiments 1-37, or a pharmaceutically acceptable salt thereof, to subject in need of treatment thereof.

Embodiment 40

A method for the treatment of a disease or disorder associated with a mutant IDH protein having a neomorphic activity comprising administration of a therapeutically effective amount of a compound according to any one of embodiments 1-37, or a pharmaceutically acceptable salt thereof, and another therapeutic agent to a subject in need of treatment thereof.

Embodiment 41

A method for the treatment of brain cancer, leukemia, skin cancer, prostate cancer, thyroid cancer, colon cancer, lung cancer or sarcoma comprising administration of a compound according to any one of previous embodiments 1-37, or a pharmaceutically acceptable salt thereof, to a subject in need of treatment thereof.

Embodiment 42

A method for the treatment of glioma, glioblastoma multiforme, paraganglioma, suprantentorial primordial neuroectodermal tumors, acute myeloid leukemia, myelodysplastic syndrome, chronic myelogenous leukemia, melanoma, prostate, thyroid, colon, lung, central chondrosarcoma, central or periosteal chondroma tumors, fibrosarcoma, or cholangiocarcinoma comprising administration of a compound according to any one of previous embodiments 1-37, or a pharmaceutically acceptable salt thereof, to a subject in need of treatment thereof.

Embodiment 43

A compound according to any one of previous embodiments 1-37, or a pharmaceutically acceptable salt thereof, for use in the treatment of brain cancer, leukemia, skin cancer, prostate cancer, thyroid cancer, colon cancer, lung cancer or sarcoma.

Embodiment 44

A compound according to any one of previous embodiments 1-37, or a pharmaceutically acceptable salt thereof, for use in the treatment of glioma, glioblastoma multiforme, paraganglioma, suprantentorial primordial neuroectodermal tumors, acute myeloid leukemia, myelodysplastic syndrome, chronic myelogenous leukemia, melanoma, prostate, thyroid, colon, lung, central chondrosarcoma, central or periosteal chondroma tumors, fibrosarcoma, or cholangiocarcinoma.

Embodiment 45

A compound according to embodiment 1 which is (R)-3-(2-(((S)-1-(5-(4-chlorophenyl)oxazol-2-yl)ethyl)amino)-5-fluoropyrimidin-4-yl)-4-(fluoromethyl)oxazolidin-2-one or a pharmaceutically acceptable salt thereof.

What is claimed is:

1. A compound having the following formula:

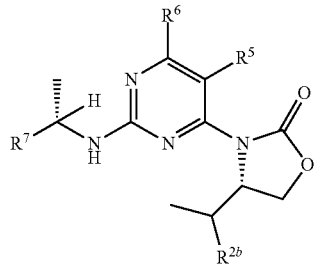

(III)

wherein $R^{2b}$ is OH, $NH_2$ or fluoro;

$R^5$ and $R^6$ are each independently hydrogen, deuterium, halo, —C(O)OCH$_3$, $C_{1-3}$ alkyl or $C_{1-3}$ haloalkyl;

$R^7$ is

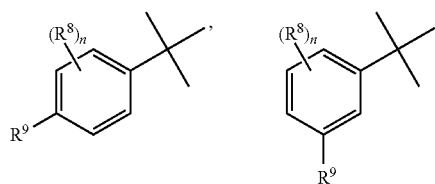

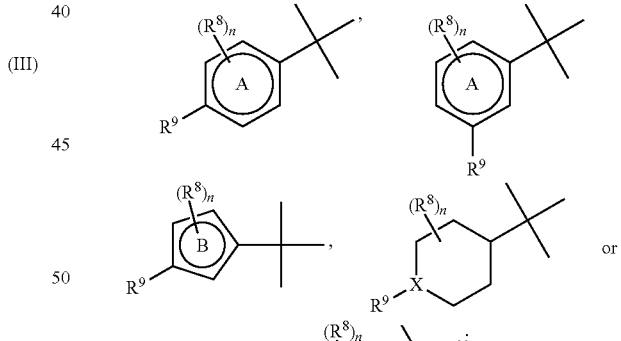

wherein:

ring A is a 6 membered heteroaryl ring having one to three nitrogen atoms;

ring B is a 5 membered heteroaryl ring having one to four heteroatoms each independently selected from the group consisting of N, O and S;

X is N or CH;

each $R^8$ is independently hydrogen, halo, $C_{1-3}$ alkyl, $C_{1-3}$ haloalkyl, $C_{1-3}$ alkoxy or $C_{1-3}$ haloalkoxy;

n is 1 or 2;

R⁹ is hydrogen, halo, C₁₋₃ haloalkyl, optionally substituted C₁₋₆ alkyl, optionally substituted C₃₋₆ cycloalkyl, optionally substituted aryl, optionally substituted 5 or 6 membered heterocyclic, optionally substituted heteroaryl, —OR⁹ᵃ, —SO₂R⁹ᵃ, —C(O)NHR⁹ᵃ, CH₂R⁹ᵇ or CHCH₃R⁹ᵇ, provided that when X is N, R⁹ is hydrogen, C₁₋₃ haloalkyl, optionally substituted C₁₋₆ alkyl, optionally substituted C₃₋₆ cycloalkyl, optionally substituted aryl, optionally substituted heteroaryl, —SO₂R⁹ᵃ or —C(O)NHR⁹ᵃ, wherein:

said C₁₋₆ alkyl is optionally substituted with one to three substituents each independently selected from the group consisting of: OH, phenyl and phenoxy, and said C₃₋₆ cycloalkyl, 5 or 6 membered heterocyclic, aryl and heteroaryl are each optionally substituted with one to three substituents each independently selected from the group consisting of: halo, hydroxyl, cyano, —NRR, C₁₋₆ alkyl, C₁₋₆ haloalkyl, C₁₋₃ alkoxy, and C₁₋₃ haloalkoxy;

R⁹ᵃ is optionally substituted C₁₋₆ alkyl, C₁₋₆ haloalkyl, optionally substituted C₃₋₆ cycloalkyl, optionally substituted phenyl, or optionally substituted heterocyclic, wherein:

said C₁₋₆ alkyl is optionally substituted with one C₃₋₆ cycloalkyl, said C₃₋₆ cycloalkyl and heterocyclic are each optionally substituted with one to three substituents each independently selected from the group consisting of: hydroxyl, CH₂OH, —NRR, cyano, C₁₋₃ alkyl, C₁₋₃ haloalkyl, and C₁₋₃ alkoxy, and said phenyl is optionally substituted with one to three substituents each independently selected from the group consisting of: halo, hydroxyl, cyano, —NRR, C₁₋₆ alkyl, C₁₋₆ haloalkyl, C₁₋₃ alkoxy, and C₁₋₃ haloalkoxy;

R⁹ᵇ is optionally substituted C₃₋₆ cycloalkyl, optionally substituted phenyl or optionally substituted heterocyclic, said C₃₋₆ cycloalkyl and heterocyclic are each optionally substituted with one to four substituents each independently selected from the group consisting of: hydroxyl, CH₂OH, —NRR, —NRC(O)CH₃, 4 to 6 membered heterocyclic, cyano, halo, C₁₋₃ alkyl, C₁₋₃ haloalkyl, and C₁₋₃ alkoxy, and said phenyl is optionally substituted with one to three substituents each independently selected from the group consisting of: halo, hydroxyl, cyano, C₁₋₆ alkyl, C₁₋₆ haloalkyl, C₁₋₃ alkoxy, and C₁₋₃ haloalkoxy; and each R is independently selected from the group consisting of H, C₁₋₃ alkyl and C₃₋₆ cycloalkyl;

or a pharmaceutically acceptable salt thereof.

2. A compound according to claim 1 wherein R⁷ is:

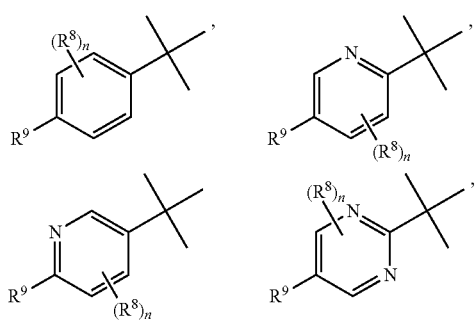

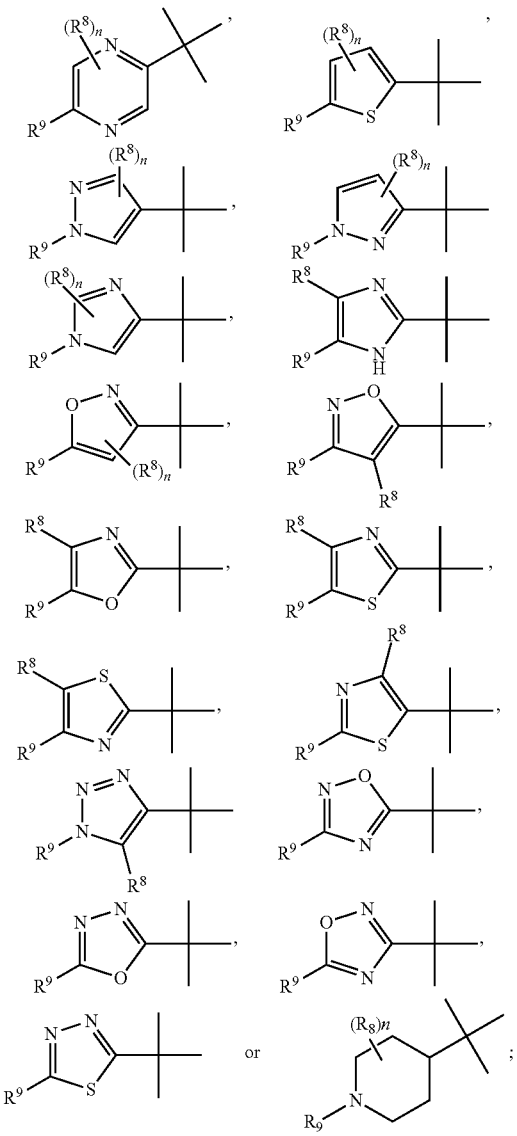

or a pharmaceutically acceptable salt thereof.

3. A compound according to claim 1 wherein R⁹ is phenyl optionally substituted with one or two substituents each independently selected from the group consisting of: fluoro, chloro, bromo, cyano, methoxy, CH₂OH, C₁₋₄ alkyl, C₁₋₄ haloalkyl and C₁₋₃ haloalkoxy; or a pharmaceutically acceptable salt thereof.

4. A compound according to claim 1 wherein R⁹ is pyrazolyl, pyridinyl, indolyl or isoquinolinyl each of which is optionally substituted; or a pharmaceutically acceptable salt thereof.

5. A compound according to claim 1 wherein R⁹ is CH₂R⁹ᵇ wherein R⁹ᵇ is piperidinyl, piperazinyl or morpholinyl each of which is optionally substituted with one to three substituents each independently selected from the group consisting of: hydroxyl, halo, CH₂OH, —NRR, cyano, C₁₋₃ alkyl, C₁₋₃ haloalkyl, and C₁₋₃ alkoxy; or a pharmaceutically acceptable salt thereof.

6. A compound according to claim 1 wherein R²ᵇ is fluoro.

7. A compound according to claim 1 wherein
R⁵ is hydrogen or halo; and
R⁶ is hydrogen, halo, methyl, CH₂F, CHF₂, or CF₃; or a pharmaceutically acceptable salt thereof.

8. A compound according to claim 7 wherein R⁵ and R⁶ are both hydrogen; or a pharmaceutically acceptable salt thereof.

9. A compound according to of claim 1 wherein $R^{2b}$ is OH; or a pharmaceutically acceptable salt thereof.

10. A compound according to claim 1 wherein $R^{2b}$ is NH₂; or a pharmaceutically acceptable salt thereof.

11. A compound according to claim 1 that is chosen from:
(R)-3-(2-(((S)-1-(1-(4-chloro-3-(trifluoromethoxy)phenyl) piperidin-4-yl)ethyl)amino)-5-fluoropyrimidin-4-yl)-4-((S)-1-hydroxyethyl)oxazolidin-2-one,
(R)-3-(5-fluoro-2-(((S)-1-(1-(2-(1,1,1-trifluoro-2-methylpropan-2-yl)pyridin-4-yl)piperidin-4-yl)ethyl)amino)pyrimidin-4-yl)-4-((S)-1-hydroxyethyl)oxazolidin-2-one,
(R)-4-((R)-1-hydroxyethyl)-3-(2-(((S)-1-phenylethyl)amino)pyrimidin-4-yl)oxazolidin-2-one,
(R)-3-(2-(((S)-1-(3-(3-chloro-4-(trifluoromethoxy)phenyl)-1,2,4-oxadiazol-5-yl)ethyl)amino)pyrimidin-4-yl)-4-((R)-1-hydroxyethyl)oxazolidin-2-one,
(R)-4-((R)-1-hydroxyethyl)-3-(2-(((S)-1-(4-phenoxyphenyl)ethyl)amino)pyrimidin-4-yl)oxazolidin-2-one,
(R)-4-((R)-1-hydroxyethyl)-3-(2-(((S)-1-(5-(3-(trifluoromethyl)phenyl)pyrazin-2-yl)ethyl)amino)pyrimidin-4-yl)oxazolidin-2-one,
(R)-3-(2-(((S)-1-(3-fluoro-4-((3,3,4-trimethylpiperazin-1-yl)methyl)phenyl)ethyl)amino)pyrimidin-4-yl)-4-((S)-1-hydroxyethyl)oxazolidin-2-one,
(R)-3-(2-(((S)-1-(4-((4,4-difluoropiperidin-1-yl)methyl)-3-fluorophenyl)ethyl)amino)pyrimidin-4-yl)-4-((S)-1-hydroxyethyl)oxazolidin-2-one,
(R)-3-(2-(((S)-1-(5-(4-fluoro-3-methylphenyl)pyridin-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(5-(3-(trifluoromethyl)phenyl)pyridin-2-yl)ethyl)amino)pyrimidin-4-yl)oxazolidin-2-one,
(R)-3-(2-(((S)-1-(6-(4-fluoro-3-methylphenyl)pyridin-3-yl)ethyl)amino)pyrimidin-4-yl)-4-((R)-1-hydroxyethyl)oxazolidin-2-one,
(R)-4-((R)-1-hydroxyethyl)-3-(2-(((S)-1-(6-(3-(trifluoromethyl)phenyl)pyridin-3-yl)ethyl)amino)pyrimidin-4-yl)oxazolidin-2-one,
(R)-3-(2-(((S)-1-(5-(4-fluoro-3-methylphenyl)pyrazin-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(2'-(trifluoromethyl)-[3,4'-bipyridin]-6-yl)ethyl)amino)pyrimidin-4-yl)oxazolidin-2-one,
(R)-4-((R)-1-hydroxyethyl)-3-(2-(((S)-1-(6'-(trifluoromethyl)-[2,3'-bipyridin]-5-yl)ethyl)amino)pyrimidin-4-yl)oxazolidin-2-one,
(R)-4-((R)-1-hydroxyethyl)-3-(2-(((S)-1-(6'-(trifluoromethyl)-[3,3'-bipyridin]-6-yl)ethyl)amino)pyrimidin-4-yl)oxazolidin-2-one,
(R)-4-((R)-1-hydroxyethyl)-3-(2-(((S)-1-(6-(trifluoromethyl)-[2,3'-bipyridin]-6'-yl)ethyl)amino)pyrimidin-4-yl)oxazolidin-2-one,
(R)-4-((R)-1-hydroxyethyl)-3-(2-(((S)-1-(4-methyl-2'-(trifluoromethyl)-[3,4'-bipyridin]-6-yl)ethyl)amino)pyrimidin-4-yl)oxazolidin-2-one,
(R)-3-(2-(((S)-1-(5-fluoro-2'-(trifluoromethyl)-[3,4'-bipyridin]-6-yl)ethyl)amino)pyrimidin-4-yl)-4-((R)-1-hydroxyethyl)oxazolidin-2-one,
(R)-4-((R)-1-hydroxyethyl)-3-(2-(((S)-1-(5-methyl-2'-(trifluoromethyl)-[3,4'-bipyridin]-6-yl)ethyl)amino)pyrimidin-4-yl)oxazolidin-2-one,
(R)-4-((R)-1-hydroxyethyl)-3-(2-(((S)-1-(2-methyl-2'-(trifluoromethyl)-[3,4'-bipyridin]-6-yl)ethyl)amino)pyrimidin-4-yl)oxazolidin-2-one,
(R)-3-(2-(((S)-1-(2'-(tert-butyl)-[3,4'-bipyridin]-6-yl)ethyl)amino)pyrimidin-4-yl)-4-((R)-1-hydroxyethyl)oxazolidin-2-one,
(R)-4-((R)-1-hydroxyethyl)-3-(2-(((S)-1-(2'-(1,1,1-trifluoro-2-methylpropan-2-yl)-[3,4'-bipyridin]-6-yl)ethyl)amino)pyrimidin-4-yl)oxazolidin-2-one,
4-(2-((S)-1-((4-((R)-4-((R)-1-hydroxyethyl)-2-oxooxazolidin-3-yl)pyrimidin-2-yl)amino)ethyl)thiazol-4-yl)benzonitrile,
(R)-3-(2-(((S)-1-(5-(4-chlorophenyl)isoxazol-3-yl)ethyl)amino)pyrimidin-4-yl)-4-((R)-1-hydroxyethyl)oxazolidin-2-one,
(R)-3-(2-(((S)-1-(4-(2,4-dichlorophenyl)thiazol-2-yl)ethyl)amino)pyrimidin-4-yl)-4-((R)-1-hydroxyethyl)oxazolidin-2-one,
(R)-3-(2-(((S)-1-(4-(4-bromophenyl)thiazol-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(4-((4-methylpiperazin-1-yl)methyl)phenyl)ethyl)amino)pyrimidin-4-yl)oxazolidin-2-one,
(R)-3-(2-(((S)-1-(54(4,4-difluoropiperidin-1-yl)methyl)pyridin-2-yl)ethyl)amino)pyrimidin-4-yl)-4-((R)-1-hydroxyethyl)oxazolidin-2-one,
(R)-3-(2-(((S)-1-(64(4,4-difluoropiperidin-1-yl)methyl)pyridin-3-yl)ethyl)amino)pyrimidin-4-yl)-4-((R)-1-hydroxyethyl)oxazolidin-2-one,
(R)-3-(2-(((S)-1-(5-(4-fluoro-3-(trifluoromethyl)phenyl)pyrimidin-2-yl)ethyl)amino)pyrimidin-4-yl)-4-((R)-1-hydroxyethyl)oxazolidin-2-one,
(R)-3-(2-(((S)-1-(5-(4-chloro-3-(trifluoromethyl)phenyl)pyrimidin-2-yl)ethyl)amino)pyrimidin-4-yl)-4-((R)-1-hydroxyethyl)oxazolidin-2-one,
(R)-3-(2-(((S)-1-(5-(3,4-dichlorophenyl)pyrimidin-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(5-(3-(trifluoromethyl)phenyl)pyrimidin-2-yl)ethyl)amino)pyrimidin-4-yl)oxazolidin-2-one,
(R)-3-(2-(((S)-1-(5-(4-chloro-3-methylphenyl)pyrimidin-2-yl)ethyl)amino)pyrimidin-4-yl)-4-((R)-1-hydroxyethyl)oxazolidin-2-one,
(R)-3-(2-(((S)-1-(5-(3-chloro-5-(trifluoromethyl)phenyl)pyrimidin-2-yl)ethyl)amino)pyrimidin-4-yl)-4-((R)-1-hydroxyethyl)oxazolidin-2-one,
(R)-3-(2-(((S)-1-(3-(4-chlorophenyl)-1,2,4-oxadiazol-5-yl)ethyl)amino)pyrimidin-4-yl)-4-((R)-1-hydroxyethyl)oxazolidin-2-one,
(R)-3-(2-(((S)-1-(5-(4-fluorophenyl)-1,3,4-oxadiazol-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(3-(2-phenoxyethyl)-1,2,4-oxadiazol-5-yl)ethyl)amino)pyrimidin-4-yl)oxazolidin-2-one,
(R)-3-(2-(((S)-1-(3-(4-fluorophenyl)-1,2,4-oxadiazol-5-yl)ethyl)amino)pyrimidin-4-yl)-4-((R)-1-hydroxyethyl)oxazolidin-2-one,
(R)-3-(2-(((S)-1-(5-(2-fluorophenyl)-1,3,4-oxadiazol-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(5-(m-tolyl)-1,3,4-oxadiazol-2-yl)ethyl)amino)pyrimidin-4-yl)oxazolidin-2-one, (R)-4-((R)-1-hydroxyethyl)-3-(2-(((S)-1-(5-(o-tolyl)-1,3,4-oxadiazol-2-yl)ethyl)amino)pyrimidin-4-yl)oxazolidin-2-one, (R)-3-(2-(((S)-1-(4-(4-chlorophenyl)-5-methylthiazol-2-yl)ethyl)amino)pyrimidin-4-yl)-4-((R)-1-hydroxyethyl)oxazolidin-2-one, (R)-3-(2-(((S)-1-(5-(3-fluorophenyl)-1,3,4-oxadiazol-2-yl)ethyl)amino)pyrimidin-4-yl)-4-((R)-1-hydroxyethyl)oxazolidin-2-one, (R)-4-((R)-1-hydroxyethyl)-3-(2-(((S)-1-(5-(pyridin-3-yl)-1,3,4-oxadiazol-2-yl)ethyl)amino)pyrimidin-4-yl)oxazolidin-2-one, (R)-3-(2-(((S)-1-(5-benzyl-1,2,4-oxadiazol-3-yl)ethyl)amino)pyrimidin-4-yl)-4-((R)-1-hydroxyethyl)oxazolidin-2-one, (R)-3-(2-(((S)-1-(5-benzyl-1,2,4-oxadiazol-3-yl)ethyl)amino)-5-fluoropyrimidin-4-yl)-4-((R)-1-hydroxyethyl)oxazolidin-2-one, (R)-3-(2-(((S)-1-(3-(4-bromophenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(3-fluoro-4-methylphenyl)-1,2,4-oxadiazol-5-yl)ethyl)amino)pyrimidin-4-yl)-4-((R)-1-hydroxyethyl)oxazolidin-2-one, (R)-3-(5-fluoro-2-(((S)-1-(3-(3-fluoro-4-methylphenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(3,4-difluorophenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(3,4-dichlorophenyl)isoxazol-5-yl)ethyl)amino)pyrimidin-4-yl)-4-((R)-1-hydroxyethyl)oxazolidin-2-one, (R)-3-(2-(((S)-1-(3-(2,4-dichlorophenyl)isoxazol-5-yl)ethyl)amino)pyrimidin-4-yl)-4-((R)-1-hydroxyethyl)oxazolidin-2-one, (R)-3-(2-(((S)-1-(3-(3,4-difluorophenyl)-1,2,4-oxadiazol-5-yl)ethyl)amino)-5-fluoropyrimidin-4-yl)-4-((R)-1-hydroxyethyl)oxazolidin-2-one, (R)-3-(2-(((S)-1-(3-(3,4-dichlorophenyl)isoxazol-5-yl)ethyl)amino)-5-fluoropyrimidin-4-yl)-4-((R)-1-hydroxyethyl)oxazolidin-2-one, (R)-3-(2-(((S)-1-(3-(2,4-dichlorophenyl)isoxazol-5-yl)ethyl)amino)-5-fluoropyrimidin-4-yl)-4-((R)-1-hydroxyethyl)oxazolidin-2-one, (R)-3-(2-(((S)-1-(4-(3-chloro-4-fluorophenyl)thiazol-2-yl)ethyl)amino)pyrimidin-4-yl)-4-((R)-1-hydroxyethyl)oxazolidin-2-one, (R)-4-((R)-1-hydroxyethyl)-3-(2-(((S)-1-(2-phenylthiazol-5-yl)ethyl)amino)pyrimidin-4-yl)oxazolidin-2-one, (R)-3-(2-(((S)-1-(3-(3-chlorophenyl)-1,2,4-oxadiazol-5-yl)ethyl)amino)pyrimidin-4-yl)-4-((R)-1-hydroxyethyl)oxazolidin-2-one, (R)-4-((R)-1-hydroxyethyl)-3-(2-(((S)-1-(3-(4-isopropylphenyl)-1,2,4-oxadiazol-5-yl)ethyl)amino)pyrimidin-4-yl)oxazolidin-2-one, (R)-4-((R)-1-hydroxyethyl)-3-(2-(((S)-1-(3-(2-(trifluoromethoxy)phenyl)-1,2,4-oxadiazol-5-yl)ethyl)amino)pyrimidin-4-yl)oxazolidin-2-one, (R)-3-(2-(((S)-1-(3-(4-fluoro-3-methylphenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(4-ethylphenyl)-1,2,4-oxadiazol-5-yl)ethyl)amino)-5-fluoropyrimidin-4-yl)-4-((R)-1-hydroxyethyl)oxazolidin-2-one, (R)-3-(2-(((S)-1-(5-(3,4-dimethylphenyl)-1,3,4-oxadiazol-2-yl)ethyl)amino)pyrimidin-4-yl)-4-((R)-1-hydroxyethyl)oxazolidin-2-one, (R)-4-((R)-1-hydroxyethyl)-3-(2-(((S)-1-(3-(isoquinolin-8-yl)-1,2,4-oxadiazol-5-yl)ethyl)amino)pyrimidin-4-yl)oxazolidin-2-one, (R)-3-(2-(((S)-1-(3-(4-chloro-2-(trifluoromethyl)phenyl)-1,2,4-oxadiazol-5-yl)ethyl)amino)pyrimidin-4-yl)-4-((R)-1-hydroxyethyl)oxazolidin-2-one, (R)-3-(5-fluoro-2-(((S)-1-(3-(4-isopropylphenyl)-1,2,4-oxadiazol-5-yl)ethyl)amino)pyrimidin-4-yl)-4-((R)-1-hydroxyethyl)oxazolidin-2-one, (R)-4-((R)-1-hydroxyethyl)-3-(2-(((S)-1-(3-(3-(trifluoromethyl)phenyl)-1,2,4-oxadiazol-5-yl)ethyl)amino)pyrimidin-4-yl)oxazolidin-2-one, (R)-3-(2-(((S)-1-(3-(4-fluoro-3-(trifluoromethoxy)phenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(3-(difluoromethoxy)phenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(4-chloro-3-methoxyphenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(2,2-difluorobenzo[d][1,3]dioxol-5-yl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(4-chloro-3-(trifluoromethyl)phenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(4-ethylphenyl)-1,2,4-oxadiazol-5-yl)ethyl)amino)pyrimidin-4-yl)-4-((R)-1-hydroxyethyl)oxazolidin-2-one, (R)-4-((R)-1-hydroxyethyl)-3-(2-(((S)-1-(3-(4-(trifluoromethyl)phenyl)-1,2,4-oxadiazol-5-yl)ethyl)amino)pyrimidin-4-yl)oxazolidin-2-one, (R)-4-((R)-1-hydroxyethyl)-3-(2-(((S)-1-(3-phenethyl-1,2,4-oxadiazol-5-yl)ethyl)amino)pyrimidin-4-yl)oxazolidin-2-one, (R)-3-(2-(((S)-1-(3-(4-chloro-3-(trifluoromethoxy)phenyl)-1,2,4-oxadiazol-5-yl)ethyl)amino)-5-fluoropyrimidin-4-yl)-4-((R)-1-hydroxyethyl)oxazolidin-2-one, (R)-4-((R)-1-hydroxyethyl)-3-(2-(((S)-1-(3-(4-(trifluoromethoxy)phenyl)-1,2,4-oxadiazol-5-yl)ethyl)amino)pyrimidin-4-yl)oxazolidin-2-one, (R)-4-((R)-1-hydroxyethyl)-3-(2-(((S)-1-(3-(3-(2,2,2-trifluoroethoxy)phenyl)-1,2,4-oxadiazol-5-yl)ethyl)amino)pyrimidin-4-yl)oxazolidin-2-one, (R)-3-(2-(((S)-1-(5-(4-chlorophenyl)-4-methyloxazol-2-yl)ethyl)amino)pyrimidin-4-yl)-4-((R)-1-hydroxyethyl)oxazolidin-2-one, (R)-3-(2-(((S)-1-(5-(4-chlorophenyl)-4-methyloxazol-2-yl)ethyl)amino)-5-fluoropyrimidin-4-yl)-4-((R)-1-hydroxyethyl)oxazolidin-2-one, (R)-3-(2-(((S)-1-(4-(4-chlorophenyl)-5-methylthiazol-2-yl)ethyl)amino)-5-fluoropyrimidin-4-yl)-4-((R)-1-hydroxyethyl)oxazolidin-2-one, (R)-3-(2-(((S)-1-(4-(4-bromophenyl)thiazol-2-yl)ethyl)amino)-5-fluoropyrimidin-4-yl)-4-((R)-1-hydroxyethyl)oxazolidin-2-one, (R)-3-(2-(((S)-1-(5-(3,4-dichlorophenyl)pyrimidin-2-yl)ethyl)amino)-5-fluoropyrimidin-4-yl)-4-((R)-1-hydroxyethyl)oxazolidin-2-one, (R)-4-((R)-1-hydroxyethyl)-3-(2-(((S)-1-(5-(3-methyl-4-(trifluoromethyl)phenyl)pyrimidin-2-yl)ethyl)amino)pyrimidin-4-yl)oxazolidin-2-one, (R)-4-((R)-1-hydroxyethyl)-3-(2-(((S)-1-(4-methyl-5-(2-(1,1,1-trifluoro-2-methylpropan-2-yl)pyridin-4-yl)thiazol-2-yl)ethyl)amino)pyrimidin-4-yl)oxazolidin-2-one, (R)-3-(2-(((S)-1-(5-(2-fluoro-3-(trifluoromethyl)phenyl)pyrimidin-2-yl)ethyl)amino)pyrimidin-4-yl)-4-((R)-1-hydroxyethyl)oxazolidin-2-one, (R)-3-(2-(((S)-1-(5-(4-chlorophenyl)oxazol-2-yl)ethyl)amino)-5-fluoropyrimidin-4-yl)-4-((R)-1-hydroxyethyl)oxazolidin-2-one, (R)-3-(2-(((S)-1-(3-(4-chlorophenyl)isoxazol-5-yl)ethyl)amino)pyrimidin-4-yl)-4-((R)-1-hydroxyethyl)oxazolidin-2-one, (R)-3-(2-(((S)-1-(5-(4-chlorophenyl)oxazol-2-yl)ethyl)amino)pyrimidin-4-yl)-4-((R)-1-hydroxyethyl)oxazolidin-2-one, (R)-3-(6-chloro-2-(((S)-1-(3-(4-chlorophenyl)-1,2,4-oxadiazol-5-yl)ethyl)amino)pyrimidin-4-yl)-4-((R)-1-hydroxyethyl)oxazolidin-2-one, (R)-3-(6-chloro-2-(((S)-1-(2-fluoro-4-(trifluoromethyl)phenyl)ethyl)amino)pyrimidin-4-yl)-4-((R)-1-hydroxyethyl)oxazolidin-2-one, (R)-3-(6-chloro-2-(((S)-1-(2-fluoro-4-(1-methyl-1H-pyrazol-4-yl)phenyl)ethyl)amino)pyrimidin-4-yl)-4-((R)-1-hydroxyethyl)oxazolidin-2-one, (R)-3-(2-(((S)-1-(3-(4-chlorophenyl)-1,2,4-oxadiazol-5-yl)ethyl)amino)-6-(difluoromethyl)pyrimidin-4-yl)-4-((R)-1-hydroxyethyl)oxazolidin-2-one, (R)-3-(2-(((S)-1-(3-(4-chlorophenyl)-1,2,4-oxadiazol-5-yl)ethyl)amino)-6-(trifluoromethyl)pyrimidin-4-yl)-4-((R)-1-hydroxyethyl)oxazolidin-2-one, (R)-3-(6-chloro-2-(((S)-1-(2,5-difluoro-4-(1-methyl-1H-pyrazol-4-yl)phenyl)ethyl)amino)pyrimidin-4-yl)-4-((R)-1-hydroxyethyl)oxazolidin-2-one, (R)-3-(6-chloro-2-(((S)-1-(5-(4-chlorophenyl)isoxazol-3-yl)ethyl)amino)pyrimidin-4-yl)-4-((R)-1-hydroxyethyl)oxazolidin-2-one, (R)-3-(6-chloro-2-(((S)-1-(5-(4-chlorophenyl)isoxazol-3-yl)ethyl)amino)pyrimidin-4-yl)-4-((R)-1-hydroxyethyl)oxazolidin-2-one, (R)-3-(6-chloro-2-(((S)-1-(5-phenylisoxazol-3-yl)ethyl)amino)pyrimidin-4-yl)-4-((R)-1-hydroxyethyl)oxazolidin-2-one, (R)-3-(6-fluoro-2-(((S)-1-(1-(4-fluorophenyl)-1H-pyrazol-4-yl)ethyl)amino)pyrimidin-4-yl)-4-((R)-1-hydroxyethyl)oxazolidin-2-one, (R)-3-(6-chloro-2-(((S)-1-(2-(4-chlorophenyl)thiazol-5-yl)ethyl)amino)pyrimidin-4-yl)-4-((R)-1-hydroxyethyl)oxazolidin-2-one, (R)-3-(2-(((S)-1-(2-(4-chlorophenyl)thiazol-5-yl)ethyl)amino)-5-fluoropyrimidin-4-yl)-4-((R)-1-hydroxyethyl)oxazolidin-2-one, (R)-3-(2-(((S)-1-(5-(4-chlorophenyl)isoxazol-3-yl)ethyl)amino)-5-fluoropyrimidin-4-yl)-4-((R)-1-hydroxyethyl)oxazolidin-2-one, (R)-3-(6-chloro-2-(((S)-1-(5-(4-chlorophenyl)-1,3,4-thiadiazol-2-yl)ethyl)amino)pyrimidin-4-yl)-4-((R)-1-hydroxyethyl)oxazolidin-2-one, (R)-3-(6-chloro-2-(((S)-1-(1-(4-chlorophenyl)-1H-pyrazol-4-yl)ethyl)amino)pyrimidin-4-yl)-4-((R)-1-hydroxyethyl)oxazolidin-2-one, (R)-3-(2-(((S)-1-(1-(4-chlorophenyl)-1H-pyrazol-4-yl)ethyl)amino)-5-fluoropyrimidin-4-yl)-4-((R)-1-hydroxyethyl)oxazolidin-2-one, (R)-3-(2-(((S)-1-(5-(4-chlorophenyl)isoxazol-3-yl)ethyl)amino)-6-(fluoromethyl)pyrimidin-4-yl)-4-((R)-1-hydroxyethyl)oxazolidin-2-one, (R)-3-(2-(((S)-1-(2-(4-chlorophenyl)thiazol-5-yl)ethyl)amino)-6-(fluoromethyl)pyrimidin-4-yl)-4-((R)-1-hydroxyethyl)oxazolidin-2-one, (R)-3-(2-(((S)-1-(2-(4-chlorophenyl)thiazol-5-yl)ethyl)amino)pyrimidin-4-yl)-4-((R)-1-hydroxyethyl)oxazolidin-2-one, (R)-3-(2-(((S)-1-(2-(4-chlorophenyl)thiazol-5-yl)ethyl)amino)pyrimidin-4-yl)-4-((R)-1-hydroxyethyl)oxazolidin-2-one, (R)-3-(2-(((S)-1-(1-(4-chlorophenyl)-1H-pyrazol-4-yl)ethyl)amino)pyrimidin-4-yl)-4-((R)-1-hydroxyethyl)oxazolidin-2-one, (R)-3-(2-(((S)-1-(1-(4-chlorophenyl)-1H-pyrazol-4-yl)ethyl)amino)pyrimidin-4-yl)-4-((R)-1-hydroxyethyl)oxazolidin-2-one, (R)-3-(6-chloro-2-(((S)-1-(3-(4-chlorophenyl)isoxazol-5-yl)ethyl)amino)pyrimidin-4-yl)-4-((R)-1-hydroxyethyl)oxazolidin-2-one, (R)-3-(2-(((S)-1-(3-(4-chlorophenyl)isoxazol-5-yl)ethyl)amino)-5-fluoropyrimidin-4-yl)-4-((R)-1-hydroxyethyl)oxazolidin-2-one, (R)-3-(2-(((S)-1-(1-(4-chlorophenyl)-1H-pyrazol-4-yl)ethyl)amino)-6-fluoropyrimidin-4-yl)-4-((R)-1-hydroxyethyl)oxazolidin-2-one, (R)-3-(2-(((S)-1-(1-(4-chlorophenyl)-1H-pyrazol-4-yl)ethyl)amino)-6-fluoropyrimidin-4-yl)-4-((R)-1-hydroxyethyl)oxazolidin-2-one, (R)-3-(6-chloro-2-(((S)-1-(5-(4-fluorophenyl)isoxazol-3-yl)ethyl)amino)pyrimidin-4-yl)-4-((R)-1-hydroxyethyl)oxazolidin-2-one, (R)-3-(6-chloro-2-(((S)-1-(5-(morpholinomethyl)isoxazol-3-yl)ethyl)amino)pyrimidin-4-yl)-4-((R)-1-hydroxyethyl)oxazolidin-2-one, (R)-3-(2-(((S)-1-(1-(4-chlorophenyl)-1H-pyrazol-4-yl)ethyl)amino)-6-methylpyrimidin-4-yl)-4-((R)-1-hydroxyethyl)oxazolidin-2-one, (R)-3-(6-chloro-2-(((S)-1-(2-(pyridin-2-yl)thiazol-5-yl)ethyl)amino)pyrimidin-4-yl)-4-((R)-1-hydroxyethyl)oxazolidin-2-one, (R)-3-(6-chloro-2-(((S)-1-(2-(pyridin-3-yl)thiazol-5-yl)ethyl)amino)pyrimidin-4-yl)-4-((R)-1-hydroxyethyl)oxazolidin-2-one, (R)-3-(6-chloro-2-(((S)-1-(2-(pyridin-4-yl)thiazol-5-yl)ethyl)amino)pyrimidin-4-yl)-4-((R)-1-hydroxyethyl)oxazolidin-2-one, (R)-3-(2-(((S)-1-(5-(4-chlorophenyl)isoxazol-3-yl)ethyl)amino)-6-methylpyrimidin-4-yl)-4-((R)-1-hydroxyethyl)oxazolidin-2-one, (R)-3-(2-(((S)-1-(2-(4-chlorophenyl)thiazol-5-yl)ethyl)amino)-6-methylpyrimidin-4-yl)-4-((R)-1-hydroxyethyl)oxazolidin-2-one, (R)-3-(2-(((S)-1-(1-(4-chlorophenyl)-1H-imidazol-4-yl)ethyl)amino)-6-methylpyrimidin-4-yl)-4-((R)-1-hydroxyethyl)oxazolidin-2-one, (R)-3-(2-(((S)-1-(3-(4-chlorophenyl)-1,2,4-oxadiazol-5-yl)ethyl)amino)-6-methylpyrimidin-4-yl)-4-((R)-1-hydroxyethyl)oxazolidin-2-one, (R)-3-(2-(((S)-1-(1-(4-chlorophenyl)-1H-pyrazol-3-yl)ethyl)amino)-6-methylpyrimidin-4-yl)-4-((R)-1-hydroxyethyl)oxazolidin-2-one, (R)-3-(2-(((S)-1-(1-(4-chlorophenyl)-1H-1,2,3-triazol-4-yl)ethyl)amino)-6-methylpyrimidin-4-yl)-4-((R)-1-hydroxyethyl)oxazolidin-2-one, (R)-3-(6-chloro-2-(((S)-1-(1-(4-chlorophenyl)-1H-1,2,3-triazol-4-yl)ethyl)amino)pyrimidin-4-yl)-4-((R)-1-hydroxyethyl)oxazolidin-2-one, (R)-3-(2-(((S)-1-(1-(4-chlorophenyl)-1H-1,2,3-triazol-4-yl)ethyl)amino)pyrimidin-4-yl)-4-((R)-1-hydroxyethyl)oxazolidin-2-one,
(R)-3-(2-(((S)-1-(4-(1,1-difluoroethyl)-2-fluorophenyl)ethyl)amino)-6-methylpyrimidin-4-yl)-4-((R)-1-hydroxyethyl)oxazolidin-2-one,
(R)-3-(2-(((S)-1-(2,5-difluoro-4-(2,2,2-trifluoroethoxy)phenyl)ethyl)amino)-6-methylpyrimidin-4-yl)-4-((R)-1-hydroxyethyl)oxazolidin-2-one,
(R)-4-((R)-1-hydroxyethyl)-3-(6-methyl-2-(((S)-1-(2-(6-methylpyridin-3-yl)thiazol-5-yl)ethyl)amino)pyrimidin-4-yl)oxazolidin-2-one,
(R)-4-((R)-1-hydroxyethyl)-3-(2-(((S)-1-(2-(6-(trifluoromethyl)pyridin-3-yl)thiazol-5-yl)ethyl)amino)pyrimidin-4-yl)oxazolidin-2-one,
(R)-4-((R)-1-hydroxyethyl)-3-(2-(((S)-1-(2-(2-(trifluoromethyl)pyridin-4-yl)thiazol-5-yl)ethyl)amino)pyrimidin-4-yl)oxazolidin-2-one,
methyl 2-(((S)-1-(2-(4-chlorophenyl)thiazol-5-yl)ethyl)amino)-6-((R)-4-((R)-1-hydroxyethyl)-2-oxooxazolidin-3-yl)pyrimidine-4-carboxylate,
(R)-3-(2-(((S)-1-(1-(4-chlorophenyl)-2-methyl-1H-imidazol-4-yl)ethyl)amino)pyrimidin-4-yl)-4-((R)-1-hydroxyethyl)oxazolidin-2-one,
(R)-3-(2-(((S)-1-(2-(4-(difluoromethyl)phenyl)thiazol-5-yl)ethyl)amino)pyrimidin-4-yl)-4-((R)-1-hydroxyethyl)oxazolidin-2-one,
(R)-3-(2-(((S)-1-(2-fluoro-4-(trifluoromethyl)phenyl)ethyl)amino)pyrimidin-4-yl)-4-((R)-1-hydroxyethyl)oxazolidin-2-one,
(R)-3-(2-(((S)-1-(4-(1-ethoxycyclopropyl)-2-fluorophenyl)ethyl)amino)pyrimidin-4-yl)-4-((R)-1-hydroxyethyl)oxazolidin-2-one,
2-chloro-N-cyclopentyl-4-((S)-1-((4-((R)-4-((R)-1-hydroxyethyl)-2-oxooxazolidin-3-yl)pyrimidin-2-yl)amino)ethyl)benzamide,
1-(3-fluoro-4-((S)-14(4-((R)-4-((R)-1-hydroxyethyl)-2-oxooxazolidin-3-yl)pyrimidin-2-yl)amino)ethyl)phenyl)cyclopropane-1-carbonitrile,
(R)-3-(2-(((S)-1-(2-fluoro-4-(1-methyl-1H-pyrazol-4-yl)phenyl)ethyl)amino)pyrimidin-4-yl)-4-((R)-1-hydroxyethyl)oxazolidin-2-one,
(R)-4-((R)-1-hydroxyethyl)-3-(2-(((S)-1-(4-(1-methyl-1H-pyrazol-4-yl)phenyl)ethyl)amino)pyrimidin-4-yl)oxazolidin-2-one,
(R)-3-(2-(((S)-1-(2-fluoro-4-(1H-pyrazol-4-yl)phenyl)ethyl)amino)pyrimidin-4-yl)-4-((R)-1-hydroxyethyl)oxazolidin-2-one,
(R)-3-(5-fluoro-2-(((S)-1-(2-fluoro-4-(trifluoromethyl)phenyl)ethyl)amino)pyrimidin-4-yl)-4-((R)-1-hydroxyethyl)oxazolidin-2-one,
(R)-3-(5-fluoro-2-(((S)-1-(2-fluoro-4-(trifluoromethyl)phenyl)ethyl)amino)pyrimidin-4-yl)-4-((R)-1-hydroxyethyl)oxazolidin-2-one,
(R)-3-(2-(((S)-1-(2-fluoro-4-(1-methylcyclopropyl)phenyl)ethyl)amino)pyrimidin-4-yl)-4-((R)-1-hydroxyethyl)oxazolidin-2-one,
(R)-3-(2-(((S)-1-(2-fluoro-4-isopropylphenyl)ethyl)amino)pyrimidin-4-yl)-4-((R)-1-hydroxyethyl)oxazolidin-2-one,
(R)-3-(5-fluoro-2-(((S)-1-(2-fluoro-4-(1-methyl-1H-pyrazol-4-yl)phenyl)ethyl)amino)pyrimidin-4-yl)-4-((R)-1-hydroxyethyl)oxazolidin-2-one,
(R)-3-(5-fluoro-2-(((S)-1-(2-fluoro-4-(1-methylcyclopropyl)phenyl)ethyl)amino)pyrimidin-4-yl)-4-((R)-1-hydroxyethyl)oxazolidin-2-one,
(R)-3-(5-fluoro-2-(((S)-1-(2-fluoro-4-(1H-pyrazol-4-yl)phenyl)ethyl)amino)pyrimidin-4-yl)-4-((R)-1-hydroxyethyl)oxazolidin-2-one,
(R)-3-(5-fluoro-2-(((S)-1-(2-fluoro-4-isopropylphenyl)ethyl)amino)pyrimidin-4-yl)-4-((R)-1-hydroxyethyl)oxazolidin-2-one,
(R)-3-(5-fluoro-2-(((S)-1-(2-fluoro-4-(2-hydroxypropan-2-yl)phenyl)ethyl)amino)pyrimidin-4-yl)-4-((R)-1-hydroxyethyl)oxazolidin-2-one,
(R)-3-(2-(((S)-1-(2,5-difluoro-4-(1-methyl-1H-pyrazol-4-yl)phenyl)ethyl)amino)-5-fluoropyrimidin-4-yl)-4-((R)-1-hydroxyethyl)oxazolidin-2-one,
(R)-3-(2-(((S)-1-(2-(4-chlorophenyl)thiazol-5-yl)ethyl)amino)pyrimidin-4-yl)-4-((S)-1-hydroxyethyl)oxazolidin-2-one,
(R)-3-(6-chloro-2-(((S)-1-(2-fluoro-4-(2-fluoropropan-2-yl)phenyl)ethyl)amino)pyrimidin-4-yl)-4-((R)-1-hydroxyethyl)oxazolidin-2-one,
(R)-3-(2-(((S)-1-(4-chloro-2-fluorophenyl)ethyl)amino)-5-fluoropyrimidin-4-yl)-4-((R)-1-hydroxyethyl)oxazolidin-2-one,
(R)-3-(2-(((S)-1-(2,5-difluoro-4-isopropylphenyl)ethyl)amino)pyrimidin-4-yl)-4-((R)-1-hydroxyethyl)oxazolidin-2-one,
(R)-3-(2-(((S)-1-(4-bromo-2,5-difluorophenyl)ethyl)amino)pyrimidin-4-yl)-4-((R)-1-hydroxyethyl)oxazolidin-2-one,
(R)-3-(2-(((S)-1-(5-chloro-6-(1,1-difluoroethyl)pyridin-3-yl)ethyl)amino)pyrimidin-4-yl)-4-((R)-1-hydroxyethyl)oxazolidin-2-one,
(R)-3-(2-(((S)-1-(5-chloro-6-(2,2,2-trifluoroethoxy)pyridin-3-yl)ethyl)amino)pyrimidin-4-yl)-4-((R)-1-hydroxyethyl)oxazolidin-2-one,
(R)-3-(2-(((S)-1-(4-bromo-2,3-difluorophenyl)ethyl)amino)pyrimidin-4-yl)-4-((R)-1-hydroxyethyl)oxazolidin-2-one,
(R)-3-(2-(((S)-1-(4-bromo-2,5-difluorophenyl)ethyl)amino)-5-fluoropyrimidin-4-yl)-4-((R)-1-hydroxyethyl)oxazolidin-2-one,
(R)-3-(2-(((S)-1-(4-bromo-2-fluorophenyl)ethyl)amino)-5-fluoropyrimidin-4-yl)-4-((R)-1-hydroxyethyl)oxazolidin-2-one,
(R)-3-(2-(((S)-1-(4-chloro-2-fluorophenyl)ethyl)amino)-5-fluoropyrimidin-4-yl)-4-((R)-1-hydroxyethyl)oxazolidin-2-one,
(R)-3-(2-(((S)-1-(5-bromo-3-fluoropyridin-2-yl)ethyl)amino)-5-fluoropyrimidin-4-yl)-4-((R)-1-hydroxyethyl)oxazolidin-2-one,
(R)-3-(2-(((S)-1-(3-(4-chlorophenyl)-1,2,4-oxadiazol-5-yl)ethyl)amino)-5-fluoropyrimidin-4-yl)-4-((R)-1-hydroxyethyl)oxazolidin-2-one,
(R)-3-(2-(((S)-1-(5-bromopyridin-2-yl)ethyl)amino)-5-fluoropyrimidin-4-yl)-4-((R)-1-hydroxyethyl)oxazolidin-2-one,
(R)-3-(2-(((S)-1-(4-bromo-3-fluorophenyl)ethyl)amino)-5-fluoropyrimidin-4-yl)-4-((R)-1-hydroxyethyl)oxazolidin-2-one,
(R)-3-(2-(((S)-1-(5-chloro-6-(1,1-difluoroethyl)pyridin-3-yl)ethyl)amino)-5-fluoropyrimidin-4-yl)-4-((R)-1-hydroxyethyl)oxazolidin-2-one,
(R)-3-(2-(((S)-1-(5-chloro-6-(2,2,2-trifluoroethoxy)pyridin-3-yl)ethyl)amino)-5-fluoropyrimidin-4-yl)-4-((R)-1-hydroxyethyl)oxazolidin-2-one,
(R)-3-(2-(((S)-1-(2,4-dichlorophenyl)ethyl)amino)-5-fluoropyrimidin-4-yl)-4-((R)-1-hydroxyethyl)oxazolidin-2-one, (R)-3-(2-(((S)-1-(6-bromopyridin-3-yl)ethyl)amino)-5-fluoropyrimidin-4-yl)-4-((R)-1-hydroxyethyl)oxazolidin-2-one,
(R)-3-(2-(((S)-1-(4-chloro-3-fluorophenyl)ethyl)amino)-5-fluoropyrimidin-4-yl)-4-((R)-1-hydroxyethyl)oxazolidin-2-one,
(R)-3-(2-(((S)-1-(3,4-dichlorophenyl)ethyl)amino)-5-fluoropyrimidin-4-yl)-4-((R)-1-hydroxyethyl)oxazolidin-2-one,
(R)-3-(2-(((S)-1-(6-chloro-5-fluoropyridin-3-yl)ethyl)amino)-5-fluoropyrimidin-4-yl)-4-((R)-1-hydroxyethyl)oxazolidin-2-one,
(R)-3-(2-(((S)-1-(5,6-dichloropyridin-3-yl)ethyl)amino)-5-fluoropyrimidin-4-yl)-4-((R)-1-hydroxyethyl)oxazolidin-2-one,
(R)-3-(2-(((S)-1-(3,5-dichloropyridin-2-yl)ethyl)amino)-5-fluoropyrimidin-4-yl)-4-((R)-1-hydroxyethyl)oxazolidin-2-one,
(R)-3-(6-chloro-2-(((S)-1-(3,5-dichloropyridin-2-yl)ethyl)amino)pyrimidin-4-yl)-4-((R)-1-hydroxyethyl)oxazolidin-2-one,
(R)-3-(6-chloro-2-(((S)-1-(3-fluoro-5-(2,2,2-trifluoroethoxy)pyridin-2-yl)ethyl)amino)pyrimidin-4-yl)-4-((R)-1-hydroxyethyl)oxazolidin-2-one,
(R)-3-(2-(((S)-1-(1-(4-chlorophenyl)-1H-pyrazol-3-yl)ethyl)amino)-5-fluoropyrimidin-4-yl)-4-((R)-1-hydroxyethyl)oxazolidin-2-one,
(R)-3-(2-(((S)-1-(1-(4-chlorophenyl)-1H-imidazol-4-yl)ethyl)amino)-5-fluoropyrimidin-4-yl)-4-((R)-1-hydroxyethyl)oxazolidin-2-one,
(R)-3-(2-(((S)-1-(2,5-difluoro-4-(2,2,2-trifluoroethoxy)phenyl)ethyl)amino)-5-fluoropyrimidin-4-yl)-4-((R)-1-hydroxyethyl)oxazolidin-2-one,
(R)-3-(5-fluoro-2-(((S)-1-(2-fluoro-4-(2,2,2-trifluoroethoxy)phenyl)ethyl)amino)pyrimidin-4-yl)-4-((R)-1-hydroxyethyl)oxazolidin-2-one,
(R)-3-(5-fluoro-2-(((S)-1-(3-fluoro-4-(2,2,2-trifluoroethoxy)phenyl)ethyl)amino)pyrimidin-4-yl)-4-((R)-1-hydroxyethyl)oxazolidin-2-one,
(R)-3-(5-fluoro-2-(((S)-1-(1-(4-fluorophenyl)-1H-pyrazol-3-yl)ethyl)amino)pyrimidin-4-yl)-4-((R)-1-hydroxyethyl)oxazolidin-2-one,
(R)-3-(5-fluoro-2-(((S)-1-(5-(2,2,2-trifluoroethoxy)pyridin-2-yl)ethyl)amino)pyrimidin-4-yl)-4-((R)-1-hydroxyethyl)oxazolidin-2-one,
(R)-3-(2-(((S)-1-(1-(4-chlorophenyl)-1H-imidazol-4-yl)ethyl)amino)pyrimidin-4-yl)-4-((R)-1-hydroxyethyl)oxazolidin-2-one,
(R)-3-(2-(((S)-1-(1-(4-chlorophenyl)-1H-pyrazol-3-yl)ethyl)amino)pyrimidin-4-yl)-4-((R)-1-hydroxyethyl)oxazolidin-2-one,
(R)-3-(6-chloro-2-(((S)-1-(1-(4-chlorophenyl)-1H-imidazol-4-yl)ethyl)amino)pyrimidin-4-yl)-4-((R)-1-hydroxyethyl)oxazolidin-2-one,
(R)-3-(6-chloro-2-(((S)-1-(1-(4-chlorophenyl)-1H-imidazol-4-yl)ethyl)amino)pyrimidin-4-yl)-4-((R)-1-hydroxyethyl)oxazolidin-2-one,
(R)-3-(6-chloro-2-(((S)-1-(1-(4-fluorophenyl)-1H-pyrazol-3-yl)ethyl)amino)pyrimidin-4-yl)-4-((R)-1-hydroxyethyl)oxazolidin-2-one,
(R)-3-(2-(((S)-1-(2,4-dichlorophenyl)ethyl)amino)pyrimidin-4-yl)-4-((R)-1-hydroxyethyl)oxazolidin-2-one,
(R)-3-(2-(((S)-1-(3,4-dichlorophenyl)ethyl)amino)pyrimidin-4-yl)-4-((R)-1-hydroxyethyl)oxazolidin-2-one,
(R)-3-(6-chloro-2-(((S)-1-(1-(4-chlorophenyl)-1H-pyrazol-3-yl)ethyl)amino)pyrimidin-4-yl)-4-((R)-1-hydroxyethyl)oxazolidin-2-one,
(R)-3-(2-(((S)-1-(2,5-difluoro-4-(2,2,2-trifluoroethoxy)phenyl)ethyl)amino)pyrimidin-4-yl)-4-((R)-1-hydroxyethyl)oxazolidin-2-one,
(R)-3-(2-(((S)-1-(2-fluoro-4-(2,2,2-trifluoroethoxy)phenyl)ethyl)amino)pyrimidin-4-yl)-4-((R)-1-hydroxyethyl)oxazolidin-2-one,
(R)-3-(2-(((S)-1-(3-fluoro-4-(2,2,2-trifluoroethoxy)phenyl)ethyl)amino)pyrimidin-4-yl)-4-((R)-1-hydroxyethyl)oxazolidin-2-one,
(R)-3-(2-(((S)-1-(5-bromopyridin-2-yl)ethyl)amino)pyrimidin-4-yl)-4-((R)-1-hydroxyethyl)oxazolidin-2-one,
(R)-3-(2-(((S)-1-(4,5-dichloro-2-fluorophenyl)ethyl)amino)pyrimidin-4-yl)-4-((R)-1-hydroxyethyl)oxazolidin-2-one,
(R)-3-(2-(((S)-1-(2,5-difluoro-4-(4-methyl-1H-imidazol-1-yl)phenyl)ethyl)amino)pyrimidin-4-yl)-4-((R)-1-hydroxyethyl)oxazolidin-2-one,
(R)-3-(5-chloro-2-(((S)-1-(4,5-dichloro-2-fluorophenyl)ethyl)amino)pyrimidin-4-yl)-4-((R)-1-hydroxyethyl)oxazolidin-2-one,
(R)-3-(2-(((S)-1-(2,5-difluoro-4-(2-methylpyridin-4-yl)phenyl)ethyl)amino)pyrimidin-4-yl)-4-((R)-1-hydroxyethyl)oxazolidin-2-one,
(R)-3-(2-(((S)-1-(2,5-difluoro-4-(6-methylpyridin-3-yl)phenyl)ethyl)amino)pyrimidin-4-yl)-4-((R)-1-hydroxyethyl)oxazolidin-2-one,
(R)-3-(2-(((S)-1-(2,5-difluoro-4-(2-(trifluoromethyl)pyridin-4-yl)phenyl)ethyl)amino)pyrimidin-4-yl)-4-((R)-1-hydroxyethyl)oxazolidin-2-one,
(R)-3-(2-(((S)-1-(2,5-difluoro-4-(6-(trifluoromethyl)pyridin-3-yl)phenyl)ethyl)amino)pyrimidin-4-yl)-4-((R)-1-hydroxyethyl)oxazolidin-2-one,
(R)-4-((R)-1-hydroxyethyl)-3-(2-(((S)-1-(4-isobutoxyphenyl)ethyl)amino)pyrimidin-4-yl)oxazolidin-2-one,
(R)-3-(5-fluoro-2-(((S)-1-(2-fluoro-4-methoxyphenyl)ethyl)amino)pyrimidin-4-yl)-4-((R)-1-hydroxyethyl)oxazolidin-2-one,
(R)-3-(2-(((S)-1-(2,3-difluorophenyl)ethyl)amino)pyrimidin-4-yl)-4-((R)-1-hydroxyethyl)oxazolidin-2-one,
(R)-3-(2-(((S)-1-(2,3-difluorophenyl)ethyl)amino)-5-fluoropyrimidin-4-yl)-4-((R)-1-hydroxyethyl)oxazolidin-2-one,
(R)-3-(2-(((S)-1-(3,4-difluorophenyl)ethyl)amino)-5-fluoropyrimidin-4-yl)-4-((R)-1-hydroxyethyl)oxazolidin-2-one,
(R)-3-(2-(((S)-1-(2,4-difluorophenyl)ethyl)amino)-5-fluoropyrimidin-4-yl)-4-((R)-1-hydroxyethyl)oxazolidin-2-one,
(R)-3-(2-(((S)-1-(3,5-difluorophenyl)ethyl)amino)-5-fluoropyrimidin-4-yl)-4-((R)-1-hydroxyethyl)oxazolidin-2-one,
(R)-3-(5-chloro-2-(((S)-1-(2'-(trifluoromethyl)-[3,4'-bipyridin]-6-yl)ethyl)amino)pyrimidin-4-yl)-4-((R)-1-hydroxyethyl)oxazolidin-2-one,
(R)-3-(5-fluoro-2-(((S)-1-(6-(2,2,2-trifluoroethoxy)pyridin-3-yl)ethyl)amino)pyrimidin-4-yl)-4-((R)-1-hydroxyethyl)oxazolidin-2-one,
(R)-3-(2-(((S)-1-(4-(difluoromethyl)-2-fluorophenyl)ethyl)amino)-5-fluoropyrimidin-4-yl)-4-((R)-1-hydroxyethyl)oxazolidin-2-one,
(R)-3-(2-(((S)-1-(4-(1,1-difluoroethyl)-2-fluorophenyl)ethyl)amino)-5-fluoropyrimidin-4-yl)-4-((R)-1-hydroxyethyl)oxazolidin-2-one,
(R)-3-(2-(((S)-1-(4-(1,1-difluoroethyl)-2-fluorophenyl)ethyl)amino)-5-fluoropyrimidin-4-yl)-4-((R)-1-hydroxyethyl)oxazolidin-2-one, (R)-3-(6-chloro-2-(((S)-1-(4-(difluoromethyl)-2-fluorophenyl)ethyl)amino)pyrimidin-4-yl)-4-((R)-1-hydroxyethyl)oxazolidin-2-one,
(R)-3-(6-chloro-2-(((S)-1-(4-(1,1-difluoroethyl)-2-fluorophenyl)ethyl)amino)pyrimidin-4-yl)-4-((R)-1-hydroxyethyl)oxazolidin-2-one,
(R)-3-(6-chloro-2-(((S)-1-(5-phenylthiophen-2-yl)ethyl)amino)pyrimidin-4-yl)-4-((R)-1-hydroxyethyl)oxazolidin-2-one,
(R)-3-(6-chloro-2-(((S)-1-(5-(pyridin-2-yl)thiophen-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(3-(((S)-tetrahydrofuran-3-yl)oxy)phenyl)ethyl)amino)pyrimidin-4-yl)oxazolidin-2-one,
(R)-4-((R)-1-hydroxyethyl)-3-(2-(((S)-1-(3-isobutoxyphenyl)ethyl)amino)pyrimidin-4-yl)oxazolidin-2-one,
(R)-3-(6-chloro-2-(((S)-1-(4-(isobutylsulfonyl)phenyl)ethyl)amino)pyrimidin-4-yl)-4-((R)-1-hydroxyethyl)oxazolidin-2-one,
(R)-4-((R)-1-hydroxyethyl)-3-(2-(((S)-1-(4-(trifluoromethoxy)phenyl)ethyl)amino)pyrimidin-4-yl)oxazolidin-2-one,
(R)-3-(2-(((S)-1-(3-fluoro-4-(trifluoromethoxy)phenyl)ethyl)amino)pyrimidin-4-yl)-4-((R)-1-hydroxyethyl)oxazolidin-2-one,
(R)-3-(2-(((S)-1-(2-fluoro-4-(trifluoromethoxy)phenyl)ethyl)amino)pyrimidin-4-yl)-4-((R)-1-hydroxyethyl)oxazolidin-2-one,
(R)-3-(2-(((S)-1-(4-(difluoromethoxy)-3-fluorophenyl)ethyl)amino)pyrimidin-4-yl)-4-((R)-1-hydroxyethyl)oxazolidin-2-one,
(R)-3-(2-(((S)-1-(4-(difluoromethoxy)-3-fluorophenyl)ethyl)amino)-5-fluoropyrimidin-4-yl)-4-((R)-1-hydroxyethyl)oxazolidin-2-one,
(R)-3-(2-(((S)-1-(4-(difluoromethoxy)phenyl)ethyl)amino)pyrimidin-4-yl)-4-((R)-1-hydroxyethyl)oxazolidin-2-one,
(R)-3-(2-(((S)-1-(4-(difluoromethoxy)-2-fluorophenyl)ethyl)amino)pyrimidin-4-yl)-4-((R)-1-hydroxyethyl)oxazolidin-2-one,
(R)-4-((R)-1-hydroxyethyl)-3-(2-(((S)-1-(3-(trifluoromethoxy)phenyl)ethyl)amino)pyrimidin-4-yl)oxazolidin-2-one,
(R)-3-(2-(((S)-1-(3-(difluoromethoxy)phenyl)ethyl)amino)pyrimidin-4-yl)-4-((R)-1-hydroxyethyl)oxazolidin-2-one,
(R)-3-(2-(((S)-1-(4-(difluoromethoxy)-2-fluorophenyl)ethyl)amino)-5-fluoropyrimidin-4-yl)-4-((R)-1-hydroxyethyl)oxazolidin-2-one,
(R)-3-(5-fluoro-2-(((S)-1-(3-(trifluoromethoxy)phenyl)ethyl)amino)pyrimidin-4-yl)-4-((R)-1-hydroxyethyl)oxazolidin-2-one,
(R)-3-(2-(((S)-1-(3-(difluoromethoxy)phenyl)ethyl)amino)-5-fluoropyrimidin-4-yl)-4-((R)-1-hydroxyethyl)oxazolidin-2-one,
(R)-4-((R)-1-hydroxyethyl)-3-(2-(((S)-1-(3-phenoxyphenyl)ethyl)amino)pyrimidin-4-yl)oxazolidin-2-one,
(R)-4-((R)-1-hydroxyethyl)-3-(2-(((S)-1-(4-isopropoxyphenyl)ethyl)amino)pyrimidin-4-yl)oxazolidin-2-one,
(R)-4-((R)-1-hydroxyethyl)-3-(2-(((S)-1-(4-isobutoxy-3-methylphenyl)ethyl)amino)pyrimidin-4-yl)oxazolidin-2-one,
(R)-3-(6-chloro-2-(((S)-1-(4-(trifluoromethoxy)phenyl)ethyl)amino)pyrimidin-4-yl)-4-((R)-1-hydroxyethyl)oxazolidin-2-one,
(R)-3-(5-fluoro-2-(((S)-1-(4-(trifluoromethoxy)phenyl)ethyl)amino)pyrimidin-4-yl)-4-((R)-1-hydroxyethyl)oxazolidin-2-one,
(R)-3-(6-chloro-2-(((S)-1-(2-fluoro-4-(trifluoromethoxy)phenyl)ethyl)amino)pyrimidin-4-yl)-4-((R)-1-hydroxyethyl)oxazolidin-2-one,
(R)-3-(5-fluoro-2-(((S)-1-(2-fluoro-4-(trifluoromethoxy)phenyl)ethyl)amino)pyrimidin-4-yl)-4-((R)-1-hydroxyethyl)oxazolidin-2-one,
(R)-3-(5-fluoro-2-(((S)-1-(2-fluoro-4-isobutoxyphenyl)ethyl)amino)pyrimidin-4-yl)-4-((R)-1-hydroxyethyl)oxazolidin-2-one,
(R)-3-(2-(((S)-1-(4-(difluoromethoxy)phenyl)ethyl)amino)-5-fluoropyrimidin-4-yl)-4-((R)-1-hydroxyethyl)oxazolidin-2-one,
(R)-3-(5-fluoro-2-(((S)-1-(3-fluoro-4-(trifluoromethoxy)phenyl)ethyl)amino)pyrimidin-4-yl)-4-((R)-1-hydroxyethyl)oxazolidin-2-one,
(R)-3-(6-chloro-2-(((S)-1-(4-(difluoromethoxy)phenyl)ethyl)amino)pyrimidin-4-yl)-4-((R)-1-hydroxyethyl)oxazolidin-2-one,
(R)-3-(6-chloro-2-(((S)-1-(3-fluoro-4-(trifluoromethoxy)phenyl)ethyl)amino)pyrimidin-4-yl)-4-((R)-1-hydroxyethyl)oxazolidin-2-one,
(R)-3-(5-fluoro-2-(((S)-1-(4-(isobutylsulfonyl)phenyl)ethyl)amino)pyrimidin-4-yl)-4-((R)-1-hydroxyethyl)oxazolidin-2-one,
(R)-3-(5-fluoro-2-(((S)-1-(4-(isopropylsulfonyl)phenyl)ethyl)amino)pyrimidin-4-yl)-4-((R)-1-hydroxyethyl)oxazolidin-2-one,
(R)-3-(6-chloro-2-(((S)-1-(4-(isopropylsulfonyl)phenyl)ethyl)amino)pyrimidin-4-yl)-4-((R)-1-hydroxyethyl)oxazolidin-2-one,
(R)-3-(2-(((S)-1-(4-(cyclopropylmethoxy)phenyl)ethyl)amino)pyrimidin-4-yl)-4-((R)-1-hydroxyethyl)oxazolidin-2-one,
(R)-3-(2-(((S)-1-(2-fluoro-4-isobutoxyphenyl)ethyl)amino)pyrimidin-4-yl)-4-((R)-1-hydroxyethyl)oxazolidin-2-one,
(S)-4-((R)-1-aminoethyl)-3-(2-(((S)-1-(2-(4-chlorophenyl)thiazol-5-yl)ethyl)amino)pyrimidin-4-yl)oxazolidin-2-one,
(S)-4-((R)-1-aminoethyl)-3-(2-(((S)-1-(2-(4-chlorophenyl)thiazol-5-yl)ethyl)amino)pyrimidin-4-yl)oxazolidin-2-one,
(S)-4-((R)-1-aminoethyl)-3-(2-(((S)-1-(1-(4-chlorophenyl)-1H-imidazol-4-yl)ethyl)amino)pyrimidin-4-yl)oxazolidin-2-one,
(S)-4-((R)-1-aminoethyl)-3-(2-(((S)-1-(5-(4-chlorophenyl)isoxazol-3-yl)ethyl)amino)pyrimidin-4-yl)oxazolidin-2-one,
(S)-4-((R)-1-aminoethyl)-3-(2-(((S)-1-(2,5-difluoro-4-(6-methylpyridin-3-yl)phenyl)ethyl)amino)pyrimidin-4-yl)oxazolidin-2-one,
(R)-3-(2-(((S)-1-(1-(4-chlorophenyl)-1H-imidazol-4-yl)ethyl)amino)pyrimidin-4-yl)-4-((R)-1-fluoroethyl)oxazolidin-2-one,
(R)-3-(2-(((S)-1-(1-(4-chlorophenyl)-1H-imidazol-4-yl)ethyl)amino)pyrimidin-4-yl)-4-((R)-1-fluoroethyl)oxazolidin-2-one,
(R)-3-(2-(((S)-1-(5-(4-chlorophenyl)isoxazol-3-yl)ethyl)amino)pyrimidin-4-yl)-4-((R)-1-fluoroethyl)oxazolidin-2-one,
(R)-3-(2-(((S)-1-(2-(4-chlorophenyl)thiazol-5-yl)ethyl)amino)pyrimidin-4-yl)-4-((R)-1-fluoroethyl)oxazolidin-2-one, (R)-3-(2-(((S)-1-(1-(4-chlorophenyl)-1H-imidazol-4-yl)ethyl)amino)pyrimidin-4-yl)-4-((S)-1-fluoroethyl)oxazolidin-2-one, (R)-3-(2-(((S)-1-(2-(4-chlorophenyl)thiazol-5-yl)ethyl)amino)pyrimidin-4-yl)-4-((S)-1-fluoroethyl)oxazolidin-2-one, (R)-3-(2-(((S)-1-(5-(4-chlorophenyl)isoxazol-3-yl)ethyl)amino)pyrimidin-4-yl)-4-((S)-1-fluoroethyl)oxazolidin-2-one, (R)-3-(2-(((S)-1-(3-(4-chlorophenyl)-1,2,4-oxadiazol-5-yl)ethyl)amino)pyrimidin-4-yl)-4-((R)-1-fluoroethyl)oxazolidin-2-one, (R)-4-((R)-1-fluoroethyl)-3-(2-(((S)-1-(2-(2-(trifluoromethyl)pyridin-4-yl)thiazol-5-yl)ethyl)amino)pyrimidin-4-yl)oxazolidin-2-one, (R)-4-((R)-1-fluoroethyl)-3-(2-(((S)-1-(2-(6-(trifluoromethyl)pyridin-3-yl)thiazol-5-yl)ethyl)amino)pyrimidin-4-yl)oxazolidin-2-one, (R)-3-(2-(((S)-1-(1-(4-chlorophenyl)-1H-pyrazol-4-yl)ethyl)amino)pyrimidin-4-yl)-4-((R)-1-fluoroethyl)oxazolidin-2-one, (R)-3-(2-(((S)-1-(2-(4-chlorophenyl)thiazol-5-yl)ethyl)amino)-5-fluoropyrimidin-4-yl)-4-((R)-1-fluoroethyl)oxazolidin-2-one, (R)-3-(2-(((S)-1-(1-(4-chlorophenyl)-1H-pyrazol-4-yl)ethyl)amino)pyrimidin-4-yl)-4-((S)-1-fluoroethyl)oxazolidin-2-one, (R)-3-(2-(((S)-1-(1-(4-chlorophenyl)-1H-pyrazol-4-yl)ethyl)amino)-5-fluoropyrimidin-4-yl)-4-((R)-1-fluoroethyl)oxazolidin-2-one, (R)-3-(2-(((S)-1-(5-(4-chlorophenyl)isoxazol-3-yl)ethyl)amino)-5-fluoropyrimidin-4-yl)-4-((R)-1-fluoroethyl)oxazolidin-2-one, (R)-3-(2-(((S)-1-(1-(4-chlorophenyl)-1H-imidazol-4-yl)ethyl)amino)-5-fluoropyrimidin-4-yl)-4-((R)-1-fluoroethyl)oxazolidin-2-one, (R)-3-(2-(((S)-1-(1-(4-chlorophenyl)-2-methyl-1H-imidazol-4-yl)ethyl)amino)pyrimidin-4-yl)-4-((S)-1-fluoroethyl)oxazolidin-2-one, (R)-4-((S)-1-fluoroethyl)-3-(2-(((S)-1-(1-(4-fluorophenyl)-1H-imidazol-4-yl)ethyl)amino)pyrimidin-4-yl)oxazolidin-2-one, (R)-4-((S)-1-fluoroethyl)-3-(2-(((S)-1-(1-(4-fluorophenyl)-1H-imidazol-4-yl)ethyl)amino)pyrimidin-4-yl)oxazolidin-2-one, (R)-3-(2-(((S)-1-(2,5-difluoro-4-(4-methyl-1H-imidazol-1-yl)phenyl)ethyl)amino)pyrimidin-4-yl)-4-((S)-1-fluoroethyl)oxazolidin-2-one, (R)-4-((S)-1-fluoroethyl)-3-(2-(((S)-1-(1-(6-(trifluoromethyl)pyridin-3-yl)-1H-pyrazol-3-yl)ethyl)amino)pyrimidin-4-yl)oxazolidin-2-one, (R)-3-(2-(((S)-1-(1-(4-chlorophenyl)-2-methyl-1H-imidazol-4-yl)ethyl)amino)pyrimidin-4-yl)-4-((R)-1-fluoroethyl)oxazolidin-2-one, (R)-4-((S)-1-hydroxyethyl)-3-(2-(((S)-1-(1-(2-(1,1,1-trifluoro-2-methylpropan-2-yl)pyridin-4-yl)piperidin-4-yl)ethyl)amino)pyrimidin-4-yl)oxazolidin-2-one, (R)-3-(2-(((S)-1-(1-(4-chloro-3-(trifluoromethoxy)phenyl)piperidin-4-yl)ethyl)amino)pyrimidin-4-yl)-4-((S)-1-hydroxyethyl)oxazolidin-2-one, (R)-4-((R)-1-hydroxyethyl)-3-(2-(((S)-1-(3-(1-methyl-1H-indol-6-yl)-1,2,4-oxadiazol-5-yl)ethyl)amino)pyrimidin-4-yl)oxazolidin-2-one, (R)-4-((R)-1-hydroxyethyl)-3-(2-(((S)-1-(3-(3-(trifluoromethoxy)phenyl)-1,2,4-oxadiazol-5-yl)ethyl)amino)pyrimidin-4-yl)oxazolidin-2-one, (R)-3-(2-(((S)-1-(3-(1,2-dimethyl-1H-indol-4-yl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(4-chloro-3-(trifluoromethoxy)phenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(4-chloro-3-methylphenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(4-bromo-3-methoxyphenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(3-(tert-butyl)phenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(2,3-dihydro-1H-inden-5-yl)-1,2,4-oxadiazol-5-yl)ethyl)amino)pyrimidin-4-yl)-4-((R)-1-hydroxyethyl)oxazolidin-2-one, (R)-3-(2-(((S)-1-(5-(4-chlorophenyl)-1,2,4-oxadiazol-3-yl)ethyl)amino)pyrimidin-4-yl)-4-((R)-1-hydroxyethyl)oxazolidin-2-one, (R)-4-((S)-1-fluoroethyl)-3-(2-(((S)-1-(2-(2-(trifluoromethyl)pyridin-4-yl)thiazol-5-yl)ethyl)amino)pyrimidin-4-yl)oxazolidin-2-one, (R)-3-(2-(((S)-1-(1-(4-(difluoromethyl)-3-fluorophenyl)-1H-imidazol-4-yl)ethyl)amino)-5-fluoropyrimidin-4-yl)-4-((S)-1-fluoroethyl)oxazolidin-2-one, (R)-3-(2-(((S)-1-(1-(4-(difluoromethyl)phenyl)-1H-imidazol-4-yl)ethyl)amino)-5-fluoropyrimidin-4-yl)-4-((S)-1-fluoroethyl)oxazolidin-2-one, (R)-3-(2-(((S)-1-(1-(4-chloro-3-fluorophenyl)-1H-imidazol-4-yl)ethyl)amino)-5-fluoropyrimidin-4-yl)-4-((S)-1-fluoroethyl)oxazolidin-2-one, (R)-3-(2-(((S)-1-(1-(3,5-difluorophenyl)-1H-imidazol-4-yl)ethyl)amino)-5-fluoropyrimidin-4-yl)-4-((S)-1-fluoroethyl)oxazolidin-2-one, (R)-3-(2-(((S)-1-(1-(4-chlorophenyl)-1H-imidazol-4-yl)ethyl)amino)-5-fluoropyrimidin-4-yl)-4-((S)-1-fluoroethyl)oxazolidin-2-one, (R)-3-(5-fluoro-2-(((S)-1-(1-(4-fluorophenyl)-1H-imidazol-4-yl)ethyl)amino)pyrimidin-4-yl)-4-((S)-1-fluoroethyl)oxazolidin-2-one, (R)-3-(2-(((S)-1-(5-(4-chlorophenyl)isoxazol-3-yl)ethyl)amino)-5-fluoropyrimidin-4-yl)-4-((S)-1-fluoroethyl)oxazolidin-2-one, (R)-3-(2-(((S)-1-(1-(4-chlorophenyl)-1H-pyrazol-4-yl)ethyl)amino)-5-fluoropyrimidin-4-yl)-4-((S)-1-fluoroethyl)oxazolidin-2-one, (R)-3-(2-(((S)-1-(1-(3,5-difluorophenyl)-1H-imidazol-4-yl)ethyl)amino)pyrimidin-4-yl)-4-((S)-1-fluoroethyl)oxazolidin-2-one, (R)-3-(2-(((S)-1-(1-(4-(difluoromethyl)-3-fluorophenyl)-1H-imidazol-4-yl)ethyl)amino)pyrimidin-4-yl)-4-((S)-1-fluoroethyl)oxazolidin-2-one, (R)-3-(2-(((S)-1-(1-(4-(difluoromethyl)phenyl)-1H-imidazol-4-yl)ethyl)amino)pyrimidin-4-yl)-4-((S)-1-fluoroethyl)oxazolidin-2-one, (R)-3-(2-(((S)-1-(1-(4-(difluoromethyl)phenyl)-1H-imidazol-4-yl)ethyl)amino)pyrimidin-4-yl)-4-((S)-1-fluoroethyl)oxazolidin-2-one, (R)-3-(2-(((S)-1-(1-(3-chloro-4-fluorophenyl)-1H-imidazol-4-yl)ethyl)amino)pyrimidin-4-yl)-4-((S)-1-fluoroethyl)oxazolidin-2-one, (R)-3-(2-(((S)-1-(1-(4-chloro-3-fluorophenyl)-1H-imidazol-4-yl)ethyl)amino)pyrimidin-4-yl)-4-((S)-1-fluoroethyl)oxazolidin-2-one, (R)-3-(2-(((S)-1-(1-(3,4-difluorophenyl)-1H-imidazol-4-yl)ethyl)amino)pyrimidin-4-yl)-4-((S)-1-fluoroethyl)oxazolidin-2-one, (R)-3-(2-(((S)-1-(2,5-difluoro-4-(1-methyl-1H-pyrazol-4-yl)phenyl)ethyl)amino)pyrimidin-4-yl)-4-((S)-1-fluoroethyl)oxazolidin-2-one, (R)-3-(5-fluoro-2-(((S)-1-(1-(4-fluorophenyl)-1H-imidazol-4-yl)ethyl)amino)pyrimidin-4-yl)-4-((R)-1-fluoroethyl)oxazolidin-2-one, (R)-3-(5-fluoro-2-(((S)-1-(5-fluoro-2'-(trifluoromethyl)-[3,4'-bipyridin]-6-yl)ethyl)amino)pyrimidin-4-yl)-4-((R)-1-fluoroethyl)oxazolidin-2-one, (R)-3-(2-(((S)-1-(5-fluoro-2'-(trifluoromethyl)-[3,4'-bipyridin]-6-yl)ethyl)amino)pyrimidin-4-yl)-4-((S)-1-fluoroethyl)oxazolidin-2-one, (R)-3-(2-(((S)-1-(5-fluoro-2'-(trifluoromethyl)-[3,4'-bipyridin]-6-yl)ethyl)amino)pyrimidin-4-yl)-4-((S)-1-fluoroethyl)oxazolidin-2-one, (R)-3-(2-(((S)-1-(5-fluoro-2'-(trifluoromethyl)-[3,4'-bipyridin]-6-yl)ethyl)amino)pyrimidin-4-yl)-4-((R)-1-fluoroethyl)oxazolidin-2-one, (R)-3-(5-fluoro-2-(((S)-1-(5-fluoro-2'-(trifluoromethyl)[3,4'-bipyridin]-6-yl)ethyl)amino)pyrimidin-4-yl)-4-((S)-1-fluoroethyl)oxazolidin-2-one, (R)-4-((S)-1-fluoroethyl)-3-(2-(((S)-1-(4-methyl-2'-(trifluoromethyl)-[3,4'-bipyridin]-6-yl)ethyl)amino)pyrimidin-4-yl)oxazolidin-2-one, (R)-3-(2-(((S)-1-(5-(2-fluoro-3-(trifluoromethyl)phenyl)pyrimidin-2-yl)ethyl)amino)pyrimidin-4-yl)-4-((S)-1-fluoroethyl)oxazolidin-2-one, (R)-4-((S)-1-fluoroethyl)-3-(2-(((S)-1-(2'-(trifluoromethyl)-[3,4'-bipyridin]-6-yl)ethyl)amino)pyrimidin-4-yl)oxazolidin-2-one, (R)-3-(2-(((S)-1-(5-(4-fluoro-3-methylphenyl)pyrimidin-2-yl)ethyl)amino)pyrimidin-4-yl)-4-((S)-1-fluoroethyl)oxazolidin-2-one, (R)-3-(5-fluoro-2-(((S)-1-(4-methyl-2'-(trifluoromethyl)-[3,4'-bipyridin]-6-yl)ethyl)amino)pyrimidin-4-yl)-4-((S)-1-fluoroethyl)oxazolidin-2-one, (R)-3-(2-(((S)-1-(1-(4-chloro-2-fluorophenyl)-1H-imidazol-4-yl)ethyl)amino)pyrimidin-4-yl)-4-((S)-1-fluoroethyl)oxazolidin-2-one, (R)-3-(2-(((S)-1-(1-(4-chloro-2-fluorophenyl)-1H-imidazol-4-yl)ethyl)amino)-5-fluoropyrimidin-4-yl)-4-((S)-1-fluoroethyl)oxazolidin-2-one, (R)-3-(2-(((S)-1-(1-(2,4-difluorophenyl)-1H-imidazol-4-yl)ethyl)amino)pyrimidin-4-yl)-4-((S)-1-fluoroethyl)oxazolidin-2-one, and (R)-3-(2-(((S)-1-(1-(2,4-difluorophenyl)-1H-imidazol-4-yl)ethyl)amino)-5-fluoropyrimidin-4-yl)-4-((S)-1-fluoroethyl)oxazolidin-2-one;

or a pharmaceutically acceptable salt thereof.

12. A pharmaceutical composition comprising a compound according to claim 1, or a pharmaceutically acceptable salt thereof, and a pharmaceutically acceptable carrier or excipient.

13. A method of treating AML (acute myeloid leukemia) comprising administering a compound according to claim 1 or a pharmaceutically acceptable salt thereof, to a subject in need thereof.

14. A method of treating AML (acute myeloid leukemia) according to claim 13, wherein the compound is chosen from:

(R)-3-(2-(((S)-1-(1-(4-chloro-3-(trifluoromethoxy)phenyl)piperidin-4-yl)ethyl)amino)-5-fluoropyrimidin-4-yl)-4-((S)-1-hydroxyethyl)oxazolidin-2-one, (R)-3-(5-fluoro-2-(((S)-1-(1-(2-(1,1,1-trifluoro-2-methylpropan-2-yl)pyridin-4-yl)piperidin-4-yl)ethyl)amino)pyrimidin-4-yl)-4-((S)-1-hydroxyethyl)oxazolidin-2-one, (R)-4-((R)-1-hydroxyethyl)-3-(2-(((S)-1-phenylethyl)amino)pyrimidin-4-yl)oxazolidin-2-one, (R)-3-(2-(((S)-1-(3-(3-chloro-4-(trifluoromethoxy)phenyl)-1,2,4-oxadiazol-5-yl)ethyl)amino)pyrimidin-4-yl)-4-((R)-1-hydroxyethyl)oxazolidin-2-one, (R)-4-((R)-1-hydroxyethyl)-3-(2-(((S)-1-(4-phenoxyphenyl)ethyl)amino)pyrimidin-4-yl)oxazolidin-2-one, (R)-4-((R)-1-hydroxyethyl)-3-(2-(((S)-1-(5-(3-(trifluoromethyl)phenyl)pyrazin-2-yl)ethyl)amino)pyrimidin-4-yl)oxazolidin-2-one, (R)-3-(2-(((S)-1-(3-fluoro-4-((3,3,4-trimethylpiperazin-1-yl)methyl)phenyl)ethyl)amino)pyrimidin-4-yl)-4-((S)-1-hydroxyethyl)oxazolidin-2-one, (R)-3-(2-(((S)-1-(4-((4,4-difluoropiperidin-1-yl)methyl)-3-fluorophenyl)ethyl)amino)pyrimidin-4-yl)-4-((S)-1-hydroxyethyl)oxazolidin-2-one, (R)-3-(2-(((S)-1-(5-(4-fluoro-3-methylphenyl)pyridin-2-yl)ethyl)amino)pyrimidin-4-yl)-4-((R)-1-hydroxyethyl)oxazolidin-2-one, (R)-4-((R)-1-hydroxyethyl)-3-(2-(((S)-1-(5-(3-(trifluoromethyl)phenyl)pyridin-2-yl)ethyl)amino)pyrimidin-4-yl)oxazolidin-2-one, (R)-3-(2-(((S)-1-(6-(4-fluoro-3-methylphenyl)pyridin-3-yl)ethyl)amino)pyrimidin-4-yl)-4-((R)-1-hydroxyethyl)oxazolidin-2-one, (R)-4-((R)-1-hydroxyethyl)-3-(2-(((S)-1-(6-(3-(trifluoromethyl)phenyl)pyridin-3-yl)ethyl)amino)pyrimidin-4-yl)oxazolidin-2-one, (R)-3-(2-(((S)-1-(5-(4-fluoro-3-methylphenyl)pyrazin-2-yl)ethyl)amino)pyrimidin-4-yl)-4-((R)-1-hydroxyethyl)oxazolidin-2-one, (R)-4-((R)-1-hydroxyethyl)-3-(2-(((S)-1-(2'-(trifluoromethyl)-[3,4'-bipyridin]-6-yl)ethyl)amino)pyrimidin-4-yl)oxazolidin-2-one, (R)-4-((R)-1-hydroxyethyl)-3-(2-(((S)-1-(6'-(trifluoromethyl)-[2,3'-bipyridin]-5-yl)ethyl)amino)pyrimidin-4-yl)oxazolidin-2-one, (R)-4-((R)-1-hydroxyethyl)-3-(2-(((S)-1-(6'-(trifluoromethyl)-[3,3'-bipyridin]-6-yl)ethyl)amino)pyrimidin-4-yl)oxazolidin-2-one, (R)-4-((R)-1-hydroxyethyl)-3-(2-(((S)-1-(6-(trifluoromethyl)-[2,3'-bipyridin]-6'-yl)ethyl)amino)pyrimidin-4-yl)oxazolidin-2-one, (R)-4-((R)-1-hydroxyethyl)-3-(2-(((S)-1-(4-methyl-2'-(trifluoromethyl)-[3,4'-bipyridin]-6-yl)ethyl)amino)pyrimidin-4-yl)oxazolidin-2-one, (R)-3-(2-(((S)-1-(5-fluoro-2'-(trifluoromethyl)-[3,4'-bipyridin]-6-yl)ethyl)amino)pyrimidin-4-yl)-4-((R)-1-hydroxyethyl)oxazolidin-2-one, (R)-4-((R)-1-hydroxyethyl)-3-(2-(((S)-1-(5-methyl-2'-(trifluoromethyl)-[3,4'-bipyridin]-6-yl)ethyl)amino)pyrimidin-4-yl)oxazolidin-2-one, (R)-4-((R)-1-hydroxyethyl)-3-(2-(((S)-1-(2-methyl-2'-(trifluoromethyl)-[3,4'-bipyridin]-6-yl)ethyl)amino)pyrimidin-4-yl)oxazolidin-2-one, (R)-3-(2-(((S)-1-(2'-(tert-butyl)-[3,4'-bipyridin]-6-yl)ethyl)amino)pyrimidin-4-yl)-4-((R)-1-hydroxyethyl)oxazolidin-2-one, (R)-4-((R)-1-hydroxyethyl)-3-(2-(((S)-1-(2'-(1,1,1-trifluoro-2-methylpropan-2-yl)-[3,4'-bipyridin]-6-yl)ethyl)amino)pyrimidin-4-yl)oxazolidin-2-one, 4-(2-(((S)-1-((4-((R)-4-((R)-1-hydroxyethyl)-2-oxooxazolidin-3-yl)pyrimidin-2-yl)amino)ethyl)thiazol-4-yl)benzonitrile,
(R)-3-(2-(((S)-1-(5-(4-chlorophenyl)isoxazol-3-yl)ethyl)amino)pyrimidin-4-yl)-4-((R)-1-hydroxyethyl)oxazolidin-2-one,
(R)-3-(2-(((S)-1-(4-(2,4-dichlorophenyl)thiazol-2-yl)ethyl)amino)pyrimidin-4-yl)-4-((R)-1-hydroxyethyl)oxazolidin-2-one,
(R)-3-(2-(((S)-1-(4-(4-bromophenyl)thiazol-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(4-((4-methylpiperazin-1-yl)methyl)phenyl)ethyl)amino)pyrimidin-4-yl)oxazolidin-2-one,
(R)-3-(2-(((S)-1-(5(4,4-difluoropiperidin-1-yl)methyl)pyridin-2-yl)ethyl)amino)pyrimidin-4-yl)-4-((R)-1-hydroxyethyl)oxazolidin-2-one,
(R)-3-(2-(((S)-1-(6(4,4-difluoropiperidin-1-yl)methyl)pyridin-3-yl)ethyl)amino)pyrimidin-4-yl)-4-((R)-1-hydroxyethyl)oxazolidin-2-one,
(R)-3-(2-(((S)-1-(5-(4-fluoro-3-(trifluoromethyl)phenyl)pyrimidin-2-yl)ethyl)amino)pyrimidin-4-yl)-4-((R)-1-hydroxyethyl)oxazolidin-2-one,
(R)-3-(2-(((S)-1-(5-(4-chloro-3-(trifluoromethyl)phenyl)pyrimidin-2-yl)ethyl)amino)pyrimidin-4-yl)-4-((R)-1-hydroxyethyl)oxazolidin-2-one,
(R)-3-(2-(((S)-1-(5-(3,4-dichlorophenyl)pyrimidin-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(5-(3-(trifluoromethyl)phenyl)pyrimidin-2-yl)ethyl)amino)pyrimidin-4-yl)oxazolidin-2-one,
(R)-3-(2-(((S)-1-(5-(4-chloro-3-methylphenyl)pyrimidin-2-yl)ethyl)amino)pyrimidin-4-yl)-4-((R)-1-hydroxyethyl)oxazolidin-2-one,
(R)-3-(2-(((S)-1-(5-(3-chloro-5-(trifluoromethyl)phenyl)pyrimidin-2-yl)ethyl)amino)pyrimidin-4-yl)-4-((R)-1-hydroxyethyl)oxazolidin-2-one,
(R)-3-(2-(((S)-1-(3-(4-chlorophenyl)-1,2,4-oxadiazol-5-yl)ethyl)amino)pyrimidin-4-yl)-4-((R)-1-hydroxyethyl)oxazolidin-2-one,
(R)-3-(2-(((S)-1-(5-(4-fluorophenyl)-1,3,4-oxadiazol-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(3-(2-phenoxyethyl)-1,2,4-oxadiazol-5-yl)ethyl)amino)pyrimidin-4-yl)oxazolidin-2-one,
(R)-3-(2-(((S)-1-(3-(4-fluorophenyl)-1,2,4-oxadiazol-5-yl)ethyl)amino)pyrimidin-4-yl)-4-((R)-1-hydroxyethyl)oxazolidin-2-one,
(R)-3-(2-(((S)-1-(5-(2-fluorophenyl)-1,3,4-oxadiazol-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(5-(m-tolyl)-1,3,4-oxadiazol-2-yl)ethyl)amino)pyrimidin-4-yl)oxazolidin-2-one,
(R)-4-((R)-1-hydroxyethyl)-3-(2-(((S)-1-(5-(o-tolyl)-1,3,4-oxadiazol-2-yl)ethyl)amino)pyrimidin-4-yl)oxazolidin-2-one,
(R)-3-(2-(((S)-1-(4-(4-chlorophenyl)-5-methylthiazol-2-yl)ethyl)amino)pyrimidin-4-yl)-4-((R)-1-hydroxyethyl)oxazolidin-2-one,
(R)-3-(2-(((S)-1-(5-(3-fluorophenyl)-1,3,4-oxadiazol-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(5-(pyridin-3-yl)-1,3,4-oxadiazol-2-yl)ethyl)amino)pyrimidin-4-yl)oxazolidin-2-one,
(R)-3-(2-(((S)-1-(5-benzyl-1,2,4-oxadiazol-3-yl)ethyl)amino)pyrimidin-4-yl)-4-((R)-1-hydroxyethyl)oxazolidin-2-one,
(R)-3-(2-(((S)-1-(5-benzyl-1,2,4-oxadiazol-3-yl)ethyl)amino)-5-fluoropyrimidin-4-yl)-4-((R)-1-hydroxyethyl)oxazolidin-2-one,
(R)-3-(2-(((S)-1-(3-(4-bromophenyl)-1,2,4-oxadiazol-5-yl)ethyl)amino)pyrimidin-4-yl)-4-((R)-1-hydroxyethyl)oxazolidin-2-one,
(R)-3-(2-(((S)-1-(3-(3-fluoro-4-methylphenyl)-1,2,4-oxadiazol-5-yl)ethyl)amino)pyrimidin-4-yl)-4-((R)-1-hydroxyethyl)oxazolidin-2-one,
(R)-3-(5-fluoro-2-(((S)-1-(3-(3-fluoro-4-methylphenyl)-1,2,4-oxadiazol-5-yl)ethyl)amino)pyrimidin-4-yl)-4-((R)-1-hydroxyethyl)oxazolidin-2-one,
(R)-3-(2-(((S)-1-(3-(3,4-difluorophenyl)-1,2,4-oxadiazol-5-yl)ethyl)amino)pyrimidin-4-yl)-4-((R)-1-hydroxyethyl)oxazolidin-2-one,
(R)-3-(2-(((S)-1-(3-(3,4-dichlorophenyl)isoxazol-5-yl)ethyl)amino)pyrimidin-4-yl)-4-((R)-1-hydroxyethyl)oxazolidin-2-one,
(R)-3-(2-(((S)-1-(3-(2,4-dichlorophenyl)isoxazol-5-yl)ethyl)amino)pyrimidin-4-yl)-4-((R)-1-hydroxyethyl)oxazolidin-2-one,
(R)-3-(2-(((S)-1-(3-(3,4-difluorophenyl)-1,2,4-oxadiazol-5-yl)ethyl)amino)-5-fluoropyrimidin-4-yl)-4-((R)-1-hydroxyethyl)oxazolidin-2-one,
(R)-3-(2-(((S)-1-(3-(3,4-dichlorophenyl)isoxazol-5-yl)ethyl)amino)-5-fluoropyrimidin-4-yl)-4-((R)-1-hydroxyethyl)oxazolidin-2-one,
(R)-3-(2-(((S)-1-(3-(2,4-dichlorophenyl)isoxazol-5-yl)ethyl)amino)-5-fluoropyrimidin-4-yl)-4-((R)-1-hydroxyethyl)oxazolidin-2-one,
(R)-3-(2-(((S)-1-(4-(3-chloro-4-fluorophenyl)thiazol-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(2-phenylthiazol-5-yl)ethyl)amino)pyrimidin-4-yl)oxazolidin-2-one,
(R)-3-(2-(((S)-1-(3-(3-chlorophenyl)-1,2,4-oxadiazol-5-yl)ethyl)amino)pyrimidin-4-yl)-4-((R)-1-hydroxyethyl)oxazolidin-2-one,
(R)-4-((R)-1-hydroxyethyl)-3-(2-(((S)-1-(3-(4-isopropylphenyl)-1,2,4-oxadiazol-5-yl)ethyl)amino)pyrimidin-4-yl)oxazolidin-2-one,
(R)-4-((R)-1-hydroxyethyl)-3-(2-(((S)-1-(3-(2-(trifluoromethoxy)phenyl)-1,2,4-oxadiazol-5-yl)ethyl)amino)pyrimidin-4-yl)oxazolidin-2-one,
(R)-3-(2-(((S)-1-(3-(4-fluoro-3-methylphenyl)-1,2,4-oxadiazol-5-yl)ethyl)amino)pyrimidin-4-yl)-4-((R)-1-hydroxyethyl)oxazolidin-2-one,
(R)-3-(2-(((S)-1-(3-(4-ethylphenyl)-1,2,4-oxadiazol-5-yl)ethyl)amino)-5-fluoropyrimidin-4-yl)-4-((R)-1-hydroxyethyl)oxazolidin-2-one,
(R)-3-(2-(((S)-1-(5-(3,4-dimethylphenyl)-1,3,4-oxadiazol-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(3-(isoquinolin-8-yl)-1,2,4-oxadiazol-5-yl)ethyl)amino)pyrimidin-4-yl)oxazolidin-2-one,
(R)-3-(2-(((S)-1-(3-(4-chloro-2-(trifluoromethyl)phenyl)-1,2,4-oxadiazol-5-yl)ethyl)amino)pyrimidin-4-yl)-4-((R)-1-hydroxyethyl)oxazolidin-2-one, (R)-3-(5-fluoro-2-(((S)-1-(3-(4-isopropylphenyl)-1,2,4-oxadiazol-5-yl)ethyl)amino)pyrimidin-4-yl)-4-((R)-1-hydroxyethyl)oxazolidin-2-one, (R)-4-((R)-1-hydroxyethyl)-3-(2-(((S)-1-(3-(3-(trifluoromethyl)phenyl)-1,2,4-oxadiazol-5-yl)ethyl)amino)pyrimidin-4-yl)oxazolidin-2-one, (R)-3-(2-(((S)-1-(3-(4-fluoro-3-(trifluoromethoxy)phenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(3-(difluoromethoxy)phenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(4-chloro-3-methoxyphenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(2,2-difluorobenzo[d][1,3]dioxol-5-yl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(4-chloro-3-(trifluoromethyl)phenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(4-ethylphenyl)-1,2,4-oxadiazol-5-yl)ethyl)amino)pyrimidin-4-yl)-4-((R)-1-hydroxyethyl)oxazolidin-2-one, (R)-4-((R)-1-hydroxyethyl)-3-(2-(((S)-1-(3-(4-(trifluoromethyl)phenyl)-1,2,4-oxadiazol-5-yl)ethyl)amino)pyrimidin-4-yl)oxazolidin-2-one, (R)-4-((R)-1-hydroxyethyl)-3-(2-(((S)-1-(3-phenethyl-1,2,4-oxadiazol-5-yl)ethyl)amino)pyrimidin-4-yl)oxazolidin-2-one, (R)-3-(2-(((S)-1-(3-(4-chloro-3-(trifluoromethoxy)phenyl)-1,2,4-oxadiazol-5-yl)ethyl)amino)-5-fluoropyrimidin-4-yl)-4-((R)-1-hydroxyethyl)oxazolidin-2-one, (R)-4-((R)-1-hydroxyethyl)-3-(2-(((S)-1-(3-(4-(trifluoromethoxy)phenyl)-1,2,4-oxadiazol-5-yl)ethyl)amino)pyrimidin-4-yl)oxazolidin-2-one, (R)-4-((R)-1-hydroxyethyl)-3-(2-(((S)-1-(3-(3-(2,2,2-trifluoroethoxy)phenyl)-1,2,4-oxadiazol-5-yl)ethyl)amino)pyrimidin-4-yl)oxazolidin-2-one, (R)-3-(2-(((S)-1-(5-(4-chlorophenyl)-4-methyloxazol-2-yl)ethyl)amino)pyrimidin-4-yl)-4-((R)-1-hydroxyethyl)oxazolidin-2-one, (R)-3-(2-(((S)-1-(5-(4-chlorophenyl)-4-methyloxazol-2-yl)ethyl)amino)-5-fluoropyrimidin-4-yl)-4-((R)-1-hydroxyethyl)oxazolidin-2-one, (R)-3-(2-(((S)-1-(4-(4-chlorophenyl)-5-methylthiazol-2-yl)ethyl)amino)-5-fluoropyrimidin-4-yl)-4-((R)-1-hydroxyethyl)oxazolidin-2-one, (R)-3-(2-(((S)-1-(4-(4-bromophenyl)thiazol-2-yl)ethyl)amino)-5-fluoropyrimidin-4-yl)-4-((R)-1-hydroxyethyl)oxazolidin-2-one, (R)-3-(2-(((S)-1-(5-(3,4-dichlorophenyl)pyrimidin-2-yl)ethyl)amino)-5-fluoropyrimidin-4-yl)-4-((R)-1-hydroxyethyl)oxazolidin-2-one, (R)-4-((R)-1-hydroxyethyl)-3-(2-(((S)-1-(5-(3-methyl-4-(trifluoromethyl)phenyl)pyrimidin-2-yl)ethyl)amino)pyrimidin-4-yl)oxazolidin-2-one, (R)-4-((R)-1-hydroxyethyl)-3-(2-(((S)-1-(4-methyl-5-(2-(1,1,1-trifluoro-2-methylpropan-2-yl)pyridin-4-yl)thiazol-2-yl)ethyl)amino)pyrimidin-4-yl)oxazolidin-2-one, (R)-3-(2-(((S)-1-(5-(2-fluoro-3-(trifluoromethyl)phenyl)pyrimidin-2-yl)ethyl)amino)pyrimidin-4-yl)-4-((R)-1-hydroxyethyl)oxazolidin-2-one, (R)-3-(2-(((S)-1-(5-(4-chlorophenyl)oxazol-2-yl)ethyl)amino)-5-fluoropyrimidin-4-yl)-4-((R)-1-hydroxyethyl)oxazolidin-2-one, (R)-3-(2-(((S)-1-(3-(4-chlorophenyl)isoxazol-5-yl)ethyl)amino)pyrimidin-4-yl)-4-((R)-1-hydroxyethyl)oxazolidin-2-one, (R)-3-(2-(((S)-1-(5-(4-chlorophenyl)oxazol-2-yl)ethyl)amino)pyrimidin-4-yl)-4-((R)-1-hydroxyethyl)oxazolidin-2-one, (R)-3-(6-chloro-2-(((S)-1-(3-(4-chlorophenyl)-1,2,4-oxadiazol-5-yl)ethyl)amino)pyrimidin-4-yl)-4-((R)-1-hydroxyethyl)oxazolidin-2-one, (R)-3-(6-chloro-2-(((S)-1-(2-fluoro-4-(trifluoromethyl)phenyl)ethyl)amino)pyrimidin-4-yl)-4-((R)-1-hydroxyethyl)oxazolidin-2-one, (R)-3-(6-chloro-2-(((S)-1-(2-fluoro-4-(1-methyl-1H-pyrazol-4-yl)phenyl)ethyl)amino)pyrimidin-4-yl)-4-((R)-1-hydroxyethyl)oxazolidin-2-one, (R)-3-(2-(((S)-1-(3-(4-chlorophenyl)-1,2,4-oxadiazol-5-yl)ethyl)amino)-6-(difluoromethyl)pyrimidin-4-yl)-4-((R)-1-hydroxyethyl)oxazolidin-2-one, (R)-3-(2-(((S)-1-(3-(4-chlorophenyl)-1,2,4-oxadiazol-5-yl)ethyl)amino)-6-(trifluoromethyl)pyrimidin-4-yl)-4-((R)-1-hydroxyethyl)oxazolidin-2-one, (R)-3-(6-chloro-2-(((S)-1-(2,5-difluoro-4-(1-methyl-1H-pyrazol-4-yl)phenyl)ethyl)amino)pyrimidin-4-yl)-4-((R)-1-hydroxyethyl)oxazolidin-2-one, (R)-3-(6-chloro-2-(((S)-1-(5-(4-chlorophenyl)isoxazol-3-yl)ethyl)amino)pyrimidin-4-yl)-4-((R)-1-hydroxyethyl)oxazolidin-2-one, (R)-3-(6-chloro-2-(((S)-1-(5-(4-chlorophenyl)isoxazol-3-yl)ethyl)amino)pyrimidin-4-yl)-4-((R)-1-hydroxyethyl)oxazolidin-2-one, (R)-3-(6-chloro-2-(((S)-1-(5-phenylisoxazol-3-yl)ethyl)amino)pyrimidin-4-yl)-4-((R)-1-hydroxyethyl)oxazolidin-2-one, (R)-3-(6-fluoro-2-(((S)-1-(1-(4-fluorophenyl)-1H-pyrazol-4-yl)ethyl)amino)pyrimidin-4-yl)-4-((R)-1-hydroxyethyl)oxazolidin-2-one, (R)-3-(6-chloro-2-(((S)-1-(2-(4-chlorophenyl)thiazol-5-yl)ethyl)amino)pyrimidin-4-yl)-4-((R)-1-hydroxyethyl)oxazolidin-2-one, (R)-3-(2-(((S)-1-(2-(4-chlorophenyl)thiazol-5-yl)ethyl)amino)-5-fluoropyrimidin-4-yl)-4-((R)-1-hydroxyethyl)oxazolidin-2-one, (R)-3-(2-(((S)-1-(5-(4-chlorophenyl)isoxazol-3-yl)ethyl)amino)-5-fluoropyrimidin-4-yl)-4-((R)-1-hydroxyethyl)oxazolidin-2-one, (R)-3-(6-chloro-2-(((S)-1-(5-(4-chlorophenyl)-1,3,4-thiadiazol-2-yl)ethyl)amino)pyrimidin-4-yl)-4-((R)-1-hydroxyethyl)oxazolidin-2-one, (R)-3-(6-chloro-2-(((S)-1-(1-(4-chlorophenyl)-1H-pyrazol-4-yl)ethyl)amino)pyrimidin-4-yl)-4-((R)-1-hydroxyethyl)oxazolidin-2-one, (R)-3-(2-(((S)-1-(1-(4-chlorophenyl)-1H-pyrazol-4-yl)ethyl)amino)-5-fluoropyrimidin-4-yl)-4-((R)-1-hydroxyethyl)oxazolidin-2-one, (R)-3-(2-(((S)-1-(5-(4-chlorophenyl)isoxazol-3-yl)ethyl)amino)-6-(fluoromethyl)pyrimidin-4-yl)-4-((R)-1-hydroxyethyl)oxazolidin-2-one, (R)-3-(2-(((S)-1-(2-(4-chlorophenyl)thiazol-5-yl)ethyl)amino)-6-(fluoromethyl)pyrimidin-4-yl)-4-((R)-1-hydroxyethyl)oxazolidin-2-one, (R)-3-(2-(((S)-1-(2-(4-chlorophenyl)thiazol-5-yl)ethyl)amino)pyrimidin-4-yl)-4-((R)-1-hydroxyethyl)oxazolidin-2-one, (R)-3-(2-(((S)-1-(2-(4-chlorophenyl)thiazol-5-yl)ethyl)amino)pyrimidin-4-yl)-4-((R)-1-hydroxyethyl)oxazolidin-2-one, (R)-3-(2-(((S)-1-(1-(4-chlorophenyl)-1H-pyrazol-4-yl)ethyl)amino)pyrimidin-4-yl)-4-((R)-1-hydroxyethyl)oxazolidin-2-one, (R)-3-(2-(((S)-1-(1-(4-chlorophenyl)-1H-pyrazol-4-yl)ethyl)amino)pyrimidin-4-yl)-4-((R)-1-hydroxyethyl)oxazolidin-2-one, (R)-3-(6-chloro-2-(((S)-1-(3-(4-chlorophenyl)isoxazol-5-yl)ethyl)amino)pyrimidin-4-yl)-4-((R)-1-hydroxyethyl)oxazolidin-2-one, (R)-3-(2-(((S)-1-(3-(4-chlorophenyl)isoxazol-5-yl)ethyl)amino)-5-fluoropyrimidin-4-yl)-4-((R)-1-hydroxyethyl)oxazolidin-2-one, (R)-3-(2-(((S)-1-(1-(4-chlorophenyl)-1H-pyrazol-4-yl)ethyl)amino)-6-fluoropyrimidin-4-yl)-4-((R)-1-hydroxyethyl)oxazolidin-2-one, (R)-3-(2-(((S)-1-(1-(4-chlorophenyl)-1H-pyrazol-4-yl)ethyl)amino)-6-fluoropyrimidin-4-yl)-4-((R)-1-hydroxyethyl)oxazolidin-2-one, (R)-3-(6-chloro-2-(((S)-1-(5-(4-fluorophenyl)isoxazol-3-yl)ethyl)amino)pyrimidin-4-yl)-4-((R)-1-hydroxyethyl)oxazolidin-2-one, (R)-3-(6-chloro-2-(((S)-1-(5-(morpholinomethyl)isoxazol-3-yl)ethyl)amino)pyrimidin-4-yl)-4-((R)-1-hydroxyethyl)oxazolidin-2-one, (R)-3-(2-(((S)-1-(1-(4-chlorophenyl)-1H-pyrazol-4-yl)ethyl)amino)-6-methylpyrimidin-4-yl)-4-((R)-1-hydroxyethyl)oxazolidin-2-one, (R)-3-(6-chloro-2-(((S)-1-(2-(pyridin-2-yl)thiazol-5-yl)ethyl)amino)pyrimidin-4-yl)-4-((R)-1-hydroxyethyl)oxazolidin-2-one, (R)-3-(6-chloro-2-(((S)-1-(2-(pyridin-3-yl)thiazol-5-yl)ethyl)amino)pyrimidin-4-yl)-4-((R)-1-hydroxyethyl)oxazolidin-2-one, (R)-3-(6-chloro-2-(((S)-1-(2-(pyridin-4-yl)thiazol-5-yl)ethyl)amino)pyrimidin-4-yl)-4-((R)-1-hydroxyethyl)oxazolidin-2-one, (R)-3-(2-(((S)-1-(5-(4-chlorophenyl)isoxazol-3-yl)ethyl)amino)-6-methylpyrimidin-4-yl)-4-((R)-1-hydroxyethyl)oxazolidin-2-one, (R)-3-(2-(((S)-1-(2-(4-chlorophenyl)thiazol-5-yl)ethyl)amino)-6-methylpyrimidin-4-yl)-4-((R)-1-hydroxyethyl)oxazolidin-2-one, (R)-3-(2-(((S)-1-(1-(4-chlorophenyl)-1H-imidazol-4-yl)ethyl)amino)-6-methylpyrimidin-4-yl)-4-((R)-1-hydroxyethyl)oxazolidin-2-one, (R)-3-(2-(((S)-1-(3-(4-chlorophenyl)-1,2,4-oxadiazol-5-yl)ethyl)amino)-6-methylpyrimidin-4-yl)-4-((R)-1-hydroxyethyl)oxazolidin-2-one, (R)-3-(2-(((S)-1-(1-(4-chlorophenyl)-1H-pyrazol-3-yl)ethyl)amino)-6-methylpyrimidin-4-yl)-4-((R)-1-hydroxyethyl)oxazolidin-2-one, (R)-3-(2-(((S)-1-(1-(4-chlorophenyl)-1H-1,2,3-triazol-4-yl)ethyl)amino)-6-methylpyrimidin-4-yl)-4-((R)-1-hydroxyethyl)oxazolidin-2-one, (R)-3-(6-chloro-2-(((S)-1-(1-(4-chlorophenyl)-1H-1,2,3-triazol-4-yl)ethyl)amino)pyrimidin-4-yl)-4-((R)-1-hydroxyethyl)oxazolidin-2-one, (R)-3-(2-(((S)-1-(1-(4-chlorophenyl)-1H-1,2,3-triazol-4-yl)ethyl)amino)pyrimidin-4-yl)-4-((R)-1-hydroxyethyl)oxazolidin-2-one, (R)-3-(2-(((S)-1-(4-(1,1-difluoroethyl)-2-fluorophenyl)ethyl)amino)-6-methylpyrimidin-4-yl)-4-((R)-1-hydroxyethyl)oxazolidin-2-one, (R)-3-(2-(((S)-1-(2,5-difluoro-4-(2,2,2-trifluoroethoxy)phenyl)ethyl)amino)-6-methylpyrimidin-4-yl)-4-((R)-1-hydroxyethyl)oxazolidin-2-one, (R)-4-((R)-1-hydroxyethyl)-3-(6-methyl-2-(((S)-1-(2-(6-methylpyridin-3-yl)thiazol-5-yl)ethyl)amino)pyrimidin-4-yl)oxazolidin-2-one, (R)-4-((R)-1-hydroxyethyl)-3-(2-(((S)-1-(2-(6-(trifluoromethyl)pyridin-3-yl)thiazol-5-yl)ethyl)amino)pyrimidin-4-yl)oxazolidin-2-one, (R)-4-((R)-1-hydroxyethyl)-3-(2-(((S)-1-(2-(2-(trifluoromethyl)pyridin-4-yl)thiazol-5-yl)ethyl)amino)pyrimidin-4-yl)oxazolidin-2-one, methyl 2-(((S)-1-(2-(4-chlorophenyl)thiazol-5-yl)ethyl)amino)-6-((R)-4-((R)-1-hydroxyethyl)-2-oxooxazolidin-3-yl)pyrimidine-4-carboxylate, (R)-3-(2-(((S)-1-(1-(4-chlorophenyl)-2-methyl-1H-imidazol-4-yl)ethyl)amino)pyrimidin-4-yl)-4-((R)-1-hydroxyethyl)oxazolidin-2-one, (R)-3-(2-(((S)-1-(2-(4-(difluoromethyl)phenyl)thiazol-5-yl)ethyl)amino)pyrimidin-4-yl)-4-((R)-1-hydroxyethyl)oxazolidin-2-one, (R)-3-(2-(((S)-1-(2-fluoro-4-(trifluoromethyl)phenyl)ethyl)amino)pyrimidin-4-yl)-4-((R)-1-hydroxyethyl)oxazolidin-2-one, (R)-3-(2-(((S)-1-(4-(1-ethoxycyclopropyl)-2-fluorophenyl)ethyl)amino)pyrimidin-4-yl)-4-((R)-1-hydroxyethyl)oxazolidin-2-one, 2-chloro-N-cyclopentyl-4-((S)-1-((4-((R)-4-((R)-1-hydroxyethyl)-2-oxooxazolidin-3-yl)pyrimidin-2-yl)amino)ethyl)benzamide, 1-(3-fluoro-4-((S)-14(4-((R)-4-((R)-1-hydroxyethyl)-2-oxooxazolidin-3-yl)pyrimidin-2-yl)amino)ethyl)phenyl)cyclopropane-1-carbonitrile, (R)-3-(2-(((S)-1-(2-fluoro-4-(1-methyl-1H-pyrazol-4-yl)phenyl)ethyl)amino)pyrimidin-4-yl)-4-((R)-1-hydroxyethyl)oxazolidin-2-one, (R)-4-((R)-1-hydroxyethyl)-3-(2-(((S)-1-(4-(1-methyl-1H-pyrazol-4-yl)phenyl)ethyl)amino)pyrimidin-4-yl)oxazolidin-2-one, (R)-3-(2-(((S)-1-(2-fluoro-4-(1H-pyrazol-4-yl)phenyl)ethyl)amino)pyrimidin-4-yl)-4-((R)-1-hydroxyethyl)oxazolidin-2-one, (R)-3-(5-fluoro-2-(((S)-1-(2-fluoro-4-(trifluoromethyl)phenyl)ethyl)amino)pyrimidin-4-yl)-4-((R)-1-hydroxyethyl)oxazolidin-2-one, (R)-3-(5-fluoro-2-(((S)-1-(2-fluoro-4-(trifluoromethyl)phenyl)ethyl)amino)pyrimidin-4-yl)-4-((R)-1-hydroxyethyl)oxazolidin-2-one, (R)-3-(2-(((S)-1-(2-fluoro-4-(1-methylcyclopropyl)phenyl)ethyl)amino)pyrimidin-4-yl)-4-((R)-1-hydroxyethyl)oxazolidin-2-one, (R)-3-(2-(((S)-1-(2-fluoro-4-isopropylphenyl)ethyl)amino)pyrimidin-4-yl)-4-((R)-1-hydroxyethyl)oxazolidin-2-one, (R)-3-(5-fluoro-2-(((S)-1-(2-fluoro-4-(1-methyl-1H-pyrazol-4-yl)phenyl)ethyl)amino)pyrimidin-4-yl)-4-((R)-1-hydroxyethyl)oxazolidin-2-one, (R)-3-(5-fluoro-2-(((S)-1-(2-fluoro-4-(1-methylcyclopropyl)phenyl)ethyl)amino)pyrimidin-4-yl)-4-((R)-1-hydroxyethyl)oxazolidin-2-one, (R)-3-(5-fluoro-2-(((S)-1-(2-fluoro-4-(1H-pyrazol-4-yl)phenyl)ethyl)amino)pyrimidin-4-yl)-4-((R)-1-hydroxyethyl)oxazolidin-2-one, (R)-3-(5-fluoro-2-(((S)-1-(2-fluoro-4-isopropylphenyl)ethyl)amino)pyrimidin-4-yl)-4-((R)-1-hydroxyethyl)oxazolidin-2-one, (R)-3-(5-fluoro-2-(((S)-1-(2-fluoro-4-(2-hydroxypropan-2-yl)phenyl)ethyl)amino)pyrimidin-4-yl)-4-((R)-1-hydroxyethyl)oxazolidin-2-one, (R)-3-(2-(((S)-1-(2,5-difluoro-4-(1-methyl-1H-pyrazol-4-yl)phenyl)ethyl)amino)-5-fluoropyrimidin-4-yl)-4-((R)-1-hydroxyethyl)oxazolidin-2-one, (R)-3-(2-(((S)-1-(2-(4-chlorophenyl)thiazol-5-yl)ethyl)amino)pyrimidin-4-yl)-4-((S)-1-hydroxyethyl)oxazolidin-2-one, (R)-3-(6-chloro-2-(((S)-1-(2-fluoro-4-(2-fluoropropan-2-yl)phenyl)ethyl)amino)pyrimidin-4-yl)-4-((R)-1-hydroxyethyl)oxazolidin-2-one, (R)-3-(2-(((S)-1-(4-chloro-2-fluorophenyl)ethyl)amino)-5-fluoropyrimidin-4-yl)-4-((R)-1-hydroxyethyl)oxazolidin-2-one, (R)-3-(2-(((S)-1-(2,5-difluoro-4-isopropylphenyl)ethyl)amino)pyrimidin-4-yl)-4-((R)-1-hydroxyethyl)oxazolidin-2-one, (R)-3-(2-(((S)-1-(4-bromo-2,5-difluorophenyl)ethyl)amino)pyrimidin-4-yl)-4-((R)-1-hydroxyethyl)oxazolidin-2-one, (R)-3-(2-(((S)-1-(5-chloro-6-(1,1-difluoroethyl)pyridin-3-yl)ethyl)amino)pyrimidin-4-yl)-4-((R)-1-hydroxyethyl)oxazolidin-2-one, (R)-3-(2-(((S)-1-(5-chloro-6-(2,2,2-trifluoroethoxy)pyridin-3-yl)ethyl)amino)pyrimidin-4-yl)-4-((R)-1-hydroxyethyl)oxazolidin-2-one, (R)-3-(2-(((S)-1-(4-bromo-2,3-difluorophenyl)ethyl)amino)pyrimidin-4-yl)-4-((R)-1-hydroxyethyl)oxazolidin-2-one, (R)-3-(2-(((S)-1-(4-bromo-2,5-difluorophenyl)ethyl)amino)-5-fluoropyrimidin-4-yl)-4-((R)-1-hydroxyethyl)oxazolidin-2-one, (R)-3-(2-(((S)-1-(4-bromo-2-fluorophenyl)ethyl)amino)-5-fluoropyrimidin-4-yl)-4-((R)-1-hydroxyethyl)oxazolidin-2-one, (R)-3-(2-(((S)-1-(4-chloro-2-fluorophenyl)ethyl)amino)-5-fluoropyrimidin-4-yl)-4-((R)-1-hydroxyethyl)oxazolidin-2-one, (R)-3-(2-(((S)-1-(5-bromo-3-fluoropyridin-2-yl)ethyl)amino)-5-fluoropyrimidin-4-yl)-4-((R)-1-hydroxyethyl)oxazolidin-2-one, (R)-3-(2-(((S)-1-(3-(4-chlorophenyl)-1,2,4-oxadiazol-5-yl)ethyl)amino)-5-fluoropyrimidin-4-yl)-4-((R)-1-hydroxyethyl)oxazolidin-2-one, (R)-3-(2-(((S)-1-(5-bromopyridin-2-yl)ethyl)amino)-5-fluoropyrimidin-4-yl)-4-((R)-1-hydroxyethyl)oxazolidin-2-one, (R)-3-(2-(((S)-1-(4-bromo-3-fluorophenyl)ethyl)amino)-5-fluoropyrimidin-4-yl)-4-((R)-1-hydroxyethyl)oxazolidin-2-one, (R)-3-(2-(((S)-1-(5-chloro-6-(1,1-difluoroethyl)pyridin-3-yl)ethyl)amino)-5-fluoropyrimidin-4-yl)-4-((R)-1-hydroxyethyl)oxazolidin-2-one, (R)-3-(2-(((S)-1-(5-chloro-6-(2,2,2-trifluoroethoxy)pyridin-3-yl)ethyl)amino)-5-fluoropyrimidin-4-yl)-4-((R)-1-hydroxyethyl)oxazolidin-2-one, (R)-3-(2-(((S)-1-(2,4-dichlorophenyl)ethyl)amino)-5-fluoropyrimidin-4-yl)-4-((R)-1-hydroxyethyl)oxazolidin-2-one, (R)-3-(2-(((S)-1-(6-bromopyridin-3-yl)ethyl)amino)-5-fluoropyrimidin-4-yl)-4-((R)-1-hydroxyethyl)oxazolidin-2-one, (R)-3-(2-(((S)-1-(4-chloro-3-fluorophenyl)ethyl)amino)-5-fluoropyrimidin-4-yl)-4-((R)-1-hydroxyethyl)oxazolidin-2-one, (R)-3-(2-(((S)-1-(3,4-dichlorophenyl)ethyl)amino)-5-fluoropyrimidin-4-yl)-4-((R)-1-hydroxyethyl)oxazolidin-2-one, (R)-3-(2-(((S)-1-(6-chloro-5-fluoropyridin-3-yl)ethyl)amino)-5-fluoropyrimidin-4-yl)-4-((R)-1-hydroxyethyl)oxazolidin-2-one, (R)-3-(2-(((S)-1-(5,6-dichloropyridin-3-yl)ethyl)amino)-5-fluoropyrimidin-4-yl)-4-((R)-1-hydroxyethyl)oxazolidin-2-one, (R)-3-(2-(((S)-1-(3,5-dichloropyridin-2-yl)ethyl)amino)-5-fluoropyrimidin-4-yl)-4-((R)-1-hydroxyethyl)oxazolidin-2-one, (R)-3-(6-chloro-2-(((S)-1-(3,5-dichloropyridin-2-yl)ethyl)amino)pyrimidin-4-yl)-4-((R)-1-hydroxyethyl)oxazolidin-2-one, (R)-3-(6-chloro-2-(((S)-1-(3-fluoro-5-(2,2,2-trifluoroethoxy)pyridin-2-yl)ethyl)amino)pyrimidin-4-yl)-4-((R)-1-hydroxyethyl)oxazolidin-2-one, (R)-3-(2-(((S)-1-(1-(4-chlorophenyl)-1H-pyrazol-3-yl)ethyl)amino)-5-fluoropyrimidin-4-yl)-4-((R)-1-hydroxyethyl)oxazolidin-2-one, (R)-3-(2-(((S)-1-(1-(4-chlorophenyl)-1H-imidazol-4-yl)ethyl)amino)-5-fluoropyrimidin-4-yl)-4-((R)-1-hydroxyethyl)oxazolidin-2-one, (R)-3-(2-(((S)-1-(2,5-difluoro-4-(2,2,2-trifluoroethoxy)phenyl)ethyl)amino)-5-fluoropyrimidin-4-yl)-4-((R)-1-hydroxyethyl)oxazolidin-2-one, (R)-3-(5-fluoro-2-(((S)-1-(2-fluoro-4-(2,2,2-trifluoroethoxy)phenyl)ethyl)amino)pyrimidin-4-yl)-4-((R)-1-hydroxyethyl)oxazolidin-2-one, (R)-3-(5-fluoro-2-(((S)-1-(3-fluoro-4-(2,2,2-trifluoroethoxy)phenyl)ethyl)amino)pyrimidin-4-yl)-4-((R)-1-hydroxyethyl)oxazolidin-2-one, (R)-3-(5-fluoro-2-(((S)-1-(1-(4-fluorophenyl)-1H-pyrazol-3-yl)ethyl)amino)pyrimidin-4-yl)-4-((R)-1-hydroxyethyl)oxazolidin-2-one, (R)-3-(5-fluoro-2-(((S)-1-(5-(2,2,2-trifluoroethoxy)pyridin-2-yl)ethyl)amino)pyrimidin-4-yl)-4-((R)-1-hydroxyethyl)oxazolidin-2-one, (R)-3-(2-(((S)-1-(1-(4-chlorophenyl)-1H-imidazol-4-yl)ethyl)amino)pyrimidin-4-yl)-4-((R)-1-hydroxyethyl)oxazolidin-2-one, (R)-3-(2-(((S)-1-(1-(4-chlorophenyl)-1H-pyrazol-3-yl)ethyl)amino)pyrimidin-4-yl)-4-((R)-1-hydroxyethyl)oxazolidin-2-one, (R)-3-(6-chloro-2-(((S)-1-(1-(4-chlorophenyl)-1H-imidazol-4-yl)ethyl)amino)pyrimidin-4-yl)-4-((R)-1-hydroxyethyl)oxazolidin-2-one, (R)-3-(6-chloro-2-(((S)-1-(1-(4-chlorophenyl)-1H-imidazol-4-yl)ethyl)amino)pyrimidin-4-yl)-4-((R)-1-hydroxyethyl)oxazolidin-2-one, (R)-3-(6-chloro-2-(((S)-1-(1-(4-fluorophenyl)-1H-pyrazol-3-yl)ethyl)amino)pyrimidin-4-yl)-4-((R)-1-hydroxyethyl)oxazolidin-2-one, (R)-3-(2-(((S)-1-(2,4-dichlorophenyl)ethyl)amino)pyrimidin-4-yl)-4-((R)-1-hydroxyethyl)oxazolidin-2-one, (R)-3-(2-(((S)-1-(3,4-dichlorophenyl)ethyl)amino)pyrimidin-4-yl)-4-((R)-1-hydroxyethyl)oxazolidin-2-one, (R)-3-(6-chloro-2-(((S)-1-(1-(4-chlorophenyl)-1H-pyrazol-3-yl)ethyl)amino)pyrimidin-4-yl)-4-((R)-1-hydroxyethyl)oxazolidin-2-one, (R)-3-(2-(((S)-1-(2,5-difluoro-4-(2,2,2-trifluoroethoxy)phenyl)ethyl)amino)pyrimidin-4-yl)-4-((R)-1-hydroxyethyl)oxazolidin-2-one, (R)-3-(2-(((S)-1-(2-fluoro-4-(2,2,2-trifluoroethoxy)phenyl)ethyl)amino)pyrimidin-4-yl)-4-((R)-1-hydroxyethyl)oxazolidin-2-one, (R)-3-(2-(((S)-1-(3-fluoro-4-(2,2,2-trifluoroethoxy)phenyl)ethyl)amino)pyrimidin-4-yl)-4-((R)-1-hydroxyethyl)oxazolidin-2-one, (R)-3-(2-(((S)-1-(5-bromopyridin-2-yl)ethyl)amino)pyrimidin-4-yl)-4-((R)-1-hydroxyethyl)oxazolidin-2-one,
(R)-3-(2-(((S)-1-(4,5-dichloro-2-fluorophenyl)ethyl)amino)pyrimidin-4-yl)-4-((R)-1-hydroxyethyl)oxazolidin-2-one,
(R)-3-(2-(((S)-1-(2,5-difluoro-4-(4-methyl-1H-imidazol-1-yl)phenyl)ethyl)amino)pyrimidin-4-yl)-4-((R)-1-hydroxyethyl)oxazolidin-2-one,
(R)-3-(5-chloro-2-(((S)-1-(4,5-dichloro-2-fluorophenyl)ethyl)amino)pyrimidin-4-yl)-4-((R)-1-hydroxyethyl)oxazolidin-2-one,
(R)-3-(2-(((S)-1-(2,5-difluoro-4-(2-methylpyridin-4-yl)phenyl)ethyl)amino)pyrimidin-4-yl)-4-((R)-1-hydroxyethyl)oxazolidin-2-one,
(R)-3-(2-(((S)-1-(2,5-difluoro-4-(6-methylpyridin-3-yl)phenyl)ethyl)amino)pyrimidin-4-yl)-4-((R)-1-hydroxyethyl)oxazolidin-2-one,
(R)-3-(2-(((S)-1-(2,5-difluoro-4-(2-(trifluoromethyl)pyridin-4-yl)phenyl)ethyl)amino)pyrimidin-4-yl)-4-((R)-1-hydroxyethyl)oxazolidin-2-one,
(R)-3-(2-(((S)-1-(2,5-difluoro-4-(6-(trifluoromethyl)pyridin-3-yl)phenyl)ethyl)amino)pyrimidin-4-yl)-4-((R)-1-hydroxyethyl)oxazolidin-2-one,
(R)-4-((R)-1-hydroxyethyl)-3-(2-(((S)-1-(4-isobutoxyphenyl)ethyl)amino)pyrimidin-4-yl)oxazolidin-2-one,
(R)-3-(5-fluoro-2-(((S)-1-(2-fluoro-4-methoxyphenyl)ethyl)amino)pyrimidin-4-yl)-4-((R)-1-hydroxyethyl)oxazolidin-2-one,
(R)-3-(2-(((S)-1-(2,3-difluorophenyl)ethyl)amino)pyrimidin-4-yl)-4-((R)-1-hydroxyethyl)oxazolidin-2-one,
(R)-3-(2-(((S)-1-(2,3-difluorophenyl)ethyl)amino)-5-fluoropyrimidin-4-yl)-4-((R)-1-hydroxyethyl)oxazolidin-2-one,
(R)-3-(2-(((S)-1-(3,4-difluorophenyl)ethyl)amino)-5-fluoropyrimidin-4-yl)-4-((R)-1-hydroxyethyl)oxazolidin-2-one,
(R)-3-(2-(((S)-1-(2,4-difluorophenyl)ethyl)amino)-5-fluoropyrimidin-4-yl)-4-((R)-1-hydroxyethyl)oxazolidin-2-one,
(R)-3-(2-(((S)-1-(3,5-difluorophenyl)ethyl)amino)-5-fluoropyrimidin-4-yl)-4-((R)-1-hydroxyethyl)oxazolidin-2-one,
(R)-3-(5-chloro-2-(((S)-1-(2'-(trifluoromethyl)-[3,4'-bipyridin]-6-yl)ethyl)amino)pyrimidin-4-yl)-4-((R)-1-hydroxyethyl)oxazolidin-2-one,
(R)-3-(5-fluoro-2-(((S)-1-(6-(2,2,2-trifluoroethoxy)pyridin-3-yl)ethyl)amino)pyrimidin-4-yl)-4-((R)-1-hydroxyethyl)oxazolidin-2-one,
(R)-3-(2-(((S)-1-(4-(difluoromethyl)-2-fluorophenyl)ethyl)amino)-5-fluoropyrimidin-4-yl)-4-((R)-1-hydroxyethyl)oxazolidin-2-one,
(R)-3-(2-(((S)-1-(4-(1,1-difluoroethyl)-2-fluorophenyl)ethyl)amino)-5-fluoropyrimidin-4-yl)-4-((R)-1-hydroxyethyl)oxazolidin-2-one,
(R)-3-(2-(((S)-1-(4-(1,1-difluoroethyl)-2-fluorophenyl)ethyl)amino)-5-fluoropyrimidin-4-yl)-4-((R)-1-hydroxyethyl)oxazolidin-2-one,
(R)-3-(6-chloro-2-(((S)-1-(4-(difluoromethyl)-2-fluorophenyl)ethyl)amino)pyrimidin-4-yl)-4-((R)-1-hydroxyethyl)oxazolidin-2-one,
(R)-3-(6-chloro-2-(((S)-1-(4-(1,1-difluoroethyl)-2-fluorophenyl)ethyl)amino)pyrimidin-4-yl)-4-((R)-1-hydroxyethyl)oxazolidin-2-one,
(R)-3-(6-chloro-2-(((S)-1-(5-phenylthiophen-2-yl)ethyl)amino)pyrimidin-4-yl)-4-((R)-1-hydroxyethyl)oxazolidin-2-one,
(R)-3-(6-chloro-2-(((S)-1-(5-(pyridin-2-yl)thiophen-2-yl)ethyl)amino)pyrimidin-4-yl)-4-((R)-1-hydroxyethyl)oxazolidin-2-one,
(R)-4-((R)-1-hydroxyethyl)-3-(2-(((S)-1-(3-(((S)-tetrahydrofuran-3-yl)oxy)phenyl)ethyl)amino)pyrimidin-4-yl)oxazolidin-2-one,
(R)-4-((R)-1-hydroxyethyl)-3-(2-(((S)-1-(3-isobutoxyphenyl)ethyl)amino)pyrimidin-4-yl)oxazolidin-2-one,
(R)-3-(6-chloro-2-(((S)-1-(4-(isobutylsulfonyl)phenyl)ethyl)amino)pyrimidin-4-yl)-4-((R)-1-hydroxyethyl)oxazolidin-2-one,
(R)-4-((R)-1-hydroxyethyl)-3-(2-(((S)-1-(4-(trifluoromethoxy)phenyl)ethyl)amino)pyrimidin-4-yl)oxazolidin-2-one,
(R)-3-(2-(((S)-1-(3-fluoro-4-(trifluoromethoxy)phenyl)ethyl)amino)pyrimidin-4-yl)-4-((R)-1-hydroxyethyl)oxazolidin-2-one,
(R)-3-(2-(((S)-1-(2-fluoro-4-(trifluoromethoxy)phenyl)ethyl)amino)pyrimidin-4-yl)-4-((R)-1-hydroxyethyl)oxazolidin-2-one,
(R)-3-(2-(((S)-1-(4-(difluoromethoxy)-3-fluorophenyl)ethyl)amino)pyrimidin-4-yl)-4-((R)-1-hydroxyethyl)oxazolidin-2-one,
(R)-3-(2-(((S)-1-(4-(difluoromethoxy)-3-fluorophenyl)ethyl)amino)-5-fluoropyrimidin-4-yl)-4-((R)-1-hydroxyethyl)oxazolidin-2-one,
(R)-3-(2-(((S)-1-(4-(difluoromethoxy)phenyl)ethyl)amino)pyrimidin-4-yl)-4-((R)-1-hydroxyethyl)oxazolidin-2-one,
(R)-3-(2-(((S)-1-(4-(difluoromethoxy)-2-fluorophenyl)ethyl)amino)pyrimidin-4-yl)-4-((R)-1-hydroxyethyl)oxazolidin-2-one,
(R)-4-((R)-1-hydroxyethyl)-3-(2-(((S)-1-(3-(trifluoromethoxy)phenyl)ethyl)amino)pyrimidin-4-yl)oxazolidin-2-one,
(R)-3-(2-(((S)-1-(3-(difluoromethoxy)phenyl)ethyl)amino)pyrimidin-4-yl)-4-((R)-1-hydroxyethyl)oxazolidin-2-one,
(R)-3-(2-(((S)-1-(4-(difluoromethoxy)-2-fluorophenyl)ethyl)amino)-5-fluoropyrimidin-4-yl)-4-((R)-1-hydroxyethyl)oxazolidin-2-one,
(R)-3-(5-fluoro-2-(((S)-1-(3-(trifluoromethoxy)phenyl)ethyl)amino)pyrimidin-4-yl)-4-((R)-1-hydroxyethyl)oxazolidin-2-one,
(R)-3-(2-(((S)-1-(3-(difluoromethoxy)phenyl)ethyl)amino)-5-fluoropyrimidin-4-yl)-4-((R)-1-hydroxyethyl)oxazolidin-2-one,
(R)-4-((R)-1-hydroxyethyl)-3-(2-(((S)-1-(3-phenoxyphenyl)ethyl)amino)pyrimidin-4-yl)oxazolidin-2-one,
(R)-4-((R)-1-hydroxyethyl)-3-(2-(((S)-1-(4-isopropoxyphenyl)ethyl)amino)pyrimidin-4-yl)oxazolidin-2-one,
(R)-4-((R)-1-hydroxyethyl)-3-(2-(((S)-1-(4-isobutoxy-3-methylphenyl)ethyl)amino)pyrimidin-4-yl)oxazolidin-2-one,
(R)-3-(6-chloro-2-(((S)-1-(4-(trifluoromethoxy)phenyl)ethyl)amino)pyrimidin-4-yl)-4-((R)-1-hydroxyethyl)oxazolidin-2-one,
(R)-3-(5-fluoro-2-(((S)-1-(4-(trifluoromethoxy)phenyl)ethyl)amino)pyrimidin-4-yl)-4-((R)-1-hydroxyethyl)oxazolidin-2-one,
(R)-3-(6-chloro-2-(((S)-1-(2-fluoro-4-(trifluoromethoxy)phenyl)ethyl)amino)pyrimidin-4-yl)-4-((R)-1-hydroxyethyl)oxazolidin-2-one,
(R)-3-(5-fluoro-2-(((S)-1-(2-fluoro-4-(trifluoromethoxy)phenyl)ethyl)amino)pyrimidin-4-yl)-4-((R)-1-hydroxyethyl)oxazolidin-2-one, (R)-3-(5-fluoro-2-(((S)-1-(2-fluoro-4-isobutoxyphenyl)ethyl)amino)pyrimidin-4-yl)-4-((R)-1-hydroxyethyl)oxazolidin-2-one,
(R)-3-(2-(((S)-1-(4-(difluoromethoxy)phenyl)ethyl)amino)-5-fluoropyrimidin-4-yl)-4-((R)-1-hydroxyethyl)oxazolidin-2-one,
(R)-3-(5-fluoro-2-(((S)-1-(3-fluoro-4-(trifluoromethoxy)phenyl)ethyl)amino)pyrimidin-4-yl)-4-((R)-1-hydroxyethyl)oxazolidin-2-one,
(R)-3-(6-chloro-2-(((S)-1-(4-(difluoromethoxy)phenyl)ethyl)amino)pyrimidin-4-yl)-4-((R)-1-hydroxyethyl)oxazolidin-2-one,
(R)-3-(6-chloro-2-(((S)-1-(3-fluoro-4-(trifluoromethoxy)phenyl)ethyl)amino)pyrimidin-4-yl)-4-((R)-1-hydroxyethyl)oxazolidin-2-one,
(R)-3-(5-fluoro-2-(((S)-1-(4-(isobutylsulfonyl)phenyl)ethyl)amino)pyrimidin-4-yl)-4-((R)-1-hydroxyethyl)oxazolidin-2-one,
(R)-3-(5-fluoro-2-(((S)-1-(4-(isopropylsulfonyl)phenyl)ethyl)amino)pyrimidin-4-yl)-4-((R)-1-hydroxyethyl)oxazolidin-2-one,
(R)-3-(6-chloro-2-(((S)-1-(4-(isopropylsulfonyl)phenyl)ethyl)amino)pyrimidin-4-yl)-4-((R)-1-hydroxyethyl)oxazolidin-2-one,
(R)-3-(2-(((S)-1-(4-(cyclopropylmethoxy)phenyl)ethyl)amino)pyrimidin-4-yl)-4-((R)-1-hydroxyethyl)oxazolidin-2-one,
(R)-3-(2-(((S)-1-(2-fluoro-4-isobutoxyphenyl)ethyl)amino)pyrimidin-4-yl)-4-((R)-1-hydroxyethyl)oxazolidin-2-one,
(S)-4-((R)-1-aminoethyl)-3-(2-(((S)-1-(2-(4-chlorophenyl)thiazol-5-yl)ethyl)amino)pyrimidin-4-yl)oxazolidin-2-one,
(S)-4-((R)-1-aminoethyl)-3-(2-(((S)-1-(2-(4-chlorophenyl)thiazol-5-yl)ethyl)amino)pyrimidin-4-yl)oxazolidin-2-one,
(S)-4-((R)-1-aminoethyl)-3-(2-(((S)-1-(1-(4-chlorophenyl)-1H-imidazol-4-yl)ethyl)amino)pyrimidin-4-yl)oxazolidin-2-one,
(S)-4-((R)-1-aminoethyl)-3-(2-(((S)-1-(5-(4-chlorophenyl)isoxazol-3-yl)ethyl)amino)pyrimidin-4-yl)oxazolidin-2-one,
(S)-4-((R)-1-aminoethyl)-3-(2-(((S)-1-(2,5-difluoro-4-(6-methylpyridin-3-yl)phenyl)ethyl)amino)pyrimidin-4-yl)oxazolidin-2-one,
(R)-3-(2-(((S)-1-(1-(4-chlorophenyl)-1H-imidazol-4-yl)ethyl)amino)pyrimidin-4-yl)-4-((R)-1-fluoroethyl)oxazolidin-2-one,
(R)-3-(2-(((S)-1-(1-(4-chlorophenyl)-1H-imidazol-4-yl)ethyl)amino)pyrimidin-4-yl)-4-((R)-1-fluoroethyl)oxazolidin-2-one,
(R)-3-(2-(((S)-1-(5-(4-chlorophenyl)isoxazol-3-yl)ethyl)amino)pyrimidin-4-yl)-4-((R)-1-fluoroethyl)oxazolidin-2-one,
(R)-3-(2-(((S)-1-(2-(4-chlorophenyl)thiazol-5-yl)ethyl)amino)pyrimidin-4-yl)-4-((R)-1-fluoroethyl)oxazolidin-2-one,
(R)-3-(2-(((S)-1-(1-(4-chlorophenyl)-1H-imidazol-4-yl)ethyl)amino)pyrimidin-4-yl)-4-((S)-1-fluoroethyl)oxazolidin-2-one,
(R)-3-(2-(((S)-1-(2-(4-chlorophenyl)thiazol-5-yl)ethyl)amino)pyrimidin-4-yl)-4-((S)-1-fluoroethyl)oxazolidin-2-one,
(R)-3-(2-(((S)-1-(5-(4-chlorophenyl)isoxazol-3-yl)ethyl)amino)pyrimidin-4-yl)-4-((S)-1-fluoroethyl)oxazolidin-2-one,
(R)-3-(2-(((S)-1-(3-(4-chlorophenyl)-1,2,4-oxadiazol-5-yl)ethyl)amino)pyrimidin-4-yl)-4-((R)-1-fluoroethyl)oxazolidin-2-one,
(R)-4-((R)-1-fluoroethyl)-3-(2-(((S)-1-(2-(2-(trifluoromethyl)pyridin-4-yl)thiazol-5-yl)ethyl)amino)pyrimidin-4-yl)oxazolidin-2-one,
(R)-4-((R)-1-fluoroethyl)-3-(2-(((S)-1-(2-(6-(trifluoromethyl)pyridin-3-yl)thiazol-5-yl)ethyl)amino)pyrimidin-4-yl)oxazolidin-2-one,
(R)-3-(2-(((S)-1-(1-(4-chlorophenyl)-1H-pyrazol-4-yl)ethyl)amino)pyrimidin-4-yl)-4-((R)-1-fluoroethyl)oxazolidin-2-one,
(R)-3-(2-(((S)-1-(2-(4-chlorophenyl)thiazol-5-yl)ethyl)amino)-5-fluoropyrimidin-4-yl)-4-((R)-1-fluoroethyl)oxazolidin-2-one,
(R)-3-(2-(((S)-1-(1-(4-chlorophenyl)-1H-pyrazol-4-yl)ethyl)amino)pyrimidin-4-yl)-4-((S)-1-fluoroethyl)oxazolidin-2-one,
(R)-3-(2-(((S)-1-(1-(4-chlorophenyl)-1H-pyrazol-4-yl)ethyl)amino)-5-fluoropyrimidin-4-yl)-4-((R)-1-fluoroethyl)oxazolidin-2-one,
(R)-3-(2-(((S)-1-(5-(4-chlorophenyl)isoxazol-3-yl)ethyl)amino)-5-fluoropyrimidin-4-yl)-4-((R)-1-fluoroethyl)oxazolidin-2-one,
(R)-3-(2-(((S)-1-(1-(4-chlorophenyl)-1H-imidazol-4-yl)ethyl)amino)-5-fluoropyrimidin-4-yl)-4-((R)-1-fluoroethyl)oxazolidin-2-one,
(R)-3-(2-(((S)-1-(1-(4-chlorophenyl)-2-methyl-1H-imidazol-4-yl)ethyl)amino)pyrimidin-4-yl)-4-((S)-1-fluoroethyl)oxazolidin-2-one,
(R)-4-((S)-1-fluoroethyl)-3-(2-(((S)-1-(1-(4-fluorophenyl)-1H-imidazol-4-yl)ethyl)amino)pyrimidin-4-yl)oxazolidin-2-one,
(R)-4-((S)-1-fluoroethyl)-3-(2-(((S)-1-(1-(4-fluorophenyl)-1H-imidazol-4-yl)ethyl)amino)pyrimidin-4-yl)oxazolidin-2-one,
(R)-3-(2-(((S)-1-(2,5-difluoro-4-(4-methyl-1H-imidazol-1-yl)phenyl)ethyl)amino)pyrimidin-4-yl)-4-((S)-1-fluoroethyl)oxazolidin-2-one,
(R)-4-((S)-1-fluoroethyl)-3-(2-(((S)-1-(6-(trifluoromethyl)pyridin-3-yl)-1H-pyrazol-3-yl)ethyl)amino)pyrimidin-4-yl)oxazolidin-2-one,
(R)-3-(2-(((S)-1-(1-(4-chlorophenyl)-2-methyl-1H-imidazol-4-yl)ethyl)amino)pyrimidin-4-yl)-4-((R)-1-fluoroethyl)oxazolidin-2-one,
(R)-4-((S)-1-hydroxyethyl)-3-(2-(((S)-1-(1-(2-(1,1,1-trifluoro-2-methylpropan-2-yl)pyridin-4-yl)piperidin-4-yl)ethyl)amino)pyrimidin-4-yl)oxazolidin-2-one,
(R)-3-(2-(((S)-1-(1-(4-chloro-3-(trifluoromethoxy)phenyl)piperidin-4-yl)ethyl)amino)pyrimidin-4-yl)-4-((S)-1-hydroxyethyl)oxazolidin-2-one,
(R)-4-((R)-1-hydroxyethyl)-3-(2-(((S)-1-(3-(1-methyl-1H-indol-6-yl)-1,2,4-oxadiazol-5-yl)ethyl)amino)pyrimidin-4-yl)oxazolidin-2-one,
(R)-4-((R)-1-hydroxyethyl)-3-(2-(((S)-1-(3-(3-(trifluoromethoxy)phenyl)-1,2,4-oxadiazol-5-yl)ethyl)amino)pyrimidin-4-yl)oxazolidin-2-one,
(R)-3-(2-(((S)-1-(3-(1,2-dimethyl-1H-indol-4-yl)-1,2,4-oxadiazol-5-yl)ethyl)amino)pyrimidin-4-yl)-4-((R)-1-hydroxyethyl)oxazolidin-2-one,
(R)-3-(2-(((S)-1-(3-(4-chloro-3-(trifluoromethoxy)phenyl)-1,2,4-oxadiazol-5-yl)ethyl)amino)pyrimidin-4-yl)-4-((R)-1-hydroxyethyl)oxazolidin-2-one,
(R)-3-(2-(((S)-1-(3-(4-chloro-3-methylphenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(4-bromo-3-methoxyphenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(3-(tert-butyl)phenyl)-1,2,4-oxadiazol-5-yl)ethyl)amino)pyrimidin-4-yl)-4-((R)-1-hydroxyethyl)oxazolidin-2-one, (R)-3-(2-(((S)-1-(3-(2,3-dihydro-1H-inden-5-yl)-1,2,4-oxadiazol-5-yl)ethyl)amino)pyrimidin-4-yl)-4-((R)-1-hydroxyethyl)oxazolidin-2-one, (R)-3-(2-(((S)-1-(5-(4-chlorophenyl)-1,2,4-oxadiazol-3-yl)ethyl)amino)pyrimidin-4-yl)-4-((R)-1-hydroxyethyl)oxazolidin-2-one, (R)-4-((S)-1-fluoroethyl)-3-(2-(((S)-1-(2-(2-(trifluoromethyl)pyridin-4-yl)thiazol-5-yl)ethyl)amino)pyrimidin-4-yl)oxazolidin-2-one, (R)-3-(2-(((S)-1-(1-(4-(difluoromethyl)-3-fluorophenyl)-1H-imidazol-4-yl)ethyl)amino)-5-fluoropyrimidin-4-yl)-4-((S)-1-fluoroethyl)oxazolidin-2-one, (R)-3-(2-(((S)-1-(1-(4-(difluoromethyl)phenyl)-1H-imidazol-4-yl)ethyl)amino)-5-fluoropyrimidin-4-yl)-4-((S)-1-fluoroethyl)oxazolidin-2-one, (R)-3-(2-(((S)-1-(1-(4-chloro-3-fluorophenyl)-1H-imidazol-4-yl)ethyl)amino)-5-fluoropyrimidin-4-yl)-4-((S)-1-fluoroethyl)oxazolidin-2-one, (R)-3-(2-(((S)-1-(1-(3,5-difluorophenyl)-1H-imidazol-4-yl)ethyl)amino)-5-fluoropyrimidin-4-yl)-4-((S)-1-fluoroethyl)oxazolidin-2-one, (R)-3-(2-(((S)-1-(1-(4-chlorophenyl)-1H-imidazol-4-yl)ethyl)amino)-5-fluoropyrimidin-4-yl)-4-((S)-1-fluoroethyl)oxazolidin-2-one, (R)-3-(5-fluoro-2-(((S)-1-(1-(4-fluorophenyl)-1H-imidazol-4-yl)ethyl)amino)pyrimidin-4-yl)-4-((S)-1-fluoroethyl)oxazolidin-2-one, (R)-3-(2-(((S)-1-(5-(4-chlorophenyl)isoxazol-3-yl)ethyl)amino)-5-fluoropyrimidin-4-yl)-4-((S)-1-fluoroethyl)oxazolidin-2-one, (R)-3-(2-(((S)-1-(1-(4-chlorophenyl)-1H-pyrazol-4-yl)ethyl)amino)-5-fluoropyrimidin-4-yl)-4-((S)-1-fluoroethyl)oxazolidin-2-one, (R)-3-(2-(((S)-1-(1-(3,5-difluorophenyl)-1H-imidazol-4-yl)ethyl)amino)pyrimidin-4-yl)-4-((S)-1-fluoroethyl)oxazolidin-2-one, (R)-3-(2-(((S)-1-(1-(4-(difluoromethyl)-3-fluorophenyl)-1H-imidazol-4-yl)ethyl)amino)pyrimidin-4-yl)-4-((S)-1-fluoroethyl)oxazolidin-2-one, (R)-3-(2-(((S)-1-(1-(4-(difluoromethyl)phenyl)-1H-imidazol-4-yl)ethyl)amino)pyrimidin-4-yl)-4-((S)-1-fluoroethyl)oxazolidin-2-one, (R)-3-(2-(((S)-1-(1-(4-(difluoromethyl)phenyl)-1H-imidazol-4-yl)ethyl)amino)pyrimidin-4-yl)-4-((S)-1-fluoroethyl)oxazolidin-2-one, (R)-3-(2-(((S)-1-(1-(3-chloro-4-fluorophenyl)-1H-imidazol-4-yl)ethyl)amino)pyrimidin-4-yl)-4-((S)-1-fluoroethyl)oxazolidin-2-one, (R)-3-(2-(((S)-1-(1-(4-chloro-3-fluorophenyl)-1H-imidazol-4-yl)ethyl)amino)pyrimidin-4-yl)-4-((S)-1-fluoroethyl)oxazolidin-2-one, (R)-3-(2-(((S)-1-(1-(3,4-difluorophenyl)-1H-imidazol-4-yl)ethyl)amino)pyrimidin-4-yl)-4-((S)-1-fluoroethyl)oxazolidin-2-one, (R)-3-(2-(((S)-1-(2,5-difluoro-4-(1-methyl-1H-pyrazol-4-yl)phenyl)ethyl)amino)pyrimidin-4-yl)-4-((S)-1-fluoroethyl)oxazolidin-2-one, (R)-3-(5-fluoro-2-(((S)-1-(1-(4-fluorophenyl)-1H-imidazol-4-yl)ethyl)amino)pyrimidin-4-yl)-4-((R)-1-fluoroethyl)oxazolidin-2-one, (R)-3-(5-fluoro-2-(((S)-1-(5-fluoro-2'-(trifluoromethyl)-[3,4'-bipyridin]-6-yl)ethyl)amino)pyrimidin-4-yl)-4-((R)-1-fluoroethyl)oxazolidin-2-one, (R)-3-(2-(((S)-1-(5-fluoro-2'-(trifluoromethyl)-[3,4'-bipyridin]-6-yl)ethyl)amino)pyrimidin-4-yl)-4-((S)-1-fluoroethyl)oxazolidin-2-one, (R)-3-(2-(((S)-1-(5-fluoro-2'-(trifluoromethyl)-[3,4'-bipyridin]-6-yl)ethyl)amino)pyrimidin-4-yl)-4-((R)-1-fluoroethyl)oxazolidin-2-one, (R)-3-(5-fluoro-2-(((S)-1-(5-fluoro-2'-(trifluoromethyl)-[3,4'-bipyridin]-6-yl)ethyl)amino)pyrimidin-4-yl)-4-((S)-1-fluoroethyl)oxazolidin-2-one, (R)-4-((S)-1-fluoroethyl)-3-(2-(((S)-1-(4-methyl-2'-(trifluoromethyl)-[3,4'-bipyridin]-6-yl)ethyl)amino)pyrimidin-4-yl)oxazolidin-2-one, (R)-3-(2-(((S)-1-(5-(2-fluoro-3-(trifluoromethyl)phenyl)pyrimidin-2-yl)ethyl)amino)pyrimidin-4-yl)-4-((S)-1-fluoroethyl)oxazolidin-2-one, (R)-4-((S)-1-fluoroethyl)-3-(2-(((S)-1-(2'-(trifluoromethyl)-[3,4'-bipyridin]-6-yl)ethyl)amino)pyrimidin-4-yl)oxazolidin-2-one, (R)-3-(2-(((S)-1-(5-(4-fluoro-3-methylphenyl)pyrimidin-2-yl)ethyl)amino)pyrimidin-4-yl)-4-((S)-1-fluoroethyl)oxazolidin-2-one, (R)-3-(5-fluoro-2-(((S)-1-(4-methyl-2'-(trifluoromethyl)-[3,4'-bipyridin]-6-yl)ethyl)amino)pyrimidin-4-yl)-4-((S)-1-fluoroethyl)oxazolidin-2-one, (R)-3-(2-(((S)-1-(1-(4-chloro-2-fluorophenyl)-1H-imidazol-4-yl)ethyl)amino)pyrimidin-4-yl)-4-((S)-1-fluoroethyl)oxazolidin-2-one, (R)-3-(2-(((S)-1-(1-(4-chloro-2-fluorophenyl)-1H-imidazol-4-yl)ethyl)amino)-5-fluoropyrimidin-4-yl)-4-((S)-1-fluoroethyl)oxazolidin-2-one, (R)-3-(2-(((S)-1-(1-(2,4-difluorophenyl)-1H-imidazol-4-yl)ethyl)amino)pyrimidin-4-yl)-4-((S)-1-fluoroethyl)oxazolidin-2-one, and (R)-3-(2-(((S)-1-(1-(2,4-difluorophenyl)-1H-imidazol-4-yl)ethyl)amino)-5-fluoropyrimidin-4-yl)-4-((S)-1-fluoroethyl)oxazolidin-2-one;

or a pharmaceutically acceptable salt thereof.

\* \* \* \* \*

SEQUENCE LISTING

<160> NUMBER OF SEQ ID NOS: 3

<210> SEQ ID NO 1
<211> LENGTH: 434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

```
Met Ala His His His His His His Ser Ala Ala Leu Glu Val Leu Phe
1               5                   10                  15

Gln Gly Pro Gly Met Ser Lys Lys Ile Ser Gly Gly Ser Val Val Glu
            20                  25                  30

Met Gln Gly Asp Glu Met Thr Arg Ile Ile Trp Glu Leu Ile Lys Glu
        35                  40                  45

Lys Leu Ile Phe Pro Tyr Val Glu Leu Asp Leu His Ser Tyr Asp Leu
    50                  55                  60

Gly Ile Glu Asn Arg Asp Ala Thr Asn Asp Gln Val Thr Lys Asp Ala
65                  70                  75                  80

Ala Glu Ala Ile Lys Lys His Asn Val Gly Val Lys Cys Ala Thr Ile
                85                  90                  95

Thr Pro Asp Glu Lys Arg Val Glu Glu Phe Lys Leu Lys Gln Met Trp
            100                 105                 110

Lys Ser Pro Asn Gly Thr Ile Arg Asn Ile Leu Gly Gly Thr Val Phe
        115                 120                 125

Arg Glu Ala Ile Ile Cys Lys Asn Ile Pro Arg Leu Val Ser Gly Trp
130                 135                 140

Val Lys Pro Ile Ile Ile Gly His His Ala Tyr Gly Asp Gln Tyr Arg
145                 150                 155                 160

Ala Thr Asp Phe Val Val Pro Gly Pro Gly Lys Val Glu Ile Thr Tyr
                165                 170                 175

Thr Pro Ser Asp Gly Thr Gln Lys Val Thr Tyr Leu Val His Asn Phe
            180                 185                 190

Glu Glu Gly Gly Gly Val Ala Met Gly Met Tyr Asn Gln Asp Lys Ser
        195                 200                 205

Ile Glu Asp Phe Ala His Ser Ser Phe Gln Met Ala Leu Ser Lys Gly
    210                 215                 220

Trp Pro Leu Tyr Leu Ser Thr Lys Asn Thr Ile Leu Lys Lys Tyr Asp
225                 230                 235                 240

Gly Arg Phe Lys Asp Ile Phe Gln Glu Ile Tyr Asp Lys Gln Tyr Lys
                245                 250                 255

Ser Gln Phe Glu Ala Gln Lys Ile Trp Tyr Glu His Arg Leu Ile Asp
            260                 265                 270

Asp Met Val Ala Gln Ala Met Lys Ser Glu Gly Gly Phe Ile Trp Ala
        275                 280                 285

Cys Lys Asn Tyr Asp Gly Asp Val Gln Ser Asp Ser Val Ala Gln Gly
    290                 295                 300

Tyr Gly Ser Leu Gly Met Met Thr Ser Val Leu Val Cys Pro Asp Gly
305                 310                 315                 320

Lys Thr Val Glu Ala Glu Ala Ala His Gly Thr Val Thr Arg His Tyr
                325                 330                 335

Arg Met Tyr Gln Lys Gly Gln Glu Thr Ser Thr Asn Pro Ile Ala Ser
            340                 345                 350
```

```
Ile Phe Ala Trp Thr Arg Gly Leu Ala His Arg Ala Lys Leu Asp Asn
            355                 360                 365

Asn Lys Glu Leu Ala Phe Phe Ala Asn Ala Leu Glu Glu Val Ser Ile
        370                 375                 380

Glu Thr Ile Glu Ala Gly Phe Met Thr Lys Asp Leu Ala Ala Cys Ile
385                 390                 395                 400

Lys Gly Leu Pro Asn Val Gln Arg Ser Asp Tyr Leu Asn Thr Phe Glu
                405                 410                 415

Phe Met Asp Lys Leu Gly Glu Asn Leu Lys Ile Lys Leu Ala Gln Ala
            420                 425                 430

Lys Leu

<210> SEQ ID NO 2
<211> LENGTH: 417
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Pro Gly Met Ser Lys Lys Ile Ser Gly Ser Val Val Glu Met
1               5                   10                  15

Gln Gly Asp Glu Met Thr Arg Ile Ile Trp Glu Leu Ile Lys Glu Lys
            20                  25                  30

Leu Ile Phe Pro Tyr Val Glu Leu Asp Leu His Ser Tyr Asp Leu Gly
        35                  40                  45

Ile Glu Asn Arg Asp Ala Thr Asn Asp Gln Val Thr Lys Asp Ala Ala
    50                  55                  60

Glu Ala Ile Lys Lys His Asn Val Gly Val Lys Cys Ala Thr Ile Thr
65                  70                  75                  80

Pro Asp Glu Lys Arg Val Glu Glu Phe Lys Leu Lys Gln Met Trp Lys
                85                  90                  95

Ser Pro Asn Gly Thr Ile Arg Asn Ile Leu Gly Gly Thr Val Phe Arg
            100                 105                 110

Glu Ala Ile Ile Cys Lys Asn Ile Pro Arg Leu Val Ser Gly Trp Val
        115                 120                 125

Lys Pro Ile Ile Ile Gly His His Ala Tyr Gly Asp Gln Tyr Arg Ala
    130                 135                 140

Thr Asp Phe Val Val Pro Gly Pro Gly Lys Val Glu Ile Thr Tyr Thr
145                 150                 155                 160

Pro Ser Asp Gly Thr Gln Lys Val Thr Tyr Leu Val His Asn Phe Glu
                165                 170                 175

Glu Gly Gly Gly Val Ala Met Gly Met Tyr Asn Gln Asp Lys Ser Ile
            180                 185                 190

Glu Asp Phe Ala His Ser Ser Phe Gln Met Ala Leu Ser Lys Gly Trp
        195                 200                 205

Pro Leu Tyr Leu Ser Thr Lys Asn Thr Ile Leu Lys Lys Tyr Asp Gly
    210                 215                 220

Arg Phe Lys Asp Ile Phe Gln Glu Ile Tyr Asp Lys Gln Tyr Lys Ser
225                 230                 235                 240

Gln Phe Glu Ala Gln Lys Ile Trp Tyr Glu His Arg Leu Ile Asp Asp
                245                 250                 255

Met Val Ala Gln Ala Met Lys Ser Glu Gly Gly Phe Ile Trp Ala Cys
            260                 265                 270
```

```
Lys Asn Tyr Asp Gly Asp Val Gln Ser Asp Ser Val Ala Gln Gly Tyr
            275                 280                 285

Gly Ser Leu Gly Met Met Thr Ser Val Leu Val Cys Pro Asp Gly Lys
        290                 295                 300

Thr Val Glu Ala Glu Ala Ala His Gly Thr Val Thr Arg His Tyr Arg
305                 310                 315                 320

Met Tyr Gln Lys Gly Gln Glu Thr Ser Thr Asn Pro Ile Ala Ser Ile
                325                 330                 335

Phe Ala Trp Thr Arg Gly Leu Ala His Arg Ala Lys Leu Asp Asn Asn
                340                 345                 350

Lys Glu Leu Ala Phe Phe Ala Asn Ala Leu Glu Glu Val Ser Ile Glu
                355                 360                 365

Thr Ile Glu Ala Gly Phe Met Thr Lys Asp Leu Ala Ala Cys Ile Lys
            370                 375                 380

Gly Leu Pro Asn Val Gln Arg Ser Asp Tyr Leu Asn Thr Phe Glu Phe
385                 390                 395                 400

Met Asp Lys Leu Gly Glu Asn Leu Lys Ile Lys Leu Ala Gln Ala Lys
                405                 410                 415

Leu

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5
```